US012773458B2

(12) United States Patent
Rastelli et al.

(10) Patent No.: US 12,773,458 B2
(45) Date of Patent: Oct. 27, 2026

(54) DIRECTED CONJUGATION TECHNOLOGIES

(71) Applicant: KLEO PHARMACEUTICALS, INC., New Haven, CT (US)

(72) Inventors: Luca Rastelli, Madison, CT (US); David Adam Spiegel, Hamden, CT (US); Matthew Ernest Welsch, New Haven, CT (US); Tetyana Berbasova, New Haven, CT (US); Michael C. Cukan, New Haven, CT (US); Lawrence Gerald Iben, Bethany, CT (US); Ada Margaret Vaill, New Haven, CT (US); Anna Bunin, New Haven, CT (US); Christian Marcel Vidal, New Haven, CT (US); Enrique Alvarez, New Haven, CT (US)

(73) Assignee: BIOHAVEN THERAPEUTICS LTD., New Haven, CT (US)

( * ) Notice: Subject to any disclaimer, the term of this patent is extended or adjusted under 35 U.S.C. 154(b) by 1083 days.

(21) Appl. No.: 17/769,924

(22) PCT Filed: Nov. 18, 2020

(86) PCT No.: PCT/US2020/061127
§ 371 (c)(1),
(2) Date: Apr. 18, 2022

(87) PCT Pub. No.: WO2021/102052
PCT Pub. Date: May 27, 2021

(65) Prior Publication Data

US 2023/0128688 A1 Apr. 27, 2023

Related U.S. Application Data

(60) Provisional application No. 63/063,902, filed on Aug. 10, 2020, provisional application No. 62/937,131, filed on Nov. 18, 2019.

(51) Int. Cl.

| | |
|---|---|
| ***A61K 47/64*** | (2017.01) |
| ***A61K 47/54*** | (2017.01) |
| ***A61K 47/65*** | (2017.01) |
| ***A61K 47/68*** | (2017.01) |

(52) U.S. Cl.
CPC .............. *A61K 47/64* (2017.08); *A61K 47/54* (2017.08); *A61K 47/65* (2017.08); *A61K 47/6849* (2017.08); *A61K 47/6879* (2017.08)

(58) Field of Classification Search
CPC ...................................................... A61K 47/64
See application file for complete search history.

(56) References Cited

U.S. PATENT DOCUMENTS

| | | | |
|---|---|---|---|
| 7,151,163 | B2 | 12/2006 | Erickson et al. |
| 9,745,339 | B2 | 8/2017 | Bittermann et al. |
| 11,135,307 | B2 | 10/2021 | Yurkovetskiy et al. |
| 2009/0286693 | A1 | 11/2009 | Chang et al. |
| 2015/0125473 | A1 | 5/2015 | Burt et al. |
| 2018/0303953 | A1 | 10/2018 | Van Berkel et al. |
| 2019/0111149 | A1 | 4/2019 | Gardiner et al. |
| 2020/0188528 | A1 | 6/2020 | Olson et al. |
| 2023/0330240 | A1 | 10/2023 | Bayden et al. |
| 2024/0335555 | A1 | 10/2024 | Kazmierski et al. |

FOREIGN PATENT DOCUMENTS

| | | | |
|---|---|---|---|
| EP | 3617235 | A1 | 3/2020 |
| WO | 2006000034 | A1 | 1/2006 |
| WO | 2012017021 | A2 | 2/2012 |
| WO | 2016033321 | A1 | 3/2016 |
| WO | 2017139329 | A1 | 8/2017 |
| WO | 2019023501 | A1 | 1/2019 |
| WO | 2019240288 | A1 | 12/2019 |
| WO | 2021003050 | A2 | 1/2021 |

OTHER PUBLICATIONS

Extended European Search Report for European Application 21775066.0 [PCT/US2021/024186] dated Sep. 16, 2024; 6 pages.
Supplementary Partial European Search Report for Application No. 22750512.0 [PCT/US2022/015390] dated Feb. 18, 2025; 6 pages.
Zhang, G. et al.; "The first-in-class peptide binder to the SARS-CoV-2 spike protein", bioRxiv, Mar. 20, 2020; DOI: 10.1101/2020.03.19.999318, available online at "www.biorxiv.org/content/10.1101/2020.03.19.99938v1.full.pdf" (2020).
Alves et al., "Oriented surface immobilization of antibodies at the conserved nucleotide binding site for enhanced antigen detection," ACS Publications, (2012), dx.doi.org/10.1021/la301887s, 9640-9648.
Choe et al., "Fc-binding ligands of immunoglobulin G: An overview of high affinity proteins and peptides." Materials, (2016), vol. 9, (No. 12). https://doi.org/10.3390/ma9120994.
Extended European Search Report for European Application 20891185.9 [PCT/US2020/061127] dated May 7, 2024; 17 pages.
Gupta et al., "Computationally designed antibody-drug conjugates self-assembled via affinity ligands," Nature Biomedical Engineering, (2019), vol. 3, 917-929.
Hui, et al., "LASIC: light activated site-specific conjugation of native IgGs," Bioconjugate Chemistry, (2015); doi: 10.1021/acs.bioconjchem.5b00275; A-E.
International Search Report for International Application No. PCT/US2022/15390 International Filing Date—Feb. 6, 2022; Date of Mailing—Aug. 24, 2022; 5 pages.

(Continued)

*Primary Examiner* — John S Kenyon
(74) *Attorney, Agent, or Firm* — CANTOR COLBURN LLP

(57) ABSTRACT

Among other things, the present disclosure provides technologies for site-directed conjugation of various moieties of interest to target agents. In some embodiments, the present disclosure utilizes target binding moieties to provide high conjugation efficiency and selectivity. In some embodiments, provided technologies are useful for preparing antibody conjugates.

20 Claims, 28 Drawing Sheets

Specification includes a Sequence Listing.

(56) References Cited

OTHER PUBLICATIONS

International Search Report; International Application No. PCT/US2021/024186; International Filing Date—Mar. 25, 2021; Date of Mailing—Aug. 6, 2021; 5 pages.

Jackson, "Processes for Constructing Homogeneous Antibody Drug Conjugates," Organic Process Research and Development, (2016), vol. 20, 852-866.

Kishimoto et al., "Site-Specific Chemical Conjugation of Antibodies by Using Affinity Peptide for the Development of Therapeutic Antibody Format," Bioconjugate Chemistry, (2019), vol. 30, 698-702.

Kruljec, et al., "Alternative Affinity Ligands for Immunoglobulins," Bioconjugate Chemistry, (2017), A-V; doi: 10.1021/acs.bioconjchem.7b00335 (e.g., Fabsorbent. triazines, etc.).

Kruljec, et al., "Development and characterization of peptide ligands of immunoglobulin G Fc region," Bioconjugate Chemistry, (2018), 1-26; doi: 10.102l/acs.bioconjchem.8b00395.

Larock, "Comprehensive Organic Transformations, A guide to functional group preparations" John Wiley & Sons, (1999), 1-145.

Muguruma, et al., "Kinetics-based structural requirements of human immunoglobulin G binding peptides," ACS Omega, (2019), A-H; doi: 10.1021/acsomega.9b01104.

Mustafaoglu, et al., "Antibody Purification via Affinity Membrane Chromatography Method Utilizing Nucleotide Binding Site Targeting With A Small Molecule," HHS Public Access, (2016), 141(24): 6571-6582.

Nelson, M. et al.; "Dual targeting of 4-1BB and OX40 with an Adaptir bispecific antibody enhances anti-tumor responses to solid tumor"; J Immunother Cancer, 8(Suppl 3) A379-A380 (2020).

Schleifer et al., "The Irnmunochemistry of Peptidoglycan; Antibodies against a Synthetic Immunogen Cross-Reacting with Peptidoglycan," Eur. J. Biochem., (1974), vol. 43, 509-519.

Smith, "March's Advanced Organic Chemistry: Reaction. Mechanisms, and Structure," John Wiley & Sons, (2001), 5th Edition.

Teng, et al., "A strategy for the generation of biomimetic ligands for affinity chromatography, combinatorial synthesis and biological evaluation of an IgG binding ligand," Journal of Molecular Recognition, (1999), vol. 12, 67-75.

Vidal, C. et al.; "A novel site-directed chemical conjugation technology confers antitumor activity via native Fc receptor to plasma immunoglobulin by attaching tumor binders"; J Immunother Cancer 8(Supp 3) A380 (2020).

Vidal, C. et al.; "KPMW135, . . . Demonstrates Increased Anti-Tumor Activity by Adding T Cell-Mediated Cytotoxicity Activity to the Existing Mechanisms of Rituximab"; Blood 136(Supp 9) 3 pp (2020); DOI:10.1182/blood-2020-142113.

Wang et al., "Engineering a Novel Antibody-Peptide Bispecific Fusion Protein Against MERS-CoV," Antibodies (2019), vol. 8, (53), 1-11.

Written Opinion for International Application PCT/US20201/024186: International Filing Date—Mar. 25, 2021; Date of Mailing—Aug. 6, 2021; 7 pages.

Written Opinion of the International Searching Authority for International Application No. PCT/US2022/15390 International Filing Date—Feb. 6, 2022; Date of Mailing—Aug. 24, 2022; 10 pages.

Yamada, et al., "AJICAP: Affinity peptide mediated regiodivergent functionalization of native antibodies," Angewandte Chemie International Edition, (2019), 16;58(17):5592-5597. doi: 10.1002/anic.201814215.

Yan et al., "Design and Study of Novel Peptide Inhibitors Against the SARS-Coronavirus Spike Protein," Understanding Biology Using Peptides, (2006), vol. 9, 335-337.

International Search Report dated Feb. 2, 2021 issued for International Application No. PCT/US2020/047287 (4 pages).

Written Opinion dated Feb. 2, 2021 issued for International Application No. PCT/US2020/047287 (8 pages).

International Preliminary Report on Patentability dated Feb. 17, 2022 issued for International Application No. PCT/US2020/047287 (9 pages).

Metallo et al. "Using Bifunctional Polymers Presenting Vancomycin and Fluorescein Groups To Direct Anti-Fluorescein Antibodies to Self-Assembled Monolayers Presenting D-Alanine-D-Alanine Groups", J. Am. Chem. Soc. 2003. vol. 125, pp. 4534-4540, entire document.

Sumranjit et al. "Recent Advances in Target Characterization and Identification by Photoaffinity Probes", Molecules 2013. vol. 18, pp. 10425-10451, especially: abstract; p. 10426, Scheme 1; p. 10427, para 3; p. 10427, Scheme 2; p. 10431, para 1; p. 10431, Figure 4, formula 9; p. 10432, Figure 5.

Vance et al. "Development, optimization and structural characterization of an efficient peptide-based photoaffinity crosslinking reaction for generation of homogeneous conjugates from wild. type antibodies", Bioconjugate Chem. Dec. 19, 2018, vol. 30(1), pp. 148-160, especially: abstract; p. 2, para 2; p. 2, para ; p. 6, para 4; p. 12, para 1; p. 15, Figure 1, compound 3a.

Walsh et al. "Site-seleclive modification strategies in antibody drug conjugates". Chem. Soc. Rev. 2021. vol. 50, pp. 1305-1353, entire document.

Brinkmann U. & Kontermann, R; "The making of bispecific antibodies"; mAbs, vol. 9, Issue No. 2; pp. 182-212; doi:10.1080/19420862.2016.1268307 (2017).

Uttamchandani, et al.; "Microarrays of Tagged Combinatorial Triazine Libraries in the Discovery of Small-Molecule Ligands of Human IgG"; J. Comb. Chem, vol. 6, Issue No. 6; pp. 862-868; DOI:10.1021/cc049900s (2004).

Xia, S. et al.; "Fusion mechanism of 2019-nCOV and fusion inhibitors targeting HR1 domain in spike protein"; Cell Mol Immunol, vol. 17; pp. 765-767; DOI:10.1038/s41423-020-0374-2 (2020).

Singapore Search Report and Written Opinion for Singapore Application 11202204154V; Date of Report: Nov. 7, 2025; 15 pages.

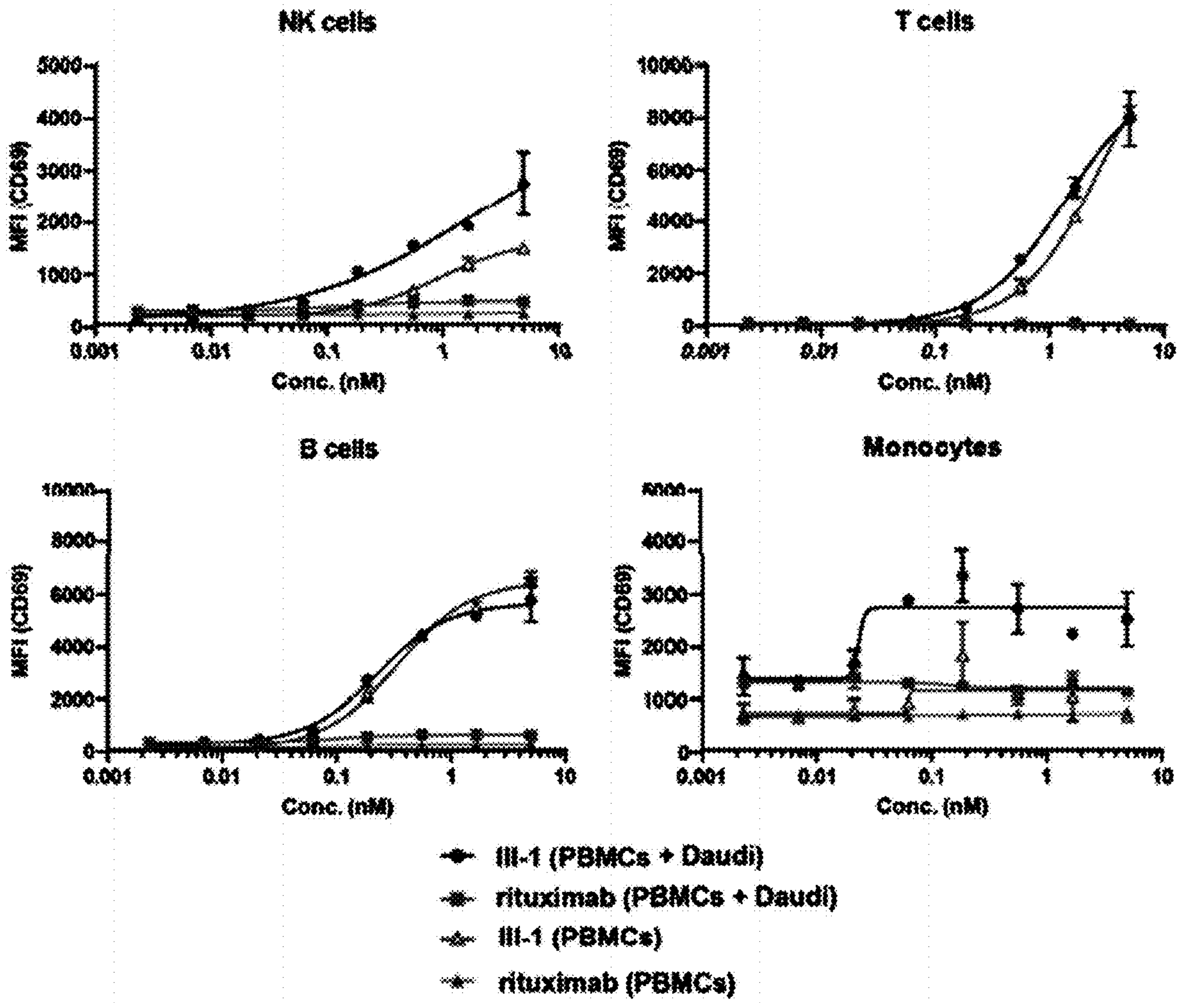
Fig. 30B
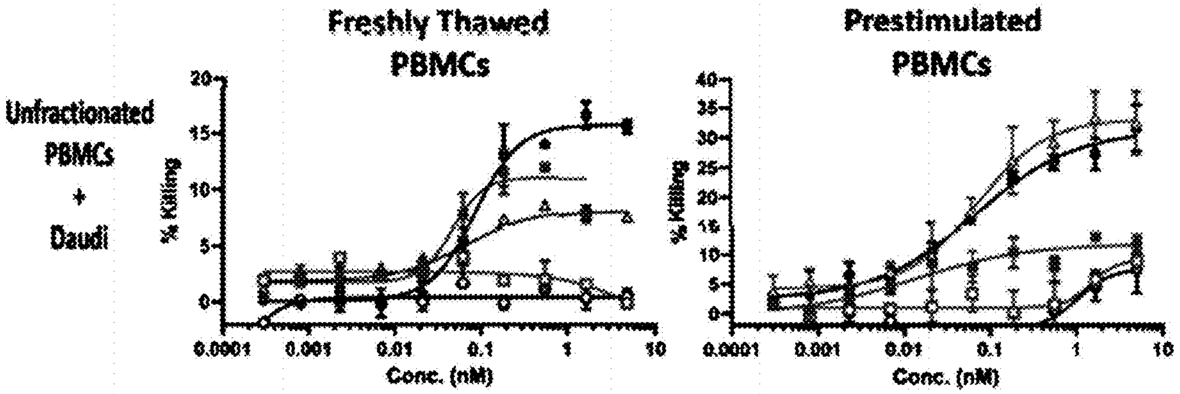
Fig. 31A.1

Fig. 31A.2

DIRECTED CONJUGATION TECHNOLOGIES

CROSS-REFERENCE TO RELATED APPLICATIONS

This application is a National Stage Entry of PCT/US2020/061127, filed Nov. 18, 2020, published as WO 2021/102052 A1, which claims the benefit of and priority to United States Provisional Application Nos. 62/937,131, filed Nov. 18, 2019, and 63/063,902, filed Aug. 10, 2020, the entirety of each of which is incorporated herein by reference.

BACKGROUND

Conjugates, e.g., protein conjugates such as antibody-drug conjugates, are useful for various purposes, e.g., as diagnostic reagents, therapeutics (e.g., antigen targeted therapeutics), etc.

SUMMARY

Among other things, the present disclosure encompasses the recognition that existing conjugation technologies can suffer from various challenges. For example, reactions conjugating moieties of interest (e.g., detection moieties, drug moieties, etc.) to target molecules (e.g., antibodies for antibody-drug conjugates) can be of low efficiency and/or have low selectivity (e.g., conjugation at various locations (e.g., various amino acid residues of antibodies) of target molecules), and product conjugate compositions are often highly heterogeneous, comprising a number of individual conjugate types each independently having its own copy number of moieties of interest, conjugation locations (e.g., different amino acid residues of proteins), etc. In some embodiments, manufacturing of conjugates involves multiple steps and includes various reactions, such as reduction, oxidation, hydrolysis, etc., and such reactions may cause undesired transformations, e.g., at one or more locations of target agent moieties (e.g., at one or more residues, and/or one or more modifications (e.g., glycans) of antibody moieties). Such undesired transformations may further lower efficiency and/or increase heterogeneity of product conjugate compositions, complicate characterization, assessment and/or purification processes and increase product cost.

In some embodiments, the present disclosure provides conjugation technologies for conjugating various moieties of interest to targets (e.g., proteins). In some embodiments, provided technologies provide directed conjugation in that moieties of interest are selectively conjugated at certain locations of targets (e.g., proteins such as antibodies). In some embodiments, provided technologies utilizes fewer steps. In some embodiments, provided technologies utilizes mild reaction conditions. In some embodiments, provided technologies include no reaction conditions such as reduction, oxidation, and/or hydrolysis. In some embodiments, provided technologies include substantially no cleavage from conjugate molecules comprising target agent moieties and moieties of interest (e.g., no cleavage of a group from target agent moieties, moieties of interest and/or linker moieties). In some embodiments, moieties of interest are detectable moieties (e.g., FITC). In some embodiments, moieties of interest are drug moieties (e.g., various drug moieties utilized in antibody-drug conjugates). In some embodiments, moieties of interest are protein moieties (e.g., antibody agents conjugated to other antibody agents (as target agent moieties)). In some embodiments, moieties of interest are or comprise reaction groups. In some embodiments, moieties of interest are or comprise reaction groups so that other moieties of interest can be further incorporated through reactions at the reaction groups.

Technologies of the present disclosure may provide various advantages. In some embodiments, the present disclosure provides improved efficiency and/or selectivity, reduced levels of heterogeneity, and/or reduced undesired transformations (e.g., through fewer steps of reactions (in some embodiments, only one), avoidance of certain reaction conditions (e.g., reduction, oxidation, hydrolysis, etc.).

In some embodiments, the present disclosure provides agents comprising moieties of interest are conjugated at certain locations of target agent moieties. In some embodiments, the present disclosure provides compositions of increased homogeneity compared to compositions from a reference technology (e.g., a technology without using target binding moieties (e.g., LG) as described in provided methods).

DETAILED DESCRIPTION OF CERTAIN EMBODIMENTS

1. Definitions

Figure 1:
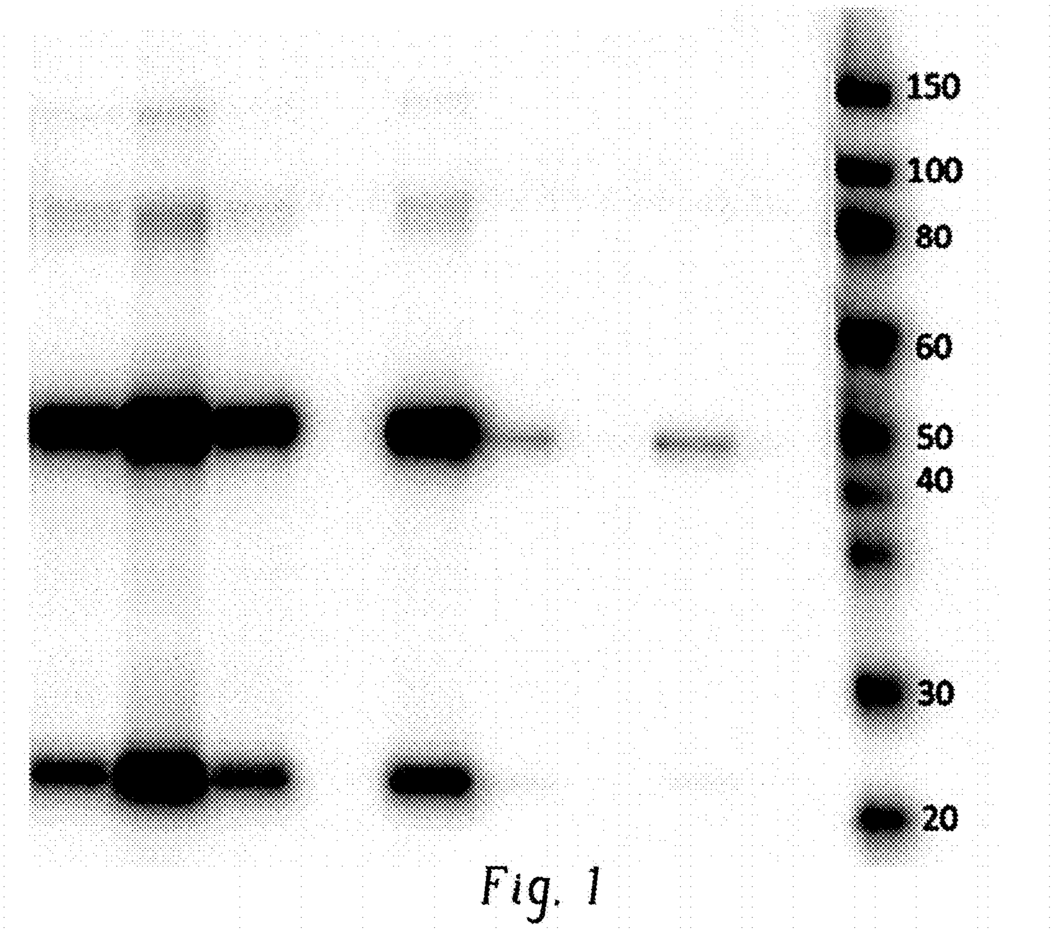
FIG. 1. Western blot data showing that provided technologies can provide various advantages (e.g., improved efficiency, improved selectivity, etc. without extra reaction steps). Reactions were set up with daratumumab using 10 M eq of indicated reagent in Bicarbonate buffer pH 8.3 for 2 h at 37° C. Reaction partners: 1: I-1; 2: I-2; 3: I-3; 4: I-4; 5: I-9; 6: I-10; 7: I-11; 8: I-15; 9: I-14.
Figure 2:
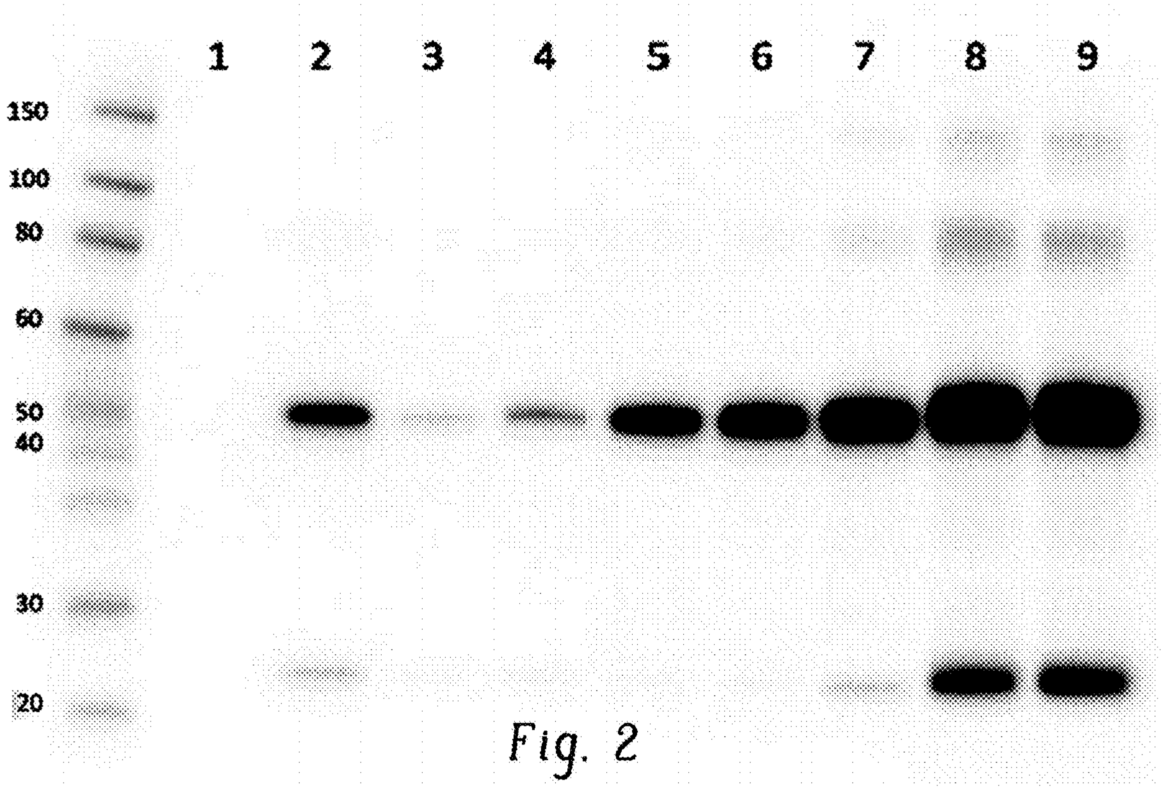
FIG. 2. Western blot data showing that provided technologies can provide various advantages (e.g., improved efficiency, improved selectivity, etc. without extra reaction steps). Reactions were set up with daratumumab using 30 M eq of indicated reagent in borate buffer pH 8.3 for 20 h at 37° C. 1: daratumumab. Reaction partners for lanes 2-9: 2: I-10; 3: I-11; 4: I-46; 5: I-24; 6: I-25; 7: I-35; 8: I-36; and 9: I-37.
Figure 3:
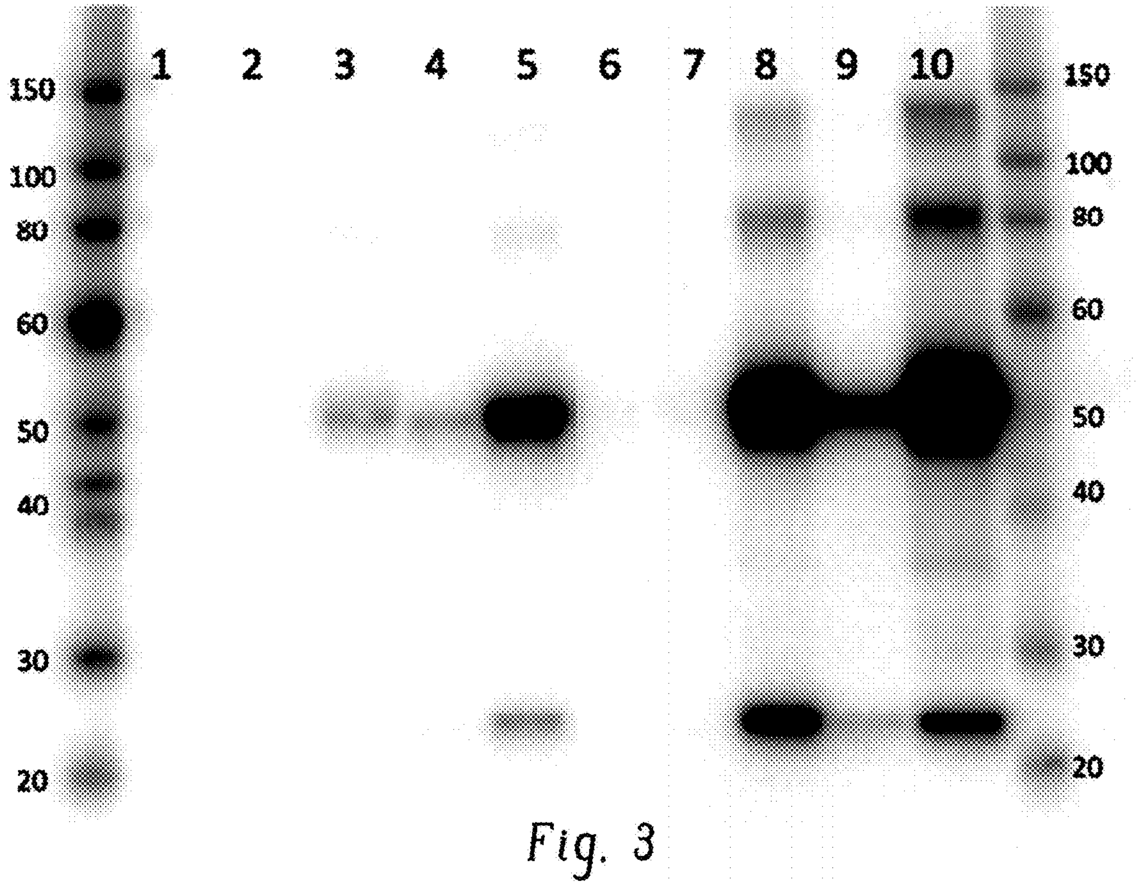
FIG. 3. Western blot data showing that provided technologies can provide various advantages (e.g., improved efficiency, improved selectivity, etc. without extra reaction steps). Reactions were set up with daratumumab using 5 M eq of indicated reagent in bicarbonate buffer pH 8.3 for 20 h at 37° C. 1: daratumumab. Reaction partners for lanes 2-10: 2: I-6; 3: I-5; 4: I-13; 5: I-17; 6: I-7; 7: I-8; 8: I-12; 9: I-16; and 10: I-35.
Figure 4:
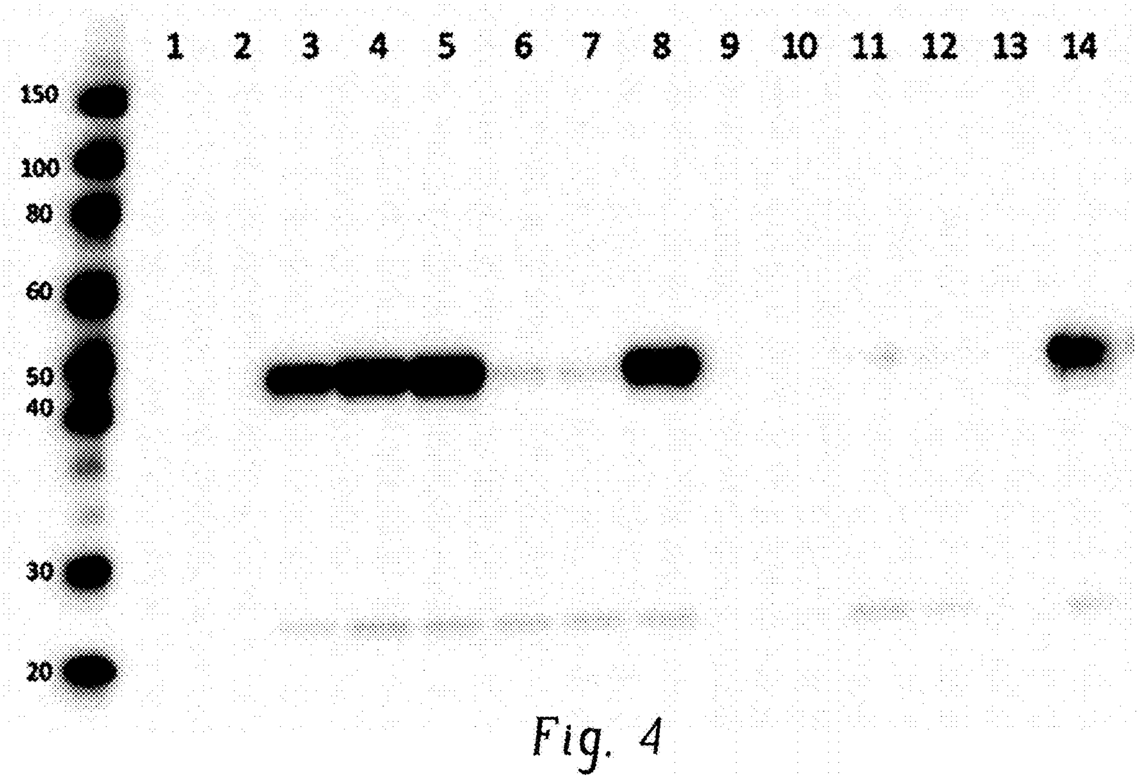
FIG. 4. Western blot data showing that provided technologies can provide various advantages (e.g., improved efficiency, improved selectivity, etc. without extra reaction steps). Reactions were set up with daratumumab using 2.5 M eq of indicated reagent in phosphate buffer saline pH 7.4 for 4 h at 25° C. 1 and 2: daratumumab. Reaction partners for lanes 3-14: 3: I-38; 4: I-39; 5: I-40; 6: I-47; 7: I-48; 8: I-49; 9: I-18; 10: I-50; 11: I-51; 12: I-52; 13: I-9; and 14: I-45.
Figure 5:
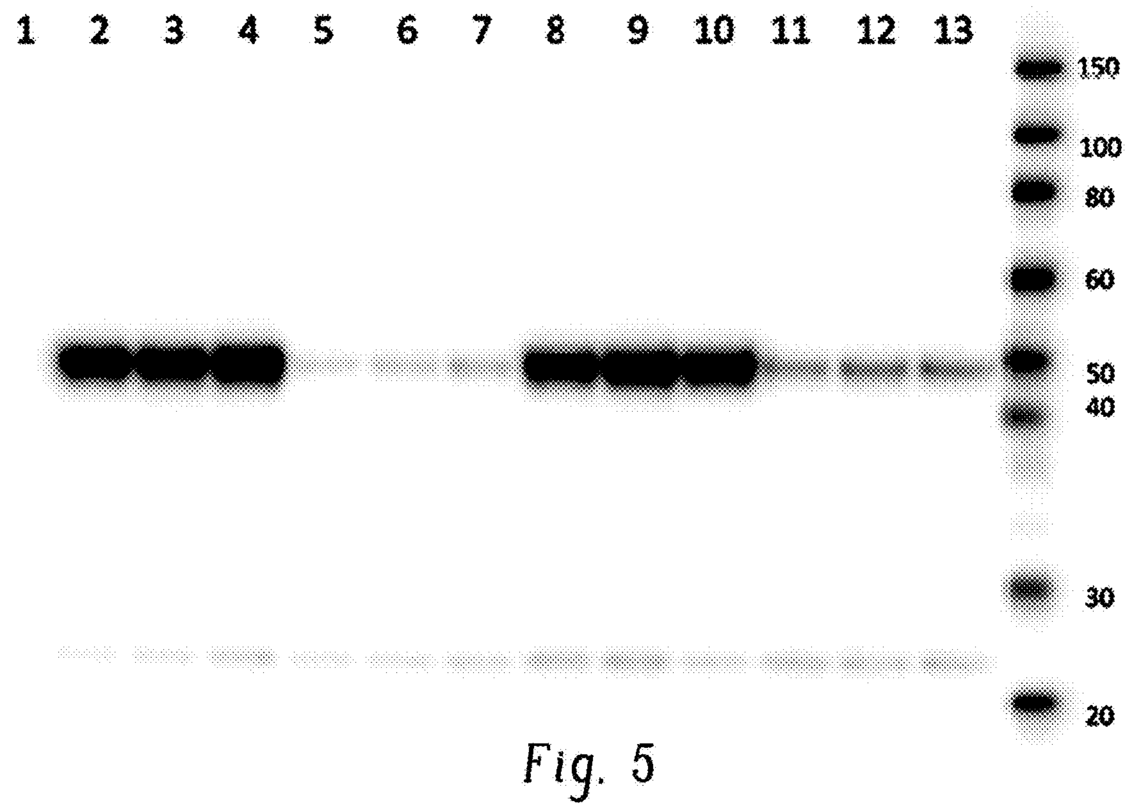
FIG. 5. Western blot data showing that provided technologies can provide various advantages (e.g., improved efficiency, improved selectivity, etc. without extra reaction steps). Reactions were as described in Table 30-8. 1: daratumumab; 2: I-45, 2.5 Eq, 1 mg/ml; 3: I-45, 3.0 Eq, 1 mg/ml; 4: I-45, 3.5 Eq, 1 mg/ml; 5: I-9, 2.5 Eq, 1 mg/ml; 6: I-9, 3.0 Eq, 1 mg/ml; 7: I-9, 3.5 Eq, 1 mg/ml; 8: I-45, 2.5 Eq, 4 mg/ml; 9: I-45, 3.0 Eq, 4 mg/ml; 10: I-45, 3.5 Eq, 4 mg/ml; 11: I-9, 2.5 Eq, 4 mg/ml; 12: I-9, 3.0 Eq, 4 mg/ml; 13: I-9, 3.5 Eq, 4 mg/ml.
Figure 6:
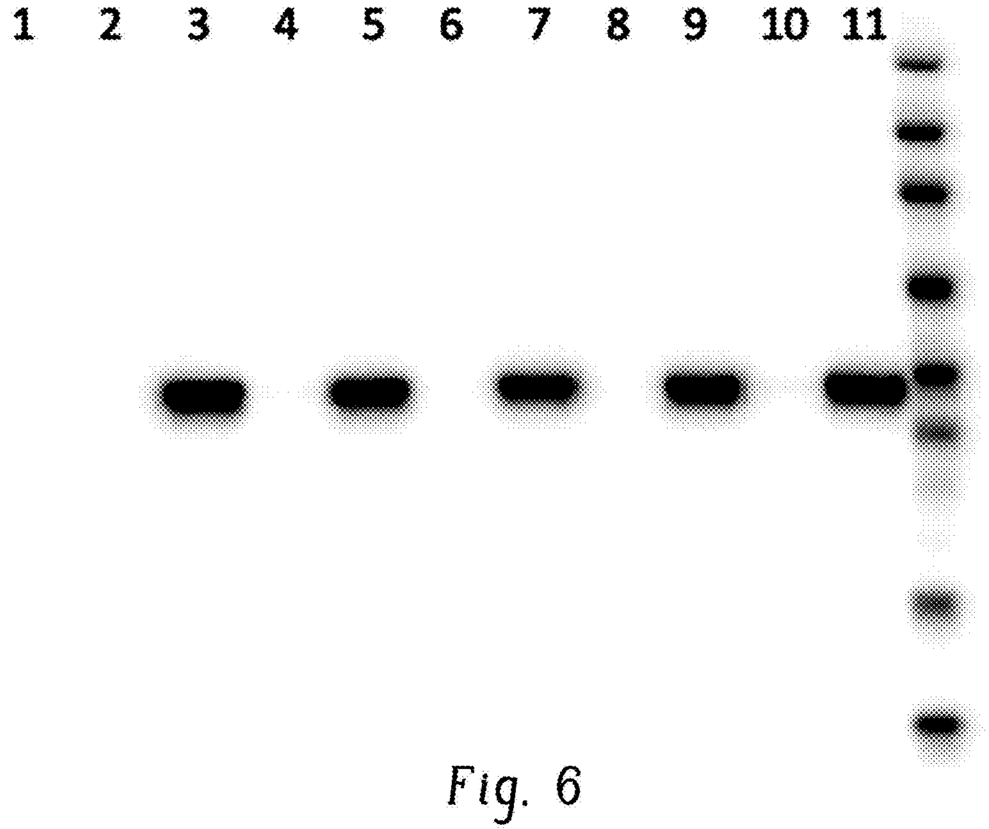
FIG. 6. Western blot data showing that provided technologies can provide various advantages (e.g., improved efficiency, improved selectivity, etc. without extra reaction steps). Certain reactions were as described in Table 30-10. 1: daratumumab; 2: I-10, PBS, pH 8.2, 25° C.; 3: I-44, PBS, pH 8.2, 25° C.; 4: I-10, PBS, pH 8.0, 25° C.; 5: I-44, PBS, pH 8.0, 25° C.; 6: I-10, PBS, pH 7.8, 25° C.; 7: I-44, PBS, pH 7.8, 25° C.; 8: I-10, PBS, pH 7.4, 30° C.; 9: I-44, PBS, pH 7.4, 30° C.; 10: I-10, PBS, pH 7.4, 37° C.; and 11: I-44, PBS, pH 7.4, 37° C.
Figure 7:
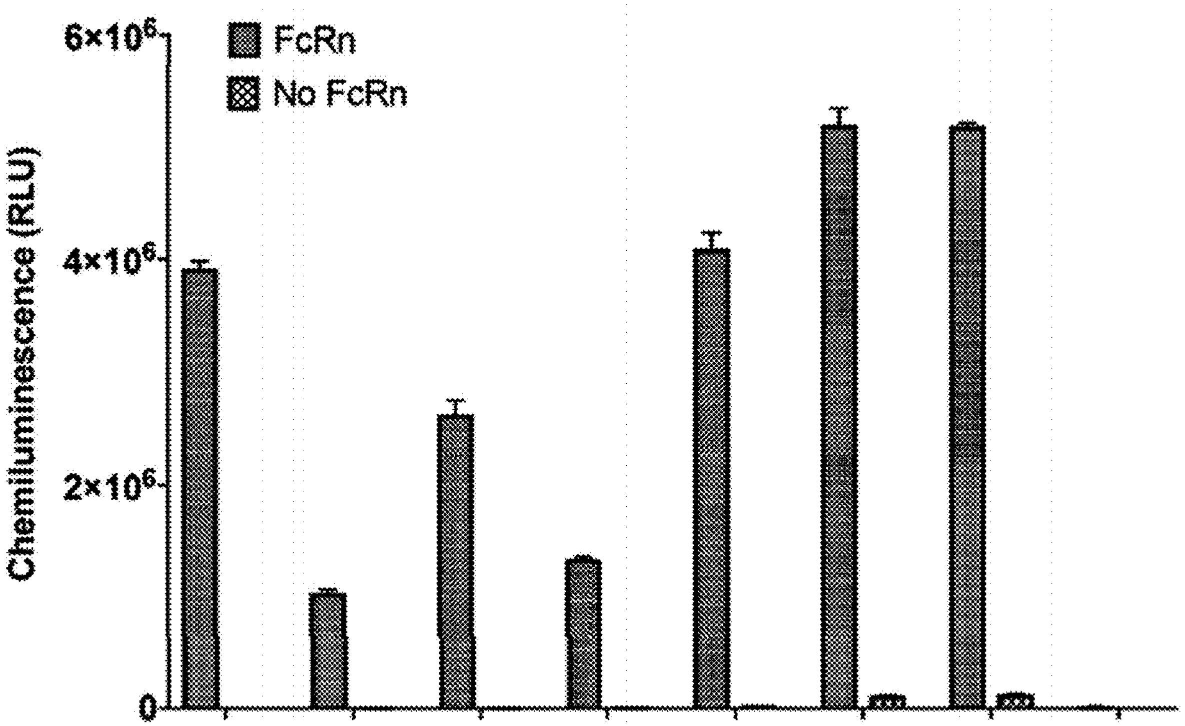
FIG. 7. Antibody conjugates maintain properties/activities of antibodies. Reactions were set up with daratumumab using 30 M eq of indicated reagent in borate buffer pH 8.3 for 20 h at 37° C. From left to right: daratumumab; conjugates using I-46; I-24; I-25, I-35, 8: I-36, and I-37; no antibody.
Figure 8:
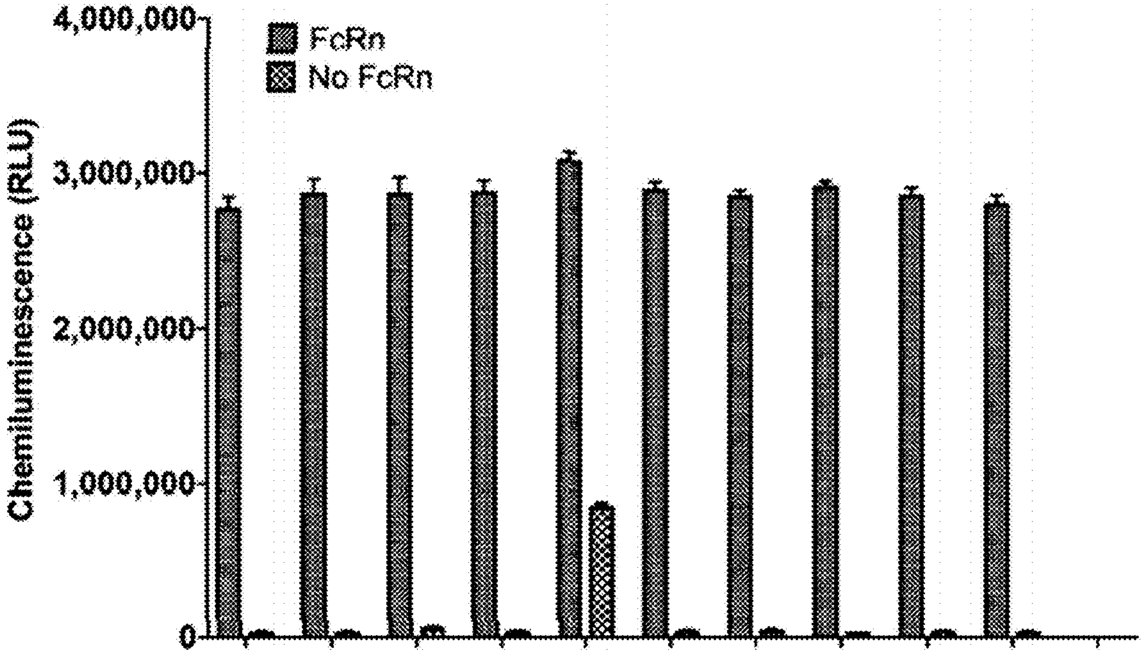
FIG. 8. Antibody conjugates maintain properties/activities of antibodies. Reactions were set up with daratumumab using 5 M eq of indicated reagent in bicarbonate buffer pH 8.3 for 20 h at 37° C. From left to right: daratumumab; conjugates using I-6, I-5, I-13, I-17, I-7, I-8, I-12, I-16, and I-35; no antibody.
Figure 9:
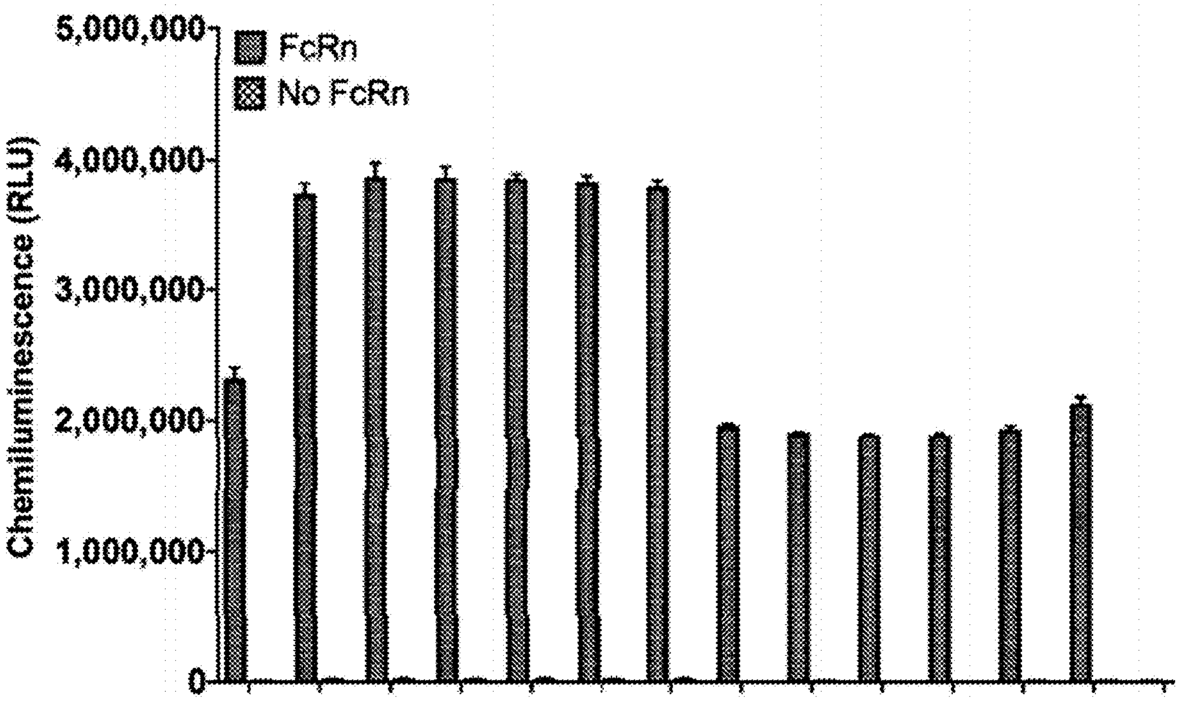
FIG. 9. Antibody conjugates maintain properties/activities of antibodies. Reactions were set up with daratumumab using 2.5 M eq of indicated reagent in phosphate buffer saline pH 7.4 for 4 h at 25° C. From left to right: daratumumab; conjugates using I-38, I-39, I-40, I-47, I-49, I-48, I-18, I-50, I-51, I-52, I-9, I-45; no antibody.
Figure 10:
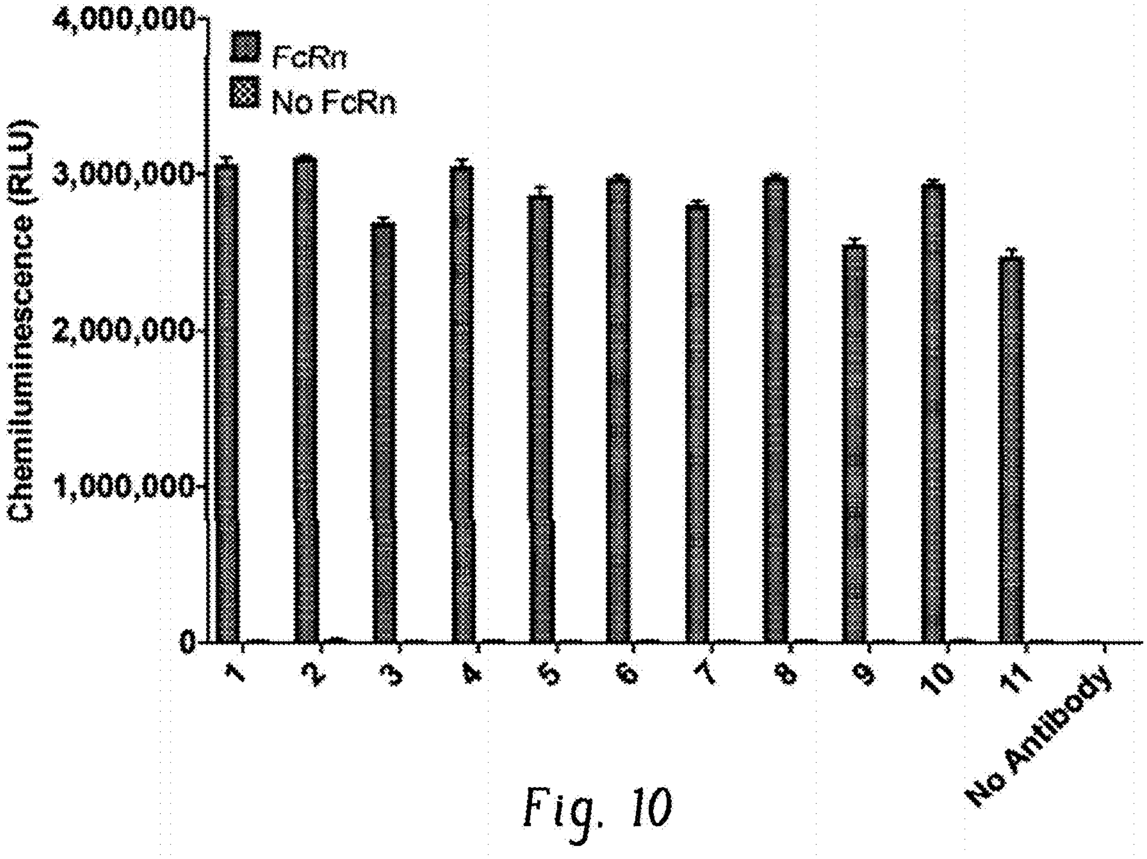
FIG. 10. Antibody conjugates maintain properties/activities of antibodies. Reactions were as described in Table 30-10. 1: daratumumab; 2: I-10, PBS, pH 8.2, 25° C.; 3: I-44, PBS, pH 8.2, 25° C.; 4: I-10, PBS, pH 8.0, 25° C.; 5: I-44, PBS, pH 8.0, 25° C.; 6: I-10, PBS, pH 7.8, 25° C.; 7: I-44, PBS, pH 7.8, 25° C.; 8: I-10, PBS, pH 7.4, 30° C.; 9: I-44, PBS, pH 7.4, 30° C.; 10: I-10, PBS, pH 7.4, 37° C.; and 11: I-44, PBS, pH 7.4, 37° C.
Figure 11:
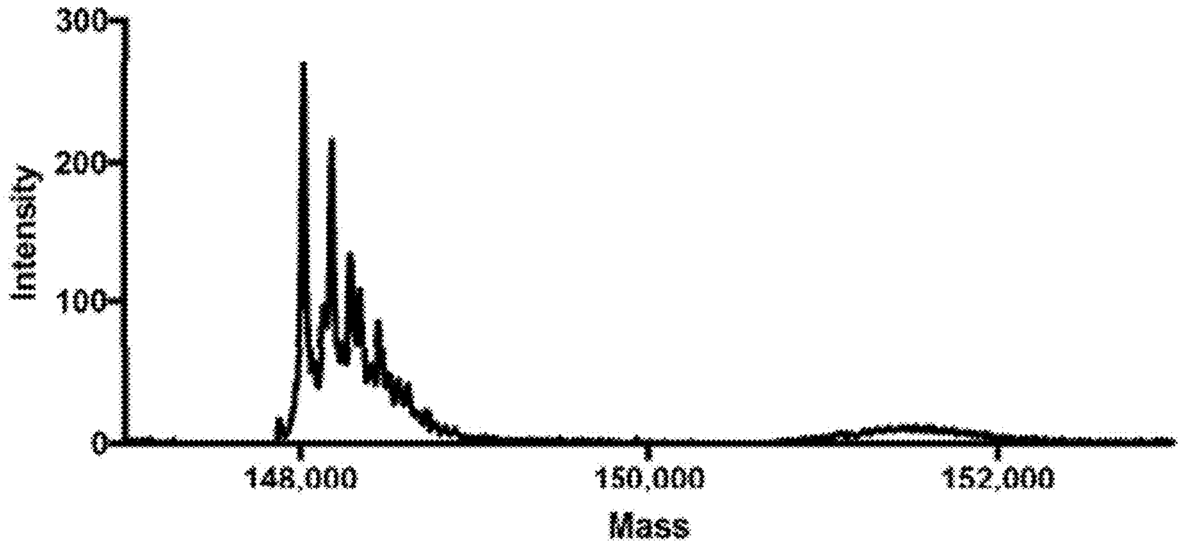
FIG. 11. Certain intact mass data of daratumumab (DAR=0) as examples.
Figure 12A:
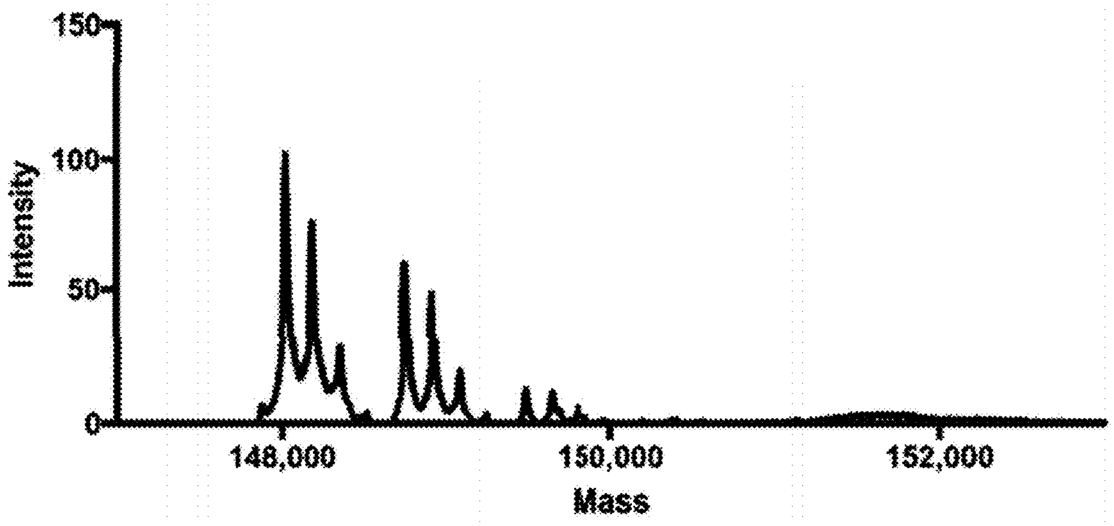
FIG. 12. Certain intact mass data of daratumumab conjugated with I-45 as examples. (a) FITC DAR is 0.43. (b) FITC DAR is 1.09. (c) FITC DAR is 0.90.
Figure 12B:
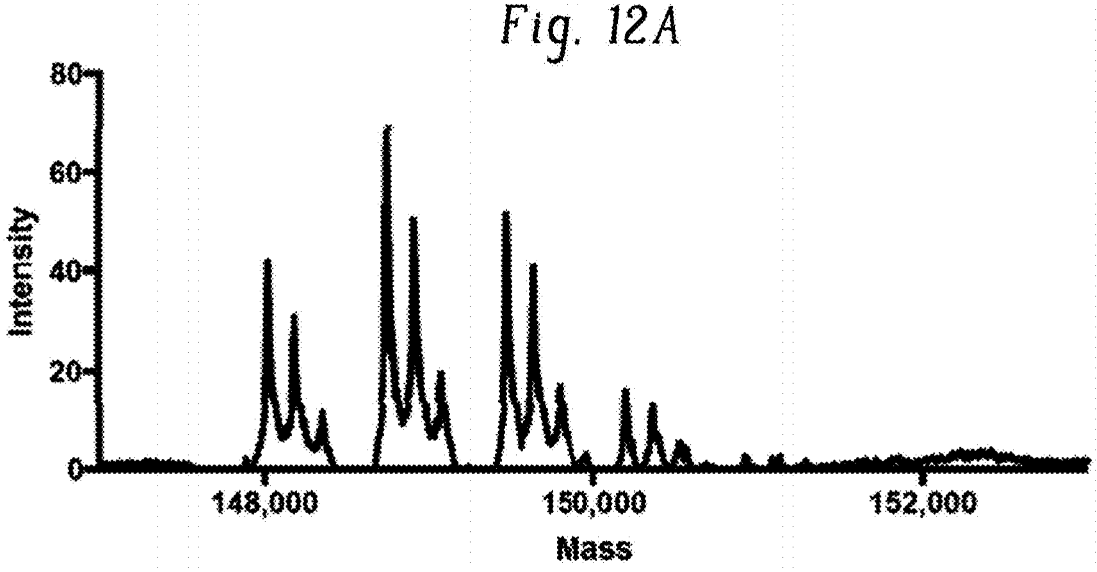
Figure 12C:
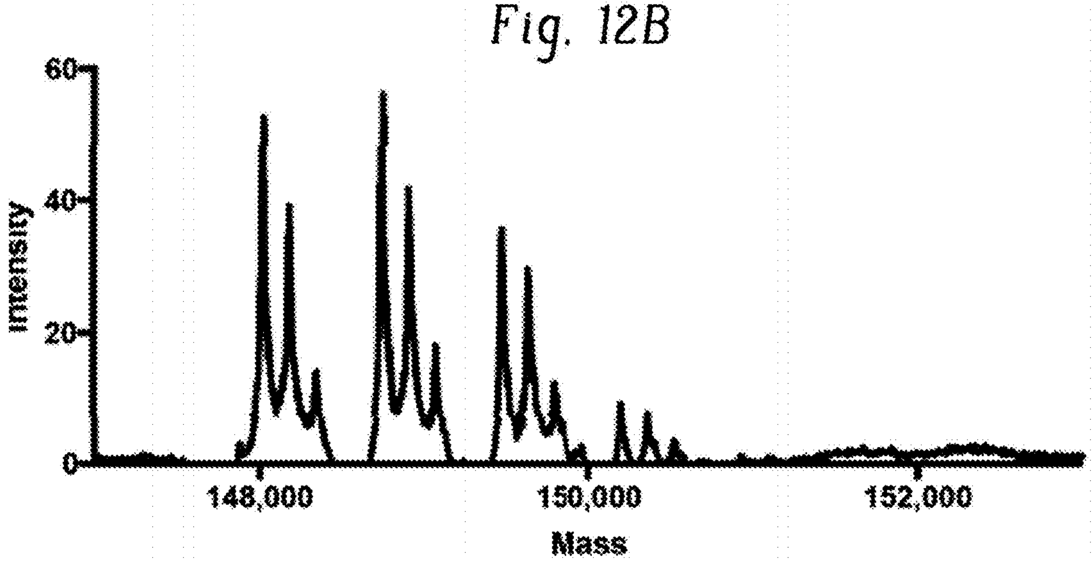

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001.

As used herein in the present disclosure, unless otherwise clear from context, (i) the term "a" or "an" may be understood to mean "at least one"; (ii) the term "or" may be understood to mean "and/or"; (iii) the terms "comprising", "comprise", "including" (whether used with "not limited to" or not), and "include" (whether used with "not limited to" or not) may be understood to encompass itemized components or steps whether presented by themselves or together with one or more additional components or steps; (iv) the term "another" may be understood to mean at least an additional/second one or more; (v) the terms "about" and "approximately" may be understood to permit standard variation as would be understood by those of ordinary skill in the art; and (vi) where ranges are provided, endpoints are included. Unless otherwise specified, compounds described herein may be provided and/or utilized in a salt form, particularly a pharmaceutically acceptable salt form.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety. In some embodiments, an agent is a compound (e.g., a small molecule, a protein, a nucleic acid, etc.). In some embodiments, an agent is a mono-, bi- or polyvalent moiety of a compound (e.g., by removing one (for a monovalent moiety) or more (for a bi- or polyvalent moiety) hydrogen atoms and/or other monovalent groups from a compound).

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: As used herein, the term "alkenyl" refers to an aliphatic group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, an alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an aliphatic group, as defined herein, having one or more triple bonds.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but is not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present disclosure is in a format selected from, but not limited to, intact IgA, IgG, IgE or IgM antibodies; bi- or multi-specific antibodies (e.g., Zybodies®, additional bi- or multi-specific antibodies described in Ulrich Brinkmann & Roland E. Kontermann (2017) The making of bispecific antibodies, mAbs, 9:2, 182-212, doi: 10.1080/19420862.2016.1268307, etc.); antibody fragments such as Fab fragments, Fab' fragments, F(ab')2 fragments, Fd' fragments, Fd fragments, and isolated CDRs or sets thereof, single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies®; minibodies; BiTE®s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; KALBITOR®s; CovX-Bodies; and CrossMabs. In some embodiments, antibodies may have enhanced Fc domains. In some embodiments, antibodies may comprise one or more unnatural amino acid residues. In some embodiments, an antibody may lack a covalent modification (e.g., attachment of a glycan) that it would have if produced naturally. In some embodiments, an antibody is an afucosylated antibody. In some embodiments, an antibody is conjugated with another entity. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted forms thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is boron, oxygen, sulfur, nitrogen, phosphorus, or silicon (including various forms of such atoms, such as oxidized forms (e.g., of nitrogen, sulfur, phosphorus, or silicon), quaternized form of a basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl) etc.). In some embodiments, a heteroatom is oxygen, sulfur or nitrogen.

Heterocycle: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Lower alkyl: The term "lower alkyl" refers to a $C_{1-4}$ straight or branched alkyl group. Example lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Optionally Substituted: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR^{\circ}$, —$SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}$ $SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$Si(R^{\circ})_3$; —$OSi(R^{\circ})_3$; —$B(R^{\circ})_2$; —$OB(R^{\circ})_2$; —$OB(OR^{\circ})_2$; —$P(R^{\circ})_2$; —$P(OR^{\circ})_2$; —$P(R^{\circ})(OR^{\circ})$; —$OP(R^{\circ})_2$; —$OP(OR^{\circ})_2$; —$OP(R^{\circ})(OR^{\circ})$; —$P(O)(R^{\circ})_2$; —$P(O)(OR^{\circ})_2$; —$OP(O)(R^{\circ})_2$; —$OP(O)(OR^{\circ})_2$; —$OP(O)(OR^{\circ})(SR^{\circ})$; —$SP(O)(R^{\circ})_2$; —$SP(O)(OR^{\circ})_2$; —$N(R^{\circ})P(O)(R^{\circ})_2$; —$N(R^{\circ})P(O)(OR^{\circ})_2$; —$P(R^{\circ})_2[B(R^{\circ})_3]$; —$P(OR^{\circ})_2[B(R^{\circ})_3]$; —$OP(R^{\circ})_2[B(R^{\circ})_3]$; —$OP(OR^{\circ})_2[B(R^{\circ})_3]$; —($C_{1-4}$ straight or branched alkylene)O—$N(R^{\circ})_2$; or —($C_{1-4}$ straight or branched alkylene)C(O)O—$N(R^{\circ})_2$, wherein each $R^{\circ}$ may be substituted as defined herein and is independently hydrogen, $C_{1-20}$ aliphatic, $C_{1-20}$ heteroaliphatic having 1-5 heteroatoms independently selected from nitrogen, oxygen, sulfur, silicon and phosphorus, —$CH_2$—($C_{6-14}$ aryl), —$O(CH_2)_{0-1}$($C_{6-14}$ aryl), —$CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^{\circ}$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)C(O)$OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of $R^{\circ}$ include ═O and ═S.

Suitable divalent substituents, e.g., on a suitable carbon atom, are independently the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of $R^*$ are independently halogen, —$R^{\bullet}$, -(halo$R^{\bullet}$), —OH, —$OR^*$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently $—R^†$, $—NR^†_2$, $—C(O)R^†$, $—C(O)OR^†$, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R^†)S(O)_2R^†$; wherein each RT is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of RT are independently halogen, $—R^•$, -(haloR$^•$), —OH, $—OR^•$, —O(haloR$^•$), —CN, —C(O)OH, $—C(O)OR^•$, $—NH_2$, $—NHR^•$, $—NR^•_2$, or $—NO_2$, wherein each $R^•$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups. In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen (e.g., in an aqueous solution with a pKa no more than about 11, 10, 9, 8, 7, 6, 5, 4, 3, or 2; in some embodiments, no more than about 7; in some embodiments, no more than about 6; in some embodiments, no more than about 5; in some embodiments, no more than about 4; in some embodiments, no more than about 3) in the acidic groups are replaced with cations.

Protecting group: The term "protecting group," as used herein, is well known in the art and includes those described in detail in *Protecting Groups in Organic Synthesis*, T. W. Greene and P. G. M. Wuts, 3$^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. June 2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group. In some embodiments, a phosphorous linkage protecting group is a group attached to the phosphorous linkage (e.g., an internucleotidic linkage) throughout oligonucleotide synthesis. In some embodiments, a protecting group is attached to a sulfur atom of an phosphorothioate group. In some embodiments, a protecting group is attached to an oxygen atom of an internucleotide phosphorothioate linkage. In some embodiments, a protecting group is attached to an oxygen atom of the internucleotide phosphate linkage. In some embodiments a protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, or 4-[N-methyl-N-(2,2,2-trifluoroacetyl)amino]butyl.

Subject: As used herein, the term "subject" refers to any organism to which a compound or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject is a human. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Therapeutic agent: As used herein, the term "therapeutic agent" in general refers to any agent that elicits a desired effect (e.g., a desired biological, clinical, or pharmacological effect) when administered to a subject. In some embodiments, an agent is considered to be a therapeutic agent if it demonstrates a statistically significant effect across an appropriate population. In some embodiments, an appropriate population is a population of subjects suffering from and/or susceptible to a disease, disorder or condition. In some embodiments, an appropriate population is a population of model organisms. In some embodiments, an appropriate population may be defined by one or more criterion such as age group, gender, genetic background, preexisting clinical conditions, prior exposure to therapy. In some embodiments, a therapeutic agent is a substance that alleviates, ameliorates, relieves, inhibits, prevents, delays onset of, reduces severity of, and/or reduces incidence of one or more symptoms or features of a disease, disorder, and/or condition in a subject when administered to the subject in an effective amount. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, a therapeutic agent is a compound described herein.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds are within the scope of the present disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of the present disclosure. Such compounds are useful, for example, as analytical tools, as probes in biological assays, or as therapeutic agents in accordance with the present disclosure.

2. Description of Exemplary Embodiments

As described herein, in some embodiments, the present disclosure provides technologies that can conjugate moieties of interest to targets with high efficiency, high selectivity, and/or reduced side transformations (e.g., due to numbers of chemical reactions and/or conditions/types of chemical reactions). In some embodiments, the present disclosure provides useful reagents and methods for conjugation, and provide product compositions with enhanced homogeneity (e.g., 10%, 20%, 30%, 40%, 50%, 60%, 70%, 80%, 90%, 100%, or 2, 3, 4, 5, 6, 7, 8, 9, 10, 11, 12, 13, 14, 15, 16, 17, 18, 19, 20 or more fold, increase of modification/conjugation at one or more desired sites of target agents, and/or 10%, 20%, 30%, 40%, 50%, 60%, 70%, 80%, 90%, 100%, or 2, 3, 4, 5, 6, 7, 8, 9, 10, 11, 12, 13, 14, 15, 16, 17, 18, 19, 20 or more fold, decrease of modification/conjugation at one or more undesired sites of target agents), purity and/or reduced undesired modifications (e.g., to certain protein residues as results of side reactions). In some embodiments, the present disclosure provides a compound of formula R-I or a salt thereof as described herein. In some embodiments, a compound of formula R-I or a salt thereof is useful for introducing a moiety of interest to a target in one step of reaction. In some embodiments, the present disclosure provides agents of formula P-I or P-II, or a salt thereof. In some embodiments, a product composition comprise a plurality of agents having the structure of formula P-I or P-II, or a salt thereof, wherein the product composition has a higher level of homogeneity of said agents compared to a reference product composition (e.g., a product composition from a method in which a compound of formula R-I or a salt thereof is replaced with a compound which has the same structure as the compound of formula R-I or a salt thereof except that each target binding moiety is replaced with —H).

In some embodiments, the present disclosure provides a method, comprising steps of:

1) contacting a target agent with a reaction partner comprising:

a first group comprising a target binding moiety that binds to a target agent, a reactive group;

a moiety of interest; and optionally one or more linker moieties;

2) forming an agent comprising:

a target agent moiety;

a moiety of interest; and optionally one or more linker moieties.

In some embodiments, a reaction group is located between a first group and a moiety of interest, and is connected to a first group and a moiety of interest independently and optionally through a linker moiety. In some embodiments, a reaction partner is a compound of formula R-I or a salt thereof. In some embodiments, a first group is or comprises a LG group as described herein. In some embodiments, a first group is or comprises a LG group as described herein.

In some embodiments, the present disclosure provides a method comprising steps of:

1) contacting a target agent with a reaction partner having the structure of formula R-I:

$$\text{LG-RG-L}^{RM}\text{-MOI,} \qquad \text{(R-I)}$$

or a salt thereof, wherein:

LG is a group comprising a target binding domain that binds to a target agent,

RG is a reactive group;

$L^{RM}$ is a linker; and

MOI is a moiety of interest; and 2) forming an agent having the structure of formula P-I:

$$\text{P-L}^{PM}\text{-MOI,} \qquad \text{(P-I)}$$

or a salt thereof, wherein:

P is a target agent moiety;

$L^{PM}$ is a linker; and

MOI is a moiety of interest.

In some embodiments, a target agent is a protein agent. In some embodiments, a target agent. In some embodiments, a target agent is an antibody. In some embodiments, a target agent is an IgG antibody. In some embodiments, a target is a protein, and a moiety of interest is conjugated at one or more lysine residues. In some embodiments, an agent of formula P-I or a salt thereof is an agent of formula P-II or a salt thereof.

In some embodiments, the present disclosure provides a method of manufacturing an agent having the structure of P-IL:

$$\text{P—N-L}^{PM}\text{-MOI,} \qquad \text{(P-II)}$$

wherein:

P—N is a protein agent moiety comprising a lysine residue;

$L^{PM}$ is a linker; and

MOI is a moiety of interest;

the method comprising:

contacting P—N with a reaction partner having a structure of formula R-I:

$$\text{LG-RG-L}^{RM}\text{-MOI,} \qquad \text{(R-I)}$$

or a salt thereof, wherein:

LG is a group comprising a protein-binding domain that binds to P—N,

RG is a reactive group;

$L^{RM}$ is a linker; and

MOI is a moiety of interest.

In some embodiments, as exemplified herein, contacting is performed under conditions and for a time sufficient for the lysine residue N to react and form a bond with an atom of RG and release LG.

Targets

Those skilled in the art after reading the present disclosure will appreciate that provided technologies herein are useful for conjugating various target agents to many types of moieties of interest. In some embodiments, provided technologies are particularly useful for conjugating protein agents with various moieties of interest. In some embodiments, target agents are or comprise nucleic acids.

In some embodiments, a target agent is or comprises a protein agent. In some embodiments, a target agent is a protein agent. In some embodiments, a target agent is a natural protein in a cell, tissue, organ or organism. In some embodiments, a target agent is an endogenous protein. In some embodiments, a target agent is an exogenous protein. In some embodiments, a target agent is a manufactured protein, e.g., a protein produced using various biotechnologies. In some embodiments, a target agent is an antibody agent. In some embodiments, a target agent is an antibody useful as therapeutics. Various such antibodies are known in the art and can be utilized as target agents. In some embodiments, an antibody is a monoclonal antibody. In some embodiments, an antibody is a polyclonal antibody. In some embodiments, an antibody is an IgG antibody. In some embodiments, an antibody is IVIG (in some embodiments, pooled from healthy donors). In some embodiments, a protein comprises a Fc region. In some embodiments, an antibody comprises a Fc region. In some embodiments, a Fc region comprises a single heavy chain or a fragment thereof. In some embodiments, a Fc region comprises two heavy chains or fragments thereof. In some embodiments, an antibody is a human antibody. In some embodiments, an antibody is a chimeric antibody. In some embodiments, an antibody is a humanized antibody. In some embodiments, an antibody is a mouse antibody.

In some embodiments, when characterizing polyclonal antibody agents or IVIG agents, either before, during or after conjugation, digestions are performed, e.g., enzyme digestions using IdeZ, IdeS, etc., so that certain regions of antibodies (e.g., Fab) are removed to provide compositions with improved homogeneity for characterization (e.g., by MS).

In some embodiments, an antibody is a therapeutic antibody, e.g., a FDA-approved antibody for therapeutic uses. In some embodiments, a therapeutic antibody is useful for treating cancer. In some embodiments, an antibody is adalimumab, alemtuzumab, atezolizumab, avelumab, ipilimumab, cetuximab, daratumumab, dinutuximab, elotuzumab, ibritumomab tiuxetan, imgatuzumab, infliximab, ipilimumab, necitumumab, obinutuzumab, ofatumumab, pertuzumab, reslizumab, rituximab, trastuzumab, mogamulizumab, AMP-224, FS-102, GSK-2857916, ARGX-111, ARGX-110, AFM-13, APN-301, BI-836826, BI-836858, enoblituzumab, otlertuzumab, veltuzumab, KHK-4083, BIW-8962, ALT-803, carotuximab, epratuzumab, inebilizumab, isatuximab, margetuximab, MOR-208, ocaratuzumab, talacotuzumab, tremelimumab, benralizumab, lumiliximab, MOR-208, Ifibatuzumab, GSK2831781, SEA-CD40, KHK-2823, or BI836858. In some embodiments, an antibody is rituximab, basiliximab, infliximab, cetuximab, siltuximab, dinutuximab, altertoxaximab, daclizumab, palivizumab, trastuzumab, alemtuzumab, omalizumab, efalizumab, bevacizumab, natalizumab, tocilizumab, eculizumab, mogamulizumab, pertuzumab, obinutuzumab, vedolizumab, pembrolizumab, mepolizumab, elotuzumab, daratumumab, ixekizumab, reslizumab, and atezolizumab, adalimumab, panitumumab, golimumab, ustekinumab, canakinumab, ofatumumab, denosumab, ipilimumab, belimumab, raxibacumab, ramucirumab, nivolumab, secukinumab, evolocumab, alirocumab, necitumumab, brodalumab, or olaratumab. In some embodiments, an antibody is daratumumab. In some embodiments, an antibody is cetuximab. In some embodiments, a provided compound or agent comprising an antibody agent moiety is useful for treating a condition, disorder or disease that may be treated by the antibody agent.

Antibodies may be prepared in a number of technologies in accordance with the present disclosure. In some embodiments, antibodies may have engineered structures compared to natural immunoglobulins. In some embodiments, antibodies may comprise certain tags for purification, identification, assessment, etc. In some embodiments, antibodies may contain fragments (e.g., CDR and/or Fe, etc.) and not full immunoglobulins. Those skilled in the art appreciate that when a site of an antibody is recited in the present disclosure (e.g., K246, K248, K288, K290, K317, etc.; unless indicated otherwise, human antibody per EU numbering), an amino acid residue may not be at the exact numbered site but may be at a site that corresponds to that numbered site per, e.g., EU numbering and/or sequence homology (e.g., homologues of the same or different species).

As those skilled in the art will appreciate, provided technologies among other things can provide directed conjugation with native targets, e.g., native antibodies. In some embodiments, target agents are or comprise native antibody agents. In some embodiments, target agents are or comprise engineered antibody agents. In some embodiments, target agents, e.g., antibodies, comprise no engineered unnatural amino acid residues.

Partner Compounds

In some embodiments, the present disclosure provides compounds each independently comprising a first group comprising a target binding moiety that binds to a target agent, a reactive group, a moiety of interest, and optionally one or more linker moieties linking such groups/moieties. In some embodiments, such a compound is useful as reaction partners for conjugating moieties of interest to targets. In some embodiments, the present disclosure provides compounds for conjugating moieties of interest to targets, e.g., various proteins. In some embodiments, provided compounds each comprise a moiety of interest, a reactive group, a target binding moiety, and optionally one or more linker moieties (linkers) linking such moieties. In some embodiments, a target binding moiety is part of a leaving group that is released upon contacting such a compound with a target and reacting a reactive group of the compound with a reactive group of a target (e.g., —$NH_2$ of a Lys residue of a target protein). As demonstrated herein, provided compounds among other things can provide improved conjugation efficiency, high selectivity, and fewer steps (in some cases, single step) to conjugation products. In some embodiments, a provided compound has the structure of formula R-I or a salt thereof:

$$\text{LG-RG-L}^{RM}\text{-MOI}, \qquad \text{(R-I)}$$

or a salt thereof, wherein:

LG is a group comprising a target binding moiety that binds to a target agent,

RG is a reactive group;

$L^{RM}$ is a linker; and

MOI is a moiety of interest.

In some embodiments, a first group is LG.

In some embodiments, LG is or comprises a target binding moiety that can bind to a target agent, and optionally a linker moiety.

As used in the present disclosure, a moiety generally refers to a part of a molecule, e.g., in an ester RCOOR', the alcohol moiety is RO—. In some embodiments, a moiety of a compound (e.g., a target agent, a protein agent, an antibody agent, etc.) retains one or more or all desirable structural features, properties, functions, and/or activities of a compound. For example, in some embodiments, a target binding moiety can bind to a target, optionally in a comparable fashion, as its corresponding target binding compound; in some embodiments, a target agent moiety maintains one or more desired structural features, properties, functions, and/or properties comparable to its corresponding target agent compound; in some embodiments, an antibody agent moiety maintains one or more desired structural features, properties, functions, and/or properties (e.g., 3-dimension structure, antigen specificity, antigen-binding capacity, and/or immunological functions, etc.) comparable to its corresponding antibody agent compound. In some embodiments, a moiety of a compound, e.g., a target agent moiety, a protein agent moiety, an antibody agent moiety, etc. is a monovalent (for a monovalent moiety), bivalent (for a bivalent moiety), or polyvalent (for a polyvalent moiety) radical of a compound, e.g., a target agent compound (for a target agent moiety), a protein agent compound (for a protein agent moiety), an antibody agent compound (for an antibody agent moiety), etc. In some embodiments, a monovalent radical is formed by removing a monovalent part (e.g., hydrogen, halogen, another monovalent group like alkyl, aryl, etc.) from a compound. In some embodiments, a bivalent or polyvalent radical is formed by removing one or more monovalent (e.g., hydrogen, halogen, monovalent groups like alkyl, aryl, etc.), bivalent and/or polyvalent parts from a compound. In some embodiments, radicals are formed by removing hydrogen atoms. In some embodiments, a moiety is monovalent. In some embodiments, a moiety is bivalent. In some embodiments, a moiety is polyvalent.

In some embodiments, LG is or comprises $R^{LG}$-$L^{LG}$-, wherein $R^{LG}$ is or comprises a target binding moiety, and $L^{LG}$ is $L^{LG1}$ as described herein. In some embodiments, $L^{LG}$ is -$L^{LG1}$-$L^{LG2}$-, wherein each of $L^{LG1}$ and $L^{LG2}$ is independently as described herein. In some embodiments, $L^{LG}$ is -$L^{LG1}$-$L^{LG2}$-$L^{LG3}$-, wherein each of $L^{LG1}$, $L^{LG2}$ and $L^{LG3}$ is independently as described herein. In some embodiments, $L^{LG}$ is -$L^{LG1}$-$L^{LG2}$-$L^{LG3}$-$L^{LG4}$-, wherein each of $L^{LG1}$, $L^{LG2}$, $L^{LG3}$ and $L^{LG4}$ is independently as described herein. In some embodiments, $L^{LG1}$ is bonded to $R^{LG}$. In some embodiments, $L^{LG1}$ is bonded to moiety of interest. In some embodiments, $L^{LG}$ is -$L^{LG1}$-, and a reactive group comprises $L^{LG2}$, $L^{LG3}$ and $L^{LG4}$. In some embodiments, $L^{LG}$ is -$L^{LG1}$-$L^{LG2}$-, and a reactive group comprises $L^{LG3}$ and $L^{LG4}$. In some embodiments, $L^{LG}$ is -$L^{LG1}$-$L^{LG2}$-$L^{LG3}$-, and a reactive group comprises $L^{LG4}$.

In some embodiments, target binding moieties, first groups, and/or LG are released after reactions, e.g., after partner compounds react with target agents. In some embodiments, a first group is released after a reaction. In some embodiments, a target binding moiety is released after a reaction. In some embodiments, LG is released after a reaction. In some embodiments, a first group is released as part of a compound having the structure of LG-H or a salt thereof. In some embodiments, a target binding moiety is released as part of a compound having the structure of LG-H or a salt thereof. In some embodiments, LG is released as part of a compound having the structure of LG-H or a salt thereof. In some embodiments, a first group is released as part of a compound having the structure of $R^{LG}$-$L^{LG1}$-$L^{LG2}$-$L^{LG3}$-$L^{LG4}$-H or a salt thereof. In some embodiments, a target binding moiety is released as part of a compound having the structure of $R^{LG}$-$L^{LG1}$-$L^{LG2}$-$L^{LG3}$-$L^{LG4}$-H or a salt thereof. In some embodiments, a target binding moiety is released as part of a compound having the structure of $R^{LG}$-$L^{LG1}$-$L^{LG2}$-$L^{LG3}$-$L^{LG4}$-H or a salt thereof, wherein $R^{LG}$ is or comprises the target binding moiety. In some embodiments, LG is released as part of a compound having the structure of $R^{LG}$-$L^{LG1}$-$L^{LG2}$-$L^{LG3}$-$L^{LG4}$-H or a salt thereof, wherein LG is $R^{LG}$-$L^{LG}$, and $L^{LG}$ is -$L^{LG1}$-, -$L^{LG1}$-$L^{LG2}$-, -$L^{LG1}$-$L^{LG2}$-$L^{LG3}$-, or -$L^{LG1}$-$L^{LG2}$-$L^{LG3}$-$L^{LG4}$. In some embodiments, LG is released as part of a compound having the structure of $R^{LG}$-$L^{LG1}$-$L^{LG2}$-$L^{LG3}$-$L^{LG4}$-H or a salt thereof, wherein LG is $R^{LG}$-$L^{LG1}$-. In some embodiments, LG is released as part of a compound having the structure of $R^{LG}$-$L^{LG1}$-$L^{LG2}$-$L^{LG3}$-$L^{LG4}$-H or a salt thereof, wherein LG is $R^{LG}$-$L^{LG1}$-$L^{LG2}$. In some embodiments, LG is released as part of a compound having the structure of $R^{LG}$-$L^{LG1}$-$L^{LG2}$-$L^{LG3}$-$L^{LG4}$-H or a salt thereof, wherein LG is $R^{LG}$-$L^{LG1}$-$L^{LG2}$-$L^{LG3}$. In some embodiments, LG is released as part of a compound having the structure of $R^{LG}$-$L^{LG1}$-$L^{LG2}$-$L^{LG3}$-$L^{LG4}$-H or a salt thereof, wherein LG is $R^{LG}$-$L^{LG1}$-$L^{LG2}$-$L^{LG3}$-$L^{LG4}$.

In some embodiments, L is a covalent bond, or a bivalent optionally substituted, linear or branched $C_{1-100}$ group comprising one or more aliphatic moieties, aryl moieties, heteroaliphatic moieties each independently having 1-20 heteroatoms, heteroaromatic moieties each independently having 1-20 heteroatoms, or any combinations of any one or more of such moieties, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue, or —[(—O—C(R')$_2$—C(R')$_2$—)$_n$]—, wherein n is 1-20. In some embodiments, L is a covalent bond, or a bivalent optionally substituted, linear or branched $C_{1-100}$ aliphatic or heteroaliphatic group 1-20 heteroatoms, wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —[(—O—C(R')$_2$—C(R')$_2$—)$_n$]—, wherein n is 1-20. In some embodiments, L is a covalent bond, or a bivalent optionally substituted, linear or branched $C_1$, $C_2$, $C_3$, $C_4$, $C_5$, $C_{10}$, $C_{15}$, $C_{20}$, $C_{25}$, $C_{30}$, $C_{40}$, $C_{50}$, $C_{60}$, $C_{1-2}$, $C_{1-5}$, $C_{1-10}$, $C_{1-15}$, $C_{1-20}$, $C_{1-30}$, $C_{1-40}$, $C_{1-50}$, $C_{1-60}$, $C_{1-70}$, $C_{1-80}$, or $C_{1-90}$ aliphatic or heteroaliphatic group 1-10 heteroatoms, wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, amino acid residues, or —[(—O—C(R')$_2$—C(R')$_2$—)$_n$]—, wherein n is 1-20. In some embodiments, L is a covalent bond, or a bivalent optionally substituted, linear or branched $C_1$, $C_2$, $C_3$, $C_4$, $C_5$, $C_{10}$, $C_{15}$, $C_{20}$, $C_{25}$, $C_{30}$, $C_{40}$, $C_{50}$, $C_{60}$, $C_{1-2}$, $C_{1-5}$, $C_{1-10}$, $C_{1-15}$, $C_{1-20}$, $C_{1-30}$, $C_{1-40}$, $C_{1-50}$, $C_{1-60}$, $C_{1-70}$, $C_{1-80}$, or $C_{1-90}$ aliphatic or heteroaliphatic group 1-10 heteroatoms, wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, amino acid residues, or —[(—O—C(R')$_2$—C(R')$_2$—)$_n$]—, wherein n is 1-10. In some embodiments, L is a covalent bond, or a bivalent optionally substituted, linear or branched $C_1$, $C_2$, $C_3$, $C_4$, $C_5$, $C_{10}$, $C_{15}$, $C_{20}$, $C_{25}$, $C_{30}$, $C_{40}$, $C_{50}$, $C_{60}$, $C_{1-2}$, $C_{1-5}$, $C_{1-10}$, $C_{1-15}$, $C_{1-20}$, $C_{1-30}$, $C_{1-40}$, $C_{1-50}$, $C_{1-60}$, $C_{1-70}$, $C_{1-80}$, or $C_{1-90}$ aliphatic group, wherein one or more methylene units of the group are optionally and independently replaced with —O—, —N(R')—, —C(O)—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, amino acid residues, or —[(—O—C(R')$_2$—C(R')$_2$—)$_n$]—, wherein n is 1-10. In some embodiments, L is a covalent bond, or a bivalent optionally substituted, linear or branched $C_1$, $C_2$, $C_3$, $C_4$, $C_5$, $C_{10}$, $C_{15}$, $C_{20}$, $C_{25}$, $C_{30}$, $C_{40}$, $C_{50}$, $C_{60}$, $C_{1-2}$, $C_{1-5}$, $C_{1-10}$, $C_{1-15}$, $C_{1-20}$, $C_{1-30}$, $C_{1-40}$, $C_{1-50}$, $C_{1-60}$, $C_{1-70}$, $C_{1-80}$, or $C_{1-90}$ aliphatic group, wherein one or more methylene units of the group are optionally and independently replaced with —O—, —N(R')—, —C(O)—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, or —[(—O—C(R')$_2$—C(R')$_2$—)$_n$]—, wherein n is 1-10. In some embodiments, L is a covalent bond, or a bivalent optionally substituted, linear or branched $C_{1-10}$ aliphatic group, wherein one or more methylene units of the group are optionally and independently replaced with —O—, —N(R')—, —C(O)—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, -Cy-, or —[(—O—C(R')$_2$—C(R')$_2$—)$_n$]—, wherein n is 1-10. In some embodiments, L is a covalent bond, or a bivalent optionally substituted, linear or branched $C_{1-10}$ aliphatic group, wherein one or more methylene units of the group are optionally and independently replaced with —O—, —N(R')—, —C(O)—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, or —[(—O—C(R')$_2$—C(R')$_2$—)$_n$]—, wherein n is 1-10. In some embodiments, L comprises no —C(O)O—. In some embodiments, L comprises no —C(O)—N(R')—. In some embodiments, L comprises no —S—. In some embodiments, L comprises no —S-Cy-. In some embodiments, L comprises no —S—S—. In some embodiments, L does not contain one or more or any of —C(O)O—, —C(O)—N(R')—, —S—, and —S—S—. In some embodiments, L does not contain one or more or any of —C(O)O—, —C(O)—N(R')—, —S-Cy-, and —S—S—. In some embodiments, L does not contain one or more or any of —C(O)O—, —S—, and —S—S—. In some embodiments, L does not contain one or more any of —C(O)O—, —S-Cy-, and —S—S—. In some embodiments, L contains none of —C(O)O—, —S—, and —S—S—. In some embodiments, L contains none of —C(O)O—, —S-Cy-, and —S—S—. In some embodiments, L contains none of —C(O)O— and —S—S—.

In some embodiments, each amino acid residue is independently a residue of an amino acid having the structure of formula A-I or a salt thereof. In some embodiments, each amino acid residue independently has the structure of —N($R^{a1}$)-$L^{a1}$-C($R^{a2}$)($R^{a3}$)-$L^{a2}$-CO— or a salt form thereof. In some embodiments, each amino acid residue independently has the structure of —N($R^{a1}$)—C($R^{a2}$)($R^{a3}$)—CO— or a salt form thereof.

In some embodiments, L is a covalent bond. In some embodiments, L is not a covalent bond.

In some embodiments, $L^{LG1}$ is a covalent bond. In some embodiments, $L^{LG1}$ is not a covalent bond. In some embodiments, $L^{LG1}$ is or comprises —(CH$_2$CH$_2$O)n-. In some embodiments, $L^{LG1}$ is or comprises —(CH$_2$)n-O—(CH$_2$CH$_2$O)n-(CH$_2$)n-, wherein each n is independently as described herein, and each —CH$_2$— is independently optionally substituted. In some embodiments, $L^{LG1}$ is —(CH$_2$)n-O—(CH$_2$CH$_2$O)n-(CH$_2$)n-, wherein each n is independently as described herein, and each —CH$_2$— is independently optionally substituted. In some embodiments, $L^{LG1}$ is —(CH$_2$)$_2$—O—(CH$_2$CH$_2$O)n-(CH$_2$)$_2$—, wherein n is as described herein, and each —CH$_2$— is independently optionally substituted. In some embodiments, $L^{LG1}$ is —(CH$_2$)$_2$—O—(CH$_2$CH$_2$O)n-(CH$_2$)$_2$—, wherein n is as described herein.

In some embodiments, $L^{LG1}$ is —CH$_2$—. In some embodiments, $L^{LG1}$ is —(CH$_2$)$_2$—. In some embodiments, $L^{LG1}$ is —(CH$_2$)$_2$—C(O)—. In some embodiments, $L^{LG1}$ is —(CH$_2$)$_2$—C(O)—NH—. In some embodiments, $L^{LG1}$ is —(CH$_2$)$_3$—. In some embodiments, $L^{LG1}$ is —(CH$_2$)$_3$NH—. In some embodiments, $L^{LG1}$ is —(CH$_2$)$_3$NH—C(O)—. In some embodiments, $L^{LG1}$ is —C(O)—(CH$_2$)$_3$NH—C(O)—. In some embodiments, $L^{LG1}$ is —C(O)—(CH$_2$)$_3$—. In some embodiments, $L^{LG1}$ is —NH—C(O)—(CH$_2$)$_3$—. In some embodiments, $L^{LG1}$ is —NHC(O)—(CH$_2$)$_3$NH—C(O)—. In some embodiments, a —CH$_2$— is bonded to a target binding moiety.

In some embodiments, $L^{LG1}$ is —CH$_2$CH$_2$—O—CH$_2$CH$_2$—O—CH$_2$CH$_2$—. In some embodiments, $L^{LG1}$ is —CH$_2$CH$_2$—O—CH$_2$CH$_2$—O—CH$_2$CH$_2$—C(O)—. In some embodiments, $L^{LG1}$ is —CH$_2$CH$_2$—O—CH$_2$CH$_2$—O—CH$_2$CH$_2$—C(O)NH—. In some embodiments, $L^{LG1}$ is —CH$_2$CH$_2$—O—CH$_2$CH$_2$—O—CH$_2$CH$_2$—C(O)NH—CH$_2$—. In some embodiments, —CH$_2$CH$_2$— is bonded to a target binding moiety.

In some embodiments, $L^{LG1}$ is —(CH$_2$CH$_2$O)n-. In some embodiments, $L^{LG1}$ is —(CH$_2$CH$_2$O)n-CH$_2$—CH$_2$—. In some embodiments, $L^{LG1}$ is —(CH$_2$CH$_2$O)n-CH$_2$—CH$_2$—C(O)—. In some embodiments, $L^{LG1}$ is (CH$_2$CH$_2$O)$_2$—CH$_2$—CH$_2$—C(O)—. In some embodiments, $L^{LG1}$ is —(CH$_2$CH$_2$O)$_4$—CH$_2$—CH$_2$—C(O)—. In some embodiments, $L^{LG1}$ is —(CH$_2$CH$_2$O)$_8$—CH$_2$—CH$_2$—C(O)—. In some embodiments, —C(O)— is bonded to a target binding moiety.

In some embodiments, $L^{LG1}$ is —N(R')—. In some embodiments, $L^{LG1}$ is —NH—. In some embodiments, $L^{LG1}$ is —NH—[(—CH$_2$CH$_2$—O—)]n-. In some embodiments, $L^{LG1}$ is —NH—[(—CH$_2$CH$_2$—O—)]n-CH$_2$CH$_2$—. In some embodiments, $L^{LG1}$ is —NH—[(—CH$_2$CH$_2$—O—)]n-CH$_2$CH$_2$—NH—. In some embodiments, $L^{LG1}$ is —NH—[(—CH$_2$CH$_2$—O—)]n-CH$_2$CH$_2$—NH—C(O)—. In some embodiments, n is 1. In some embodiments, n is 2. In some embodiments, n is 3. In some embodiments, n is 4. In some embodiments, n is 5. In some embodiments, $L^{LG1}$ is —NH—CH$_2$CH$_2$—O—. In some embodiments, $L^{LG1}$ is —NH—CH$_2$CH$_2$—O—CH$_2$CH$_2$—. In some embodiments, $L^{LG1}$ is NH—CH$_2$CH$_2$—O—CH$_2$CH$_2$—NH—. In some embodiments, $L^{LG1}$ is —NH—CH$_2$CH$_2$—O—CH$_2$CH$_2$—NH—C(O)—.

In some embodiments, $L^{LG1}$ is —NH—[(—CH$_2$CH$_2$—O—)]$_2$—. In some embodiments, $L^{LG1}$ is —NH—[(—CH$_2$CH$_2$—O—)]$_2$—CH$_2$CH$_2$—. In some embodiments, $L^{LG1}$ is —NH—[(—CH$_2$CH$_2$—O—)]$_2$—CH$_2$CH$_2$—NH—. In some embodiments, $L^{LG1}$ is —NH—[(—CH$_2$CH$_2$—O—)]$_2$—CH$_2$CH$_2$—NH—C(O)—.

In some embodiments, $L^{LG1}$ is —NH—[(—CH$_2$CH$_2$—O—)]$_3$—. In some embodiments, $L^{LG1}$ is —NH—[(—CH$_2$CH$_2$—O—)]$_3$—CH$_2$CH$_2$—. In some embodiments, $L^{LG1}$ is —NH—[(—CH$_2$CH$_2$—O—)]$_3$—CH$_2$CH$_2$—NH—. In some embodiments, $L^{LG1}$ is —NH—[(—CH$_2$CH$_2$—O—)]$_3$—CH$_2$CH$_2$—NH—C(O)—. In some embodiments, $L^{LG1}$ is —NH—[(—CH$_2$CH$_2$—O—)]$_4$—. In some embodiments, $L^{LG1}$ is —NH—[(—CH$_2$CH$_2$—O—)]$_4$—CH$_2$CH$_2$—. In some embodiments, $L^{LG1}$ is —NH—[(—CH$_2$CH$_2$—O—)]$_4$—CH$_2$CH$_2$—NH—. In some embodiments, $L^{LG1}$ is —NH—[(—CH$_2$CH$_2$—O—)]$_4$—CH$_2$CH$_2$—NH—C(O)—. In some embodiments, $L^{LG1}$ is —NH—[(—CH$_2$CH$_2$—O—)]$_5$—. In some embodiments, $L^{LG1}$ is —NH—[(—CH$_2$CH$_2$—O—)]$_5$—CH$_2$CH$_2$—. In some embodiments, $L^{LG1}$ is —NH—[(—CH$_2$CH$_2$—O—)]$_5$—CH$_2$CH$_2$—NH—. In some embodiments, $L^{LG1}$ is —NH—[(—CH$_2$CH$_2$—O—)]$_5$—CH$_2$CH$_2$—NH—C(O)—. In some embodiments, —NH— is bonded to a target binding moiety.

In some embodiments, $L^{LG1}$ is —CH$_2$—. In some embodiments, $L^{LG1}$ is —CH$_2$CH$_2$—. In some embodiments, $L^{LG1}$ is —$CH_2CH_2NH$—. In some embodiments, $L^{LG1}$ is —$CH_2CH_2NH$—(CO)—. In some embodiments, —$CH_2$— is bonded to a target binding moiety.

In some embodiments, $L^{LG1}$ is —$CH_2$—. In some embodiments, $L^{LG1}$ is —$CH_2C(O)$—. In some embodiments, $L^{LG1}$ is —$CH_2C(O)NH$—. In some embodiments, $L^{LG1}$ is —$CH_2(CO)NHCH_2$—. In some embodiments, —$CH_2$—C(O)— is bonded to a target binding moiety at —$CH_2$—.

In some embodiments, $L^{LG2}$ is a covalent bond. In some embodiments, $L^{LG2}$ is not a covalent bond. In some embodiments, $L^{LG2}$ is —N(R')C(O)—. In some embodiments, $L^{LG2}$ is —NHC(O)—. In some embodiments, $L^{LG2}$ is —$(CH_2)$n-N(R')C(O)—, wherein —$(CH_2)$n- is optionally substituted. In some embodiments, $L^{LG2}$ is —$(CH_2)$n-OC(O)—, wherein —$(CH_2)$n- is optionally substituted. In some embodiments, $L^{LG2}$ is —$(CH_2)$n-OC(O)N(R')—, wherein —$(CH_2)$n- is optionally substituted. In some embodiments, $L^{LG2}$ is —$(CH_2)$n-OC(O)NH—, wherein —$(CH_2)$n- is optionally substituted. In some embodiments, n is 1-10, e.g., 1, 2, 3, 4, 5, 6, 7, 8, 9, or 10. In some embodiments, n is 1. In some embodiments, n is 2. In some embodiments, n is 3. In some embodiments, —$(CH_2)$n- is substituted. In some embodiments, —$(CH_2)$n- is unsubstituted. In some embodiments, $L^{LG2}$ is —$CH_2N(CH_2CH_2CH_2S(O)_2OH)$—C(O)—. In some embodiments, $L^{LG2}$ is —C(O)—$NHCH_2$—. In some embodiments, $L^{LG2}$ is —C(O)—$NHCH_2CH_2$—. In some embodiments, $L^{LG2}$ is —C(O)O—$CH_2$—. In some embodiments, $L^{LG2}$ is —NH—C(O)O—$CH_2$—. In some embodiments, —C(O)— is bonded to $L^{LG3}$. In some embodiments, —N(R')—, —NH—, or an optionally substituted —$CH_2$— unit (of optionally substituted —$(CH_2)$n-) is bonded to $L^{LG3}$.

In some embodiments, $L^{LG2}$ is —N(R')—. In some embodiments, $L^{LG2}$ is —N(R)—. In some embodiments, $L^{LG2}$ is —NH—.

In some embodiments, $L^{LG2}$ is optionally substituted bivalent $C_{1-6}$ aliphatic. In some embodiments, $L^{LG2}$ is —$CH_2$—. In some embodiments, $L^{LG2}$ is —$CH_2NH$—. In some embodiments, $L^{LG2}$ is —$CH_2NH$—C(O)—. In some embodiments, $L^{LG2}$ is —$CH_2NH$—C(O)—$CH_2$—.

In some embodiments, $L^{LG3}$ is or comprises an optionally substituted aryl ring. In some embodiments, $L^{LG3}$ is or comprises an optionally substituted phenyl ring. In some embodiments, $L^{LG3}$ is a phenyl ring substituted with one or more electron-withdrawing groups. As appreciated by those skilled in the art, various electron-withdrawing groups are known in the art and may be utilized in accordance with the present disclosure. In some embodiments, an electron-withdrawing group is halogen. In some embodiments, an electron-withdrawing group is —F. In some embodiments, it is —Cl. In some embodiments, it is —Br. In some embodiments, it is —I. In some embodiments, an electron-withdrawing group comprises an X═Y double bond, wherein X is bonded to the group to which the electron-withdrawing group is a substituent, and at least one of X and Y is a heteroatom. In some embodiments, X is a heteroatom. In some embodiments, Y is a heteroatom. In some embodiments, each of X and Y is independently a heteroatom. In some embodiments, Y is O. In some embodiments, Y is S. In some embodiments, X is C. In some embodiments, X is N. In some embodiments, X is P. In some embodiments, X is S. In some embodiments, X═Y is C═O. In some embodiments, X═Y is N═O. In some embodiments, X═Y is S═O. In some embodiments, X═Y is P═O. In some embodiments, an electron-withdrawing group is —C(O)-L-R'. In some embodiments, an electron-withdrawing group is —C(O)—R'. In some embodiments, it is —$NO_2$. In some embodiments, it is —S(O)-L-R'. In some embodiments, it is —S(O)—R'. In some embodiments, it is —$S(O)_2$-L-R'. In some embodiments, it is —$S(O)_2$—O—R'. In some embodiments, it is —$S(O)_2$—$N(R')_2$. In some embodiments, it is —P(O)$(-L-R')_2$. In some embodiments, it is —P(O)$(R')_2$. In some embodiments, it is —P(O)$(OR')_2$. In some embodiments, it is —P(O)$[N(R')_2]_2$.

In some embodiments, $L^{LG3}$ is -$L^{LG3a}$-$L^{LG3b}$, wherein $L^{LG3a}$ is a covalent bond or —C(O)O—$CH_2$—, wherein —$CH_2$— is optionally substituted, and $L^{LG3b}$ is an optionally substituted aryl ring. In some embodiments, $L^{LG3a}$ is bonded to $L^{LG2}$, and $L^{LG3b}$ is bonded to $L^{LG4}$.

In some embodiments, $L^{LG3a}$ is a covalent bond. In some embodiments, $L^{LG3a}$ is —C(O)O—$CH_2$—, wherein —$CH_2$— is optionally substituted. In some embodiments, $L^{LG3a}$ is —C(O)O—$CH_2$—, wherein —$CH_2$— is substituted. In some embodiments, $L^{LG3a}$ is —C(O)O—$CH_2$—, wherein —$CH_2$— is unsubstituted.

In some embodiments, a first group, a target binding moiety, and/or LG is released as part of a compound having the structure of $R^{LG}$-$L^{LG1}$-$L^{LG2}$-H or a salt thereof.

In some embodiments, $L^{LG3b}$ is an optionally substituted phenyl ring. In some embodiments, at least one substituent is an electron-withdrawing group as described herein.

In some embodiments, $L^{LG3}$ is

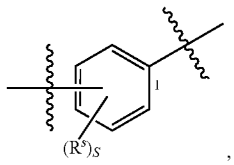

, wherein s is 0-4, each $R^s$ is independently halogen, —$NO_2$, -L-R', —C(O)-L-R', —S(O)-L-R', —$S(O)_2$-L-R', or —P(O)$(-L-R')_2$. In some embodiments, C1 is bonded to $L^{LG4}$. In some embodiments, $L^{LG3}$ is

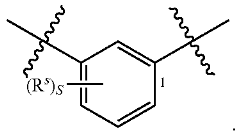

.

In some embodiments, $L^{LG3}$ is

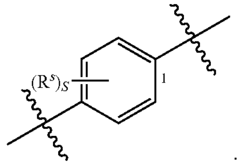

.

In some embodiments, $L^{LG3}$ is

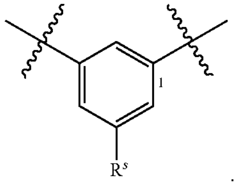

In some embodiments, $L^{LG3}$ is

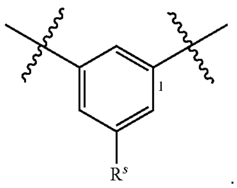

In some embodiments, $L^{LG3}$ is

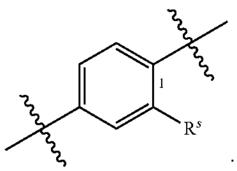

In some embodiments, $L^{LG3}$ is

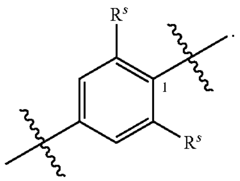

In some embodiments, $L^{LG3b}$ is

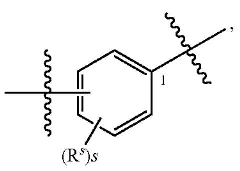

wherein s is 0-4, each $R^s$ is independently halogen, —$NO_2$, -L-R', —C(O)-L-R', —S(O)-L-R', —$S(O)_2$-L-R', or —P(O)(-L-R')$_2$. In some embodiments, C1 is bonded to $L^{LG4}$. In some embodiments, $L^{LG3b}$ is

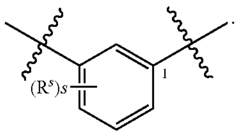

In some embodiments, $L^{LG3b}$ is

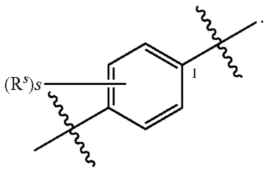

In some embodiments, $L^{LG3b}$ is

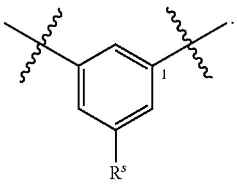

In some embodiments, $L^{LG3b}$ is

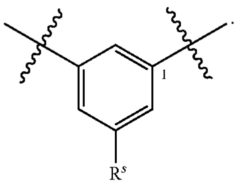

In some embodiments, $L^{LG3b}$ is

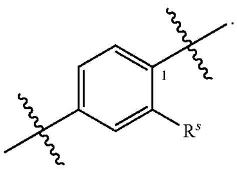

In some embodiments, $L^{LG3b}$ is

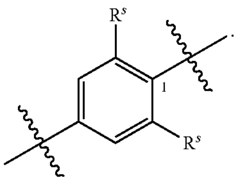

In some embodiments, s is 0. In some embodiments, s is 1-4. In some embodiments, s is 1. In some embodiments, s is 2. In some embodiments, s is 3. In some embodiments, s is 4.

In some embodiments, s is 1-4, and at least one $R^s$ is an electron-withdrawing group, e.g., an electron-withdrawing group described above. In some embodiments, at least one $R^s$ is —$NO_2$. In some embodiments, at least one $R^s$ is —F. In some embodiments, each $R^s$ is independently an electron-withdrawing group. In some embodiments, each $R^s$ is —$NO_2$. In some embodiments, each $R^s$ is —F.

In some embodiments, an electron-withdrawing group or $R^s$ is at C2. In some embodiments, an electron-withdrawing group or $R^s$ is at C3. In some embodiments, an electron-withdrawing group or $R^s$ is at C4. In some embodiments, an electron-withdrawing group or $R^s$ is at C2 and C5.

In some embodiments, $L^{LG3}$ is

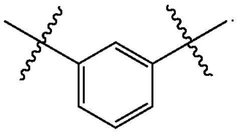 [SMILES: *c1cccc(*)c1]

In some embodiments, $L^{LG3}$ is

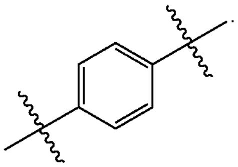 [SMILES: *c1ccc(*)cc1]

In some embodiments, $L^{LG3}$ is

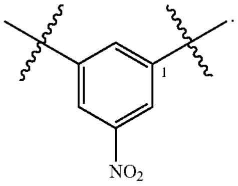 [SMILES: *c1cc(*)cc([N+](=O)[O-])c1]

In some embodiments, $L^{LG3}$ is

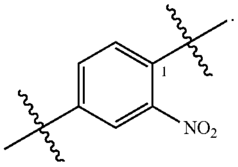 [SMILES: *c1ccc(*)c([N+](=O)[O-])c1]

In some embodiments, $L^{LG3}$ is

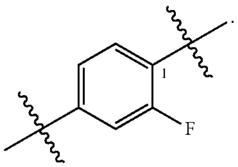 [SMILES: *c1ccc(*)c(F)c1]

In some embodiments, $L^{LG3}$ is

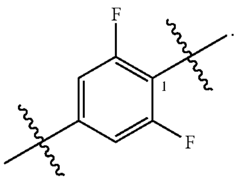 [SMILES: *c1cc(F)c(*)c(F)c1]

In some embodiments, $L^{LG3}$ is

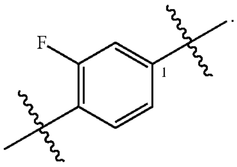 [SMILES: *c1ccc(*)c(F)c1]

In some embodiments, $L^{LG3}$ is

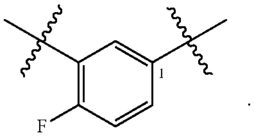 [SMILES: *c1ccc(F)c(*)c1]

In some embodiments, $L^{LG3b}$ is

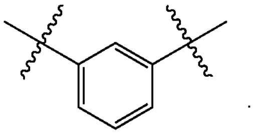 [SMILES: *c1cccc(*)c1]

In some embodiments, $L^{LG3b}$ is

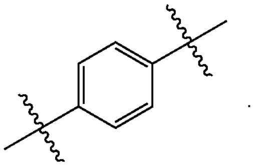 [SMILES: *c1ccc(*)cc1]

In some embodiments, $L^{LG3b}$ is

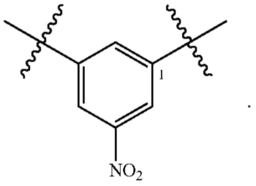 [SMILES: *c1cc(*)cc([N+](=O)[O-])c1]

In some embodiments, $L^{LG3b}$ is

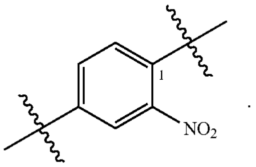 [SMILES: *c1ccc(*)c([N+](=O)[O-])c1]

In some embodiments, $L^{LG3b}$ is

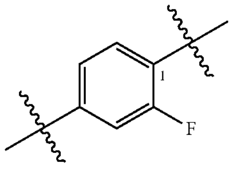
.

In some embodiments, $L^{LG3b}$ is

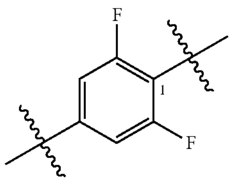
.

In some embodiments, $L^{LG3b}$ is

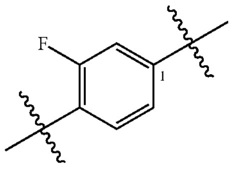
.

In some embodiments, $L^{LG3b}$ is

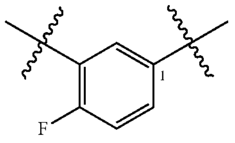
.

In some embodiments, $L^{LG3b}$ is optionally substituted

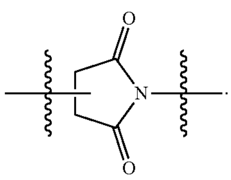
.

In some embodiments, the nitrogen atom is boned to $L^{LG4}$ which is —O—. In some embodiments, the nitrogen atom is boned to $L^{LG4}$ which is —O—, and $-L^{RG1}-L^{RG2}-$ is —C(O)—.

In some embodiments, $-L^{LG4}-L^{RG1}-L^{RG2}-$ is —O—C(O)—. In some embodiments, $-L^{LG4}-L^{RG1}-L^{RG2}-$ is —S—C(O)—. In some embodiments, $-L^{LG4}-L^{RG1}-L^{RG2}-$ is —S—C(O)—.

In some embodiments, $L^{LG4}$ is a covalent bond. In some embodiments, $L^{LG4}$ is not a covalent bond. In some embodiments, $L^{LG4}$ is —O—. In some embodiments, $L^{LG4}$ is —N(R')—. In some embodiments, $L^{LG4}$ is —NH—. In some embodiments, $L^{LG4}$ is —$N(CH_3)$—. In some embodiments, $L^{LG4}$ is —N(R')—, and $L^{LG3}$ is —O—. In some embodiments, R' is optionally substituted $C_{1-6}$ alkyl. In some embodiments, $L^{LG4}$ is —S—.

As described herein, in some embodiments, $R^{LG}$ is or comprises a target binding moiety. In some embodiments, $R^{LG}$ is or comprises a protein binding moiety. In some embodiments, $R^{LG}$ is or comprises an antibody binding moiety. In some embodiments, $R^{LG}$ is a target binding moiety. In some embodiments, $R^{LG}$ is a protein binding moiety. In some embodiments, $R^{LG}$ is an antibody binding moiety.

In some embodiments, $R^{LG}$ is or comprises

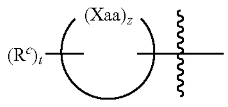

as described herein. In some embodiments, $R^{LG}$ is or comprises $R^c$-(Xaa)z- as described herein. In some embodiments, $R^{LG}$ is or comprises a small molecule moiety. In some embodiments, $R^{LG}$ is or comprises a peptide agent. In some embodiments, $R^{LG}$ is or comprises a nucleic acid agent. In some embodiments, $R^{LG}$ is or comprises an aptamer agent. In some embodiments, a target binding moiety is or comprises

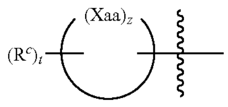

as described herein. In some embodiments, a protein binding moiety is or comprises

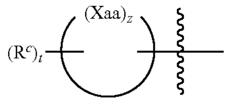

as described herein. In some embodiments, an antibody binding moiety is or comprises

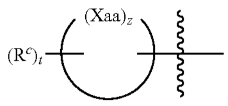

as described herein. In some embodiments, a target binding moiety is or comprises $R^c$-(Xaa)z- as described herein. In some embodiments, a protein binding moiety is or comprises $R^c$-(Xaa)z- as described herein. In some embodiments, an antibody binding moiety is or comprises $R^c$-(Xaa)z- as described herein.

Target Binding Moieties

As appreciated by those skilled in the art, various target binding moieties can be utilized in accordance with the present disclosure. Various technologies are also available in the art for developing and assessing target binding moieties and can be utilized in accordance with the present disclosure.

In some embodiments, a target binding moiety is or comprises a small molecule moiety. In some embodiments, a target binding moiety is or comprises a polymeric moiety.

In some embodiments, a target binding moiety is or comprises nucleic acid or fragments thereof. In some embodiments, a target binding moiety is or comprises a peptide moiety. In some embodiments, a target binding moiety is a polypeptide moiety.

In some embodiments, provided technologies comprise one and no more than one target binding moiety. In some embodiments, provided technologies comprise two or more target binding moieties. For example, in some embodiments, provided compounds may comprise two or more target binding moieties that can bind to target antibody agents.

a. Small Molecules

In some embodiments, a target binding moiety is or comprises a small molecule moiety that can selectively bind to a target agent. Small molecule binders to target agents including various protein agents are widely known in the art and can be utilized in accordance with the present disclosure. In some embodiments, a small molecule binder is or is a moiety of a therapeutic agent, e.g., a drug, an antibody-drug conjugate, etc.

In some embodiments, a target binding moiety is a small molecule moiety. In some embodiments, a small molecule moiety has a molecular weight no more than 8000, 7000, 6000, 5000, 4000, 3000, 2000, 1500, 1000, 900, 800, 700, or 600. In some embodiments, a small molecule moiety has a molecular weight no more than 8000. In some embodiments, a small molecule moiety has a molecular weight no more than 7000. In some embodiments, a small molecule moiety has a molecular weight no more than 6000. In some embodiments, a small molecule moiety has a molecular weight no more than 5000. In some embodiments, a small molecule moiety has a molecular weight no more than 4000. In some embodiments, a small molecule moiety has a molecular weight no more than 3000. In some embodiments, a small molecule moiety has a molecular weight no more than 2000. In some embodiments, a small molecule moiety has a molecular weight no more than 1500. In some embodiments, a small molecule moiety has a molecular weight no more than 1000. In some embodiments, a small molecule moiety has a molecular weight no more than 900.

b. Peptide Agents

In some embodiments, a target binding moiety is or comprises a peptide agent. In some embodiments, a target binding moiety is a peptide moiety. In some embodiments, a peptide moiety can either be linier or cyclic. In some embodiments, a target binding moiety is or comprises a cyclic peptide moiety. Various peptide target binding moieties are known in the art and can be utilized in accordance with the present disclosure.

In some embodiments, a target binding moiety is or comprises a peptide aptamer agent.

c. Aptamer Agents

In some embodiments, a target binding moiety is or comprises a nucleic acid agent. In some embodiments, a target binding moiety is or comprises an oligonucleotide moiety. In some embodiments, a target binding moiety is or comprises an aptamer agent. Various aptamer agents are known in the art or can be readily developed using common technologies, and can be utilized in provided technologies in accordance with the present disclosure.

In some embodiments, a target binding moiety is an antibody binding moiety. Such target binding moieties are, among other things, for conjugating moieties of interest to antibody agents.

Antibody Binding Moieties

In some embodiments, targets are antibody agents. In some embodiments, target binding moieties are antibody binding moieties. In some embodiments, provided compounds and/or agents comprise antibody binding moieties. Various antibody binding moieties can be utilized in accordance with the present disclosure. In some embodiments, antibody binding moieties are universal antibody binding moieties which can bind to antibodies having different Fab regions and different specificity. Among other things, compounds comprising such antibody binding moieties may be utilized for conjugation with antibodies having different specificity. In some embodiments, antibody binding moieties of the present disclosure, e.g., universal antibody binding moieties, bind to Fc regions. In some embodiments, binding of antibody binding moieties to Fc regions can happen at the same time as binding of Fc receptors, e.g., CD16a, to the same Fc regions (e.g., may at different locations/amino acid residues of the same Fc regions). In some embodiments, upon binding of antibody binding moieties, e.g., those in provided agents, compounds, methods, etc., an Fc region can still interact with Fc receptors and perform one or more or all of its immune activities, including recruitment of immune cells (e.g., effector cells such as NK cells), and/or triggering, generating, encouraging, and/or enhancing immune system activities toward target cells, tissues, objects and/or entities, for example, antibody-dependent cell-mediated cytotoxicity (ADCC) and/or ADCP.

Various antibody binding moieties including universal antibody binding moieties can be utilized in accordance with the present disclosure. Certain antibody binding moieties and technologies for identifying and/or assessing antibody binding moieties are described in WO/2019/023501 and WO/2019/136442, and are incorporated herein by reference. Those skilled in the art appreciates that additional technologies in the art may be suitable for identifying and/or assessing antibody binding moieties in accordance with the present disclosure. In some embodiments, an antibody binding moiety comprises one or more amino acid residues, each independently natural or unnatural.

In some embodiments, a target binding moiety, e.g., a protein binding moiety (e.g., an antibody binding moiety (e.g., a universal antibody binding moiety)), has the structure of

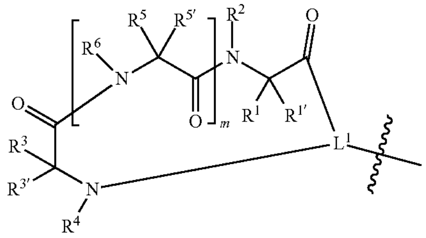

or a salt form thereof, wherein:

each of $R^1$, $R^3$ and $R^5$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:

$R^1$ and $R^{1'}$ are optionally taken together with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;

$R^3$ and $R^{3'}$ are optionally taken together with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;

an $R^5$ group and the $R^{5'}$ group attached to the same carbon atom are optionally taken together with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur; or two $R^5$ groups are optionally taken together with their intervening atoms to form a $C_{1-10}$ optionally substituted bivalent straight or branched saturated or unsaturated hydrocarbon chain wherein 1-3 methylene units of the chain are independently and optionally replaced with —S—, —SS—, —N(R)—, —O—, —C(O)—, —OC(O)—, —C(O)O—, —C(O)N(R)—, —N(R)C(O)—, —S(O)—, —$S(O)_2$—, or -$Cy^1$-, wherein each -$Cy^1$- is independently a 5-6 membered heteroarylenyl with 1-4 heteroatoms independently selected from nitrogen, oxygen or sulfur;

each of $R^{1'}$, $R^{3'}$ and $R^{5'}$ is independently hydrogen or optionally substituted $C_{1-3}$ aliphatic;

each of $R^2$, $R^4$ and $R^6$ is independently hydrogen, or optionally substituted $C_{1-4}$ aliphatic, or:

$R^2$ and $R^1$ are optionally taken together with their intervening atoms to form a 4-8 membered, optionally substituted saturated or partially unsaturated monocyclic heterocyclic ring having 1-2 heteroatoms independently selected from nitrogen, oxygen, or sulfur;

$R^4$ and $R^3$ are optionally taken together with their intervening atoms to form a 4-8 membered optionally substituted saturated or partially unsaturated monocyclic heterocyclic ring having 1-2 heteroatoms independently selected from nitrogen, oxygen, or sulfur; or an $R^6$ group and its adjacent $R^5$ group are optionally taken together with their intervening atoms to form a 4-8 membered optionally substituted saturated or partially unsaturated monocyclic heterocyclic ring having 1-2 heteroatoms independently selected from nitrogen, oxygen, or sulfur;

$L^1$ is a trivalent linker moiety; and each of m and n is independently 1, 2, 3, 4, 5, 6, 7, 8, 9, 10, 11, 12, 13, 14, 15, 16, 17, 18, 19, or 20.

In some embodiments, $L^1$ is an optionally substituted trivalent group selected from $C_1$-$C_{20}$ aliphatic or $C_1$-$C_{20}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

In some embodiments, a target binding moiety, e.g. a protein binding moiety (e.g., an antibody binding moiety (e.g., a universal antibody binding moiety)), has the structure of

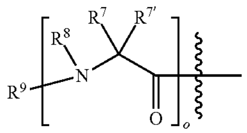

or a salt form thereof, wherein:

each of $R^7$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:

an $R^7$ group and the $R^{7'}$ group attached to the same carbon atom are optionally taken together with their intervening carbon atom to form a 3-8 membered optionally substituted saturated or partially unsaturated spirocyclic carbocyclic ring or a 3-8 membered optionally substituted saturated or partially unsaturated spirocyclic heterocyclic ring having 1-2 heteroatoms independently selected from nitrogen, oxygen, or sulfur;

each of $R^{7'}$ is independently hydrogen or optionally substituted $C_{1-3}$ aliphatic;

each of $R^8$ is independently hydrogen, or optionally substituted $C_{1-4}$ aliphatic, or:

an $R^8$ group and its adjacent $R^7$ group are optionally taken together with their intervening atoms to form a 4-8 membered optionally substituted saturated or partially unsaturated monocyclic heterocyclic ring having 1-2 heteroatoms independently selected from nitrogen, oxygen, or sulfur; and $R^9$ is hydrogen, optionally substituted $C_{1-3}$ aliphatic, or —C(O)—.

In some embodiments, an antibody binding moiety, e.g., a universal antibody binding moiety is or comprises a peptide moiety, e.g., a moiety having the structure of $R^c$-(Xaa)z- or a salt form thereof, wherein each of $R^c$, z and Xaa is independently as described herein. In some embodiments, one or more Xaa are independently an unnatural amino acid residue. In some embodiments, side chains of two or more amino acid residues may be linked together to form bridges. For example, in some embodiments, side chains of two cysteine residues may form a disulfide bridge comprising —S—S— (which, as in many proteins, can be formed by two —SH groups).

In some embodiments, a target binding moiety, e.g. a protein binding moiety (e.g., an antibody binding moiety (e.g., a universal antibody binding moiety)), is or comprises a cyclic peptide moiety, e.g., a moiety having the structure of

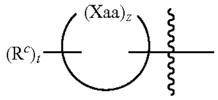

or a salt form thereof, wherein:

each Xaa is independently a residue of an amino acid or an amino acid analog;

t is 0-50;

z is 1-50;

L is a linker moiety;

each $R^c$ is independently -$L^a$-R';

each $L^a$ is independently a covalent bond, or an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent monocyclic, bicyclic or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —$CO_2$R, or —$SO_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, a heteroatom is independently selected from oxygen, nitrogen, sulfur, phosphorus and silicon.

In some embodiments, a target binding moiety is or comprises $R^c$-(Xaa)z- or a salt form thereof, wherein each variable is as described herein. In some embodiments, a protein binding moiety is or comprises $R^c$-(Xaa)z- or a salt form thereof, wherein each variable is as described herein. In some embodiments, an antibody binding moiety, e.g., a universal antibody binding moiety, is or comprises $R^c$-(Xaa)z- or a salt form thereof, wherein each variable is as described herein. In some embodiments, a target binding moiety is or comprises

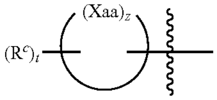

or a salt form thereof, wherein each variable is as described herein. In some embodiments, a protein binding moiety is or comprises

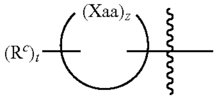

or a salt form thereof, wherein each variable is as described herein. In some embodiments, an antibody binding moiety, e.g., a universal antibody binding moiety, is or comprises

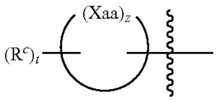

or a salt form thereof, wherein each variable is as described herein. In some embodiments, an antibody binding moiety, e.g., a universal antibody binding moiety is $R^c$-(Xaa)z- or

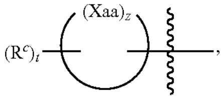, or a salt form thereof, and is or comprises a peptide unit. In some embodiments, -(Xaa)z- is or comprises a peptide unit. In some embodiments, amino acid residues may form bridges, e.g., connections formed by side chains optionally through linker moieties (e.g., L); for example, as in many polypeptides, cysteine residues may form disulfide bridges. In some embodiments, a peptide unit comprises an amino acid residue (e.g., at physiological pH about 7.4, "positively charged amino acid residue", $Xaa^P$), e.g., a residue of an amino acid of formula A-I that has a positively charged side chain. In some embodiments, a peptide unit comprises R. In some embodiments, at least one Xaa is R. In some embodiments, a peptide unit is or comprises APAR. In some embodiments, a peptide unit is or comprises RAPA. In some embodiments, a peptide unit comprises an amino acid residue, e.g., a residue of an amino acid of formula A-I, that has a side chain comprising an aromatic group ("aromatic amino acid residue", $Xaa^A$). In some embodiments, a peptide unit comprises a positively charged amino acid residue and an aromatic amino acid residue. In some embodiments, a peptide unit comprises W. In some embodiments, a peptide unit comprises a positively charged amino acid residue and an aromatic amino acid residue. In some embodiments, a peptide unit is or comprises $Xaa^{A}XaaXaa^{P}Xaa^{P}$. In some embodiments, a peptide unit is or comprises $Xaa^{P}Xaa^{P}XaaXaa^{A}$. In some embodiments, a peptide unit is or comprises $Xaa^{P}Xaa^{A}Xaa^{P}$. In some embodiments, a peptide unit is or comprises two or more $Xaa^{P}Xaa^{A}Xaa^{P}$. In some embodiments, a peptide unit is or comprises $Xaa^{P}Xaa^{A}Xaa^{P}XaaXaa^{P}Xaa^{A}Xaa^{P}$. In some embodiments, a peptide unit is or comprises $Xaa^{P}Xaa^{P}Xaa^{A}Xaa^{A}Xaa^{P}$. In some embodiments, a peptide unit is or comprises $Xaa^{P}Xaa^{P}Xaa^{P}Xaa^{A}$. In some embodiments, a peptide unit is or comprises two or more $Xaa^{A}Xaa^{A}Xaa^{P}$. In some embodiments, a peptide residue comprises one or more proline residues. In some embodiments, a peptide unit is or comprises HWRGWA. In some embodiments, a peptide unit is or comprises WGRR. In some embodiments, a peptide unit is or comprises RRGW. In some embodiments, a peptide unit is or comprises NKFRGKYK. In some embodiments, a peptide unit is or comprises NRFRGKYK. In some embodiments, a peptide unit is or comprises NARKFYK. In some embodiments, a peptide unit is or comprises NARKFYKG. In some embodiments, a peptide unit is or comprises HWRGWV. In some embodiments, a peptide unit is or comprises KHFRNKD. In some embodiments, a peptide unit comprises a positively charged amino acid residue, an aromatic amino acid residue, and an amino acid residue, e.g., a residue of an amino acid of formula A-I, that has a negatively charged side chain (e.g., at physiological pH about 7.4, "negatively charged amino acid residue", $Xaa^{N}$). In some embodiments, a peptide unit comprises RHRFNKD. In some embodiments, a peptide unit is RHRFNKD. In some embodiments, a peptide unit comprises TY. In some embodiments, a peptide unit is TY. In some embodiments, a peptide unit comprises TYK. In some embodiments, a peptide unit is TYK. In some embodiments, a peptide unit comprises RTY. In some embodiments, a peptide unit is RTY. In some embodiments, a peptide unit comprises RTYK. In some embodiments, a peptide unit is RTYK. In some embodiments, a peptide unit is or comprises a sequence selected from PAM. In some embodiments, a peptide unit comprises WHL. In some embodiments, a peptide unit is WHL. In some embodiments, a peptide unit is or comprises WXL, wherein X is an amino acid residue as described herein, e.g., one suitable for connection with another moiety (e.g., an amino acid residue comprising —COOH or a salt or activated form thereof such as D, E, etc.). In some embodiments, a peptide unit comprises WDL. In some embodiments, a peptide unit is WDL. In some embodiments, a peptide unit comprises ELVW. In some embodiments, a peptide unit is ELVW. In some embodiments, a peptide unit comprises GELVW. In some embodiments, a peptide unit is GELVW. In some embodiments, a peptide unit is or comprises a sequence selected from AWHLGELVW. In some embodiments, a peptide unit is or comprises AWHLGELVW. In some embodiments, a peptide unit is or comprises a sequence selected from AWDLGELVW. In some embodiments, a peptide unit is or comprises AWDLGELVW. In some embodiments, a peptide unit is or comprises AWXLGELVW, wherein X is an amino acid residue as described herein, e.g., one suitable for connection with another moiety (e.g., an amino acid residue comprising —COOH or a salt or activated form thereof such as D, E, etc.). In some embodiments, a peptide unit is or comprises a sequence selected from DCAWHLGELVWCT, wherein the two cysteine residues can form a disulfide bond as found in natural proteins. In some embodiments, a peptide unit is or comprises DCAWHLGELVWCT, wherein the two cysteine residues can form a disulfide bond as found in natural proteins. In some embodiments, a peptide unit is or comprises a sequence selected from DCAWXLGELVWCT, wherein the two cysteine residues can form a disulfide bond as found in natural proteins, and X is an amino acid residue as described herein, e.g., one suitable for connection with another moiety (e.g., an amino acid residue comprising —COOH or a salt or activated form thereof such as D, E, etc.). In some embodiments, a peptide unit is or comprises DCAWXLGELVWCT, wherein the two cysteine residues can form a disulfide bond as found in natural proteins, and X is an amino acid residue as described herein, e.g., one suitable for connection with another moiety (e.g., an amino acid residue comprising —COOH or a salt or activated form thereof such as D, E, etc.). In some embodiments, X comprises —COOH or a salt or activated form thereof in its side chain. In some embodiments, a peptide unit is or comprises a sequence selected from DCAWDLGELVWCT, wherein the two cysteine residues can form a disulfide bond as found in natural proteins. In some embodiments, a peptide unit is or comprises DCAWDLGELVWCT, wherein the two cysteine residues can form a disulfide bond as found in natural proteins. In some embodiments, a peptide unit is or comprises a sequence selected from Fc-III. In some embodiments, a peptide unit is or comprises Fc-III. In some embodiments, a peptide unit is or comprises a sequence selected from DpLpAWXLGELVW, wherein X is an amino acid residue as described herein, e.g., one suitable for connection with another moiety (e.g., an amino acid residue comprising —COOH or a salt or activated form thereof such as D, E, etc.). In some embodiments, a peptide unit is or comprises DpLpAWXLGELVW, wherein X is an amino acid residue as described herein, e.g., one suitable for connection with another moiety (e.g., an amino acid residue comprising —COOH or a salt or activated form thereof such as D, E, etc.). In some embodiments, a peptide unit is or comprises a sequence selected from DpLpAWDLGELVW. In some embodiments, a peptide unit is or comprises DpLpAWDLGELVW. In some embodiments, a peptide unit is or comprises a sequence selected from DpLpAWHLGELVW, wherein the two cysteine residues can form a disulfide bond as found in natural proteins. In some embodiments, a peptide unit is or comprises DpLpAWHLGELVW (e.g., FcBP-1), wherein the two cysteine residues can form a disulfide bond as found in natural proteins. In some embodiments, a peptide unit is or comprises a sequence selected from FcBP-1. In some embodiments, a peptide unit is or comprises a sequence selected from DpLpDCAWXLGELVWCT, wherein the two cysteine residues can form a disulfide bond as found in natural proteins, and X is an amino acid residue as described herein, e.g., one suitable for connection with another moiety (e.g., an amino acid residue comprising —COOH or a salt or activated form thereof such as D, E, etc.). In some embodiments, a peptide unit is or comprises DpLpDCAWXLGELVWCT, wherein the two cysteine residues can form a disulfide bond as found in natural proteins, and X is an amino acid residue as described herein, e.g., one suitable for connection with another moiety (e.g., an amino acid residue comprising —COOH or a salt or activated form thereof such as D, E, etc.). In some embodiments, a peptide unit is or comprises a sequence selected from DpLpDCAWHLGELVWCT, wherein the two cysteine residues can form a disulfide bond as found in natural proteins. In some embodiments, a peptide unit is or comprises DpLpDCAWHLGELVWCT (e.g., FcBP-2), wherein the two cysteine residues can form a disulfide bond as found in natural proteins. In some embodiments, a peptide unit is or comprises a sequence selected from DpLpDCAW-DLGELVWCT, wherein the two cysteine residues can form a disulfide bond as found in natural proteins. In some embodiments, a peptide unit is or comprises DpLpDCAW-DLGELVWCT, wherein the two cysteine residues can form a disulfide bond as found in natural proteins. In some embodiments, a peptide unit is or comprises a sequence selected from FcBP-2. In some embodiments, a peptide unit is or comprises a sequence selected from CDCAWXLGELVWCTC, wherein the first and the last cysteines, and the two cysteines in the middle of the sequence, can each independently form a disulfide bond as in natural proteins, and X is an amino acid residue as described herein, e.g., one suitable for connection with another moiety (e.g., an amino acid residue comprising —COOH or a salt or activated form thereof such as D, E, etc.). In some embodiments, a peptide unit is or comprises CDCAWXLGELVWCTC, wherein the first and the last cysteines, and the two cysteines in the middle of the sequence, can each independently form a disulfide bond as in natural proteins, and X is an amino acid residue as described herein, e.g., one suitable for connection with another moiety (e.g., an amino acid residue comprising —COOH or a salt or activated form thereof such as D, E, etc.). In some embodiments, a peptide unit is or comprises a sequence selected from CDCAWHLGELVWCTC, wherein the first and the last cysteines, and the two cysteines in the middle of the sequence, can each independently form a disulfide bond as in natural proteins. In some embodiments, a peptide unit is or comprises CDCAWHLGELVWCTC, wherein the first and the last cysteines, and the two cysteines in the middle of the sequence, can each independently form a disulfide bond as in natural proteins. In some embodiments, a peptide unit is or comprises a sequence selected from CDCAW-DLGELVWCTC, wherein the first and the last cysteines, and the two cysteines in the middle of the sequence, can each independently form a disulfide bond as in natural proteins. In some embodiments, a peptide unit is or comprises CDCAWDLGELVWCTC, wherein the first and the last cysteines, and the two cysteines in the middle of the sequence, can each independently form a disulfide bond as in natural proteins. In some embodiments, a peptide unit is or comprises a sequence selected from Fc-III-4c. In some embodiments, a peptide unit is or comprises a sequence selected from FcRM. In some embodiments, a peptide unit is or comprises a cyclic peptide unit. In some embodiments, a cyclic peptide unit comprises amide group formed by an amino group of a side chain and the C-terminus —COOH. It is appreciated by those skilled in the art that in various embodiments, when a peptide unit is connected to another moiety, an amino acid residue of a peptide unit may be connected through various positions, e.g., its backbone, its side chain, etc. In some embodiments, an amino acid residue is modified for connection. In some embodiments, an amino acid residue is replaced with another suitable residue for connection while maintaining one or more properties and/or activities a peptide unit (e.g., binding to an antibody as described herein). For example, in some embodiments, an amino acid residue is replaced with an amino acid residue with a side chain comprising —COOH or a salt or activated form thereof (e.g., side chain being —$CH_2$—COOH or a salt or activated form thereof). As exemplified herein, in various sequences H may be replaced with D (e.g., in various peptide units comprising WHL). In some embodiments, a peptide unit is connected to another moiety through —COOH or a salt or activated form thereof, e.g., through formation of e.g., —CON(R')—. In some embodiments, R' is —H. In some embodiments, —COOH is in a side chain of an amino acid residue. In some embodiments, in a sequence described herein (e.g., DCAWHLGELVWCT), 1-5 (e.g., 1, 2, 3, 4, or 5) amino acid residues may be independently and optionally replaced with another amino acid residue, 1-5 (e.g., 1, 2, 3, 4, or 5) amino acid residues may be independently and optionally deleted, and/or 1-5 (e.g., 1, 2, 3, 4, or 5) amino acid residues may be independently and optionally inserted. In some embodiments, a peptide moiety is connected to the rest of a molecule through its N-terminus. In some embodiments, it is connected to the rest of a molecule through its C-terminus. In some embodiments, it is connected to the rest of a molecule through a side chain of an amino acid residue (e.g., various X residues as described in the present disclosure). In some embodiments, two cysteine residues may independently and optionally form a disulfide bond. In some embodiments, the total number of replacement, deletion and insertion is no more than 10 (e.g., 0, or no more than 1, 2, 3, 4, 5, 6, 7, 8, 9, or 10). In some embodiments, the total number is 0. In some embodiments, the total number is no more than 1. In some embodiments, the total number is no more than 2. In some embodiments, the total number is no more than 3. In some embodiments, the total number is no more than 4. In some embodiments, the total number is no more than 5. In some embodiments, the total number is no more than 6. In some embodiments, the total number is no more than 7. In some embodiments, the total number is no more than 8. In some embodiments, the total number is no more than 9. In some embodiments, the total number is no more than 10. In some embodiments, there are no insertions. In some embodiments, there are no deletions.

In some embodiments, -(Xaa)z- is or comprises $[X^1]_{p1}[X^{12}]_{p2}$—$X^3X^4X^5X^6X^7X^8X^9X^{10}X^{11}X^{12}$—$[X^{13}]_{p13}$—$[X^{14}]_{p14}[X^{15}]_{p15}[X^{16}]_{p16}$, wherein each of $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue, e.g., of an amino acid of formula A-I, and each of p1, p2, p13, p14, p15 and p16 is independently 0, 1, 2, 3, 4, 5, 6, 7, 8, 9, or 10. In some embodiments, each of $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue of an amino acid of formula A-I. In some embodiments, each of $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently a natural amino acid residue. In some embodiments, one or more of $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently an unnatural amino acid residue as described in the present disclosure.

In some embodiments, a peptide unit comprises a functional group in an amino acid residue that can react with a functional group of another amino acid residue. In some embodiments, a peptide unit comprises an amino acid residue with a side chain which comprises a functional group that can react with another functional group of the side chain of another amino acid residue to form a linkage (e.g., see moieties described in Table A-1, Table 1, etc.). In some embodiments, one functional group of one amino acid residue is connected to a functional group of another amino acid residue to form a linkage (or bridge). Linkages are bonded to backbone atoms of peptide units and comprise no backbone atoms. In some embodiments, a peptide unit comprises a linkage formed by two side chains of non-neighboring amino acid residues. In some embodiments, a linkage is bonded to two backbone atoms of two non-neighboring amino acid residues. In some embodiments, both backbone atoms bonded to a linkage are carbon atoms. In some embodiments, a linkage has the structure of $L^b$, wherein $L^b$ is $L^a$ as described in the present disclosure, wherein $L^a$ is not a covalent bond. In some embodiments, $L^a$ comprises -Cy-. In some embodiments, $L^a$ comprises -Cy-, wherein -Cy- is optionally substituted heteroaryl. In some embodiments, -Cy- is

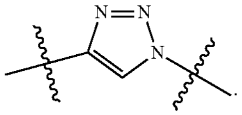 [SMILES: *c1cn(*)nn1]

In some embodiments, $L^a$ is

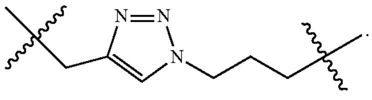 [SMILES: *CCCn1cc(C*)nn1]

In some embodiments, such an $L^a$ can be formed by a —$N_3$ group of the side chain of one amino acid residue, and the -≡- of the side chain of another amino acid residue. In some embodiments, a linkage is formed through connection of two thiol groups, e.g., of two cysteine residues. In some embodiments, $L^a$ comprises —S—S—. In some embodiments, $L^a$ is —$CH_2$—S—S—$CH_2$—. In some embodiments, a linkage is formed through connection of an amino group (e.g., —$NH_2$ in the side chain of a lysine residue) and a carboxylic acid group (e.g., —COOH in the side chain of an aspartic acid or glutamic acid residue). In some embodiments, $L^a$ comprises —C(O)—N(R')—. In some embodiments, $L^a$ comprise —C(O)—NH—. In some embodiments, $L^a$ is —$CH_2CONH$—$(CH_2)_3$—. In some embodiments, $L^a$ comprises —C(O)—N(R')—, wherein R' is R, and is taken together with an R group on the peptide backbone to form a ring (e.g., in A-34). In some embodiments, $L^a$ is —$(CH_2)_2$—N(R')—CO—$(CH_2)_2$—. In some embodiments, -Cy- is optionally substituted phenylene. In some embodiments, -Cy- is optionally substituted 1,2-phenylene. In some embodiments, $L^a$ is

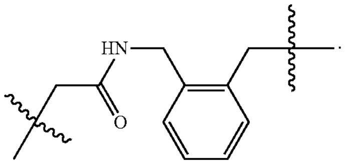 [SMILES: *CC(=O)NCc1ccccc1C*]

In some embodiments, $L^a$ is

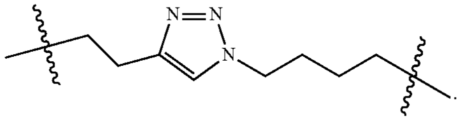 [SMILES: *CCCCn1cc(CC*)nn1]

In some embodiments, $L^a$ is optionally substituted bivalent $C_{2-20}$ bivalent aliphatic. In some embodiments, $L^a$ is optionally substituted —$(CH_2)_9$—CH═CH—$(CH_2)_9$—. In some embodiments, $L^a$ is —$(CH_2)_3$—CH═CH—$(CH_2)_3$—.

In some embodiments, two amino acid residues bonded to a linkage are separated by 1, 2, 3, 4, 5, 6, 7, 8, 9, 10, 11, 12, 13, 14, 15, or more than 15 amino acid residues between them (excluding the two amino acid residues bonded to the linkage). In some embodiments, the number is 1. In some embodiments, the number is 2. In some embodiments, the number is 3. In some embodiments, the number is 4. In some embodiments, the number is 5. In some embodiments, the number is 6. In some embodiments, the number is 7. In some embodiments, the number is 8. In some embodiments, the number is 9. In some embodiments, the number is 10. In some embodiments, the number is 11. In some embodiments, the number is 12. In some embodiments, the number is 13. In some embodiments, the number is 14. In some embodiments, the number is 15.

In some embodiments, each of p1, p2, p13, p14, p15 and p16 is 0. In some embodiments, -(Xaa)z- is or comprises —$X^3X^4X^5X^6X^7X^8X^9X^{10}X^{11}X^{12}$—, wherein:

each of $X^3$, $X^4$, $X^5$, $X^6$, $X^7$, $X^8$, $X^9$, $X^{10}$, $X^{11}$, and $X^{12}$ is independently an amino acid residue;

$X^6$ is $Xaa^A$ or $Xaa^P$;

$X^9$ is $Xaa^N$; and $X^{12}$ is $Xaa^A$ or $Xaa^P$.

In some embodiments, each of $X^3$, $X^4$, $X^5$, $X^6$, $X^7$, $X^8$, $X^9$, $X^{10}$, $X^{11}$, and $X^{12}$ is independently an amino acid residue of an amino acid of formula A-I as described in the present disclosure. In some embodiments, $X^5$ is $Xaa^A$ or $Xaa^P$. In some embodiments, $X^5$ is $Xaa^A$. In some embodiments, $X^5$ is $Xaa^P$. In some embodiments, $X^5$ is an amino acid residue whose side chain comprises an optionally substituted saturated, partially saturated or aromatic ring. In some embodiments, $X^5$ is

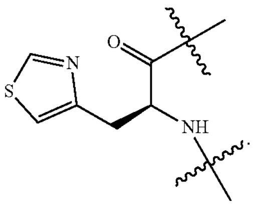 [SMILES: *N[C@@H](Cc1cscn1)C(*)=O]

In some embodiments, $X^5$ is

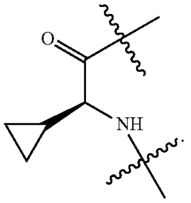 [SMILES: *N[C@H](C(*)=O)C1CC1]

In some embodiments, $X^6$ is $Xaa^A$. In some embodiments, $X^6$ is $Xaa^P$. In some embodiments, $X^6$ is His. In some embodiments, $X^{12}$ is $Xaa^A$. In some embodiments, $X^{12}$ is $Xaa^P$. In some embodiments, $X^9$ is Asp. In some embodiments, $X^9$ is Glu. In some embodiments, $X^{12}$ is

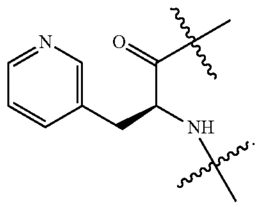 [SMILES: *N[C@@H](Cc1cccnc1)C(*)=O]

In some embodiments, $X^{12}$ is

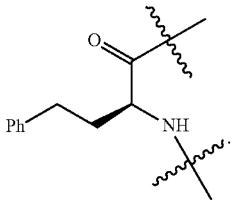 [SMILES: *N[C@@H](CCc1ccccc1)C(*)=O]

In some embodiments, each of $X^7$, $X^{10}$, and $X^{11}$ is independently an amino acid residue with a hydrophobic side chain ("hydrophobic amino acid residue", $Xaa^H$). In some embodiments, $X^7$ is $Xaa^H$. In some embodiments, $X^7$ is

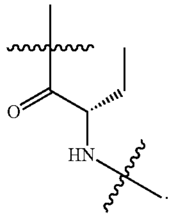 [SMILES: *N[C@@H](CC)C(*)=O]

In some embodiments, $X^7$ is Val. In some embodiments, $X^{10}$ is $Xaa^H$. In some embodiments, $X^{10}$ is Met. In some embodiments, $X^{10}$ is

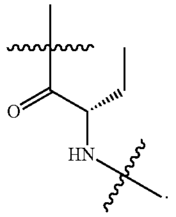 [SMILES: *N[C@@H](CC)C(*)=O]

In some embodiments, $X^{11}$ is $Xaa^H$. In some embodiments, $X^{11}$ is

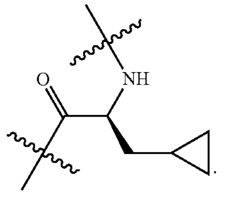 [SMILES: *N[C@@H](CC1CC1)C(*)=O]

In some embodiments, $X^8$ is Gly. In some embodiments, $X^4$ is Pro. In some embodiments, $X^3$ is Lys. In some embodiments, the —COOH of $X^{12}$ forms an amide bond with the side chain amino group of Lys ($X^3$), and the other amino group of the Lys ($X^3$) is connected to a linker moiety and then a target binding moiety.

In some embodiments, -(Xaa)z- is or comprises —$X^3X^4X^5X^6X^7X^8X^9X^{10}X^{11}X^{12}$—, wherein:

each of $X^3$, $X^4$, $X^5$, $X^6$, $X^7$, $X^8$, $X^9$, $X^{10}$, $X^{11}$, and $X^{12}$ is independently an amino acid residue;

at least two amino acid residues are connected through one or more linkages $L^b$;

$L^b$ is an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, wherein $L^b$ is bonded to a backbone atom of one amino acid residue and a backbone atom of another amino acid residue, and comprises no backbone atoms;

$X^6$ is $Xaa^A$ or $Xaa^P$;

$X^9$ is $Xaa^N$; and $X^{12}$ is $Xaa^A$ or $Xaa^P$.

In some embodiments, each of $X^3$, $X^4$, $X^5$, $X^6$, $X^7$, $X^8$, $X^9$, $X^{10}$, $X^{11}$, and $X^{12}$ is independently an amino acid residue of an amino acid of formula A-I as described in the present disclosure. In some embodiments, two non-neighboring amino acid residues are connected by $L^b$. In some embodiments, $X^5$ and $X^{10}$ are connected by $L^b$. In some embodiments, there is one linkage $L^b$. In some embodiments, $X^6$ is $Xaa^A$. In some embodiments, $X^6$ is $Xaa^P$. In some embodiments, $X^6$ is His. In some embodiments, $X^9$ is Asp. In some embodiments, $X^9$ is Glu. In some embodiments, $X^{12}$ is $Xaa^A$. In some embodiments, $X^{12}$ is

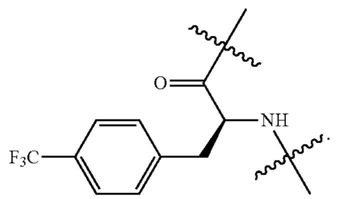 [SMILES: *N[C@@H](Cc1ccc(C(F)(F)F)cc1)C(*)=O]

In some embodiments, $X^{12}$ is

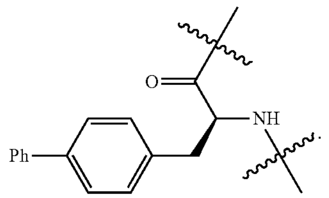 [SMILES: *N[C@@H](Cc1ccc(-c2ccccc2)cc1)C(*)=O]

In some embodiments, $X^{12}$ is

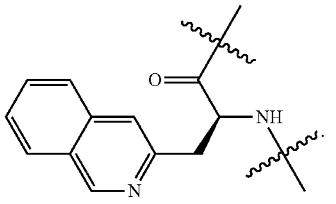 [SMILES: *N[C@@H](Cc1cc2ccccc2cn1)C(*)=O]

In some embodiments, each of $X^4$, $X^7$, and $X^{11}$ is independently $Xaa^H$. In some embodiments, $X^4$ is $Xaa^H$. In some embodiments, $X^4$ is Ala. In some embodiments, $X^7$ is $Xaa^H$. In some embodiments, $X^7$ is

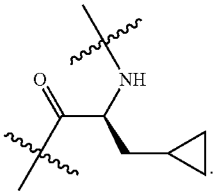 [SMILES: *N[C@@H](CC1CC1)C(*)=O]

In some embodiments, $X^{11}$ is $Xaa^H$. In some embodiments, $X^{11}$ is

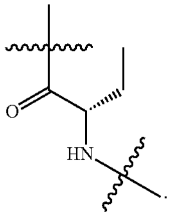 [SMILES: *N[C@@H](CC)C(*)=O]

In some embodiments, $X^8$ is Gly. In some embodiments, $X^3$ is Lys. In some embodiments, the —COOH of $X^{12}$ forms an amide bond with the side chain amino group of Lys ($X^3$), and the other amino group of the Lys ($X^3$) is connected to a linker moiety and then a target binding moiety. In some embodiments, $L^b$ is

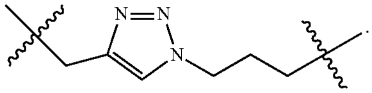 [SMILES: *CCCn1cc(C*)nn1]

In some embodiments, $L^b$ is

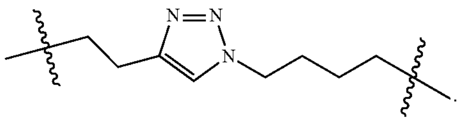 [SMILES: *CCCCn1cc(CC*)nn1]

In some embodiments, $L^b$ connects two alpha-carbon atoms of two different amino acid residues. In some embodiments, both $X^5$ and $X^{10}$ are Cys, and the two —SH groups of their side chains form —S—S— ($L^b$ is —$CH_2$—S—S—$CH_2$—).

In some embodiments, -(Xaa)z- is or comprises —$X^2X^3X^4X^5X^6X^7X^8X^9X^{10}X^{11}X^{12}$—, wherein:

each of $X^2$, $X^3$, $X^4$, $X^5$, $X^6$, $X^7$, $X^8$, $X^9$, $X^{10}$, $X^{11}$, and $X^{12}$ is independently an amino acid residue;

at least two amino acid residues are connected through one or more linkages $L^b$;

$L^b$ is an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, wherein $L^b$ is bonded to a backbone atom of one amino acid residue and a backbone atom of another amino acid residue, and comprises no backbone atoms;

$X^4$ is $Xaa^A$.

$X^5$ is $Xaa^A$ or $Xaa^P$;

$X^8$ is $Xaa^N$; and $X^{11}$ is $Xaa^A$.

In some embodiments, each of $X^2$, $X^3$, $X^4$, $X^5$, $X^6$, $X^7$, $X^8$, $X^9$, $X^{10}$, $X^{11}$, and $X^{12}$ is independently an amino acid residue of an amino acid of formula A-I as described in the present disclosure. In some embodiments, two non-neighboring amino acid residues are connected by $L^b$. In some embodiments, there is one linkage $L^b$. In some embodiments, $X^2$ and $X^{12}$ are connected by $L^b$. In some embodiments, $L^b$ is —$CH_2$—S—S—$CH_2$—. In some embodiments, $L^b$ is —$CH_2$—$CH_2$—S—$CH_2$—. In some embodiments, $L^b$ is

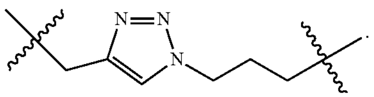 [SMILES: *CCCn1cc(C*)nn1]

In some embodiments, $L^b$ is

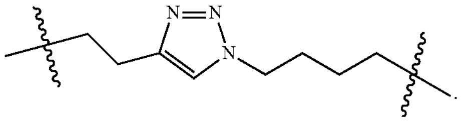 [SMILES: *CCCCn1cc(CC*)nn1]

In some embodiments, $L^b$ is —$CH_2CH_2CO$—N(R')—$CH_2CH_2$—. In some embodiments, R' are taken together with an R group on the backbone atom that —N(R')—$CH_2CH_2$— is bonded to form a ring, e.g., as in A-34. In some embodiments, a formed ring is 3-, 4-, 5-, 6-, 7- or 8-membered. In some embodiments, a formed ring is monocyclic. In some embodiments, a formed ring is saturated. In some embodiments, $L^b$ is

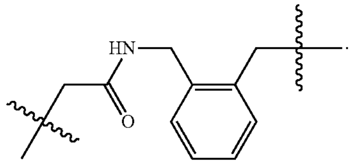 [SMILES: *CC(=O)NCc1ccccc1C*]

In some embodiments, $L^b$ connects two alpha-carbon atoms of two different amino acid residues. In some embodiments, $X^4$ is $Xaa^A$. In some embodiments, $X^4$ is Tyr. In some embodiments, $X^5$ is $Xaa^A$. In some embodiments, $X^5$ is $Xaa^P$. In some embodiments, $X^5$ is His. In some embodiments, $X^8$ is Asp. In some embodiments, $X^8$ is Glu. $X^{11}$ is Tyr. In some embodiments, both $X^2$ and $X^{12}$ are Cys, and the two —SH groups of their side chains form —S—S— ($L^b$ is —$CH_2$—S—S—$CH_2$—). In some embodiments, each of $X^3$, $X^6$, $X^9$, and $X^{10}$ is independently $Xaa^H$. In some embodiments, $X^3$ is $Xaa^H$. In some embodiments, $X^3$ is Ala. In some embodiments, $X^6$ is $Xaa^H$. In some embodiments, $X^6$ is Leu. In some embodiments, $X^9$ is $Xaa^H$. In some embodiments, $X^9$ is Leu. In some embodiments, $X^9$ is

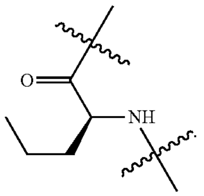 [SMILES: *N[C@@H](CCC)C(*)=O]

In some embodiments, $X^{10}$ is $Xaa^H$. In some embodiments, $X^{10}$ is Val. In some embodiments, $X^{10}$ is

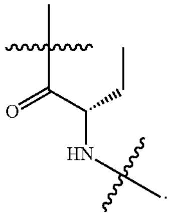 [SMILES: *N[C@@H](CC)C(*)=O]

In some embodiments, $X^7$ is Gly. In some embodiments, p1 is 1. In some embodiments, $X^1$ is Asp. In some embodiments, p13 is 1. In some embodiments, p14, p15 and p16 are 0. In some embodiments, $X^{13}$ is an amino acid residue comprising a polar uncharged side chain (e.g., at physiological pH, "polar uncharged amino acid residue", $Xaa^L$). In some embodiments, $X^{13}$ is Thr. In some embodiments, $X^{13}$ is Val. In some embodiments, p13 is 0. In some embodiments, $R^c$ is —$NHCH_2CH(OH)CH_3$. In some embodiments, $R^c$ is (R)—$NHCH_2CH(OH)CH_3$. In some embodiments, $R^c$ is (S)—$NHCH_2CH(OH)CH_3$.

In some embodiments, -(Xaa)z- is or comprises —$X^2X^3X^4X^5X^6X^7X^8X^9X^{10}X^{11}X^{12}$—, wherein:

each of $X^2$, $X^3$, $X^4$, $X^5$, $X^6$, $X^7$, $X^8$, $X^9$, $X^{10}$, $X^{11}$, and $X^{12}$ is independently an amino acid residue;

at least two amino acid residues are connected through one or more linkages $L^b$;

$L^b$ is an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—, wherein $L^b$ is bonded to a backbone atom of one amino acid residue and a backbone atom of another amino acid residue, and comprises no backbone atoms;

$X^5$ is $Xaa^A$ or $Xaa^P$;

$X^8$ is $Xaa^N$; and $X^{11}$ is $Xaa^A$.

In some embodiments, each of $X^2$, $X^3$, $X^4$, $X^5$, $X^6$, $X^7$, $X^8$, $X^9$, $X^{10}$, $X^{11}$, and $X^{12}$ is independently an amino acid residue of an amino acid of formula A-I as described in the present disclosure. In some embodiments, two non-neighboring amino acid residues are connected by $L^b$. In some embodiments, there is one linkage $L^b$. In some embodiments, there are two or more linkages $L^b$. In some embodiments, there are two linkages $L^b$. In some embodiments, $X^{12}$ and $X^{12}$ are connected by $L^b$. In some embodiments, $X^4$ and $X^9$ are connected by $L^b$. In some embodiments, $X^4$ and $X^{10}$ are connected by $L^b$. In some embodiments, $L^b$ is —$CH_2$—S—S—$CH_2$—. In some embodiments, $L^b$ is

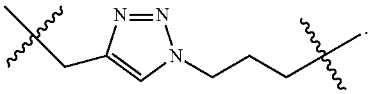 [SMILES: *CCCn1cc(C*)nn1]

In some embodiments, $L^b$ is

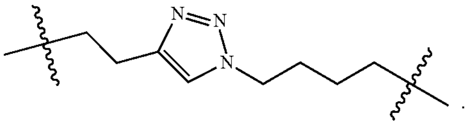 [SMILES: *CCCCn1cc(CC*)nn1]

In some embodiments, both $X^{12}$ and $X^{12}$ are Cys, and the two —SH groups of their side chains form —S—S— ($L^b$ is —$CH_2$—S—S—$CH_2$—). In some embodiments, both $X^4$ and $X^{10}$ are Cys, and the two —SH groups of their side chains form —S—S— ($L^b$ is —$CH_2$—S—S—$CH_2$—). In some embodiments, $X^4$ and $X^9$ are connected by $L^b$, wherein $L^b$ is

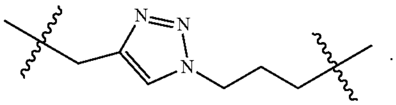 [SMILES: *CCCn1cc(C*)nn1]

In some embodiments, $X^4$ and $X^9$ are connected by $L^b$, wherein $L^b$ is

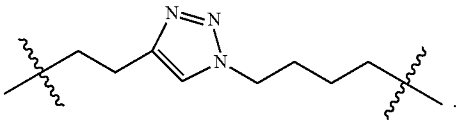 [SMILES: *CCCCn1cc(CC*)nn1]

In some embodiments, $X^5$ is $Xaa^A$. In some embodiments, $X^5$ is $Xaa^P$. In some embodiments, $X^5$ is His. In some embodiments, $X^8$ is Asp. In some embodiments, $X^8$ is Glu. In some embodiments, $X^{11}$ is Tyr. In some embodiments, $X^{11}$ is N

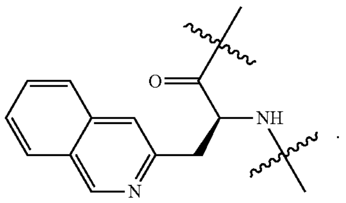 [SMILES: *N[C@@H](Cc1cc2ccccc2cn1)C(*)=O]

In some embodiments, $X^2$ and $X^{12}$ are connected by $L^b$, wherein $L^b$ is —$CH_2$—S—$CH_2CH_2$—. In some embodiments, $L^b$ connects two alpha-carbon atoms of two different amino acid residues. In some embodiments, each of $X^3$, $X^6$, and $X^9$ is independently $Xaa^H$. In some embodiments, $X^3$ is $Xaa^H$. In some embodiments, $X^3$ is Ala. In some embodiments, $X^6$ is $Xaa^H$. In some embodiments, $X^6$ is Leu. In some embodiments, $X^6$ is

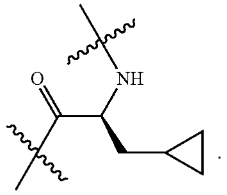 [SMILES: *N[C@@H](CC1CC1)C(*)=O]

In some embodiments, $X^9$ is $Xaa^H$. In some embodiments, $X^9$ is Leu. In some embodiments, $X^9$ is

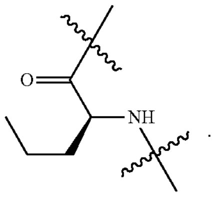 [SMILES: *N[C@@H](CCC)C(*)=O]

In some embodiments, $X^{10}$ is $Xaa^H$. In some embodiments, $X^{10}$ is Val. In some embodiments, $X^7$ is Gly. In some embodiments, p1 is 1. In some embodiments, $X^1$ is $Xaa^N$. In some embodiments, $X^1$ is Asp. In some embodiments, $X^1$ is Glu. In some embodiments, p13 is 1. In some embodiments, p14, p15 and p16 are 0. In some embodiments, $X^{13}$ is $Xaa^L$. In some embodiments, $X^{13}$ is Thr. In some embodiments, $X^{13}$ is Val.

In some embodiments, -(Xaa)z- is or comprises —$X^2X^3X^4X^5X^6X^7X^8X^9X^{10}X^{11}X^{12}X^{13}X^{14}X^{15}X^{16}$—, wherein:

each of $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, and $X^{16}$ is independently an amino acid residue;

at least two amino acid residues are connected through a linkage $L^b$;

$L^b$ is an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, wherein $L^b$ is bonded to a backbone atom of one amino acid residue and a backbone atom of another amino acid residue, and comprises no backbone atoms;

$X^3$ is $Xaa^N$;

$X^6$ is $Xaa^A$;

$X^7$ is $Xaa^A$ or $Xaa^P$;

$X^9$ is $Xaa^N$; and $X^{13}$ is $Xaa^A$.

In some embodiments, each of $X^2$, $X^3$, $X^4$, $X^5$, $X^6$, $X^7$, $X^8$, $X^9$, $X^{10}$, $X^{11}$, and $X^{12}$ is independently an amino acid residue of an amino acid of formula A-I as described in the present disclosure. In some embodiments, two non-neighboring amino acid residues are connected by $L^b$. In some embodiments, there is one linkage $L^b$. In some embodiments, there are two or more linkages $L^b$. In some embodiments, there are two linkages $L^b$. In some embodiments, $X^2$ are connected to $X^{16}$ by $L^b$. In some embodiments, $X^4$ are connected to $X^{14}$ by $L^b$. In some embodiments, both $X^2$ and $X^{16}$ are Cys, and the two —SH groups of their side chains form —S—S— ($L^b$ is —$CH_2$—S—S—$CH_2$—). In some embodiments, both $X^4$ and $X^{14}$ are Cys, and the two —SH groups of their side chains form —S—S— ($L^b$ is —$CH_2$—S—S—$CH_2$—). In some embodiments, $L^b$ connects two alpha-carbon atoms of two different amino acid residues. In some embodiments, $X^3$ is Asp. In some embodiments, $X^3$ is Glu. In some embodiments, $X^5$ is $Xaa^H$. In some embodiments, $X^5$ is Ala. In some embodiments, $X^6$ is $Xaa^A$. In some embodiments, $X^6$ is Tyr. In some embodiments, $X^7$ is $Xaa^A$. In some embodiments, $X^7$ is $Xaa^P$. In some embodiments, $X^7$ is His. In some embodiments, $X^7$ is $Xaa^H$. In some embodiments, $X^7$ is Ala. In some embodiments, $X^9$ is Gly. In some embodiments, $X^{10}$ is Asp. In some embodiments, $X^{10}$ is Glu. In some embodiments, $X^{11}$ is $Xaa^H$. In some embodiments, $X^{11}$ is Leu. In some embodiments, $X^{12}$ is $Xaa^H$. In some embodiments, $X^{12}$ is Val. In some embodiments, $X^{13}$ is $Xaa^A$. In some embodiments, $X^{13}$ is Tyr. In some embodiments, $X^{15}$ is $Xaa^L$. In some embodiments, $X^{15}$ is Thr. In some embodiments, $X^{15}$ is Val. In some embodiments, p1 is 1. In some embodiments, In some embodiments, $X^1$ is $Xaa^N$. In some embodiments, $X^1$ is Asp. In some embodiments, $X^1$ is Glu.

As appreciated by those skilled in the art, an amino acid residue may be replaced by another amino acid residue having similar properties, e.g., one $Xaa^H$ (e.g., Val, Leu, etc.) may be replaced with another $Xaa^H$ (e.g., Leu, Ile, Ala, etc.), one $Xaa^A$ may be replaced with another $Xaa^A$, one $Xaa^P$ may be replaced with another $Xaa^P$, one $Xaa^N$ may be replaced with another $Xaa^N$, one $Xaa^L$ may be replaced with another $Xaa^L$, etc.

In some embodiments, a target binding moiety is or comprises optionally substituted moiety of Table A-1. In some embodiments, a protein binding moiety is or comprises optionally substituted moiety of Table A-1. In some embodiments, an antibody binding moiety, e.g., a universal antibody binding moiety, is or comprises optionally substituted moiety of Table A-1. In some embodiments, a target binding moiety is selected from able A-1. In some embodiments, a protein binding moiety is selected from able A-1. In some embodiments, an antibody binding moiety, e.g., a universal antibody binding moiety, is selected from able A-1. In some embodiments, C-terminus and/or N-terminus are optionally capped (e.g., for C-terminus, by converting —COOH into —C(O)N(R')$_2$ like —C(O)$NH_2$; for N-terminus, by adding R'C(O)— like $CH_3$C(O)— to an amino group).

TABLE A-1
| Exemplary antibody binding moieties. | |
|---|---|
| 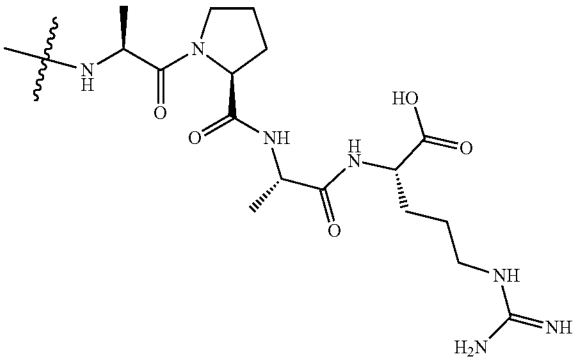 [SMILES: *N[C@@H](C)C(=O)N1CCC[C@H]1C(=O)N[C@@H](C)C(=O)N[C@@H](CCCNC(=N)N)C(=O)O] | A-1 |
| 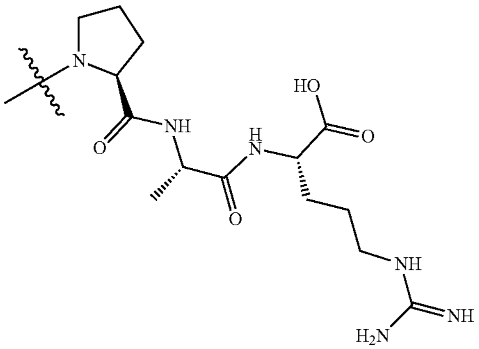 [SMILES: *N1CCC[C@H]1C(=O)N[C@@H](C)C(=O)N[C@@H](CCCNC(=N)N)C(=O)O] | A-2 |
| 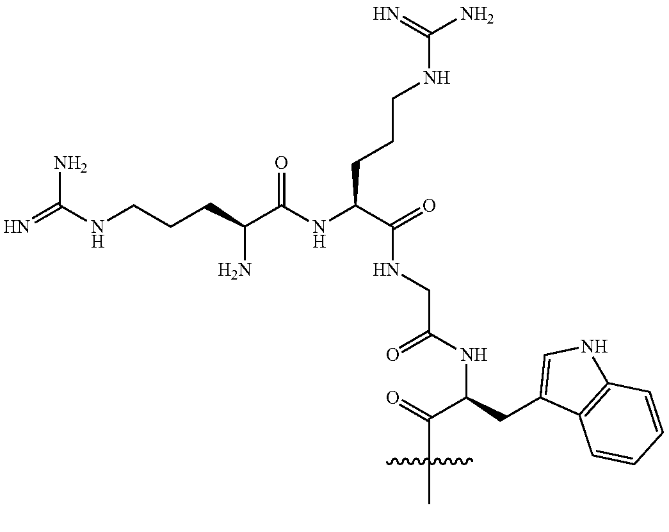 [SMILES: *C(=O)[C@H](Cc1c[nH]c2ccccc12)NC(=O)CNC(=O)[C@H](CCCNC(=N)N)NC(=O)[C@@H](N)CCCNC(=N)N] | A-3 |

TABLE A-1-continued
| Exemplary antibody binding moieties. |
| --- |
A-4
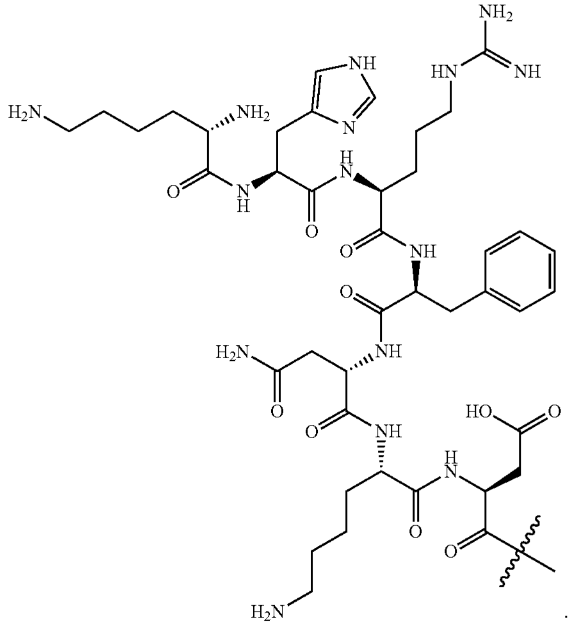 [SMILES: *C(=O)[C@H](CC(=O)O)NC(=O)[C@H](CCCCN)NC(=O)[C@H](CC(N)=O)NC(=O)[C@H](Cc1ccccc1)NC(=O)[C@H](CCCNC(=N)N)NC(=O)[C@H](Cc1c[nH]cn1)NC(=O)[C@@H](N)CCCCN]
A-5
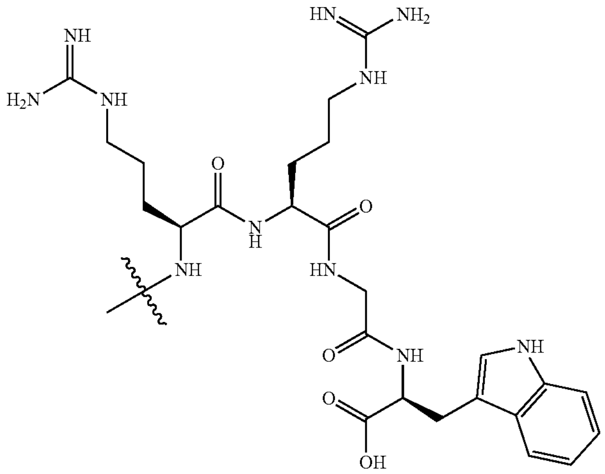 [SMILES: *N[C@@H](CCCNC(=N)N)C(=O)N[C@@H](CCCNC(=N)N)C(=O)NCC(=O)N[C@@H](Cc1c[nH]c2ccccc12)C(=O)O]
A-6
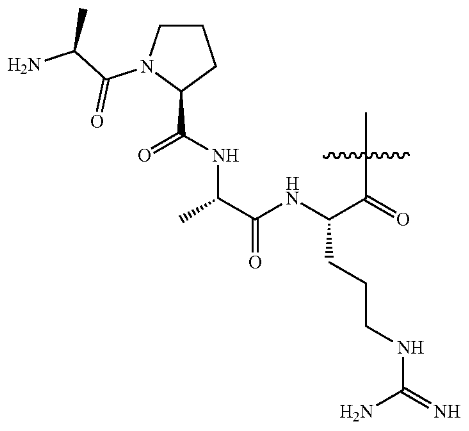 [SMILES: *C(=O)[C@H](CCCNC(=N)N)NC(=O)[C@H](C)NC(=O)[C@@H]1CCCN1C(=O)[C@H](C)N]

TABLE A-1-continued
| Exemplary antibody binding moieties. |
| --- |
A-7
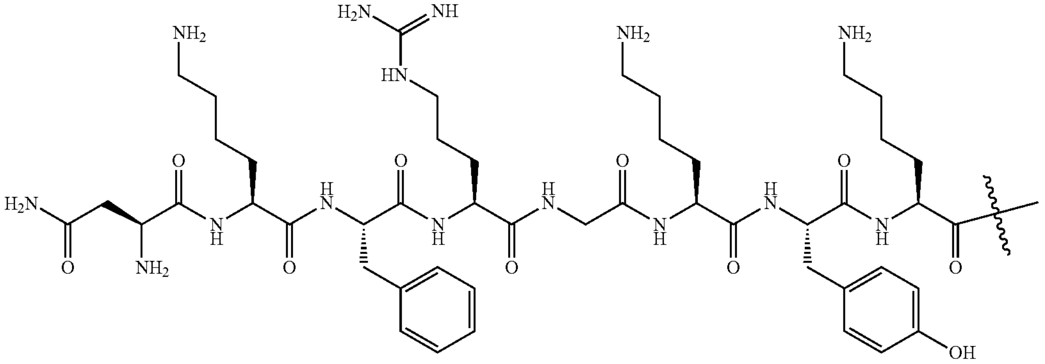 [SMILES: *C(=O)[C@H](CCCCN)NC(=O)[C@H](Cc1ccc(O)cc1)NC(=O)[C@H](CCCCN)NC(=O)CNC(=O)[C@H](CCCNC(=N)N)NC(=O)[C@H](Cc1ccccc1)NC(=O)[C@H](CCCCN)NC(=O)[C@@H](N)CC(N)=O]
A-8
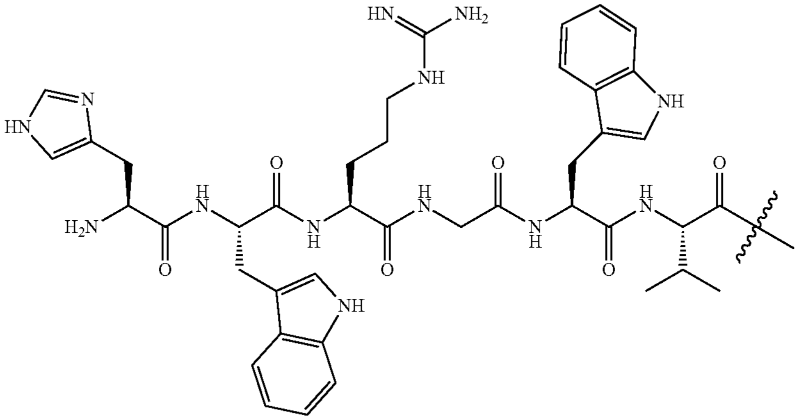 [SMILES: *C(=O)[C@@H](NC(=O)[C@H](Cc1c[nH]c2ccccc12)NC(=O)CNC(=O)[C@H](CCCNC(=N)N)NC(=O)[C@H](Cc1c[nH]c2ccccc12)NC(=O)[C@@H](N)Cc1c[nH]cn1)C(C)C]
A-9
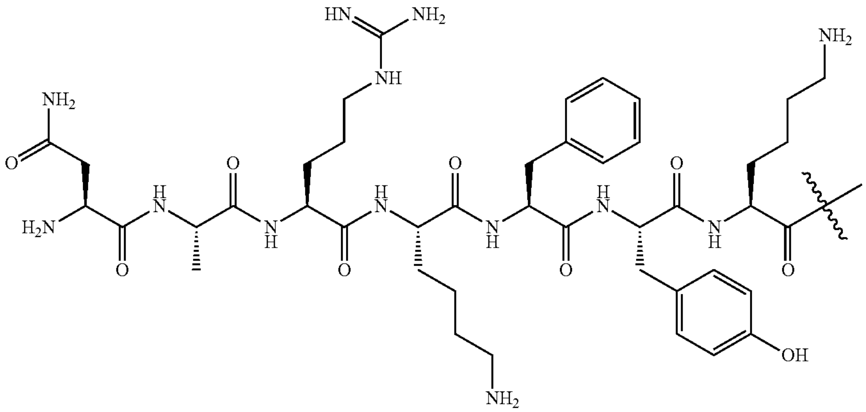 [SMILES: *C(=O)[C@H](CCCCN)NC(=O)[C@H](Cc1ccc(O)cc1)NC(=O)[C@H](Cc1ccccc1)NC(=O)[C@H](CCCCN)NC(=O)[C@H](CCCNC(=N)N)NC(=O)[C@H](C)NC(=O)[C@@H](N)CC(N)=O]

TABLE A-1-continued
| Exemplary antibody binding moieties. |
| --- |
A-10
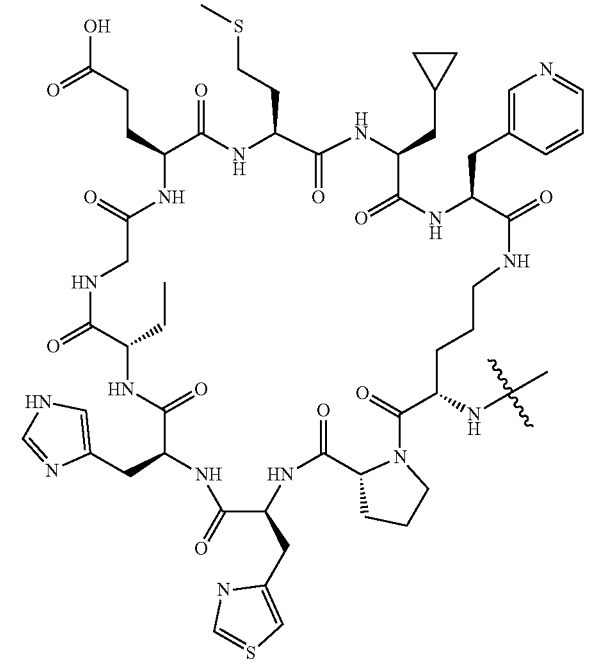
A-11
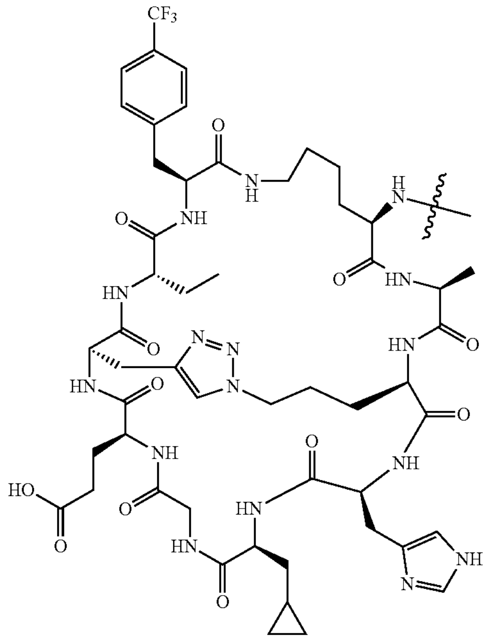 [SMILES: *N[C@@H]1CCCCNC(=O)[C@H](Cc2ccc(C(F)(F)F)cc2)NC(=O)[C@H](CC)NC(=O)[C@H]2Cc3cn(nn3)CCC[C@@H](NC(=O)[C@H](C)NC1=O)C(=O)N[C@@H](Cc1c[nH]cn1)C(=O)N[C@@H](CC1CC1)C(=O)NCC(=O)N[C@@H](CCC(=O)O)C(=O)N2]

TABLE A-1-continued
| Exemplary antibody binding moieties. |
| --- |
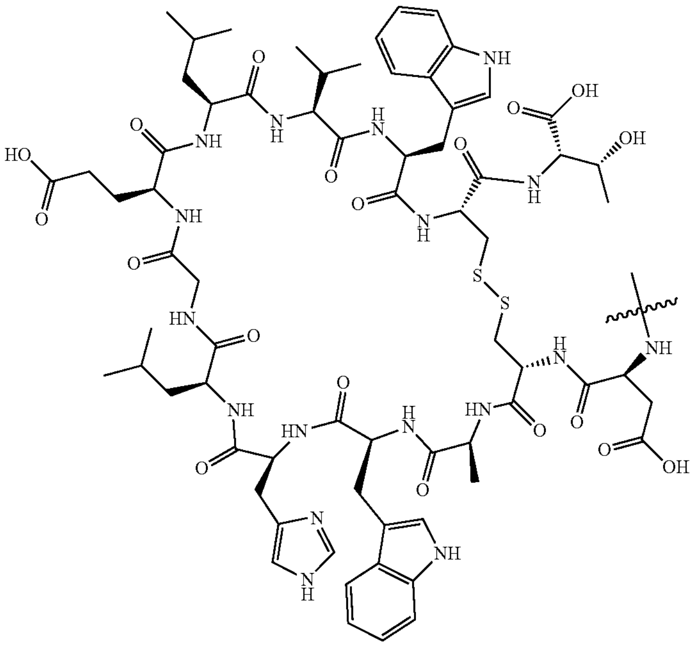 [SMILES: *N[C@@H](CC(=O)O)C(=O)N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]
A-12
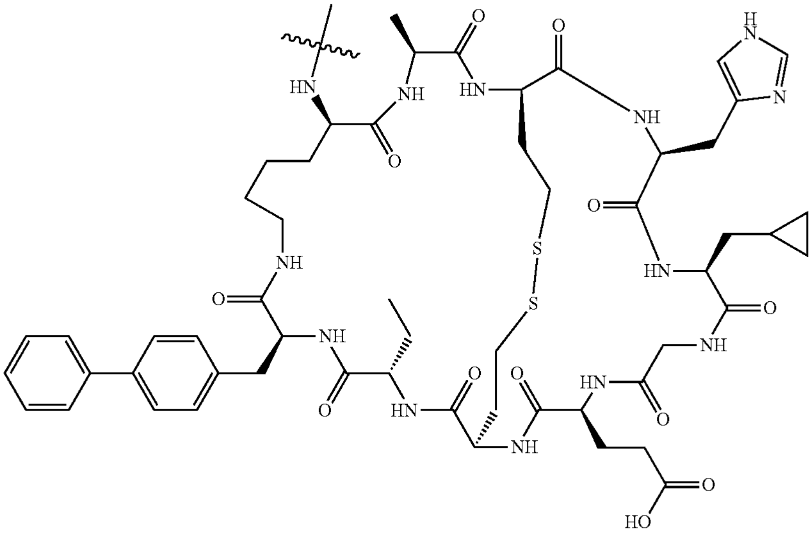 [SMILES: *N[C@@H]1CCCCNC(=O)[C@H](Cc2ccc(-c3ccccc3)cc2)NC(=O)[C@H](CC)NC(=O)[C@H]2CCSSCC[C@@H](NC(=O)[C@H](C)NC1=O)C(=O)N[C@@H](Cc1c[nH]cn1)C(=O)N[C@@H](CC1CC1)C(=O)NCC(=O)N[C@@H](CCC(=O)O)C(=O)N2]
A-13

TABLE A-1-continued
| Exemplary antibody binding moieties. | |
|---|---|
| 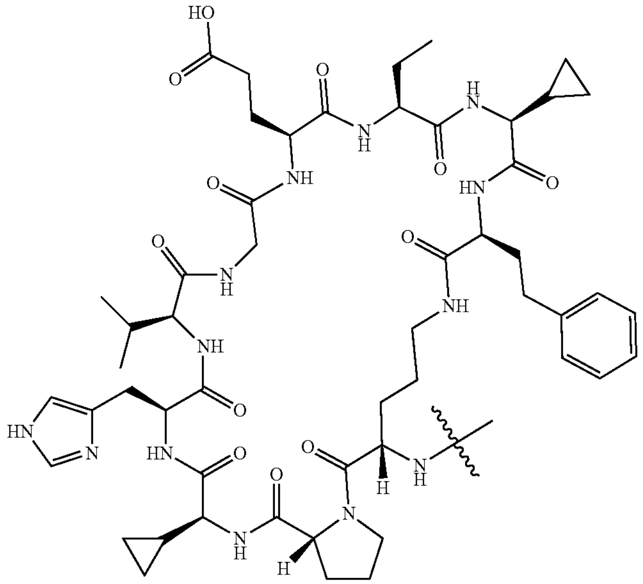 [SMILES: *N[C@H]1CCCNC(=O)[C@H](CCc2ccccc2)NC(=O)[C@H](C2CC2)NC(=O)[C@H](CC)NC(=O)[C@H](CCC(=O)O)NC(=O)CNC(=O)[C@H](C(C)C)NC(=O)[C@H](Cc2c[nH]cn2)NC(=O)[C@H](C2CC2)NC(=O)[C@H]2CCCN2C1=O] | A-14 |
| 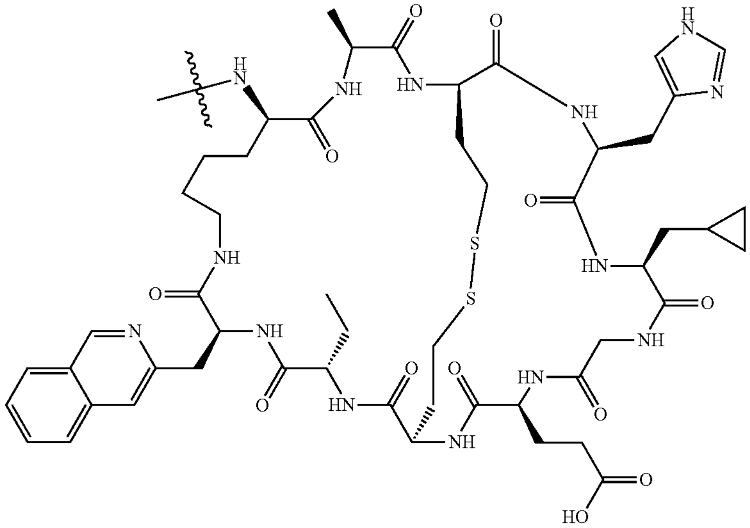 [SMILES: *N[C@@H]1CCCCNC(=O)[C@H](Cc2cc3ccccc3cn2)NC(=O)[C@H](CC)NC(=O)[C@H]2CCSSCC[C@@H](NC(=O)[C@H](C)NC1=O)C(=O)N[C@@H](Cc1c[nH]cn1)C(=O)N[C@@H](CC1CC1)C(=O)NCC(=O)N[C@@H](CCC(=O)O)C(=O)N2] | A-15 |

TABLE A-1-continued
| Exemplary antibody binding moieties. |
| --- |
A-16
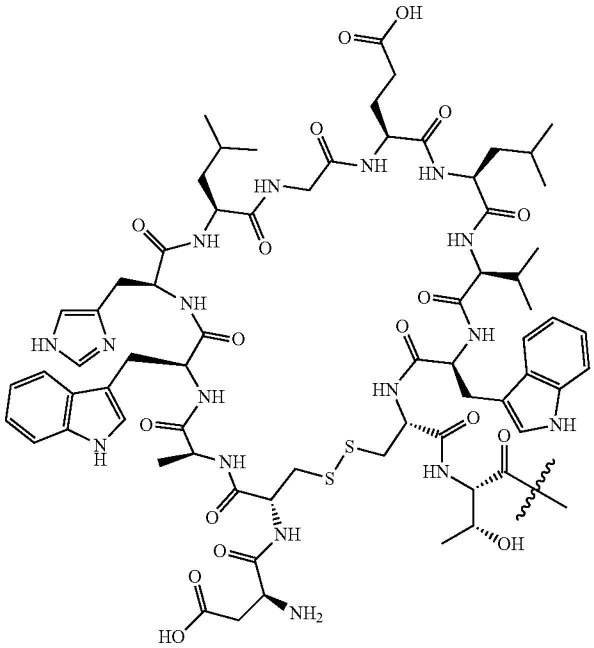 [SMILES: *C(=O)[C@@H](NC(=O)[C@@H]1CSSC[C@H](NC(=O)[C@@H](N)CC(=O)O)C(=O)N[C@@H](C)C(=O)N[C@@H](Cc2c[nH]c3ccccc23)C(=O)N[C@@H](Cc2c[nH]cn2)C(=O)N[C@@H](CC(C)C)C(=O)NCC(=O)N[C@@H](CCC(=O)O)C(=O)N[C@@H](CC(C)C)C(=O)N[C@@H](C(C)C)C(=O)N[C@@H](Cc2c[nH]c3ccccc23)C(=O)N1)[C@@H](C)O]
A-17
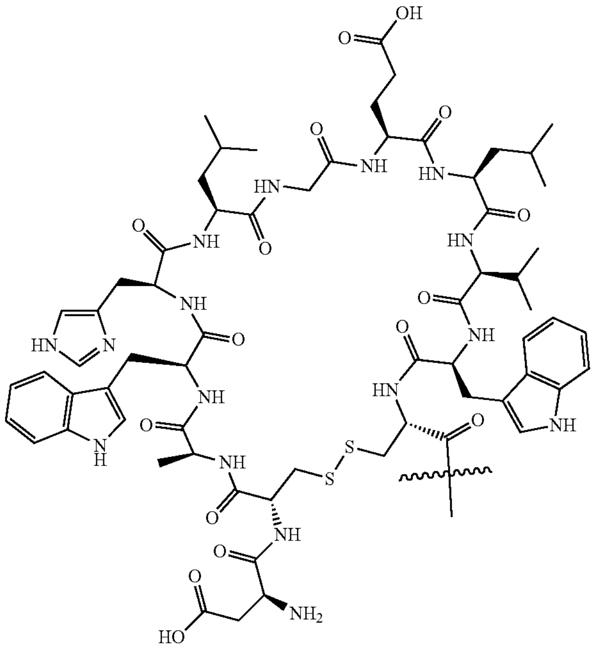 [SMILES: *C(=O)[C@@H]1CSSC[C@H](NC(=O)[C@@H](N)CC(=O)O)C(=O)N[C@@H](C)C(=O)N[C@@H](Cc2c[nH]c3ccccc23)C(=O)N[C@@H](Cc2c[nH]cn2)C(=O)N[C@@H](CC(C)C)C(=O)NCC(=O)N[C@@H](CCC(=O)O)C(=O)N[C@@H](CC(C)C)C(=O)N[C@@H](C(C)C)C(=O)N[C@@H](Cc2c[nH]c3ccccc23)C(=O)N1]

TABLE A-1-continued
| Exemplary antibody binding moieties. |
| --- |
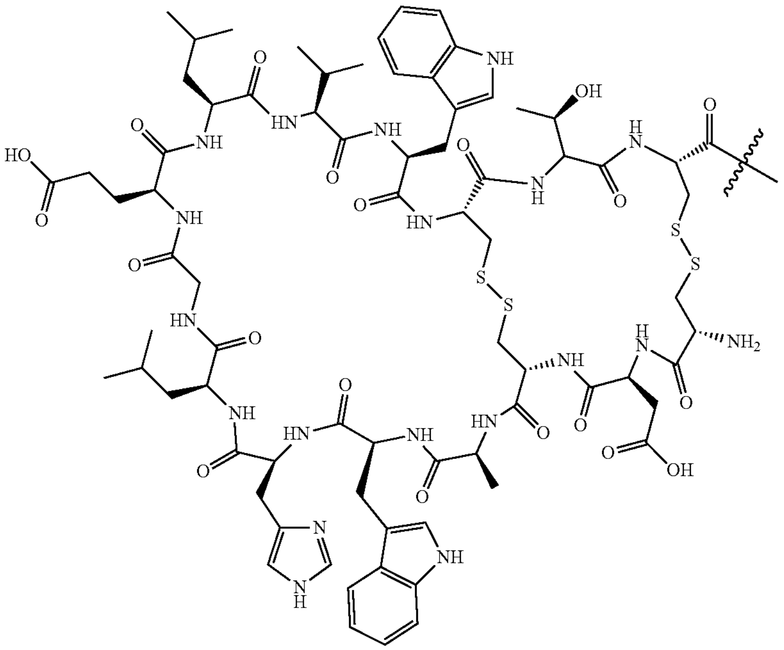 [SMILES: *C(=O)[C@@H]1CSSC[C@H](N)C(=O)N[C@@H](CC(=O)O)C(=O)N[C@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc3c[nH]cn3)NC(=O)[C@H](Cc3c[nH]c4ccccc34)NC(=O)[C@H](C)NC2=O)C(=O)NC([C@@H](C)O)C(=O)N1]
A-18
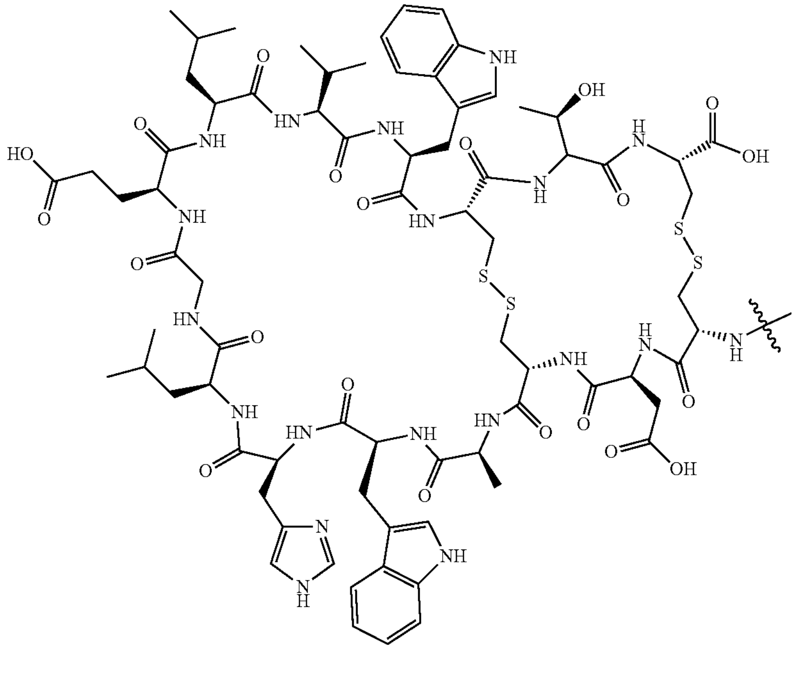 [SMILES: *N[C@H]1CSSC[C@@H](C(=O)O)NC(=O)C([C@@H](C)O)NC(=O)[C@@H]2CSSC[C@H](NC(=O)[C@H](CC(=O)O)NC1=O)C(=O)N[C@@H](C)C(=O)N[C@@H](Cc1c[nH]c3ccccc13)C(=O)N[C@@H](Cc1c[nH]cn1)C(=O)N[C@@H](CC(C)C)C(=O)NCC(=O)N[C@@H](CCC(=O)O)C(=O)N[C@@H](CC(C)C)C(=O)N[C@@H](C(C)C)C(=O)N[C@@H](Cc1c[nH]c3ccccc13)C(=O)N2]
A-19

TABLE A-1-continued
| Exemplary antibody binding moieties. |
| --- |
A-20
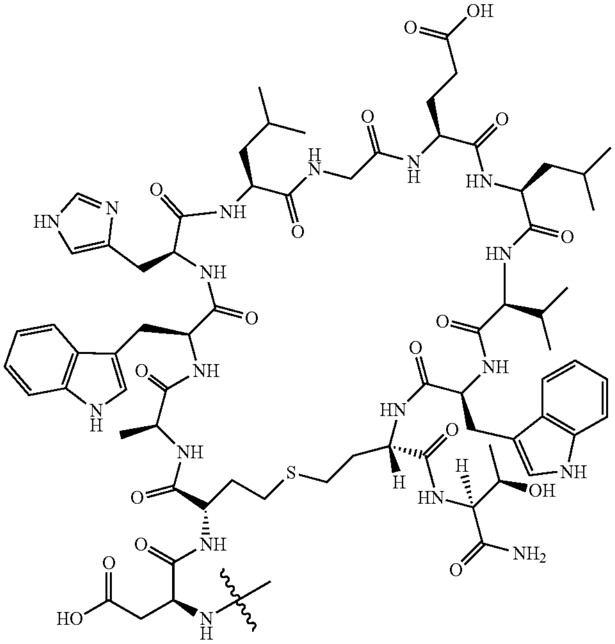
A-21
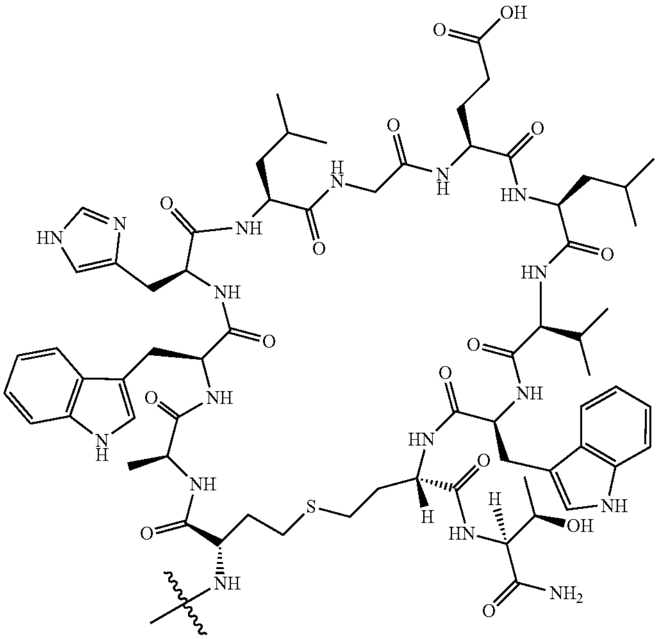

TABLE A-1-continued
| Exemplary antibody binding moieties. |
| --- |
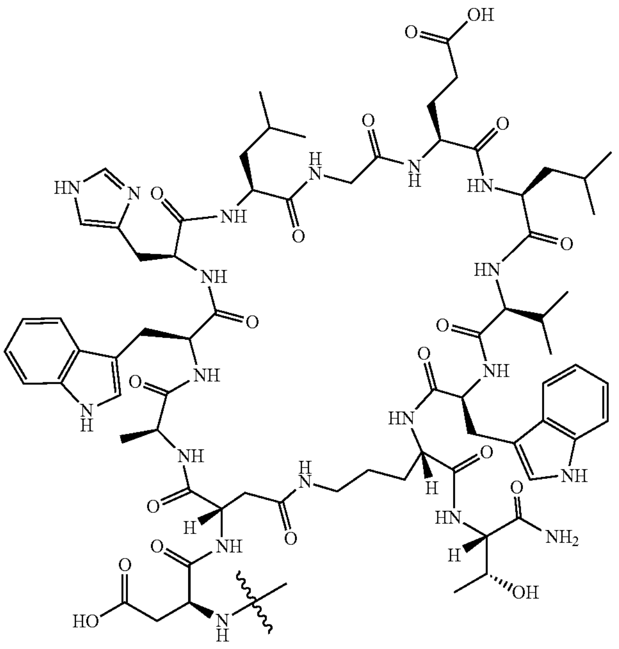 [SMILES: *N[C@@H](CC(=O)O)C(=O)N[C@H]1CC(=O)NCCC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]
A-22
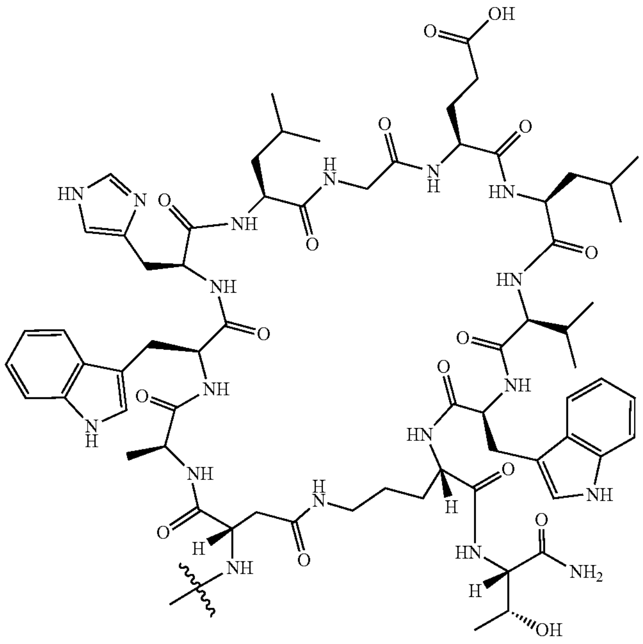 [SMILES: *N[C@H]1CC(=O)NCCC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]
A-23

TABLE A-1-continued
| Exemplary antibody binding moieties. | |
|---|---|
| 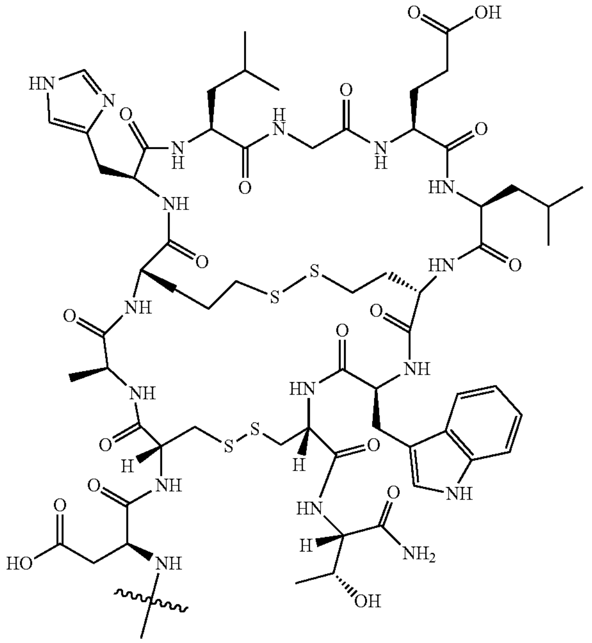 [SMILES: *N[C@@H](CC(=O)O)C(=O)N[C@H]1CSSC[C@@H](C(=O)N[C@H](C(N)=O)[C@@H](C)O)NC(=O)[C@H](Cc2c[nH]c3ccccc23)NC(=O)[C@@H]2CCSSCCC[C@H](NC(=O)[C@H](C)NC1=O)C(=O)N[C@@H](Cc1c[nH]cn1)C(=O)N[C@@H](CC(C)C)C(=O)NCC(=O)N[C@@H](CCC(=O)O)C(=O)N[C@@H](CC(C)C)C(=O)N2] | A-24 |
| 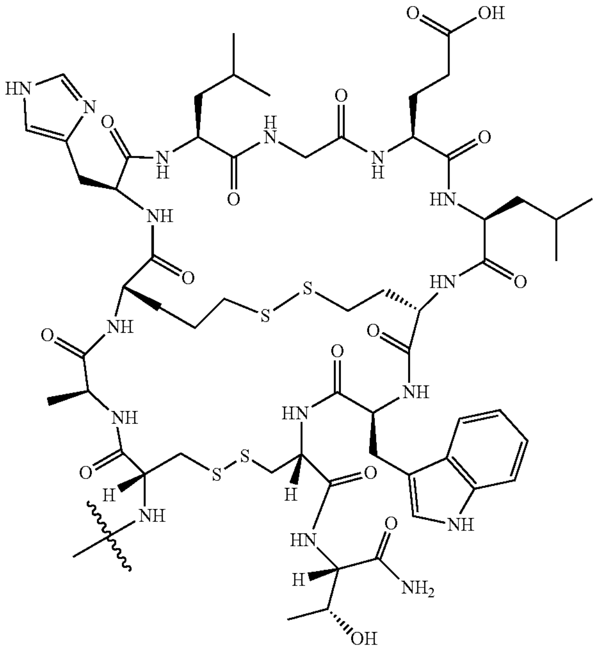 [SMILES: *N[C@H]1CSSC[C@@H](C(=O)N[C@H](C(N)=O)[C@@H](C)O)NC(=O)[C@H](Cc2c[nH]c3ccccc23)NC(=O)[C@@H]2CCSSCCC[C@H](NC(=O)[C@H](C)NC1=O)C(=O)N[C@@H](Cc1c[nH]cn1)C(=O)N[C@@H](CC(C)C)C(=O)NCC(=O)N[C@@H](CCC(=O)O)C(=O)N[C@@H](CC(C)C)C(=O)N2] | A-25 |

TABLE A-1-continued
| Exemplary antibody binding moieties. |
|---|
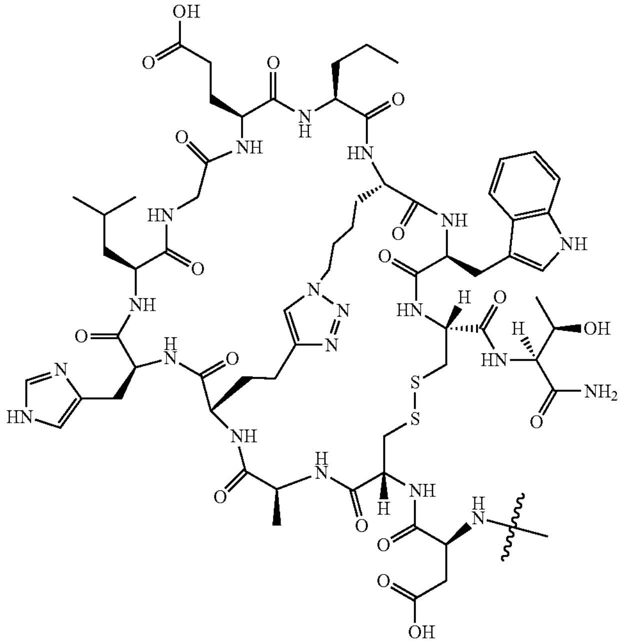 [SMILES: *N[C@@H](CC(=O)O)C(=O)N[C@H]1CSSC[C@@H](C(=O)N[C@H](C(N)=O)[C@@H](C)O)NC(=O)[C@H](Cc2c[nH]c3ccccc23)NC(=O)[C@@H]2CCCCn3cc(nn3)CC[C@H](NC(=O)[C@H](C)NC1=O)C(=O)N[C@@H](Cc1c[nH]cn1)C(=O)N[C@@H](CC(C)C)C(=O)NCC(=O)N[C@@H](CCC(=O)O)C(=O)N[C@@H](CCC)C(=O)N2]
A-26
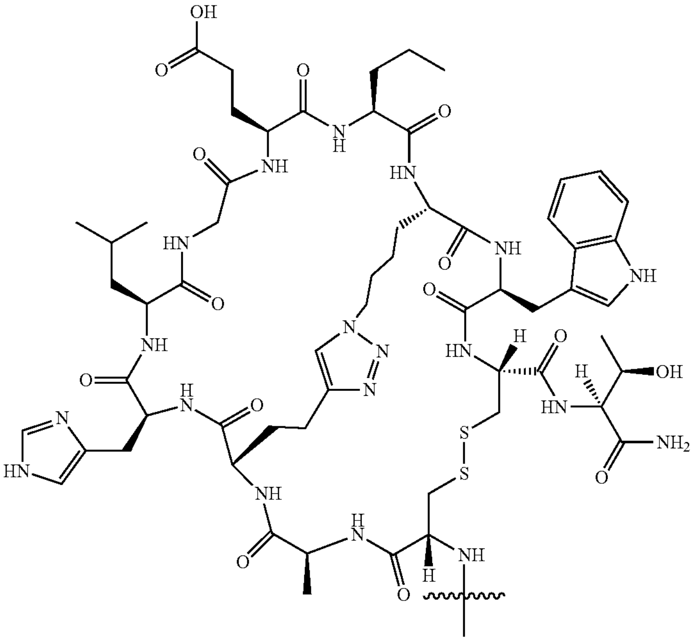 [SMILES: *N[C@H]1CSSC[C@@H](C(=O)N[C@H](C(N)=O)[C@@H](C)O)NC(=O)[C@H](Cc2c[nH]c3ccccc23)NC(=O)[C@@H]2CCCCn3cc(nn3)CC[C@H](NC(=O)[C@H](C)NC1=O)C(=O)N[C@@H](Cc1c[nH]cn1)C(=O)N[C@@H](CC(C)C)C(=O)NCC(=O)N[C@@H](CCC(=O)O)C(=O)N[C@@H](CCC)C(=O)N2]
A-27

TABLE A-1-continued
| Exemplary antibody binding moieties. |
| --- |
A-28
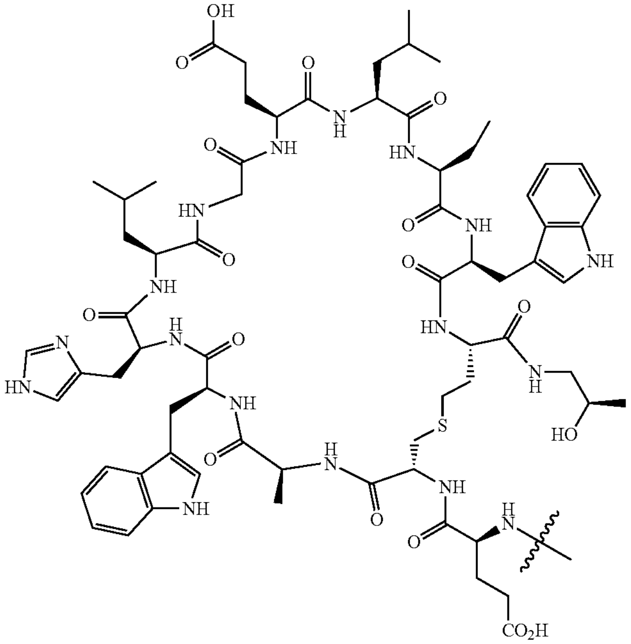 [SMILES: *N[C@@H](CCC(=O)O)C(=O)N[C@H]1CSCC[C@@H](C(=O)NC[C@@H](C)O)NC(=O)[C@H](Cc2c[nH]c3ccccc23)NC(=O)[C@H](CC)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]
A-29
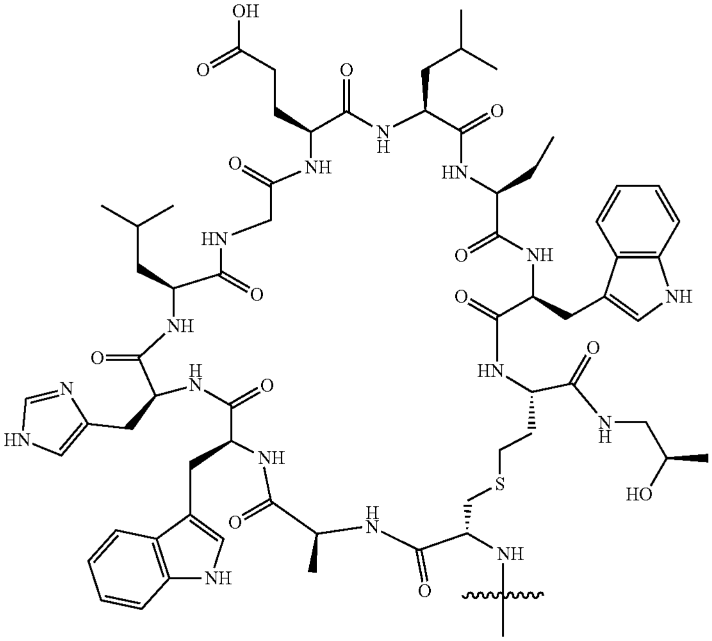 [SMILES: *N[C@H]1CSCC[C@@H](C(=O)NC[C@@H](C)O)NC(=O)[C@H](Cc2c[nH]c3ccccc23)NC(=O)[C@H](CC)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]

TABLE A-1-continued
Exemplary antibody binding moieties.
A-30
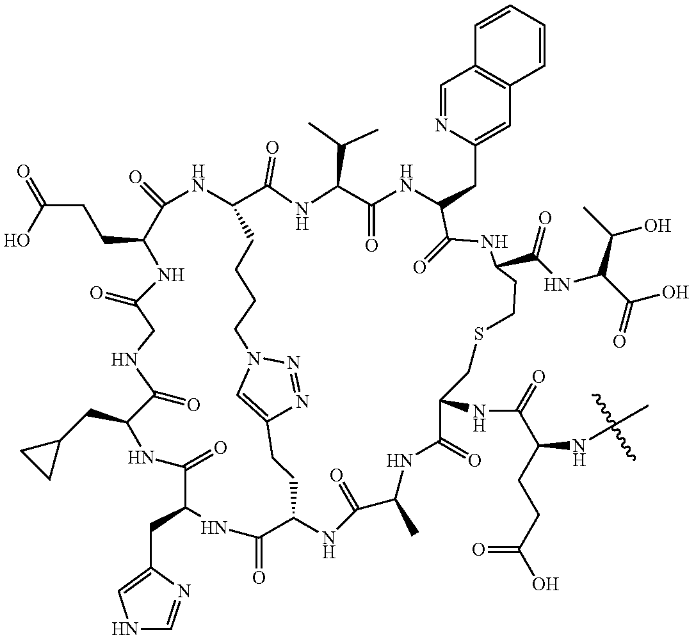
A-31
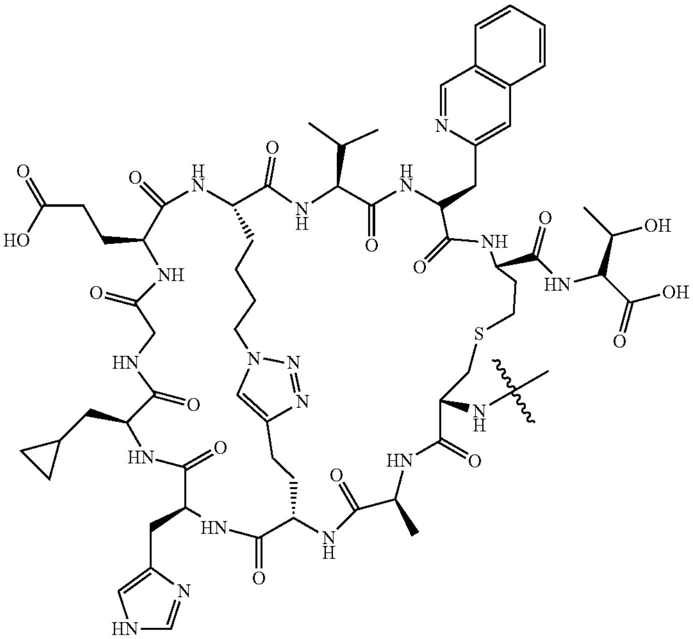

TABLE A-1-continued
| Exemplary antibody binding moieties. |
| --- |
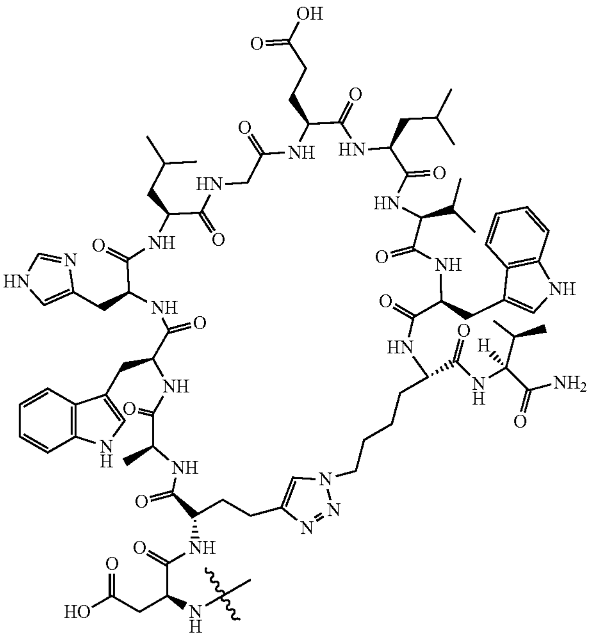
A-32
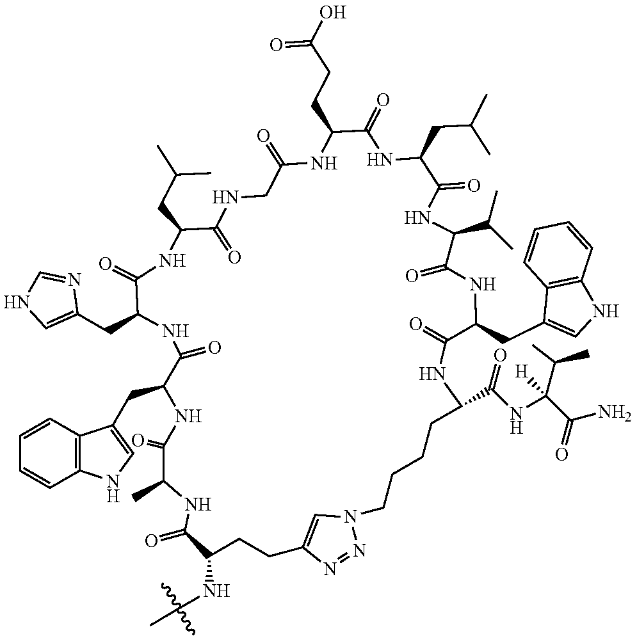
A-33

TABLE A-1-continued
| Exemplary antibody binding moieties. |
| --- |
A-34
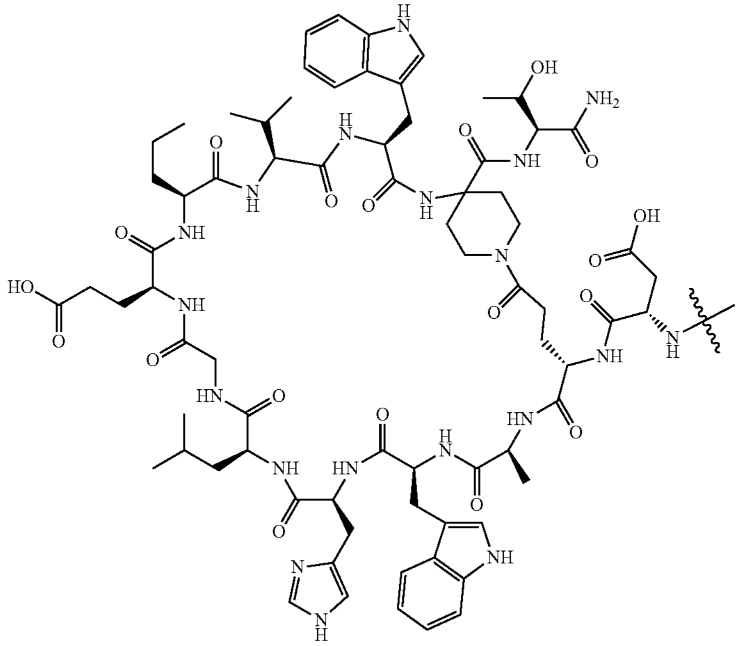 [SMILES: *N[C@@H](CC(=O)O)C(=O)N[C@H]1CCC(=O)N2CCC(C(=O)N[C@H](C(N)=O)C(C)O)(CC2)NC(=O)[C@H](Cc2c[nH]c3ccccc23)NC(=O)[C@H](C(C)C)NC(=O)[C@H](CCC)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]
A-35
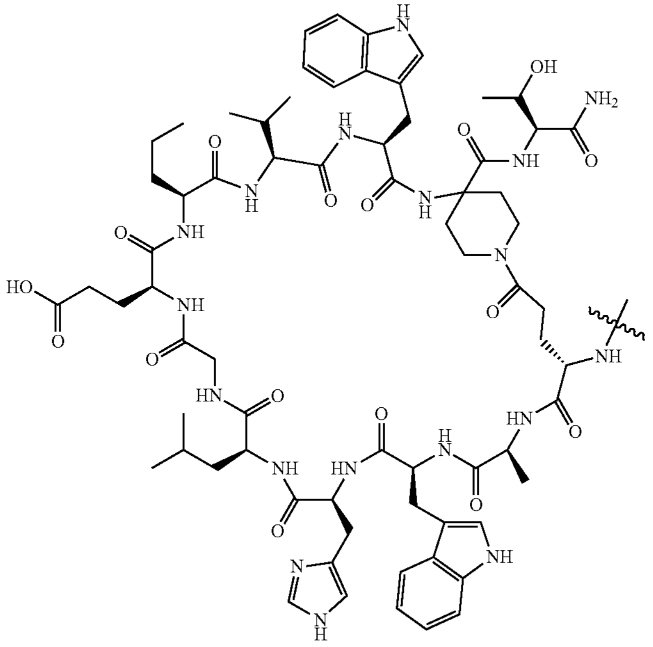 [SMILES: *N[C@H]1CCC(=O)N2CCC(C(=O)N[C@H](C(N)=O)C(C)O)(CC2)NC(=O)[C@H](Cc2c[nH]c3ccccc23)NC(=O)[C@H](C(C)C)NC(=O)[C@H](CCC)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]

TABLE A-1-continued
| Exemplary antibody binding moieties. |
| --- |
A-36
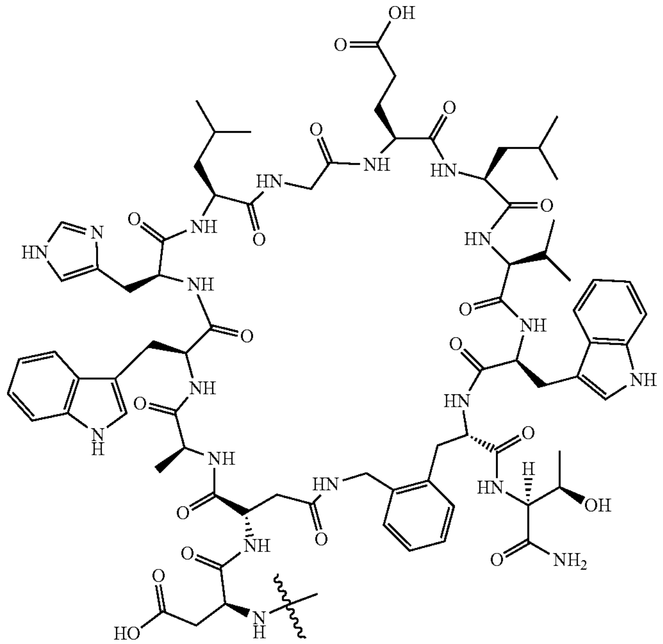
A-37
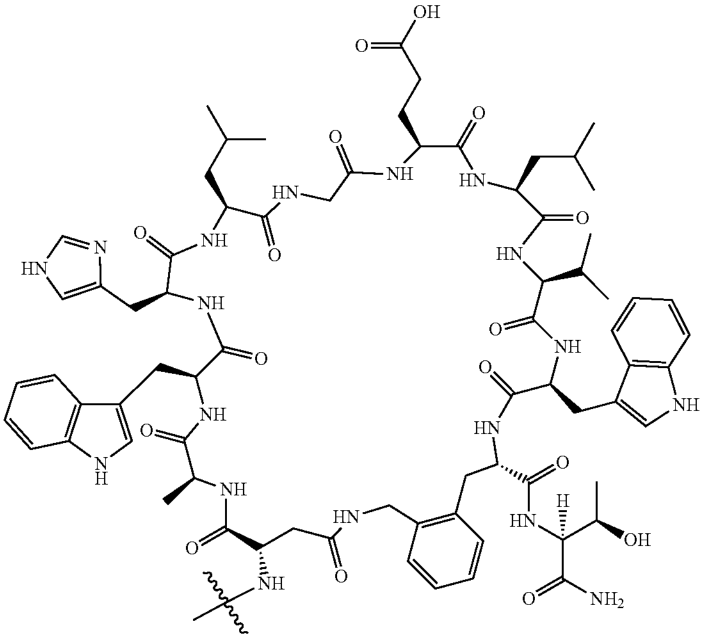

TABLE A-1-continued
| Exemplary antibody binding moieties. |
| --- |
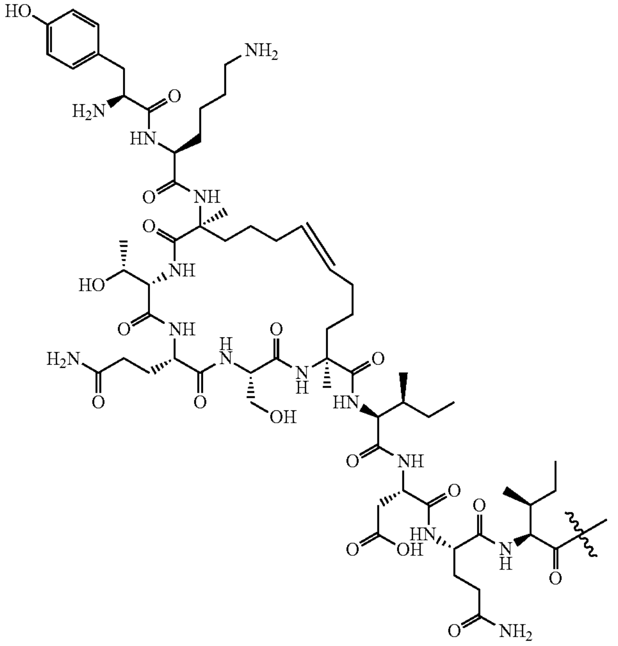 [SMILES: *C(=O)[C@@H](NC(=O)[C@H](CCC(N)=O)NC(=O)[C@H](CC(=O)O)NC(=O)[C@@H](NC(=O)[C@]1(C)CCC/C=C/CCC[C@](C)(NC(=O)[C@H](CCCCN)NC(=O)[C@@H](N)Cc2ccc(O)cc2)C(=O)N[C@@H]([C@@H](C)O)C(=O)N[C@@H](CCC(N)=O)C(=O)N[C@@H](CO)C(=O)N1)[C@@H](C)CC)[C@@H](C)CC]
A-38
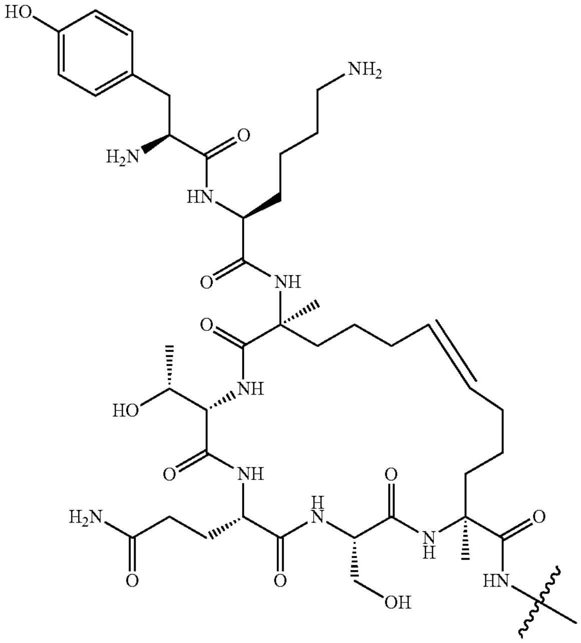 [SMILES: *NC(=O)[C@]1(C)CCC/C=C/CCC[C@](C)(NC(=O)[C@H](CCCCN)NC(=O)[C@@H](N)Cc2ccc(O)cc2)C(=O)N[C@@H]([C@@H](C)O)C(=O)N[C@@H](CCC(N)=O)C(=O)N[C@@H](CO)C(=O)N1]
A-39

TABLE A-1-continued
Exemplary antibody binding moieties.
A-40
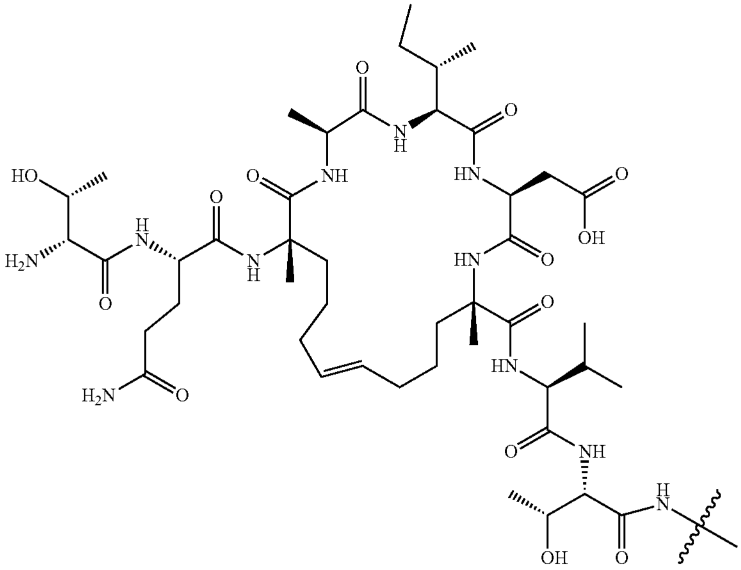 [SMILES: *NC(=O)[C@@H](NC(=O)[C@@H](NC(=O)[C@]1(C)CCC/C=C/CCC[C@](C)(NC(=O)[C@H](CCC(N)=O)NC(=O)[C@H](N)[C@@H](C)O)C(=O)N[C@@H](C)C(=O)N[C@@H]([C@@H](C)CC)C(=O)N[C@@H](CC(=O)O)C(=O)N1)C(C)C)[C@@H](C)O]
A-41
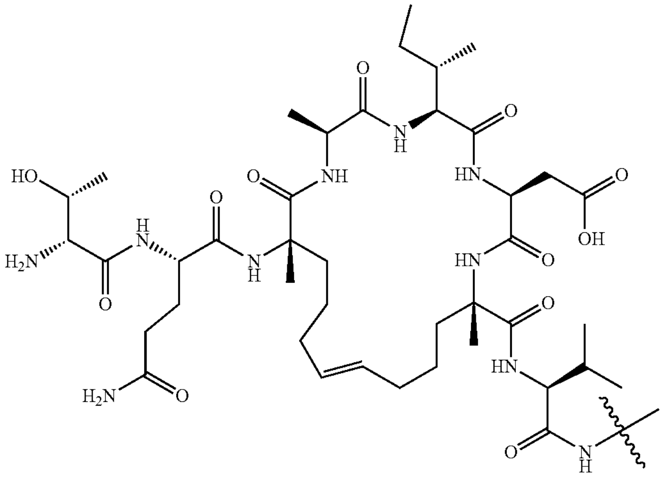 [SMILES: *NC(=O)[C@@H](NC(=O)[C@]1(C)CCC/C=C/CCC[C@](C)(NC(=O)[C@H](CCC(N)=O)NC(=O)[C@H](N)[C@@H](C)O)C(=O)N[C@@H](C)C(=O)N[C@@H]([C@@H](C)CC)C(=O)N[C@@H](CC(=O)O)C(=O)N1)C(C)C]
A-42
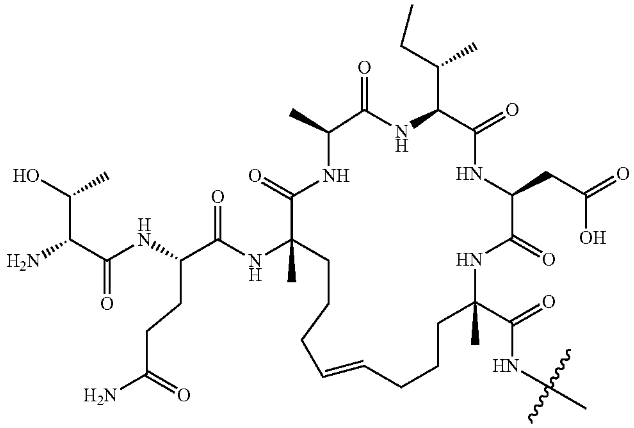 [SMILES: *NC(=O)[C@]1(C)CCC/C=C/CCC[C@](C)(NC(=O)[C@H](CCC(N)=O)NC(=O)[C@H](N)[C@@H](C)O)C(=O)N[C@@H](C)C(=O)N[C@@H]([C@@H](C)CC)C(=O)N[C@@H](CC(=O)O)C(=O)N1]

TABLE A-1-continued
Exemplary antibody binding moieties.
A-43
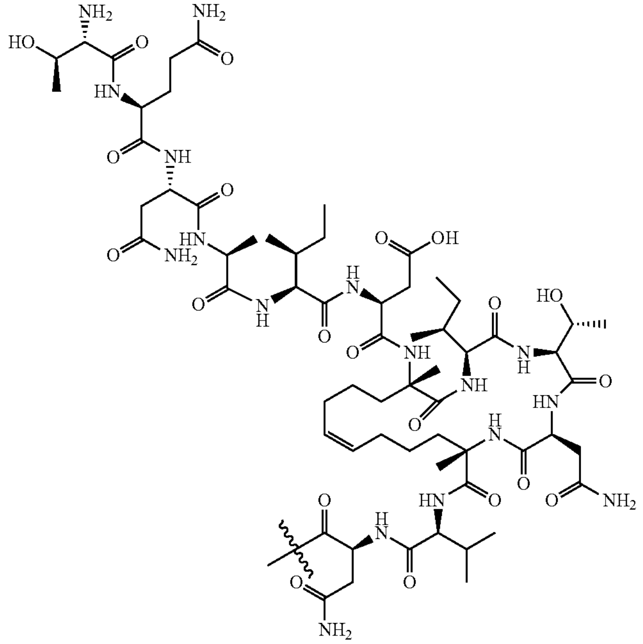 [SMILES: *C(=O)[C@H](CC(N)=O)NC(=O)[C@@H](NC(=O)[C@]1(C)CCC/C=C\CCC[C@](C)(NC(=O)[C@H](CC(=O)O)NC(=O)[C@@H](NC(=O)[C@H](C)NC(=O)[C@H](CC(N)=O)NC(=O)[C@H](CCC(N)=O)NC(=O)[C@@H](N)[C@@H](C)O)[C@@H](C)CC)C(=O)N[C@@H]([C@@H](C)CC)C(=O)N[C@@H]([C@@H](C)O)C(=O)N[C@@H](CC(N)=O)C(=O)N1)C(C)C]
A-44
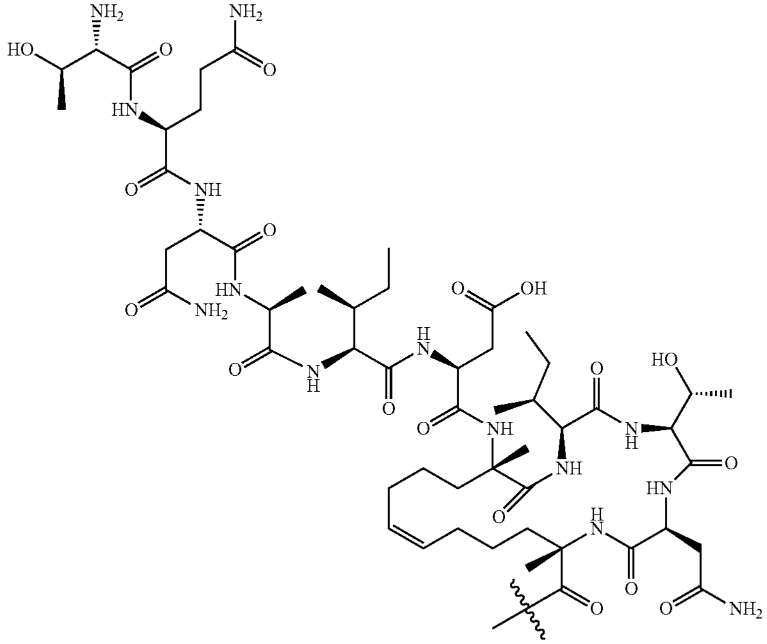 [SMILES: *C(=O)[C@]1(C)CCC/C=C\CCC[C@](C)(NC(=O)[C@H](CC(=O)O)NC(=O)[C@@H](NC(=O)[C@H](C)NC(=O)[C@H](CC(N)=O)NC(=O)[C@H](CCC(N)=O)NC(=O)[C@@H](N)[C@@H](C)O)[C@@H](C)CC)C(=O)N[C@@H]([C@@H](C)CC)C(=O)N[C@@H]([C@@H](C)O)C(=O)N[C@@H](CC(N)=O)C(=O)N1]

TABLE A-1-continued
| Exemplary antibody binding moieties. |
| --- |
A-45
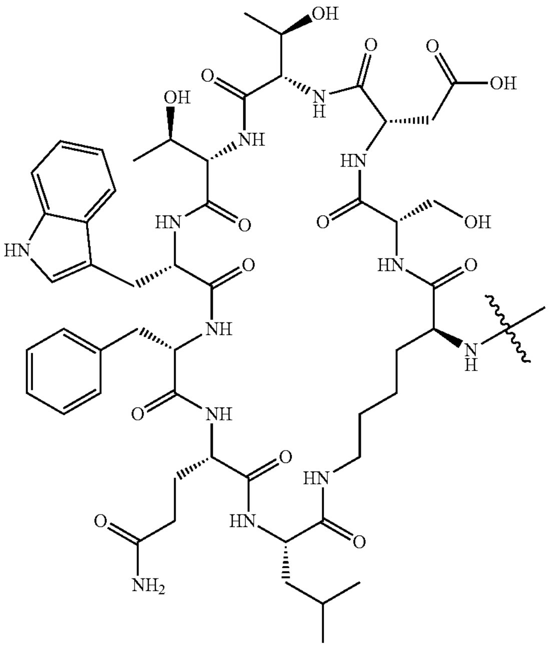 [SMILES: *N[C@H]1CCCCNC(=O)[C@H](CC(C)C)NC(=O)[C@H](CCC(N)=O)NC(=O)[C@H](Cc2ccccc2)NC(=O)[C@H](Cc2c[nH]c3ccccc23)NC(=O)[C@H]([C@@H](C)O)NC(=O)[C@H]([C@@H](C)O)NC(=O)[C@H](CC(=O)O)NC(=O)[C@H](CO)NC1=O]
A-46
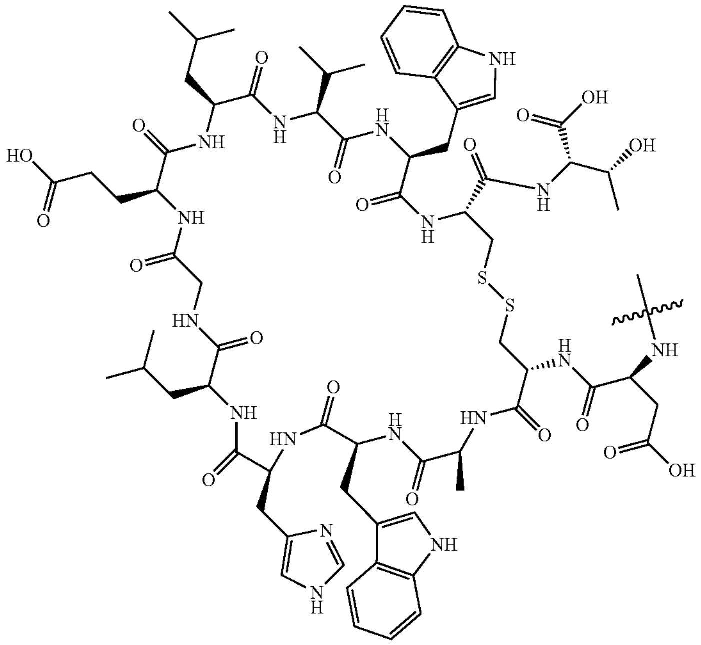 [SMILES: *N[C@@H](CC(=O)O)C(=O)N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]

TABLE A-1-continued
Exemplary antibody binding moieties.
A-47
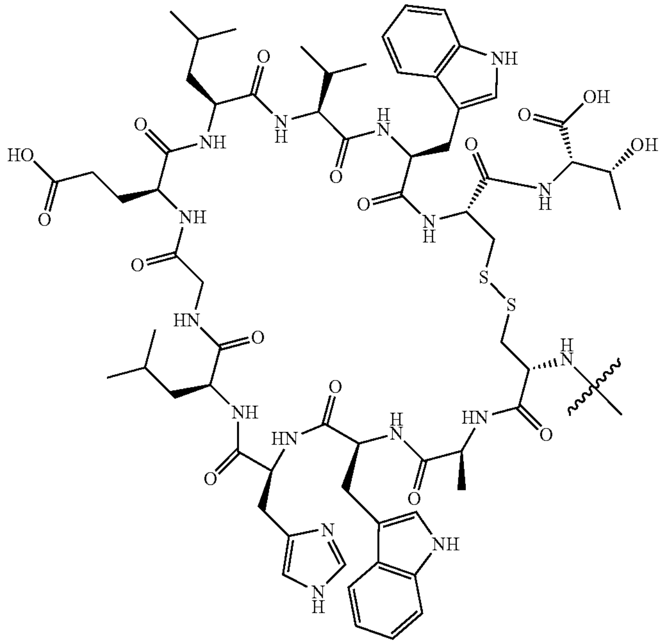 [SMILES: *N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O]
A-48
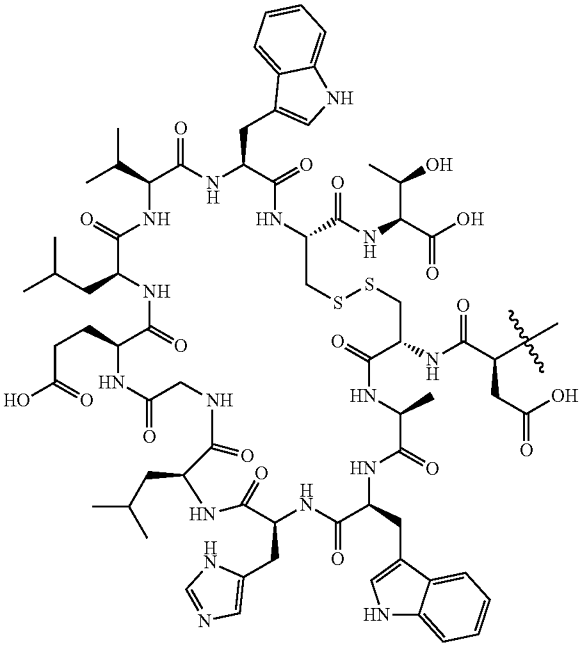 [SMILES: *[C@@H](CC(=O)O)C(=O)N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC1=O]

TABLE A-1-continued

| Exemplary antibody binding moieties. |
| --- |
| 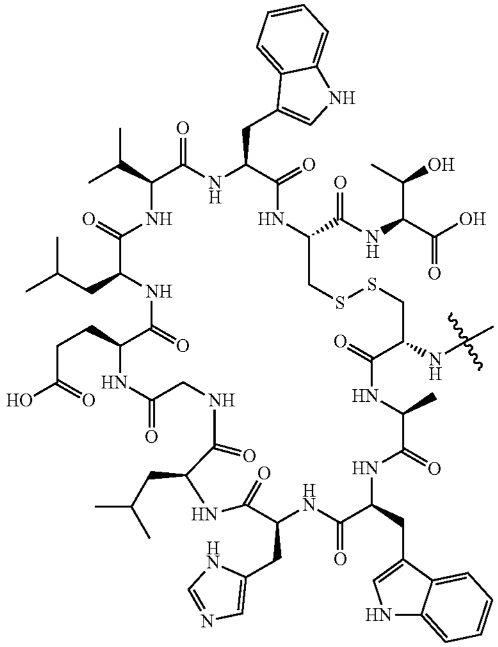 [SMILES: *N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC1=O] A-49 |

In some embodiments, a target binding moiety is an antibody binding moiety described herein. In some embodiments, a protein binding moiety is an antibody binding moiety described herein. In some embodiments, —COOH and/or amino groups of amino acid residues, e.g., those at the C-terminus or N-terminus, is optionally capped. For example, in some embodiments, a —COOH group (e.g., a C-terminus —COOH) is amidated (e.g., converted into $—CON(R')_2$, e.g., —C(O)NHR (e.g., $—C(O)NH_2$)), and in some embodiments, an amino group, e.g. $—NH_2$ (e.g., a N-terminus $—NH_2$) is capped with R'— or R'C(O)— (e.g., in some embodiments, by conversion $—NH_2$ into —NHR' (e.g., —NHC(O)R, (e.g., $—NHC(O)CH_3$))).

In some embodiments, a target binding moiety is or comprises optionally substituted A-1. In some embodiments, a target binding moiety is or comprises optionally substituted A-2. In some embodiments, a target binding moiety is or comprises optionally substituted A-3. In some embodiments, a target binding moiety is or comprises optionally substituted A-4. In some embodiments, a target binding moiety is or comprises optionally substituted A-5. In some embodiments, a target binding moiety is or comprises optionally substituted A-6. In some embodiments, a target binding moiety is or comprises optionally substituted A-7. In some embodiments, a target binding moiety is or comprises optionally substituted A-8. In some embodiments, a target binding moiety is or comprises optionally substituted A-9. In some embodiments, a target binding moiety is or comprises optionally substituted A-10. In some embodiments, a target binding moiety is or comprises optionally substituted A-11. In some embodiments, a target binding moiety is or comprises optionally substituted A-12. In some embodiments, a target binding moiety is or comprises optionally substituted A-13. In some embodiments, a target binding moiety is or comprises optionally substituted A-14. In some embodiments, a target binding moiety is or comprises optionally substituted A-15. In some embodiments, a target binding moiety is or comprises optionally substituted A-16. In some embodiments, a target binding moiety is or comprises optionally substituted A-17. In some embodiments, a target binding moiety is or comprises optionally substituted A-18. In some embodiments, a target binding moiety is or comprises optionally substituted A-19. In some embodiments, a target binding moiety is or comprises optionally substituted A-20. In some embodiments, a target binding moiety is or comprises optionally substituted A-21. In some embodiments, a target binding moiety is or comprises optionally substituted A-22. In some embodiments, a target binding moiety is or comprises optionally substituted A-23. In some embodiments, a target binding moiety is or comprises optionally substituted A-24. In some embodiments, a target binding moiety is or comprises optionally substituted A-25. In some embodiments, a target binding moiety is or comprises optionally substituted A-26. In some embodiments, a target binding moiety is or comprises optionally substituted A-27. In some embodiments, a target binding moiety is or comprises optionally substituted A-28. In some embodiments, a target binding moiety is or comprises optionally substituted A-29. In some embodiments, a target binding moiety is or comprises optionally substituted A-30. In some embodiments, a target binding moiety is or comprises optionally substituted A-31. In some embodiments, a target binding moiety is or comprises optionally substituted A-32. In some embodiments, a target binding moiety is or comprises optionally substituted A-33. In some embodiments, a target binding moiety is or comprises optionally substituted A-34. In some embodiments, a target binding moiety is or comprises optionally substituted A-35. In some embodiments, a target binding moiety is or comprises optionally substituted A-36. In some embodiments, a target binding moiety is or comprises optionally substituted A-37. In some embodiments, a target binding moiety is or comprises optionally substituted A-38. In some embodiments, a target binding moiety is or comprises optionally substituted A-39.

In some embodiments, a target binding moiety is or comprises optionally substituted A-40. In some embodiments, a target binding moiety is or comprises optionally substituted A-41. In some embodiments, a target binding moiety is or comprises optionally substituted A-42. In some embodiments, a target binding moiety is or comprises optionally substituted A-43. In some embodiments, a target binding moiety is or comprises optionally substituted A-44. In some embodiments, a target binding moiety is or comprises optionally substituted A-45. In some embodiments, a target binding moiety is or comprises optionally substituted A-46. In some embodiments, a target binding moiety is or comprises optionally substituted A-47. In some embodiments, a target binding moiety is or comprises optionally substituted A-48. In some embodiments, a target binding moiety is or comprises optionally substituted A-49. In some embodiments, such a target binding moiety is an antibody binding moiety. In some embodiments, such a target binding moiety is a universal antibody binding moiety.

In some embodiments, a target binding moiety is A-1. In some embodiments, a target binding moiety is A-2. In some embodiments, a target binding moiety is A-3. In some embodiments, a target binding moiety is A-4. In some embodiments, a target binding moiety is A-5. In some embodiments, a target binding moiety is A-6. In some embodiments, a target binding moiety is A-7. In some embodiments, a target binding moiety is A-8. In some embodiments, a target binding moiety is A-9. In some embodiments, a target binding moiety is A-10. In some embodiments, a target binding moiety is A-11. In some embodiments, a target binding moiety is A-12. In some embodiments, a target binding moiety is A-13. In some embodiments, a target binding moiety is A-14. In some embodiments, a target binding moiety is A-15. In some embodiments, a target binding moiety is A-16. In some embodiments, a target binding moiety is A-17. In some embodiments, a target binding moiety is A-18. In some embodiments, a target binding moiety is A-19. In some embodiments, a target binding moiety is A-20. In some embodiments, a target binding moiety is A-21. In some embodiments, a target binding moiety is A-22. In some embodiments, a target binding moiety is A-23. In some embodiments, a target binding moiety is A-24. In some embodiments, a target binding moiety is A-25. In some embodiments, a target binding moiety is A-26. In some embodiments, a target binding moiety is A-27. In some embodiments, a target binding moiety is A-28. In some embodiments, a target binding moiety is A-29. In some embodiments, a target binding moiety is A-30. In some embodiments, a target binding moiety is A-31. In some embodiments, a target binding moiety is A-32. In some embodiments, a target binding moiety is A-33. In some embodiments, a target binding moiety is A-34. In some embodiments, a target binding moiety is A-35. In some embodiments, a target binding moiety is A-36. In some embodiments, a target binding moiety is A-37. In some embodiments, a target binding moiety is A-38. In some embodiments, a target binding moiety is A-39. In some embodiments, a target binding moiety is A-40. In some embodiments, a target binding moiety is A-41. In some embodiments, a target binding moiety is A-42. In some embodiments, a target binding moiety is A-43. In some embodiments, a target binding moiety is A-44. In some embodiments, a target binding moiety is A-45. In some embodiments, a target binding moiety is A-46. In some embodiments, a target binding moiety is A-47. In some embodiments, a target binding moiety is A-48. In some embodiments, a target binding moiety is A-49. In some embodiments, such a target binding moiety is an antibody binding moiety. In some embodiments, such a target binding moiety is a universal antibody binding moiety.

In some embodiments, a target binding moiety, e.g., a protein binding moiety (e.g., an antibody binding moiety (e.g., a universal antibody binding moiety)) comprises a peptide unit, and is connected to a linker moiety through the C-terminus of the peptide unit. In some embodiments, it is connected to a linker moiety through the N-terminus of the peptide unit. In some embodiments, it is connected to a linker through a side chain group of the peptide unit. In some embodiments, an antibody binding moiety, e.g., a universal antibody binding moiety comprises a peptide unit, and is connected to a target binding moiety optionally through a linker moiety through the C-terminus of the peptide unit. In some embodiments, a target binding moiety, e.g., a protein binding moiety (e.g., an antibody binding moiety (e.g., a universal antibody binding moiety)) comprises a peptide unit, and is connected to a target binding moiety optionally through a linker moiety through the N-terminus of the peptide unit. In some embodiments, In some embodiments, a target binding moiety, e.g., a protein binding moiety (e.g., an antibody binding moiety (e.g., a universal antibody binding moiety)) comprises a peptide unit, and is connected to a target binding moiety optionally through a linker moiety through a side chain of the peptide unit.

In some embodiments, a target binding moiety is or comprises (DCAWHLGELVWCT)-, wherein 1-5 (e.g., 1, 2, 3, 4, or 5) amino acid residues may be independently and optionally replaced with another amino acid residue, 1-5 (e.g., 1, 2, 3, 4, or 5) amino acid residues may be independently and optionally deleted, and/or 1-5 (e.g., 1, 2, 3, 4, or 5) amino acid residues may be independently and optionally inserted. In some embodiments, it is connected to the rest of a molecule through its N-terminus. In some embodiments, it is connected to the rest of a molecule through its C-terminus. In some embodiments, it is connected to the rest of a molecule through a side chain of an amino acid residue (e.g., various X residues as described in the present disclosure). In some embodiments, two cysteine residues form a disulfide bond. In some embodiments, a target binding moiety is or comprises

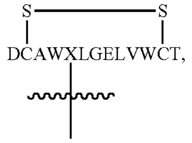

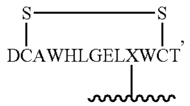

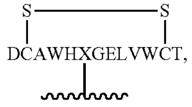

or

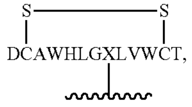

wherein X is an amino acid residue bonded to the rest of a compound or agent, and wherein 1-5 (e.g., 1, 2, 3, 4, or 5) amino acid residues may be independently and optionally replaced with another amino acid residue, 1-5 (e.g., 1, 2, 3, 4, or 5) amino acid residues may be independently and optionally deleted, and/or 1-5 (e.g., 1, 2, 3, 4, or 5) amino acid residues may be independently and optionally inserted. In some embodiments, the total number of replacement, deletion and insertion is no more than 10 (e.g., 0, or no more than 1, 2, 3, 4, 5, 6, 7, 8, 9, or 10). In some embodiments, the total number is 0. In some embodiments, the total number is no more than 1. In some embodiments, the total number is no more than 2. In some embodiments, the total number is no more than 3. In some embodiments, the total number is no more than 4. In some embodiments, the total number is no more than 5. In some embodiments, the total number is no more than 6. In some embodiments, the total number is no more than 7. In some embodiments, the total number is no more than 8. In some embodiments, the total number is no more than 9. In some embodiments, the total number is no more than 10. In some embodiments, there are no insertions. In some embodiments, there are no deletions. In some embodiments, there are no replacements. In some embodiments, a target binding moiety is or comprises

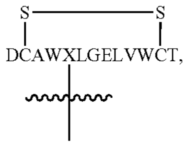

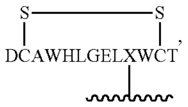

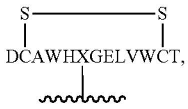

or

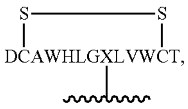

wherein X is an amino acid residue bonded to the rest of a compound or agent. In some embodiments, X is —N(R')—CH(–)—C(O)—. In some embodiments, X is —N(R')—CH(-$L^{LG1}$-)-C(O)—. In some embodiments, X is —N(R')—CH(-$L^{LG1}$-$L^{LG2}$-)—C(O)—. In some embodiments, X is —N(R')—CH(-$L^{LG1}$-$L^{LG2}$-$L^{LG3}$-)—C(O)—. In some embodiments, X is —N(R')—CH(-$L^{LG1}$-$L^{LG2}$-$L^{LG3}$-$L^{LG4}$-)—C(O)—. In some embodiments, a target binding moiety is or comprises

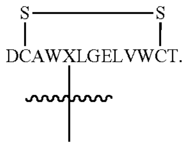

In some embodiments, a target binding moiety is or comprises

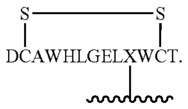

In some embodiments, a target binding moiety is or comprises

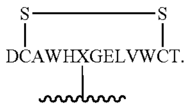

In some embodiments, a target binding moiety is or comprises

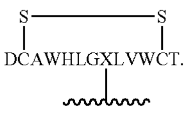

In some embodiments, X is a residue of

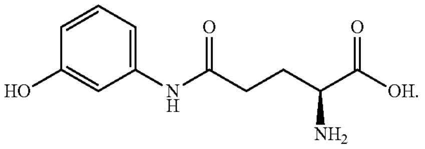 [SMILES: N[C@@H](CCC(=O)Nc1cccc(O)c1)C(=O)O]

In some embodiments, X is a residue of

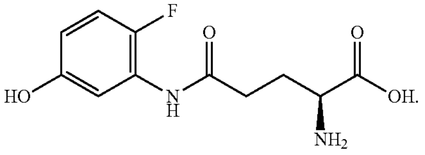 [SMILES: N[C@@H](CCC(=O)Nc1cc(O)ccc1F)C(=O)O]

In some embodiments, X is a residue of

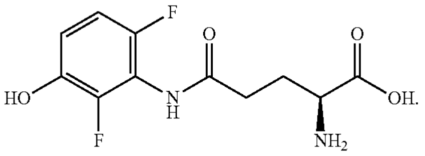 [SMILES: N[C@@H](CCC(=O)Nc1c(F)ccc(O)c1F)C(=O)O]

In some embodiments, X is a residue of

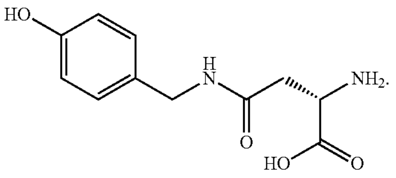 [SMILES: N[C@@H](CC(=O)NCc1ccc(O)cc1)C(=O)O]

In some embodiments, X is a residue of

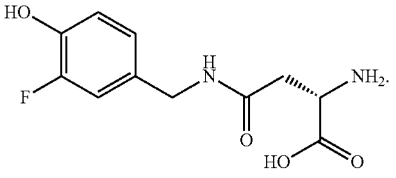 [SMILES: N[C@@H](CC(=O)NCc1ccc(O)c(F)c1)C(=O)O]

In some embodiments, X is a residue of

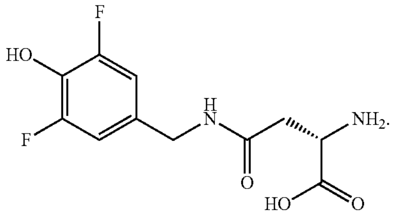 [SMILES: N[C@@H](CC(=O)NCc1cc(F)c(O)c(F)c1)C(=O)O]

In some embodiments, X is a residue of

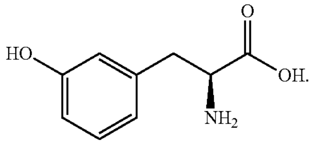

In some embodiments, X is a residue of

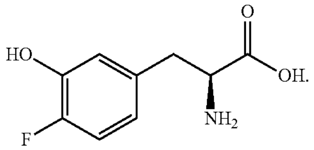

In some embodiments, X is a residue of

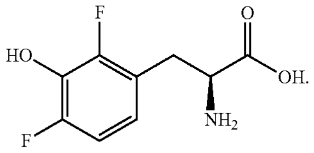

In some embodiments, X is K. In some embodiments, X is D. In some embodiments, X is a residue of Dab. In some embodiments, X is E. In some embodiments, X is a residue of

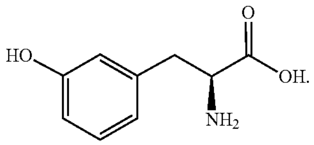 [SMILES: N[C@@H](Cc1cccc(O)c1)C(=O)O]

In some embodiments, the present disclosure provides an amino acid having the structure of

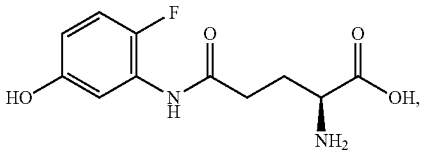

-continued

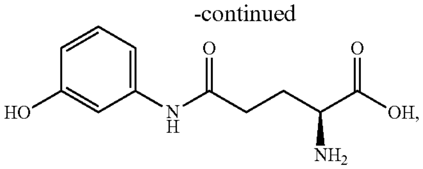

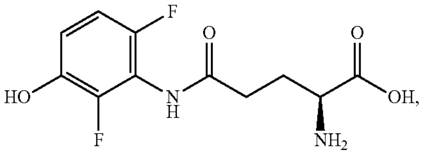

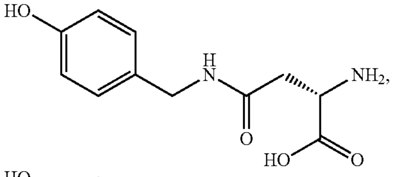

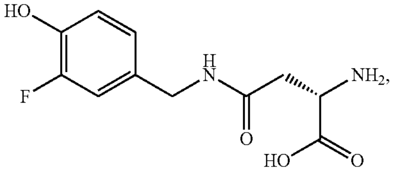

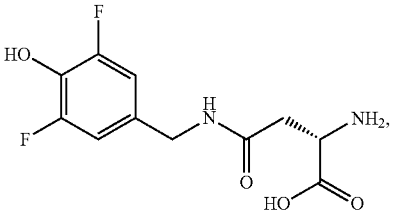

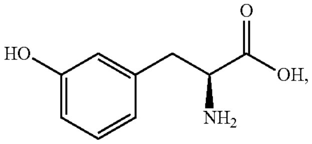

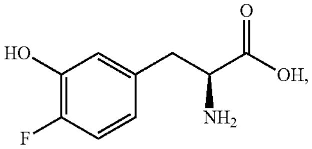 [SMILES: N[C@@H](Cc1ccc(F)c(O)c1)C(=O)O]

or

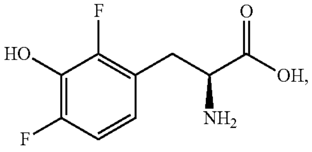 [SMILES: N[C@@H](Cc1ccc(F)c(O)c1F)C(=O)O]

or a salt thereof, or an ester thereof, or an activated ester thereof, or a stereoisomer thereof, or an ester or an activated ester of a stereoisomer. In some embodiments, such target binding moieties are antibody binding moieties.

In some embodiments, an antibody binding moiety, e.g., a universal antibody binding moiety, is or comprises a small molecule entity, with a molecular weight of, e.g., less than 10000, 9000, 8000, 7000, 6000, 5000, 4000, 3000, 2000, 1500, 1000, etc. Suitable such antibody binding moieties include small molecule Fc binder moieties, e.g., those described in U.S. Pat. No. 9,745,339, US 201/30131321, etc. In some embodiments, an antibody binding moiety is of such a structure that its corresponding compound is a compound described in U.S. Pat. No. 9,745,339 or US 2013/0131321, the compounds of each of which are independently incorporated herein by reference. In some embodiments, an antibody binding moiety ABT is of such a structure that H-ABT is a compound described in U.S. Pat. No. 9,745,339 or US 2013/0131321, the compounds of each of which are independently incorporated herein by reference. In some embodiments, such a compound can bind to an antibody. In some embodiments, such a compound can bind to Fc region of an antibody.

In some embodiments, a target binding moiety is or comprises optionally substituted

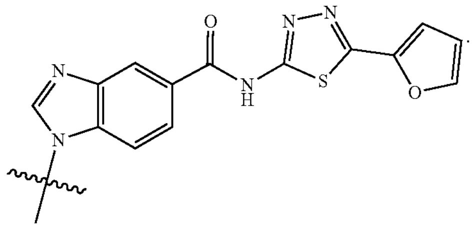 [SMILES: *n1cnc2cc(C(=O)Nc3nnc(-c4ccco4)s3)ccc21]

In some embodiments, a target binding moiety is or comprises

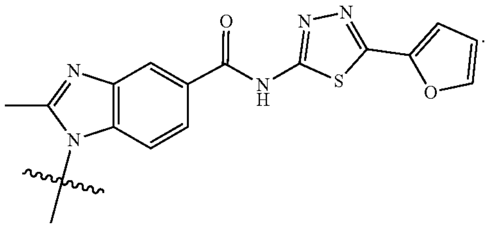 [SMILES: *n1c(C)nc2cc(C(=O)Nc3nnc(-c4ccco4)s3)ccc21]

In some embodiments, a target binding moiety is or comprises optionally substituted

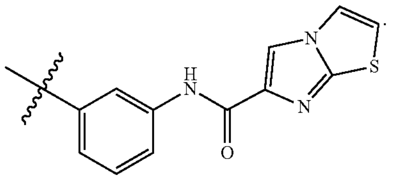 [SMILES: *c1cccc(NC(=O)c2cn3ccsc3n2)c1]

In some embodiments, a target binding moiety is or comprises

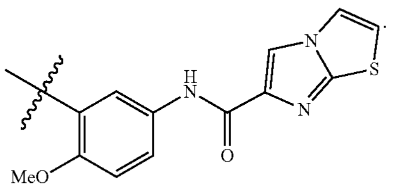 [SMILES: *c1cc(NC(=O)c2cn3ccsc3n2)ccc1OC]

In some embodiments, a target binding moiety is or comprises

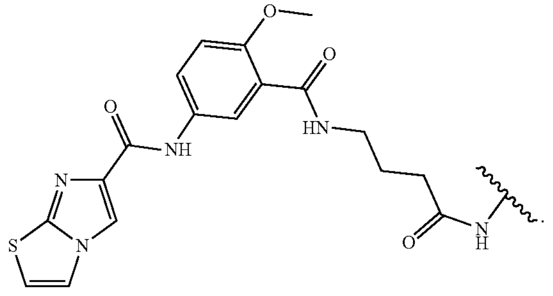 [SMILES: *NC(=O)CCCNC(=O)c1cc(NC(=O)c2cn3ccsc3n2)ccc1OC]

In some embodiments, a target binding moiety is or comprises optionally substituted

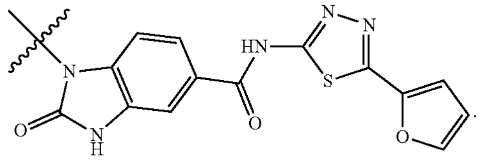 [SMILES: *n1c(=O)[nH]c2cc(C(=O)Nc3nnc(-c4ccco4)s3)ccc21]

In some embodiments, a target binding moiety is or comprises

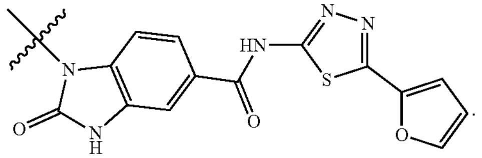 [SMILES: *n1c(=O)[nH]c2cc(C(=O)Nc3nnc(-c4ccco4)s3)ccc21]

In some embodiments, a target binding moiety is or comprises optionally substituted

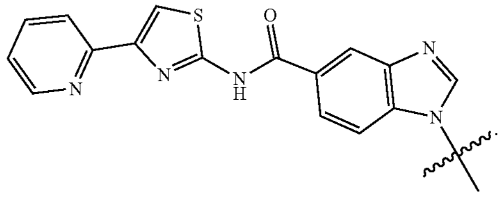 [SMILES: *n1cnc2cc(C(=O)Nc3nc(-c4ccccn4)cs3)ccc21]

In some embodiments, a target binding moiety is or comprises

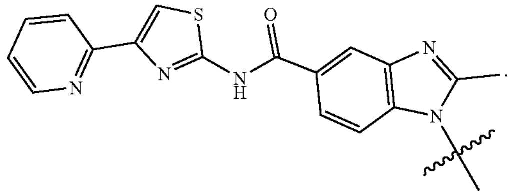 [SMILES: *n1c(C)nc2cc(C(=O)Nc3nc(-c4ccccn4)cs3)ccc21]

In some embodiments, target binding moiety is or comprises

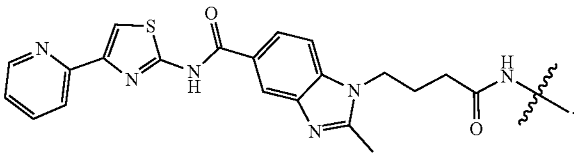 [SMILES: *NC(=O)CCCn1c(C)nc2cc(C(=O)Nc3nc(-c4ccccn4)cs3)ccc21]

In some embodiments, a target binding moiety is or comprises

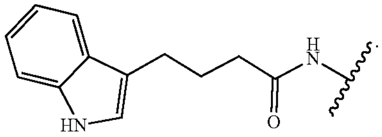 [SMILES: *NC(=O)CCCc1c[nH]c2ccccc12]

In some embodiments, target binding moiety is or comprises optionally substituted

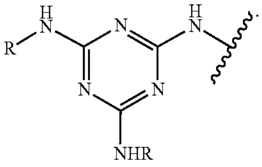

In some embodiments, target binding moiety is or comprises optionally substituted

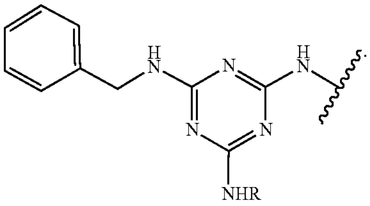

In some embodiments, target binding moiety is or comprises

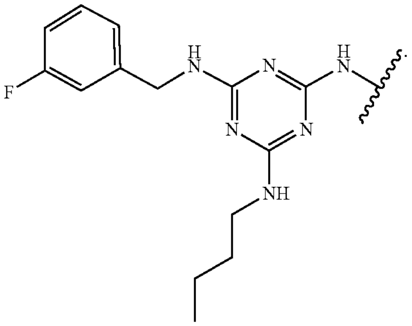 [SMILES: *Nc1nc(NCCCC)nc(NCc2cccc(F)c2)n1]

In some embodiments, a target binding moiety is or comprises optionally substituted

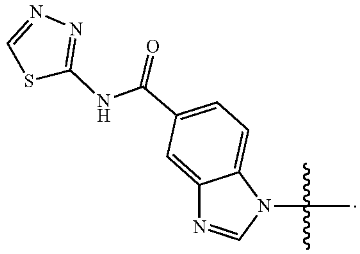 [SMILES: *n1cnc2cc(C(=O)Nc3nncs3)ccc21]

In some embodiments, a target binding moiety is or comprises

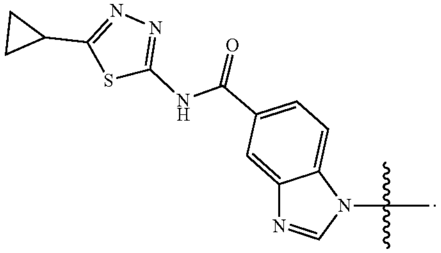 [SMILES: *n1cnc2cc(C(=O)Nc3nnc(C4CC4)s3)ccc21]

In some embodiments, a target binding moiety is or comprises

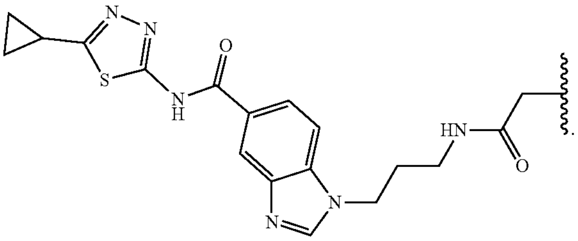 [SMILES: *CC(=O)NCCCn1cnc2cc(C(=O)Nc3nnc(C4CC4)s3)ccc21]

In some embodiments, a target binding moiety is or comprises optionally substituted

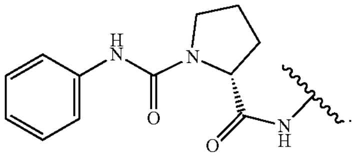 [SMILES: *NC(=O)[C@H]1CCCN1C(=O)Nc1ccccc1]

In some embodiments, a target binding moiety is or comprises

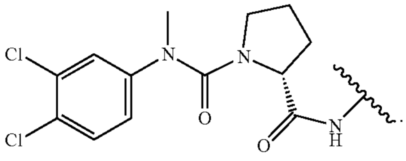 [SMILES: *NC(=O)[C@H]1CCCN1C(=O)N(C)c1ccc(Cl)c(Cl)c1]

In some embodiments, a target binding moiety is or comprises optionally substituted

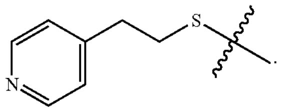 [SMILES: *SCCc1ccncc1]

In some embodiments, a target binding moiety is or comprises

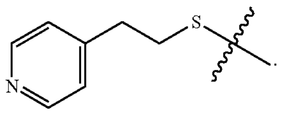 [SMILES: *SCCc1ccncc1]

In some embodiments, such target binding moieties are antibody binding moieties.

In some embodiments, target binding moiety is or comprises

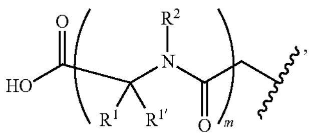

wherein each variable is independently as described herein. In some embodiments, m is 4 to 13. In some embodiments, a target binding moiety is or comprises

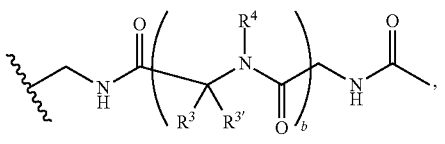

wherein b is 1-20, and each other variable is independently as described herein. In some embodiments, b is 4-13. In some embodiments, a target binding moiety, e.g., $R^c$-(Xaa)z-, is or comprises

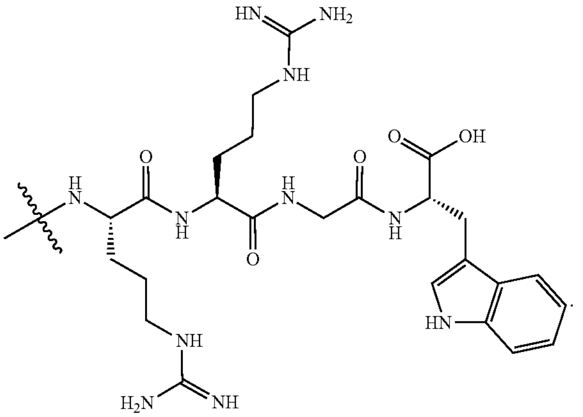 [SMILES: *N[C@@H](CCCNC(=N)N)C(=O)N[C@@H](CCCNC(=N)N)C(=O)NCC(=O)N[C@@H](Cc1c[nH]c2ccccc12)C(=O)O]

In some embodiments, a target binding moiety, e.g., $R^C$-(Xaa)z-, is or comprises

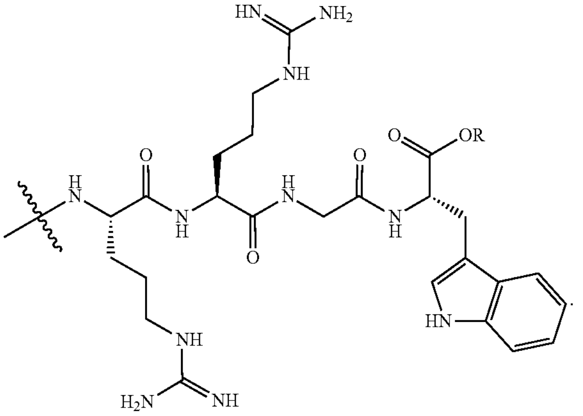

In some embodiments, a target binding moiety, e.g., $R^c$-(Xaa)z-, is or comprises

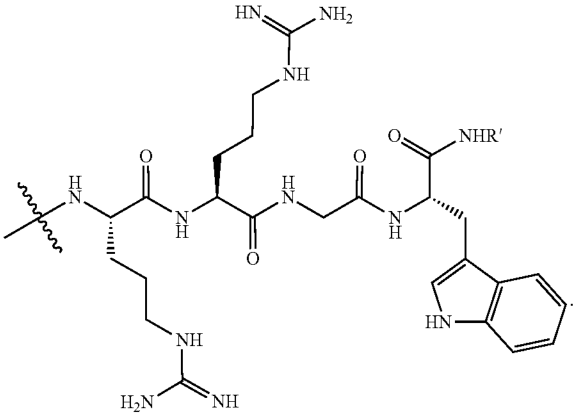

In some embodiments, a target binding moiety, e.g., $R^c$-(Xaa)z-, is or comprises

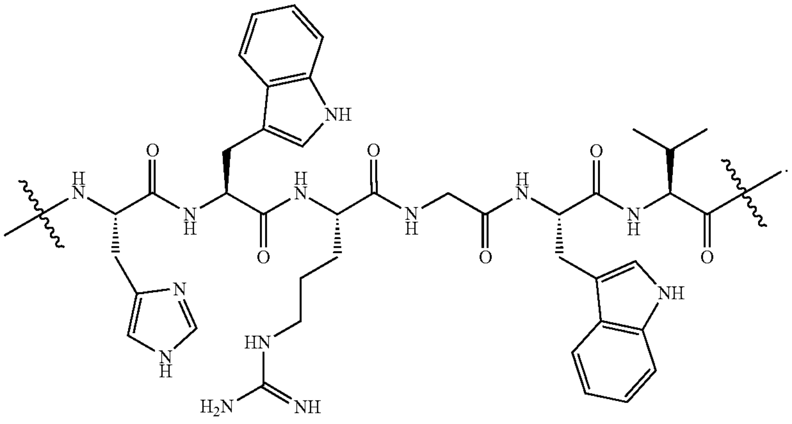 [SMILES: *N[C@@H](Cc1c[nH]cn1)C(=O)N[C@@H](Cc1c[nH]c2ccccc12)C(=O)N[C@@H](CCCNC(=N)N)C(=O)NCC(=O)N[C@@H](Cc1c[nH]c2ccccc12)C(=O)N[C@H](C(*)=O)C(C)C]
In some embodiments, a target binding moiety, e.g., $R^c$-(Xaa)z-, is or comprises
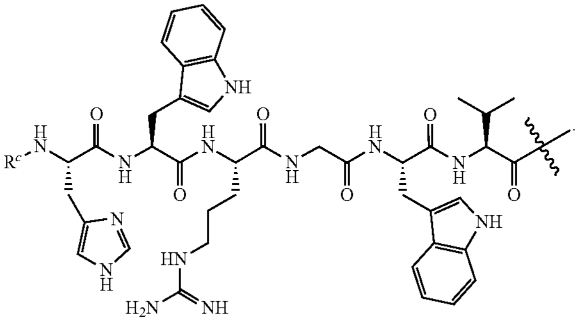
In some embodiments, a target binding moiety, e.g., $R^c$-(Xaa)z-, is or comprises
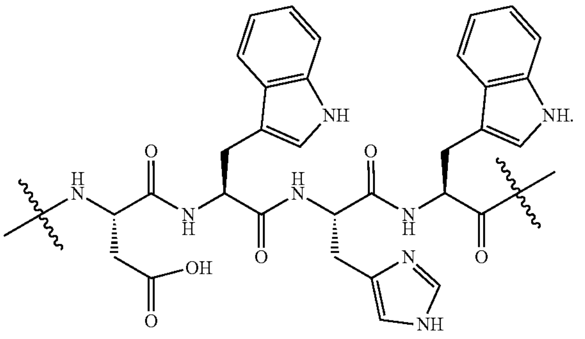
In some embodiment a target binding moiety, e.g., $R^c$-(Xaa) z-, is or comprises
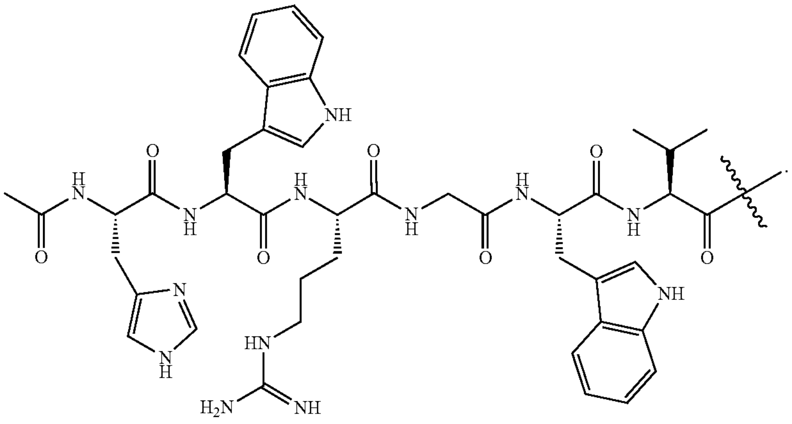 [SMILES: *C(=O)[C@@H](NC(=O)[C@H](Cc1c[nH]c2ccccc12)NC(=O)CNC(=O)[C@H](CCCNC(=N)N)NC(=O)[C@H](Cc1c[nH]c2ccccc12)NC(=O)[C@H](Cc1c[nH]cn1)NC(C)=O)C(C)C]
In some embodiments, a target binding moiety, e.g., $R^c$-(Xaa)z-, is or comprises

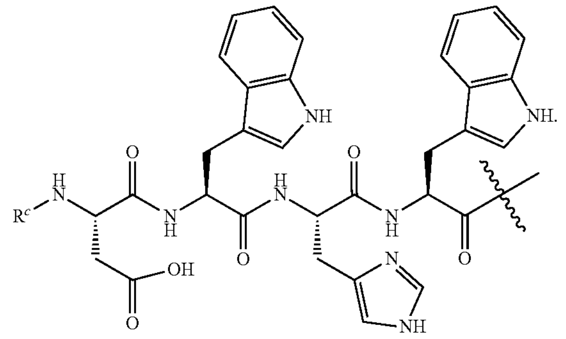

In some embodiments, a target binding moiety, e.g., $R^c$-(Xaa)z-, is or comprises

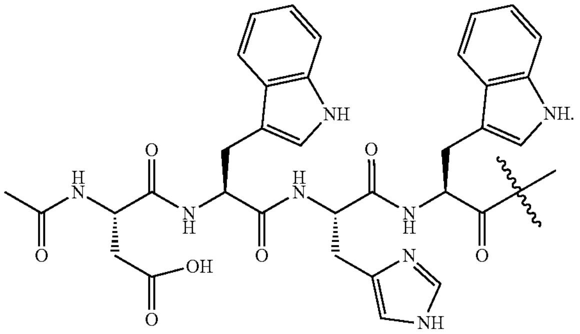 [SMILES: *C(=O)[C@H](Cc1c[nH]c2ccccc12)NC(=O)[C@H](Cc1c[nH]cn1)NC(=O)[C@H](Cc1c[nH]c2ccccc12)NC(=O)[C@H](CC(=O)O)NC(C)=O]

In some embodiments, a target binding moiety, e.g., $R^c$-(Xaa)z-, is or comprises

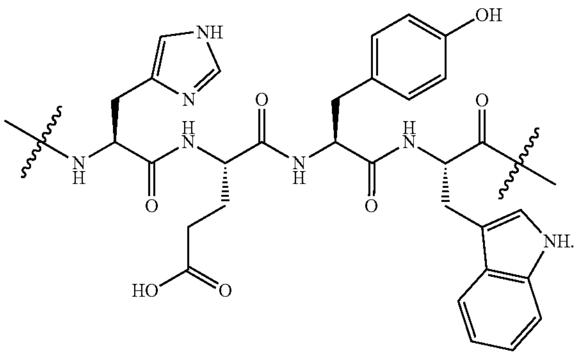 [SMILES: *N[C@@H](Cc1c[nH]cn1)C(=O)N[C@@H](CCC(=O)O)C(=O)N[C@@H](Cc1ccc(O)cc1)C(=O)N[C@@H](Cc1c[nH]c2ccccc12)C(*)=O]

In some embodiments, a target binding moiety, e.g., $R^c$-(Xaa)z-, is or comprises

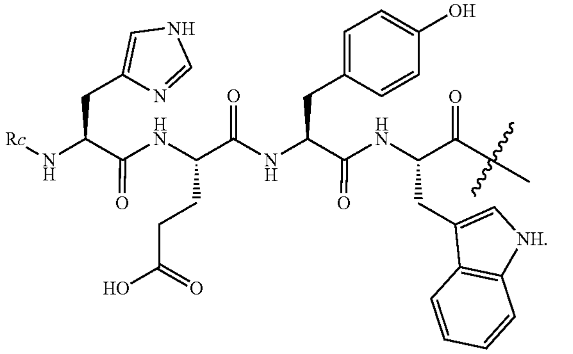

In some embodiments, a target binding moiety, e.g., $R^c$-(Xaa)z-, is or comprises

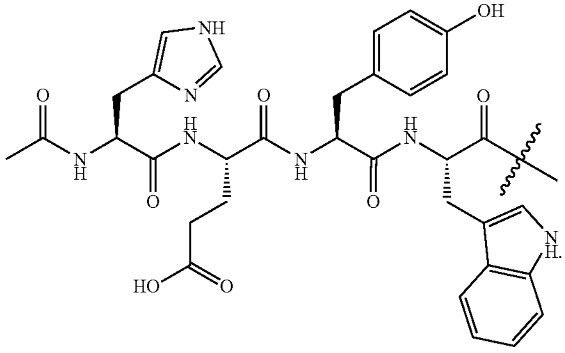 [SMILES: *C(=O)[C@H](Cc1c[nH]c2ccccc12)NC(=O)[C@H](Cc1ccc(O)cc1)NC(=O)[C@H](CCC(=O)O)NC(=O)[C@H](Cc1c[nH]cn1)NC(C)=O]

In some embodiments, a target binding moiety, e.g., $R^c$-(Xaa)z-, is or comprises

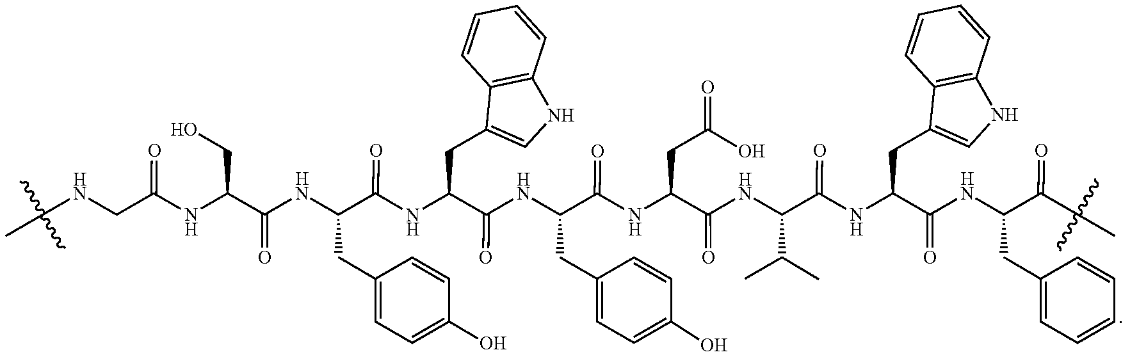 [SMILES: *NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(*)=O)C(C)C]
In some embodiments, a target binding moiety, e.g., $R^c$-(Xaa)z-, is or comprises
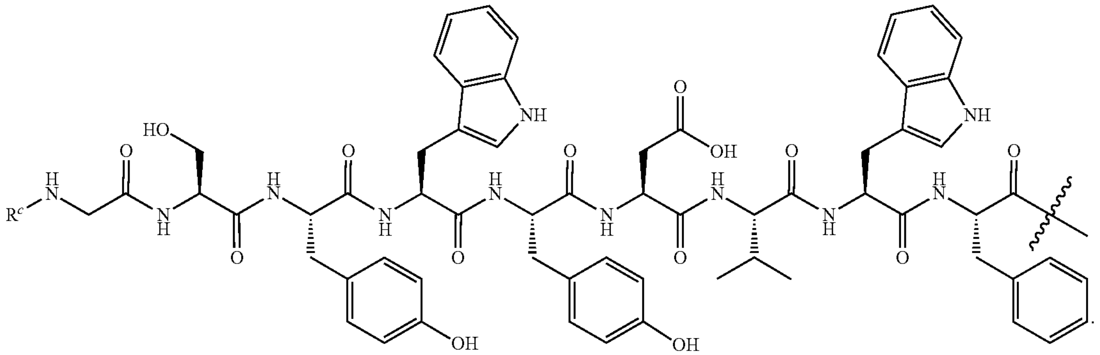
In some embodiments, a target binding moiety, e.g., $R^c$-(Xaa)z-, is or comprises
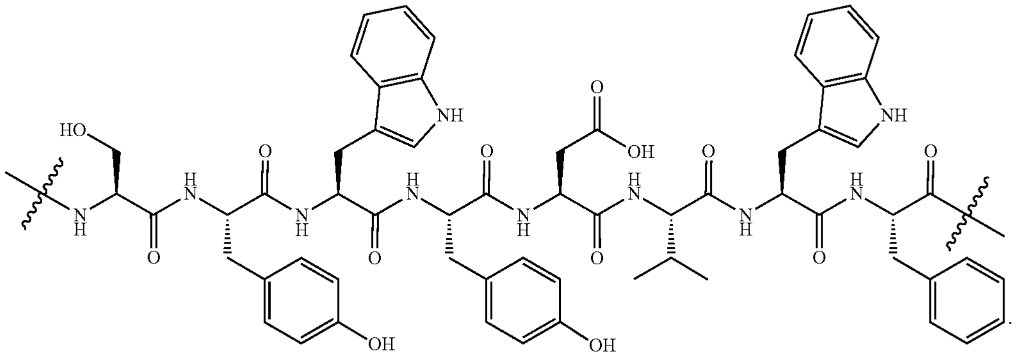 [SMILES: *N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(*)=O)C(C)C]
In some embodiments, a target binding moiety, e.g., $R^c$-(Xaa)z-, is or comprises

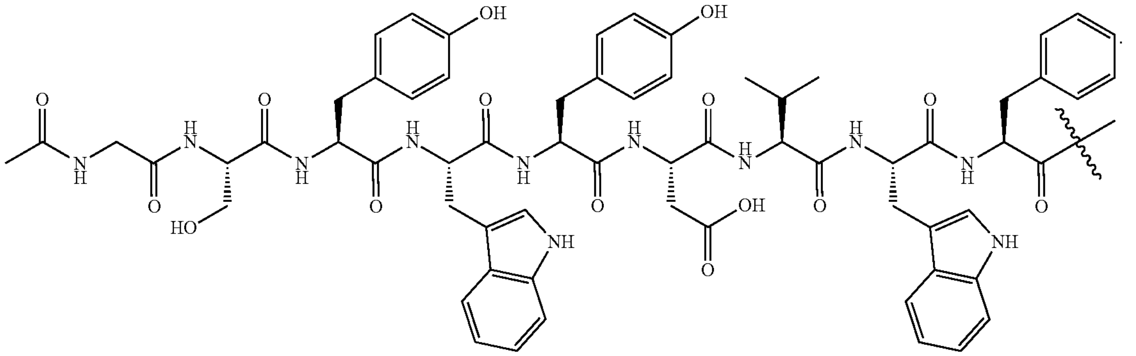 [SMILES: *C(=O)[C@H](Cc1ccccc1)NC(=O)[C@H](Cc1c[nH]c2ccccc12)NC(=O)[C@@H](NC(=O)[C@H](CC(=O)O)NC(=O)[C@H](Cc1ccc(O)cc1)NC(=O)[C@H](Cc1c[nH]c2ccccc12)NC(=O)[C@H](Cc1ccc(O)cc1)NC(=O)[C@H](CO)NC(=O)CNC(C)=O)C(C)C]

In some embodiments, a target binding moiety, e.g., $R^c$-(Xaa)z-, is or comprises

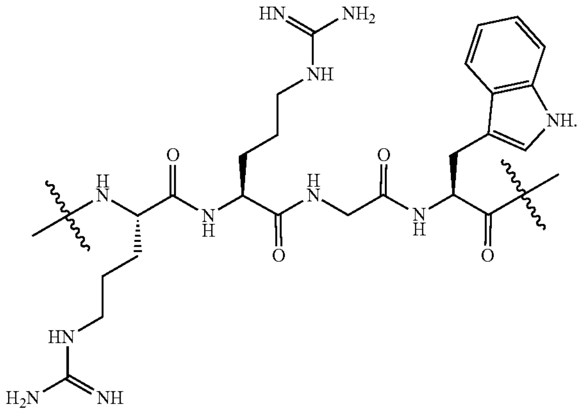 [SMILES: *N[C@@H](CCCNC(=N)N)C(=O)N[C@@H](CCCNC(=N)N)C(=O)NCC(=O)N[C@@H](Cc1c[nH]c2ccccc12)C(*)=O]

In some embodiments, a target binding moiety, e.g., $R^c$-(Xaa)z-, is or comprises

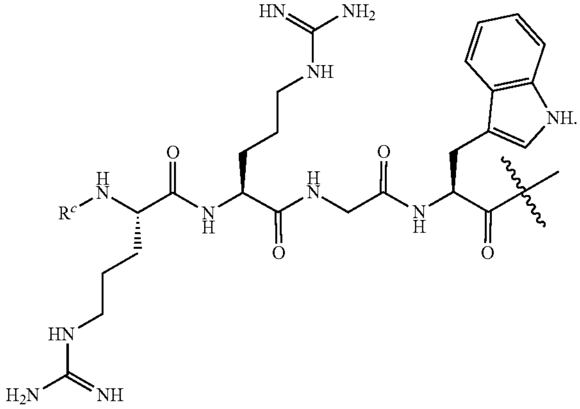

In some embodiments, a target binding moiety, e.g., $R^c$-(Xaa)z-, is or comprises

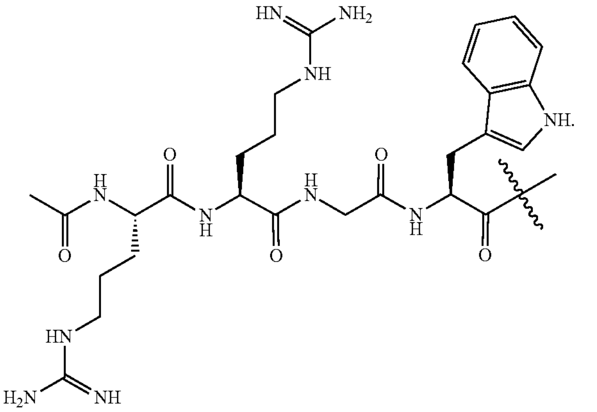 [SMILES: *C(=O)[C@H](Cc1c[nH]c2ccccc12)NC(=O)CNC(=O)[C@H](CCCNC(=N)N)NC(=O)[C@H](CCCNC(=N)N)NC(C)=O]

In some embodiments, —NH— is bonded to a $R^c$ group. In some embodiments, $R^c$ is R—C(O)—. In some embodiments, $R^c$ is $CH_3C(O)$—. In some embodiments, such target binding moieties are antibody binding moieties.

In some embodiments, a target binding moiety, e.g.,

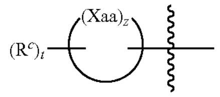

or $R^c$-(Xaa)z-, is or comprises
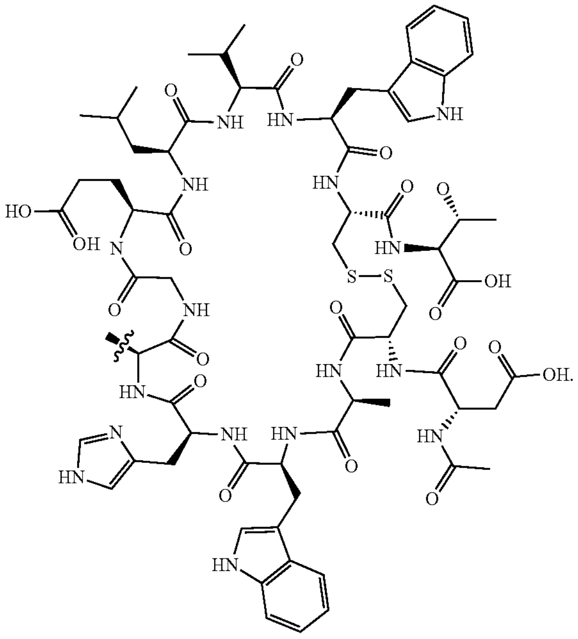
In some embodiments, a target binding moiety, e.g.,
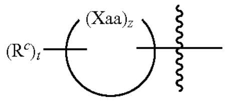
or $R^c$-(Xaa)z-, is or comprises
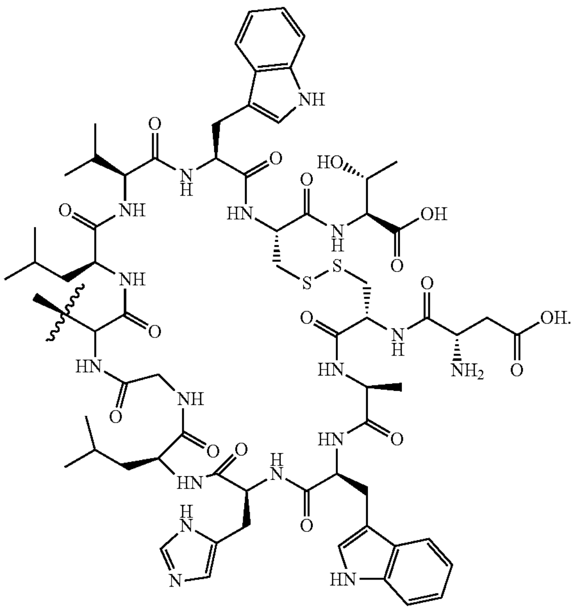 [SMILES: *C1NC(=O)CNC(=O)[C@H](CC(C)C)NC(=O)[C@H](Cc2cnc[nH]2)NC(=O)[C@H](Cc2c[nH]c3ccccc23)NC(=O)[C@H](C)NC(=O)[C@@H](NC(=O)[C@@H](N)CC(=O)O)CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC1=O]
In some embodiments, a target binding moiety, e.g.,
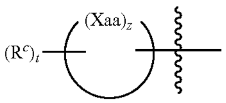
or $R^c$-(Xaa)z-, is or comprises
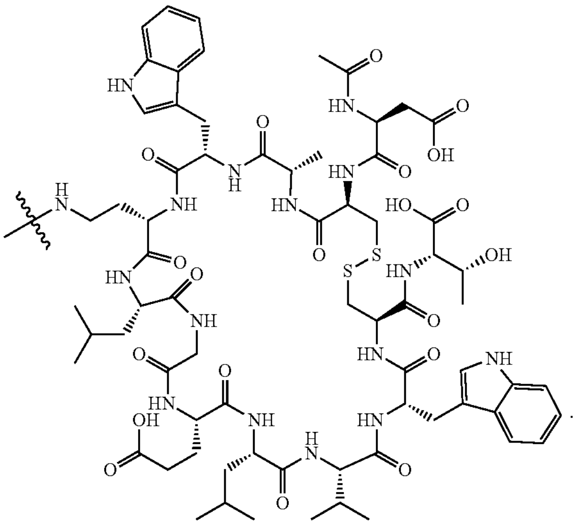 [SMILES: *NCC[C@@H]1NC(=O)[C@H](Cc2c[nH]c3ccccc23)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC1=O]
In some embodiments, a target binding moiety, e.g.,
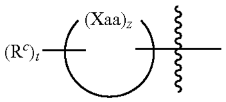
or $R^c$-(Xaa)z-, is or comprises
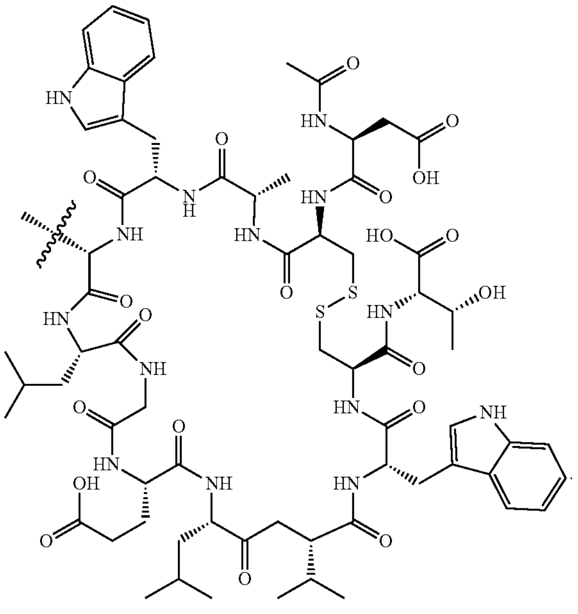 [SMILES: *[C@@H]1NC(=O)[C@H](Cc2c[nH]c3ccccc23)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc2c[nH]c3ccccc23)NC(=O)[C@H](C(C)C)CC(=O)[C@H](CC(C)C)NC(=O)[C@H](CCC(=O)O)NC(=O)CNC(=O)[C@H](CC(C)C)NC1=O]

In some embodiments, a target binding moiety, e.g.,
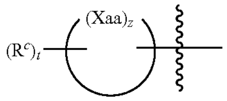
or $R^c$-(Xaa)z-, is or comprises
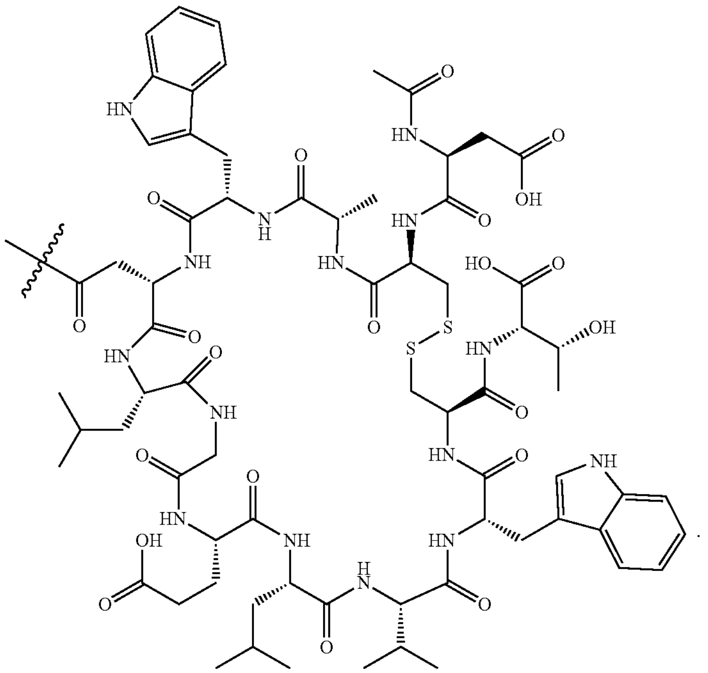 [SMILES: *C(=O)C[C@@H]1NC(=O)[C@H](Cc2c[nH]c3ccccc23)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC1=O]
In some embodiments, a target binding moiety, e.g.,
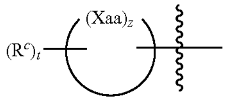

or $R^c$-(Xaa)z-, is or comprises
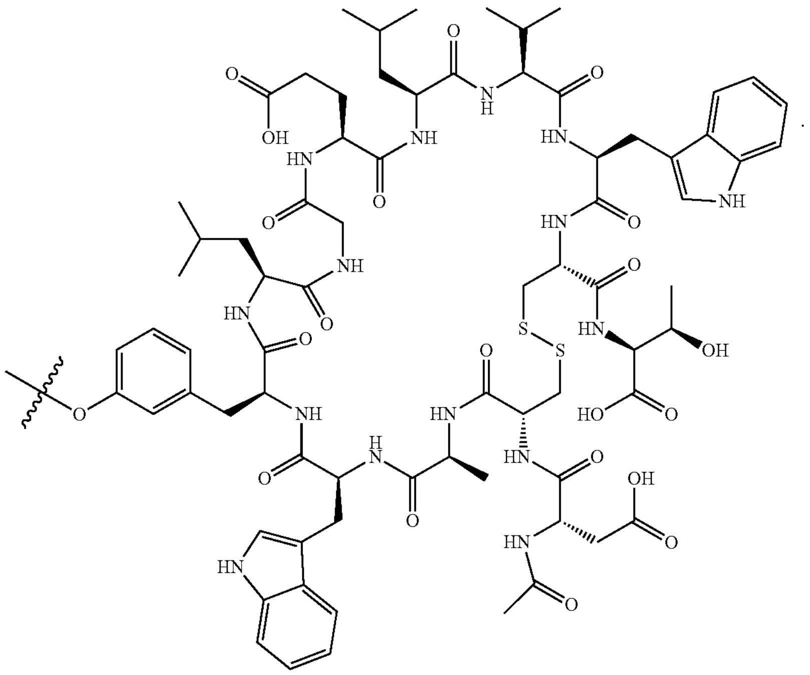 [SMILES: *Oc1cccc(C[C@@H]2NC(=O)[C@H](Cc3c[nH]c4ccccc34)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC(=O)[C@H](CC(C)C)NC2=O)c1]
In some embodiments, a target binding moiety, e.g.
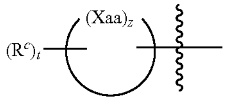
or $R^c$-(Xaa)z-, is or comprises
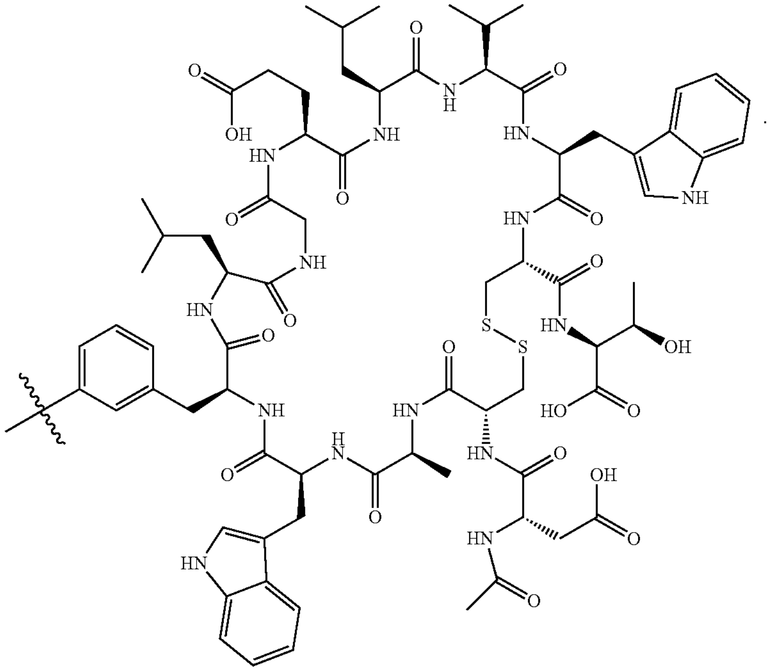 [SMILES: *c1cccc(C[C@@H]2NC(=O)[C@H](Cc3c[nH]c4ccccc34)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC(=O)[C@H](CC(C)C)NC2=O)c1]
In some embodiments, a target binding moiety, e.g.,
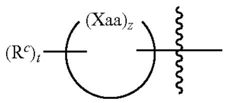

or $R^c$-(Xaa)z-, is or comprises

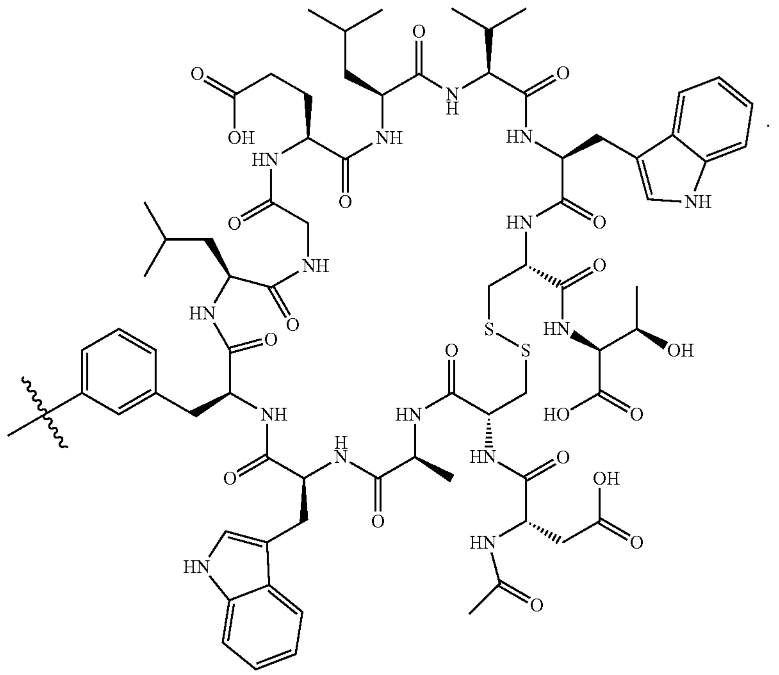 [SMILES: *c1cccc(C[C@@H]2NC(=O)[C@H](Cc3c[nH]c4ccccc34)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC(=O)[C@H](CC(C)C)NC2=O)c1]

In some embodiments, a target binding moiety, e.g.,

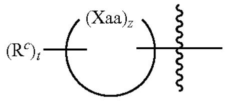

or $R^c$-(Xaa)z-, is or comprises

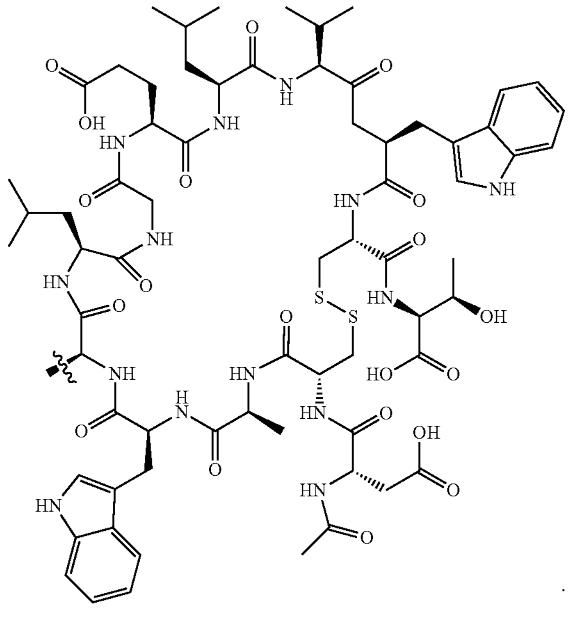

In some embodiments, such target binding moieties are antibody binding moieties.

In some embodiments, a target binding moiety, e.g., $R^c$-(Xaa)z-, is or comprises a Z33 peptide moiety. In some embodiments, a target binding moiety, e.g., $R^c$-(Xaa)z-, is or comprises -FNMQQQRRFYEALHDPNLNEEQRNAKIKSIRDD-$NH_2$ or a fragment thereof. In some embodiments, a target binding moiety, e.g., $R^c$-(Xaa)z-, is or comprises FNMQCQRRFYEALHDPNLNEEQRNAKIKSIRDDC or a fragment thereof. In some embodiments, a target binding moiety, e.g.,

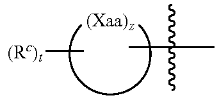

or $R^c$-(Xaa)z-, is or comprises a moiety of a peptide such as FNMQCQRRFYEALHDPNLNEEQRNAKIKSIRDDC, RGNCAYHRGQLVWCTYH, RGNCAYHKGQLVWCTYH, RGNCKYHRGQLVWCTYH, RGNCAWHRGKLVWCTYH, RGNCKWHRGELVWCTYH, RGNCKWHRGQLVWCTYH, RGNCKYHLGELVWCTYH, RGNCKYHLGQLVWCTYH, DCKWHLGELVWCT, DCKYHLGELVWCT, DCKWHRGELVWCT, DCKWHLGQLVWCT, DCKYHRGELVWCT, DCKYHLGQLVWCT, DCKWHRGQLVWCT, DCKYHRGQLVWCT, FNKQCQRRFYEALHDPNLNEEQRNARIRSIRDDC, FNMQCQRRFYEALHDPNLNEEQRNARIRSIKDDC, FNMQCQRRFYEALHDPNLNKEQRNARIRSIRDDC, FNMQCQRRFYEALHDPNLNEEQRNARIRSIRDDC, RGNCAWHLGQLVWCKYH, RGNCAWHLGELVWCKYH, RGNCAYHLGQLVWCTKH, RGNCAYHLGQLVWCTYK, RGNCAYHRGQLVWCTKH, KNMQCQRRFYEALHDPNLNEEQRNARIRSIRDDC, FNMQCQKRFYEALHDPNLNEEQRNARIRSIRDDC, FNMQCQRRFYEAKHDPNLNEEQRNARIRSIRDDC,FNMQCQRRF- YEALHDPNLNEEQRKARIRSIRDDC, FNMQCQRRFYEALHDPNLNKEQRNARIRSIRDDC, FNMQCQRRFYEALHDPNLNEEQRNARIRSIKDDC, FNKQ CQRRFYEALHDPNLNEEQRNARIRSIRDDC, FNMQCKRRFYEALHDPNLNEEQRNARIRSIRDDC, FNMQCQRRFYEALHDPNLNEEQRNARIRSIRKDC, Fc-III, FcBP-2, Fc-III-4C,

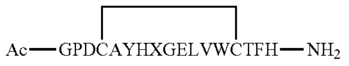

(X=K or R), etc., wherein two cysteine residues may optionally form a disulfide bond. In some embodiments, in a peptide described herein, two cysteine residues form a disulfide bond. In some embodiments, a peptide, such as Z33, FNMQCQRRFYEALHDPNLNEEQRNAKIKSIRDDC, RGNCAYHRGQLVWCTYH, RGNCKYHRGQLVWCTYH, RGNCAYHKGQLVWCTYH, RGNCAWHRGKLVWCTYH, RGNCKWHRGQLVWCTYH, RGNCKWHRGELVWCTYH, RGNCKYHLGELVWCTYH, RGNCKYHLGQLVWCTYH, DCKWHLGELVWCT, DCKYHLGELVWCT, DCKWHRGELVWCT, DCKWHLGQLVWCT, DCKYHRGELVWCT, DCKYHLGQLVWCT, DCKWHRGQLVWCT, DCKYHRGQLVWCT, FNKQCQRRFYEALHDPNLNEEQRNARIRSIRDDC, FNMQCQRRFYEALHDPNLNEEQRNARIRSIKDDC, FNMQCQRRFYEALHDPNLNKEQRNARIRSIRDDC, FNMQCQRRFYEALHDPNLNEEQRNARIRSIRDDC, RGNCAWHLGQLVWCKYH, RGNCAWHLGELVWCKYH, RGNCAYHLGQLVWCTKH, RGNCAYHLGQLVWCTYK, RGNCAYHRGQLVWCTKH, KNMQCQRRFYEALHDPNLNEEQRNARIRSIRDDC, FNMQCQKRFYEALHDPNLNEEQRNARIRSIRDDC, FNMQCQRRFYEAKHDPNLNEEQRNARIRSIRDDC, FNMQCQRRFYEALHDPNLNEEQRKARIRSIRDDC, FNMQCQRRFYEALHDPNLNKEQRNARIRSIRDDC, FNMQCQRRFYEALHDPNLNEEQRNARIRSIKDDC, FNKQ CQRRFYEALHDPNLNEEQRNARIRSIRDDC, FNMQCKRRFYEALHDPNLNEEQRNARIRSIRDDC, FNMQCQRRFYEALHDPNLNEEQRNARIRSIRKDC, Fc-III, FcBP-2, Fc-III-4C,

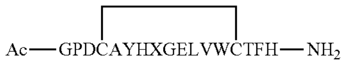

(X=K or R), etc., is connected through its N-terminus, C-terminus, or a side chain (e.g., of K (e.g., of underlined K residues in RGNCAYHKGQLVWCTYH, RGNCKYHRGQLVWCTYH, RGNCAWHRGKLVWCTYH, RGNCKWHRGELVWCTYH, RGNCKWHRGQLVWCTYH, RGNCKYHLGELVWCTYH, RGNCKYHLGQLVWCTYH, DCKWHLGELVWCT, DCKYHLGELVWCT, DCKWHRGELVWCT, DCKWHLGQLVWCT, DCKYHRGELVWCT, DCKYHLGQLVWCT, DCKWHRGQLVWCT, DCKYHRGQLVWCT, RGNCAWHLGQLVWCKYH, FNKQCQRRFYEALHDPNLNEEQRNARIRSIRDDC, FNMQCQRRFYEALHDPNLNEEQRNARIRSIKDDC, FNMQCQRRFYEALHDPNLNKEQRNARIRSIRDDC, RGNCAWHLGELVWCKYH, RGNCAYHLGQLVWCTKH, RGNCAYHLGQLVWCTYK RGNCAYHRGQLVWCTKH, KNMQCQRRFYEALHDPNLNEEQRNARIRSIRDDC, FNMQCQKRFYEALHDPNLNEEQRNARIRSIRDDC, FNMQCQRRFYEAKHDPNLNEEQRNARIRSIRDDC, FNMQCQRRFYEALHDPNLNEEQRKARIRSIRDDC, FNMQCQRRFYEALHDPNLNKEQRNARIRSIRDDC, FNMQCQRRFYEALHDPNLNEEQRNARIRSIKDDC, FNKQCQRRFYEALHDPNLNEEQRNARIRSIRDDC, FNMQCKRRFYEALHDPNLNEEQRNARIRSIRDDC, FNMQCQRRFYEALHDPNLNEEQRNARIRSIRKDC, etc.)). In some embodiments, one or more amino acid residues of a sequence may be independently and optionally replaced (e.g., 1-5), deleted (e.g., 1-5) and/or inserted (e.g., 1-5) as described herein. In some embodiments, a target binding moiety, e.g.,

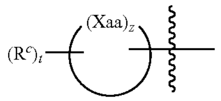

or $R^c$-(Xaa)z-, is or comprises —CXYHXXXLVWC—, —XCXYHXXXLVWC—, —CXYHXXXLVWCX—, —$X_{0-3}$CXYHXXXLVWC$X_{0-3}$—, —XCXYHXXXLVWCXXX—XXXCXYHXXXLVWCXXX—, wherein each X is independently an amino acid residue, and the two C residues optionally form a disulfide bond. In some embodiments, $X^8$ (the X after H) is Orn. In some embodiments, $X^8$ is Dab. In some embodiments, $X^8$ is Lys(Ac). In some embodiments, $X^8$ is Orn(Ac). In some embodiments, $X^8$ is Dab(Ac). In some embodiments, $X^8$ is Arg. In some embodiments, $X^8$ is Nle. In some embodiments, $X^8$ is Nva. In some embodiments, $X^8$ is Val. In some embodiments, $X^8$ is Tle. In some embodiments, $X^8$ is Leu. In some embodiments, $X^8$ is Ala(tBu). In some embodiments, $X^8$ is Cha. In some embodiments, $X^8$ is Phe. In some embodiments, a target binding moiety, e.g.,

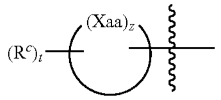

or $R^c$-(Xaa)z-, is or comprises DCAWHLGELVWCT. In some embodiments, a C-terminus and/or a N-terminus of a protein agent/peptide agent moiety are independently capped (e.g., RC(O)— such as $CH_3C(O)$— for N-terminus, —$N(R')_2$ such as —$NH_2$ for C-terminus, etc.). In some embodiments, such target binding moieties are antibody binding moieties. In some embodiments, as described herein, a residue may be modified or replaced for connection with another moiety, e.g., in some embodiments, H may be replaced with an amino acid residue comprises a side chain that contain —COOH or a salt or activated form thereof (e.g., D).

In some embodiments, a target binding moiety, e.g.,

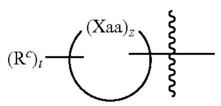

or $R^c$-(Xaa)z-, is or comprises $(X_{1-3})$—C—$(X_2)$—H-(Xaa1)-G-(Xaa2)-L-V—W—C—$(X_{1-3})$, wherein each of X and Xaa is independently an amino acid residue and optionally not a cysteine residue. In some embodiments, Xaa1 is R, L, L, D, E, a 2-amino suberic acid residue, or a diaminopropionic acid residue. In some embodiments, Xaa2 is L, D, E, N, or Q. In some embodiments, Xaa1 is a lysine residue, a cysteine residue, an aspartic acid residue, a glutamic acid residue, a 2-amino suberic acid residue, or a diaminopropionic acid residue. In some embodiments, Xaa2 is a glutamic acid residue or an aspartic acid residue. In some embodiments, Xaa1 is an arginine residue or a leucine residue. In some embodiments, Xaa2 is a lysine residue, a glutamine residue, or an aspartic acid residue. In some embodiments, such target binding moieties are antibody binding moieties.

In some embodiments, a target binding moiety, e.g.,

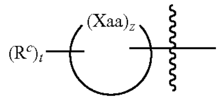

or $R^c$-(Xaa)z-, is or comprises (X1-3)-C-(Xaa3)-(xaa4)-H-(Xaa1)-G-(Xaa2)-L-V—W—C-(Xaa5)-(Xaa6)-(Xaa7), wherein each of X and Xaa is independently an amino acid residue and optionally not a cysteine residue. In some embodiments, Xaa3 is an alanine residue or a lysine residue. In some embodiments, Xaa4 is a tryptophan residue or a tyrosine residue. In some embodiments, Xaa1 is an arginine residue, a leucine residue, a lysine residue, an aspartic acid residue, a glutamic acid residue, a 2-amino suberic acid residue, or a diaminopropionic acid residue. In some embodiments, Xaa2 is a lysine residue, a glutamine residue, a glutamic acid residue, an asparagine residue, or an aspartic acid residue. In some embodiments, Xaa5 is a threonine residue or a lysine residue. In some embodiments, Xaa6 is a tyrosine residue, a lysine residue, or absent. In some embodiments, Xaa7 is a histidine residue, a lysine residue, or absent. In some embodiments, such target binding moieties are antibody binding moieties.

In some embodiments, a target binding moiety, e.g.,

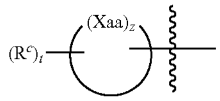

or $R^c$-(Xaa)z-, is or comprises D-C-(Xaa3)-(Xaa4)-H-(Xaa1)-G-(Xaa2)-L-V—W—C-(Xaa5)-(Xaa6)-(Xaa7), wherein each of X and Xaa is independently an amino acid residue and optionally not a cysteine residue. In some embodiments, Xaa3 is an alanine residue or a lysine residue. In some embodiments, Xaa4 is a tryptophan residue or a tyrosine residue. In some embodiments, Xaa1 is an arginine residue, a leucine residue, a lysine residue, an aspartic acid residue, a glutamic acid residue, a 2-amino suberic acid residue, or a diaminopropionic acid residue. In some embodiments, Xaa2 is a lysine residue, a glutamine residue, a glutamic acid residue, an asparagine residue, or an aspartic acid residue. In some embodiments, Xaa5 is a threonine residue or a lysine residue. In some embodiments, Xaa6 is a tyrosine residue, a lysine residue, or absent. In some embodiments, Xaa7 is a histidine residue, a lysine residue, or absent. In some embodiments, such target binding moieties are antibody binding moieties.

In some embodiments, a target binding moiety, e.g.,

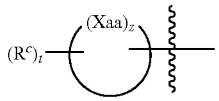

or $R^c$-(Xaa)z-, is or comprises D-C-(Xaa3)-(Xaa4)-H-(Xaa1)-G-(Xaa2)-L-V—W—C-T, wherein each of X and Xaa is independently an amino acid residue and optionally not a cysteine residue. In some embodiments, Xaa3 is an alanine residue or a lysine residue. In some embodiments, Xaa4 is a tryptophan residue or a tyrosine residue. In some embodiments, Xaa1 is an arginine residue, a leucine residue, a lysine residue, an aspartic acid residue, a glutamic acid residue, a 2-amino suberic acid residue, or a diaminopropionic acid residue. In some embodiments, Xaa2 is a lysine residue, a glutamine residue, a glutamic acid residue, an asparagine residue, or an aspartic acid residue. In some embodiments, such target binding moieties are antibody binding moieties.

In some embodiments, a target binding moiety, e.g.

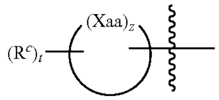

or $R^c$-(Xaa)z-, is or comprises R-G-N—C-(Xaa3)-(Xaa4)-H-(Xaa1)-G-(Xaa2)-L-V—W—C-(Xaa5)-(Xaa6)-(Xaa7), wherein each of X and Xaa is independently an amino acid residue and optionally not a cysteine residue. In some embodiments, Xaa3 is an alanine residue or a lysine residue. In some embodiments, Xaa4 is a tryptophan residue or a tyrosine residue. In some embodiments, Xaa1 is an arginine residue, a leucine residue, a lysine residue, an aspartic acid residue, a glutamic acid residue, a 2-amino suberic acid residue, or a diaminopropionic acid residue. In some embodiments, Xaa2 is a lysine residue, a glutamine residue, a glutamic acid residue, an asparagine residue, or an aspartic acid residue. In some embodiments, Xaa5 is a threonine residue or a lysine residue. In some embodiments, Xaa6 is a tyrosine residue, a lysine residue, or absent. In some embodiments, Xaa7 is a histidine residue, a lysine residue, or absent. In some embodiments, such target binding moieties are antibody binding moieties.

In some embodiments, target binding moieties, e.g., various target binding moieties described above, are protein binding moieties. In some embodiments, target binding moieties are antibody binding moieties. In some embodiments, LG is or comprises such a target binding moiety. In some embodiments, LG is or comprises a protein binding moiety. In some embodiments, LG is or comprises an antibody binding moiety.

In some embodiments, target binding moieties, e.g., antibody binding moieties, and useful technologies for developing and/or assessing such moieties are described in, e.g., Alves, Langmuir 2012, 28, 9640-9648; Choe et al., Materials 2016, 9, 994; doi: 10.3390/ma9120994; Gupta et al., Nature Biomedical Engineering, vol. 3, 2019, 917-929; Muguruma, et al., ACS Omega 2019, 4, 14390-14397, doi: 10.1021/acsomega.9b01104; Yamada, et al., Angew Chem Int Ed Engl. 2019 Apr. 16; 58(17):5592-5597, doi: 10.1002/anie.201814215; Kruljec, et al., Bioconjug Chem. 2017, 28(8): 2009-2030, doi: 10.1021/acs.bioconjchem.7b00335 (e.g., Fabsorbent, triazines, etc.); Kruljec, et al., Bioconjugate Chem. 2018, 29, 8, 2763-2775, doi: 10.1021/acs.bioconjchem.8b00395; WO2012017021A2, etc., the binding moieties (e.g., antibody binding moieties) of each of which are incorporated herein by reference.

In some embodiments, a target binding moiety, e.g., a protein binding moiety (e.g., an antibody binding moiety), is an affinity substance described in AU 2018259856 or WO 2018199337, the affinity substance of each of which is incorporated herein by reference.

In some embodiments, a target binding moiety, e.g., an antibody binding moiety, is or comprises an adapter protein agent, e.g., as described in Hui, et al., Bioconjugate Chem. 2015, 26, 1456-1460, doi: 10.1021/acs.bioconjchem.5b00275. In some embodiments, when utilized in accordance with the present disclosure, adapter proteins do not require reactive residues (e.g., BPA) to achieve one or more or all advantages.

In some embodiments, target binding moiety, e.g., an antibody binding moiety is or comprises a triazine moiety, e.g., one described in US 2009/0286693. In some embodiments, a target binding moiety, e.g., an antibody binding moiety is of such a structure that its corresponding compound is a compound described in US 2009/0286693, the compounds of which are independently incorporated herein by reference. In some embodiments, a target binding moiety, e.g., an antibody binding moiety, is ABT. In some embodiments, ABT is of such a structure that H-ABT is a compound described in US 2009/0286693, the compounds of which are independently incorporated herein by reference. In some embodiments, such a compound can bind to an antibody. In some embodiments, such a compound can bind to Fc region of an antibody.

In some embodiments, a target binding moiety, e.g., an antibody binding moiety is or comprises a triazine moiety, e.g., one described in Teng, et al., A strategy for the generation of biomimetic ligands for affinity chromatography. Combinatorial synthesis and biological evaluation of an IgG binding ligand, *J. Mol. Recognit.* 1999; 12:67-75 ("Teng"). In some embodiments, a target binding moiety, e.g., an antibody binding moiety is of such a structure that its corresponding compound is a compound described in Teng, the compounds of which are independently incorporated herein by reference. In some embodiments, a target binding moiety, e.g., an antibody binding moiety, ABT is of such a structure that H-ABT is a compound described in Teng, the compounds of which are independently incorporated herein by reference. In some embodiments, such a compound can bind to an antibody. In some embodiments, such a compound can bind to Fc region of an antibody.

In some embodiments, v target binding moiety, e.g., an antibody binding moiety is a triazine moiety, e.g., one described in Uttamchandani, et al., Microarrays of Tagged Combinatorial Triazine Libraries in the Discovery of Small-Molecule Ligands of Human IgG, *J Comb Chem.* 2004 November-December; 6(6):862-8 ("Uttamchandani"). In some embodiments, a target binding moiety, e.g., an antibody binding moiety is of such a structure that its corresponding compound is a compound described in Uttamchandani, the compounds of which are independently incorporated herein by reference. In some embodiments, a target binding moiety, e.g., an antibody binding moiety, ABT is of such a structure that H-ABT is a compound described in Uttamchandani, the compounds of which are independently incorporated herein by reference. In some embodiments, such a compound can bind to an antibody. In some embodiments, such a compound can bind to Fc region of an antibody.

In some embodiments, an antibody binding moiety binds to one or more binding sites of protein A. In some embodiments, an antibody binding moiety binds to one or more binding sites of protein G. In some embodiments, an antibody binding moiety binds to one or more binding sites of protein L. In some embodiments, an antibody binding moiety binds to one or more binding sites of protein Z. In some embodiments, an antibody binding moiety binds to one or more binding sites of protein LG. In some embodiments, an antibody binding moiety binds to one or more binding sites of protein LA. In some embodiments, an antibody binding moiety binds to one or more binding sites of protein AG. In some embodiments, an antibody binding moiety is described in Choe, W., Durgannavar, T. A., & Chung, S. J. (2016). Fc-binding ligands of immunoglobulin G: An overview of high affinity proteins and peptides. Materials, 9(12). https://doi.org/10.3390/ma9120994.

In some embodiments, a target binding moiety, e.g., an antibody binding moiety can bind to a nucleotide-binding site. In some embodiments, a target binding moiety, e.g., an antibody binding moiety is a small molecule moiety that can bind to a nucleotide-binding site. In some embodiments, a small molecule is tryptamine. In some embodiments, a target binding moiety, e.g., an antibody binding moiety, ABT is of such a structure that H-ABT is tryptamine. Certain useful technologies were described in Mustafaoglu, et al., Antibody Purification via Affinity Membrane Chromatography Method Utilizing Nucleotide Binding Site Targeting With A Small Molecule, Analyst. 2016 Nov. 28; 141(24): 6571-6582.

Many technologies are available for identifying and/or assessing and/or characterizing target binding moieties, including protein binding moieties (e.g., antibody binding moieties such as universal antibody binding moieties), and/or their utilization in provided technologies, e.g., those described in WO/2019/023501, the technologies of which are incorporated herein by reference. In some embodiments, an antibody binding moiety is a moiety (e.g., small molecule moiety, peptide moiety, nucleic acid moiety, etc.) that can selectively bind to IgG, and when used in provided technologies can provide and/or stimulate ADCC and/or ADCP. In some embodiments, peptide display technologies (e.g., phase display, non-cellular display, etc.) can be utilized to identify antibody binding moieties. In some embodiments, an antibody binding moiety is a moiety (e.g., small molecule moiety, peptide moiety, nucleic acid moiety, etc.) that can bind to IgG and optionally can compete with known antibody binders, e.g., protein A, protein G, protein L, etc.

As appreciated by those skilled in the art, antibodies of various properties and activities (e.g., antibodies recognizing different antigens, having optional modifications, etc.) may be targeted by antibody binding moieties described in the present disclosure. In some embodiments, such antibodies include antibodies administered to a subject, e.g., for therapeutic purposes. In some embodiments, antibody binding moieties described herein may bind antibodies toward different antigens and are useful for conjugating moieties of interest with various antibodies.

In some embodiments, a target binding moiety, e.g., an antibody binding moiety, is or comprises a meditope agent moiety. In some embodiments, a meditope agent is described in, e.g., US 2019/0111149.

In some embodiments, a target binding moiety, e.g., an antibody binding moiety, can bind to human IgG. In some embodiments, a target binding moiety, e.g., an antibody binding moiety, can bind to rabbit IgG. In some embodiments, a target binding moiety, e.g., an antibody binding moiety, binds to IgG1. In some embodiments, a target binding moiety, e.g., an antibody binding moiety, binds to IgG2. In some embodiments, a target binding moiety, e.g., an antibody binding moiety, binds to IgG3. In some embodiments, a target binding moiety, e.g., an antibody binding moiety, binds to IgG4. In some embodiments, a target binding moiety, e.g., an antibody binding moiety, binds to IgG1, IgG2 and/or IgG4. In some embodiments, a target binding moiety, e.g., an antibody binding moiety, binds to IgG1, IgG2 and IgG4.

In some embodiments

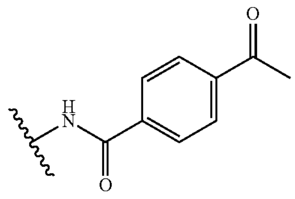 [SMILES: *NC(=O)c1ccc(C(C)=O)cc1]

is utilized in a reference technology as a non-target binding moiety. In some embodiments, $CH_3$— is utilized in a reference technology a non-target binding moiety. In some embodiments, $CH_3C(O)$— is utilized in a reference technology a non-target binding moiety. In some embodiments, $CH_3C(O)NH$— is utilized in a reference technology a non-target binding moiety. In some embodiments, $CH_3C(O)NHCH_2$— is utilized in a reference technology a non-target binding moiety. In some embodiments, $CH_3CH_2$— is utilized in a reference technology a non-target binding moiety. In some embodiments, $CH_3CH_2NH$— is utilized in a reference technology a non-target binding moiety. In some embodiments, $CH_3CH_2NHC(O)$— is utilized in a reference technology a non-target binding moiety.

In some embodiments, target binding moieties (e.g., antibody binding moieties) bind to targets (e.g., antibody agents for antibody binding moieties) with a Kd that is about 1 mM-1 pM or less. In some embodiments, a Kd is about 1 mM, 0.5 mM, 0.2 mM, 0.1 mM, 0.05 mM, 0.02 mM, 0.01 mM, 0.005 mM, 0.002 mM, 0.001 mM, 500 nM, 200 nM, 100 nM, 50 nM, 20 nM, 10 nM, 5 nM, 2 nM, 1 nM, 0.5 nM, 0.2 nM, 0.1 nM, or less. In some embodiments, Kd is about 1 mM or less. In some embodiments, Kd is about 0.5 mM or less. In some embodiments, Kd is about 0.1 mM or less. In some embodiments, Kd is about 0.05 mM or less. In some embodiments, Kd is about 0.01 mM or less. In some embodiments, Kd is about 0.005 mM or less. In some embodiments, Kd is about 0.001 mM or less. In some embodiments, Kd is about 500 nM or less. In some embodiments, Kd is about 200 nM or less. In some embodiments, Kd is about 100 nM or less. In some embodiments, Kd is about 50 nM or less. In some embodiments, Kd is about 20 nM or less. In some embodiments, Kd is about 10 nM or less. In some embodiments, Kd is about 5 nM or less. In some embodiments, Kd is about 2 nM or less. In some embodiments, Kd is about 1 nM or less. For example, in some embodiments, antibody binding moieties bind to IgG antibody agents with Kd described herein.

Amino Acids

In some embodiments, provided compounds and agents may comprise one or more amino acid moieties, e.g., in antibody binding moieties, linker moieties, etc. Amino acid moieties can either be those of natural amino acids or unnatural amino acids. In some embodiments, an amino acid has the structure of formula A-I:

$NH(R^{a1})-L^{a1}-C(R^{a2})(R^{a3})-L^{a2}-COOH$, A-I or a salt thereof, wherein:

each of $R^{a1}$, $R^{a2}$ and $R^{a3}$ is independently $-L^a-R'$ or an amino acid side chain;

each of $L^{a1}$ and $L^{a2}$ is independently $L^a$;

each $L^a$ is independently a covalent bond, or an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—;

each -Cy- is independently an optionally substituted bivalent monocyclic, bicyclic or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —$CO_2R$, or —$SO_2R$;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, an amino acid residue, e.g., of an amino acid having the structure of formula A-I, has the structure of —$N(R^{a1})-L^{a1}-C(R^{a2})(R^{a3})-L^{a2}-CO$—. In some embodiments, each amino acid residue in a peptide independently has the structure of —$N(R^{a1})-L^{a1}-C(R^{a2})(R^{a3})-L^{a2}-CO$—.

In some embodiments, the present disclosure provides a derivative of an amino acid of formula A-I or a salt thereof. In some embodiments, a derivative is an ester. In some embodiments, the present disclosure provides a compound of formula $NH(R^{a1})$-$L^{a1}$-$C(R^{a2})(R^{a3})$-$L^{a2}$-$COOR^{CT}$ or salt thereof, wherein $R^{CT}$ is R' and each other variable is independently as described herein. In some embodiments, $R^{CT}$ is R. In some embodiments, $R^{CT}$ is optionally substituted aliphatic. In some embodiments, $R^{CT}$ is t-butyl.

In some embodiments, $L^{a1}$ is a covalent bond. In some embodiments, a compound of formula A-I is of the structure $NH(R^{a1})$—$C(R^{a2})(R^{a3})$-$L^{a2}$-COOH. In some embodiments, $L^{a2}$ is —$CH_2SCH_2$—.

In some embodiments, $L^{a2}$ is a covalent bond. In some embodiments, a compound of formula A-I is of the structure $NH(R^{a1})$-$L^{a1}$-$C(R^{a2})(R^{a3})$—COOH. In some embodiments, an amino acid residue has the structure of —$N(R^{a1})$-$L^{a1}$-$C(R^{a2})(R^{a3})$—CO—. In some embodiments, $L^{a1}$ is —$CH_2CH_2S$—. In some embodiments, $L^{a1}$ is —$CH_2CH_2S$—, wherein the $CH_2$ is bonded to $NH(R^{a1})$.

In some embodiments, $L^{a1}$ is a covalent bond and $L^{a2}$ is a covalent bond. In some embodiments, a compound of formula A-I is of the structure $NH(R^{a1})$—$C(R^{a2})(R^{a3})$—COOH. In some embodiments, a compound of formula A-I is of the structure $NH(R^{a1})$—$CH(R^{a2})$—COOH. In some embodiments, a compound of formula A-I is of the structure $NH(R^{a1})$—$CH(R^{a3})$—COOH. In some embodiments, a compound of formula A-I is of the structure $NH_2$—$CH(R^{a2})$—COOH. In some embodiments, a compound of formula A-I is of the structure $NH_2$—$CH(R^{a3})$—COOH. In some embodiments, an amino acid residue has the structure of —$N(R^{a1})$—$C(R^{a2})(R^{a3})$—CO—. In some embodiments, an amino acid residue has the structure of —$N(R^{a1})$—$CH(R^{a2})$—CO—. In some embodiments, an amino acid residue has the structure of —$N(R^{a1})$—$CH(R^{a3})$—CO—. In some embodiments, an amino acid residue has the structure of —NH—$CH(R^{a2})$—CO—. In some embodiments, an amino acid residue has the structure of —NH—$CH(R^{a3})$—CO—.

In some embodiments, $L^a$ is a covalent bond. In some embodiments, $L^a$ is optionally substituted $C_{1-6}$ bivalent aliphatic. In some embodiments, $L^a$ is optionally substituted $C_{1-6}$ alkylene. In some embodiments, $L^a$ is —$CH_2$—. In some embodiments, $L^a$ is —$CH_2CH_2$—. In some embodiments, $L^a$ is —$CH_2CH_2CH_2$—.

In some embodiments, $L^a$ is bivalent optionally substituted $C_{1-20}$ aliphatic, wherein one or more methylene units are independently replaced with —C(O)—, —N(R')—, -Cy-, and/or —O—. In some embodiments, $L^a$ is bivalent optionally substituted $C_{1-20}$ aliphatic, wherein one or more methylene units are independently replaced with —C(O)N(R')—, -Cy-, and —O—. In some embodiments, $L^a$ is bivalent optionally substituted $C_{1-20}$ aliphatic, wherein two or more methylene units are independently replaced with —C(O)N(R')—, and -Cy- in addition to other optional replacements. In some embodiments, -Cy- is optionally substituted. In some embodiments, -Cy- is optionally substituted with an electron-withdrawing group as described herein. In some embodiments, -Cy- is substituted with one or more —F. In some embodiments, -Cy- is optionally substituted 1,3-phenylene. In some embodiments, -Cy- is optionally substituted 1,4-phenylene. In some embodiments, $L^a$ is or comprises

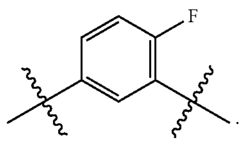 [SMILES: *c1ccc(F)c(*)c1]

In some embodiments, $L^a$ is or comprises

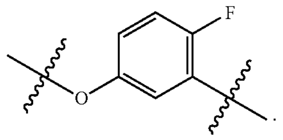 [SMILES: *Oc1ccc(F)c(*)c1]

In some embodiments, $L^a$ is or comprises

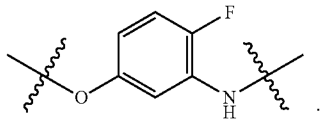 [SMILES: *Nc1cc(O*)ccc1F]

In some embodiments, $L^a$ is or comprises

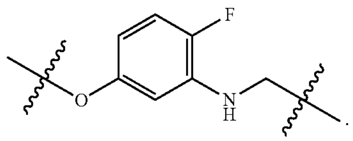 [SMILES: *CNc1cc(O*)ccc1F]

In some embodiments, $L^a$ is or comprises

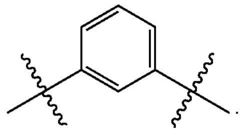 [SMILES: *c1cccc(*)c1]

In some embodiments, $L^a$ is or comprises

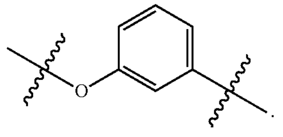 [SMILES: *Oc1cccc(*)c1]

In some embodiments, $L^a$ is or comprises

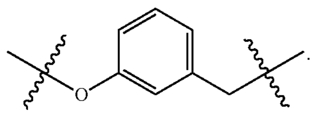 [SMILES: *Cc1cccc(O*)c1]

In some embodiments, $L^a$ is or comprises

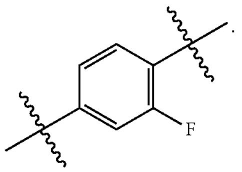 [SMILES: *c1ccc(*)c(F)c1]

In some embodiments, $L^a$ is or comprises

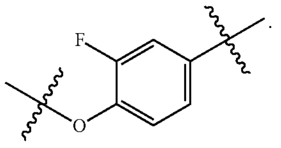 [SMILES: *Oc1ccc(*)cc1F]

In some embodiments, $L^a$ is or comprises

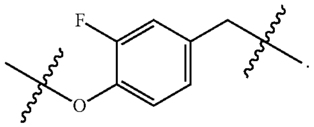 [SMILES: *Cc1ccc(O*)c(F)c1]

In some embodiments, $L^a$ is or comprises

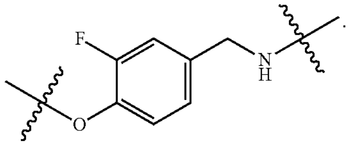 [SMILES: *NCc1ccc(O*)c(F)c1]

In some embodiments, $L^a$ is or comprises

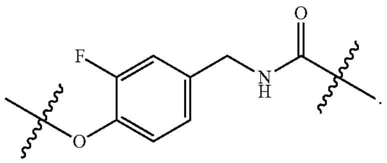 [SMILES: *Oc1ccc(CNC(*)=O)cc1F]

In some embodiments, $L^a$ is or comprise

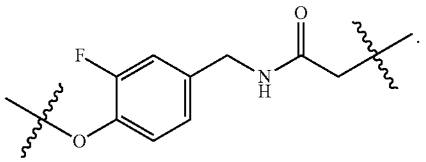 [SMILES: *CC(=O)NCc1ccc(O*)c(F)c1]

In some embodiments, $L^a$ is or comprises

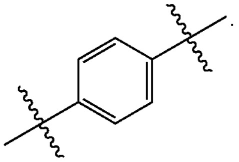 [SMILES: *c1ccc(*)cc1]

In some embodiments, $L^a$ is or comprises

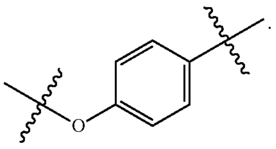 [SMILES: *Oc1ccc(*)cc1]

In some embodiments, $L^a$ is or comprises

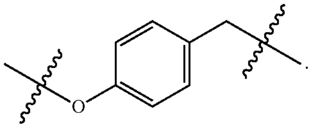 [SMILES: *Cc1ccc(O*)cc1]

In some embodiments, $L^a$ is or comprises

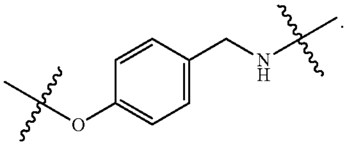 [SMILES: *NCc1ccc(O*)cc1]

In some embodiments, $L^a$ is or comprises

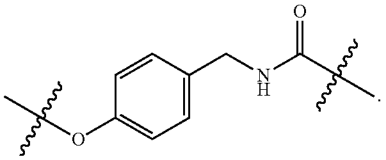 [SMILES: *Oc1ccc(CNC(*)=O)cc1]

In some embodiments, $L^a$ is or comprises

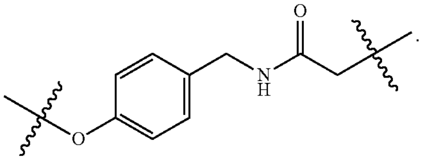 [SMILES: *CC(=O)NCc1ccc(O*)cc1]

In some embodiments, R' is R. In some embodiments, $R^{a1}$ is R, wherein R is as described in the present disclosure. In some embodiments, $R^{a1}$ is R, wherein R methyl. In some embodiments, $R^{a2}$ is R, wherein R is as described in the present disclosure. In some embodiments, $R^{a3}$ is R, wherein R is as described in the present disclosure. In some embodiments, each of $R^{a1}$, $R^{a2}$, and $R^{a3}$ is independently R, wherein R is as described in the present disclosure.

In some embodiments, $R^{a1}$ is hydrogen. In some embodiments, $R^{a1}$ is a protective group. In some embodiments, $R^{a1}$ is -Fmoc. In some embodiments, $R^{a1}$ is -Dde.

In some embodiments, each of $R^{a1}$, $R^{a2}$ and $R^{a3}$ is independently $-L^{a}-R'$.

In some embodiments, $R^{a2}$ is hydrogen. In some embodiments, $R^{a3}$ is hydrogen. In some embodiments, $R^{a1}$ is hydrogen, and at least one of $R^{a2}$ and $R^{a3}$ is hydrogen. In some embodiments, $R^{a1}$ is hydrogen, one of $R^{a2}$ and $R^{a3}$ is hydrogen, and the other is not hydrogen. In some embodiments, $R^{a2}$ is $-L^{a}-R$ and $R^{a3}$ is —H. In some embodiments, $R^{a3}$ is $-L^{a}-R$ and $R^{a2}$ is —H. In some embodiments, $R^{a2}$ is $—CH_2—R$ and $R^{a3}$ is —H. In some embodiments, $R^{a3}$ is $—CH_2—R$ and $R^{a2}$ is —H. In some embodiments, $R^{a2}$ is R and $R^{a3}$ is —H. In some embodiments, $R^{a3}$ is R and $R^{a2}$ is —H.

In some embodiments, $R^{a2}$ is $-L^{a}-R$, wherein R is as described in the present disclosure. In some embodiments, $R^{a2}$ is $-L^{a}-R$, wherein R is an optionally substituted group selected from $C_{3-30}$ cycloaliphatic, $C_{5-30}$ aryl, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon. In some embodiments, $R^{a2}$ is $-L^{a}-R$, wherein R is an optionally substituted group selected from $C_{6-30}$ aryl and 5-30 membered heteroaryl having 1-10 heteroatoms independently selected from oxygen, nitrogen, sulfur, phosphorus and silicon. In some embodiments, $R^{a2}$ is a side chain of an amino acid. In some embodiments, $R^{a2}$ is a side chain of a standard amino acid.

In some embodiments, $R^{a3}$ is $-L^{a}-R$, wherein R is as described in the present disclosure. In some embodiments, $R^{a3}$ is $-L^{a}-R$, wherein R is an optionally substituted group selected from $C_{3-30}$ cycloaliphatic, $C_{5-30}$ aryl, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon. In some embodiments, $R^{a3}$ is $-L^{a}-R$, wherein R is an optionally substituted group selected from $C_{6-30}$ aryl and 5-30 membered heteroaryl having 1-10 heteroatoms independently selected from oxygen, nitrogen, sulfur, phosphorus and silicon. In some embodiments, $R^{a3}$ is a side chain of an amino acid. In some embodiments, $R^{a3}$ is a side chain of a standard amino acid.

In some embodiments, one or $R^{a2}$ and $R^{a3}$ is —H. In some embodiments, one or $R^{a2}$ and $R^{a3}$ is $-L^{a}-R$, wherein $L^{a}$ is as described herein. In some embodiments, $L^{a}$ is not a covalent bond. In some embodiments, one or more methylene units of $L^{a}$ are independently and optionally replaced as described herein, e.g., with —C(O)—, —N(R')—, —O—, —C(O)—N(R')— and/or -Cy-, etc. In some embodiments, $L^{a}$ is or comprises —C(O)—, —N(R')— and -Cy-. In some embodiments, $L^{a}$ is or comprises —C(O)N(R')— and -Cy-. In some embodiments, as described herein, -Cy- is substituted and one or more substituents are independently an electron-withdrawing group.

In some embodiments, an amino acid side chain is $R^{a2}$ or $R^{a3}$. In some embodiments, an amino acid side chain is or comprises $-L^{LG1}-L^{LG2}-L^{LG3}-L^{LG4}-H$. In some embodiments, an amino acid side chain is or comprises $-L^{LG2}-L^{LG3}-L^{LG4}-H$. In some embodiments, an amino acid side chain is or comprises $-L^{LG3}-L^{LG4}-H$. In some embodiments, an amino acid side chain is or comprises $-L^{LG4}-H$. In some embodiments, such a side chain is

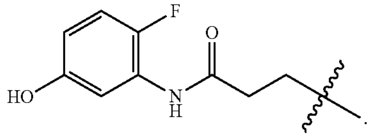 [SMILES: *CCC(=O)Nc1cc(O)ccc1F]

In some embodiments, such a side chain is

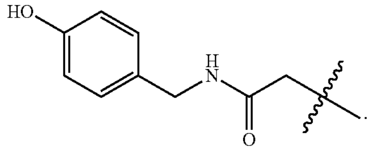 [SMILES: *CC(=O)NCc1ccc(O)cc1]

In some embodiments, such a side chain is

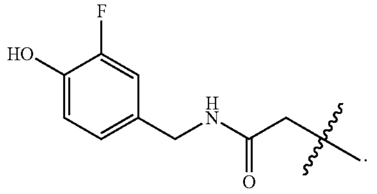 [SMILES: *CC(=O)NCc1ccc(O)c(F)c1]

In some embodiments, such a side chain is

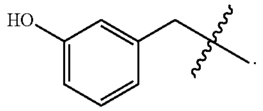 [SMILES: *Cc1cccc(O)c1]

In some embodiments, R is an optionally substituted $C_{1-6}$ aliphatic. In some embodiments, R is an optionally substituted $C_{1-6}$ alkyl. In some embodiments, R is $—CH_3$. In some embodiments, R is optionally substituted pentyl. In some embodiments, R is n-pentyl.

In some embodiments, R is a cyclic group. In some embodiments, R is an optionally substituted $C_{3-30}$ cycloaliphatic group. In some embodiments, R is cyclopropyl.

In some embodiments, R is an optionally substituted aromatic group, and an amino acid residue of an amino acid of formula A-I is a $Xaa^{A}$. In some embodiments, $R^{a2}$ or $R^{a3}$ is $—CH_2—R$, wherein R is an optionally substituted aryl or heteroaryl group. In some embodiments, R is optionally substituted phenyl. In some embodiments, R is phenyl. In some embodiments, R is optionally substituted phenyl. In some embodiments, R is 4-trifluoromethylphenyl. In some embodiments, R is 4-phenylphenyl. In some embodiments, R is optionally substituted 5-30 membered heteroaryl having 1-10 heteroatoms independently selected from oxygen, nitrogen, sulfur, phosphorus and silicon. In some embodiments, R is optionally substituted 5-14 membered heteroaryl having 1-5 heteroatoms independently selected from oxygen, nitrogen, and sulfur. In some embodiments, R is

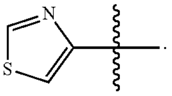 [SMILES: *c1cscn1]

In some embodiments, R is optionally substituted pyridinyl. In some embodiments, R is 1-pyridinyl. In some embodiments, R is 2-pyridinyl. In some embodiments, R is 3-pyridinyl. In some embodiments, R is

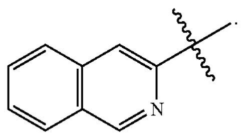 [SMILES: *c1cc2ccccc2cn1]

In some embodiments, R' is —COOH. In some embodiments, a compound of and an amino acid residue of an amino acid of formula A-I is a $Xaa^N$.

In some embodiments, R' is —$NH_2$. In some embodiments, a compound of an amino acid residue of an amino acid of formula A-I is a Xaa.

In some embodiments, $R^{a2}$ or $R^{a3}$ is R, wherein R is $C_{1-20}$ aliphatic as described in the present disclosure. In some embodiments, a compound of an amino acid residue of an amino acid of formula A-I is a $Xaa^H$. In some embodiments, R is —$CH_3$. In some embodiments, R is ethyl. In some embodiments, R is propyl. In some embodiments, R is n-propyl. In some embodiments, R is butyl. In some embodiments, R is n-butyl. In some embodiments, R is pentyl. In some embodiments, R is n-pentyl. In some embodiments, R is cyclopropyl.

In some embodiments, two or more of $R^{a1}$, $R^{a2}$, and $R^{a3}$ are R and are taken together to form an optionally substituted ring as described in the present disclosure.

In some embodiments, $R^{a1}$ and one of $R^{a2}$ and $R^{a3}$ are R and are taken together to form an optionally substituted 3-6 membered ring having no additional ring heteroatom other than the nitrogen atom to which $R^{a1}$ is bonded to. In some embodiments, a formed ring is a 5-membered ring as in proline.

In some embodiments, $R^{a2}$ and $R^{a3}$ are R and are taken together to form an optionally substituted 3-6 membered ring as described in the present disclosure. In some embodiments, $R^{a2}$ and $R^{a3}$ are R and are taken together to form an optionally substituted 3-6 membered ring having one or more nitrogen ring atom. In some embodiments, $R^{a2}$ and $R^{a3}$ are R and are taken together to form an optionally substituted 3-6 membered ring having one and no more than one ring heteroatom which is a nitrogen atom. In some embodiments, a ring is a saturated ring.

In some embodiments, an amino acid is a natural amino acid. In some embodiments, an amino acid is an unnatural amino acid. In some embodiments, an amino acid is an alpha-amino acid. In some embodiments, an amino acid is a beta-amino acid. In some embodiments, a compound of formula A-I is a natural amino acid. In some embodiments, a compound of formula A-I is an unnatural amino acid.

In some embodiments, an amino acid comprises a hydrophobic side chain. In some embodiments, an amino acid with a hydrophobic side chain is A, V, I, L, M, F, Y or W. In some embodiments, an amino acid with a hydrophobic side chain is A, V, I, L, M, or F. In some embodiments, an amino acid with a hydrophobic side chain is A, V, I, L, or M. In some embodiments, an amino acid with a hydrophobic side chain is A, V, I, or L. In some embodiments, a hydrophobic side chain is R wherein R is $C_{1-10}$ aliphatic. In some embodiments, R is $C_{1-10}$ alkyl. In some embodiments, R is methyl. In some embodiments, R is ethyl. In some embodiments, R is propyl. In some embodiments, R is butyl. In some embodiments, R is pentyl. In some embodiments, R is n-pentyl. In some embodiments, an amino acid with a hydrophobic side chain is $NH_2CH(CH_2CH_2CH_2CH_2CH_3)COOH$. In some embodiments, an amino acid with a hydrophobic side chain is (S)—$NH_2CH(CH_2CH_2CH_2CH_2CH_3)COOH$. In some embodiments, an amino acid with a hydrophobic side chain is (R)—$NH_2CH(CH_2CH_2CH_2CH_2CH_3)COOH$. In some embodiments, a hydrophobic side chain is —$CH_2R$ wherein R is optionally substituted phenyl. In some embodiments, R is phenyl. In some embodiments, R is phenyl substituted with one or more hydrocarbon group. In some embodiments, R is 4-phenylphenyl. In some embodiments, an amino acid with a hydrophobic side chain is $NH_2CH(CH_2$-4-phenylphenyl)COOH. In some embodiments, an amino acid with a hydrophobic side chain is (S)—$NH_2CH(CH_2$-4-phenylphenyl)COOH. In some embodiments, an amino acid with a hydrophobic side chain is (R)—$NH_2CH(CH_2$-4-phenylphenyl)COOH.

In some embodiments, an amino acid comprises a positively charged side chain (e.g., at physiological pH) as described herein. In some embodiments, such an amino acid comprises a basic nitrogen in its side chain. In some embodiments, such an amino acid is Arg, His or Lys. In some embodiments, such an amino acid is Arg. In some embodiments, such an amino acid is His. In some embodiments, such an amino acid is Lys.

In some embodiments, an amino acid comprises a negatively charged side chain (e.g., at physiological pH) as described herein. In some embodiments, such an amino acid comprises a —COOH in its side chain. In some embodiments, such an amino acid is Asp. In some embodiments, such an amino acid is Glu.

In some embodiments, an amino acid comprises a side chain comprising an aromatic group as described herein. In some embodiments, such an amino acid is Phe, Tyr, Trp, or His. In some embodiments, such an amino acid is Phe. In some embodiments, such an amino acid is Tyr. In some embodiments, such an amino acid is Trp. In some embodiments, such an amino acid is His. In some embodiments, such an amino acid is $NH_2$—$CH(CH_2$-4-phenylphenyl)-COOH. In some embodiments, such an amino acid is (S)—$NH_2$—$CH(CH_2$-4-phenylphenyl)-COOH. In some embodiments, such an amino acid is (R)—$NH_2$—$CH(CH_2$-4-phenylphenyl)-COOH.

In some embodiments, an amino acid is

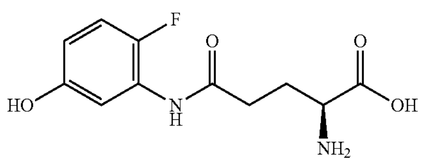 [SMILES: N[C@@H](CCC(=O)Nc1cc(O)ccc1F)C(=O)O]

or a salt thereof. In some embodiments, an amino acid is

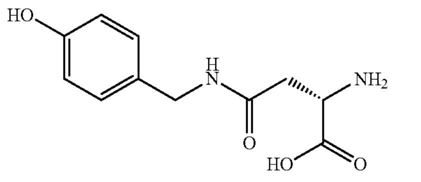 [SMILES: N[C@@H](CC(=O)NCc1ccc(O)cc1)C(=O)O]

or a salt thereof. In some embodiments, an amino acid is

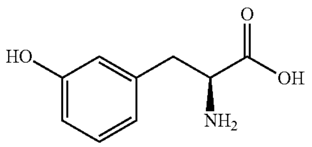 [SMILES: N[C@@H](Cc1cccc(O)c1)C(=O)O]

or a salt thereof. In some embodiments, an amino acid is

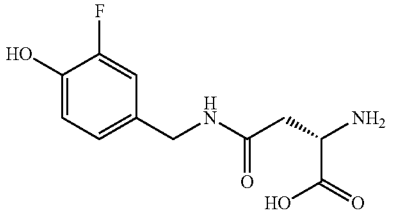 [SMILES: N[C@@H](CC(=O)NCc1ccc(O)c(F)c1)C(=O)O]

or a salt thereof. In some embodiments, an amino acid is

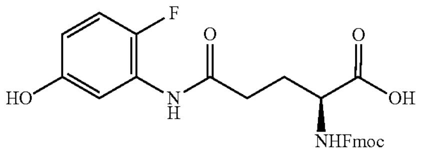

or a salt thereof. In some embodiments, an amino acid is

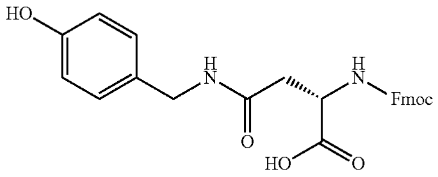

or a salt thereof. In some embodiments, an amino acid is

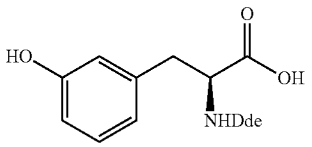

or a salt thereof. In some embodiments, an amino acid is

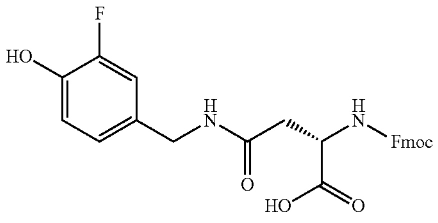

or a salt thereof. In some embodiments, a provided compound is

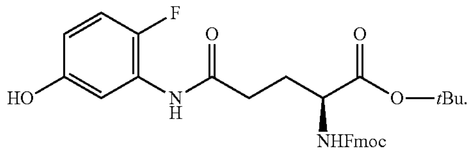

In some embodiments, the present disclosure provides polypeptide agents comprising one or more amino acid residues described in the present disclosure.

Reactive Group

In some embodiments, provided compounds, e.g., those useful as reaction partners, comprise reactive groups (e.g., RG). As exemplified herein, in many embodiments, in provided compounds reactive groups (e.g., RG) are located between first groups (e.g., LG) and moieties of interest (e.g., MOI), and are optionally and independently linked to first groups and moieties of interest via linkers. In some embodiments, RG is a reaction group as described herein.

In some embodiments, as demonstrated herein, reactive groups when utilized in compounds that comprise no target binding moieties react slowly and provide low level of, in some embodiments, substantially no conjugation of moieties of interest with target agents. As demonstrated herein, combination of reactive groups with target binding moieties in the same compounds, e.g., as in compounds of formula R-I or salts thereof, can, among other things, promote reactions between reactive groups and target agents, enhance reaction efficiency, reduce side reactions, and/or improve reaction selectivity (e.g., in terms of target sites wherein conjugation of moieties of interest with target agents occurs).

Figure 15:
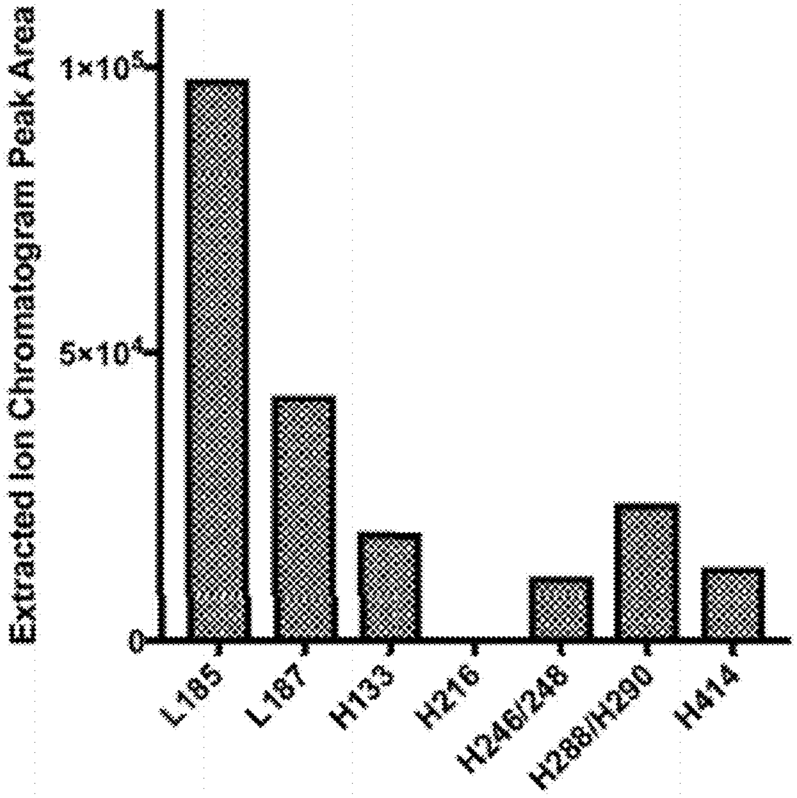
FIG. 15. Certain peptide mapping data of daratumumab conjugated with I-9 (containing no antibody binding moiety that binds to daratumumab) as examples. FITC DAR is 0.44.
Figure 16A:
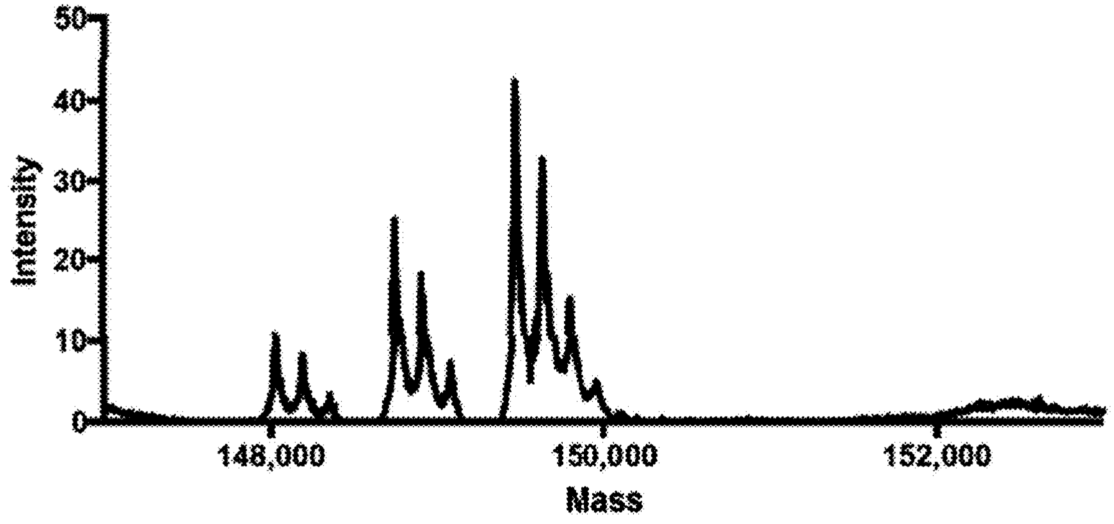
FIG. 16. Certain intact mass data of daratumumab conjugated with I-44 as examples. (a) Phosphate buffer saline, pH 8.2, 25° C., 20 h, 2.5 M eq I-44, FITC DAR 1.14. (b) Phosphate buffer saline, pH 7.4, 30° C., 20 h, 2.5 M eq I-44. FITC DAR 1.15. (c) Phosphate buffer saline, pH 7.4, 37 C, 20 h, 2.5 M eq I-44. FITC DAR 1.66. (d) Borate buffer pH 8.2 25 C, 20 h, 2.5 M eq I-44. FITC DAR 1.42. (e) Borate buffer pH 8.2 25 C, 20 h, 2.5 M eq I-44. FITC DAR 0.21.
Figure 16B:
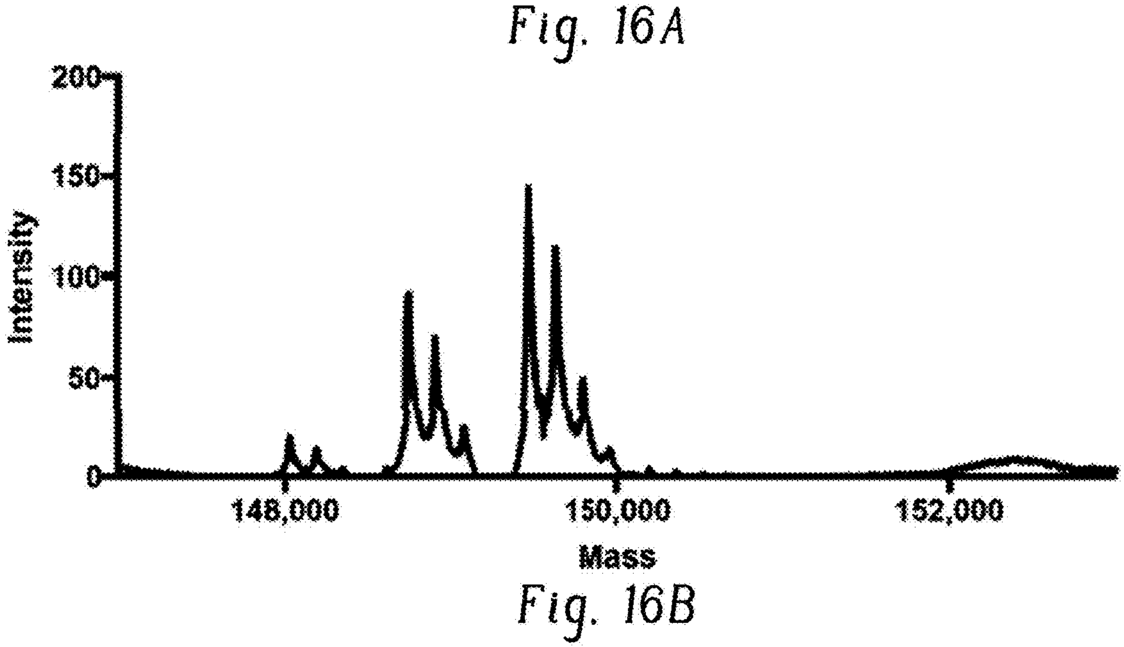
Figure 16C:
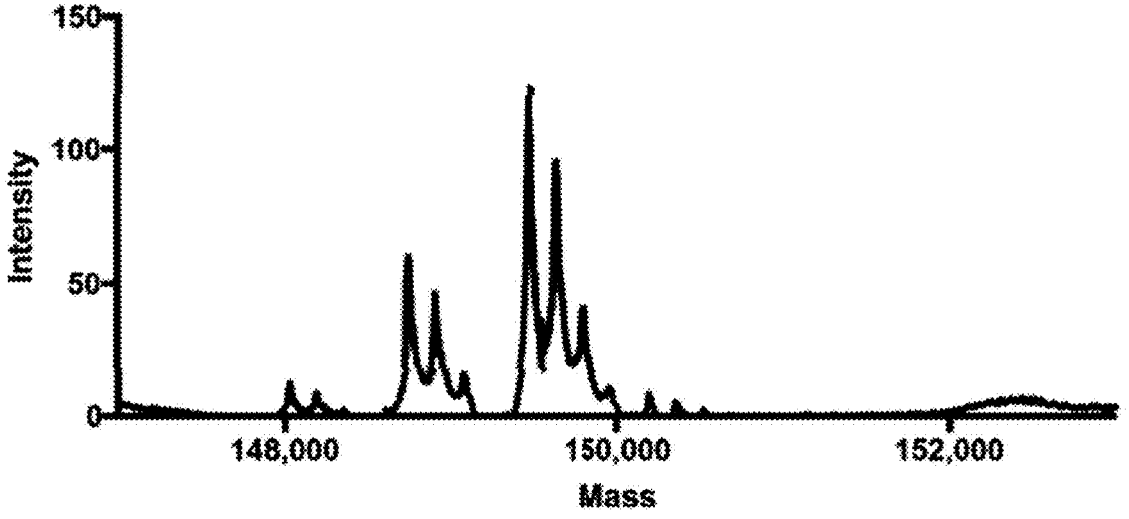
Figure 16D:
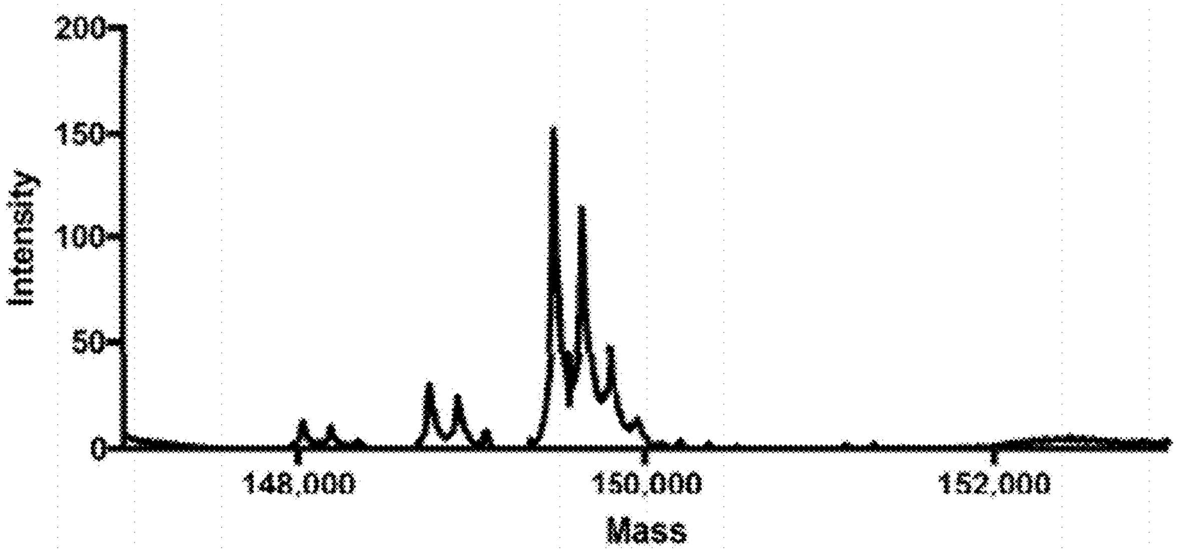
Figure 16E:
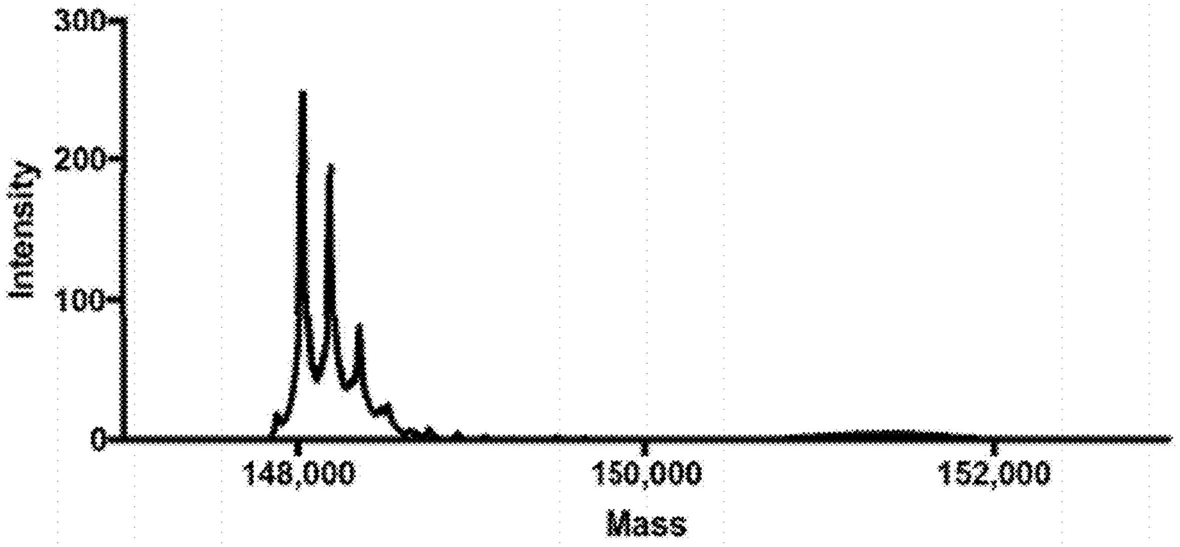

Reactive groups in provided compounds can react with various types of groups in target agents. In some embodiments, reactive groups in provided compounds selectively react with amino groups of target agents, e.g., —$NH_2$ groups on side chains of lysine residues of proteins. In some embodiments, reactive groups when utilized in provided compounds, e.g., those of formula R-I or salts thereof, selectively react with particular sites of target agents, e.g., as shown in examples herein, one or more of K246, K248, K288, K290, K317, etc. of IgG1, K251, K 253, etc. for IgG2, K239, K241 for IgG4, etc. In some embodiments, a site is K246 or K248 of an antibody heavy chain. In some embodiments, sites are K246 and/or K248 of an antibody heavy chain. In some embodiments, a site is K246 of an antibody heavy chain. In some embodiments, a site is K248 of an antibody heavy chain. In some embodiments, a site is K288 or K290 of an antibody heavy chain. In some embodiments, a site is K288 of an antibody heavy chain. In some embodiments, a site is K290 of an antibody heavy chain. In some embodiments, a site is K317. In some embodiments, a site is K414 of an antibody heavy chain. In some embodiments, a site is K185 of an antibody light chain. In some embodiments, a site is K187 of an antibody light chain. In some embodiments, sites are K251 and/or K253 of an IgG2 heavy chain. In some embodiments, a site is K251 of an IgG2 heavy chain. In some embodiments, a site is K253 of an IgG2 heavy chain. In some embodiments, sites are K239 and/or K241 of an IgG4 heavy chain. In some embodiments, a site is K239 of an IgG4 heavy chain. In some embodiments, a site is K241 of an IgG4 heavy chain. In some embodiments, conjugation selectively occurs at one or more heavy chain sites over light chain sites. In some embodiments, for technologies without target binding moieties, conjugation occurs at light chain sites more than heavy chain sites (e.g., see FIG. 15).

In some embodiments, a reactive group, e.g., RG, is or comprises an ester group. In some embodiments, a reactive group, e.g., RG, is or comprises an electrophilic group, e.g., a Michael acceptor.

In some embodiments, a reactive group, e.g., RG, is or comprises $-L^{RG1}-L^{RG2}-$, wherein each of $L^{RG1}$ and $L^{RG2}$ is independently L as described herein. In some embodiments, a reactive group, e.g., RG, is or comprises $-L^{LG4}-L^{RG1}-L^{RG2}-$, wherein each variable is as described herein. In some embodiments, a reactive group, e.g., RG, is or comprises $-L^{LG3}-L^{LG4}-L^{RG1}-L^{RG2}-$, wherein each variable is as described herein. In some embodiments, a reactive group, e.g., RG, is or comprises $-L^{LG2}-L^{LG3}-L^{LG4}-L^{RG1}-L^{RG2}-$, wherein each variable is as described herein. In some embodiments, a reactive group, e.g., RG, is or comprises $-L^{LG4}-L^{RG2}-$, wherein each variable is as described herein. In some embodiments, a reactive group, e.g., RG, is or comprises $-L^{LG3}-L^{LG4}-L^{RG2}-$, wherein each variable is as described herein. In some embodiments, a reactive group, e.g., RG, is or comprises $-L^{LG2}-L^{LG3}-L^{LG4}-L^{RG2}-$, wherein each variable is as described herein.

In some embodiments, as described herein, $L^{LG4}$ is —O—. In some embodiments, $L^{LG4}$ is —N(R)—. In some embodiments, $L^{LG4}$ is —NH—.

In some embodiments, as described herein, $L^{LG3}$ is or comprises an optionally substituted aryl ring. In some embodiments, $L^{LG3}$ is or comprises a phenyl ring. In some embodiments, an aryl or phenyl ring is substituted. In some embodiments, a substituent is a electron-withdrawing group as described herein, e.g., $-NO_2$, —F, etc.

In some embodiments, $L^{RG1}$ is a covalent bond. In some embodiments, $L^{RG1}$ is not a covalent bond. In some embodiments, $L^{RG1}$ is $-S(O)_2-$.

In some embodiments, $L^{RG2}$ is —C(O)—. In some embodiments, a reactive group is or comprises $-L^{LG4}-C(O)-$, wherein each variable is as described herein. In some embodiments, a reactive group is or comprises $-L^{LG3}-L^{LG4}-C(O)-$, wherein each variable is as described herein. In some embodiments, a reactive group is or comprises $-L^{LG2}-L^{LG3}-L^{LG4}-C(O)-$, wherein each variable is as described herein.

In some embodiments, $L^{RG2}$ is $-L^{RG3}-C(=CR^{RG1}R^{RG2})-CR^{RG3}R^{RG4}-$, wherein each of $R^{RG1}$, $R^{RG2}$, $R^{RG3}$ and $R^{RG4}$ is independently -L-R', and $L^{RG3}$ is —C(O)—, —C(O)O—, —C(O)N(R')—, —S(O)—, $-S(O)_2-$, —P(O)(OR')—, —P(O)(SR')—, or $-P(O)(N(R')_2)-$. In some embodiments, each of $R^{RG1}R^{RG2}$, $R^{RG3}$ and $R^{RG4}$ is independently R'. In some embodiments, one or more of $R^{RG1}$, $R^{RG2}$, $R^{RG3}$ and $R^{RG4}$ is independently —H. In some embodiments, $L^{RG3}$ is —C(O)—. In some embodiments, $L^{RG3}$ is —C(O)O—. In some embodiments, —O—, —N(R')—, etc. of $L^{RG3}$ is bonded to $L^{PM}$.

In some embodiments, $R^{RG1}$ is —H. In some embodiments, $R^{RG3}$ is —H.

In some embodiments, $L^{RG2}$ is optionally substituted $-L^{RG3}-C(=CHR^{RG2})-CHR^{RG4}-$, wherein each variable is as described herein.

In some embodiments, $R^{RG2}$ and $R^{RG4}$ are taken together with their intervening atoms to form an optionally substituted ring as described herein. In some embodiments, a formed ring is an optionally substituted 3-10 membered monocyclic or bicyclic ring having 0-5 heteroatoms. In some embodiments, a formed ring is an optionally substituted 3-10 membered cycloaliphatic ring. In some embodiments, a formed ring is an optionally substituted 3-8 membered cycloaliphatic ring. In some embodiments, a formed ring is an optionally substituted 5-8 membered cycloaliphatic ring. In some embodiments, a formed ring is an optionally substituted 5-membered cycloaliphatic ring. In some embodiments, a formed ring is an optionally substituted 6-membered cycloaliphatic ring. In some embodiments, a formed ring is an optionally substituted 7-membered cycloaliphatic ring. In some embodiments, a formed ring is substituted. In some embodiments, a formed ring is not substituted. In some embodiments, a formed ring contains no additional unsaturation in addition to the double bond in $C(=CHR^{RG2})$ or $C(=CR^{RG1}R^{RG2})$.

In some embodiments, $-C(=CHR^{RG2})-CHR^{RG4}$ or $-C(=CR^{RG1}R^{RG2})-CR^{RG3}R^{RG4}$ is optionally substituted

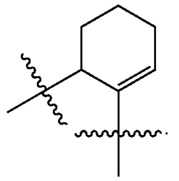 [SMILES: *C1=CCCCC1*]

In some embodiments, $-C(=CHR^{RG2})-CHR^{RG4}$ or $-C(=CR^{RG1}R^{RG2})-CR^{RG3}R^{RG4}$ is

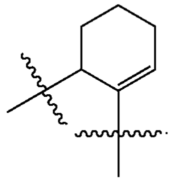 [SMILES: *C1=CCCCC1*]

In some embodiments, $-C(=CHR^{RG2})CHR^{RG4}-L-$ or $-C(=CR^{RG1}R^{RG2})-CR^{RG3}R^{RG4}-L^{RG3}-$ is optionally substituted

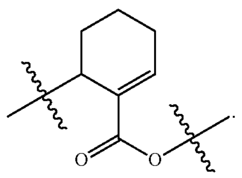 [SMILES: *OC(=O)C1=CCCCC1*]

In some embodiments, $-C(=CHR^{RG2})-CHR^{RG4}-L^{RG3}-$ or $-C(=CR^{RG1}R^{RG2})-CR^{RG3}R^{RG4}-L^{RG3}-$ is

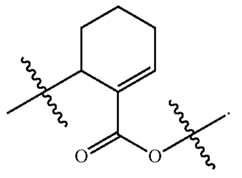

In some embodiments, $-L^{RG1}-C(=CHR^{RG2})-CHR^{RG4}-L^{RG3}-$ or $-L^{RG1}-C(=CR^{RG1}R^{RG2})-CR^{RG3}R^{RG4}-L^{RG3}-$ is optionally substituted

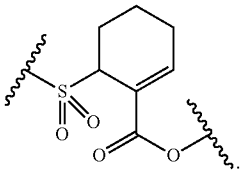 [SMILES: *OC(=O)C1=CCCCC1S(*)(=O)=O]

In some embodiments, $-L^{RG1}-C(=CHR^{RG2})-CHR^{RG4}-L^{RG3}-$ or $-L^{RG1}-C(=CR^{RG1}R^{RG2})-CR^{RG3}R^{RG4}-L^{RG3}-$ is optionally substituted

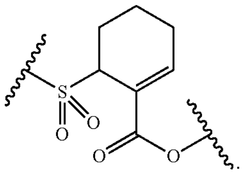 [SMILES: *OC(=O)C1=CCCCC1S(*)(=O)=O]

In some embodiments, a reactive group is a structure selected from the Table below. In some embodiments, $-L^{LG2}-L^{LG3}-L^{LG4}-L^{RG1}-L^{RG2}-$ is a structure selected from the Table below. In some embodiments, $-L^{LG2}-L^{LG3}-L^{LG4}-RG-$ is a structure selected from the Table below.

TABLE RG-1

| Certain structures as examples. |
| --- |
| 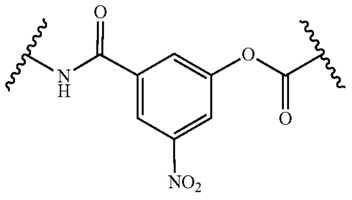 [SMILES: *NC(=O)c1cc(OC(*)=O)cc([N+](=O)[O-])c1] |
| 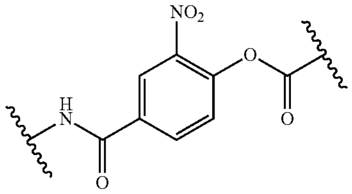 [SMILES: *NC(=O)c1ccc(OC(*)=O)c([N+](=O)[O-])c1] |
| 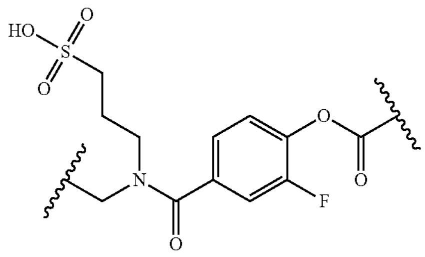 [SMILES: *CN(CCCS(=O)(=O)O)C(=O)c1ccc(OC(*)=O)c(F)c1] |
| 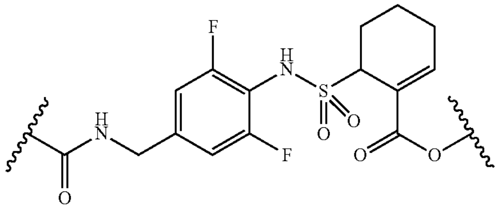 [SMILES: *OC(=O)C1=CCCCC1S(=O)(=O)Nc1c(F)cc(CNC(*)=O)cc1F] |

TABLE RG-1-continued

| Certain structures as examples. |
| --- |
| 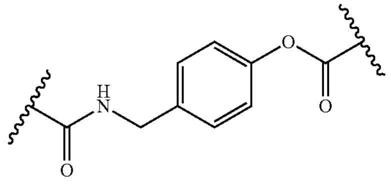 [SMILES: *C(=O)NCc1ccc(OC(*)=O)cc1] |
| 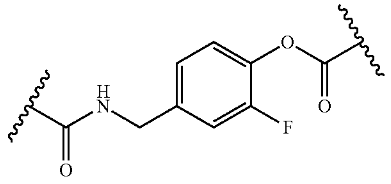 [SMILES: *C(=O)NCc1ccc(OC(*)=O)c(F)c1] |
| 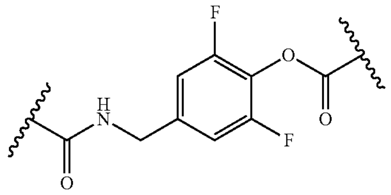 [SMILES: *C(=O)NCc1cc(F)c(OC(*)=O)c(F)c1] |
| 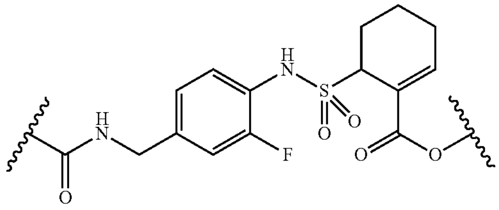 [SMILES: *OC(=O)C1=CCCCC1S(=O)(=O)Nc1ccc(CNC(*)=O)cc1F] |
| 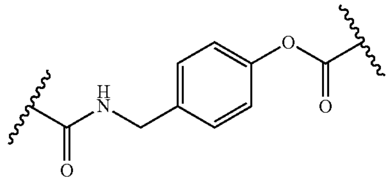 [SMILES: *C(=O)NCc1ccc(OC(*)=O)cc1] |
| 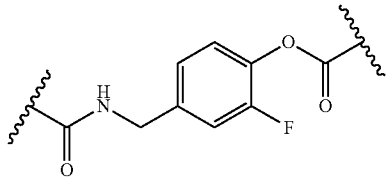 [SMILES: *C(=O)NCc1ccc(OC(*)=O)c(F)c1] |
| 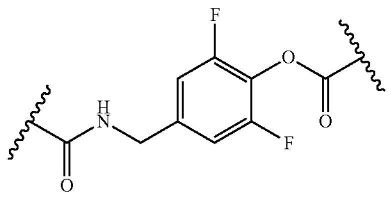 [SMILES: *C(=O)NCc1cc(F)c(OC(*)=O)c(F)c1] |

TABLE RG-1-continued
| Certain structures as examples. |
| --- |
| 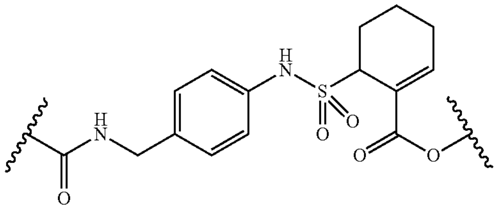 [SMILES: *OC(=O)C1=CCCCC1S(=O)(=O)Nc1ccc(CNC(*)=O)cc1] |
| 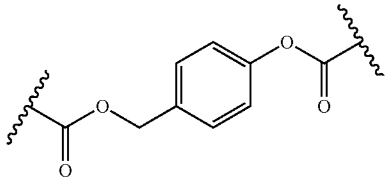 [SMILES: *C(=O)OCc1ccc(OC(*)=O)cc1] |
| 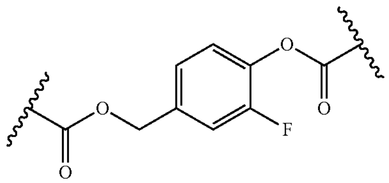 [SMILES: *C(=O)OCc1ccc(OC(*)=O)c(F)c1] |
| 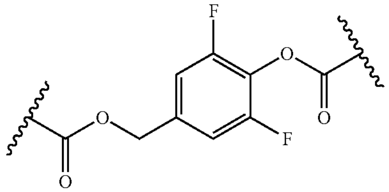 [SMILES: *C(=O)OCc1cc(F)c(OC(*)=O)c(F)c1] |
| 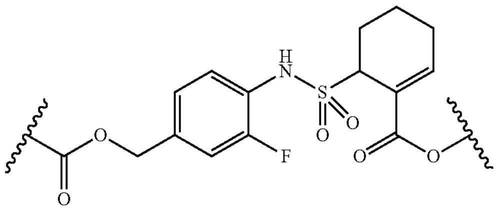 [SMILES: *OC(=O)C1=CCCCC1S(=O)(=O)Nc1ccc(COC(*)=O)cc1F] |
| 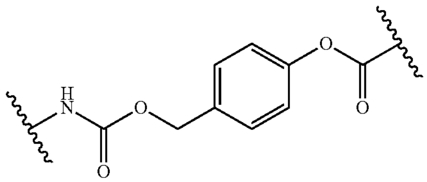 [SMILES: *NC(=O)OCc1ccc(OC(*)=O)cc1] |
| 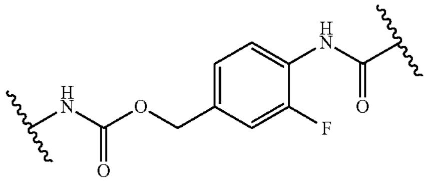 [SMILES: *NC(=O)OCc1ccc(NC(*)=O)c(F)c1] |
TABLE RG-1-continued
| Certain structures as examples. |
| --- |
| 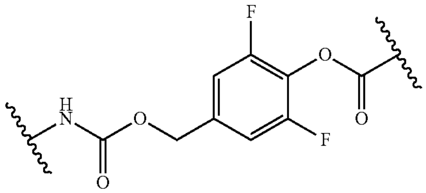 [SMILES: *NC(=O)OCc1cc(F)c(OC(*)=O)c(F)c1] |
| 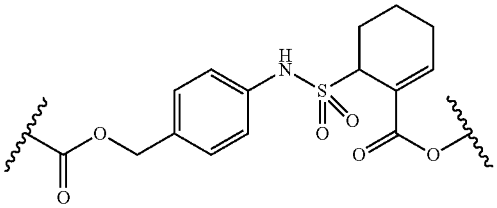 [SMILES: *OC(=O)C1=CCCCC1S(=O)(=O)Nc1ccc(COC(*)=O)cc1] |
| 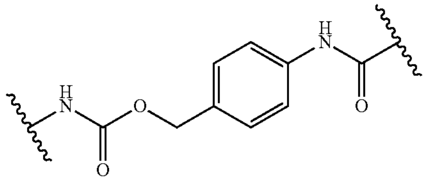 [SMILES: *NC(=O)OCc1ccc(NC(*)=O)cc1] |
| 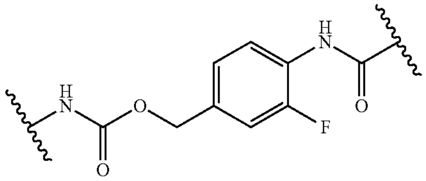 [SMILES: *NC(=O)OCc1ccc(NC(*)=O)c(F)c1] |
| 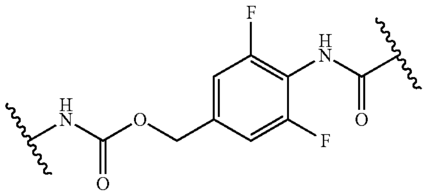 [SMILES: *NC(=O)OCc1cc(F)c(NC(*)=O)c(F)c1] |
| 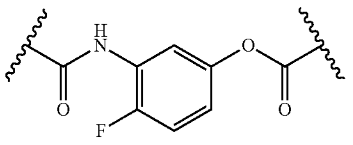 [SMILES: *C(=O)Nc1cc(OC(*)=O)ccc1F] |
| 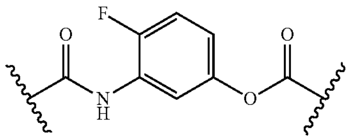 [SMILES: *C(=O)Nc1cc(OC(*)=O)ccc1F] |
| 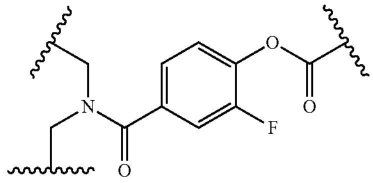 [SMILES: *CN(C*)C(=O)c1ccc(OC(*)=O)c(F)c1] |
| and |

TABLE RG-1-continued

| Certain structures as examples. |
|---|
| 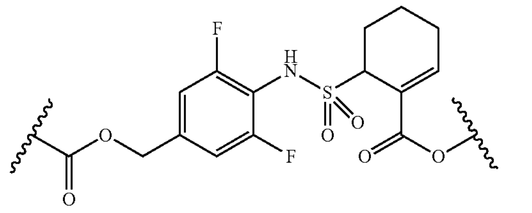 [SMILES: *OC(=O)C1=CCCCC1S(=O)(=O)Nc1c(F)cc(COC(*)=O)cc1F] |

In some embodiments, $-L^{LG4}-L^{RG2}-$ is —O—C(O)—. In some embodiments, $-L^{LG4}-L^{RG2}$ is —S—C(O)—. In some embodiments, $-L^{LG4}-L^{RG1}-L^{RG2}-$ is —S—C(O)—.

In some embodiments, $-L^{LG4}-L^{RG2}-$ is —N(−)—C(O)—, wherein N is a ring atom of an optionally substituted heteroaryl ring. In some embodiments, $-L^{LG4}-L^{RG2}-$ is —N(−)—C(O)—, wherein N is a ring atom of $L^{LG4}$ which is or comprises an optionally substituted heteroaryl ring. In some embodiments, $-L^{LG4}-L^{RG2}-$ is —N(−)—C(O)—O—, wherein N is a ring atom of $L^{LG4}$ which is or comprises an optionally substituted heteroaryl ring.

In some embodiments, $L^{RG2}$ is optionally substituted —$CH_2$—C(O)—, wherein —$CH_2$— is bonded to an electron-withdrawing group comprising or connected to a target binding moiety. In some embodiments, $L^{RG2}$ is optionally substituted —$CH_2$— bonded to an electron-withdrawing group comprising or connected to a target binding moiety. In some embodiments, $L^{RG1}$ is an electron-withdrawing group. In some embodiments, $L^{RG1}$ is —C(O)—. In some embodiments, $L^{RG1}$ is —S(O)—. In some embodiments, $L^{RG1}$ is —$S(O)_2$—. In some embodiments, $L^{RG1}$ is —P(O(OR)—. In some embodiments, $L^{RG1}$ is —P(O(SR)—. In some embodiments, $L^{RG1}$ is —P(O(N(R)$_2$)—. In some embodiments, $L^{RG1}$ is —OP(O(OR)—. In some embodiments, $L^{RG1}$ is —OP(O(SR)—. In some embodiments, $L^{RG1}$ is —OP(O(N(R)$_2$)—.

In some embodiments, $L^{RG2}$ is optionally substituted —$CH_2$—C(O)—, wherein —$CH_2$— is bonded to a leaving group comprising or connected to a target binding moiety. In some embodiments, $L^{RG2}$ is optionally substituted —$CH_2$— bonded to a leaving group comprising or connected to a target binding moiety. In some embodiments, $L^{RG1}$ is —O—C(O)—. In some embodiments, $L^{RG1}$ is —OS(O)$_2$—. In some embodiments, $L^{RG1}$ is —OP(O(OR)—. In some embodiments, $L^{RG1}$ is —OP(O(SR)—. In some embodiments, $L^{RG1}$ is —OP(O(N(R)$_2$)—.

In some embodiments, a reactive group reacts with an amino group of a target agent. In some embodiments, an amino group is —$NH_2$ of the side chain of a lysine residue.

In some embodiments, a target agent is a protein agent. In some embodiments, a target agent is an antibody agent. In some embodiments, a reactive group reacts with an amino acid residue of such protein or antibody agent. In some embodiments, an amino acid residue is a lysine residue. In some embodiments, a reactive group reacts with —$NH_2$ of the side chain of a lysine residue. In some embodiments, a reactive group is or comprises —C(O)—O—, it reacts with —$NH_2$ (e.g., of the side chain of a lysine residue), and forms an amide group —C(O)—O— with the —$NH_2$.

Linker Moieties

In some embodiments, moieties are optionally connected to each other through linker moieties. For example, in some embodiments, a reactive group, e.g., RG, is connected to a moiety of interest, e.g., MOI, through a linker, e.g., $L^{RM}$. In some embodiments, a moiety, e.g., LG, may also comprise one or more linkers, e.g., $L^{LG1}$, $L^{LG2}$, $L^{LG3}$, $L^{LG4}$, etc., to link various portions. In some embodiments, $L^{LG}$ is a linker moiety described herein. In some embodiments, $L^{LG1}$ is a linker moiety described herein. In some embodiments, $L^{LG2}$ is a linker moiety described herein. In some embodiments, $L^{LG3}$ is a linker moiety described herein. In some embodiments, $L^{LG4}$ is a linker moiety described herein. In some embodiments, $L^{RM}$ is a linker moiety described herein. In some embodiments, $L^{PM}$ is L as described herein. In some embodiments, $L^{PM}$ is a linker moiety described herein. In some embodiments, $L^{PM}$ is L as described herein.

Linker moieties of various types and/or for various purposes, e.g., those utilized in antibody-drug conjugates, etc., may be utilized in accordance with the present disclosure.

Linker moieties can be either bivalent or polyvalent depending on how they are used. In some embodiments, a linker moiety is bivalent. In some embodiments, a linker is polyvalent and connecting more than two moieties.

In some embodiments, a linker moiety, e.g., $L^z$ (wherein z represents superscript text; e.g., $L^{PM}$, $L^{RM}$, $L^{LG}$, $L^{LG1}$, etc.), is or comprises L.

In some embodiments, L is a covalent bond, or a bivalent or polyvalent optionally substituted, linear or branched $C_{1-100}$ group comprising one or more aliphatic, aryl, heteroaliphatic having 1-20 heteroatoms, heteroaromatic having 1-20 heteroatoms, or any combinations thereof, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue, or —[(—O—C(R')$_2$—C(R')$_2$—)$_n$]—, wherein n is 1-20. In some embodiments, each amino acid residue is independently a residue of an amino acid having the structure of formula A-I or a salt thereof. In some embodiments, each amino acid residue independently has the structure of —N($R^{a1}$)-$L^{a1}$-C($R^{a2}$)($R^{a3}$)-$L^{a2}$-CO— or a salt form thereof.

In some embodiments, L is bivalent. In some embodiments, L is a covalent bond.

In some embodiments, L is a bivalent or optionally substituted, linear or branched group selected from $C_{1-00}$ aliphatic and $C_{1-100}$ heteroaliphatic having 1-50 heteroatoms, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—C(R')$_2$—C(R')$_2$—)$_n$]—.

In some embodiments, L is a bivalent or optionally substituted, linear or branched group selected from $C_{1-20}$ aliphatic and $C_{1-20}$ heteroaliphatic having 1-10 heteroatoms, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—C(R')$_2$—C(R')$_2$—)$_n$]—.

In some embodiments, L is a bivalent or optionally substituted, linear or branched group selected from $C_{1-20}$ aliphatic wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—C(R')$_2$—C(R')$_2$—)$_n$]—.

In some embodiments, L is a bivalent or optionally substituted, linear or branched group selected from $C_{1-20}$ aliphatic wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, an amino acid residue or —[(—O—C(R')$_2$—C(R')$_2$—)$_n$]—.

In some embodiments, L is a bivalent or optionally substituted, linear or branched group selected from $C_{1-20}$ aliphatic wherein one or more methylene units of the group are optionally and independently replaced with —C≡C—, -Cy-, —C(R')$_2$—, —O—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, an amino acid residue or —[(—O—C(R')$_2$—C(R')$_2$—)$_n$]—.

In some embodiments, a linker moiety, e.g., L, $L^{PM}$ $L^{RM}$, etc., comprises an acidic group, e.g., —S(O)$_2$OH.

In some embodiments, L is or comprises —[(—O—C(R')$_2$—C(R')$_2$—)$_n$]—. In some embodiments, L is or comprises —[(—O—CH$_2$—CH$_2$—)$_n$]—. In some embodiments, L is —[(—CH$_2$—CH$_2$—O)$_6$]—CH$_2$—CH$_2$—. In some embodiments, L is —[(—CH$_2$—CH$_2$—O)$_8$]—CH$_2$—CH$_2$—. In some embodiments, —CH$_2$—CH$_2$—O— is bonded to a target binding moiety at a —CH$_2$—. In some embodiments, —CH$_2$—CH$_2$—O— is bonded to a moiety of interest at a —CH$_2$—. In some embodiments, $L^{PM}$ is such L as described herein. In some embodiments, $L^{RM}$ is such L as described herein.

In some embodiments, a linker moiety is trivalent or polyvalent. For example, in some embodiments, a linker moiety is L as described herein and L is trivalent or polyvalent. In some embodiments, L is trivalent. For example, in some embodiments, L is —CH$_2$—N(—CH$_2$—)—C(O)—.

In some embodiments, L is or comprises a bioorthogonal or enzymatic reaction product moiety. In some embodiments, L is or comprise an optionally substituted triazole moiety (which is optionally part of a bi- or poly-cyclic ring system). In some embodiments, L is or comprises LPXTG. In some embodiments, L is or comprises LPETG. In some embodiments, L is or comprises LPXT(G)n, wherein n is 1, 2, 3, 4, 5, 6, 7, 8, 9, or 10. In some embodiments, L is or comprises LPET(G)n, wherein n is 1, 2, 3, 4, 5, 6, 7, 8, 9, or 10.

In some embodiments, provided compounds/agents (e.g., reaction partners, agents (e.g., products of provided methods and/or steps therein) comprise no cleavable groups (except one or more reactive groups and/or moieties therein) that could be cleaved under conditions that would not substantially damage or transform target agents and/or agents comprising target agent moieties (e.g., conjugation products comprising target agent moieties). In some embodiments, provided compounds/agents (e.g., reaction partners, agents (e.g., products of provided methods and/or steps therein) comprise no cleavable groups (except one or more reactive groups and/or moieties therein) that could be cleaved under conditions that would not render target agents and/or agents comprising target agent moieties (e.g., conjugation products comprising target agent moieties) for one or more uses (e.g., for use as diagnostic agents, therapeutic agents, etc.). In some embodiments, provided compounds/agents (e.g., reaction partners, agents (e.g., products of provided methods and/or steps therein) comprise no cleavable groups which can be cleaved under bioorthogonal conditions. In some embodiments, provided compounds/agents (e.g., reaction partners, agents (e.g., products of provided methods and/or steps therein) comprise no cleavable groups which can be cleaved without substantively damaging and/or transforming proteins. In some embodiments, a cleavable group is or comprises —S—, —S—S—, —S-Cy-, —C(O)—O—, —C(O)—S—, acetal moiety, —N═N—, imine moiety, —CH═N—, —P(O)(OR)O— moiety, —P(O)(OR)—N(R)—moiety, —C(O)—CH$_2$—C(COOH)═CHC(O)— moiety, —CHOH—CHOH— moiety, —Se— moiety, Si bonded to two oxygen atoms, —C(O)—CH$_2$— wherein the —CH$_2$— is bonded to a benzylic carbon wherein the phenyl ring of the benzyl group is substituted with —NO$_2$—, —C(O)—CH$_2$— wherein the —CH$_2$— is bonded to a benzylic carbon wherein the phenyl ring of the benzyl group is substituted with —NO$_2$— at o-position, or —C(O)—N(−)— moiety, wherein N is a ring atom of a heteroaryl ring. In some embodiments, a cleavable group is or comprises —S—S—, —S—CH$_2$-Cy-, —S-Cy-, —C(O)—O—, —C(O)—S—, acetal moiety, —N═N—, imine moiety, —CH═N—, —P(O)(OR)O— moiety, —P(O)(OR)—N(R)— moiety, —C(O)—CH$_2$—C(COOH)═CHC(O)— moiety, —CHOH—CHOH— moiety, —Se— moiety, Si bonded to two oxygen atoms, —C(O)—CH$_2$— wherein the —CH$_2$— is bonded to a benzylic carbon wherein the phenyl ring of the benzyl group is substituted with —NO$_2$—, —C(O)—CH$_2$— wherein the —CH$_2$— is bonded to a benzylic carbon wherein the phenyl ring of the benzyl group is substituted with —NO$_2$— at o-position, or —C(O)—N(−)— moiety, wherein N is a ring atom of a heteroaryl ring. In some embodiments, a cleavage group is a cleavable linker or a cleavable portion described in WO 2018199337A1 or AU 2018259856, the cleavable linkers and cleavable portions of each of which is incorporated herein by reference. In some embodiments, a cleavage group is:

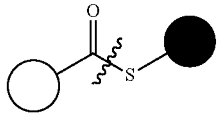

-continued

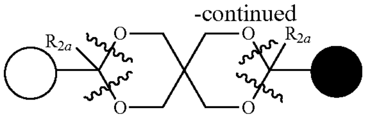
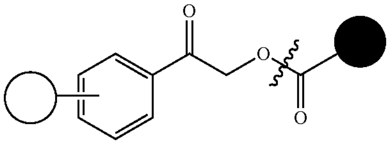
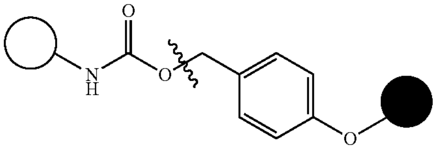
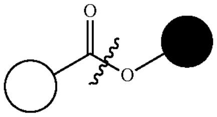
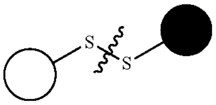
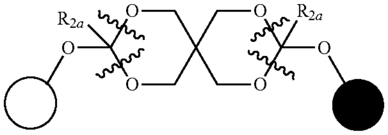
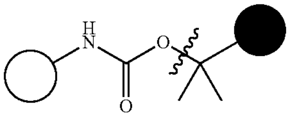
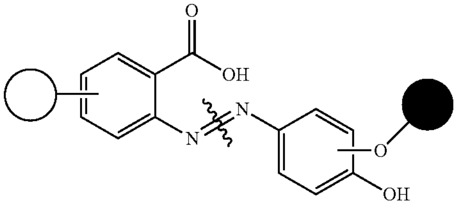
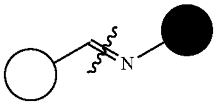
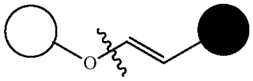
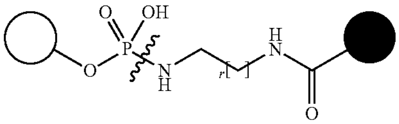
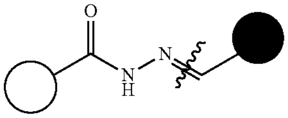
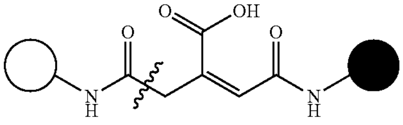
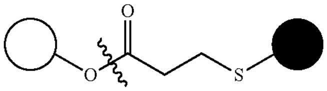
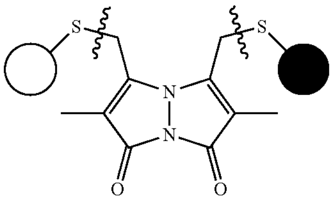

-continued

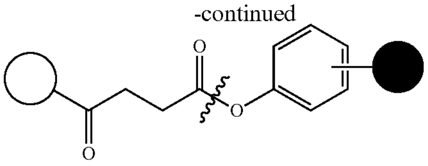
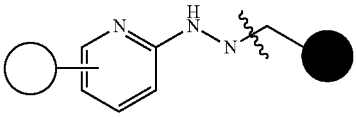
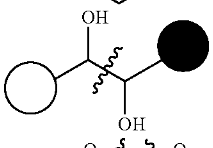
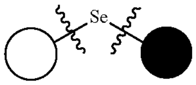
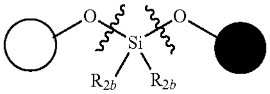
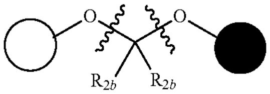
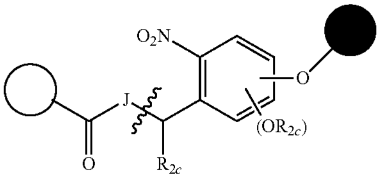
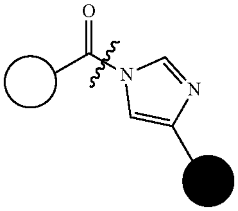
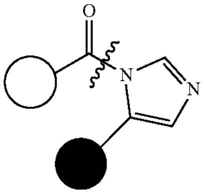
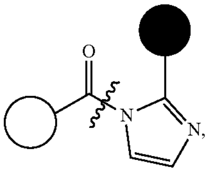

wherein:

a wavy line orthogonal to the bond indicates a potential cleavage site, $R^{2a}$, $R^{2b}$ and $R^{2c}$ are the same or different and each is independently:

(i) a hydrogen atom or a halogen atom;

(ii) a monovalent hydrocarbon group;

(iii) aralkyl;

(iv) a monovalent heterocyclic group;

(v) $R_c$—O—, $R_c$—C(O)—, $R_c$—O—C(O)—, or $R_c$—C(O)—O—, wherein $R_c$ is hydrogen or a monovalent hydrocarbon group;

(vi) —$NR_dR_e$, —$NR_dR_e$—C(O)—, —$NR_dR_e$—C(O)O—, —$NR_d$—C(O)—, —$NR_d$—C(O)O—, or $R_d$—C(O)—$NR_e$—, wherein $R_d$ and $R_e$ are the same or different and each is a hydrogen atom or a monovalent hydrocarbon group; or (vii) selected from a group consisting of a nitro group, a sulfuric acid group, a sulfonic acid group, a cyano group, and a carboxyl group;

J is —$CH_2$—, —O—, or —S—;

r is any integer of 1 to 4;

white circle and black circle are independently a bond connect to other moieties;

In some embodiments, a linker moiety does not contain a cleavage group above. In some embodiments, a linker moiety does not contain one or more or any of the following moieties: —S—, —S—S—, —S—$CH_2$-Cy-, —S-Cy-, —C(O)—O—, —C(O)—S—, acetal moiety, —N═N—, imine moiety, —CH═N—, —P(O)(OR)O— moiety, —P(O)(OR)—N(R)— moiety, —C(O)—$CH_2$—C(COOH)═CHC(O)— moiety, —CHOH—CHOH— moiety, —Se— moiety, Si bonded to two oxygen atoms, —C(O)—$CH_2$— wherein the —$CH_2$— is bonded to a benzylic carbon wherein the phenyl ring of the benzyl group is substituted with —$NO_2$—, —C(O)—$CH_2$— wherein the —$CH_2$— is bonded to a benzylic carbon wherein the phenyl ring of the benzyl group is substituted with —$NO_2$— at o-position, or —C(O)—N(−)— moiety, wherein N is a ring atom of a heteroaryl ring. In some embodiments, a linker moiety does not contain one or more or any of the following moieties: —S—S—, —S—$CH_2$-Cy-, —S-Cy-, —C(O)—O—, —C(O)—S—, acetal moiety, —N═N—, imine moiety, —CH═N—, —P(O)(OR)O— moiety, —P(O)(OR)—N(R)— moiety, —C(O)—$CH_2$—C(COOH)═CHC(O)— moiety, —CHOH—CHOH— moiety, —Se— moiety, Si bonded to two oxygen atoms, —C(O)—$CH_2$— wherein the —$CH_2$— is bonded to a benzylic carbon wherein the phenyl ring of the benzyl group is substituted with —$NO_2$—, —C(O)—$CH_2$— wherein the —$CH_2$— is bonded to a benzylic carbon wherein the phenyl ring of the benzyl group is substituted with —$NO_2$— at o-position, or —C(O)—N(−)— moiety, wherein N is a ring atom of a heteroaryl ring. In some embodiments, a linker moiety comprises no —S—. In some embodiments, a linker moiety comprises no —S—S— (optionally except a disulfide moiety formed by two amino acid residues, in some embodiments, optionally except a disulfide moiety formed by two cysteine residues). In some embodiments, a linker moiety comprises no —S-Cy-. In some embodiments, a linker moiety comprises no —S—$CH_2$-Cy-. In some embodiments, a linker moiety comprises no —C(O)—O—. In some embodiments, a linker moiety comprises no —C(O)—S—. In some embodiments, a linker moiety comprises no acetal moiety. In some embodiments, a linker moiety comprises no —N═N—. In some embodiments, a linker moiety comprises no imine moiety. In some embodiments, a linker moiety comprises no —CH═N— (optionally except in a ring, in some embodiments, optionally except in a heteroaryl ring). In some embodiments, a linker moiety comprises no —P(O)(OR)O— moiety. In some embodiments, a linker moiety comprises no —P(O)(OR)—N(R)—moiety. In some embodiments, a linker moiety comprises no —C(O)—$CH_2$—C(COOH)═CHC(O)— moiety. In some embodiments, a linker moiety comprises no —CHOH—CHOH— moiety. In some embodiments, a linker moiety comprises no —Se— moiety. In some embodiments, a linker moiety comprises no Si bonded to two oxygen atoms. In some embodiments, a linker moiety comprises no —C(O)—$CH_2$—, wherein the —$CH_2$— is bonded to a benzylic carbon, wherein the phenyl ring of the benzyl group is substituted with —$NO_2$—. In some embodiments, a linker moiety comprises no —C(O)—$CH_2$—, wherein the —$CH_2$— is bonded to a benzylic carbon, wherein the phenyl ring of the benzyl group is substituted with —$NO_2$— at o-position. In some embodiments, a linker moiety comprise no —C(O)—N(−)— moiety, wherein N is a ring atom of a heteroaryl ring. In some embodiments, a linker moiety does not contain any of these groups. In some embodiments, $L^{RM}$ is such a linker moiety. In some embodiments, $L^{PM}$ is such a linker moiety. In some embodiments, $L^{LG}$ is such a linker moiety. In some embodiments, an agent of the present disclosure does not contain one or more or all of such moieties.

In some embodiments, L is a covalent bond. In some embodiments, L is a bivalent optionally substituted, linear or branched $C_{1-100}$ aliphatic group wherein one or more methylene units of the group are optionally and independently replaced. In some embodiments, L is a bivalent optionally substituted, linear or branched $C_{6-100}$ arylaliphatic group wherein one or more methylene units of the group are optionally and independently replaced. In some embodiments, L is a bivalent optionally substituted, linear or branched $C_{5-100}$ heteroarylaliphatic group having 1-20 heteroatoms wherein one or more methylene units of the group are optionally and independently replaced. In some embodiments, L is a bivalent optionally substituted, linear or branched $C_{1-100}$ heteroaliphatic group having 1-20 heteroatoms wherein one or more methylene units of the group are optionally and independently replaced.

In some embodiments, a linker moiety (e.g., L) is or comprises one or more (e.g., 1, 2, 3, 4, 5, 6, 7, 8, 9, 10, 11, 12, 13, 14, 15, 16, 17, 18, 19, 20 or more) polyethylene glycol units. In some embodiments, a linker moiety is or comprises —$(CH_2CH_2O)_n$—, wherein n is as described in the present disclosure. In some embodiments, one or more methylene units of L are independently replaced with —$(CH_2CH_2O)_n$—.

As described herein, in some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

In some embodiments, a linker moiety (e.g., L) is or comprises one or more (e.g., 1, 2, 3, 4, 5, 6, 7, 8, 9, 10, 11, 12, 13, 14, 15, 16, 17, 18, 19, 20 or more) amino acid residues. As used in the present disclosure, "one or more" can be 1-100, 1-50, 1-40, 1-30, 1-20, 1-10, 1-5, 1, 2, 3, 4, 5, 6, 7, 8, 9, 10, 11, 12, 13, 14, 15, 16, 17, 18, 19, or 20 or more. In some embodiments, one or more methylene units of L are independently replaced with an amino acid residue. In some embodiments, one or more methylene units of L are independently replaced with an amino acid residue, wherein the amino acid residue is of an amino acid of formula A-I or a salt thereof. In some embodiments, one or more methylene units of L are independently replaced with an amino acid residue, wherein each amino acid residue independently has the structure of —N($R^{a1}$)-$L^{a1}$-C($R^{a2}$)($R^{a3}$)-$L^{a2}$-CO— or a salt form thereof.

In some embodiments, a linker moiety comprises one or more moieties, e.g., amino, carbonyl, etc., that can be utilized for connection with other moieties. In some embodiments, a linker moiety comprises one or more —NR'—, wherein R' is as described in the present disclosure. In some embodiments, —NR'— improves solubility. In some embodiments, —NR'— serves as connection points to another moiety. In some embodiments, R' is —H. In some embodiments, one or more methylene units of L are independently replaced with —NR'—, wherein R' is as described in the present disclosure.

In some embodiments, a linker moiety, e.g., L, comprises a —C(O)— group, which can be utilized for connections with a moiety. In some embodiments, one or more methylene units of L are independently replaced with —C(O)—.

In some embodiments, a linker moiety, e.g., L, comprises a —NR'— group, which can be utilized for connections with a moiety. In some embodiments, one or more methylene units of L are independently replaced with —N(R')—.

In some embodiments, a linker moiety, e.g., L, comprises a —C(O)NR'— group, which can be utilized for connections with a moiety. In some embodiments, one or more methylene units of L are independently replaced with —C(O)N(R')—.

In some embodiments, a linker moiety, e.g., L, comprises a —$C(R')_2$— group. In some embodiments, one or more methylene units of L are independently replaced with —$C(R')_2$—. In some embodiments, —$C(R')_2$— is —CHR'—. In some embodiments, R' is —$(CH_2)_2C(O)NH(CH_2)_{11}COOH$. In some embodiments, R' is —$(CH_2)_2COOH$. In some embodiments, R' is —COOH.

In some embodiments, a linker moiety is or comprises one or more ring moieties, e.g., one or more methylene units of L are replaced with -Cy-. In some embodiments, a linker moiety, e.g., L, comprises an aryl ring. In some embodiments, a linker moiety, e.g., L, comprises an heteroaryl ring. In some embodiments, a linker moiety, e.g., L, comprises an aliphatic ring. In some embodiments, a linker moiety, e.g., L, comprises an heterocyclyl ring. In some embodiments, a linker moiety, e.g., L, comprises a polycyclic ring. In some embodiments, a ring in a linker moiety, e.g., L, is 3-20 membered. In some embodiments, a ring is 5-membered. In some embodiments, a ring is 6-membered. In some embodiments, a ring in a linker is product of a cycloaddition reaction (e.g., click chemistry, and variants thereof) utilized to link different moieties together.

In some embodiments, a linker moiety (e.g., L) is or comprises

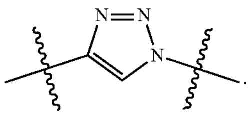 [SMILES: *c1cn(*)nn1]

In some embodiments, a methylene unit of L is replaced with

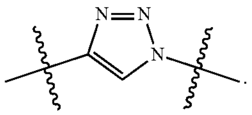 [SMILES: *c1cn(*)nn1]

In some embodiments, a methylene unit of L is replaced with -Cy-. In some embodiments, -Cy- is

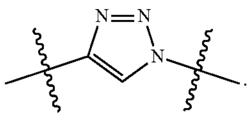 [SMILES: *c1cn(*)nn1]

In some embodiments, a linker moiety (e.g., L) is or comprises -Cy-. In some embodiments, a methylene unit of L is replaced with -Cy-. In some embodiments, -Cy- is

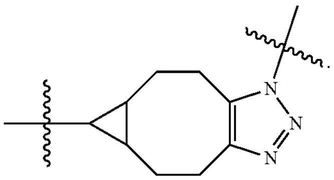 [SMILES: *C1C2CCc3nnn(*)c3CCC12]

In some embodiments, -Cy- is

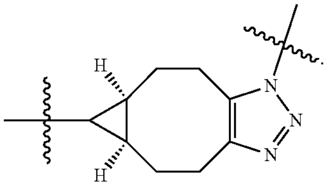

In some embodiments, -Cy is

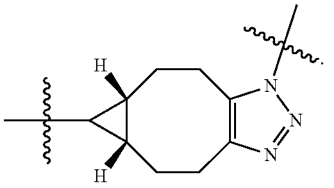

In some embodiments, a linker moiety, e.g., L, in a provided agent, e.g., a compound in Table 1, comprises

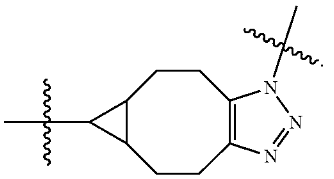

In some embodiments,

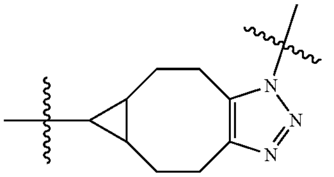 [SMILES: *C1C2CCc3nnn(*)c3CCC12]

is

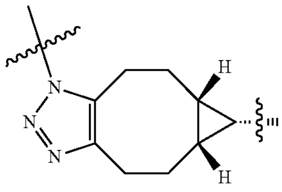 or

-continued

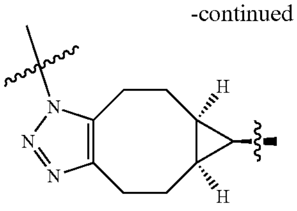

in the structure. In some embodiments,

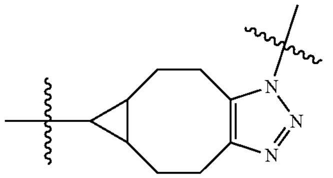 [SMILES: *C1C2CCc3nnn(*)c3CCC12]

is

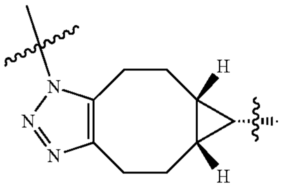

In some embodiments

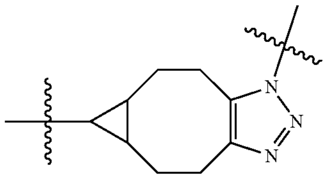 [SMILES: *C1C2CCc3nnn(*)c3CCC12]

is

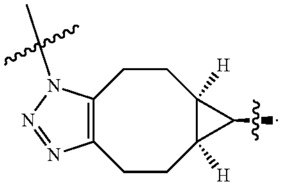

In some embodiments, a linker moiety is as described in Table 1. In some embodiments, L is $L^1$ ad present disclosure. In some embodiments, L is $L^b$ as described in the present disclosure.

In some embodiments, $L^{RM}$ is a covalent bond. In some embodiments, $L^{RM}$ is not a covalent bond. In some embodiments, $L^{RM}$ is or comprises $-(CH_2CH_2O)n-$. In some embodiments, $L^{RM}$ is or comprises $-(CH_2)n-O-(CH_2CH_2O)n-(CH_2)n-$, wherein each n is independently as described herein, and each $-CH_2-$ is independently optionally substituted. In some embodiments, $L^{RM}$ is $-(CH_2)n-O-(CH_2CH_2O)n-(CH_2)n-$, wherein each n is independently as described herein, and each $-CH_2-$ is independently optionally substituted. In some embodiments, $L^{RM}$ is $-(CH_2)_2-O-(CH_2CH_2O)n-(CH_2)_2-$, wherein n is as described herein, and each $-CH_2-$ is independently optionally substituted. In some embodiments, $L^{RM}$ is $-(CH_2)_2-O-(CH_2CH_2O)n-(CH_2)_2-$, wherein n is as described herein.

In some embodiments, $L^{PM}$ is a covalent bond. In some embodiments, $L^{PM}$ is not a covalent bond. In some embodiments, $L^{PM}$ is or comprises $-(CH_2CH_2O)n-$. In some embodiments, $L^{PM}$ is or comprises $-(CH_2)n-O-(CH_2CH_2O)n-(CH_2)n-$, wherein each n is independently as described herein, and each $-CH_2-$ is independently optionally substituted. In some embodiments, $L^{PM}$ is $-(CH_2)n-O-(CH_2CH_2O)n-(CH_2)n-$, wherein each n is independently as described herein, and each $-CH_2-$ is independently optionally substituted. In some embodiments, $L^{PM}$ is $-(CH_2)_2-O-(CH_2CH_2O)n-(CH_2)_2-$, wherein n is as described herein, and each $-CH_2-$ is independently optionally substituted. In some embodiments, $L^{PM}$ is $-(CH_2)_2-O-(CH_2CH_2O)n-(CH_2)_2-$, wherein n is as described herein.

In some embodiments, $L^{PM}$ (e.g., in a product of a first and a second agents) is or comprises a reaction product moiety formed a first reactive moiety and a second reactive moiety.

In some embodiments, a linker moiety (e.g., $L^{PM}$ in a product of a first and a second agents) is or comprises

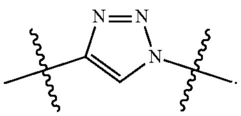

In some embodiments, a methylene unit of a linker moiety, e.g., L or a linker moiety that can be L (e.g., $L^{RM}$, $L^{PM}$, etc.) is replaced with -Cy-. In some embodiments, -Cy is optionally substituted

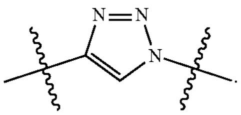

In some embodiments, -Cy- is

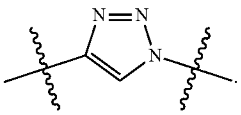

In some embodiments, -Cy- is

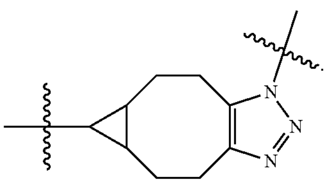

In some embodiments, -Cy- is

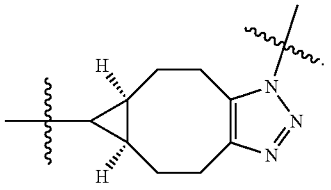

In some embodiments, -Cy- is

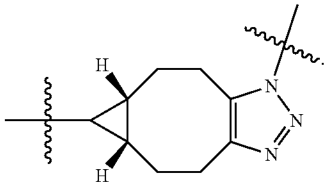

Moieties of Interest

Those skilled in the art reading the present disclosure will appreciate that various types of moieties of interest can be utilized for various purposes in accordance with the present disclosure.

For example, in some embodiments, moieties of interest are or comprise detectable moieties. Among other things, such moieties can be useful for detection, quantification, diagnosis, treatment, etc. In some embodiments, a moiety of interest is or comprises a radioactive label. In some embodiments, a moiety of interest is or comprises a label that can be detected through spectroscopy. In some embodiments, a moiety of interest is or comprises a fluorophore such as FITC moiety. In some embodiments, a moiety of interest is or comprises

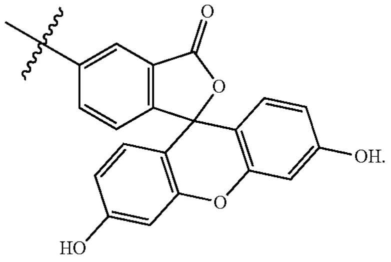 [SMILES: *c1ccc2c(c1)C(=O)OC21c2ccc(O)cc2Oc2cc(O)ccc21]

In some embodiments, a moiety of interest is or comprises

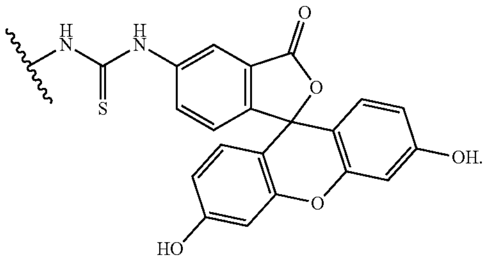 [SMILES: *NC(=S)Nc1ccc2c(c1)C(=O)OC21c2ccc(O)cc2Oc2cc(O)ccc21]

In some embodiments, a moiety of interest is or comprise a moiety of an enzyme, e.g., peroxidase, alkaline phosphatase, luciferase, b-galactosidase, etc. In some embodiments, a moiety of interest is or comprises an affinity substance, e.g., streptavidin, biotin, etc.

In some embodiments, moieties of interest are or comprise therapeutic agent moieties. In some embodiments, a moiety of interest is or comprises a drug moiety, e.g., a drug moiety in an antibody-drug conjugate. In some embodiments, a moiety of interest is or comprises a toxic agent. In some embodiments, a moiety of interest is or comprises a cytotoxic agent. In some embodiments, a moiety of interest is or comprises an anti-cancer agent. In some embodiments, an anti-cancer agent is a chemotherapeutic agent. In some embodiments, an anti-cancer agent is selected from DNA injuring agents, antimetabolites, enzyme inhibitors, DNA intercalating agents, DNA cleaving agents, topoisomerase inhibitors, DNA binding inhibitors, tubulin binding inhibitors, cytotoxic nucleosides, and platinum compounds. In some embodiments, an anti-cancer agent is selected from toxins that include bacteriotoxins (e.g., diphtheria toxin) and phytotoxins (e.g., ricin). In some embodiments, a therapeutic agent is an antimitotic agent. In some embodiments, a therapeutic agent is a maytansinoid agent. In some embodiments, a moiety of interest is or comprises DM1 agent. In some embodiments, a moiety of interest is or comprises DM4 agent. In some embodiments, a therapeutic agent is an auristatin agent. In some embodiments, a moiety of interest is or comprises monomethyl auristatin-E agent. In some embodiments, a moiety of interest is or comprises monomethyl auristatin-F agent. In some embodiments, a moiety of interest is exatecan or a derivative thereof (e.g., DXd). In some embodiments, a therapeutic agent is a DNA interacting agent. In some embodiments, a moiety of interest is or comprises a calicheamicin agent. In some embodiments, a moiety of interest is or comprises a CC-1065 agent or an analog thereof. In some embodiments, a moiety of interest is or comprises a duocarmycin agent. In some embodiments, a therapeutic agent is a transcription inhibitor agent. In some embodiments, a moiety of interest is or comprises a amatoxin agent. As appreciated by those skilled in the art, various therapeutic agents, e.g., anti-cancer agents including many approved drugs by FDA, EMA, etc., may be utilized in accordance with the present disclosure. In some embodiments, a therapeutic agent is a small molecule. In some embodiments, a therapeutic agent is or comprises a peptide. In some embodiments, a therapeutic agent is or comprises a protein. In some embodiments, a therapeutic agent is or comprises a nucleic acid agent (e.g., an oligonucleotide, RNA therapeutics etc.). In some embodiments, a moiety of interest is or comprises a small molecule moiety. In some embodiments, a moiety of interest is or comprises a polypeptide moiety. In some embodiments, a moiety of interest is or comprises a nucleic acid moiety. In some embodiments, a moiety of interest is or comprises an oligonucleotide moiety. In some embodiments, a moiety of interest is or comprises a carbohydrate moiety. In some embodiments, a moiety of interest is or comprises a lipid moiety. In some embodiments, a provided compound or agent comprising a therapeutic agent moiety is useful for treating a condition, disorder or disease that may be treated by the therapeutic agent.

In some embodiments, moieties of interest are or comprise moieties that can interact and/or recruit other agents, such as proteins, nucleic acids, cells, etc. In some embodiments, moieties of interest interact with proteins expressed by certain cell types, e.g., immune cells, disease cells, etc. In some embodiments, moieties of interest are immune cell binders. In some embodiments, moieties of interest recruit immune cells. In some embodiments, moieties of interest trigger, promote and/or enhance one or more immune activities, e.g., for removing, killing, and/or inhibiting desired targets (e.g., cancer cells, antigens, etc.). In some embodiments, moieties of interest interact, recruit and/or bind to disease cells, and trigger, promote and/or enhance removing, killing, and/or inhibiting disease cells.

In some embodiments, a moiety of interest is or comprises a small molecule agent (e.g., one can bind specifically to its protein targets, cells targets, etc.). In some embodiments, a moiety of interest is or comprises a peptide or protein agent (e.g., scFv, a peptide binder to specific target, etc.). In some embodiments, a moiety of interest is or comprises a nucleic acid agent (e.g., an oligonucleotide, mRNA, etc.). In some embodiments, a moiety of interest is or comprises a carbohydrate agent. In some embodiments, a moiety of interest is or comprises a lipid agent.

In some embodiments, a moiety of interest is or comprises a protein complex (e.g., Fab). In some embodiments, a moiety of interest is or comprises a fluorophore. In some embodiments, a moiety of interest is or comprises a cytotoxic small molecule agent. In some embodiments, a moiety of interest is or comprises a cytotoxic peptide agent.

In some embodiments, a moiety of interest is an adjuvant. Those skilled in the art will appreciate various adjuvants can be utilized as moieties of interest in accordance with the present disclosure. In some embodiments, an adjuvant is one described in US20190015516. In some embodiments, a moiety of interest stimulates an immune system.

In some embodiments, a moiety of interest is or comprises a particle. In some embodiments, a particle is or comprises a nanoparticle. In some embodiments, a moiety of interest is or comprises a nanoparticle. In some embodiments, a particle is or comprises a gold-nanoparticle. In some embodiments, a particle is or comprises superparamagnetic iron oxide (SPIO) nanoparticles. In some embodiments, a moiety of interest is or comprises a theranostic agent which comprises one or more gold- and superparamagnetic iron oxide nanoparticles.

In some embodiments, a moiety of interest is or comprises a nucleic acid moiety. In some embodiments, a moiety of interest is or comprises an oligonucleotide. In some embodiments, a moiety of interest is or comprises an aptamers. In some embodiments, a moiety of interest is or comprises a DNA and/or RNA aptamers. In some embodiments, an aptamers is or comprises double stranded or single stranded DNA sequence or RNA sequence. In some embodiments, such sequences are partially or completely defined. In some embodiments, an aptamers is or comprises Pegaptanib. In some embodiments, the present disclosure provides an agent having the structure of I-66, I-67, I-68, or I-69, or a salt thereof.

In some embodiments, a moiety of interest is an antibody agent. In some embodiments, a moiety of interest is or comprises an antibody fragment. In some embodiments, a moiety of interest is an antibody agent moiety that does not contain a region to which a target binding moiety binds. In some embodiments, a moiety of interest is an antibody agent that contains no Fc region. In some embodiments, a moiety of interest is or comprises a scFv. In some embodiments, a scFv is for a different antigen than an antibody target agent.

In some embodiments, moieties of interest are or comprise reactive moieties, particularly those reaction partners for bioorthogonal reactions. Suitable reactive moieties, including those for bioorthogonal reactions, are widely known in the art and can be utilized herein. In some embodiments, a bioorthogonal reaction is a cycloaddition reaction, e.g., click chemistry. In some embodiments, a moiety of interest is or comprises —$N_3$. In some embodiments, a moiety of interest is or comprises an alkyne. In some embodiments, a moiety of interest is or comprises an alkyne suitable for metal-free click chemistry. For example, in some embodiments, a moiety of interest is or comprises optionally substituted

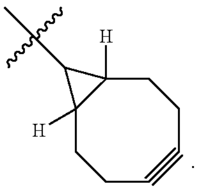 [SMILES: *C1C2CCC#CCCC12]

In some embodiments, a moiety of interest is or comprises

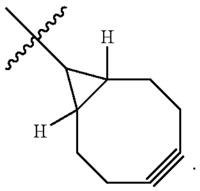 [SMILES: *C1C2CCC#CCCC12]

In some embodiments, a moiety of interest is or comprises

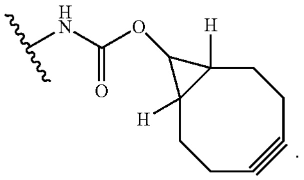 [SMILES: *NC(=O)OC1C2CCC#CCCC21]

In some embodiments, a moiety of interest is or comprises optionally substituted

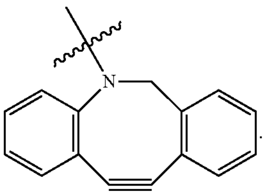 [SMILES: *N1Cc2ccccc2C#Cc2ccccc21]

In some embodiments, a moiety of interest is or comprises

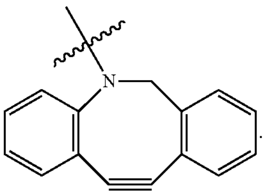 [SMILES: *N1Cc2ccccc2C#Cc2ccccc21]

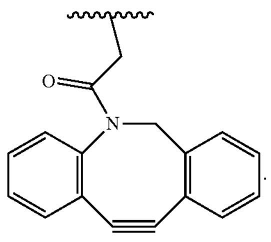 [SMILES: *CC(=O)N1Cc2ccccc2C#Cc2ccccc21]

In some embodiments, a moiety of interest is or comprises an aldehyde, ketone, alkoxyamine, or hydrazide moiety.

In some embodiments, a moiety of interest improves one or more properties and/or activities of a target agent. In some embodiments, a moiety of interest is or comprises a stability enhancer. In some embodiments, a moiety of interest improves one or more pharmacodynamic and/or pharmacokinetic properties of a target agent.

In some embodiments, a moiety of interest is or comprises a peptide tag, e.g., for detection, transformation, etc. In some embodiments, a peptide tag is or comprises GGGGG and can serve as substrate for Sortase A mediated reaction with, e.g., LPETG tagged protein. In some embodiments, a peptide tag is or comprises LPXTG. In some embodiments, a peptide tag is or comprises LPETG. In some embodiments, a moiety of interest is or comprises (G)n, wherein n is 1-10. In some embodiments, a first G is the N-terminal residue. In some embodiments, a moiety of interest is or comprises LPXTG, wherein X is an amino acid residue. In some embodiments, a moiety of interest is or comprises LPETG. In some embodiments, a moiety of interest is or comprises LPXTG-(X)n, wherein each X is independently an amino acid residue, and n is 1-10. In some embodiments, a moiety of interest is or comprises LPETG-(X)n, wherein each X is independently an amino acid residue, and n is 1-10. In some embodiments, n is 1, 2, 3, 4, 5, 6, 7, 8, 9 or 10. In some embodiments, n is 2. In some embodiments, n is 3. In some embodiments, n is 4. In some embodiments, n is 5. In some embodiments, n is 2-10. In some embodiments, n is 2-5. In some embodiments, n is 3-10. In some embodiments, n is 3-5.

As those skilled in the art will appreciate, various peptide tags are available and may be utilized in accordance with the present disclosure.

In some embodiments, a provided method further comprises:

reacting a first agent comprising a first reactive moiety, e.g., in a first moiety of interest, with a second agent comprising a second reactive moiety. In various embodiments, a first reactive moiety is in a first moiety of interest, e.g., which can be incorporated through a method described herein (e.g., via contacting with a compound having the structure of formula R-I or a salt thereof).

In some embodiments, a first moiety of interest is in a compound which comprises no target binding moieties. In some embodiments, a first moiety of interest is in a compound of formula P-I or P-II, or a salt thereof. In some embodiments, a first moiety of interest is in a compound of R-I or a salt thereof. In some embodiments, a first agent has the structure of formula P-I or P-II, or a sat thereof.

In some embodiments, a second agent comprises a peptide moiety which is linked to a second reactive moiety optionally through a linker. In some embodiments, a second agent comprises a peptide moiety which is linked to a second reactive moiety optionally through a linker. In some embodiments, a second agent comprises an antibody agent moiety which is linked to a second reactive moiety optionally through a linker.

In some embodiments, a second moiety of interest is in a compound which comprises no target binding moieties. In some embodiments, a second moiety of interest is in a compound of formula P-I or P-II, or a salt thereof. In some embodiments, a second moiety of interest is in a compound of R-I or a salt thereof. In some embodiments, a second agent has the structure of formula P-I or P-II, or a sat thereof. In some embodiments, a second reactive moiety is in a moiety of interest of a second agent. In some embodiments, a second agent comprises a target agent moiety as described herein. For example, in some embodiments, a target agent moiety in a second agent is or comprises a peptide moiety. In some embodiments, a target agent moiety in a second agent is or comprises an antibody agent moiety as described herein. In some embodiments, it comprises a scFv moiety. In some embodiments, a target agent moiety in a second agent provides different specificity compared to that of a first agent. In some embodiments, such first and second agents react with each other to provide various product agents comprising moieties having different specificities as described herein.

In some embodiments, a reaction between a first reactive moiety and a second reactive moiety is a bioorthogonal reaction. In some embodiments, a reaction is a cycloaddition reaction. In some embodiments, a reaction is a [3+2] reaction. Suitable such reactions and corresponding first and second reactive moieties are widely known in the art and can be utilized in accordance with the present disclosure. In some embodiments, a first reactive moiety is or comprises —$N_3$, and a second reactive moiety is or comprises -≡- (e.g., an alkyne moiety suitable for click chemistry, including those suitable for metal-free click chemistry). In some embodiments, a second reactive moiety is or comprises —$N_3$, and a first reactive moiety is or comprises -≡- (e.g., an alkyne moiety suitable for click chemistry, including those suitable for metal-free click chemistry).

As described herein, in some embodiments, a reaction between a first reactive moiety and a second reactive moiety is an enzymatic reaction. In some embodiments, a reaction is a sortase-mediated reaction. In some embodiments, each of the first and second reactive moiety independently is or comprises a substrate moiety for a reaction, e.g., an enzymatic reaction. For example, in some embodiments, for a sortase-mediated conjugation, a reactive moiety is or comprises (G)n (e.g., n is 3, 4, 5, etc.), and a reactive moiety is or comprises LPXTG (e.g., LPETG). In some embodiments, a reactive moiety is or comprises LPXTG-(X)n (e.g., LPETG-(X)n, LPETG-XX, etc.). Those skilled in the art reading the present disclosure will appreciate that various reactive moieties can be utilized in accordance with the present disclosure for conjugation, via either enzymatic and/or non-enzymatic pathways. In some embodiments, a compound comprising a first reactive moiety is I-53, I-54, I-55, I-56, I-57, or I-58, or a salt thereof. In some embodiments, a compound comprising a second reactive moiety is or comprises METDTLLLWVLLLWVPGSTGEVQLVES-GGGLVQPGGSLKLSCAASGFTFNTYAMNWVRQAPG KGLEWVGRIRSKYNNYATYYADSVKGRFTISRDD-SKNTLYLQMNSLRAEDTAVYYCVRHGNFG NSYV-SWFAYWGQGTLVTVSSGGGGSGGGGSGGGGSQAV-VTQEPSLTVSPGGTVTLTCGSSTGA VTTSNYANW-VQQKPGQAPRGLIGGTNKRAPGVPARFSGSLLGG-KAALTLSGAQPEDEAEYYCALWYSNLWVFGGGT- KLTVLGSEQKLISEEDLGSGGGGSLPETGGSHH-HHHH (SEQ ID NO: 1) or a fragment thereof, or a sequence that shares 60%, 70%, 80%, 85%, 90%, 91%, 92%, 93%, 94%, 95%, 96%, 97%, 98%, or 99% homology with SEQ ID NO: 1 or a fragment thereof, or a salt thereof. In some embodiments, a compound comprising a second reactive moiety is compound II-I: METDTLLLWVLLLWVPGST-GEVQLVESGGGLVQPGGSLKLSCAASGFTFN-TYAMNWVRQAPG KGLEWVGRIRSKYNNYATYY-ADSVKGRFTISRDDSKNTLYLQMNSLRAEDTAVYY-CVRHGNFG NSYVSWFAYWGQGTLVTVSSGGGGSG-GGGSGGGGSQAVVTQEPSLTVSPGGTVTLTCGSSTGA VTTSNYANWVQQKPGQAPRGLIGGTNKRAPGVPAR-FSGSLLGGKAALTLSGAQPEDEAEYYCA LWYSNLW-VFGGGTKLTVLGSEQKLISEEDLGSGGGGSL-PETGGSHHHHHH (SEQ ID NO: 1), or a salt thereof.

In some embodiments, a second agent is or comprises a second moiety of interest which is a moiety of interest as described herein. In some embodiments, a second reactive moiety and a second moiety of interest is connected through a linker (e.g., a linker as described herein (e.g., $L^{PM}$, L, etc. as described herein). In some embodiments, a second moiety of interest is as described herein (e.g., a detection moiety, a therapeutic moiety, a moiety of interest which can interact, recognize and/or bind proteins, nucleic acids, immune cells, disease cells, etc.). In some embodiments, a second moiety of interest is or comprises an antibody agent. In some embodiments, a second moiety of interest is or comprises a scFv antibody agent. In some embodiments, such an antibody agent has different specificity compared to the initial target antibody agent. Thus, in some embodiments, the present disclosure provides bispecific antibody agents, compositions, and methods thereof. In some embodiments, a target agent is or comprises a first antibody agent, and it is conjugated with a moiety of interest comprising a first reactive moiety. In some embodiments, an agent comprising a first antibody agent and a first reactive moiety is reacted with a second agent comprising a second reactive moiety and a second moiety of interest which is or comprises a second antibody agent to provide an agent comprising a first and a second antibody agents. In some embodiments, a first and a second antibody agents are different. In some embodiments, they are the same.

In some embodiments, an agent comprises two or more antibody agent moieties. In some embodiments, antibody agent moieties in a single agent molecule have different target specificity. In some embodiments, some or all antibody agent moieties in a single agent molecule have the same target specificity. In some embodiments, an agent as described herein is or comprises moieties having different target specificity (e.g., antibody moieties having different target specificity). In some embodiments, an agent is a bispecific antibody agent. In some embodiments, an agent comprises a first moiety (e.g., a first antibody agent moiety) and a second moiety (e.g., a second antibody agent moiety). In some embodiments, a first moiety (e.g., a first antibody agent moiety) is or comprises IgG or a fragment thereof. In some embodiments, a first moiety (e.g., a first antibody agent moiety) is or comprises an antibody agent moiety or a fragment thereof (e.g., Fc region or a fragment thereof) to which a target binding moiety may bind. In some embodiments, a second moiety (e.g., a second antibody agent moiety) is or comprises IgG or a fragment thereof. In some embodiments, a second moiety (e.g., a second antibody agent moiety) is or comprises an antibody agent moiety or a fragment thereof (e.g., Fc region or a fragment thereof) to which a target binding moiety may bind. In some embodiments, an antibody agent moiety, e.g., a second antibody agent moiety, comprises no moiety to which a target binding moiety may bind. In some embodiments, an antibody agent moiety, e.g., a second antibody agent moiety, comprises no Fc moiety to which a target binding moiety may bind. In some embodiments, an antibody agent moiety, e.g., a second antibody agent moiety, is or comprises scFv. In some embodiments, a first moiety is or comprises an agent moiety of a first agent. In some embodiments, a second moiety is or comprises a moiety of interest of a second agent. In some embodiments, a first agent, e.g., one comprising a first antibody agent moiety, is contacted with a second agent, e.g., one comprising a second antibody agent moiety, to provide an agent comprising two or more moieties having target specificity (e.g., antibody agent moieties).

In some embodiments, a moiety, e.g., a first moiety, is or comprises an antibody agent moiety that binds to a target (e.g., a protein, lipid, carbohydrate, object, etc.) associated with a condition, disorder or disease (e.g., cancer). In some embodiments, a moiety, e.g., a first moiety, is or comprises a moiety of an antibody agent suitable for preventing or treating a condition, disorder or disease, e.g., cancer. In some embodiments, a moiety, e.g., a first moiety, is or comprises a moiety of an antibody agent which targets cancer cells, tissues, organs, etc. For example, in some embodiments, a first moiety is or comprises a moiety of an anti-CD20 antibody or a fragment thereof. In some embodiments, a first moiety is or comprises rituximab or a fragment thereof. In some embodiments, a moiety, e.g., a second moiety, is a second moiety of interest. In some embodiments, a moiety, e.g., a second moiety, is or comprises an antibody agent moiety that can recruit and/or activate an immune activity, e.g. one or more immune cells. In some embodiments, a moiety, e.g., a second moiety, is or comprises an antibody agent moiety which can recruit and/or activate T cells. In some embodiments, a moiety, e.g., a second moiety is or comprises a moiety of an anti-CD3 antibody or fragment thereof. In some embodiments, an anti-CD3 antibody is a CD3-directed scFv. In some embodiments, a moiety, e.g., a first moiety, is a target agent moiety. In some embodiments, a provided agent comprises an anti-CD20 moiety and an anti-CD3 moiety. In some embodiments, a provided agent comprises an anti-CD20 moiety and an anti-CD3 moiety, wherein the two moieties are linked by a linker. In some embodiments, a linker comprises moieties that are not amino acid residues. In some embodiments, a linker comprises moieties that are not natural proteinogenic amino acid residues. In some embodiments, a linker is a linker moiety as described herein. Those skilled in the art will appreciate that agents comprising two or more target-specific moieties (e.g., antibody agent moieties) can be prepared with various benefits and characteristics according to the present disclosure, e.g., high site specificity, high homogeneity, low level of damages, low levels or substantially absence of reduction of desired properties and/or activities (e.g., target binding, recruitment and/or activation of immune activities, etc.), etc. Those skilled in the art will also appreciate that provided technologies can readily conjugate antibody agents, e.g., those readily available (e.g., "off-the-shelf" therapeutic antibodies) with other moieties, e.g., in some embodies other antibody agents, to, e.g., produce bispecific agents. In some embodiments, a first and a second moiety is linked by a linker as described herein.

In some embodiments, a provided product agent comprises a linker moiety connecting a target agent moiety and a second moiety of interest (e.g., two antibody agent moieties). In some embodiments, a linker is or comprises one or more of $L^{RG2}$, $L^{PM}$ or fragments thereof, and one or more moiety formed by a first and second reactive moieties (e.g., for click chemistry, a triazole moiety). In some embodiments, a linker is or comprises a product linker moiety, e.g., one formed by a reaction between a first and a second reactive moiety. In some embodiments, a product linker moiety is or comprise LPXTG. In some embodiments, a product linker moiety is or comprise LPXT(G)n, wherein n is 1, 2, 3, 4, 5, 6, 7, 8, 9, or 10. In some embodiments, a product linker moiety is or comprises a bioorthogonal reaction product moiety, e.g., a click chemistry reaction product moiety.

In some embodiments, an agent comprising a second reactive moiety and a second moiety of interest is prepared using a technology provided herein. In some embodiments, a second moiety of interest is or comprises a protein agent moiety. In some embodiments, a second moiety of interest is or comprises an antibody agent moiety. In some embodiments, a second moiety of interest (e.g., a protein agent (e.g., an antibody agent)) can serve as a target agent moiety, and a second reactive moiety can serve as a moiety of interest (e.g., MOI in a compound of formula R-I or a salt thereof), for utilization of certain provided methods (e.g., comprising reacting target agents (e.g., protein agents (e.g., antibody agents, etc.)) with reaction partners comprising moieties of interest (e.g., those that are or comprise second reactive moieties), reactive groups and target binding moieties that can bind to target agents to provide second agents).

In some embodiments, each of a first agent and a second agent is independently and optionally an agent of formula P-I or P-II, or a salt thereof. In some embodiments, each of a first agent and a second agent is independently an agent of formula P-I or P-II, or a salt thereof. In some embodiments, at least one of a first agent and a second agent is prepared using a method of the present disclosure. In some embodiments, each of a first agent and a second agent is independently prepared using a method of the present disclosure. In some embodiments, a target agent moiety of a first agent is an antibody agent. In some embodiments, a moiety of interest of a first agent is or comprises a first reactive moiety. In some embodiments, a target agent moiety of a second agent is an antibody agent. In some embodiments, a moiety of interest of a second agent is or comprises a second reactive moiety. As described herein, in many embodiments, a first reactive moiety and a second reactive moiety can react with each to provide a product agent. In some embodiments, a reaction between a first and a second reactive moieties is or comprises a reaction compatible with target agents in the first and second agents, e.g., compatible with protein agents (e.g., antibody agents). In some embodiments, such a reaction is a bioorthogonal reaction. In some embodiments, such a reaction is a cycloaddition reaction. In some embodiments, such a reaction is a click reaction. In some embodiments, such a reaction is a metal free click reaction. In some embodiments, a product agent is of formula P-I or P-II, or a salt thereof. In some embodiments, in a product agent of formula P-I or P-II, or a salt thereof, a target agent moiety is a protein agent (e.g., an antibody agent), and in some embodiments, a target agent moiety of a first agent. In some embodiments, in a product agent of formula P-I or P-II, or a salt thereof, a moiety of interest is a protein agent (e.g., an antibody agent), and in some embodiments, a target agent moiety of a second agent. In some embodiments, a product agent comprises two or more antibody agents. In some embodiments, the two or more antibody agents have different antigen specificity. In some embodiments, the two or more antibody agents are toward different antigens. In some embodiments, a provided method comprises:

reacting a first agent which has the structure of formula P-I or P-II, or a salt thereof with a second agent which has the structure of formula P-I or P-II, or a salt thereof to provide a product agent.

In some embodiments, wherein a first agent is an agent of formula P-I or P-II, or a salt thereof, a first agent and a product agent share the same target agent (P or P—N), a different linker $L^{PM}$ and a different MOI (e.g., in some embodiments, MOI of a first agent is or comprises a reactive group, which MOI of a product agent of a first and second agents is or comprises a target agent moiety (e.g., an antibody agent moiety) of a second agent. In some embodiments, $L^{PM}$ of a product agent is or comprises a product moiety of a first reactive moiety and a second reactive moiety. For example, in some embodiments, when a reaction is or comprises a click reaction, $L^{PM}$ in a product agent is or comprises a triazole moiety (e.g.,

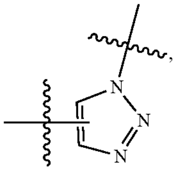

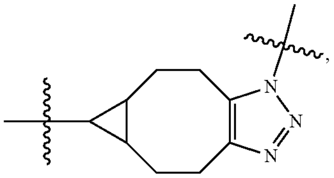

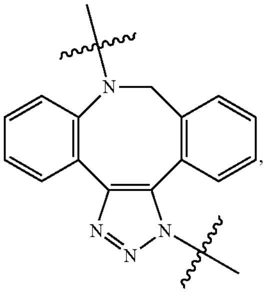

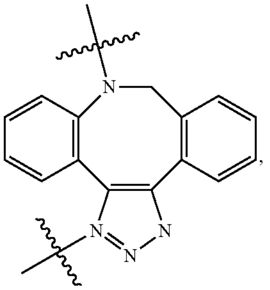

etc.).

Methods and Products

In some embodiments, provided technologies comprise contacting a target agent (e.g., to which a moiety of interest is to be attached) with a reaction partner. In some embodiments, contact is performed under conditions and for a time so that a target agent react with a reaction partner to form an agent as a product. Many reaction conditions/reaction times in the art may be assessed and utilized if suitable for desired purposes in accordance with the present disclosure; certain such conditions, reaction times, assessment, etc. are described in the Examples.

In some embodiments, an agent formed comprises a target agent moiety, a moiety of interest and optionally a linker moiety connecting a target agent moiety and a moiety of interest. In some embodiments, a target agent moiety is derived from a target agent (e.g., by removing one or more —H from a target agent). In some embodiments, a target agent moiety maintains one or more, most, or substantially all structural features and/or biological functions of a target agent. For example, in some embodiments, a target agent is an antibody agent, and a target agent moiety in a formed agent is a corresponding antibody agent moiety and maintains major functions of the antibody agent, e.g., interacting with various receptors (e.g., Fc receptors such as FcRn), recognizing antigen with specificity, triggering, promoting, and/or enhancing immunological activities toward diseased cells, etc., as the antibody agent. In some embodiments, a formed agent provides one or more functions beyond those of a target agent, for example, from a moiety of interest and/or a formed agent as a whole.

In some embodiments, an agent formed has the structure of formula P-I or P-II, or a salt thereof. In some embodiments, a moiety of interest in a formed agent (e.g., MOI of formula P-I or P-II, or a salt thereof) is the same as a moiety of interest in a reaction partner (e.g., MOI of formula R-I or a salt thereof) utilized to prepare a formed agent. In some embodiments, P is a protein moiety. In some embodiments, P is an antibody moiety.

In some embodiments, linker moieties (or a part thereof) connected to moieties of interest may also be transferred from reaction partners (e.g., $L^{RM}$ of formula R-I or a salt thereof). In some embodiments, a linker moiety in a formed agent (e.g., $L^{PM}$) is or comprises a linker moiety in a reaction partner (e.g., one between a reactive group and a moiety of interest, e.g., $L^{RM}$). In some embodiments, $L^{PM}$ is or comprises $L^{RM}$. In some embodiments, $L^{PM}$ is $-L^{RM}-L^{RG2}-$. In some embodiments, $L^{RG2}$ is —C(O)—. In some embodiments, $L^{RG2}$ is —C(O)—, and is bonded to —NH— of a target agent moiety, e.g., —NH— in a side chain of a lysine residue of a protein moiety, which in some embodiments, is an antibody moiety.

Reaction partners, e.g., compounds of formula R-I or salts thereof, typically do not contain moieties that can react with reactive groups under conditions under which reactive groups react with target agents. In some embodiments, to the extent that some moieties in reaction partners may react with reactive groups under conditions under which reactive groups react with target agents, reactions between such moieties and reactive groups are significantly slower and/or less efficient compared to reactions between reactive groups and target agents. In some embodiments, reactions between such moieties and reactive groups do not significantly reduce (e.g., no more than about 5%, 10%, 15%, 20%, 25%, 30%, 40%, 50%, 60%, 70%, 80%, 90%, etc. of reduction) efficiencies, yields, rates, and/or conversions, etc., of reactions between reactive groups and target agents. In some embodiments, reactive groups (e.g., ester groups, activated carboxylic acid derivatives, etc.) react with amino groups (e.g., —$NH_2$ groups) of target agents (e.g., protein agents such as antibody agents). In some embodiments, reaction partners, e.g., compounds of formula R-I or salts thereof, do not contain amine groups. In some embodiments, compounds of formula R-I or salts thereof (or portions thereof, such as $R^{LG}$, $L^{LG}$, $L^{LG1}$, $L^{LG2}$, $L^{LG3}$, $L^{LG4}$, $L^{RG1}$, $L^{RG2}$, $L^{RM}$, and/or MOI) do not contain amine groups. In some embodiments, they do not contain primary amine groups (—$NH_2$). In some embodiments, they do not contain —$CH_2NH_2$. In some embodiments, they do not contain —$CH_2CH_2NH_2$. In some embodiments, they do not contain —$CH_2CH_2CH_2NH_2$. In some embodiments, they do not contain —$CH_2CH_2CH_2CH_2NH_2$. In some embodiments, amine groups, e.g., primary amine groups, are capped (e.g., by introduction of acyl groups (e.g., R—C(O)— (e.g., acetyl)) to form amide groups) to prevent or reduce undesired reactions.

In some embodiments, reactions are performed in buffer systems. In some embodiments, buffer systems of present disclosure maintains structures and/or functions of target agents, moiety of interest, etc. In some embodiments, a buffer is a phosphate buffer. In some embodiments, a buffer is a PBS buffer. In some embodiments, a buffer is a borate buffer. In some embodiments, buffers of the present disclosure provide and optionally maintain certain pH value or range. For example, in some embodiments, a useful pH is about 7-9, e.g., 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 9.0, etc. In some embodiments, a pH is 7.4. In some embodiments, a pH is 7.5. In some embodiments, a pH is 7.8. In some embodiments, a pH is 8.0. In some embodiments, a pH is 8.2. In some embodiments, a pH is 8.3.

Provided technologies can provide various advantages. Among other things, in some embodiments, connection of a moiety of interest in a provided reaction partner (e.g., a compound comprising a reactive group located between a first group and a moiety of interest (e.g., a compound of formula R-I or a salt thereof)) to a target agent and release of a target binding moiety in a provided reaction partner can be achieved in one reaction and/or in one pot. Thus, in many embodiments, no separate reactions/steps are performed to remove target binding moieties. As appreciated by those skilled in the art, by performing connection of moiety of interest and release of target binding moiety in a single reaction/operation, provided technologies can avoid separate steps for target binding moiety removal and can improve overall efficiency (e.g., by simplify operations, increasing overall yield, etc.), reduce manufacturing cost, improve product purity (e.g., by avoiding exposure to target binding moiety removal conditions, which typically involve one or more of reduction, oxidation, hydrolysis (e.g., of ester groups), etc., conditions and may damage target agent moieties (e.g., for protein agent moieties, protein amino acid residues, overall structures, and/or post-translational modifications (e.g., glycans of antibodies) thereof. Indeed, as demonstrated herein, provided technologies among other things can provided improved efficiency (e.g., in terms of reaction rates and/or conversion percentages), increased yield, increased purity/homogeneity, and/or enhanced selectivity, particularly compared to reference technologies wherein a reaction partner containing no target binding moieties is used, without introducing step(s) for target binding moiety removal (e.g., target binding moiety is removed in the same step as moiety of interest conjugation).

In some embodiments, the present disclosure provides products of provided processes, which, among other things, contain low levels of damage to target agent moieties compared to processes comprising steps which are performed for target binding moiety removal but not for substantial moiety of interest conjugation. In some embodiments, provided product compositions have high homogeneity compared to reference product compositions (e.g., those from technologies without using target binding moieties, or utilizing extra step(s) for target binding moiety removal (e.g., not utilizing reaction partners described herein which comprise a reactive group located between a target binding moiety and a moiety of interest).

In some embodiments, a product agent is an agent comprising:

a target agent moiety;

a moiety of interest; and optionally one or more linker moieties.

In some embodiments, a target agent moiety is a protein agent moiety. In some embodiments, a target agent moiety is an antibody agent moiety. In some embodiments, an antibody agent moiety comprises IgG Fc region. In some embodiments, a target agent moiety is connected to a moiety of interest through an amino group optionally through a linker. In some embodiments, it is through a lysine residue wherein the amino group of the side chain is connected to a moiety of interest optionally through a linker (e.g., forming —NH—C(O)— as part of an amide group, a carbamate group, etc.).

In some embodiments, selected locations of target agents are utilized for conjugation. For example, in some embodiments, K246 or K248 of an antibody agent (EU numbering, or corresponding residues) are conjugation locations. In some embodiments, a conjugation location is K246 of heavy chain (unless otherwise specified, locations herein include corresponding residues in, e.g., modified sequence (e.g., longer, shorter, rearranged, etc., sequences)). In some embodiments, a location is K248 of heavy chain. In some embodiments, a location is K288 or K290 of heavy chain. In some embodiments, a location is K288 of heavy chain. In some embodiments, a location is K290 of heavy chain. In some embodiments, a location is K317.

In some embodiments, when target agents are antibody agents, heavy chains are selectively labeled over light chains.

Among other things, the present disclosure can provide controlled moiety of interest/target agent ratios (e.g., for antibody-drug conjugates, drug/antibody ratio (DAR)). In some embodiments, a ratio is about 0.5-6, e.g., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, 4.5, 5.0, 5.5, etc.). In some embodiments, a ratio is about 0.5-2.5. In some embodiments, a ratio is about 0.5-2. In some embodiments, a ratio is about 1-2. In some embodiments, a ratio is about 1.5-2. In some embodiments, a ratio is of moieties of interest conjugated to target agent moieties and target agent moieties conjugated to moieties of interest. In some embodiments, a ratio is of moieties of interest conjugated to target agent moieties and all target agent moieties in a composition.

In some embodiments, in provided agents (e.g., agents of formula P-I or P-II, or a salt thereof) substantially all conjugation sites of target agent moieties have the same modifications (e.g., all share the same moieties of interest optionally connected through the same linker moieties). In some embodiments, no conjugation sites bear different modifications (e.g., different moieties of interest and/or no moieties of interest and/or different linker moieties).

In some embodiments, in provided compositions comprising a plurality of provided agents (e.g., agents of formula P-I or P-II, or a salt thereof) substantially all conjugation sites of target agent moieties have the same modifications (e.g., all share the same moieties of interest optionally connected through the same linker moieties). In some embodiments, no conjugation sites bear different modifications (e.g., different moieties of interest and/or no moieties of interest and/or different linker moieties). In some embodiments, such compositions do not contain agents that share the same (or substantially the same) target agent moieties but different modifications (e.g., different moieties of interest and/or no moieties of interest and/or different linker moieties). In some embodiments, agents that share the same (or substantially the same) target agent moieties but different modifications (e.g., different moieties of interest and/or no moieties of interest and/or different linker moieties) are intermediates of multiple-step preparations (e.g., comprising steps for removal of target binding moieties in addition to steps for moiety of interest conjugation) of final product agents.

In some embodiments, the present disclosure provides a composition comprising a plurality of agents each of which independently comprising:

a target agent moiety, a moiety of interest, and optionally a linker moiety linking a target agent moiety and a moiety of interest; wherein agents of the plurality share the same or substantially the same target agent moiety, and a common modification independently at at least one common location; and wherein about 1%-100% of all agents that comprise a target agent moiety and a moiety of interest are agents of the plurality.

In some embodiments, a target agent moiety is or comprises a protein moiety. In some embodiments, agents of the plurality share common modifications (e.g., conjugations of moieties of interest optionally through linker moieties) independently at at least one amino acid residues. In some embodiments, agents of the plurality are each independently of formula P-I or P-II, or a salt thereof.

In some embodiments, the present disclosure provides a composition comprising a plurality of agents each of which independently comprising:

a protein agent moiety, a moiety of interest, and optionally a linker moiety linking a protein agent moiety and a moiety of interest; wherein protein agent moieties of agents of the plurality comprise a common amino acid sequence, and agents of the plurality share a common modification independently at at least one common amino acid residue of protein agent moieties; and wherein about 1%-100% of all agents that comprise a protein agent moiety that comprise the common amino acid sequence and a moiety of interest are agents of the plurality.

In some embodiments, agents of the plurality are each independently of formula P-I or P-II, or a salt thereof. In some embodiments, each protein agent moiety is independently an antibody agent moiety.

In some embodiments, the present disclosure provides a composition comprising a plurality of agents each of which independently comprising:

an antibody agent moiety, a moiety of interest, and optionally a linker moiety linking an antibody agent moiety and a moiety of interest; wherein antibody agent moieties of agents of the plurality comprise a common amino acid sequence or can bind to a common antigen, and agents of the plurality share a common modification independently at at least one common amino acid residue of protein agent moieties; and wherein about 1%-100% of all agents that comprise an antibody agent moiety that comprise the common amino acid sequence or can bind to the common antigen and a moiety of interest are agents of the plurality.

In some embodiments, agents of the plurality are each independently of formula P-I or P-II, or a salt thereof. In some embodiments, antibody agent moieties of agents of the plurality comprise a common amino acid sequence. In some embodiments, antibody agent moieties of agents of the plurality comprise a common amino acid sequence in a Fc region. In some embodiments, antibody agent moieties of agents of the plurality comprise a common Fc region. In some embodiments, antibody agent moieties of agents of the plurality can bind a common antigen specifically. In some embodiments, antibody agent moieties are monoclonal antibody moieties. In some embodiments, antibody agent moieties are polyclonal antibody moieties. In some embodiments, antibody agent moieties bind to two or more different antigents. In some embodiments, antibody agent moieties bind to two or more different proteins. In some embodiments, antibody agent moieties are IVIG moieties.

As used in the present disclosure, in some embodiments, “at least one” or “one or more” is 1-1000, 1-500, 1-200, 1-100, 1-90, 1-80, 1-70, 1-60, 1-50, 1-40, 1-30, 1-20, 1-10, 1-5, or about 1, 2, 3, 4, 5, 6, 7, 8, 9, 10, 11, 12, 13, 14, 15, 16, 17, 18, 19, 20, or more. In some embodiments, it is one. In some embodiments, it is two or more. In some embodiments, it is about 3. In some embodiments, it is about 4. In some embodiments, it is about 5. In some embodiments, it is about 6. In some embodiments, it is about 7. In some embodiments, it is about 8. In some embodiments, it is about 9. In some embodiments, it is about 10. In some embodiments, it is about 10 or more.

In some embodiments, a common amino acid sequence comprises 1-1000, 1-500, 1-400, 1-300, 1-200, 1-100, 1-50, 10-1000, 10-500, 10-400, 10-300, 10-200, 10-100, 10-50, 20-1000, 20-500, 20-400, 20-300, 20-200, 20-100, 20-50, 50-1000, 50-500, 50-400, 50-300, 50-200, 50-100, 1, 2, 3, 4, 5, 6, 7, 8, 9, 10, 11, 12, 13, 14, 15, 16, 17, 18, 19, 20, 25, 30, 40, 50, 60, 70, 80, 90, 100, 110, 120, 130, 140, 150, 200, 250, 300, 400, 500, 600 or more amino acid residues. In some embodiments, a length is at least 5 amino acid residues. In some embodiments, a length is at least 10 amino acid residues. In some embodiments, a length is at least 50 amino acid residues. In some embodiments, a length is at least 100 amino acid residues. In some embodiments, a length is at least 150 amino acid residues. In some embodiments, a length is at least 200 amino acid residues. In some embodiments, a length is at least 300 amino acid residues. In some embodiments, a length is at least 400 amino acid residues. In some embodiments, a length is at least 500 amino acid residues. In some embodiments, a length is at least 600 amino acid residues.

In some embodiments, a common amino acid sequence is at least 10%-100%, 50%-100%, 50%, 55%, 60%, 65%, 70%, 75%, 80%, 85%, 90%, 91%, 92%, 93%, 94%, 95%, 96%, 97%, 98% or 99% of an amino acid sequence of a target agent moiety, a protein agent moiety, an antibody agent moiety, etc. In some embodiments, it is 100%.

In some embodiments, protein agent moieties share a high percentage of amino acid sequence homology. In some embodiments, it is 50%-100%. In some embodiments, it is 50%. In some embodiments, it is 60%. In some embodiments, it is 70%. In some embodiments, it is 80%. In some embodiments, it is 90%. In some embodiments, it is 91%. In some embodiments, it is 50%. In some embodiments, it is 92%. In some embodiments, it is 93%. In some embodiments, it is 94%. In some embodiments, it is 95%. In some embodiments, it is 96%. In some embodiments, it is 97%. In some embodiments, it is 98%. In some embodiments, it is 99%. In some embodiments, it is 100%. In some embodiments, it is at least 50%. In some embodiments, it is at least 60%. In some embodiments, it is at least 70%. In some embodiments, it is at least 80%. In some embodiments, it is at least 90%. In some embodiments, it is at least 91%. In some embodiments, it is at least 50%. In some embodiments, it is at least 92%. In some embodiments, it is at least 93%. In some embodiments, it is at least 94%. In some embodiments, it is at least 95%. In some embodiments, it is at least 96%. In some embodiments, it is at least 97%. In some embodiments, it is at least 98%. In some embodiments, it is at least 99%.

In some embodiments, a protein agent moiety or an antibody agent moiety is or comprises a protein complex. In some embodiments, at least one or each individual chain shares a common amino acid sequence and/or has a homology as described herein.

In some embodiments, agents of a plurality share a common moiety of interest. In some embodiments, each agent of a plurality is independently an agent of formula P-I or P-II, or a salt thereof. In some embodiments, each agent of a plurality is independently an agent of formula P-I or P-II, or a salt thereof, wherein MOI is the same for each agent of the plurality. In some embodiments, agents of a plurality are products of methods described herein. In some embodiments, compositions comprising agents of a plurality are products of methods described herein.

In some embodiments, a modification is or comprises a moiety of interest and optionally a linker. In some embodiments, a modification is or comprises -$L^{PM}$-MOI.

In some embodiments, agents of the plurality share a common modification independently at at least one location. In some embodiments, a modification is or comprises a moiety of interest and optionally a linker connecting the moiety of interest. As described herein, each location independently has its common modification. In some embodiments, common modifications at two or more or all locations comprise a common moiety of interest. In some embodiments, common modifications are the same. In some embodiments, agents of the plurality share a common modification at each location which has a modification that is or comprises a moiety of interest and optionally a linker. In some embodiments, agents of the plurality share a common modification at each location which has a modification that is or comprises -$L^{PM}$-MOI.

In some embodiments, protein agents (e.g., antibody agents) share a common modification at least one amino acid residue. In some embodiments, agents of the plurality share a common modification at each location which has a modification that is or comprises a moiety of interest and optionally a linker. In some embodiments, agents of the plurality share a common modification at each location which has a modification that is or comprises -$L^{PM}$-MOI.

In some embodiments, a location is selected from K246, K248, K288, K290, K317 of antibody agents and locations corresponding thereto. In some embodiments, a location is selected from K246 and K248, and locations corresponding thereto. In some embodiments, a location is selected from K288 and K290, and locations corresponding thereto. In some embodiments, a location is K246 or a location corresponding thereto. In some embodiments, a location is K248 or a location corresponding thereto. In some embodiments, a location is K288 or a location corresponding thereto. In some embodiments, a location is K290 or a location corresponding thereto. In some embodiments, a location is K317 or a location corresponding thereto. In some embodiments, a location is K185 of light chain or a location corresponding thereto. In some embodiments, a location is K187 of light chain or a location corresponding thereto. In some embodiments, a location is K133 of heavy chain or a location corresponding thereto. In some embodiments, a location is K246 or K248 of heavy chain or a location corresponding thereto. In some embodiments, a location is K414 of heavy chain or a location corresponding thereto.

In some embodiments, about 1%-100% of all agents that comprise a target agent moiety and a moiety of interest are agents of the plurality. In some embodiments, about 1%-100% of all agents that comprise a protein agent moiety that comprise the common amino acid sequence and a moiety of interest are agents of the plurality. In some embodiments, about 1%-100% of all agents that comprise an antibody agent moiety that comprise the common amino acid sequence or can bind to the common antigen and a moiety of interest are agents of the plurality. In some embodiments, about 1%-100% of all agents that comprise a target agent moiety are agents of the plurality. In some embodiments, about 1%-100% of all agents that comprise a protein agent moiety that comprise the common amino acid sequence are agents of the plurality. In some embodiments, about 1%-100% of all agents that comprise an antibody agent moiety that comprise the common amino acid sequence or can bind to the common antigen are agents of the plurality. In some embodiments, it is 50%-100%. In some embodiments, it is 50%. In some embodiments, it is 60%. In some embodiments, it is 70%. In some embodiments, it is 80%. In some embodiments, it is 90%. In some embodiments, it is 91%. In some embodiments, it is 50%. In some embodiments, it is 92%. In some embodiments, it is 93%. In some embodiments, it is 94%. In some embodiments, it is 95%. In some embodiments, it is 96%. In some embodiments, it is 97%. In some embodiments, it is 98%. In some embodiments, it is 99%. In some embodiments, it is 100%. In some embodiments, it is at least 50%. In some embodiments, it is at least 60%. In some embodiments, it is at least 70%. In some embodiments, it is at least 80%. In some embodiments, it is at least 90%. In some embodiments, it is at least 91%. In some embodiments, it is at least 50%. In some embodiments, it is at least 92%. In some embodiments, it is at least 93%. In some embodiments, it is at least 94%. In some embodiments, it is at least 95%. In some embodiments, it is at least 96%. In some embodiments, it is at least 97%. In some embodiments, it is at least 98%. In some embodiments, it is at least 99%.

In some embodiments, provided agents, compounds, etc., e.g., those of formula R-I, P-I, P-II, etc. and salts thereof have high purity. In some embodiments, it is 50%-100%. In some embodiments, it is 50%. In some embodiments, it is 60%. In some embodiments, it is 70%. In some embodiments, it is 80%. In some embodiments, it is 90%. In some embodiments, it is 91%. In some embodiments, it is 50%. In some embodiments, it is 92%. In some embodiments, it is 93%. In some embodiments, it is 94%. In some embodiments, it is 95%. In some embodiments, it is 96%. In some embodiments, it is 97%. In some embodiments, it is 98%. In some embodiments, it is 99%. In some embodiments, it is 100%. In some embodiments, it is at least 50%. In some embodiments, it is at least 60%. In some embodiments, it is at least 70%. In some embodiments, it is at least 80%. In some embodiments, it is at least 90%. In some embodiments, it is at least 91%. In some embodiments, it is at least 50%. In some embodiments, it is at least 92%. In some embodiments, it is at least 93%. In some embodiments, it is at least 94%. In some embodiments, it is at least 95%. In some embodiments, it is at least 96%. In some embodiments, it is at least 97%. In some embodiments, it is at least 98%. In some embodiments, it is at least 99%.

In some embodiments, the present disclosure provides product agent compositions comprising product agents (e.g., agents of formula P-I or P-II, or a salt thereof). In some embodiments, a product agent composition (e.g., a formed agent composition from certain methods) comprises a product agent comprising a target agent moiety and a moiety of interest and optionally a linker (e.g., an agent of formula P-I or P-II, or a salt thereof), a released target binding moiety (e.g., a compound comprising $R^{LG}$-$(L^{LG1})_{0-1}$-$(L^{LG2})_{0-1}$-$(L^{LG3})_{0-1}$-$(L^{LG4})_{0-1}$-) or a compound comprising a released target binding moiety (e.g., a compound having the structure of $R^{LG}$-$(L^{LG1})_{0-1}$-$(L^{LG2})_{0-1}$-$(L^{LG3})_{0-1}$-$(L^{LG4})_{0-1}$-H or a salt thereof), and a reaction partner (e.g., a compound of formula R-I or a salt thereof). In some embodiments, released target binding moieties may bind to target agent moieties in target agents and/or formed product agents. Various technologies are available to separate released target binding moieties from target agent moieties in accordance with the present disclosure, for example, in some embodiments, contacting a composition with a composition comprising glycine at certain pH.

Certain Embodiments of Variables

As examples, exemplary embodiments of variables are described throughout the present disclosure. As appreciated by those skilled in the art, embodiments for different variables may be optionally combined.

In some embodiments, ABT is an antibody binding moiety as described herein. In some embodiments, an ABT is an ABT of a compound selected from those depicted in Table 1. In some embodiments, an ABT is a moiety selected from Table A-1. In some embodiments, an ABT is a moiety described in Table 1.

In some embodiments, L is a linker moiety of a compound selected from those depicted in Table 1.

In some embodiments, each of $R^1$, $R^3$ and $R^5$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or: $R^1$ and $R^{1'}$ are optionally taken together with their intervening carbon atom to form a 3-8 membered saturated or partially unsaturated spirocyclic carbocyclic ring or a 4-8 membered saturated or partially unsaturated spirocyclic heterocyclic ring having 1-2 heteroatoms independently selected from nitrogen, oxygen, or sulfur; $R^3$ and $R^{3'}$ are optionally taken together with their intervening carbon atom to form a 3-8 membered saturated or partially unsaturated spirocyclic carbocyclic ring or a 4-8 membered saturated or partially unsaturated spirocyclic heterocyclic ring having 1-2 heteroatoms independently selected from nitrogen, oxygen, or sulfur; an $R^5$ group and the $R^{5'}$ group attached to the same carbon atom are optionally taken together with their intervening carbon atom to form a 3-8 membered saturated or partially unsaturated spirocyclic carbocyclic ring or a 4-8 membered saturated or partially unsaturated spirocyclic heterocyclic ring having 1-2 heteroatoms independently selected from nitrogen, oxygen, or sulfur; or two $R^5$ groups are optionally taken together with their intervening atoms to form a $C_{1-10}$ bivalent straight or branched saturated or unsaturated hydrocarbon chain wherein 1-3 methylene units of the chain are independently and optionally replaced with —S—, —SS—, —N(R)—, —O—, —C(O)—, —OC(O)—, —C(O)O—, —C(O)N(R)—, —N(R)C(O)—, —S(O)—, —$S(O)_2$—, or -$Cy^1$-, wherein each -$Cy^1$- is independently a 5-6 membered heteroarylenyl with 1-4 heteroatoms independently selected from nitrogen, oxygen or sulfur.

In some embodiments, $R^1$ is hydrogen. In some embodiments, $R^1$ is optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^1$ is an optionally substituted $C_{1-6}$ aliphatic group. In some embodiments, $R^1$ is an optionally substituted 3-8 membered saturated or partially unsaturated monocyclic carbocyclic ring. In some embodiments, $R^1$ is an optionally substituted phenyl. In some embodiments, $R^1$ is an optionally substituted 8-10 membered bicyclic aromatic carbocyclic ring. In some embodiments, $R^1$ is an optionally substituted 4-8 membered saturated or partially unsaturated monocyclic heterocyclic ring having 1-2 heteroatoms independently selected from nitrogen, oxygen, or sulfur. In some embodiments, $R^1$ is an optionally substituted 5-6 membered monocyclic heteroaromatic ring having 1-4 heteroatoms independently selected from nitrogen, oxygen, or sulfur. In some embodiments, $R^1$ is an optionally substituted 8-10 membered bicyclic heteroaromatic ring having 1-5 heteroatoms independently selected from nitrogen, oxygen, or sulfur.

In some embodiments, $R^1$ is

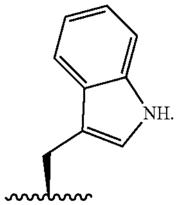

In some embodiments, $R^1$ is

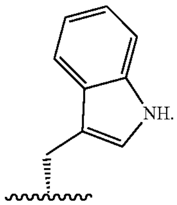

In some embodiments, $R^1$ is

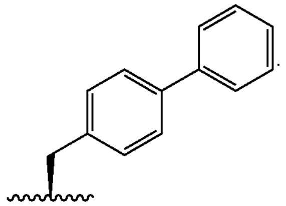

In some embodiments, $R^1$ is

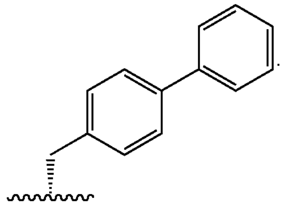

In some embodiments, $R^1$ is

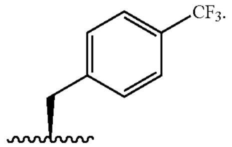

In some embodiments, $R^1$ is

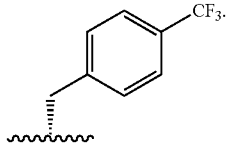

In some embodiments, $R^1$ is

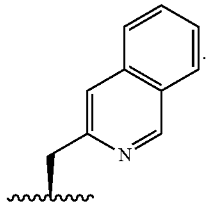

In some embodiments, $R^1$ is

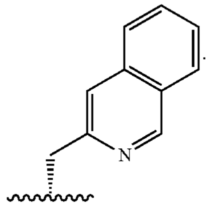

In some embodiments, $R^1$ is

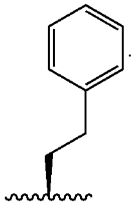

In some embodiments, $R^1$ is

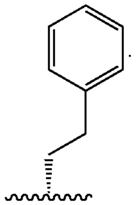

In some embodiments, $R^1$ is

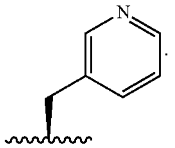

In some embodiments, $R^1$ is

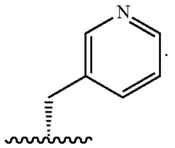

In some embodiments, $R^1$ is

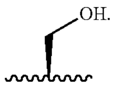

In some embodiments, $R^1$ is

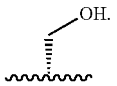

In some embodiments, $R^1$ is

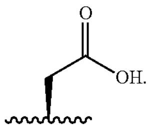

In some embodiments, $R^1$ is

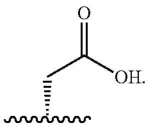

In some embodiments, $R^1$ is

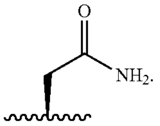

In some embodiments, $R^1$ is

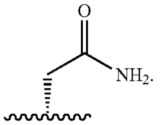

In some embodiments, $R^1$ is

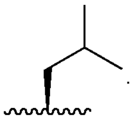

In some embodiments, $R^1$ is

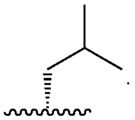

In some embodiments, $R^1$ and $R^{1'}$ are optionally taken together with their intervening carbon atom to form a 3-8 membered saturated or partially unsaturated spirocyclic carbocyclic ring. In some embodiments, $R^1$ and $R^{1'}$ are optionally taken together with their intervening carbon atom to form a 4-8 membered saturated or partially unsaturated spirocyclic heterocyclic ring having 1-2 heteroatoms independently selected from nitrogen, oxygen, or sulfur.

In some embodiments, $R^1$ is selected from those depicted in Table 1.

In some embodiments, R is $R^1$ as described in the present disclosure. In some embodiments, $R^{a2}$ is $R^1$ as described in the present disclosure. In some embodiments, $R^{a3}$ is $R^1$ as described in the present disclosure.

In some embodiments, $R^3$ is hydrogen. In some embodiments, $R^3$ is optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^3$ is an optionally substituted $C_{1-6}$ aliphatic group. In some embodiments, $R^3$ is an optionally substituted 3-8 membered saturated or partially unsaturated monocyclic carbocyclic ring. In some embodiments, $R^3$ is an optionally substituted phenyl. In some embodiments, $R^3$ is an optionally substituted 8-10 membered bicyclic aromatic carbocyclic ring. In some embodiments, $R^3$ is an optionally substituted 4-8 membered saturated or partially unsaturated monocyclic heterocyclic ring having 1-2 heteroatoms independently selected from nitrogen, oxygen, or sulfur. In some embodiments, $R^3$ is an optionally substituted 5-6 membered monocyclic heteroaromatic ring having 1-4 heteroatoms independently selected from nitrogen, oxygen, or sulfur. In some embodiments, $R^3$ is an optionally substituted 8-10 membered bicyclic heteroaromatic ring having 1-5 heteroatoms independently selected from nitrogen, oxygen, or sulfur.

In some embodiments, $R^3$ is methyl. In some embodiments, $R^3$ is

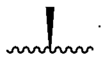.

In some embodiments, $R^3$ is

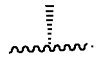.

In some embodiments, $R^3$ is

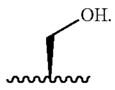.

In some embodiments, $R^3$ is

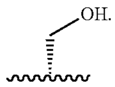.

In some embodiments, $R^3$ is

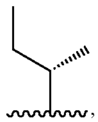, wherein the site of attachment has (S) stereochemistry. In some embodiments, $R^3$ is

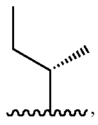, wherein the site of attachment has (R) stereochemistry. In some embodiments, $R^3$ is

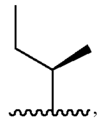, wherein the site of attachment has (S) stereochemistry. In some embodiments, $R^3$ is

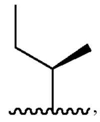, wherein the site of attachment has (R) stereochemistry.

In some embodiments, $R^3$ is

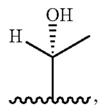, wherein the site of attachment has (S) stereochemistry. In some embodiments, $R^3$ is

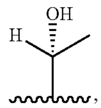, wherein the site of attachment has (R) stereochemistry.

In some embodiments, $R^3$ and $R^{3'}$ are optionally taken together with their intervening carbon atom to form a 3-8 membered saturated or partially unsaturated spirocyclic carbocyclic ring. In some embodiments, $R^3$ and $R^{3'}$ are optionally taken together with their intervening carbon atom to form a 4-8 membered saturated or partially unsaturated spirocyclic heterocyclic ring having 1-2 heteroatoms independently selected from nitrogen, oxygen, or sulfur.

In some embodiments, $R^3$ is selected from those depicted in Table 1.

In some embodiments, R is $R^2$ as described in the present disclosure. In some embodiments, $R^{a2}$ is $R^2$ as described in the present disclosure. In some embodiments, $R^{a3}$ is $R^2$ as described in the present disclosure.

In some embodiments, $R^5$ is hydrogen. In some embodiments, $R^5$ is optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^5$ is an optionally substituted $C_{1-6}$ aliphatic group. In some embodiments, $R^5$ is an optionally substituted 3-8 membered saturated or partially unsaturated monocyclic carbocyclic ring. In some embodiments, $R^5$ is an optionally substituted phenyl. In some embodiments, $R^5$ is an optionally substituted 8-10 membered bicyclic aromatic carbocyclic ring. In some embodiments, $R^5$ is an optionally substituted 4-8 membered saturated or partially unsaturated monocyclic heterocyclic ring having 1-2 heteroatoms independently selected from nitrogen, oxygen, or sulfur. In some embodiments, $R^5$ is an optionally substituted 5-6 membered monocyclic heteroaromatic ring having 1-4 heteroatoms independently selected from nitrogen, oxygen, or sulfur. In some embodiments, $R^5$ is an optionally substituted 8-10 membered bicyclic heteroaromatic ring having 1-5 heteroatoms independently selected from nitrogen, oxygen, or sulfur.

In some embodiments, $R^5$ is methyl. In some embodiments, $R^5$ is

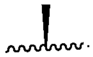.

In some embodiments, $R^5$ is

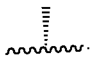.

In some embodiments, $R^5$ is

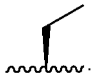.

In some embodiments, $R^5$ is

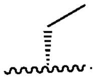.

In some embodiments, $R^5$ is

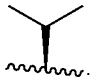.

In some embodiments, $R^5$ is

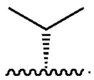.

In some embodiments, $R^5$ is

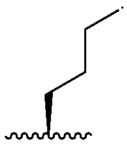.

In some embodiments, $R^5$ is

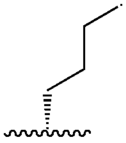

In some embodiments, $R^5$ is

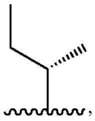, wherein the site of attachment has (S) stereochemistry. In some embodiments, $R^5$ is

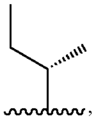, wherein the site of attachment has (R) stereochemistry. In some embodiments, $R^5$ is

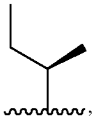, wherein the site of attachment has (S) stereochemistry. In some embodiments, $R^5$

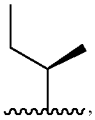, wherein the site of attachment has (R) stereochemistry. In some embodiments, $R^5$ is

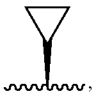,

In some embodiments, $R^5$ is

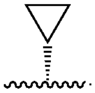.

In some embodiments, $R^5$ is

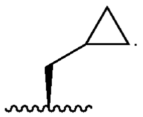

In some embodiments, $R^5$ is

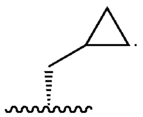

In some embodiments, $R^5$ is

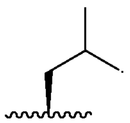

In some embodiments, $R^5$ is

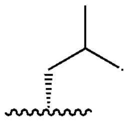

In some embodiments, $R^5$ is

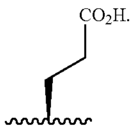

In some embodiments, $R^5$ is

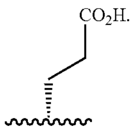

In some embodiments, $R^5$ is

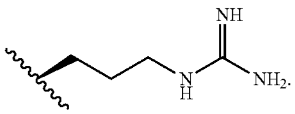

In some embodiments, $R^5$ is

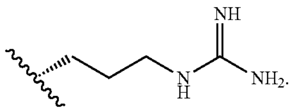

In some embodiments, $R^5$ is

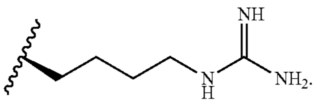

In some embodiments, $R^5$ is

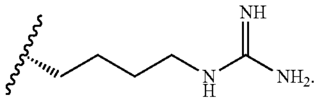

In some embodiments, $R^5$ is

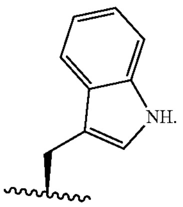

In some embodiments, $R^5$ is

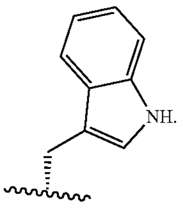

In some embodiments, $R^5$ is

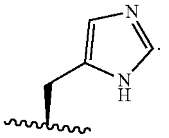

In some embodiments, $R^5$ is

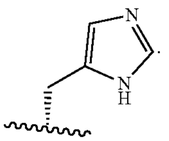

In some embodiments, $R^5$ is

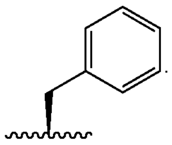

In some embodiments, $R^5$ is

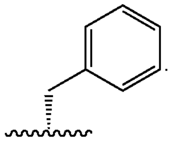

In some embodiments, $R^5$ is

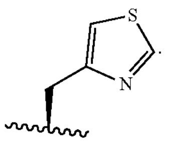

In some embodiments, $R^5$ is

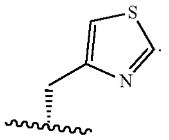

In some embodiments, $R^5$ is

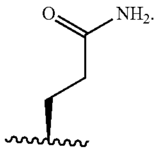

In some embodiments, $R^4$ is 5

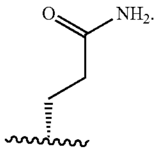

In some embodiments, $R^5$ is

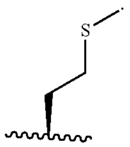

In some embodiments, $R^5$ is

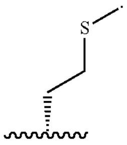

In some embodiments, $R^5$ is

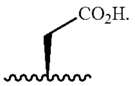

In some embodiments $R^5$ is

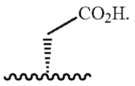

In some embodiments $R^4$ is

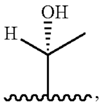

wherein the site of attachment has (S) stereochemistry.

In some embodiments, $R^4$ is

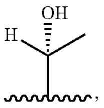

wherein the site of attachment has (R) stereochemistry.

In some embodiments, $R^5$ and the $R^{5'}$ group attached to the same carbon atom are optionally taken together with their intervening carbon atom to form a 3-8 membered saturated or partially unsaturated spirocyclic carbocyclic ring. In some embodiments, $R^5$ and the $R^{5'}$ group attached to the same carbon atom are optionally taken together with their intervening carbon atom to form a 4-8 membered saturated or partially unsaturated spirocyclic heterocyclic ring having 1-2 heteroatoms independently selected from nitrogen, oxygen, or sulfur.

In some embodiments, two $R^5$ groups are taken together with their intervening atoms to form a $C_{1-10}$ bivalent straight or branched saturated or unsaturated hydrocarbon chain wherein 1-3 methylene units of the chain are independently and optionally replaced with —S—, —SS—, —N(R)—, —O—, —C(O)—, —OC(O)—, —C(O)O—, —C(O)N(R)—, —N(R)C(O)—, —S(O)—, $—S(O)_2—$, or $-Cy^1-$, wherein each $-Cy^1$ is independently a 5-6 membered heteroarylenyl with 1-4 heteroatoms independently selected from nitrogen, oxygen or sulfur.

In some embodiments, two $R^5$ groups are taken together with their intervening atoms to form

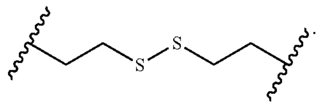 [SMILES: *CCSSCC*]

In some embodiments, two $R^5$ groups are taken together with their intervening atoms to form

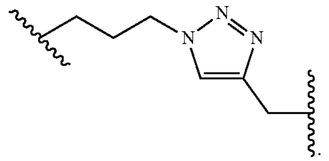 [SMILES: *CCCn1cc(C*)nn1]

In some embodiments, two $R^5$ groups are taken together with their intervening atoms to form

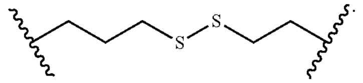 [SMILES: *CCCSSCC*]

In some embodiments, two $R^5$ groups are taken together with their intervening atoms to form

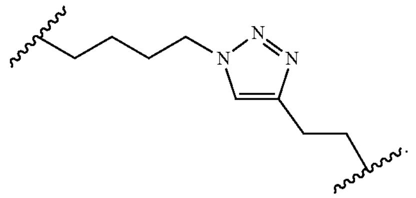 [SMILES: *CCCCn1cc(CC*)nn1]

In some embodiments, $R^5$ is selected from those depicted in Table 1.

In some embodiments, R is $R^5$ as described in the present disclosure. In some embodiments, $R^{a2}$ is $R^5$ as described in the present disclosure. In some embodiments, $R^{a3}$ is $R^5$ as described in the present disclosure.

In some embodiments, each of $R^{1'}$, $R^{3'}$ and $R^{5'}$ is independently hydrogen or $C_{1-3}$ aliphatic.

In some embodiments, $R^{1'}$ is hydrogen. In some embodiments, $R^{1'}$ is $C_{1-3}$ aliphatic.

In some embodiments, $R^{1'}$ is methyl. In some embodiments, $R^{1'}$ is ethyl. In some embodiments, $R^{1'}$ is n-propyl. In some embodiments, $R^{1'}$ is isopropyl. In some embodiments, $R^{1'}$ is cyclopropyl.

In some embodiments, $R^{1'}$ is selected from those depicted in Table 1.

In some embodiments, $R^{3'}$ is hydrogen. In some embodiments, $R^{3'}$ is $C_{1-3}$ aliphatic.

In some embodiments, $R^{3'}$ is methyl. In some embodiments, $R^{3'}$ is ethyl. In some embodiments, $R^{3'}$ is n-propyl. In some embodiments, $R^{3'}$ is isopropyl. In some embodiments, $R^{3'}$ is cyclopropyl.

In some embodiments, $R^{3'}$ is selected from those depicted in Table 1.

In some embodiments, $R^{5'}$ is hydrogen. In some embodiments, $R^{5'}$ is $C_{1-3}$ aliphatic.

In some embodiments, $R^{5'}$ is methyl. In some embodiments, $R^{5'}$ is ethyl. In some embodiments, $R^{5'}$ is n-propyl. In some embodiments, $R^{5'}$ is isopropyl. In some embodiments, $R^{5'}$ is cyclopropyl.

In some embodiments, $R^{5'}$ is selected from those depicted in Table 1.

In some embodiments, each of $R^2$, $R^4$ and $R^6$ is independently hydrogen, or $C_{1-4}$ aliphatic, or: $R^2$ and $R^1$ are optionally taken together with their intervening atoms to form a 4-8 membered saturated or partially unsaturated monocyclic heterocyclic ring having 1-2 heteroatoms independently selected from nitrogen, oxygen, or sulfur; $R^4$ and $R^3$ are optionally taken together with their intervening atoms to form a 4-8 membered saturated or partially unsaturated monocyclic heterocyclic ring having 1-2 heteroatoms independently selected from nitrogen, oxygen, or sulfur; or an $R^6$ group and its adjacent $R^5$ group are optionally taken together with their intervening atoms to form a 4-8 membered saturated or partially unsaturated monocyclic heterocyclic ring having 1-2 heteroatoms independently selected from nitrogen, oxygen, or sulfur.

In some embodiments, $R^2$ is hydrogen. In some embodiments, $R^2$ is $C_{1-4}$ aliphatic. In some embodiments, $R^2$ is methyl. In some embodiments, $R^2$ is ethyl. In some embodiments, $R^2$ is n-propyl. In some embodiments, $R^2$ is isopropyl. In some embodiments, $R^2$ is n-butyl. In some embodiments, $R^2$ is isobutyl. In some embodiments, $R^2$ is tert-butyl.

In some embodiments, $R^2$ and $R^1$ are taken together with their intervening atoms to form a 4-8 membered saturated or partially unsaturated monocyclic heterocyclic ring having 1-2 heteroatoms independently selected from nitrogen, oxygen, or sulfur.

In some embodiments, $R^2$ and $R^1$ are taken together with their intervening atoms to form

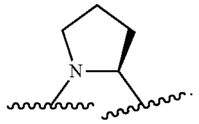 [SMILES: *[C@@H]1CCCN1*]

In some embodiments, $R^2$ and $R^1$ are taken together with their intervening atoms to form

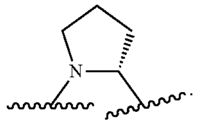 [SMILES: *[C@H]1CCCN1*]

In some embodiments, $R^2$ is selected from those depicted in Table 1.

In some embodiments, $R^4$ is hydrogen. In some embodiments, $R^4$ is $C_{1-4}$ aliphatic. In some embodiments, $R^4$ is methyl. In some embodiments, $R^4$ is ethyl. In some embodiments, $R^4$ is n-propyl. In some embodiments, $R^4$ is isopropyl. In some embodiments, $R^4$ is n-butyl. In some embodiments, $R^4$ is isobutyl. In some embodiments, $R^4$ is tert-butyl.

In some embodiments, $R^4$ and $R^3$ are taken together with their intervening atoms to form a 4-8 membered saturated or partially unsaturated monocyclic heterocyclic ring having 1-2 heteroatoms independently selected from nitrogen, oxygen, or sulfur.

In some embodiments, $R^4$ and $R^3$ are taken together with their intervening atoms to form

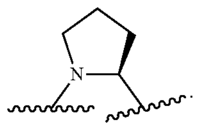 [SMILES: *[C@@H]1CCCN1*]

In some embodiments, $R^4$ and $R^3$ are taken together with their intervening atoms to form

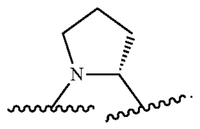

In some embodiments, $R^4$ is selected from those depicted in Table 1.

In some embodiments, $R^6$ is hydrogen. In some embodiments, $R^6$ is $C_{1-4}$ aliphatic. In some embodiments, $R^6$ is methyl. In some embodiments, $R^6$ is ethyl. In some embodiments, $R^6$ is n-propyl. In some embodiments, $R^6$ is isopropyl. In some embodiments, $R^6$ is n-butyl. In some embodiments, $R^6$ is isobutyl. In some embodiments, $R^6$ is tert-butyl.

In some embodiments, an $R^6$ group and its adjacent $R^5$ group are taken together with their intervening atoms to form a 4-8 membered saturated or partially unsaturated monocyclic heterocyclic ring having 1-2 heteroatoms independently selected from nitrogen, oxygen, or sulfur.

In some embodiments, an $R^6$ group and its adjacent $R^5$ group are taken together with their intervening atoms to form

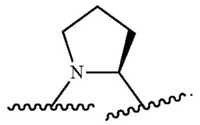 [SMILES: *[C@@H]1CCCN1*]

In some embodiments, an $R^6$ group and its adjacent $R^5$ group are taken together with their intervening atoms to form

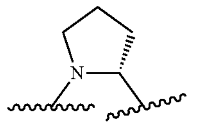 [SMILES: *[C@H]1CCCN1*]

In some embodiments, $R^6$ is selected from those depicted in Table 1.

In some embodiments, R is $R^{1'}$ as described in the present disclosure. In some embodiments, $R^{a2}$ is $R^{1'}$ as described in the present disclosure. In some embodiments, $R^{a3}$ is $R^{1'}$ as described in the present disclosure. In some embodiments, R is $R^{3'}$ as described in the present disclosure. In some embodiments, $R^{a2}$ is $R^{3'}$ as described in the present disclosure. In some embodiments, $R^{a3}$ is $R^{3'}$ as described in the present disclosure. In some embodiments, R is $R^2$ as described in the present disclosure. In some embodiments, $R^{a2}$ is $R^2$ as described in the present disclosure. In some embodiments, $R^{a3}$ is $R^2$ as described in the present disclosure. In some embodiments, R is $R^4$ as described in the present disclosure. In some embodiments, $R^{a2}$ is $R^4$ as described in the present disclosure. In some embodiments, $R^{a3}$ is $R^4$ as described in the present disclosure. In some embodiments, R is $R^6$ as described in the present disclosure. In some embodiments, $R^{a2}$ is $R^6$ as described in the present disclosure. In some embodiments, $R^{a3}$ is $R^6$ as described in the present disclosure.

In some embodiments, $L^1$ is

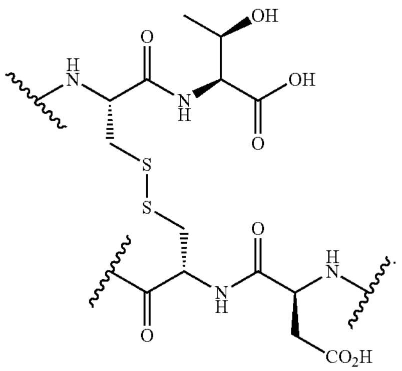 [SMILES: *N[C@@H](CC(=O)O)C(=O)N[C@@H](CSSC[C@H](N*)C(=O)N[C@H](C(=O)O)[C@@H](C)O)C(*)=O]

In some embodiments, $L^1$ is

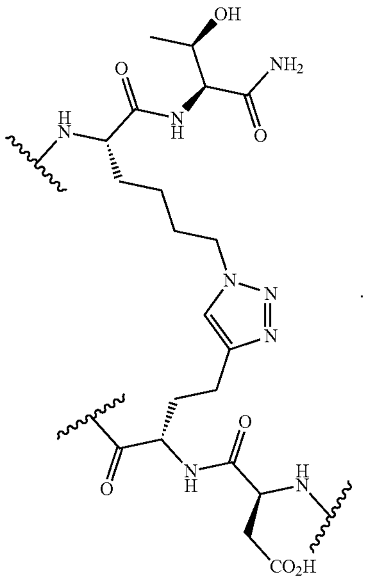 [SMILES: *N[C@@H](CC(=O)O)C(=O)N[C@@H](CCc1cn(CCCC[C@H](N*)C(=O)N[C@H](C(N)=O)[C@@H](C)O)nn1)C(*)=O]

In some embodiments, $L^1$ is
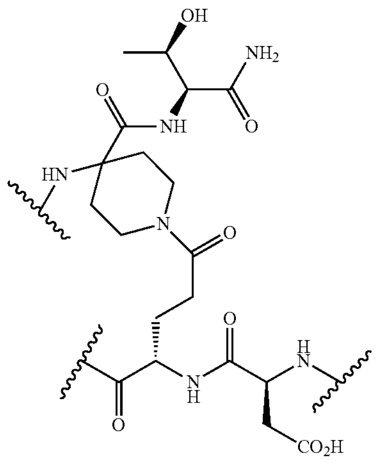
.
In some embodiments, $L^1$ is
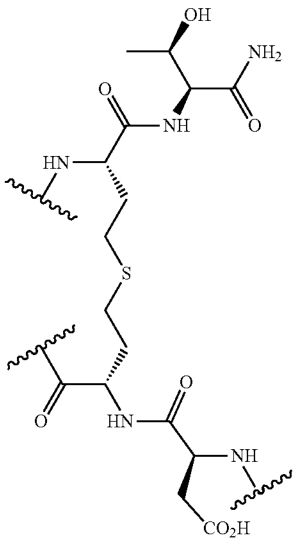
.
In some embodiments, $L^1$ is
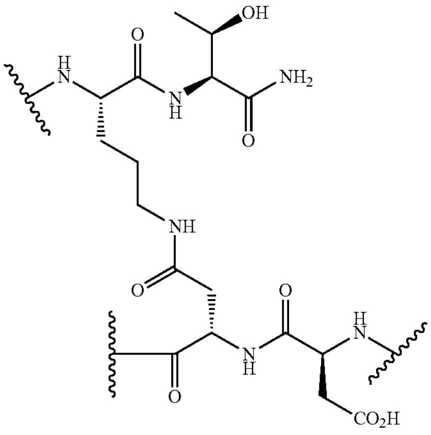
.
In some embodiments, $L^1$ is
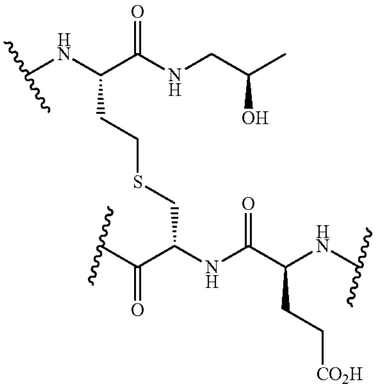
.
In some embodiments, $L^1$ is
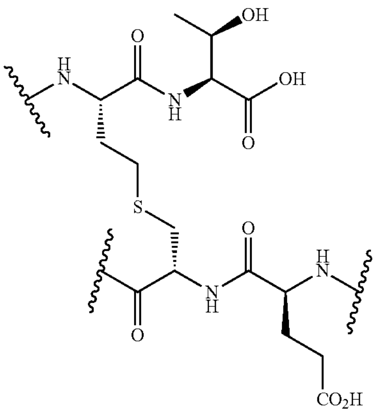
.
In some embodiments, $L^1$ is
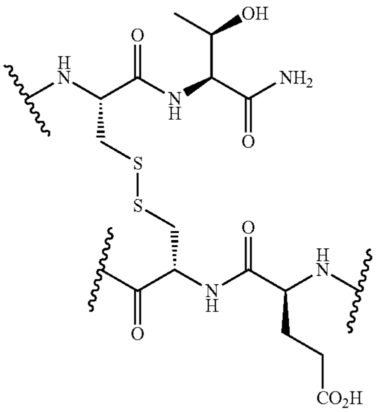
.

In some embodiments, $L^1$ is
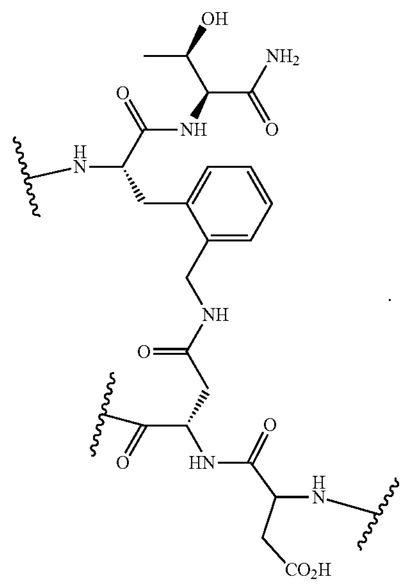 [SMILES: *NC(CC(=O)O)C(=O)N[C@@H](CC(=O)NCc1ccccc1C[C@H](N*)C(=O)N[C@H](C(N)=O)[C@@H](C)O)C(*)=O]
In some embodiments, $L^1$ is
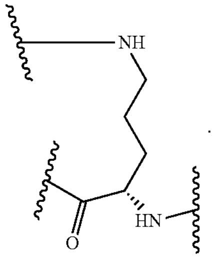 [SMILES: *NCCC[C@H](N*)C(*)=O]
In some embodiments, $L^1$ is
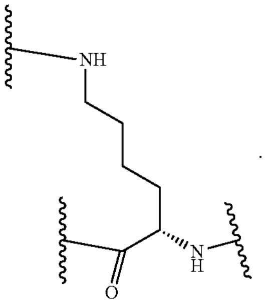 [SMILES: *NCCCC[C@H](N*)C(*)=O]
In some embodiments, $L^1$ is
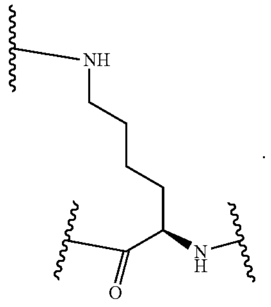 [SMILES: *NCCCC[C@@H](N*)C(*)=O]
In some embodiments, $L^1$ is
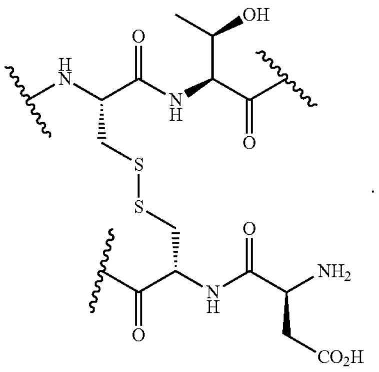 [SMILES: *N[C@@H](CSSC[C@H](NC(=O)[C@@H](N)CC(=O)O)C(*)=O)C(=O)N[C@H](C(*)=O)[C@@H](C)O]
In some embodiments, $L^1$ is
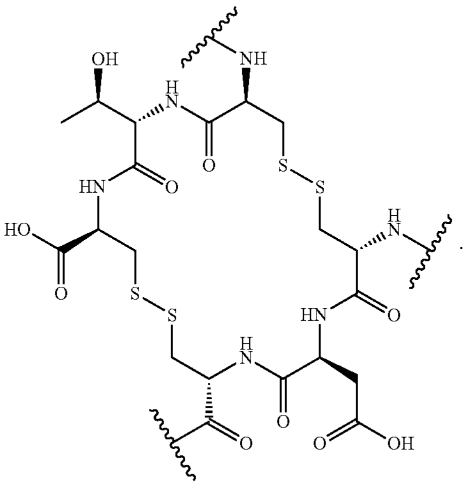 [SMILES: *N[C@H]1CSSC[C@H](N*)C(=O)N[C@@H]([C@@H](C)O)C(=O)N[C@H](C(=O)O)CSSC[C@@H](C(*)=O)NC(=O)[C@H](CC(=O)O)NC1=O]

In some embodiments, $L^1$ is
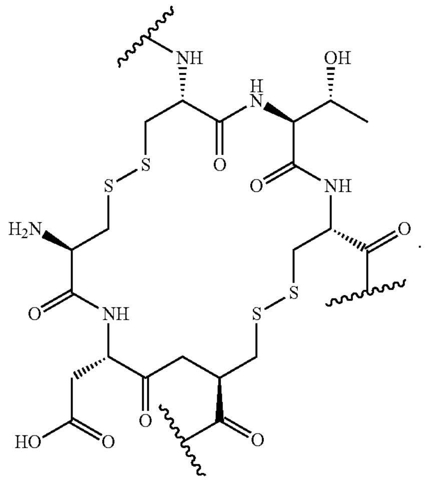 [SMILES: *N[C@H]1CSSC[C@H](N)C(=O)N[C@@H](CC(=O)O)C(=O)C[C@H](C(*)=O)CSSC[C@@H](C(*)=O)NC(=O)[C@H]([C@@H](C)O)NC1=O]
In some embodiments, $L^1$ is
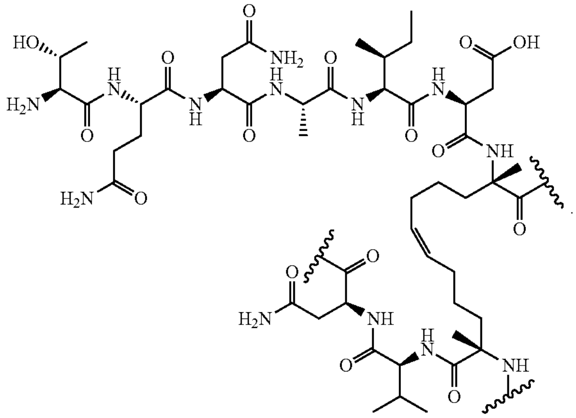 [SMILES: *N[C@@](C)(CCC/C=C\CCC[C@](C)(NC(=O)[C@H](CC(=O)O)NC(=O)[C@@H](NC(=O)[C@H](C)NC(=O)[C@H](CC(N)=O)NC(=O)[C@H](CCC(N)=O)NC(=O)[C@@H](N)[C@@H](C)O)[C@@H](C)CC)C(*)=O)C(=O)N[C@H](C(=O)N[C@@H](CC(N)=O)C(*)=O)C(C)C]
In some embodiments, $L^1$ is
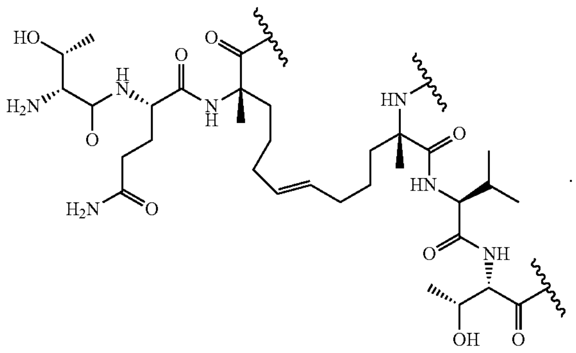 [SMILES: *N[C@@](C)(CCC/C=C/CCC[C@](C)(NC(=O)[C@H](CCC(N)=O)NC(O)[C@H](N)[C@@H](C)O)C(*)=O)C(=O)N[C@H](C(=O)N[C@H](C(*)=O)[C@@H](C)O)C(C)C]

In some embodiments, $L^1$ is
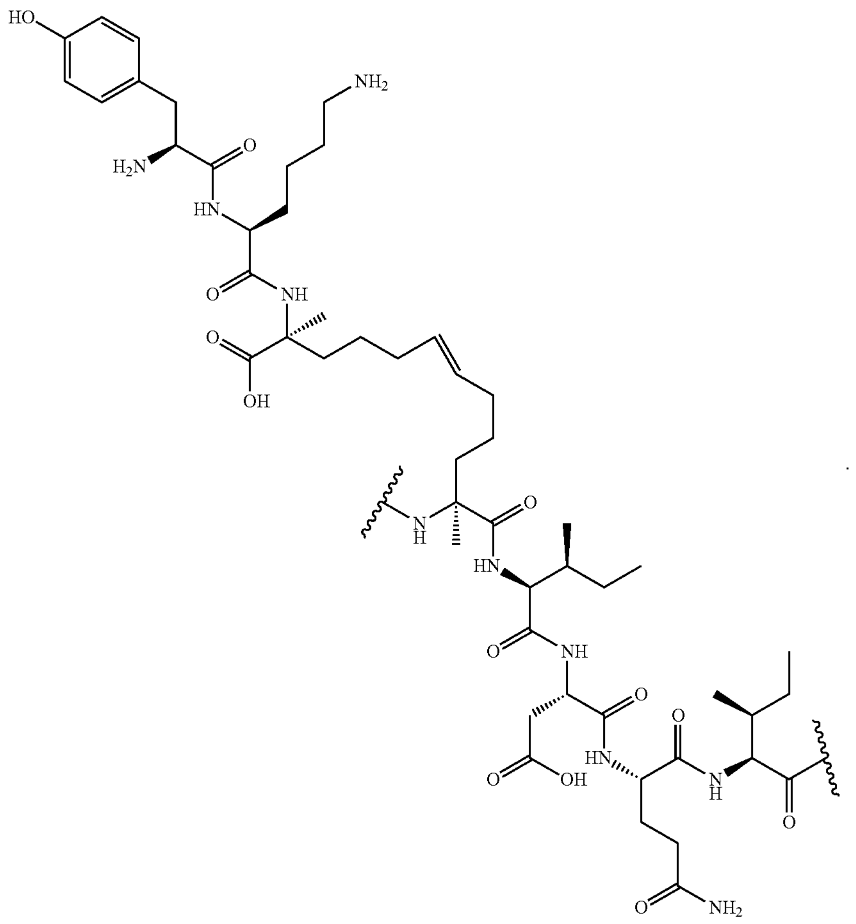 [SMILES: *N[C@@](C)(CCC/C=C/CCC[C@](C)(NC(=O)[C@H](CCCCN)NC(=O)[C@@H](N)Cc1ccc(O)cc1)C(=O)O)C(=O)N[C@H](C(=O)N[C@@H](CC(=O)O)C(=O)N[C@@H](CCC(N)=O)C(=O)N[C@H](C(*)=O)[C@@H](C)CC)[C@@H](C)CC]
In some embodiments, $L^1$ is
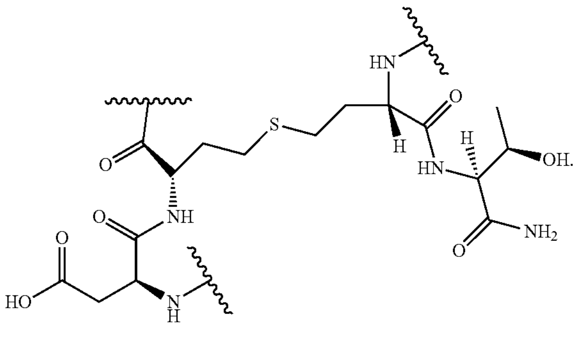
In some embodiments, $L^1$ is
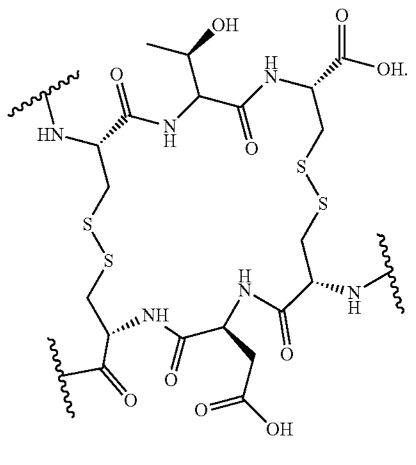 [SMILES: *N[C@H]1CSSC[C@@H](C(*)=O)NC(=O)[C@H](CC(=O)O)NC(=O)[C@@H](N*)CSSC[C@@H](C(=O)O)NC(=O)C([C@@H](C)O)NC1=O]

In some embodiments, $L^1$ is

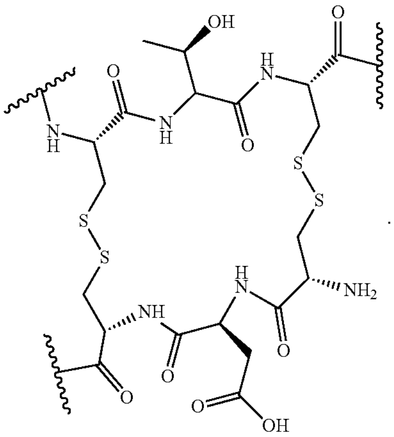 [SMILES: *N[C@H]1CSSC[C@@H](C(*)=O)NC(=O)[C@H](CC(=O)O)NC(=O)[C@@H](N)CSSC[C@@H](C(*)=O)NC(=O)C([C@@H](C)O)NC1=O]

In some embodiments, $L^1$ is

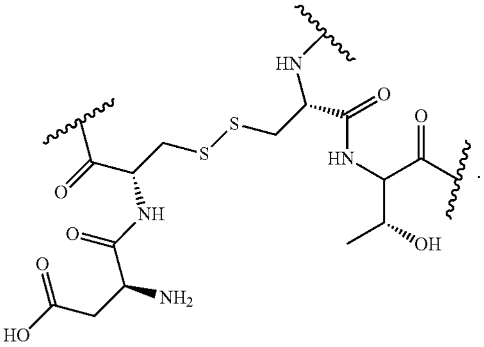 [SMILES: *N[C@@H](CSSC[C@H](NC(=O)[C@@H](N)CC(=O)O)C(*)=O)C(=O)NC(C(*)=O)[C@@H](C)O]

In some embodiments, L is a covalent bond or a $C_{1-10}$ bivalent straight or branched saturated or unsaturated hydrocarbon chain wherein 1-3 methylene units of the chain are independently and optionally replaced with —S—, —N(R)—, —O—, —C(O)—, —OC(O)—, —C(O)O—, —C(O)N(R)—, —N(R)C(O)—, —S(O)—, —$S(O)_2$—,

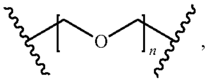
,
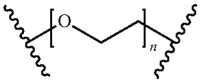
,
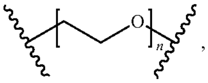
, or -$Cy^1$-, wherein each -$Cy^1$ is independently a 5-6 membered heteroarylenyl with 1-4 heteroatoms independently selected from nitrogen, oxygen or sulfur.

In some embodiments, L is a covalent bond. In some embodiments, L is a $C_{1-10}$ bivalent straight or branched saturated or unsaturated hydrocarbon chain wherein 1-3 methylene units of the chain are independently and optionally replaced with —S—, —N(R)—, —O—, —C(O)—, —OC(O)—, —C(O)O—, —C(O)N(R)—, —N(R)C(O)—, —S(O)—, —$S(O)_2$—,

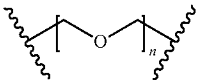
,
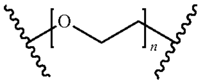
,
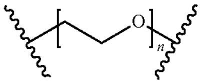
, or -$Cy^1$-, wherein each -$Cy^1$- is independently a 5-6 membered heteroarylenyl with 1-4 heteroatoms independently selected from nitrogen, oxygen or sulfur.

In some embodiments, L is

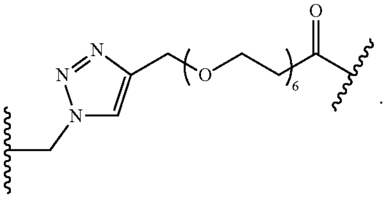

In some embodiments, L is

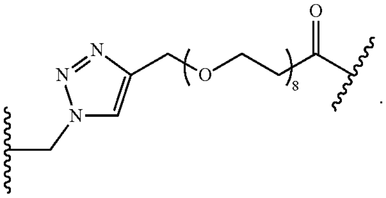

In some embodiments, L is

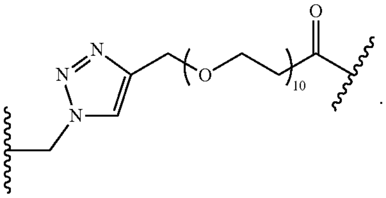

In some embodiments, L is

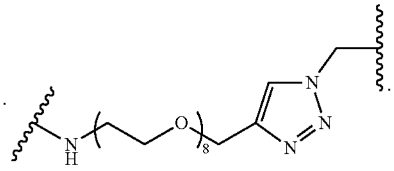

In some embodiments, L is

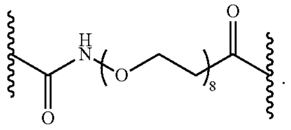

In some embodiments, L is

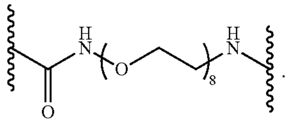

In some embodiments, each of m and n is independently 1, 2, 3, 4, 5, 6, 7, 8, 9, or 10.

In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, m is selected from those depicted in Table 1.

In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is selected from those depicted in Table 1.

In some embodiments, each of $R^7$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or: an $R^7$ group and the $R^7$ group attached to the same carbon atom are optionally taken together with their intervening carbon atom to form a 3-8 membered saturated or partially unsaturated spirocyclic carbocyclic ring or a 4-8 membered saturated or partially unsaturated spirocyclic heterocyclic ring having 1-2 heteroatoms independently selected from nitrogen, oxygen, or sulfur.

In some embodiments, $R^7$ is hydrogen. In some embodiments, $R^7$ is optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^7$ is an optionally substituted $C_{1-6}$ aliphatic group. In some embodiments, $R^7$ is an optionally substituted 3-8 membered saturated or partially unsaturated monocyclic carbocyclic ring. In some embodiments, $R^7$ is an optionally substituted phenyl. In some embodiments, $R^7$ is an optionally substituted 8-10 membered bicyclic aromatic carbocyclic ring. In some embodiments, $R^7$ is an optionally substituted 4-8 membered saturated or partially unsaturated monocyclic heterocyclic ring having 1-2 heteroatoms independently selected from nitrogen, oxygen, or sulfur. In some embodiments, $R^7$ is an optionally substituted 5-6 membered monocyclic heteroaromatic ring having 1-4 heteroatoms independently selected from nitrogen, oxygen, or sulfur. In some embodiments, $R^7$ is an optionally substituted 8-10 membered bicyclic heteroaromatic ring having 1-5 heteroatoms independently selected from nitrogen, oxygen, or sulfur.

In some embodiments, $R^7$ is methyl. In some embodiments, $R^7$ is

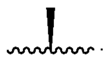

In some embodiments, $R^7$ is

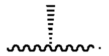

In some embodiments, $R^7$ is

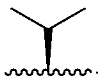

In some embodiments, $R^7$ is

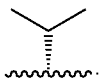

In some embodiments, $R^7$ is

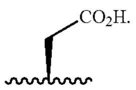

In some embodiments, $R^7$ is

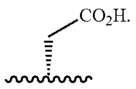

In some embodiments, $R^7$ is
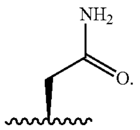
In some embodiments, $R^7$ is
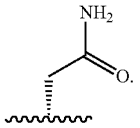
In some embodiments, $R^7$ is
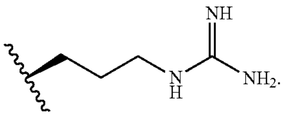
In some embodiments, $R^7$ is
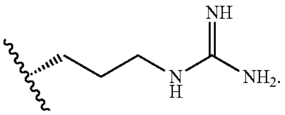
In some embodiments, $R^7$ is
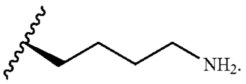
In some embodiments, $R^7$ is
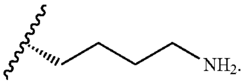
In some embodiments, $R^7$ is
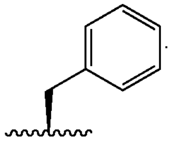
In some embodiments, $R^7$ is
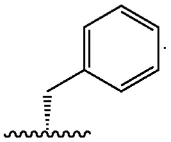
In some embodiments, $R^7$ is
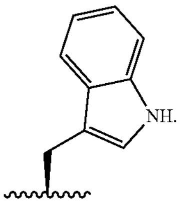
In some embodiments, $R^7$ is
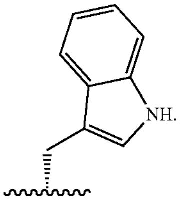
In some embodiments, $R^7$ is
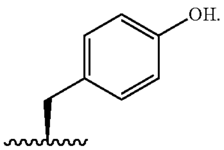
In some embodiments, $R^7$ is
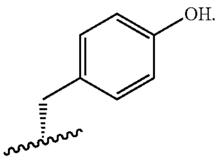
In some embodiments, $R^7$ is
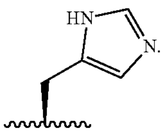

In some embodiments, $R^7$ is

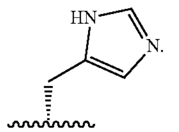

In some embodiments, an $R^7$ group and the $R^{7'}$ group attached to the same carbon atom are taken together with their intervening carbon atom to form a 3-8 membered saturated or partially unsaturated spirocyclic carbocyclic ring. In some embodiments, an $R^7$ group and the $R^{7'}$ group attached to the same carbon atom are taken together with their intervening carbon atom to form a 4-8 membered saturated or partially unsaturated spirocyclic heterocyclic ring having 1-2 heteroatoms independently selected from nitrogen, oxygen, or sulfur.

In some embodiments, $R^7$ is selected from those depicted in Table 1.

In some embodiments, each of $R^{7'}$ is independently hydrogen or $C_{1-3}$ aliphatic.

In some embodiments, $R^{7'}$ is hydrogen. In some embodiments, $R^{7'}$ is methyl. In some embodiments, $R^{7'}$ is ethyl. In some embodiments, $R^{7'}$ is n-propyl. In some embodiments, $R^{7'}$ is isopropyl.

In some embodiments, $R^{7'}$ is selected from those depicted in Table 1.

In some embodiments, each of $R^8$ is independently hydrogen, or $C_{1-4}$ aliphatic, or: an $R^8$ group and its adjacent $R^7$ group are optionally taken together with their intervening atoms to form a 4-8 membered saturated or partially unsaturated monocyclic heterocyclic ring having 1-2 heteroatoms independently selected from nitrogen, oxygen, or sulfur.

In some embodiments, $R^8$ is hydrogen. In some embodiments, $R^8$ is $C_{1-4}$ aliphatic. In some embodiments, $R^8$ is methyl. In some embodiments, $R^8$ is ethyl. In some embodiments, $R^8$ is n-propyl. In some embodiments, $R^8$ is isopropyl. In some embodiments, $R^8$ is n-butyl. In some embodiments, $R^8$ is isobutyl. In some embodiments, $R^8$ is tert-butyl.

In some embodiments, an $R^8$ group and its adjacent $R^7$ group are taken together with their intervening atoms to form a 4-8 membered saturated or partially unsaturated monocyclic heterocyclic ring having 1-2 heteroatoms independently selected from nitrogen, oxygen, or sulfur.

In some embodiments, an $R^8$ group and its adjacent $R^7$ group are taken together with their intervening atoms to form

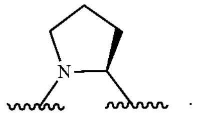 [SMILES: *[C@@H]1CCCN1*]

In some embodiments, an $R^8$ group and its adjacent $R^7$ group are taken together with their intervening atoms to form

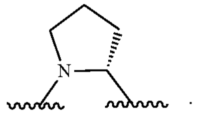 [SMILES: *[C@H]1CCCN1*]

In some embodiments, $R^8$ is selected from those depicted in Table 1.

In some embodiments, $R^9$ is hydrogen, $C_{1-3}$ aliphatic, or —$C(O)C_{1-3}$ aliphatic.

In some embodiments, $R^9$ is hydrogen. In some embodiments, $R^9$ is $C_{1-3}$ aliphatic. In some embodiments, $R^9$ is —$C(O)C_{1-3}$ aliphatic.

In some embodiments, $R^9$ is methyl. In some embodiments, $R^9$ is ethyl. In some embodiments, $R^9$ is n-propyl. In some embodiments, $R^9$ is isopropyl. In some embodiments, $R^9$ is cyclopropyl.

In some embodiments, $R^9$ is —C(O)Me. In some embodiments, $R^9$ is —C(O)Et. In some embodiments, $R^9$ is —$C(O)CH_2CH_2CH_3$. In some embodiments, $R^9$ is —$C(O)CH(CH_3)_2$. In some embodiments, $R^9$ is —C(O)cyclopropyl.

In some embodiments, $R^9$ is selected from those depicted in Table 1.

In some embodiments, R is $R^7$ as described in the present disclosure. In some embodiments, $R^{a2}$ is $R^7$ as described in the present disclosure. In some embodiments, $R^{a3}$ is $R^7$ as described in the present disclosure. In some embodiments, R is $R^{7'}$ as described in the present disclosure. In some embodiments, $R^{a2}$ is $R^{7'}$ as described in the present disclosure. In some embodiments, $R^{a3}$ is $R^{7'}$ as described in the present disclosure. In some embodiments, R is $R^8$ as described in the present disclosure. In some embodiments, $R^{a2}$ is $R^8$ as described in the present disclosure. In some embodiments, $R^{a3}$ is $R^8$ as described in the present disclosure. In some embodiments, R is $R^{8'}$ as described in the present disclosure. In some embodiments, $R^{a2}$ is $R^{8'}$ as described in the present disclosure. In some embodiments, $R^{a3}$ is $R^{8'}$ as described in the present disclosure. In some embodiments, R is $R^9$ as described in the present disclosure. In some embodiments, $R^{a2}$ is $R^9$ as described in the present disclosure. In some embodiments, $R^{a3}$ is $R^9$ as described in the present disclosure.

In some embodiments, o is 1, 2, 3, 4, 5, 6, 7, 8, 9, or 10. In some embodiments, o is 1. In some embodiments, o is 2. In some embodiments, o is 3. In some embodiments, o is 4. In some embodiments, o is 5. In some embodiments, o is 6. In some embodiments, o is 7. In some embodiments, o is 8. In some embodiments, o is 9. In some embodiments, o is 10.

In some embodiments, o is selected from those depicted in Table 1.

In some embodiments, $R^{a1}$ is R as described in the present disclosure. In some embodiments, $R^{a1}$ is optionally substituted $C_{1-4}$ aliphatic. In some embodiments, $R^{a1}$ is optionally substituted $C_{1-4}$ alkyl. In some embodiments, $R^{a1}$ is methyl.

In some embodiments, $L^{a1}$ is $L^a$ as described in the present disclosure. In some embodiments, $L^{a1}$ is a covalent bond.

In some embodiments, $L^{a2}$ is $L^a$ as described in the present disclosure. In some embodiments, $L^{a2}$ is a covalent bond.

In some embodiments, $L^T$ is $L^a$ as described herein. In some embodiments, $L^T$ is L as described herein. In some embodiments, $L^T$ is a covalent bond. In some embodiments, $L^T$ is —$CH_2$—C(O)—. In some embodiments, $L^T$ links a —S— of a side chain (e.g., through —$CH_2$) with the amino group of an amino acid residue (e.g., through —C(O)—).

In some embodiments, $L^a$ is a covalent bond. In some embodiments, $L^a$ is an optionally substituted bivalent group selected from $C_1$-$C_{10}$ aliphatic or $C_1$-$C_{10}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, $L^a$ is an optionally substituted bivalent group selected from $C_1$-$C_5$ aliphatic or $C_1$-$C_5$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —, -Cy-, —O—, —S—, —S—S—, —N(R')—, —C(O)—, —$C_2$—, —$S(O)_2N(R')$—, —C(O)S—, or —C(O)O—. In some embodiments, $L^a$ is an optionally substituted bivalent $C_1$-$C_5$ aliphatic, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, $L^a$ is an optionally substituted bivalent $C_1$-$C_5$ aliphatic. In some embodiments, $L^a$ is an optionally substituted bivalent $C_1$-$C_5$ heteroaliphatic having 1-3 heteroatoms independently selected from nitrogen, oxygen and sulfur.

In some embodiments, $R^{a2}$ is R as described in the present disclosure. In some embodiments, $R^{a2}$ is a side chain of a natural amino acid. In some embodiments, $R^{a3}$ is R as described in the present disclosure. In some embodiments, $R^{a3}$ is a side chain of a natural amino acid. In some embodiments, one of $R^{a2}$ and $R^{a3}$ is hydrogen. In some embodiments, $R^{a2}$ and/or $R^{a3}$ are R, wherein R is optionally substituted $C_{1-8}$ aliphatic or aryl. In some embodiments, R is optionally substituted linear $C_{2-8}$ alkyl. In some embodiments, R is linear $C_{2-8}$ alkyl. In some embodiments, R is optionally substituted branched $C_{2-8}$ alkyl. In some embodiments, R is branched $C_{2-8}$ alkyl. In some embodiments, R is n-pentyl. In some embodiments, R is optionally substituted phenyl. In some embodiments, R is optionally substituted —$CH_2$-phenyl. In some embodiments, R is 4-phenylphenyl-$CH_2$—.

In some embodiments, each -Cy- is independently an optionally substituted bivalent monocyclic, bicyclic or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon. In some embodiments, each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon. In some embodiments, -Cy- is an optionally substituted ring as described in the present disclosure, for example, for R and $Cy^L$, but is bivalent.

In some embodiments, -Cy- is monocyclic. In some embodiments, -Cy- is bicyclic. In some embodiments, -Cy- is polycyclic. In some embodiments, -Cy- is saturated. In some embodiments, -Cy- is partially unsaturated. In some embodiments, -Cy- is aromatic. In some embodiments, -Cy- comprises a saturated monocyclic moiety. In some embodiments, -Cy- comprises a partially unsaturated monocyclic moiety. In some embodiments, -Cy- comprises an aromatic monocyclic moiety. In some embodiments, -Cy- comprises a combination of a saturated, a partially unsaturated, and/or an aromatic cyclic moiety. In some embodiments, -Cy- is or comprises 3-membered ring. In some embodiments, -Cy- is or comprises 4-membered ring. In some embodiments, -Cy- is or comprises 5-membered ring. In some embodiments, -Cy- is or comprises 6-membered ring. In some embodiments, -Cy- is or comprises 7-membered ring. In some embodiments, -Cy- is or comprises 8-membered ring. In some embodiments, -Cy- is or comprises 9-membered ring. In some embodiments, -Cy- is or comprises 10-membered ring. In some embodiments, -Cy- is or comprises 11-membered ring. In some embodiments, -Cy- is or comprises 12-membered ring. In some embodiments, -Cy- is or comprises 13-membered ring. In some embodiments, -Cy- is or comprises 14-membered ring. In some embodiments, -Cy- is or comprises 15-membered ring. In some embodiments, -Cy- is or comprises 16-membered ring. In some embodiments, -Cy- is or comprises 17-membered ring. In some embodiments, -Cy- is or comprises 18-membered ring. In some embodiments, -Cy- is or comprises 19-membered ring. In some embodiments, -Cy- is or comprises 20-membered ring.

In some embodiments, -Cy- is or comprises an optionally substituted bivalent $C_{3-20}$ cycloaliphatic ring. In some embodiments, -Cy- is or comprises an optionally substituted bivalent, saturated $C_{3-20}$ cycloaliphatic ring. In some embodiments, -Cy- is or comprises an optionally substituted bivalent, partially unsaturated $C_{3-20}$ cycloaliphatic ring. In some embodiments, -Cy-H is optionally substituted cycloaliphatic as described in the present disclosure, for example, cycloaliphatic embodiments for R.

In some embodiments, -Cy- is or comprises an optionally substituted $C_{6-20}$ aryl ring. In some embodiments, -Cy- is or comprises optionally substituted phenylene. In some embodiments, -Cy is or comprises optionally substituted 1,2-phenylene. In some embodiments, -Cy- is or comprises optionally substituted 1,3-phenylene. In some embodiments, -Cy- is or comprises optionally substituted 1,4-phenylene. In some embodiments, -Cy- is or comprises an optionally substituted bivalent naphthalene ring. In some embodiments, -Cy-H is optionally substituted aryl as described in the present disclosure, for example, aryl embodiments for R.

In some embodiments, -Cy- is or comprises an optionally substituted bivalent 5-20 membered heteroaryl ring having 1-10 heteroatoms independently selected from oxygen, nitrogen, sulfur, phosphorus and silicon. In some embodiments, -Cy- is or comprises an optionally substituted bivalent 5-20 membered heteroaryl ring having 1-10 heteroatoms independently selected from oxygen, nitrogen, and sulfur. In some embodiments, -Cy- is or comprises an optionally substituted bivalent 5-6 membered heteroaryl ring having 1-4 heteroatoms independently selected from oxygen, nitrogen, sulfur. In some embodiments, -Cy- is or comprises an optionally substituted bivalent 5-6 membered heteroaryl ring having 1-3 heteroatoms independently selected from oxygen, nitrogen, sulfur. In some embodiments, -Cy- is or comprises an optionally substituted bivalent 5-6 membered heteroaryl ring having 1-2 heteroatoms independently selected from oxygen, nitrogen, sulfur. In some embodiments, -Cy- is or comprises an optionally substituted bivalent 5-6 membered heteroaryl ring having one heteroatom independently selected from oxygen, nitrogen, sulfur. In some embodiments, -Cy-H is optionally substituted heteroaryl as described in the present disclosure, for example, heteroaryl embodiments for R. In some embodiments, -Cy- is

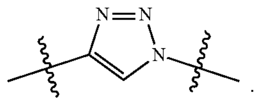 [SMILES: *c1cn(*)nn1]

In some embodiments, -Cy- is or comprises an optionally substituted bivalent 3-20 membered heterocyclyl ring having 1-10 heteroatoms independently selected from oxygen, nitrogen, sulfur, phosphorus and silicon. In some embodiments, -Cy- is or comprises an optionally substituted bivalent 3-20 membered heterocyclyl ring having 1-10 heteroatoms independently selected from oxygen, nitrogen, and sulfur. In some embodiments, -Cy- is or comprises an optionally substituted bivalent 3-6 membered heterocyclyl ring having 1-4 heteroatoms independently selected from oxygen, nitrogen, sulfur. In some embodiments, -Cy- is or comprises an optionally substituted bivalent 5-6 membered heterocyclyl ring having 1-4 heteroatoms independently selected from oxygen, nitrogen, sulfur. In some embodiments, -Cy- is or comprises an optionally substituted bivalent 5-6 membered heterocyclyl ring having 1-3 heteroatoms independently selected from oxygen, nitrogen, sulfur. In some embodiments, -Cy- is or comprises an optionally substituted bivalent 5-6 membered heterocyclyl ring having 1-2 heteroatoms independently selected from oxygen, nitrogen, sulfur. In some embodiments, -Cy- is or comprises an optionally substituted bivalent 5-6 membered heterocyclyl ring having one heteroatom independently selected from oxygen, nitrogen, sulfur. In some embodiments, -Cy- is or comprises an optionally substituted saturated bivalent heterocyclyl group. In some embodiments, -Cy- is or comprises an optionally substituted partially unsaturated bivalent heterocyclyl group. In some embodiments, -Cy-H is optionally substituted heterocyclyl as described in the present disclosure, for example, heterocyclyl embodiments for R.

In some embodiments, -Cy- is

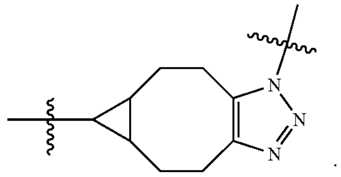 [SMILES: *C1C2CCc3nnn(*)c3CCC12]

In some embodiments, -Cy- is

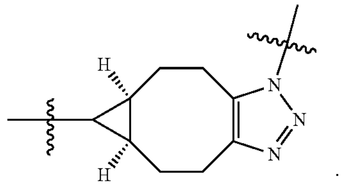 [SMILES: *C1[C@H]2CCc3c(nnn3*)CC[C@@H]12]

In some embodiments, -Cy- is

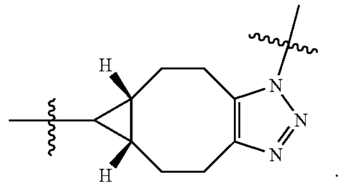 [SMILES: *C1[C@H]2CCc3nnn(*)c3CC[C@@H]12]

In some embodiments, -Cy is

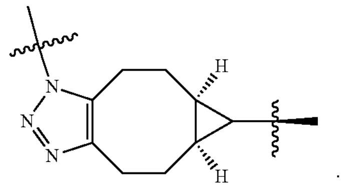 [SMILES: *C1[C@H]2CCc3nnn(*)c3CC[C@@H]12]

In some embodiments, -Cy- is

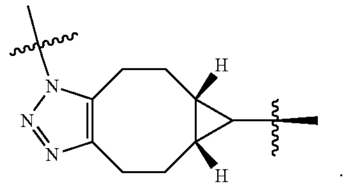 [SMILES: *C1[C@H]2CCc3c(nnn3*)CC[C@@H]12]

In some embodiments, each Xaa is independently an amino acid residue. In some embodiments, each Xaa is independently an amino acid residue of an amino acid of formula A-I.

In some embodiments, t is 0. In some embodiments, t is 1-50. In some embodiments, t is z as described in the present disclosure.

In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10. In some embodiments, y is 11. In some embodiments, y is 12. In some embodiments, y is 13. In some embodiments, y is 14. In some embodiments, y is 15. In some embodiments, y is 16. In some embodiments, y is 17. In some embodiments, y is 18. In some embodiments, y is 19. In some embodiments, y is 20. In some embodiments, y is greater than 20.

In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10. In some embodiments, z is 11. In some embodiments, z is 12. In some embodiments, z is 13. In some embodiments, z is 14. In some embodiments, z is 15. In some embodiments, z is 16. In some embodiments, z is 17. In some embodiments, z is 18. In some embodiments, z is 19. In some embodiments, z is 20. In some embodiments, z is greater than 20.

In some embodiments, $R^c$ is R' as described in the present disclosure. In some embodiments, $R^c$ is R as described in the present disclosure. In some embodiments, $R^c$ is $—N(R')_2$, wherein each R' is independently as described in the present disclosure. In some embodiments, $R^c$ is —$NH_2$. In some embodiments, $R^c$ is R—C(O)—, wherein R is as described in the present disclosure. In some embodiments, $R^c$ is —H.

In some embodiments, $L^b$ is $L^a$ as described in the present disclosure. In some embodiments, $L^b$ comprises -Cy-. In some embodiments, $L^b$ comprises a double bond. In some embodiments, $L^b$ comprises —S—. In some embodiments, $L^b$ comprises —S—S—. In some embodiments, $L^b$ comprises —C(O)—N(R')—.

In some embodiments, R' is —R, —C(O)R, —C(O)OR, or —$S(O)_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —$S(O)_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ is aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is $-(CH_2)_2CN$.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted $C_{1-30}$ heteroaliphatic having 1-10 heteroatoms independently selected from oxygen, nitrogen, sulfur, phosphorus and silicon. In some embodiments, R is optionally substituted $C_{1-20}$ heteroaliphatic having 1-10 heteroatoms. In some embodiments, R is optionally substituted $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted $C_{1-30}$ heteroaliphatic comprising 1-10 groups independently selected from

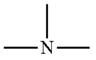,

—N═, ≡N, —S—, —S(O)—, —S(O)$_2$—, —O—, ═O,

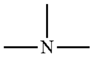, 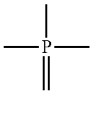, and 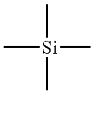,

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. In some embodiments, R is an optionally substituted 5-membered heteroaryl ring having three heteroatoms independently selected from nitrogen, oxygen, and sulfur. In some embodiments, R is an optionally substituted 5-membered heteroaryl ring having four heteroatoms independently selected from nitrogen, oxygen, and sulfur.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In certain embodiments, R is an optionally substituted 6,6-fused heteroaryl ring having 1-4 heteroatoms independently selected from nitrogen, oxygen, and sulfur.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur. In some embodiments, R is an optionally substituted 5,6-fused heteroaryl ring having 1-5 heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C═O is formed. In some embodiments, —C═C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

Exemplary compounds are set forth in Table 1.

TABLE 1
Certain compounds/agents as examples.
Table 1a.
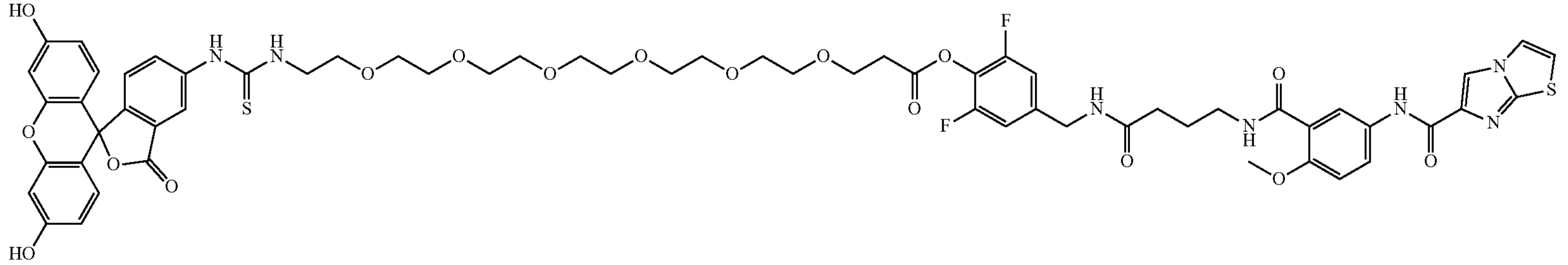 [SMILES: COc1ccc(NC(=O)c2cn3ccsc3n2)cc1C(=O)NCCCC(=O)NCc1cc(F)c(OC(=O)CCOCCOCCOCCOCCOCCOCCNC(=S)Nc2ccc3c(c2)C(=O)OC32c3ccc(O)cc3Oc3cc(O)ccc32)c(F)c1]
I-1
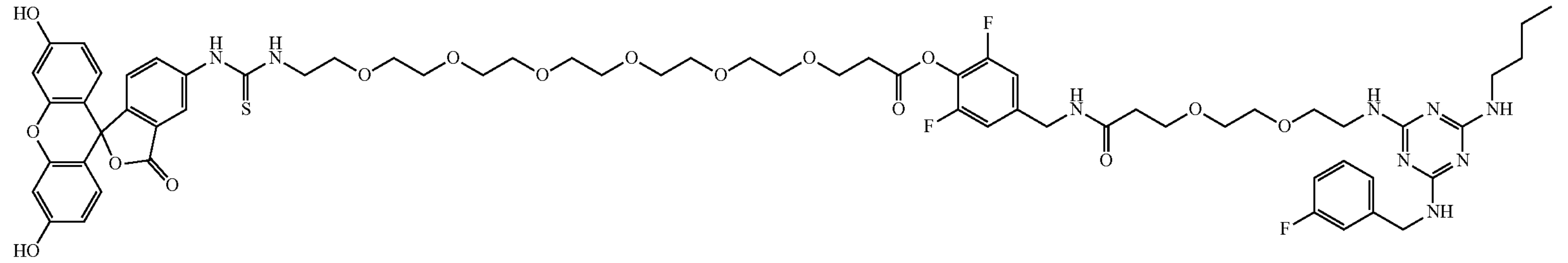 [SMILES: CCCCNc1nc(NCCOCCOCCC(=O)NCc2cc(F)c(OC(=O)CCOCCOCCOCCOCCOCCOCCNC(=S)Nc3ccc4c(c3)C(=O)OC43c4ccc(O)cc4Oc4cc(O)ccc43)c(F)c2)nc(NCc2cccc(F)c2)n1]
I-2
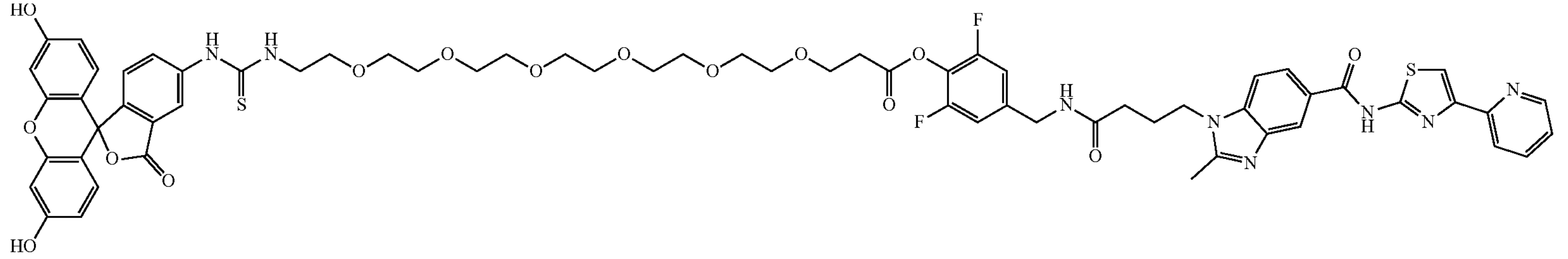 [SMILES: Cc1nc2cc(C(=O)Nc3nc(-c4ccccn4)cs3)ccc2n1CCCC(=O)NCc1cc(F)c(OC(=O)CCOCCOCCOCCOCCOCCOCCNC(=S)Nc2ccc3c(c2)C(=O)OC32c3ccc(O)cc3Oc3cc(O)ccc32)c(F)c1]
I-3

TABLE 1-continued
| Certain compounds/agents as examples. | |
|---|---|
| 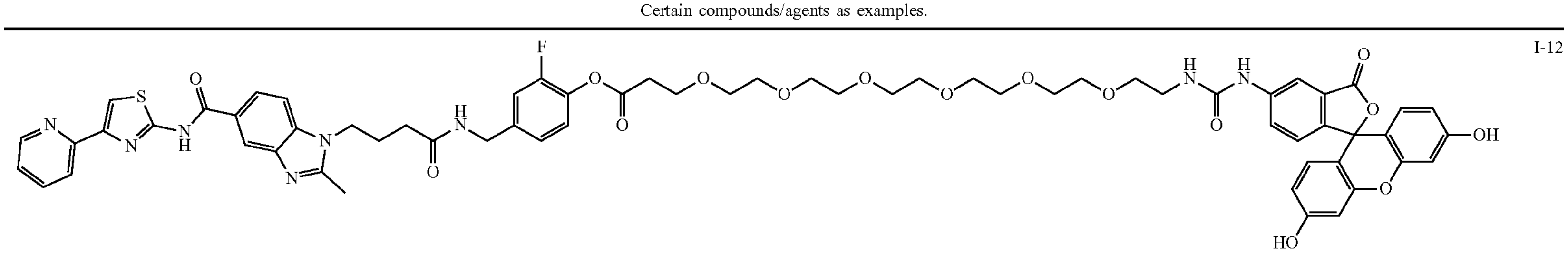 | I-12 |
| 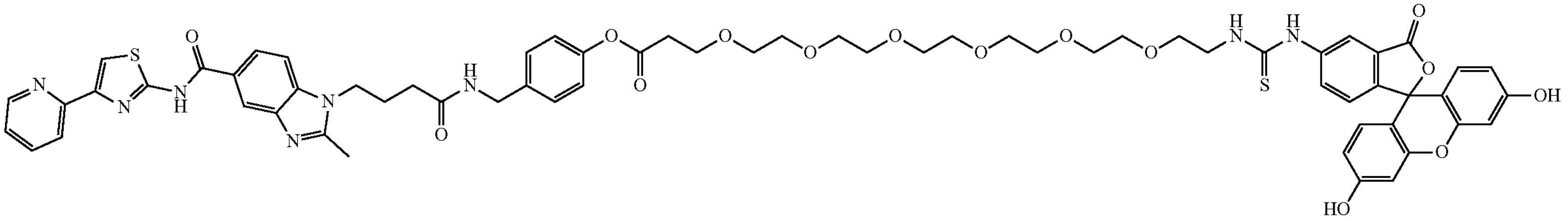 [SMILES: Cc1nc2cc(C(=O)Nc3nc(-c4ccccn4)cs3)ccc2n1CCCC(=O)NCc1ccc(OC(=O)CCOCCOCCOCCOCCOCCOCCNC(=S)Nc2ccc3c(c2)C(=O)OC32c3ccc(O)cc3Oc3cc(O)ccc32)cc1] | I-13 |
| 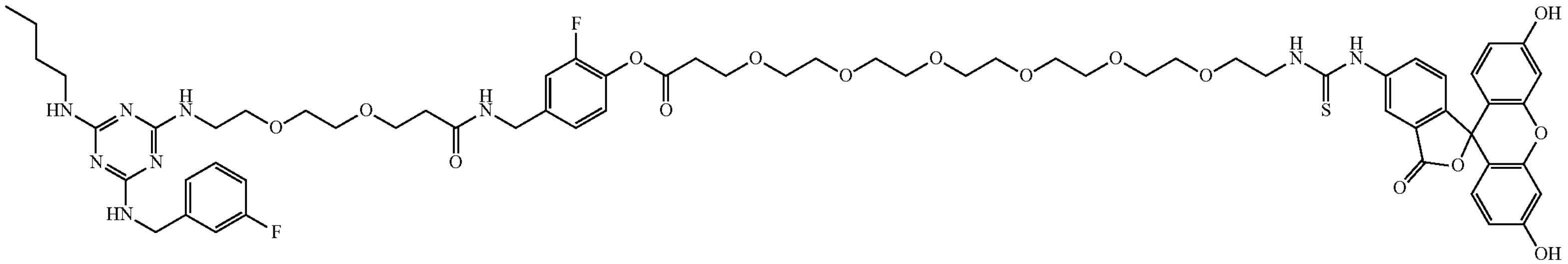 [SMILES: CCCCNc1nc(NCCOCCOCCC(=O)NCc2ccc(OC(=O)CCOCCOCCOCCOCCOCCOCCNC(=S)Nc3ccc4c(c3)C(=O)OC43c4ccc(O)cc4Oc4cc(O)ccc43)c(F)c2)nc(NCc2cccc(F)c2)n1] | I-14 |
| 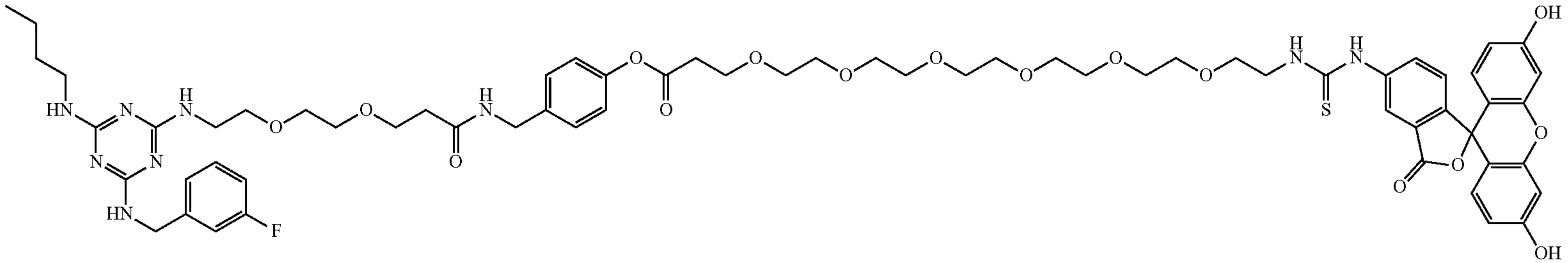 [SMILES: CCCCNc1nc(NCCOCCOCCC(=O)NCc2ccc(OC(=O)CCOCCOCCOCCOCCOCCOCCNC(=S)Nc3ccc4c(c3)C(=O)OC43c4ccc(O)cc4Oc4cc(O)ccc43)cc2)nc(NCc2cccc(F)c2)n1] | I-15 |

TABLE 1-continued
Certain compounds/agents as examples.
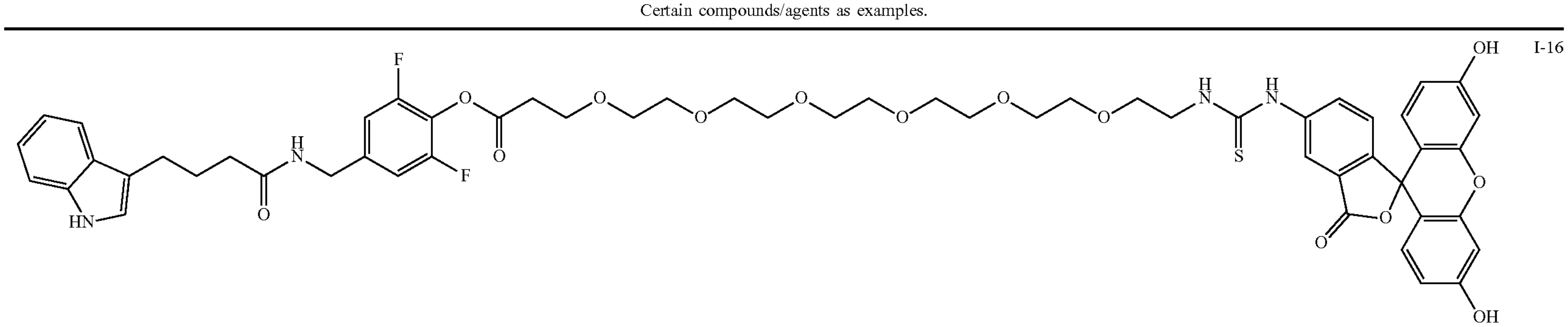
I-16
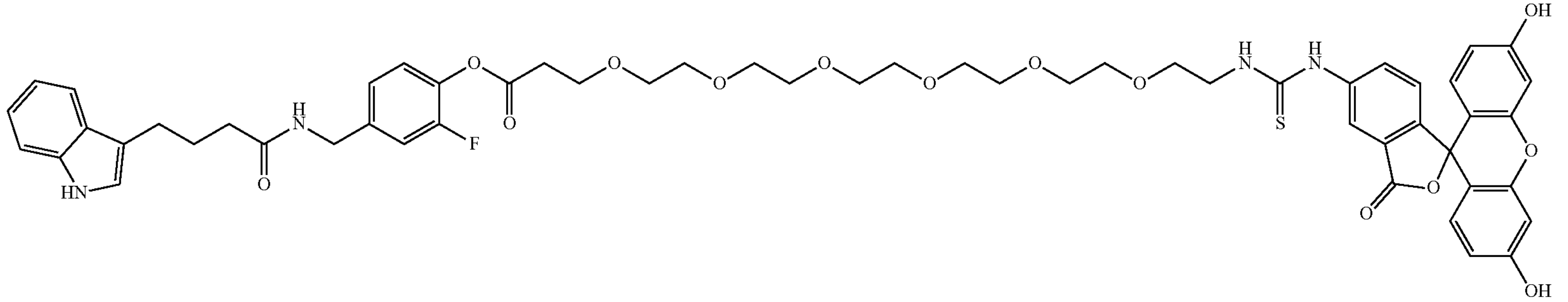 [SMILES: O=C(CCCc1c[nH]c2ccccc12)NCc1ccc(OC(=O)CCOCCOCCOCCOCCOCCOCCNC(=S)Nc2ccc3c(c2)C(=O)OC32c3ccc(O)cc3Oc3cc(O)ccc32)c(F)c1]
I-17
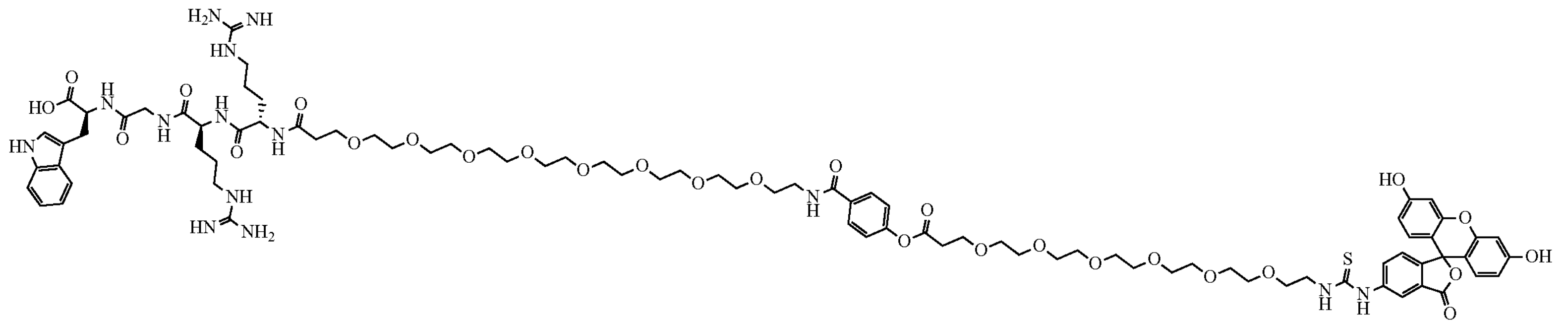 [SMILES: N=C(N)NCCC[C@H](NC(=O)CCOCCOCCOCCOCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)cc1)C(=O)N[C@@H](CCCNC(=N)N)C(=O)NCC(=O)N[C@@H](Cc1c[nH]c2ccccc12)C(=O)O]
I-21

TABLE 1-continued
| Certain compounds/agents as examples. |
| --- |
| 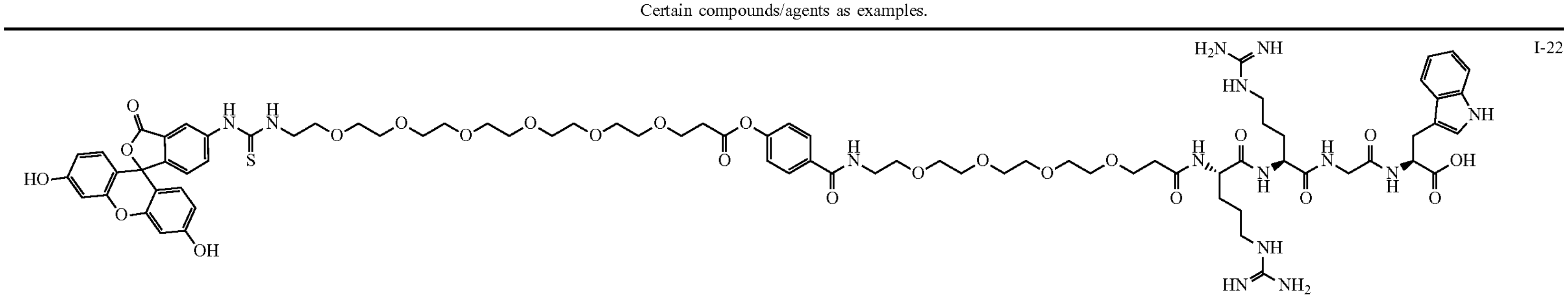 I-22 |
| 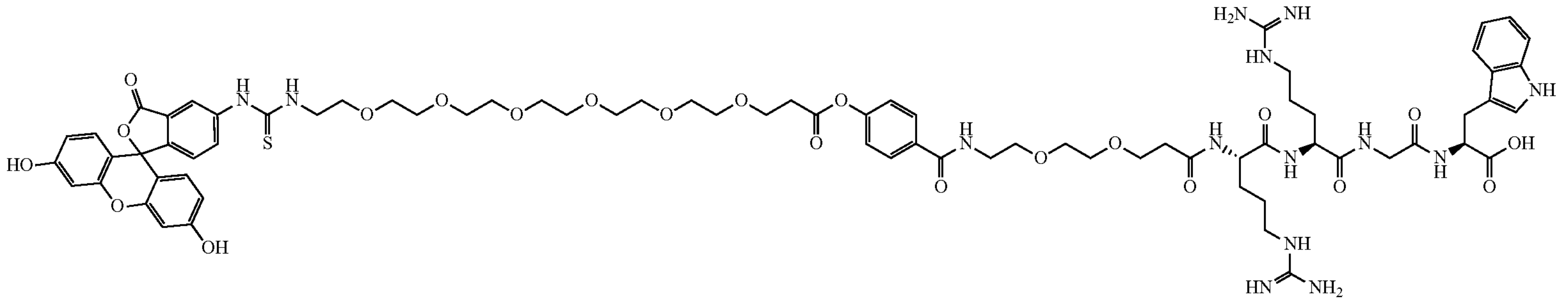 [SMILES: N=C(N)NCCC[C@H](NC(=O)CCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)cc1)C(=O)N[C@@H](CCCNC(=N)N)C(=O)NCC(=O)N[C@@H](Cc1c[nH]c2ccccc12)C(=O)O] I-23 |

TABLE 1-continued
Certain compounds/agents as examples.
I-24
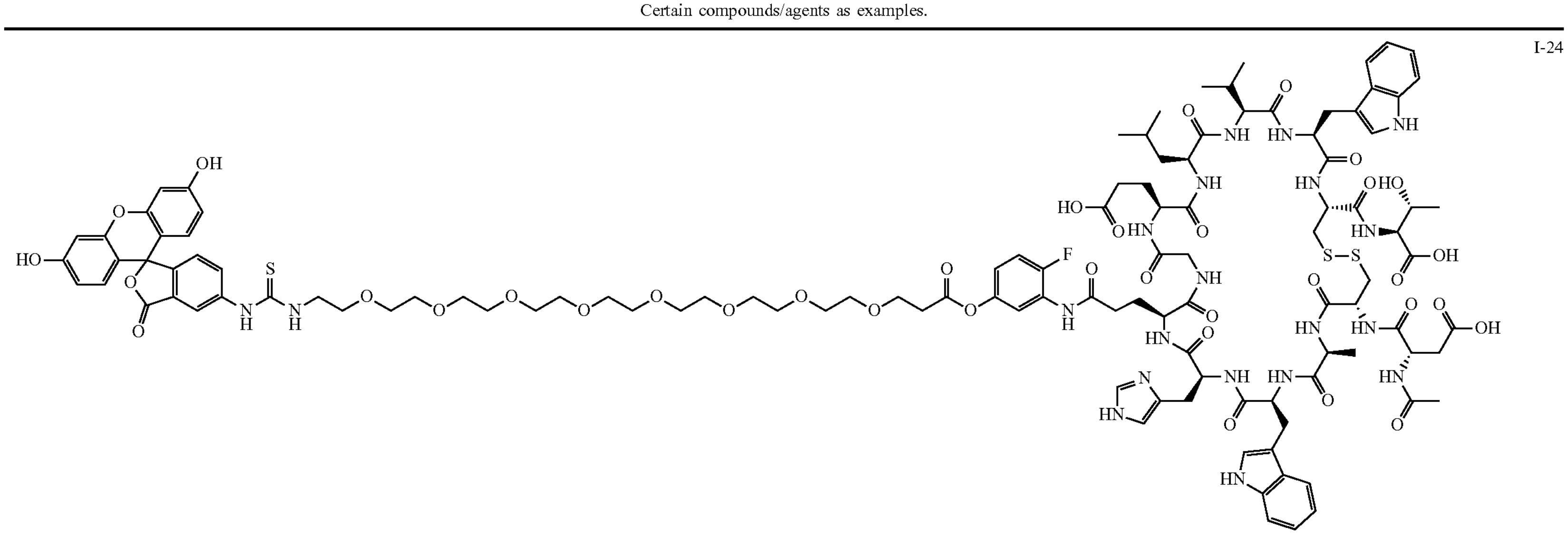
I-25
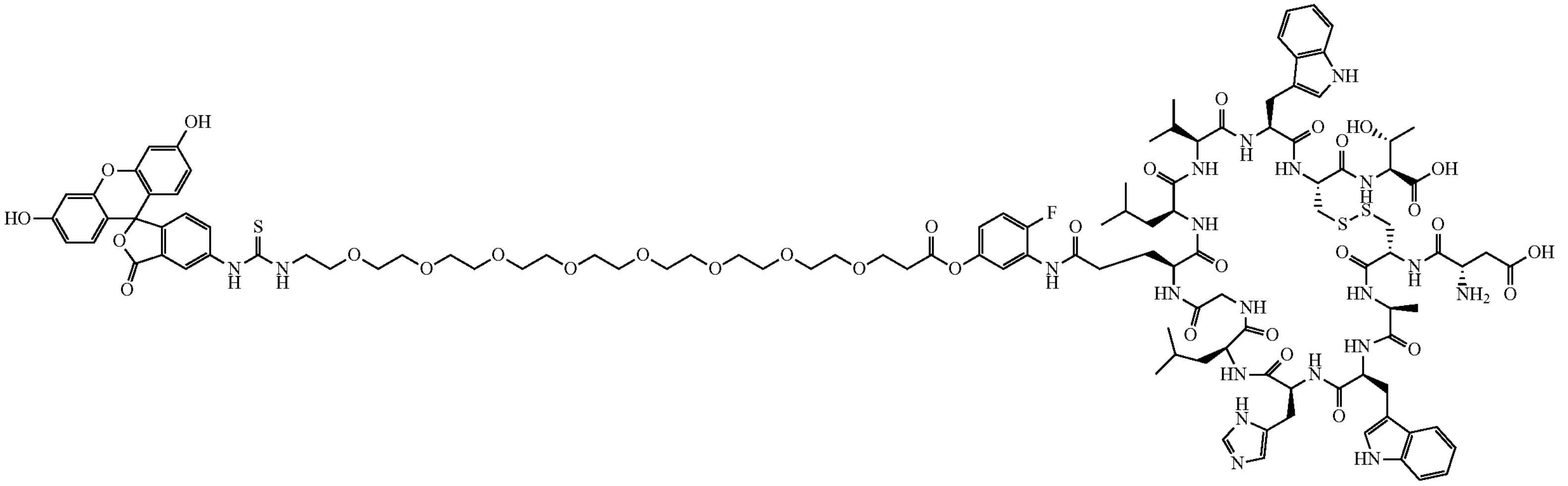 [SMILES: CC(C)C[C@@H]1NC(=O)[C@H](Cc2cnc[nH]2)NC(=O)[C@H](Cc2c[nH]c3ccccc23)NC(=O)[C@H](C)NC(=O)[C@@H](NC(=O)[C@@H](N)CC(=O)O)CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)Nc2cc(OC(=O)CCOCCOCCOCCOCCOCCOCCOCCOCCNC(=S)Nc3ccc4c(c3)C(=O)OC43c4ccc(O)cc4Oc4cc(O)ccc43)ccc2F)NC(=O)CNC1=O]

TABLE 1-continued
Certain compounds/agents as examples.
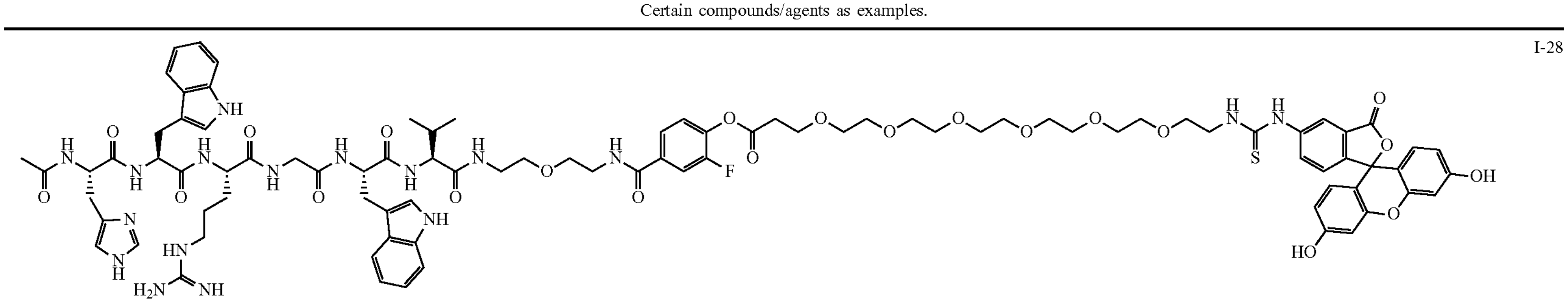
I-28
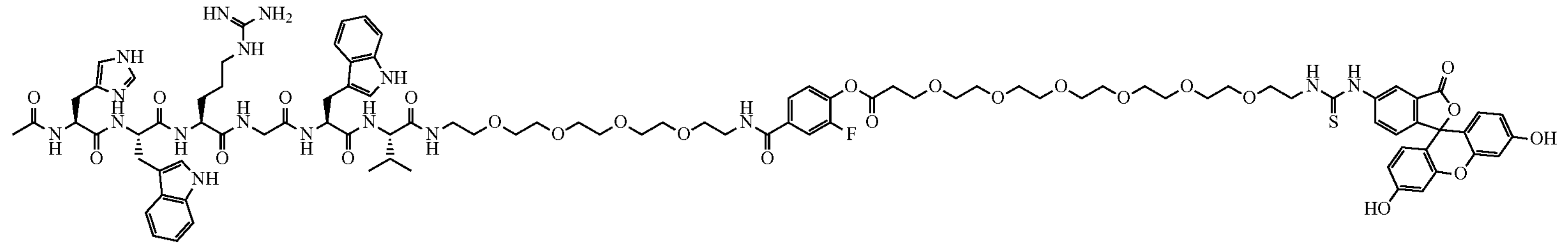 [SMILES: CC(=O)N[C@@H](Cc1c[nH]cn1)C(=O)N[C@@H](Cc1c[nH]c2ccccc12)C(=O)N[C@@H](CCCNC(=N)N)C(=O)NCC(=O)N[C@@H](Cc1c[nH]c2ccccc12)C(=O)N[C@H](C(=O)NCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C]
I-29
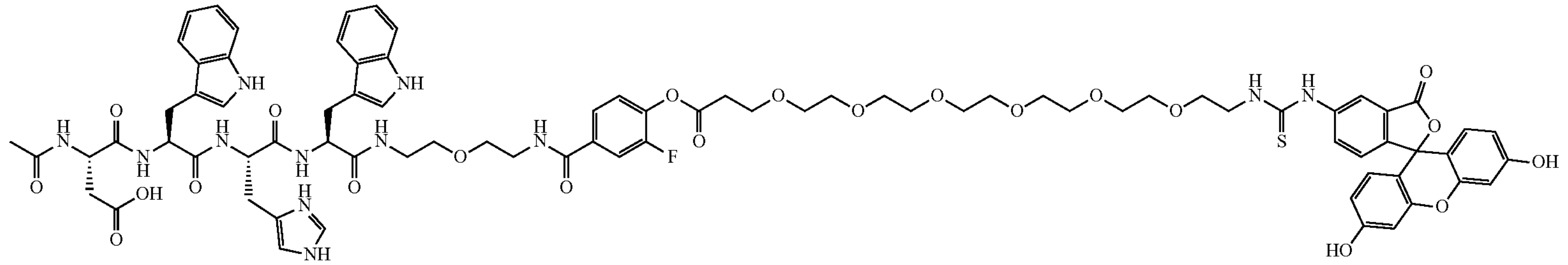
I-30
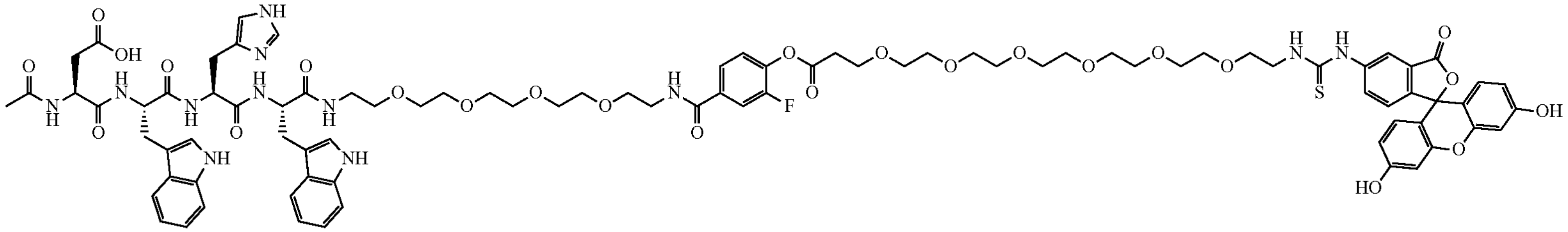 [SMILES: CC(=O)N[C@@H](CC(=O)O)C(=O)N[C@@H](Cc1c[nH]c2ccccc12)C(=O)N[C@@H](Cc1c[nH]cn1)C(=O)N[C@@H](Cc1c[nH]c2ccccc12)C(=O)NCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1]
I-31

TABLE 1-continued
| Certain compounds/agents as examples. | |
|---|---|
| 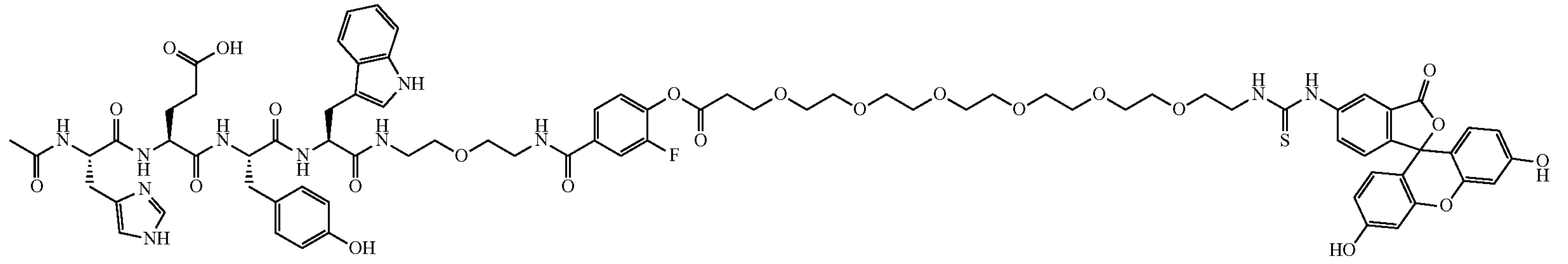 [SMILES: CC(=O)N[C@@H](Cc1c[nH]cn1)C(=O)N[C@@H](CCC(=O)O)C(=O)N[C@@H](Cc1ccc(O)cc1)C(=O)N[C@@H](Cc1c[nH]c2ccccc12)C(=O)NCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1] | I-32 |
| 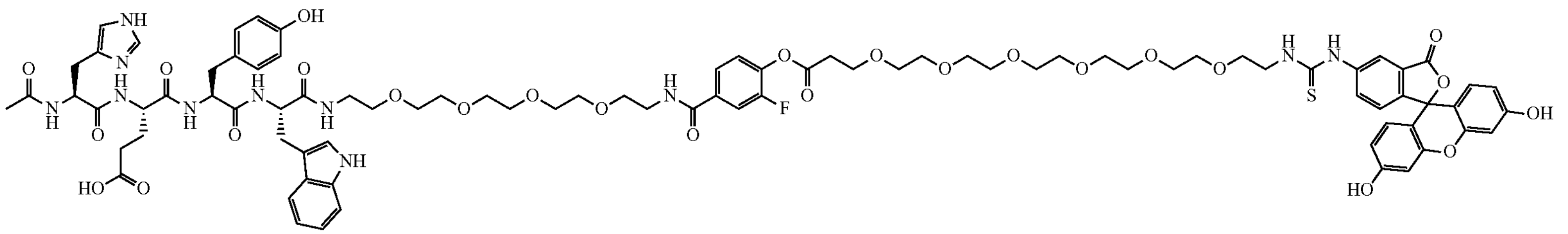 [SMILES: CC(=O)N[C@@H](Cc1c[nH]cn1)C(=O)N[C@@H](CCC(=O)O)C(=O)N[C@@H](Cc1ccc(O)cc1)C(=O)N[C@@H](Cc1c[nH]c2ccccc12)C(=O)NCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1] | I-33 |
| 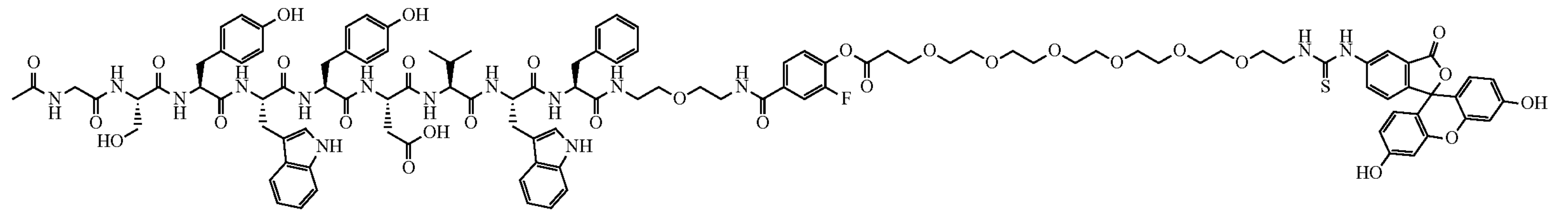 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C] | I-34 |
| 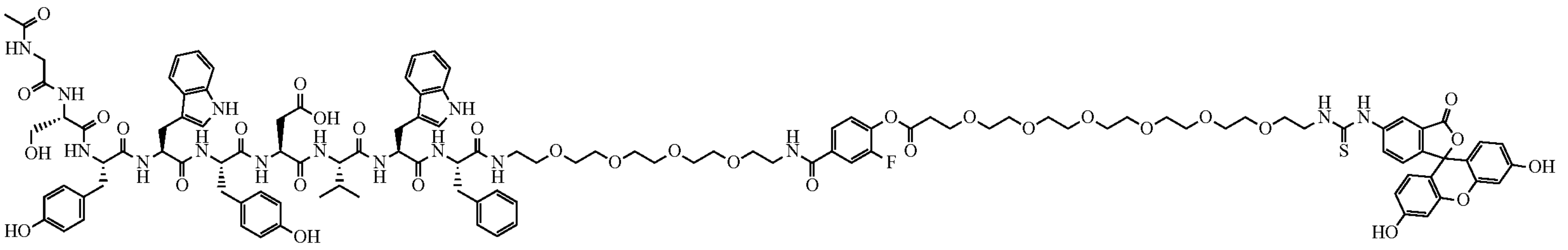 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C] | I-35 |

TABLE 1-continued
Certain compounds/agents as examples.
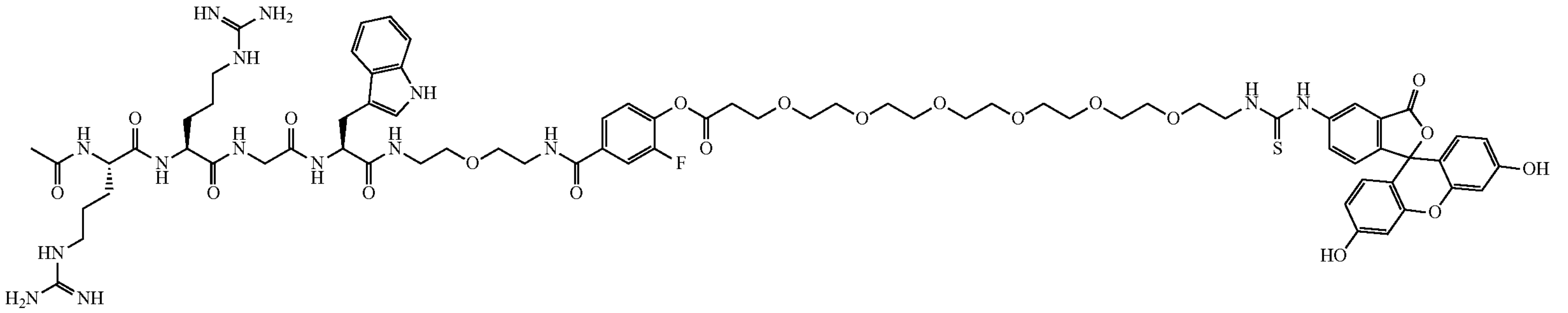 [SMILES: CC(=O)N[C@@H](CCCNC(=N)N)C(=O)N[C@@H](CCCNC(=N)N)C(=O)NCC(=O)N[C@@H](Cc1c[nH]c2ccccc12)C(=O)NCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1]
I-36
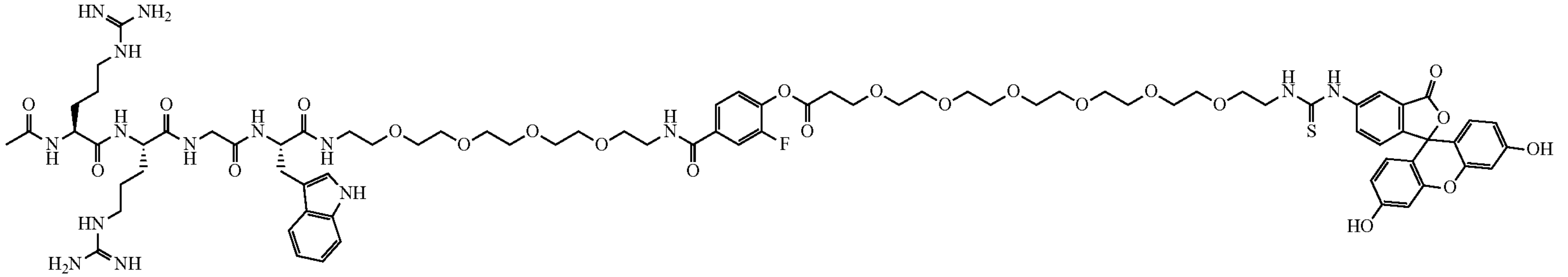 [SMILES: CC(=O)N[C@@H](CCCNC(=N)N)C(=O)N[C@@H](CCCNC(=N)N)C(=O)NCC(=O)N[C@@H](Cc1c[nH]c2ccccc12)C(=O)NCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1]
I-37
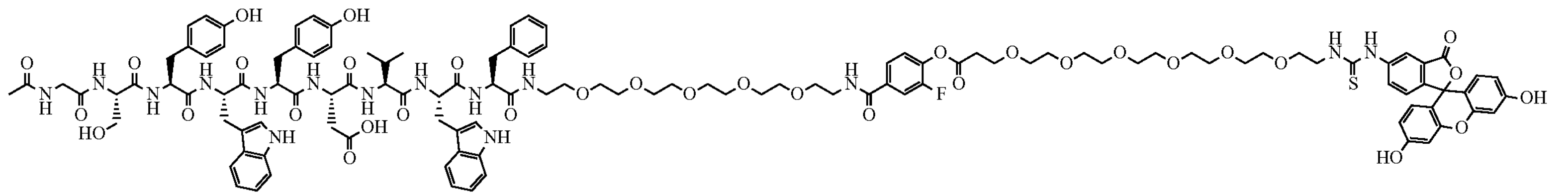 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C]
I-38
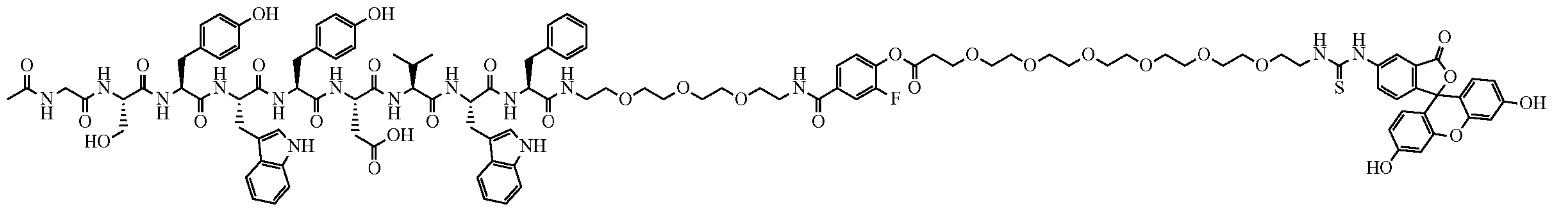 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C]
I-39

TABLE 1-continued
Certain compounds/agents as examples.
I-40
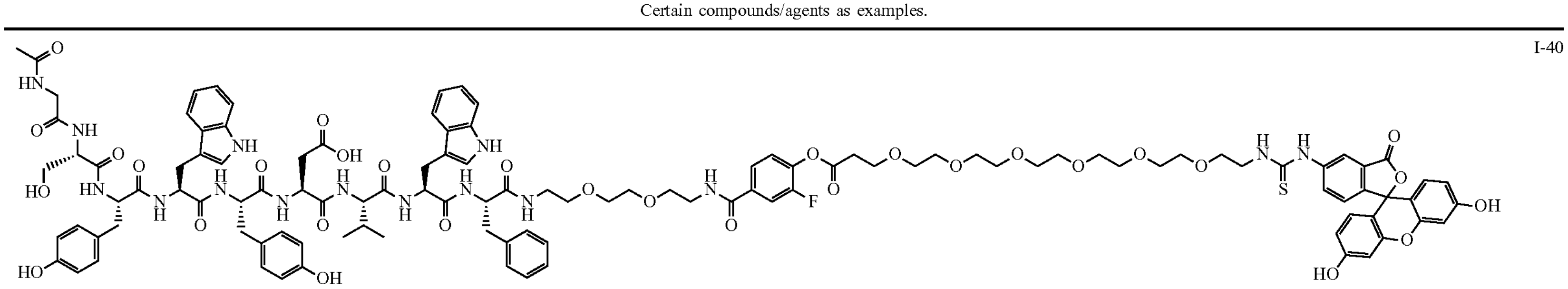
I-41
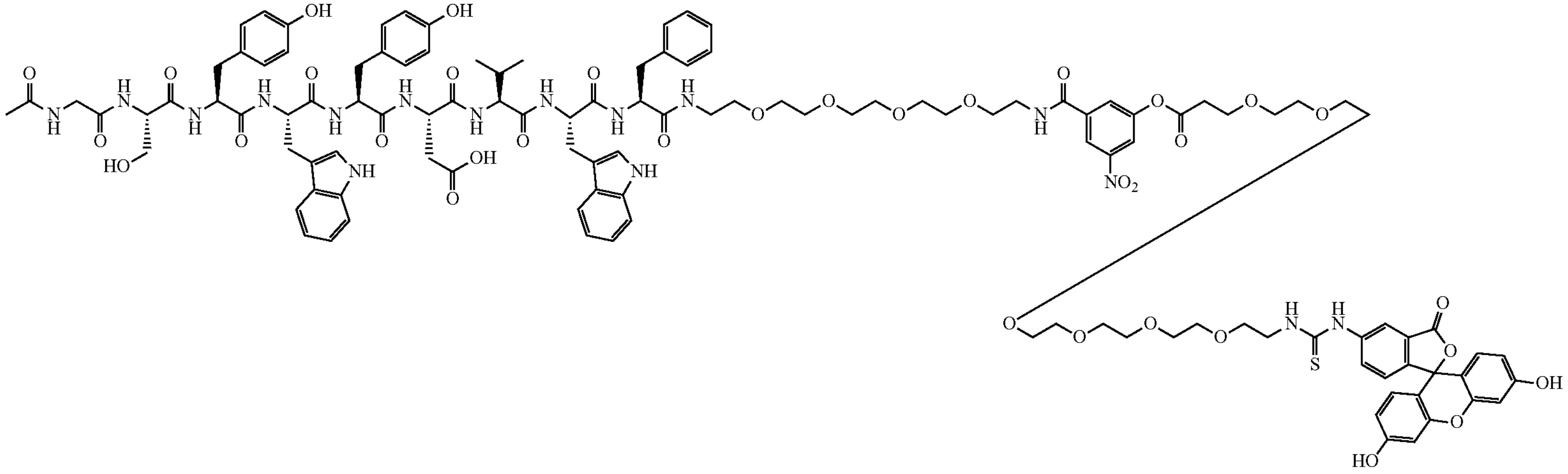 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCOCCOCCOCCNC(=O)c1cc(OC(=O)CCOCCOCCOCCOCCOCCOCCNC(=S)Nc2ccc3c(c2)C(=O)OC32c3ccc(O)cc3Oc3cc(O)ccc32)cc([N+](=O)[O-])c1)C(C)C]

TABLE 1-continued
Certain compounds/agents as examples.
I-42
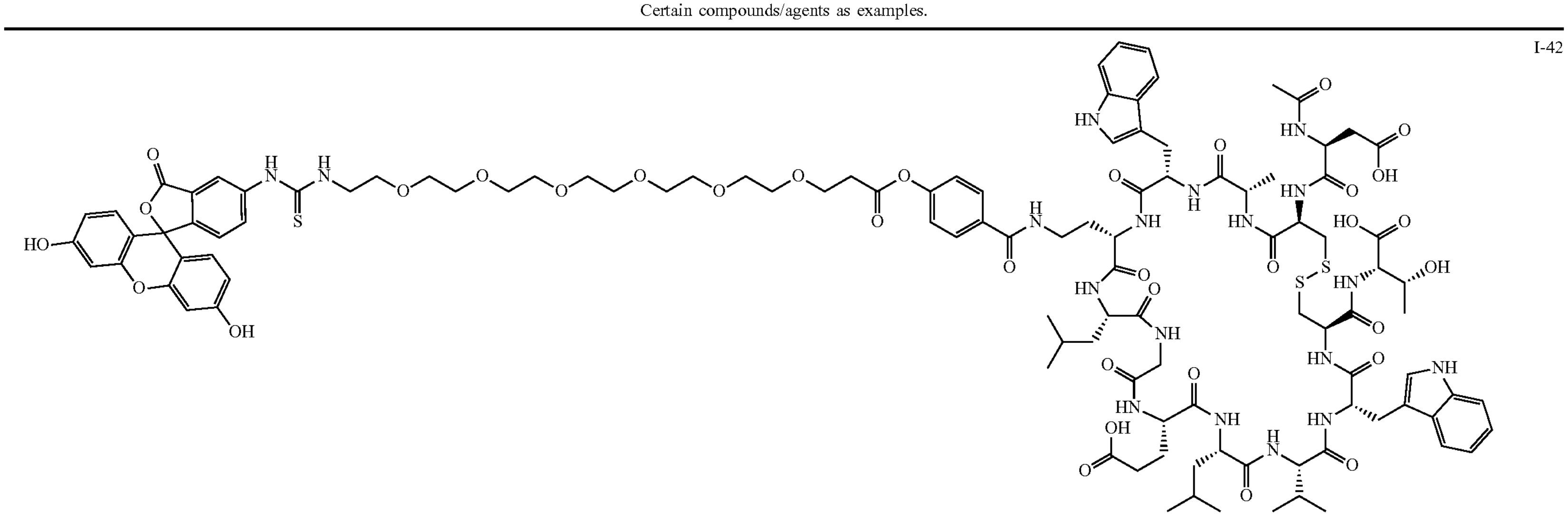
I-43
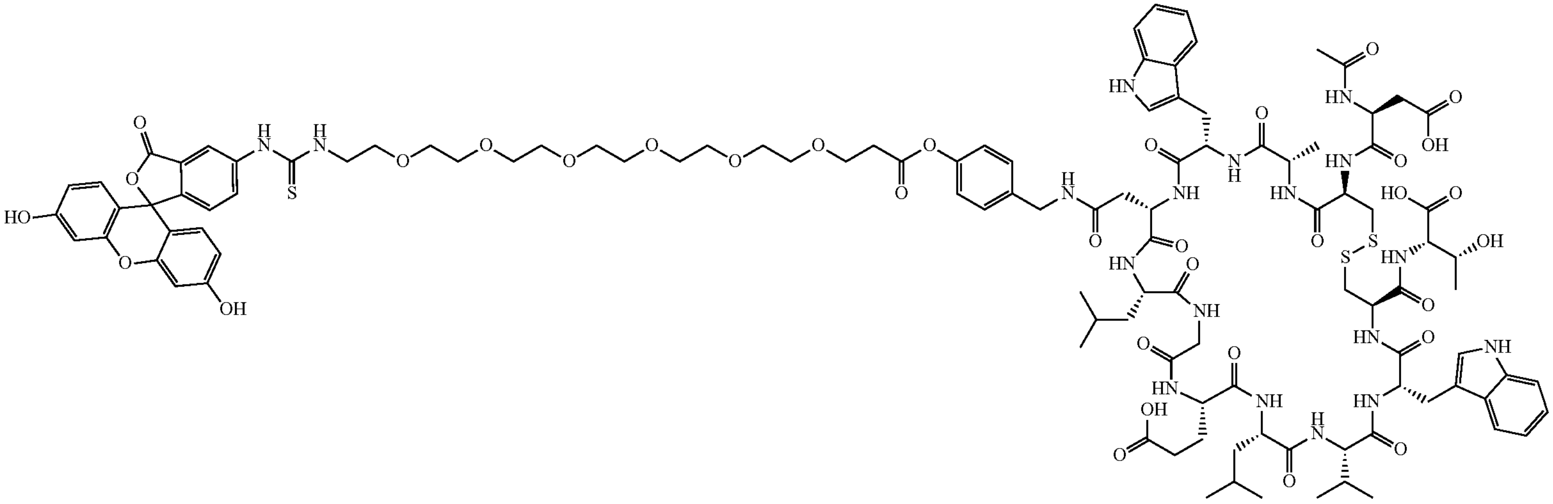 [SMILES: CC(=O)N[C@@H](CC(=O)O)C(=O)N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](CC(=O)NCc2ccc(OC(=O)CCOCCOCCOCCOCCOCCOCCNC(=S)Nc3ccc4c(c3)C(=O)OC43c4ccc(O)cc4Oc4cc(O)ccc43)cc2)NC(=O)[C@H](Cc2c[nH]c3ccccc23)NC(=O)[C@H](C)NC1=O]

TABLE 1-continued
Certain compounds/agents as examples.
I-44
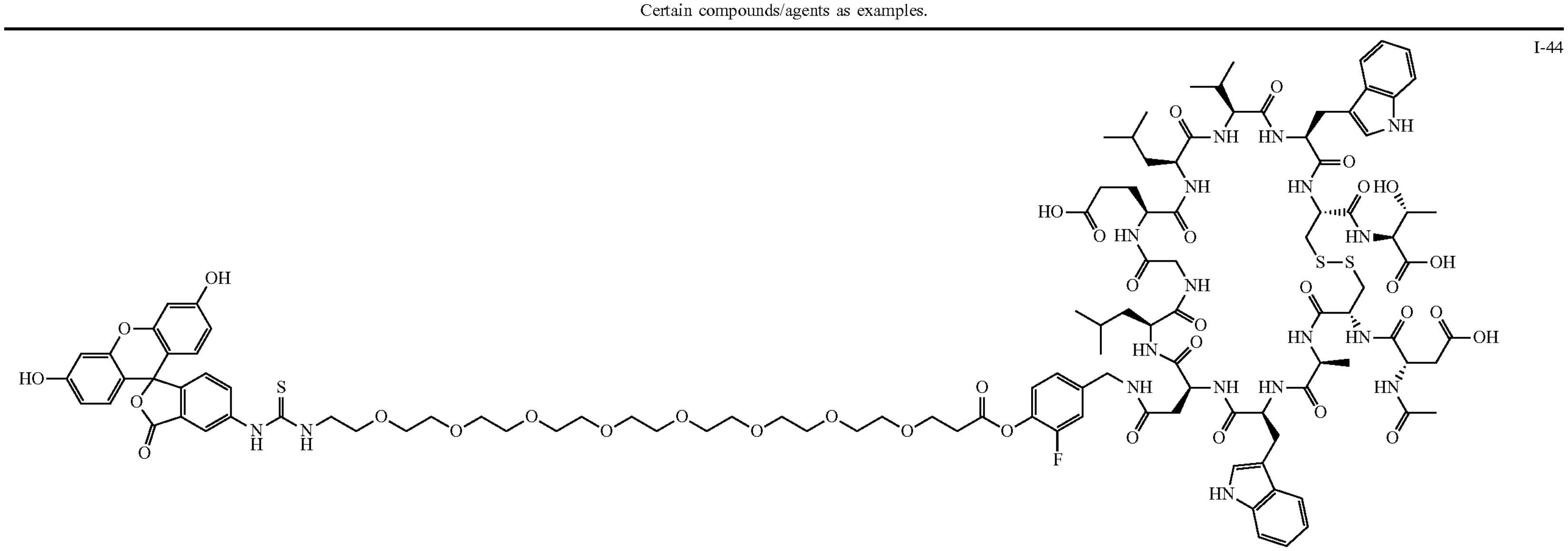
I-45
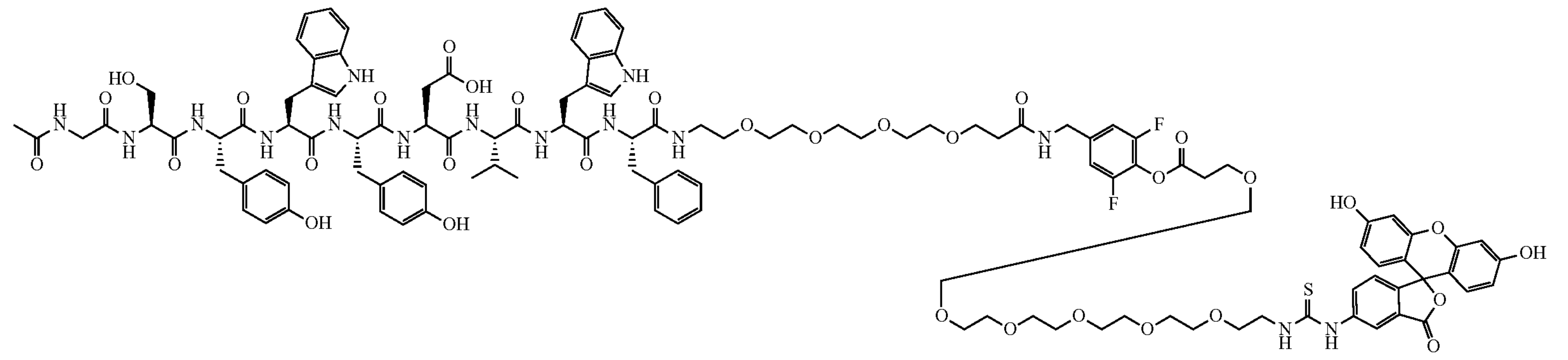 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCOCCOCCOCCC(=O)NCc1cc(F)c(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C]

TABLE 1-continued
| Certain compounds/agents as examples. |
| --- |
| 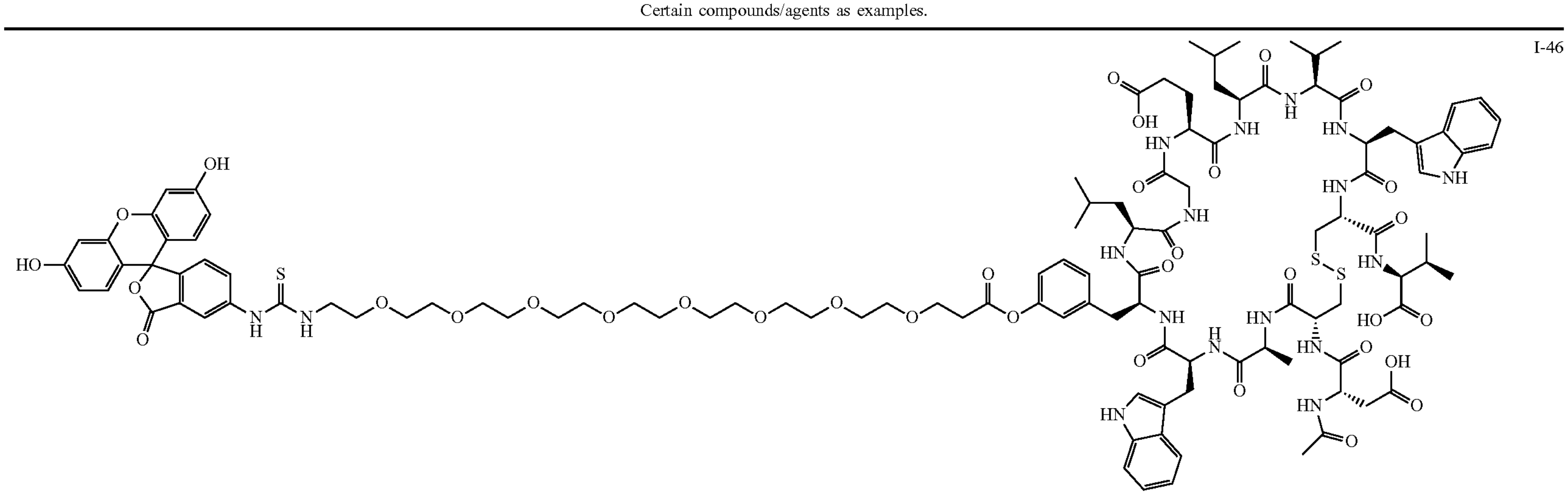 I-46 |
| 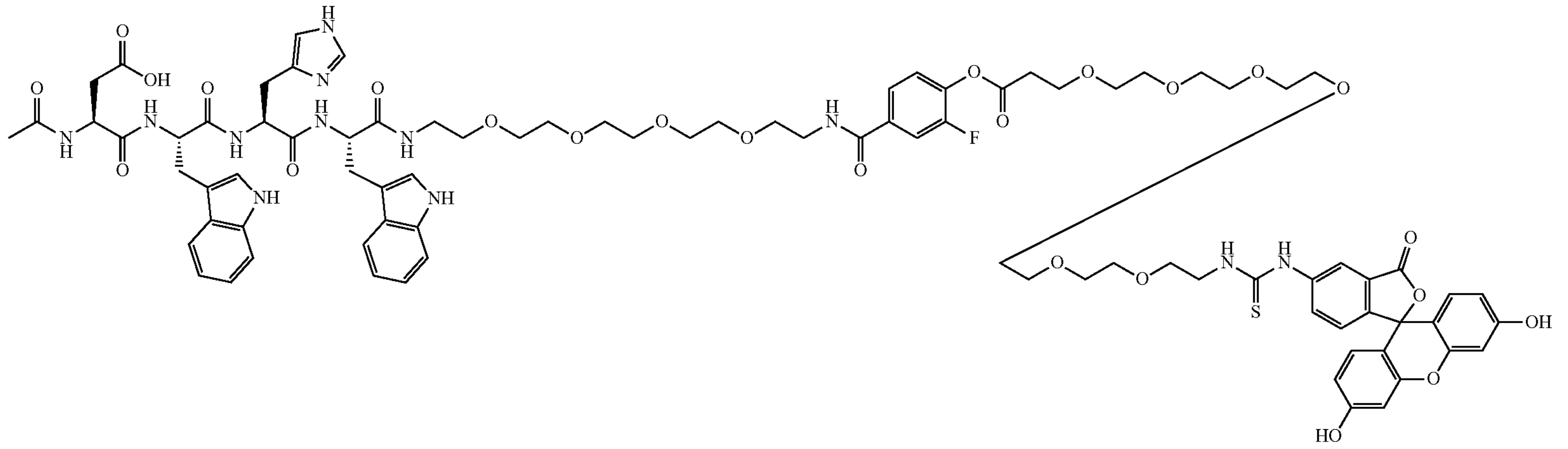 [SMILES: CC(=O)N[C@@H](CC(=O)O)C(=O)N[C@@H](Cc1c[nH]c2ccccc12)C(=O)N[C@@H](Cc1c[nH]cn1)C(=O)N[C@@H](Cc1c[nH]c2ccccc12)C(=O)NCCOCCOCCOCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1] I-47 |

TABLE 1-continued
Certain compounds/agents as examples.
I-48
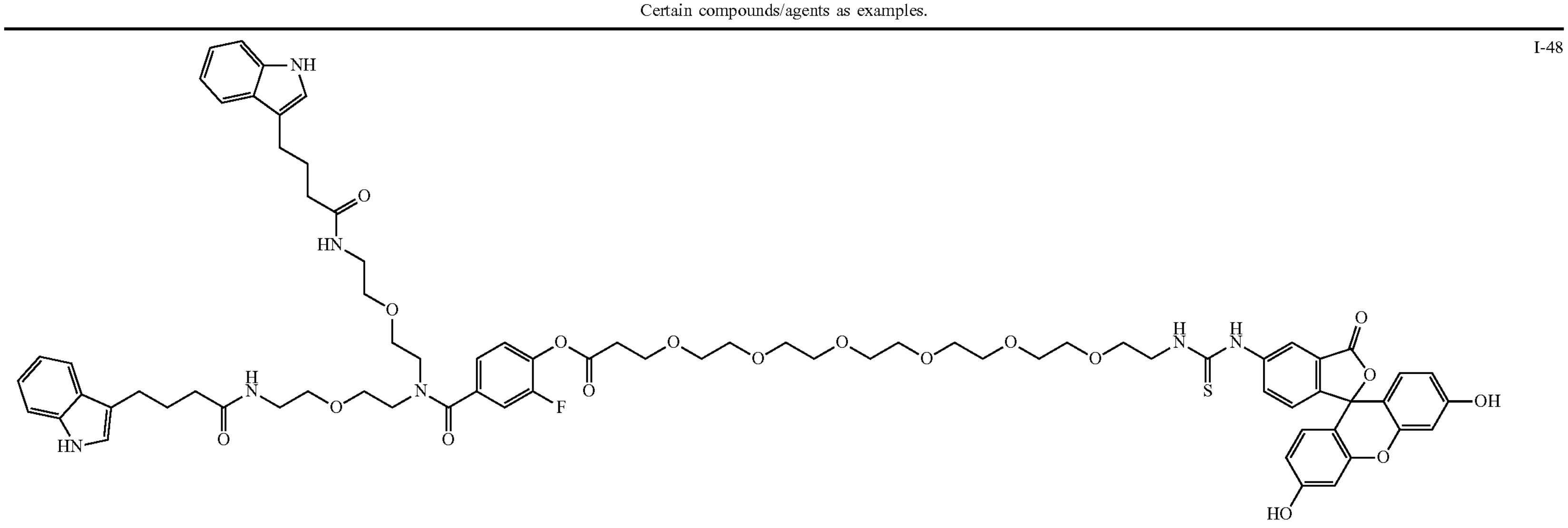
I-49
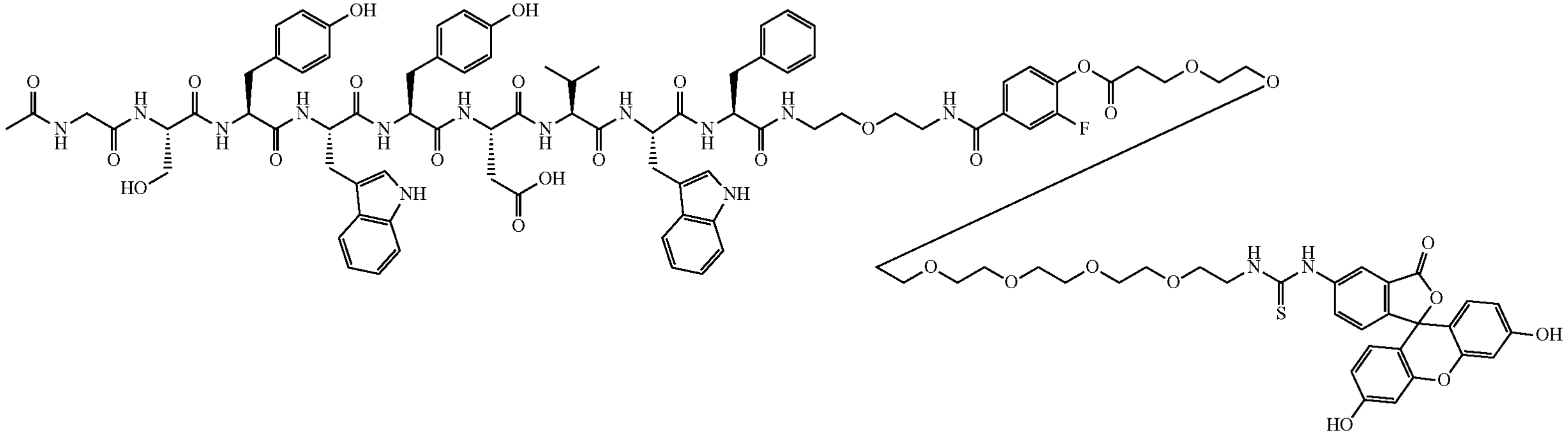 [SMILES: CC(=O)NCC(=O)N[C@@H](CO)C(=O)N[C@@H](Cc1ccc(O)cc1)C(=O)N[C@@H](Cc1c[nH]c2ccccc12)C(=O)N[C@@H](Cc1ccc(O)cc1)C(=O)N[C@@H](CC(=O)O)C(=O)N[C@H](C(=O)N[C@@H](Cc1c[nH]c2ccccc12)C(=O)N[C@@H](Cc1ccccc1)C(=O)NCCOCCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1)C(C)C]

TABLE 1-continued
| Certain compounds/agents as examples. |
| --- |
| I-50 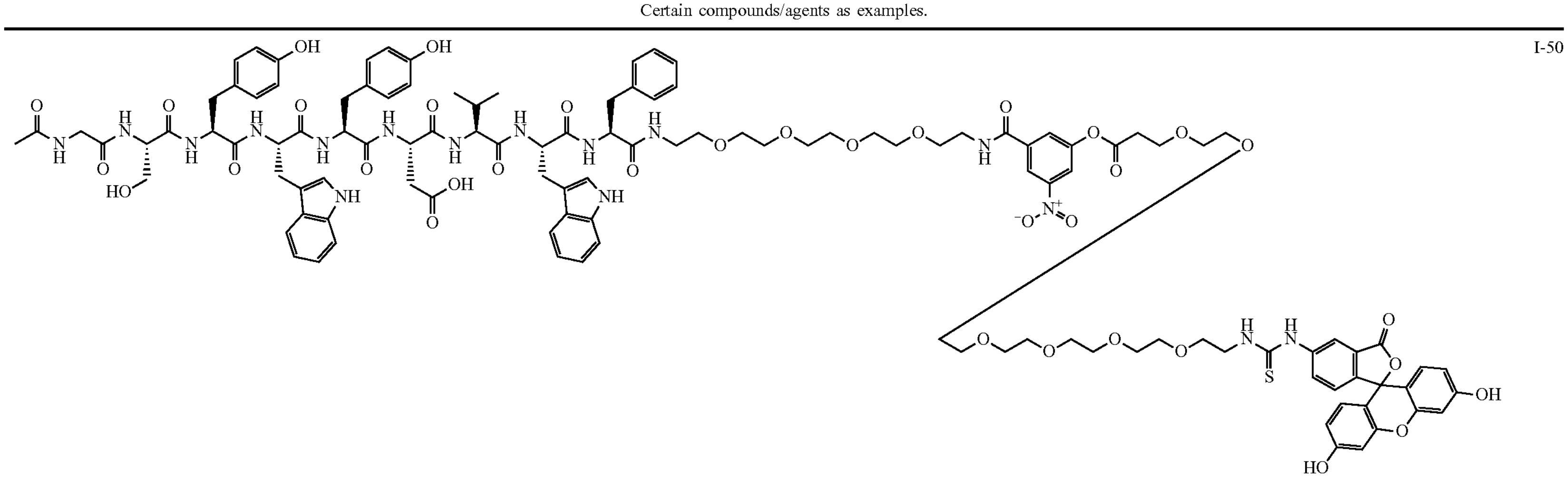 |
| I-53 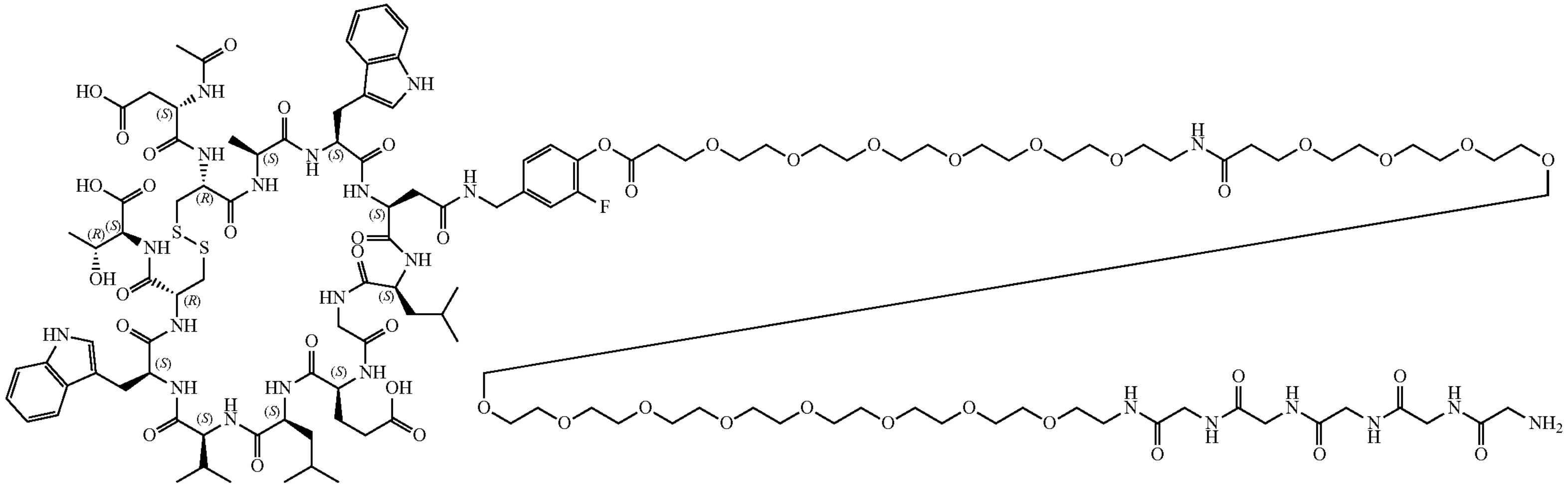 |

TABLE 1-continued
| Certain compounds/agents as examples. |
| --- |
| 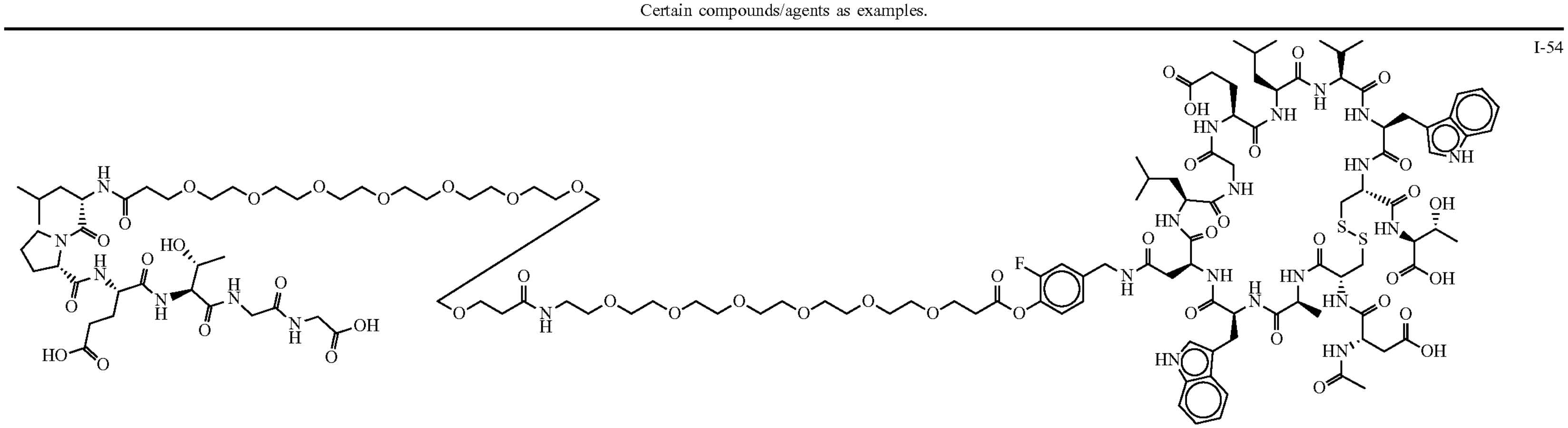 I-54 |
| 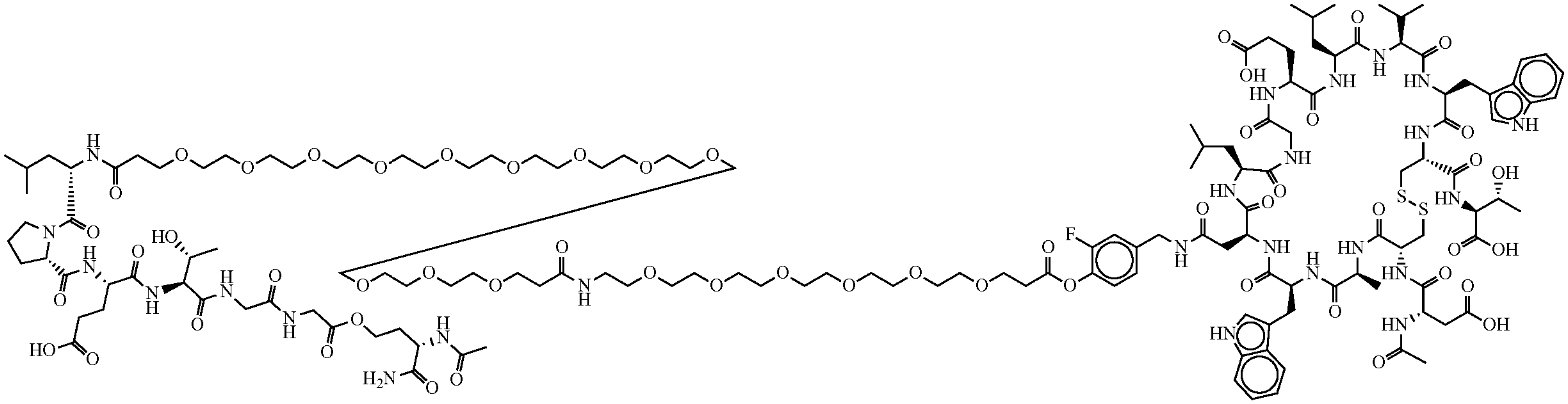 I-55 |

TABLE 1-continued
| Certain compounds/agents as examples. |
| --- |
| 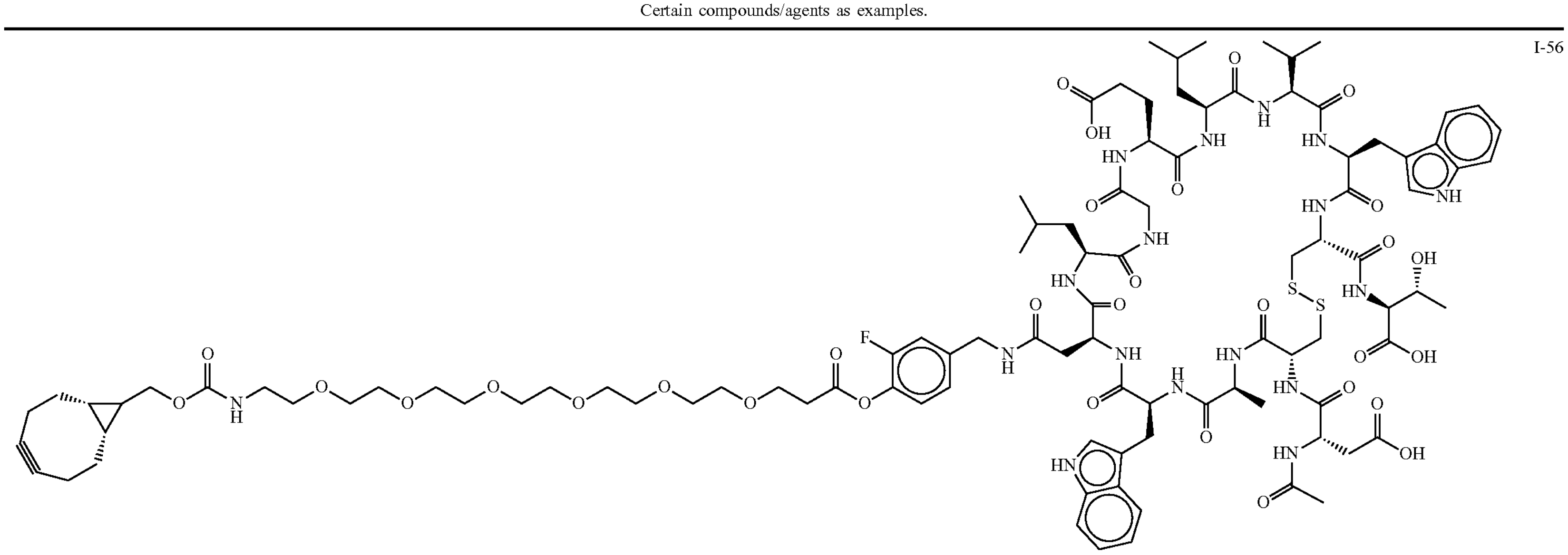 I-56 |
| 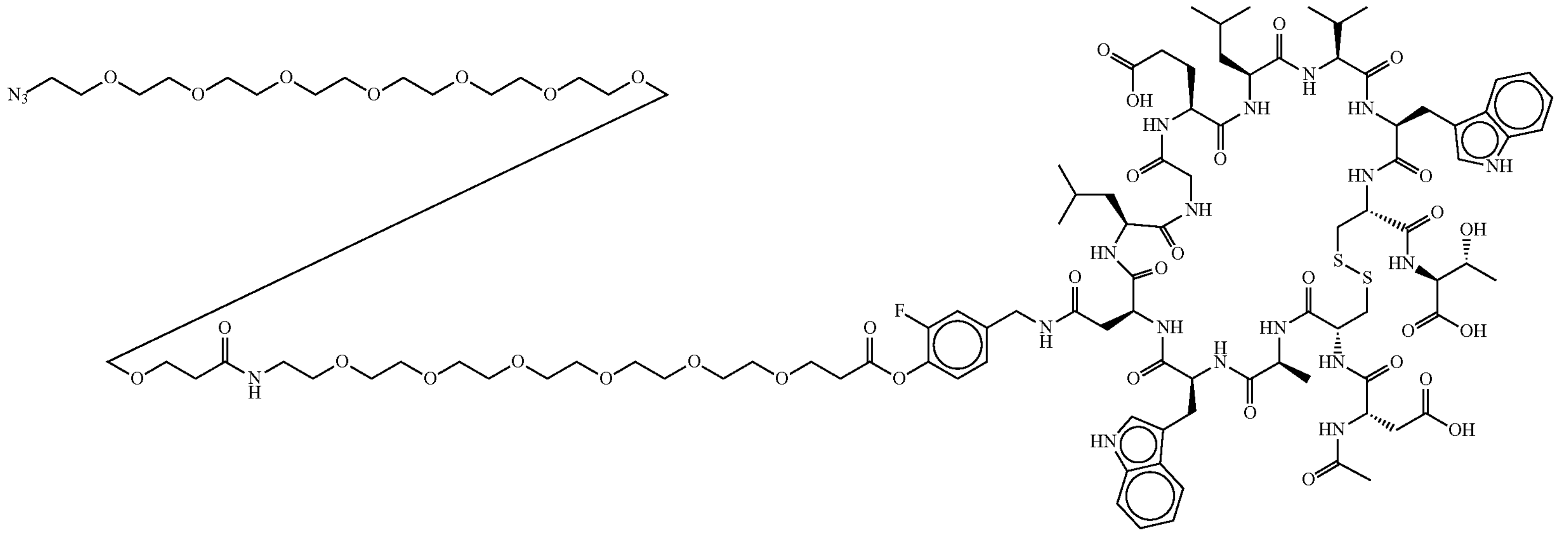 I-57 |

TABLE 1-continued
Certain compounds/agents as examples.
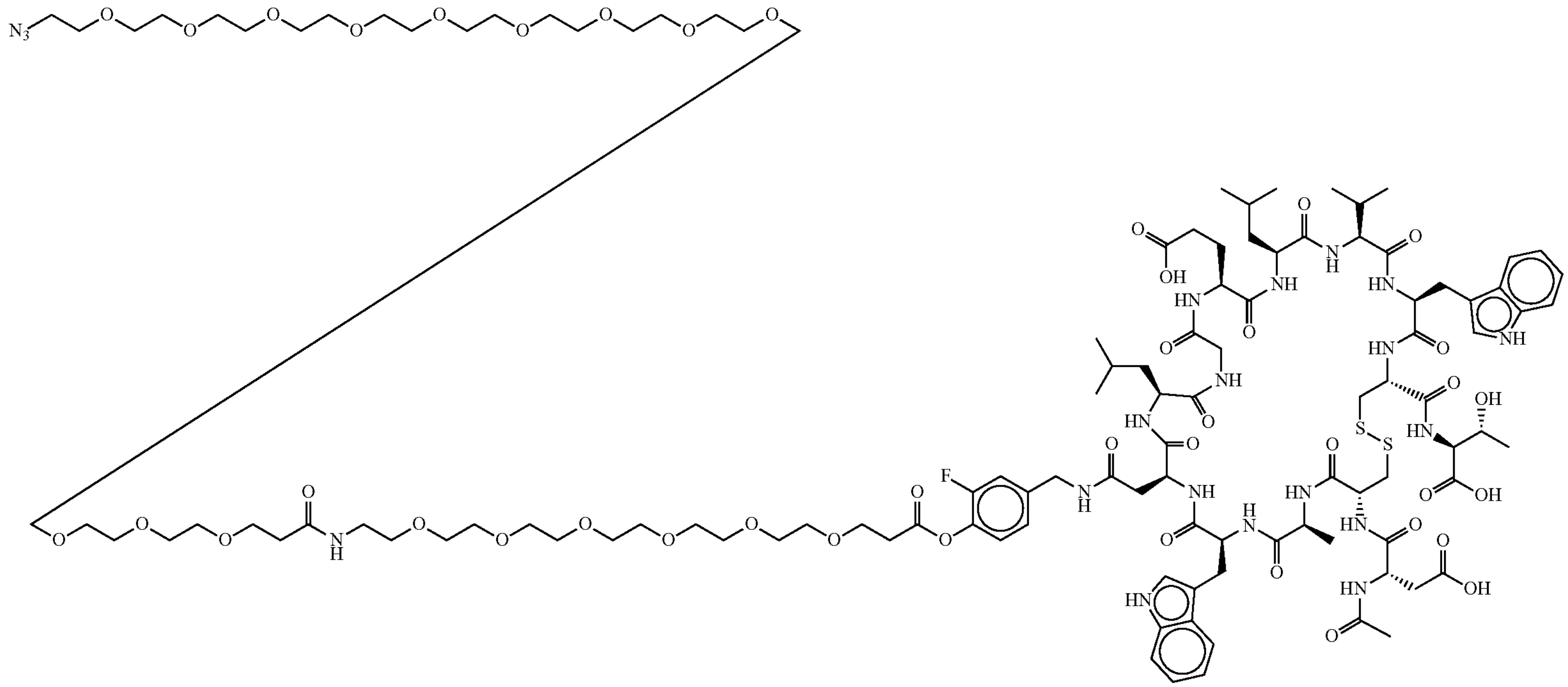
I-58

TABLE 1-continued
| Certain compounds/agents as examples. | |
|---|---|
| 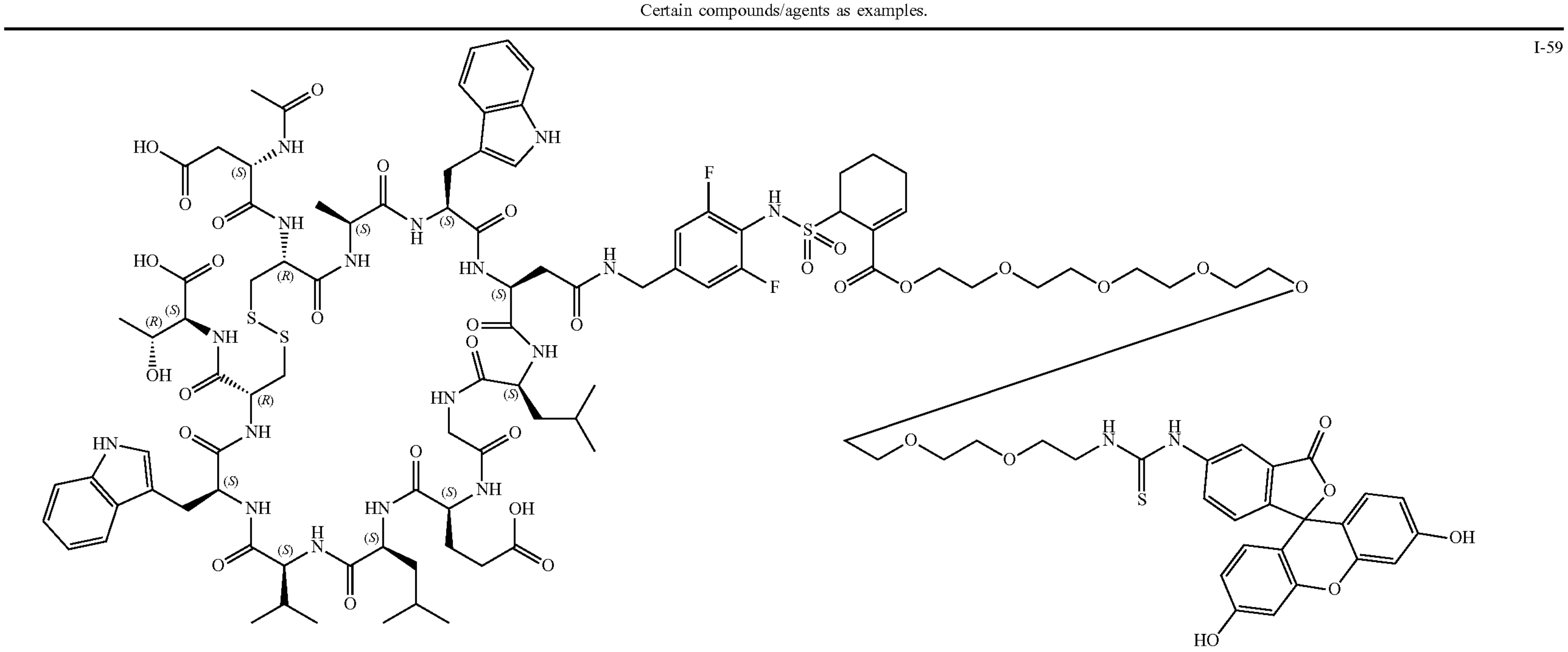 | I-59 |

TABLE 1-continued
Certain compounds/agents as examples.
I-61
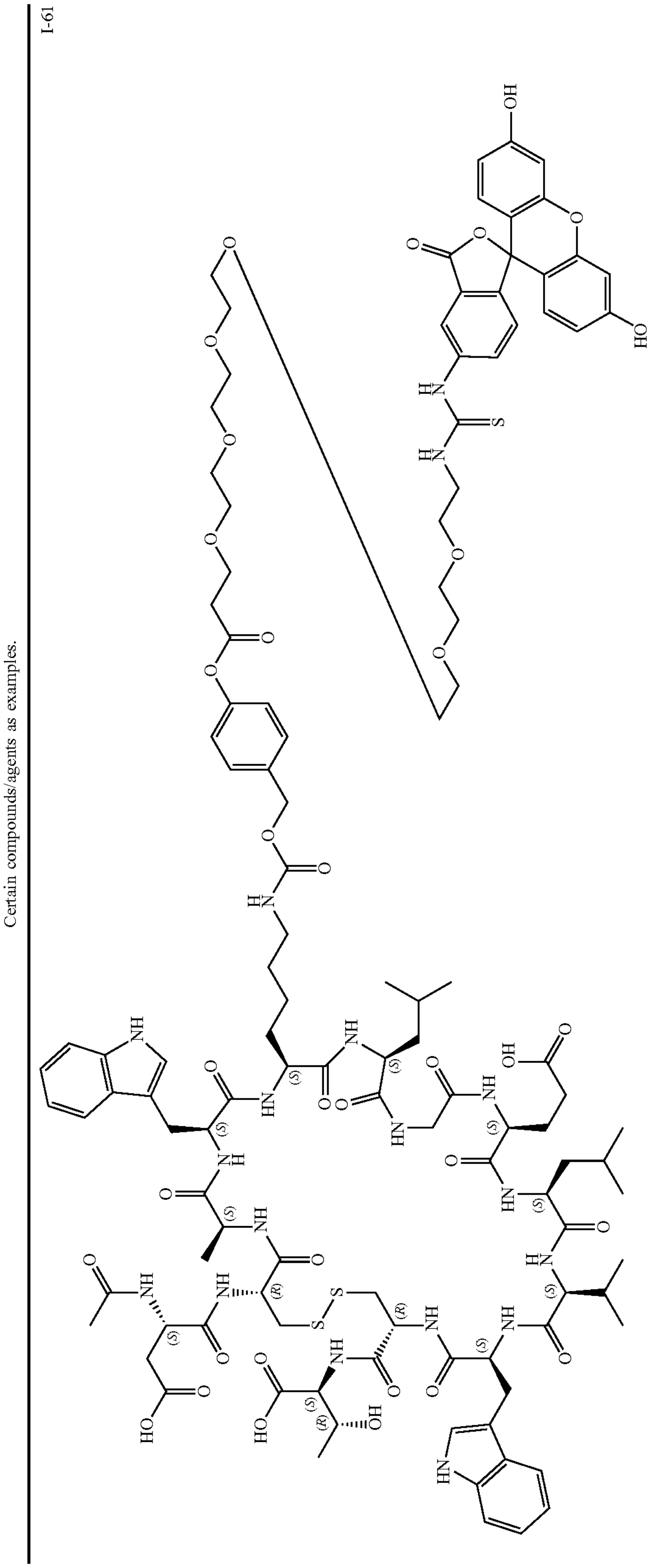

TABLE 1-continued
| Certain compounds/agents as examples. |
| --- |
| I-63 |
| 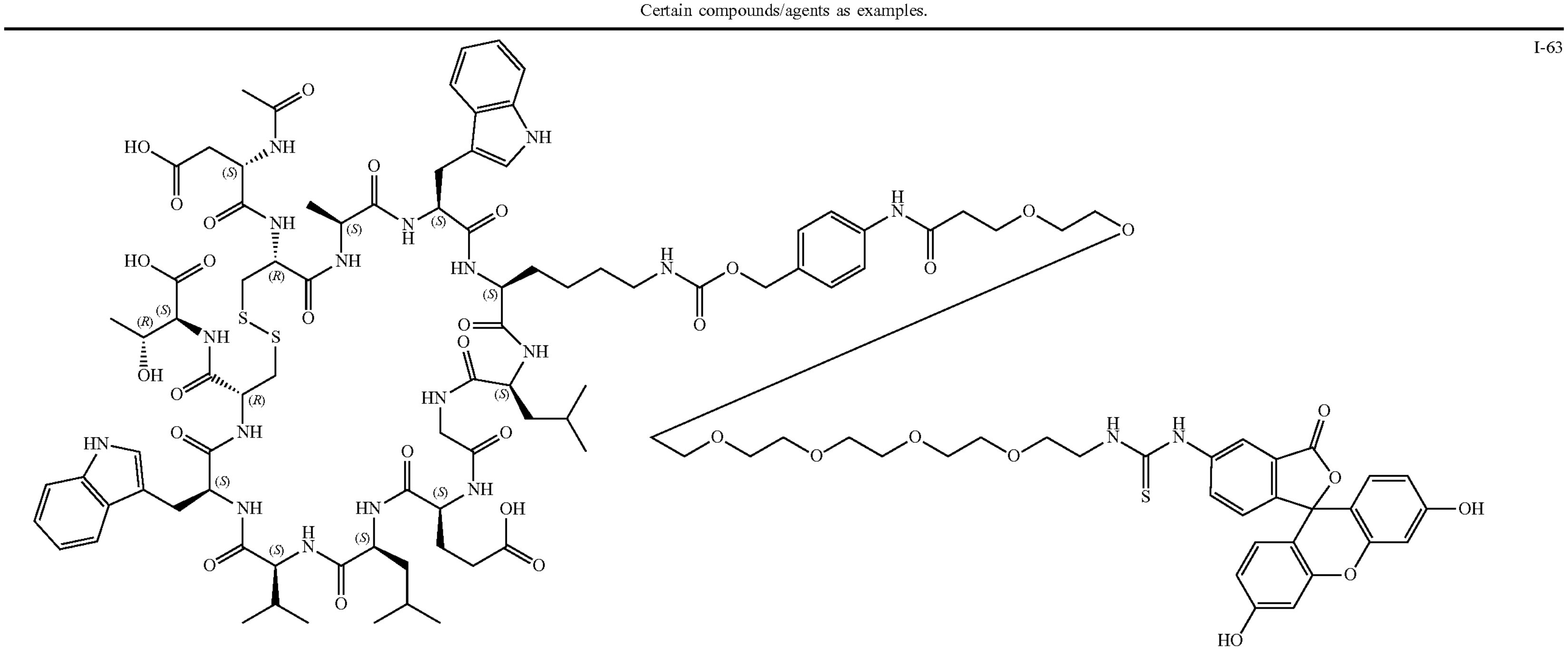 |

TABLE 1-continued
| Certain compounds/agents as examples. | |
|---|---|
| 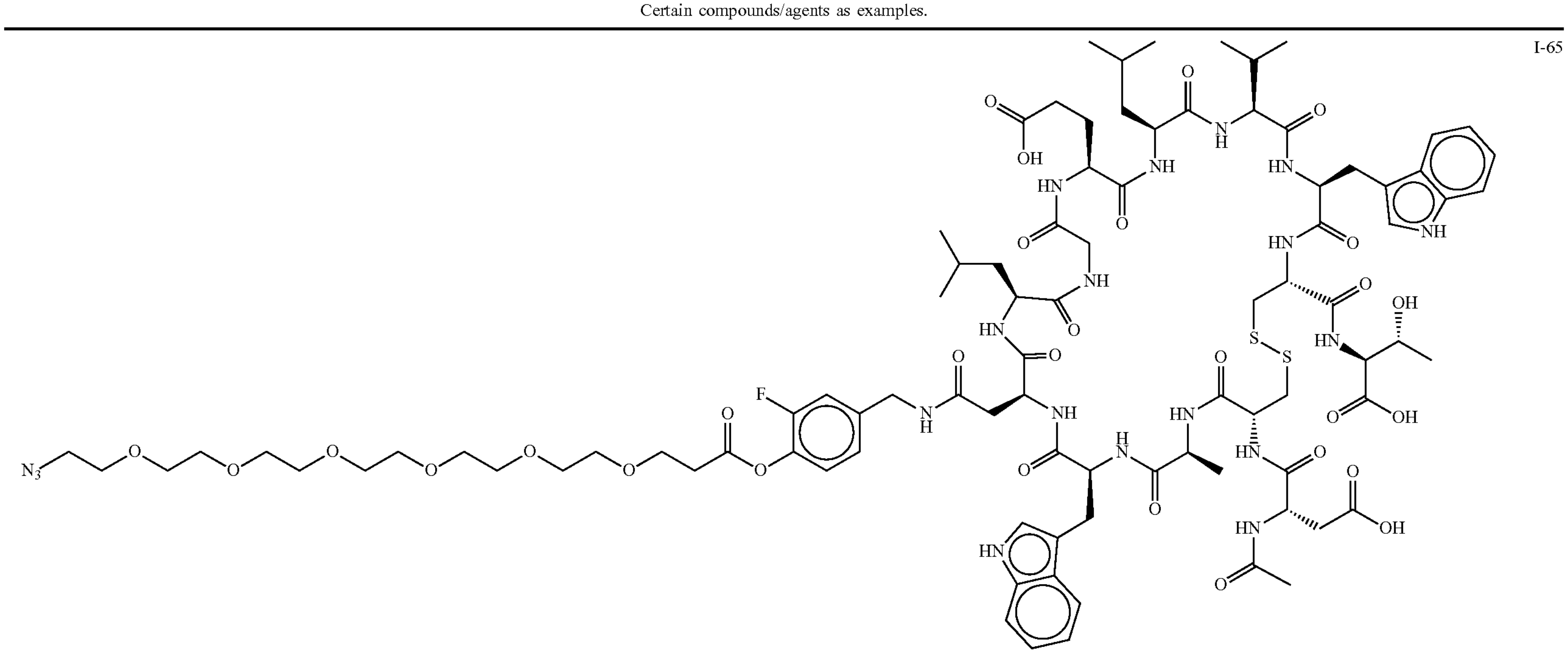 | I-65 |

TABLE 1-continued
| Certain compounds/agents as examples. | |
|---|---|
| 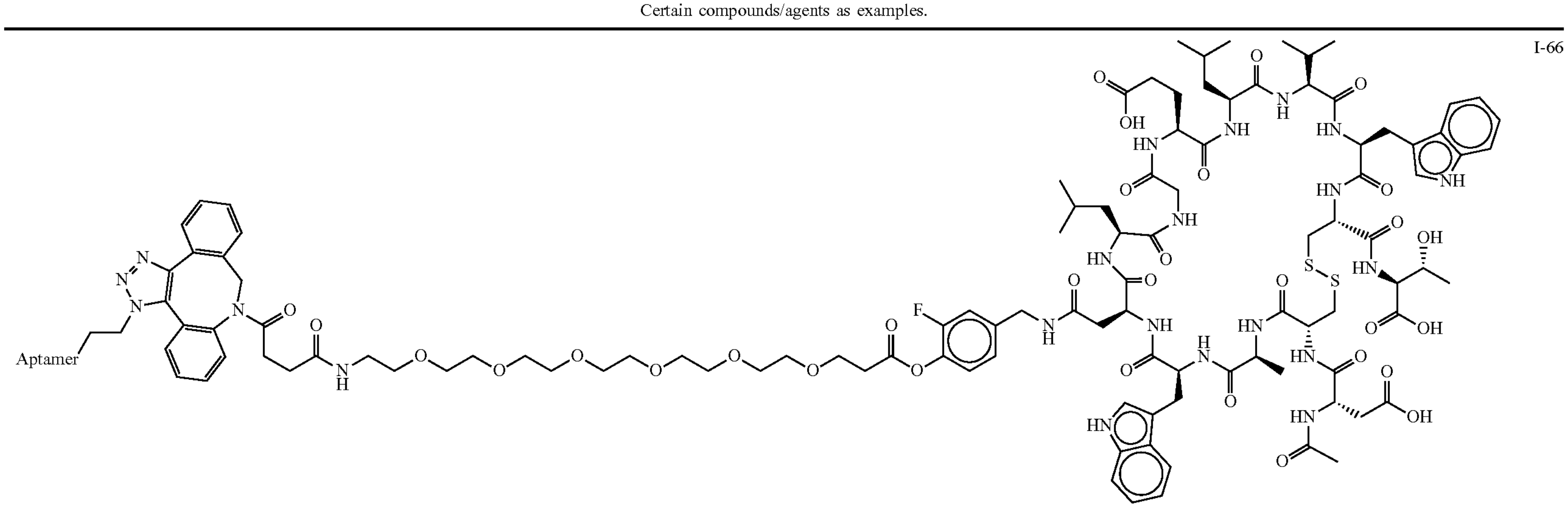 | I-66 |
| 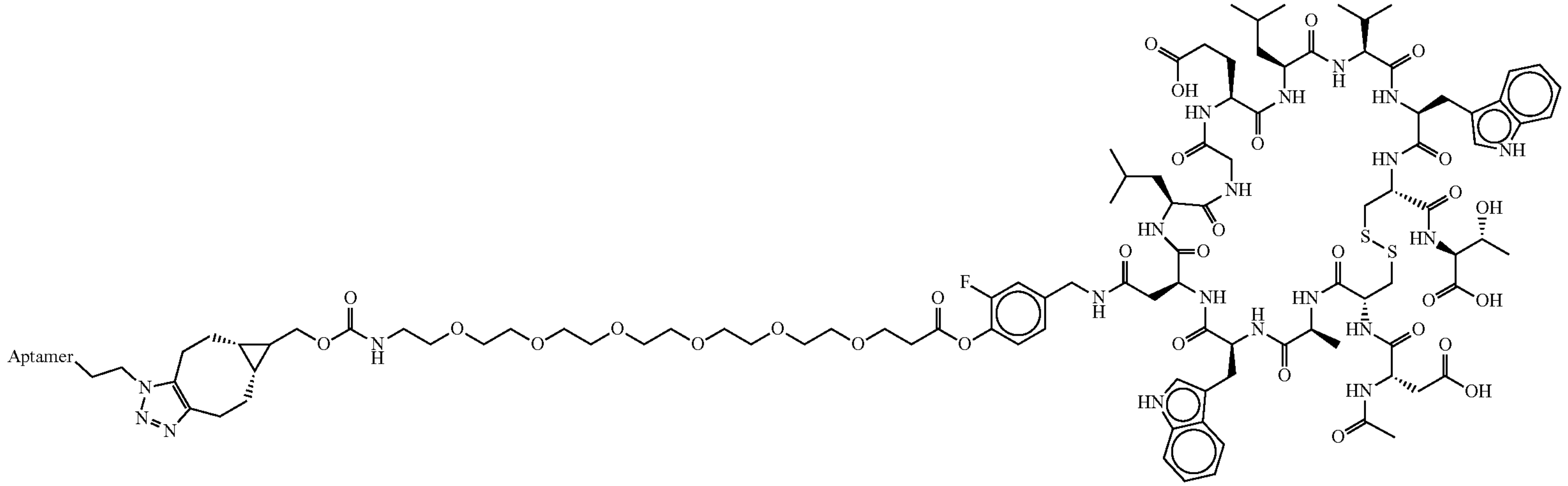 | I-67 |

TABLE 1-continued
Certain compounds/agents as examples.
I-68
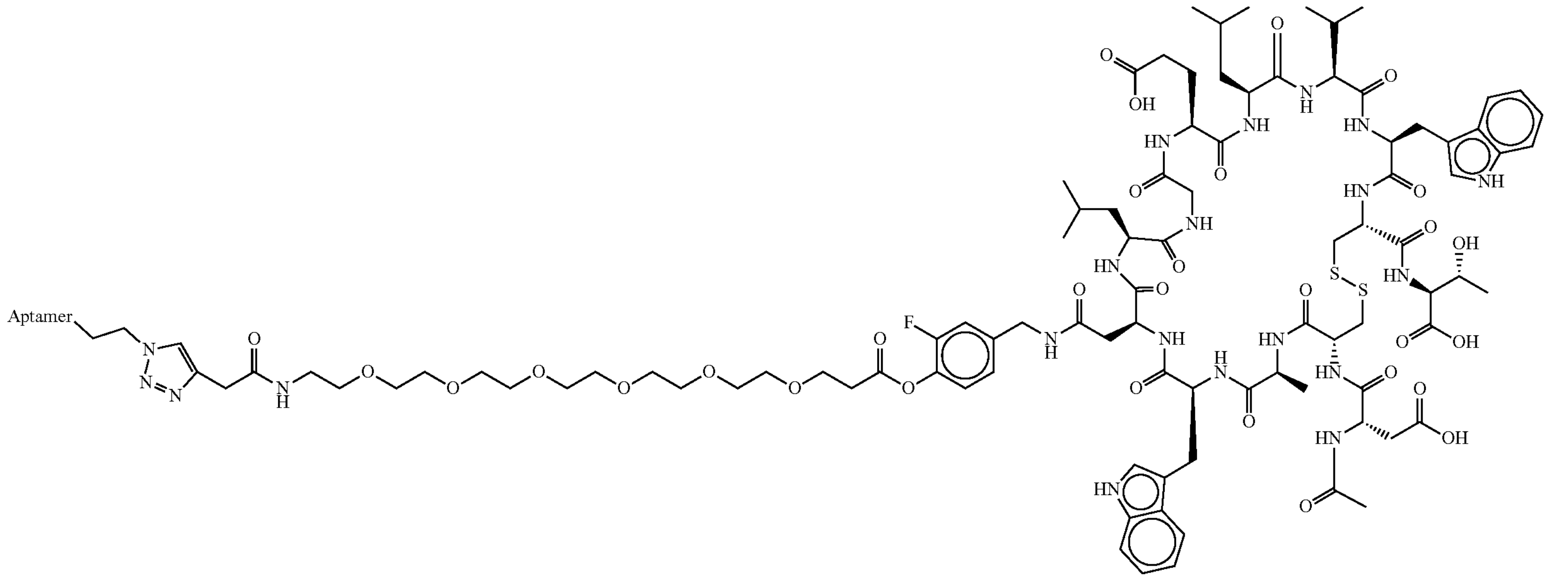

TABLE 1-continued
Certain compounds/agents as examples.
I-69
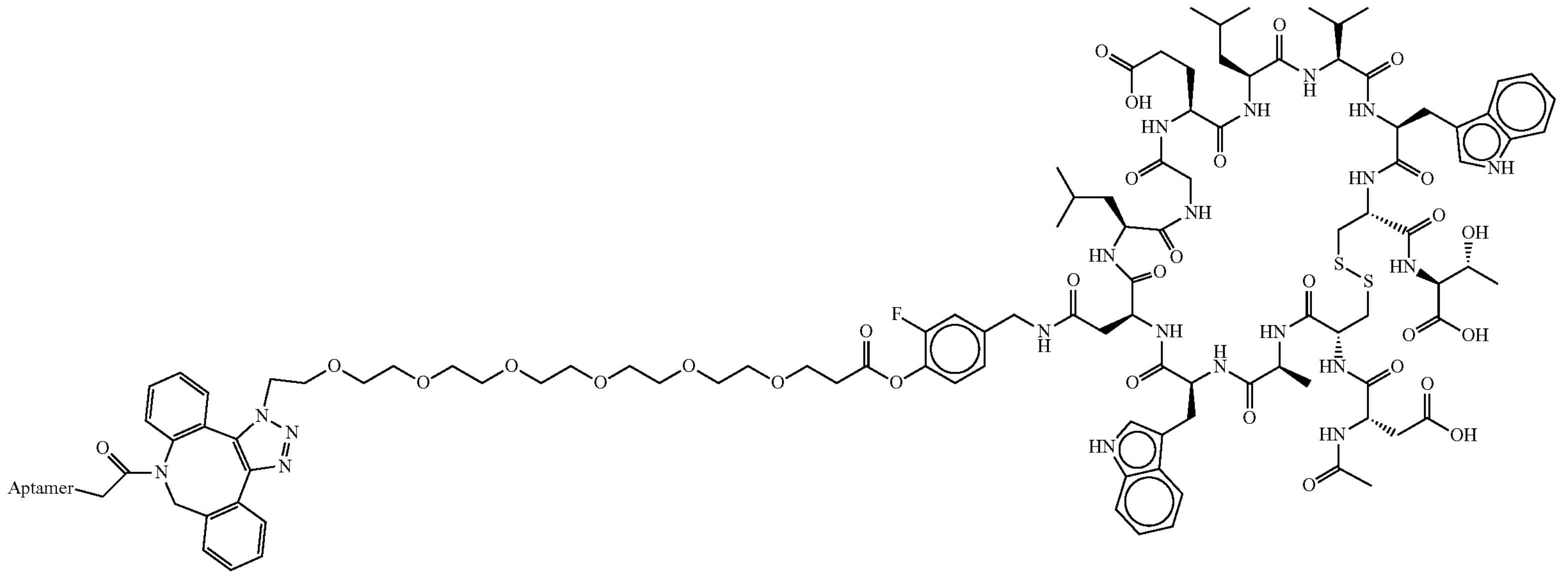
Table 1b.
I-9
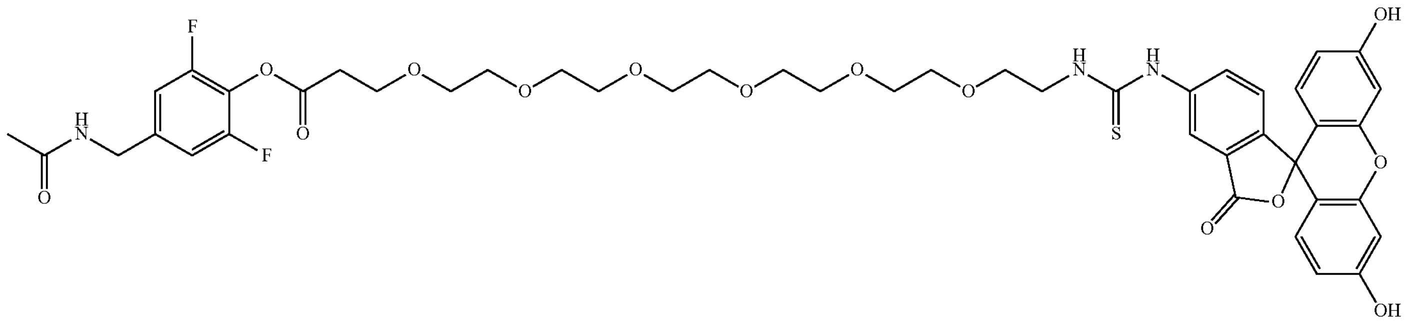 [SMILES: CC(=O)NCc1cc(F)c(OC(=O)CCOCCOCCOCCOCCOCCOCCNC(=S)Nc2ccc3c(c2)C(=O)OC32c3ccc(O)cc3Oc3cc(O)ccc32)c(F)c1]

TABLE 1-continued
| Certain compounds/agents as examples. | |
|---|---|
| 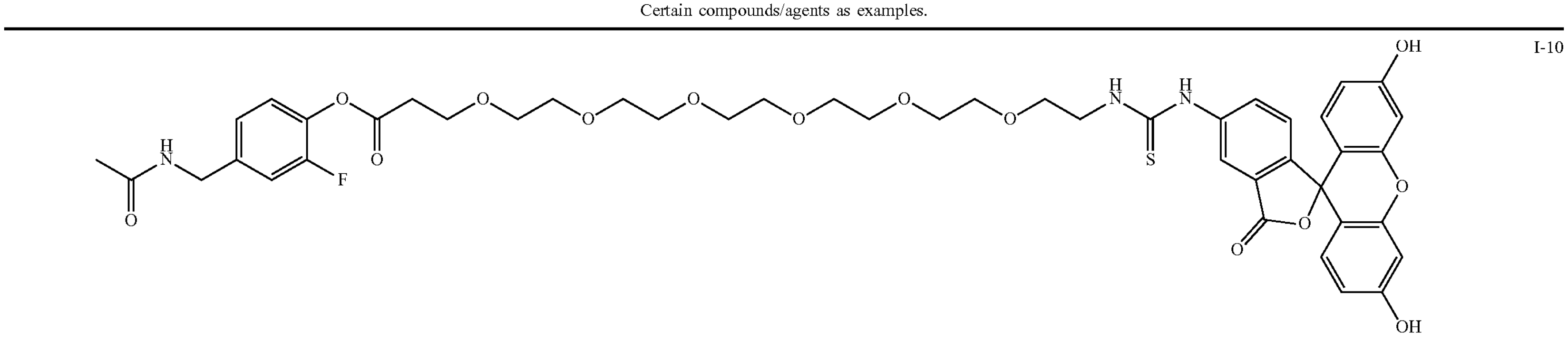 | I-10 |
| 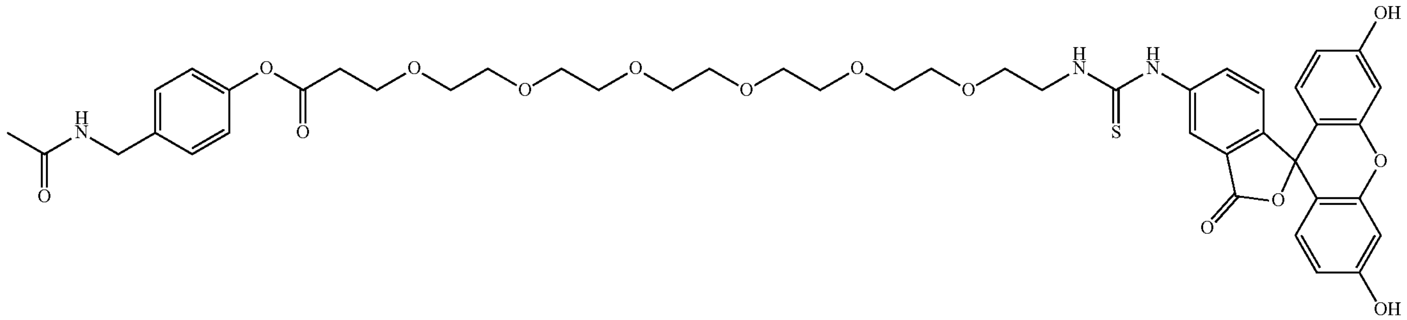 [SMILES: CC(=O)NCc1ccc(OC(=O)CCOCCOCCOCCOCCOCCOCCNC(=S)Nc2ccc3c(c2)C(=O)OC32c3ccc(O)cc3Oc3cc(O)ccc32)cc1] | I-11 |
| 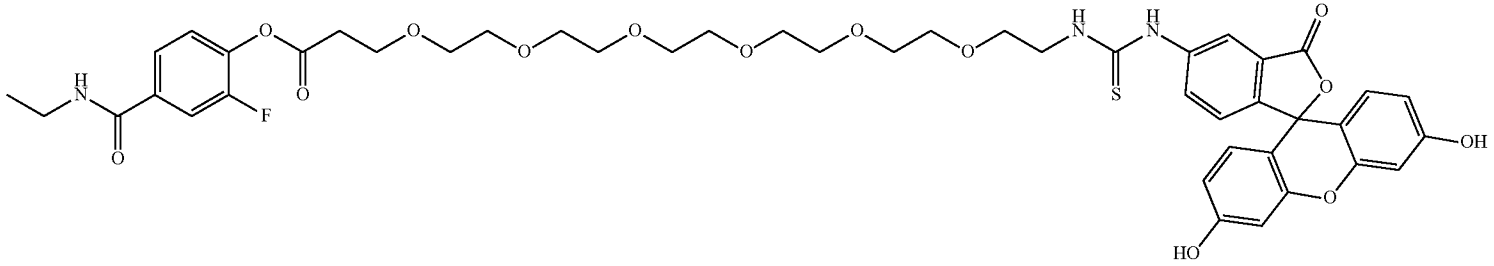 [SMILES: CCNC(=O)c1ccc(OC(=O)CCOCCOCCOCCOCCOCCOCCNC(=S)Nc2ccc3c(c2)C(=O)OC32c3ccc(O)cc3Oc3cc(O)ccc32)c(F)c1] | I-18 |

TABLE 1-continued
| Certain compounds/agents as examples. | |
| --- | --- |
| 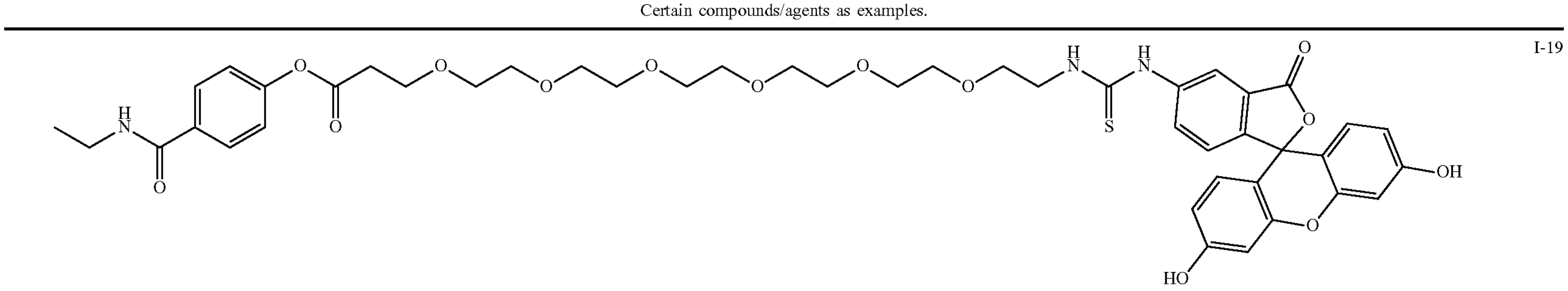 | I-19 |
| 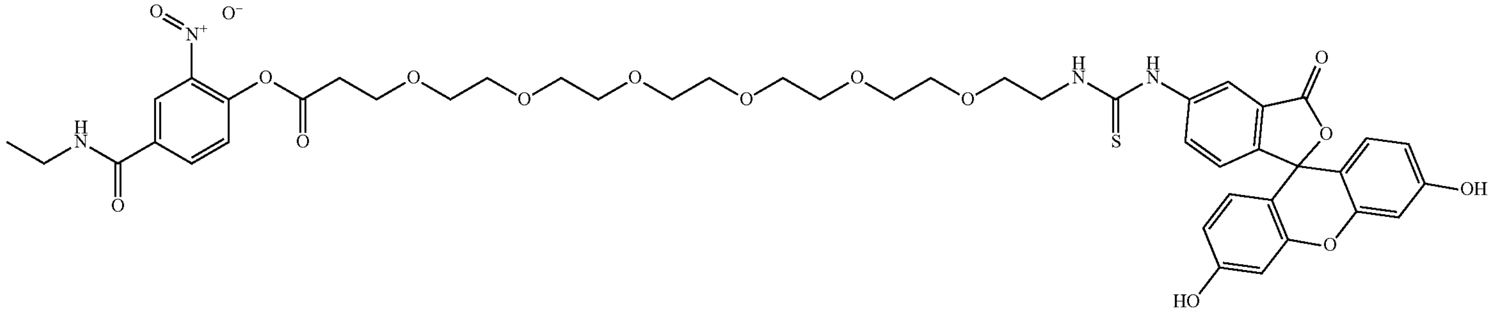 | I-51 |
| 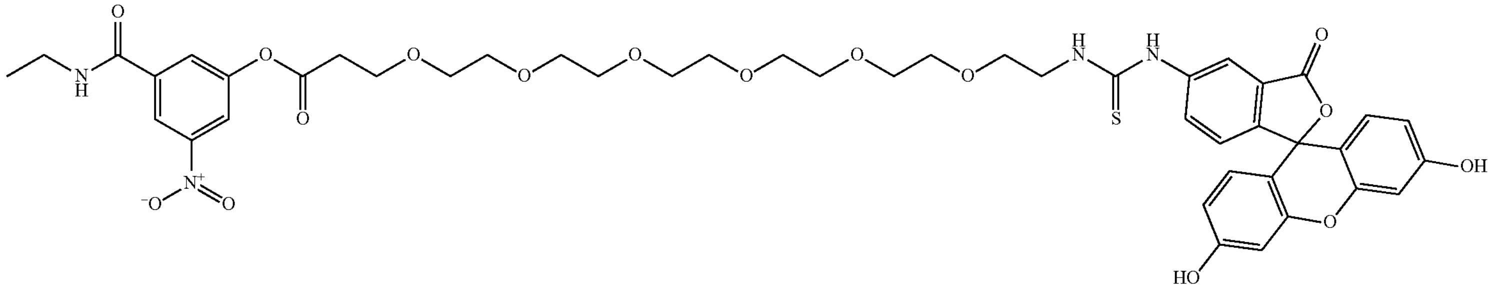 | I-52 |

TABLE 1-continued
| Certain compounds/agents as examples. | |
| --- | --- |
| 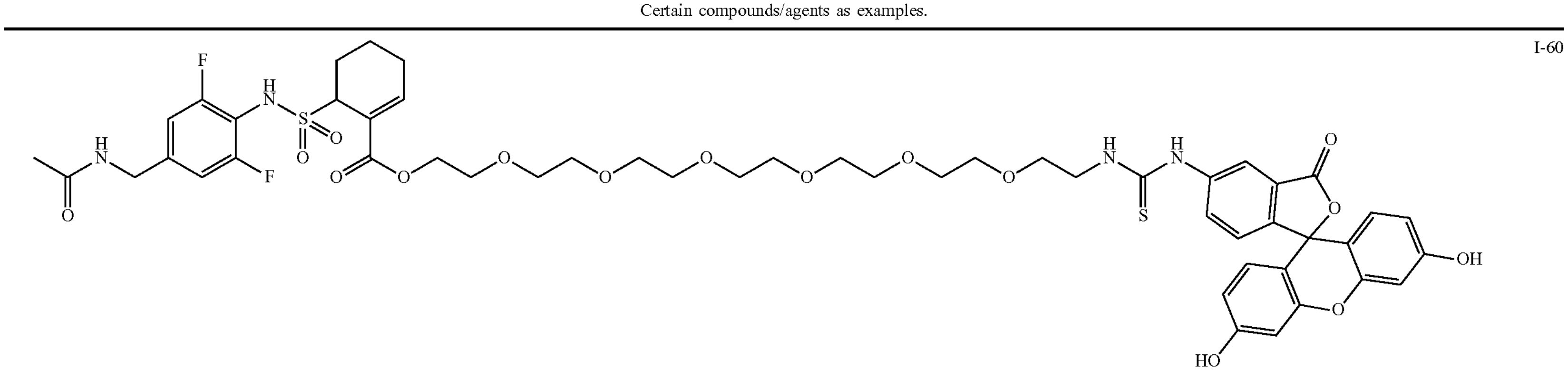 | I-60 |
| 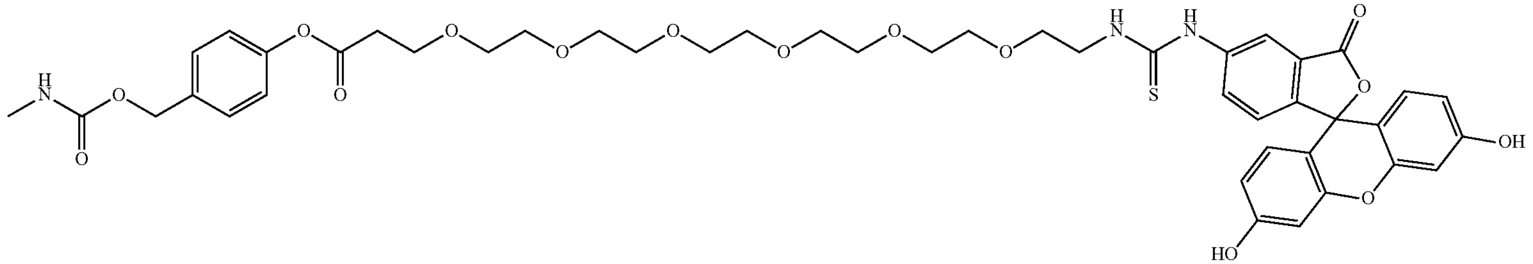 [SMILES: CNC(=O)OCc1ccc(OC(=O)CCOCCOCCOCCOCCOCCOCCNC(=S)Nc2ccc3c(c2)C(=O)OC32c3ccc(O)cc3Oc3cc(O)ccc32)cc1] | I-62 |
| 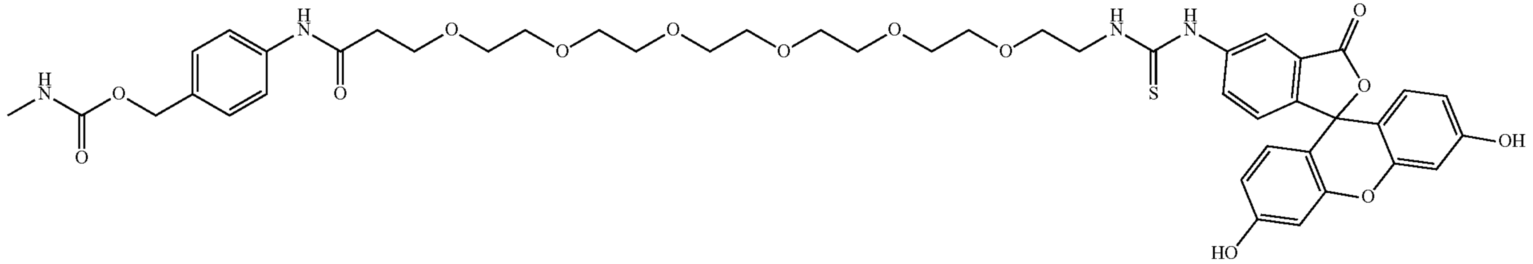 [SMILES: CNC(=O)OCc1ccc(NC(=O)CCOCCOCCOCCOCCOCCOCCNC(=S)Nc2ccc3c(c2)C(=O)OC32c3ccc(O)cc3Oc3cc(O)ccc32)cc1] | I-64 |
Table 1c.

TABLE 1-continued
Certain compounds/agents as examples.
I-4
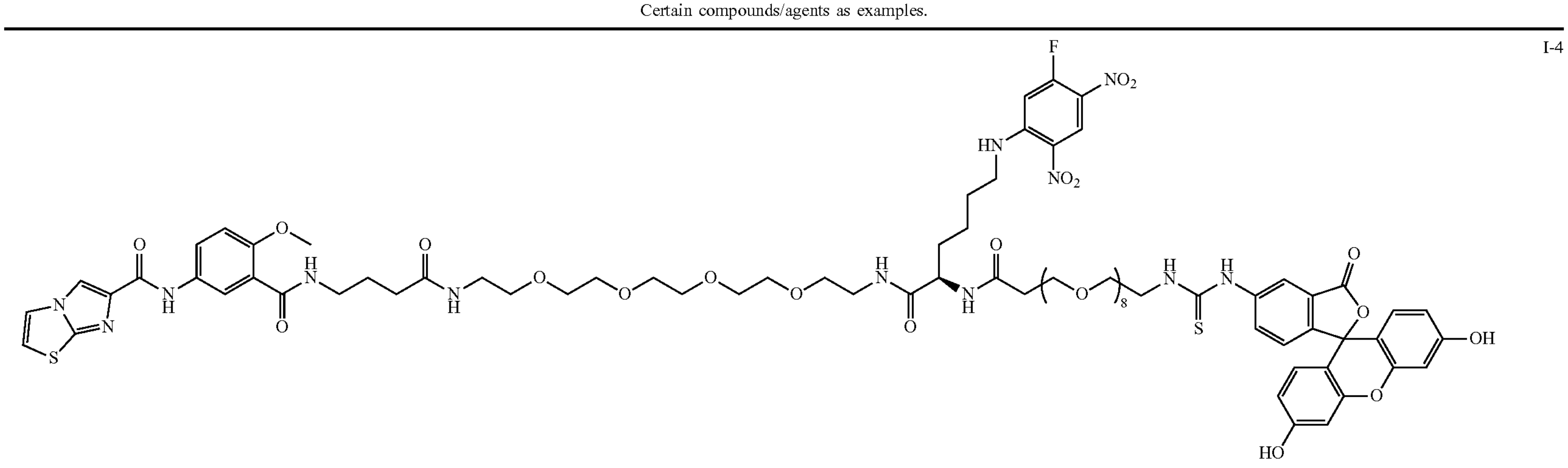
I-5
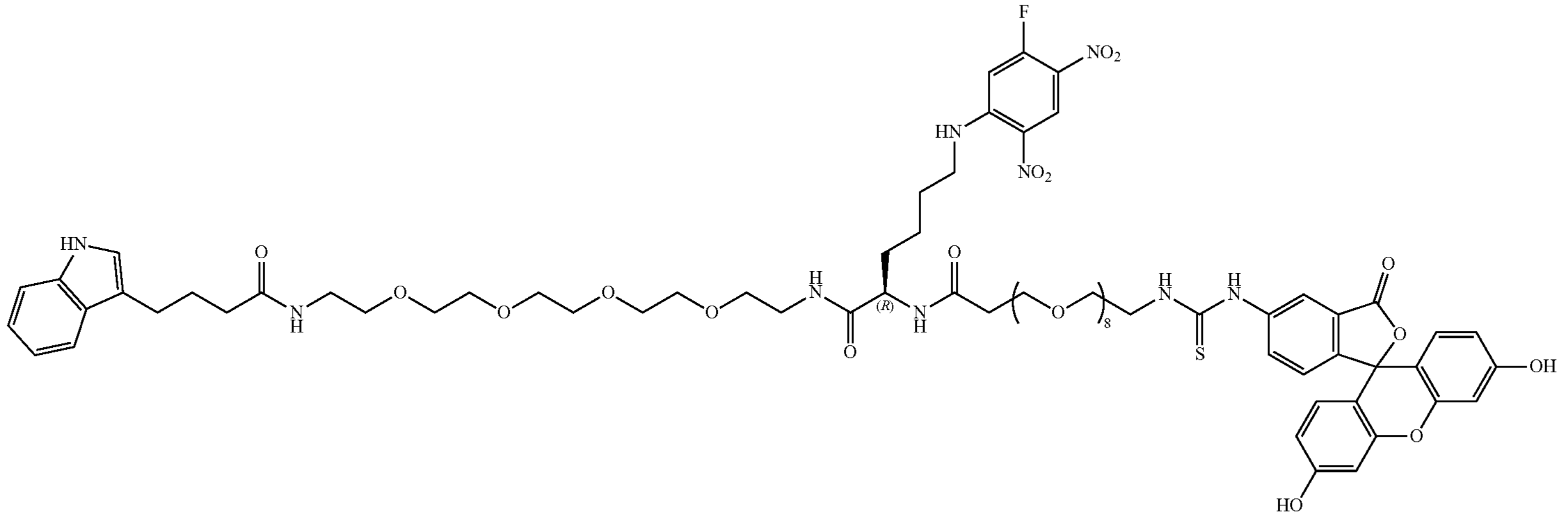

TABLE 1-continued
| Certain compounds/agents as examples. |
| --- |
| 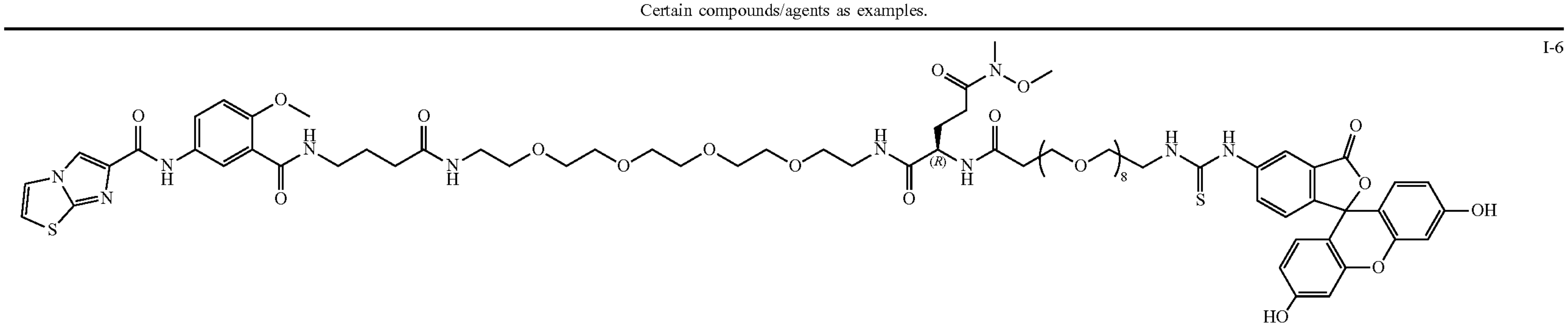 I-6 |
| 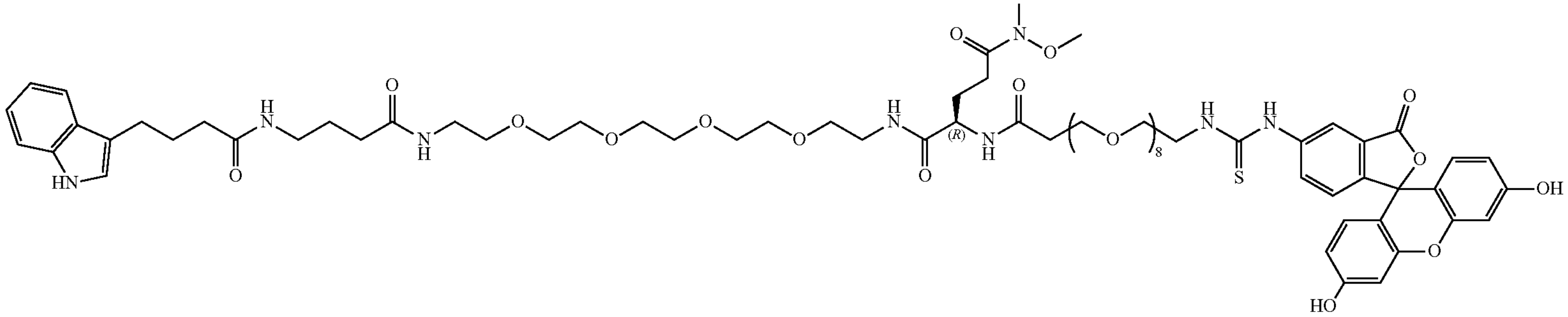 I-7 |
| 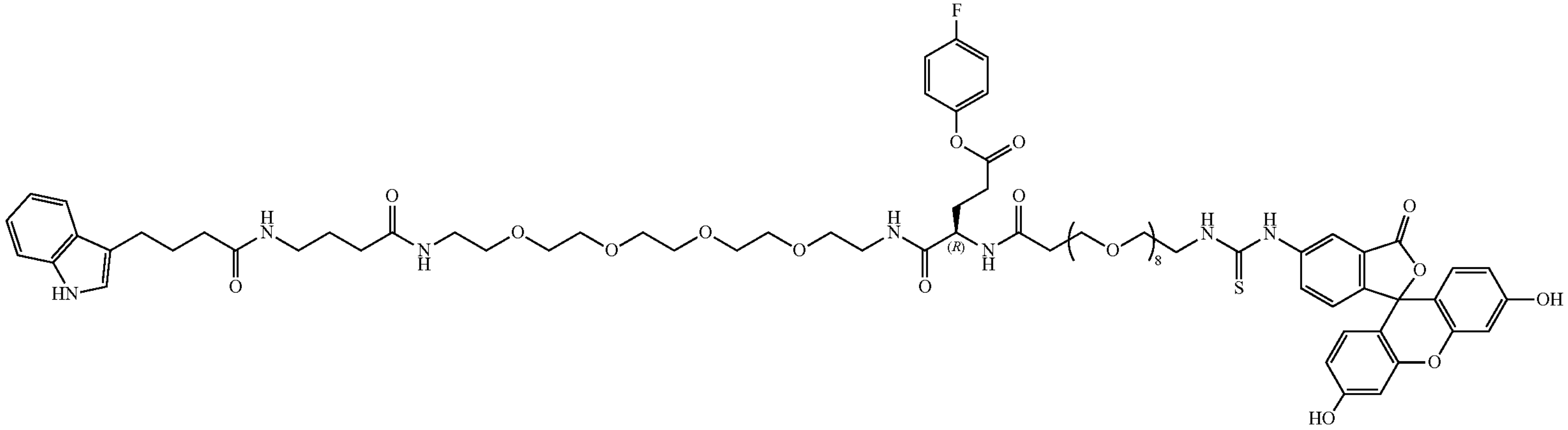 I-8 |

TABLE 1-continued
| Certain compounds/agents as examples. | |
|---|---|
| 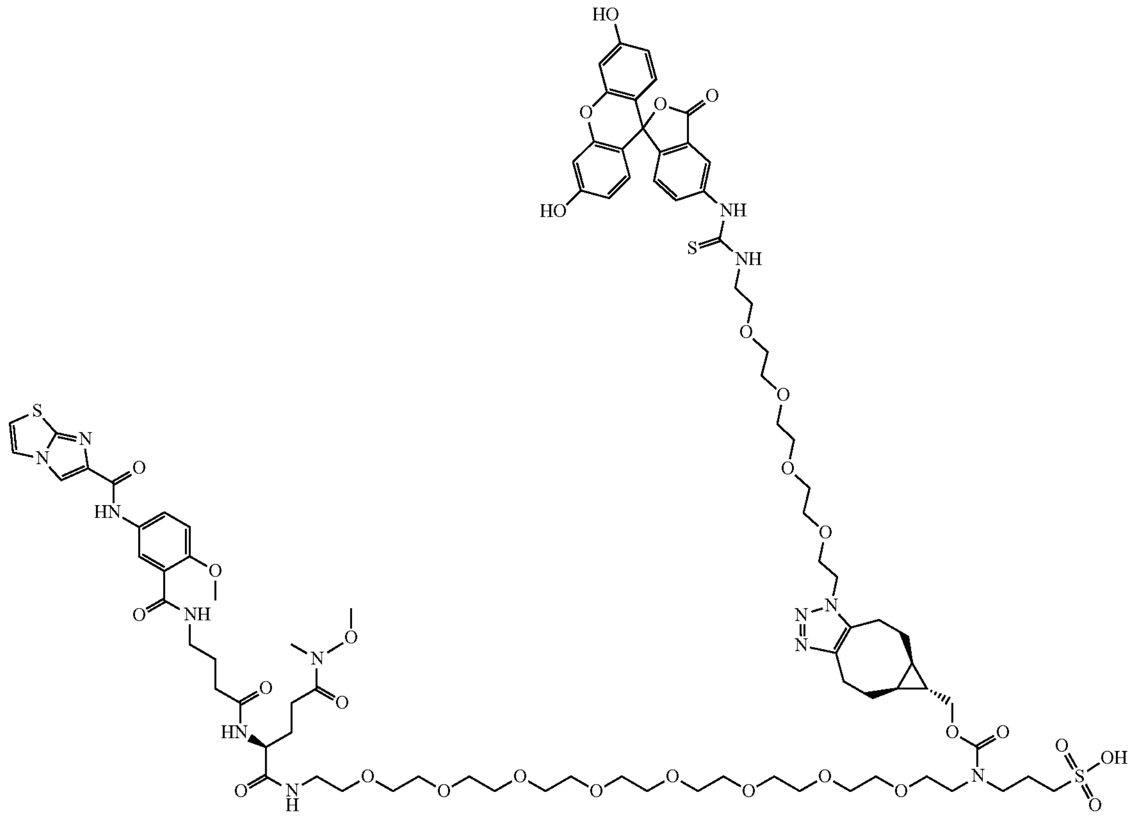 [SMILES: COc1ccc(NC(=O)c2cn3ccsc3n2)cc1C(=O)NCCCC(=O)N[C@@H](CCC(=O)N(C)OC)C(=O)NCCOCCOCCOCCOCCOCCOCCOCCOCCN(CCCS(=O)(=O)O)C(=O)OC[C@H]1[C@@H]2CCc3c(nnn3CCOCCOCCOCCOCCNC(=S)Nc3ccc4c(c3)C(=O)OC43c4ccc(O)cc4Oc4cc(O)ccc43)CC[C@@H]21] | I-20 |

TABLE 1-continued
Certain compounds/agents as examples.
I-26
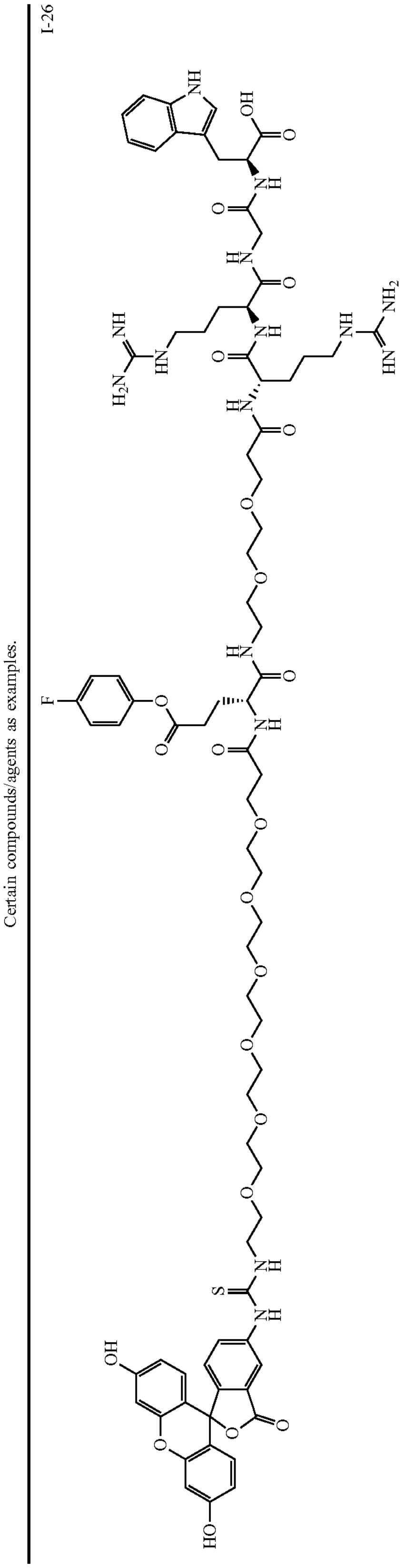
I-27
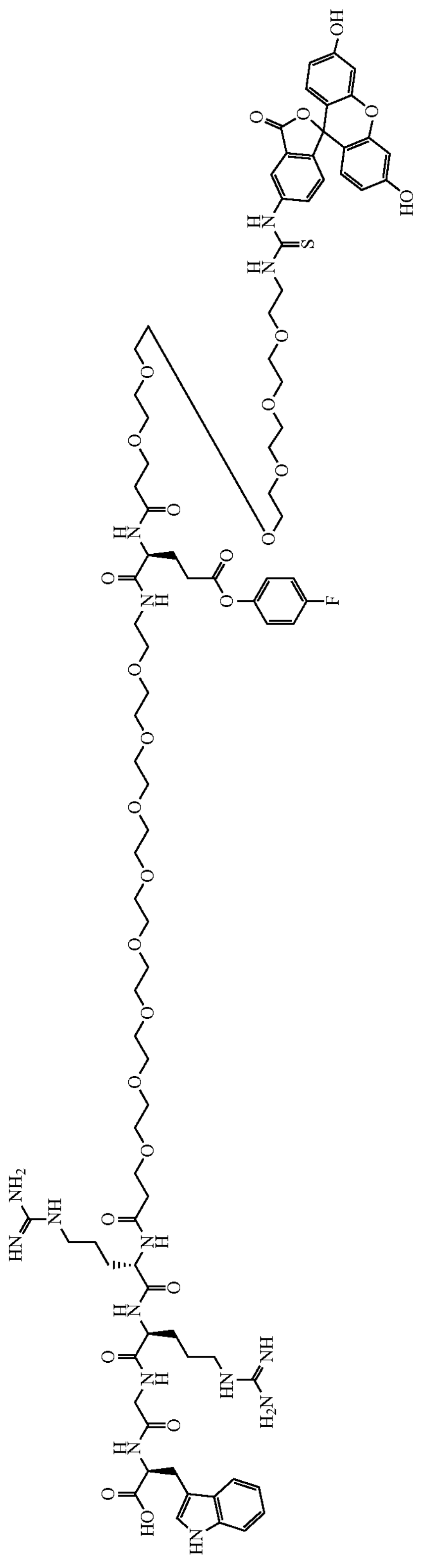

In some embodiments, a reaction partner is a compound of Table 1a or Table 1b. In some embodiments, a reaction partner comprising a target binding moiety and a moiety of interest, e.g., a compound of formula R-I or a salt thereof, is a compound in Table 1a. In some embodiments, a compound comprising an antibody binding moiety and a moiety of interest is a compound of Table 1a. In some embodiments, compound of Table 1b does not contain antibody binding moiety and may be utilized as reference for corresponding reaction partner compounds. In some embodiments, the present disclosure provides technologies for assessing properties and/or activities of reactive groups. In some embodiments, compounds of Table 1c are useful for assessing properties and/or activities of reactive groups thereon, e.g.,

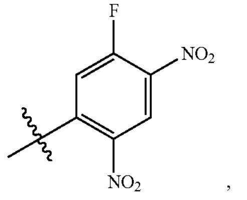 [SMILES: *c1cc(F)c([N+](=O)[O-])cc1[N+](=O)[O-]]

, $—C(O)N(CH_3)O(CH_3)$,

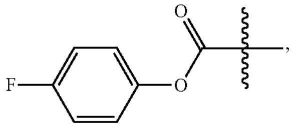

, etc.

In some embodiments, the present disclosure provides a compound set forth in Table 1, above, or a pharmaceutically acceptable salt thereof. In some embodiments, the present disclosure provides a composition which comprises or delivers a compound set forth in Table 1, above, or a pharmaceutically acceptable salt thereof. In some embodiments, the present disclosure provides an antibody-antibody conjugate as described herein. In some embodiments, the present disclosure provides an antibody-antibody conjugate comprising a linker as described herein (e.g., a linker lack of —S—S—). In some embodiments, the present disclosure provides a composition which comprises or delivers a provided antibody-antibody conjugate. In some embodiments, a provided composition is a pharmaceutical composition.

In some embodiments, the present disclosure provides technologies (e.g., compounds, methods, etc.) useful for preparing compounds, agents, compositions, etc. as described herein. In some embodiments, provided compounds are useful for preparing compounds of formula R-I or a salt thereof. In some embodiments, a compound has the structure of LG-$R^{LG}$—H or a salt thereof. In some embodiments, a compound has the structure of LG-$L^{LG1}$-H or a salt thereof. In some embodiments, a compound has the structure of LG-$L^{LG1}$-$L^{LG2}$-H or a salt thereof. In some embodiments, a compound has the structure of LG-$L^{LG1}$-$L^{LG2}$-$L^{LG3}$-H or a salt thereof. In some embodiments, a compound has the structure of LG-$L^{LG1}$-$L^{LG2}$-$L^{LG3}$-$L^{LG4}$-H or a salt thereof. In some embodiments, a compound has the structure of LG-$L^{LG1}$-$L^{LG2}$-$L^{LG3}$-$L^{LG4}$-RG-H or a salt thereof. In some embodiments, a compound has the structure of LG-$L^{LG1}$-$L^{LG2}$-$L^{LG3}$-$L^{LG4}$-$L^{RG1}$-H or a salt thereof. In some embodiments, a compound has the structure of LG-$L^{LG1}$-$L^{LG2}$-$L^{LG3}$-$L^{LG4}$-$L^{RG1}$-$L^{RG2}$-H or a salt thereof. In some embodiments, a compound has the structure of LG-$L^{LG1}$-$L^{LG2}$-$L^{LG3}$-$L^{LG4}$-$L^{RG1}$-$L^{RG2}$-$L^{RM}$-H or a salt thereof. In some embodiments, a compound has the structure of LG-$L^{LG1}$-$L^{LG2}$-$L^{LG3}$-$L^{LG4}$-$L^{RG1}$-$L^{RG2}$-$L^{PM}$-H or a salt thereof. For example, in some embodiments, a compound is

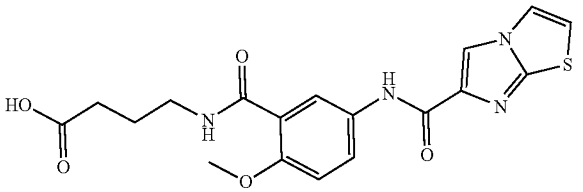 [SMILES: COc1ccc(NC(=O)c2cn3ccsc3n2)cc1C(=O)NCCCC(=O)O]

or a salt thereof. In some embodiments, a compound is

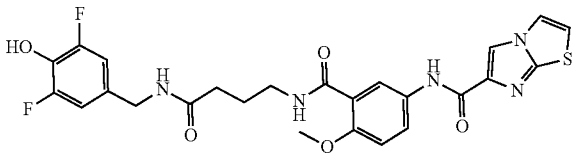 [SMILES: COc1ccc(NC(=O)c2cn3ccsc3n2)cc1C(=O)NCCCC(=O)NCc1cc(F)c(O)c(F)c1]

or a salt thereof. In some embodiments, a compound is

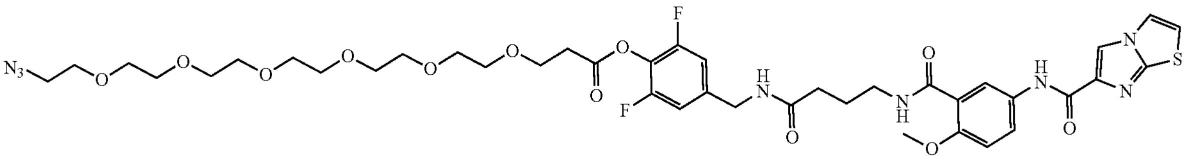 [SMILES: COc1ccc(NC(=O)c2cn3ccsc3n2)cc1C(=O)NCCCC(=O)NCc1cc(F)c(OC(=O)CCOCCOCCOCCOCCOCCOCCN=[N+]=[N-])c(F)c1]

or a salt thereof. In some embodiments, a compound is

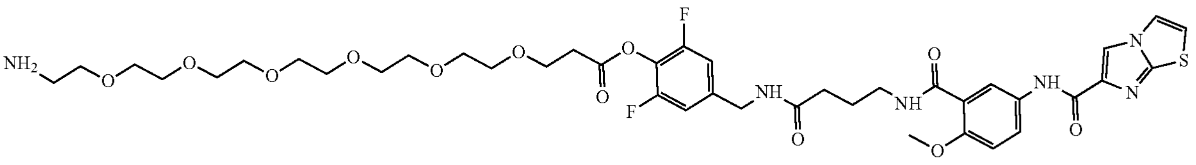 [SMILES: COc1ccc(NC(=O)c2cn3ccsc3n2)cc1C(=O)NCCCC(=O)NCc1cc(F)c(OC(=O)CCOCCOCCOCCOCCOCCOCCN)c(F)c1]

or a salt thereof. In some embodiments, a compound is one described in an Example as described herein.

General Methods, Reagents and Conditions

Various technologies may be utilized to provide compounds and agents herein in accordance with the present disclosure.

In some embodiments, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $5^{th}$ Edition, John Wiley & Sons, 2001, *Comprehensive Organic Transformations*, R. C. Larock, $2^{nd}$ Edition, John Wiley & Sons, 1999, and *Protecting Groups in Organic Synthesis*, T. W. Greene and P. G. M. Wuts, $3^{rd}$ edition, John Wiley & Sons, 1999, the entirety of each of which is hereby incorporated herein by reference.

In some embodiments, leaving groups include but are not limited to, halogens (e.g. fluoride, chloride, bromide, iodide), sulfonates (e.g. mesylate, tosylate, benzenesulfonate, brosylate, nosylate, triflate), diazonium, and the like.

In some embodiments, an oxygen protecting group includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that compounds/agents may contain one or more stereocenters, and may be present as a racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

One of skill in the art will appreciate that various functional groups present in compounds of the present disclosure such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the present disclosure are described below in the Exemplification.

Uses, Formulation and Administration

Compounds, agents, compositions, etc. of the present disclosure may be provided as in various forms according to desired uses. In some embodiments, they are provided as pharmaceutical compositions. As appreciated by those skilled in the art, in many instances, pharmaceutical compositions comprise controlled amounts and are manufactured for administration to subjects such as human patients. In some embodiments, the present disclosure provides a composition comprising a compound, an agent, and/or a composition described herein or a pharmaceutically acceptable derivative thereof and a pharmaceutically acceptable carrier. In some embodiments, the present disclosure provides a pharmaceutical composition comprising a compound, agent or composition of the present disclosure and a pharmaceutically acceptable carrier. In some embodiments, the present disclosure provides a pharmaceutical composition comprising a therapeutically effective amount of a compound, an agent or a composition of the present disclosure and a pharmaceutically acceptable carrier. In some embodiments, a pharmaceutical composition is packaged for storage, transportation, administration, etc. In some embodiments, a pharmaceutical composition does not contain a significant amount of organic solvents (e.g., total amount of organic solvents no more than 50%, 40%, 30%, 25%, 20%, 15%, 10%, 5%, 4%, 3%, 2%, or 1% of weight and/or volume of a pharmaceutical composition).

In some embodiments, a pharmaceutically acceptable carrier is or comprises a non-toxic carrier, adjuvant, or vehicle that does not destroy the pharmacological activity of the compound with which it is formulated. Pharmaceutically acceptable carriers, adjuvants or vehicles that may be include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, a pharmaceutically acceptable derivative is a non-toxic salt, ester, salt of an ester or other derivative of a compound that, upon administration to a recipient, is capable of providing, either directly or indirectly, a compound or an active metabolite or residue thereof.

Compositions may be administered orally, parenterally, by inhalation spray, topically, rectally, nasally, buccally, vaginally or via an implanted reservoir. In some embodiments, parenteral administration includes subcutaneous, intravenous, intramuscular, intra-articular, intra-synovial, intrasternal, intrathecal, intrahepatic, intralesional and intracranial injection or infusion techniques. In some embodiments, compositions are administered orally, intraperitoneally or intravenously. Sterile injectable forms of compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

In some embodiments, a bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, pharmaceutically acceptable compositions may be administered in the form of suppositories for rectal administration. In some embodiments, these can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

In some embodiments, pharmaceutically acceptable compositions may be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions are formulated for oral administration. Such formulations may be administered with or without food. In some embodiments, pharmaceutically acceptable compositions are administered without food. In other embodiments, pharmaceutically acceptable compositions are administered with food.

Amounts of compounds that may be combined with the carrier materials to produce a composition in a single dosage form will vary depending upon the host treated, the particular mode of administration. In some embodiments, provided compositions are formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

The amount of a compound of the present disclosure in the composition will also depend upon the particular compound in the composition.

Technologies (e.g., compounds, agents, compositions) of the present disclosure can be utilized for various purposes, e.g., detection, diagnosis, therapy, etc. In some embodiments, provided technologies are useful for treating conditions, disorders or diseases, e.g., various cancers. In some embodiments, provided technologies comprise target binding moieties, e.g., antibody agent moieties, that can bind antigens of cancer cells. In some embodiments, a target binding moiety is an antibody agent moiety. In some embodiments, an antibody agent is a therapeutic agent. Among other things, various antibody agents, including many developed and/or approved (e.g., by FDA, EMA, etc.) as therapeutics can be utilized in accordance with the present disclosure to provide therapeutics for various diseases.

Among other things, the present disclosure provides the following embodiments:

1. A compound having the structure of formula R-I:

$$LG\text{-}RG\text{-}L^{RM}\text{-}MOI, \qquad (R\text{-}I)$$

or a salt thereof, wherein:

LG is a group comprising a target binding moiety that binds to a target agent,

RG is a reactive group;

$L^{RM}$ is a linker; and

MOI is a moiety of interest.

2. A compound having the structure of formula R-I:

$$LG\text{-}RG\text{-}L^{RM}\text{-}MOI, \qquad (R\text{-}I)$$

or a salt thereof, wherein:

LG is $R^{LG}$-$L^{LG}$.

$R^{LG}$ is

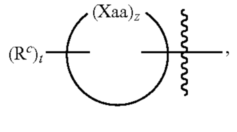

$R^c$-(Xaa)z-, a nucleic acid moiety, or a small molecule moiety;

each Xaa is independently a residue of an amino acid or an amino acid analog;

t is 0-50;

z is 1-50;

each $R^c$ is independently -$L^a$-R';

each of a and b is independently 1-200;

each $L^a$ is independently a covalent bond, or an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent monocyclic, bicyclic or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

$L^{LG}$ is -$L^{LG1}$-, -$L^{LG1}$-$L^{LG2}$-, -$L^{LG1}$-$L^{LG2}$-$L^{LG3}$-, or -$L^{LG1}$-$L^{LG2}$-$L^{LG3}$-$L^{LG4}$-;

RG is -$L^{RG1}$-$L^{RG2}$-; -$L^{LG4}$-$L^{RG1}$-$L^{RG2}$-, -$L^{LG3}$-$L^{LG4}$-$L^{RG1}$-$L^{RG2}$-, -$L^{LG2}$-$L^{LG3}$-$L^{LG4}$-$L^{RG1}$-$L^{RG2}$-;

each of $L^{LG1}$, $L^{LG2}$, $L^{LG3}$, $L^{LG4}$, $L^{RG1}$, $L^{RG2}$, and $L^{RM}$ is independently L;

each L is independently a covalent bond, or a bivalent optionally substituted, linear or branched $C_{1-100}$ group comprising one or more aliphatic moieties, aryl moieties, heteroaliphatic moieties each independently having 1-20 heteroatoms, heteroaromatic moieties each independently having 1-20 heteroatoms, or any combinations of any one or more of such moieties, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue, or —[(—O—C(R')$_2$—C(R')$_2$—)$_n$]—, wherein n is 1-20;

each R' is independently —R, —C(O)R, —CO$_2$R, or —SO$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms; and MOI is a moiety of interest.

3. The compound of any one of the preceding embodiments, wherein LG is or comprises a target binding moiety that binds to a target agent, wherein a target agent is a protein agent.

4. The compound of any one of the preceding embodiments, wherein LG is or comprises a target binding moiety that binds to a target agent, wherein a target agent is an antibody agent.

5. The compound of any one of the preceding embodiments, wherein LG is or comprises a target binding moiety that binds to a Fc region.

6. The compound of any one of the preceding embodiments, wherein each L is independently a covalent bond, or a bivalent optionally substituted, linear or branched aliphatic group or heteroaliphatic group having 1-10 heteroatoms, wherein one or more methylene units of the group are optionally and independently replaced with —C≡C—, -Cy-, —$C(R')_2$—, —O—, —S—, —S—S—, —N(R')—, —C(O)—, —C(S)—, —C(NR')—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue, or —[(—O—$C(R')_2$—$C(R')_2$—$)_n$]—, wherein n is 1-20.

7. The compound of any one of the preceding embodiments, wherein LG is $R^{LG}$-$L^{LG}$-, wherein $R^{LG}$ is or comprises a target binding moiety, wherein $L^{LG}$ is $L^{LG1}$, wherein $L^{LG1}$ is L.

8. The compound of any one of the preceding embodiments, wherein RG is or comprises -$L^{LG2}$-$L^{LG3}$-$L^{LG4}$-$L^{RG1}$-$L^{RG2}$-, wherein each of $L^{LG2}$, $L^{LG3}$, $L^{LG4}$, $L^{RG1}$, $L^{RG2}$ is independently L.

9. The compound of any one of the preceding embodiments, wherein LG is $R^{LG}$-$L^{LG}$-, wherein $R^{LG}$ is or comprises a target binding moiety, wherein $L^{LG}$ is $L^{LG1}$-$L^{LG2}$-.

10. The compound of any one of the preceding embodiments, wherein RG is or comprises -$L^{LG3}$-$L^{LG4}$-$L^{RG1}$-$L^{RG2}$-.

11. The compound of any one of the preceding embodiments, wherein LG is $R^{LG}$-$L^{LG}$-, wherein $R^{LG}$ is or comprises a target binding moiety, wherein $L^{LG}$ is $L^{LG1}$-$L^{LG2}$-$L^{LG3}$-.

12. The compound of any one of the preceding embodiments, wherein RG is or comprises -$L^{LG4}$-$L^{RG1}$-$L^{RG2}$-.

13. The compound of any one of the preceding embodiments, wherein LG is $R^{LG}$-$L^{LG}$-, wherein $R^{LG}$ is or comprises a target binding moiety, wherein $L^{LG}$ is $L^{LG1}$-$L^{LG2}$-$L^{LG3}$-$L^{LG4}$-.

14. The compound of any one of the preceding embodiments, wherein RG is or comprises -$L^{RG1}$-$L^{RG2}$-.

15. The compound of any one of the preceding embodiments, wherein $R^{LG}$ is

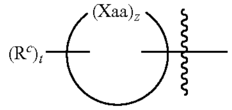

or $R^c$-(Xaa)z-.

16. The compound of any one of the preceding embodiments, wherein $R^{LG}$ is or comprises WXL, wherein X is an amino acid residue.

17. The compound of any one of the preceding embodiments, wherein $R^{LG}$ is or comprises AWXLGELVW, wherein X is an amino acid residue.

18. The compound of any one of the preceding embodiments, wherein $R^{LG}$ is or comprises DpLpAWXLGELVW, wherein X is an amino acid residue.

19. The compound of any one of the preceding embodiments, wherein $R^{LG}$ is or comprises DCAWXLGELVWCT, wherein the two cysteine residues optionally form a disulfide bond, and X is an amino acid residue.

20. The compound of any one of the preceding embodiments, wherein $R^{LG}$ is or comprises DpLpDCAWXLGELVWCT, wherein the two cysteine residues optionally form a disulfide bond, and X is an amino acid residue.

21. The compound of any one of the preceding embodiments, wherein $R^{LG}$ is or comprises CDCAWXLGELVWCTC, wherein the first and the last cysteines, and the two cysteines in the middle of the sequence, are each independently and optionally form a disulfide bond, and X is an amino acid residue.

22. The compound of any one of embodiments 16-21, wherein $R^{LG}$ is or comprises WXL, wherein X is an amino acid residue.

23. The compound of embodiment 15, wherein $R^{LG}$ is selected from Table A-1.

24. The compound of embodiment 15, wherein $R^{LG}$ is

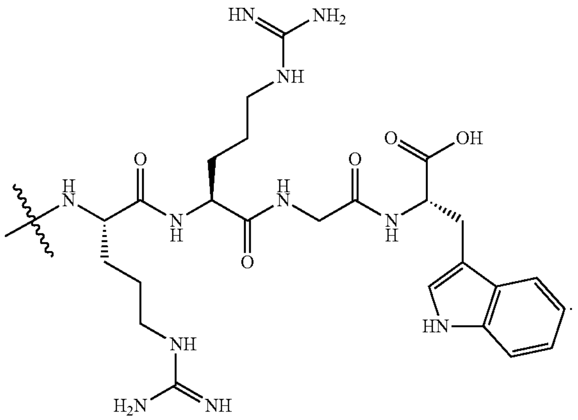 [SMILES: *N[C@@H](CCCNC(=N)N)C(=O)N[C@@H](CCCNC(=N)N)C(=O)NCC(=O)N[C@@H](Cc1c[nH]c2ccccc12)C(=O)O]

25. The compound of embodiment 15, wherein $R^{LG}$ is

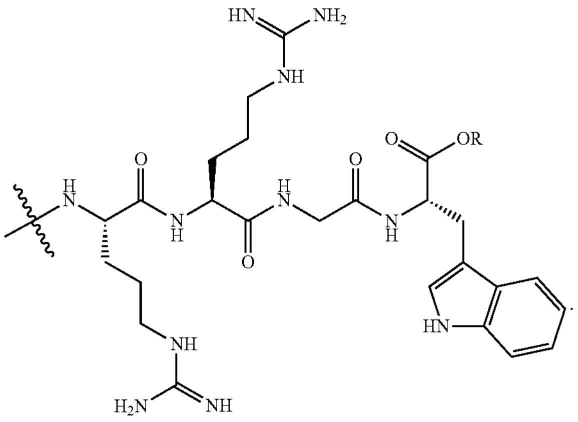

26. The compound of embodiment 15, wherein $R^{LG}$ is

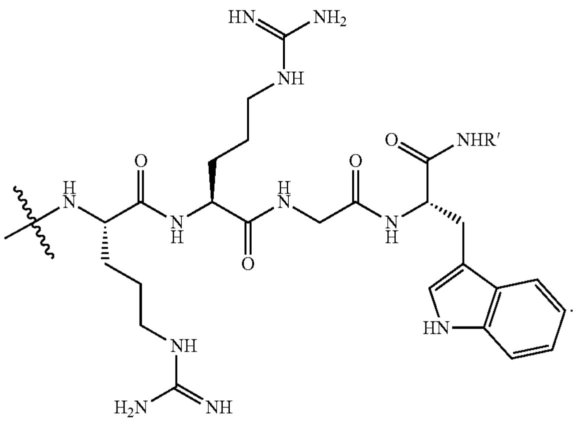

27. The compound of embodiment 15, wherein $R^{LG}$ is
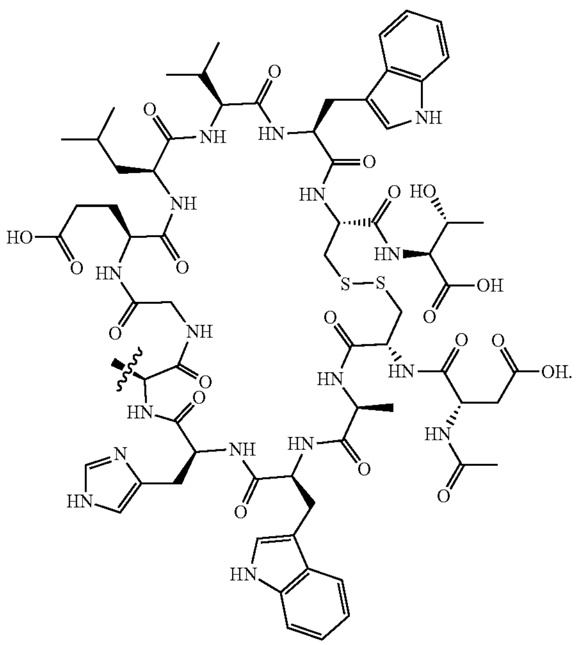
28. The compound of embodiment 15, wherein $R^{LG}$ is
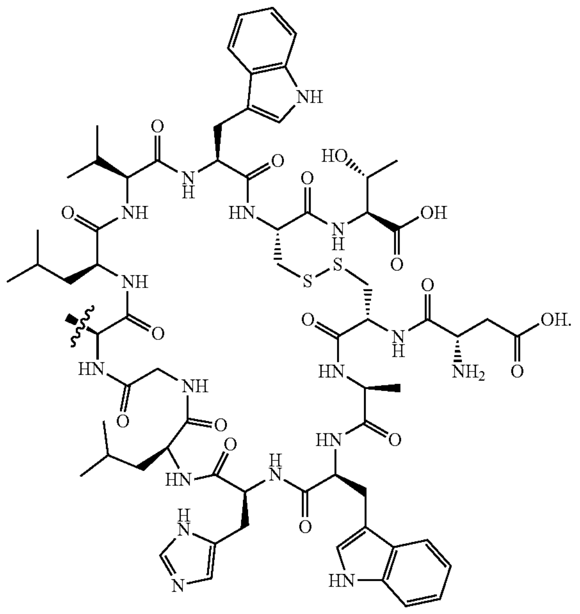
29. The compound of embodiment 15, wherein $R^{LG}$ is
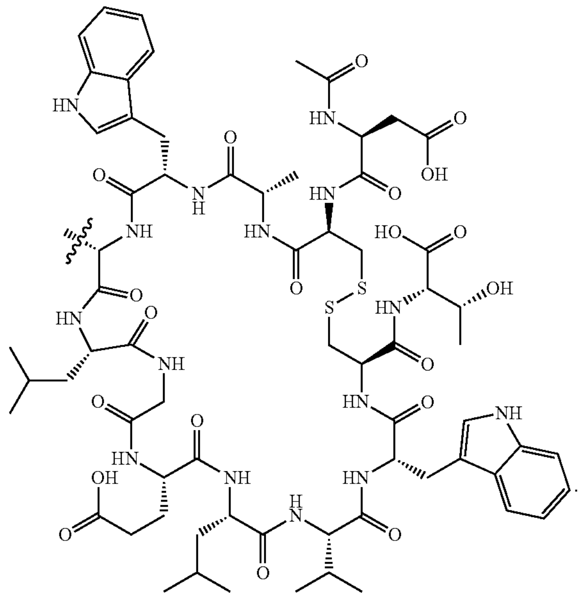
30. The compound of embodiment 15, wherein $R^{LG}$ is
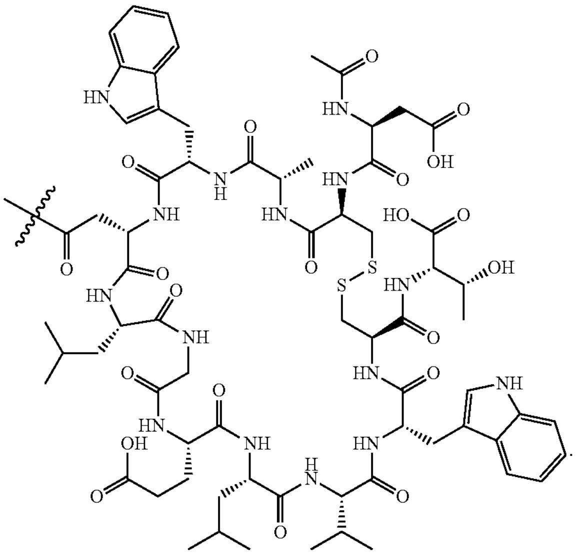 [SMILES: *C(=O)C[C@@H]1NC(=O)[C@H](Cc2c[nH]c3ccccc23)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC1=O]

31. The compound of embodiment 15, wherein $R^{LG}$ is
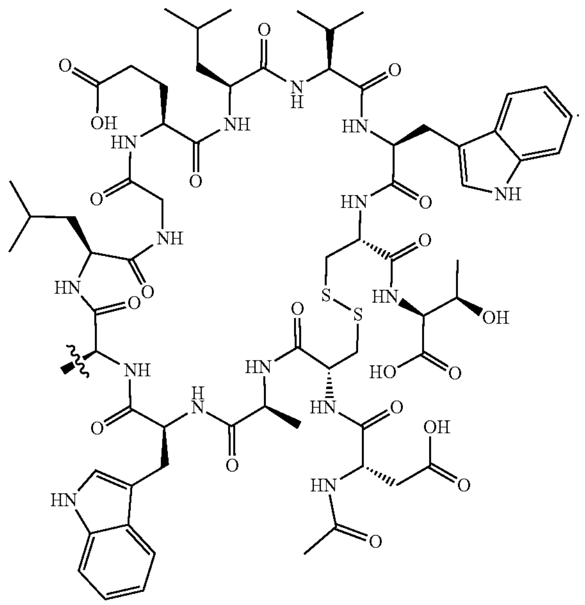
32. The compound of embodiment 15, wherein $R^{LG}$ is
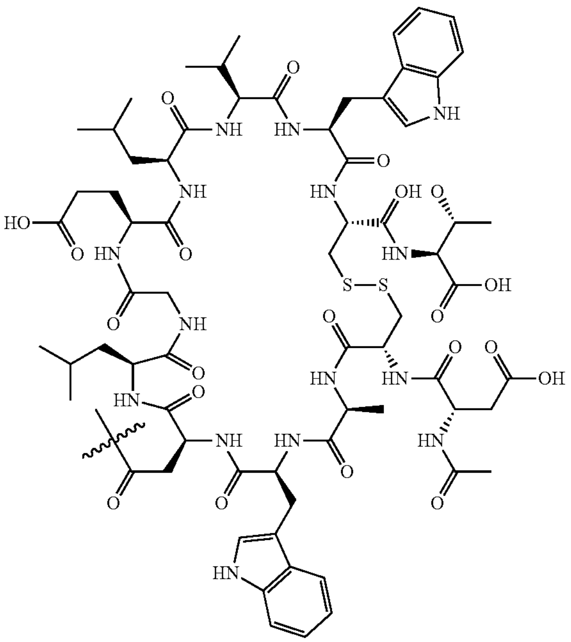 [SMILES: *C(=O)C[C@@H]1NC(=O)[C@H](Cc2c[nH]c3ccccc23)NC(=O)[C@H](C)NC(=O)[C@@H](NC(=O)[C@H](CC(=O)O)NC(C)=O)CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC1=O]
33. The compound of embodiment 15, wherein $R^{LG}$ is
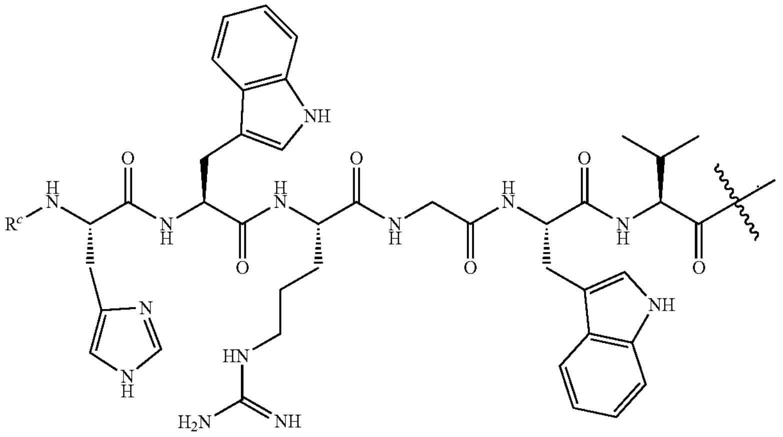
34. The compound of embodiment 15, wherein $R^{LG}$ is
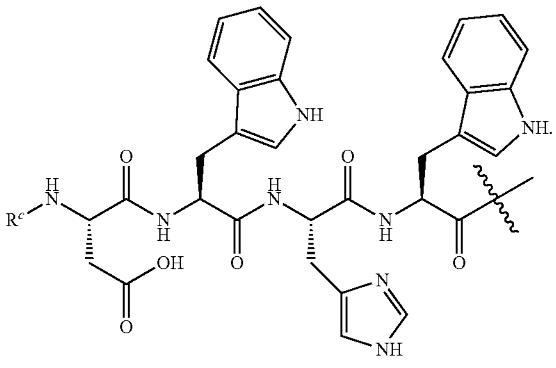

35. The compound of embodiment 15, wherein $R^{LG}$ is

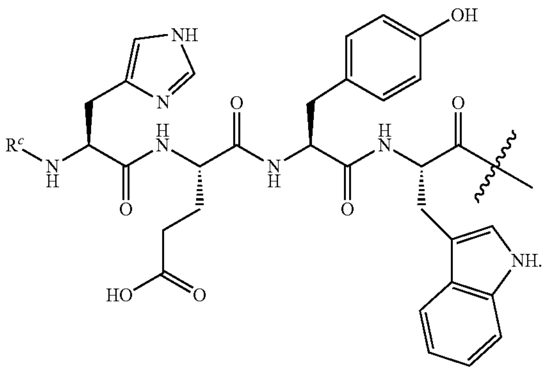

41. The compound of embodiment 40, wherein $R^{LG}$ is optionally substituted

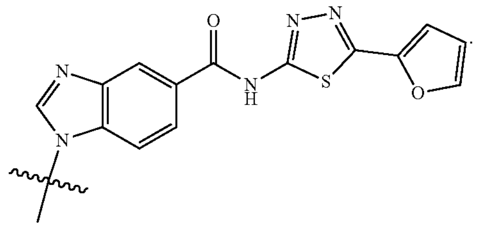

36. The compound of embodiment 15, wherein $R^{LG}$ is

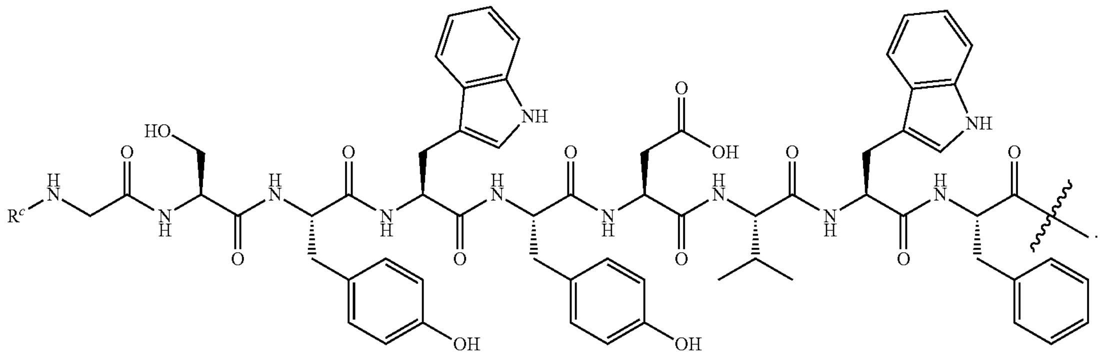

37. The compound of embodiment 15, wherein $R^{LG}$ is

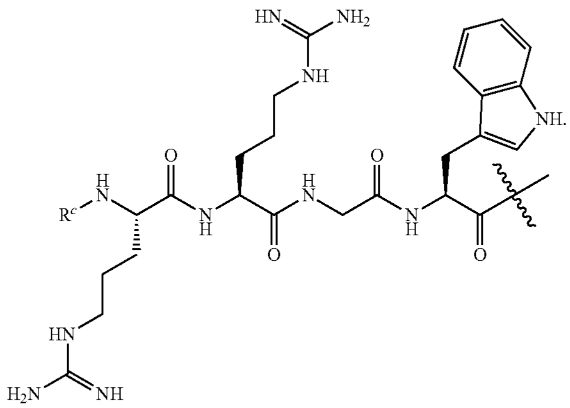

38. The compound of any one of embodiments 33-37, wherein $R^c$ is R—C(O)—, wherein R is optionally substituted $C_{1-6}$ aliphatic.

39. The compound of any one of embodiments 33-37, wherein $R^c$ is $CH_3C(O)$—.

40. The compound of any one of embodiments 1-14, wherein $R^{LG}$ is a small molecule moiety.

42. The compound of embodiment 40, wherein $R^{LG}$ is

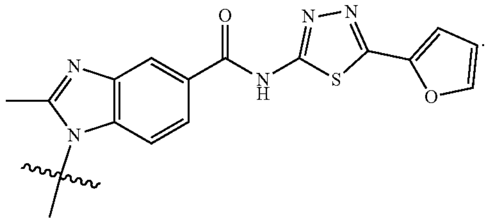 [SMILES: *n1c(C)nc2cc(C(=O)Nc3nnc(-c4ccco4)s3)ccc21]

43. The compound of embodiment 40, wherein $R^{LG}$ is optionally substituted

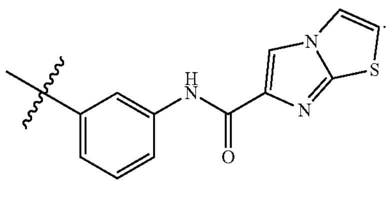 [SMILES: *c1cccc(NC(=O)c2cn3ccsc3n2)c1]

44. The compound of embodiment 40, wherein $R^{LG}$ is

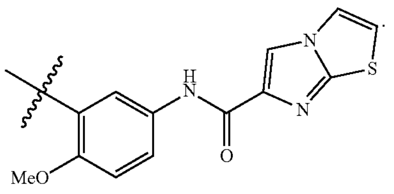 [SMILES: *c1cc(NC(=O)c2cn3ccsc3n2)ccc1OC]

45. The compound of embodiment 40, wherein $R^{LG}$ is

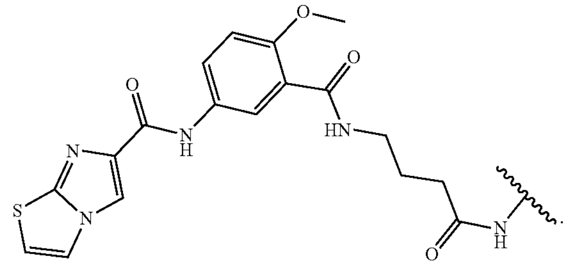 [SMILES: *NC(=O)CCCNC(=O)c1cc(NC(=O)c2cn3ccsc3n2)ccc1OC]

46. The compound of embodiment 40, wherein $R^{LG}$ is optionally substituted

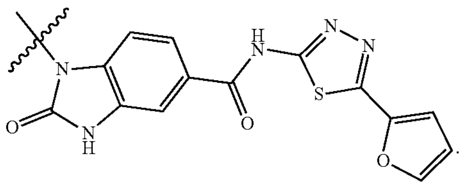 [SMILES: *n1c(=O)[nH]c2cc(C(=O)Nc3nnc(-c4ccco4)s3)ccc21]

47. The compound of embodiment 40, wherein $R^{LG}$ is

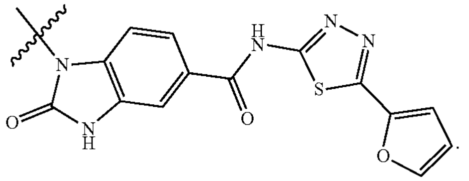 [SMILES: *n1c(=O)[nH]c2cc(C(=O)Nc3nnc(-c4ccco4)s3)ccc21]

48. The compound of embodiment 40, wherein $R^{LG}$ is optionally substituted

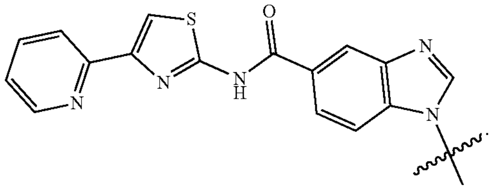

49. The compound of embodiment 40, wherein $R^{LG}$ is

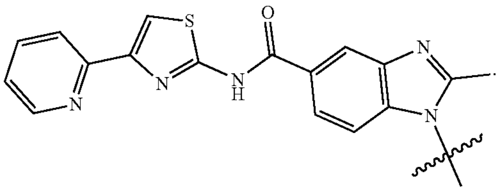

50. The compound of embodiment 40, wherein $R^{LG}$ is

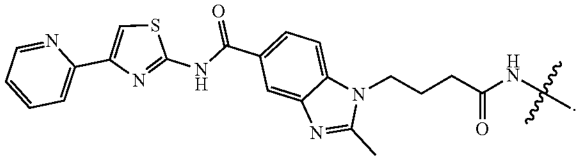

51. The compound of embodiment 40, wherein $R^{LG}$ is optionally substituted

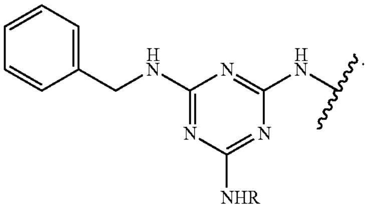

52. The compound of embodiment 40, wherein $R^{LG}$ is

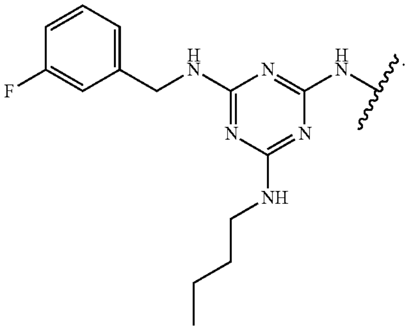 [SMILES: *Nc1nc(NCCCC)nc(NCc2cccc(F)c2)n1]

53. The compound of embodiment 40, wherein $R^{LG}$ is optionally substituted

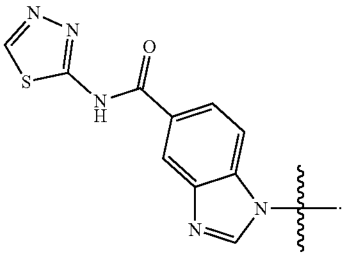

54. The compound of embodiment 40, wherein $R^{LG}$ is

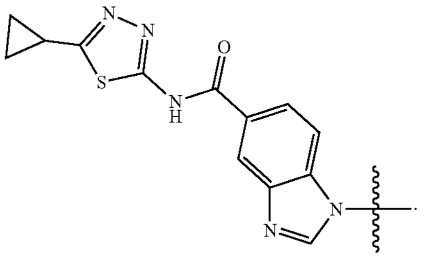

55. The compound of embodiment 40, wherein $R^{LG}$ is

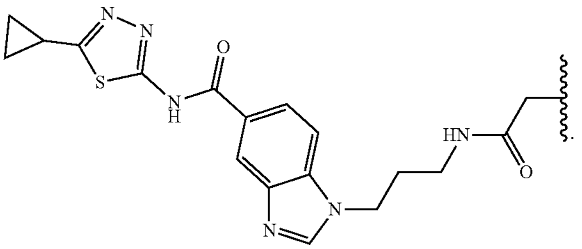 [SMILES: *CC(=O)NCCCn1cnc2cc(C(=O)Nc3nnc(C4CC4)s3)ccc21]

56. The compound of embodiment 40, wherein $R^{LG}$ is optionally substituted

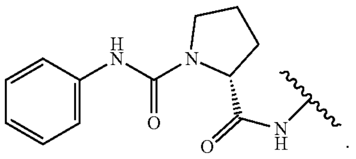 [SMILES: *NC(=O)[C@H]1CCCN1C(=O)Nc1ccccc1]

57. The compound of embodiment 40, wherein $R^{LG}$ is

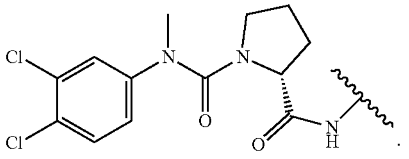 [SMILES: *NC(=O)[C@H]1CCCN1C(=O)N(C)c1ccc(Cl)c(Cl)c1]

58. The compound of any one of the preceding embodiments, wherein $L^{LG1}$ is a covalent bond.

59. The compound of any one of embodiments 1-14, wherein $L^{LG1}$ is or comprises —$(CH_2CH_2O)n$-.

60. The compound of any one of embodiments 1-14, wherein $L^{LG1}$ is or comprises —$(CH_2)n$-O—$(CH_2CH_2O)n$-$(CH_2)n$-, wherein each n is independently 1-10, and each —$CH_2$— is independently optionally substituted.

61. The compound of any one of the preceding embodiments, wherein $L^{LG2}$ is or comprises —NR'—.

62. The compound of any one of the preceding embodiments, wherein $L^{LG2}$ is or comprises —C(O)—.

63. The compound of any one of the preceding embodiments, wherein $L^{LG2}$ is or comprises —NR'C(O)—.

64. The compound of any one of the preceding embodiments, wherein $L^{LG2}$ is or comprises —$(CH_2)n$-OC(O)N(R')—, wherein —$(CH_2)n$- is optionally substituted.

65. The compound of any one of embodiments 1-60, wherein $L^{LG2}$ is a covalent bond.

66. The compound of any one of embodiments 1-60, wherein $L^{LG2}$ is —$CH_2N(CH_2CH_2CH_2S(O)_2OH)$—C(O)—.

67. The compound of any one of embodiments 1-60, wherein $L^{LG2}$ is —C(O)—$NHCH_2$—.

68. The compound of any one of embodiments 1-60, wherein $L^{LG2}$ is —C(O)O—$CH_2$—.

69. The compound of any one of embodiments 1-60, wherein $L^{LG2}$ is —NH—C(O)O—$CH_2$—.

70. The compound of any one of embodiments 62-63 and 66-69, wherein —C(O)— is bonded to $L^{LG3}$.

71. The compound of any one of the preceding embodiments, wherein $L^{LG3}$ is or comprises an optionally substituted aryl ring.

72. The compound of any one of the preceding embodiments, wherein $L^{LG3}$ is or comprises an optionally substituted phenyl ring.

73. The compound of any one of embodiments 71-72, wherein the ring is substituted, and one or more substituents are independently an electron-withdrawing group.

74. The compound of embodiment 73, wherein a substituent is —F.

75. The compound of embodiment 73, wherein a substituent is —$NO_2$.

76. The compound of any one of embodiments 1-75, wherein $L^{LG3}$ is

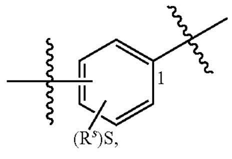

wherein s is 0-4, each $R^s$ is independently halogen, —$NO_2$, -L-R', —C(O)-L-R', —S(O)-L-R', —$S(O)_2$-L-R', or —P(O)(-L-R')$_2$.

77. The compound of any one of embodiments 1-75, wherein $L^{LG3}$ is

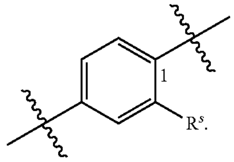

78. The compound of any one of embodiments 1-75, wherein $L^{LG3}$ is

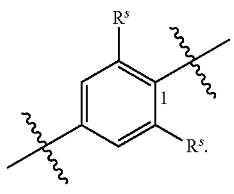

79. The compound of any one of embodiments 1-71, wherein $L^{LG3}$ is

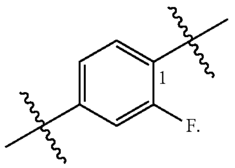 [SMILES: *c1ccc(*)c(F)c1]

80. The compound of any one of embodiments 1-71, wherein $L^{LG3}$ is

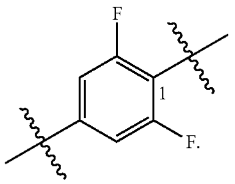 [SMILES: *c1cc(F)c(*)c(F)c1]

81. The compound of any one of embodiments 76-80, wherein C1 is bonded to $L^{LG4}$.

82. The compound of any one of embodiments 1-70, wherein $L^{LG3}$ is a covalent bond.

83. The compound of any one of the preceding embodiments, wherein $L^{LG4}$ is or comprises —O—.

84. The compound of any one of the preceding embodiments, wherein $L^{LG4}$ is or comprises —NR'—.

85. The compound of any one of embodiments 1-83, wherein $L^{LG4}$ is —O—.

86. The compound of any one of embodiments 1-83, wherein $L^{LG4}$ is —NH—.

87. The compound of any one of embodiments 1-83, wherein $L^{LG4}$ is a covalent bond.

88. The compound of any one of the preceding embodiments, wherein $L^{RG1}$ is a covalent bond.

89. The compound of any one of embodiments 1-88, wherein $L^{RG1}$ is or comprises $—S(O)_2—$.

90. The compound of any one of the preceding embodiments, wherein $L^{RG2}$ is or comprises —C(O)—.

91. The compound of any one of the preceding embodiments, wherein $L^{RG2}$ is or comprises $-L^{RG3}-C({=}CR^{RG1}R^{RG2})—CR^{RG3}R^{RG4}—$, wherein each of $R^{RG1}$, $R^{RG2}$, $R^{RG3}$ and $R^{RG4}$ is independently -L-R', and $L^{RG3}$ is —C(O)—, —C(O)O—, —C(O)N(R')—, —S(O)—, $—S(O)_2—$, —P(O)(OR')—, —P(O)(SR')—, or $—P(O)(N(R')_2)—$.

92. The compound of any one of the preceding embodiments, wherein $L^{RG2}$ is or comprises optionally substituted $-L^{RG3}-C({=}CHR^{RG2})—CHR^{RG4}—$.

93. The compound of embodiment 91 or 92, wherein $R^{RG2}$ and $R^{RG4}$ are taken together with their intervening atoms to form an optionally substituted 3-10 membered monocyclic or bicyclic ring having 0-5 heteroatoms.

94. The compound of embodiment 91 or 92, wherein $—C({=}CHR^{RG2})—CHR^{RG4}$ or $—C({=}CR^{RG1}R^{RG2})—CR^{RG3}R^{RG4}$ is optionally substituted

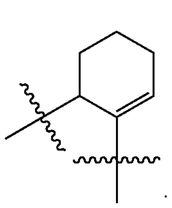

95. The compound of any one of embodiments 1-89, wherein $L^{RG2}$ is —C(O)—.

96. The compound of any one of embodiments 1-89, wherein $L^{RG2}$ is

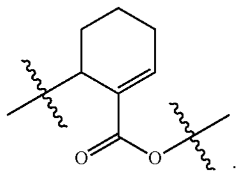 [SMILES: *OC(=O)C1=CCCCC1*]

97. The compound of any one of embodiments 1-89, wherein $-L^{LG1}-L^{RG2}-$ is —C(O)—.

98. The compound of any one of embodiments 1-89, wherein $-L^{LG1}-L^{RG2}-$ is

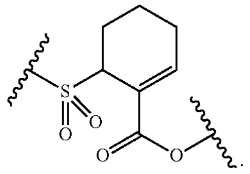 [SMILES: *OC(=O)C1=CCCCC1S(*)(=O)=O]

99. The compound of any one of the preceding embodiments, wherein $L^{PM}$ is or comprises $—(CH_2CH_2O)n-$.

100. The compound of any one of the preceding embodiments, wherein $L^{PM}$ is or comprises $—(CH_2)n-O—(CH_2CH_2O)n-(CH_2)n-$, wherein each n is independently 1-10, and each $—CH_2—$ is independently optionally substituted.

101. The compound of any one of the preceding embodiments, wherein a moiety of interest is or comprises a detectable moiety.

102. The compound of any one of the preceding embodiments, wherein a moiety of interest is or comprises a fluorophore.

103. The compound of any one of the preceding embodiments, wherein a moiety of interest is or comprises

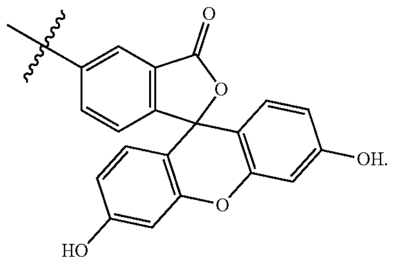 [SMILES: *c1ccc2c(c1)C(=O)OC21c2ccc(O)cc2Oc2cc(O)ccc21]

104. The compound of any one of the preceding embodiments, wherein a moiety of interest is or comprises a therapeutic agent.

105. The compound of any one of the preceding embodiments, wherein a moiety of interest is or comprises a cytotoxic agent.

106. The compound of any one of the preceding embodiments, wherein a moiety of interest is or comprises a moiety that can bind to a protein, nucleic acid or a cell.

107. The compound of any one of the preceding embodiments, wherein a moiety of interest is or comprises a moiety that can bind to immune cells.

108. The compound of any one of the preceding embodiments, wherein a moiety of interest is or comprises a small molecule moiety.

109. The compound of any one of the preceding embodiments, wherein a moiety of interest is or comprises a peptide moiety.

110. The compound of any one of the preceding embodiments, wherein a moiety of interest is or comprises a reactive moiety.

111. The compound of any one of the preceding embodiments, wherein a moiety of interest is or comprises a reactive moiety suitable for a bioorthogonal reaction.

112. The compound of any one of embodiments 110-111, wherein a reactive moiety is or comprises $-N_3$.

113. The compound of any one of embodiments 110-111, wherein a reactive moiety is or comprises an alkyne moiety.

114. The compound of any one of embodiments 110-111, wherein a reactive moiety is or comprises optionally substituted

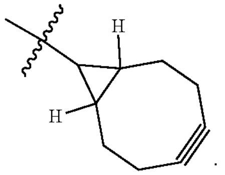 [SMILES: *C1C2CCC#CCCC12]

115. The compound of any one of embodiments 110-111, wherein a reactive moiety is or comprises optionally substituted

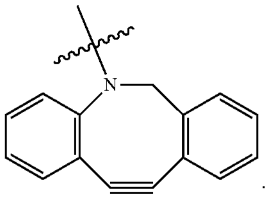 [SMILES: *N1Cc2ccccc2C#Cc2ccccc21]

116. The compound of any one of the preceding embodiments, wherein the compound comprises no cleavable groups whose cleavage can release LG except one or more optionally in RG.

117. The compound of any one of the preceding embodiments, wherein the compound comprises no —S—S—, acetal or imine groups except in RG or MOI.

118. The compound of any one of the preceding embodiments, wherein the compound comprises no —S—S—, acetal or imine groups except that the compound may have —S—S— formed by two amino acid residues.

119. The compound of any one of the preceding embodiments, wherein the compound comprises no —S—S—, acetal or imine groups except that the compound may have —S—S— formed by cysteine residues.

120. The compound of any one of the preceding embodiments, wherein the compound comprises no —S—S—, acetal or imine groups.

121. The compound of any one of the preceding embodiments, wherein the compound comprises one or more groups selected from:

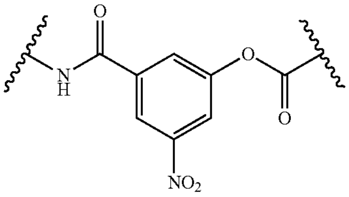

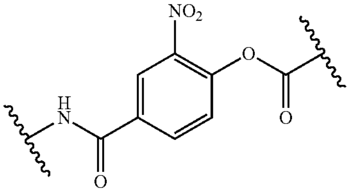

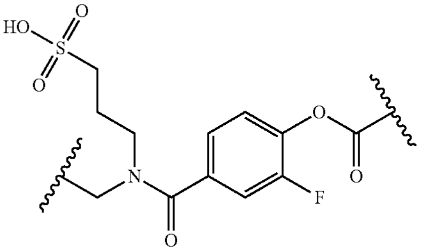

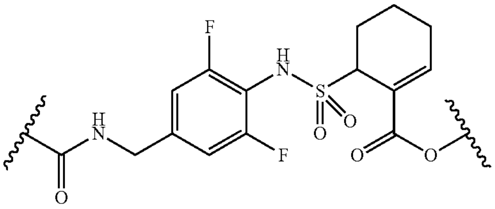

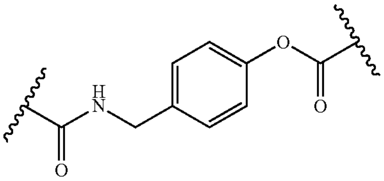

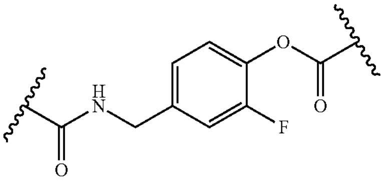

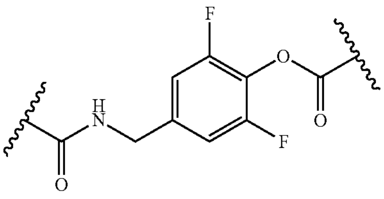

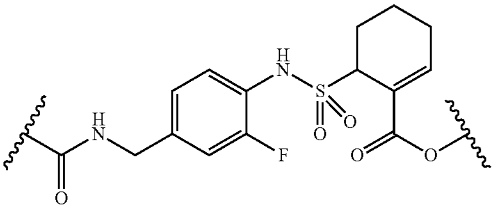

-continued
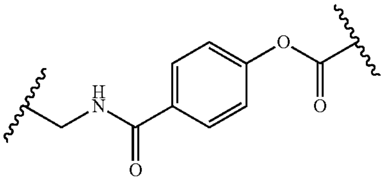
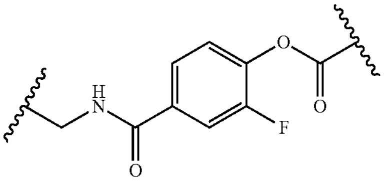
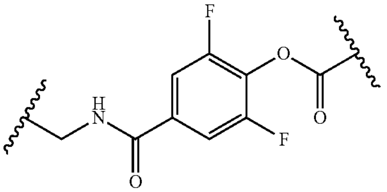
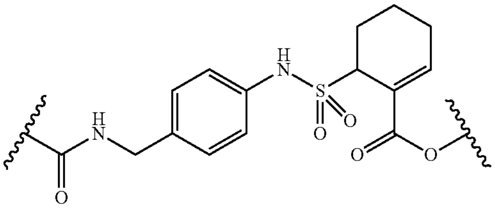
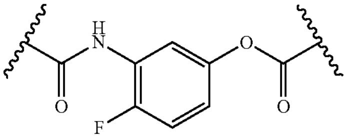
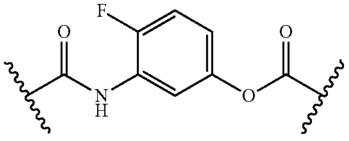
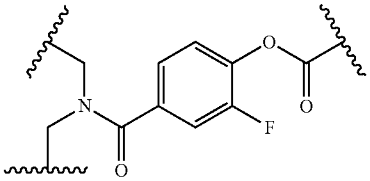
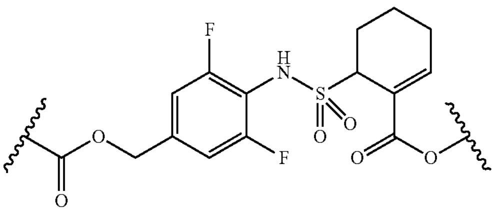
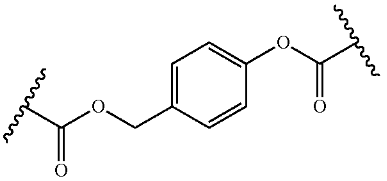
-continued
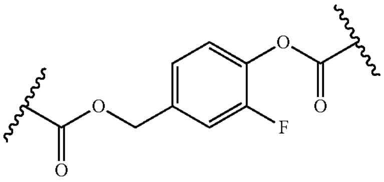
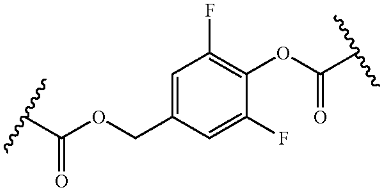
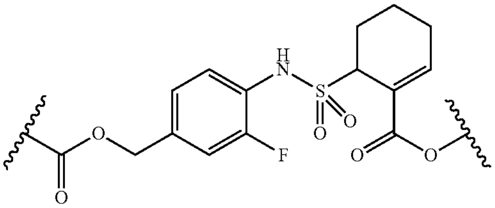
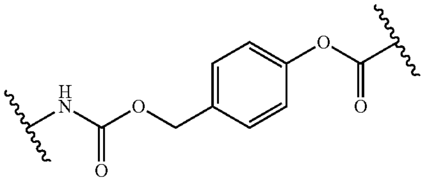
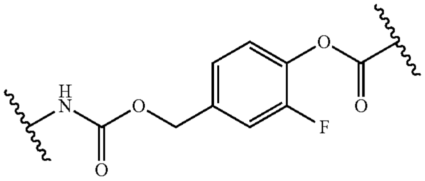
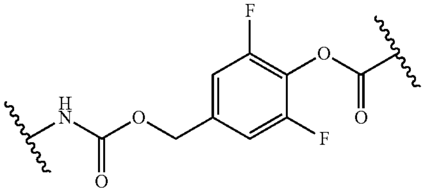
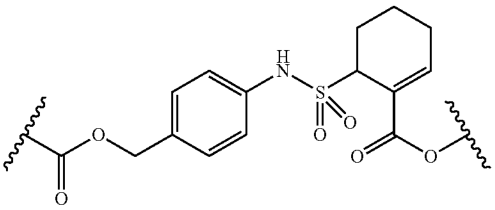
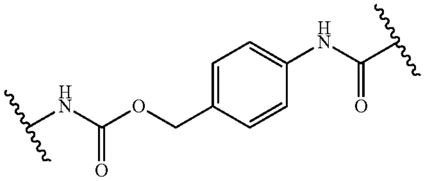
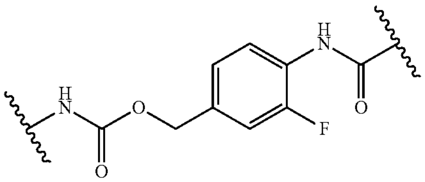

-continued
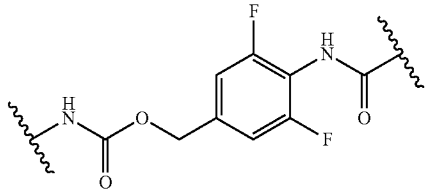.
122. The compound of any one of the preceding embodiments, wherein $-L^{LG2}-L^{LG3}-L^{LG4}-RG-$ is a structure selected from:
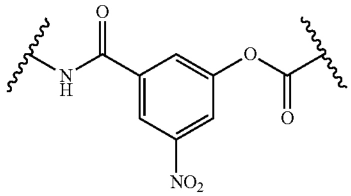
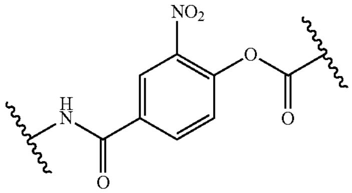
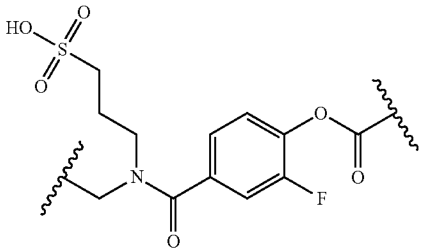
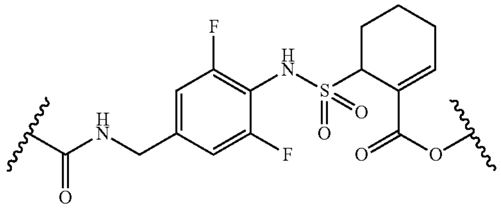
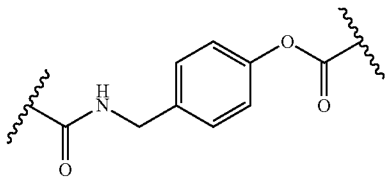
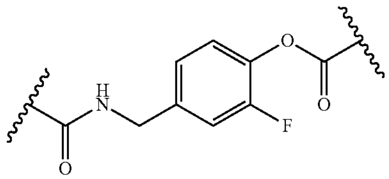
-continued
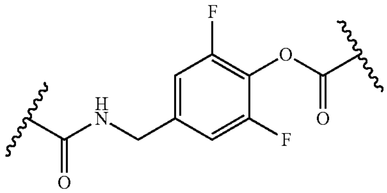
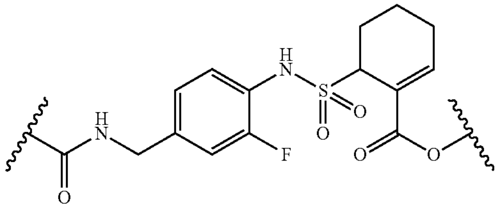
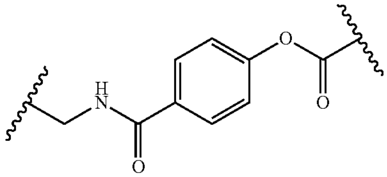
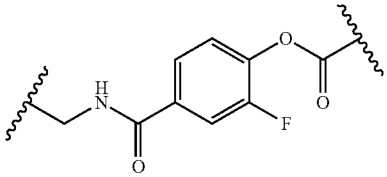
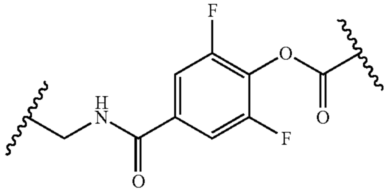
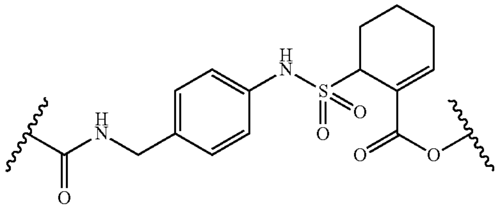
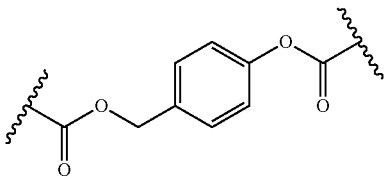
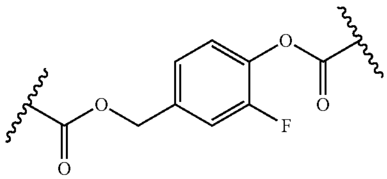
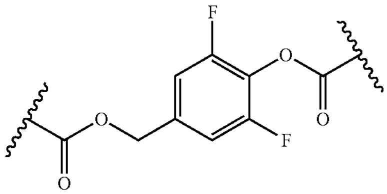

-continued

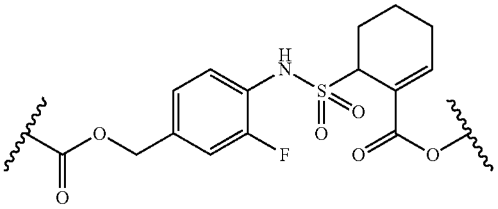

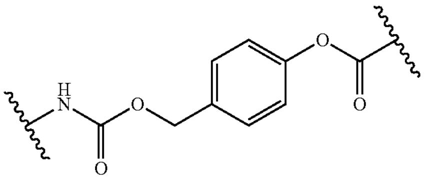

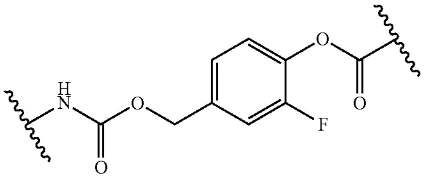

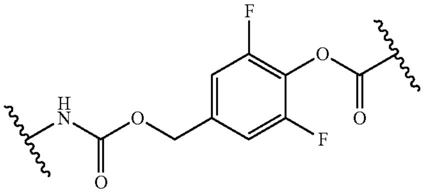

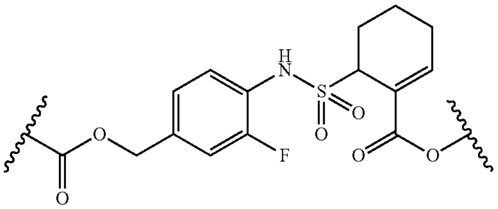

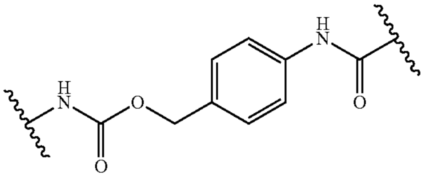

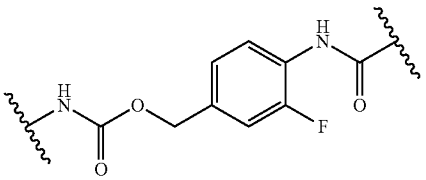

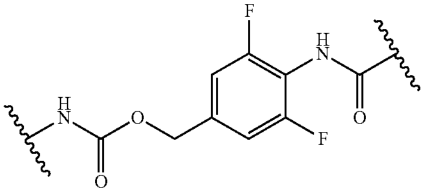

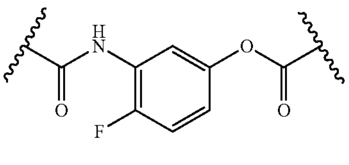

-continued

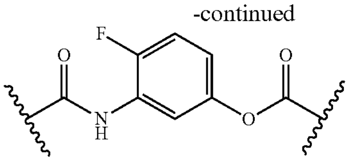

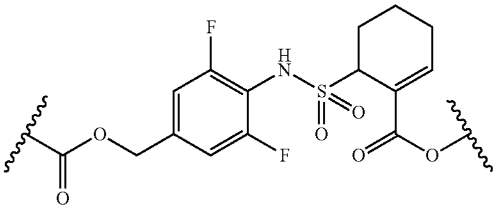

.

123. A compound selected from Table 1a or a salt thereof.

124. A compound, wherein the compound is 1-10 or a salt thereof.

125. A compound, wherein the compound is 1-12 or a salt thereof.

126. A compound, wherein the compound is 1-17 or a salt thereof.

127. A compound, wherein the compound is 1-24 or a salt thereof.

128. A compound, wherein the compound is 1-25 or a salt thereof.

129. A compound, wherein the compound is 1-35 or a salt thereof.

130. A compound, wherein the compound is 1-36 or a salt thereof.

131. A compound, wherein the compound is 1-37 or a salt thereof.

132. A compound, wherein the compound is 1-38 or a salt thereof.

133. A compound, wherein the compound is 1-39 or a salt thereof.

134. A compound, wherein the compound is 1-40 or a salt thereof.

135. A compound, wherein the compound is 1-40 or a salt thereof.

136. A compound, wherein the compound is 1-44 or a salt thereof.

137. A compound, wherein the compound is 1-49 or a salt thereof.

138. A compound selected from Table 1b or a salt thereof.

139. A compound selected from Table 1c or a salt thereof.

140. A compound comprising:

a first group comprising a target binding moiety that binds to a target agent, a reactive group;

a moiety of interest; and optionally one or more linker moieties;

wherein a reaction group is located between a first group and a moiety of interest, and is connected to a first group and a moiety of interest independently and optionally through a linker moiety.

141. The compound of embodiment 140, wherein a reaction group is located between a first group and a moiety of interest, and is connected to a first group and a moiety of interest independently and optionally through a linker moiety.

142. The compound of any one of embodiments 140-141, wherein a first group is LG in any one of embodiments 1-139.

143. The compound of any one of embodiments 140-142, wherein a reactive group is RG in any one of embodiments 1-139.

144. The compound of any one of embodiments 140-143, wherein a moiety of interest is a moiety of interest in any one of embodiments 1-139.

145. The compound of any one of embodiments 140-144, wherein the compound is a compound of any one of embodiments 1-139.

146. The compound of any one of the preceding embodiments, wherein the compound comprises two or more target binding moieties.

147. A method, comprising steps of:

1) contacting a target agent with a reaction partner comprising:

a first group comprising a target binding moiety that binds to a target agent, a reactive group;

a moiety of interest; and optionally one or more linker moieties;

2) forming an agent comprising:

a target agent moiety;

a moiety of interest; and optionally one or more linker moieties.

148. The method of embodiment 147, wherein a reaction group is located between a first group and a moiety of interest, and is connected to a first group and a moiety of interest independently and optionally through a linker moiety.

149. A method of preparing an agent having the structure of P-I:

$$P\text{-}L^{PM}\text{-}MOI, \qquad (P\text{-}I)$$

or a salt thereof, wherein:

P is a target agent moiety;

$L^{PM}$ is a linker; and

MOI is a moiety of interest.

comprising steps of 1) contacting a target agent with a reaction partner having the structure of formula R-I:

$$LG\text{-}RG\text{-}L^{RM}\text{-}MOI, \qquad (R\text{-}I)$$

or a salt thereof, wherein:

LG is a group comprising a target binding moiety that binds to a target agent,

RG is a reactive group;

$L^{RM}$ is a linker; and

MOI is a moiety of interest; and 2) forming an agent having the structure of formula P-I.

150. A method of preparing an agent having the structure of P-IL:

$$P—N\text{-}L^{PM}\text{-}MOI, \qquad (P\text{-}II)$$

wherein:

P—N is a protein agent moiety comprising a lysine residue;

$L^{PM}$ is a linker; and

MOI is a moiety of interest;

the method comprising:

contacting P—N with a reaction partner having a structure of formula R-I:

$$LG\text{-}RG\text{-}L^{RM}\text{-}MOI, \qquad (R\text{-}I)$$

or a salt thereof, wherein:

LG is a group comprising a protein-binding moiety that binds to P—N,

RG is a reactive group;

$L^{RM}$ is a linker; and

MOI is a moiety of interest.

151. The method of any one of the proceeding embodiments, wherein a target agent is or comprises a protein agent.

152. The method of any one of the proceeding embodiments, wherein a target agent is or comprises an antibody agent.

153. The method of embodiment 152, wherein a moiety of interest is selectively attached to the antibody agent at K246 or K248 or a corresponding location.

154. The method of embodiment 152, wherein a moiety of interest is selectively attached to the antibody agent at K288 or K290 or a corresponding location.

155. The method of embodiment 152, wherein a moiety of interest is selectively attached to the antibody agent at K251 or K253 of an IgG2 heavy chain or a corresponding location.

156. The method of embodiment 152, wherein a moiety of interest is selectively attached to the antibody agent at K239 or K241 of an IgG4 heavy chain or a corresponding location.

157. The method of embodiment 152, wherein a moiety of interest is selectively attached to the antibody agent at K317 or a corresponding location.

158. The method of embodiment 152, wherein a moiety of interest is selectively attached to the antibody agent at heavy chain residue(s) over light chain residue(s).

159. The method of any one of the proceeding embodiments, wherein a target agent is or comprise an IgG antibody agent.

160. The method of any one of the proceeding embodiments, wherein a target agent is or comprises an Fc region.

161. The method of any one of the preceding embodiments, wherein a reaction partner is a compound of any one embodiments 1-146.

162. The method of any one of the preceding embodiments, wherein the contacting and forming steps are performed in one pot.

163. The method of any one of the preceding embodiments, wherein the contacting and forming steps are performed in one chemical reaction.

164. The method of any one of the preceding embodiments, wherein the method comprises no reactions which are directed primarily to cleavage of a functional group in an agent comprising a target agent moiety.

165. The method of any one of the preceding embodiments, wherein the method comprises no reactions which are directed primarily to cleavage of a functional group in $L^{RM}$ or $L^{PM}$.

166. The method of any one of the preceding embodiments, wherein the method comprises no reactions which are directed primarily to reduction of a functional group in an agent comprising target agent moiety.

167. The method of any one of the preceding embodiments, wherein the method comprises no reactions which are directed primarily to reduction of a functional group in $L^{RM}$ or $L^{PM}$.

168. The method of any one of the preceding embodiments, wherein the method comprises no reactions which are directed primarily to oxidation of a functional group in an agent comprising a target agent moiety.

169. The method of any one of the preceding embodiments, wherein the method comprises no reactions which are directed primarily to oxidation of a functional group in $L^{RM}$ or $L^{PM}$.

170. The method of any one of the preceding embodiments, wherein the method comprises no reactions which are directed primarily to hydrolysis of a functional group in an agent comprising a target agent moiety.

171. The method of any one of the preceding embodiments, wherein the method comprises no reactions which are directed primarily to hydrolysis of a functional group in $L^{RM}$ or $L^{PM}$.

172. The method of any one of the preceding embodiments, wherein the method comprises no reactions which are directed primarily to hydrolysis of an ester group in $L^{RM}$ or $L^{PM}$.

173. The method of any one of embodiments 164-172, wherein a target agent moiety is a protein agent moiety.

174. The method of any one of embodiments 164-172, wherein a target agent moiety is an antibody agent moiety.

175. The method of any one of the proceeding embodiments, wherein contacting is performed under conditions and for a time sufficient for a lysine residue of a target agent to react with a reactive group of a reaction partner.

176. The method of any one of the proceeding embodiments, wherein contacting is performed under conditions and for a time sufficient for a lysine residue of a target agent to react and form a bond with an atom of RG and release LG.

177. The method of any one of the preceding embodiments, wherein the agent and the reaction partner share the same moiety of interest.

178. The method of any one of the preceding embodiments, wherein moiety of interest is or comprises an antibody agent.

179. The method of any one of the preceding embodiments, wherein moiety of interest is or comprises a reactive moiety.

180. The method of any one of the preceding embodiments, wherein moiety of interest is or comprises an azide.

181. The method of any one of the preceding embodiments, wherein moiety of interest is or comprises an alkyne.

182. The method of any one of embodiments 147-181, wherein moiety of interest is or comprises an alkyne.

183. The method of embodiment 182, wherein moiety of interest is or comprises

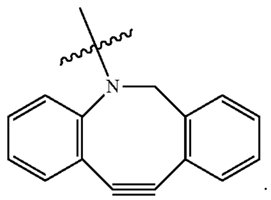 [SMILES: *N1Cc2ccccc2C#Cc2ccccc21]

184. The method of any one of the preceding embodiments, comprising reacting a first agent comprising a first reactive moiety in a first moiety of interest with a second agent comprising a second reactive moiety.

185. The method of any one of the preceding embodiments, wherein a second agent comprises a second reactive moiety and a peptide moiety.

186. The method of any one of the preceding embodiments, wherein a second agent comprises a second reactive moiety and a protein moiety.

187. The method of any one of the preceding embodiments, wherein a second agent comprises a second reactive moiety and an antibody agent moiety.

188. The method of any one of the preceding embodiments, comprising reacting a first agent comprising a first reactive moiety in a first moiety of interest with a second agent comprising a second reactive moiety in a second moiety of interest.

189. The method of any one of embodiments 184-188, wherein the first agent is a product of a method of any one of embodiments 147-183.

190. The method of any one of embodiments 184-188, wherein the second agent is a product of a method of any one of embodiments 147-183.

191. The method of any one of embodiments 184-188, wherein each of the first and the second agent is independently a product of a method of any one of embodiments 147-183.

192. A method, comprising reacting a first agent comprising a first reactive moiety in a first moiety of interest with a second agent comprising a second reactive moiety in a second moiety of interest, wherein the first agent is prepared by a method of any one of embodiments 147-183.

193. A method, comprising reacting a first agent comprising a first reactive moiety in a first moiety of interest with a second agent comprising a second reactive moiety in a second moiety of interest, wherein the second agents is prepared by a method of any one of embodiments 147-183.

194. A method, comprising reacting a first agent comprising a first reactive moiety in a first moiety of interest with a second agent comprising a second reactive moiety in a second moiety of interest, wherein each of the first and the second agents is independently prepared by a method of any one of embodiments 147-183.

195. The method of any one of embodiments 184-194, wherein each of the first and the second agents independently has the structure of formula P-I or P-II, or a salt thereof.

196. The method of any one of embodiments 184-195, wherein the target agent moiety of the first agent is an antibody agent moiety.

197. The method of any one of embodiments 184-196, wherein the target agent moiety of the second agent is an antibody agent moiety.

198. The method of any one of embodiments 196-197, wherein the first and the second target moieties are independently antibody agent moieties toward different antigens.

199. The method of any one of embodiments 196-197, wherein the first and the second target moieties are independently antibody agent moieties toward different proteins.

200. The method of any one of embodiments 184-199, wherein the first agent comprises an anti-CD20 agent moiety.

201. The method of any one of embodiments 184-199, wherein the first agent comprises rituximab.

202. The method of any one of embodiments 184-199, wherein the first agent comprises trastuzumab.

203. The method of any one of embodiments 184-202, wherein the second agent comprises an anti-CD3 agent moiety.

204. The method of any one of embodiments 184-202, wherein the second agent comprises scFv.

205. The method of any one of embodiments 184-202, wherein the second agent comprises a peptide whose sequence is SEQ ID NO: 1 or a fragment thereof.

206. The method of any one of embodiments 184-202, wherein the second agent comprises cetuximab.

207. The method of any one of embodiments 184-206, wherein one of the first reactive and the second moieties is or comprises (G)n, wherein n is 1-10, and the other is or comprises LPXTG, wherein X is an amino acid residue.

208. The method of any one of embodiments 184-206, wherein the first reactive moiety is or comprise (G)n, wherein n is 1-10, and the second reactive moiety is or comprises LPXTG, wherein X is an amino acid residue.

209. The method of any one of embodiments 184-206, wherein the second reactive moiety is or comprise (G)n, wherein n is 1-10, and the first reactive moiety is or comprises LPXTG, wherein X is an amino acid residue.

210. The method of any one of embodiments 207-209, wherein n is 2.

211. The method of any one of embodiments 207-209, wherein n is 3.

212. The method of any one of embodiments 207-209, wherein n is 4.

213. The method of any one of embodiments 207-209, wherein n is 5.

214. The method of any one of embodiments 207-213, wherein a reactive moiety that is or comprises LPXTG is or comprises LPXTG-(X)n, wherein each X is independently an amino acid residue, wherein n is 1-10.

215. The method of embodiment 214, wherein n in (X)n is 1.

216. The method of embodiment 214, wherein n in (X)n is 2.

217. The method of embodiment 214, wherein n in (X)n is 3.

218. The method of embodiment 214, wherein n in (X)n is 4.

219. The method of embodiment 214, wherein n in (X)n is 5.

220. The method of any one of embodiments 207-219, wherein LPXTG is LPETG.

221. The method of any one of embodiments 184-206, wherein one of the first reactive and the second moieties is or comprises —$N_3$, and the other is or comprises an alkyne.

222. The method of any one of embodiments 184-206, wherein one of the first reactive and the second moieties is or comprises —$N_3$, and the other is or comprises

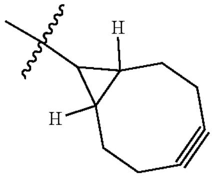

or

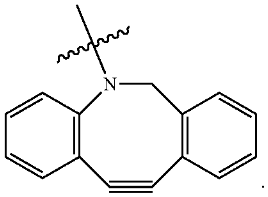

.

223. The method of any one of embodiments 184-222, wherein a product formed by a reaction of a first and a second agents is an agent of formula P-I or P-II, or a salt thereof, wherein the target agent moiety is or is derived from the target agent moiety of the first or the second agents, while the moiety of interest is derived from the target agent moiety of the other of the first or the second agents.

224. A product prepared by a method of any one of embodiments 147-223.

225. The product of embodiment 224, wherein the product is or comprise an agent of formula P-I or P-II, or a salt thereof.

226. The product of embodiment 224, wherein the product is a composition comprising an agent of formula P-I or P-II, or a salt thereof.

227. The product of any one of embodiments 225-226, wherein the agent does not contain —S-Cy-, wherein -Cy- is optionally substituted 5-membered monocyclic ring, does not contain —S—S— which is not formed by cysteine residues and does not contain —SH or salt form thereof that is not of a cysteine residue.

228. The product of any one of embodiments 224-226, wherein the product is a pharmaceutical composition.

229. A composition provides a plurality of agents each of which independently comprising:

a target agent moiety, a moiety of interest, and optionally a linker moiety linking a target agent moiety and a moiety of interest; wherein agents of the plurality share the same or substantially the same target agent moiety, and a common modification independently at at least one common location; and wherein about 1%-100% of all agents that comprise a target agent moiety and a moiety of interest are agents of the plurality.

230. A composition provides a plurality of agents each of which independently comprising:

a protein agent moiety, a moiety of interest, and optionally a linker moiety linking a protein agent moiety and a moiety of interest; wherein protein agent moieties of agents of the plurality comprise a common amino acid sequence, and agents of the plurality share a common modification independently at at least one common amino acid residue of protein agent moieties; and wherein about 1%-100% of all agents that comprise a protein agent moiety that comprise the common amino acid sequence and a moiety of interest are agents of the plurality.

231. A composition provides a plurality of agents each of which independently comprising:

an antibody agent moiety, a moiety of interest, and optionally a linker moiety linking an antibody agent moiety and a moiety of interest; wherein antibody agent moieties of agents of the plurality comprise a common amino acid sequence or can bind to a common antigen, and agents of the plurality share a common modification independently at at least one common amino acid residue of protein agent moieties; and wherein about 1%-100% of all agents that comprise an antibody agent moiety that comprise the common amino acid sequence or can bind to the common antigen and a moiety of interest are agents of the plurality.

232. The composition of embodiment 231, wherein antibody agent moieties of agents of the plurality can bind to a common antigen.

233. The composition of embodiment 231, wherein antibody agent moieties of agents of the plurality can bind to two or more different antigens.

234. The composition of any one of embodiments 231-233, wherein antibody agent moieties of agents of the plurality comprise a common amino acid sequence.

235. The composition of any one of embodiments 231-233, wherein antibody agent moieties of agents of the plurality comprise a common amino acid sequence in a Fc region.

236. The composition of any one of embodiments 231-233, wherein antibody agent moieties of agents of the plurality comprise a common Fc region.

237. The composition of any one of the preceding embodiments, wherein a target, protein or antibody agent moiety is or comprises an anti-CD20 agent moiety.

238. The composition of any one of the preceding embodiments, wherein a target, protein or antibody agent moiety is or comprises an anti-CD20 agent moiety.

239. The composition of any one of the preceding embodiments, wherein a target, protein or antibody agent moiety is or comprises rituximab.

240. The composition of any one of embodiments 229-234, wherein a target, protein or antibody agent moiety is or comprises trastuzumab.

241. The composition of any one of embodiments 233-236, wherein antibody agent moieties of agents of the plurality are IVIG moieties.

242. The composition of any one of the preceding embodiments, wherein agents of the plurality comprises a common moiety of interest.

243. The composition of any one of embodiments 229-242, wherein each agent of the plurality is independently an agent of formula P-I or P-II, or a salt thereof.

244. The composition of any one of embodiments 229-243, wherein a moiety of interest is or comprises a detectable moiety.

245. The composition of any one of embodiments 229-243, wherein a moiety of interest is or comprises a reactive moiety.

246. The composition of any one of embodiments 229-243, wherein a moiety of interest is or comprises a reactive moiety which does not react with a target agent moiety, a protein agent moiety or an antibody moiety agent.

247. The composition of any one of embodiments 229-243, wherein a moiety of interest is or comprises a reactive moiety which does not react with an antibody moiety agent.

248. The composition of embodiment 245, wherein the reactive moiety is $—N_3$.

249. The composition of embodiment 245, wherein the reactive moiety is -≡-.

250. The composition of embodiment 245, wherein the reactive moiety is

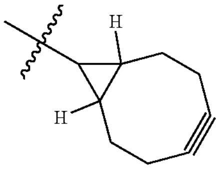

or

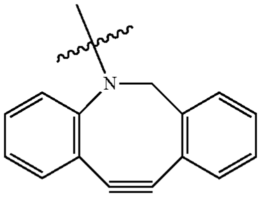

.

251. The composition of any one of embodiments 229-243, wherein a moiety of interest is or comprises a therapeutic agent moiety.

252. The composition of any one of embodiments 229-243, wherein a moiety of interest is or comprises a drug moiety.

253. The composition of any one of embodiments 229-243, wherein a moiety of interest is or comprises a cytotoxic moiety.

254. The composition of any one of embodiments 229-243, wherein a moiety of interest is or comprises a peptide moiety.

255. The composition of any one of embodiments 229-243, wherein a moiety of interest is or comprises a protein moiety.

256. The composition of any one of embodiments 229-243, wherein a moiety of interest is or comprises an antibody agent.

257. The composition of any one of embodiments 229-243, wherein a moiety of interest is or comprises a scFv agent.

258. The composition of any one of embodiments 229-243, wherein a moiety of interest is or comprises an anti-CD3 agent.

259. The composition of any one of embodiments 229-243, wherein a moiety of interest is or comprises a peptide whose sequence is SEQ ID NO: 1 or a fragment thereof.

260. The composition of any one of embodiments 229-243, wherein a moiety of interest is or comprises cetuximab.

261. The composition of any one of embodiments 229-260, wherein the linker is not a natural amino acid peptide linker.

262. The composition of any one of embodiments 229-261, wherein the linker is or comprises LPXT(G)n, wherein n is 1-10.

263. The composition of any one of embodiments 229-261, wherein the linker is or comprises LPET(G)n, wherein n is I-10.

264. The composition of embodiment 262 or 263, wherein n is 1.

265. The composition of embodiment 262 or 263, wherein n is 2.

266. 270 The composition of embodiment 262 or 263, wherein n is 3.

267. The composition of embodiment 262 or 263, wherein n is 4.

268. The composition of embodiment 262 or 263, wherein n is 5.

269. The composition of any one of embodiments 229-268, wherein a linker comprise one or more $—CH_2—CH_2—O—$.

270. The composition of any one of embodiments 229-269, wherein a linker comprise a triazole ring.

271. The composition of any one of embodiments 230-270, wherein the common amino acid sequence comprises about 1-500 or more amino acid residues.

272. The composition of any one of embodiments 230-270, wherein the common amino acid sequence comprises 10 or more amino acid residues.

273. The composition of any one of embodiments 230-270, wherein the common amino acid sequence comprises 20 or more amino acid residues.

274. The composition of any one of embodiments 230-270, wherein the common amino acid sequence comprises 50 or more amino acid residues.

275. The composition of any one of embodiments 230-274, wherein the common amino acid sequence comprises one or more amino acid residues selected from K246 and K248 of an IgG1 heavy chain and amino acid residues corresponding thereto, K251 and K253 of an IgG2 heavy chain and amino acid residues corresponding thereto, and K239 and K241 of an IgG4 heavy chain and amino acid residues corresponding thereto.

276. The composition of any one of embodiments 230-275, wherein the common amino acid sequence is at least 10%-100% of that of the protein or antibody agent moiety.

277. The composition of any one of embodiments 230-275, wherein the common amino acid sequence is at least 50%-100% of that of the protein or antibody agent moiety.

278. The composition of any one of embodiments 230-275, wherein the protein agent moieties or the antibody agent moieties of agents of the plurality are of at least 50% amino acid sequence homology.

279. The composition of any one of embodiments 230-275, wherein the protein agent moieties or the antibody agent moieties of agents of the plurality are of at least 80% amino acid sequence homology.

280. The composition of any one of embodiments 230-275, wherein the protein agent moieties or the antibody agent moieties of agents of the plurality are of at least 90% amino acid sequence homology.

281. The composition of any one of the preceding embodiments, wherein a common modification is or comprises a moiety of interest and optionally a linker.

282. The composition of any one of the preceding embodiments, wherein all common modifications comprises a common moiety of interest and optionally a common linker.

283. The composition of any one of embodiments 230-282, wherein a common amino acid residue is K246 of an antibody heavy chain or an amino acid residue corresponding thereto.

284. The composition of any one of embodiments 230-283, wherein a common amino acid residue is K248 of an antibody heavy chain or an amino acid residue corresponding thereto.

285. The composition of any one of embodiments 230-284, wherein a common amino acid residue is K288 of an antibody heavy chain or an amino acid residue corresponding thereto.

286. The composition of any one of embodiments 230-285, wherein a common amino acid residue is K290 of an antibody heavy chain or an amino acid residue corresponding thereto.

287. The composition of any one of embodiments 230-286, wherein a common amino acid residue is K317 of an antibody heavy chain or an amino acid residue corresponding thereto.

288. The composition of any one of embodiments 230-287, wherein a common amino acid residue is K133 of an antibody heavy chain or an amino acid residue corresponding thereto.

289. The composition of any one of embodiments 230-288, wherein a common amino acid residue is K144 of an antibody heavy chain or an amino acid residue corresponding thereto.

290. The composition of any one of embodiments 230-289, wherein a common amino acid residue is K133 of an antibody heavy chain or an amino acid residue corresponding thereto.

291. The composition of any one of embodiments 230-290, wherein a common amino acid residue is K185 of an antibody light chain or an amino acid residue corresponding thereto.

292. The composition of any one of embodiments 230-291, wherein a common amino acid residue is K187 of an antibody light chain or an amino acid residue corresponding thereto.

293. The composition of any one of embodiments 230-292, wherein a common amino acid residue is K251 of an IgG2 antibody heavy chain or an amino acid residue corresponding thereto.

294. The composition of any one of embodiments 230-293, wherein a common amino acid residue is K253 of an IgG2 antibody heavy chain or an amino acid residue corresponding thereto.

295. The composition of any one of embodiments 230-294, wherein a common amino acid residue is K239 of an IgG4 antibody heavy chain or an amino acid residue corresponding thereto.

296. The composition of any one of embodiments 230-295, wherein a common amino acid residue is K241 of an IgG4 antibody heavy chain or an amino acid residue corresponding thereto.

297. The composition of any one of the preceding embodiments, wherein at least about 2% of all agents that comprise a target agent moiety and a moiety of interest are agents of the plurality, or at least about 2% of all agents that comprise a protein agent moiety that comprise the common amino acid sequence and a moiety of interest are agents of the plurality, or at least about 2% of all agents that comprise an antibody agent moiety that comprise the common amino acid sequence or can bind to the common antigen and a moiety of interest are agents of the plurality.

298. The composition of any one of the preceding embodiments, wherein about 1%-100% of all agents that comprise a target agent moiety are agents of the plurality, or at least about 1%-100% of all agents that comprise a protein agent moiety that comprise the common amino acid sequence are agents of the plurality, or about 1%-100% of all agents that comprise an antibody agent moiety that comprise the common amino acid sequence or can bind to the common antigen are agents of the plurality.

299. The composition of any one of embodiments 297-298, wherein the percentage is at least about 5%.

300. The composition of any one of embodiments 297-298, wherein the percentage is at least about 10%.

301. The composition of any one of embodiments 297-298, wherein the percentage is at least about 20%.

302. The composition of any one of embodiments 297-298, wherein the percentage is at least about 25%.

303. The composition of any one of embodiments 297-298, wherein the percentage is at least about 50%.

304. The composition of any one of embodiments 297-298, wherein the percentage is at least about 60%, 65%, 70%, 75%, 80%, 85%, 90% or 95%.

305. The composition of any one of the preceding embodiments, wherein each agent of the plurality does not contain —S-Cy-, wherein -Cy- is optionally substituted 5-membered monocyclic ring, does not contain —S—S— which is not formed by cysteine residues and does not contain —SH or salt form thereof that is not of a cysteine residue.

306. The composition of any one of the preceding embodiments, wherein each agent of the plurality does not contain $—S—CH_2—CH_2—$.

307. The composition of any one the preceding embodiments, wherein each agent of the plurality does not contain a moiety that can specifically bind to an antibody agent.

308. The composition of any one the preceding embodiments, wherein each agent of the plurality independently comprises an antibody agent moiety, and each agent can independently bind to an Fc receptor.

309. The composition of any one of the preceding embodiments, wherein the composition is a product of a method of any one of the preceding embodiments.

310. The composition of any one of the preceding embodiments, wherein the composition is a pharmaceutical composition.

311. An agent, wherein the agent is an agent of the plurality of any one of embodiments 229-309.

312. A pharmaceutical composition, comprising an agent of embodiment 311 and a pharmaceutically acceptable carrier.

313. The composition of embodiment 310 or 312, wherein the composition is in a solid form.

314. The composition of embodiment 310 or 312, wherein the composition is in a liquid form, and contains no more than 5%, 10%, 15%, 20%, 25%, 30%, 35%, 40%, 45% or 50% (v/v) organic solvents.

315. The method, product, composition or agent of any one of the preceding embodiments, wherein the ratio of moieties of interest conjugated to target agent moieties and target agent moieties, or the ratio of moieties of interest conjugated to protein agent moieties and protein agent moieties, or the ratio of moieties of interest conjugated to antibody agent moieties and antibody agent moieties, is about 0.5-6.

316. The method, product, composition or agent of any embodiment 315, wherein the ratio is about 0.5-2.5.

317. The method, product, composition or agent of any embodiment 315, wherein the ratio is about 0.5, 0.6, 0.7, 0.8, 0.9, 1.0, 1.1, 1.2, 1.3, 1.4, 1.5, 1.6, 1.7, 1.8, 1.9, 2.0, 2.5 or 3.

318. The compound, method, product, composition or agent of any one of the preceding embodiments, wherein each heteroatom is independently selected from oxygen, nitrogen, sulfur, phosphorus and silicon.

319. A compound, wherein the compound is

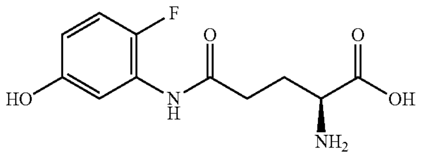 [SMILES: N[C@@H](CCC(=O)Nc1cc(O)ccc1F)C(=O)O]

or a salt thereof.

320. A compound, wherein the compound is

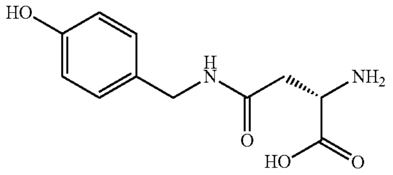 [SMILES: N[C@@H](CC(=O)NCc1ccc(O)cc1)C(=O)O]

or a salt thereof.

321. A compound, wherein the compound is

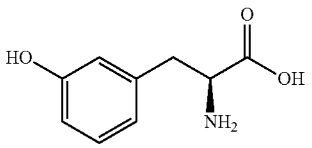 [SMILES: N[C@@H](Cc1cccc(O)c1)C(=O)O]

or a salt thereof.

322. A compound, wherein the compound is

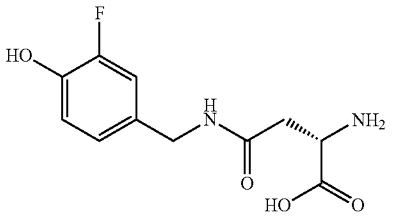 [SMILES: N[C@@H](CC(=O)NCc1ccc(O)c(F)c1)C(=O)O]

or a salt thereof.

323. A compound, wherein the compound is

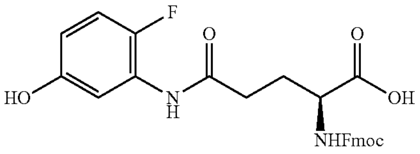

or a salt thereof.

324. A compound, wherein the compound is

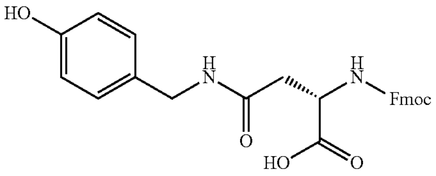

or a salt thereof.

325. A compound, wherein the compound is

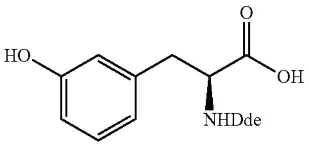

or a salt thereof.

326. A compound, wherein the compound is

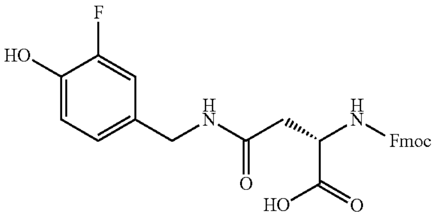

or a salt thereof.

327. A compound, wherein the compound is

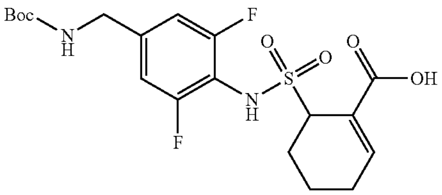 [SMILES: CC(C)(C)OC(=O)NCc1cc(F)c(NS(=O)(=O)C2CCCC=C2C(=O)O)c(F)c1]

or a salt thereof.

328. A compound, wherein the compound is

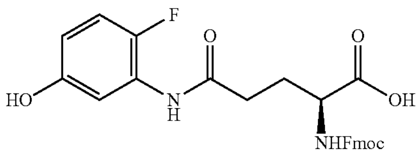

or a salt thereof.

329. A compound, wherein the compound is

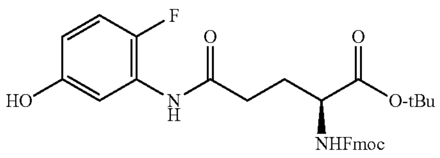

or a salt thereof.

330. An ester of a compound of any one of embodiments 319-329.

331. An agent comprising an amino acid residue of a compound of any one of embodiments 319-329.

332. The agent of embodiment 331, wherein the agent has the structure of formula R-I or a salt thereof.

333. A polypeptide agent comprising an amino acid residue of a compound of any one of embodiments 319-329.

334. A method for preparing a compound, comprising providing a compound of any one of embodiments 319-329.

335. The method of embodiment 334, wherein the compound is an agent of any one of embodiments 331-333.

EXEMPLIFICATION

As depicted in the Examples below, in certain exemplary embodiments, compounds, agents, compositions, etc. are prepared and/or assessed according to the following procedures as examples. It will be appreciated that, although the general methods depict the synthesis of certain compounds, agents, compositions of the present disclosure, the following general methods, and other methods known to one of ordinary skill in the art, can be applied to in accordance with the present disclosure to provide technologies of the present disclosure.

Example 1. Exemplary Synthesis of Compound I-1

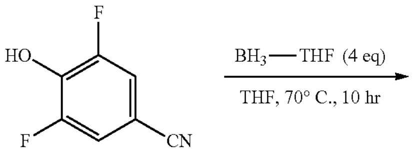

1

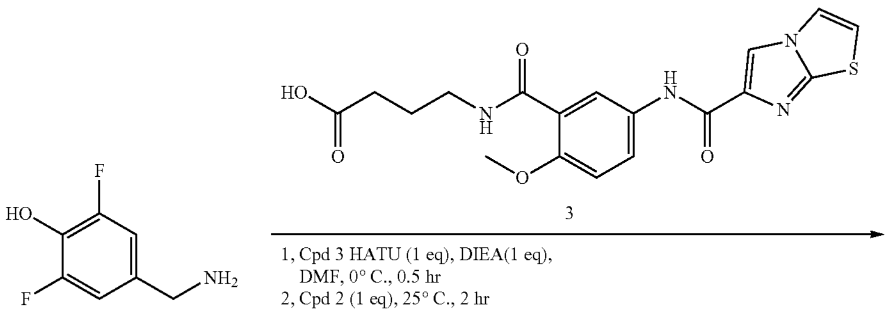

2

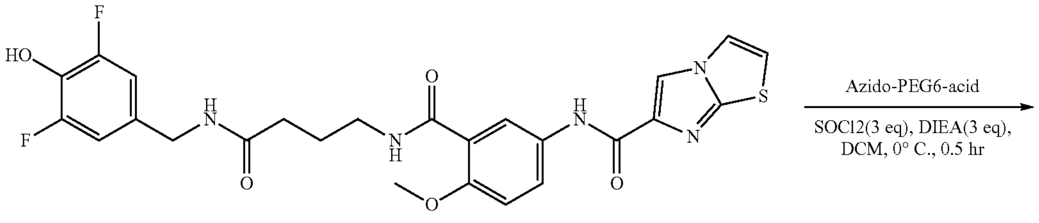

4

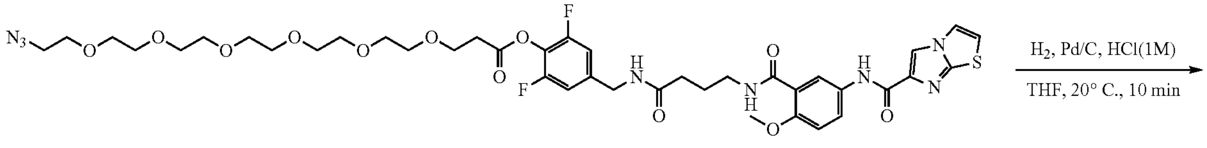

5

-continued

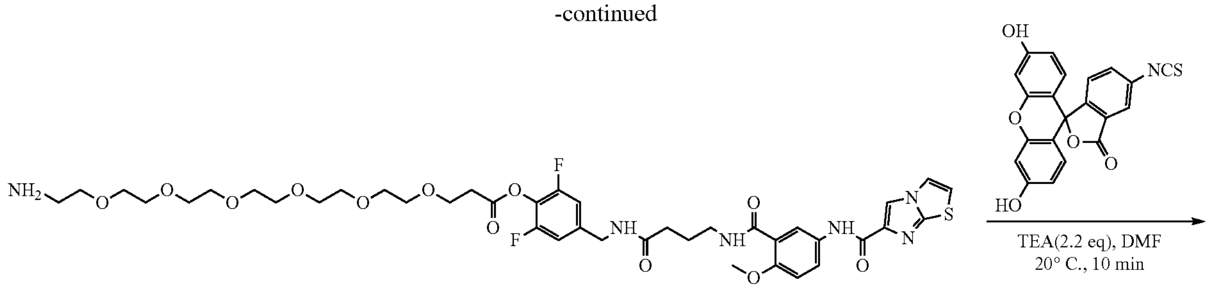

6

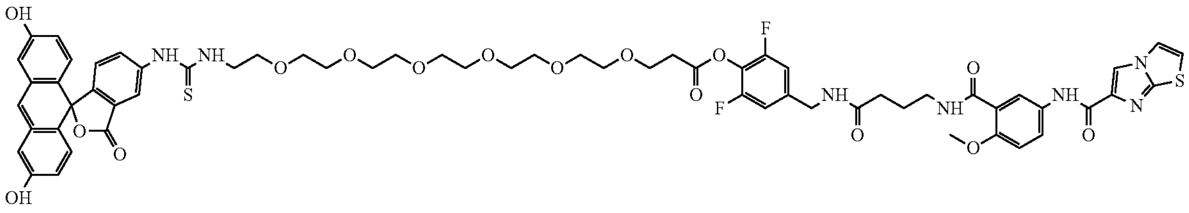

I-1

General Procedure for Preparation of Compound 2:

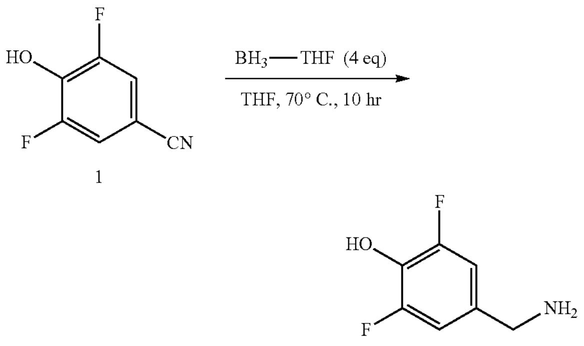

1

2

The $BH_3$·THF (1 M, 1.29 mL, 4 eq) was added carefully to a solution of compound 1 (50 mg, 322.37 umol, 1 eq) in anhydrous THF (5 mL). The resultant solution was stirred and heated to reflux for 10 hr (70° C.). TLC (Plate 1, Petroleum ether:Ethyl acetate=1:1, $R_f$=0.01) indicated compound 1 was consumed completely one new spot formed. After the mixture was cooled, 6 N HCl (2 mL) was carefully added to the solution, and heating was continued at reflux for 30 min. The mixture was concentrated under reduced pressure to give a residue. Compound 2 (40 mg, crude, HCl) was obtained as a white solid checked by HNMR. $^1$H NMR (400 MHz, METHANOL-d4) δ ppm 7.17-6.97 (m, 2H), 4.12-3.96 (m, 2H), 3.73 (s, 1H), 3.63-3.51 (m, 1H), 1.93-1.78 (m, 1H), 1.59 (br t, J=2.7 Hz, 1H), 1.40 (s, 1H).

General Procedure for Preparation of Compound 4:

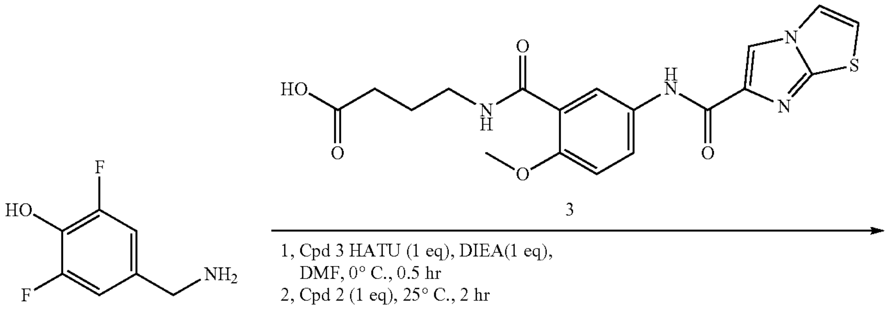

3

2

-continued

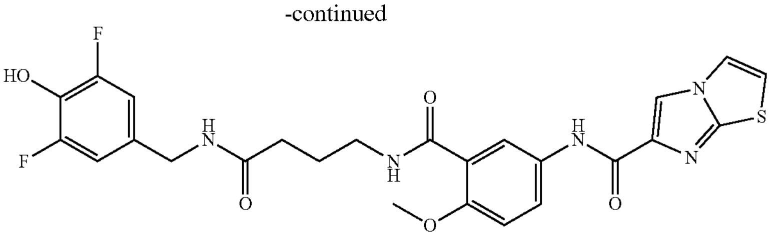

4

To a compound 3 (500 mg, 968.15 umol, 1 eq, TFA) in DMF (3 mL) was added HATU (368.12 mg, 968.15 umol, 1 eq) and DIEA (500.51 mg, 3.87 mmol, 674.54 uL, 4 eq) at 0° C. for 0.5 hr. The mixture was added compound 2 (378.73 mg, 968.15 umol, 1 eq, HCl) in DMF (2 mL). The mixture was stirred at 25° C. for 2 hr. LC-MS showed compound 3 was consumed completely and desired mass was detected. The reaction mixture was purified directly. The residue was purified by prep-HPLC (TFA condition; column: Phenomenex luna C18 250*50 mm*10 um; mobile phase: [water (0.1% TFA)-ACN]; B %: 20%-50%, 10 min). Compound 4 (460 mg, 846.30 umol, 87.41% yield) was obtained as yellow oil checked by HNMR. LCMS: RT=1.794 min, MS cal.: 543.14, $[M+H]^+$=544.2. $^1$H NMR (400 MHz, DMSO-$d_6$) δ ppm 10.14-10.08 (m, 1H), 8.37-8.32 (m, 1H), 8.25-8.20 (m, 1H), 8.02-7.98 (m, 1H), 7.90-7.84 (m, 1H), 7.46-7.41 (m, 1H), 7.13-7.06 (m, 1H), 6.93-6.88 (m, 1H), 4.19-4.15 (m, 2H), 3.88-3.85 (m, 3H), 3.32-3.20 (m, 2H), 2.26-2.19 (m, 2H), 1.82-1.73 (m, 2H).

General Procedure for Preparation of Compound 5:

Solution 1: To a solution of Azido-PEG6-acid (300 mg, 790.71 umol, 1 eq) in DCM (3 mL) was added SOCl2 (282.21 mg, 2.37 mmol, 172.08 uL, 3 eq) at 0° C. for 5 min. The mixture was concentrated to dryness. The crude product was dissolved with DCM (1 mL). Solution 2: To a solution of compound 4 (429.78 mg, 790.71 umol, 1 eq) in DCM (3 mL) was added DIEA (306.58 mg, 2.37 mmol, 413.18 uL, 3 eq) at 0° C. The solution 1 was added with solution 2 at 0° C. The mixture was stirred at 25° C. for 0.5 hr. LC-MS showed desired mass was detected. The mixture was purified directly. The residue was purified by prep-HPLC (TFA condition; column: Phenomenex luna C18 250*50 mm*10 um; mobile phase: [water (0.1% TFA)-ACN]; B %: 30%-60%, 10 min). Compound 5 (570 mg, 591.52 umol, 74.81% yield, 93.91% purity) was obtained as pink oil checked by LCMS and HNMR. LCMS: RT=2.367 min, MS cal.: 904.32, $[M/2+H]^+$=453.3. LCMS: RT=2.356 min, MS cal.: 904.32, $[M/2+H]^+$=453.4. $^1$H NMR (400 MHz, DMSO-$d_6$) δ ppm 10.14-10.06 (m, 1H), 8.48-8.40 (m, 1H), 8.36-8.32 (m, 1H), 8.26-8.17 (m, 1H), 8.03-7.94 (m, 1H), 7.94-7.81 (m, 1H), 7.48-7.38 (m, 1H), 7.21-7.01 (m, 3H), 4.33-4.25 (m, 2H), 3.89-3.83 (m, 3H), 3.80-3.71 (m, 3H), 3.67-3.52 (m, 27H), 3.52-3.45 (m, 16H), 3.41-3.36 (m, 2H), 3.33-3.24 (m, 3H), 2.99-2.88 (m, 3H), 2.29-2.22 (m, 2H), 1.86-1.72 (m, 2H), 1.29-1.20 (m, 1H).

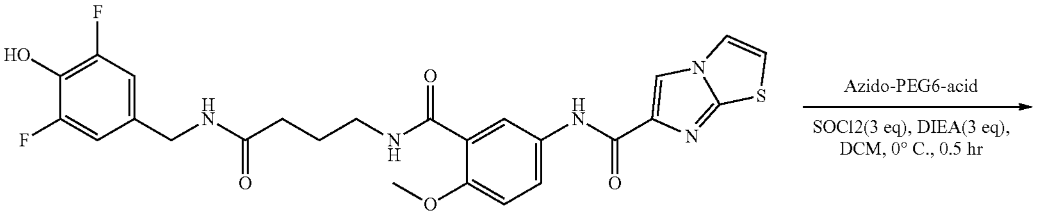

4

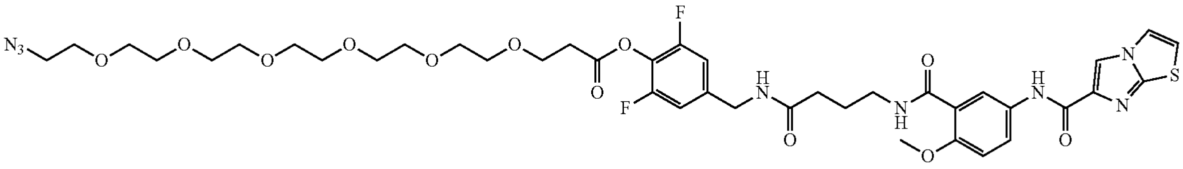

5

General Procedure for Preparation of Compound 6:

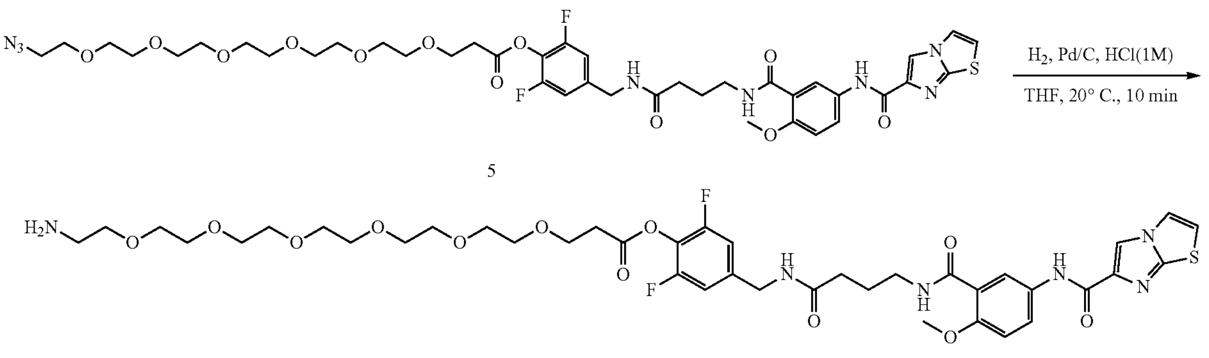

5

6

To a solution of compound 5 (500 mg, 552.53 umol, 1 eq) in THF (10 mL) was added Pd/C (500 mg, 552.53 umol, 10% purity, 1 eq) and HCl (1 M, 2.00 mL, 3.62 eq) under $N_2$. The suspension was degassed under vacuum and purged with $H_2$ several times. The mixture was stirred under $H_2$ (15 psi) at 25° C. for 10 min. LC-MS showed desired mass was detected. The mixture was filtered and filtrate was added with $NaHCO_3$ to pH 5-6. The filtrate was lyophilized to give a solid. The residue was purified by prep-HPLC (TFA condition; column: Nano-micro Kromasil C18 100*40 mm 10 um; mobile phase: [water (0.1% TFA)-ACN]; B %: 15%-50%, 7 min). Compound 6 (240 mg, 273.06 umol, 49.42% yield) was obtained as yellow oil checked by HNMR. LCMS: RT=1.865 min, MS cal.: 878.33, $[1/2M+H]^+$=440.3. $^1H$ NMR (400 MHz, DMSO-$d_6$) δ ppm 10.13-10.08 (m, 1H), 8.48-8.42 (m, 1H), 8.36-8.30 (m, 1H), 8.25-8.17 (m, 2H), 8.02-7.96 (m, 1H), 7.90-7.84 (m, 1H), 7.75-7.65 (m, 2H), 7.45-7.41 (m, 1H), 7.20-7.02 (m, 3H), 4.32-4.26 (m, 2H), 3.89-3.83 (m, 3H), 3.79-3.73 (m, 2H), 3.63-3.55 (m, 10H), 3.54-3.49 (m, 31H), 3.35-3.25 (m, 3H), 3.02-2.90 (m, 4H), 2.30-2.22 (m, 2H), 1.85-1.69 (m, 2H).

General Procedure for Preparation of Compound I-1:

To a solution of compound 6 (90 mg, 102.40 umol, 1 eq) in DMF (1 mL) was added compound 6A (39.87 mg, 102.40 umol, 1 eq). The mixture was added with TEA (22.80 mg, 225.27 umol, 31.36 uL, 2.2 eq). The mixture was stirred at 20° C. for 10 min. LC-MS showed desired mass was detected. The reaction mixture was purified directly. The residue was purified by prep-HPLC (TFA condition; column: Phenomenex Luna C18 100*30 mm*5 um; mobile phase: [water (0.1% TFA)-ACN]; B %: 40%-60%, 10 min). Compound I-1 (15.21 mg, 11.75 umol, 11.48% yield, 98% purity) was obtained as yellow solid checked by HNMR, HPLC and QC-LCMS. LCMS: RT=2.429 min, MS cal.: 1267.37, $[1/2M+H]^+$=635.1. QCLCMS: RT=3.092 min, MS cal.: 1267.37, $[1/2M+H]^+$=634.8. HPLC: Rt=3.009. $^1H$ NMR (400 MHz, DMSO-$d_6$) δ ppm 10.14-10.10 (m, 1H), 10.08-10.02 (m, 1H), 8.49-8.40 (m, 1H), 8.36-8.33 (m, 1H), 8.31-8.26 (m, 1H), 8.25-8.17 (m, 2H), 8.14-8.05 (m, 1H), 8.02-7.97 (m, 1H), 7.90-7.82 (m, 1H), 7.79-7.69 (m, 1H), 7.45-7.41 (m, 1H), 7.21-7.07 (m, 4H), 6.70-6.65 (m, 2H), 6.63-6.54 (m, 4H), 4.33-4.24 (m, 2H), 3.89-3.83 (m, 3H), 3.77-3.72 (m, 2H), 3.72-3.65 (m, 2H), 3.65-3.59 (m, 2H), 3.58-3.55 (m, 4H), 3.55-3.47 (m, 16H), 3.33-3.22 (m, 2H), 2.98-2.88 (m, 2H), 2.31-2.21 (m, 2H), 1.89-1.70 (m, 2H).

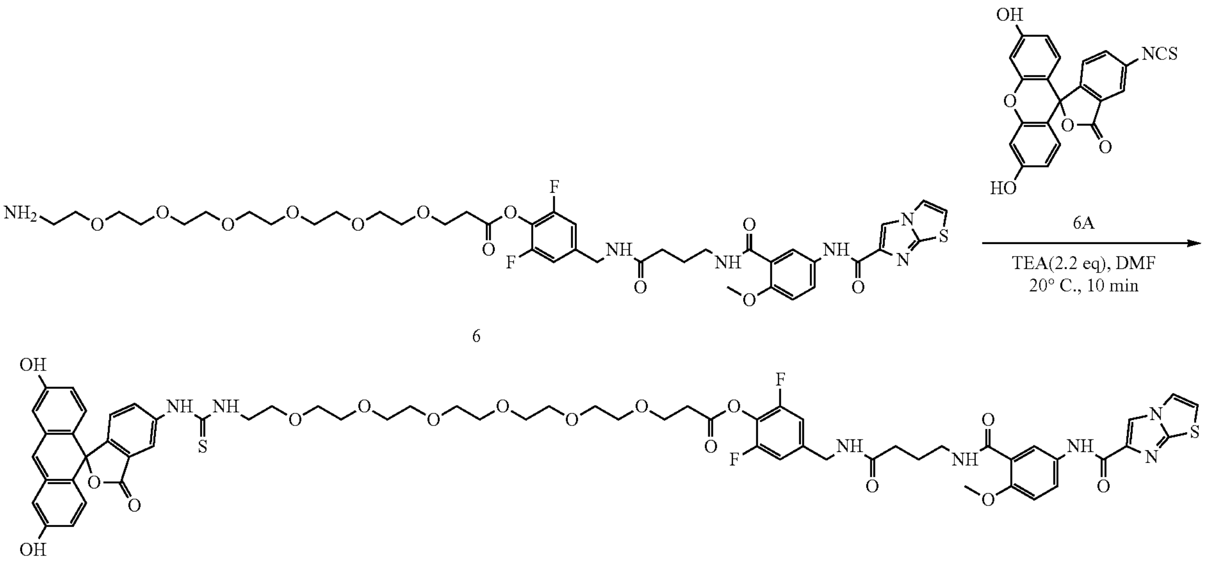

6

I-1

Example 2. Exemplary Synthesis of Compound I-2
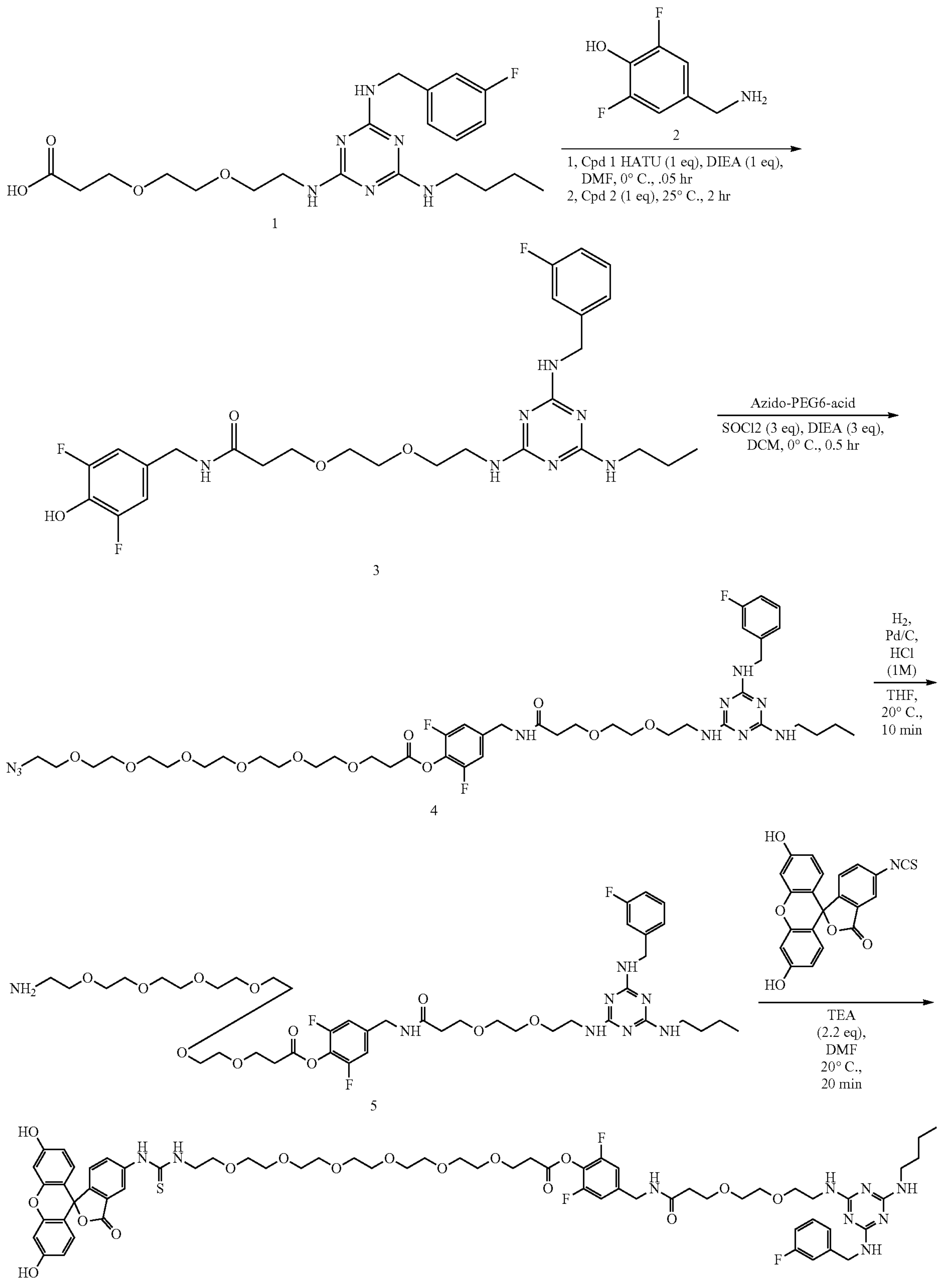
1 2 3 4 5 I-2

General Procedure for Preparation of Compound 3:

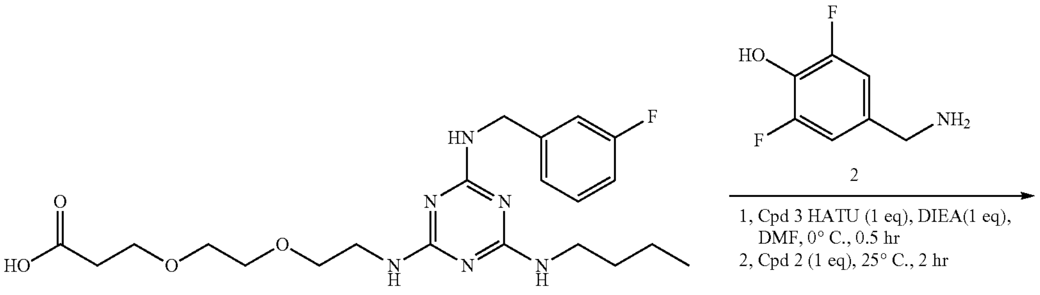

2

1

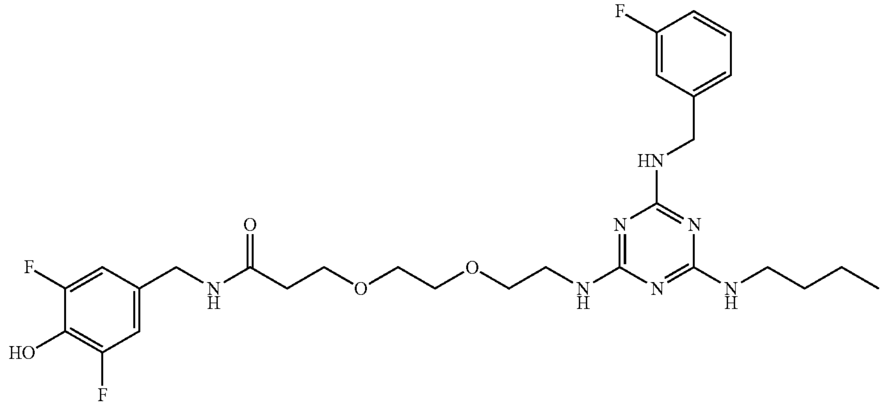

3

To a solution of compound 1 (500 mg, 893.03 umol, 1 eq, 3 M HCl) in DMF (3 mL) was added HATU (339.56 mg, 893.03 umol, 1 eq) and DIEA (577.08 mg, 4.47 mmol, 777.73 uL, 5 eq) at 0° C. for 0.5 hr. To the mixture was added compound 2 (349.34 mg, 893.03 umol, 1 eq, HCl). The mixture was stirred at 25° C. for 2 hr. LC-MS showed compound 1 was consumed completely and desired mass was detected. The reaction mixture was purified directly. The residue was purified by prep-HPLC (TFA condition; column: Nano-micro Kromasil C18 100*40 mm*10 um; mobile phase: [water (0.1% TFA)-ACN]; B %: 26%-56%, 7 min). Compound 3 (470 mg, 794.42 umol, 88.96% yield) was obtained as yellow oil checked by HNMR. LCMS: RT=2.174 min, MS cal.: 591.63, $[M+H]^+$=592.4. $^1H$ NMR (400 MHz, DMSO-$d_6$) δ ppm 10.09-9.95 (m, 1H), 8.96-8.62 (m, 1H), 8.44-8.25 (m, 1H), 8.20-7.87 (m, 1H), 8.25-7.86 (m, 1H), 7.46-7.32 (m, 1H), 7.25-7.02 (m, 3H), 6.97-6.82 (m, 2H), 4.65-4.41 (m, 2H), 4.21-4.13 (m, 2H), 3.70-3.61 (m, 2H), 3.58-3.49 (m, 5H), 3.48-3.36 (m, 4H), 3.33-3.18 (m, 2H), 2.42-2.33 (m, 2H), 1.59-1.41 (m, 1H), 1.40-1.15 (m, 2H), 1.41-1.13 (m, 3H), 0.94-0.85 (m, 2H), 0.96-0.75 (m, 3H), 0.96-0.75 (m, 3H).

General Procedure for Preparation of Compound 4:

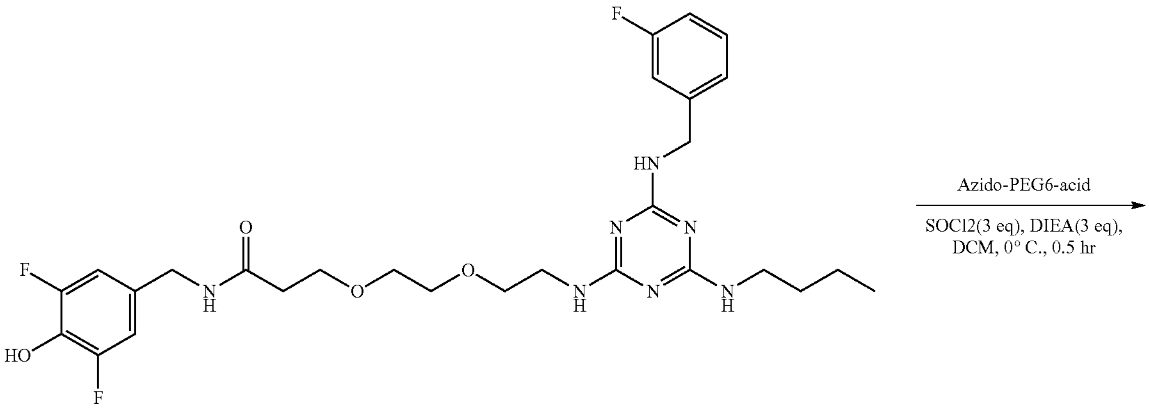

3

-continued

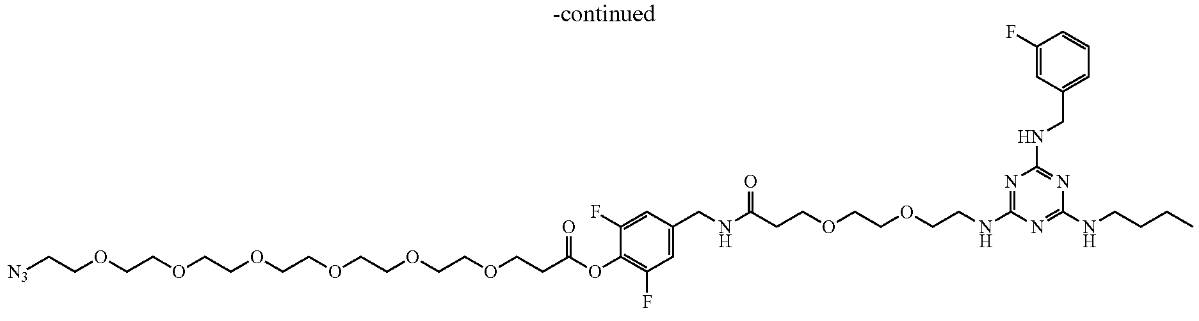

4

Solution 1: To a solution of Azido-PEG6-acid (280 mg, 738.00 umol, 1 eq) in DCM (3 mL) was added $SOCl_2$ (263.40 mg, 2.21 mmol, 160.61 uL, 3 eq) at 0° C. for 5 min. The mixture was concentrated to dryness. The crude product was dissolved with DCM (1 mL). Solution 2: To a solution of compound 3 (436.62 mg, 738.00 umol, 1 eq) in DCM (3 mL) was added DIEA (286.14 mg, 2.21 mmol, 385.64 uL, 3 eq) at 0° C. The compound 3 was added with solution 2 at 0° C. The mixture was stirred at 25° C. for 0.5 hr. LC-MS showed compound 3 was consumed completely and desired mass was detected. The mixture was purified directly. The residue was purified by prep-HPLC (TFA condition; column: Phenomenex luna C18 250*50 mm*10 um; mobile phase: [water (0.1% TFA)-ACN]; B %: 30%-60%, 10 min). Compound 4 (550 mg, 551.72 umol, 74.76% yield, 95.6% purity) was obtained as yellow oil checked by LCMS. LCMS: RT=1.398 min, MS cal.: 952.46, $[(M-N2)/2+H]^+$= 463.3. LCMS: RT=1.361 min, MS cal.: 952.46, $[M+H]^+$= 935.5.

General Procedure for Preparation of Compound 5:

To a solution of compound 4 (500 mg, 524.65 umol, 1 eq) in THF (10 mL) was added Pd/C (500 mg, 524.65 umol, 10% purity, 1 eq) and HCl (1 M, 2 mL, 3.81 eq) under $N_2$. The suspension was degassed under vacuum and purged with $H_2$ several times. The mixture was stirred under $H_2$ (15 psi) at 25° C. for 10 min. LC-MS showed desired mass was detected. The mixture was filtered and filtrate was added with $NaHCO_3$ to pH 5-6. The filtrate was lyophilized to give a solid. The residue was purified by prep-HPLC (TFA condition; column: Phenomenex luna C18 250*50 mm*10 um; mobile phase: [water (0.1% TFA)-ACN]; B %: 20%-50%, 10 min). Compound 5 (240 mg, 258.90 umol, 49.35% yield) was obtained as pink oil checked by HNMR. LCMS: RT=2.176 min, MS cal.: 926.47, [1/2M+H]=464.4. $^1H$ NMR (400 MHz, DMSO-$d_6$) δ ppm 8.55-8.45 (m, 1H), 7.82-7.68 (m, 2H), 7.42-7.34 (m, 1H), 7.21-7.06 (m, 5H), 4.59-4.44 (m, 2H), 4.32-4.23 (m, 2H), 3.80-3.72 (m, 5H), 3.69-3.48 (m, 37H), 3.54-3.48 (m, 21H), 3.03-2.91 (m, 4H), 1.55-1.42 (m, 1H), 1.38-1.25 (m, 2H), 1.27-1.16 (m, 1H), 1.25-1.12 (m, 1H), 0.92-0.77 (m, 3H).

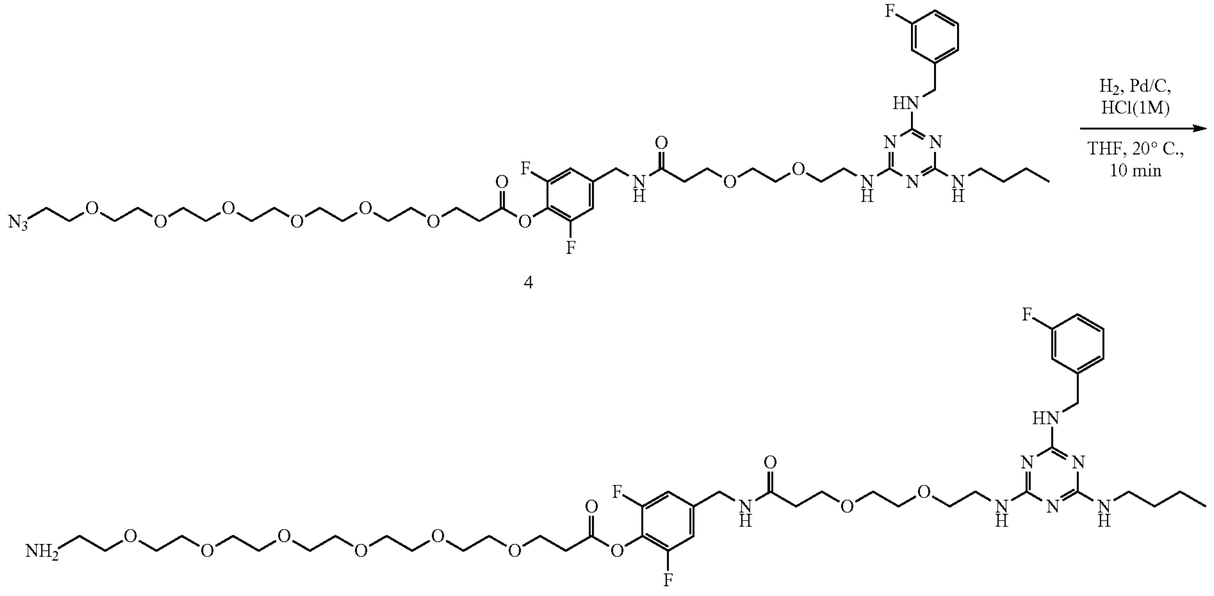

4

5

General Procedure for Preparation of Compound I-2:

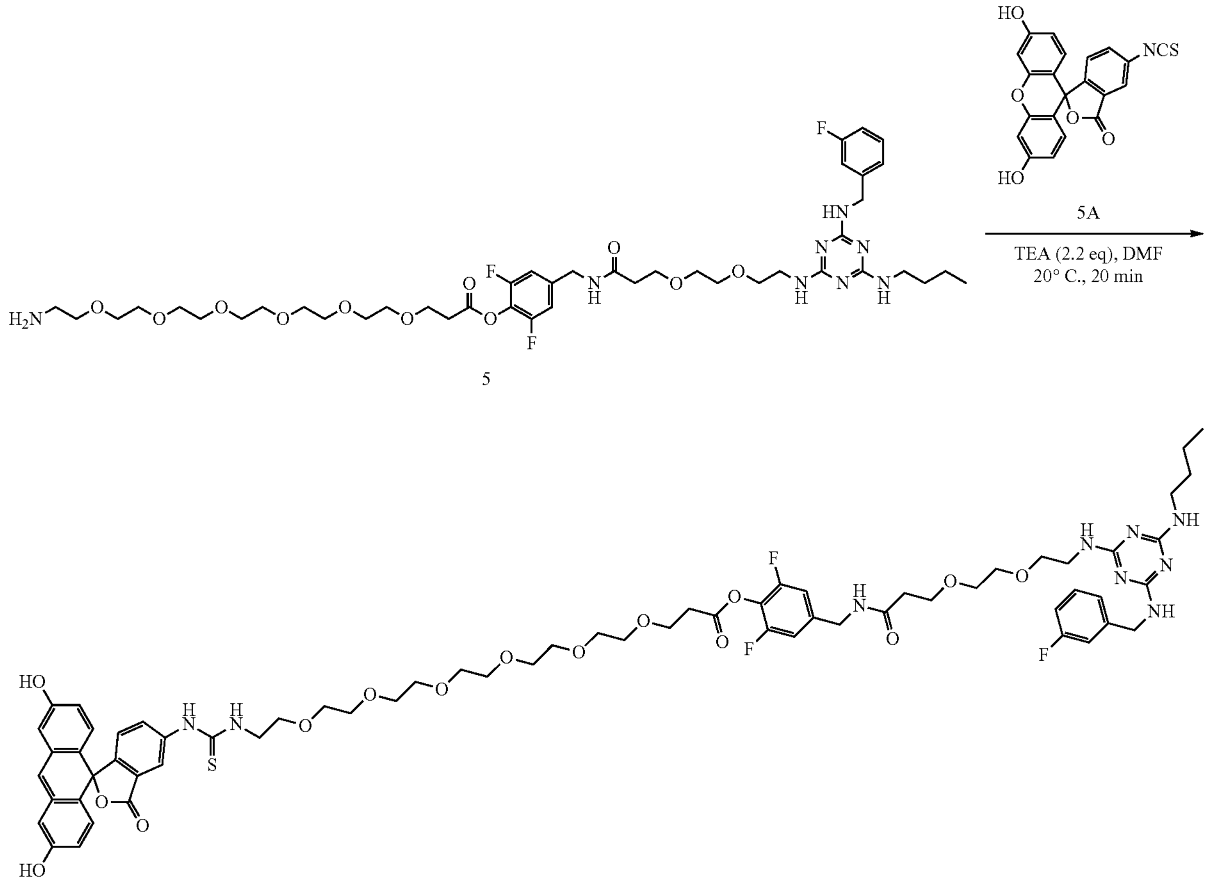

I-2

To a solution of compound 5 (90 mg, 85.44 umol, 1 eq) and compound 5A (33.27 mg, 85.44 umol, 1 eq) in DMF (1 mL) was added TEA (19.02 mg, 187.96 umol, 26.16 uL, 2.2 eq). The mixture was stirred at 20° C. for 20 min. LC-MS showed desired mass was detected. The reaction mixture was purified directly. The residue was purified by prep-HPLC (TFA condition; column: Phenomenex Luna C18 100*30 mm*5 um; mobile phase: [water (0.1% TFA)-ACN]; B %: 20%-50%, 10 min). Compound I-2 (13.27 mg, 9.96 umol, 11.66% yield, 98.83% purity) was obtained as yellow solid checked by HPLC, QC-LCMS and HNMR. LCMS: RT=2.676 min, MS cal.: 1315.51, $[1/2M+H]^+$=659.1. QCLCMS: RT=3.297 min, MS cal.: 1315.51, $[1/2M+H]^+$ =658.9. HPLC: Rt=3.273. $^1H$ NMR (400 MHz, METHANOL-$d_4$) δ ppm 8.35-8.27 (m, 1H), 7.93-7.81 (m, 1H), 7.37-7.29 (m, 1H), 7.24-7.19 (m, 1H), 7.17-7.09 (m, 1H), 7.09-7.04 (m, 1H), 7.03-6.90 (m, 5H), 7.04-6.89 (m, 6H), 6.88-6.81 (m, 2H), 6.76-6.68 (m, 2H), 4.60-4.54 (m, 2H), 4.39-4.34 (m, 2H), 3.84-3.74 (m, 6H), 3.73-3.69 (m, 3H), 3.68-3.64 (m, 5H), 3.63-3.56 (m, 24H), 3.48 (br s, 3H), 2.89-2.83 (m, 2H), 2.56-2.49 (m, 2H), 1.61-1.51 (m, 1H), 1.50-1.44 (m, 1H), 1.41-1.33 (m, 1H), 1.33-1.26 (m, 1H), 1.33-1.25 (m, 1H), 0.98-0.91 (m, 2H), 0.90-0.85 (m, 1H), 0.91-0.85 (m, 1H), 1.00-0.77 (m, 4H).

Example 3. Exemplary Synthesis of Compound I-3

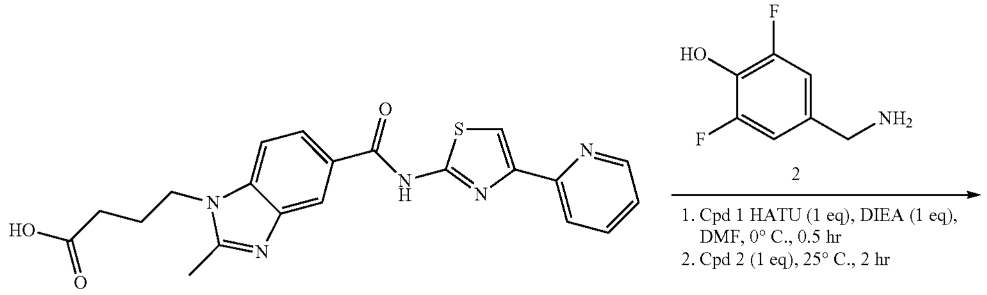

1

-continued
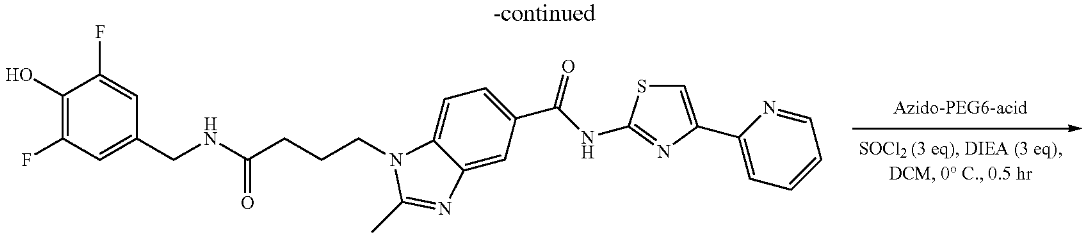
3
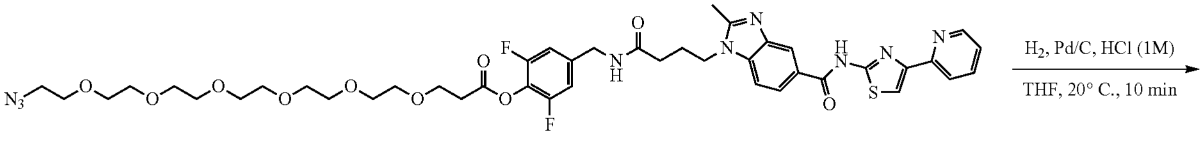
4
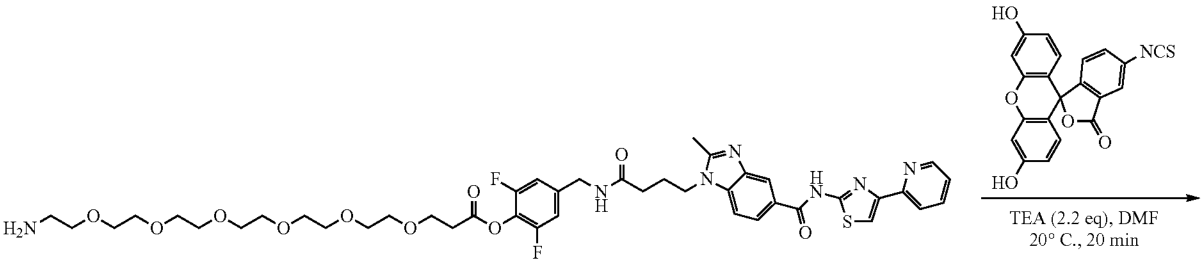
5
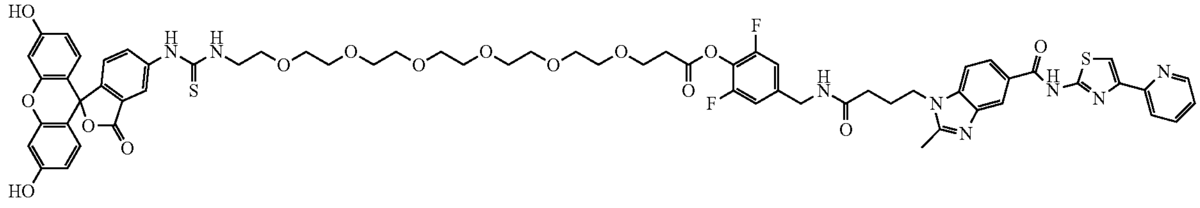
I-3
General Procedure for Preparation of Compound:
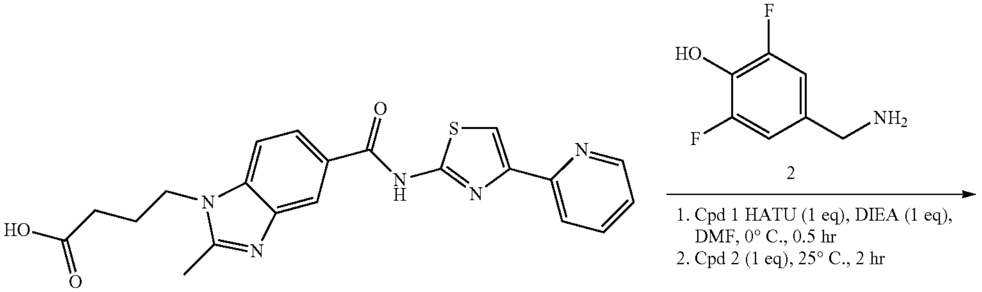
1
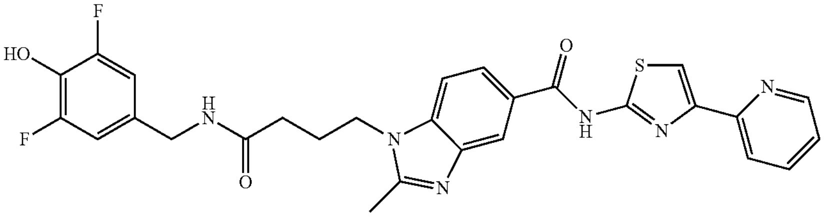
3

To a solution of compound 1 (400 mg, 746.97 umol, 1 eq, TFA) in DCM (10 mL) was added HATU (312.42 mg, 821.67 umol, 1.1 eq) and DIEA (386.16 mg, 2.99 mmol, 520.42 uL, 4 eq) at 0° C. for 0.5 hr. To the mixture was added compound 2 (321.43 mg, 821.67 umol, 1.1 eq, HCl) in DMF (2 mL). The mixture was stirred at 25° C. for 2 hr. LC-MS showed desired mass was detected. The mixture was concentrated under reduced pressure to give a residue. The reaction mixture was purified directly. The residue was purified by prep-HPLC (column: Phenomenex Luna C18 200*40 mm*10 um; mobile phase: [water (0.1% TFA)-ACN]; B %: 5%-35%, 10 min). Compound 3 (250 mg, 444.37 umol, 59.49% yield) was obtained as yellow oil checked by HNMR. LCMS: RT=0.954 min, MS cal.: 526.16, $[1/2M+H]^+$=282.1. $^1H$ NMR (400 MHz, DMSO-$d_6$) δ ppm 13.08-12.95 (m, 1H), 8.68-8.61 (m, 1H), 8.57-8.50 (m, 1H), 8.41-8.31 (m, 1H), 8.31-8.20 (m, 1H), 8.09-8.01 (m, 2H), 7.99-7.90 (m, 2H), 7.46-7.31 (m, 1H), 6.98-6.81 (m, 2H), 4.50-4.37 (m, 3H), 4.14 (br d, J=5.7 Hz, 4H), 2.88-2.78 (m, 3H), 2.70-2.63 (m, 1H), 2.36-2.28 (m, 3H), 2.10-2.00 (m, 3H).

General Procedure for Preparation of Compound 4:

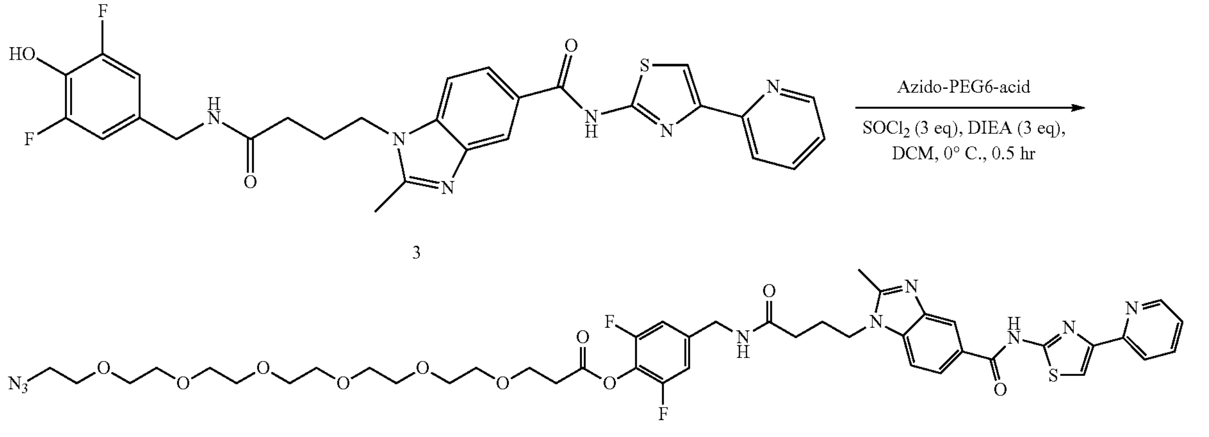

3

4

Solution 1: To a solution of Azido-PEG6-acid (340 mg, 896.14 umol, 1 eq) in DCM (5 mL) was added SOCl2 (319.84 mg, 2.69 mmol, 195.03 uL, 3 eq) at 0° C. for 5 min. The mixture was concentrated to dryness. The crude product was dissolved with DCM (1 mL). Solution 2: To a solution of compound 3 (504.16 mg, 896.14 umol, 1 eq) in DCM (5 mL) was added DIEA (347.45 mg, 2.69 mmol, 468.26 uL, 3 eq) at 0° C. Solution 2 was added to solution 1 at 0° C. The mixture was stirred at 25° C. for 0.5 hr. LC-MS showed desired mass was detected. The mixture was concentrated under reduced pressure to give a residue. The mixture was used next step directly. The residue was purified by prep-HPLC (column: Welch Xtimate C18 250*50 mm*10 um; mobile phase: [water (0.1% TFA)-ACN]; B %: 15%-45%, 10 min). Compound 4 (600 mg, 649.37 umol, 72.46% yield) was obtained as yellow solid. LCMS: RT=1.819 min, MS cal.: 923.34, $[1/2M+H]^+$=462.9.

General Procedure for Preparation of Compound 5:

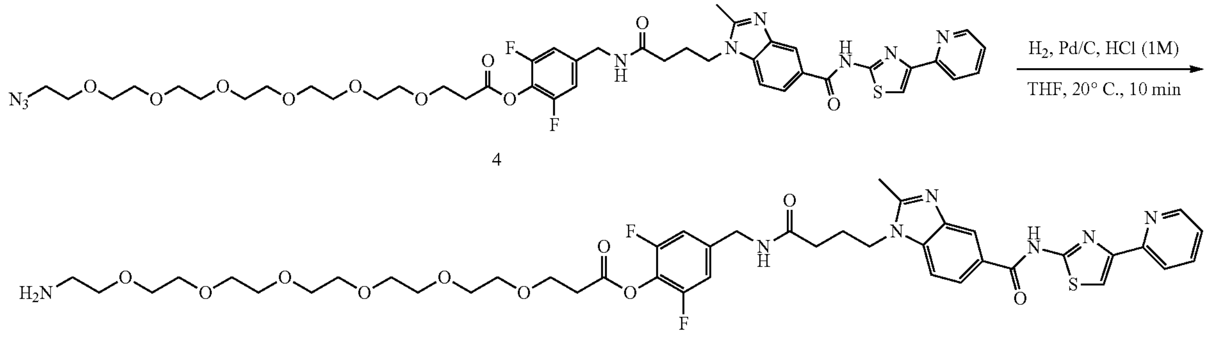

4

5

To a solution of compound 4 (300 mg, 324.68 umol, 1 eq) in THF (10 mL) was added Pd/C (400 mg, 324.68 umol, 10% purity, 1 eq) and HCl (1 M, 1.62 mL, 5 eq) under $N_2$. The suspension was degassed under vacuum and purged with $H_2$ several times. The mixture was stirred under $H_2$ (15 psi) at 25° C. for 10 min. LC-MS showed desired mass was detected. The mixture was filtered and filtrate was concentrated under reduced pressure to give a residue. The residue was purified by prep-HPLC (TFA condition; column: Nano-micro Kromasil C18 100*40 mm 10 um; mobile phase: [water (0.1% TFA)-ACN]; B %: 8%-38%, 9 min). Compound 5 (200 mg, 222.72 umol, 68.60% yield) was obtained as white solid. LCMS: RT=0.996 min, MS cal.: 897.35, $[1/2M+H]^+$=449.8.

General Procedure for Preparation of Compound I-3:

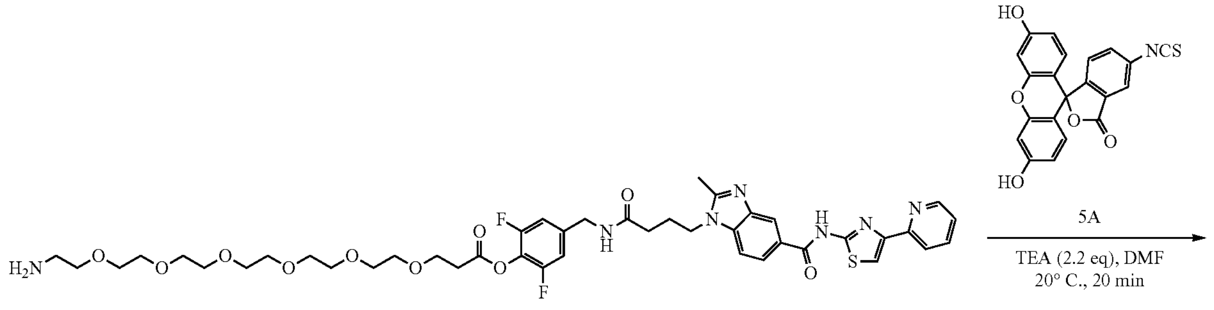

5

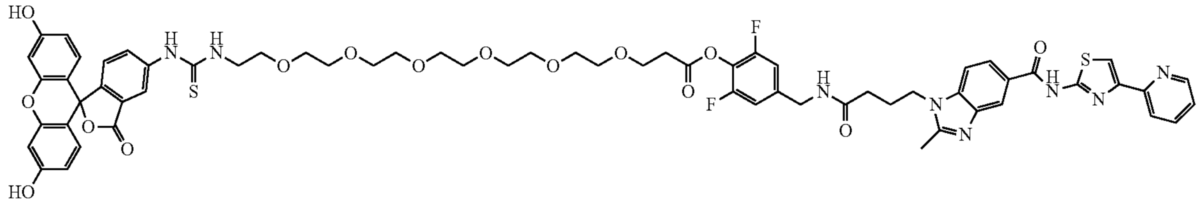

I-3

To a solution of compound 5 (60 mg, 66.82 umol, 1 eq) and compound 5A (26.02 mg, 66.82 umol, 1 eq) in DMF (1 mL) was added TEA (6.76 mg, 66.82 umol, 9.30 uL, 1 eq). The mixture was stirred at 25° C. for 10 min. LC-MS showed desired mass was detected. The reaction mixture was concentrated under reduced pressure to give a residue. The residue was purified by prep-HPLC (TFA condition; column: Welch Ultimate AQ-C18 150*30 mm*5 um; mobile phase: [water (0.1% TFA)-ACN]; B %: 35%-65%, 12 min). Compound I-3 (11.48 mg, 8.90 umol, 13.33% yield, 99.85% purity) was obtained as yellow solid checked by HPLC, HNMR and QC-LCMS. LCMS: RT=2.047 min, MS cal.: 1286.39, $[1/2M+H]^+$=644.6. QCLCMS: RT=3.151 min, MS cal.: 1286.39, $[1/2M+H]^+$=644.3. HPLC: Rt=2.444. $^1H$ NMR (400 MHz, DMSO-$d_6$) δ ppm 13.02-12.95 (m, 1H), 10.16-10.07 (m, 1H), 10.07-9.99 (m, 1H), 8.66-8.62 (m, 1H), 8.55-8.51 (m, 1H), 8.49-8.43 (m, 1H), 8.31-8.23 (m, 2H), 8.09-8.02 (m, 2H), 7.98-7.91 (m, 2H), 7.77-7.70 (m, 1H), 7.41-7.35 (m, 1H), 7.20-7.16 (m, 1H), 7.15-7.10 (m, 2H), 6.69-6.66 (m, 2H), 6.62-6.61 (m, 1H), 6.60-6.59 (m, 1H), 6.58-6.56 (m, 2H), 6.56-6.54 (m, 1H), 4.48-4.40 (m, 3H), 4.28-4.24 (m, 3H), 3.76-3.70 (m, 4H), 3.62-3.59 (m, 2H), 3.58-3.55 (m, 4H), 3.54-3.46 (m, 18H), 2.97-2.88 (m, 2H), 2.86-2.77 (m, 3H), 2.41-2.31 (m, 5H), 2.12-2.01 (m, 3H).

Example 4. Exemplary Synthesis of Compound I-4

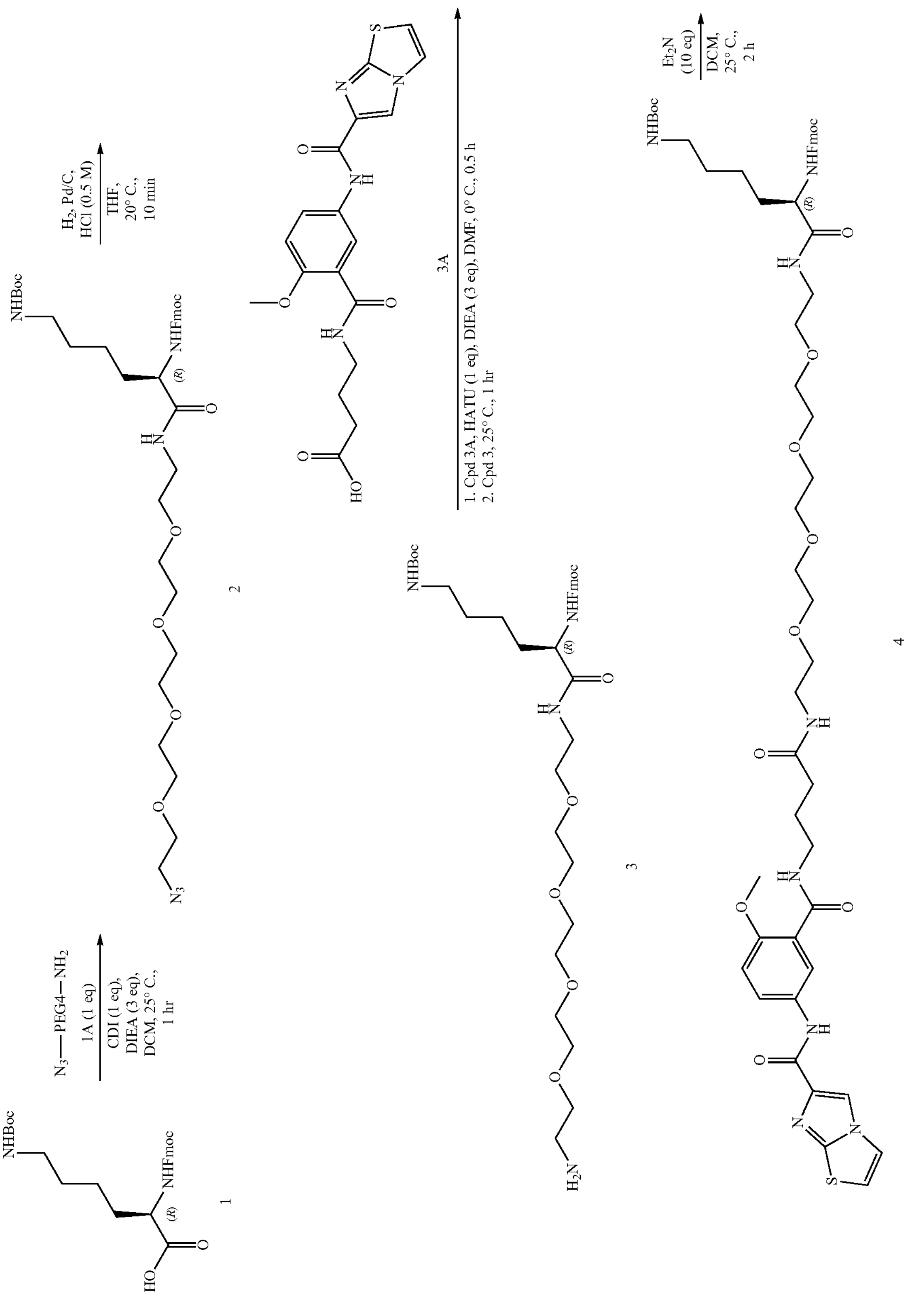
1
2
3
4

-continued
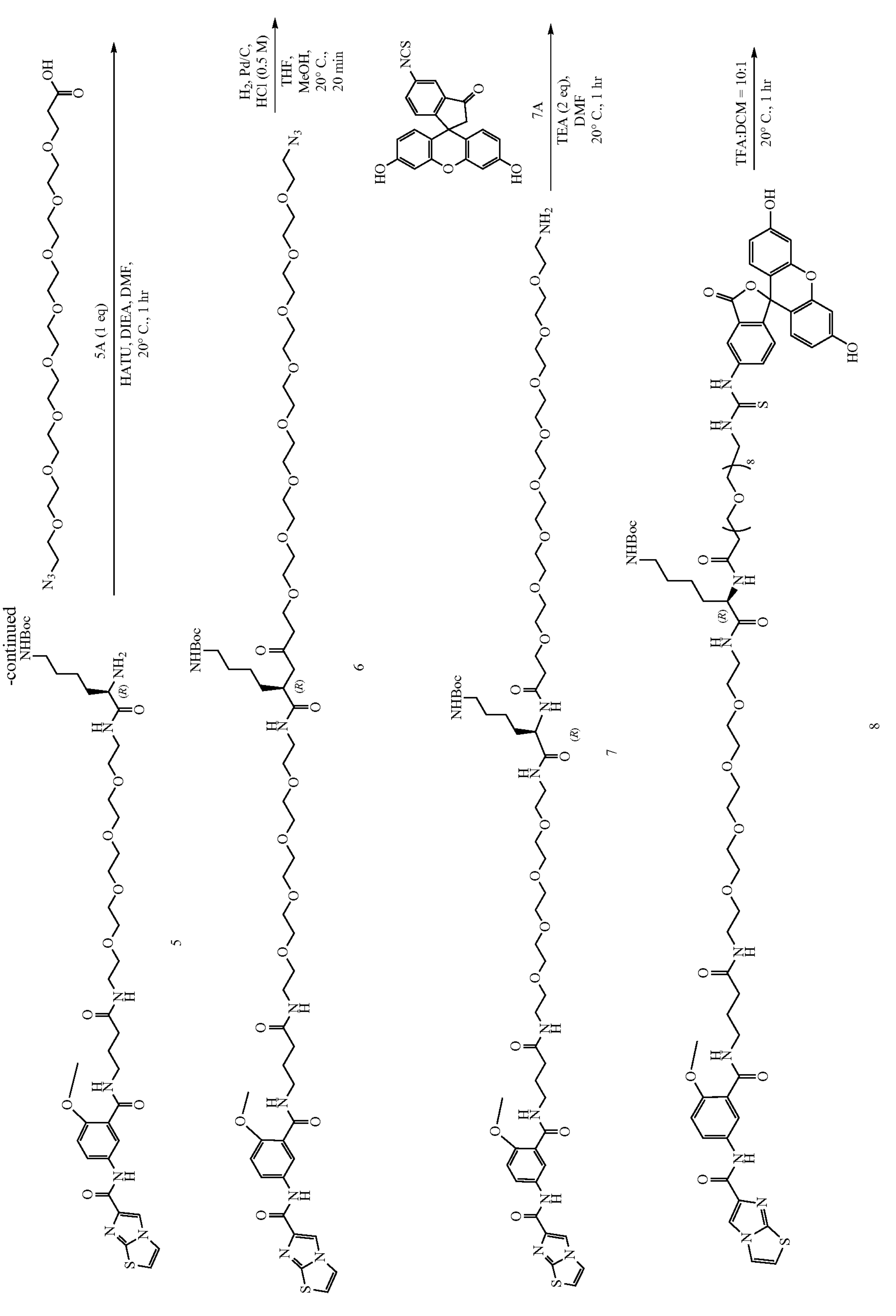
5
6
7
8

-continued
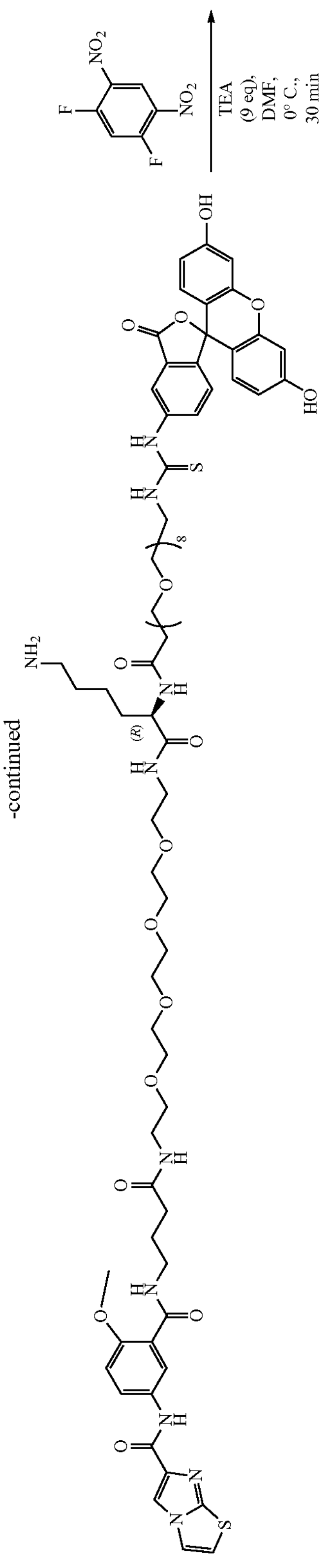
9
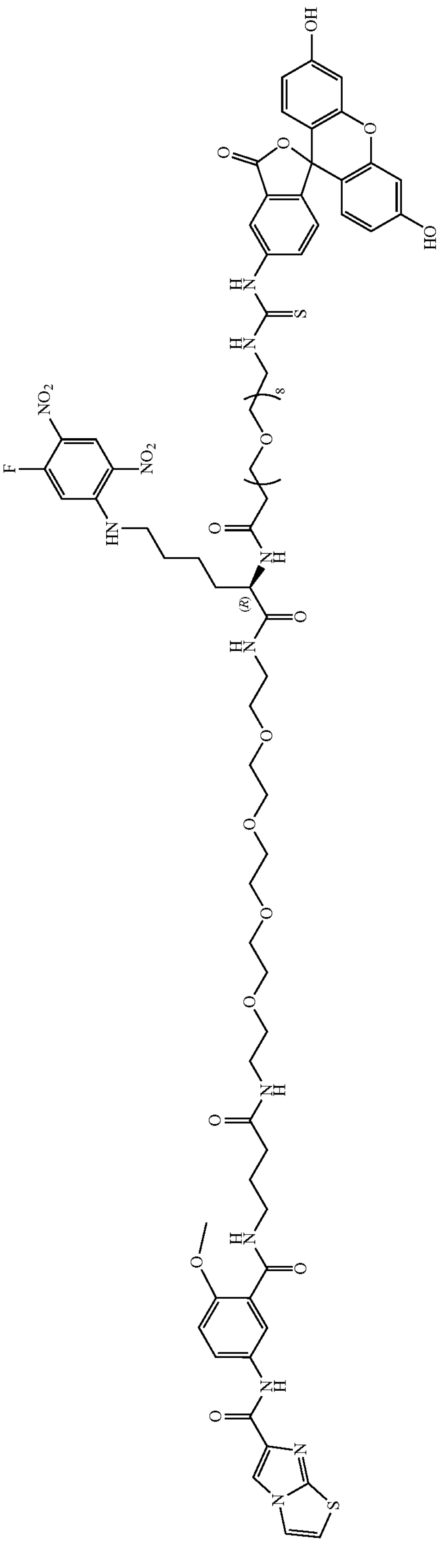
I-4

General Procedure for Preparation of Compound 2:

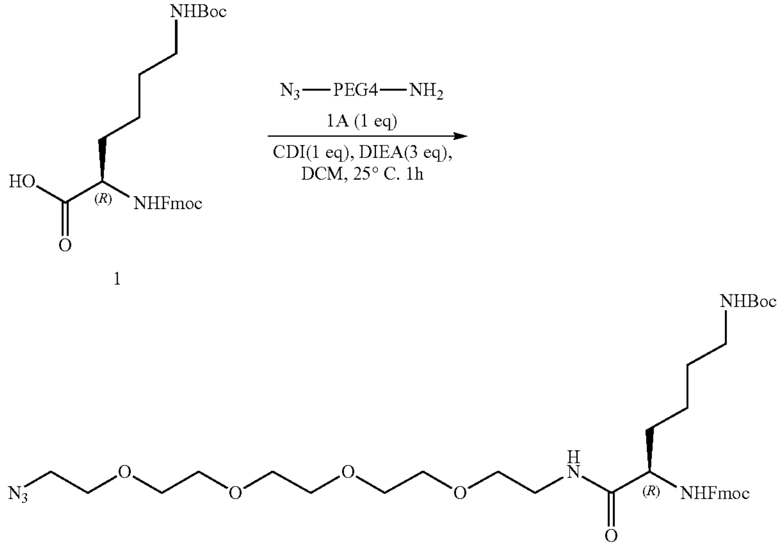

1

2

To a solution of compound 1 (2 g, 4.27 mmol, 1 eq) in DCM (15 mL) was added CDI (692.14 mg, 4.27 mmol, 1 eq) and DIEA (1.66 g, 12.81 mmol, 2.23 mL, 3 eq). Then compound 1A (1.12 g, 4.27 mmol, 1 eq) was added to the reaction mixture. The mixture was stirred at 25° C. for 1 hr. LC-MS showed Reactant 1 was consumed completely and one main peak with desired mass was detected. The residue was diluted with $H_2O$ 20 mL and extracted with DCM (20 mL*3). The combined organic layers were washed with brine (20 mL*3), dried over $Na_2SO_4$, filtered and concentrated under reduced pressure to give a residue. Compound 2 (2.2 g, 3.09 mmol, 72.30% yield) was obtained as a white solid. LCMS: RT=3.185 min, MS cal.: 712.38, $[M+H]^+$=713.4.

General Procedure for Preparation of Compound 3:

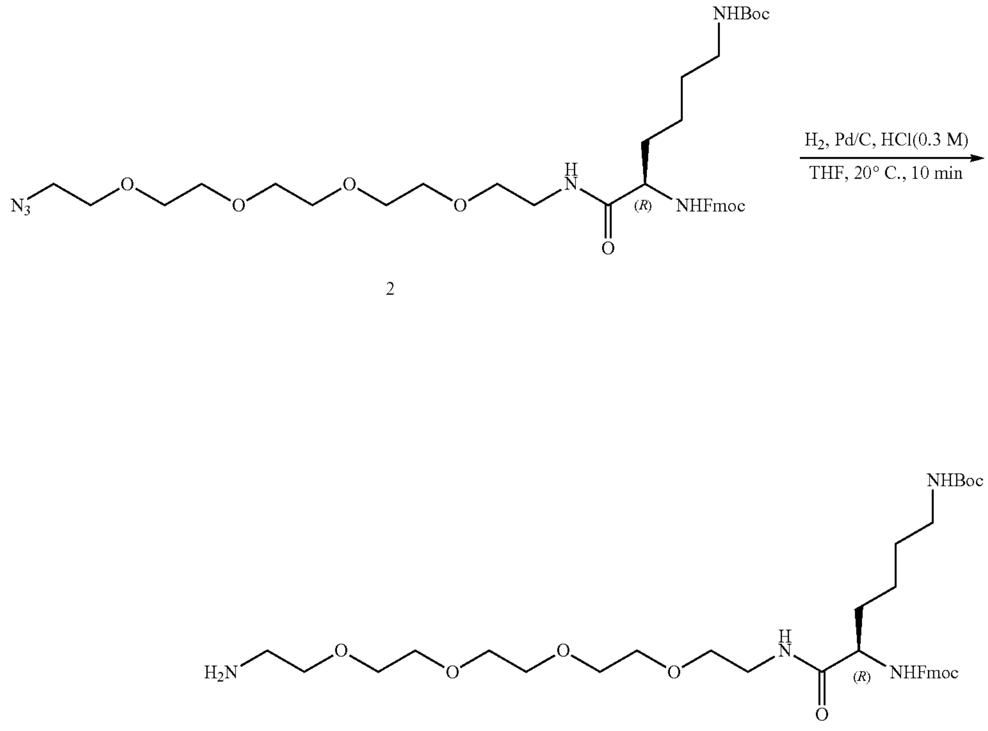

2

3

To a solution of compound 2 (1.4 g, 1.96 mmol, 1 eq) in THF (50 mL) was added Pd/C (1 g, 10% purity) and HCl (0.3 M, 32.73 mL, 5 eq) under $N_2$ atmosphere. The suspension was degassed and purged with $H_2$ 3 times. The mixture was stirred under $H_2$ (15 Psi) at 20° C. for 10 min. LC-MS showed desired mass was detected. The mixture was filtered and filtrate was lyophilized to give a white solid. Compound 3 (1.4 g, 1.45 mmol, 73.92% yield, 75% purity, HCl) was obtained as a white solid checked by HNMR. LCMS: RT=1.208 min, MS cal.: 686.39, $[M+H]^+$=687.4. $^1H$ NMR (400 MHz, DMSO-$d_6$) δ ppm 8.04-7.94 (m, 2H), 7.93-7.85 (m, 2H), 7.77-7.66 (m, 2H), 7.48-7.38 (m, 3H), 7.36-7.25 (m, 2H), 6.81-6.73 (m, 1H), 4.31-4.18 (m, 3H), 3.97-3.87 (m, 1H), 3.61-3.57 (m, 1H), 3.57-3.51 (m, 1H), 3.57-3.44 (m, 1H), 3.41-3.38 (m, 1H), 3.41-3.37 (m, 1H), 3.25-3.14 (m, 2H), 2.98-2.83 (m, 3H), 1.65-1.46 (m, 2H), 1.41-1.33 (m, 9H), 1.27-1.14 (m, 1H).

General Procedure for Preparation of Compound 4:

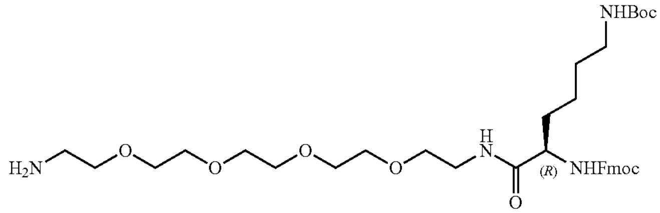

3

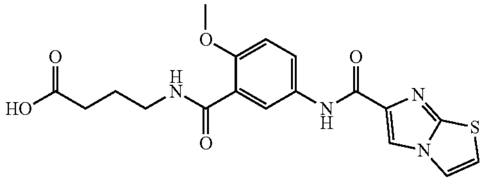

3A

1. Cpd 3A, HATU ( 1 eq), DIEA (3 eq), DMF, 0° C., 0.5 hr
2. Cpd 3, 25° C., 1 h

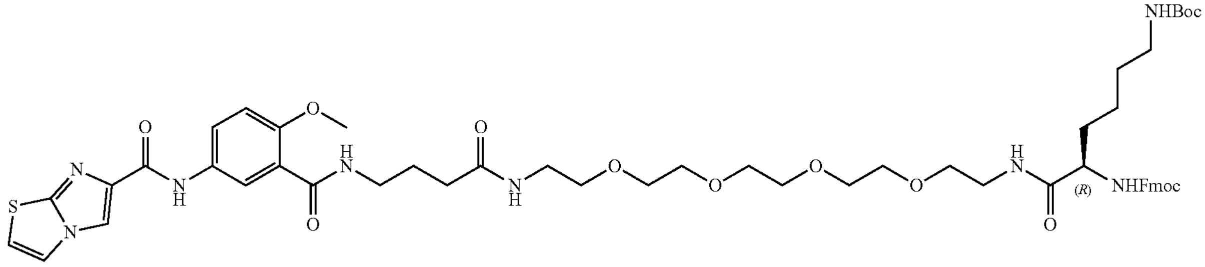

4

To a solution of compound 3A (500 mg, 968.15 umol, 1 eq, TFA) in DMF (1 mL) was added HATU (368.12 mg, 968.15 umol, 1 eq) at 0° C. for 0.5 hr. The mixture was combined with Compound 3 (778.07 mg, 968.15 umol, 1 eq, HCl) and TEA (293.90 mg, 2.90 mmol, 404.27 uL, 3 eq). The mixture was stirred at 25° C. for 1 hr. LC-MS showed desired mass was detected. The combined reaction mixture was poured into HCl (0.5 M) (20 mL) and extracted with ethyl acetate (20 mL*2). The combined organic phase was concentrated in vacuo to give a residue. The residue was purified by column chromatography ($SiO_2$, Dichloromethane:Methanol=100/1 to 5/1, Rf=0.59). Compound 4 (900 mg, 840.15 umol, 86.78% yield) was obtained as a pink solid checked by HNMR. LCMS: RT=2.852 min, MS cal.: 1070.48, $[1/2M+H]^+$=536.4. $^1H$ NMR (400 MHz, DMSO-$d_6$) δ ppm 10.13-10.04 (m, 1H), 8.35-8.30 (m, 1H), 8.24-8.14 (m, 2H), 8.01-7.95 (m, 1H), 7.94-7.82 (m, 6H), 7.76-7.68 (m, 2H), 7.45-7.36 (m, 4H), 7.35-7.28 (m, 2H), 7.12-7.05 (m, 1H), 6.79-6.70 (m, 1H), 4.27-4.16 (m, 3H), 4.06-3.99 (m, 1H), 3.95-3.88 (m, 1H), 3.87-3.83 (m, 3H), 3.52-3.43 (m, 13H), 3.41-3.36 (m, 5H), 3.29-3.23 (m, 3H), 3.21-3.15 (m, 4H), 2.93-2.79 (m, 3H), 2.17-2.11 (m, 2H), 2.00-1.96 (m, 1H), 1.77-1.69 (m, 2H), 1.62-1.46 (m, 3H), 1.40-1.32 (m, 12H), 1.20-1.15 (m, 2H).

General Procedure for Preparation of Compound 5:

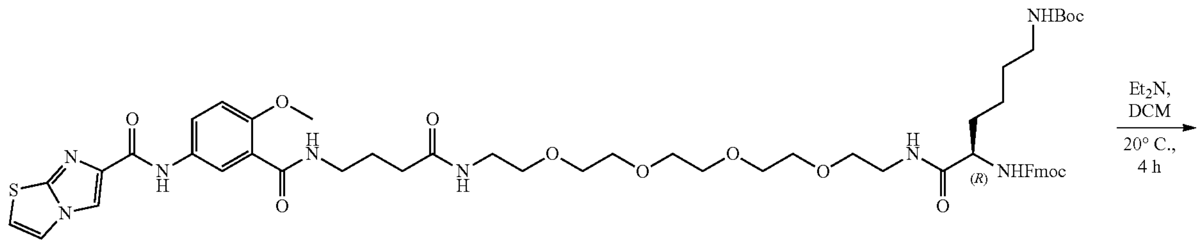

4

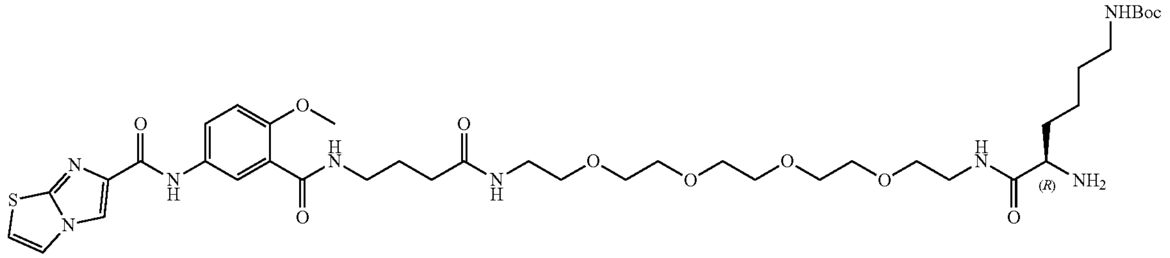

5

To a solution of compound 4 (600 mg, 560.10 umol, 1 eq) in DCM (2 mL) was added $Et_2NH$ (2.13 g, 29.12 mmol, 3.00 mL, 51.99 eq). The mixture was stirred at 20° C. for 4 hr. TLC indicated compound 4 was consumed completely and one new spot formed. LC-MS showed compound 4 was consumed completely and desired mass was detected. The reaction mixture was concentrated under reduced pressure to give a residue. Compound 5 (475.52 mg, 560.09 umol, 100% yield) was used into the next step without further purification checked by HNMR. LCMS: RT=1.830 min, MS cal.: 848.41, $[M+H]^+$=849.4. $^1H$ NMR (400 MHz, CHLOROFORM-d) δ ppm 9.15-9.04 (m, 1H), 8.29-8.06 (m, 4H), 7.80-7.67 (m, 3H), 7.54-7.47 (m, 1H), 7.42-7.31 (m, 3H), 7.09-6.93 (m, 2H), 6.13-6.01 (m, 2H), 5.38-5.26 (m, 1H), 4.05-3.94 (m, 3H), 3.76-3.61 (m, 13H), 3.60-3.53 (m, 5H), 3.51-3.38 (m, 6H), 3.18-3.05 (m, 1H), 3.05-2.96 (m, 1H), 2.36-2.20 (m, 3H), 2.00-1.89 (m, 4H), 1.46-1.33 (m, 16H), 1.29-1.20 (m, 3H), 0.94-0.73 (m, 6H).

General Procedure for Preparation of Compound 6:

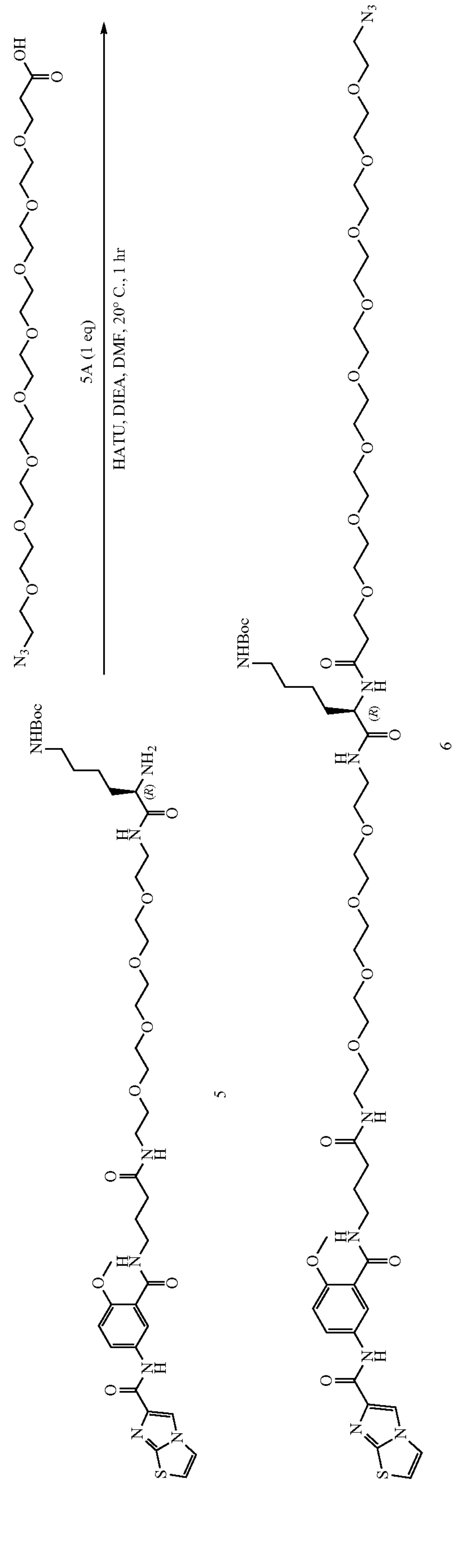
5
6

To a solution of compound 5A (310 mg, 663.09 umol, 1.2 eq) in DCM (3 mL) was added HATU (210.10 mg, 552.57 umol, 1 eq) and TEA (139.79 mg, 1.38 mmol, 192.28 uL, 2.5 eq) at 0° C. for 0.5 hr. The mixture was added with compound 5 (469.14 mg, 552.57 umol, 1 eq). The mixture was stirred at 0° C. for 1 hr. LC-MS showed desired mass was detected. The residue was washed with NH4Cl 10 ml (10 mL*2) and extracted with DCM 40 mL (40 mL*3). The combined organic layers were washed with brine 20 mL, dried over $Na_2SO_4$, filtered and concentrated under reduced pressure to give a residue. Compound 6 (700 mg, 539.08 umol, 97.56% yield) was used into the next step without further purification (yellow oil). LCMS: RT=2.372 min, MS cal.: 1297.65, $[M+H]^+$=650.1.

General Procedure for Preparation of Compound 7:

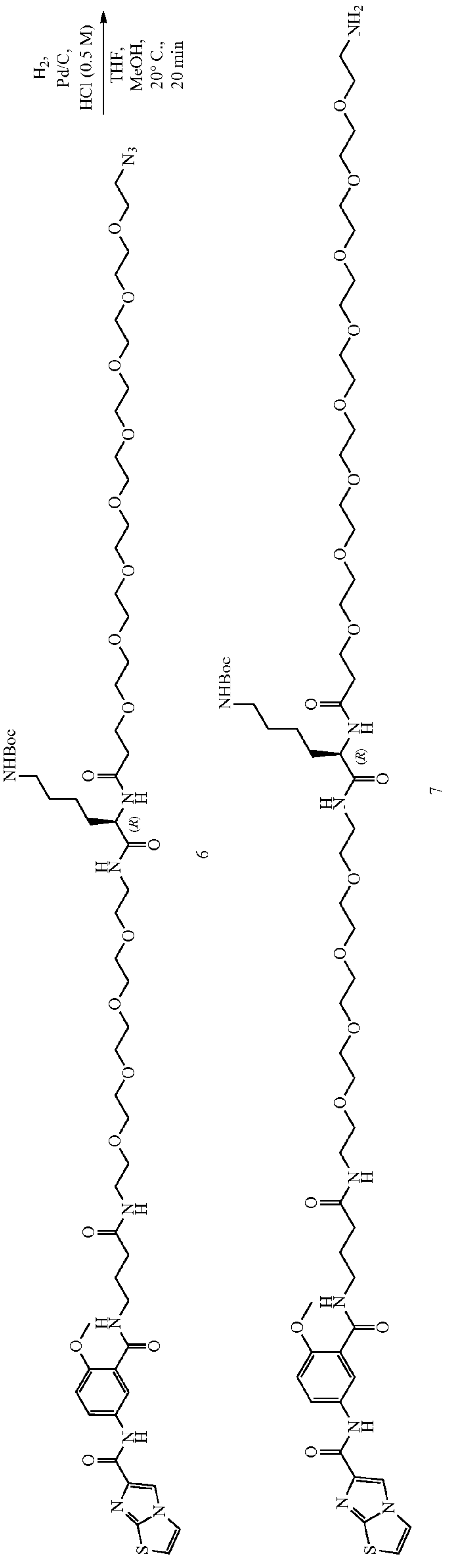
6
7

To a solution compound 6 (100 mg, 77.01 umol, 1 eq) in THF (1 mL) and MeOH (0.5 mL) was added Pd/C (100 mg, 77.01 umol, 10% purity, 1 eq) and HCl (0.5 M, 462.07 uL, 3 eq) under $N_2$. The suspension was degassed under vacuum and purged with H2 several times. The mixture was stirred under $H_2$ (15 psi) at 25° C. for 10 min. LC-MS showed desired mass was detected. The mixture was filtered and filtrate was extracted with MTBE 10 mL. The pH was adjusted to around 8-9 by progressively adding sat. $NaHCO_3$. The aqueous layer was extracted with DCM 20 mL (20 mL*2). The combined organic layers were washed with brine 20 mL, dried over $Na_2SO_4$, filtered and concentrated under reduced pressure to give a residue. Compound 7 (40 mg, 9.12 umol, 11.84% yield, 29% purity) was obtained as yellow oil checked by LCMS. LCMS: RT=1.973 min, MS cal.: 1271.66, $[1/2M+H]^+$=637.2. LCMS: RT=1.919 min, MS cal.: 1271.66, $[1/2M+H]^+$=637.1.

General Procedure for Preparation of Compound 8:

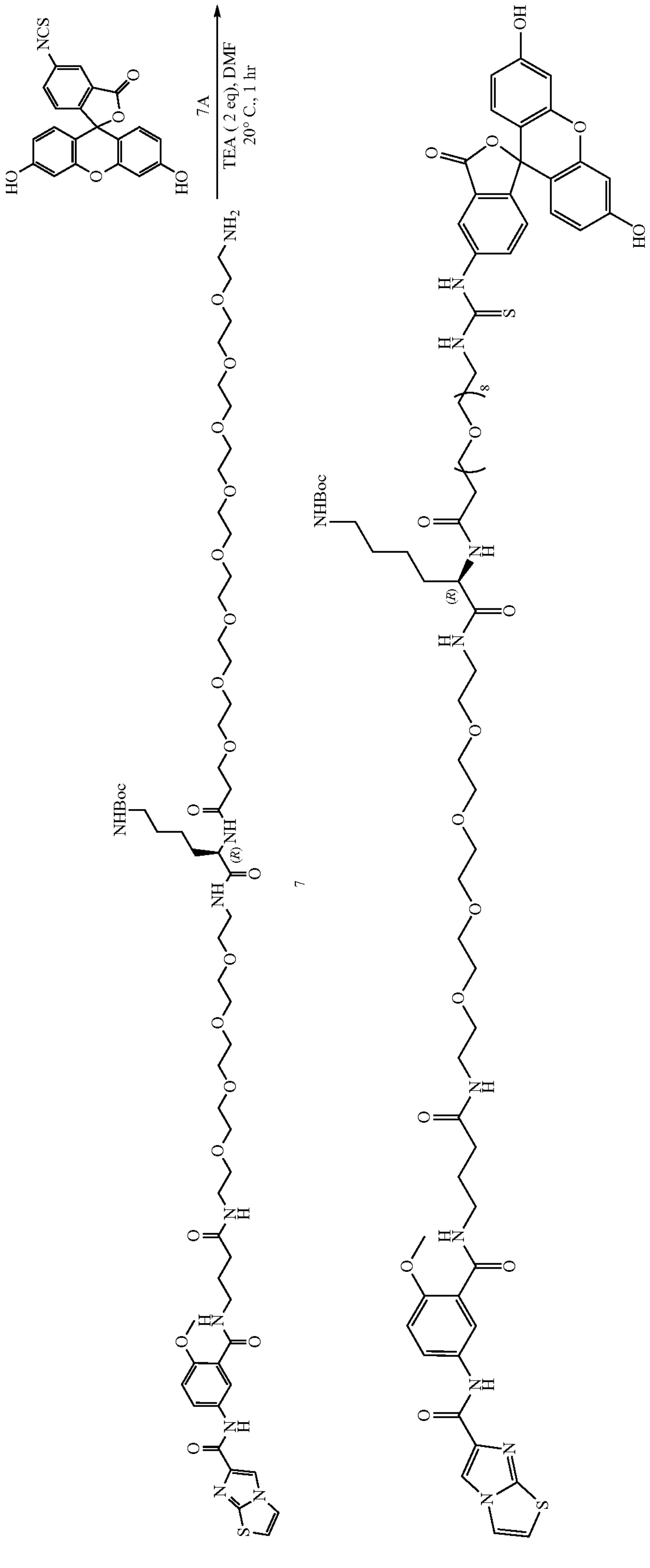
7
8

To a solution of compound 7 (200 mg, 157.17 umol, 1 eq) in DMF (2 mL) was added TEA (31.81 mg, 314.34 umol, 43.75 uL, 2 eq) and compound 7A (60 mg, 154.09 umol, 0.98 eq). The mixture was stirred at 20° C. for 1 hr. LC-MS showed desired mass was detected. The mixture was purified directly. The residue was purified by prep-HPLC (column: Nano-micro Kromasil C18 100*30 mm 5 um; mobile phase: [water (0.1% TFA)-ACN]; B %: 30%-55%, 10 min). Compound 8 (100 mg, 53.55 umol, 34.07% yield, 89% purity) was obtained as yellow solid checked by HNMR and LCMS. LCMS: RT=1.805 min, MS cal.: 1660.69, $[1/2M+H]^+$=831.8. LCMS: RT=1.265 min, MS cal.: 1660.69, $[1/2M+H]^+$=831.8. $^1$H NMR (400 MHz, DMSO-$d_6$) δ ppm 10.12-10.07 (m, 1H), 10.05-9.98 (m, 1H), 8.35-8.30 (m, 1H), 8.28-8.24 (m, 1H), 8.22-8.17 (m, 2H), 7.99-7.96 (m, 1H), 7.94-7.87 (m, 3H), 7.87-7.80 (m, 1H), 7.74-7.67 (m, 1H), 7.44-7.37 (m, 1H), 7.18-7.13 (m, 1H), 7.10-7.06 (m, 1H), 6.75-6.69 (m, 1H), 6.67-6.62 (m, 2H), 6.62-6.51 (m, 4H), 3.87-3.79 (m, 4H), 3.60-3.50 (m, 95H), 3.51-3.44 (m, 51H), 3.40-3.32 (m, 5H), 3.28-3.20 (m, 2H), 3.20-3.10 (m, 4H), 2.88-2.80 (m, 2H), 2.44-2.26 (m, 2H), 2.17-2.08 (m, 2H), 1.76-1.68 (m, 2H), 1.61-1.50 (m, 1H), 1.49-1.40 (m, 1H), 1.38-1.29 (m, 12H), 1.23-1.10 (m, 2H).

General Procedure for Preparation of Compound 9:

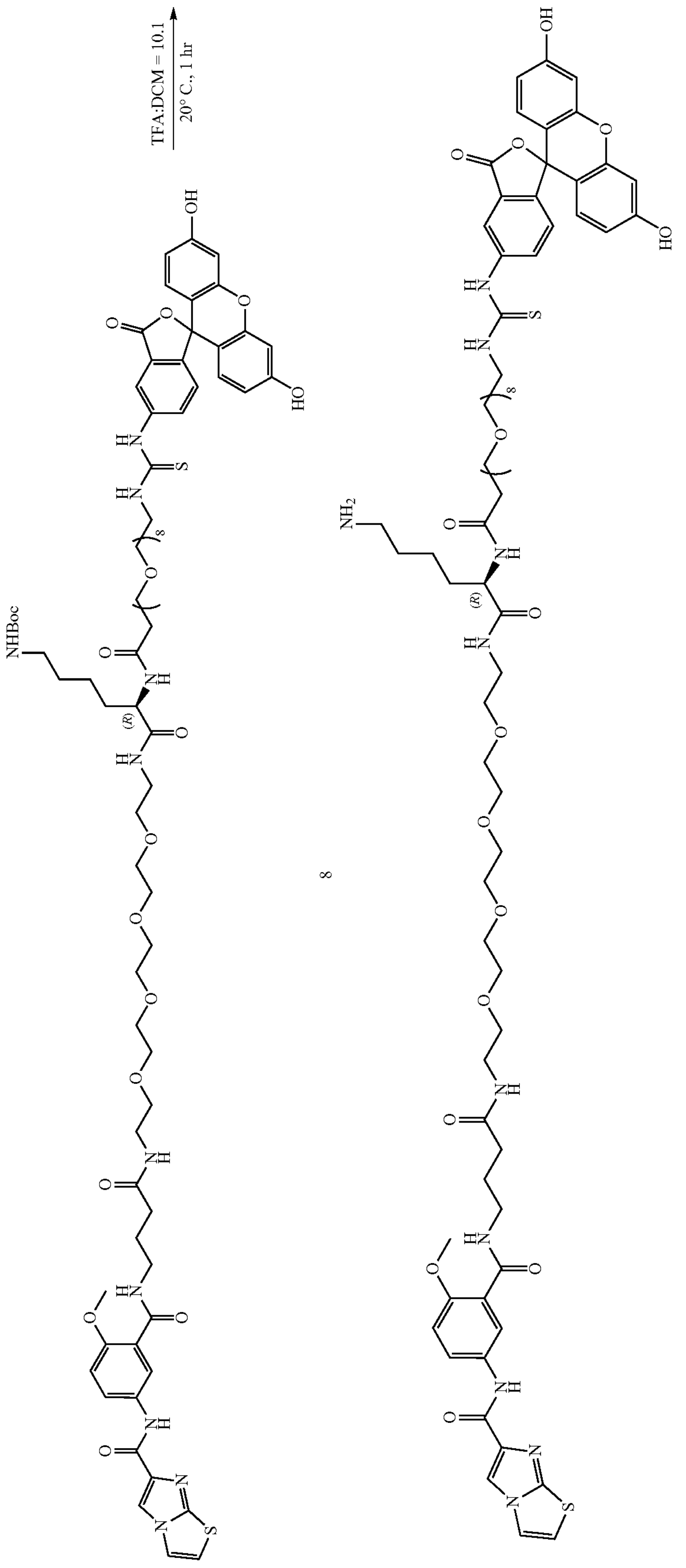
8
9

To a solution of compound 8 (6 mg, 3.61 umol, 1 eq) in DCM (0.5 mL) was added TFA (61.60 mg, 540.24 umol, 0.04 mL, 149.64 eq). The mixture was stirred at 20° C. for 0.5 hr. LC-MS showed desired mass was detected. The reaction mixture was dried under nitrogen gas. Compound 9 (5.64 mg, 3.61 umol, 100% yield) was obtained as yellow solid. LCMS: Rt=1.153 min, MS cal.: 1560.64, $[1/2M+H]^+$= 781.7.

General Procedure for Preparation of Compound I-4:

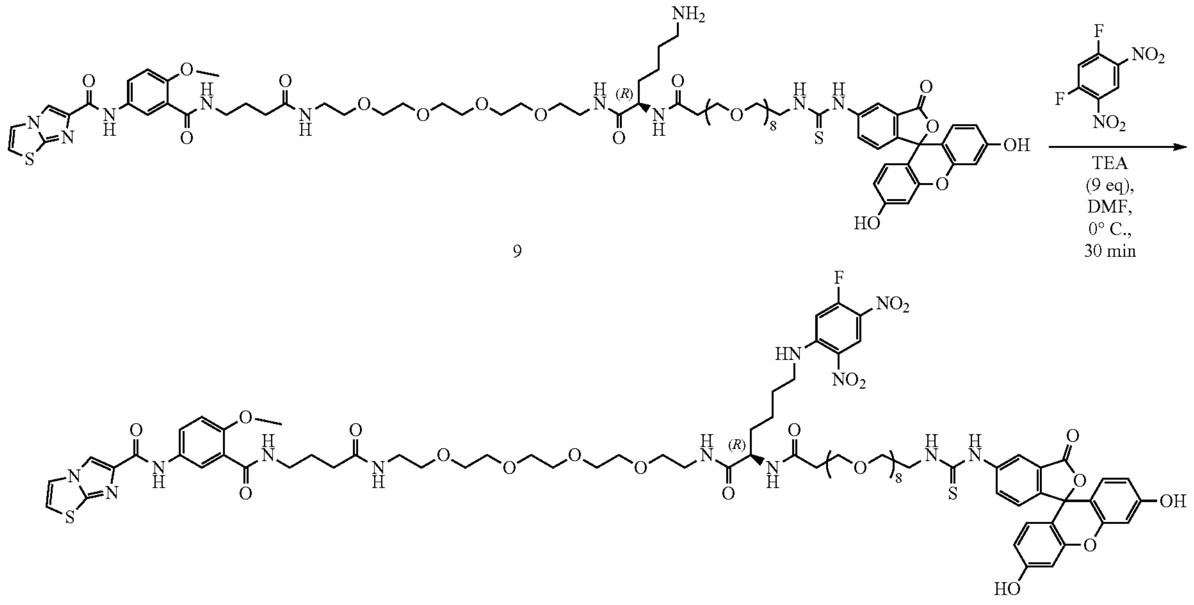

9

I-4

To a solution of compound 9 (18.8 mg, 12.04 umol, 1 eq) in DMF (1 mL) was added TEA (10.96 mg, 108.34 umol, 15.08 uL, 9 eq). The mixture was combined with 1,5-difluoro-2,4-dinitro-benzene (2.46 mg, 12.04 umol, 2.94e-1 uL, 1 eq) at 0° C. The mixture was stirred at 0° C. for 30 min. LC-MS showed desired mass was detected. The mixture was purified directly. The residue was purified by prep-HPLC (TFA condition; column: Nano-micro Kromasil C18 80*25 mm*3 um; mobile phase: [water (0.1% TFA)-ACN]; B %: 35%-55%, 10 min). Compound I-4 (1.02 mg, 5.38e-1 umol, 4.47% yield, 92% purity) was obtained as yellow solid checked by HPLC, MS and HNMR. LCMS: RT=2.591 min, MS cal.: 1744.63, $[1/2M+H]^+$=873.8. MS: MS cal.: 1744.63, $[1/2M+H]^+$=874.0. HPLC: RT=3.003 min. $^1H$ NMR (400 MHz, DMSO-$d_6$) δ ppm 10.17-10.07 (m, 2H), 10.06-9.99 (m, 1H), 8.91-8.79 (m, 2H), 8.34-8.30 (m, 1H), 8.30-8.25 (m, 1H), 8.30-8.24 (m, 1H), 8.23-8.15 (m, 2H), 8.12-8.04 (m, 1H), 8.01-7.93 (m, 2H), 7.92-7.83 (m, 2H), 7.77-7.69 (m, 1H), 7.44-7.40 (m, 1H), 7.24-7.14 (m, 1H), 7.12-7.05 (m, 1H), 6.98-6.92 (m, 1H), 6.70-6.64 (m, 2H), 6.62-6.52 (m, 3H), 4.29-4.20 (m, 1H), 3.90-3.83 (m, 3H), 3.64-3.36 (m, 206H), 3.33-3.24 (m, 11H), 3.22-3.13 (m, 7H), 2.40-2.26 (m, 6H), 2.17-2.08 (m, 3H), 1.80-1.70 (m, 2H), 1.66-1.44 (m, 4H), 1.37-1.26 (m, 2H), 1.26-1.19 (m, 2H).

Example 5. Exemplary Synthesis of Compound I-5

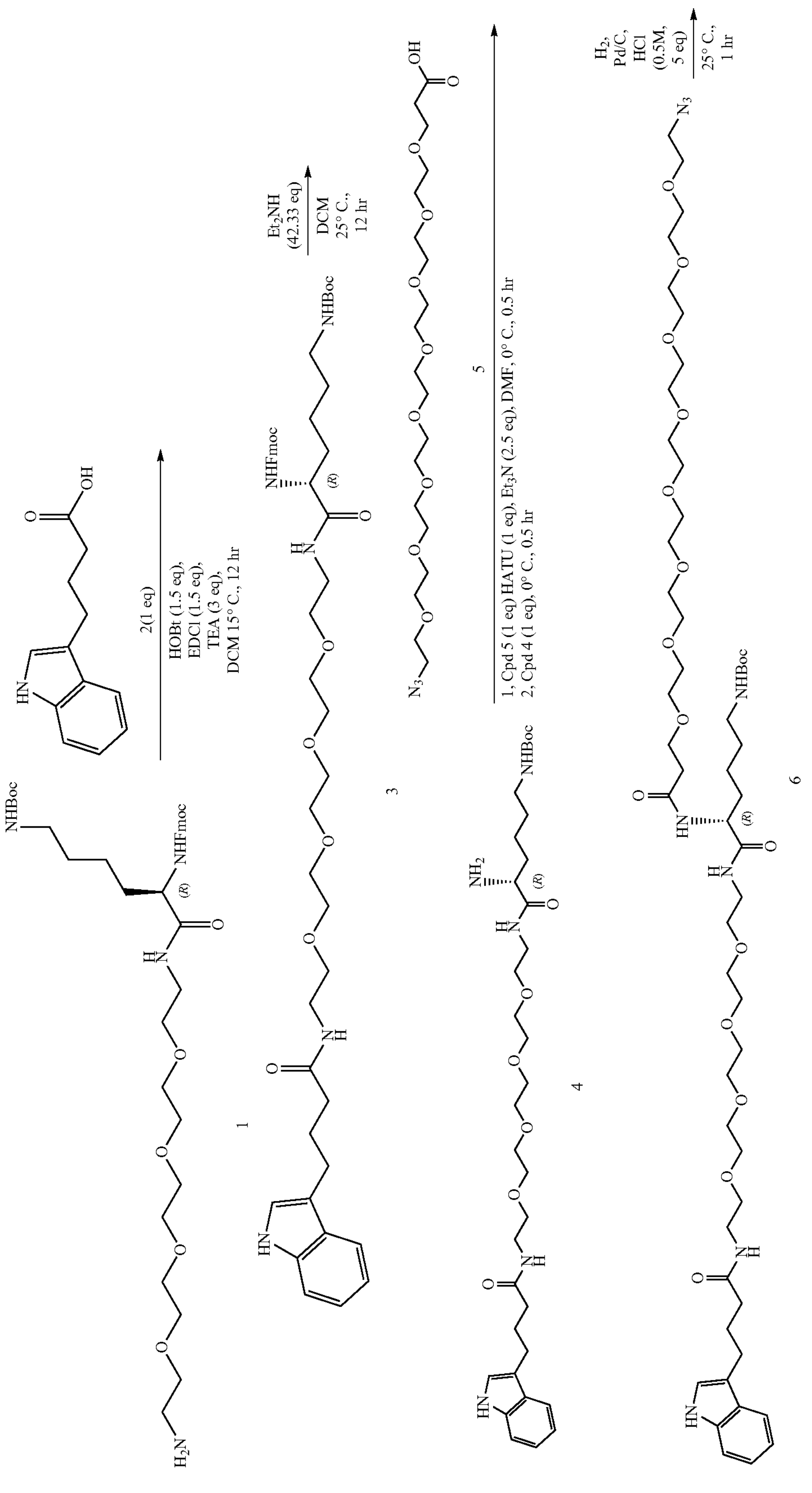
1
2(1 eq)
HOBt (1.5 eq),
EDCl (1.5 eq),
TEA (3 eq),
DCM 15° C., 12 hr
3
Et2NH
(42.33 eq)
DCM
25° C.,
12 hr
4
5
1, Cpd 5 (1 eq) HATU (1 eq), Et3N (2.5 eq), DMF, 0° C., 0.5 hr
2, Cpd 4 (1 eq), 0° C., 0.5 hr
6
H2,
Pd/C,
HCl
(0.5M,
5 eq)
25° C.,
1 hr -continued
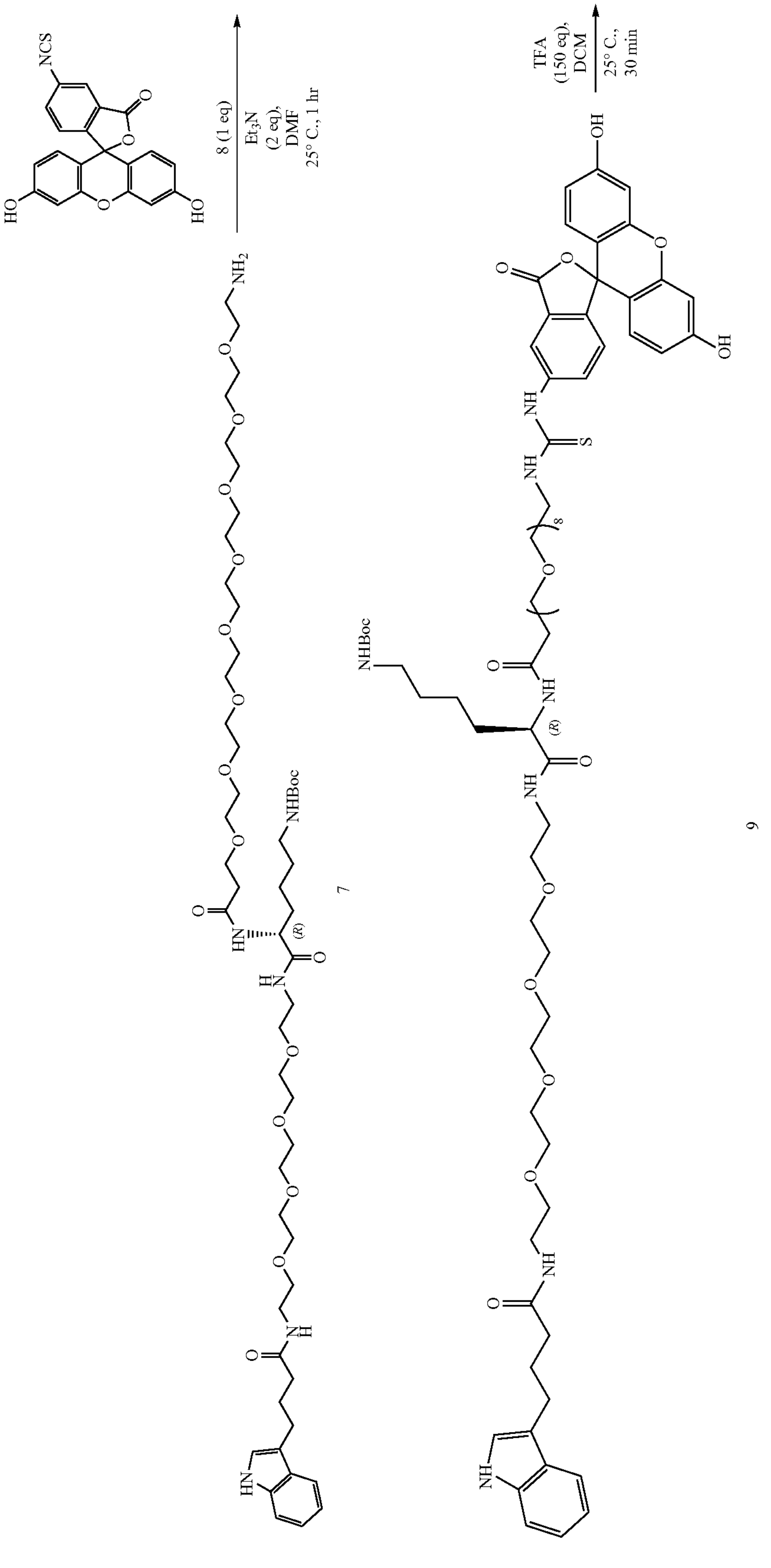
7
9

-continued
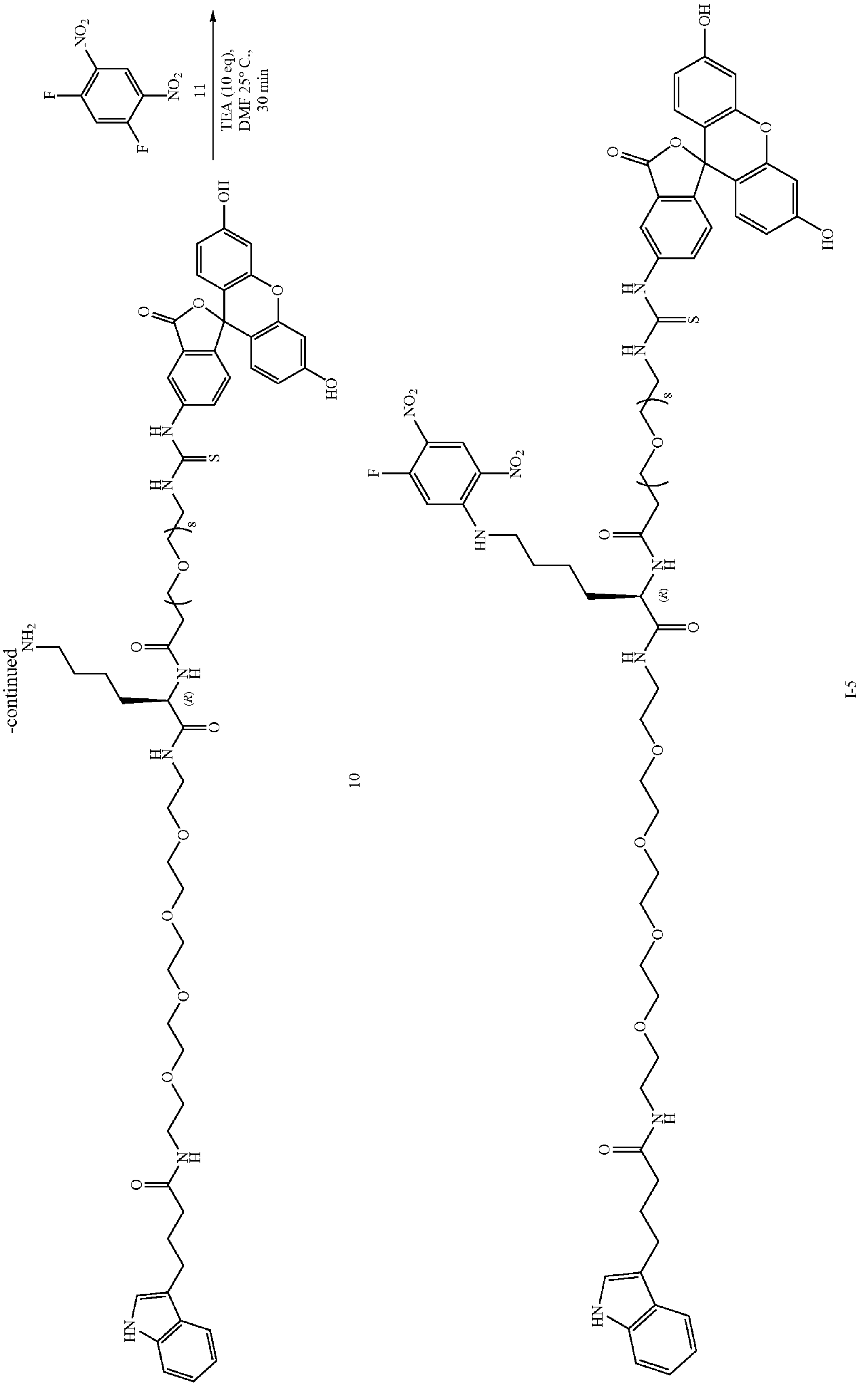
10
I-5

General Procedure for Preparation of Compound 3:

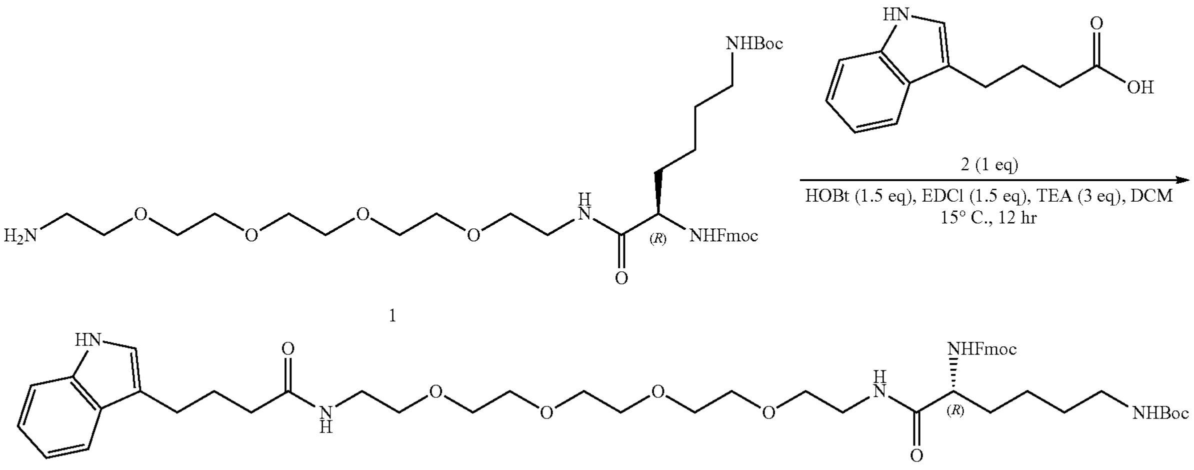

1

3

To a solution of compound 1 (1 g, 1.31 mmol, 1 eq) in DCM (40 mL) was added TEA (397.79 mg, 3.93 mmol, 547.16 uL, 3 eq), EDCI (376.80 mg, 1.97 mmol, 1.5 eq), Compound 2 (266.31 mg, 1.31 mmol, 1 eq) and HOBt (265.59 mg, 1.97 mmol, 1.5 eq). The mixture was stirred at 15° C. for 12 hr. LC-MS (Rt=1.489 min) showed compound 1 was consumed completely and one main peak with desired mass was detected. The reaction mixture was partitioned between DCM (40 mL) and 0.5 M HCl (40 mL). The organic phase was separated, washed with brine 40 mL, dried over $Na_2SO_4$, filtered and concentrated under reduced pressure to give a residue. The residue was purified by column chromatography ($SiO_2$, Dichloromethane:Methanol=80:1 to 20:1). Compound 3 (900 mg, 940.31 umol, 71.76% yield) was obtained as a yellow solid. LCMS: RT=1.489 min, MS cal.: 871.5, $[M+H]^+$=872.5. $^1$H NMR (400 MHz, METHANOL-d4) δ ppm 7.77-7.87 (m, 2H) 7.63-7.72 (m, 2H) 7.50-7.57 (m, 1H) 7.37-7.44 (m, 2H) 7.28-7.35 (m, 3H) 6.94-7.12 (m, 3H) 4.33-4.48 (m, 2H) 4.18-4.29 (m, 1H) 4.00-4.11 (m, 1H) 3.42-3.65 (m, 19H) 3.18-3.27 (m, 1H) 2.99-3.09 (m, 2H) 2.73-2.84 (m, 2H) 2.22-2.33 (m, 2H) 1.96-2.07 (m, 2H) 1.68-1.82 (m, 1H) 1.55-1.68 (m, 2H) 1.39-1.54 (m, 14H) 1.28-1.36 (m, 3H).

General Procedure for Preparation of Compound 4:

To a solution of compound 3 (900 mg, 1.03 mmol, 1 eq) in DCM (9 mL) was added $Et_2NH$ (3.19 g, 43.69 mmol, 4.50 mL, 42.33 eq). The mixture was stirred at 25° C. for 12 hr. LC-MS (Rt=1.970 min) showed compound 3 was consumed completely and one main peak with desired mass was detected. The reaction mixture was concentrated under reduced pressure to remove solvent. The residue was used for the next step directly. Compound 4 (670.64 mg, 1.03 mmol, 100.00% yield) was obtained as a yellow oil. LCMS: RT=1.970 min, MS cal.: 649.6, $[M+H]^+$=650.4. $^1$H NMR (400 MHz, CHLOROFORM-d) δ 8.43-8.53 (m, 1H) 7.60-7.71 (m, 2H) 7.50-7.56 (m, 1H) 7.37-7.44 (m, 1H) 7.21-7.35 (m, 4H) 7.07-7.14 (m, 1H) 7.00-7.05 (m, 1H) 6.95-6.99 (m, 1H) 5.98-6.05 (m, 1H) 3.51-3.63 (m, 9H) 3.43-3.50 (m, 3H) 3.30-3.41 (m, 3H) 3.16-3.22 (m, 1H) 2.99-3.08 (m, 1H) 2.84-2.98 (m, 3H) 2.69-2.80 (m, 1H) 2.09-2.23 (m, 2H) 1.93-2.07 (m, 2H) 1.66-1.81 (m, 2H) 0.92-1.08 (m, 1H) 0.68-0.87 (m, 1H).

General Procedure for Preparation of Compound 6:

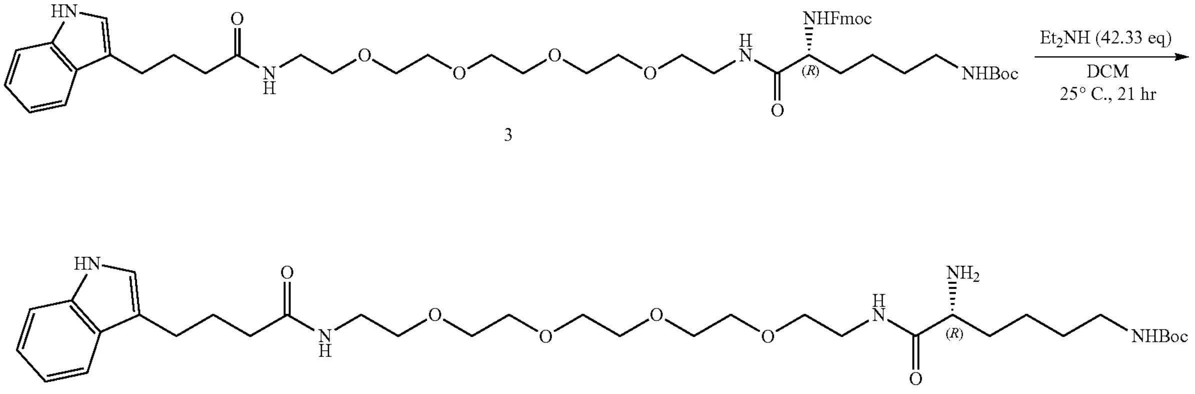

3

4

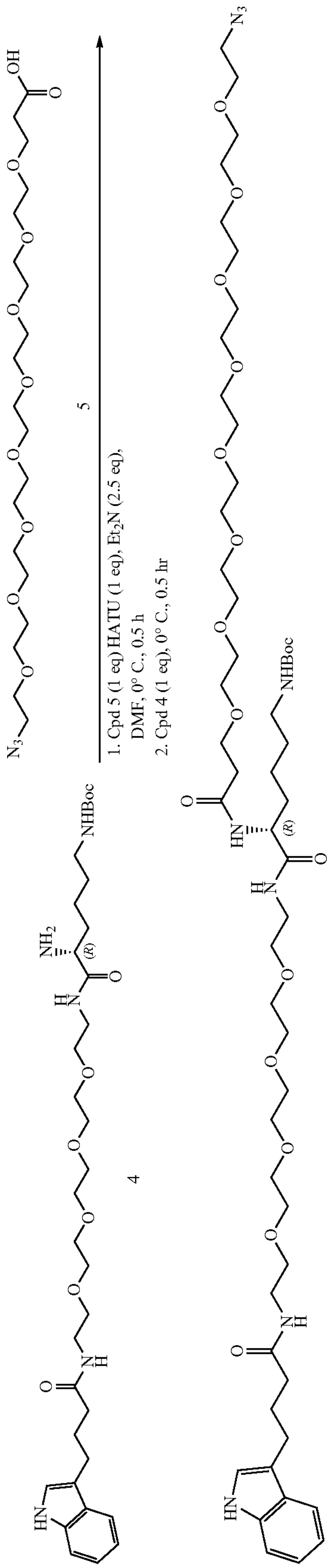
4
5
6

To a solution of compound 5 (730 mg, 1.56 mmol, 1.5 eq) in DCM (10 mL) was added $Et_3N$ (263.34 mg, 2.60 mmol, 362.23 uL, 2.5 eq) and HATU (395.81 mg, 1.04 mmol, 1 eq). The mixture was stirred at 0° C. for 30 min. The compound 4 (676.44 mg, 1.04 mmol, 1 eq) was added to the reaction mixture. The mixture was stirred at 0° C. for 30 min. LC-MS (Rt=1.365 min) showed compound 4 was consumed completely and one main peak with desired mass was detected. The reaction mixture was partitioned between DCM (10 mL) and $H_2O$ (10 mL). The combined organic layers were washed with $NH_4Cl$ (10 mL), dried over $Na_2SO_4$, filtered and concentrated under reduced pressure to give a residue. The residue was purified by column chromatography ($SiO_2$, Dichloromethane:Methanol=50:1 to 1:1). Compound 6 (1.1 g, 1.00 mmol, 96.12% yield) was obtained as a yellow oil. LCMS: RT=1.317 min, MS cal.: 1098.6, $[M/2+H]^+$=550.6. $^1H$ NMR (400 MHz, CHLOROFORM-d) δ 8.58-8.64 (m, 1H) 7.93-7.98 (m, 8H) 7.61-7.69 (m, 4H) 7.49-7.53 (m, 2H) 7.27-7.34 (m, 4H) 7.22-7.27 (m, 3H) 7.05-7.12 (m, 2H) 6.95-7.04 (m, 3H) 6.72-6.82 (m, 2H) 6.26-6.32 (m, 1H) 5.99-6.03 (m, 2H) 4.64-4.76 (m, 1H) 4.21-4.30 (m, 2H) 3.67-3.67 (m, 1H) 3.50-3.62 (m, 122H) 3.24-3.39 (m, 18H) 3.11-3.18 (m, 3H) 2.81 (s, 44H) 2.79-2.85 (m, 1H) 2.71-2.75 (m, 11H) 2.52-2.58 (m, 3H) 2.36-2.44 (m, 3H) 2.12-2.19 (m, 3H) 1.95-2.03 (m, 3H) 1.33-1.41 (m, 23H) 1.28-1.33 (m, 5H) 1.08-1.13 (m, 3H) 1.01-1.06 (m, 3H).

General Procedure for Preparation of Compound 7:

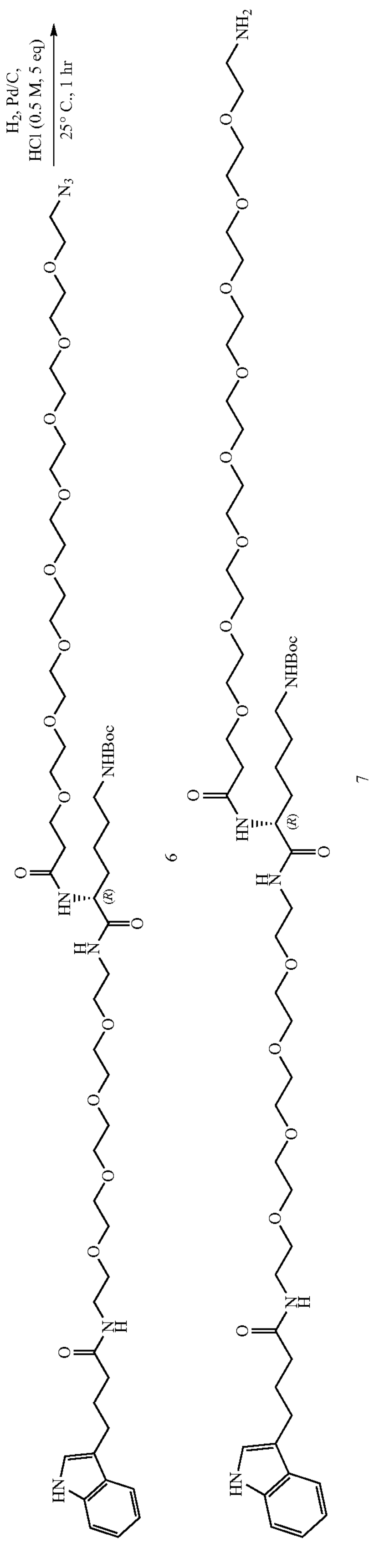
6
7

To a solution of compound 6 (500 mg, 454.83 umol, 1 eq) in THF (5 mL) was added HCl (0.5 M, 4.55 mL, 5 eq) and Pd/C (454.83 umol, 500 mg). The mixture was stirred at 25° C. for 1 hr. LC-MS (Rt=2.109 min) showed compound 6 was consumed completely and one main peak with desired mass was detected. To the reaction mixture was added ethyl acetate 20 mL. The organic phase was separated. The aqueous phase was basified to pH 8 with $NaHCO_3$, and subsequently extracted with DCM (30 ml*6). The combined organic phases were washed with brine (20 mL), dried over $Na_2SO_4$, filtered and concentrated under reduced pressure to give a residue. Compound 7 (480 mg, 447.21 umol, 98.33% yield) was obtained as a yellow oil. LCMS: RT=2.109 min, MS cal.: 1072.7, $[M/2+H]^+$=537.6.

General Procedure for Preparation of Compound 9

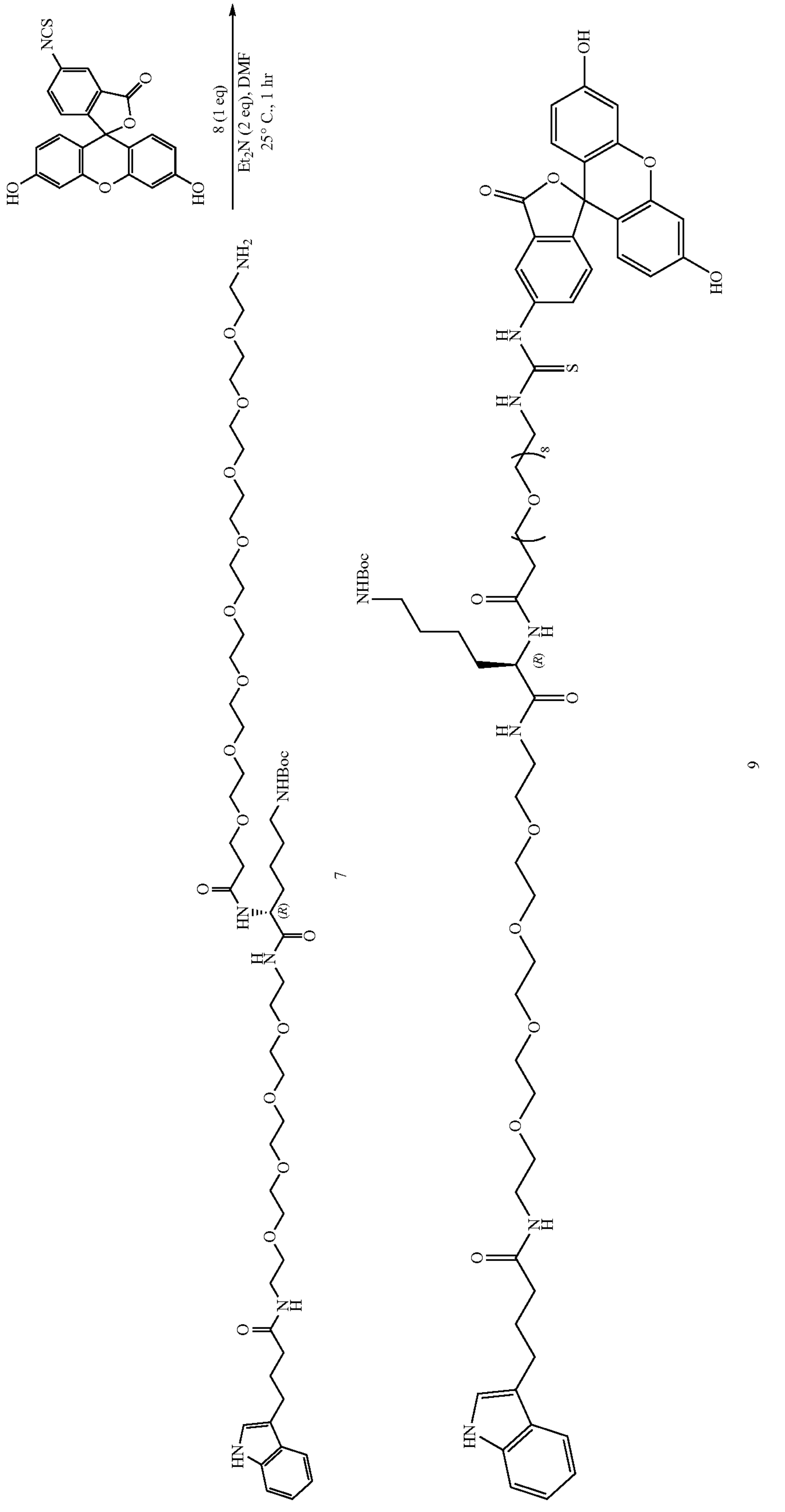
7
9

To a solution of compound 7 (220 mg, 204.97 umol, 1 eq) in DMF (3 mL) was added $Et_3N$ (41.48 mg, 409.95 umol, 57.06 uL, 2 eq) and compound 8 (79.81 mg, 204.97 umol, 1 eq). The mixture was stirred at 25° C. for 1 hr. LC-MS (Rt=1.308 min) showed compound 7 was consumed completely and one main peak with desired mass was detected. The reaction mixture was concentrated under reduced pressure to remove solvent. The residue was purified by prep-HPLC (basic condition: column: Waters Xbridge Prep OBD C18 150*40 mm*10 um; mobile phase: [water (0.04% $NH_3H_2O$+10 mM $NH_4HCO_3$)-ACN]; B %: 10%-40%, 10 min). Compound 7 (100 mg, 68.37 umol, 33.35% yield) was obtained as a yellow solid. LCMS: RT=1.308 min, MS cal.: 1461.7, $[M/2+H]^+$=732.2.

General Procedure for Preparation of Compound 10:

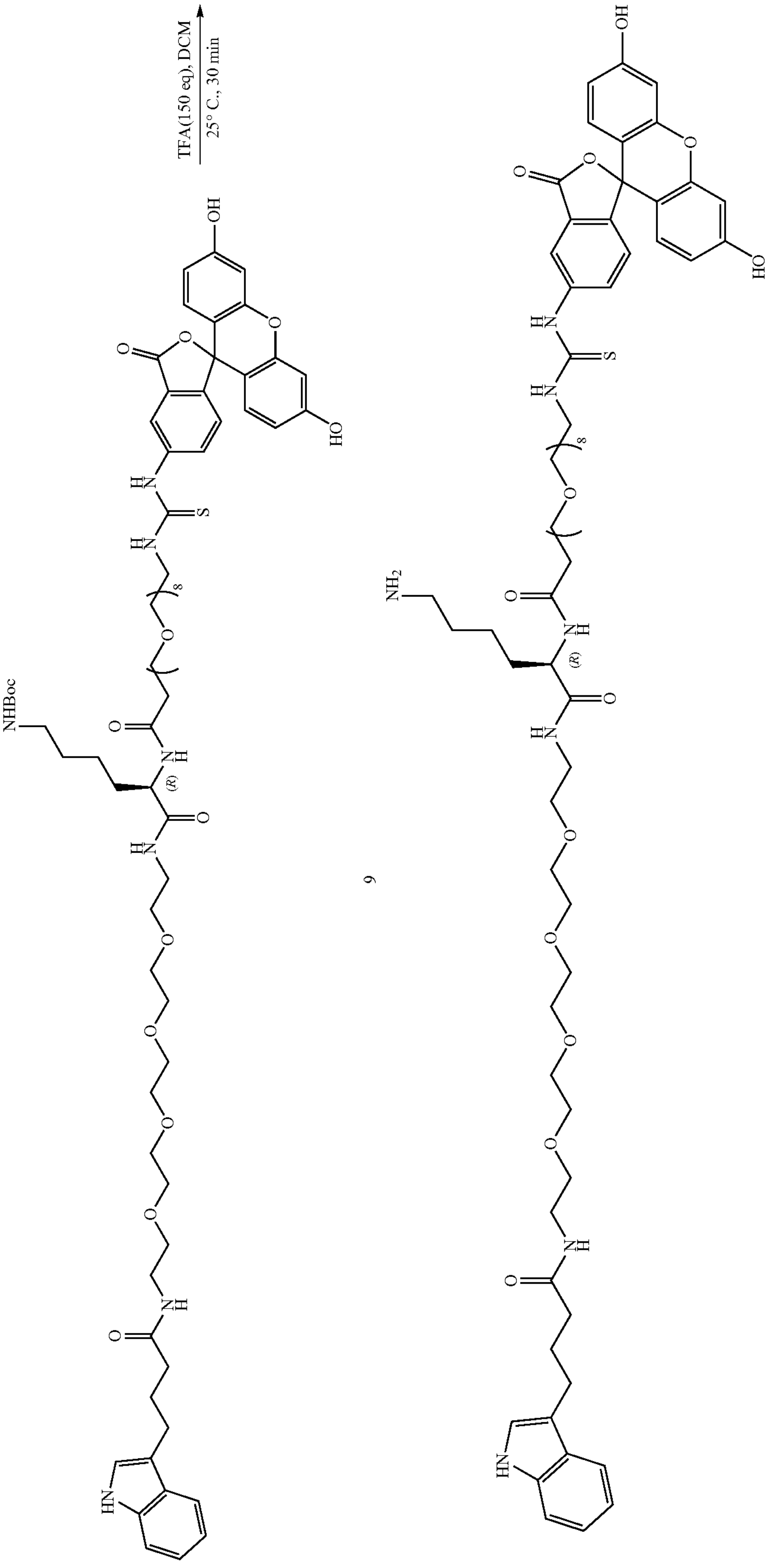
9
10

A mixture of compound 9 (60 mg, 41.02 umol, 1 eq) and TFA (154.00 mg, 1.35 mmol, 0.1 mL, 32.93 eq) in DCM (1 mL) was degassed and purged with $N_2$ 3 times, and then stirred at 20° C. for 1 hr under $N_2$ atmosphere. LCMS showed the starting material was consumed completely. The reaction mixture was filtered and the filtrate was concentrated. Compound 10 (55.89 mg, crude) was obtained as a yellow oil. LCMS: RT=1.171 min, MS cal.: 1053.4, $[M2+H]^+$=682.2.

General Procedure for Preparation of Compound I-5:

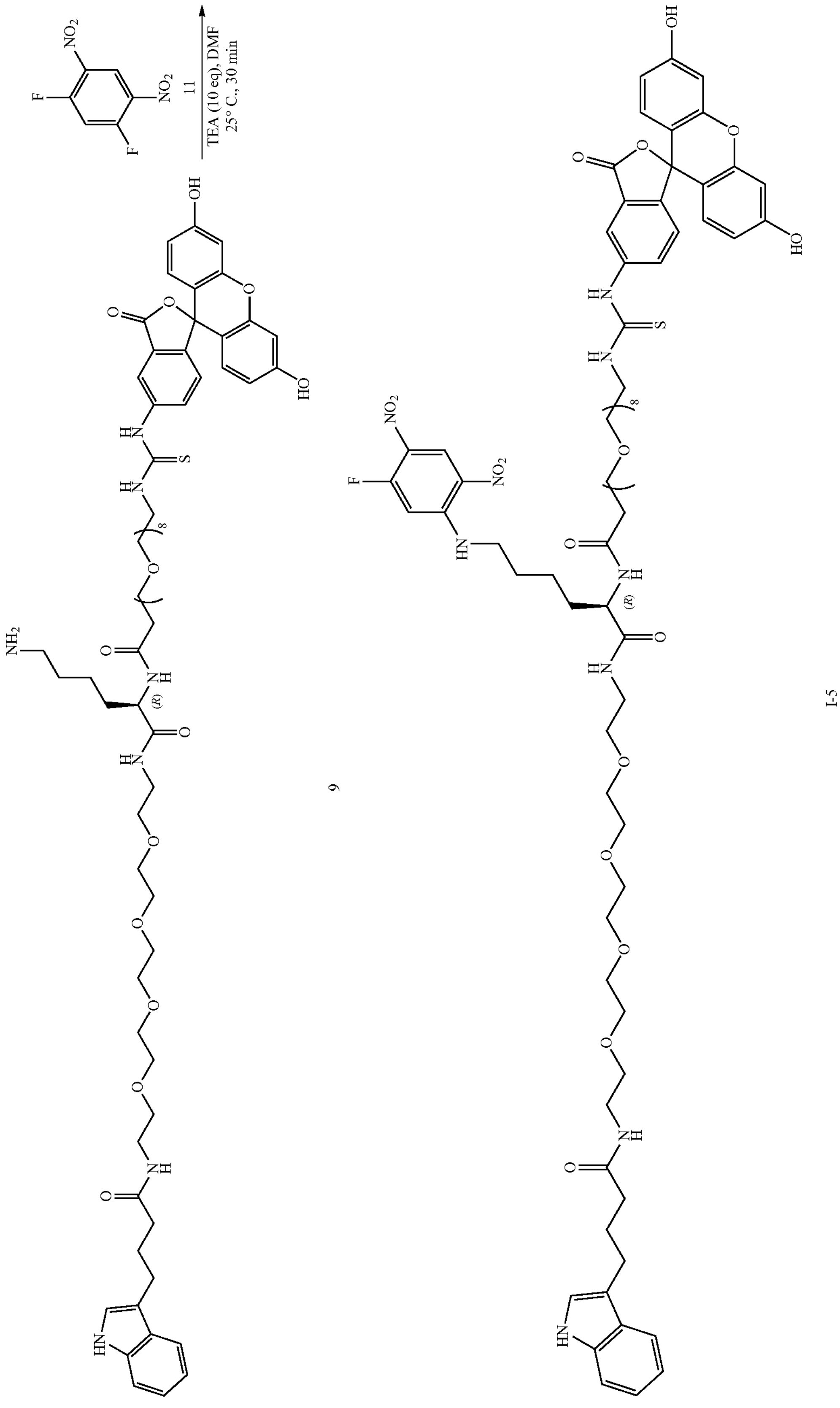
9
I-5

To a solution of Compound 10 (55.89 mg, 37.85 umol, 1 eq, TFA) in DMF (1 mL) was added Et3N (38.30 mg, 378.50 umol, 52.68 uL, 10 eq) and compound 11 (7.72 mg, 37.85 umol, 1 eq). The mixture was stirred at 25° C. for 30 min. LCMS showed the starting material was consumed completely. HPLC (RT=2.160 min) showed the starting material was consumed completely. The reaction mixture was filtered and the filter was concentrated. The crude product was purified by reversed-phase HPLC (column: Waters Xbridge BEH C18 100*30 mm*10 um; mobile phase: [water (0.1% TFA)-ACN]; B %: 250%-85%, 10 min). Compound I-5 (2.68 mg, 1.73 umol, 4.58% yield) was obtained as a white solid. LCMS: RT=2.822 min, MS cal.: 1234.7, $[M/2+H]^+$=774.2. HPLC: RT=3.160 min. $^1H$ NMR (400 MHz, DMSO-$d_6$) δ ppm 9.98-10.22 (m, 3H) 8.84-8.92 (m, 2H) 8.27 (s, 1H) 8.09 (br s, 1H) 7.94-8.01 (m, 2H) 7.81-7.87 (m, 1H) 7.74 (br d, J=6.36 Hz, 1H) 7.48 (d, J=7.46 Hz, 1H) 7.31 (d, J=8.19 Hz, 1H) 7.02-7.24 (m, 6H) 6.92-6.99 (m, 2H) 6.67 (d, J=2.20 Hz, 2H) 6.54-6.62 (m, 5H) 4.20-4.31 (m, 2H) 3.69 (br s, 5H) 3.57 (br s, 13H) 3.12-3.27 (m, 7H) 2.55-2.73 (m, 9H) 2.52-2.55 (m, 12H) 2.32-2.45 (m, 9H) 2.08-2.15 (m, 2H) 1.80-1.88 (m, 2H) 1.46-1.68 (m, 5H) 1.16-1.40 (m, 4H). MS: $[M/2+H]^+$=773.9.

Example 6. Exemplary Synthesis of Compound I-6

General Procedure for Preparation of Fragment 7:

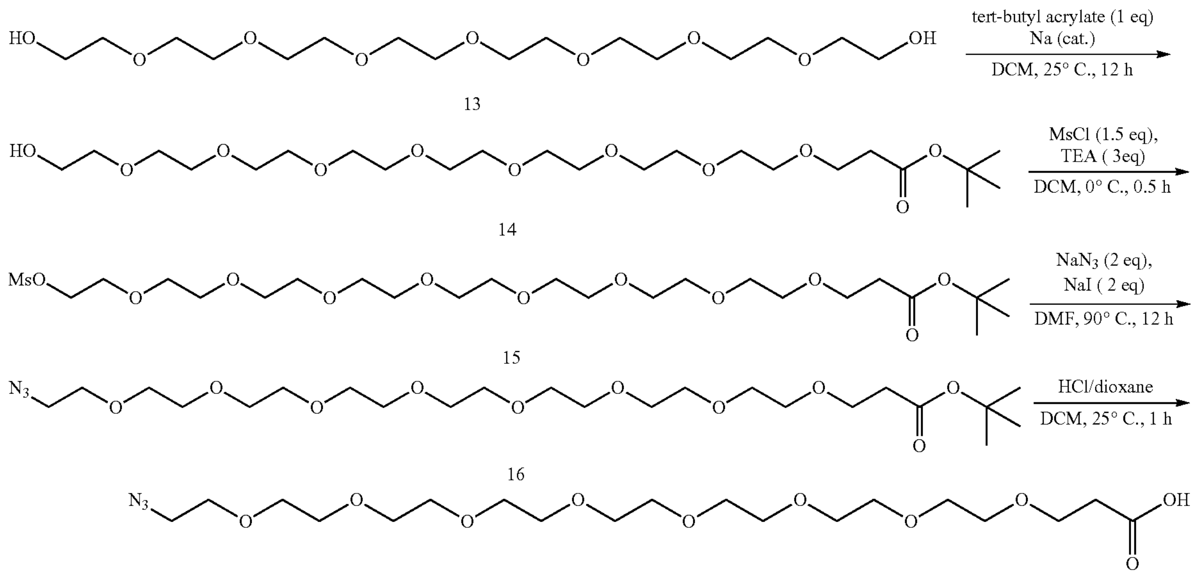

13

14

15

16

7

General Procedure for Preparation of Compound I-6:

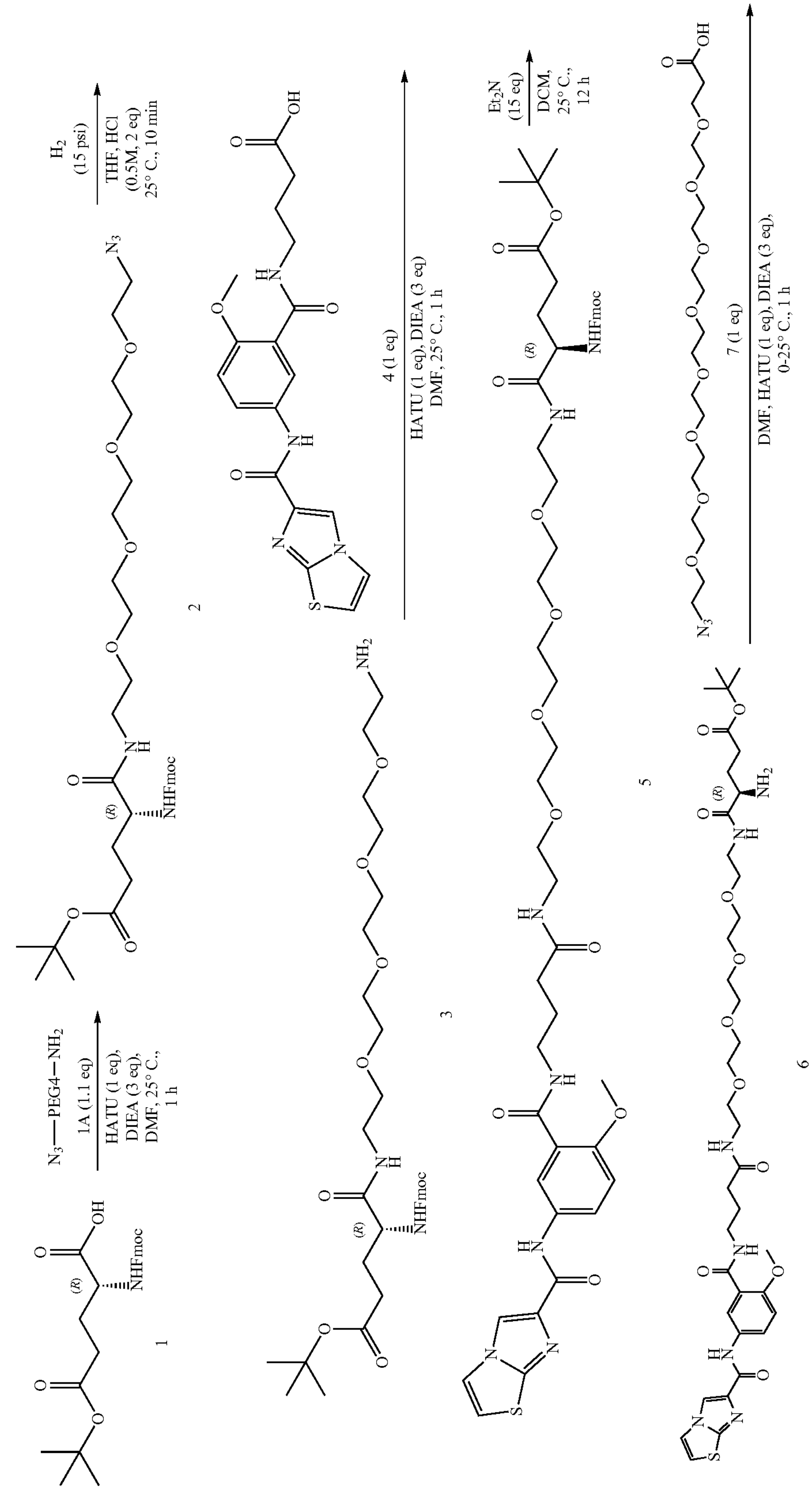
1 2 3 5 6

-continued
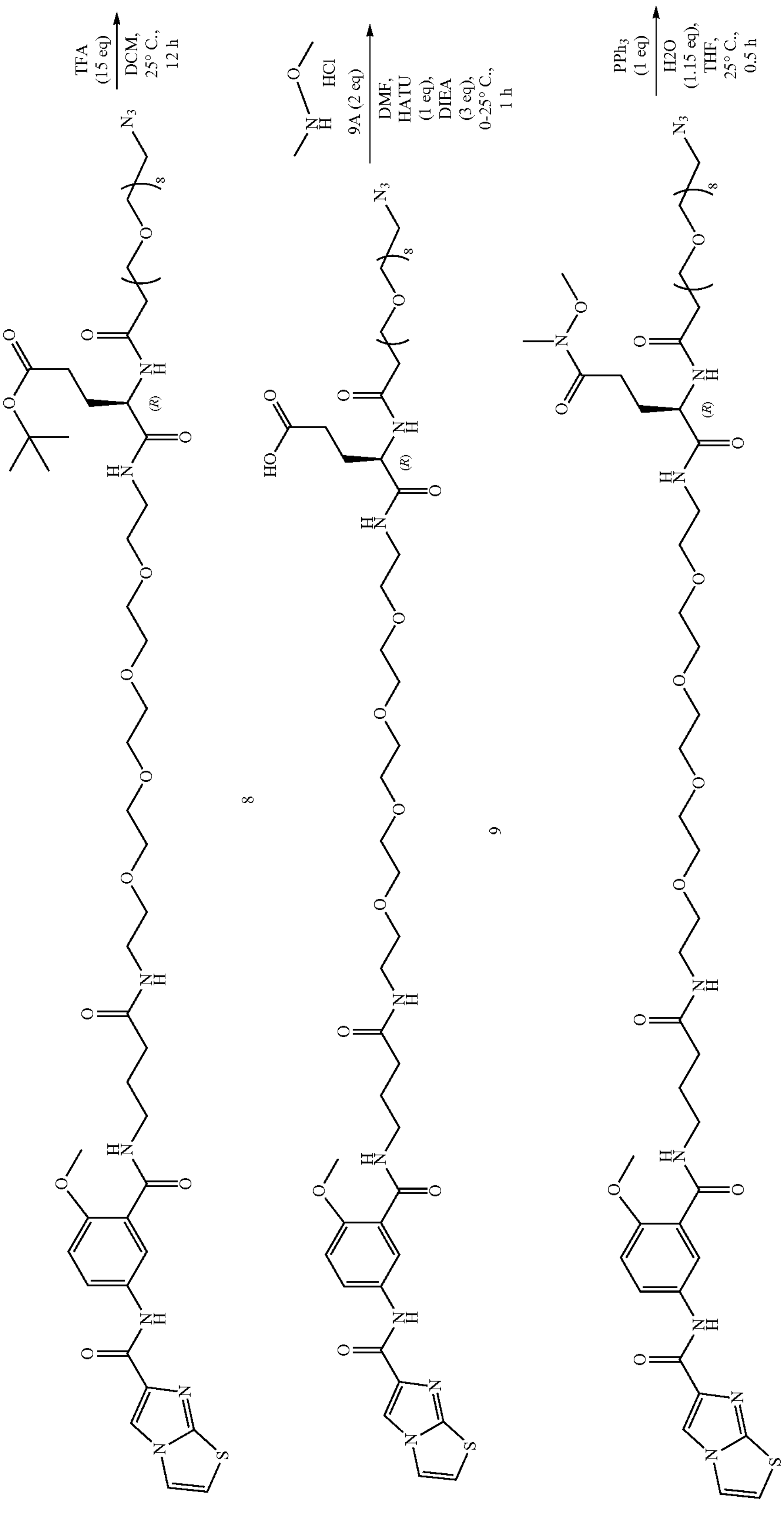
8
9
10

-continued
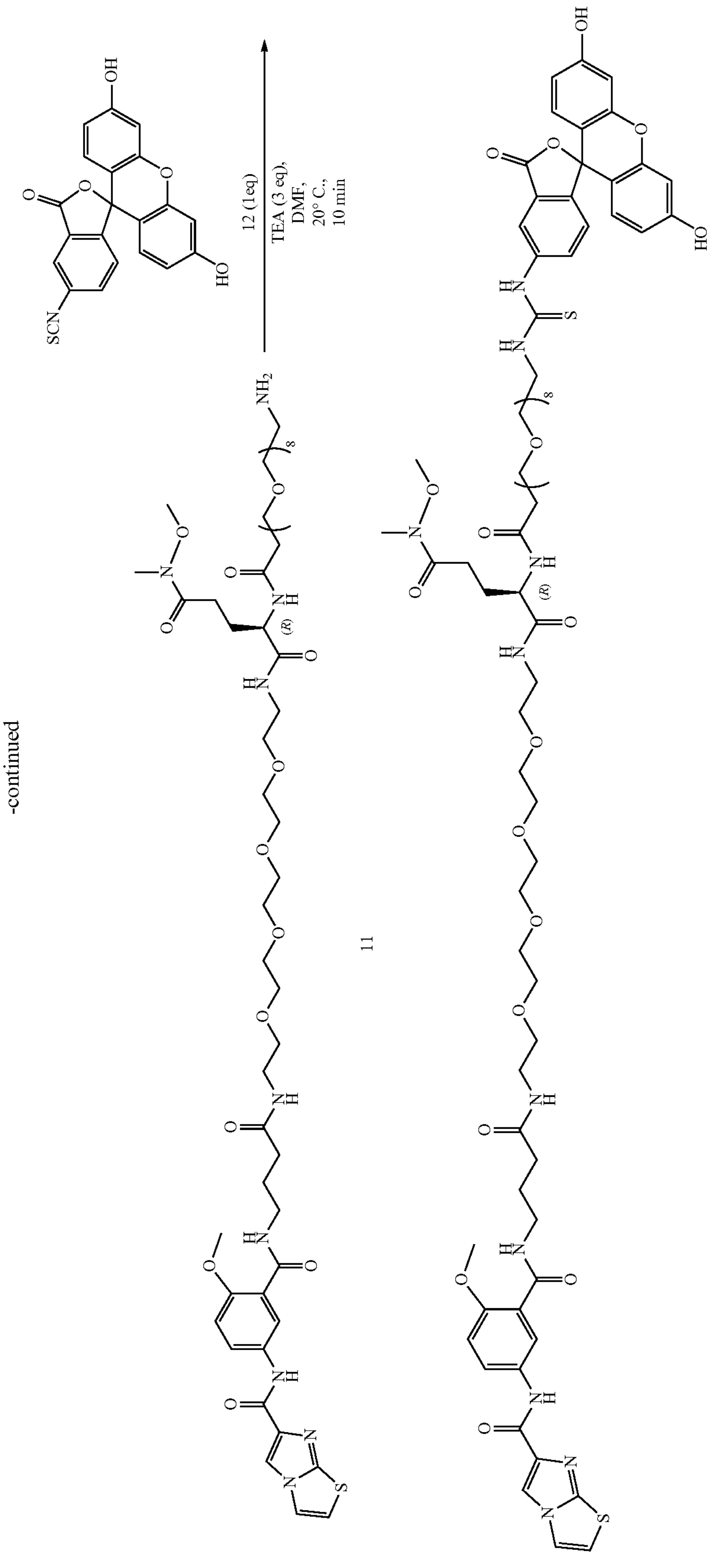
11
I-6

General Procedure for Preparation of Compound 14:

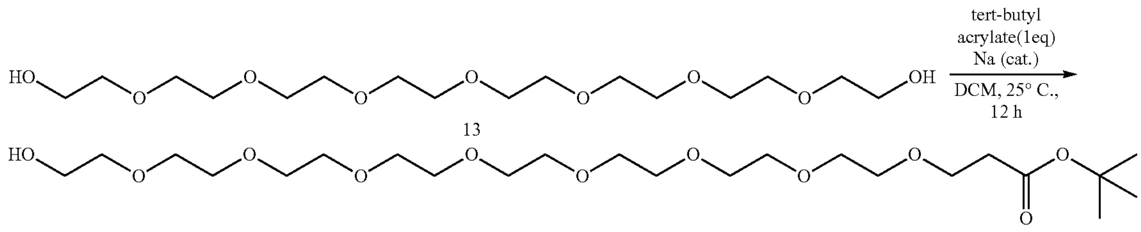

13

14

To a solution of compound 13 (16 g, 43.19 mmol, 1 eq) in DCM (70 mL) was added Na (29.79 mg, 1.30 mmol, 30.71 uL, 0.03 eq) and tert-butyl acrylate (5.54 g, 43.19 mmol, 6.27 mL, 1 eq). The mixture was stirred at 25° C. for 12 hr. TLC (Dichloromethane:Methanol=10:1 $R_f$=0.43) showed the reaction was complete. The reaction mixture was concentrated under reduced pressure to remove DCM. The residue was diluted with $H_2O$ 100 mL and extracted with EtOAc (200 mL*3). The combined organic layers were washed with brine (300 mL*1), dried over $Na_2SO_4$, filtered and concentrated under reduced pressure to give a residue. Compound 14 (16 g, 35.20 mmol, 81.49% yield) was obtained as a yellow oil.

General Procedure for Preparation of Compound 15:

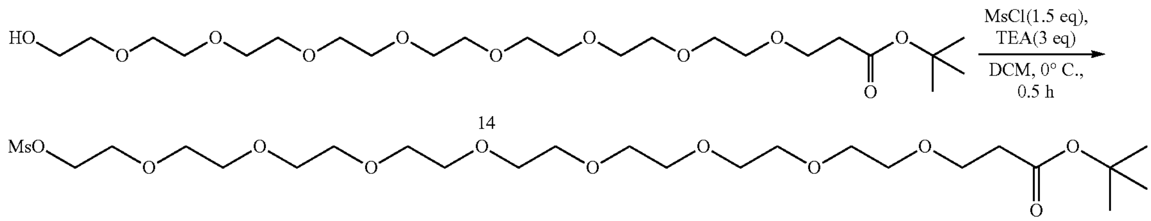

14

15

To a solution of compound 14 (17 g, 34.10 mmol, 1 eq) in DCM (130 mL) was added MsCl (5.86 g, 51.14 mmol, 3.96 mL, 1.5 eq) and TEA (10.35 g, 102.29 mmol, 14.24 mL, 3 eq). The mixture was stirred at 0° C. for 0.5 hr. TLC (Dichloromethane:Methanol=10:1 $R_f$=0.6) showed the reaction was complete. The residue was diluted with $H_2O$ 300 mL and extracted with DCM (200 mL*2). The combined organic layers were washed with 0.5 M HCl (200 mL*2), dried over $Na_2SO_4$, filtered and concentrated under reduced pressure to give a residue. Compound 15 (19 g, 32.95 mmol, 96.63% yield) was obtained as a yellow oil.

General Procedure for Preparation of Compound 16:

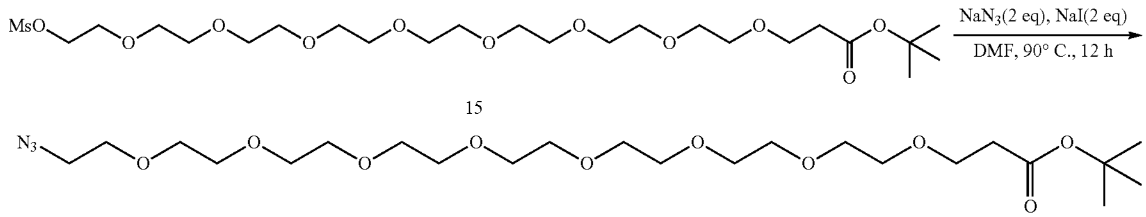

15

16

To a solution of compound 15 (19 g, 32.95 mmol, 1 eq) in DMF (190 mL) was added $NaN_3$ (4.28 g, 65.89 mmol, 2 eq) and NaI (9.88 g, 65.89 mmol, 2 eq). The mixture was stirred at 90° C. for 12 hr. TLC (Dichloromethane:Methanol=10:1 $R_f$=0.6) showed the reaction was complete. The residue was diluted with $H_2O$ 500 mL and extracted with EtOAc (500 mL*3). The combined organic layers were washed with brine (500 mL*1), dried over $Na_2SO_4$, filtered and concentrated under reduced pressure to give a residue. Compound 16 (17 g, 32.47 mmol, 98.54% yield) was obtained as a yellow oil.

General Procedure for Preparation of Compound 7:

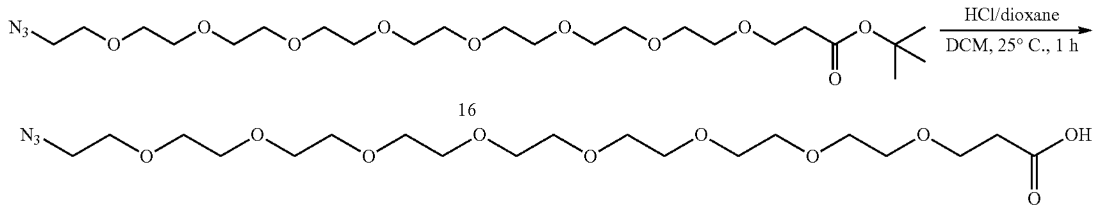

16

7

Three reactions were run in parallel. To a solution of compound 16 (6 g, 11.46 mmol, 1 eq) in DCM (120 mL) was added HCl/dioxane (4 M, 48.00 mL, 16.76 eq). The mixture was stirred at 25° C. for 0.5 hr. TLC (Dichloromethane: Methanol=10:1 $R_f$=0.1) showed the reaction was complete. The three reactions were worked up together. The reaction mixture was concentrated under reduced pressure to give a residue. The residue was purified by column chromatography ($SiO_2$, DCM:MeOH=200/1 to 1/1). Compound 7 (10 g, 21.39 mmol, 62.22% yield) was obtained as a yellow oil.

General Procedure for Preparation of Compound 2:

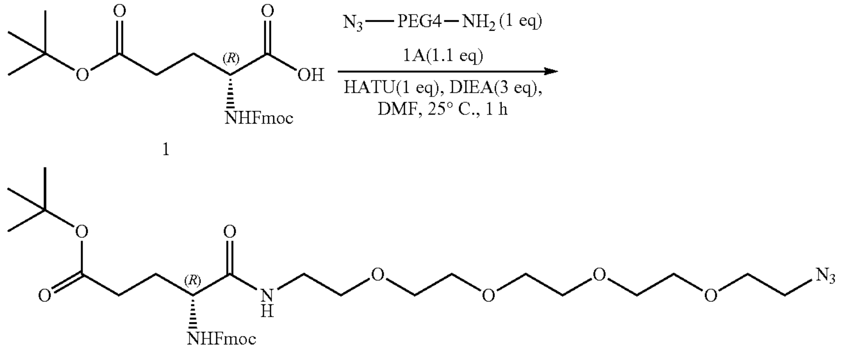

1

2

To a solution of compound 1 (6 g, 14.10 mmol, 1 eq) in DMF (40 mL) was added HATU (5.36 g, 14.10 mmol, 1 eq) and DIEA (5.47 g, 42.31 mmol, 7.37 mL, 3 eq). The mixture was stirred at 25° C. for 0.5 hr. Then compound 1A (4.07 g, 15.51 mmol, 1.1 eq) was added to it. The mixture was stirred at 25° C. for 0.5 hr. LC-MS showed compound 1 was consumed completely and one main peak with desired mass was detected. The mixture was diluted with 0.5 M HCl (200 mL) and extracted with MTBE (200 mL*3). The combined organic layers were washed with brine (200 mL*1), dried over $Na_2SO_4$, filtered and concentrated under reduced pressure to give a residue. The residue was purified by column chromatography ($SiO_2$, Petroleum ether:Ethyl acetate=20:1 to 0:1). Compound 2 (6 g, 8.85 mmol, 62.76% yield, 98.8% purity) was obtained as a white solid. LCMS: RT=1.526 min, MS cal.: 669.34, $[M+H]^+$=670.3.

General Procedure for Preparation of Compound 3:

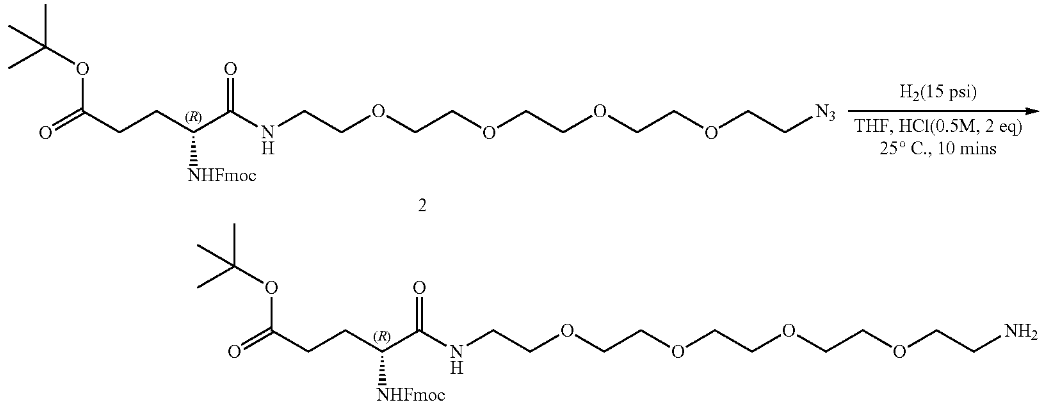

2

3

To a solution of compound 2 (3 g, 4.48 mmol, 1 eq) in THF (80 mL) was added Pd/C (5 g, 4.48 mmol, 10% purity, 1 eq) and HCl (0.5 M, 17.92 mL, 2 eq) under $N_2$. The suspension was degassed under vacuum and purged with $H_2$ several times. The mixture was stirred under $H_2$ (15 psi) at 25° C. for 10 min. LC-MS showed compound 2 was consumed completely and one main peak with desired mass was detected. It was filtered and concentrated under reduced pressure to give a residue. Compound 3 (2.8 g, 4.12 mmol, 91.90% yield, HCl) was obtained as a white solid. LCMS: RT=2.157 min, MS cal.: 643.35, $[M+H]^+$=644.4.

General Procedure for Preparation of Compound 5:

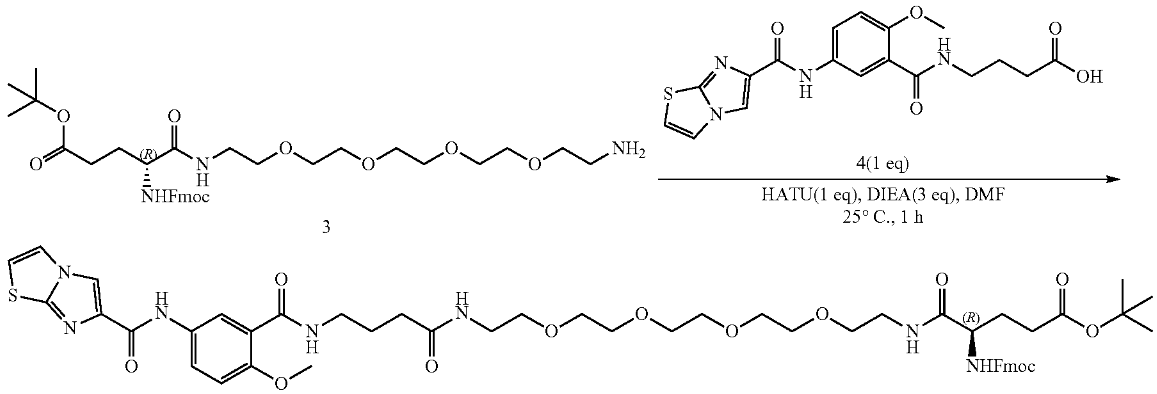

3

5

To a solution of compound 4 (1.7 g, 3.29 mmol, 1 eq, TFA) in DMF (15 mL) was added HATU (1.25 g, 3.29 mmol, 1 eq) and DIEA (1.28 g, 9.88 mmol, 1.72 mL, 3 eq). The mixture was stirred at 25° C. for 0.5 hr. Then compound 3 (6.72 g, 4.94 mmol, 1.5 eq, HCl) was added to the reaction mixture. The mixture was stirred at 25° C. for 0.5 hr. LC-MS showed compound 4 was consumed completely and one main peak with desired mass was detected. Added the reaction mixture to 50 mL 1 M HCl, extracted with EtOAc (50 mL*3). The combined organic layers were washed with brine (50 mL*1), dried over $Na_2SO_4$, filtered and concentrated under reduced pressure to give a residue. The residue was purified by column chromatography ($SiO_2$, DCM: MeOH=100:1 to 0:1). Compound 5 (2.8 g, 4.12 mmol, 91.90% yield, HCl) was obtained as a yellow solid. LCMS: RT=2.903 min, MS cal.: 1027.44, $[M/2+H]^+$=514.9.

General Procedure for Preparation of Compound 6:

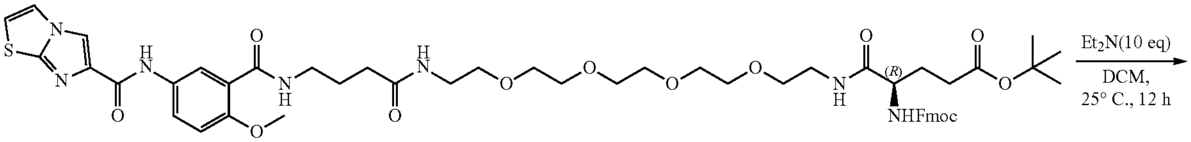

5

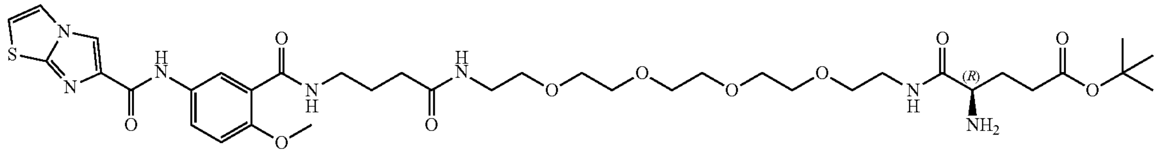

6

To a solution of compound 5 (1.5 g, 1.46 mmol, 1 eq) in DCM (6 mL) was added $Et_2NH$ (1.07 g, 14.59 mmol, 1.50 mL, 10 eq). The mixture was stirred at 25° C. for 12 hr. LC-MS showed compound 5 was consumed completely and one main peak with desired mass was detected. It was concentrated under reduced pressure to give a residue. Compound 6 (1 g, 1.24 mmol, 85.05% yield) was obtained as a yellow solid. LCMS: RT=1.081 min, MS cal.: 805.37, $[M+H]^+$=806.4.

General Procedure for Preparation of Compound 8:

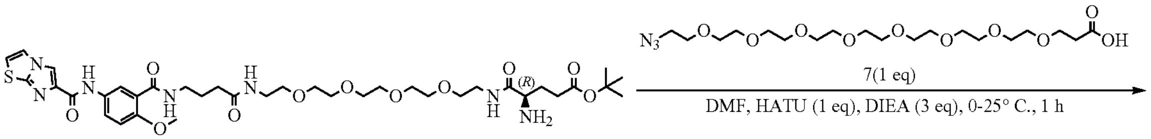

6

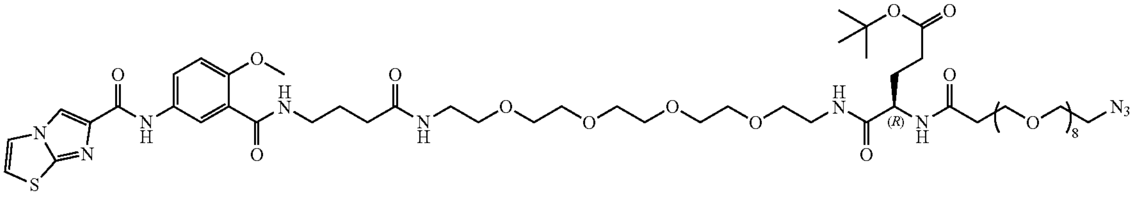

8

To a solution of compound 7 (1 g, 2.14 mmol, 1 eq) in DMF (2 mL) was added HATU (813.31 mg, 2.14 mmol, 1 eq) and DIEA (829.35 mg, 6.42 mmol, 1.12 mL, 3 eq). The mixture was stirred at 0° C. for 0.5 hr. Then compound 6 (1.72 g, 2.14 mmol, 1 eq) was added to the reaction mixture. The mixture was stirred at 25° C. for 0.5 hr. TLC (Dichloromethane:Methanol=10:1 $R_f$=0.24) showed it was finished. Added the reaction mixture to $H_2O$ (10 mL), extracted with EtOAc (10 mL*3). The combined organic layers were washed with brine (10 mL*1), dried over $Na_2SO_4$, filtered and concentrated under reduced pressure to give a residue. The residue was purified by column chromatography ($SiO_2$, DCM:MeOH=200:1 to 5:1). Compound 8 (1 g, 673.87 umol, 31.50% yield, 84.6% purity) was obtained as a yellow solid.

General Procedure for Preparation of Compound 9:

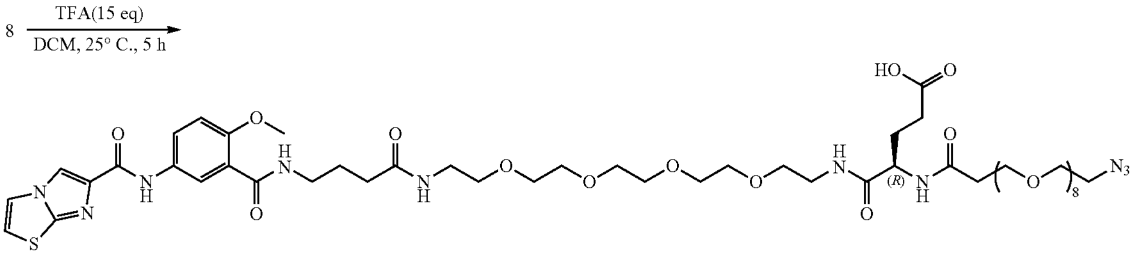

9

To a solution of compound 8 (0.3 g, 238.96 umol, 1 eq) in DCM (5 mL) was added TFA (408.71 mg, 3.58 mmol, 265.39 uL, 15 eq). The mixture was stirred at 25° C. for 5 hr. TLC (Dichloromethane:Methanol=10:1 $R_f$=0.1) showed it was finished. The reaction mixture was concentrated under reduced pressure to give a residue. Compound 9 (250 mg, 208.45 umol, 87.23% yield) was obtained as a yellow oil.

General Procedure for Preparation of Compound 10:

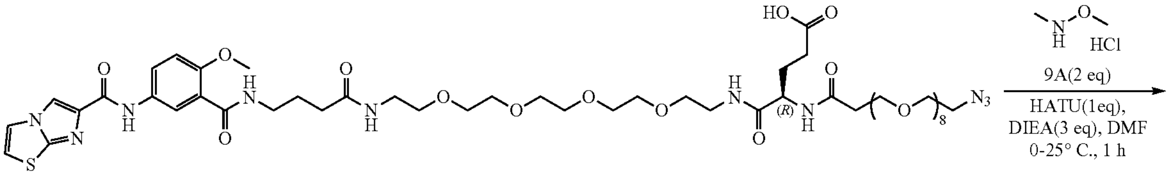

9

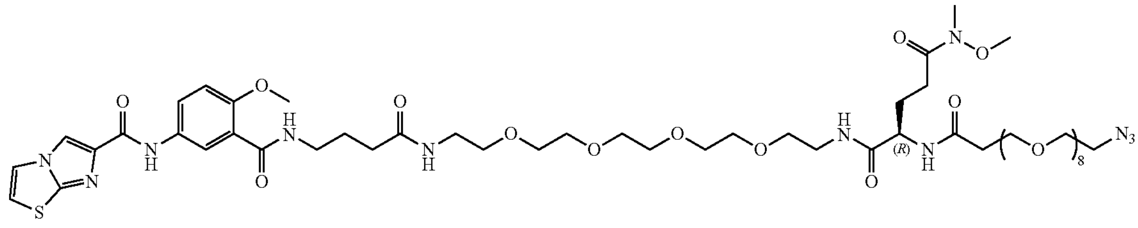

10

To a solution of compound 9 (0.19 g, 158.42 umol, 1 eq) in DMF (2 mL) was added HATU (60.24 mg, 158.42 umol, 1 eq) and DIEA (61.43 mg, 475.27 umol, 82.78 uL, 3 eq). The mixture was stirred at 0° C. for 0.5 hr. Then compound 9A (30.91 mg, 316.85 umol, 2 eq, HCl) was added to the reaction mixture. The mixture was stirred at 0° C. for 0.5 hr. LC-MS showed Reactant 1 was consumed completely and one main peak with desired mass was detected. The residue was diluted with $H_2O$ (10 mL) and extracted with EtOAc (20 mL*3). The combined organic layers were washed with brine (20 mL*1), dried over $Na_2SO_4$, filtered and concentrated under reduced pressure to give a residue. The residue was purified by prep-HPLC (TFA condition: column: Nano-micro Kromasil C18 80*25 mm*3 um; mobile phase: [water (0.1% TFA)-ACN]; B %: 20%-40%, 10 min). Compound 10 (0.1 g, 80.49 umol, 50.81% yield) was obtained as a white solid. LCMS: RT=2.030 min, MS cal.: 1241.58, $[M/2+H]^+$=622.0.

General Procedure for Preparation of Compound 11:

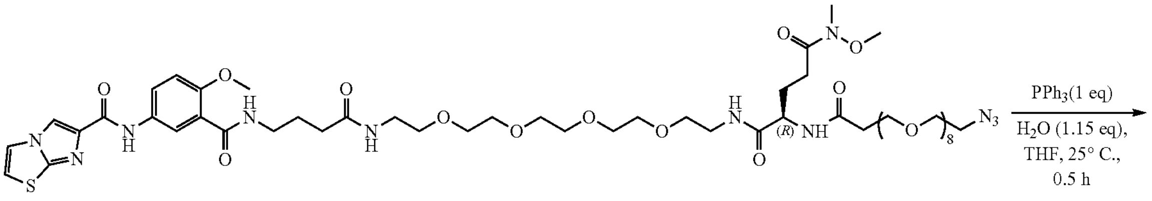

10

-continued

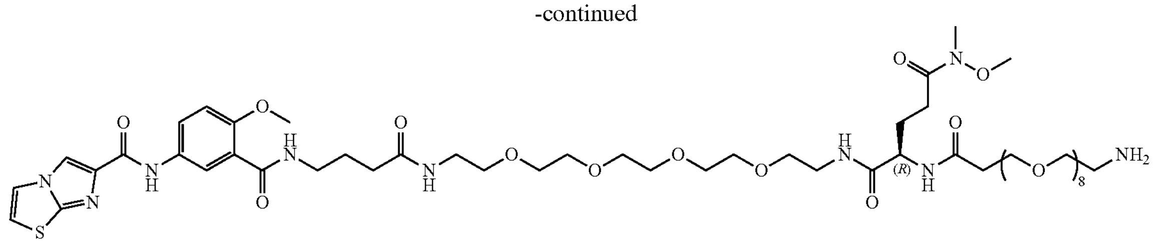

11

To a solution of compound 10 (5 mg, 4.02 umol, 1 eq) in THF (3 mL) was added $PPh_3$ (1.06 mg, 4.02 umol, 1 eq) and $H_2O$ (83.33 ug, 4.63 umol, 8.33e-2 uL, 1.15 eq). The mixture was stirred at 25° C. for 0.5 hr. LC-MS showed compound 10 was consumed completely and a main peak desired mass was detected. The mixture was diluted with $H_2O$ (10 mL), extracted with DCM (10 mL*3). The combined organic layer was washed with $H_2O$ (20 mL), brine (20 mL), dried over $Na_2SO_4$, filtered and the filtrate was concentrated to give a crude product. Compound 11 (4 mg, 3.29 umol, 81.71% yield) was obtained as a yellow oil. LCMS: RT=1.025 min, MS cal.: 1215.59, $[M/2+H]^+$=609.1.

General Procedure for Preparation of Compound I-6:

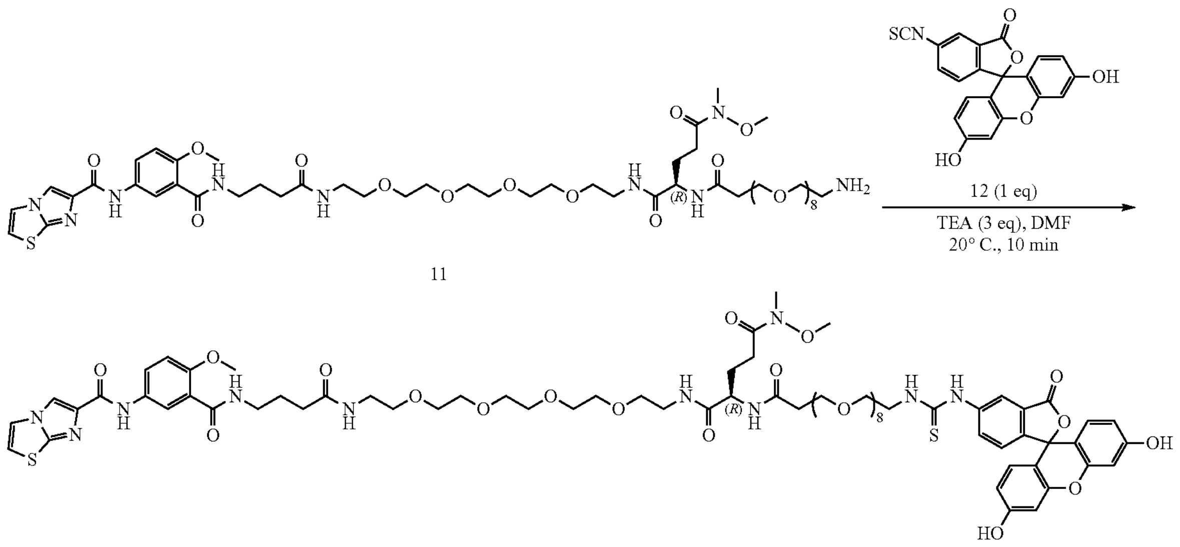

11

I-6

To a solution of compound 11 (6 mg, 4.93 umol, 1 eq) in DMF (2 mL) was added TEA (1.50 mg, 14.80 umol, 2.06 uL, 3 eq) and compound 12 (1.92 mg, 4.93 umol, 1 eq). The mixture was stirred at 25° C. for 10 min. LC-MS showed compound 11 was consumed completely and one main peak with desired mass was detected. The mixture was diluted with $H_2O$ (5 mL), extracted with DCM (5 mL*3). The combined organic layer was washed with $H_2O$ (10 mL), brine (10 mL), dried over $Na_2SO_4$, filtered and the filtrate was concentrated to give a crude product. The residue was purified by prep-HPLC (TFA condition: column: Welch Ultimate AQ-C18 150*30 mm*5 um; mobile phase: [water (0.1% TFA)-ACN]; B %: 30%-60%, 12 min). Compound I-6 (1.41 mg, $8.87*10^{-1}$ umol, 17.98% yield) was obtained as a yellow solid. LCMS: RT=2.217 min, MS cal.: 1604.63, $[M/2+H]^+$=803.7. HPLC: RT=2.930 min. $^1H$ NMR (400 MHz, DMSO-d6) δ ppm 10.02 (br s, 1H) 8.33 (s, 1H) 8.27 (s, 1H) 8.18-8.23 (m, 1H) 8.08 (br s, 1H) 7.96-8.03 (m, 1H) 7.84-7.93 (m, 2H) 7.73 (br d, J=8.44 Hz, 1H) 7.42 (d, J=4.52 Hz, 1H) 7.18 (d, J=8.56 Hz, 1H) 7.09 (d, J=8.93 Hz, 1H) 6.67 (d, J=2.08 Hz, 1H) 6.53-6.62 (m, 3H) 4.24 (br d, J=5.50 Hz, 1H) 3.86 (s, 3H) 3.45-3.72 (m, 57H) 3.39 (br d, J=2.45 Hz, 5H) 3.15-3.30 (m, 7H) 3.06 (s, 2H) 2.30-2.42 (m, 11H) 2.10-2.27 (m, 12H) 1.69-1.90 (m, 4H).

Example 7. Exemplary Synthesis of Compound I-7

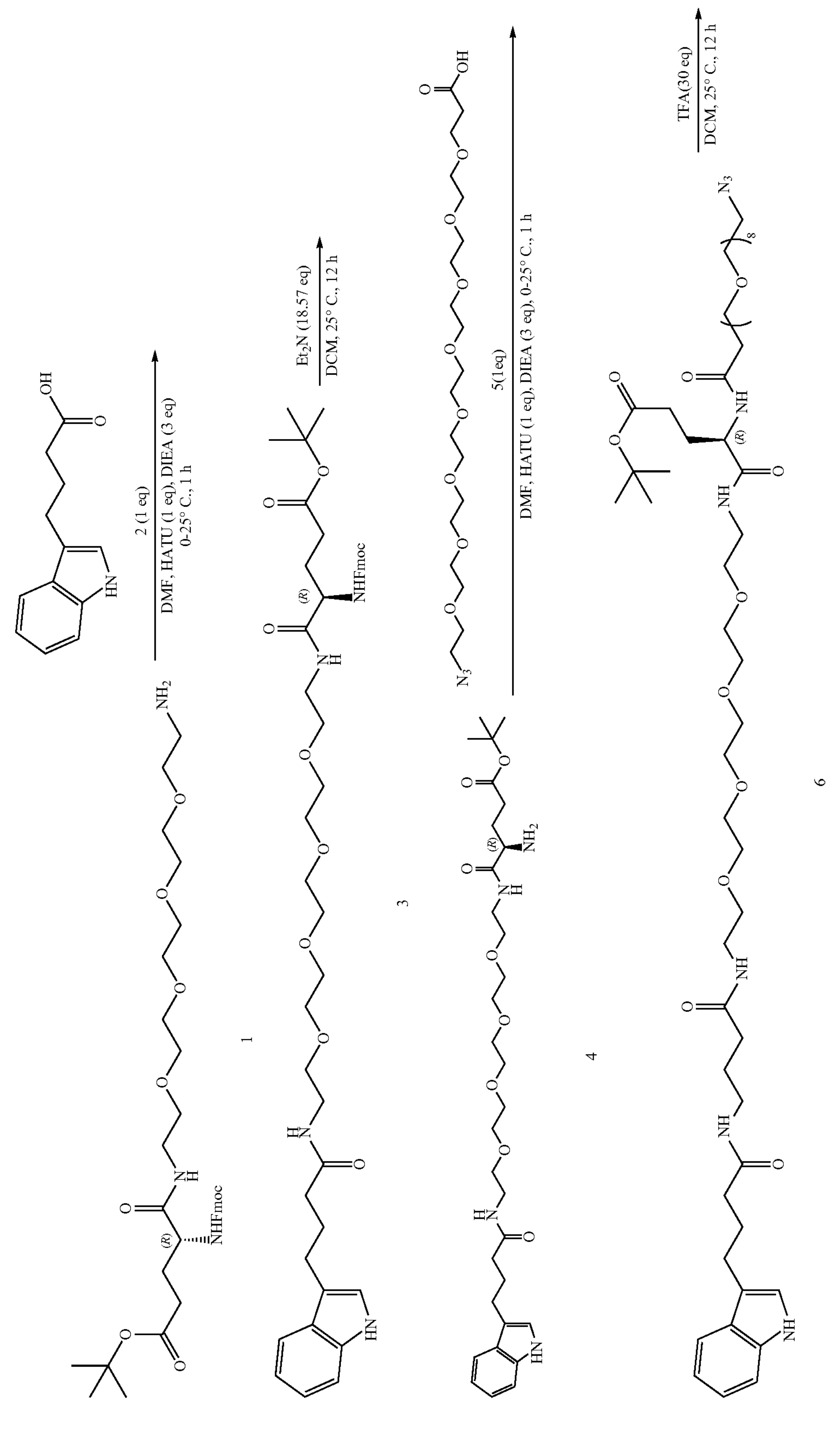
2 (1 eq)
DMF, HATU (1 eq), DIEA (3 eq)
0-25° C., 1 h
1
Et$_2$N (18.57 eq)
DCM, 25° C., 12 h
3
5(1eq)
DMF, HATU (1 eq), DIEA (3 eq), 0-25° C., 1 h
4
TFA(30 eq)
DCM, 25° C., 12 h
6

-continued
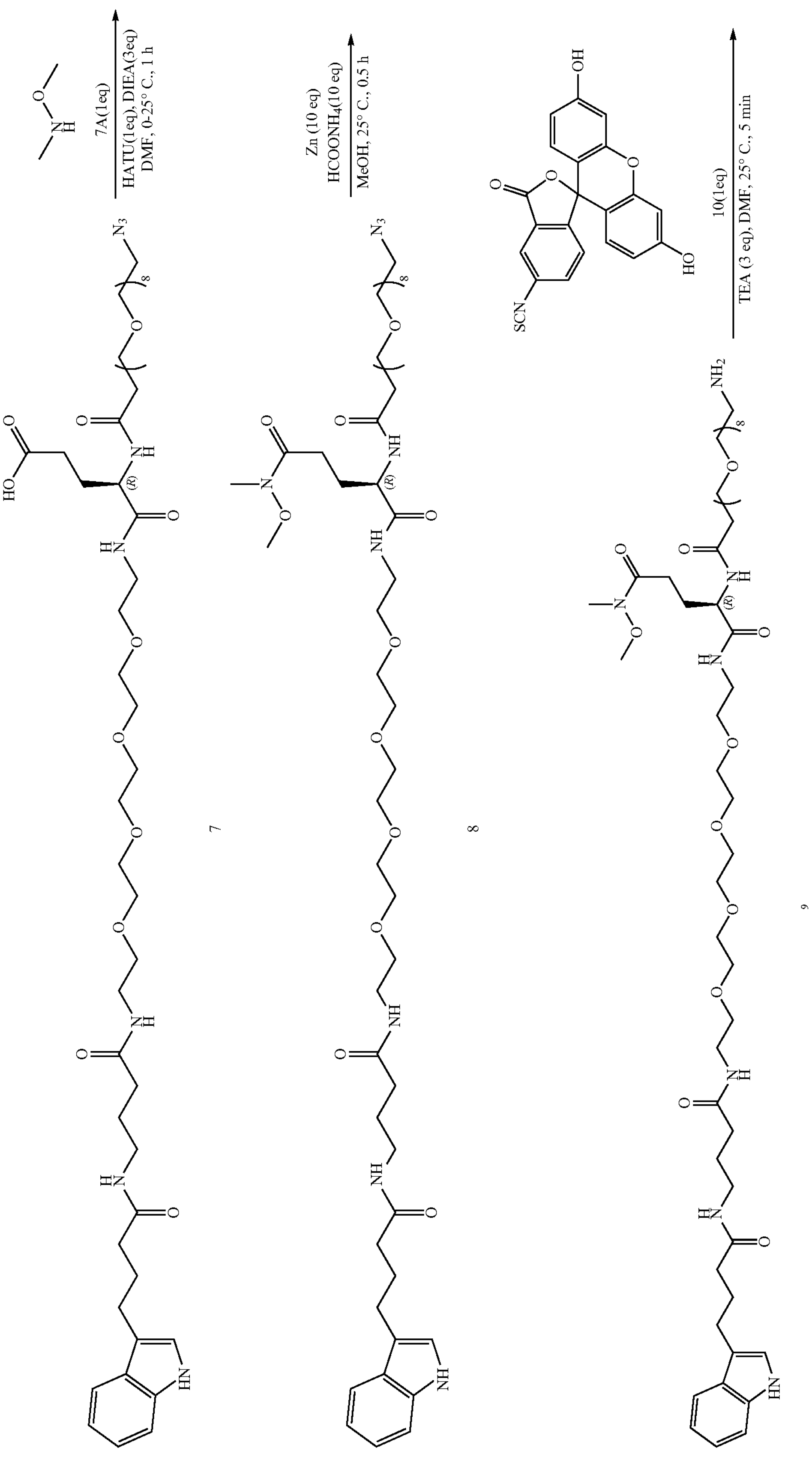
7
8
9

-continued
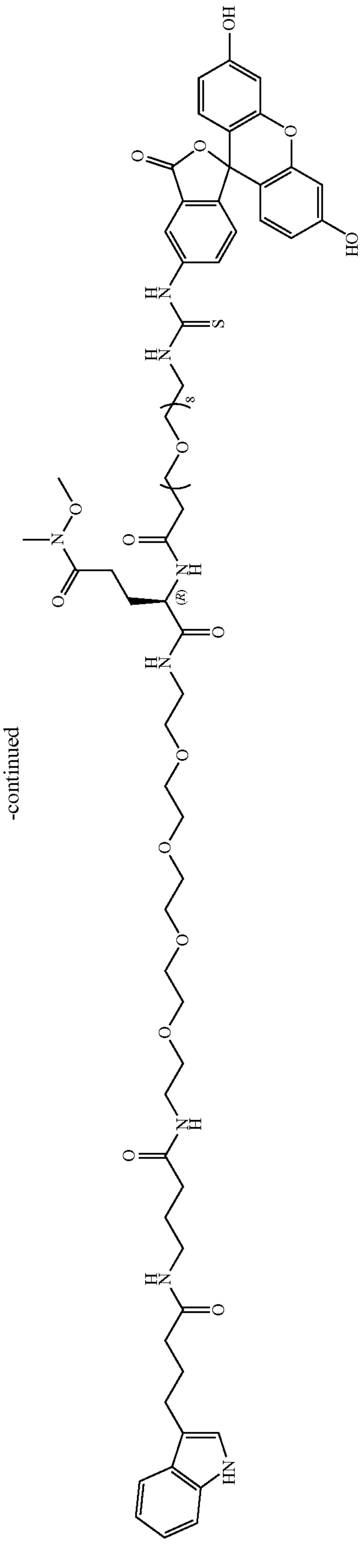
I-7

General Procedure for Preparation of Compound 3:

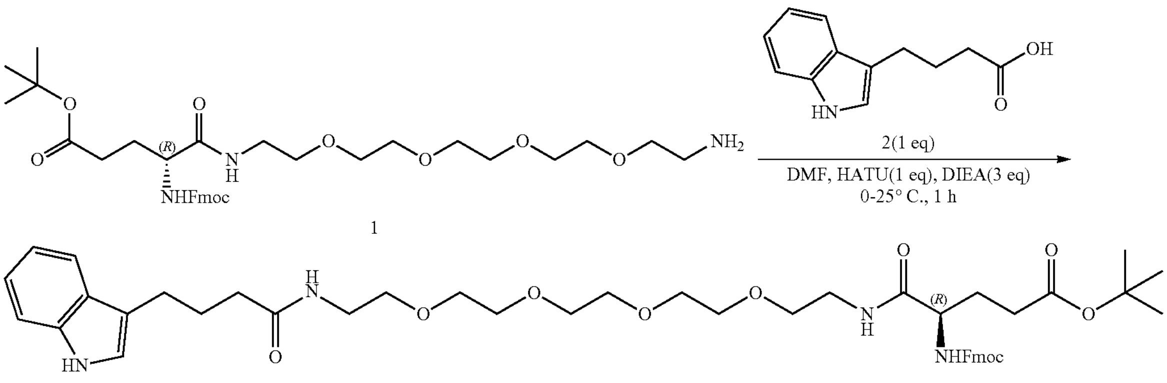

1

3

To a solution of compound 2 (433.23 mg, 2.13 mmol, 1 eq) in DMF (23 mL) was added HATU (891.57 mg, 2.34 mmol, 1.1 eq) and DIEA (826.50 mg, 6.39 mmol, 1.11 mL, 3 eq). The mixture was stirred at 0° C. for 0.5 hr. Then compound 1 (2.9 g, 2.13 mmol, 1 eq, HCl) was added to the reaction mixture. The mixture was stirred at 25° C. for 0.5 hr. LC-MS showed compound 2 was consumed completely and one main peak with desired m/z was detected. The residue was diluted with 0.5 M HCl 25 mL and extracted with EtOAc (70 mL*3). Dried over $Na_2SO_4$, filtered and concentrated under reduced pressure to give a residue. The residue was purified by column chromatography ($SiO_2$, DCM:MeOH=100:1 to 20:1). Compound 3 (0.7 g, 844.40 umol, 39.61% yield) was obtained as a yellow solid. LCMS: RT=3.241 min, MS cal.: 828.43, $[M+H]^+$=829.4.

General Procedure for Preparation of Compound 4:

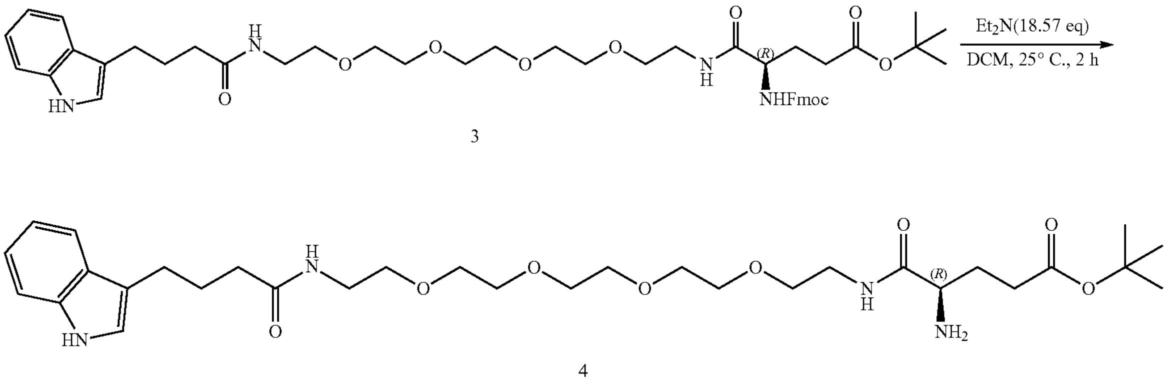

3

4

Two reactions were run in parallel. A mixture of compound 3 (0.65 g, 784.09 umol, 1 eq) and $Et_2NH$ (1.07 g, 14.56 mmol, 1.5 mL, 18.57 eq) in DCM (5 mL) was degassed and purged with $N_2$ 3 times, and the mixture was then stirred at 25° C. for 2 hr under $N_2$ atmosphere. LC-MS showed compound 3 was consumed completely and one main peak with desired m/z was detected. The two reactions were worked up together. The reaction mixture was concentrated under reduced pressure to give a residue. Compound 4 (900 mg, 1.48 mmol, 94.59% yield) was obtained as a yellow oil. LCMS: RT=1.833 min, MS cal.: 606.36, $[M+H]^+$= 607.4.

General Procedure for Preparation of Compound 6:

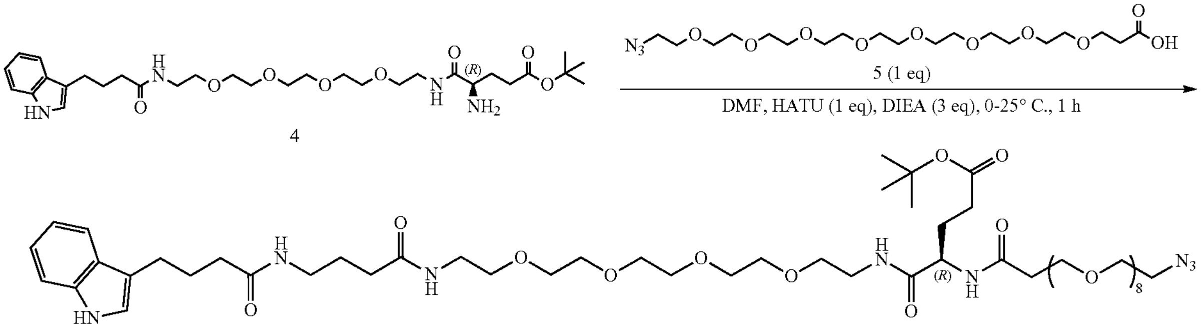

4

6

To a solution of compound 5 (690.01 mg, 1.48 mmol, 1 eq) in DMF (20 mL) was added DIEA (572.26 mg, 4.43 mmol, 771.24 uL, 3 eq) and HATU (561.20 mg, 1.48 mmol, 1 eq). The mixture was stirred at 0° C. for 0.5 hr. Then compound 4 (600 mg, 988.88 umol, 0.67 eq) was added to the reaction mixture. The mixture was stirred at 25° C. for 0.5 hr. LC-MS showed compound 5 was consumed completely and one main peak with desired m/z was detected. The residue was diluted with $H_2O$ (60 mL) and extracted with ethyl acetate (60 mL*3). The organic layer was dried over $Na_2SO_4$, filtered and concentrated under reduced pressure to give a residue. The residue was purified by column chromatography ($SiO_2$, Dichloromethane:Methanol=100:1 to 10:1). Compound 6 (1.5 g, 1.42 mmol, 96.22% yield) was obtained as a yellow oil. LCMS: RT=2.368 min, MS cal.: 1055.6, $[M/2+H]^+$=529.1.

General Procedure for Preparation of Compound 7:

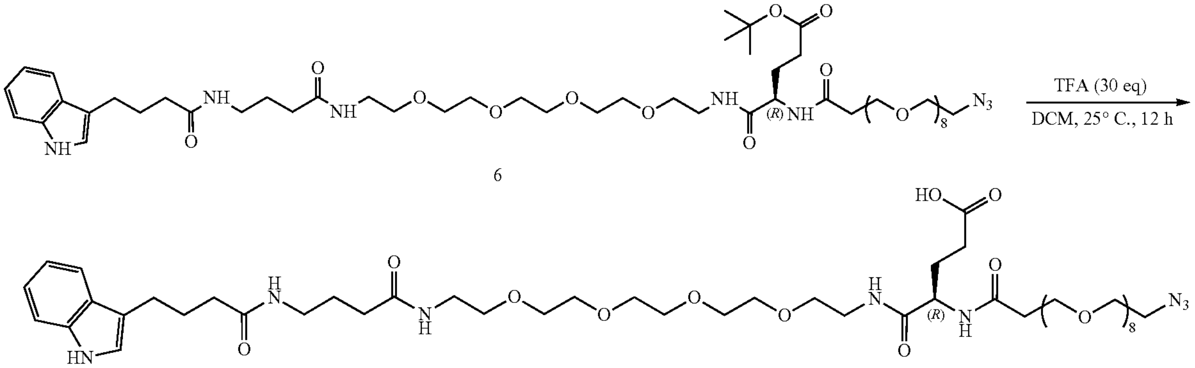

6

7

A mixture of compound 6 (100 mg, 94.68 umol, 1 eq) and TFA (323.85 mg, 2.84 mmol, 210.30 uL, 30 eq) in DCM (5 mL) was degassed and purged with $N_2$ 3 times, and the mixture was then stirred at 25° C. for 12 hr under $N_2$ atmosphere. LC-MS showed compound 6 was consumed completely several new peaks were observed. Approximately 42.52% of desired compound was detected. The reaction mixture was concentrated under reduced pressure to give a residue. The residue was purified by prep-HPLC (TFA condition). Compound 7 (92 mg, 91.99 umol, 48.58% yield) was obtained as a colorless oil. LCMS: RT=2.135 min, MS cal.: 999.54, $[M/2+H]^+$=501.0.

General Procedure for Preparation of Compound 8:

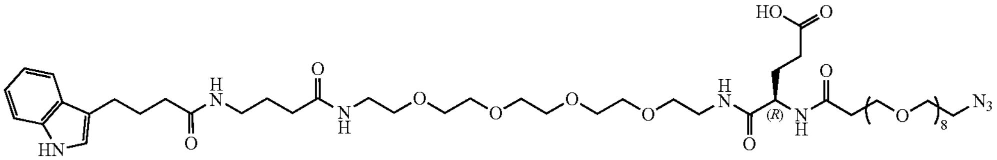

7

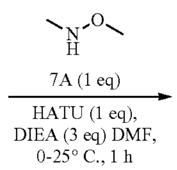

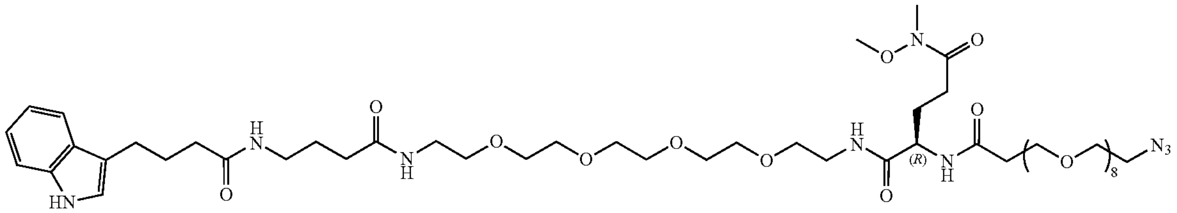

8

To a solution of compound 7 (50 mg, 49.99 umol, 1 eq) in DMF (1 mL) was added DIEA (19.38 mg, 149.98 umol, 26.12 uL, 3 eq) and HATU (19.01 mg, 49.99 umol, 1 eq). The mixture was stirred at 0° C. for 0.5 hr. Then compound 7A (9.75 mg, 99.99 umol, 2 eq, HCl) was added to the reaction mixture. The mixture was stirred at 25° C. for 0.5 hr. LC-MS showed compound 7 was consumed completely and one main peak with desired m/z or desired mass was detected. The reaction mixture was filtered and the filtrate was purified by prep-HPLC. The mixture was purified by prep-HPLC (TFA condition). Compound 8 (20 mg, 19.17 umol, 38.35% yield) was obtained as a colorless oil. LCMS: RT=2.236 min, MS cal.: 1043.2, $[M/2+H]^+$=522.5.

General Procedure for Preparation of Compound 9:

8

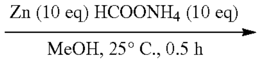

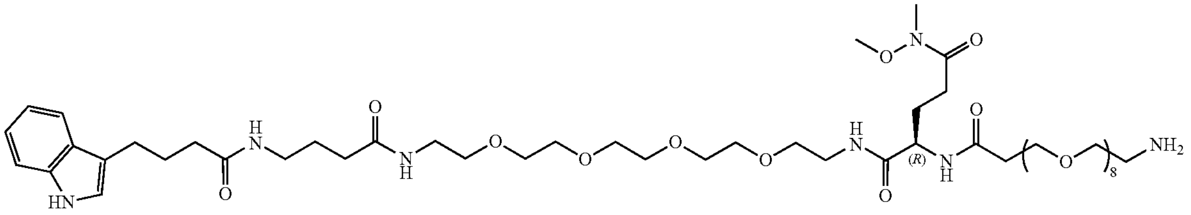

9

To a solution of Compound 8 (40 mg, 38.34 umol, 1 eq) in MeOH (2 mL) was added Zn (25.07 mg, 383.43 umol, 10 eq) and $HCOONH_4$ (24.18 mg, 383.43 umol, 10 eq). The mixture was stirred at 25° C. for 0.5 hr. LC-MS showed Reactant 1 was consumed completely and one main peak with desired mass was detected. The reaction mixture was filtered and concentrated under reduced pressure to give a residue. Compound 9 (38 mg, 37.36 umol, 97.43% yield) was obtained as a yellow oil. LCMS: RT=1.748 min, MS cal.: 1016.59, $[M/2+H]^+$=509.5.

General Procedure for Preparation of Compound I-7:

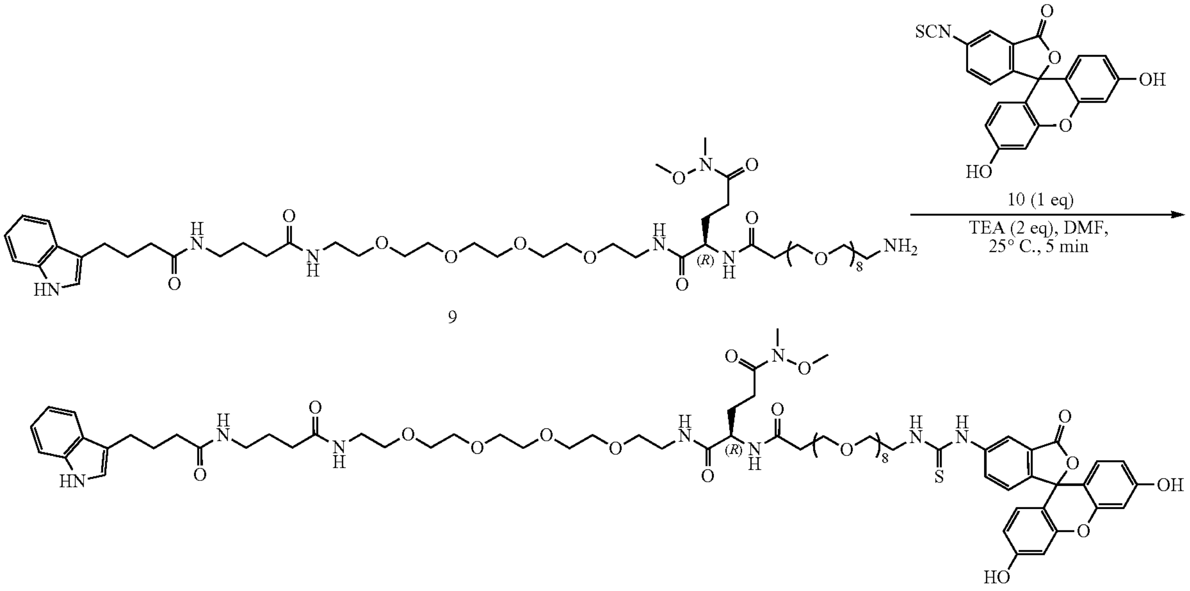

9

I-7

To a solution of compound 9 (10 mg, 9.83 umol, 1 eq) in DMF (0.5 mL) was added TEA (1.99 mg, 19.66 umol, 2.74 uL, 2 eq) and compound 10 (3.83 mg, 9.83 umol, 1 eq). The mixture was stirred at 25° C. for 5 min. LC-MS showed Reactant 1 was consumed completely. Several new peaks were shown on LC-MS. Approximately 19.07% of desired compound was detected. The reaction mixture was filtered and concentrated under reduced pressure to give a residue. The residue was purified by prep-HPLC (neutral condition: column: Waters Xbridge BEH C18 100*30 mm*10 um; mobile phase: [water (0.04% NH3H2O)-ACN]; B %: 1%-30%, 10 min). Compound I-7 (1.68 mg, 1.19 umol, 12.15% yield) was obtained as a yellow solid. L CMS: RT=2.403 min, MS cal.: 1405.63, $[M/2+H]^+$=704.2. HPLC: RT=1.610 min. $^1$H NMR (400 MHz, DMSO-d6) δ ppm 10.73 (s, 1H) 8.41 (s, 1H) 8.24-8.31 (m, 1H) 8.01 (br d, J=8.44 Hz, 1H) 7.81-7.94 (m, 2H) 7.73 (br d, J=9.41 Hz, 1H) 7.48 (d, J=8.44 Hz, 1H) 7.31 (d, J=8.07 Hz, 1H) 7.17 (d, J=8.07 Hz, 1H) 7.01-7.10 (m, 2H) 6.91-6.98 (m, 1H) 6.67 (d, J=1.96 Hz, 2H) 6.52-6.62 (m, 5H) 4.24 (br d, J=5.75 Hz, 1H) 3.68 (br s, 2H) 3.55-3.63 (m, 11H) 3.45-3.52 (m, 38H) 3.13-3.23 (m, 5H) 3.06 (s, 3H) 2.60-2.69 (m, 4H) 2.30-2.40 (m, 5H) 2.13 (t, J=7.40 Hz, 2H) 1.66-1.90 (m, 4H).

Example 8. Exemplary Synthesis of Compound I-8

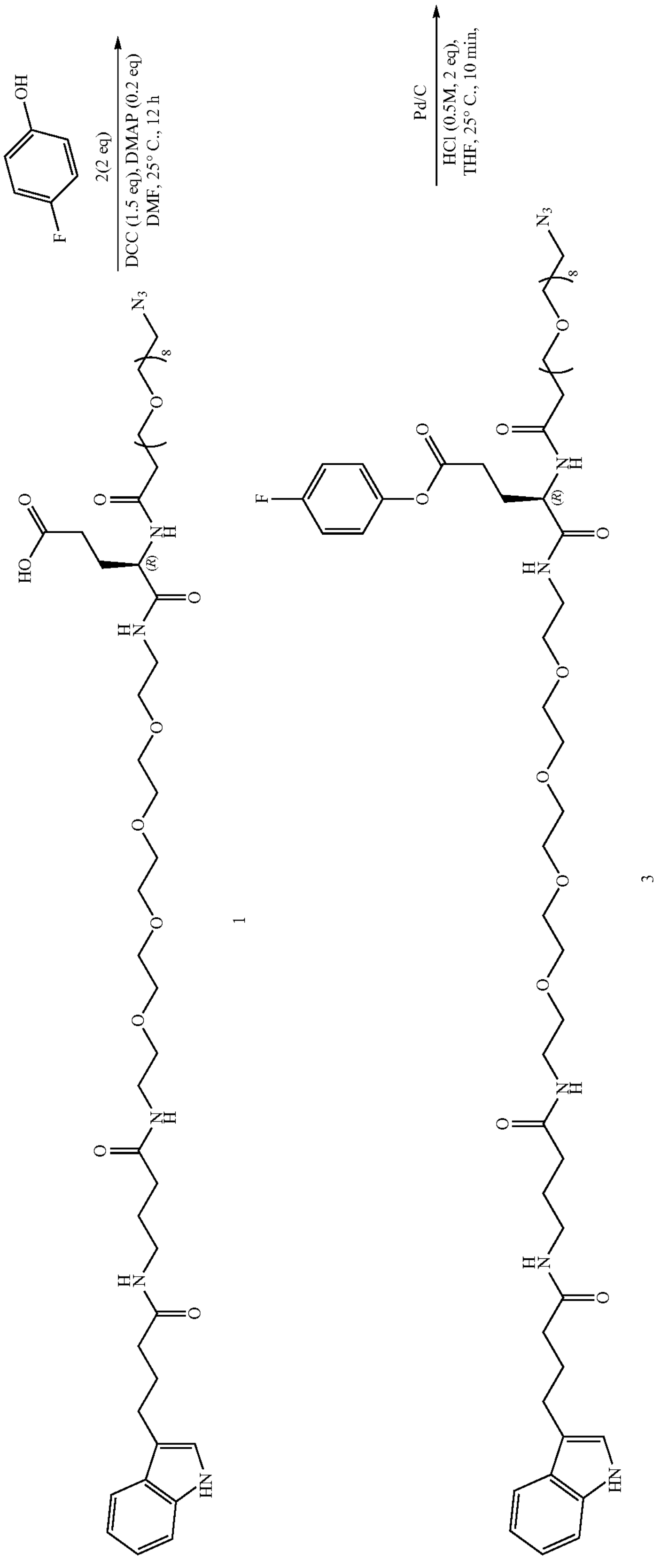
1
3

-continued
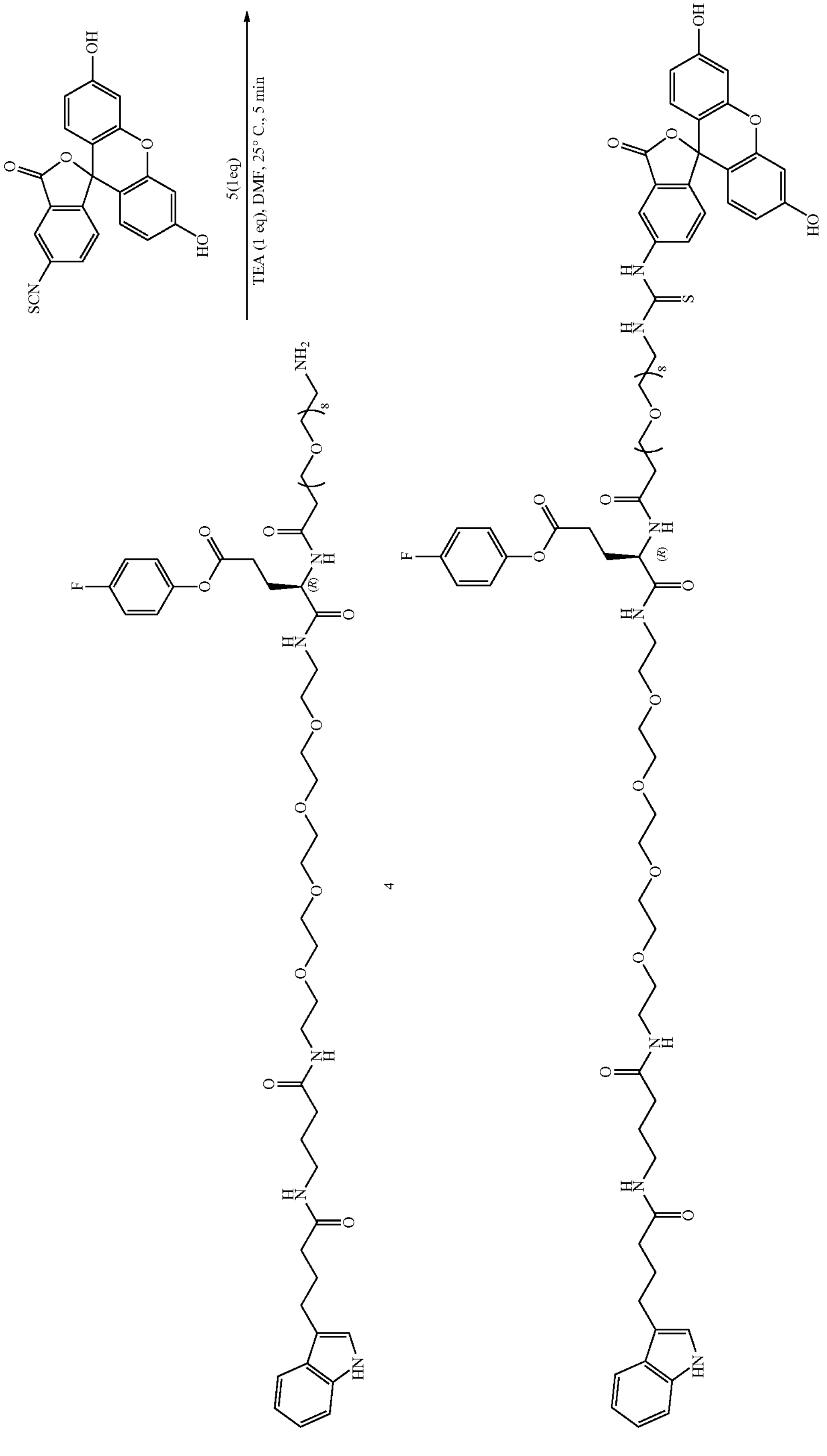
4
I-8

General Procedure for Preparation of Compound 3:

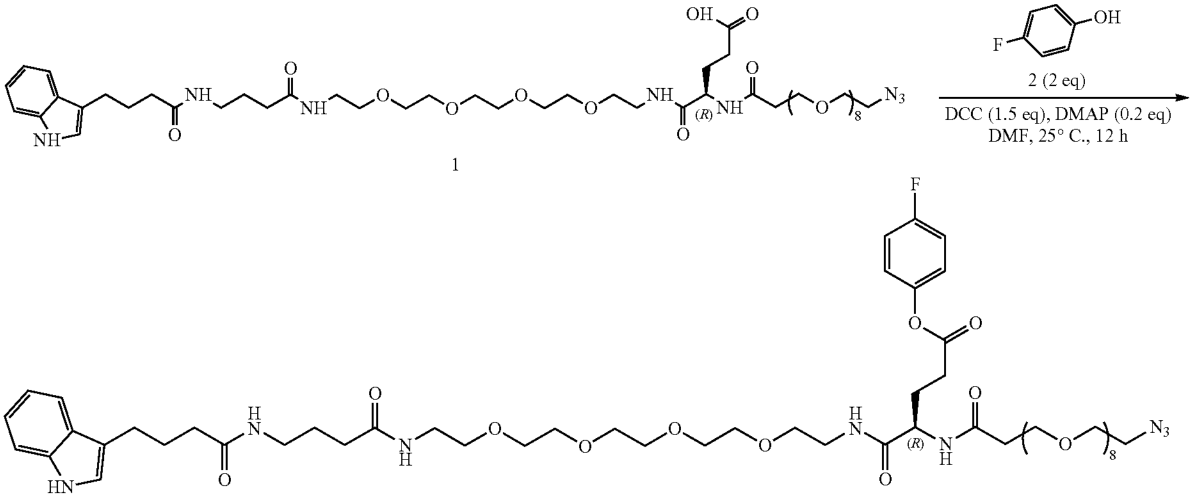

1

3

To a solution of compound 1 (80 mg, 79.99 umol, 1 eq) and compound 2 (17.93 mg, 159.98 umol, 2 eq) in DCM (2 mL) was added DCC (24.76 mg, 119.98 umol, 24.27 uL, 1.5 eq) and DMAP (1.95 mg, 16.00 umol, 0.2 eq). The mixture was stirred at 25° C. for 12 hr. LC-MS showed compound 1 was consumed completely and one main peak with desired mass was detected. The reaction mixture was dried under nitrogen gas. The residue was purified by prep-HPLC (TFA condition: column: Nano-micro Kromasil C18 80*25 mm*3 um; mobile phase: [water (0.1% TFA)-ACN]; B %: 32%-62%, 7 min). Compound 3 (50 mg, 45.69 umol, 57.13% yield) was obtained as a yellow oil. LCMS: RT=2.499 min, MS cal.: 1093.56, $[M/2+H]^+$=580.0.

General Procedure for Preparation of Compound 4:

To a solution of compound 3 (20 mg, 18.28 umol, 1 eq) in THF (2 mL) was added Pd/C (10 mg, 18.28 umol, 10% purity, 1 eq) and HCl (0.5 M, 73.11 uL, 2 eq) under $N_2$. The suspension was degassed under vacuum and purged with $H_2$ several times. The mixture was stirred under $H_2$ (15 psi) at 25° C. for 10 min. LC-MS showed Reactant 1 was consumed completely and one main peak with desired mass was detected. Filtered and concentrated under reduced pressure to give a residue. Compound 4 (19 mg, 17.79 umol, 97.31% yield) was obtained as a white solid. LCMS: RT=2.013 min, MS cal.: 1067.57, $[M/2+H]^+$=535.0.

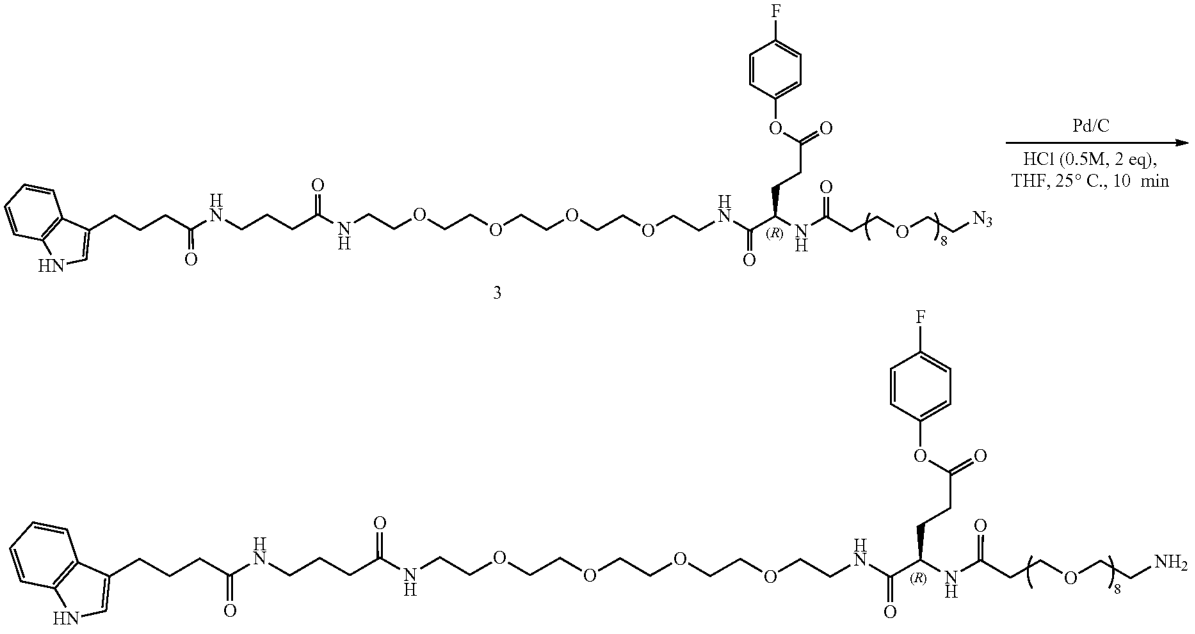

3

4

General Procedure for Preparation of Compound I-8:

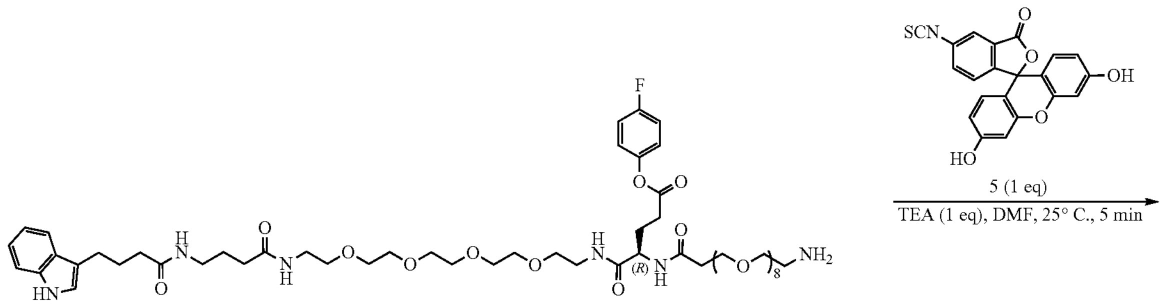

4

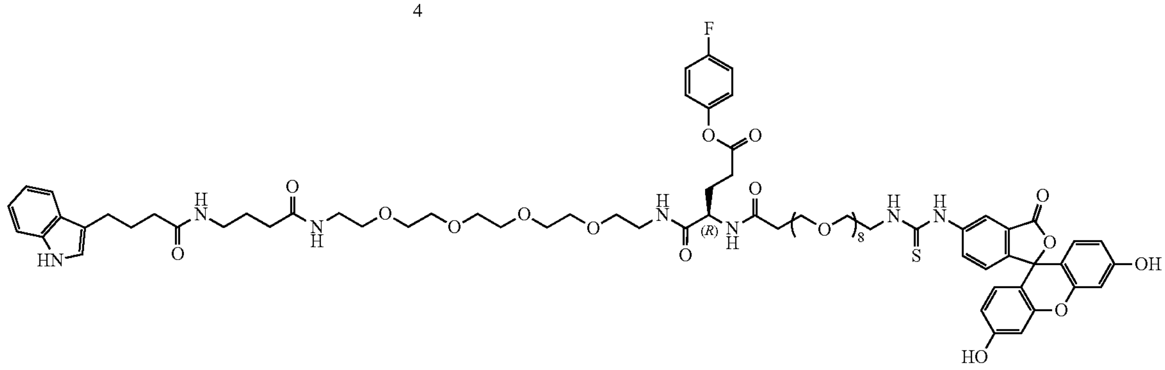

I-8

To a solution of compound 4 (20 mg, 18.10 umol, 1 eq, HCl) and compound 5 (7.05 mg, 18.10 umol, 1 eq) in DMF (1 mL) was added TEA (1.83 mg, 18.10 umol, 2.52 uL, 1 eq). The mixture was stirred at 25° C. for 5 min. LC-MS showed Reactant 1 was consumed completely. Approximately 23.73% of desired compound was detected. The reaction mixture was filtered and concentrated under reduced pressure to give a residue. The residue was purified by prep-HPLC (TFA condition: column: Phenomenex Luna C18 100*30 mm*5 um; mobile phase: [water (0.1% TFA)-ACN]; B %: 35%-55%, 12 min). Compound I-8 (2.08 mg, 1.43 umol, 7.88% yield) was obtained as a yellow solid. LCMS: RT=2.845 min, MS cal.: 1456.6, $[M/2+H]^+$=729.7. HPLC: RT=3.857 min. $^1H$ NMR (400 MHz, DMSO-d6) δ ppm 10.74 (br s, 1H) 10.00-10.22 (m, 2H) 8.27 (s, 1H) 7.99-8.13 (m, 3H) 7.70-7.88 (m, 2H) 7.48 (d, J=7.82 Hz, 1H) 6.90-7.34 (m, 8H) 6.67 (d, J=1.96 Hz, 2H) 6.53-6.62 (m, 3H) 5.58 (br s, 2H) 4.35 (br d, J=5.62 Hz, 1H) 3.68 (br s, 2H) 3.45-3.62 (m, 48H) 3.14-3.24 (m, 2H) 2.13 (br t, J=7.70 Hz, 3H) 1.94-2.05 (m, 2H) 1.80-1.88 (m, 2H) 1.71 (br d, J=12.35 Hz, 6H) 1.57-1.65 (m, 6H) 1.50 (br d, J=12.72 Hz, 3H) 1.18-1.28 (m, 6H) 0.98-1.16 (m, 10H).

Example 9. Exemplary Synthesis of Compound I-9

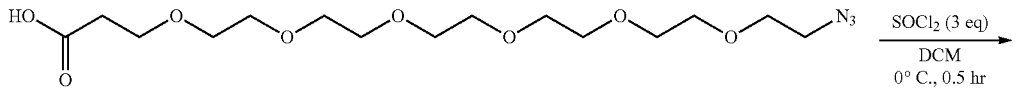

1

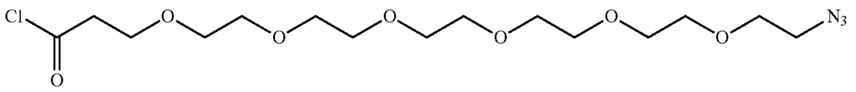

2

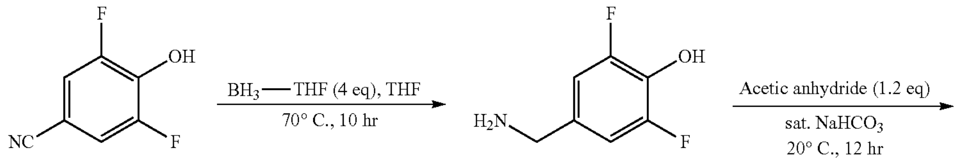

3 4

-continued

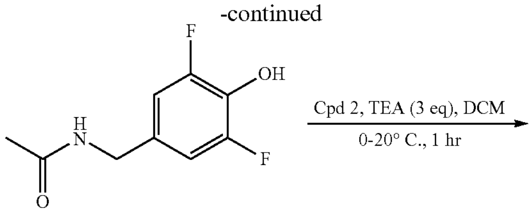

5

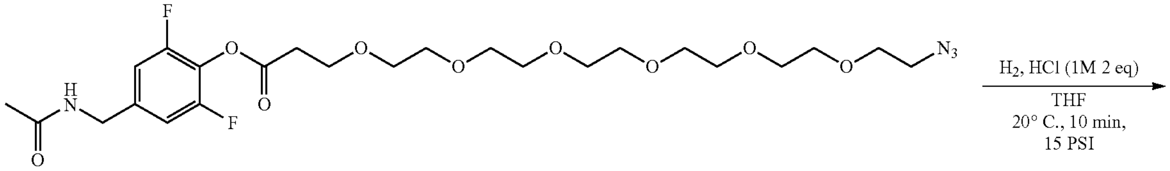

6

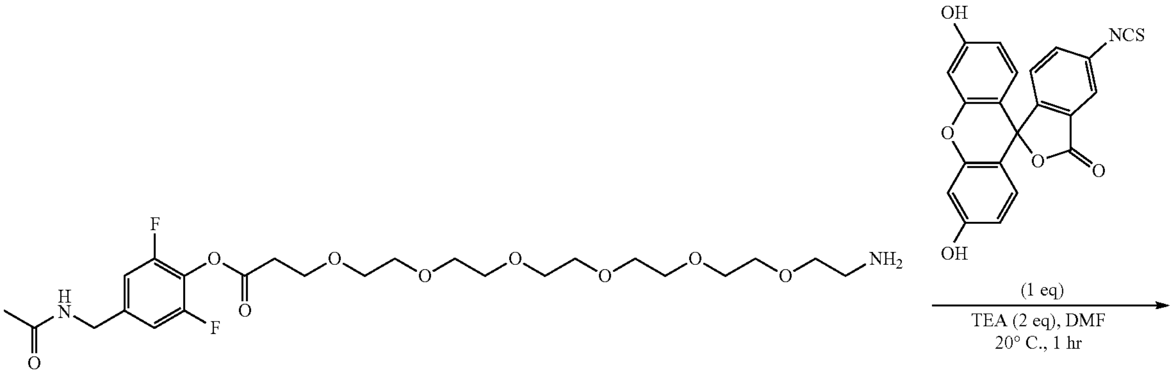

7

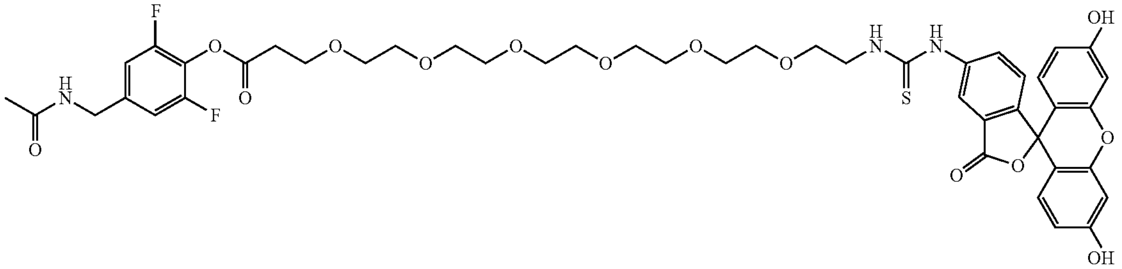

I-9

General Procedure for Preparation of Compound 2:

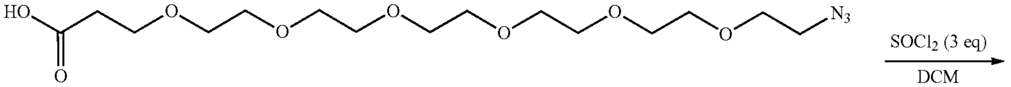

1

DCM
0° C., 0.5 hr

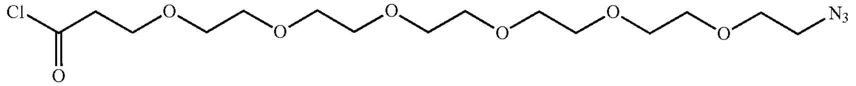

2

A mixture of compound 1 (140 mg, 369.00 umol, 1 eq), $SOCl_2$ (131.70 mg, 1.11 mmol, 80.30 uL, 3 eq) in DCM (2 mL) at 0° C. was degassed and purged with $N_2$ 3 times, and then the mixture was stirred at 0-20° C. for 0.5 hr under $N_2$ atmosphere. TLC (Dichloromethane:Methanol=10:1 $R_f$=0.46) indicated compound 1 was consumed completely. The reaction mixture was concentrated to give the crude product. Compound 2 (146.81 mg, crude) was obtained as a yellow oil.

General Procedure for Preparation of Compound 4:

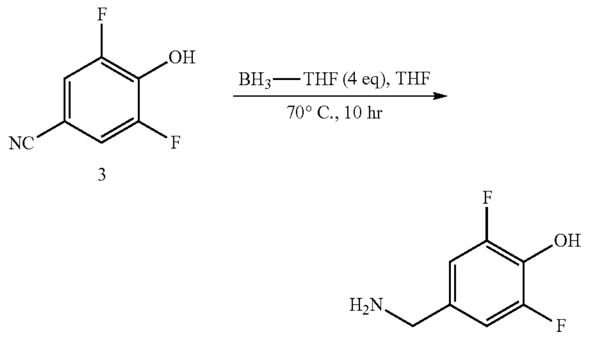

3

4

$BH_3$-THF (1 M, 25.79 mL, 4 eq) was added carefully to a solution of compound 3 (1 g, 6.45 mmol, 1 eq) in anhydrous THF (70 mL). The resultant solution was stirred and heated to reflux for 10 hr (70° C.). TLC (Petroleum ether:Ethyl acetate=1:1, $R_f$=0.01) indicated compound 3 was consumed completely and one new spot formed. After the mixture was cooled, 6 N HCl (2 mL) was carefully added to the solution, and heating was continued at reflux for 30 min. The mixture was concentrated under reduced pressure to give a residue. Compound 4 (2.5 g, crude, HCl) was obtained as a white solid.

General Procedure for Preparation of Compound 5:

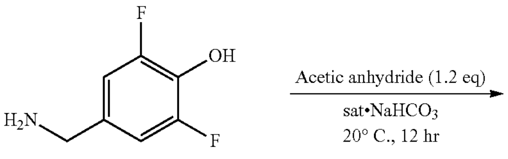

4

-continued

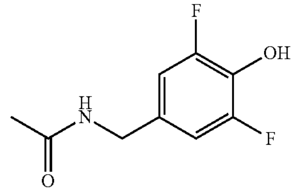

5

A mixture of compound 4 (270 mg, 690.20 umol, 1 eq, HCl), acetic anhydride (84.55 mg, 828.25 umol, 77.57 uL, 1.2 eq) in $NaHCO_3$ (5 mL) was degassed and purged with $N_2$ 3 times, and then the mixture was stirred at 20° C. for 24 hr under $N_2$ atmosphere. LCMS showed the starting material was consumed completely. TLC indicated compound 4 was consumed completely. The reaction mixture was acidified to pH 4-5 with 1M HCl. The reaction mixture was extracted with EtOAc (30 mL*2). The combined organic layers were washed with brine (30 mL), dried over $Na_2SO_4$, filtered and concentrated under reduced pressure to give a residue. The residue was purified by column chromatography ($SiO_2$, Petroleum ether:Ethyl acetate=10:1 to 1:3). Compound 5 (67 mg, 333.05 umol, 48.25% yield) was obtained as a white solid. LCMS: RT=0.609 min, MS cal.: 201.0, $[M+H]^+$= 202.2. $^1$H NMR (400 MHz, DMSO-$d_6$) δ ppm 9.99 (s, 1H) 8.28 (br s, 1H) 6.83-6.93 (m, 2H) 4.12 (d, J=5.95 Hz, 2H) 1.84 (s, 3H).

General Procedure for Preparation of Compound 6:

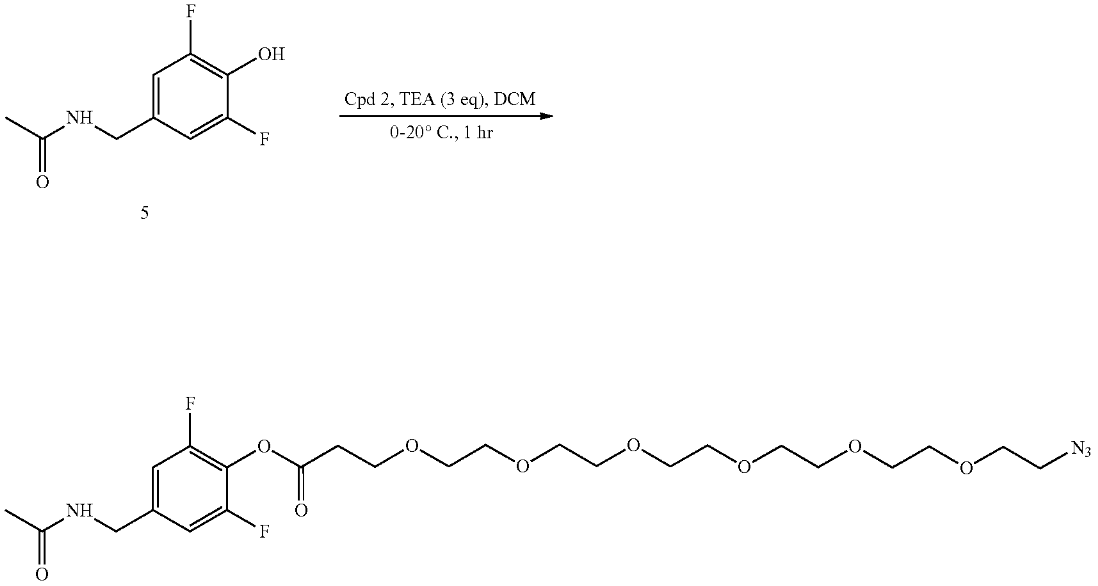

5

6

To a solution of compound 5 (67 mg, 333.05 umol, 1 eq) in DCM (1 mL) was added TEA (101.10 mg, 999.16 umol, 139.07 uL, 3 eq), and then compound 2 (145.76 mg, 366.36 umol, 1.1 eq) in DCM (1 mL) was added at 0° C. The resulting mixture was stirred at 20° C. for 2 hr. LCMS showed the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 35%-65%, 12 min). Compound 6 (100 mg, 177.76 umol, 53.37% yield) was obtained as a yellow oil. LCMS: RT=2.129 min, MS cal.: 562.2, $[M+H]^+$=563.3. $^1H$ NMR (400 MHz, CHLOROFORM-d) δ ppm 6.84 (d, J=7.95 Hz, 2H) 5.86 (br s, 1H) 4.33 (d, J=6.11 Hz, 2H) 3.81 (t, J=6.42 Hz, 2H) 3.53-3.64 (m, 23H) 3.32 (br t, J=5.01 Hz, 3H) 2.85 (t, J=6.36 Hz, 2H) 1.99 (s, 3H) 1.50 (s, 2H).

General Procedure for Preparation of Compound 7:

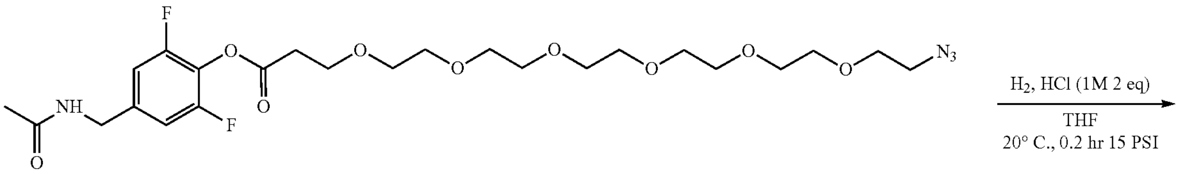

6

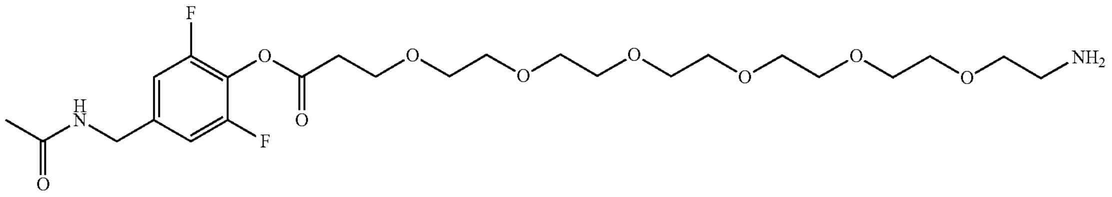

7

To a solution of compound 6 (100 mg, 177.76 umol, 1 eq) in THF (3 mL) was added HCl (0.5 M, 711.04 uL, 2 eq) and Pd/C (100 mg, 177.76 umol, 10% purity, 1.00 eq) under $N_2$. The suspension was degassed under vacuum and purged with $H_2$ several times. The mixture was stirred under $H_2$ (15 psi) at 20° C. for 0.2 hours. LCMS showed the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 15%-45%, 12 min). Compound 7 (60 mg, 111.82 umol, 62.91% yield) was obtained as a white oil. LCMS: RT=1.272 min, MS cal.: 536.2, $[M+H]^+$=537.3. $^1H$ NMR (400 MHz, CHLOROFORM-d) δ ppm 7.79 (br s, 3H) 6.98 (br d, J=8.19 Hz, 2H) 6.72 (br s, 1H) 4.42 (d, J=5.99 Hz, 2H) 3.88 (t, J=5.93 Hz, 2H) 3.80-3.85 (m, 2H) 3.72-3.76 (m, 2H) 3.65-3.71 (m, 12H) 3.13 (br s, 2H) 2.92 (t, J=5.87 Hz, 2H) 2.68 (br s, 4H) 2.08 (s, 3H).

General Procedure for Preparation of Compound I-9:

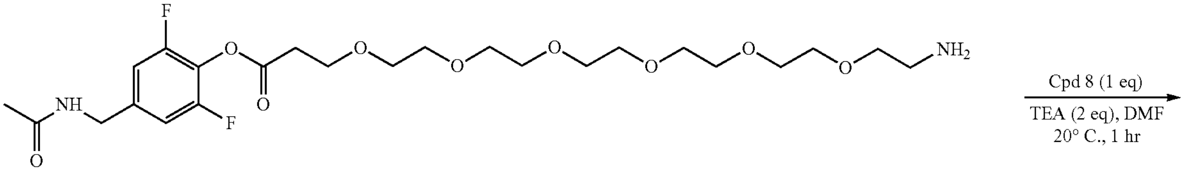

7

-continued

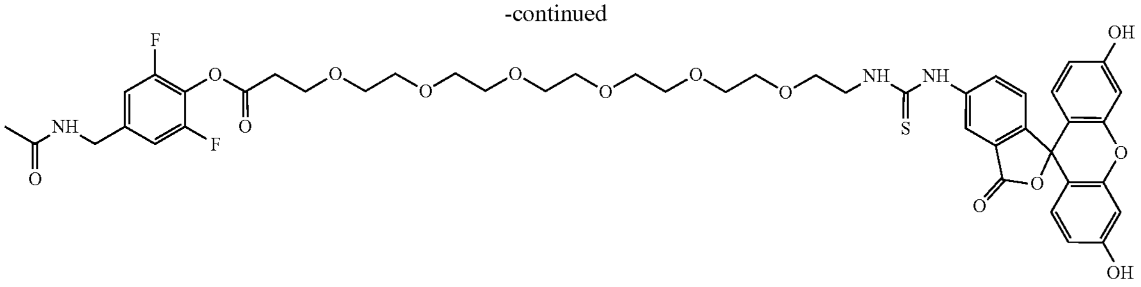

I-9

A mixture of compound 7 (20 mg, 37.27 umol, 1 eq), compound 8 (14.51 mg, 37.27 umol, 1 eq), $Et_3N$ (3.77 mg, 37.27 umol, 5.19 uL, 1 eq), in DMF (1.5 mL) was degassed and purged with $N_2$ 3 times, and the mixture was then stirred at 20° C. for 1 hr under $N_2$ atmosphere. LCMS showed the starting material was consumed completely. HPLC showed the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 40%-70%, 12 min). Compound I-9 (8 mg, 8.64 umol, 23.18% yield) was obtained as a yellow solid. LCMS: RT=2.350 min, MS cal.: 925.2, $[M/2+H]^+$=463.8. HPLC: RT=2.521 min. $^1$H NMR (400 MHz, DMSO-$d_6$) δ ppm 10.03 (br s, 1H) 8.42 (br t, J=5.50 Hz, 1H) 8.27 (s, 1H) 8.09 (br s, 1H) 7.74 (br d, J=7.70 Hz, 1H) 7.18 (d, J=8.19 Hz, 1H) 7.12 (d, J=8.80 Hz, 2H) 6.67 (d, J=1.83 Hz, 2H) 6.53-6.62 (m, 4H) 4.25 (d, J=5.99 Hz, 2H) 3.55-3.63 (m, 8H) 3.45-3.53 (m, 17H) 2.93 (t, J=5.93 Hz, 2H) 1.89 (s, 3H). MS: $[M/2+H]^+$=463.9.

Example 10. Exemplary Synthesis of Compound I-10

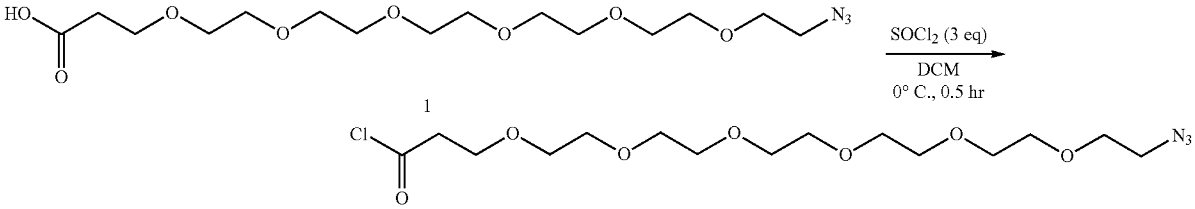

1

2

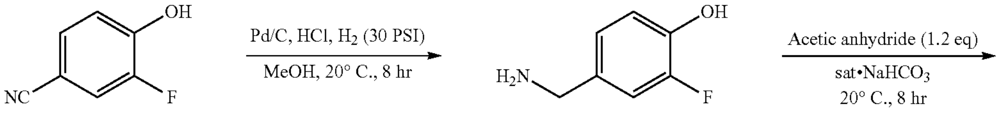

3

4

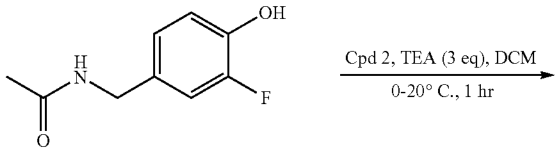

5

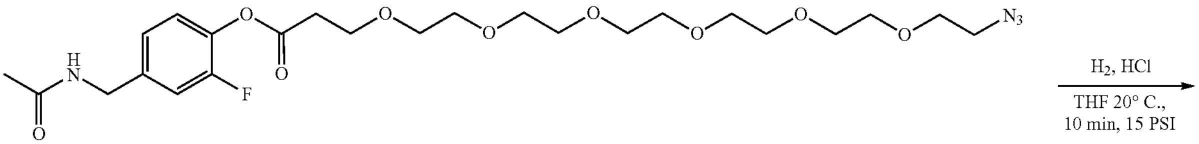

6

-continued

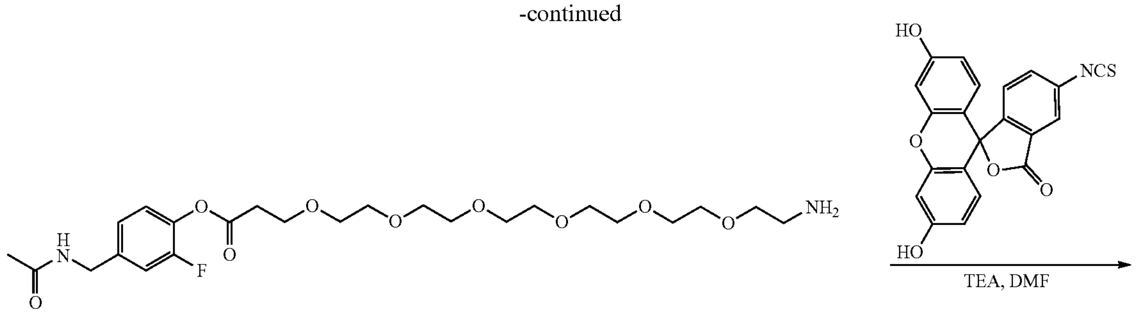

7

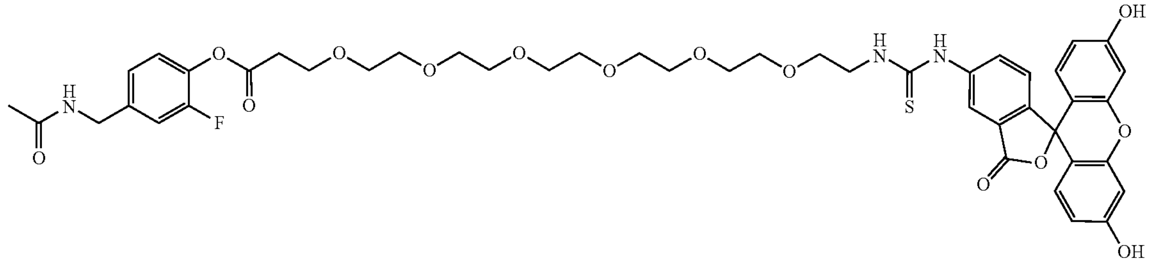

I-10

General Procedure for Preparation of Compound 2:

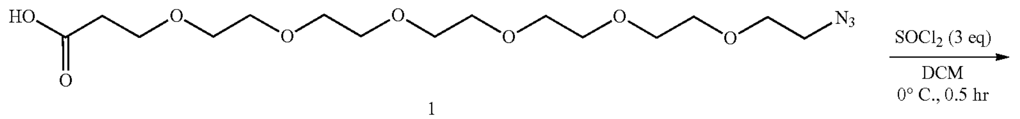

1

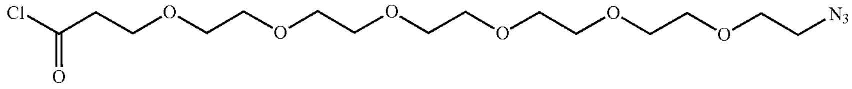

2

To a solution of compound 1 (100 mg, 263.57 umol, 1 eq) in DCM (1 mL) was added $SOCl_2$ (94.07 mg, 790.71 umol, 57.36 uL, 3 eq) at 0° C. The resulting mixture was stirred at 0° C. for 0.5 hr. TLC showed the reaction was complete. The reaction mixture was concentrated directly. The crude product compound 2 (104 mg, 261.40 umol, 99.18% yield) was used into the next step without further purification.

General Procedure for Preparation of Compound 4:

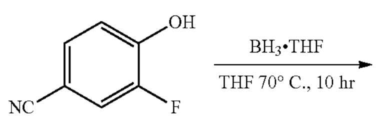

3

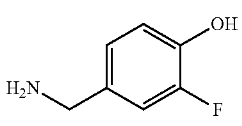

4

$BH_3$-THF (1 M, 29.17 mL, 4 eq) was added carefully to a solution of compound 3 (1 g, 7.29 mmol, 1 eq) in anhydrous THF (50 mL). The resultant solution was stirred and heated to reflux for 10 hr (70° C.). TLC (Petroleum ether:Ethyl acetate=1:1, $R_f$=0.01) indicated compound 3 was consumed completely and one new spot formed. After the mixture was cooled to room temperature, 6 N HCl (2 mL) was carefully added to the solution, and it was heated to reflux for 30 min. The mixture was concentrated under reduced pressure to give a residue. Compound 4 (2.3 g, 6.48 mmol, 88.78% yield, 50% purity, HCl) was obtained as a white solid.

General Procedure for Preparation of Compound 5:

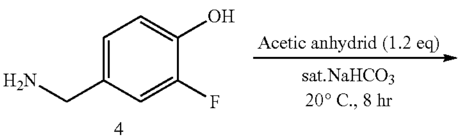

4

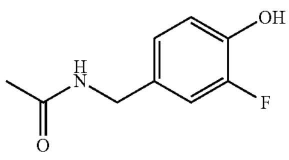

5

A mixture of compound 4 (1 g, 2.82 mmol, 1 eq, HCl), acetyl acetate (316.15 mg, 3.10 mmol, 290.04 uL, 1.1 eq) in $NaHCO_3$ (10 mL) was degassed and purged with $N_2$ 3 times, and the mixture was then stirred at 20° C. for 8 hr under $N_2$ atmosphere. LCMS showed the starting material was consumed completely. TLC indicated compound 4 was consumed completely. The reaction mixture was acidified to pH 4-5 with 1 M HCl. The reaction mixture was extracted with EtOAc (30 mL*2). The combined organic layers were washed with brine (30 mL), dried over $Na_2SO_4$, filtered and concentrated under reduced pressure to give a residue. The residue was purified by column chromatography ($SiO_2$, Petroleum ether:Ethyl acetate=20:1 to 1:2). Compound 5 (250 mg, 1.36 mmol, 48.48% yield) was obtained as a white solid. LCMS: RT=0.413 min, MS cal.: 183.0, $[M+H]^+$=184.0. $^1H$ NMR (400 MHz, DMSO-$d_6$) δ ppm 9.76 (s, 1H) 8.32 (br s, 1H) 7.03-7.09 (m, 1H) 6.90-6.95 (m, 2H) 4.19 (d, J=5.87 Hz, 2H) 1.91 (s, 3H).

General Procedure for Preparation of Compound 6:

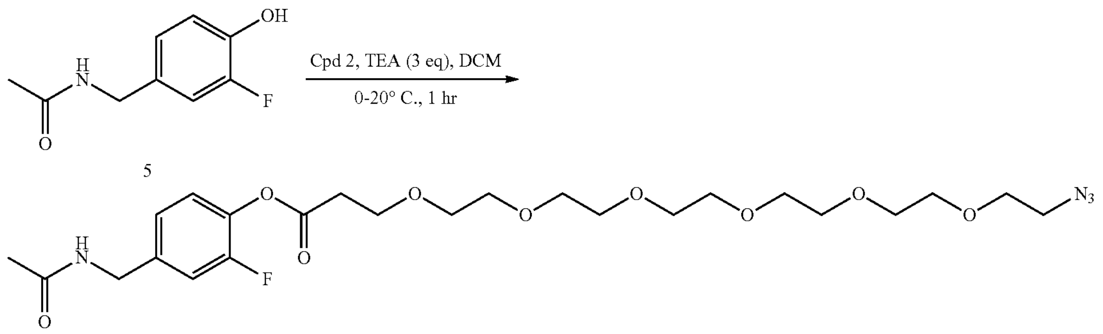

5

6

To a solution of compound 2 (104 mg, 261.40 umol, 1 eq) in DCM (1 mL) was added TEA (79.35 mg, 784.20 umol, 109.15 uL, 3 eq) at 0° C. and then compound 5 (47.88 mg, 261.40 umol, 1 eq) in DCM (1 mL) was added at 0° C. The resulting mixture was stirred at 20° C. for 2 hr. LCMS showed formation of desired product. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 25%-55%, 12 min). Compound 6 (82 mg, 150.58 umol, 57.60% yield) was obtained as a white oil. LCMS: RT=1.789 min, MS cal.: 544.2, $[M+H]^+$=545.5. $^1H$ NMR (400 MHz, CHLOROFORM-d) δ ppm 7.04-7.17 (m, 3H) 5.92 (br s, 1H) 4.44 (d, J=5.87 Hz, 2H) 3.89 (t, J=6.36 Hz, 2H) 3.60-3.73 (m, 24H) 3.40 (br t, J=5.07 Hz, 3H) 2.90 (t, J=6.36 Hz, 2H) 2.44 (br s, 2H) 2.07 (s, 3H).

General Procedure for Preparation of Compound 7:

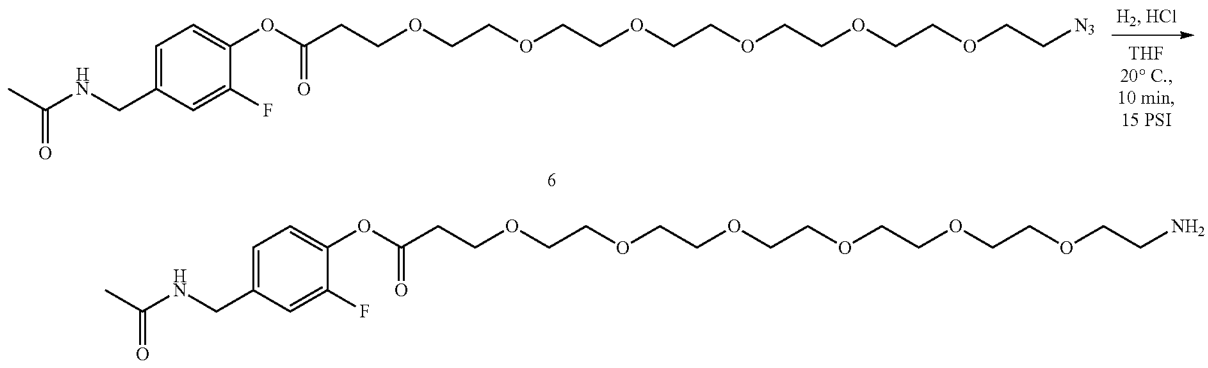

6

7

To a solution of compound 6 (82 mg, 150.58 umol, 1 eq) in THF (5 mL) was added HCl (1 M, 301.16 uL, 2 eq) and Pd/C (150.58 umol, 10% purity, 1 eq) under $N_2$. The suspension was degassed under vacuum and purged with $H_2$ several times. The mixture was stirred under $H_2$ (15 psi) at 20° C. for 10 min. LCMS showed the starting material was consumed completely. The reaction mixture was dried under nitrogen gas. The crude product was purified by reversed-phase HPLC (column: Welch Ultimate AQ-C18 150*30 mm*5 um; mobile phase: [water (0.1% TFA)-ACN]; B %: 12%-42%, 12 min). Compound 7 (4 mg, 7.71 umol, 5.12% yield) was obtained as a white oil. LCMS: RT=1.356 min, MS cal.: 518.2, $[M+H]^+$=519.2. $^1H$ NMR (400 MHz, CHLOROFORM-d) δ ppm 7.94 (br s, 1H) 7.05-7.18 (m, 1H) 6.31 (br s, 1H) 4.43 (d, J=5.75 Hz, 1H) 3.78-3.91 (m, 2H) 3.56-3.77 (m, 10H) 3.11 (br s, 1H) 2.88 (t, J=5.93 Hz, 1H) 2.06 (s, 1H) 1.61 (br s, 3H).

General Procedure for Preparation of Compound I-10:

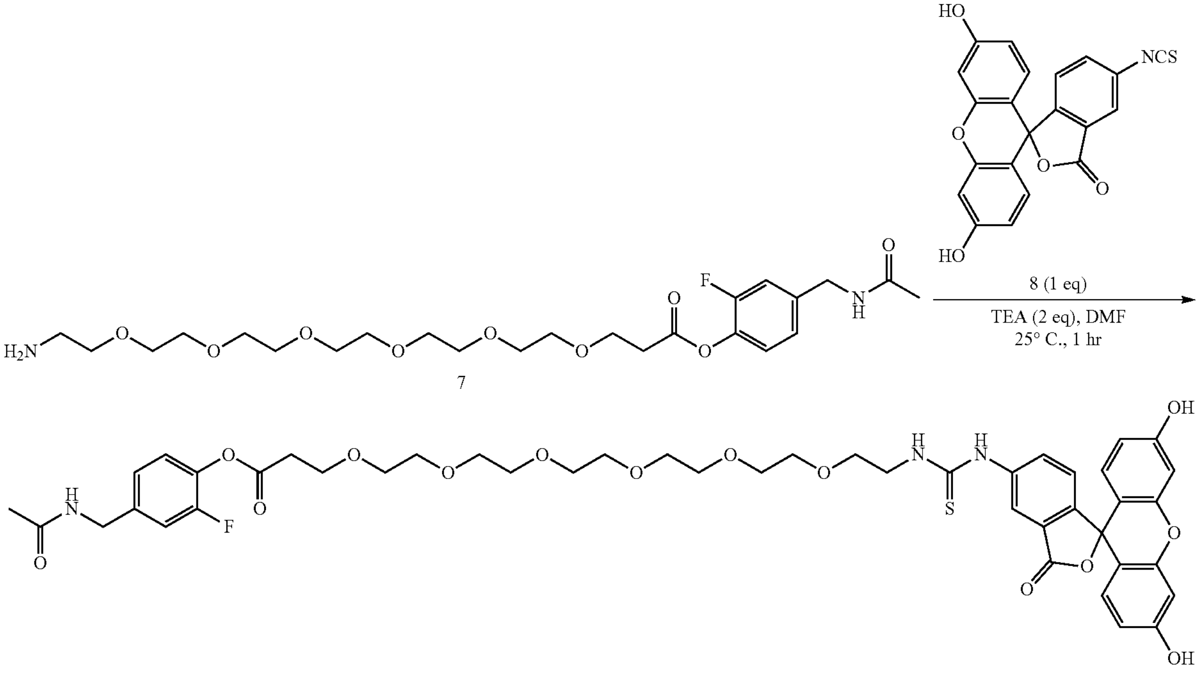

7

I-10

A mixture of compound 7 (4 mg, 7.71 umol, 1 eq), compound 8 (3.00 mg, 7.71 umol, 1 eq), TEA (1.56 mg, 15.43 umol, 2.15 uL, 2 eq) in DMF (0.2 mL) was degassed and purged with $N_2$ 3 times, and the mixture was then stirred at 25° C. for 1 hr under $N_2$ atmosphere. LCMS showed the starting material was consumed completely. HPLC showed the starting material was consumed completely. The reaction mixture was filtered and the filtrate was crude product. The crude product was purified by reversed-phase HPLC (column: Welch Ultimate AQ-C18 150*30 mm*5 um; mobile phase: [water (0.1% TFA)-ACN]; B %: 30%-60%, 12 min). Compound I-10 (1.35 mg, 1.49 umol, 19.28% yield) was obtained as a yellow solid. LCMS: RT=2.294 min, MS cal.: 907.3, $[M/2+H]^+$=454.8. HPLC: RT=2.496 min. $^1H$ NMR (400 MHz, DMSO-$d_6$) δ ppm 9.89-10.27 (m, 2H) 8.40 (br s, 1H) 8.27 (br s, 1H) 8.08 (br s, 1H) 7.72 (br s, 1H) 7.14-7.24 (m, 3H) 7.10 (br d, J=7.95 Hz, 1H) 6.67 (br s, 2H) 6.58 (q, J=8.35 Hz, 4H) 4.24 (br d, J=4.77 Hz, 2H) 3.64-3.77 (m, 5H) 3.55-3.64 (m, 9H) 3.50-3.55 (m, 13H) 2.86 (br s, 2H) 1.88 (s, 3H). MS: $[M/2+H]^+$=455.0.

Example 11. Exemplary Synthesis of Compound I-11
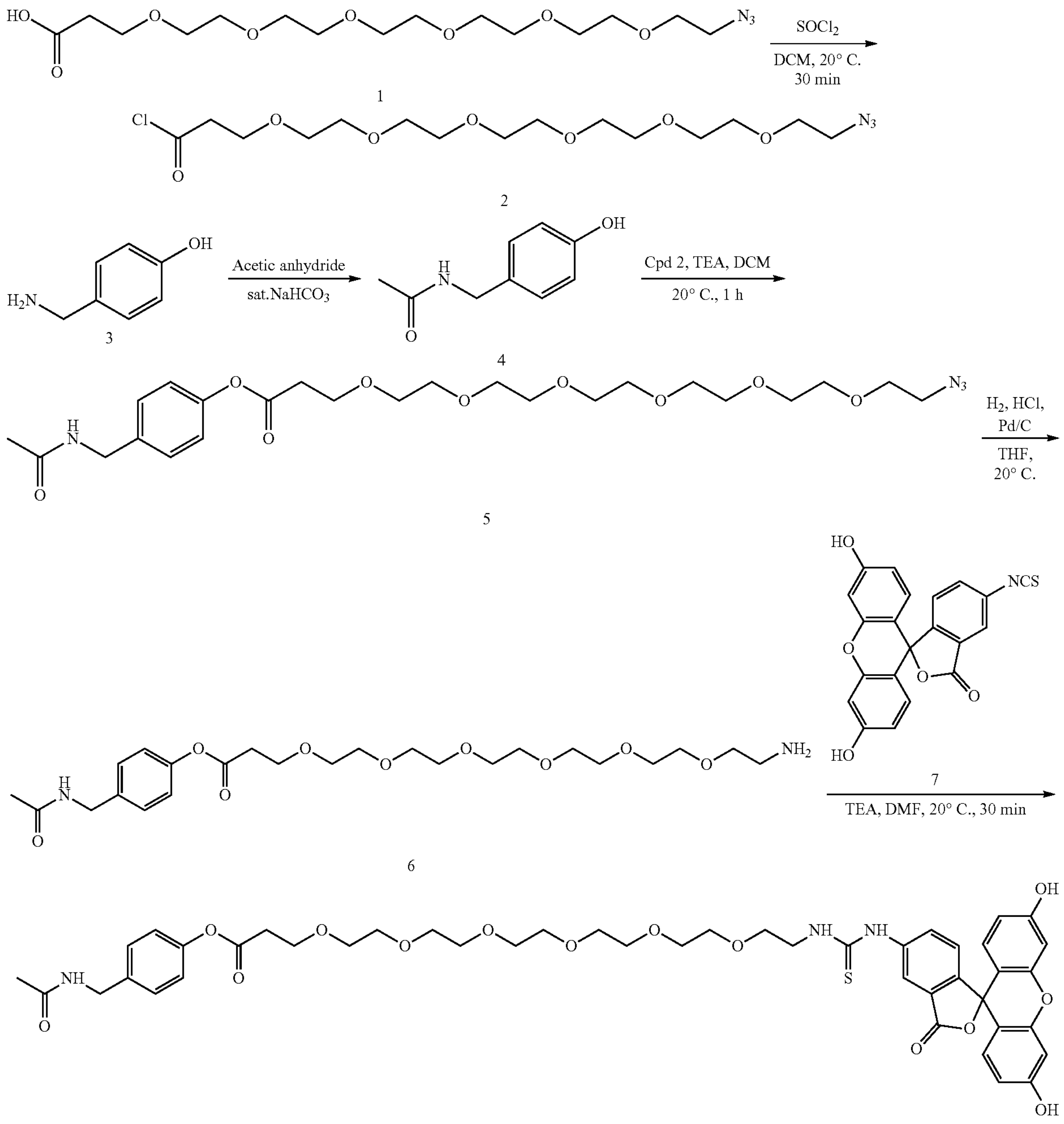
I-11
General Procedure for Preparation of Compound 2:
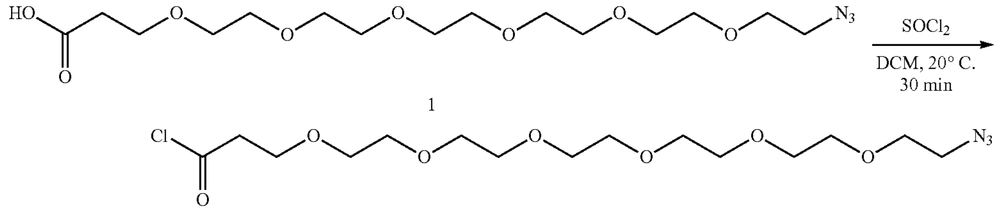
2

To a solution of compound 1 (100 mg, 263.57 umol, 1 eq) in $SOCl_2$ (94.07 mg, 790.71 umol, 57.36 uL, 3 eq) was added DCM (1 mL) in one portion at 0° C. under $N_2$. The mixture was stirred at 20° C. for 30 min. TLC (Dichloromethane:Methanol=10:1, $R_f$=0.5) indicated compound 1 was consumed completely and one new major spot formed. The reaction mixture was filtered and concentrated under reduced pressure to give a residue. The crude product compound 2 (104.86 mg, 263.57 umol, 100.00% yield) was used into the next step without further purification. Compound 2 (104.86 mg, 263.57 umol, 100.00% yield) was obtained as a colorless oil.

General Procedure for Preparation of Compound 4:

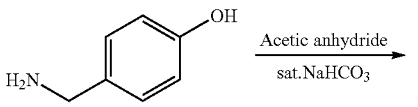

3

-continued

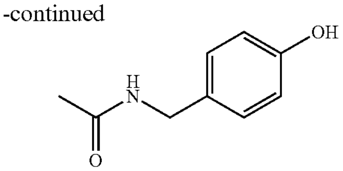

4

To a solution of compound 3 (300 mg, 2.44 mmol, 1 eq) in sat. $NaHCO_3$ (3 mL) was added $Ac_2O$ (273.56 mg, 2.68 mmol, 250.97 uL, 1.1 eq). The mixture was stirred at 20° C. for 10 hr. TLC showed formation of desired product (Petroleum ether:Ethyl acetate=0:1, $R_f$=0.05). The reaction mixture was acidified to pH 4 with 1M HCl, then the mixture was extracted with EtOAc (5 mL*3). The combined organic layer was washed with brine (5 mL), dried over $Na_2SO_4$, filtered and the filtrate was concentrated. The residue was purified by column chromatography ($SiO_2$, Petroleum ether/Ethyl acetate=20/1 to 1/1) (Petroleum ether:Ethyl acetate=0:1, $R_f$=0.64). Compound 4 (200 mg, 1.21 mmol, 49.70% yield) was obtained as a yellow solid.

General Procedure for Preparation of Compound 5:

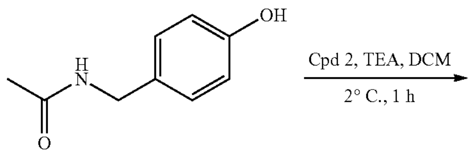

4

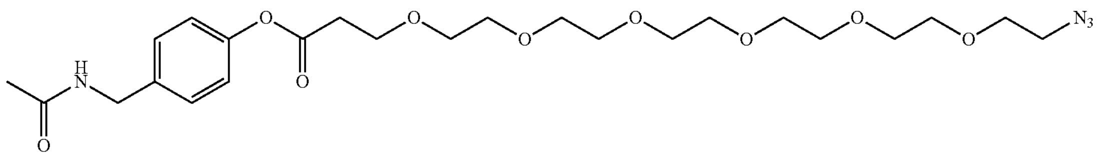

5

To a solution of compound 4 (47.98 mg, 261.40 umol, 1 eq) and TEA (79.35 mg, 784.21 umol, 109.15 uL, 3 eq) in DCM (1 mL) was added compound 2 (104.00 mg, 261.40 umol, 1 eq) in DCM (1 mL) slowly at 0° C. under $N_2$. The mixture was stirred at 20° C. for 1 hr. TLC (Dichloromethane:Methanol=10:1, $R_f$=0.3) indicated compound 4 was consumed completely and one new major spot formed. The mixture was concentrated. The residue was purified by prep-HPLC (column: Nano-micro Kromasil C18 80*5 mm*3 um; mobile phase: [water (0.1% TFA)-ACN]; B %: 20%-40%, 10 min). Compound 5 (48 mg, 91.15 umol, 34.87% yield) was obtained as a colorless oil. LCMS: RT=1.148 min, MS cal.: 526.2 $[M+H]^+$=527.2. $^1H$ NMR (400 MHz, CHLOROFORM-d) δ ppm 2.03 (s, 3H) 2.85 (t, J=6.28 Hz, 2H) 3.40 (d, J=5.07 Hz, 1H) 3.62-3.71 (m, 22H) 3.87 (t, J=6.28 Hz, 2H) 4.43 (d, J=5.73 Hz, 2H) 5.78 (br s, 1H) 7.07 (d, J=8.38 Hz, 2H) 7.30 (d, J=8.38 Hz, 2H).

General Procedure for Preparation of Compound I-11:

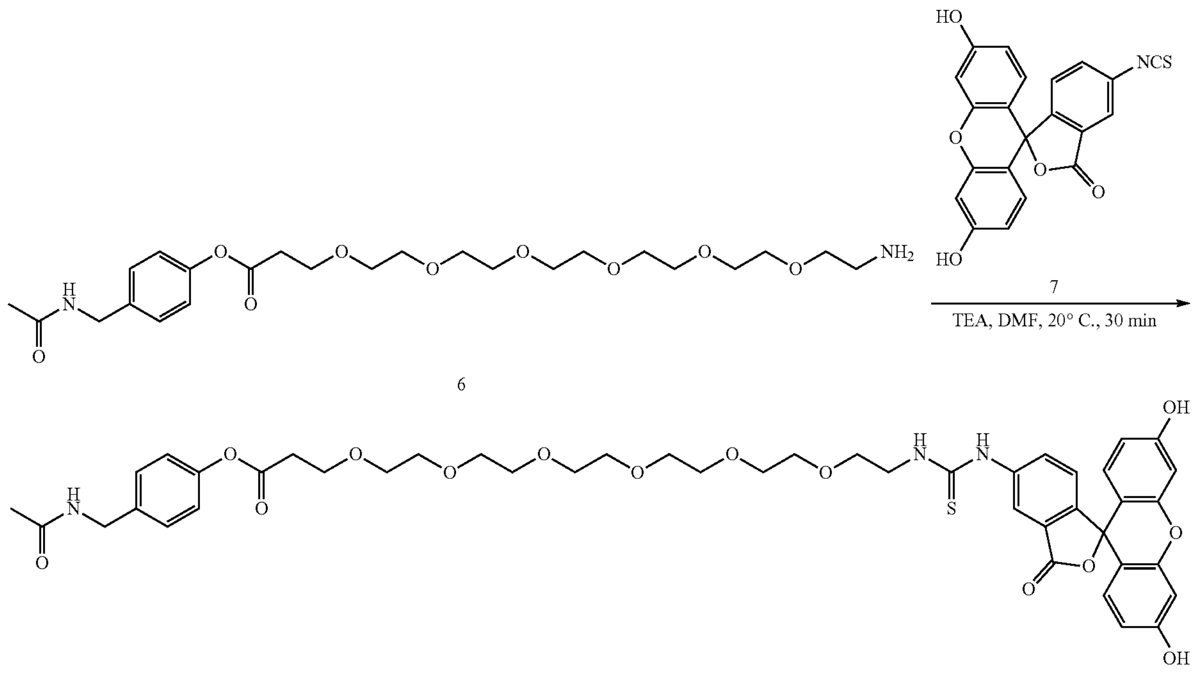

6

I-11

To a solution of compound 6 (30 mg, 48.81 umol, 1 eq, TFA) and compound 7 (19.01 mg, 48.81 umol, 1 eq) in DMF (0.5 mL) was added TEA (4.94 mg, 48.81 umol, 6.79 uL, 1 eq) in one portion at 0° C. under $N_2$. The mixture was stirred at 20° C. for 0.5 hr. LCMS showed compound 6 was consumed completely and desired mass was detected. The reaction mixture was concentrated. The residue was purified by prep-HPLC (column: Welch Ultimate AQ-C18 150*30 mm*5 um; mobile phase: [water (0.1% TFA)-ACN]; B %: 30%-60%, 12 min). Compound I-11 (4.05 mg, 4.55 umol, 9.32% yield) was obtained as a yellow solid. LCMS: RT=2.083 min, MS cal.: 889.3 $[M+H]^+$=890.3; $[M/2+H]^+$=445.9. HPLC: RT=2.767 min. $^1H$ NMR (400 MHz, DMSO-$d^6$) δ ppm 1.86 (s, 3H) 2.80 (t, J=6.17 Hz, 2H) 3.41-3.65 (m, 22H) 3.66-3.77 (m, 4H) 4.23 (d, J=5.95 Hz, 2H) 6.51-6.63 (m, 4H) 6.67 (d, J=2.21 Hz, 2H) 7.04 (d, J=8.38 Hz, 2H) 7.18 (d, J=8.16 Hz, 1H) 7.27 (d, J=8.38 Hz, 2H) 7.73 (br d, J=8.16 Hz, 1H) 8.08 (br s, 1H) 8.27 (s, 1H) 8.35 (br t, J=5.95 Hz, 1H) 9.97-10.21 (m, 3H). MS: MS cal.: 889.3 $[M/2+H]^+$=445.9; $[M+H]^+$=890.5.

Example 12. Exemplary Synthesis of Compound I-12

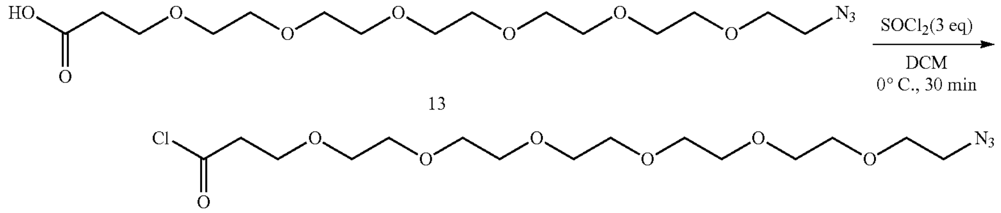

13

14

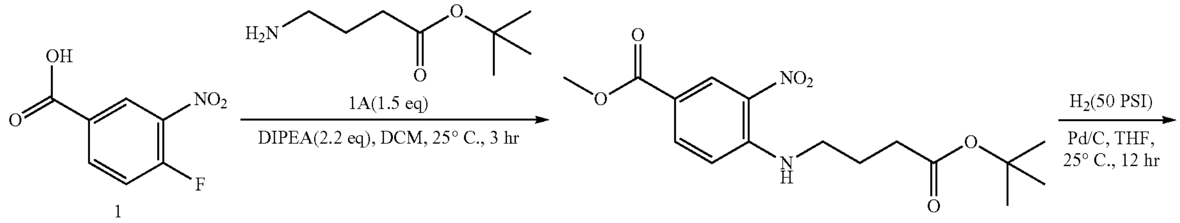

1

2

-continued
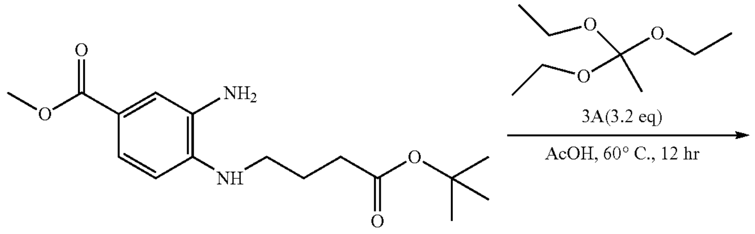
3
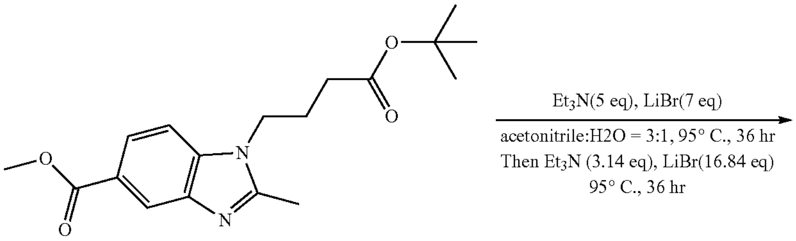
4
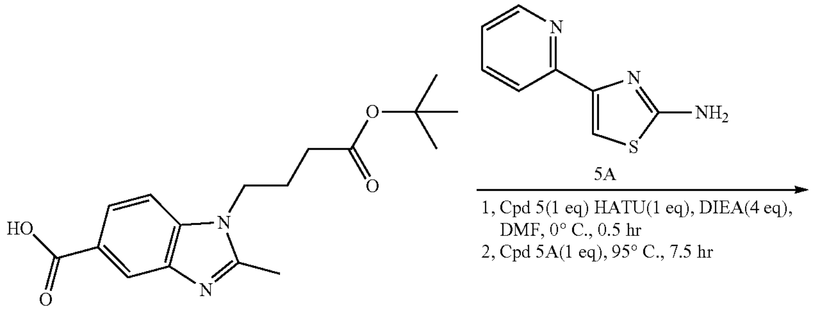
5
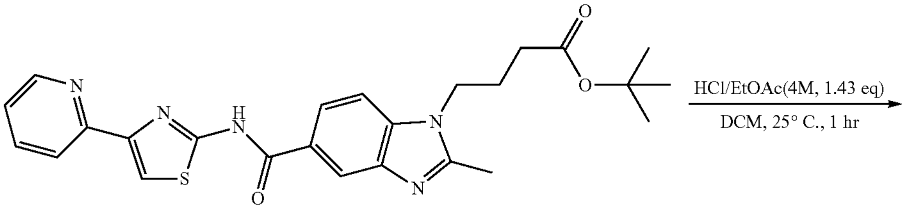
6
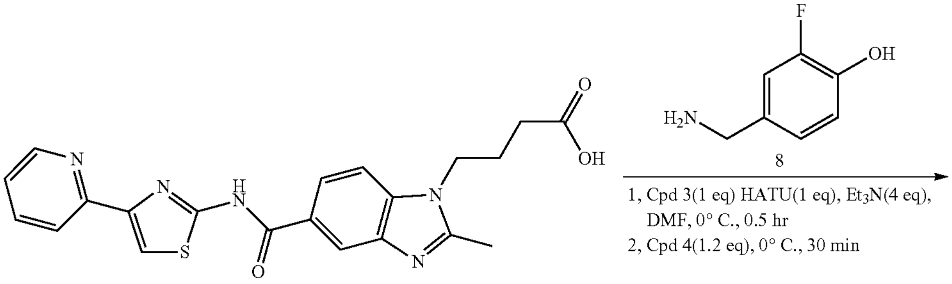
7
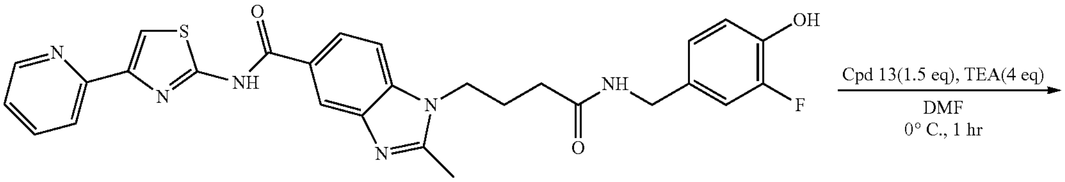
9

-continued

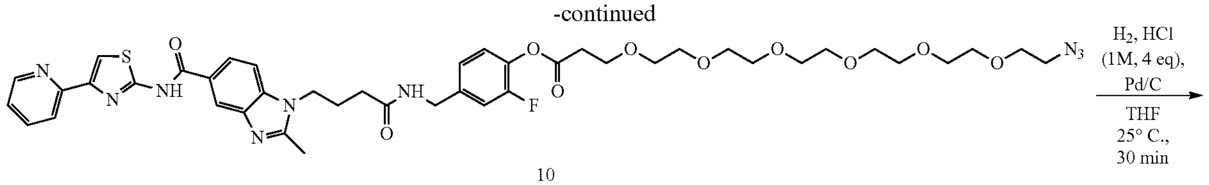

10

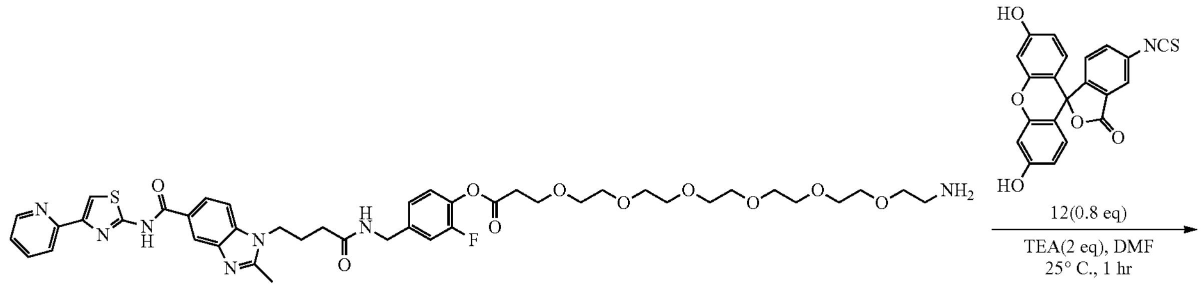

11

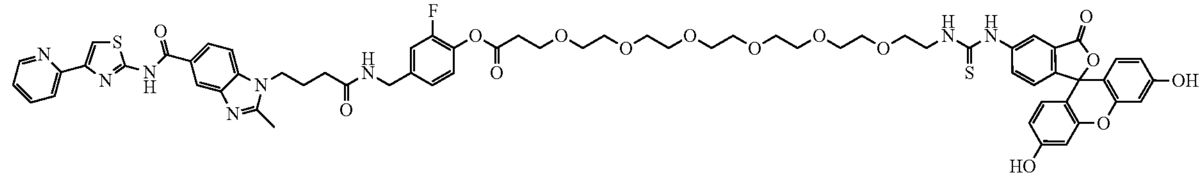

I-12

General Procedure for Preparation of Compound 13:

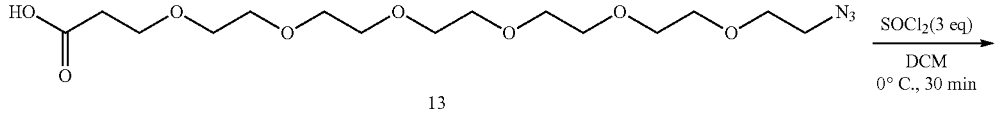

13

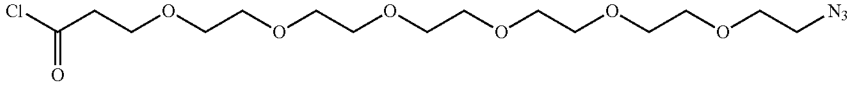

14

To a solution of compound 13 (80 mg, 210.86 umol, 1 eq) in DCM (2 mL) was added $SOCl_2$ (75.26 mg, 632.57 umol, 45.89 uL, 3 eq). The mixture was stirred at 0° C. for 30 min. TLC (Dichloromethane:Methanol=10:1, $R_f$=0.57) indicated compound 13 was consumed completely and one new spot formed. The reaction mixture was concentrated under reduced pressure to give a residue. Compound 14 (83 mg, 208.62 umol, 98.94% yield) was obtained as a yellow oil.

General Procedure for Preparation of Compound 2:

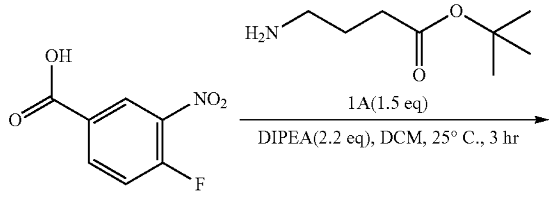

1

-continued

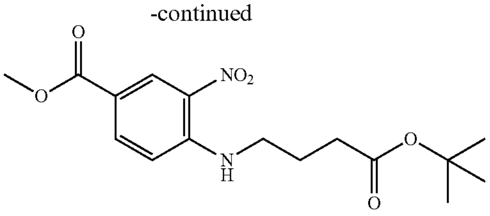

2

To a solution of compound 1 (20 g, 100.43 mmol, 1 eq) and compound 1A (19.65 g, 100.43 mmol, 1 eq, HCl) in DCM (150 mL) was added DIPEA (28.56 g, 220.95 mmol, 38.49 mL, 2.2 eq). The mixture was stirred at 25° C. for 3 hr. TLC (Petroleum ether:Ethyl acetate=3:1, $R_f$=0.24) indicated compound 1 was consumed completely and one new spot formed. The reaction was clean according to TLC. To the reaction mixture was added DCM (50 mL). The mixture was then washed with 0.2 M HCl (100 mL*2), the combined organic layers were dried over $Na_2SO_4$, filtered and concentrated under reduced pressure to give a residue. The residue was used directly next step. Compound 2 (33 g, 97.53 mmol, 97.11% yield) was obtained as a yellow solid.

General Procedure for Preparation of Compound 3:

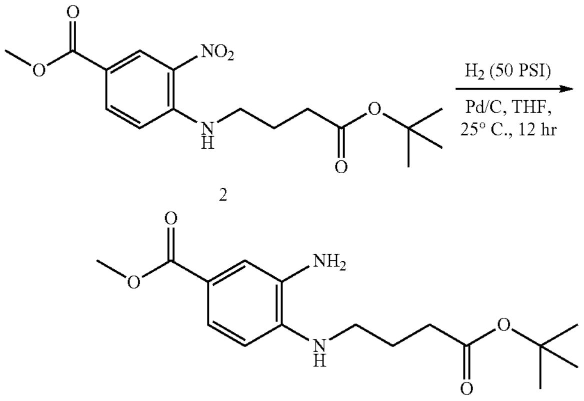

2

3

A mixture of compound 2 (30 g, 88.66 mmol, 1 eq) and Pd/C (88.66 mmol, 10% purity, 1 g) in THF (80 mL) was degassed and purged with $H_2$ 3 times, and the mixture was then stirred at 25° C. for 12 hr under $H_2$ atmosphere. TLC (Ethyl acetate, $R_f$=0.5) indicated compound 2 was consumed completely and one new spot formed. The reaction was clean according to TLC. The reaction mixture was concentrated under reduced pressure to give a residue. Compound 3 (27 g, 87.56 mmol, 98.75% yield) was obtained as a yellow solid.

General Procedure for Preparation of Compound 4:

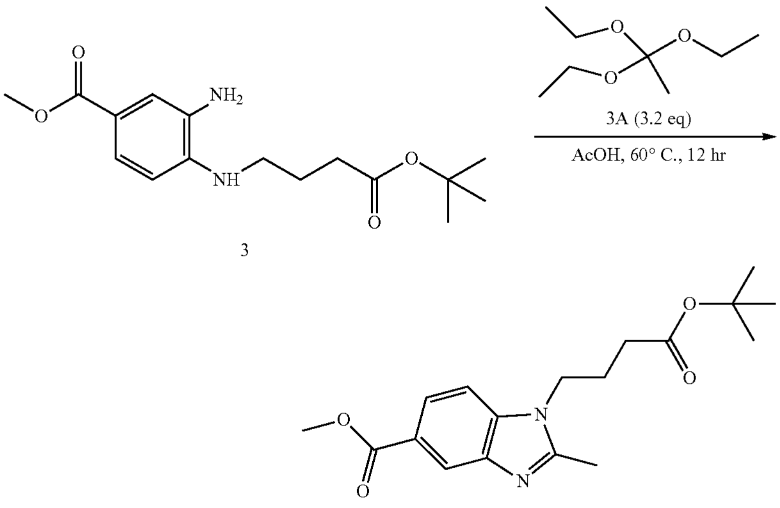

3

4

A mixture of compound 3 (27 g, 87.56 mmol, 1 eq) and compound 3A (45.45 g, 280.18 mmol, 51.36 mL, 3.2 eq) was prepared in AcOH (300 mL). The mixture was stirred at 60° C. for 12 hr. TLC (Ethyl acetate, $R_f$=0.42) indicated compound 3 was consumed completely and one spot formed. The reaction was clean according to TLC. The reaction mixture was partitioned between EtOAc (150 mL) and $H_2O$ (150 mL). The organic phase was separated, dried over $Na_2SO_4$, filtered and concentrated under reduced pressure to give a residue. Compound 4 (24 g, 72.20 mmol, 82.47% yield) was obtained as a yellow solid.

General Procedure for Preparation of Compound 5:

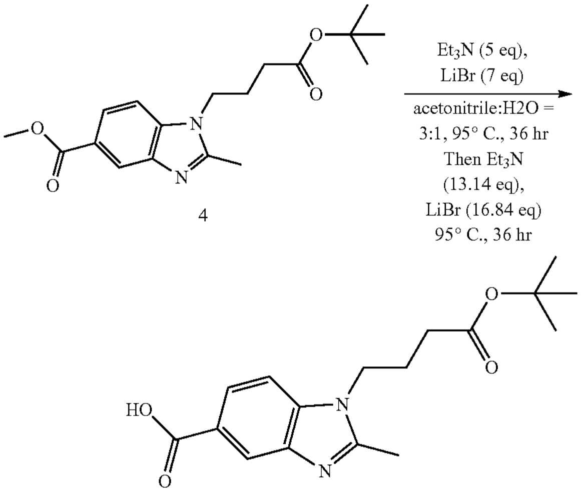

4

5

Three reactions were run in parallel. To a solution of compound 4 (10 g, 30.08 mmol, 1 eq) in acetonitrile (900 mL) and $H_2O$ (300 mL) was added $Et_3N$ (15.22 g, 150.42 mmol, 20.94 mL, 5 eq) and LiBr (18.29 g, 210.59 mmol, 5.29 mL, 7 eq). The mixture was stirred at 95° C. for 36 hr. $Et_3N$ (40.00 g, 395.30 mmol, 55.02 mL, 13.14 eq) and LiBr (44.00 g, 506.65 mmol, 12.72 mL, 16.84 eq) was added to the reaction mixture. The mixture was stirred at 95° C. for 36 hr. LC-MS showed compound 4 was consumed completely and one main peak with desired mass was detected. The three reactions were worked up together. The reaction mixture was concentrated under reduced pressure to remove solvent. The residue was dissolved by water (200 ml), the aqueous phase was acidified to pH 5 with aqueous HCl and a solid formed. Filtered to give a filter cake. The filter cake was recovered with MePh (3*200 ml), and the resultant solution was concentrated in vacuum to give product. Compound 5 (15 g, 47.12 mmol, 52.20% yield) was obtained as a yellow solid. LCMS: RT=1.108 min, MS cal.: 318.2, $[M+H]^+$=319.1.

General Procedure for Preparation of Compound 6:

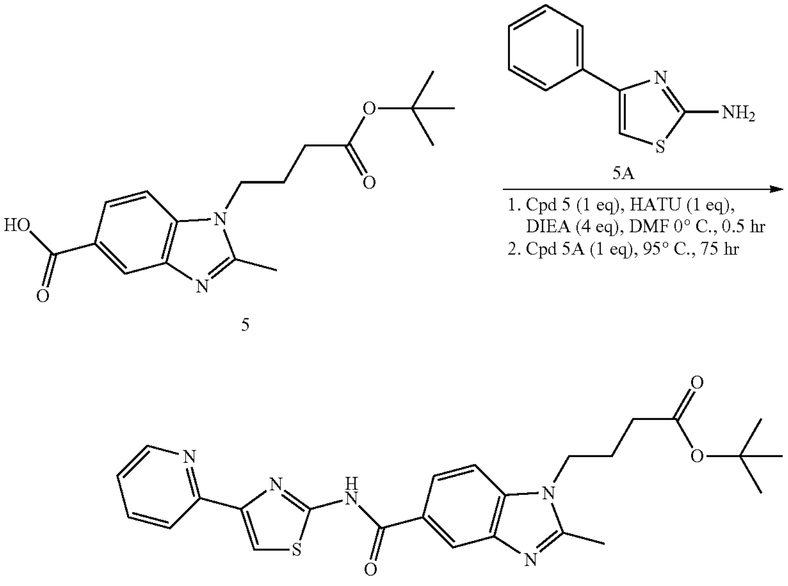

5A

5

6

To a solution of compound 5 (16 g, 50.26 mmol, 1 eq) in DMF (100 mL) was added HATU (19.11 g, 50.26 mmol, 1 eq) and DIEA (25.98 g, 201.03 mmol, 35.02 mL, 4 eq). The mixture was stirred at 0° C. for 0.5 hr. Then compound 5A (8.91 g, 50.26 mmol, 1 eq) was added to the reaction mixture, the mixture was stirred at 90° C. for 7.5 hr. LC-MS showed compound 5 was consumed completely and one main peak with desired mass was detected. The residue was diluted with $H_2O$ (500 mL) and extracted with EtOAc (500 mL*2). The combined organic layers were washed with brine (100 mL), dried over $Na_2SO_4$, filtered and concentrated under reduced pressure to give a residue. The residue was purified by column chromatography ($SiO_2$, DCM: MeOH=200/1 to 0:1). Compound 6 (19 g, 39.78 mmol, 79.16% yield) was obtained as a white solid. LCMS: RT=1.639 min, MS cal.: 477.2, $[M+H]^+$=478.0.

General Procedure for Preparation of Compound 7:

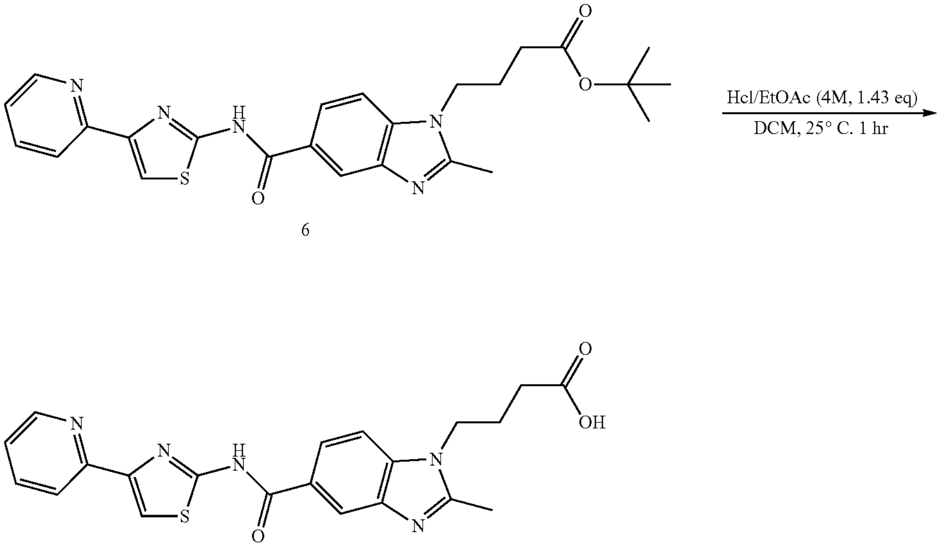

6

7

To a solution of compound 6 (4 g, 8.38 mmol, 1 eq) in DCM (5 mL) was added HCl/EtOAc (4 M, 3 mL, 1.43 eq). The mixture was stirred at 25° C. for 1 hr. TLC (Dichloromethane:Methanol=10:1, Rf=0.24) showed the reaction was complete. The reaction mixture was concentrated under reduced pressure to give a residue. Compound 7 (4.3 g, 8.03 mmol, 95.87% yield, TFA) was obtained as a white solid.

General Procedure for Preparation of Compound 9:

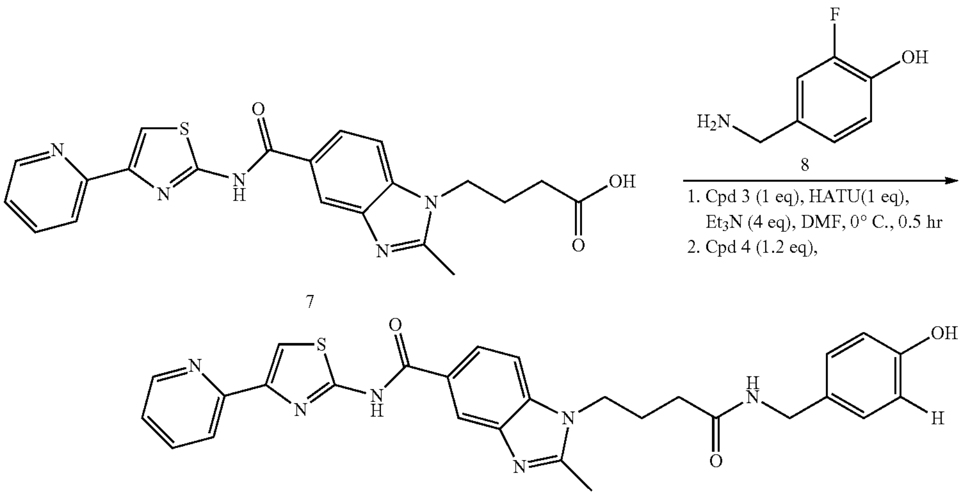

7

9

To a solution of compound 7 (250 mg, 466.86 umol, 1 eq, TFA) in DMF (5 mL) was added $Et_3N$ (188.97 mg, 1.87 mmol, 259.93 uL, 4 eq) and HATU (177.51 mg, 466.86 umol, 1 eq). The mixture was stirred at 0° C. for 30 min. The reaction mixture was added dropwise to compound 8 (199.00 mg, 560.23 umol, 1.2 eq, HCl) at 0° C. The mixture was stirred at 0° C. for 30 min. LC-MS (Rt=0.966 min) showed compound 7 was consumed completely and one main peak desired mass was detected. The reaction mixture concentrated under reduced pressure to give a residue. The residue was purified by prep-HPLC (TFA condition: column: Nano-micro Kromasil C18 80*25 mm*3 um; mobile phase: [water (0.1% TFA)-ACN]; B %: 5%-45%, 7 min). Compound 9 (280 mg, 425.13 umol, 91.06% yield, TFA) was obtained as a white solid. LCMS: RT=0.966 min, MS cal.: 544.2, $[M+H]^+$=545.3. $[M/2+H]^+$=273.2. $^1H$ NMR (400 MHz, DMSO-$d_6$) δ 8.50-8.68 (m, 2H) 8.20-8.36 (m, 2H) 7.90-8.10 (m, 3H) 7.35-7.43 (m, 1H) 6.96-7.05 (m, 1H) 6.82-6.92 (m, 2H) 4.36-4.48 (m, 2H) 4.10-4.17 (m, 3H) 2.74-2.86 (m, 3H) 2.26-2.37 (m, 2H) 2.01-2.12 (m, 2H).

General Procedure for Preparation of Compound 10:

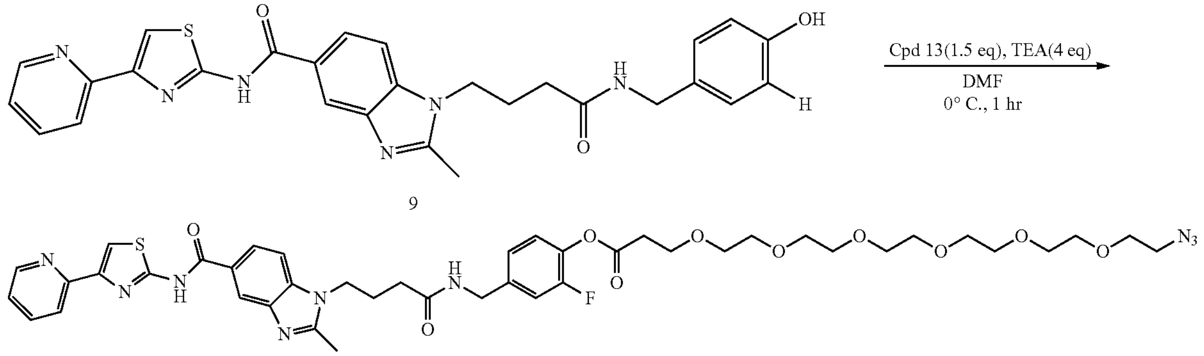

9

10

To a solution of compound 13 (82.19 mg, 206.57 umol, 1.5 eq) in DMF (2 mL) was added $Et_3N$ (55.74 mg, 550.86 umol, 76.67 uL, 4 eq) and compound 9 (75 mg, 137.72 umol, 1 eq, TFA). The mixture was stirred at 0° C. for 1 hr. LC-MS (Rt=1.769 min) showed compound 9 was consumed completely and one main peak with desired mass was detected. The reaction mixture was concentrated under reduced pressure to give a residue. The residue was purified by prep-HPLC (TFA condition: column: Nano-micro Kromasil C18 80*25 mm*3 um; mobile phase: [water (0.1% TFA)-ACN]; B %: 15%-60%, 7 min). Compound 10 (90 mg, 99.34 umol, 72.13% yield) was obtained as a white solid. LCMS: RT=1.290 min, MS cal.: 905.4, $[M/2+H]^+$=453.8.

General Procedure for Preparation of Compound 11:

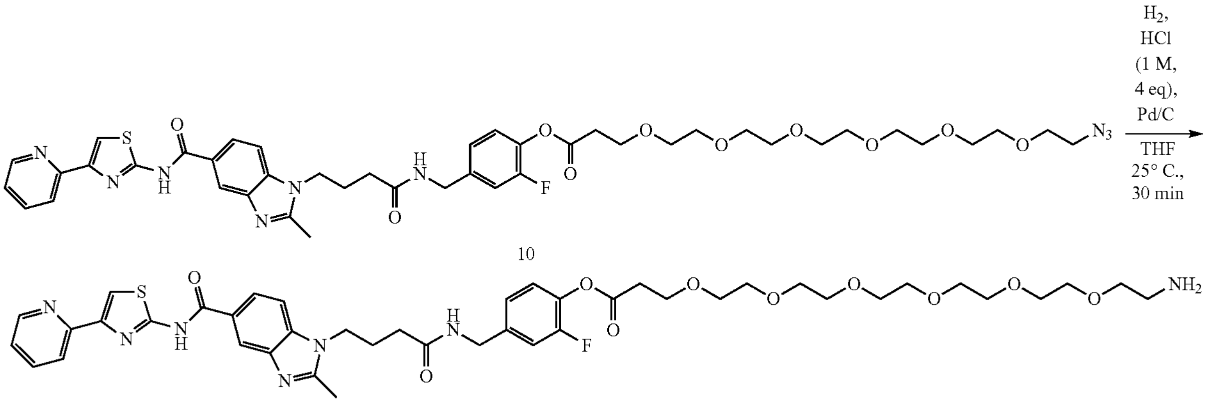

10

11

A mixture of compound 10 (90 mg, 99.34 umol, 1 eq), HCl (1 M, 397.36 uL, 4 eq), and Pd/C (90 mg, 10% purity) in THF (3 mL) was degassed and purged with $H_2$ 3 times, and the mixture was then stirred at 25° C. for 30 min under $H_2$ atmosphere. LC-MS (Rt=1.473 min) showed compound 10 was consumed completely and one main peak with desired mass was detected. The suspension was filtered and the filter cake was washed with THF (5 mL×3). The combined filtrates were concentrated to dryness to give product as a white solid. The residue was purified by prep-HPLC (TFA condition: column: Nano-micro Kromasil C18 80*25 mm*3 um; mobile phase: [water (0.1% TFA)-ACN]; B %: 5%-45%, 7 min). Compound 11 (30 mg, 34.09 umol, 34.32% yield) was obtained as a white solid. LCMS: RT=1.473 min, MS cal.: 879.4, $[M/2+H]^+$=440.9. $^1$H NMR (400 MHz, DMSO-d6) δ 12.90-12.98 (m, 1H) 8.61-8.67 (m, 1H) 8.50-8.53 (m, 1H) 8.42-8.49 (m, 1H) 8.17-8.23 (m, 1H) 8.04-8.09 (m, 1H) 7.90-7.97 (m, 3H) 7.65-7.81 (m, 2H) 7.35-7.42 (m, 1H) 7.16-7.26 (m, 2H) 7.07-7.14 (m, 1H) 4.34-4.44 (m, 2H) 4.23-4.29 (m, 2H) 3.71-3.77 (m, 4H) 3.55-3.60 (m, 24H) 2.94-3.02 (m, 2H) 2.83-2.90 (m, 2H) 2.73-2.79 (m, 3H) 2.00-2.11 (m, 2H).

General Procedure for Preparation of Compound I-12:

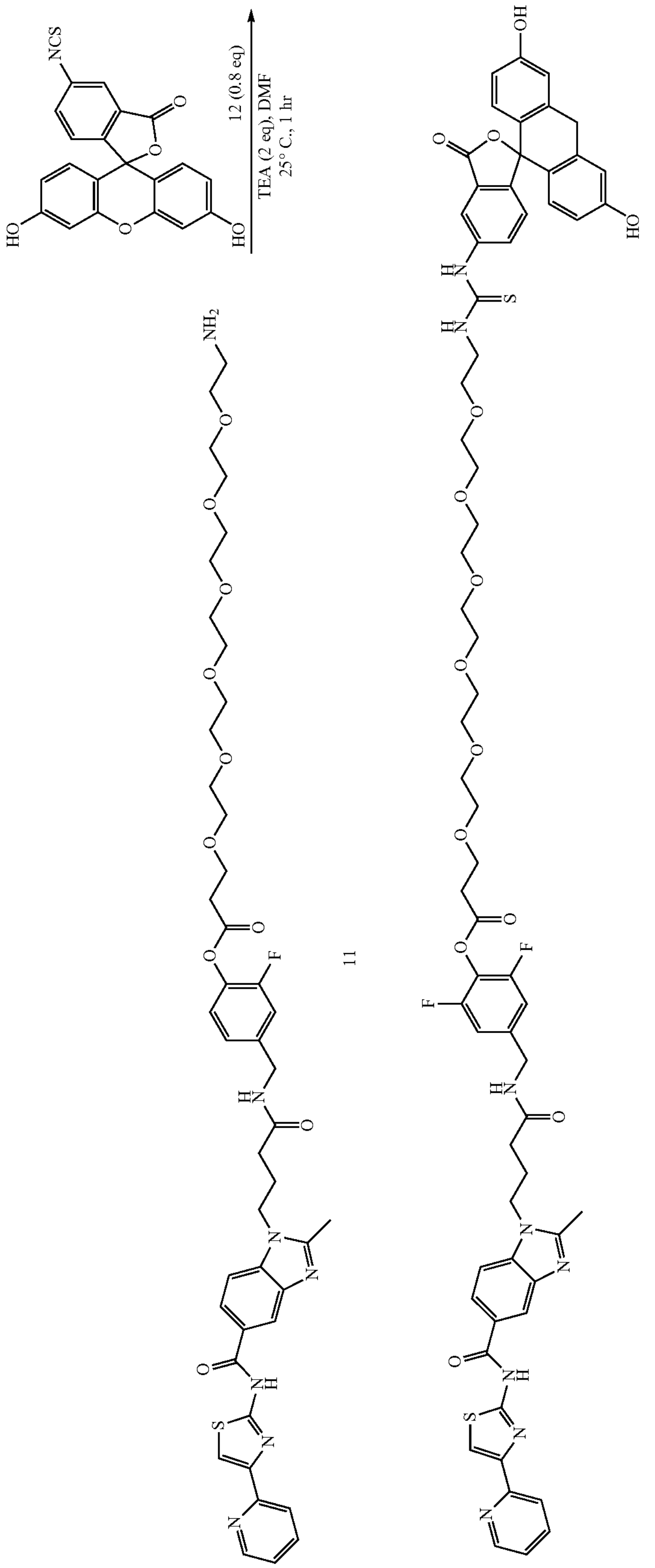
11
I-12

To a solution of compound 11 (30 mg, 34.09 umol, 1 eq, TFA) and compound 12 (10.62 mg, 27.27 umol, 0.8 eq) in DMF (1 mL) was added $Et_3N$ (6.90 mg, 68.18 umol, 9.49 uL, 2 eq). The mixture was stirred at 25° C. for 1 hr. LC-MS (Rt=2.071 min) showed compound 11 was consumed completely and one main peak with desired mass was detected. The reaction mixture was concentrated under reduced pressure to give a residue. The residue was purified by prep-HPLC (TFA condition; column: Welch Ultimate AQ-C18 150*30 mm*5 um; mobile phase: [water (0.1% TFA)-ACN]; B %: 25%-55%, 12 min). Compound I-12 (3.80 mg, 2.99 umol, 8.78% yield) was obtained as a white solid. LCMS: RT=2.071 min, MS cal.: 1268.4, $[M/2+H]^+$=635.6, $[M/3+H]^+$=424.1. MS: MS cal.: 1268.4, $[M/2+H]^+$=635.3. $^1H$ NMR (400 MHz, DMSO-d6) δ 12.97-13.06 (m, 1H) 9.99-10.26 (m, 2H) 8.62-8.67 (m, 1H) 8.51-8.56 (m, 1H) 8.41-8.49 (m, 1H) 8.23-8.30 (m, 2H) 8.09-8.15 (m, 1H) 8.02-8.09 (m, 2H) 7.91-7.98 (m, 2H) 7.70-7.77 (m, 1H) 7.36-7.42 (m, 1H) 7.17-7.24 (m, 2H) 7.06-7.13 (m, 1H) 6.65-6.70 (m, 2H) 6.54-6.63 (m, 3H) 4.40-4.48 (m, 2H) 4.22-4.27 (m, 2H) 3.72-3.76 (m, 2H) 3.46-3.64 (m, 21H) 2.85-2.89 (m, 1H) 2.78-2.84 (m, 3H) 2.31-2.36 (m, 2H) 2.02-2.13 (m, 2H). HPLC: The retention time of the product was 2.521 min.

Example 13. Exemplary Synthesis of Compound I-13

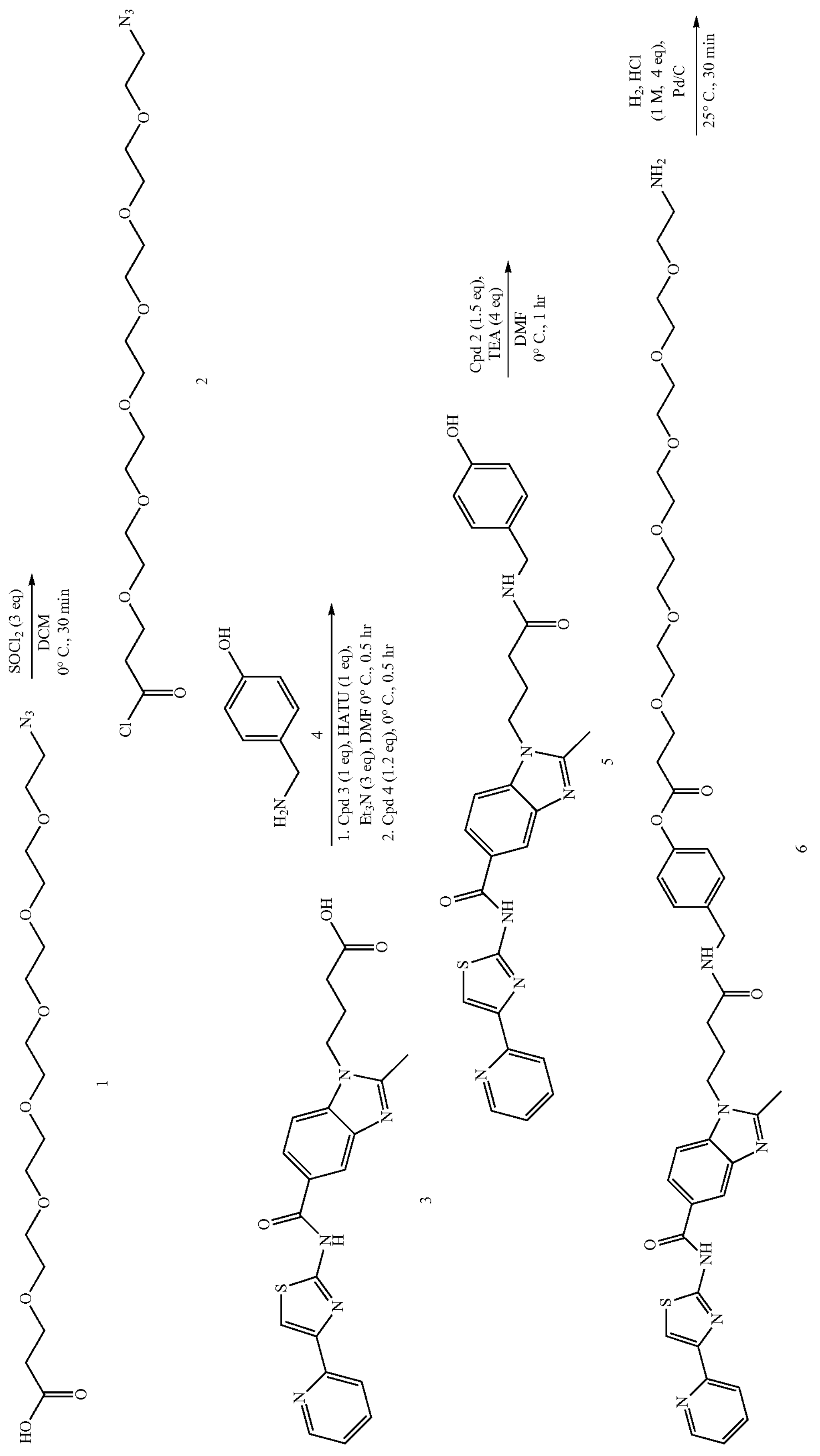
SOCl2 (3 eq)
DCM
0° C., 30 min
1
2
4
1. Cpd 3 (1 eq), HATU (1 eq),
Et3N (3 eq), DMF 0° C., 0.5 hr
2. Cpd 4 (1.2 eq), 0° C., 0.5 hr
3
Cpd 2 (1.5 eq),
TEA (4 eq)
DMF
0° C., 1 hr
5
H2, HCl
(1 M, 4 eq),
Pd/C
25° C., 30 min
6

-continued
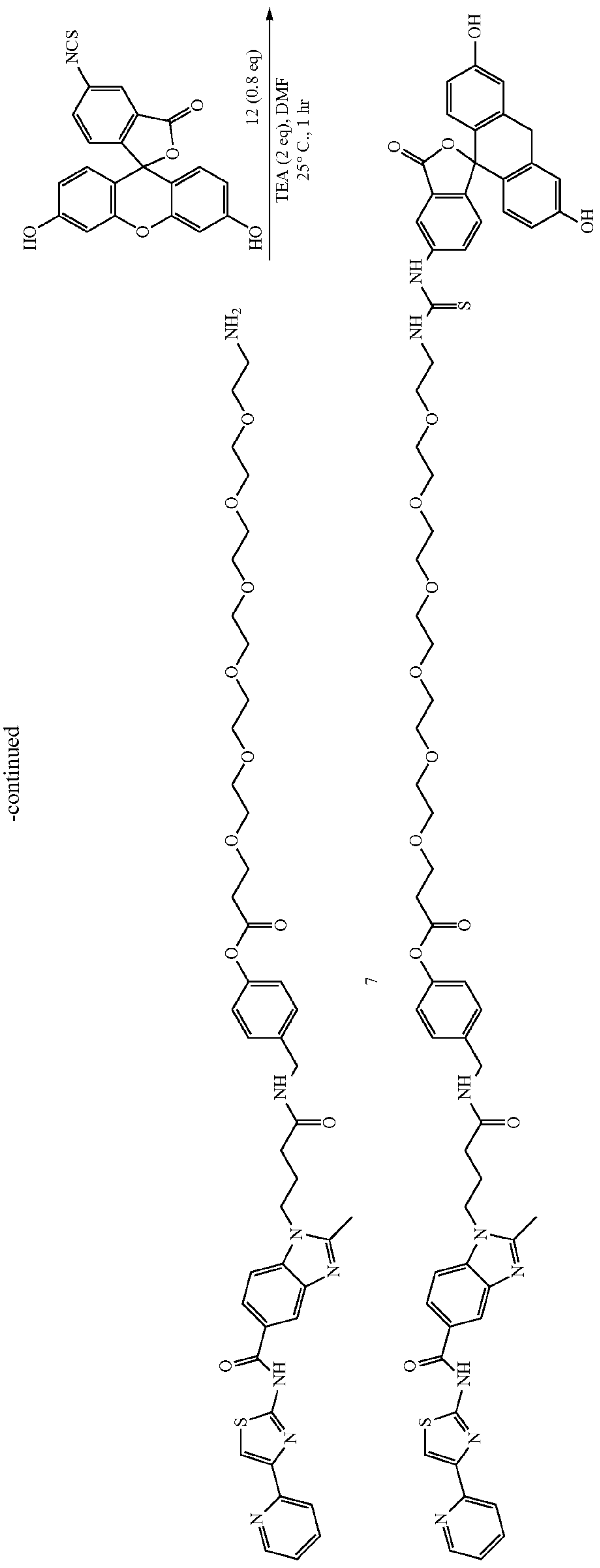
7
I-13

General Procedure for Preparation of Compound:

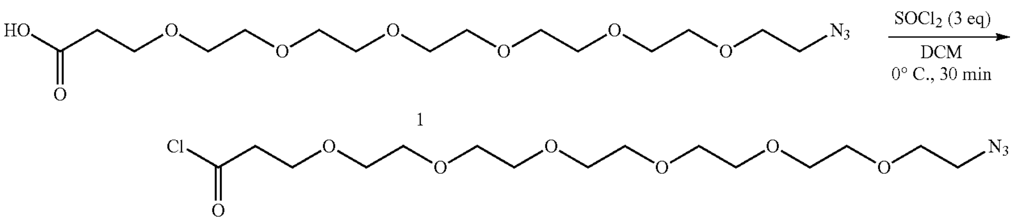

1

2

To a solution of compound 1 (80 mg, 210.86 umol, 1 eq) in DCM (2 mL) was added $SOCl_2$ (75.26 mg, 632.57 umol, 45.89 uL, 3 eq). The mixture was stirred at 0° C. for 30 min. TLC (Dichloromethane:Methanol=10:1, $R_f$=0.57) indicated compound 1 was consumed completely and one new spot formed. The reaction mixture was concentrated under reduced pressure to give a residue. Compound 2 (83 mg, 208.62 umol, 98.94% yield) was obtained as a yellow oil.

General Procedure for Preparation of Compound 5:

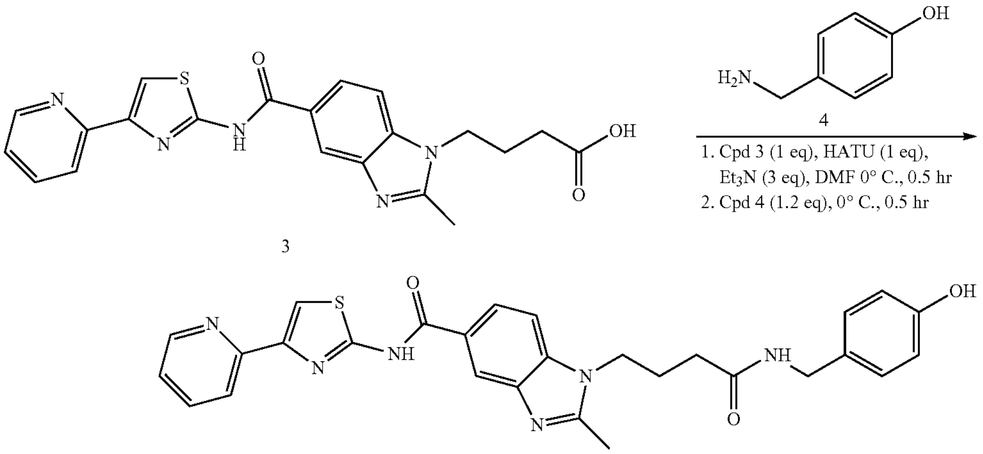

3

5

To a solution of compound 3 (300 mg, 560.23 umol, 1 eq, TFA) in DMF (5 mL) was added $Et_3N$ (170.07 mg, 1.68 mmol, 233.93 uL, 3 eq) and HATU (213.02 mg, 560.23 umol, 1 eq). The mixture was stirred at 0° C. for 30 min. The reaction mixture was added dropwise to compound 4 (89.69 mg, 728.30 umol, 1.3 eq) at 0° C. The mixture was stirred at 0° C. for 30 min. LC-MS (Rt=0.979 min) showed compound 3 was consumed completely and one main peak desired mass was detected. The reaction mixture concentrated under reduced pressure to give a residue. The residue was purified by prep-HPLC (TFA condition: column: Welch Ultimate AQ-C18 150*30 mm*5 um; mobile phase: [water (0.1% TFA)-ACN]; B %: 10%-40%, 12 min). Compound 5 (280 mg, 437.07 umol, 78.02% yield, TFA) was obtained as a white solid. LCMS: RT=0.979 min, MS cal.: 526.2, $[M+H]^+$=527.2. $[M/2+H]^+$=264.1. $^1H$ NMR (400 MHz, DMSO-d6) δ 12.95-13.15 (m, 1H) 8.62-8.74 (m, 1H) 8.52-8.59 (m, 1H) 8.18-8.40 (m, 2H) 8.03-8.14 (m, 2H) 7.88-8.02 (m, 2H) 7.34-7.49 (m, 1H) 6.98-7.15 (m, 2H) 6.60-6.79 (m, 2H) 4.35-4.54 (m, 2H) 4.07-4.17 (m, 2H) 2.75-2.92 (m, 3H) 2.23-2.39 (m, 2H) 1.96-2.15 (m, 2H).

General Procedure for Preparation of Compound 6:

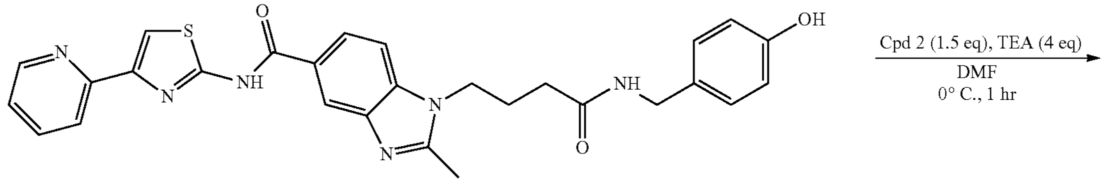

5

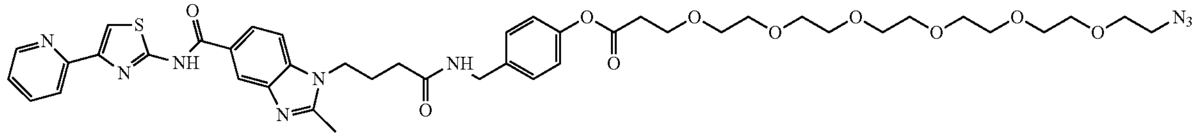

6

To a solution of compound 2 (74.52 mg, 187.32 umol, 1.5 eq) in DMF (2 mL) was added $Et_3N$ (50.55 mg, 499.51 umol, 69.53 uL, 4 eq) and compound 5 (80 mg, 124.88 umol, 1 eq, TFA). The mixture was stirred at 0° C. for 1 hr. LC-MS (Rt=1.769 min) showed ~50% of compound 5 remaining and ~50% of desired compound. The reaction mixture was filtered and concentrated under reduced pressure to give a residue. The residue was purified by prep-HPLC (TFA condition: column: Nano-micro Kromasil C18 80*25 mm*3 um; mobile phase: [water (0.1% TFA)-ACN]; B %: 10%-54%, 7 min). Compound 6 (50 mg, 56.31 umol, 45.09% yield) was obtained as a white solid. LCMS: RT=1.769 min, MS cal.: 887.4, $[M/2+H]^+$=444.9.

General Procedure for Preparation of Compound 7:

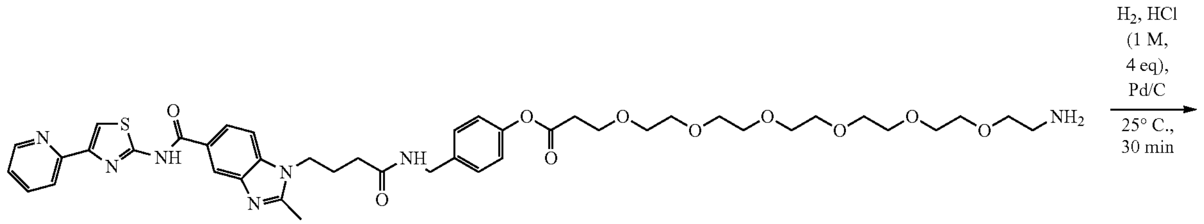

6

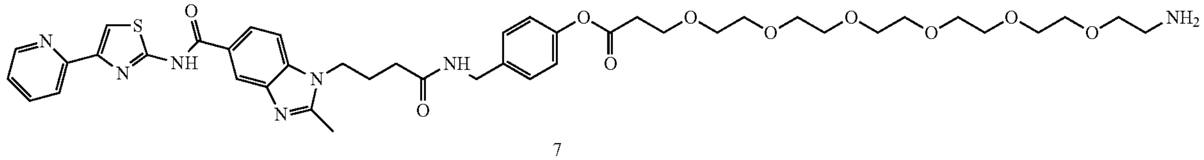

7

A mixture of compound 6 (160 mg, 180.18 umol, 1 eq), HCl (1 M, 720.72 uL, 4 eq), and Pd/C (160 mg, 10% purity) in THF (3 mL) was degassed and purged with $H_2$ 3 times, and then the mixture was stirred at 25° C. for 30 min under $H_2$ atmosphere. LC-MS (Rt=0.968 min) showed compound 6 was consumed completely and one main peak with desired mass was detected. The reaction mixture was concentrated under reduced pressure to give a residue. The residue was purified by prep-HPLC (TFA condition: column: Nano-micro Kromasil C18 80*25 mm*3 um; mobile phase: [water (0.1% TFA)-ACN]; B %: 10%-40%, 7 min). Compound 7 (45 mg, 52.20 umol, 28.97% yield) was obtained as a white solid. LCMS: RT=1.413 min, MS cal.: 861.4, $[M/2+H]^+$ =431.9. $^1$H NMR (400 MHz, DMSO-d6) δ 12.87-12.99 (m, 1H) 8.60-8.68 (m, 1H) 8.49-8.55 (m, 1H) 8.38-8.45 (m, 1H) 8.17-8.24 (m, 1H) 8.03-8.08 (m, 1H) 7.88-7.98 (m, 2H) 7.63-7.83 (m, 2H) 7.35-7.42 (m, 1H) 7.23-7.31 (m, 1H) 7.02-7.09 (m, 1H) 4.35-4.45 (m, 1H) 4.22-4.27 (m, 1H) 3.44-3.68 (m, 29H) 2.96-3.03 (m, 2H) 2.78-2.84 (m, 3H) 2.72-2.78 (m, 3H) 2.25-2.33 (m, 2H) 2.00-2.11 (m, 1H).

General Procedure for Preparation of I-13:

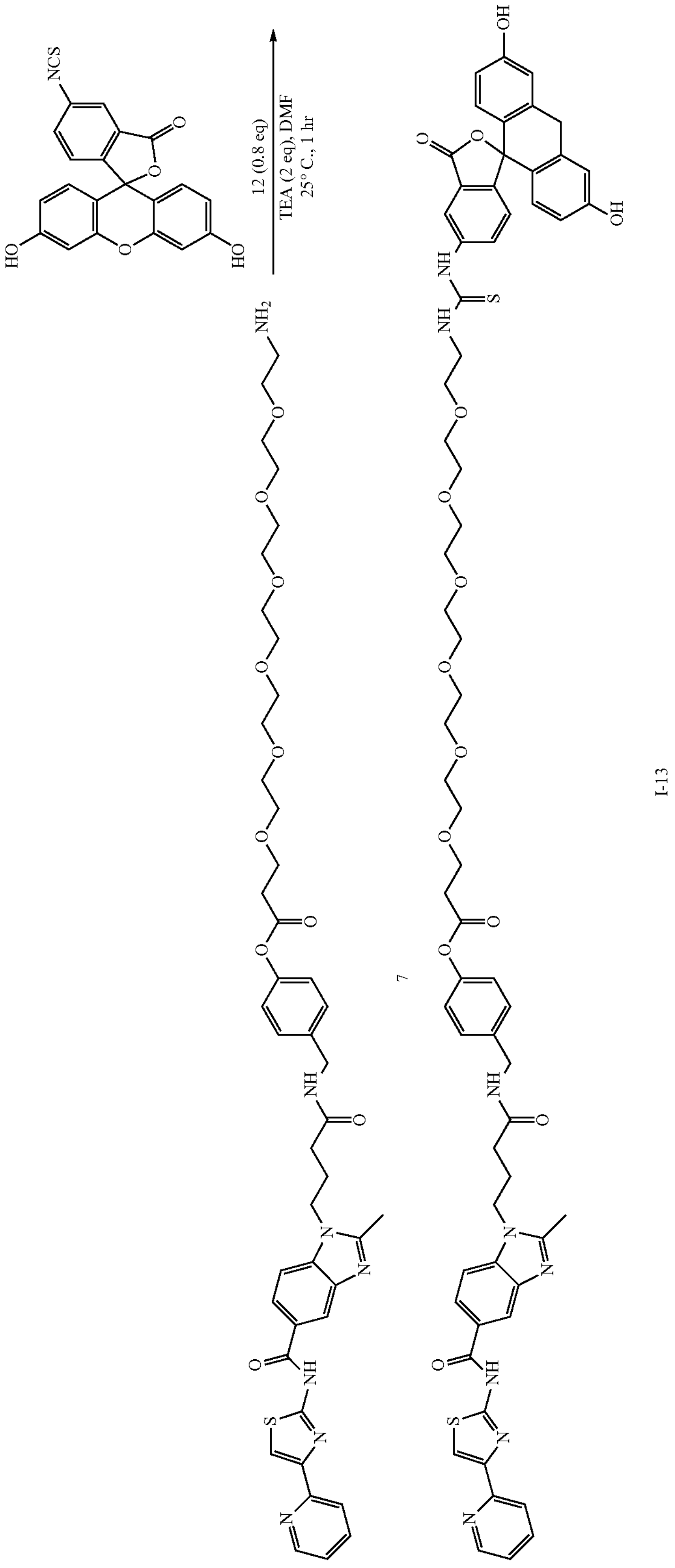
7
I-13

To a solution of compound 7 (45 mg, 46.11 umol, 1 eq, TFA) and compound 8 (14.36 mg, 36.88 umol, 0.8 eq) in DMF (1 mL) was added $Et_3N$ (9.33 mg, 92.21 umol, 12.83 uL, 2 eq). The mixture was stirred at 25° C. for 1 hr. LC-MS (Rt=1.240 min) showed compound 7 was consumed completely and one main peak with desired mass was detected. The reaction mixture was concentrated under reduced pressure to give a residue. The residue was purified by prep-HPLC (TFA condition; Welch Ultimate AQ-C18 150*30 mm*5 um, water (0.1% TFA)-ACN). Compound I-13 (3.83 mg, 3.06 umol, 6.64% yield) was obtained as a white solid. LCMS: RT=1.240 min, MS cal.: 1250.4, $[M/2+H]^+$=626.4, $[M/3+H]^+$=417.9. MS: MS cal.: v1250.4, $[M/2+H]^+$=626.8. $^1$H NMR (400 MHz, DMSO-d6) δ12.96-13.08 (m, 1H) 10.14 (br s, 2H) 8.63-8.66 (m, 1H) 8.52-8.56 (m, 1H) 8.35-8.44 (m, 1H) 8.24-8.30 (m, 1H) 8.10-8.14 (m, 1H) 8.03-8.09 (m, 1H) 7.91-7.98 (m, 1H) 7.71-7.78 (m, 1H) 7.36-7.43 (m, 1H) 7.22-7.30 (m, 1H) 7.16-7.21 (m, 1H) 7.00-7.07 (m, 1H) 6.66-6.70 (m, 1H) 6.53-6.64 (m, 3H) 4.40-4.48 (m, 2H) 4.21-4.28 (m, 3H) 3.68-3.75 (m, 4H) 3.44-3.68 (m, 19H) 2.75-2.91 (m, 4H) 2.30-2.36 (m, 3H) 2.04-2.14 (m, 3H). HPLC: The retention time of the product was 2.209 min in HPLC.

Example 14. Exemplary Synthesis of Compound I-14

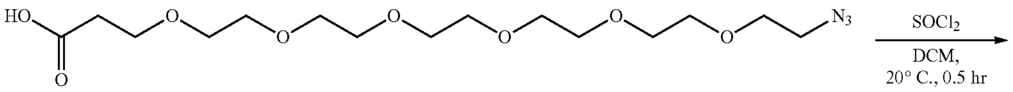

1

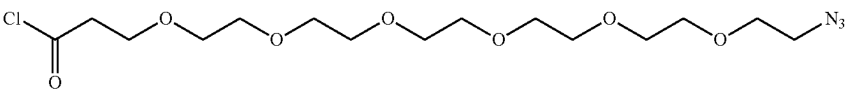

2

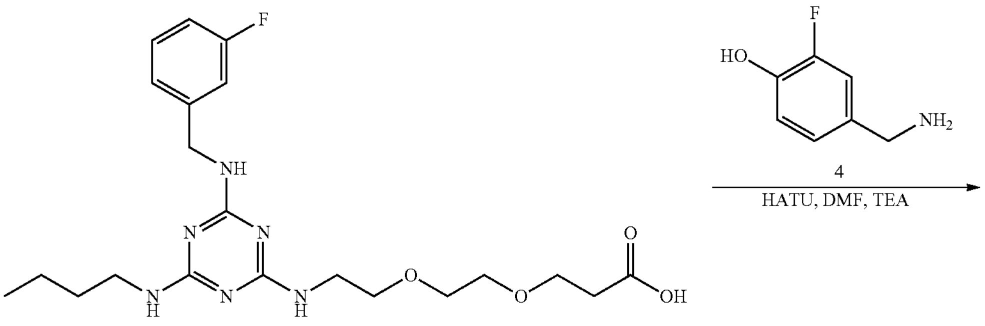

3

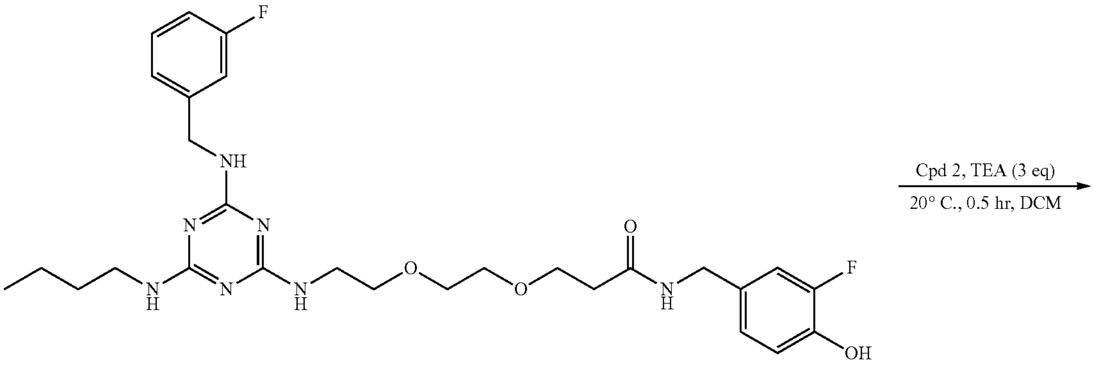

5

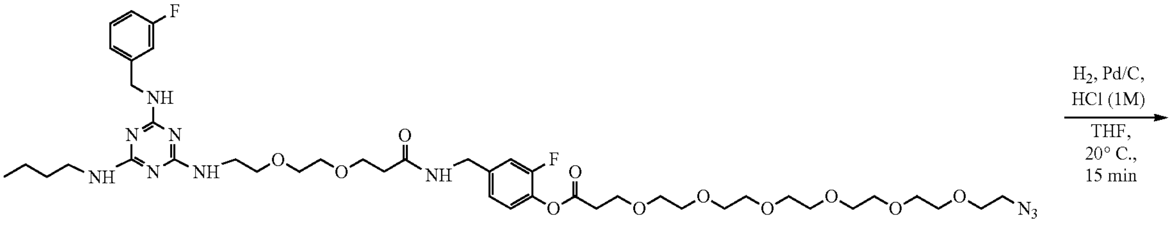

6

-continued

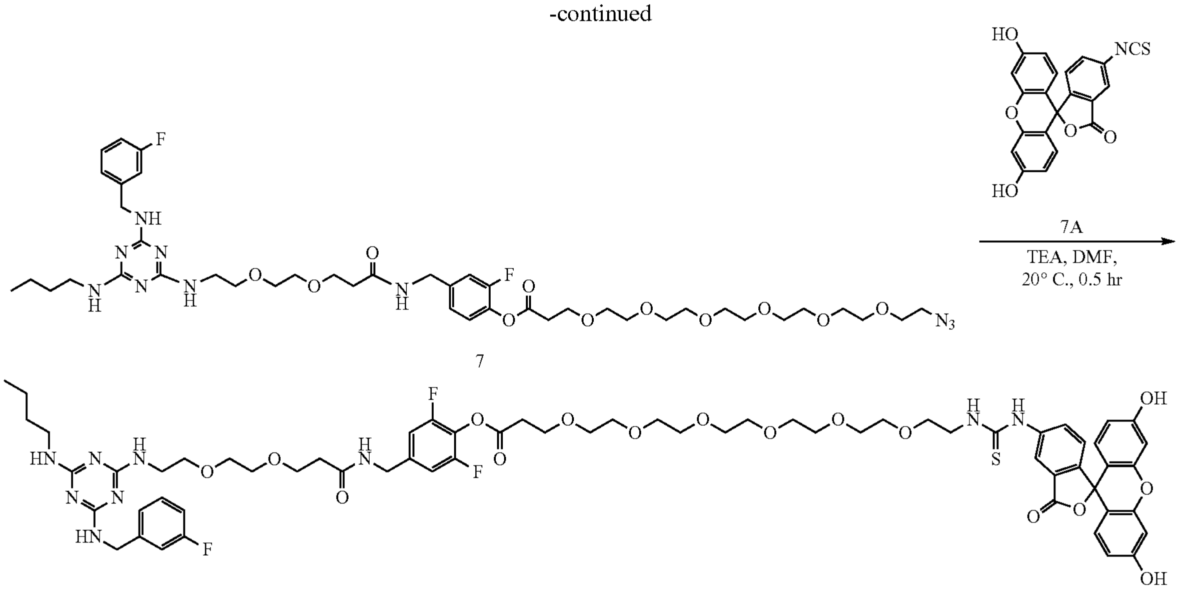

7

I-14

General Procedure for Preparation of Compound 2:

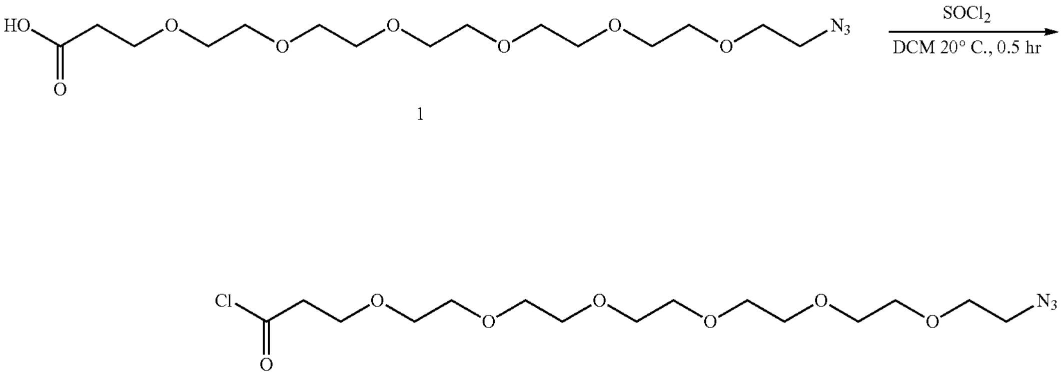

1

2

To a solution of compound 1 (250 mg, 658.93 umol, 1 eq) in DCM (0.5 mL) was added $SOCl_2$ (235.18 mg, 1.98 mmol, 143.40 uL, 3 eq) in one portion at 0° C. under $N_2$. The mixture was stirred at 20° C. for 30 min. TLC (Dichloromethane:Methanol=10:1, $R_f$=0.6) indicated compound 1 was consumed completely and one new spot formed. The reaction mixture was concentrated to give compound 2 (260 mg, 653.51 umol, 99.18% yield) as a colorless oil.

General Procedure for Preparation of Compound 5:

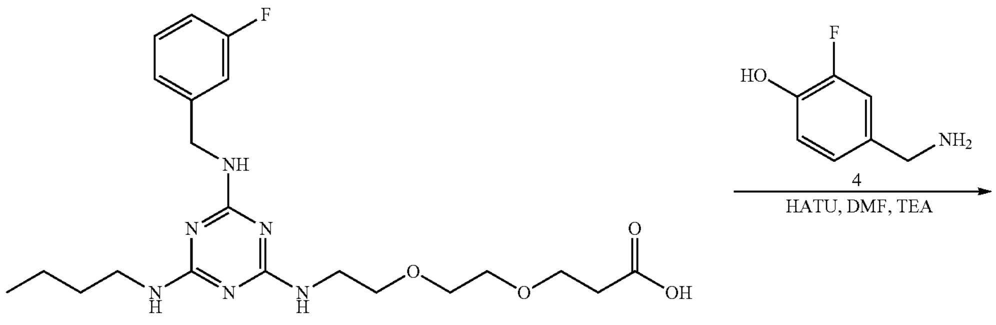

3

-continued

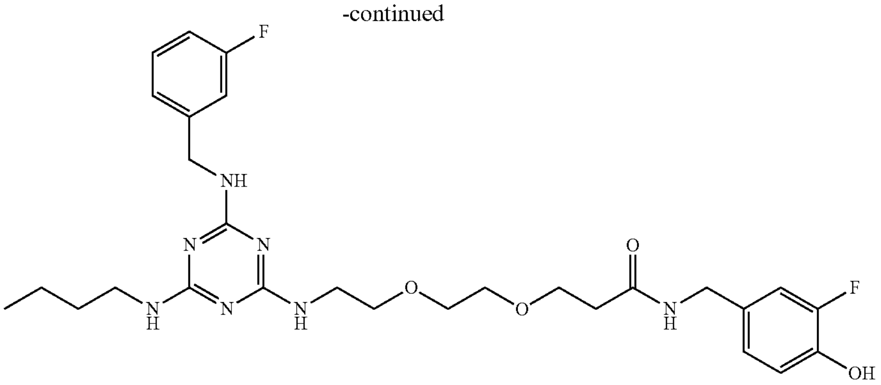

5

To a solution of compound 3 (300 mg, 535.82 umol, 1 eq, 3HCl) in DMF (2 mL) was added HATU (203.74 mg, 535.82 umol, 1 eq) and $Et_3N$ (325.32 mg, 3.21 mmol, 447.48 uL, 6 eq) in one portion at 0° C. under $N_2$. The mixture was stirred at 0° C. for 30 min, then the mixture was added to a solution of compound 4 (228.39 mg, 642.98 umol, 1.2 eq, HCl) in DMF (1 mL) at 0° C. under $N_2$. The mixture was stirred at 20° C. for 30 min. LCMS showed compound 3 was consumed completely and desired mass was detected. The reaction mixture was purified by prep-HPLC (column: Nano-micro Kromasil C18 80*25 mm*3 um; mobile phase: [water (0.1% TFA)-ACN]; B %: 20%-60%, 7 min) to give compound 5 (300 mg, 327.62 umol, 61.14% yield, 3TFA) was obtained as a pink oil. LCMS: RT=2.141 min, MS cal.: 573.3, $[M+H]^+$=574.3. $^1$H NMR (400 MHz, CHLOROFORM-d) δ ppm 7.29-7.42 (m, 2H) 6.95-7.16 (m, 5H) 6.85-6.95 (m, 2H) 4.50-4.65 (m, 2H) 4.35 (br d, J=5.26 Hz, 2H) 3.76 (br s, 2H) 3.50-3.68 (m, 5H) 3.27-3.49 (m, 6H) 2.53 (br t, J=5.14 Hz, 2H) 1.55 (br d, J=7.46 Hz, 2H) 1.28-1.43 (m, 2H) 0.87-0.99 (m, 3H).

General Procedure for Preparation of Compound 6:

To a solution of compound 5 (300 mg, 327.62 umol, 1 eq, 3TFA) in DCM (4 mL) was added compound 2 (156.41 mg, 393.14 umol, 1.2 eq) and $Et_3N$ (165.76 mg, 1.64 mmol, 228.00 uL, 5 eq) in one portion at 0° C. under $N_2$. The mixture was stirred at 0° C. for 0.5 hour. LCMS showed compound 5 was consumed completely and desired mass was detected. The reaction mixture was acidified with TFA to pH 6-7, and was concentrated. The residue was purified by prep-HPLC (column: Nano-micro Kromasil C18 80*25 mm*3 um; mobile phase: [water (0.1% TFA)-ACN]; B %: 20%-76%, 7 min) to give compound 6 (300 mg, 234.91 umol, 71.70% yield, 3TFA) as a colorless oil. LCMS: RT=2.514 min, MS cal.: 934.5, $[M+H]^+$=935.5. $^1$H NMR (400 MHz, CHLOROFORM-d) δ ppm 7.31 (br s, 2H) 6.92-7.20 (m, 6H) 4.59 (br d, J=5.75 Hz, 2H) 4.42 (br d, J=5.75 Hz, 1H) 4.33-4.49 (m, 1H) 3.75-3.92 (m, 3H) 3.30-3.73 (m, 38H) 2.81-2.91 (m, 2H) 2.55 (br d, J=5.01 Hz, 2H) 1.55 (dt, J=14.18, 7.09 Hz, 2H) 1.22-1.44 (m, 2H) 0.83-1.00 (m, 3H).

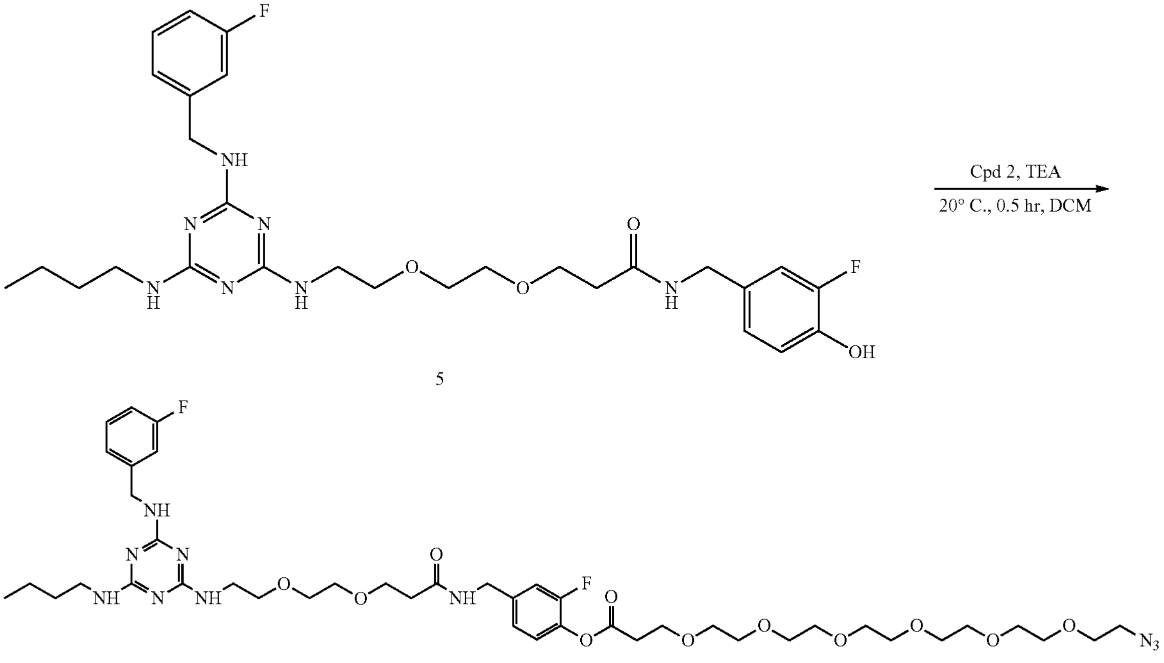

5

6

General Procedure for Preparation of Compound 7:

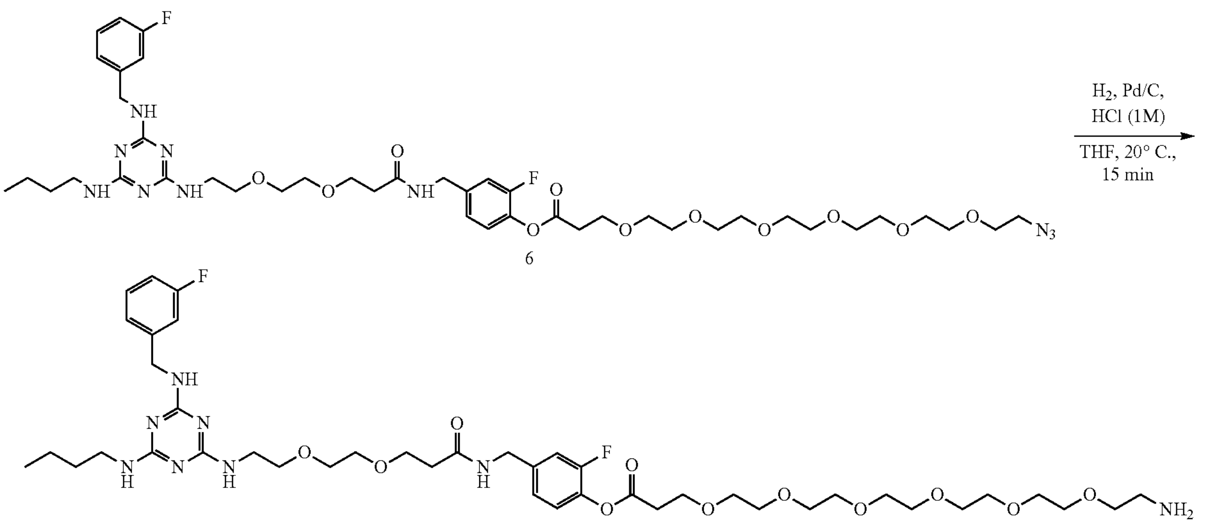

6

7

To a solution of compound 6 (100 mg, 106.95 umol, 1 eq) in THF (3 mL) was added Pd/C (100 mg, 106.95 umol, 10% purity) and HCl (1 M, 427.80 uL, 4 eq) under $N_2$. The suspension was degassed under vacuum and purged with $H_2$ several times. The mixture was stirred under $H_2$ (215.60 ug, 106.95 umol) (15 psi) at 20° C. for 15 min. LCMS showed compound 6 was consumed completely and desired mass was detected. The reaction mixture was basified with aq $NaHCO_3$ to pH 5-6, filtered, and concentrated. The residue was purified by prep-HPLC (column: Welch Ultimate AQ-C18 150*30 mm*5 um; mobile phase: [water (0.1% TFA)-CAN]; B %: 25%-55%, 12 min) to give compound 7 (60 mg, 66.00 umol, 61.72% yield) as a colorless oil. LCMS: RT=2.027 min, MS cal.: 908.5, $[M+H]/2^+$=455.4. $^1$H NMR (400 MHz, CHLOROFORM-d) δ ppm 7.78 (br s, 3H) 7.52 (br d, J=8.56 Hz, 1H) 6.94-7.16 (m, 6H) 4.52-4.65 (m, 2H) 4.41 (br d, J=5.50 Hz, 2H) 3.77-3.89 (m, 6H) 3.27-3.75 (m, 33H) 2.87 (br d, J=5.50 Hz, 3H) 2.56 (br s, 3H) 1.55 (br dd, J=14.79, 7.09 Hz, 2H) 1.28-1.43 (m, 2H) 0.87-0.97 (m, 2H) 0.84-0.97 (m, 1H).

General Procedure for Preparation of Compound I-14:

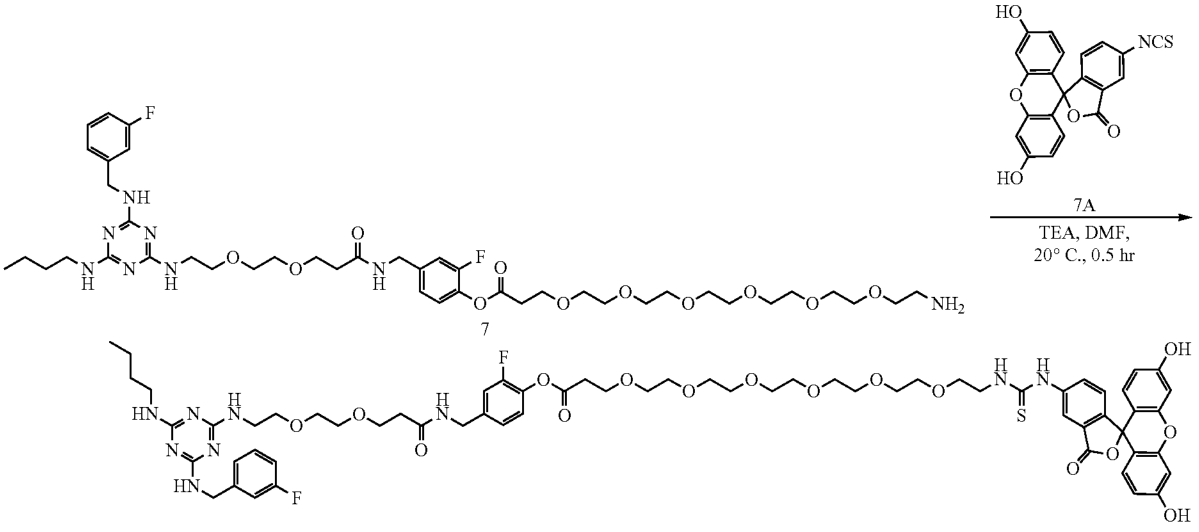

7

I-14

To a mixture of compound 7 (60 mg, 47.96 umol, 1 eq, 3TFA) and compound 7A (18.67 mg, 47.96 umol, 1 eq) in DMF (1 mL) was added $Et_3N$ (4.85 mg, 47.96 umol, 6.68 uL, 1 eq) at 20° C. under $N_2$. The mixture was stirred at 20° C. for 15 min, then was added $Et_3N$ (4.85 mg, 47.96 umol, 6.68 uL, 1 eq) at 20° C. and stirred for 15 min. LCMS showed compound 7 was consumed completely and desired mass was detected. The reaction mixture was acidified with TFA to pH 6. The mixture was purified by prep-HPLC (column: Welch Ultimate AQ-C18 150*30 mm*5 um; mobile phase: [water (0.1% TFA)-ACN]; B %: 48%-58%, 12 min) to give compound I-14 (4.66 mg, 3.59 umol, 7.48% yield) as a yellow solid. LCMS: RT=1.368 min, MS cal.:

1297.5, [M+H]/2⁺=650.0. HPLC: RT=3.123 min. MS: MS cal.: 1297.5, [M+H]/$2^+$=650.3. $^1$H NMR (400 MHz, DMSO-$d_6$) δ ppm 10.06 (br s, 1H) 9.97-10.27 (m, 1H) 8.56-8.96 (m, 1H) 8.45 (br d, J=5.95 Hz, 1H) 8.27 (s, 1H) 8.13 (br s, 1H) 7.83-8.05 (m, 1H) 7.74 (br d, J=8.16 Hz, 1H) 7.34-7.43 (m, 1H) 7.04-7.24 (m, 7H) 6.67 (d, J=2.21 Hz, 2H) 6.52-6.62 (m, 4H) 4.51 (br d, J=14.77 Hz, 2H) 4.27 (br d, J=5.29 Hz, 2H) 3.16-3.75 (m, 38H) 2.85 (t, J=6.06 Hz, 2H) 2.35-2.42 (m, 2H) 1.43-1.56 (m, 1H) 1.15-1.42 (m, 3H) 0.77-0.92 (m, 2H) 0.76-0.93 (m, 1H).
Example 15. Exemplary Synthesis of Compound I-15
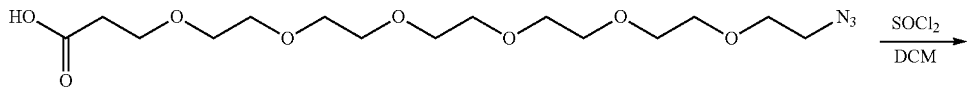
1
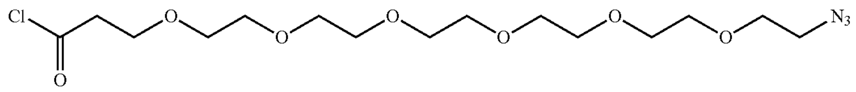
2
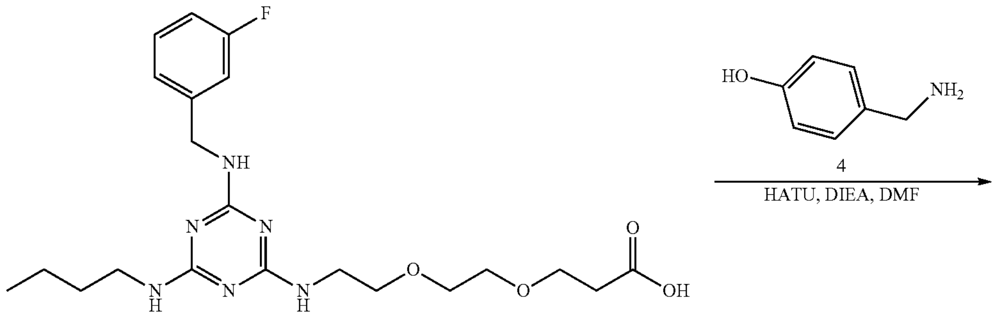
3
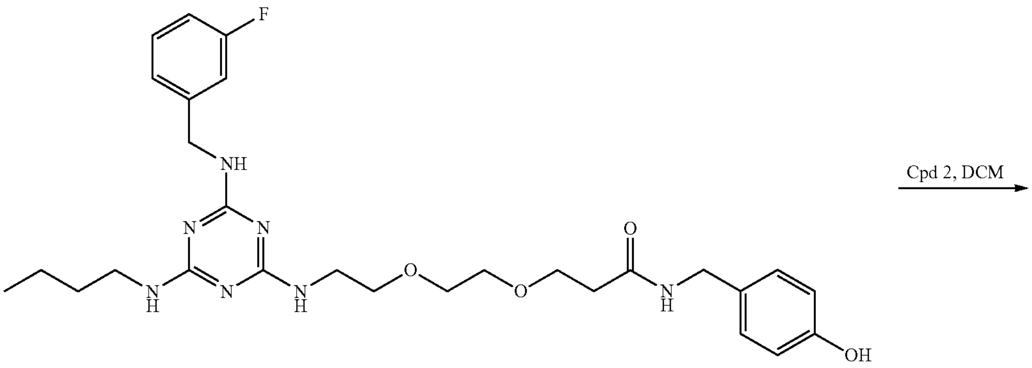
5
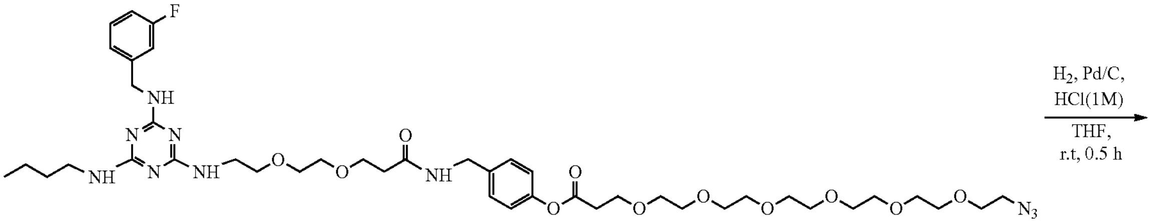
6

-continued

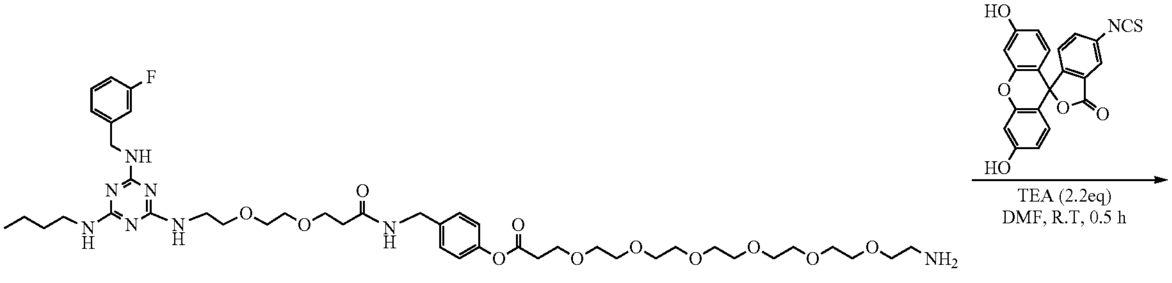

7

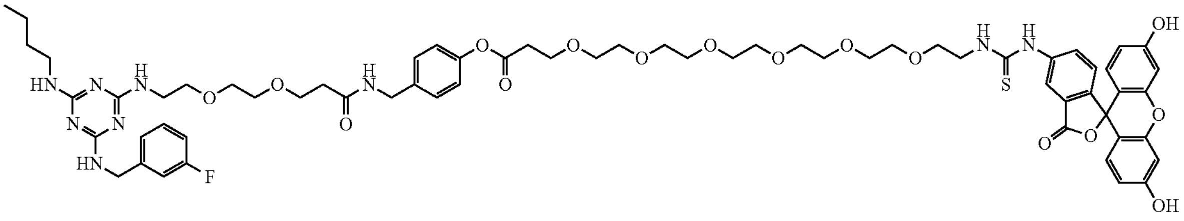

I-15

General Procedure for Preparation of Compound 2:

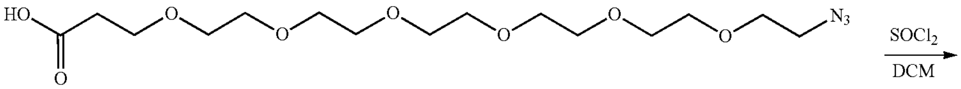

1

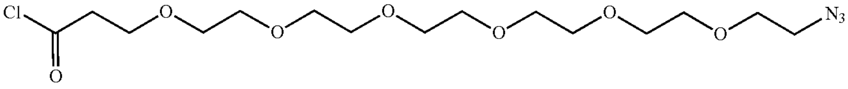

2

To a solution of compound 1 (110 mg, 289.93 umol, 1 eq) in DCM (1 mL) was added $SOCl_2$ (103.48 mg, 869.78 umol, 63.10 uL, 3 eq) in one portion at 0° C. under $N_2$. The mixture was stirred at 20° C. for 30 min. TLC (Dichloromethane: Methanol=10:1, $R_f$=0.64) indicated starting material was consumed completely and one new spot formed. The solvent was removed to give compound 2 (116 mg, crude) as colorless oil, used for next step directly.

General Procedure for Preparation of Compound 5:

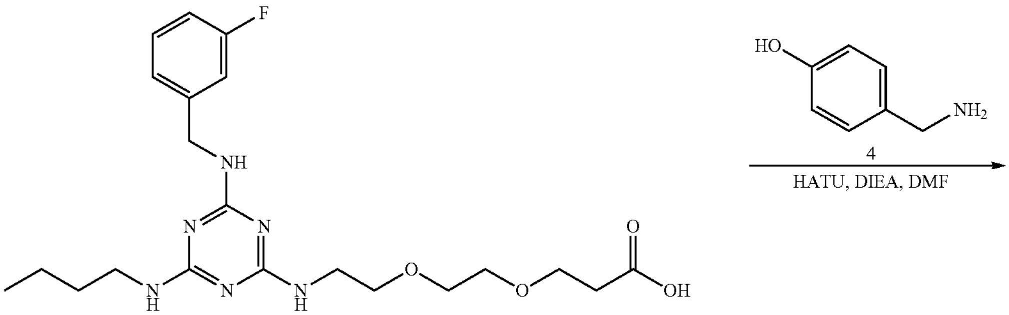

3

-continued

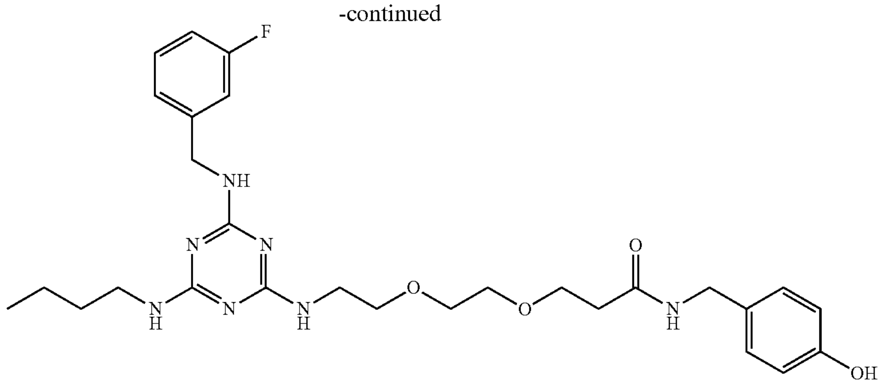

5

To a solution of compound 3 (300 mg, 535.82 umol, 1 eq, 3HCl) in DMF (3 mL) was added HATU (224.11 mg, 589.40 umol, 1.1 eq) and DIEA (415.50 mg, 3.21 mmol, 559.97 uL, 6 eq) in one portion at 0° C. under $N_2$. The mixture was stirred at 0° C. for 20 min, then the mixture was slowly added to a solution of compound 4 (79.18 mg, 642.98 umol, 1.2 eq) in DMF (0.5 mL) at 0° C. and the mixture was stirred at 20° C. for 1 hour. LCMS showed starting material was consumed completely and one main peak with desired mass was detected. The reaction was filtered and the filtrate was purified by pre-HPLC (TFA condition) to give compound 5 (200 mg, 222.79 umol, 41.58% yield, 3TFA) as brown oil. LCMS: RT=2.189 min, MS cal.: 555.3, $[M+H]^+$=556.3. $^1$H NMR: (400 MHz, DMSO-$d_6$) δ ppm 9.28 (br s, 1H) 7.81-8.92 (m, 4H) 7.30-7.46 (m, 1H) 6.96-7.25 (m, 5H) 6.69 (d, J=8.31 Hz, 2H) 4.51 (br d, J=11.37 Hz, 2H) 4.14 (br d, J=5.50 Hz, 2H) 3.10-3.71 (m, 12H) 2.35 (br d, J=4.28 Hz, 2H) 1.12-1.58 (m, 4H) 0.74-0.97 (m, 3H).

General Procedure for Preparation of Compound 6:

To a solution of compound 5 (200 mg, 222.79 umol, 1 eq, 3TFA) in DCM (2 mL) was added TEA (135.26 mg, 1.34 mmol, 186.06 uL, 6 eq) in one portion at 0° C. under $N_2$. Then a solution of compound 2 (106.36 mg, 267.35 umol, 1.2 eq) in DCM (1 mL) was slowly added to the reaction mixture and the mixture was stirred at 20° C. for 0.5 hr. LCMS showed ~20% of compound 5 remained and ~70% of desired compound had formed. The solvent was removed to give residue and the residue was purified by pre-HPLC (TFA condition) to give compound 6 (200 mg, 193.98 umol, 87.07% yield, TFA) as light yellow oil. LCMS: RT=1.445 min, MS cal.: 916.5, $[M+H]^+$=917.7. $^1$H NMR: (400 MHz, DMSO-$d_6$) δ ppm 8.40 (br d, J=5.50 Hz, 1H) 7.37 (br d, J=5.99 Hz, 1H) 7.27 (d, J=8.31 Hz, 2H) 6.99-7.20 (m, 5H) 4.50 (br d, J=11.25 Hz, 2H) 4.26 (br d, J=5.75 Hz, 2H) 3.73 (t, J=6.17 Hz, 2H) 3.57-3.66 (m, 5H) 3.44-3.57 (m, 32H) 3.26 (br s, 1H) 2.80 (t, J=6.11 Hz, 2H) 2.44 (br t, J=6.42 Hz, 1H) 2.38 (br d, J=4.40 Hz, 2H) 1.13-1.55 (m, 4H) 0.72-0.94 (m, 3H).

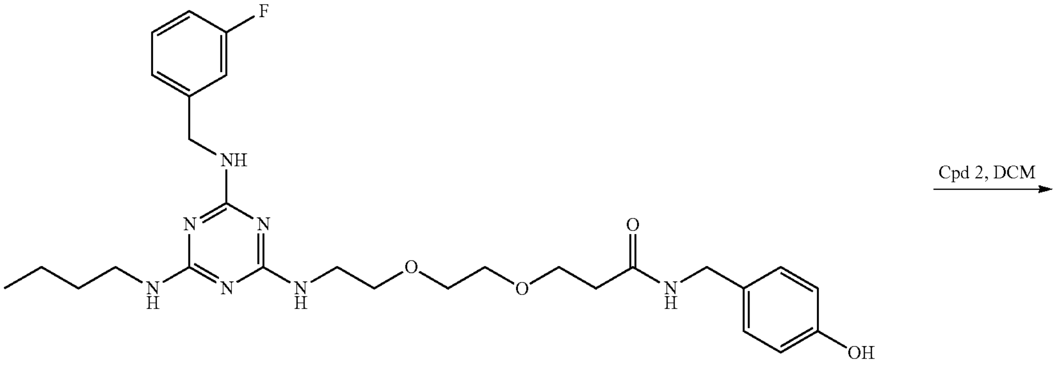

5

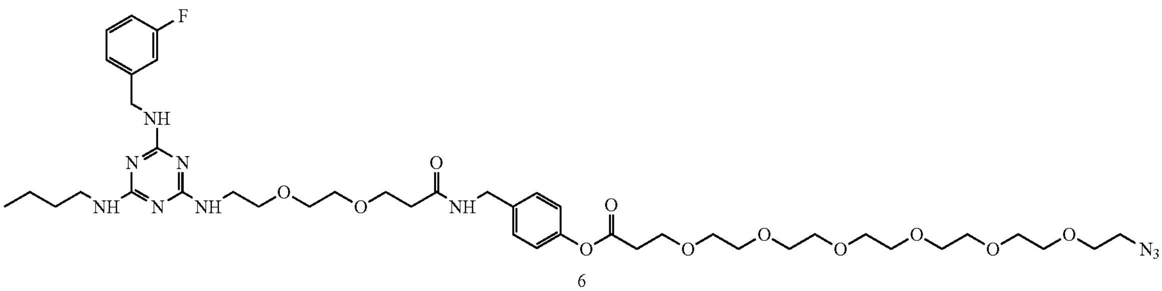

6

General Procedure for Preparation of Compound 7:

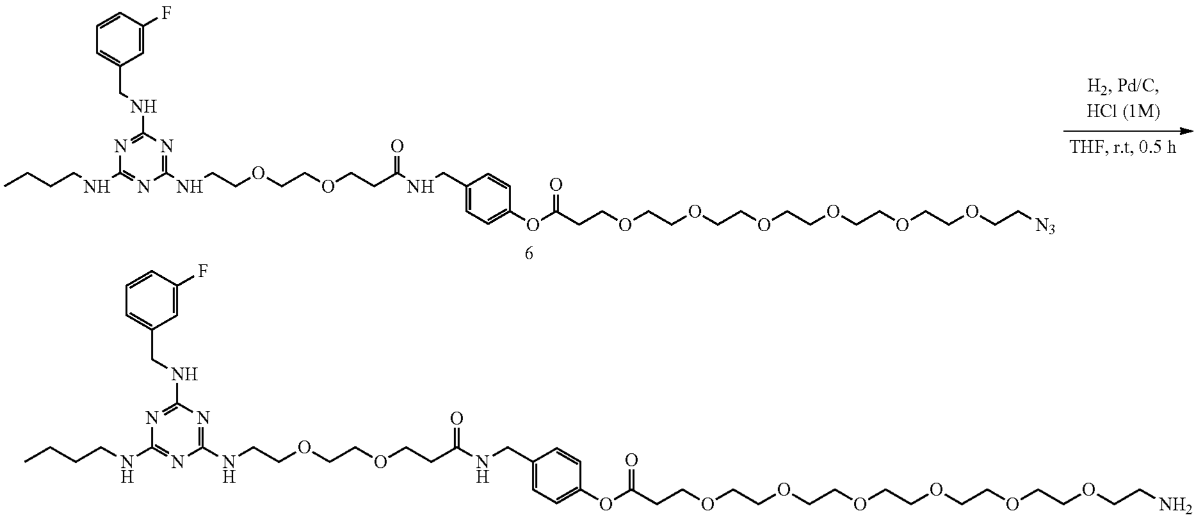

6

7

To a mixture of compound 6 (170 mg, 164.88 umol, 1 eq, TFA) and HCl (1 M, 659.52 uL, 4 eq) in THF (5 mL) was added Pd/C (24 mg, 10% purity) under $N_2$. The suspension was degassed under vacuum and purged with $H_2$ several times. The mixture was stirred under $H_2$ (15 psi) at 20° C. for 0.5 hours. LCMS showed starting material was consumed completely and one main peak with desired mass was detected. The reaction mixture was filtered and the filtrate was concentrated to give residue and the residue was purified by pre-HPLC (TFA condition) to give compound 7 (100 mg, 99.50 umol, 60.35% yield, TFA) as colorless oil. LCMS: RT=2.018 min, MS cal.: 980.5, $[M+H]^+$=891.5. $^1H$ NMR: (400 MHz, DMSO-$d_6$) δ ppm 8.41 (br d, J=6.11 Hz, 1H) 7.76 (br s, 3H) 7.32-7.43 (m, 1H) 7.27 (d, J=8.44 Hz, 2H) 6.99-7.20 (m, 5H) 4.50 (br d, J=10.76 Hz, 2H) 4.26 (br d, J=5.75 Hz, 2H) 3.73 (t, J=6.17 Hz, 3H) 3.53-3.66 (m, 21H) 3.34-3.51 (m, 14H) 2.92-3.04 (m, 2H) 2.80 (t, J=6.17 Hz, 2H) 2.38 (br d, J=3.42 Hz, 2H) 1.15-1.55 (m, 4H) 0.76-0.95 (m, 3H).

General Procedure for Preparation of Compound I-15:

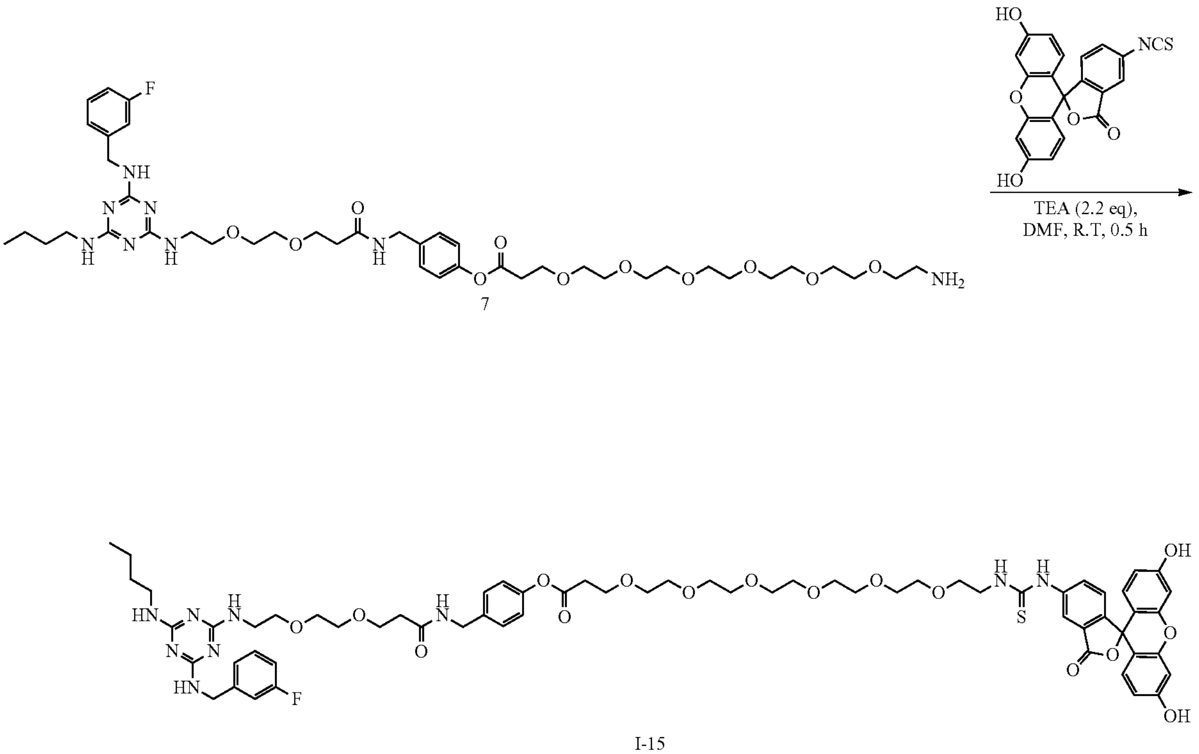

7

I-15

To a mixture of compound 7 (100 mg, 112.23 umol, 1 eq) and 3',6'-dihydroxy-6-isothiocyanato-spiro[isobenzofuran-3,9'-xanthene]-1-one (34.96 mg, 89.78 umol, 0.8 eq) in DMF (1 mL) was added TEA (11.36 mg, 112.23 umol, 15.62 uL, 1 eq) slowly at 20° C. under $N_2$. After stirring for 5 min, TEA (13.63 mg, 134.67 umol, 18.75 uL, 1.2 eq) was slowly added to the mixture and the mixture was stirred at 20° C. for 0.5 hours. LCMS showed starting material was consumed completely and one main peak with desired mass was detected. The mixture was acidified with TFA to pH 5-6, then the solvent was removed to give a residue and the residue was purified by pre-HPLC (TFA condition) to give compound I-15 (7.08 mg, 5.53 umol, 4.93% yield) as brown solid. LCMS: RT=2.582 min, MS cal.: 1279.5, $[M/2+H]^+$=641.0. MS: MS cal.: 1279.5, $[M/2+H]^+$=641.3, $[M/3+H]^+$=427.9. $^1$H NMR: (400 MHz, DMSO-$d_6$) δ ppm 9.99-10.27 (m, 2H) 8.45-8.97 (m, 1H) 8.40 (br d, J=5.62 Hz, 1H) 8.21-8.32 (m, 1H) 8.13 (br s, 1H) 7.95 (br s, 1H) 7.74 (br d, J=8.19 Hz, 1H) 7.32-7.43 (m, 1H) 7.26 (d, J=8.44 Hz, 2H) 6.98-7.21 (m, 6H) 6.67 (d, J=2.08 Hz, 2H) 6.52-6.62 (m, 4H) 4.46-4.56 (m, 2H) 4.26 (br d, J=5.01 Hz, 2H) 3.35-3.77 (m, 33H) 3.27 (br s, 2H) 2.79 (t, J=6.11 Hz, 2H) 2.34-2.41 (m, 2H) 1.11-1.58 (m, 3H) 1.11-1.58 (m, 1H) 0.70-0.95 (m, 3H).

Example 16. Exemplary Synthesis of Compound I-16

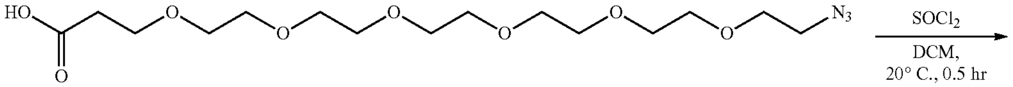

1

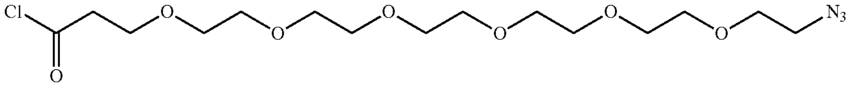

2

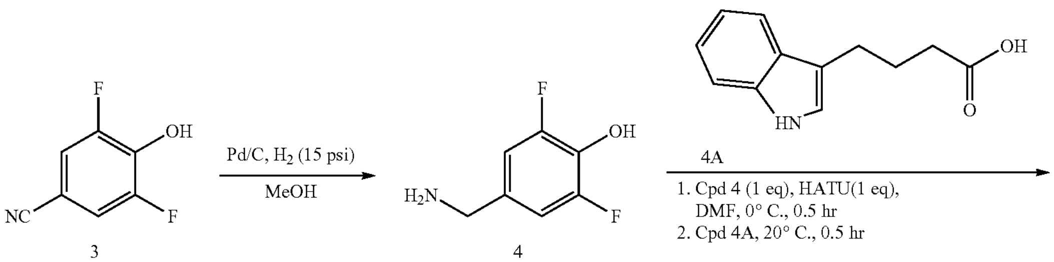

3 4

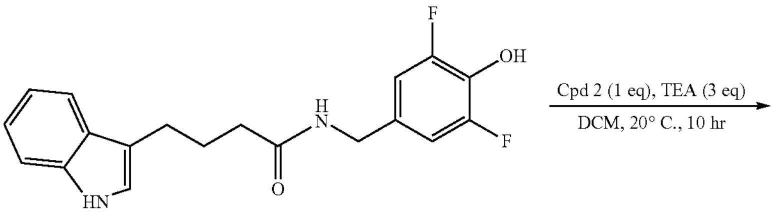

5

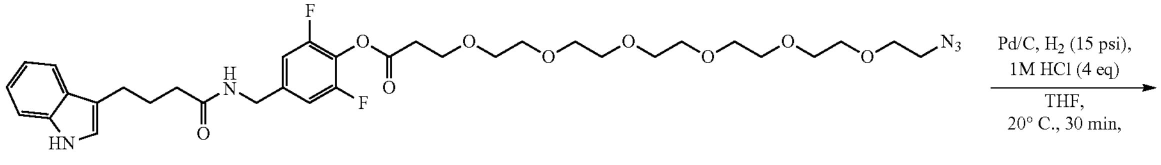

6

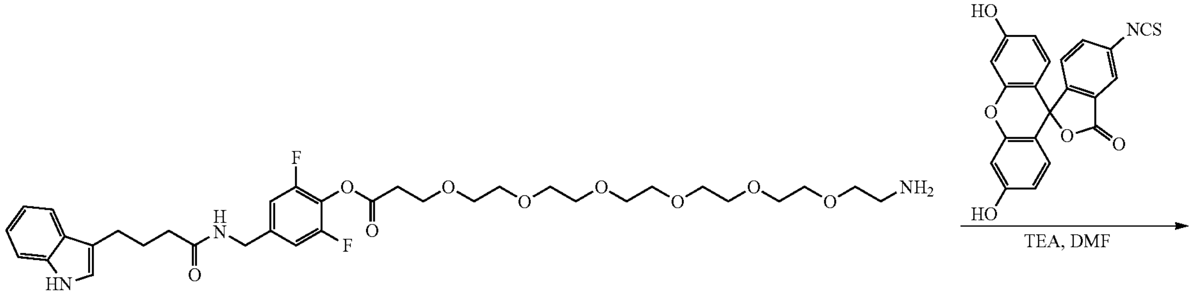

7

-continued

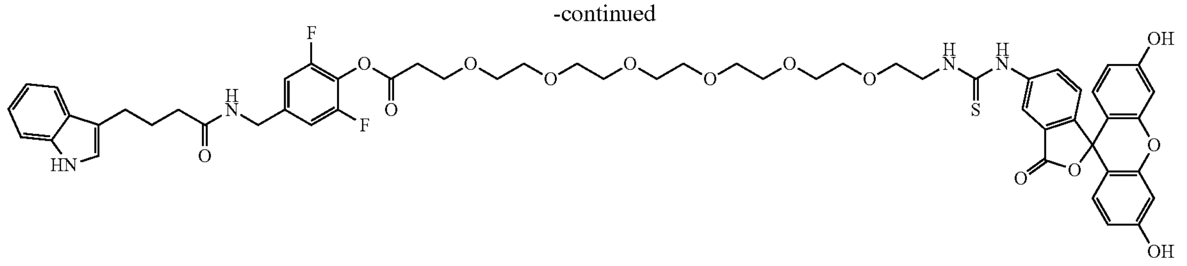

I-16

General Procedure for Preparation of Compound 2:

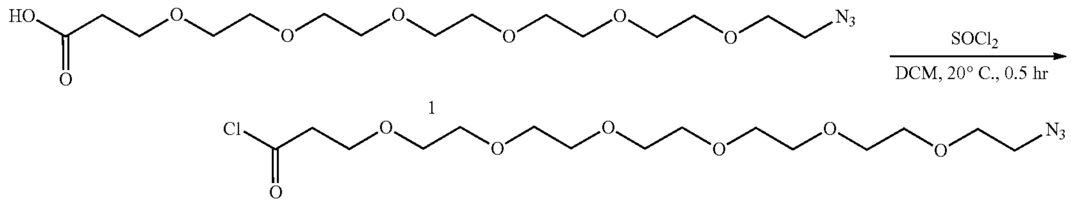

To a solution of compound 1 (150 mg, 395.36 umol, 1 eq) m DCM (1 mL was added $SOCl_2$ (282.22 mg, 2.37 mmol, 172.08 uL, 6 eq) in one portion at 0° C. under $N_2$. The mixture was stirred at 20° C. for 30 min. TLC (Dichloromethane:Methanol=10:1, $R_f$=0.5) indicated compound 1 was consumed completely and one new major spot was formed. The reaction mixture was concentrated. The crude product was used in the next step without further purification. Compound 2 (157 mg, 394.62 umol, 99.81% yield) was obtained as a colorless oil.

General Procedure for Preparation of Compound 4:

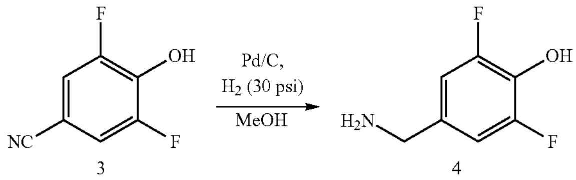

To a solution of compound 3 (500 mg, 3.22 mmol, 1 eq) in MeOH (15 mL) was added Pd/C (50 mg, 10% purity) and HCl (12 M, 2 mL, 7.44 eq) under $N_2$. The suspension was degassed under vacuum and purged with H2 several times. The mixture was stirred under $H_2$ (15 psi) at 20° C. for 1 hr. TLC showed the reaction was complete (Petroleum ether: Ethyl acetate=1:1, $R_f$=0.57). The reaction mixture was filtered and the filtrate was concentrated to give compound 4 (0.35 g, 2.20 mmol, 68.23% yield) as a yellow solid.

General Procedure for Preparation of Compound 5:

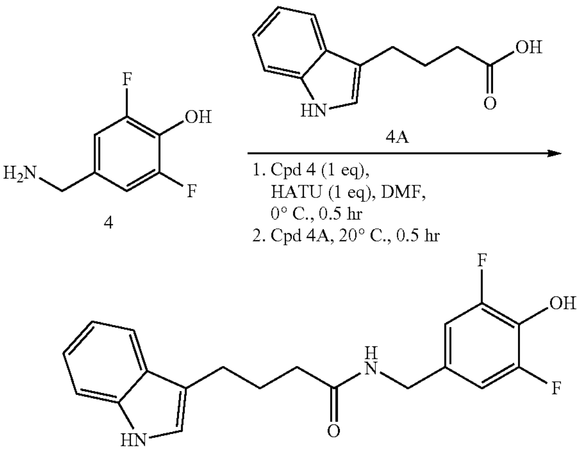

To a solution of compound 4A (300 mg, 1.48 mmol, 1 eq) in DMF (2 mL) was added HATU (561.26 mg, 1.48 mmol, 1 eq) and Et3N (597.47 mg, 5.90 mmol, 821.83 uL, 4 eq) in one portion at 0° C. under $N_2$. The mixture was stirred at 0° C. for 30 min, then the mixture was added to compound 4 (320.80 mg, 1.48 mmol, 1 eq, HCl) in DMF (1 mL) at 0° C. and stirred at 20° C. for 30 min. LCMS showed compound 4 was consumed completely and desired mass was detected. The reaction mixture was purified by prep-HPLC (column: Phenomenex Luna C18 100*30 mm*5 um; mobile phase: [water (0.1% TFA)-ACN]; B %: 25%-50%, 12 min) to give compound 5 (250 mg, 726.00 umol, 49.18% yield) as a white solid. LCMS: RT=1.891 min, MS cal.: 344.1, $[M+H]^+$= 345.2.

General Procedure for Preparation of Compound 6:

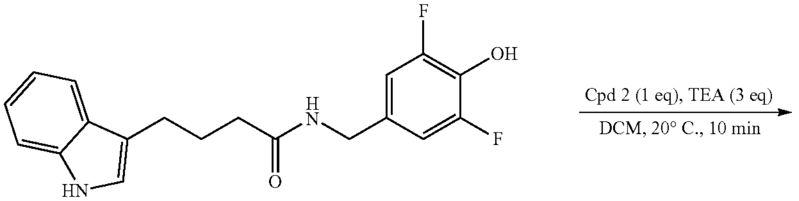

5

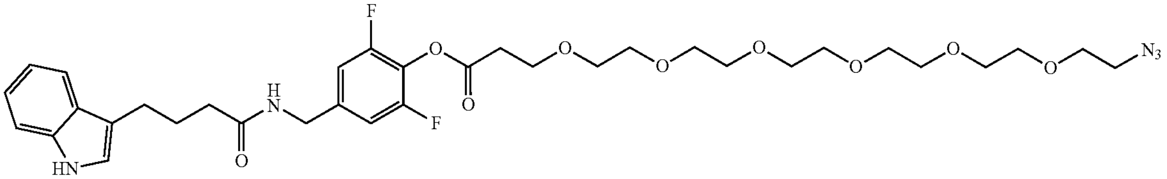

6

To a mixture of compound 5 (130 mg, 377.52 umol, 1 eq) and compound 2 (150.20 mg, 377.52 umol, 1 eq) in DCM (2 mL) was added TEA (114.60 mg, 1.13 mmol, 157.64 uL, 3 eq) slowly at 0° C. under $N_2$. The mixture was stirred at 20° C. for 10 hours. TLC (Dichloromethane:MeOH=0:1, $R_f$=0.6) showed that the starting material was consumed completely. The reaction mixture was concentrated. The residue was purified by prep-HPLC (column: Welch Ultimate AQ-C18 150*30 mm*5 um; mobile phase: [water (0.1% TFA)-ACN]; B %: 42%-72%, 12 min) to give compound 6 (140 mg, 198.37 umol, 52.55% yield) as a white oil.

General Procedure for Preparation of Compound 7:

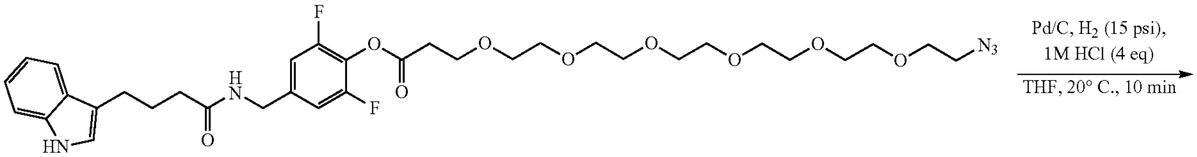

6

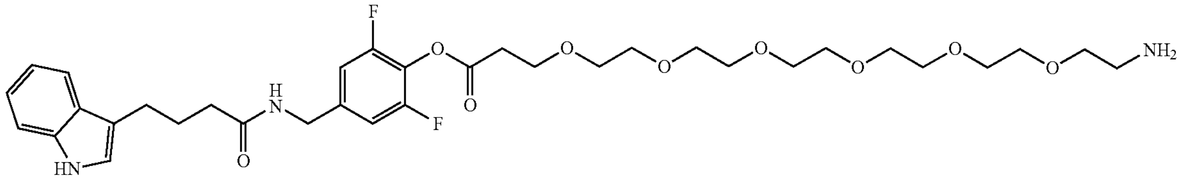

7

To a solution of compound 6 (130 mg, 184.20 umol, 1 eq) in THF (3 mL) was added HCl (1 M, 736.81 uL, 4 eq) and Pd/C (50 mg, 10% purity). The mixture was stirred at 20° C. for 10 min under $H_2$ (15 psi). LCMS showed formation of desired product. The reaction mixture was filtered and the filtrate was purified directly by prep-HPLC (column: Nano-micro Kromasil C18 80*25 mm*3 um; mobile phase: [water (0.1% TFA)-ACN]; B %: 18%-52%, 7 min) to give compound 7 (45 mg, 66.20 umol, 35.94% yield) as a colorless oil. LCMS: RT=2.071 min, MS cal.: 679.3, $[M+H]/2^+$=680.4.

General Procedure for Preparation of Compound I-16:

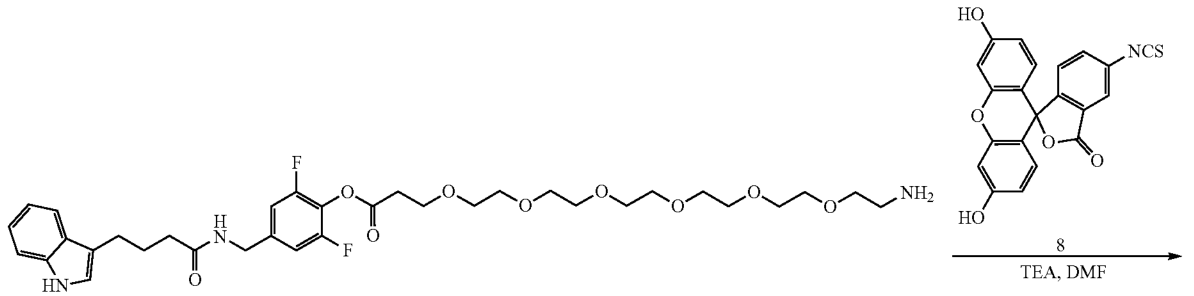

8

7

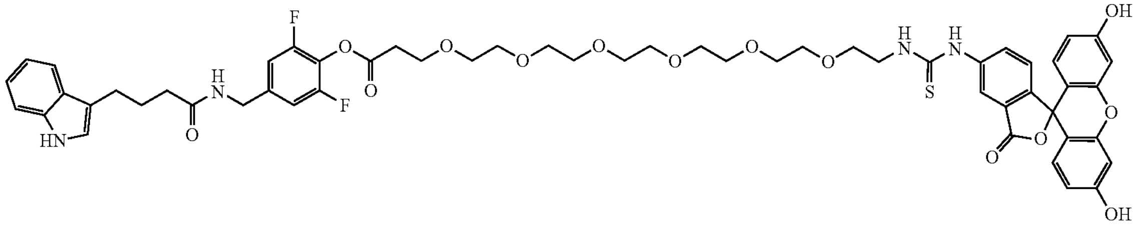

I-16

To a solution of compound 7 (40 mg, 50.39 umol, 1 eq, TFA) in DMF (0.5 mL) was added compound 8 (19.62 mg, 50.39 umol, 1 eq) and TEA (5.10 mg, 50.39 umol, 7.01 uL, 1 eq). The mixture was stirred at 20° C. for 0.5 hr. LCMS showed formation of desired product. The reaction mixture was filtered and the filtrate was purified directly by prep-HPLC (column: Welch Ultimate AQ-C18 150*30 mm*5 um; mobile phase: [water (0.1% TFA)-ACN]; B %: 45%-75%, 12 min) to give Compound I-16 (5.31 mg, 4.86 umol, 9.65% yield, 97.9% purity) as a yellow solid. LCMS: RT=2.622 min, MS cal.: 1068.3, $[M+H]/2^{+}$=535.5. $^{1}$H NMR (400 MHz, DMSO-d6) δ ppm 10.76 (br s, 1H) 9.95-10.23 (m, 2H) 8.37-8.45 (m, 1H) 8.27 (s, 1H) 8.09 (br s, 1H) 7.73 (br d, J=6.60 Hz, 1H) 7.48 (br d, J=8.07 Hz, 1H) 7.32 (d, J=8.07 Hz, 1H) 7.08-7.22 (m, 3H) 7.05 (br t, J=7.46 Hz, 1H) 6.90-6.98 (m, 1H) 6.67 (d, J=1.96 Hz, 2H) 6.51-6.63 (m, 3H) 4.27 (br d, J=5.38 Hz, 2H) 3.40-3.64 (m, 27H) 2.87-2.98 (m, 2H) 2.62-2.72 (m, 2H) 2.16-2.27 (m, 5H) 1.83-1.99 (m, 2H). HPLC: RT=3.216 min. MS: MS cal.: 1068.3, $[M+H]/2^{+}$=535.6.

Example 17. Exemplary Synthesis of Compound I-17

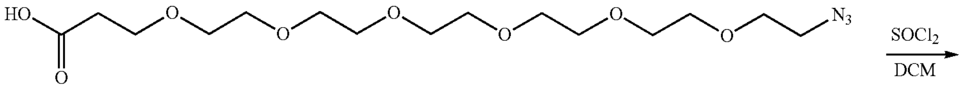

1

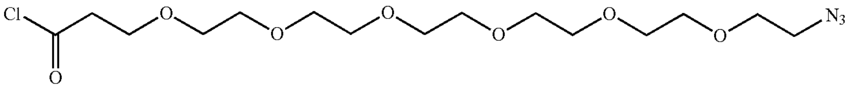

2

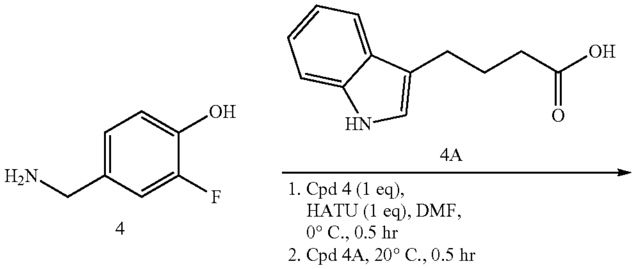

4A

4

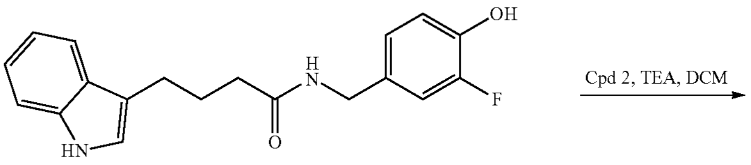

5

-continued

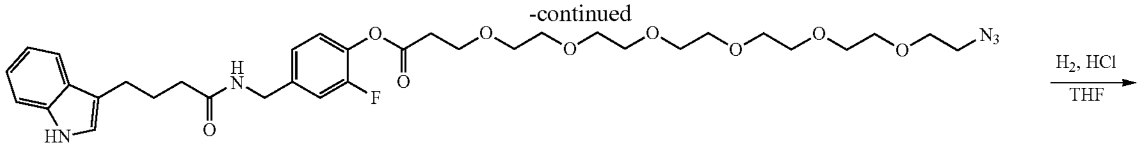

6

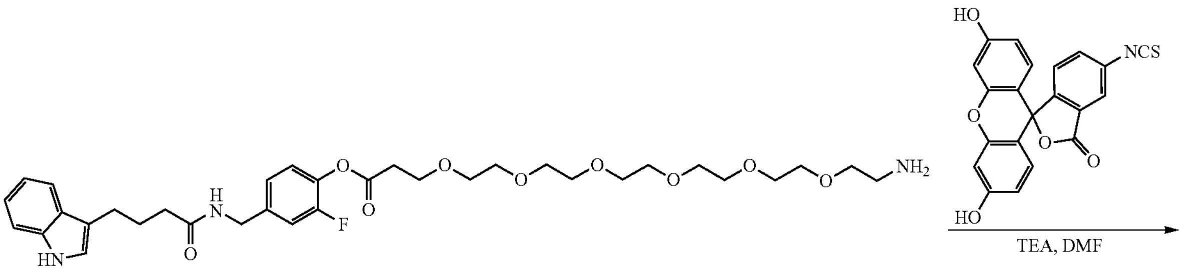

7

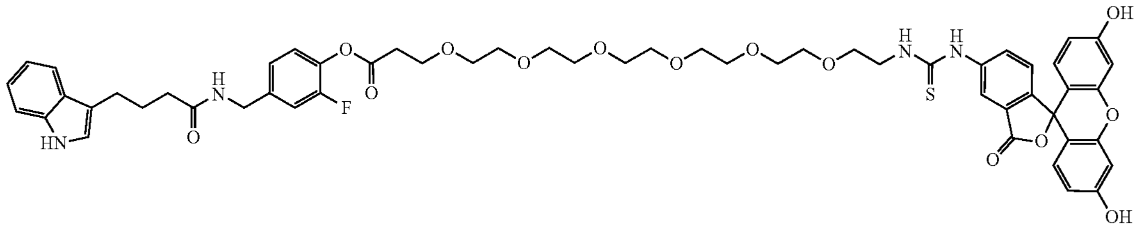

I-17

General Procedure for Preparation of Compound 2:

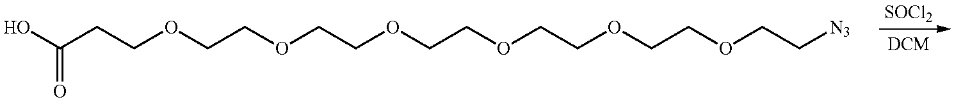

1

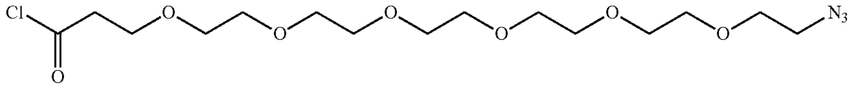

2

To a solution of compound 1 (500 mg, 1.32 mmol, 1 eq) in DCM (1 mL) was added $SOCl_2$ (470.36 mg, 3.95 mmol, 286.80 uL, 3 eq) in one portion at 0° C. under $N_2$. The mixture was stirred at 20° C. for 30 min. TLC (Dichloromethane:Methanol=10:1, $R_f$=0.64) indicated starting material was consumed completely and one new spot formed. The solvent was removed to give compound 2 (520 mg, crude) as colorless oil, used for next step directly.

General Procedure for Preparation of Compound 5:

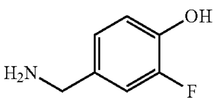

3

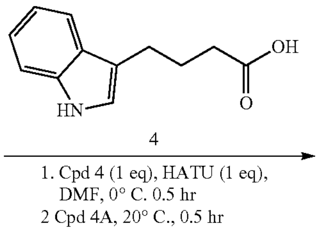

-continued

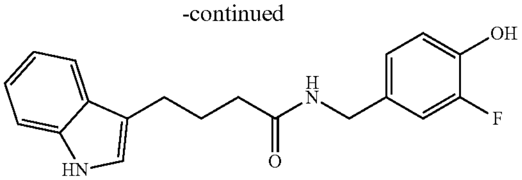

5

To a solution of compound 4 (260 mg, 1.28 mmol, 1 eq) in DMF (2 mL) was added HATU (535.07 mg, 1.41 mmol, 1.1 eq) and DIEA (496.02 mg, 3.84 mmol, 668.49 uL, 3 eq) in one portion at 0° C. under $N_2$. The mixture was stirred at 0° C. for 30 min, then the mixture was slowly added to a solution of compound 3 (433.35 mg, 1.54 mmol, 1.2 eq) in DMF (2 mL) at 0° C. and the mixture was stirred at 20° C. for 1 hour. LCMS showed starting material was consumed completely and one main peak with desired mass was detected. The reaction mixture was filtered and the filtrate was concentrated to give residue and the residue was purified by pre-HPLC (TFA condition) to give compound 5 (330 mg, 1.01 mmol, 79.04% yield) as white solid. LCMS:

RT=1.843 min, MS cal.: 326.1, $[M+H]^+$=327.2. $^1H$ NMR: (400 MHz, DMSO-$d_6$) δ ppm 10.74 (br s, 1H) 9.66 (br s, 1H) 8.24 (s, 1H) 7.47 (d, J=7.83 Hz, 1H) 7.32 (d, J=8.19 Hz, 1H) 6.84-7.10 (m, 5H) 4.15 (d, J=5.75 Hz, 2H) 2.66 (br t, J=7.27 Hz, 2H) 2.18 (br t, J=7.58 Hz, 2H) 1.82-1.94 (m, 1H) 1.82-1.94 (m, 1H).

General Procedure for Preparation of Compound 6:

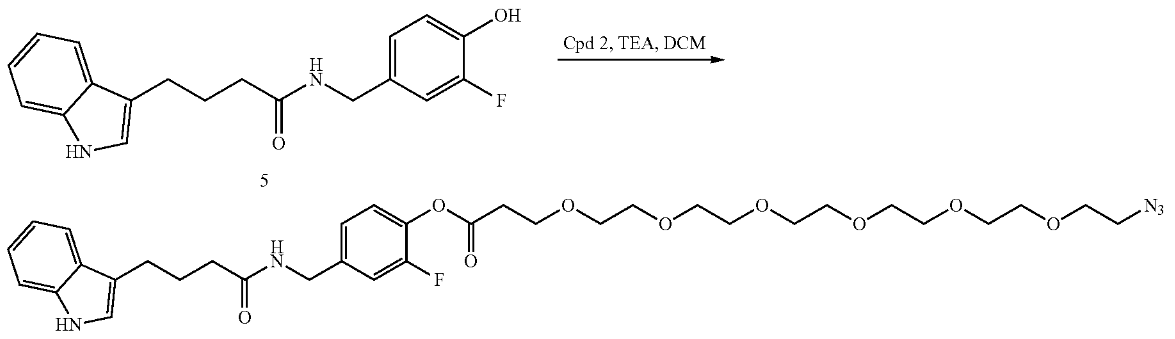

5

6

To a solution of compound 5 (330 mg, 1.01 mmol, 1 eq) in DCM (2 mL) was added TEA (613.90 mg, 6.07 mmol, 844.43 uL, 6 eq) in one portion at 0° C. under $N_2$. Then a solution of compound 2 (482.74 mg, 1.21 mmol, 1.2 eq) in DCM (2 mL) was slowly added to the reaction mixture and the mixture was stirred at 20° C. for 0.5 hours. LCMS showed the main peak with desired mass was detected. The solvent was removed to give residue and the residue was purified by pre-HPLC (TFA condition) to give compound 6 (400 mg, 581.60 umol, 57.52% yield) as colorless oil. LCMS: RT=2.476 min, MS cal.: 687.3, $[M+H]^+$=688.4. $^1H$ NMR: (400 MHz, DMSO-$d_6$) δ ppm 10.76 (br s, 1H) 8.39 (t, J=5.99 Hz, 1H) 7.49 (d, J=7.83 Hz, 1H) 7.33 (d, J=8.07 Hz, 1H) 7.17-7.25 (m, 2H) 7.09-7.13 (m, 2H) 7.06 (t, J=7.15 Hz, 1H) 6.93-6.99 (m, 1H) 4.28 (d, J=5.50 Hz, 2H) 3.75 (t, J=6.11 Hz, 2H) 3.58-3.61 (m, 2H) 3.49-3.57 (m, 22H) 3.35-3.42 (m, 2H) 2.87 (t, J=6.11 Hz, 2H) 2.68 (t, J=7.46 Hz, 2H) 2.23 (t, J=7.46 Hz, 2H) 1.91 (quin, J=7.49 Hz, 2H).

General Procedure for Preparation of Compound 7:

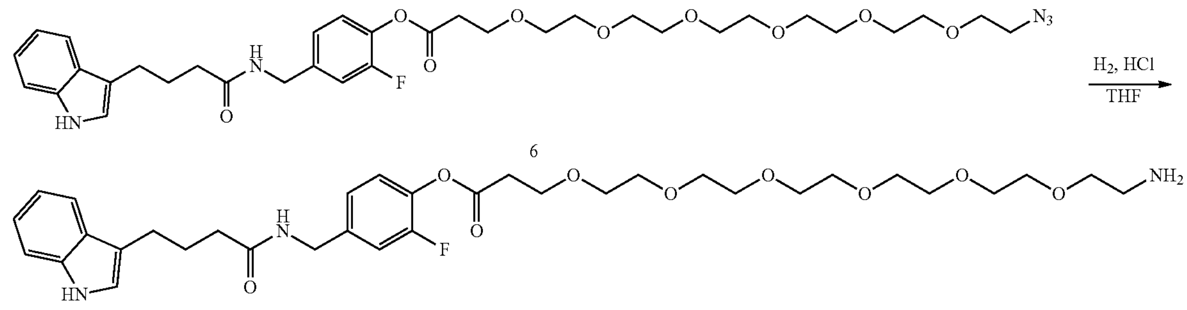

6

7

To a solution of compound 6 (120 mg, 174.48 umol, 1 eq) and HCl (1 M, 523.44 uL, 3 eq) in THF (5 mL) was added Pd/C (120 mg, 10% purity) under $N_2$. The suspension was degassed under vacuum and purged with $H_2$ several times. The mixture was stirred under $H_2$ (15 psi) at 20° C. for 0.5 hours. LCMS showed one main peak with desired mass was detected. The reaction mixture was filtered and the filtrate was basified with sat. $NaHCO_3$ aq. to pH 5-6, then the mixture was concentrated to give residue and the residue was purified by pre-HPLC (TFA condition) to give compound 7 (70 mg, 105.78 umol, 60.63% yield) as colorless oil. LCMS: RT=2.005 min, MS cal.: 661.3, $[M+H]^+$=662.4. $^1H$ NMR: (400 MHz, CHLOROFORM-d) δ ppm 8.54 (br s, 1H) 7.90 (br s, 2H) 7.57 (d, J=7.82 Hz, 1H) 7.35 (d, J=8.07 Hz, 1H) 7.13-7.19 (m, 1H) 7.01-7.11 (m, 4H) 6.95 (d, J=1.71 Hz, 1H) 6.36 (br t, J=5.81 Hz, 1H) 4.35 (d, J=5.99 Hz, 2H) 3.85 (t, J=5.93 Hz, 2H) 3.69-3.75 (m, 2H) 3.52-3.68 (m, 20H) 3.07 (br s, 2H) 2.73-2.91 (m, 4H) 2.23-2.31 (m, 2H) 2.07 (quin, J=7.34 Hz, 2H).

General Procedure for Preparation of Compound I-17:

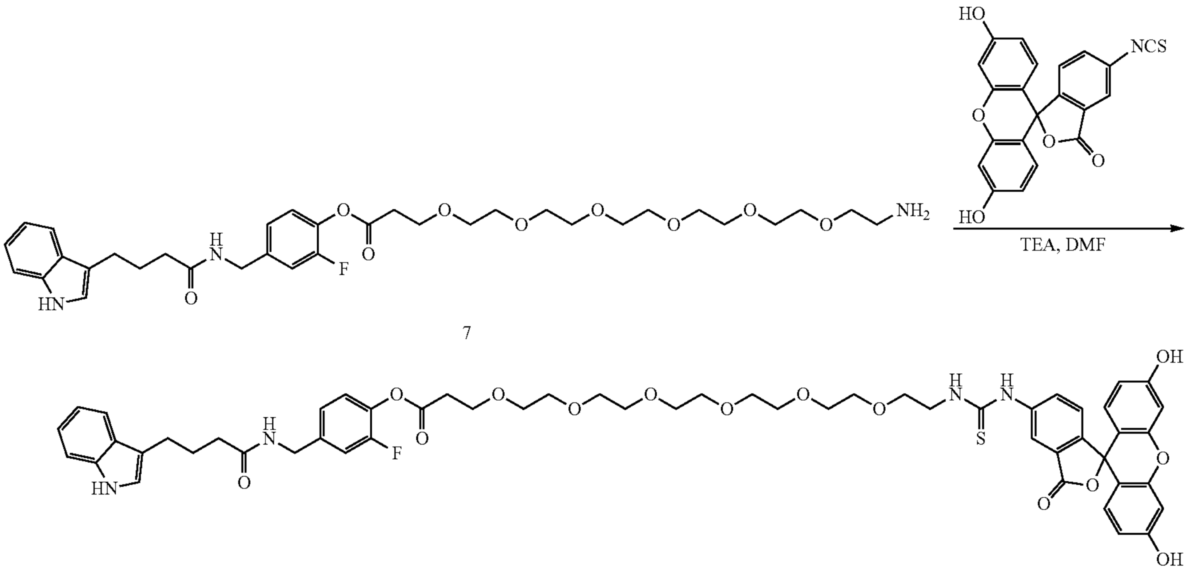

7

I-17

To a mixture of compound 7 (70 mg, 105.78 umol, 1 eq) and 3',6'-dihydroxy-6-isothiocyanato-spiro[isobenzofuran-3,9'-xanthene]-1-one (32.95 mg, 84.62 umol, 0.8 eq) in DMF (1 mL) was added TEA (10.70 mg, 105.78 umol, 14.72 uL, 1 eq) slowly at 20° C. under $N_2$. After stirring for 5 min, TEA (12.84 mg, 126.94 umol, 17.67 uL, 1.2 eq) was slowly added to the mixture and the mixture was stirred at 20° C. for 0.5 hours. LCMS showed starting material was consumed completely and one main peak with desired mass was detected. The mixture was acidified with TFA to pH 5-6, then the solvent was removed to give residue. The residue was purified by pre-HPLC (TFA condition) to give compound I-17 (8.42 mg, 8.01 umol, 7.57% yield) as brown solid. LCMS: RT=2.781 min, MS cal.: 1050.4, $[M/2+H]^+$=526.4. MS: MS cal.: 1050.4, $[M/2+H]^+$=526.6. $^1H$ NMR: (400 MHz, DMSO-$d_6$) δ ppm 10.74 (br s, 1H) 9.94-10.25 (m, 2H) 8.37 (t, J=6.24 Hz, 1H) 8.27 (s, 1H) 8.08 (br s, 1H) 7.73 (br d, J=7.70 Hz, 1H) 7.48 (d, J=7.95 Hz, 1H) 7.32 (d, J=8.07 Hz, 1H) 7.15-7.23 (m, 3H) 7.07-7.12 (m, 2H) 7.04 (t, J=7.15 Hz, 1H) 6.92-6.98 (m, 1H) 6.67 (d, J=2.20 Hz, 2H) 6.52-6.63 (m, 4H) 4.27 (d, J=5.87 Hz, 2H) 3.73 (t, J=6.11 Hz, 2H) 3.68 (br s, 2H) 3.58-3.63 (m, 2H) 3.47-3.57 (m, 22H) 2.81-2.89 (m, 2H) 2.66-2.71 (m, 2H) 2.22 (t, J=7.46 Hz, 2H) 1.90 (quin, J=7.49 Hz, 2H).

Example 18. Exemplary Synthesis of Compound I-18

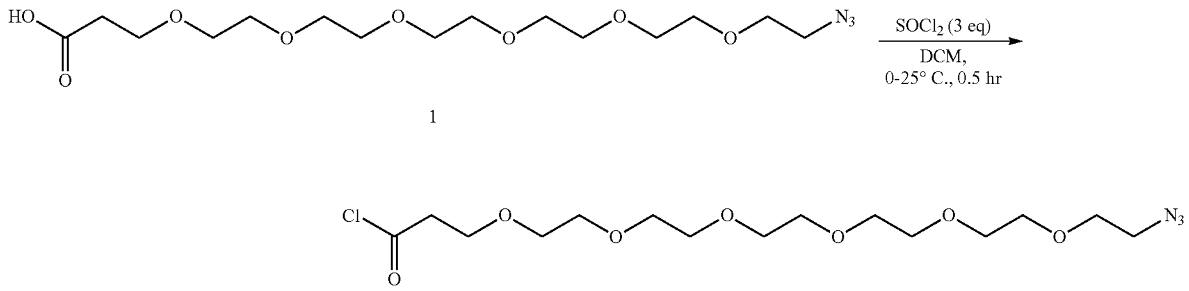

1

2

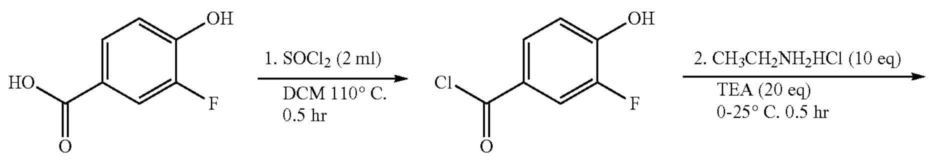

3

4

-continued

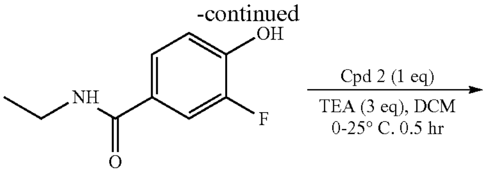

5

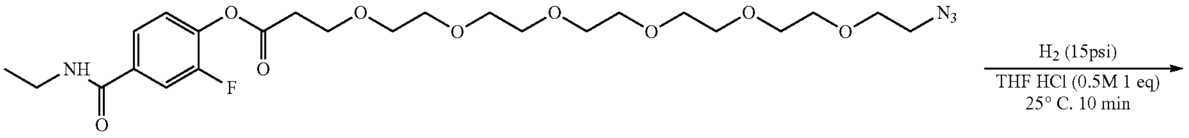

6

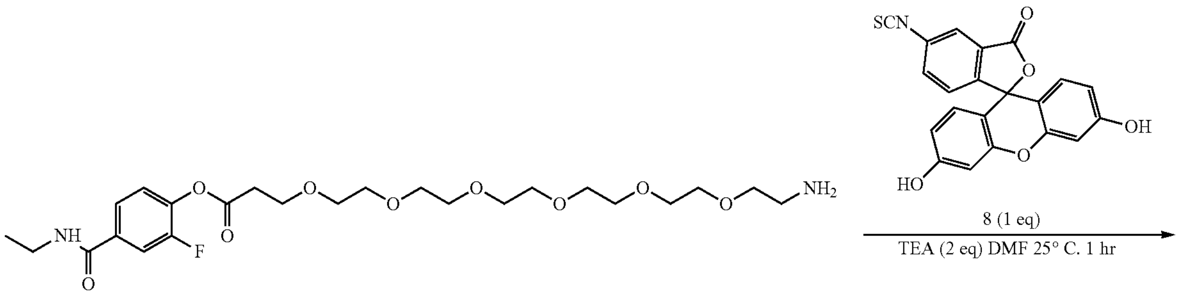

7

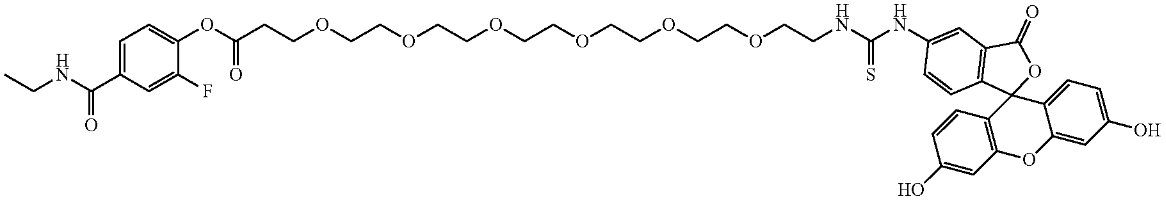

I-18

General Procedure for Preparation of Compound 2:

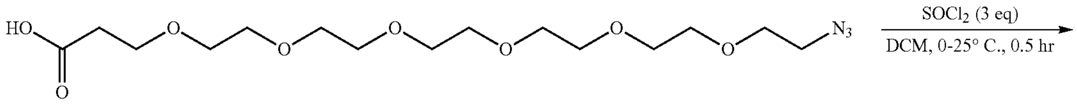

1

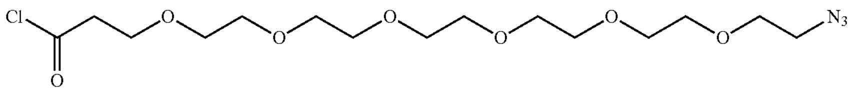

2

A mixture of compound 1 (130 mg, 342.64 umol, 1 eq) and $SOCl_2$ (122.29 mg, 1.03 mmol, 74.57 uL, 3 eq) in DCM (2 mL) at 0° C. was degassed and purged with $N_2$ 3 times, and the mixture was then stirred at 20° C. for 0.5 hr under $N_2$ atmosphere. TLC (Dichloromethane:Methanol=10:1 $R_f$=0.46) indicated compound 1 was consumed completely. The reaction mixture was co-evaporated with DCM three times to remove excess $SOCl_2$. Compound 2 (136 mg, crude) was obtained as a yellow oil.

General Procedure for Preparation of Compound 4:

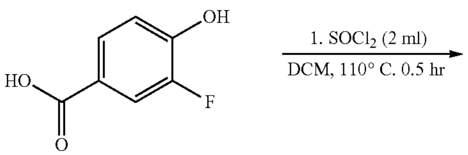

3

-continued

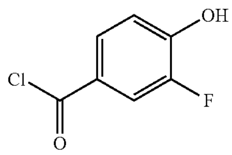

4

A mixture of compound 3 (100 mg, 640.57 umol, 1 eq) in $SOCl_2$ (3.28 g, 27.57 mmol, 2 mL, 43.04 eq) was degassed and purged with $N_2$ 3 times, and the mixture was then stirred at 110° C. for 0.5 hr under $N_2$ atmosphere. TLC (Dichloromethane:Methanol=10:1 $R_f$=0.38) indicated compound 3 was consumed completely. The reaction mixture was co-evaporated with DCM three times to remove excess $SOCl_2$. Compound 4 (112 mg, crude) was obtained as a white oil.

General Procedure for Preparation of Compound 5:

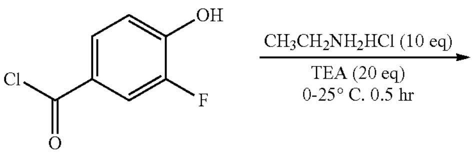

4

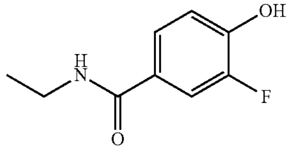

5

To a solution of $CH_3CH_2NH_2HCl$ (518.54 mg, 6.36 mmol, 10 eq) in DCM (2 mL) was added TEA (1.29 g, 12.72 mmol, 1.77 mL, 20 eq) at 0° C. After addition, the mixture was stirred at this temperature for 10 min, and then a solution of compound 4 (111 mg, 635.90 umol, 1 eq) in DCM (1 mL) was added dropwise at 0° C. The resulting mixture was stirred at 0° C. for 1 hr. LCMS showed the starting material was consumed completely. To the reaction mixture was added DCM (10 mL) and $H_2O$ (5 ml). The organic phase was separated, the water phase was acidified with 1 M HCl to pH 3-4, and the aqueous phase was extracted with DCM twice, each time with 10 mL. All organic phases were combined, washed once with saturated salt water (10 mL), dried anhydrous sodium sulfate, filtered and spun dry. Compound 5 (60 mg, 327.55 umol, 51.51% yield) was obtained as a yellow oil. LCMS: RT=0.799 min, MS cal.: 183.0, $[M+H]^+$=184.2. $^1H$ NMR (400 MHz, DMSO-$d_6$) δ ppm 10.47 (br s, 1H) 8.35 (br s, 1H) 7.69 (dd, J=12.41, 1.90 Hz, 1H) 7.60 (br d, J=8.44 Hz, 1H) 7.00-7.09 (m, 1H) 3.27-3.34 (m, 2H) 1.16 (t, J=7.15 Hz, 3H).

General Procedure for Preparation of Compound 6:

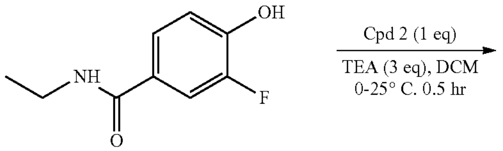

5

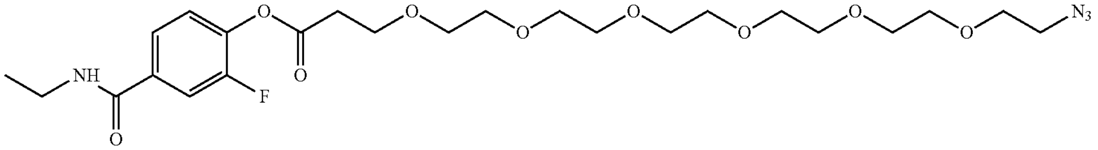

6

To a solution of compound 5 (60 mg, 327.55 umol, 1 eq) in DCM (1 mL) was added TEA (99.43 mg, 982.64 umol, 136.77 uL, 3 eq) at 0° C. After addition, the mixture was stirred at this temperature for 0.5 hr, and then a solution of compound 2 (130.32 mg, 327.55 umol, 1 eq) in DCM (1 mL) was added at 0° C. The resulting mixture was stirred at 20° C. for 1 hr. LCMS showed the starting material was consumed completely. The reaction mixture was dried under nitrogen gas. The crude product was purified by reversed-phase HPLC (column: Welch Ultimate AQ-C18 150*30 mm*5 um; mobile phase: [water (0.1% TFA)-ACN]; B %: 27%-57%, 12 min). Compound 6 (90 mg, 165.27 umol, 50.46% yield) was obtained as a white oil. LCMS: RT=2.130 min, MS cal.: 544.2, $[M+H]^+$=545.3. $^1H$ NMR (400 MHz, CHLOROFORM-d) δ ppm 7.64 (br d, J=10.39 Hz, 1H) 7.56 (br d, J=9.54 Hz, 1H) 6.12 (br s, 1H) 3.90 (t, J=6.36 Hz, 2H) 3.63-3.75 (m, 24H) 3.48-3.56 (m, 2H) 3.40 (br t, J=5.01 Hz, 2H) 2.92 (t, J=6.30 Hz, 2H) 1.28 (t, J=7.21 Hz, 3H).

General Procedure for Preparation of Compound 7:

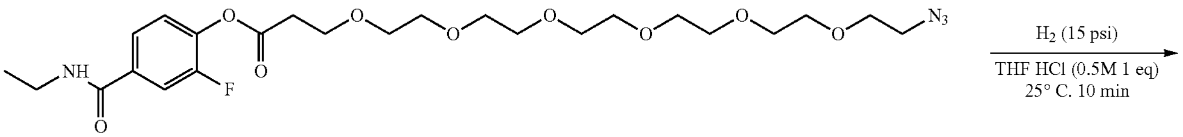

6

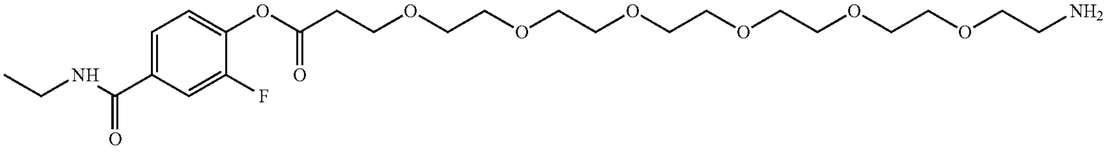

7

To a solution of compound 6 (60 mg, 110.18 umol, 1 eq) in THF (3 mL) was added Pd/C (60 mg, 10% purity) and HCl (0.5 M, 220.36 uL, 1 eq) under $N_2$. The suspension was degassed under vacuum and purged with $H_2$ several times. The mixture was stirred under $H_2$ (15 psi) at 25° C. for 10 min. LCMS showed the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 15%-40%, 12 min). Compound 7 (50 mg, 96.42 umol, 87.51% yield) was obtained as a white oil. LCMS: RT=1.426 min, MS cal.: 518.2, $[M+H]^+$=519.3. $^1H$ NMR (400 MHz, CHLOROFORM-d) δ ppm 7.86-8.08 (m, 2H) 7.73 (d, J=10.64 Hz, 1H) 7.65 (d, J=7.82 Hz, 1H) 3.90 (t, J=5.93 Hz, 2H) 3.78-3.86 (m, 2H) 3.58-3.78 (m, 20H) 3.47-3.57 (m, 2H) 3.13 (br s, 1H) 3.09-3.17 (m, 1H) 2.91 (t, J=5.93 Hz, 2H) 1.29 (t, J=7.27 Hz, 4H).

General Procedure for Preparation of Compound I-18:

A mixture of compound 7 (40 mg, 77.14 umol, 1 eq), compound 8 (30.03 mg, 77.14 umol, 1 eq), and TEA (15.61 mg, 154.27 umol, 21.47 uL, 2 eq) in DMF (0.8 mL) was degassed and purged with $N_2$ 3 times, and the mixture was then stirred at 25° C. for 1 hr under $N_2$ atmosphere. LCMS showed the starting material was consumed completely. HPLC showed the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 35%-65%, 12 min). Compound I-18 (5 mg, 4.89 umol, 6.34% yield, TFA) was obtained as a yellow solid. LCMS: RT=2.427 min, MS cal.: 907.3, $[M/2+H]^+$=454.9. HPLC: RT=3.566 min. $^1H$ NMR (400 MHz, DMSO-$d_6$) δ ppm 10.00-10.22 (m, 2H) 8.58 (br s, 1H) 8.27 (s, 1H) 8.10 (br s, 1H) 7.80 (br d, J=11.25 Hz, 1H) 7.73 (br d, J=7.70 Hz, 2H) 7.38 (t, J=8.01 Hz, 1H) 7.19 (d, J=8.31 Hz, 1H) 6.68 (d, J=1.96 Hz, 2H) 6.53-6.65 (m, 4H) 3.47-3.62 (m, 27H) 3.23-3.36 (m, 2H) 2.90 (t, J=6.05 Hz, 2H) 1.12 (t, J=7.21 Hz, 3H). MS: $[M/2+H]^+$=455.1.

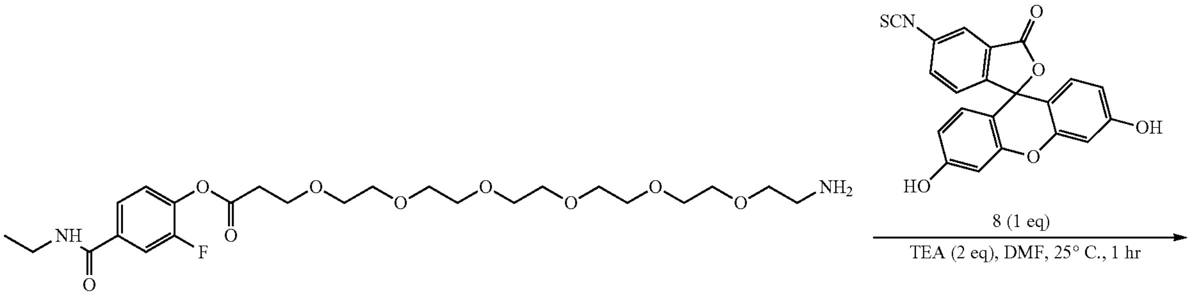

7

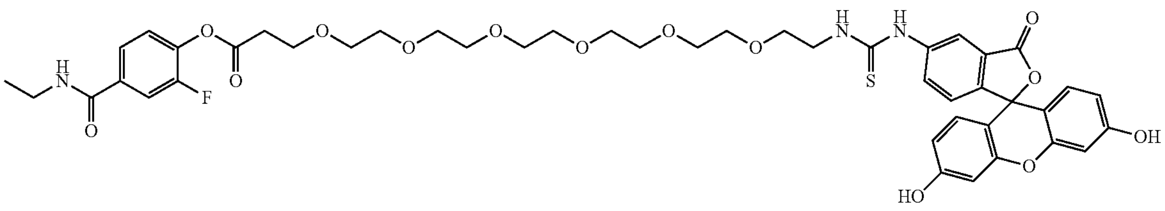

I-18

Example 19. Exemplary Synthesis of Compound I-19
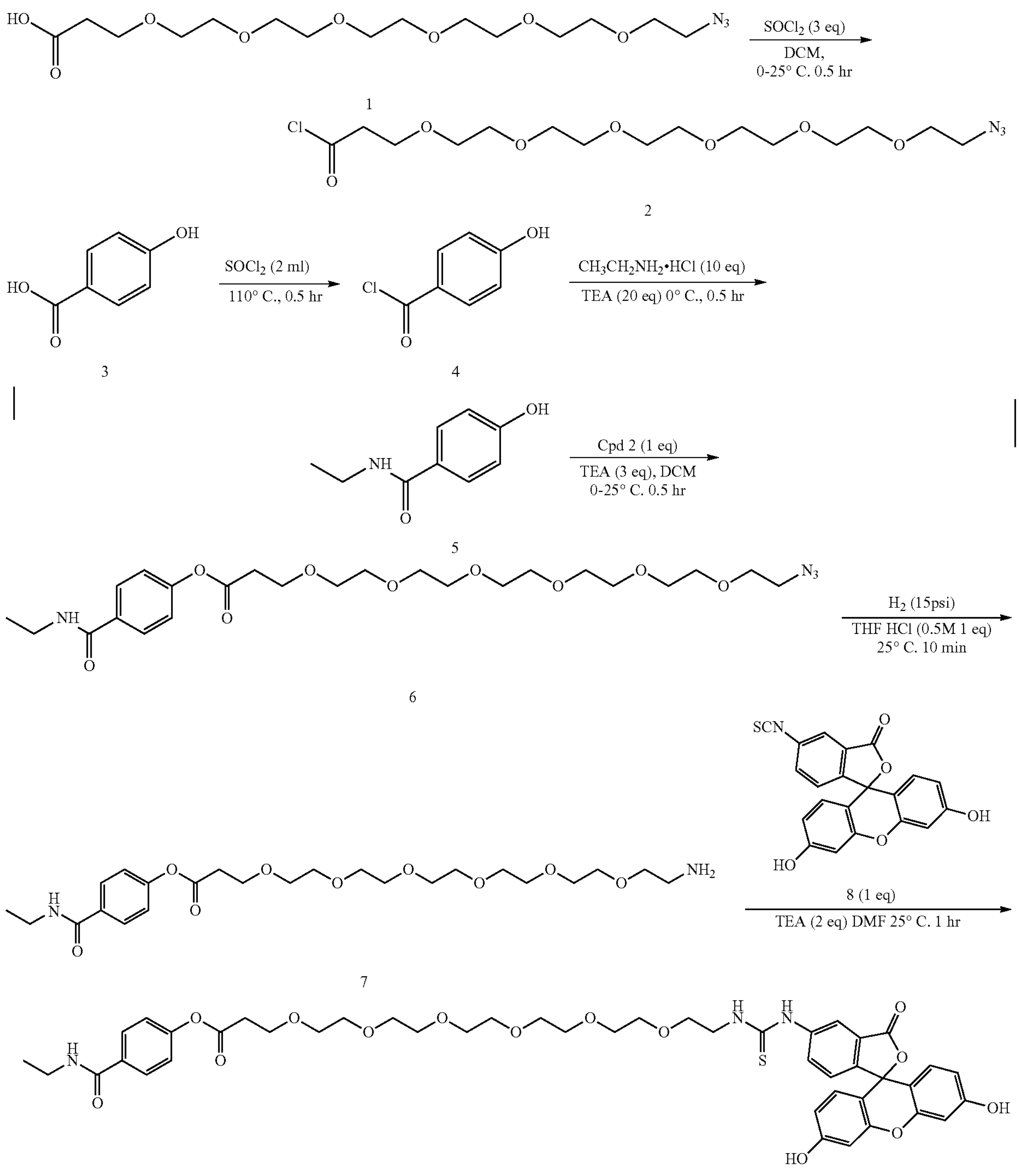
1
2
3
4
5
6
7
I-19
General Procedure for Preparation of Compound 2:
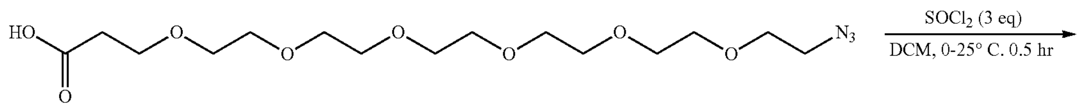
1

-continued

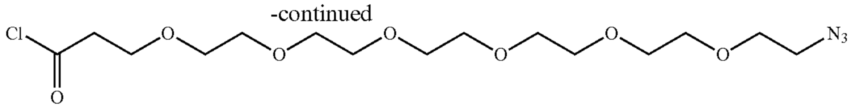

2

A mixture of compound 1 (160 mg, 421.71 umol, 1 eq) and $SOCl_2$ (150.51 mg, 1.27 mmol, 91.78 uL, 3 eq) in DCM (2 mL) at 0° C. was degassed and purged with $N_2$ 3 times, and then the mixture was stirred at 20° C. for 0.5 hr under $N_2$ atmosphere. TLC (Dichloromethane:Methanol=10:1 $R_f$=0.46) indicated compound 1 was consumed completely. The reaction mixture was concentrated to give the crude product. Compound 2 (167 mg, crude) was obtained as a yellow oil.

General Procedure for Preparation of Compound 4:

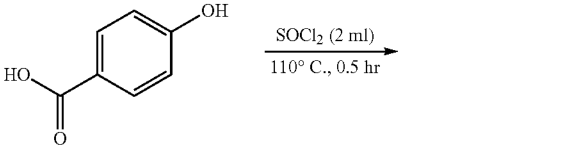

3

4

A mixture of compound 3 (300 mg, 2.17 mmol, 1 eq) in $SOCl_2$ (3.28 g, 27.57 mmol, 2 mL, 12.69 eq) was degassed and purged with $N_2$ 3 times, and then the mixture was stirred at 110° C. for 0.5 hr under $N_2$ atmosphere. TLC (Petroleum ether:Ethyl acetate=10:1 $R_f$=0.36) indicated compound 3 was consumed completely. The reaction mixture was co-evaporated with DCM three times to remove excess $SOCl_2$. Compound 4 (340 mg, crude) was obtained as yellow oil.

General Procedure for Preparation of Compound 5:

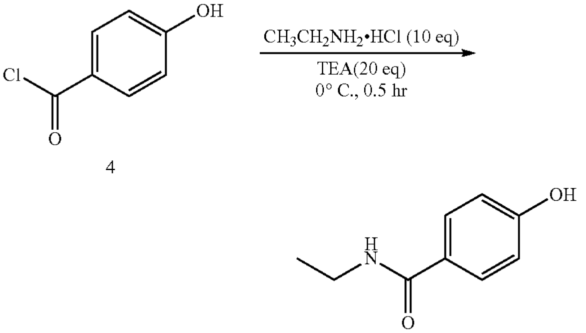

4

5

To a solution of $CH_3CH_2NH_2HCl$ (1.77 g, 21.72 mmol, 10 eq) in DCM (2 mL) was added TEA (4.39 g, 43.43 mmol, 6.05 mL, 20 eq) at 0° C. After addition, the mixture was stirred at this temperature for 10 min, and then a solution of compound 4 (340 mg, 2.17 mmol, 1 eq) in DCM (1 mL) was added dropwise at 0° C. The resulting mixture was stirred at 0° C. for 1 hr. LCMS showed that the starting material was consumed completely. The reaction mixture was filtered and the filtrate was concentrated. The crude product was purified by reversed-phase HPLC (column: Nano-micro Kromasil C18 80*25 mm*3 um; mobile phase: [water (0.1% TFA)-ACN]; B %: 1%-25%, 7 min). Compound 5 (70 mg, 423.76 umol, 19.51% yield) was obtained as a white oil. LCMS: RT=0.561 min, MS cal.: 165.0, $[M+H]^+$=166.1.

General Procedure for Preparation of Compound 6:

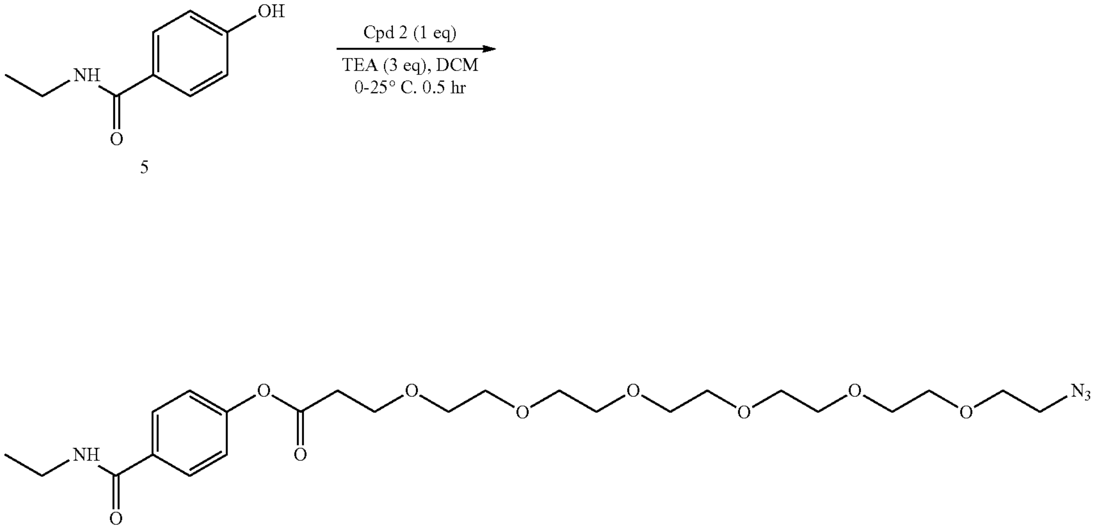

5

6

To a solution of compound 5 (66 mg, 399.54 umol, 1 eq) in DCM (3 mL) was added TEA (121.29 mg, 1.20 mmol, 166.84 uL, 3 eq) at 0° C. After addition, the mixture was stirred at this temperature for 0.5 hr, and then a solution of compound 2 (158.96 mg, 399.54 umol, 1 eq) in DCM (1 mL) was added at 0° C. The resulting mixture was stirred at 20° C. for 1 hr. LCMS showed the starting material was consumed completely. The reaction mixture was dried under nitrogen gas. The crude product was purified by reversed-phase HPLC (column: Welch Ultimate AQ-C18 150*30 mm*5 um; mobile phase: [water (0.1% TFA)-ACN]; B %: 25%-55%, 12 min). Compound 6 (100 mg, 189.91 umol, 47.53% yield) was obtained as a white oil. LCMS: RT=2.038 min, MS cal.: 526.2, $[M+H]^+$=527.3. $^1H$ NMR (400 MHz, CHLOROFORM-d) δ ppm 7.80 (d, J=8.56 Hz, 2H) 7.15-7.20 (m, 2H) 6.14 (br s, 1H) 3.88 (t, J=6.30 Hz, 2H) 3.59-3.72 (m, 23H) 3.44-3.54 (m, 2H) 3.35-3.42 (m, 2H) 2.80-2.89 (m, 2H) 1.26 (t, J=7.21 Hz, 3H).

General Procedure for Preparation of Compound 7:

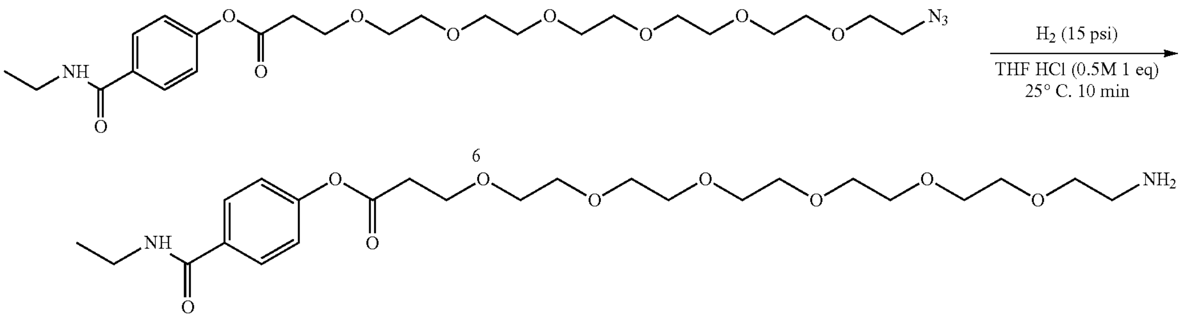

6

7

To a mixture of compound 6 (75 mg, 142.43 umol, 1 eq) and HCl (0.5 M, 284.86 uL, 1 eq) in THF (1 mL) was added Pd/C (10% purity, 1 eq) under $N_2$. The suspension was degassed under vacuum and purged with $H_2$ several times. The mixture was stirred under $H_2$ (15 psi) at 25° C. for 20 min. LCMS showed that the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 13%-43%, 12 min). Compound 7 (60 mg, 119.86 umol, 84.15% yield) was obtained as a white oil. LCMS: RT=1.400 min, MS cal.: 500.2, $[M+H]^+$=501.3.

General Procedure for Preparation of Compound I-19:

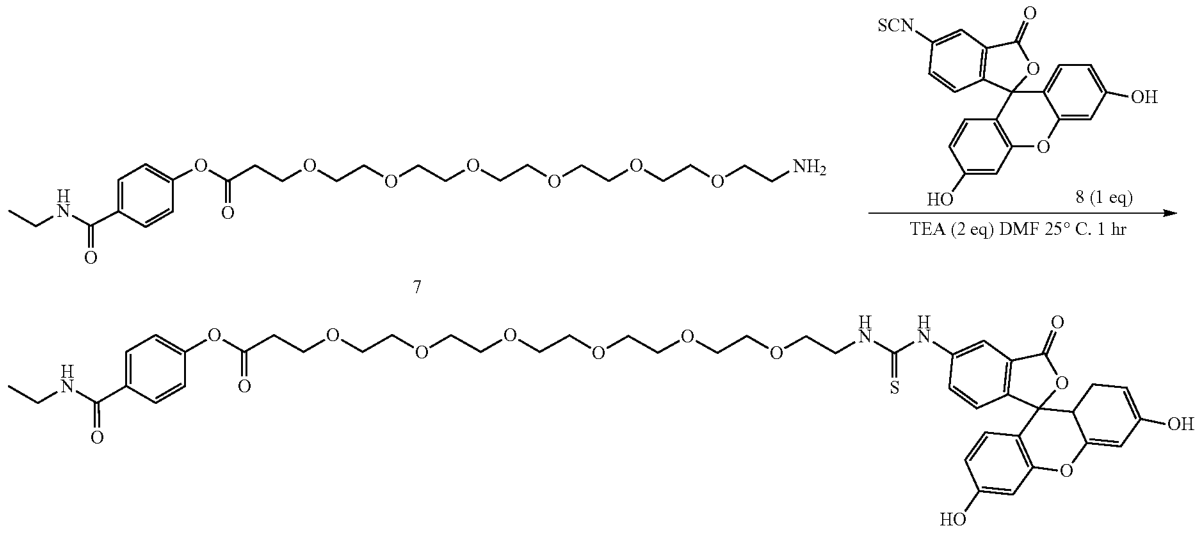

7

I-19

A mixture of compound 7 (30 mg, 59.93 umol, 1 eq), compound 8 (23.34 mg, 59.93 umol, 1 eq), and TEA (12.13 mg, 119.86 umol, 16.68 uL, 2 eq) in DMF (1 mL) was degassed and purged with $N_2$ 3 times, and the mixture was then stirred at 25° C. for 1 hr under $N_2$ atmosphere. LCMS (product: RT=2.337 min; M/2+1=445.9) showed that the starting material was consumed completely. HPLC showed the starting material was consumed completely. The reaction mixture was filtered and the filtrate was concentrated. The crude product was purified by reversed-phase HPLC (column: Welch Ultimate AQ-C18 150*30 mm*5 um; mobile phase: [water (0.1% TFA)-ACN]; B %: 30%-60%, 12 min).

Compound I-19 (5 mg, 4.98 umol, 8.31% yield, TFA) was obtained as a yellow solid. LCMS: RT=2.337 min, MS cal.: 889.3, $[M/2+H]^+$=445.9. HPLC: RT=3.469 min. $^1H$ NMR (400 MHz, DMSO-$d_6$) δ ppm 10.03 (br s, 1H) 8.47 (t, J=5.44 Hz, 1H) 8.28 (s, 1H) 8.09 (br s, 1H) 7.88 (d, J=8.68 Hz, 2H) 7.75 (br d, J=8.93 Hz, 1H) 7.16-7.22 (m, 3H) 6.68 (d, J=2.08 Hz, 2H) 6.53-6.63 (m, 4H) 3.75 (t, J=6.11 Hz, 3H) 3.69 (br s, 2H) 3.60-3.65 (m, 2H) 3.53-3.60 (m, 8H) 3.46-3.53 (m, 13H) 3.24-3.32 (m, 2H) 2.84 (t, J=6.11 Hz, 2H) 1.12 (t, J=7.15 Hz, 3H). MS: $[M/2+H]^+$=446.0.

Example 20. Exemplary Synthesis of Compound I-20

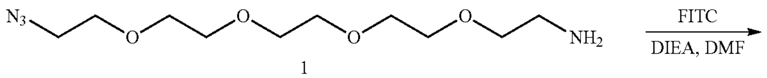

1

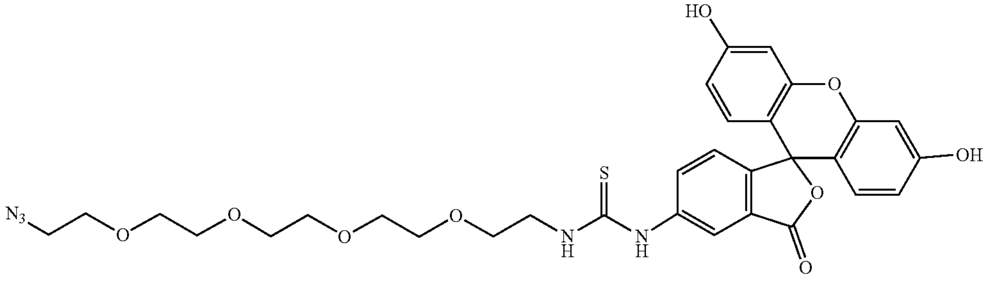

2

A mixture of compound 1 (163.2 mg, 419.3 umol), FITC (0.10 g, 381.2 umol), DIEA (98.5 mg, 762.4 umol, 132.8 uL) in DMF (0.5 mL) was stirred at 15° C. for 2 hrs. The mixture was purified by flash C18 (ISCO®; 120 g SepaFlash® C18 Flash Column, Eluent of 0~90% MeCN/$H_2O$ ether gradient @ 75 mL/min) to get compound 2 (300 mg, 1.43 mmol, 90.0% purity, 52.2% yield) as a yellow solid.

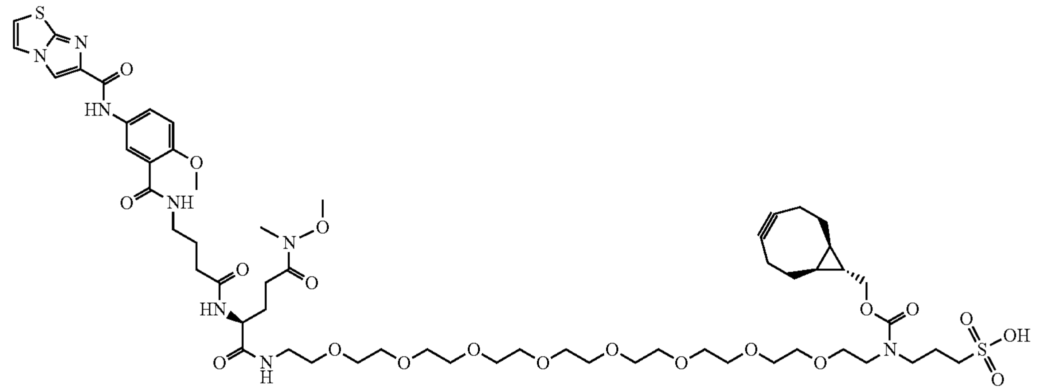

3

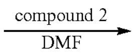

-continued

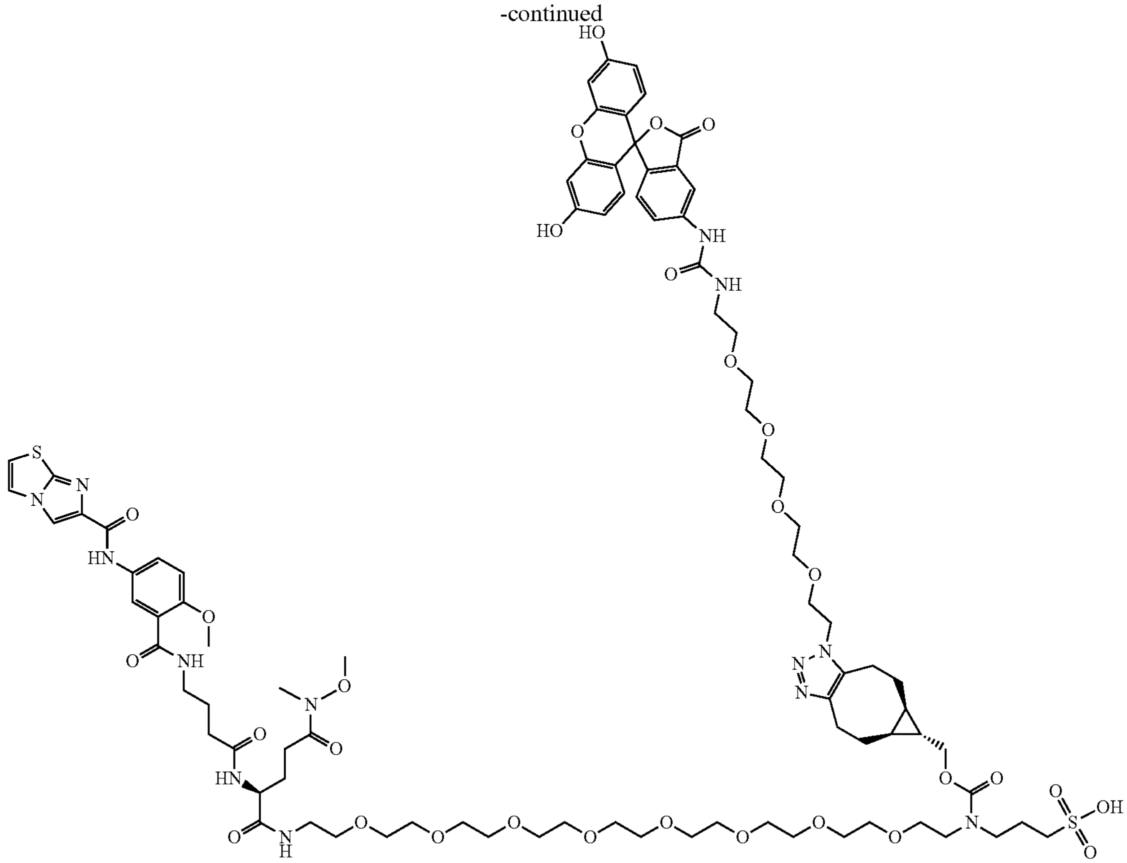

I-20

A solution of compound 3 (7.3 mg, 5.78 umol), compound 2 (3.7 mg, 5.78 umol) in DMF (0.1 mL) was stirred at 15° C. for 16 hrs. The mixture was purified by prep-HPLC (neutral condition, $NH_4OAc$) directly to get compound I-20 (1.8 mg, 8.44e-1 umol, 90.1% purity, 14.6% yield, $NH_4OAc$) as a yellow solid. MS: m/z 959.6 $[M+2H]^{2+}$. An example purification procedure:

| Purification condition | |
|---|---|
| Sample Preparation | Dissolve in $MeCN/H_2O$ |
| Instrument | Gilson GX-215 |
| Mobile Phase | A: $H_2O$ (0.075% TFA in $H_2O$) |
| B: MeCN | |

-continued

| Purification condition | |
|---|---|
| Gradient | 20-50%-60 min. Retention time: 40 min |
| Column | Luna25 * 200 mm, C18 10 um, 110A + Gemin150 * 30 mm, C18 5 um,110A |
| Flow Rate | 20 mL/min |
| Wavelength | 220/254 nm |
| Oven Tem. | Room temperature |

Example 21. Exemplary Synthesis of Compounds I-21, I-22 and I-23

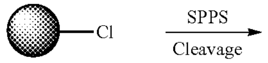

-continued

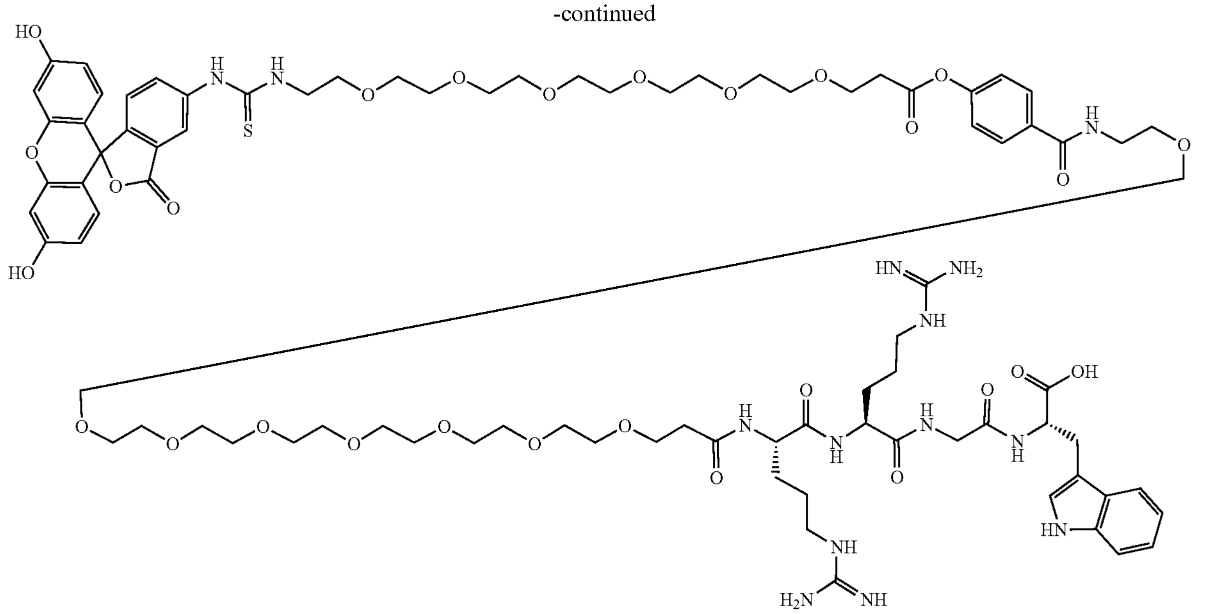

I-21

Peptide was synthesized using standard Fmoc chemistry. One procedure is described below as an example:

1) Add DCM to a vessel containing CTC Resin (0.20 mmol, 0.20 g, 1.0 mmol/g) and Fmoc-Trp(Boc)-OH (0.085 g, 0.16 mmol, 0.8 eq) with $N_2$ bubbling.
2) Add DIEA (6.0 eq) dropwise and mix for 2 hrs.
3) Add MeOH (0.50 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

One synthesized scale was 0.2 mmol.

| # | Materials | Coupling reagents |
|---|---|---|
| 1 | Fmoc-Trp(Boc)-OH (3.0 eq) | DIEA(6.0 eq) |
| 2 | Fmoc-Gly-OH (3.0 eq) | HBTU (2.85 eq) and DIEA(6.0 eq) |
| 3 | Fmoc-Arg(Pbf)-OH (3.0 eq) | HBTU (2.85 eq) and DIEA(6.0 eq) |
| 4 | Fmoc-Arg(Pbf)-OH (3.0 eq) | HBTU (2.85 eq) and DIEA(6.0 eq) |
| 5 | Fmoc-PEG8-$CH_2CH_2COOH$ (3.0 eq) | HBTU (2.85 eq) and DIEA(6.0 eq) |
| 6 | 4-hydroxybenzoic acid (3.0 eq) | DIC (3.0 eq) and HOBt(3.0 eq) |
| 7 | Fmoc-PEG6-$CH_2CH_2COOH$ | DIC (3.0 eq) and HOBt(3.0 eq), (3.0 eq) DMAP (3.0 eq) |
| 8 | FITC (2.0 eq) | DIEA (4.0 eq) |

20% piperidine in DMF was used for Fmoc deprotection for 30 mins. For the $7^{th}$ Fmoc deprotection was 2 mins. The coupling reaction was monitored by ninhydrin test, and the resin was washed with DMF for 5 times. After the last coupling, the resin was washed with MeOH for 3 times, and then dried under vacuum. The peptide was handled in dark after FITC coupling.

Peptide Cleavage and Purification. One procedure is described below as an example:

1) Add cleavage cocktail (97.5% TFA/2.5% $H_2O$) to the flask containing the side chain protected peptide at room temperature and stir for 2 hr.
2) The mixture was filtered, and the solution was concentrated under reduced pressure to remove solvent.
3) Purify the crude peptide by prep-HPLC (TFA condition) to give the I-21 (6.4 mg, 96.8% purity, 3.47% yield). MS: m/z 921.8 $[M+2H]^{2+}$.

In some embodiments, peptides were purified using conditions below as an example"

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$) |
| | B: MeCN |
| Gradient | 20-50%-60 min. Retention time: 45 min |
| Column | Luna25 * 200 mm, C18 10 um, 110A + |
| | Gemin150 * 30 mm, C18 5 um, 110A |
| Flow Rate | 20 mL/min |
| Wavelength | 220/254 nm |
| Oven Tem. | Room temperature |

I-22 and I-23 were prepared using a similar process, and the materials used in cycle 5 were Fmoc-PEG4-$CH_2CH_2COOH$ and Fmoc-PEG2-$CH_2CH_2COOH$ respectively. In one preparation, purity for I-22 was about 96%, MS: m/z 555.9 $[M+3H]^{3+}$. In one preparation, purity for I-23 was about 93%, MS: m/z 526.6 $[M+3H]^{3+}$.

Example 22. Exemplary Synthesis of Compounds I-24 and I-25

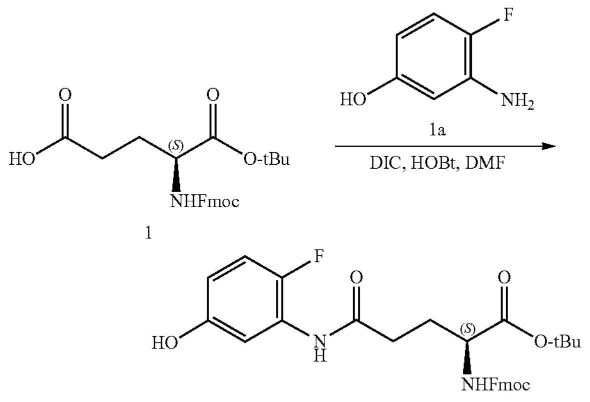

1

2

A mixture of compound 1 (2.00 g, 4.70 mmol), compound 1a (597.5 mg, 4.70 mmol), EDCI (1.80 g, 9.40 mmol), HOBt (1.27 g, 9.40 mmol) in DCM (20 mL) was stirred at 15° C. for 16 hrs. The solvent was then diluted with DCM (100 mL), washed with 1 M HCl (50 mL), $H_2O$ (50 mL), brine (50 mL), dried over anhydrous $Na_2SO_4$, concentrated under reduced pressure. The residue was purified by column chromatography ($SiO_2$, DCM:MeOH=50/1 to 10/1) to get compound 2 (2.00 g, 3.74 mmol, 79.59% yield) as a white solid.

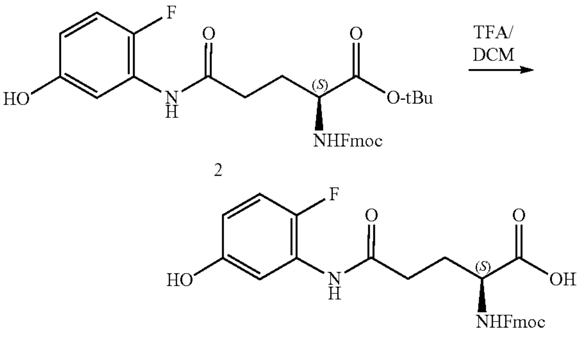

2

3

A mixture of compound 2 (2.00 g, 3.74 mmol) in DCM (20 mL) and TFA (20 mL) was stirred at 15° C. for 0.5 hr. The solvent was removed under reduced pressure. The residue was purified by flash C18 (ISCO®; 120 g Sepa-Flash® C18 Flash Column, Eluent of 0~90% MeCN/$H_2O$ ether gradient @75 mL/min) to get compound 3 (1.00 g, 2.09 mmol, 55.8% yield) as a white solid.

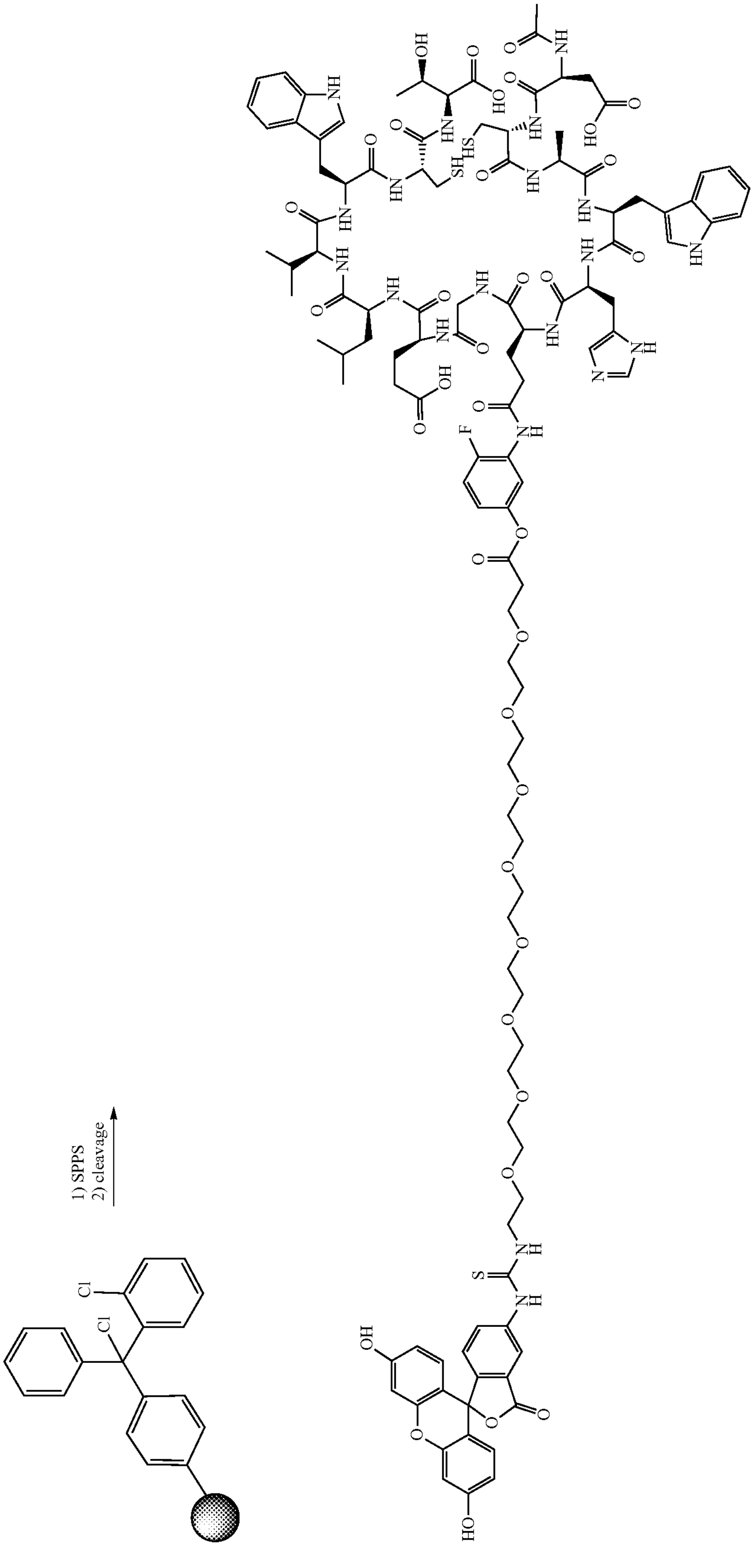
4

In some embodiments, peptide was prepared using the procedure below:

1) Add DCM to the vessel containing CTC Resin (0.10 mmol, 0.10 g, 1.0 mmol/g) and Fmoc-Thr(tBu)-OH (39.7 mg, 0.10 mmol, 1.0 eq) with $N_2$ bubbling.
2) Add DIEA (6.0 eq) dropwise and mix for 2 hrs.
3) Add MeOH (0.10 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

Synthesized scale: 0.10 mmol.

| # | Materials | Coupling reagents |
|---|---|---|
| 1 | Fmoc-Thr(tBu)-OH (0.8 eq) | DIEA(6.0 eq) |
| 2 | Fmoc-Cys(Trt)-OH (3.0 eq) | HBTU (2.85 eq) and DIEA(6.0 eq) |
| 3 | Fmoc-Trp(Boc)-OH (3.0 eq) | HBTU (2.85 eq) and DIEA(6.0 eq) |
| 4 | Fmoc-Val-OH (3.0 eq) | HBTU (2.85 eq) and DIEA(6.0 eq) |
| 5 | Fmoc-Leu-OH (3.0 eq) | HBTU (2.85 eq) and DIEA(6.0 eq) |
| 6 | Fmoc-Glu(OtBu)-OH (3.0 eq) | HBTU (2.85 eq) and DIEA(6.0 eq) |
| 7 | Fmoc-Gly-OH (3.0 eq) | HBTU (2.85 eq) and DIEA(6.0 eq) |
| 8 | Compound 3 (3.0 eq) | DIC (3.0 eq) and HOBt (3.0 eq) |
| 9 | Fmoc-His(Trt)-OH (3.0 eq) | DIC (3.0 eq) and HOBt (3.0 eq) |
| 10 | Fmoc-Trp(Boc)-OH (3.0 eq) | DIC (3.0 eq) and HOBt (3.0 eq) |
| 11 | Fmoc-Ala-OH (3.0 eq) | DIC (3.0 eq) and HOBt (3.0 eq) |
| 12 | Fmoc-Cys(Trt)-OH (3.0 eq) | DIC (3.0 eq) and HOBt (3.0 eq) |
| 13 | Fmoc-Asp(OtBu)-OH (3.0 eq) | DIC (3.0 eq) and HOBt (3.0 eq) |
| 14 | 10%$AC_2O$/5%NMM/85%DMF (10 mL) | N/A |
| 15 | Fmoc-NH-$PEG_6$-$CH_2CH_2COOH$ (3.0 eq) | DIC (3.0 eq), HOBt (3.0 eq), DMAP (3.0 eq) |
| 16 | FITC (2.0 eq) | DIEA (4.0 eq) |

20% piperidine in DMF was used for Fmoc deprotection for 30 mins. Coupling reactions were monitored by ninhydrin test, and the resin was washed with DMF for 5 times. After the last amino acid coupling, the resin was washed with MeOH for 3 times, and then dried under vacuum. After FITC couple, the peptide was handled in dark. In some embodiments, peptide was cleaved and purified using the following procedure:

1) Add cleavage cocktail (92.5% TFA/2.5%3-mercaptopropanoic acid/2.5% $H_2O$/2.5% TIS) to the flask containing the side chain protected peptide at room temperature and the mixture was stirred for 1 hr.
2) The peptide is precipitated with cold isopropyl ether and collected by centrifugation (3 mins at 3000 rpm).
3) The precipitate is washed with cold isopropyl ether for two additional times.
4) Dry the crude peptide under vacuum for 1 hr.
5) To get compound 4 (100.0 mg, crude) as a yellow solid.

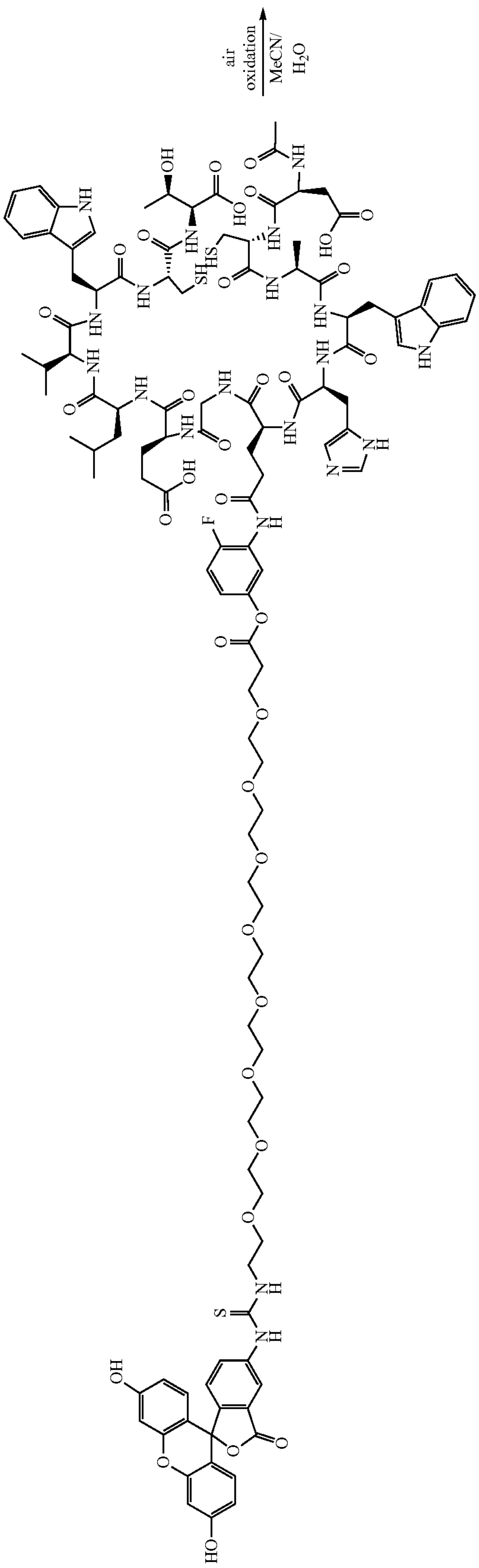
4

-continued
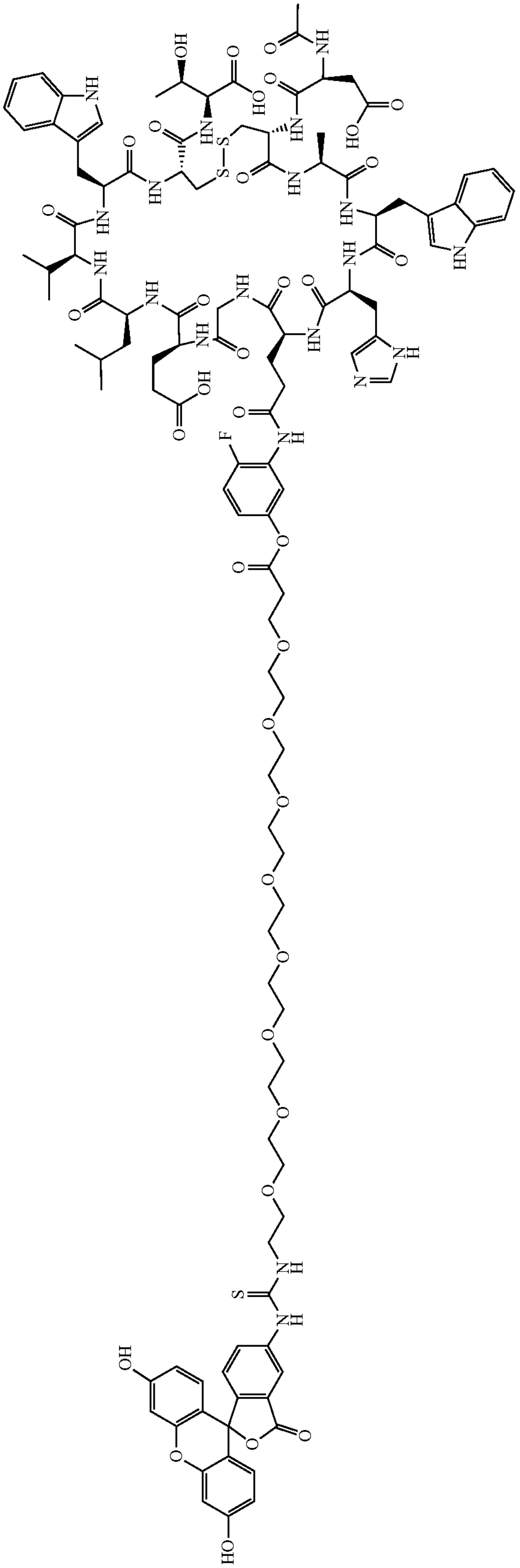
I-24

A mixture of compound 4 (100.0 mg, 39.8 umol) in MeCN/$H_2O$ (1:1, 100 mL) was stirred at 15° C. in darkness to let the disulfide form by air oxidation for 16 hrs. The solution was acidified by 1 M HCl to pH=3, dried in lyophilization. The residue was purified by prep-HPLC (acid condition, TFA) to get I-24 (2.5 mg, 9.96e-1 umol, 2.5% yield, 95.4% purity) as a yellow solid. MS: m/z 837.7 $[M+3H]^{3+}$. A purification procedure is described below as an example:

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$)<br>B: MeCN |
| Gradient | 30-60%-60 min. Retention time: 38 min |
| Column | Luna25 * 200 mm, C18 10 um, 110 A+<br>30Gemin150 * 30 mm, C18 5 um,110A |
| Flow Rate | 20 mL/min |
| Wavelength | 220/254 nm |
| Oven Tem. | Room temperature |

I-25 was synthesized using a similar procedure using corresponding amino acids (in a preparation, purity was about 94%; MS: m/z 832.5 $[M+3H]^{3+}$).

Example 23. Exemplary Synthesis of Compounds I-26 and I-27

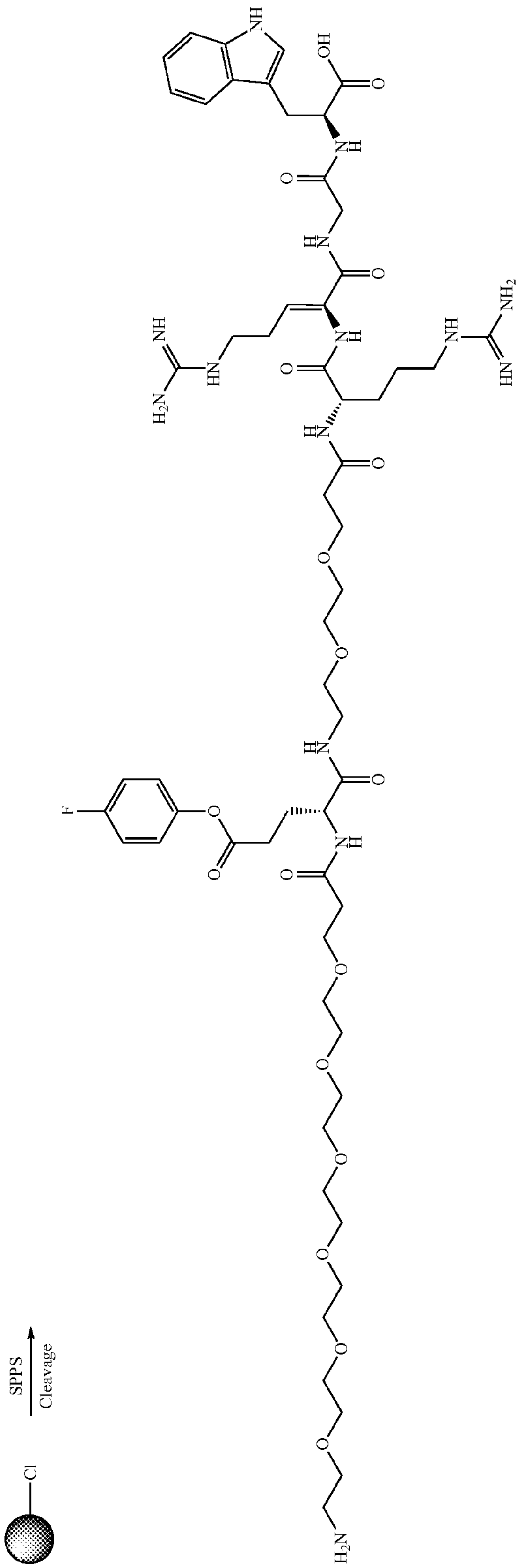
1

Peptide was synthesized using standard Fmoc chemistry. A procedure is described below as an example:

1) Add DCM to the vessel containing CTC Resin (0.20 mmol, 0.20 g, 1.0 mmol/g) and Fmoc-Trp(Boc)-OH (0.085 g, 0.16 mmol, 0.8 eq) with $N_2$ bubbling.
2) Add DIEA (6.0 eq) dropwise and mix for 2 hrs.
3) Add MeOH (0.50 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

Synthesized scale: 0.2 mmol.

| # | Materials | Coupling reagents |
|---|---|---|
| 1 | Fmoc-Trp(Boc)-OH (3.0 eq) | DIEA(6.0 eq) |
| 2 | Fmoc-Gly-OH (3.0 eq) | HBTU (2.85 eq) and DIEA(6.0 eq) |
| 3 | Fmoc-Arg(Pbf)-OH (3.0 eq) | HBTU (2.85 eq) and DIEA(6.0 eq) |
| 4 | Fmoc-Arg(Pbf)-OH (3.0 eq) | HBTU (2.85 eq) and DIEA(6.0 eq) |
| 5 | Fmoc-PEG2-$CH_2CH_2COOH$ (3.0 eq) | HBTU (2.85 eq) and DIEA(6.0 eq) |

-continued

| # | Materials | Coupling reagents |
|---|---|---|
| 6 | Fmoc-D-G1u(OA11)-OH (3.0 eq) | HBTU (2.85 eq) and DIEA(6.0 eq) |
| 7 | Boc-PEG6-$CH_2CH_2COOH$ (3.0 eq) | DIC (3.0 eq) and HOBt(3.0 eq), DMAP (3.0 eq) |
| 8 | 4-fluorophenol (3.0 eq) | DIC (3.0 eq) and HOBt(3.0 eq) |

$Pd(PPh_3)_4$ and phenylsilane were used for removing ally group on the sidechain of D-Glu. 20% piperidine in DMF was used for Fmoc deprotection for 30 mins. Coupling reactions were monitored by ninhydrin test, and the resin was washed with DMF for 5 times. After the last amino acid coupling, the resin was washed with MeOH for 3 times, and then dried under vacuum. A useful procedure for cleavage and purification is described below:

1) Add cleavage cocktail (97.5% TFA/2.5% $H_2O$) to the flask containing the side chain protected peptide at room temperature and stir for 2 hr.
2) The cleavage mixture was filtered, and the solution was concentrated under reduced pressure to remove solvent.
3) Purify the crude peptide by prep-HPLC (TFA condition) to give the compound 1 (90 mg).

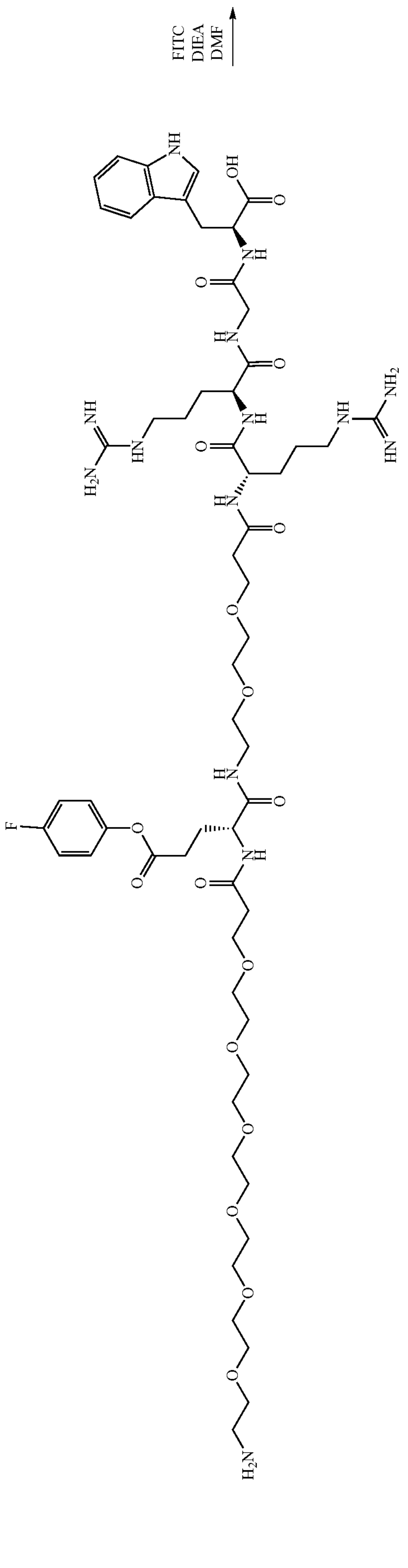
1
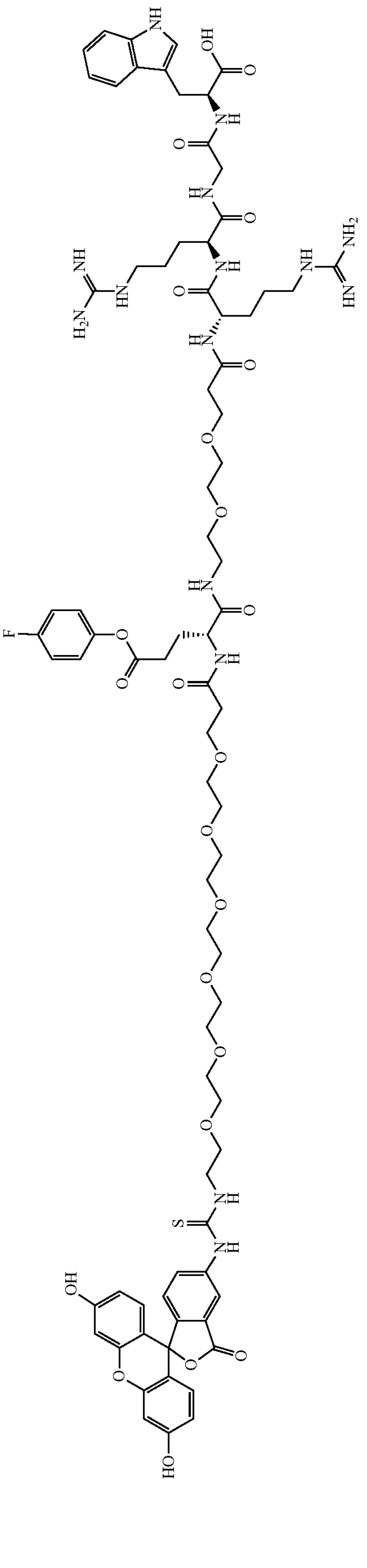
I-26

A solution of compound 1 (90 mg, 69.69 umol), FITC (32.6 mg, 83.63 umol) added DIEA (27.02 mg, 209.07 umol, 36.42 uL) in DMF (1 mL), was stirred at 25° C. for 2 hrs. The residue was purified by prep-HPLC (TFA condition) directly to get I-26 (53.2 mg, 40.6% yield, 95.2% purity) as a yellow solid. MS: m/z 560.2 $[M+3H]^{3+}$. A purification procedure is described below as an example:

| Purification condition | |
|---|---|
| Sample Preparation | Dissolve in $MeCN/H_2O$ |
| Instrument | Gilson GX-215 |
| Mobile Phase | A: $H_2O$ (0.075% TFA in $H_2O$)<br>B: MeCN |
| Gradient | 25-55%-60 min. Retention time: 48 min |
| Column | Luna25 * 200 mm, C18 10 um, 110A + 30Gemin150 * 30 mm, C18 5 um,110A |
| Flow Rate | 20 mL/min |
| Wavelength | 220/254 nm |
| Oven Tem. | Room temperature |

I-27 was prepared using a similar process, in which Fmoc-PEG8-$CH_2CH_2COOH$ was used in cycle 5 (in a preparation, purity was about 95%; MS: m/z 649$[M+3H]^{3+}$.

Example 24. Exemplary Synthesis of Compounds I-28 to I-41

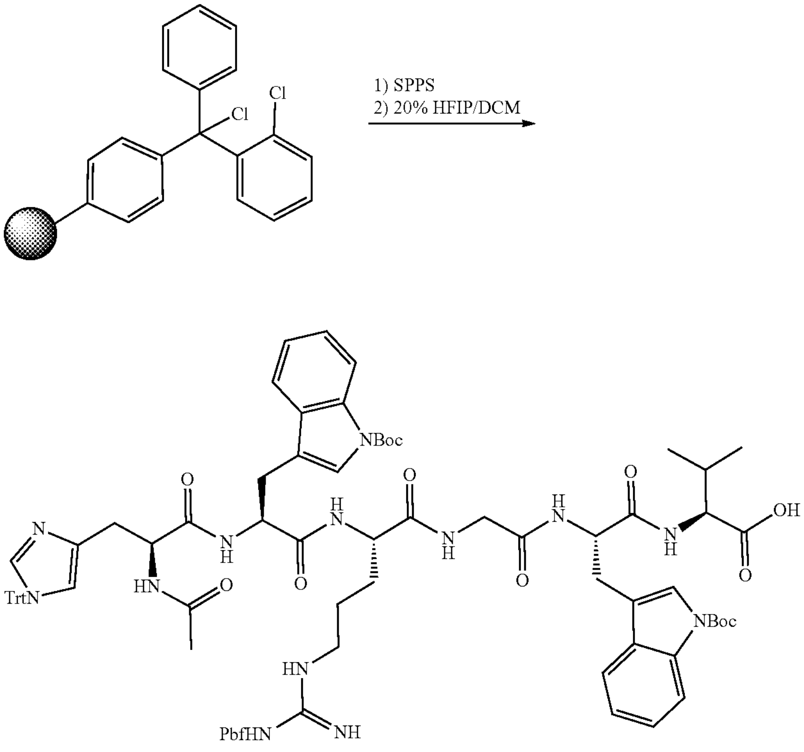

2

Peptide was synthesized using standard Fmoc chemistry. A procedure is described below as an example:

1) Add DCM (5.0 mL) to the vessel containing CTC Resin (0.50 mmol, 0.50 g, 1.0 mmol/g) and Fmoc-Val-OH (0.136 g, 0.40 mmol, 0.8 eq) with $N_2$ bubbling.
2) Add DIEA (4.0 eq) dropwise and mix for 2 hrs.
3) Add MeOH (0.5 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

Synthesized scale: 0.5 mmol.

| # | Materials | Coupling reagents |
|---|---|---|
| 1 | Fmoc-Val-OH (0.8 eq) | DIEA(4.0 eq) |
| 2 | Fmoc-Trp(Boc)-OH (3.0 eq) | HBTU (2.85 eq) and DIEA(6.0 eq) |
| 3 | Fmoc-Gly-OH (3.0 eq) | HBTU (2.85 eq) and DIEA(6.0 eq) |
| 4 | Fmoc-Arg(Pbf)-OH (3.0 eq) | HBTU (2.85 eq) and DIEA(6.0 eq) |
| 5 | Fmoc-Trp(Boc)-OH (3.0 eq) | HBTU (2.85 eq) and DIEA(6.0 eq) |
| 6 | Fmoc-His(Trt)-OH (3.0 eq) | HBTU (2.85 eq) and DIEA(6.0 eq) |
| 7 | $Ac_2O$ | $Ac_2O$/NMM/DMF (10/5/85, 10 mL) |

20% piperidine in DMF was used for Fmoc deprotection for 30 mins. The coupling reaction was monitored by ninhydrin test, and the resin was washed with DMF for 5 times. After the last amino acid coupling, the resin was washed with MeOH for 3 times, and then dried under vacuum. In some embodiments, peptide was cleaved and purified using the following procedure:

The peptide resin was treated with the 20% HFIP/DCM (20 mL) for 0.5 hr twice. After filtered, the combined filterate was concentrated under reduced pressure.

The residue was first dissolved in MeCN (5 mL) and then fully protected peptide was precipitated with cold $H_2O$ (50 mL). After filtrated, the solid fraction was dried by lyophilization to get compound 2 (707 mg, 95.0% purity, 85.2% yield).

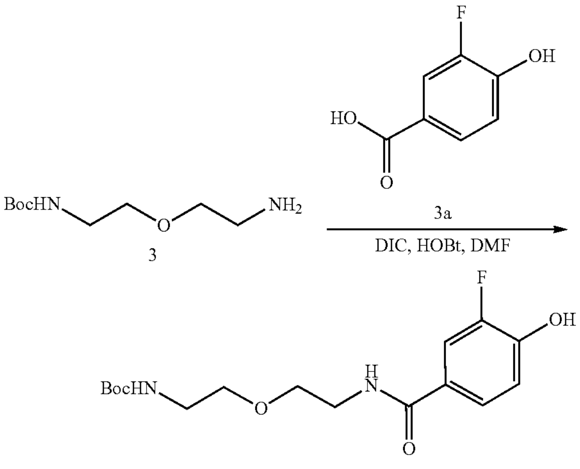

3 4

A mixture of compound 3 (0.50 g, 2.45 mmol), compound 3a (420 mg, 2.69 mmol), DIC (463 mg, 3.67 mmol, 568 uL), HOBt (496 mg, 3.67 mmol) in DMF (5 mL) was stirred at 15° C. for 2 hrs. The mixture was purified by flash C18 (ISCO®; 120 g SepaFlash® C18 Flash Column, Eluent of 0~90% MeCN/$H_2O$ ether gradient @ 75 mL/min) directly to get compound 4 (700 mg, 2.04 mmol, 83.5% yield) as a colorless oil.

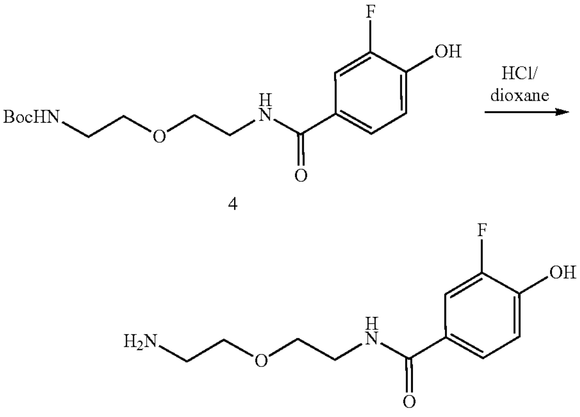

4 5

A mixture of compound 4 (700 mg, 2.04 mmol) in HCl/dioxane (4 M, 10 mL) was stirred at 15° C. for 0.5 hr. The mixture was filtered, and the solid was dried by lyophilization to get compound 5 (HCl salt, 400 mg, 1.65 mmol, 80.7% yield) as a white solid.

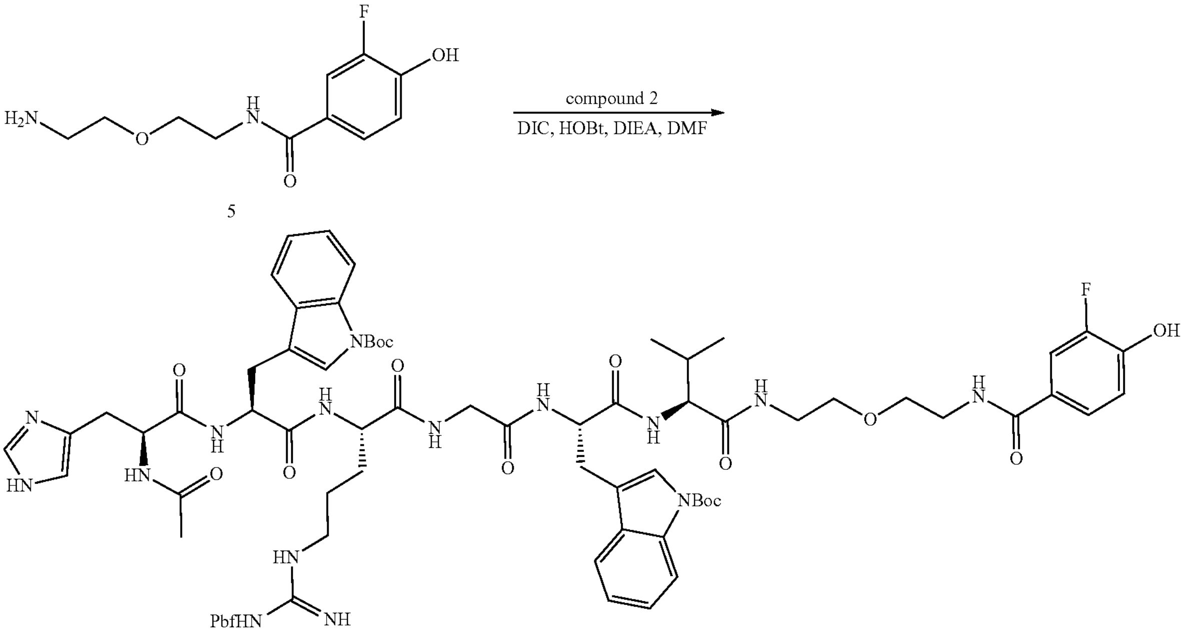

5 6

A mixture of compound 2 (150 mg, 95.13 umol), compound 5 (26.5 mg, 95.1 umol, HCl), DIC (18.0 mg, 142.7 umol, 22.1 uL), HOBt (19.3 mg, 142.7 umol), DIEA (18.4 mg, 142.7 umol, 24.8 uL) in DMF (2 mL) was stirred at 15° C. for 3 hrs. The mixture was purified by flash C18 (ISCO®; 120 g SepaFlash® C18 Flash Column, Eluent of 0~90% MeOH/$H_2O$ ether gradient @ 75 mL/min) directly to get compound 6 (150 mg, 83.2 umol, 87.4% yield) as a white solid.

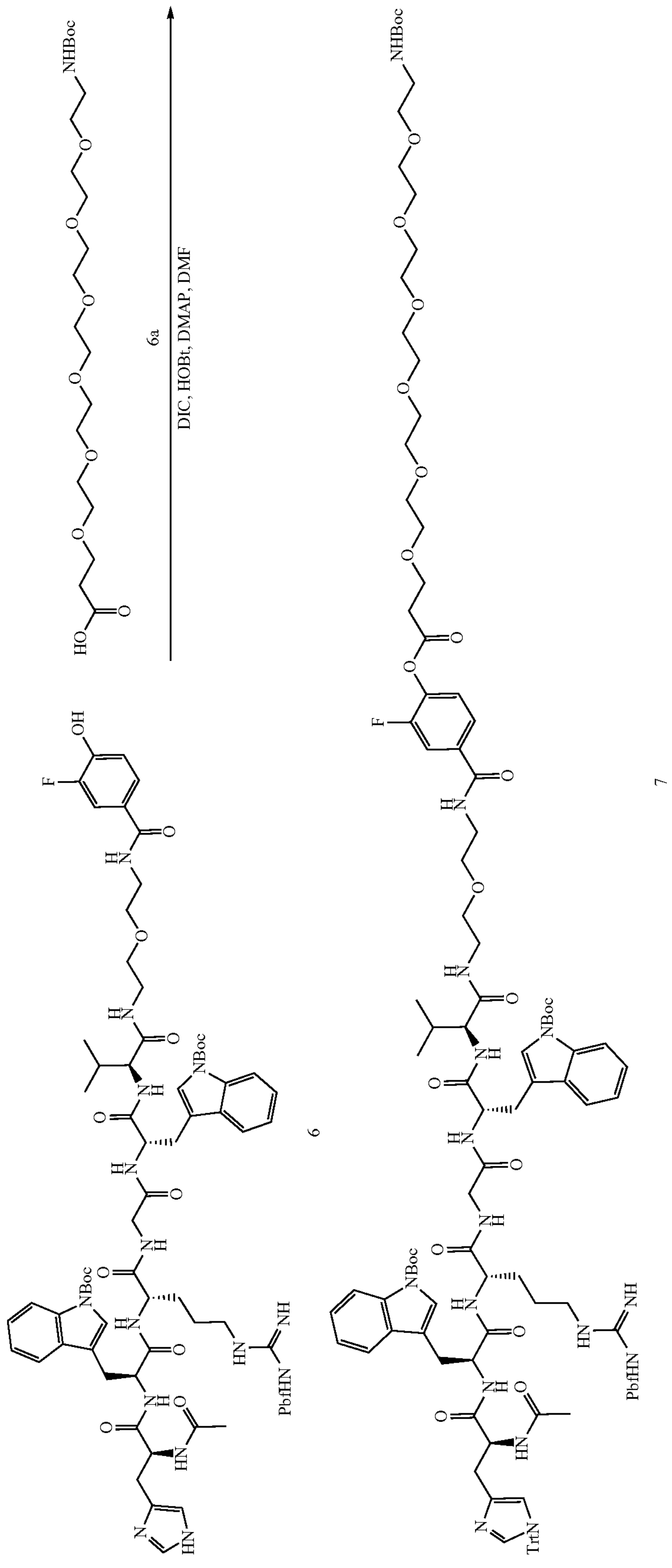
6
7

A solution of compound 6 (150 mg, 83.2 umol), compound 6a (75.4 mg, 166.4 umol), DIC (21.0 mg, 166.4 umol, 25.7 uL), HOBt (22.5 mg, 166 umol), DMAP (10.2 mg, 83.2 umol) in DMF (1 mL) was stirred at 15° C. for 16 hrs. The mixture was then added to 0.5 M HCl (cold, 30 mL), there appeared lot of white solid. The mixture was centrifuged (3 mins at 3000 rpm), and the liquid fraction was discarded. The solid was dried in lyophilization to get compound 7 (100 mg, 44.6 umol, 53.7% yield) as a white solid.

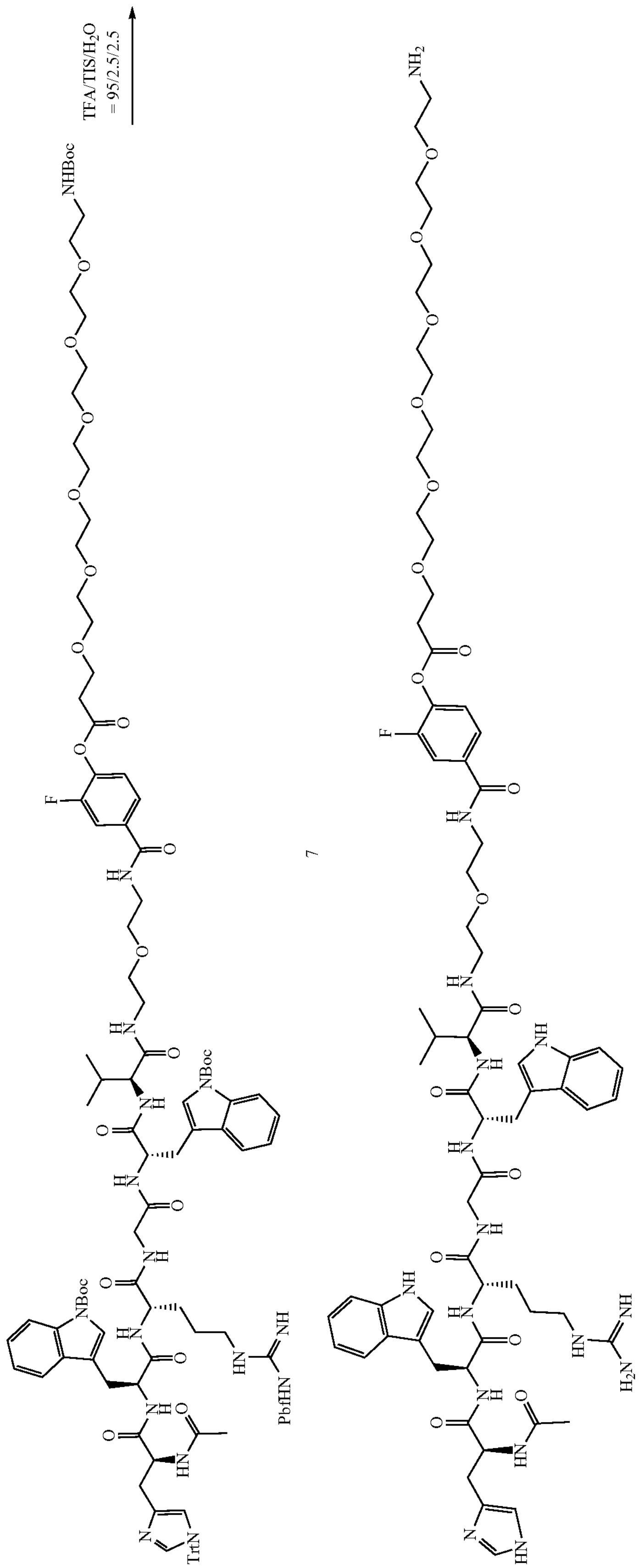
7
8

A mixture of compound 7 (100 mg, 44.7 umol) in TFA (4.81 g, 42.2 mmol, 3.13 mL), triisopropylsilane (72.3 mg, 456.4 umol, 93.7 uL) and $H_2O$ (93.7 mg, 5.20 mmol, 93.7 uL) was stirred at 15° C. for 1 hr. The mixture was precipitated with cold isopropyl ether (50 mL), centrifuged (3 mins at 3000 rpm) and washed two times with isopropyl ether, dried under vacuum 2 hrs. The residue was purified by prep-HPLC (acid condition, TFA) to get compound 8 (50.0 mg, 34.6 umol, 77.5% yield) as a white solid.

-continued

| Compound | Purity | MS |
|---|---|---|
| I-31 | 95.1% | 883.6 $[M + 2H]^{2+}$ |
| I-32 | 98.8% | 813 $[M + 2H]^{2+}$ |
| I-33 | 96.2% | 879 $[M + 2H]^{2+}$ |
| I-34 | 98.3% | 1107.5 $[M + 2H]^{2+}$ |
| I-35 | 99.1% | 1173.3 $[M + 2H]^{2+}$ |

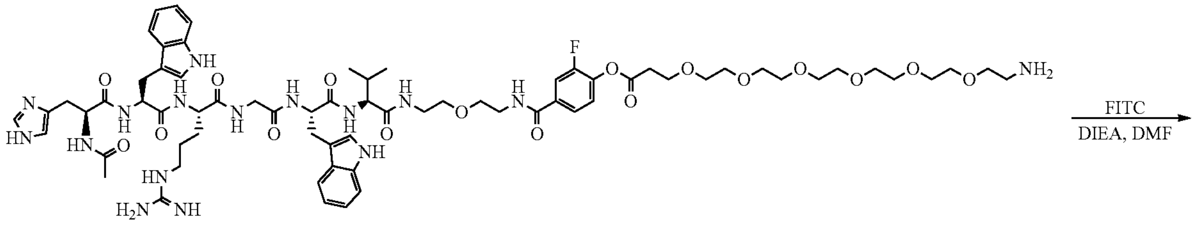

8

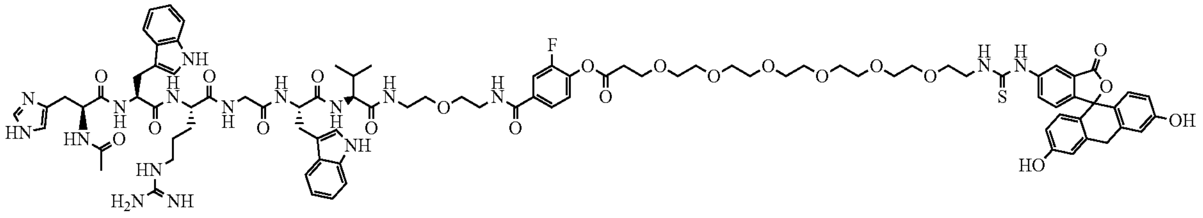

I-28

A mixture of compound 8 (40.0 mg, 27.7 umol), FITC (10.8 mg, 27.7 umol), DIEA (10.7 mg, 83.2 umol, 14.5 uL) in DMF (0.5 mL) was stirred at 15° C. for 1 hr in darkness. The mixture was purified by prep-HPLC (acid condition, TFA) directly to get I-28 (13.0 mg, 6.55 umol, 23.6% yield, 98.2% purity, TFA) as a yellow solid. MS: m/z 916 [M+2H] 2+. A purification procedure is described below as an example:

-continued

| Compound | Purity | MS |
|---|---|---|
| I-36 | 99.7% | 783 $[M + 2H]^{2+}$ |
| I-37 | 98.0% | 849.1 $[M + 3H]^{3+}$ |
| I-38 | 95.2% | 1195.5 $[M + 2H]^{2+}$ |
| I-39 | 95.7% | 1151.6 $[M + 2H]^{2+}$ |

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$) |
| | B: MeCN |
| Gradient | 30-60%-60 min. Retention time: 35 min |
| Column | Luna25*200 mm, C18 10 um, 110A + Gemin150*30 mm, C18 5 um, 110A |
| Flow Rate | 20 mL/min |
| Wavelength | 220/254 nm |
| Oven Tem. | Room temperature |

Various compounds were prepared using similar procedures with corresponding amino acids. Purity and MS data from certain preparations are presented below.

| Compound | Purity | MS |
|---|---|---|
| I-29 | 97.5% | 982.5 $[M + 2H]^{2+}$ |
| I-30 | 98.0% | 817.5 $[M + 2H]^{2+}$ |

-continued

| Compound | Purity | MS |
|---|---|---|
| I-40 | 97.1% | 1129.3 $[M + 2H]^{2+}$ |
| I-41 | 97.4% | 1187.0 $[M + 2H]^{2+}$ |

Example 25. Exemplary Synthesis of Compound I-42

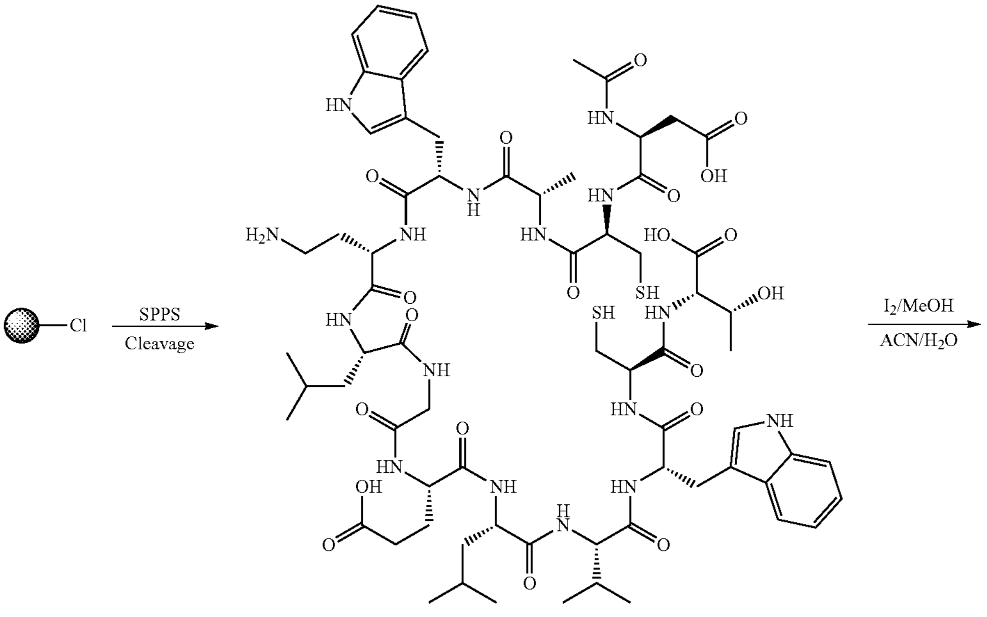

1

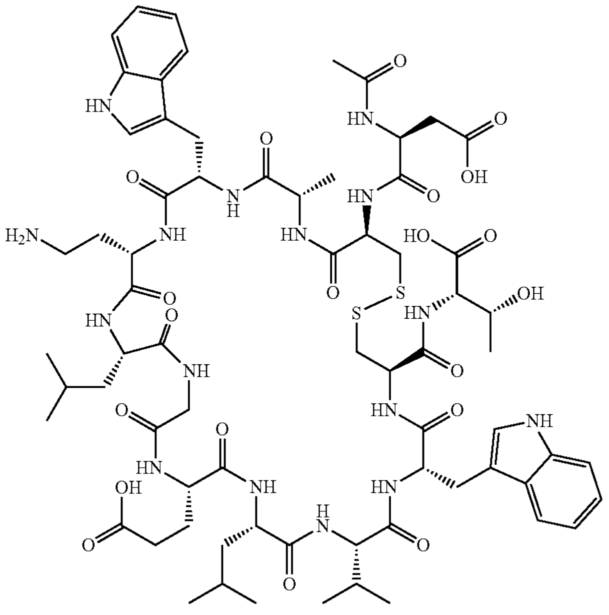

2

Peptide was synthesized using standard Fmoc chemistry. A procedure is described below as an example:

1) Add DCM to the vessel containing CTC Resin (0.50 mmol, 0.50 g, 1.0 mmol/g) and Fmoc-Thr(tBu)-OH (0.159 g, 0.40 mmol, 0.80 eq) with $N_2$ bubbling.
2) Add DIEA (6.0 eq) dropwise and mix for 2 hrs.
3) Add MeOH (0.50 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

Synthesized scale: 0.50 mmol.

| # | Materials | Coupling reagents |
|---|---|---|
| 1 | Fmoc-Thr(tBu)—OH (0.8 eq) | DIEA(6.0 eq) |
| 2 | Fmoc-Cys(Trt)-OH (3.0 eq) | HBTU (2.85 eq) and DIEA(6.0 eq) |
| 3 | Fmoc-Trp(Boc)-OH (3.0 eq) | HBTU (2.85 eq) and DIEA(6.0 eq) |
| 4 | Fmoc-Val-OH (3.0 eq) | HBTU (2.85 eq) and DIEA(6.0 eq) |
| 5 | Fmoc-Leu-OH (3.0 eq) | HBTU (2.85 eq) and DIEA(6.0 eq) |
| 6 | Fmoc-Glu(OtBu)—OH (3.0 eq) | HBTU (2.85 eq) and DIEA(6.0 eq) |
| 7 | Fmoc-Gly-OH (3.0 eq) | HBTU (2.85 eq) and DIEA(6.0 eq) |
| 8 | Fmoc-Leu-OH (3.0 eq) | HBTU (2.85 eq) and DIEA(6.0 eq) |

-continued

| # | Materials | Coupling reagents |
|---|---|---|
| 9 | Fmoc-Dab(Boc)-OH (3.0 eq) | HBTU (2.85 eq) and DIEA(6.0 eq) |
| 10 | Fmoc-Trp(Boc)-OH (3.0 eq) | HATU (2.85 eq) and DIEA(6.0 eq) |
| 11 | Fmoc-Ala-OH (3.0 eq) | HATU (2.85 eq) and DIEA(6.0 eq) |
| 12 | Fmoc-Cys(Trt)-OH (3.0 eq) | HATU (2.85 eq) and DIEA(6.0 eq) |
| 13 | Fmoc-Asp(OtBu)—OH (3.0 eq) | HATU (2.85 eq) and DIEA(6.0 eq) |
| 14 | 10% $AC_2O$/85% DMF/5% NMM (20 mL) | N/A |

20% piperidine in DMF was used for Fmoc deprotection for 30 mins. Coupling reactions were monitored by ninhydrin test, and the resin was washed with DMF for 5 times. After the last amino acid coupling, the resin was washed with MeOH for 3 times, and then dried under vacuum. In some embodiments, peptide was cleaved and purified using the following procedure:

1) Add cleavage cocktail (92.5% TFA/2.5%3-mercaptopropanoic acid/2.5% $H_2O$/2.5% TIS) to the flask containing the side chain protected peptide at room temperature and the mixture was stirred for 2 hrs.
2) The peptide is precipitated with cold isopropyl ether and collected by centrifugation (3 mins at 3000 rpm).
3) The precipitate is washed with cold isopropyl ether for two additional times.
4) Dry the crude peptide under vacuum for 2 hrs.
5) Dissolve the crude peptide in ACN/$H_2O$ (1:1, 150 mL in total).
6) Iodine (0.1 M in MeOH) was added dropwise to vigorously stirring peptide solution until yellow color persists. After 10 mins, Sodium thiosulfate (0.1 M in water) was added dropwise until yellow color disappeared, where the completion of the reaction was indicated by LCMS. The mixture was lyophilized to give the crude powder.
7) Purify the crude peptide by prep-HPLC (TFA condition) to give the compound 2 (120 mg).

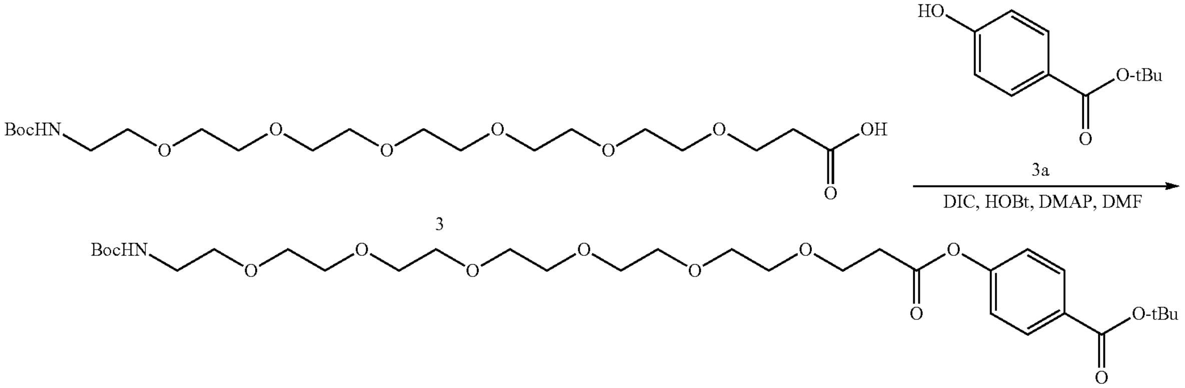

3

4

A mixture of compound 3 (1.00 g, 2.20 mmol), compound 3a (856.5 mg, 4.41 mmol), HOBt (893.8 mg, 6.61 mmol), DMAP (808.1 mg, 6.61 mmol), EDCI (1.27 g, 6.61 mmol) in DMF (1.00 mL) was stirred at 15° C. for 16 hrs. The mixture was purified by flash C18 (ISCO®; 120 g Sepa-Flash® C18 Flash Column, Eluent of 0~90% MeCN/$H_2O$ ether gradient @ 75 mL/min) directly to get compound 4 (1.20 g, 90.0% purity, 86.0% yield) as a white solid.

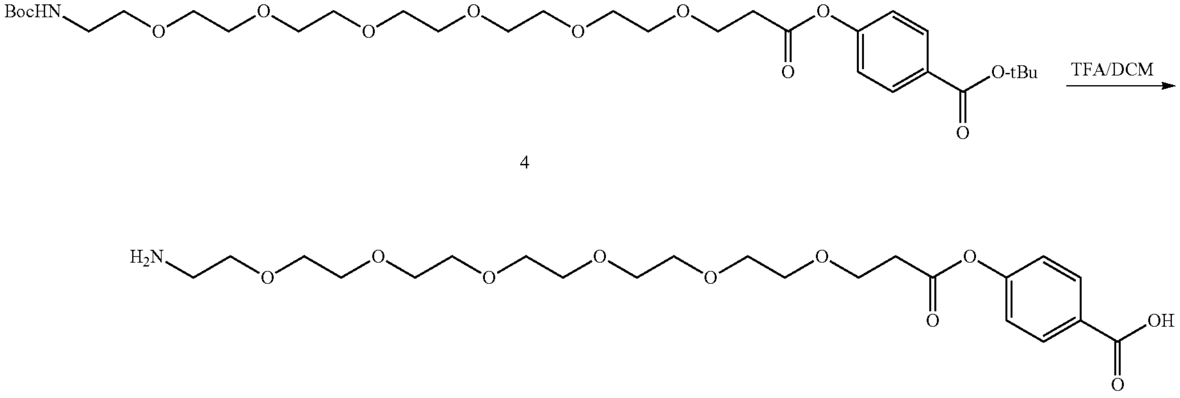

4

5

A mixture of compound 4 (1.20 g, 1.91 mmol) in TFA (36.96 g, 324.1 mmol, 24.0 mL), $H_2O$ (1.20 g, 66.6 mmol, 1.20 mL) was stirred at 15° C. for 0.5 hr. The solvent was removed under reduced pressure. The residue was purified by flash C18 (ISCO®; 120 g SepaFlash® C18 Flash Column, Eluent of 0-90% $MeCN/H_2O$ ether gradient @ 75 mL/min) to get compound 5 (0.83 g, 90.0% purity, 74.1% yield, TFA) as a colorless oil.

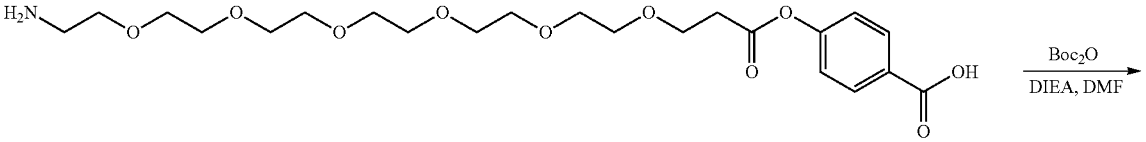

5

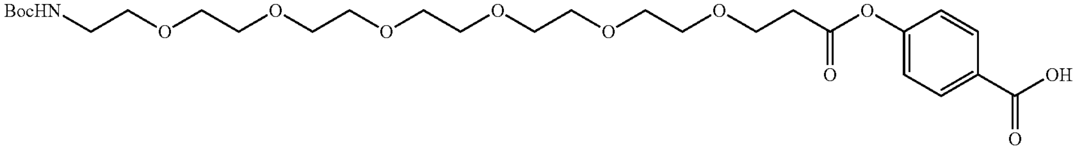

6

To a mixture of compound 5 (0.57 g, 970.15 umol, TFA), DIEA (376.1 mg, 2.91 mmol, 506.9 uL) in DMF (5.0 mL) was added $Boc_2O$ (317.6 mg, 1.46 mmol, 334.3 uL) at 0° C., then the mixture was stirred at 15° C. for 2 hrs. The mixture was purified by flash C18 (ISCO®; 120 g SepaFlash® C18 Flash Column, Eluent of 0~90% $MeCN/H_2O$ ether gradient @ 75 mL/min) directly to get compound 6 (230 mg, 400.9 umol, 41.3% yield) as a colorless oil.

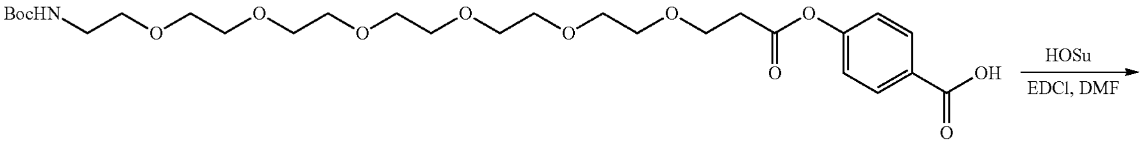

6

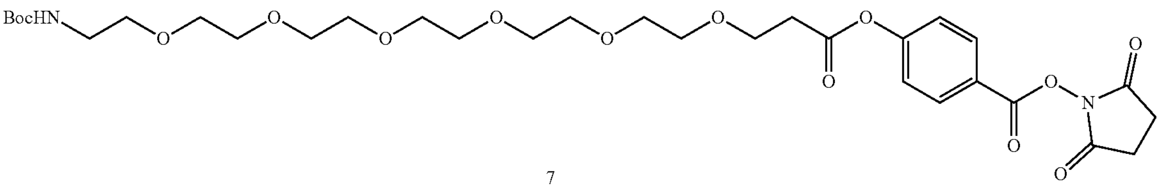

7

A mixture of compound 6 (230 mg, 400.9 umol), HOSu (69.2 mg, 601.4 umol), EDCI (153.7 mg, 801.9 umol) in DMF (1.0 mL) was stirred at 15° C. for 1 hr. The mixture was purified by flash C18 (ISCO®; 120 g SepaFlash® C18 Flash Column, Eluent of 0~90% $MeCN/H_2O$ ether gradient @ 75 mL/min) directly to get compound 7 (150 mg, 223.6 umol, 55.7% yield) as a colorless oil.

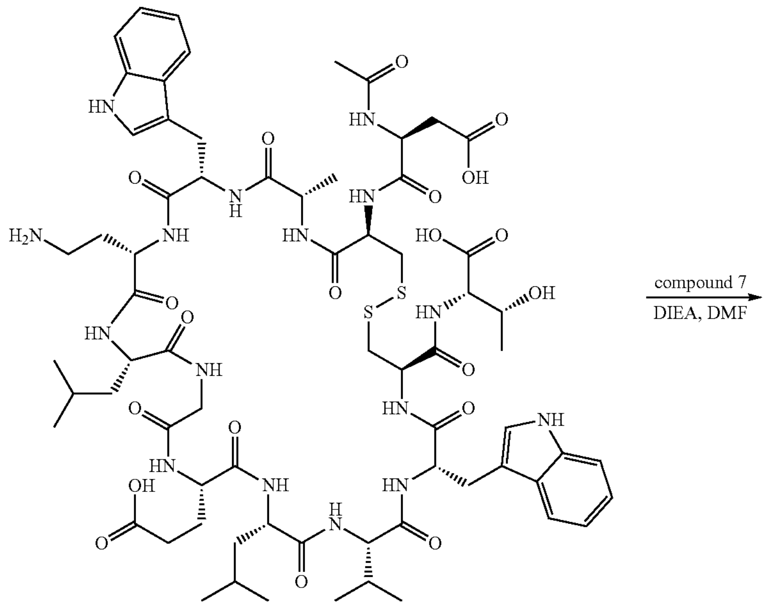
2
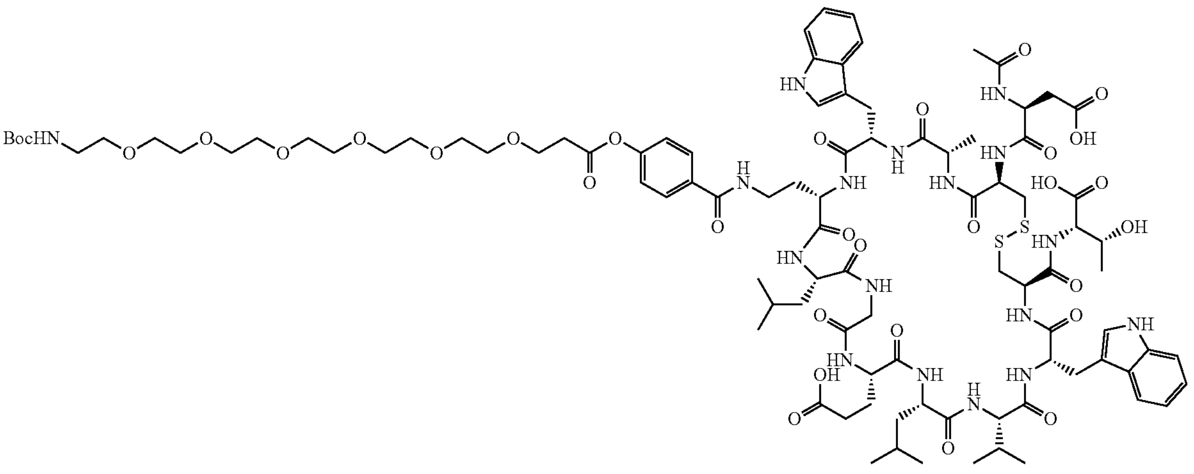
8
A mixture of compound 2 (24.6 mg, 14.9 umol, TFA), compound 7 (10.0 mg, 14.9 umol), DIEA (9.6 mg, 74.5 umol, 12.9 uL) in DMF (0.2 mL) was stirred at 15° C. for 1 hr. The mixture was purified by prep-HPLC (acid condition, TFA) directly to get compound 8 (3.3 mg, 1.58 umol, 10.5% yield) as a white solid.

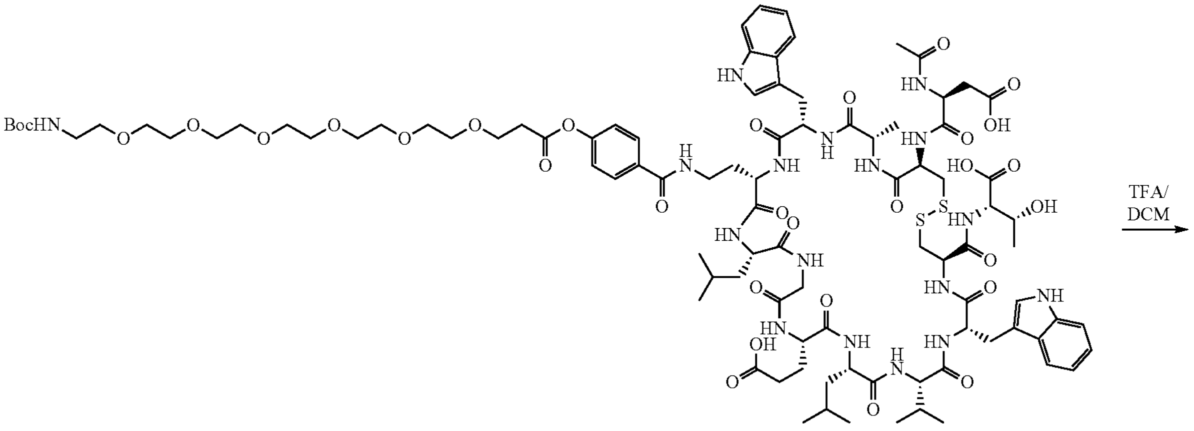
8
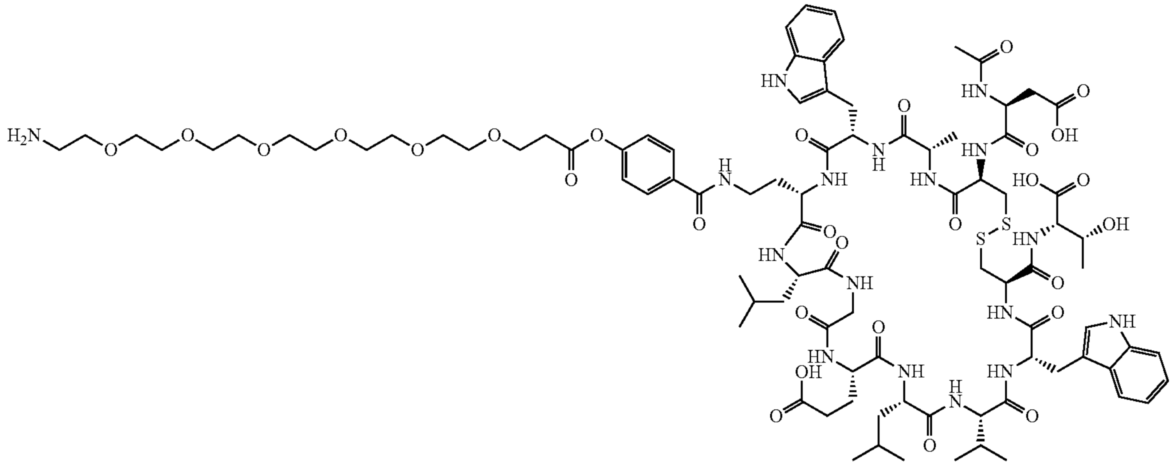
9
A mixture of compound 8 (3.3 mg, 1.58 umol) in TFA (770.0 mg, 6.75 mmol, 0.50 mL) and DCM (0.5 mL) was stirred at 15° C. for 0.5 hr. The solvent was removed under reduced pressure to get compound 9 (3.0 mg, crude, TFA) as a colorless oil.

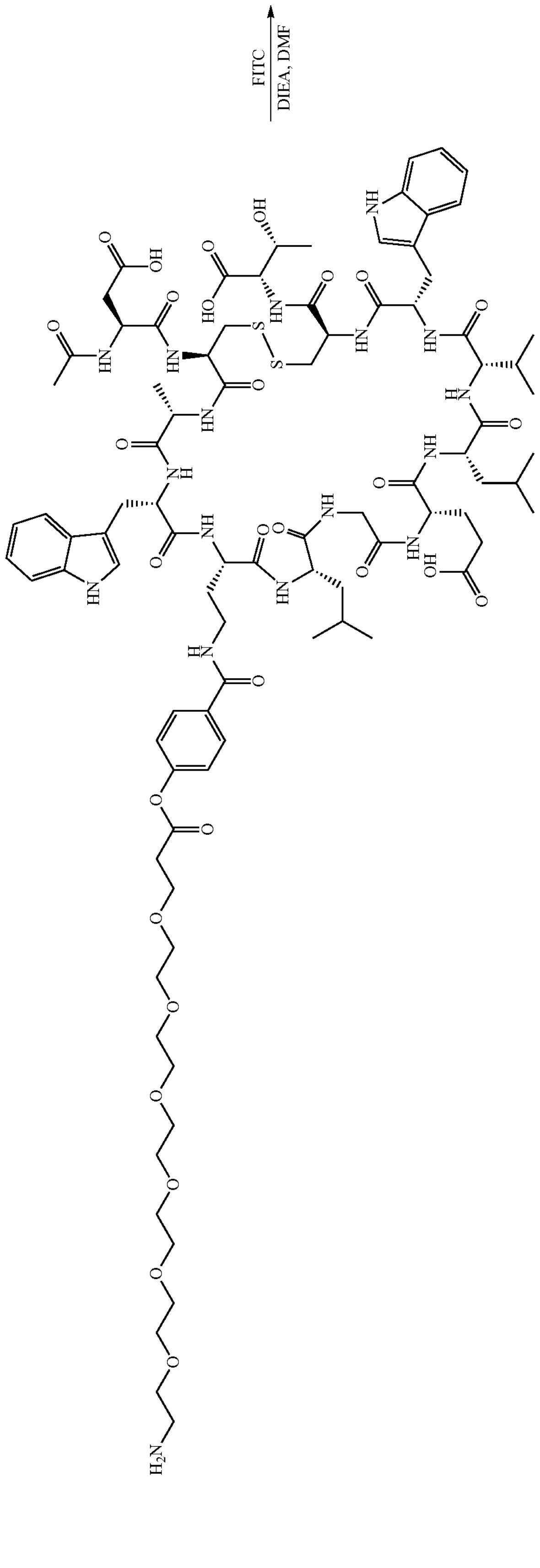
9

-continued
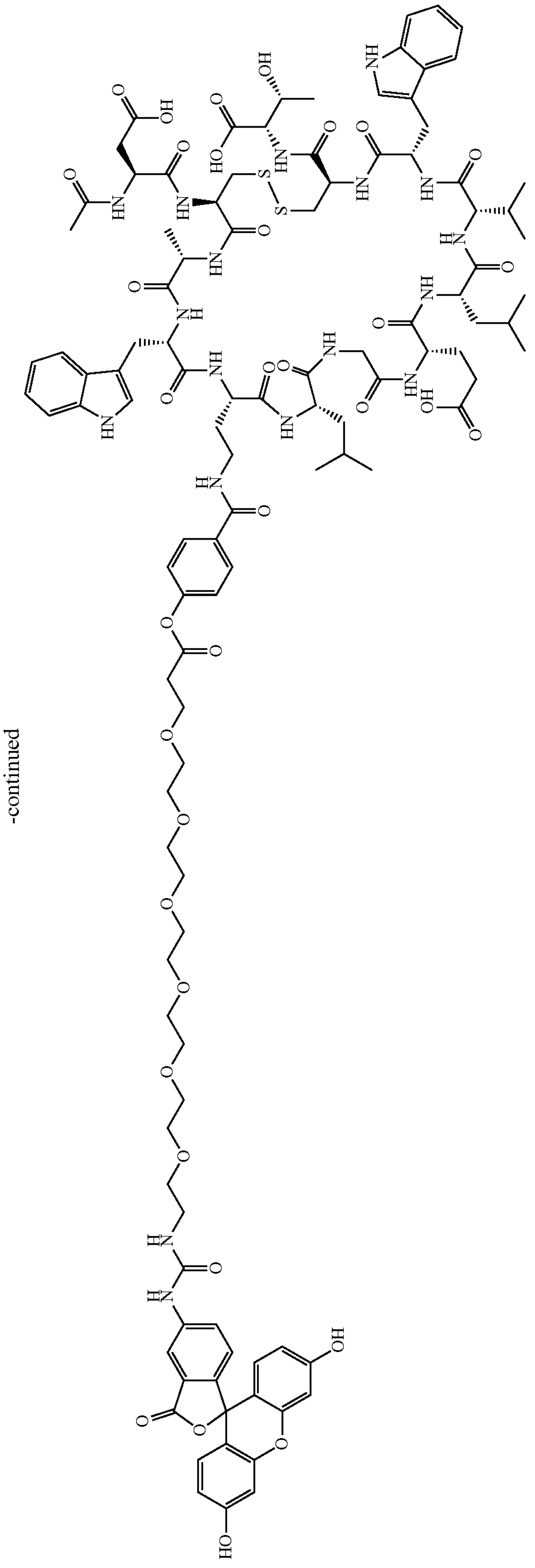
I-42

A mixture of compound 9 (3.0 mg, 1.51 umol), FITC (0.6 mg, 1.51 umol), DIEA (7.53 umol, 1.3 uL) in DMF (0.1 mL) was stirred at 15° C. for 1 hr in darkness. The mixture was purified by prep-HPLC (TFA condition) directly to get I-42 (2.1 mg, 9.06e-1 umol, 98.3% purity, 60.1% yield) as a yellow solid. MS: m/z 1191 $[M+2H]^{2+}$. In some embodiments, peptide was cleaved and purified using the following procedure:

| Purification condition | |
|---|---|
| Sample Preparation | Dissolve in $MeCN/H_2O$ |
| Instrument | Gilson GX-215 |
| Mobile Phase | A: $H_2O$ (0.075% TFA in $H_2O$) |
| | B: MeCN |
| Gradient | 40-70%-60 min. Retention time: 40 min |
| Column | Luna25*200 mm, C18 10 um, 110A + |
| | Gemin150*30 mm, C18 5 um, 110A° |
| Flow Rate | 20 mL/min |
| Wavelength | 220/254 nm |
| Oven Tem. | Room temperature |

Example 26. Exemplary Synthesis of Compound I-43

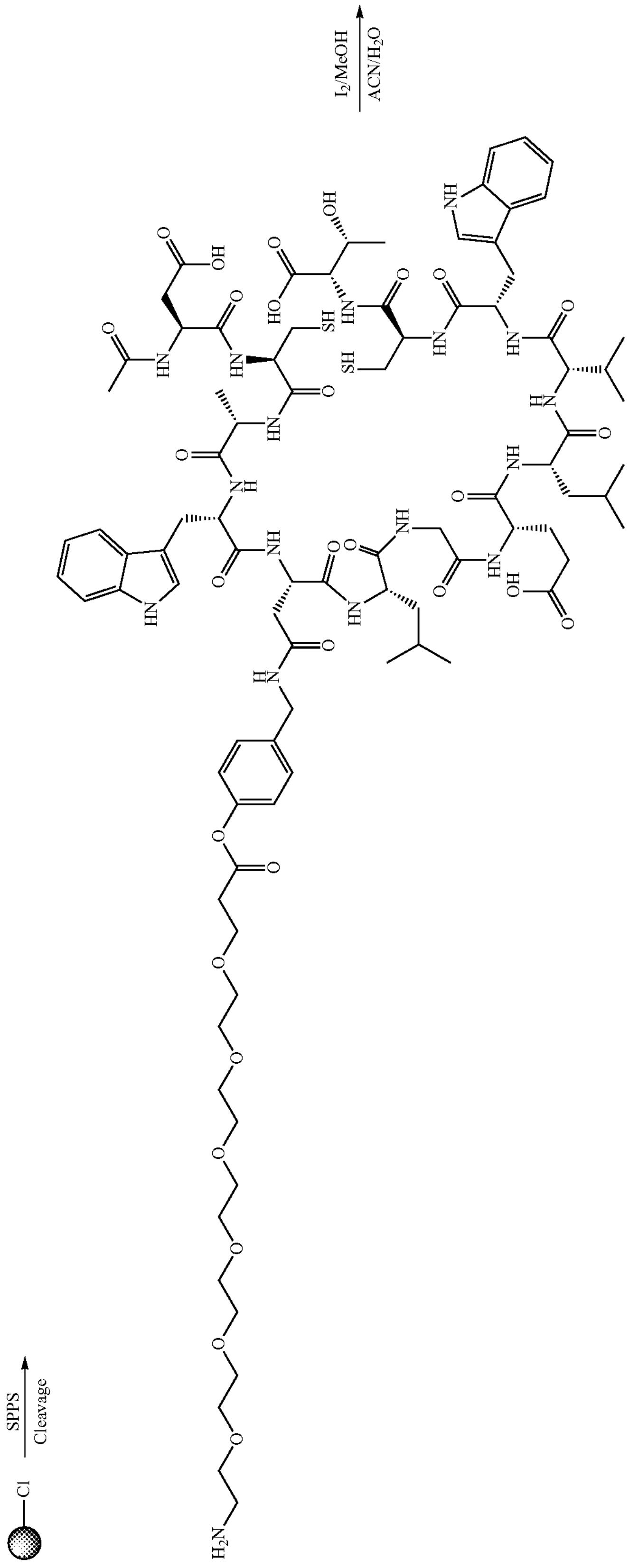
1

-continued
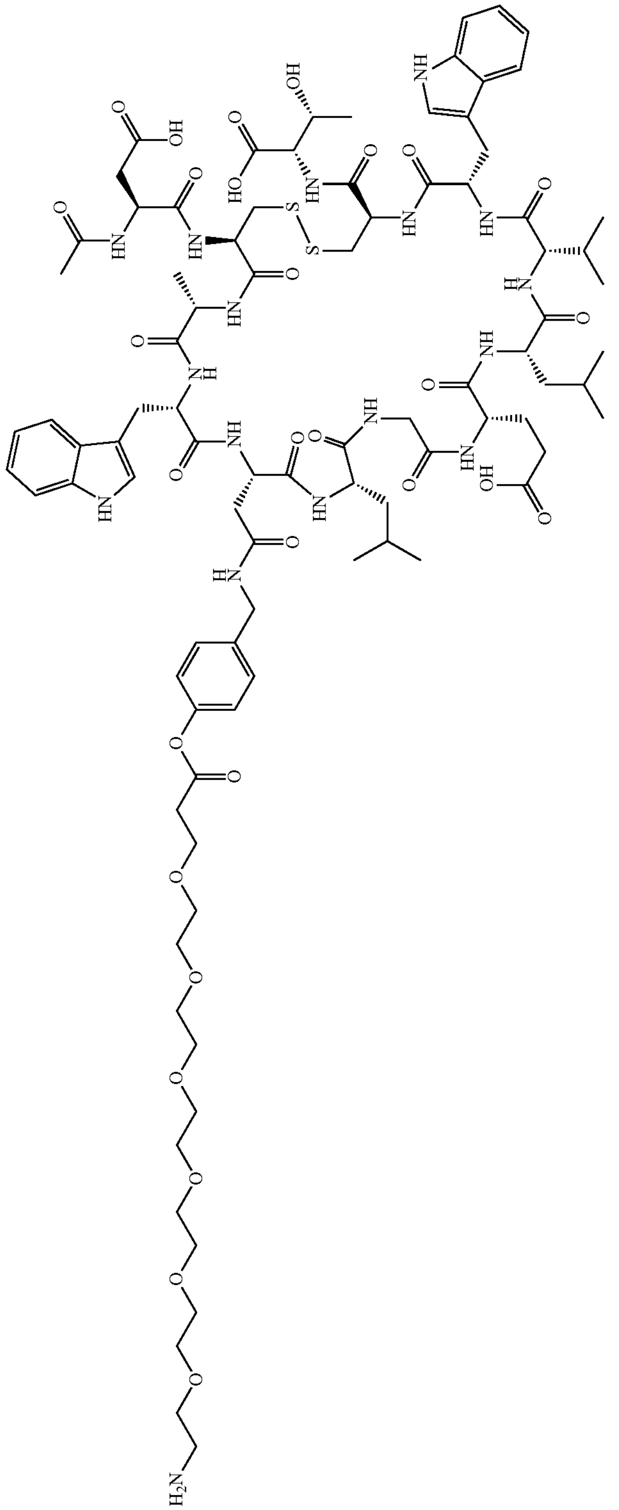
2

Peptide was synthesized using standard Fmoc chemistry. A procedure is described below as an example:

1) Add DCM to the vessel containing CTC Resin (0.500 mmol, 0.500 g, 1.00 mmol/g) and Fmoc-Thr(tBu)-OH (159 mg, 0.400 mmol, 0.80 eq) with $N_2$ bubbling.
2) Add DIEA (4.00 eq) dropwise and mix for 2 hours.
3) Add MeOH (0.500 mL) and mix for 30 min.
4) Drain and wash with DMF for 5 times.
5) Add 20% piperidine/DMF and react on 30 min.
6) Drain and wash with DMF for 5 times.
7) Add Fmoc-amino acid solution and mix for 30 see first, then add activation solution, and the coupling reaction lasts for 1 hr with continuous $N_2$ bubbling.
8) Repeat step 4 to 7 for next amino acid coupling.

| # | Materials | Coupling reagents |
|---|---|---|
| 1 | Fmoc-Thr(tBu)-OH (0.80 eq) | DIEA (4.00 eq) |
| 2 | Fmoc-Cys(Trt)-OH (3.00 eq) | HBTU(2.85 eq) and DIEA (6.00 eq) |
| 3 | Fmoc-Trp(Boc)-OH (3.00 eq) | HBTU(2.85 eq) and DIEA (6.00 eq) |
| 4 | Fmoc-Val-OH (3.00 eq) | HBTU(2.85 eq) and DIEA (6.00 eq) |
| 5 | Fmoc-Leu-OH (3.00 eq) | HBTU(2.85 eq) and DIEA (6.00 eq) |
| 6 | Fmoc-Glu(OtBu)-OH (3.00 eq) | HBTU(2.85 eq) and DIEA (6.00 eq) |
| 7 | Fmoc-Gly-OH (3.00 eq) | HBTU(2.85 eq) and DIEA (6.00 eq) |
| 8 | Fmoc-Leu-OH (3.00 eq) | HBTU(2.85 eq) and DIEA (6.00 eq) |
| 9 | 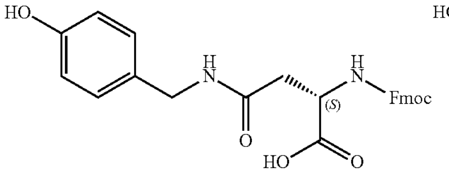 (3.00 eq) | HOBt(3.00 eq) and DIC (3.00 eq) |
| 10 | Fmoc-Trp(Boc)-OH (3.00 eq) | HOBt(3.00 eq) and DIC (3.00 eq) |
| 11 | Fmoc-Ala-OH (3.00 eq) | HOBt(3.00 eq) and DIC (3.00 eq) |
| 12 | Fmoc-Cys(Trt)-OH (3.00 eq) | HOBt(3.00 eq) and DIC (3.00 eq) |
| 13 | Fmoc-Asp(OtBu)-OH (3.00 eq) | HOBt(3.00 eq) and DIC (3.00 eq) |
| 14 | $AC_2O$:NMM:DMF = 10:5:85 (10 mL) | / |
| 15 | Boc-PEG6-$CH_2CH_2COOH$ (3.00 eq) | HOBt(3.00 eq), DIC (3.00 eq) and DMAP(3.00 eq) |

a) Synthesis scale: 0.5 mmol
b) 20% piperidine in DMF was used for Fmoc deprotection for 30 min.
c) Coupling reactions were monitored by ninhydrin test.
d) After the 14$^{th}$ cycle, 3% $NH_2NH_2 \cdot H_2O$/DMF (10 mL) added and bubbling for 20 min
e) After last coupling, the resin was washed with MeOH for 3 times, and then dried under vacuum.

Peptide Cleavage and Purification:

1) Add cleavage cocktail (92.5% TFA/2.5%3-mercaptopropanoic acid/2.5% $H_2O$/2.5% TIS) to the flask containing the side chain protected peptide at room temperature and stir for 2 hr.
2) The peptide is precipitated with cold isopropyl ether and collected by centrifugation (3 min at 3000 rpm).
3) The precipitate is washed with cold isopropyl ether for two additional times.
4) Dry the crude peptide under vacuum for 2 hr.
5) Dissolve the crude peptide in ACN/$H_2O$ (1:1, 150 mL in total)
6) Iodine (0.1 M in MeOH) was added dropwise to vigorously stirring peptide solution until yellow color persists. After 10 minutes, Sodium thiosulfate (0.1 M in water) was added dropwise until yellow color disappears, where the completion of the reaction is indicated by LCMS. The mixture was lyophilized to give the crude powder.
7) Purify the crude peptide by prep-HPLC (TFA condition) to give the compound 2 (22.4 mg).

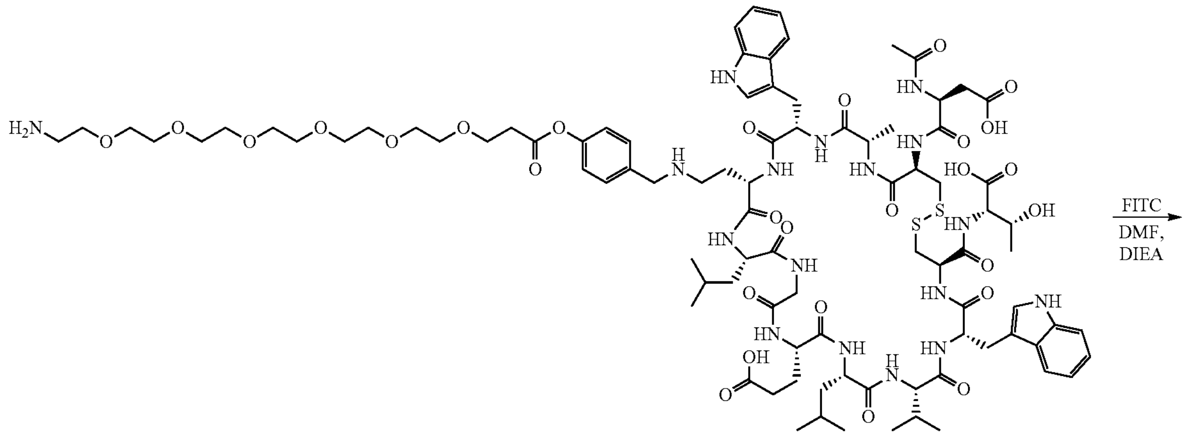

2

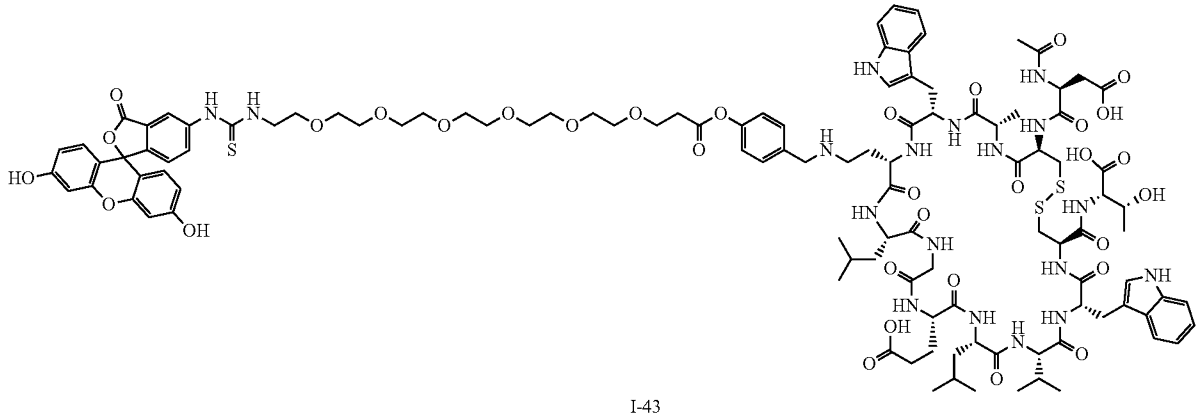

I-43

A mixture of compound 2 (22.4 mg, 1.00 eq) and FITC (4.38 mg, 1.00 eq) was dissolved in DMF (1 mL), and then DIEA (6.00 eq) was added slowly. The mixture was stirred at 20° C. for 2 hr. LCMS showed the reaction was complete. The mixture was then directly purified by prep-HPLC (TFA condition), and I-43 (16.7 mg, 96.0% purity, 59.8% yield) was obtained as a yellow solid. MS: m/z 794.2 $[M+3H]^{3+}$. A purification procedure is described below as an example:

| Separation condition | |
|---|---|
| Sample Preparation | Dissolve in DMF |
| Instrument | Gilson GX-215 |

-continued

| Separation condition | |
|---|---|
| Mobile Phase | A: $H_2O$ (0.075% TFA in $H_2O$)<br>B: $CH_3CN$ |
| Gradient | 35-65%-60 min. Retention time: 48 min |
| Column | Luna C 18, 25*200 mm, 10 um, 110 A + Gemini C 18, 150*30 mm, 5 um, 110 A |
| Flow Rate | 20 mL/min |
| Wavelength | 220/254 nm |
| Oven Tem. | Room temperature |

Example 27. Exemplary Synthesis of Compound I-44

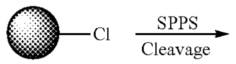

-continued

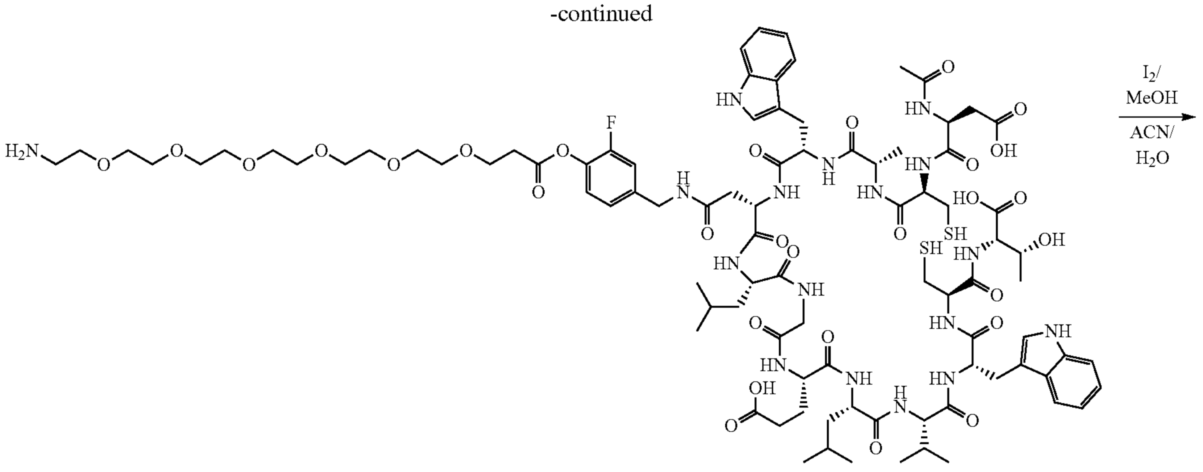

1

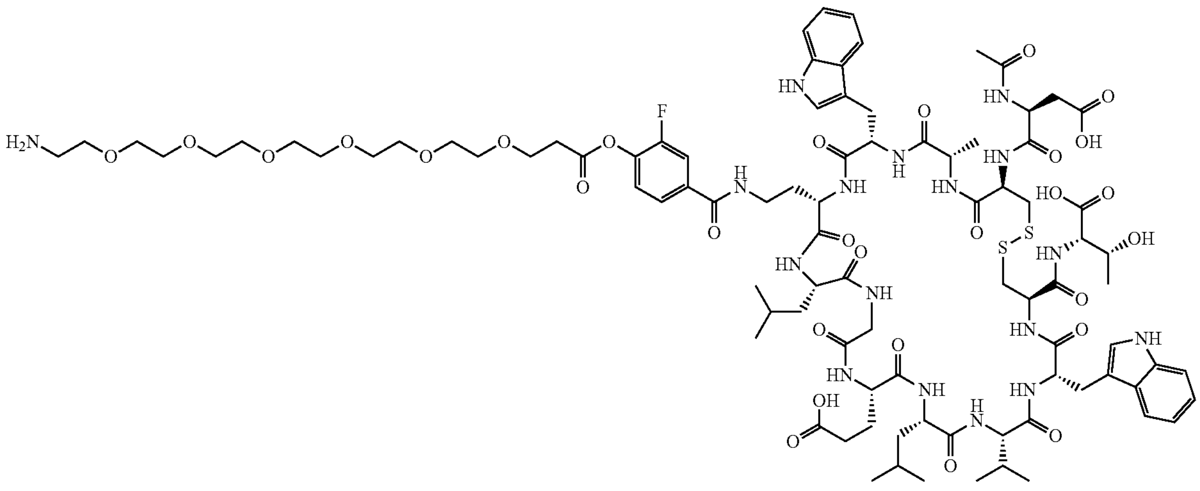

2

Peptide was synthesized using standard Fmoc chemistry. A procedure is described below as an example:

1) Add DCM to the vessel containing CTC Resin (0.500 mmol, 0.500 g, 1.00 mmol/g) and Fmoc-Thr(tBu)-OH (159 mg, 0.400 mmol, 0.80 eq) with $N_2$ bubbling.
2) Add DIEA (4.00 eq) dropwise and mix for 2 hours.
3) Add MeOH (0.500 mL) and mix for 30 min.
4) Drain and wash with DMF for 5 times.
5) Add 20% piperidine/DMF and react on 30 min.
6) Drain and wash with DMF for 5 times.
7) Add Fmoc-amino acid solution and mix for 30 see first, then add activation solution, and the coupling reaction lasts for 1 hr with continuous $N_2$ bubbling.
8) Repeat step 4 to 7 for next amino acid coupling.

| # | Materials | Coupling reagents |
|---|---|---|
| 1 | Fmoc-Thr(tBu)-OH ( 0.80 eq) | DIEA (4.00 eq) |
| 2 | Fmoc-Cys(Trt)-OH (3.00 eq) | HBTU(2.85 eq) and DIEA (6.00 eq) |
| 3 | Fmoc-Trp(Boc)-OH (3.00 eq) | HBTU(2.85 eq) and DIEA (6.00 eq) |
| 4 | Fmoc-Val-OH (3.00 eq) | HBTU(2.85 eq) and DIEA (6.00 eq) |
| 5 | Fmoc-Leu-OH (3.00 eq) | HBTU(2.85 eq) and DIEA (6.00 eq) |
| 6 | Fmoc-Glu(OtBu)-OH (3.00 eq) | HBTU(2.85 eq) and DIEA (6.00 eq) |
| 7 | Fmoc-Gly-OH (3.00 eq) | HBTU(2.85 eq) and DIEA (6.00 eq) |
| 8 | Fmoc-Leu-OH (3.00 eq) | HBTU(2.85 eq) and DIEA (6.00 eq) |

-continued

| # | Materials | Coupling reagents |
|---|---|---|
| 9 | 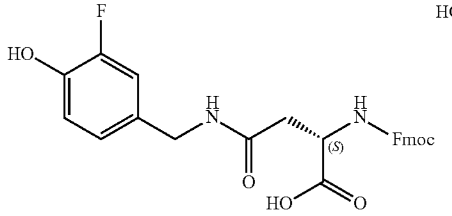 (3.00 eq) | HOBt(3.00 eq) and DIC (3.00 eq) |
| | Fmoc-Trp(Boc)-OH (3.00 eq) | HOBt(3.00 eq) and DIC (3.00 eq) |
| 10 | | |
| 11 | Fmoc-Ala-OH (3.00 eq) | HOBt(3.00 eq) and DIC (3.00 eq) |
| 12 | Fmoc-Cys(Trt)-OH (3.00 eq) | HOBt(3.00 eq) and DIC (3.00 eq) |
| 13 | Fmoc-Asp(OtBu)-OH (3.00 eq) | HOBt(3.00 eq) and DIC (3.00 eq) |
| 14 | $AC_2O$:NMM:DMF = 10:5:85 (10 mL) | / |
| 15 | Boc-PEG6-$CH_2CH_2COOH$ (3.00 eq) | HOBt (3.00 eq), DIC (3.00 eq) and DMAP(3.00 eq) |

a) Synthesis scale: 0.5 mmol
b) 20% piperidine in DMF was used for Fmoc deprotection for 30 min.
c) The coupling reaction was monitored by ninhydrin test.
d) After the 14$^{th}$ cycle, 3% $NH_2NH_2 \cdot H_2O$/DMF (10 mL) was added and mixed with bubbling for 20 min.
e) After last coupling, the resin was washed with MeOH for 3 times, and then dried under vacuum.

In some embodiments, peptide was cleaved and purified using the following procedure:

4) Add cleavage cocktail (92.5% TFA/2.5%3-mercaptopropanoic acid/2.5% $H_2O$/2.5% TIS) to the flask containing the side chain protected peptide at room temperature and stir for 2 hr.
5) The peptide is precipitated with cold isopropyl ether and collected by centrifugation (3 min at 3000 rpm).
6) The precipitate is washed with cold isopropyl ether for two additional times.
7) Dry the crude peptide under vacuum for 2 hr.
8) Dissolve the crude peptide in ACN/$H_2O$ (1:1, 150 mL in total)
9) Iodine (0.1 M in MeOH) was added dropwise to vigorously stirring peptide solution until yellow color persists. After 10 minutes, Sodium thiosulfate (0.1 M in water) was added dropwise until yellow color disappears, where the completion of the reaction is indicated by LCMS. The mixture was lyophilized to give the crude powder.
10) Purify the crude peptide by prep-HPLC (TFA condition) to give the compound 2 (48.0 mg).

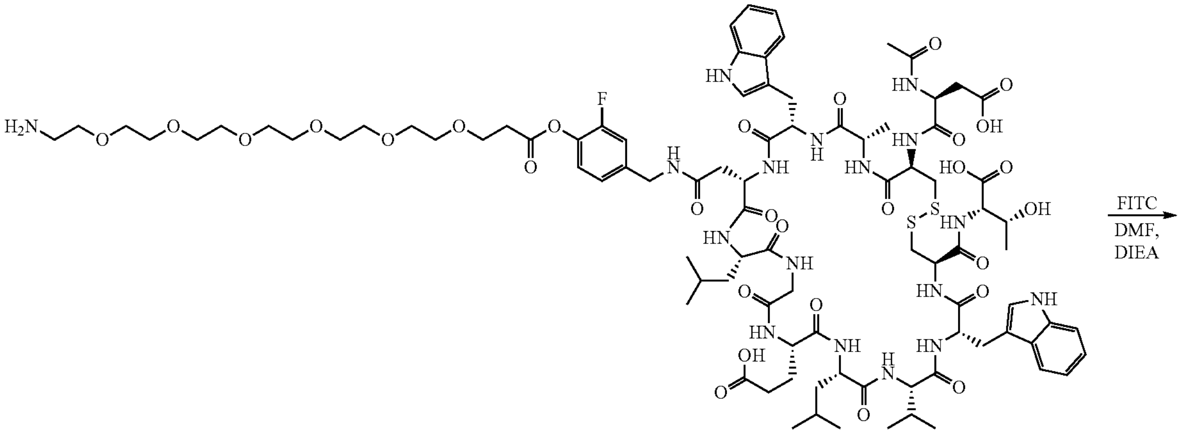

2

-continued

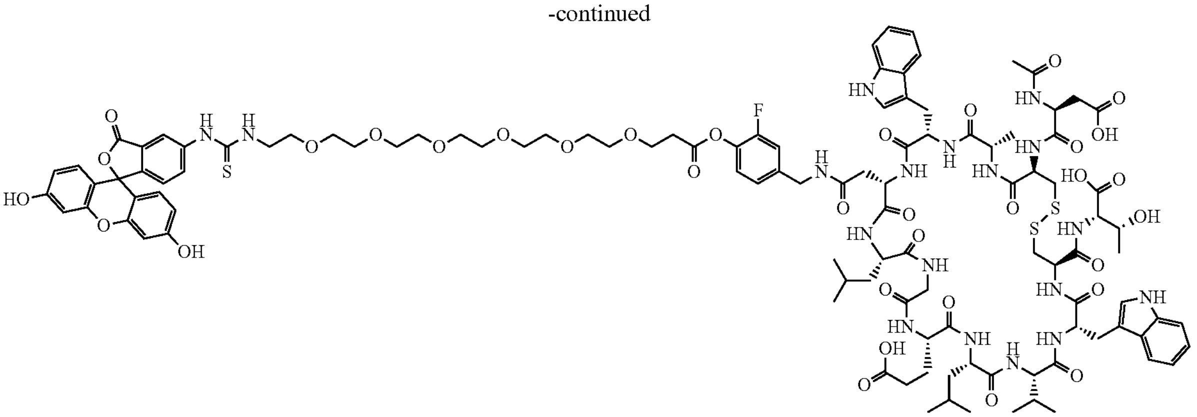

I-44

A mixture of compound 2 (48.0 mg, 1.00 eq) and FITC (9.29 mg, 1.00 eq) was dissolved in DMF (1 mL), and then DIEA (6.00 eq) was added slowly. The mixture was stirred at 20° C. for 2 hr. LCMS showed the reaction was complete. The mixture was then directly purified by prep-HPLC (TFA condition), and I-44 (32.1 mg, 97.0% purity, 83.7% yield) was obtained as a yellow solid. MS: m/z 1200 $[M+2H]^{2+}$. A purification procedure is described below as an example:

| Separation condition | |
|---|---|
| Sample Preparation | Dissolve in DMF |
| Instrument | Gilson GX-215 |
| Mobile Phase | A: $H_2O$ (0.075% TFA in $H_2O$)<br>B: $CH_3CN$ |
| Gradient | 35-65%-60 min. Retention time: 48 min |
| Column | Luna C 18, 25*200 mm, 10 um, 110 A + Gemini C 18, 150*30 mm, 5 um, 110 A |
| Flow Rate | 20 mL/min |
| Wavelength | 220/254 nm |
| Oven Tem. | Room temperature |

Example 28. Exemplary Synthesis of Compound I-45

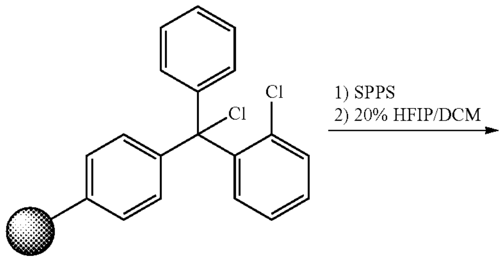

3

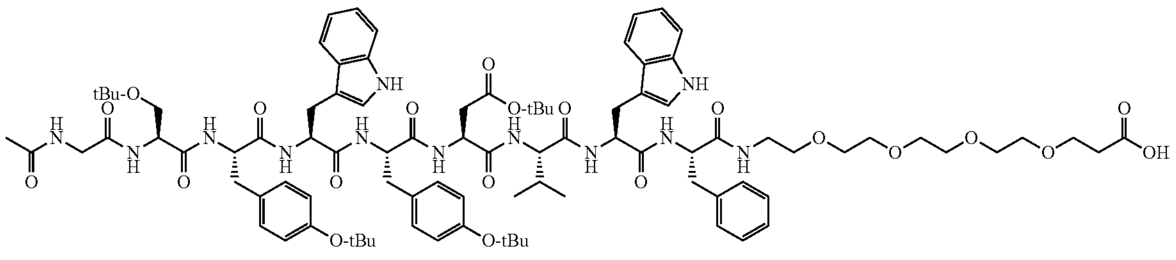

4

Peptide was synthesized using standard Fmoc chemistry. A procedure is described below as an example:

1) Add DCM to the vessel containing CTC Resin (1.00 mmol, 1.00 g, 1.0 mmol/g) and Fmoc-NH-$PEG_4$-COOH (0.39 g, 0.80 mmol, 0.8 eq) with $N_2$ bubbling.
2) Add DIEA (4.0 eq) dropwise and mix for 2 hrs.
3) Add MeOH (1 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

Synthesized scale 1.0 mmol.

| # | Materials | Coupling reagents |
|---|---|---|
| 1 | Fmoc-NH-PEG4-COOH (0.8 eq) | DIEA (4.0 eq) |
| 2 | Fmoc-Phe-OH (3.0 eq) | HBTU (2.85 eq) and DIEA(6.0 eq) |
| 3 | Fmoc-Trp-OH (3.0 eq) | HBTU (2.85 eq) and DIEA(6.0 eq) |
| 4 | Fmoc-Val-OH (3.0 eq) | HBTU (2.85 eq) and DIEA(6.0 eq) |
| 5 | Fmoc-Asp(OtBu)—OH (3.0 eq) | HBTU (2.85 eq) and DIEA(6.0 eq) |
| 6 | Fmoc-Tyr(tBu)—OH (3.0 eq) | HBTU (2.85 eq) and DIEA(6.0 eq) |
| 7 | Fmoc-Trp-OH (3.0 eq) | HBTU (2.85 eq) and DIEA(6.0 eq) |
| 8 | Fmoc-Tyr(tBu)—OH (3.0 eq) | HBTU (2.85 eq) and DIEA(6.0 eq) |
| 9 | Fmoc-Ser(tBu)—OH (3.0 eq) | HBTU (2.85 eq) and DIEA(6.0 eq) |
| 10 | Fmoc-Gly-OH (3.0 eq) | HBTU (2.85 eq) and DIEA(6.0 eq) |
| 11 | $Ac_2O$ | $Ac_2O$/NMM/DMF (10/5/85, 10 mL) |

20% piperidine in DMF was used for Fmoc deprotection for 30 mins. Coupling reactions were monitored by ninhydrin test, and the resin was washed with DMF for 5 times. After the last amino acid coupling, the resin was washed with MeOH for 3 times, and then dried under vacuum. In some embodiments, peptide was cleaved and purified using the following procedure:

1) The peptide resin was treated with the 20% HFIP/DCM (20 mL) for 30 mins twice. After filtered, the combined filterate was concentrated under reduced pressure to produce a residue.
2) The residue was dissolved in MeCN (5 mL). The solution was precipitated with cold $H_2O$ (50 mL), after filtrated, the solid was dried in lyophilization.
3) To get compound 4 (800 mg, 95.0% purity, 58.4% yield).

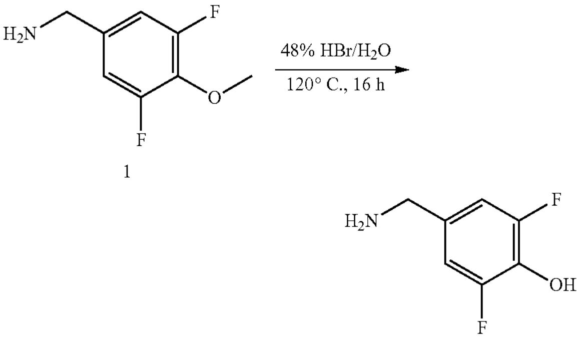

1

2

A solution of compound 1 (0.30 g, 1.73 mmol) in HBr/$H_2O$ (29.8 g, 176 mmol, 20 mL) was stirred at 120° C. for 16 hrs. The solvent was removed under reduced pressure, and the residue was triturated in MeCN (10 mL). After filtration, the solid was dried in lyophilization to get compound 2 (200 mg, 833.1 umol, 48.1% yield, HBr) as a brown solid. $^1H$ NMR: (400 MHz DMSO-$d_6$) δ ppm 10.43 (s, 1H) 8.16 (s, 2H) 7.13-7.26 (m, 2H) 3.96 (s, 2H).

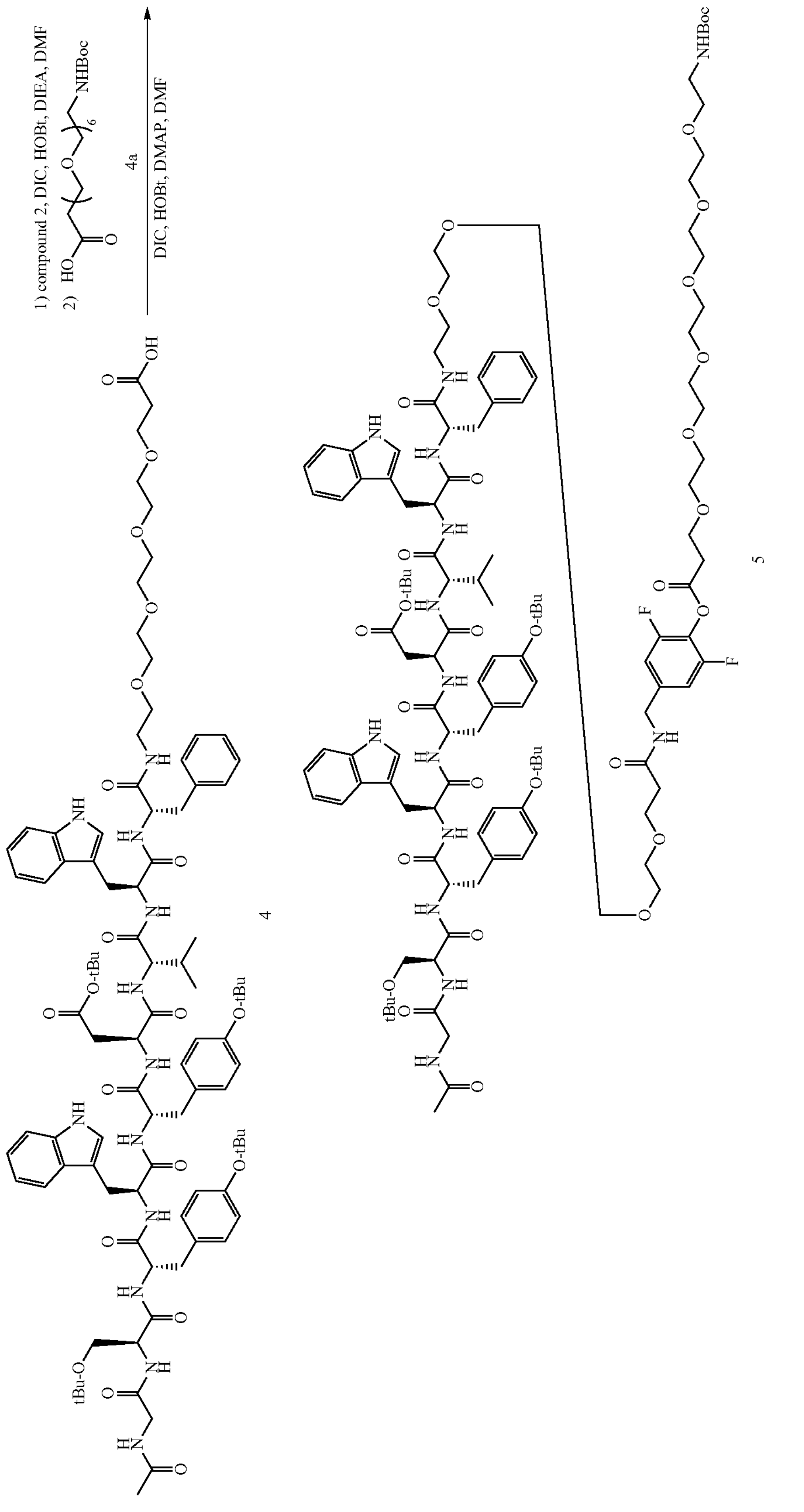
4
5

A mixture of compound 4 (400 mg, 230.4 umol), compound 2 (82.9 mg, 345.6 umol, HBr), DIC (43.6 mg, 345.6 umol, 53.2 uL), HOBt (62.3 mg, 460.8 umol), DIEA (59.5 mg, 460.8 umol, 80.3 uL) in DMF (5 mL) was stirred at 15° C. for 3 hrs. The mixture was added then added with compound 4a (104.5 mg, 230.4 umol), DMAP (56.3 mg, 460.8 umol), DIC (87.2 mg, 691.2 umol, 107.0 uL) at 15° C., and the resulting mixture was stirred at 15° C. for additional 16 hrs. The mixture was precipitated with 1 M HCl (cold, 40 mL) and centrifuged (3 mins at 3000 rpm), dried in lyophilization to get compound 5 (532 mg, crude) as a white solid.

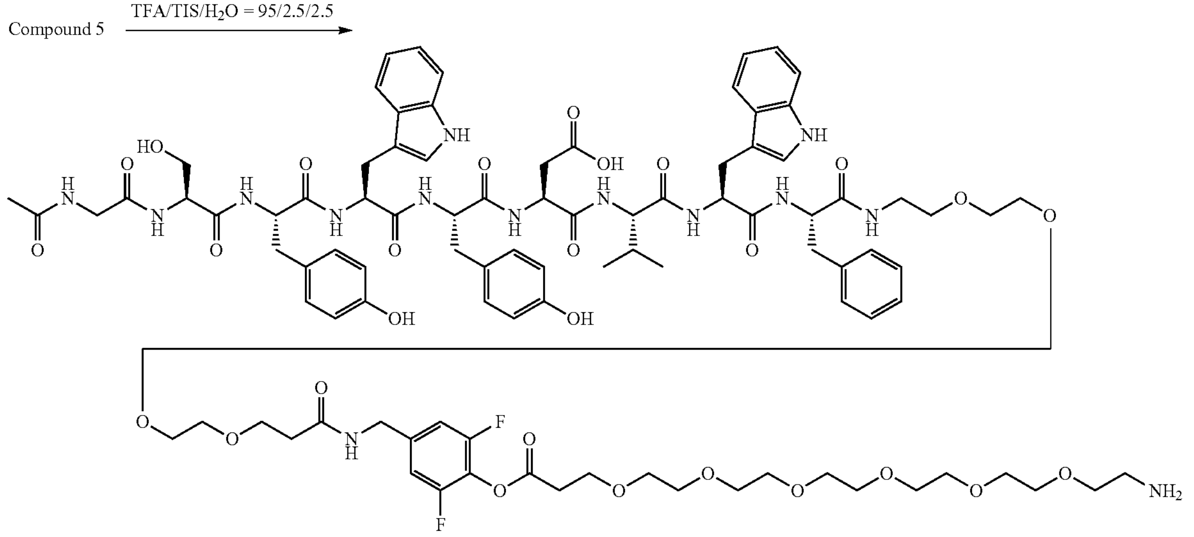

6

A mixture of compound 6 (532 mg, 230.2 umol) in TFA (24.6 g, 215.5 mmol, 15.9 mL), triisopropylsilane (307.6 mg, 1.94 mmol, 399 uL), $H_2O$ (399 mg, 22.1 mmol, 399 uL) was stirred at 15° C. for 1 hr. The mixture was precipitated with isopropyl ether (cold, 50 mL) and centrifuged (3 mins at 3000 rpm), washed with isopropyl ether for two additional times (50 mL), dried the crude peptide under vacuum 2 hrs. The residue was purified by prep-HPLC (acid condition, TFA) to get compound 7 (43.0 mg, 21.6 umol, 9.4% yield) as a white solid.

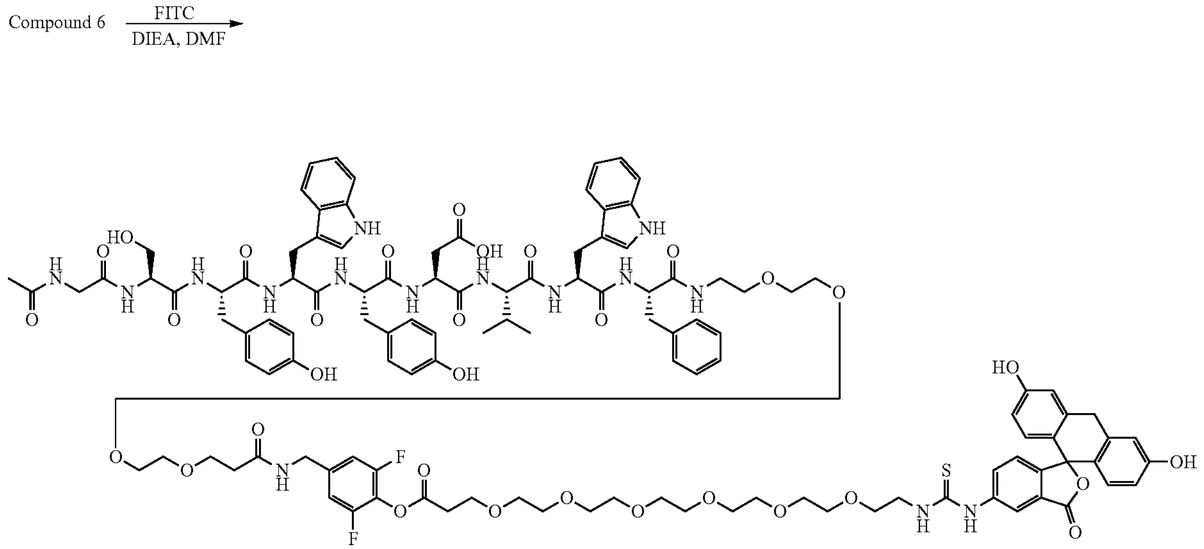

I-45

A mixture of compound 7 (43.0 mg, 21.9 umol), FITC (8.5 mg, 21.9 umol), DIEA (5.7 mg, 43.9 umol, 7.6 uL) in DMF (0.5 mL) was stirred at 15° C. for 1 hr. The mixture was purified by prep-HPLC (acid condition, TFA) to get I-45 (29.1 mg, 95.5% purity, 60.5% yield, TFA salt) as a yellow solid. MS: m/z 1189.4$[M+2H]^{2+}$. A purification procedure is described below as an example:

| Purification condition | |
|---|---|
| Sample Preparation | Dissolve in $MeCN/H_2O$ |
| Instrument | Gilson GX-215 |
| Mobile Phase | A: $H_2O$ (0.075% TFA in $H_2O$) |
| | B: MeCN |
| Gradient | 30-60%-60 min. Retention time: 33 min |
| Column | Luna25*200 mm, C18 10 um, 110A + |
| | Gemin150*30 mm, C18 5 um, 110A |
| Flow Rate | 20 mL/min |
| Wavelength | 220/254 nm |
| Oven Tem. | Room temperature |

Example 29. Exemplary Synthesis of Compound I-46

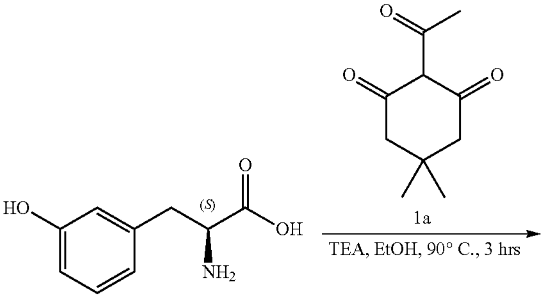

1

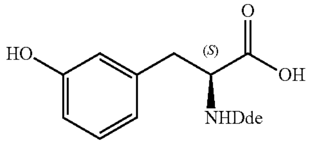

2

A mixture of compound 1 (0.30 g, 1.66 mmol), compound 1a (301.7 mg, 1.66 mmol), TEA (251.3 mg, 2.48 mmol, 345.6 uL) in EtOH (40 mL) was stirred at 90° C. for 3 hrs. The solvent was removed under reduced pressure. The residue was triturated in 1 M HCl (20 mL) for 10 mins, after filtered, the solid was dried by lyophilization to get compound 2 (500.0 mg, crude) as a white solid.

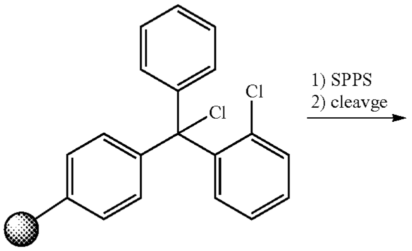

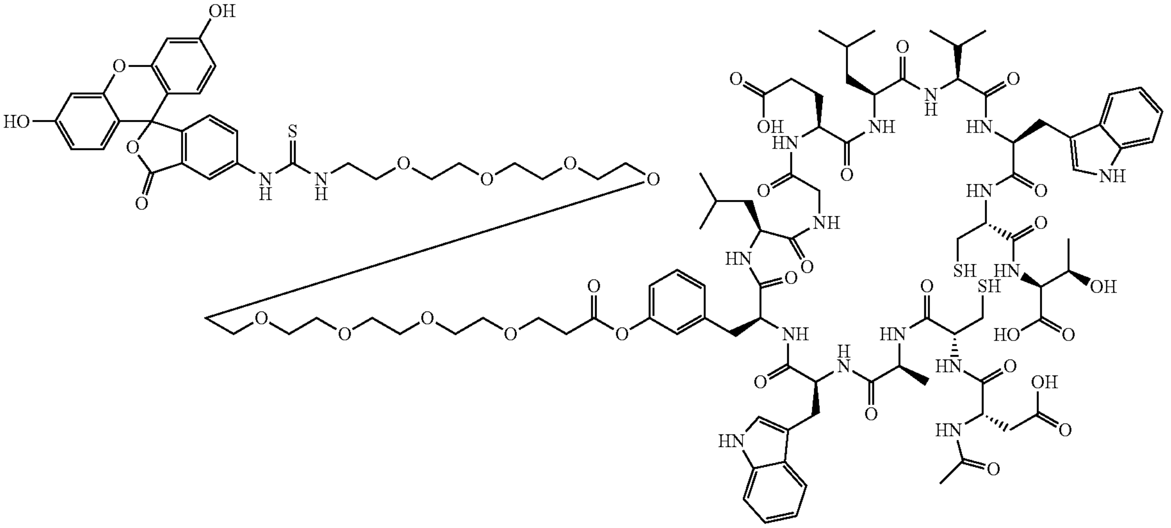

Peptide was synthesized using standard Fmoc chemistry. A procedure is described below as an example:

1) Add DCM to the vessel containing CTC Resin (0.10 mmol, 0.10 g, 1.0 mmol/g) and Fmoc-Thr(tBu)-OH (39.7 mg, 0.10 mmol, 1.0 eq) with $N_2$ bubbling.
2) Add DIEA (6.0 eq) dropwise and mix for 2 hrs.
3) Add MeOH (0.10 mL) and mix for 30 mins.
4) Drain and wash with DMF for 5 times.
5) Add 20% piperidine/DMF and mix for 30 mins.
6) Drain and then DMF wash 30 seconds with 5 times.
7) Add Fmoc-amino acid solution and mix 30 seconds, then add activation buffer, $N_2$ bubbling for about 1 hr.
8) Add 20% piperidine/DMF and mix for 30 mins.
9) Repeat step 4 to 8 for next amino acid coupling.

Synthesized scale: 0.10 mmol.

| # | Materials | Coupling reagents |
|---|---|---|
| 1 | Fmoc-Thr(tBu)—OH (0.8 eq) | DIEA(6.0 eq) |
| 2 | Fmoc-Cys(Trt)-OH (3.0 eq) | HBTU (2.85 eq) and DIEA(6.0 eq) |
| 3 | Fmoc-Trp(Boc)-OH (3.0 eq) | HBTU (2.85 eq) and DIEA(6.0 eq) |
| 4 | Fmoc-Val-OH (3.0 eq) | HBTU (2.85 eq) and DIEA(6.0 eq) |
| 5 | Fmoc-Leu-OH (3.0 eq) | HBTU (2.85 eq) and DIEA(6.0 eq) |
| 6 | Fmoc-Glu(OtBu)—OH (3.0 eq) | HBTU (2.85 eq) and DIEA(6.0 eq) |
| 7 | Fmoc-Gly-OH (3.0 eq) | HBTU (2.85 eq) and DIEA(6.0 eq) |
| 8 | Fmoc-Leu-OH (3.0 eq) | HBTU (2.85 eq) and DIEA(6.0 eq) |
| 9 | Compound 2 (3.0 eq) | DIC (3.0 eq) and HOBt (3.0 eq) |
| 10 | Fmoc-Trp(Boc)-OH (3.0 eq) | DIC (3.0 eq) and HOBt (3.0 eq) |
| 11 | Fmoc-Ala-OH (3.0 eq) | DIC (3.0 eq) and HOBt (3.0 eq) |
| 12 | Fmoc-Cys(Trt)-OH (3.0 eq) | DIC (3.0 eq) and HOBt (3.0 eq) |
| 13 | Fmoc-Asp(OtBu)—OH (3.0 eq) | DIC (3.0 eq) and HOBt (3.0 eq) |
| 14 | 10% $AC_2O$/5% NMM/85% DMF (10 mL) | N/A |
| 15 | Fmoc-NH-$PEG_6$-$CH_2CH_2COOH$ (3 .0 eq) | DIC (3.0 eq), HOBt (3.0 eq), DMAP (3.0 eq) |
| 16 | FITC (2.0 eq) | DIEA (4.0 eq) |

20% piperidine in DMF was used for Fmoc deprotection for 30 mins. 3% hydrazine hydrate in DMF was used for Dde deprotection for 30 mins. The coupling reaction was monitored by ninhydrin test, and the resin was washed with DMF for 5 times. After the last coupling, the resin was washed with MeOH for 3 times, and then dried under vacuum. After FITC coupling, the peptide was handled in dark. In some embodiments, peptide was cleaved and purified using the following procedure:

11) Add cleavage cocktail (92.5% TFA/2.5%3-mercaptopropanoic acid/2.5% $H_2O$/2.5% TIS) to the flask containing the side chain protected peptide at room temperature and the mixture was stirred for 1 hr.
12) The peptide is precipitated with cold isopropyl ether and collected by centrifugation (3 mins at 3000 rpm).
13) The precipitate is washed with cold isopropyl ether for two additional times.
14) Dry the crude peptide under vacuum for 2 hrs.
15) To get compound 3 (100.0 mg, crude) as a yellow solid.

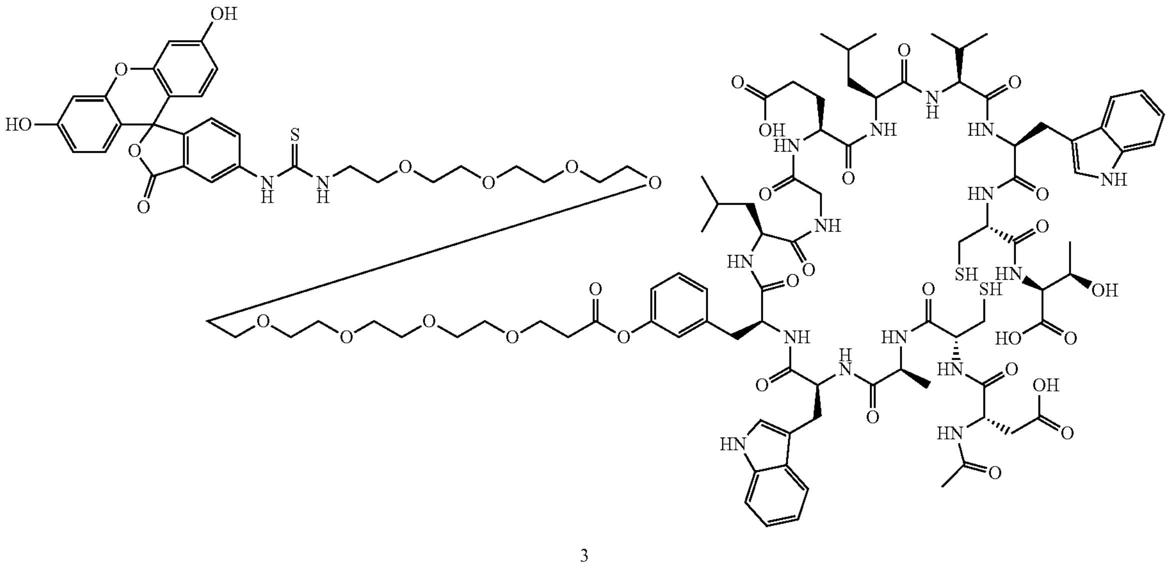

3 air oxidation | $MeCN/H_2O$

-continued

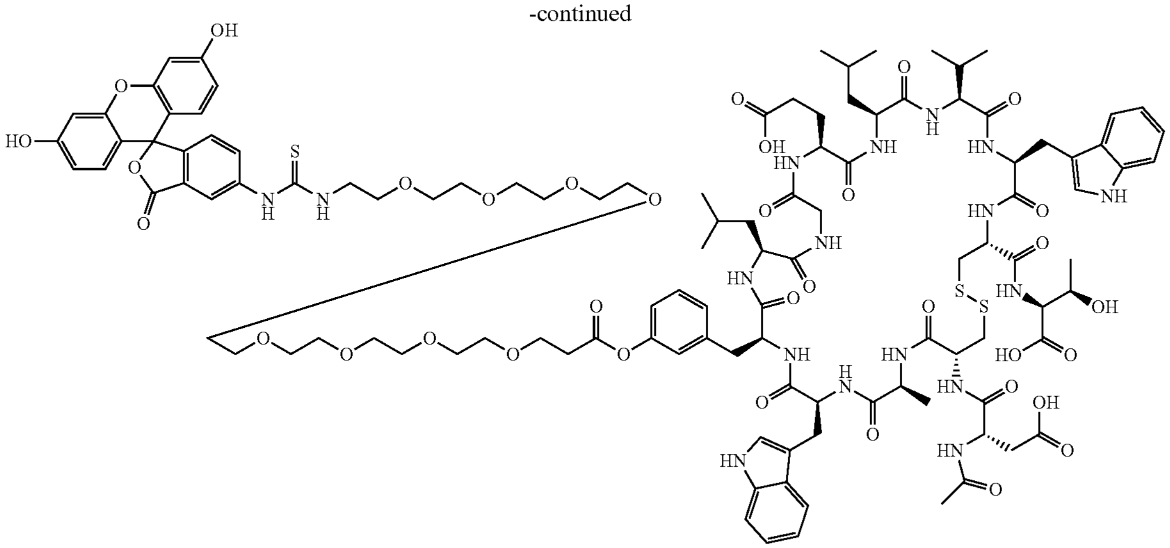

I-46

Compound 3 (100.0 mg, 41.43 umol) was dissolved in a mixture of MeCN (50 mL) and $H_2O$ (50 mL), and stirred at 15° C. in darkness to let the disulfide form by air oxidation for 16 hrs. The solution was acidified by 1 M HCl to pH=3, dried under lyophilization. The residue was purified by prep-HPLC (acid condition, TFA) to get compound I-46 (1.1 mg, 4.33e-1 umol, 1.0% yield, 91.8% purity) as a yellow solid. MS: m/z 1207.0 $[M+2H]^{2+}$. A purification procedure is described below as an example:

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$) |
| | B: MeCN |
| Gradient | 35-65%-60 min. Retention time: 40 min |
| Column | Luna25*200 mm, C18 10 um, 110A + Gemini150*30 mm, C18 5 um, 110A° |
| Flow Rate | 20 mL/min |
| Wavelength | 220/254 nm |
| Oven Tem. | Room temperature |

Example 30. Provided Technologies Provide Significantly Improved Efficiency

Among other things, provided technologies can provide increased efficiency (e.g., higher rates and/or yields) and/or selectivity. Data from certain assessment are provided herein as examples.

In some embodiments, a target agent is a protein agent. In some embodiments, a target agent is an antibody agent. In some embodiments, the present disclosure provides technologies for conjugating moieties of interest to antibodies, e.g., daratumumab, cetuximab, etc.

In some embodiments, reaction partners, e.g., compounds of formula R-I or salts thereof ere dissolved in DMSO to 5 mM stock solution.

In some embodiments, reactions are set up with 300 micrograms of antibody. In some embodiments, various conditions, including various buffers, reagent equivalents, reaction time, reaction temperature and reaction concentrations can be utilized.

As an example, one reaction is 300 microliter reaction with 1 mg/mL of antibody in PBS. Peptide I-45 (1 microliter of 5 mM stock in DMSO, 2.5 molar equivalents relative to daratumumab) was diluted in 284 microliters of PBS buffer (10 mM phosphate, 150 mM sodium chloride, pH 7.4), then 15 microliters of daratumumab (20 mg/mL stock) was added to the reaction mixture followed by incubation at room temperature in the dark. After 4 h reaction buffer was exchanged using Amicon Ultra centrifuge filter (30 KDa MWCO, 0.5 mL volume). First, glycine buffer (100 mM, pH 2.1) was used for buffer exchange to ensure dissociation of target binding moieties after reaction. Then, phosphate buffer saline (pH 7.4) was used for further buffer exchange and storage.

In another example, a reaction is 300 microliter reaction with 1 mg/mL of antibody in borate buffer. Peptide I-44 (1.2 microliter of 5 mM stock in DMSO, 3.0 molar equivalents relative to daratumumab) was diluted in 284 microliters of Borate buffer (100 mM borate, pH 8.3), then 15 microliters of daratumumab (20 mg/mL stock) was added to the reaction mixture followed by incubation at room temperature in the dark. After 20 h reaction buffer was exchanged using Amicon Ultra centrifuge filter (30 KDa MWCO, 0.5 mL volume). First, glycine buffer (100 mM, pH 2.1) was used for buffer exchange to ensure dissociation of target binding moieties after reaction. Then, phosphate buffer saline (10 mM phosphate, 150 mM sodium chloride, pH 7.4) was used for further buffer exchange and storage.

Various technologies can be utilized for assessment of reaction results in accordance with the present disclosure.

As demonstrated herein, provided technologies, among other things, can provide increased conjugation efficiency and selectivity without requiring extra reaction steps. In some embodiments, provided technologies can selectively conjugate desired moieties of interest at selective residue(s) of antibody agents. Among other things, technologies of the present disclosure can provide agents with improved properties and/or activities (e.g., improved purity, homogeneity, etc.) with high efficiency.

In some embodiments, a useful technology is absorbance based DAR analysis. DAR (ratio of moieties of interest and target agent moieties (e.g., antibody agent moieties) was calculated for various antibody conjugates, e.g., in various reagent screening/assessment methods. Various agents comprising target binding moieties were assessed for conjugation efficiency as reaction partners with targets, e.g. protein agents such as antibody agents, compared to reagents with the same reactive groups but without target binding moieties. In various ratio determination 'Drug'/moiety of interest is fluorescein isothiocyanate (FITC) dye conjugated to target agents, e.g., antibody agents. DAR molar ratio is defined as a ratio of moles of drug/moiety of interest to moles of target agent/antibody. Molarity is calculated from absorbance of FITC ($A_{485}$) and antibody ($A_{280}$) of conjugated product, and extinction coefficients of FITC and antibody using Beer-Lambert law. Correction coefficient 0.35 was used to correct for absorbance of FITC at 280 nm. Biotek Synergy H1 microplate reader and Take3 microvolume plate were used for absorbance measurements. Concentration of antibody was at least 3 mg/mL for optimal signal-to-noise in the readings. Certain target binding moieties that can provide higher DAR compared to equivalent controls (absence of target binding moieties) were selected as hits for further analysis. Certain assessment data were provided below as examples.

TABLE 30-1

Certain data.

| Compound | DAR |
|---|---|
| I-20 | 0.72 |
| I-21 | 0.18 |
| I-22 | −0.18 |
| I-23 | 0.14 |

Reactions were set up with daratumumab using 10 M eq of indicated reagent in Bicarbonate buffer pH 8.3 for 20 h at 25° C. DAR is Drug to antibody ratio, in this case "Drug" is FITC and DAR is measured using FITC absorbance.

TABLE 30-2

Certain data.

| Compound | DAR |
|---|---|
| I-1 | 1.00 |
| I-2 | 1.76 |
| I-3 | 1.39 |
| I-4 | 0.24 |
| I-9 | 1.10 |
| I-10 | 0.14 |
| I-11 | 0.14 |
| I-14 | 0.29 |
| I-15 | 0.74 |

Reactions were set up with daratumumab using 10 M eq of indicated reagent in Bicarbonate buffer pH 8.3 for 2 h at 37° C. DAR is Drug to antibody ratio, in this case "Drug" is FITC and DAR is measured using FITC absorbance.

TABLE 30-3

Certain data.

| Compound | DAR |
|---|---|
| I-10 | 0.98 |
| I-11 | 0.14 |
| I-46 | 0.43 |
| I-24 | 0.83 |

TABLE 30-3-continued

Certain data.

| Compound | DAR |
|---|---|
| I-25 | 1.25 |
| I-26 | −0.10 |
| I-27 | −0.02 |
| I-30 | 0.22 |
| I-32 | 0.28 |
| I-33 | 0.33 |
| I-35 | 2.05 |
| I-36 | 5.03 |
| I-37 | 5.49 |

Reactions were set up with daratumumab using 30 M eq of indicated reagent in borate buffer pH 8.3 for 20 h at 37° C. DAR is Drug to antibody ratio, in this case "Drug" is FITC and DAR is measured using FITC absorbance.

TABLE 30-4

Certain data.

| Compound | DAR |
|---|---|
| I-6 | 0.00 |
| I-5 | 0.15 |
| I-13 | 0.09 |
| I-17 | 0.37 |
| I-7 | 0.01 |
| I-8 | 0.04 |
| I-12 | 1.44 |
| I-16 | 0.30 |

Reactions were set up with daratumumab using 5 M eq of indicated reagent in bicarbonate buffer pH 8.3 for 20 h at 37° C. DAR is Drug to antibody ratio, in this case "Drug" is FITC and DAR is measured using FITC absorbance.

TABLE 30-5

Certain data.

| Reagent M eq | Temp. (° C.) | Time | Buffer | pH | DAR with I-18 | DAR with I-35 | Fold |
|---|---|---|---|---|---|---|---|
| 2.5 | 25 | 4 h | PBS | 7.4 | 0.05 | 0.25 | 5.46 |
| 5 | 25 | 4 h | PBS | 7.4 | 0.08 | 0.29 | 3.89 |
| 10 | 25 | 4 h | PBS | 7.4 | 0.15 | 0.54 | 3.57 |
| 2.5 | 25 | 4 h | Borate | 8.3 | 0.35 | 0.60 | 1.75 |
| 5 | 25 | 4 h | Borate | 8.3 | 0.42 | 0.99 | 2.37 |
| 10 | 25 | 4 h | Borate | 8.3 | 0.77 | 1.56 | 2.02 |
| 2.5 | 25 | 4 h | Acetate | 6.2 | 0.08 | 0.20 | 2.65 |
| 5 | 25 | 4 h | Acetate | 6.2 | 0.14 | 0.23 | 1.64 |
| 10 | 25 | 2 h | Acetate | 6.2 | 0.12 | 0.47 | 3.94 |

DAR is Drug to antibody ratio, in this case "Drug" is FITC and DAR is measured using FITC absorbance. As shown in the table above, provided technologies can significantly enhance conjugation compared to control technologies comprising no target binding moieties for the target antibody.

TABLE 30-6

Certain data.

| Compound | DAR |
|---|---|
| I-46 | 0.15 |
| I-24 | 0.05 |
| I-25 | 0.10 |

TABLE 30-6-continued

| Certain data. | |
|---|---|
| Compound | DAR |
| I-18 | 0.15 |
| I-35 | 0.30 |

Reactions were set up with daratumumab using 5 M eq of indicated reagent in phosphate buffer saline pH 7.4 for 4 h at 25° C. DAR is Drug to antibody ratio, in this case "Drug" is FITC and DAR is measured using FITC absorbance.

TABLE 30-7

| Certain data. | |
|---|---|
| Compound | DAR |
| I-9 | 0.06 |
| I-45 | 0.64 |
| I-18 | 0.05 |
| I-38 | 0.52 |
| I-39 | 0.36 |
| I-40 | 0.40 |
| I-43 | 0.26 |
| I-11 | 0.05 |
| I-44 | 0.59 |
| I-10 | 0.08 |
| I-42 | 0.13 |
| I-19 | 0.20 |

Reactions were set up with daratumumab using 2.5 M eq of indicated reagent in phosphate buffer saline pH 7.4 for 4 h at 25° C. DAR is Drug to antibody ratio, in this case "Drug" is FITC and DAR is measured using FITC absorbance. As demonstrated herein, various reagents comprising target binding moieties can provide higher level of conjugation (higher ratios of moieties of interest/target agent moieties) compared to reference reagents comprising no target binding moieties.

TABLE 30-8

Certain data.

| Antibody conc. | Reagent M eq | Temp. (° C.) | Time | Buffer | pH | DAR I-9 | DAR I-45 | Fold |
|---|---|---|---|---|---|---|---|---|
| 1 mg/mL | 2.5 | 25 | 20 h | PBS | 7.4 | 0.19 | 0.90 | 4.78 |
| 1 mg/mL | 3 | 25 | 20 h | PBS | 7.4 | 0.18 | 0.96 | 5.31 |
| 1 mg/mL | 3.5 | 25 | 20 h | PBS | 7.4 | 0.24 | 1.06 | 4.39 |
| 4 mg/mL | 2.5 | 25 | 20 h | PBS | 7.4 | 0.37 | 1.04 | 2.81 |
| 4 mg/mL | 3 | 25 | 20 h | PBS | 7.4 | 0.49 | 1.09 | 2.23 |
| 4 mg/mL | 3.5 | 25 | 20 h | PBS | 7.4 | 0.44 | 1.06 | 2.40 |

Reactions were set up with daratumumab. DAR is Drug to antibody ratio, in this case "Drug" is FIT and DAR is measured using FITC absorbance. As demonstrated herein, provided technologies can provide improved conjugation under various conditions.

TABLE 30-9

Certain data.

| Compound | DAR Daratumumab | DAR Cetuximab |
|---|---|---|
| I-9 | 0.06 | 0.03 |
| I-45 | 0.64 | 0.70 |

TABLE 30-9-continued

Certain data.

| Compound | DAR Daratumumab | DAR Cetuximab |
|---|---|---|
| I-18 | 0.05 | 0.04 |
| I-38 | 0.52 | 0.31 |
| I-39 | 0.36 | 0.46 |
| I-40 | 0.40 | 0.69 |

Reactions were set up with antibodies using 2.5 M eq of indicated reagent in phosphate buffer saline pH 7.4 for 4 h at 25° C. DAR is Drug to antibody ratio, in this case "Drug" is FITC and DAR is measured using FITC absorbance. As demonstrated herein, provided technologies comprising target binding moieties can provided significantly improved conjugation for various target agents including different antibody reagents.

TABLE 30-10

Certain data.

| Reagent M eq | Temp. (° C.) | Time | Buffer | pH | DAR (I-10) | DAR (I-44) | Fold |
|---|---|---|---|---|---|---|---|
| 2.5 | 25 C. | 4 h | PBS | 7.4 | 0.08 | 0.59 | 7.79 |
| 2.5 | 25 C. | 20 h | PBS | 7.4 | 0.07 | 1.09 | 16.08 |
| 2.5 | 25 C. | 20 h | Borate | 8.2 | 0.21 | 1.42 | 6.83 |
| 2.5 | 25 C. | 20 h | PBS | 8.2 | 0.03 | 1.14 | 36.42 |
| 2.5 | 25 C. | 20 h | PBS | 8.0 | 0.06 | 0.99 | 15.39 |
| 2.5 | 25 C. | 20 h | PBS | 7.8 | 0.15 | 1.00 | 6.58 |
| 2.5 | 30 C. | 20 h | PBS | 7.4 | 0.05 | 1.15 | 21.43 |
| 2.5 | 37 C. | 20 h | PBS | 7.4 | 0.17 | 1.66 | 9.77 |

Reactions were set up with daratumumab to under various conditions. DAR is Drug to antibody ratio, in this case "Drug" is FITC and DAR is measured using FITC absorbance. As demonstrated herein, provided technologies comprising target binding moieties (e.g., I-44) toward target agents (e.g., daratumumab) can provide significantly more conjugation compared to reference technologies comprising no target binding moieties toward target agents (e.g., I-10) under various conditions. Among other things, the present disclosure provides technologies for assess various conditions to better achieve desired results (e.g., DAR, fold increase over reference technologies, etc.).

Example 31. Provided Technologies Provide Significantly Improved Selectivity

Among other things, provided technologies can provide significantly improved selectivity with respect to conjugation sites when target agents have multiple sites available for conjugations. For example, as demonstrated herein, under various conditions various provided technologies selectively conjugate on certain chains of antibody agents, and/or selective residues of antibody agents. Among other things, the present disclosure provides data showing that efficiency and/or selectivity can be optimized in accordance with the present disclosure.

In some embodiments, western blot was utilized to assess antibody conjugation locations (e.g., heavy chain, light chain, etc.). Certain data were presented in the Figures. As shown, technologies of the present disclosure can provide various levels of selectivity. In some embodiments, various technologies provide selectivity for heavy chains over light chains.

In some embodiments, for western blot, samples were first run on NuPage denaturing gel (e.g., Invitrogen, NP0321). Samples were loaded in amount of 50 ng per well. After band separation the gel was transferred on nitrocellulose membrane (Invitrogen, IB23002) using iBlot. The membrane was blocked with 5% dry milk in PBST buffer (PBS pH 7.4 with 0.1% Tween 20). In some embodiments, for detection of fluorescein conjugated light and heavy chains, primary antibody was mouse anti-fluorescein antibody (EMD Millipore, MAB045) in 1:2500 dilution, and secondary antibody was goat anti-mouse IgG conjugated with HRP (Southern Biotech, 1038-05) in 1:20000 dilution. Detection reagent for antibodies on the nitrocellulose membrane was done using SuperSignal West Femto Chemiluminescent Substrate (Thermo Fisher, 34096). The membrane was imaged on Azure Biosystems c500 for chemiluminescent signal.

In some embodiments, technologies for assessing provided technologies are or comprise mass spectrometry optionally with chromatography technologies (e.g., HPLC, UPLC, etc.). For example, various product agents were assessed by mass spectrometry, e.g., in some embodiments, using Sciex X500 QTOF system equipped with Agilent ZORBAX RRHD (300SB-C8, 2.1×50 mm, 1.8 um) column. In some embodiments, liquid chromatography was utilized together with MS. In one example: mobile phase buffers were A=0.1% Formic acid in water, B=acetonitrile. Protocol conditions were 0-1 min, 2% B; 1-7 min, 2-40% B; 7-7.5 min, 40-80% B; 7.5-9 min, 80% B; 9-9.5 min, 80-2% B; 9.5-10.5 min, 2% B; flow rate was 0.25 mL/min; concentration of the conjugates was 0.1 mg/min; injection volume was 0.01 mL. In some embodiments, BioTool kit was used for intact mass analysis. In some embodiments, mass range was 147,000-155,000 and m/z 2200-3400.

In some embodiments, peptide mapping analysis was utilized for assessment of provided technologies. In some embodiments, conjugated and unconjugated daratumumab was digested into peptides using trypsin, and peptides comprising conjugation were quantified by ion mass. In some embodiments, trypsin digestion were performed as below:

1. Aliquot 25-50 mcg of total protein sample into a clean protein lo-bind Eppendorf tube.
2. Exchange sample buffer to Smart digest buffer using 7 kDa MWCO gel filtration columns and protocol provided by Thermo Scientific.
3. Add any necessary Smart digest buffer to the buffer exchanged sample to achieve a final volume of 100 mcL.
4. Add 5 mcL of Smart Trypsin solution to the buffer exchanged sample.
5. Digest protein for 15 minutes at 70° C. in a dry bath (Add water to well to ensure proper thermal transfer to sample).
6. Remove sample from bath and allow to cool to room temperature.
7. Add 1 mcL of TCEP Bond Breaker solution to the protein sample.
8. Incubate at room temperature for 30 minutes (away from light).
9. Add 10 mcL of 5% aqueous TFA to the sample to acidify and vortex.
10. Spin down the sample for 3 minutes in a bench top centrifuge at 12,000 rcf.
11. Transfer the sample to a clean autosampler tube, careful to not disturb any undigested protein pellet.

In some embodiments, instrument conditions for analysis was:

LC:

Waters Acquity I-Class UPLC

Mobile phases:

A: 0.05% aqueous TFA

B: 0.05% TFA in acetonitrile

Column:

ACQUITY UPLC Peptide BEH C18 Column, 300 Å, 1.7 μm, 2.1 mm×100 mm

Gradient:

Hold 2% B for the 1$^{st}$ minute 2-65% B over 1-60 minutes

MS:

Thermo LTQ Orbitrap Velos Pro

MS1, parent ions, resolution of 30000 at 400 Da; range: 300-2000 Da, used a lock mass to ensure accuracy within 5 ppm Data-dependent method with a 20000 total ion count threshold to trigger fragmentation of the parent ion.

Collision energy of 35 eV (standard collision energy for peptide mapping)

Figure 13A:
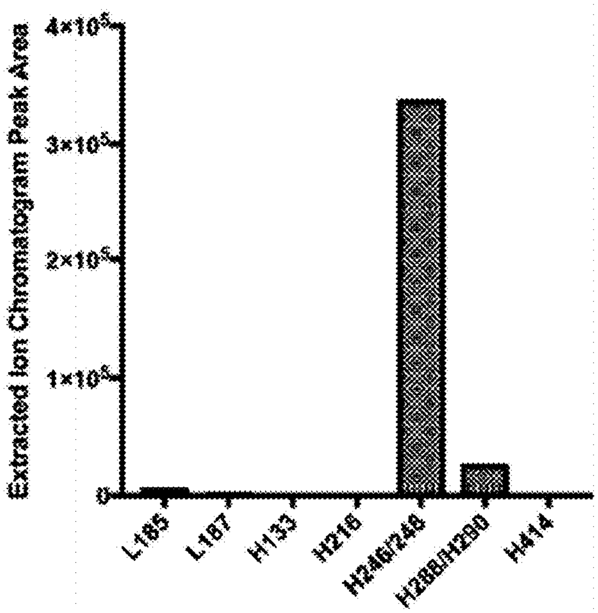
FIG. 13. Certain peptide mapping data of daratumumab conjugated with I-45 as examples. (a) FITC DAR is 0.43. (b) FITC DAR is 1.09. (c) FITC DAR is 0.90.
Figure 13B:
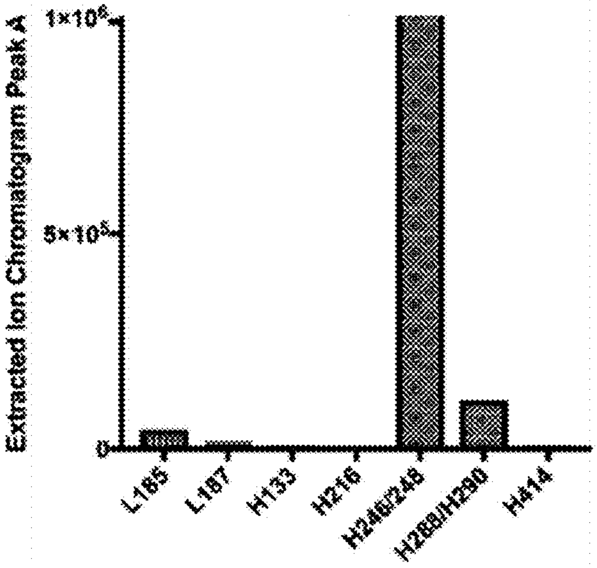
Figure 13C:
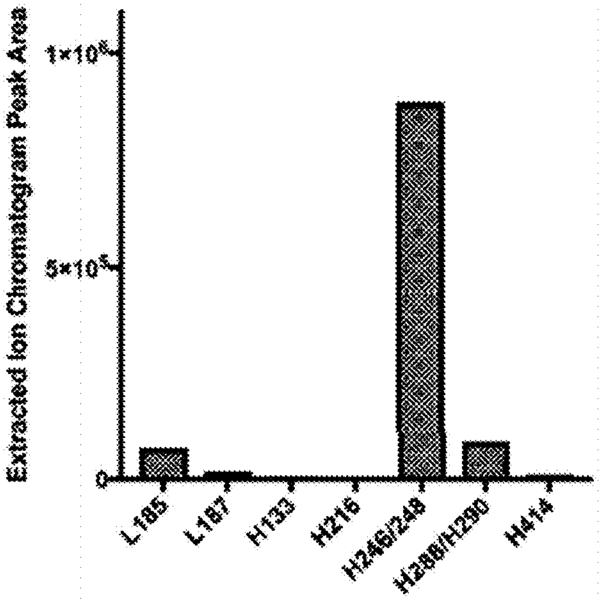
Figure 14:
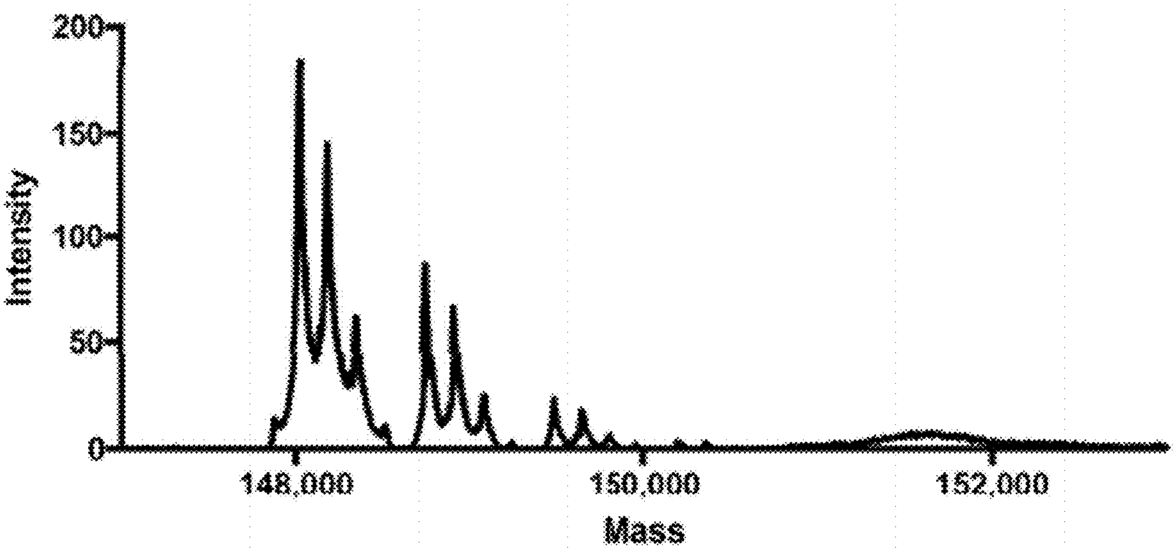
FIG. 14. Certain intact mass data of daratumumab conjugated with I-9 as examples.

Various MS data were presented in the Figures as examples. In some embodiments, conjugation selectively occurred at K246/K248 of antibody heavy chains, e.g., when I-40 or I-45 was utilized (e.g., see FIG. 13). In some embodiments, conjugation sites include K246 of heavy chains. In some embodiments, conjugation sites include K248 of heavy chains. In some embodiments, conjugation sites include K288/K290 of heavy chains. In some embodiments, conjugation sites include K288 of heavy chains. In some embodiments, conjugation sites include K290 of heavy chains. In some embodiments, conjugation sites include K185 of light chains. In some embodiments, conjugation sites include K187 of light chains. In some embodiments, conjugation sites include K414 of heavy chains.

Figure 22A:
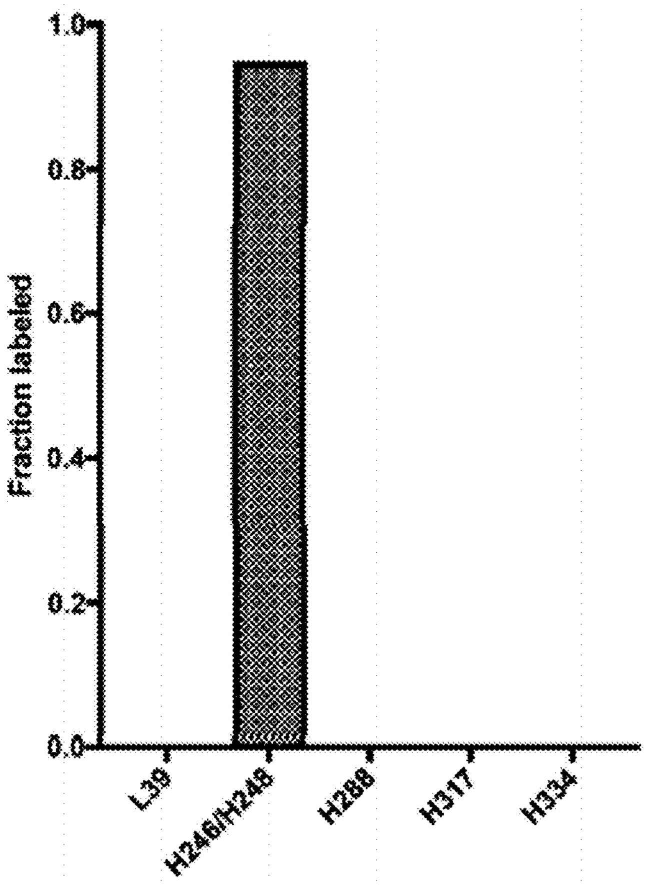
FIG. 22. Provided technologies can provide selective conjugation at certain sites. As shown, I-44 can selectively provide conjugation at sites 246 or 248 of heavy chains (A) compared to a reference compound, e.g., I-10 (B).
Figure 22B:
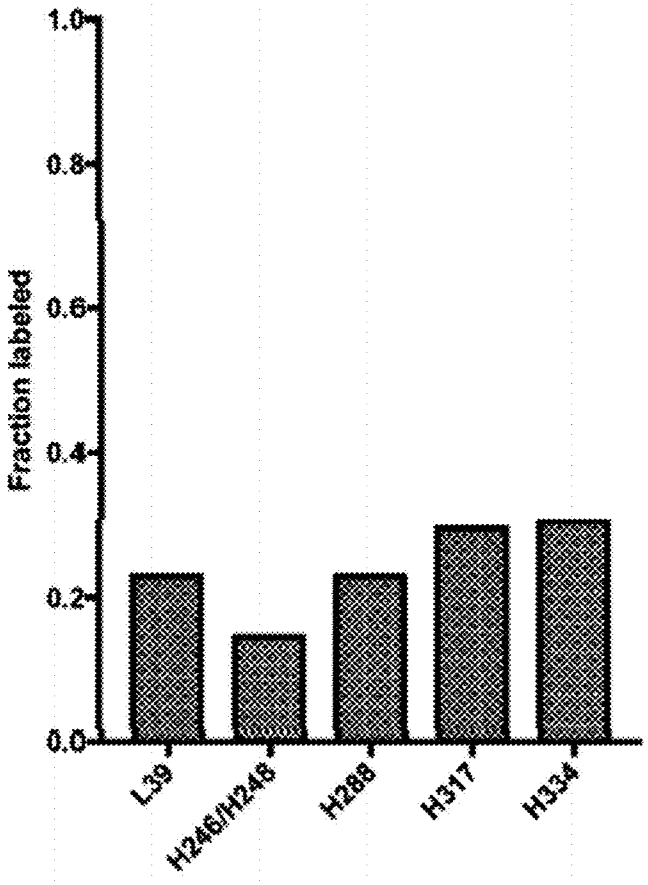
Figure 27A:
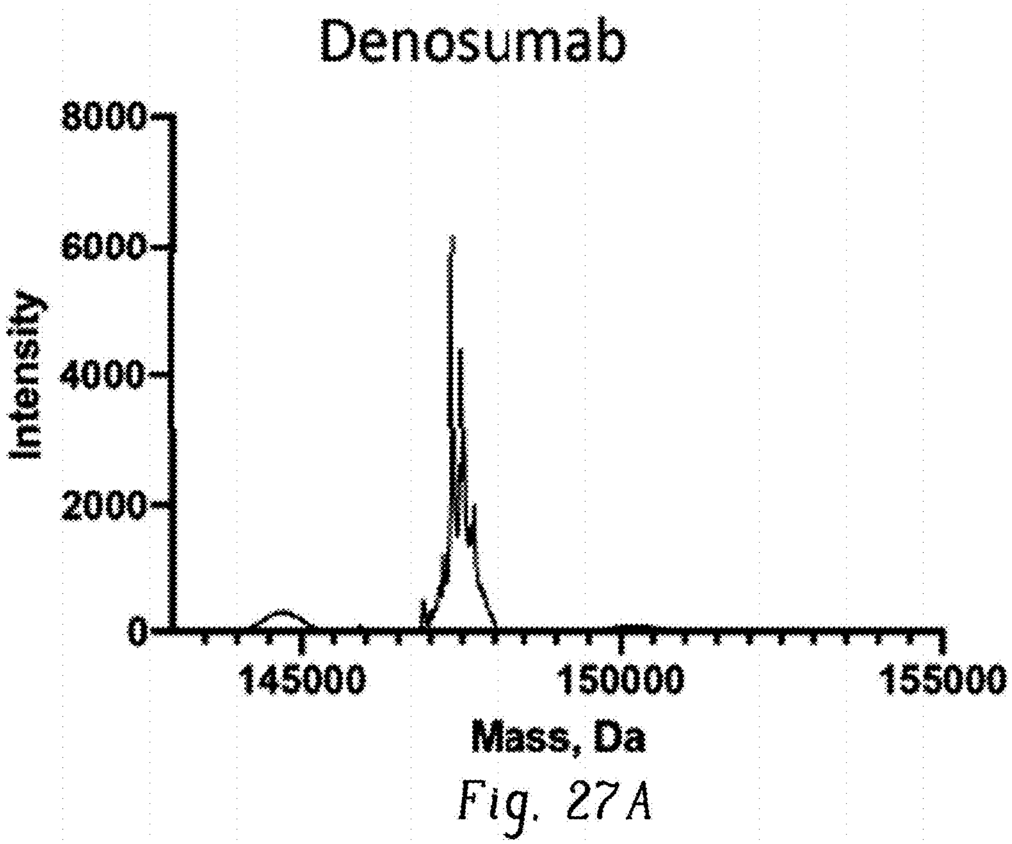
FIG. 27. Provided technologies can provide highly efficient and/or selective conjugation for various types of antibody agents. As demonstrated herein, provided technologies (e.g., I-44) among other things can provide specific conjugation for an IgG2 antibody Denosumab.
Figure 27B:
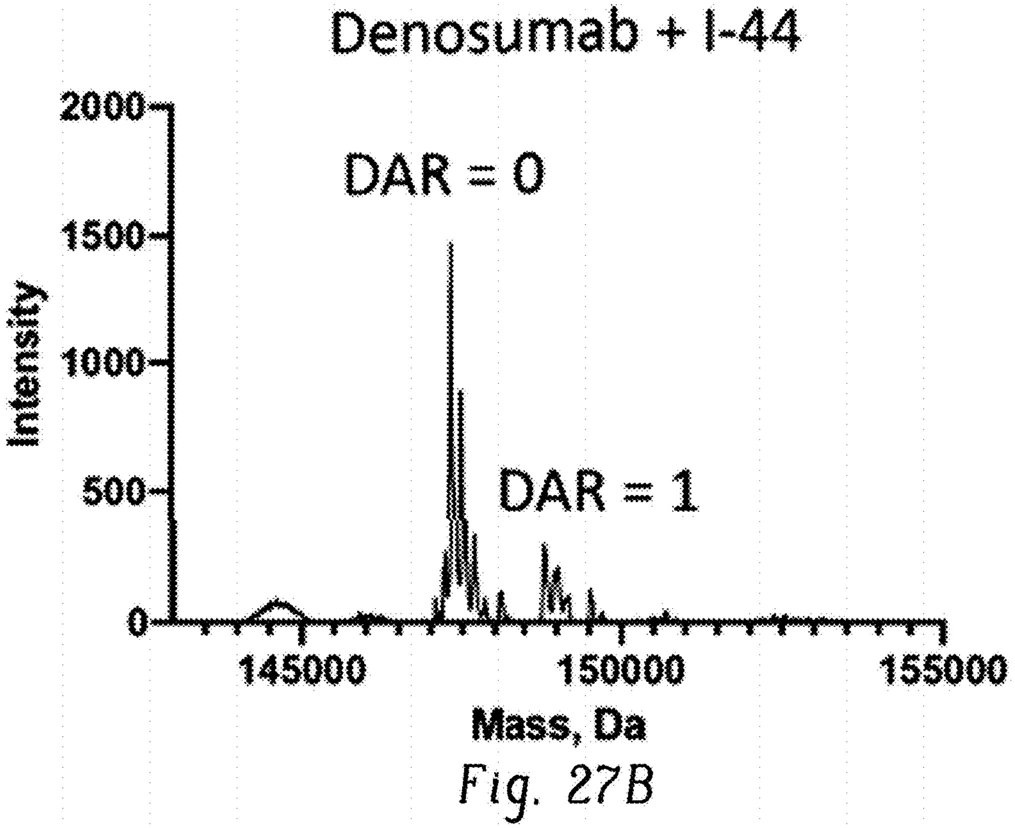
Figure 27C:
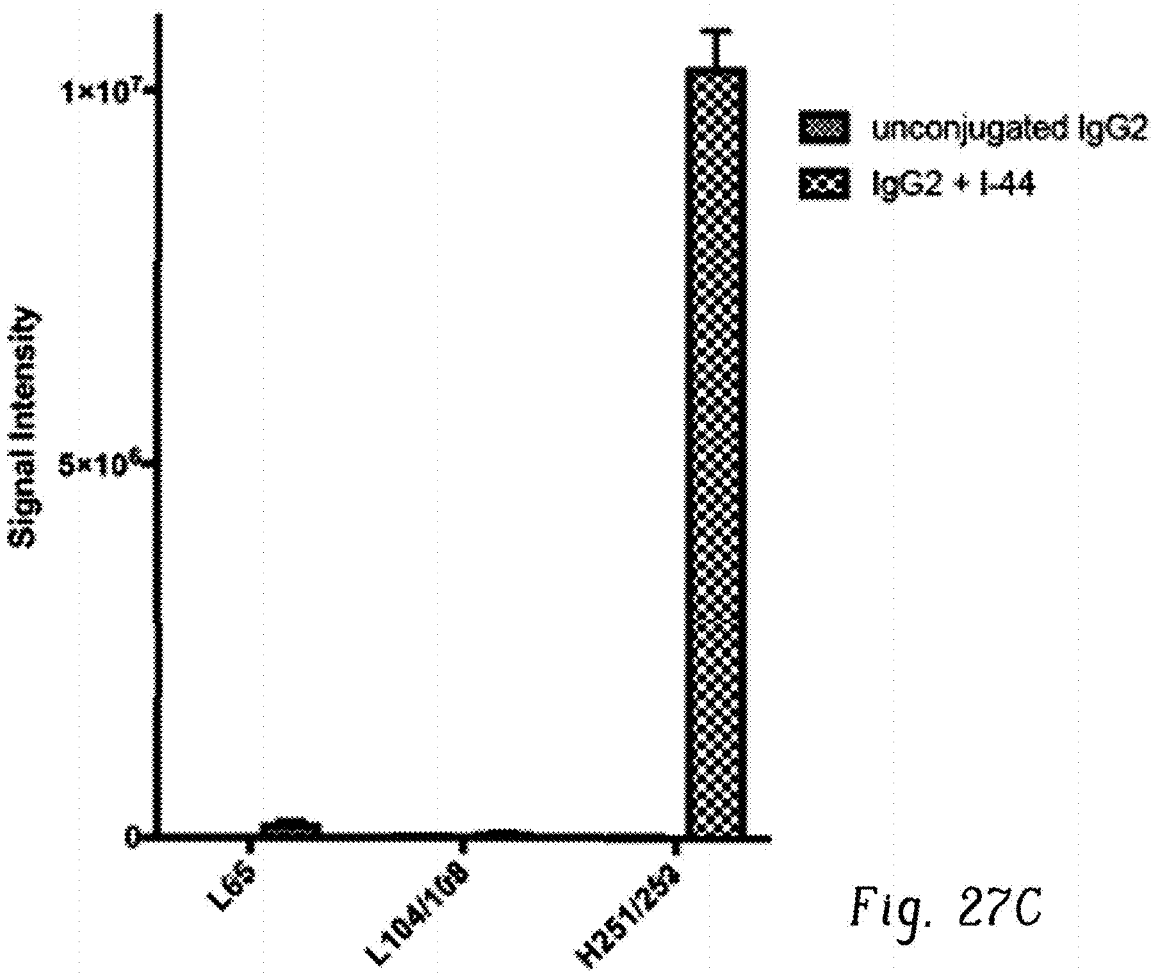
Figure 28A:
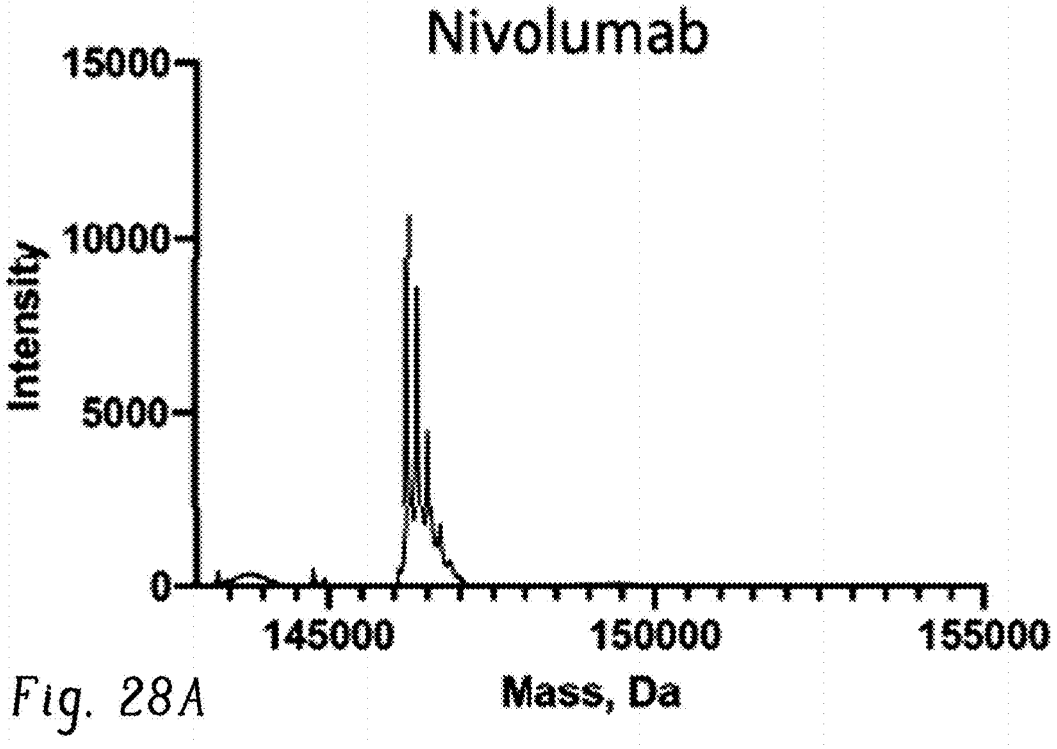
FIG. 28. Provided technologies can provide highly efficient and/or selective conjugation for various types of antibody agents. As demonstrated herein, provided technologies (e.g., I-44) can among other things provide efficient and specific conjugation for an IgG4 antibody Nivolumab.
Figure 28B:
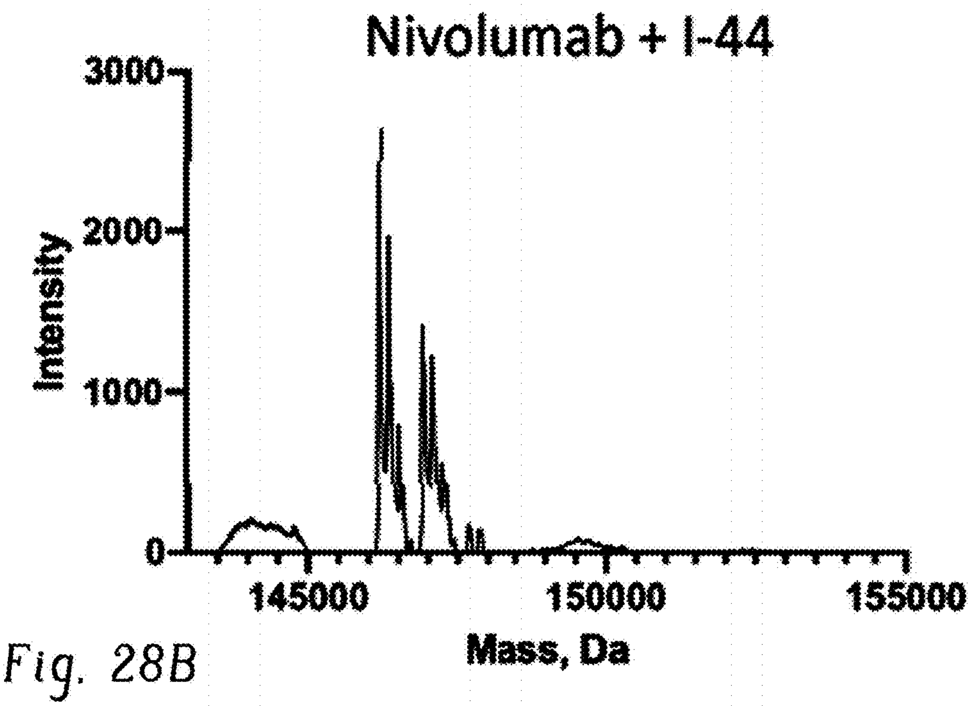
Figure 28C:
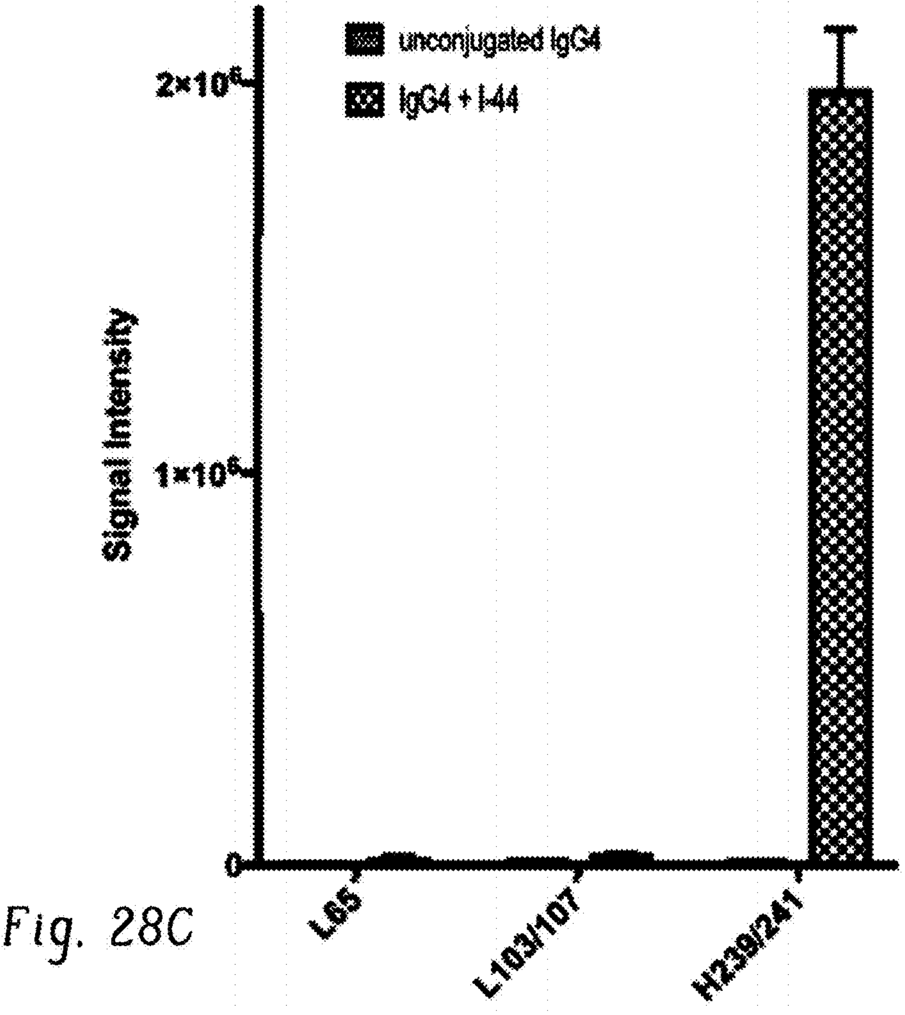

Additional data confirmed that provided technologies can provide efficient and/or selective conjugation to various types of antibody agents (e.g., monoclonal antibody agents, polyclonal antibody agents, pooled antibody agents such as IVIG, IgG1, IgG2, IgG3, and/or IgG4 antibody agents, etc.). For example, data in FIG. 22 confirm that I-44 can efficiently and selectively provide conjugation at K246 and/or K248 of the heavy chain (compared to non-specific conjugation, e.g., by using I-10). In some embodiments, provided technologies, e.g., 1-44, were utilized for conjugation with Denosumab (IgG2) (e.g., see FIG. 27) and Nivolumab (IgG4) (e.g., see FIG. 28). As confirmed herein, in some embodiments, residue 251 and/or 253 of a heavy chain of IgG2 is selectively conjugated; in some embodiments, residue 239 and/or 241 of a heavy chain of IgG2 is selectively conjugated. Those skilled in the art reading the present disclosure will appreciate that various types of antibodies can also be conjugated with high efficiency and/or selectivity in accordance with the present disclosure (e.g., using compounds and methods that comprise suitable target binding moieties for such antibodies, and various reactive moieties and optionally linker moieties as described herein). A useful protocol for peptide mapping is described below as an example; those skilled in the art that other protocols, including various modifications and variations of the protocol described below, may also be utilized in accordance with the present disclosure:

1. Quantify proteins, e.g., with Pierce 660 reagent.
2. In low-bind Eppendorf tubes dilute 10 ug of sample in 100 uL of Tris 50 mM pH 8.0.

3. Reduce proteins by adding 10 mM DTT (dithiothreitol) for 15 minutes at 60° C. in a block heater.
4. Add 15 mM iodoacetamide for alkylation at room temperature for 30 minutes in the dark.
5. Quench the reaction by adding 10 mM DTT.
6. Digest proteins with 0.33 μg of α-chymotrypsin (Sigma) over night at 37° C. in a thermoshaker.
7. Acidify samples with 2 uL of 100% formic acid.
8. Purify peptides on a Strata-X reversed phase SPE (Phenomenex). Peptide were eluted with 60% acetonitrile with 2% formic acid.
9. Dry eluted peptides under nitrogen stream.
10. Reconstitute peptides in 25 uL of mobile phase A.
11. Dilute peptides 1:10 in mobile phase A before injection on LC-MS, e.g., according to the parameters below.

Instrument for analysis as example:
LC: Eksigent microLC200 (Sciex)
Mobile phases:
A: 0.2% formic acid and 3% DMSO in water
B: 0.2% formic acid and 3% DMSO in ethanol
Column: Luna Omega PS column 0.3 mm i.d., 3 μm particles, 100 mm (Phenomenex)
Gradient: 2-48% B over 25 minutes at 6 ul/minutes flow rate.
MS: ABSciex TripleTOF 6600+
MS1 (range 350-1250 Da), resolution 35000
DDA method with a 500 cps threshold.

As described herein, provided technologies can provide highly efficient and/or selective (e.g., with respect to conjugation sites) conjugation for various types of antibody agents (e.g., monoclonal antibody agents, polyclonal antibody agents, or pooled antibody agents such as IVIG). Among other things, the present disclosure provides data confirming that technologies of the present disclosure can provide highly efficient and/or selective conjugation of IgG2 and IgG4 antibodies (e.g., see FIG. 27 for certain conjugation data for Denosumab (IgG2), and FIG. 28 for certain conjugation data for Nivolumab (IgG4)). In some embodiments, reactions were performed in borate buffer pH 8.2, 2.5 M eq of reagent to antibody, 20 h, 25° C. Those skilled in the art reading the present disclosure will appreciate that other types of antibodies can also be conjugated with high efficiency and/or selectivity in accordance with the present disclosure (e.g., using compounds and methods that comprise suitable target binding moieties for such antibodies, and various reactive moieties and optionally linker moieties as described herein).

Example 32. Provided Product Agents Maintain Properties and Functions of Target Agents Among other things, provided technologies utilize mild conditions, short pathways (e.g., no separate removal of target binding moieties), etc., and provide conjugation at directed sites and product agents that maintain one or more or all desired properties and/or activities of target agents (e.g., antibody agents). As demonstrated in the Figures (e.g., FIGS. 7, 8, 9, 10, etc.), provided agents comprising antibody agent moieties can maintain interactions with Fc receptors (e.g., FcRn).

Various technologies are useful for assess properties and/or activities of target agents (e.g., antibody agents). For example, in some embodiments, ELISA assay were utilized to assess binding between provided agents and FcRn receptor. In one example, high binding 96-well plate (e.g., Costar 3922) was coated with neutravidin (Thermo Fisher, 31000) in PBS buffer (pH 7.4), blocked with 5% bovine serum albumin in PBST buffer pH 7.4 (PBS buffer pH 7.4 with 0.05% tween 20), followed by immobilization of Avi-tagged FcRn protein (Acro Biosystems, FCM-H82W4) in PBST buffer pH 6.0. After washing with PBST pH 6.0, antibody (e.g., daratumumab, Erbitux, etc.) and its conjugates were bound to FcRn on the plate in PBST pH 6.0. All bound antibodies and conjugates were detected in PBST pH 6.0 using anti-human F(ab)2 antibody conjugated with HRP. Detection reagent was SuperSignal ELISA Pico Chemiluminescent Substrate (Thermo fisher, 37069) followed by luminescence read on Biotek Synergy H1 microplate reader.

Example 33. Exemplary Synthesis of Compound I-53

Among other things, the present disclosure provides technologies for preparing compounds described herein. A preparation of I-53 is described below as an example.

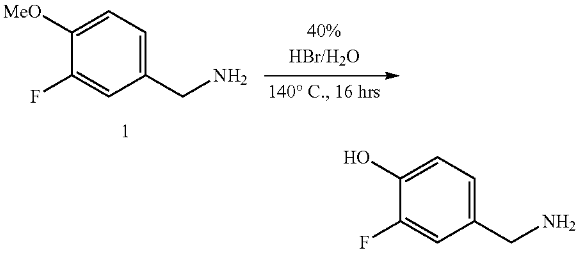

1
2

A mixture of compound 1 (3.00 g, 19.3 mmol) in HBr/$H_2O$ (149.0 g, 736.6 mmol, 100 mL, 40% purity) was stirred at 140° C. for 16 hrs. The solvent was removed at 70° C. under reduced pressure, the residue was triturated in MeCN (30 mL) for 10 mins. After filtered, the solid was dried via lyophilization to get compound 2 (4.00 g, 18.0 mmol, 93.17% yield, HBr) as a brown solid. $^1H$ NMR: ES9329-522-P1B (400 MHz DMSO-$d_6$): δ ppm 10.06 (s, 1H) 8.11 (s, 3H) 7.30 (dd, J=12.17, 1.63 Hz, 1H) 7.09 (d, J=8.28 Hz, 1H) 6.93-7.04 (m, 1H) 3.93 (q, J=5.27 Hz, 1H) 3.87-4.00 (m, 1H).

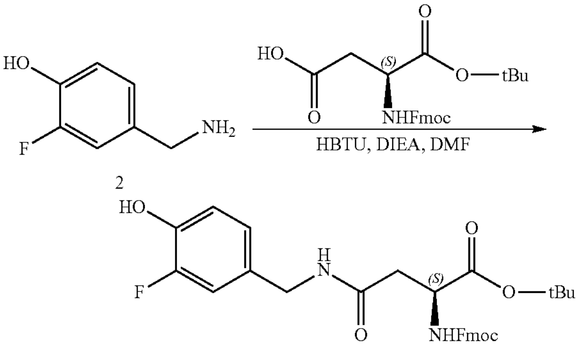

2
3

A mixture of compound 2 (3.00 g, 13.51 mmol, HBr, 1.00 eq), compound 2a (5.56 g, 13.51 mmol, 1.00 eq), HBTU (5.12 g, 13.51 mmol, 1.00 eq), DIEA (5.24 g, 40.5 mmol, 7.06 mL, 3.00 eq) in DMF (50 mL) was stirred at 15° C. for 1 hr. The mixture was added to 0.5 M HCl (cold, 500 mL), and there appeared lots of white solid. After filtered, the solid was dried via lyophilization to get compound 3 (7.00 g, crude) as a white solid.

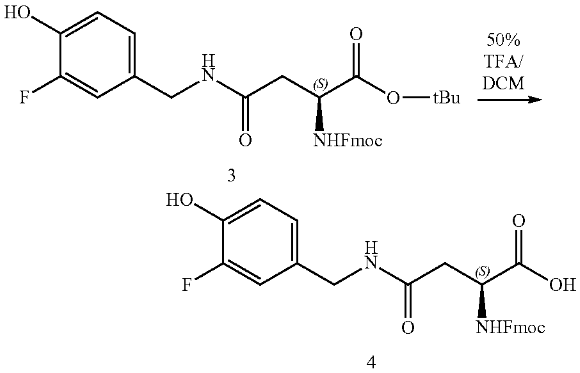

A mixture of compound 3 (7.00 g, 13.0 mmol) in TFA (61.60 g, 540.2 mmol, 40 mL) and DCM (40 mL) was stirred at 15° C. for 0.5 hr. The solvent was removed under reduced pressure. The residue was purified by flash C18 (ISCO®; 120 g SepaFlash® C18 Flash Column, Eluent of 0~90% $MeCN/H_2O$ gradient @ 75 mL/min) directly to get compound 4 (5.00 g, 10.4 mmol, 79.8% yield) as a white solid. $^1H$ NMR: ES9329-561-P1C (400 MHz DMSO-$d_6$): δ ppm 12.68 (s, 1H) 9.67 (s, 1H) 8.33 (t, J=5.65 Hz, 1H) 7.90 (d, J=7.28 Hz, 2H) 7.71 (d, J=7.28 Hz, 2H) 7.39-7.47 (m, 2H) 7.29-7.37 (m, 2H) 7.02 (d, J=12.05 Hz, 1H) 6.84-6.90 (m, 2H) 4.36-4.47 (m, 1H) 4.26-4.30 (m, 2H) 4.20-4.25 (m, 1H) 4.17 (s, 2H) 1.88-2.06 (m, 1H) 1.24 (s, 3H).

resin was washed with DMF (20 mL)*5. Then 20% piperidine in DMF (20 mL) was added and the mixture was bubbled with $N_2$ for 30 mins at 15° C. Then the mixture was filtered to obtain the resin. The resin was washed with DMF (20 mL)*5 before proceeding to next step.

2) Coupling: A solution of Fmoc-PEG12-$CH_2CH_2COOH$ (1.26 g, 1.50 eq), HATU (0.541 g, 1.43 eq) in DMF (10 mL) was added to the resin with $N_2$ bubbling. Then DIEA (3.00 eq) was added to the mixture dropwise and bubbled with $N_2$ for 30 mins at 15° C. The coupling reaction was monitored by ninhydrin test, if it showed colorless, the coupling was completed. The resin was then washed with DMF (20 mL)*5.

3) De-protection: 20% piperidine in DMF (20 mL) was added to the resin and the mixture was bubbled with $N_2$ for 30 mins at 15° C. The resin was then washed with DMF (20 mL)*5. The De-protection reaction was monitored by ninhydrin test, if it showed blue or other brownish red, the reaction was completed.

4) Repeat Step 2 and 3 for all other amino acids: (2-4 in the table below).

| # | Materials | Coupling reagents |
|---|---|---|
| 1 | Fmoc-PEG6-$CH_2CH_2COOH$ (1.00 eq) | DIEA (4.00 eq) |
| 2 | Fmoc-PEG12-$CH_2CH_2COOH$ (1.50 eq) | HATU (1.43 eq) and DIEA (3.00 eq) |
| 3 | Fmoc-Gly-OH (3.00 eq) | HBTU (2.85 eq) and DIEA (6.00 eq) |
| 4 | Boc-Gly-Gly-Gly-OH (3.00 eq) | HATU (2.85 eq) and DIEA (6.00 eq) |

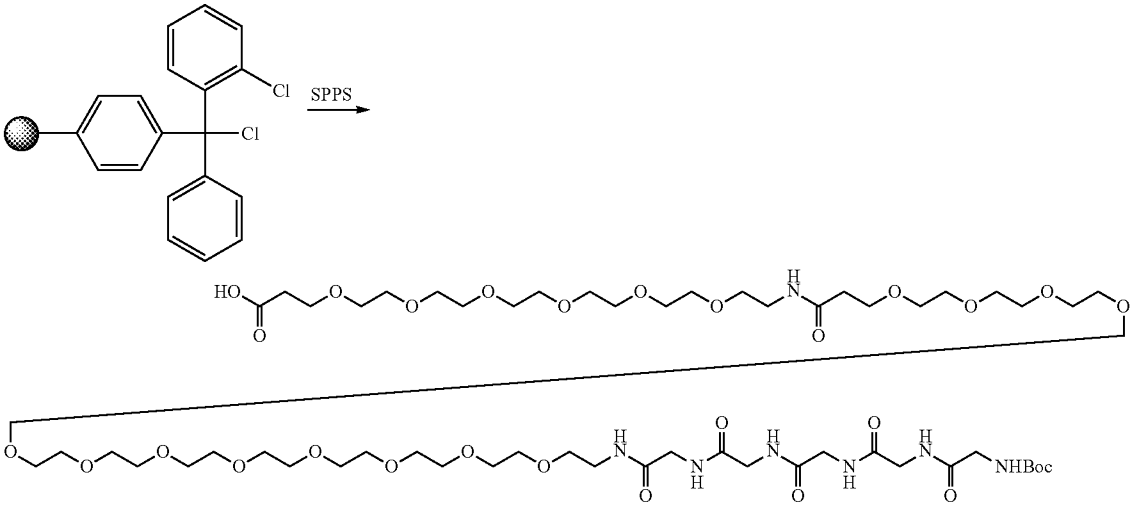

5

In some embodiments, peptide was prepared using the procedure below using Fmoc chemistry.

1) Resin preparation: To the vessel containing CTC Resin (1.0 mmol, 1.0 g, 1.00 mmol/g) and Fmoc-PEG6-$CH_2CH_2COOH$ (0.575 g, 1.0 mmol, 1.00 eq) in DCM (5 mL) was added DIEA (4.00 eq) dropwise and mix for 2 hrs with $N_2$ bubbling at 15° C. Then added MeOH (1.0 mL) and bubbled with $N_2$ for another 30 mins. The Peptide Cleavage and Purification: Add cleavage buffer (20% HFIP/DCM, 30 mL) to the flask containing the side chain protected peptide at room temperature and stirred for 30 mins. Filter and collect the filtrate. The mixture was concentrated under reduced pressure to remove solvent. The residue was lyophilized to give the crude compound 5 (802 mg).

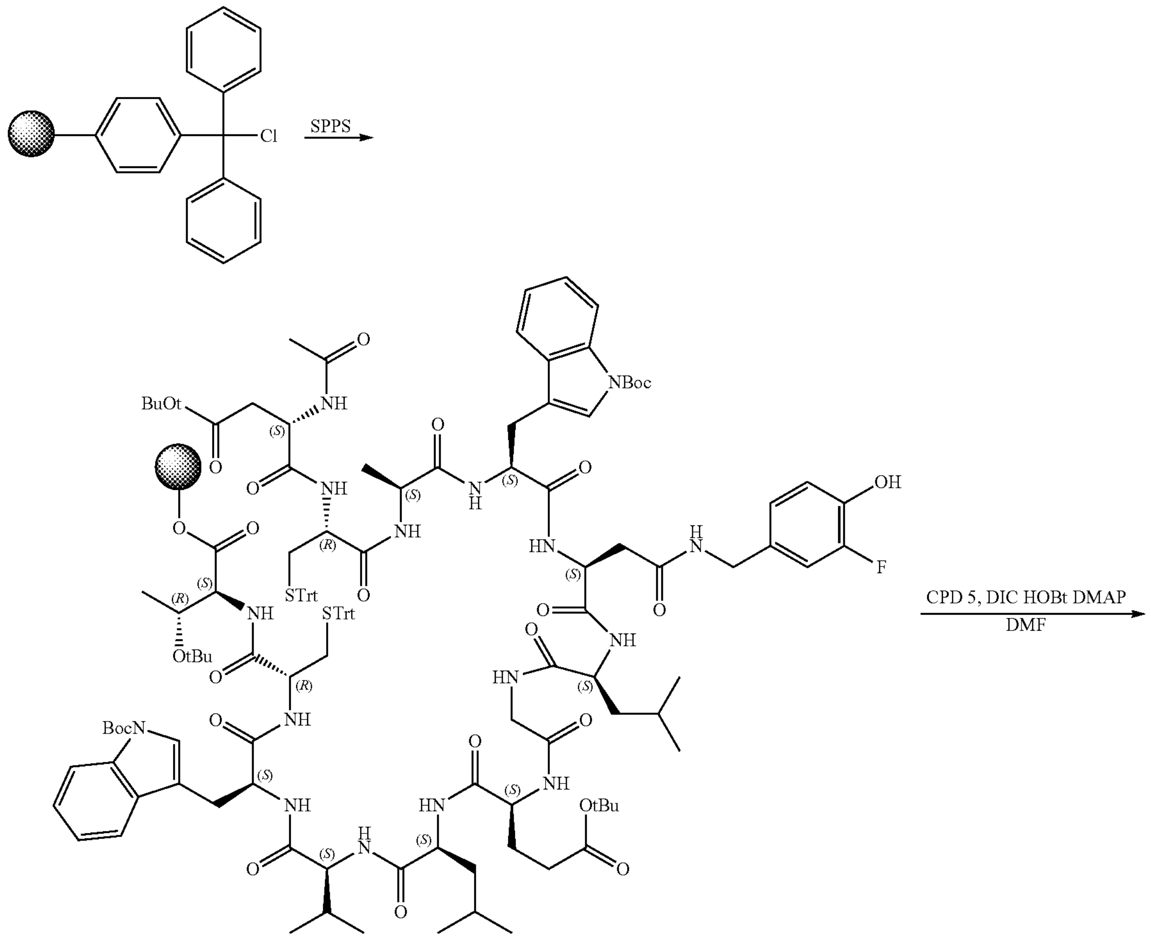
6
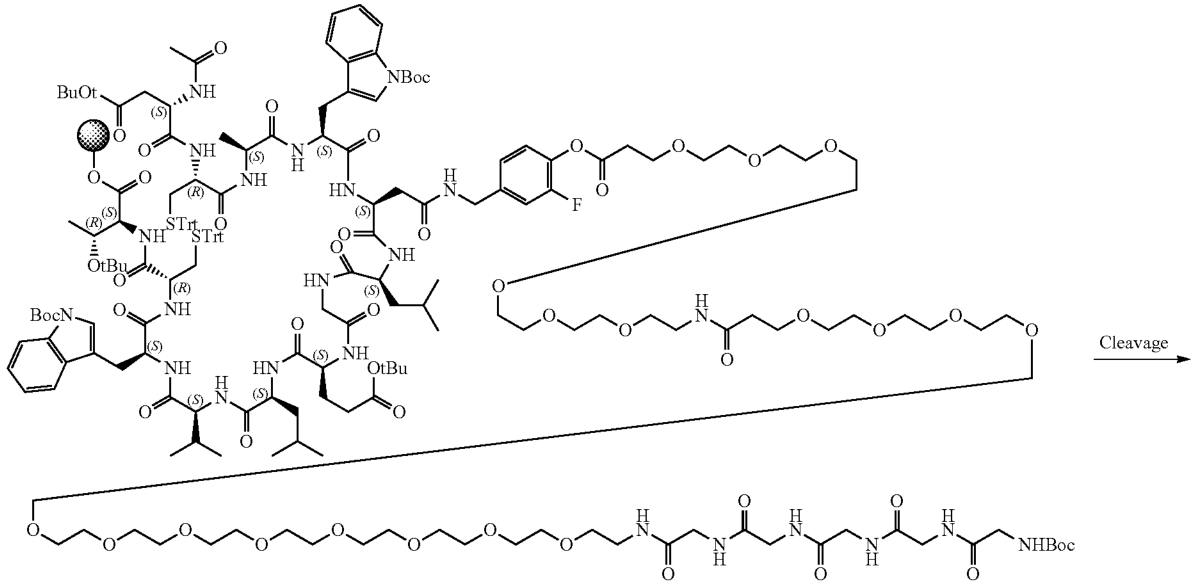
7

-continued

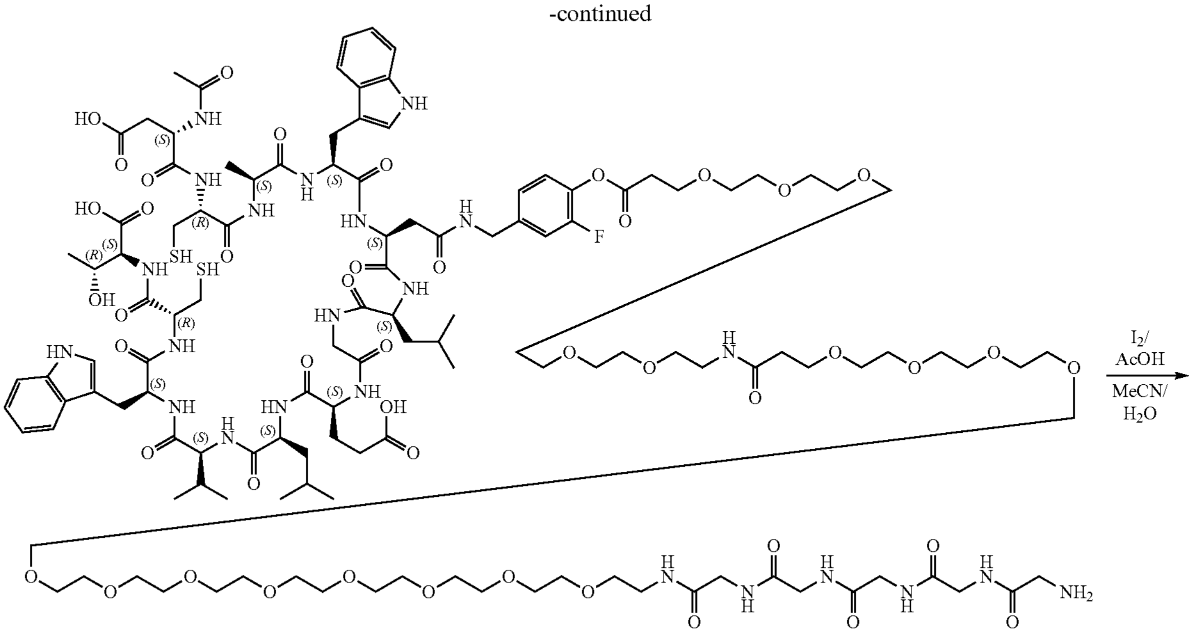

8

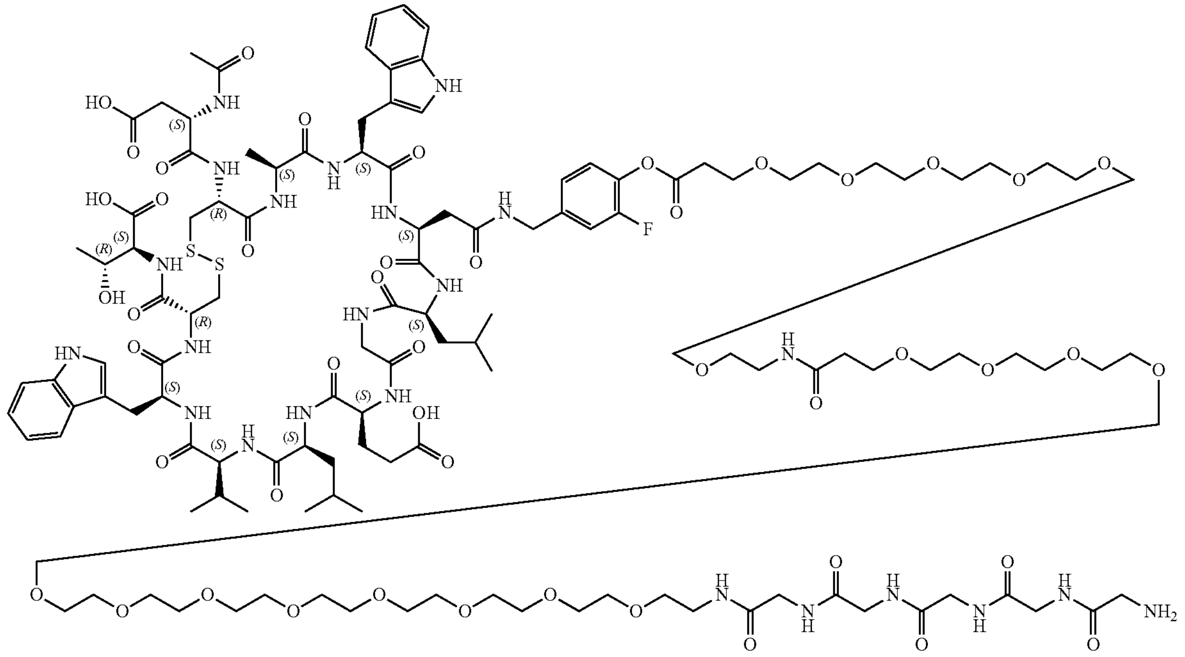

I-53

In some embodiments, peptide was prepared using the procedure below using Fmoc chemistry.

1) Resin preparation: To the vessel containing CTC Resin (0.3 mmol, 0.3 g, 1.00 mmol/g) and Fmoc-Thr(tBu)-OH (0.119 g, 1.0 mmol, 1.00 eq) in DCM (5 mL) was added DIEA (4.00 eq) dropwise and mix for 2 hrs with $N_2$ bubbling at 15° C. Then added MeOH (0.5 mL) and bubbled with $N_2$ for another 30 mins. The resin was washed with DMF (10 mL)*5. Then 20% piperidine in DMF (10 mL) was added and the mixture was bubbled with $N_2$ for 30 mins at 15° C. Then the mixture was filtered to obtain the resin. The resin was washed with DMF (10 mL)*5 before proceeding to next step.

2) Coupling: A solution of Fmoc-Cys(Trt)-OH (0.527 g, 3.00 eq), HBTU (0.324 g, 2.85 eq) in DMF (3 mL) was added to the resin with $N_2$ bubbling. Then DIEA (6.00 eq) was added to the mixture dropwise and bubbled with $N_2$ for 30 mins at 15° C. The coupling reaction was monitored by ninhydrin test, if it showed colorless, the coupling was complete. If it was not complete, the coupling was repeated one more time till ninhydrin test showed colorless. The resin was then washed with DMF (10 mL)*5.

3) De-protection: 20% piperidine in DMF (10 mL) was added to the resin and the mixture was bubbled with $N_2$ for 30 mins at 15° C. The resin was then washed with DMF (10 mL)*5. The De-protection reaction was monitored by ninhydrin test, if it showed blue or other brownish red, the reaction was complete.

4) Repeat Step 2 and 3 for all other amino acids: (2-13 in the Table below).

5) Acetylation: After Fmoc-Asp(OtBu)-OH was coupled to the sequence, the resin was washed with DMF, and Fmoc was removed. Then the resin was washed with DMF 5 times, DCM 5 times, and then a mixed solution contained Ac2O/NMM/DMF (V/V/V, 10/5/85, 20 mL in total) was added to the resin and the reaction lasted for 20 min. Ninhydrin test showed no free amine was detected.

Coupling for the last position: A solution of compound 5 (802 mg, 0.6 mmol, 2.00 eq), DIC (2.00 eq), HOBt (2.00 eq) and DMAP (2.00 eq) was added to resin and the mixture was bubbled with $N_2$ for 36 hrs. The coupling reaction was monitored by LCMS after a mini-cleavage, almost 50% was desired MS. The resin was then washed with DMF (10 mL)*5, MeOH (10 mL)*5, and then dried under vacuum.

| # | Materials | Coupling reagents |
|---|---|---|
| 1 | Fmoc-Thr(tBu)OH (1.00 eq) | DIEA (4.00 eq) |
| 2 | Fmoc-Cys(Trt)OH (3.00 eq) | HBTU (2.85 eq) and DIEA (6.00 eq) |
| 3 | Fmoc-Trp-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OtBu)-OH (3.00 eq) | HBTU (2.85 eq) and DIEA (6.00 eq) |
| 7 | Fmoc-Gly-OH (3.00 eq) | HBTU (2.85 eq) and DIEA (6.00 eq) |
| 8 | Fmoc-Leu-OH (3.00 eq) | HBTU (2.85 eq) and DIEA (6.00 eq) |
| 9 | Compound 4 (2.00 eq) | DIC (2.00 eq) and HOBt (2.00 eq) |
| 10 | Fmoc-Trp-OH (3.00 eq) | DIC (3.00 eq) and HOBt (3.00 eq) |
| 11 | Fmoc-Ala-OH (3.00 eq) | DIC (3.00 eq) and HOBt (3.00 eq) |
| 12 | Fmoc-Cys(Trt)-OH (3.00 eq) | DIC (3.00 eq) and HOBt (3.00 eq) |
| 13 | Fmoc-Asp(OtBu)-OH (3.00 eq) | DIC (3.00 eq) and HOBt (3.00 eq) |
| 14 | $Ac_2O$ | $Ac_2O$/NMM/DMF (10/5/85, 20 mL) |
| 15 | Compound 5(2.00 eq) | DIC (2.00 eq), HOBt (2.00 eq) and DMAP (2.00 eq) |

Peptide Cleavage and Purification: Add cleavage buffer (95TFA/2.5Tis/2.5% $H_2O$, 15 mL) to the flask containing the side chain protected peptide at room temperature and stirred for 1 hr. Filter and collect the filtrate. The peptide is precipitated with cold isopropyl ether (100 mL) and centrifuged (3 mins at 3000 rpm). Isopropyl ether washes two additional times, and dry the crude peptide under vacuum for 2 hrs. The residue was purified prep-HPLC (acid condition, TFA) to get compound 420 (17.3 mg, 1.99% yield, 95.3% purity) as a white solid. LCMS+ESI observed (m/z, major peaks): 1447.8, 965.5, 724.4. A purification protocol is presented below as an example:

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$)<br>B: MeCN |
| Gradient | 15-45%-60 min. Retention time: 51 min |
| Column | Luna 25*200 mm, C 18 10 um,110 Å + Gemin 150*30 mm, C18 5 um,110 Å |
| Flow Rate | 20 mL/min |
| Wavelength | 220/254 nm |
| Oven Tem. | Room temperature |

Various other compounds were also prepared, for example compounds I-54, I-55, I-56, I-57, I-58, etc.

Example 34. Preparation of Agents Comprising Multiple Antibody Agent Moieties Among other things, the present disclosure provides technologies for preparation of agents comprising moieties having different specificity, e.g., antibody moieties toward different antigens. In some embodiments, such agents can be prepared, as described herein, by reacting a first compound that comprises a target agent moiety which is or comprises a first antibody agent moiety, a first moiety of interest which is or comprises a first reactive moiety, and optionally a linker moiety, with a second compound that comprises a second reactive moiety and a second antibody agent. In some embodiments, each of the first and second agents is independently a compound of formula P-I or P-II, or a salt thereof. Among other things, provided technologies provides various advantages, e.g., they can readily conjugate existing antibody agents with other antibody agents to provide agents comprising multiple antibody agent moieties which option have different specificity. In some embodiments, a product agent is a bispecific antibody agent. Described herein is an example confirming various effects and/or advantages of provided technologies.

A first agent comprising a first antibody agent moiety, e.g., an anti-CD20 agent moiety such as rituximab utilized in the present Example, was conjugated with a second agent comprising a second antibody agent moiety, e.g., a CD3-directed ScFv (SP34) to provide a bispecific agent, in this Example, CD20×CD3. Various antibody agents, including those of various structures/formats and/or useful for therapeutic and/or diagnostic applications, may be conjugated, for example, rituximab is a chimeric monoclonal antibody useful for, e.g., treatment of B-cell lymphomas and lymphocytic leukemias. In some embodiments, the present disclosure provides technologies, e.g., mAb therapy enhancer (MATE™) technologies that can provide efficient site-directed chemical conjugation to "off-the-shelf" therapeutic antibody agents, e.g. various mAbs, and allow development of various bispecific therapeutic agents. Among other things, technologies of the present disclosure, e.g., MATE technologies, provide chemical engineering of antibody agents, e.g., various existing antibodies, without the need to create new DNA vectors or genetic engineering of master cell lines. In some embodiments, advantages of provided technologies include 1) site-directed conjugation specificity, and/or 2) no requirement of genetic engineering, compared to certain existing methods that 1) lack site-directed conjugation specificity by indiscriminately binding/conjugating to available amino acid residues, and/or 2) require genetic engineering to create conjugate tags. In some embodiments, a useful technology is described below, wherein a tag comprising a reactive moiety is introduced to an agent comprising a first antibody agent moiety and is utilized to conjugate with an agent comprising a second antibody agent moiety. In some embodiments, an enzymatic conjugation is promoted by a sortase.

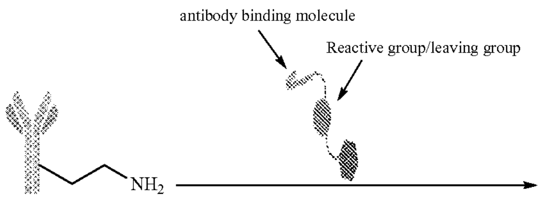

-continued
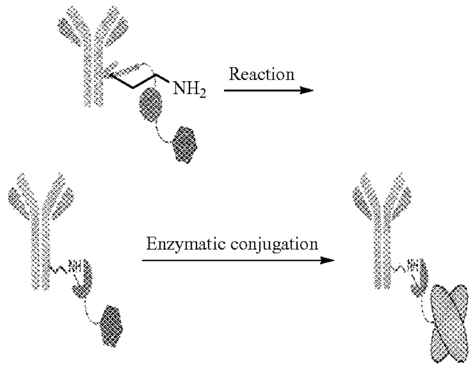
In some embodiments a useful scheme is depicted below:

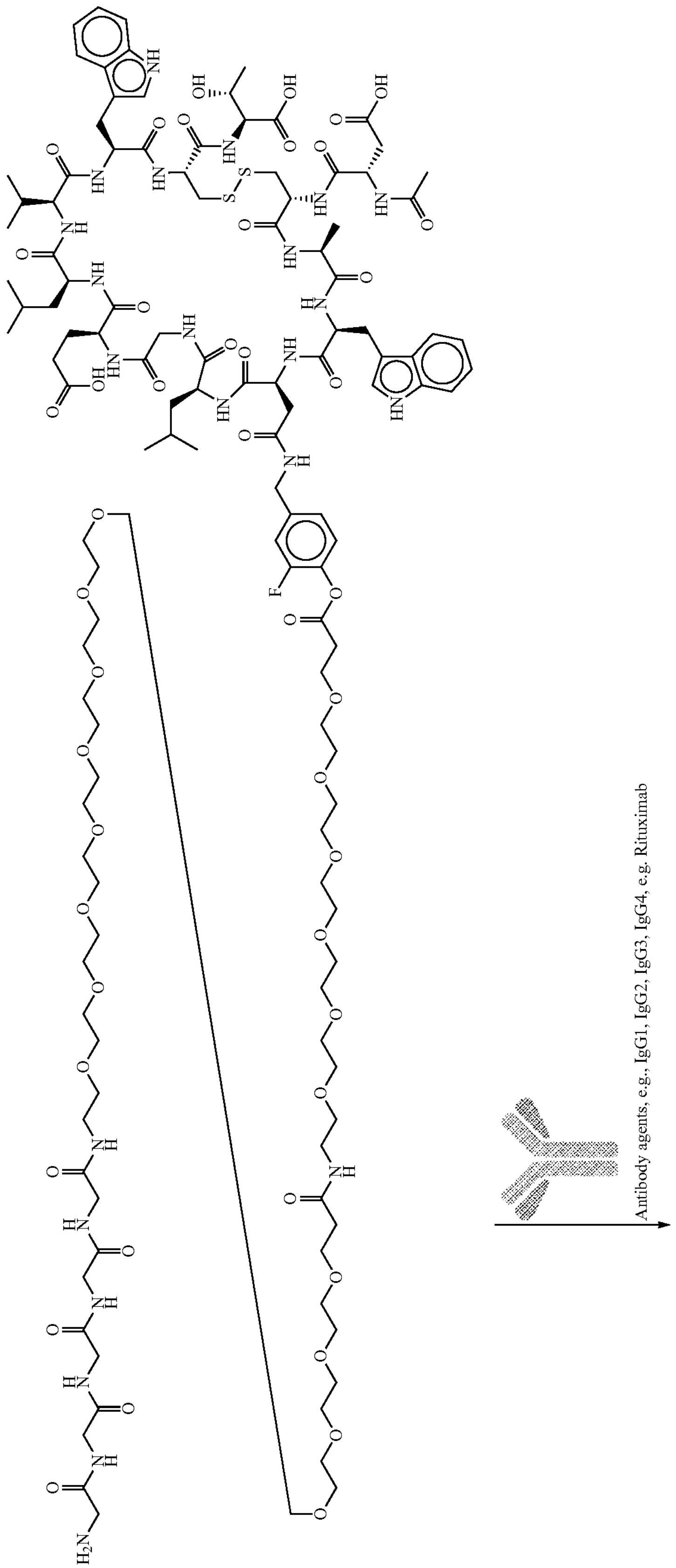
Antibody agents, e.g., IgG1, IgG2, IgG3, IgG4, e.g. Rituximab

-continued
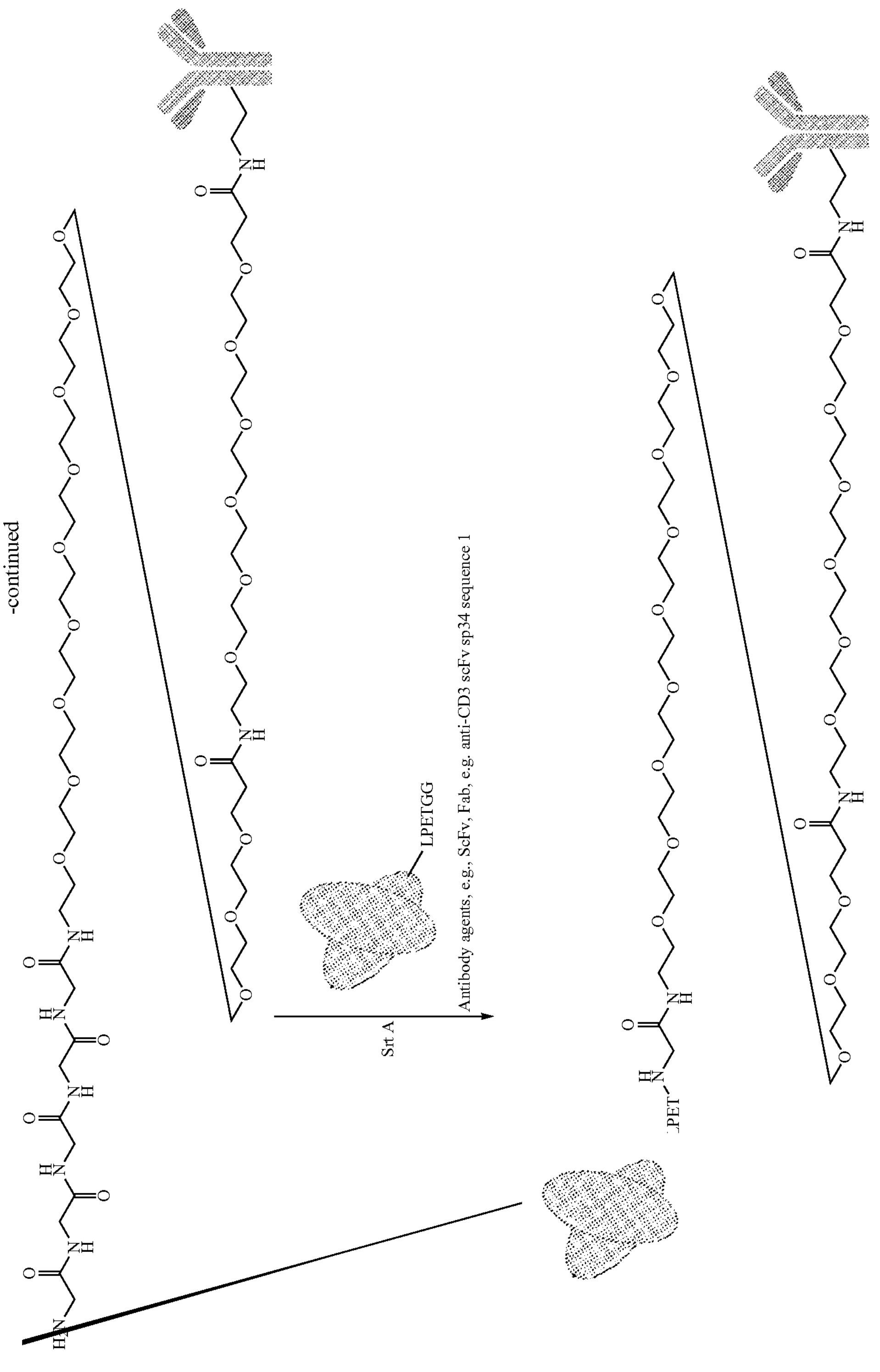

In some embodiments, a useful scheme is depicted below:

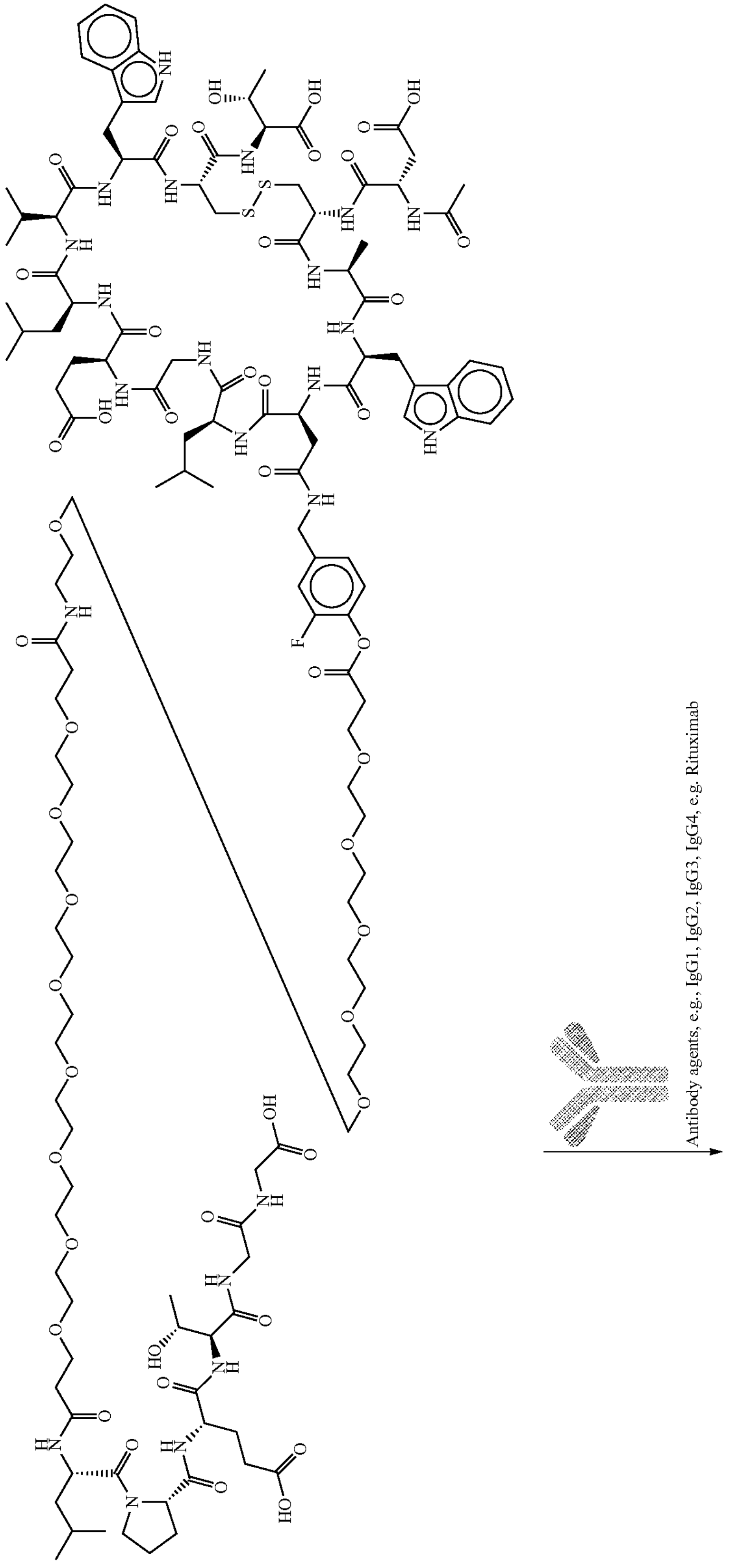
Antibody agents, e.g., IgG1, IgG2, IgG3, IgG4, e.g. Rituximab

-continued
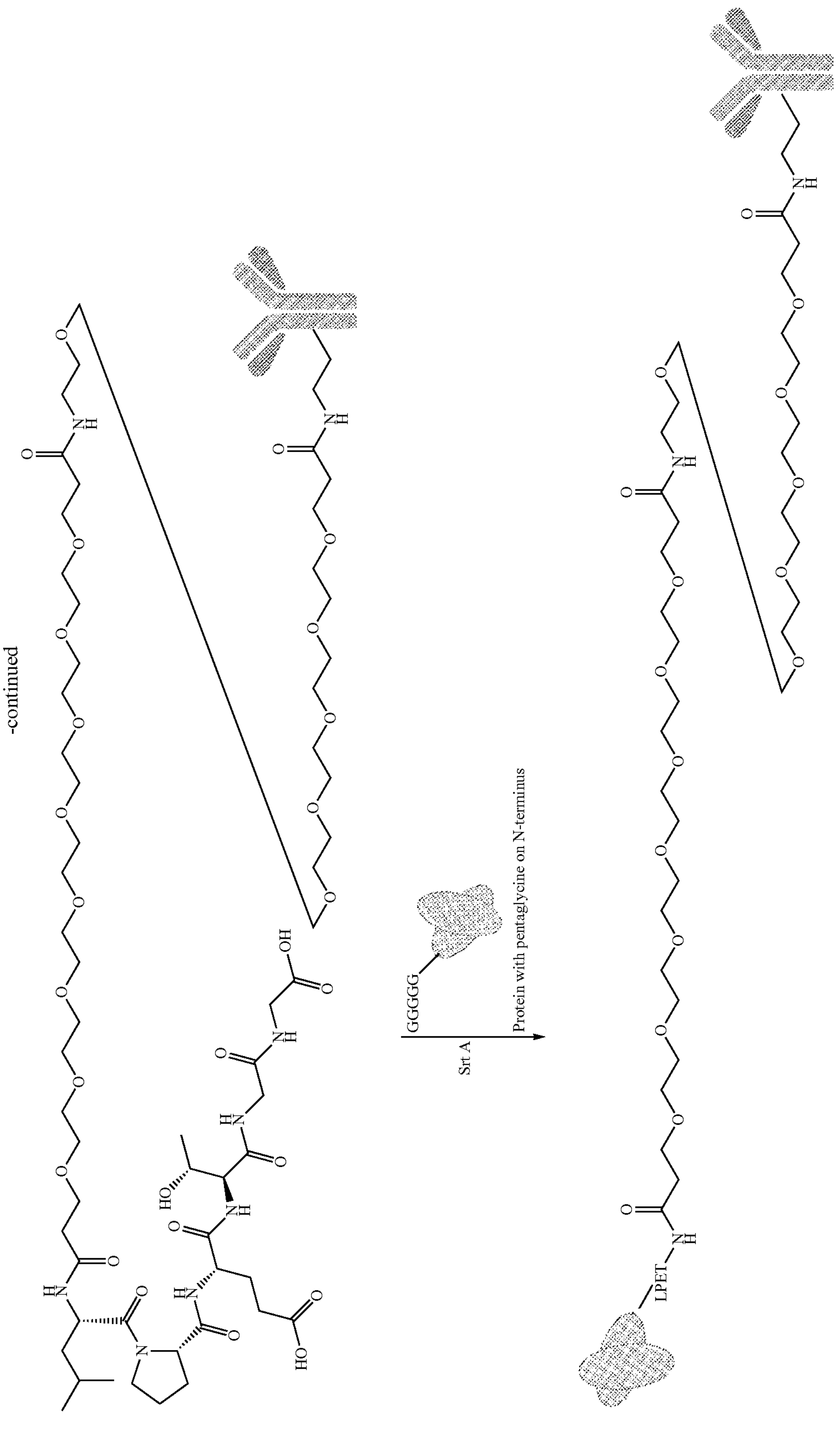

In some embodiments, a useful scheme is depicted below:
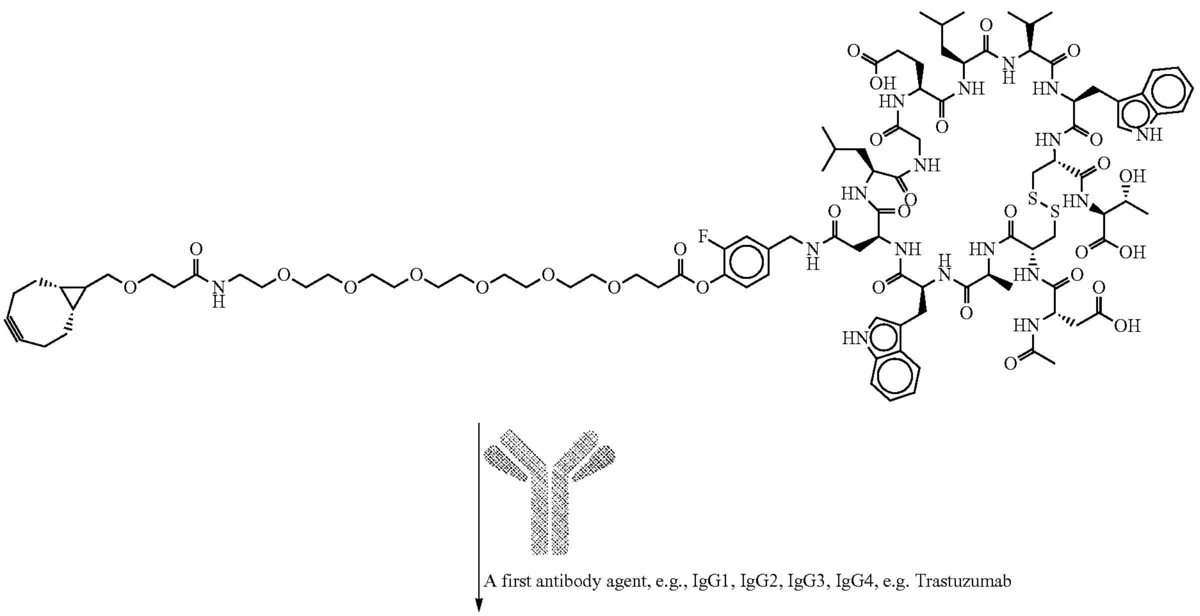
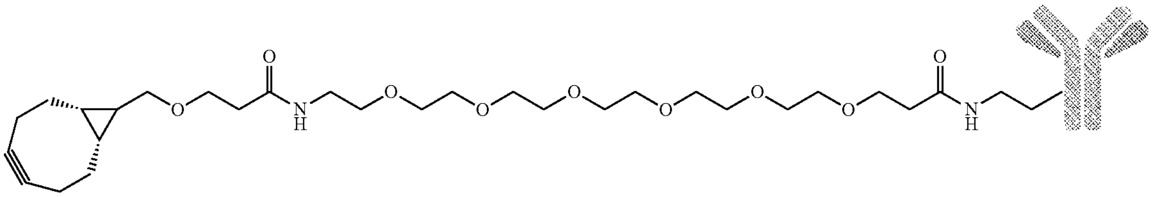
A first agent
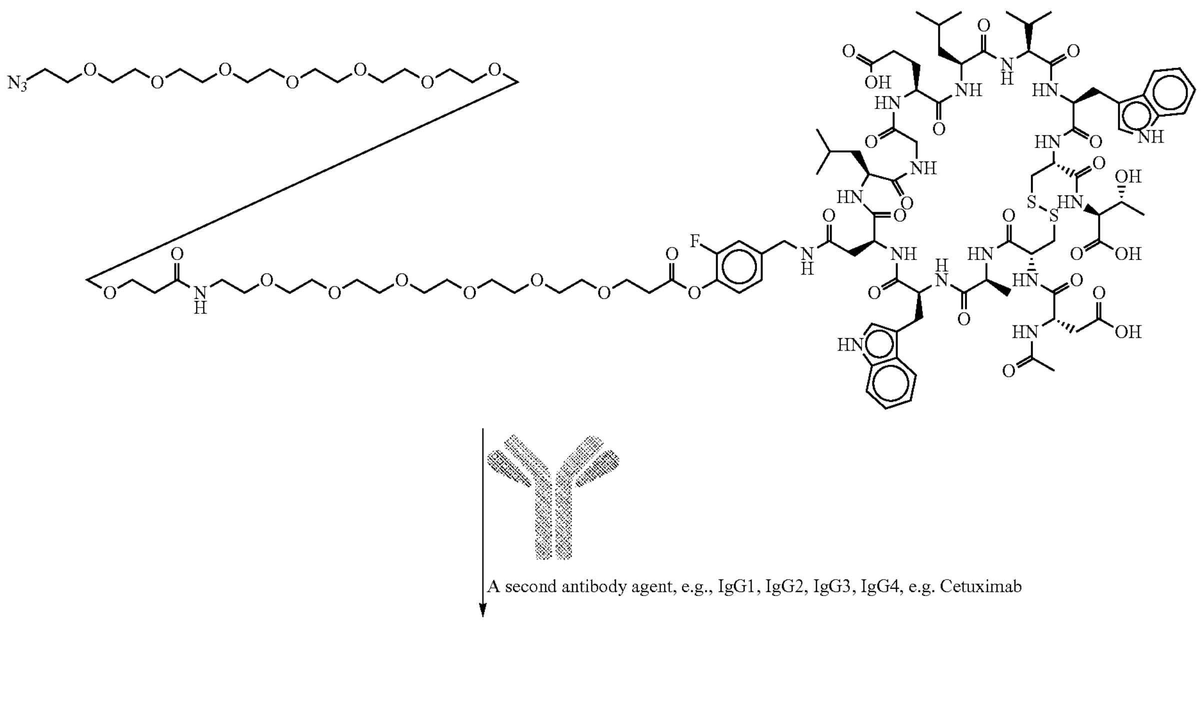

-continued

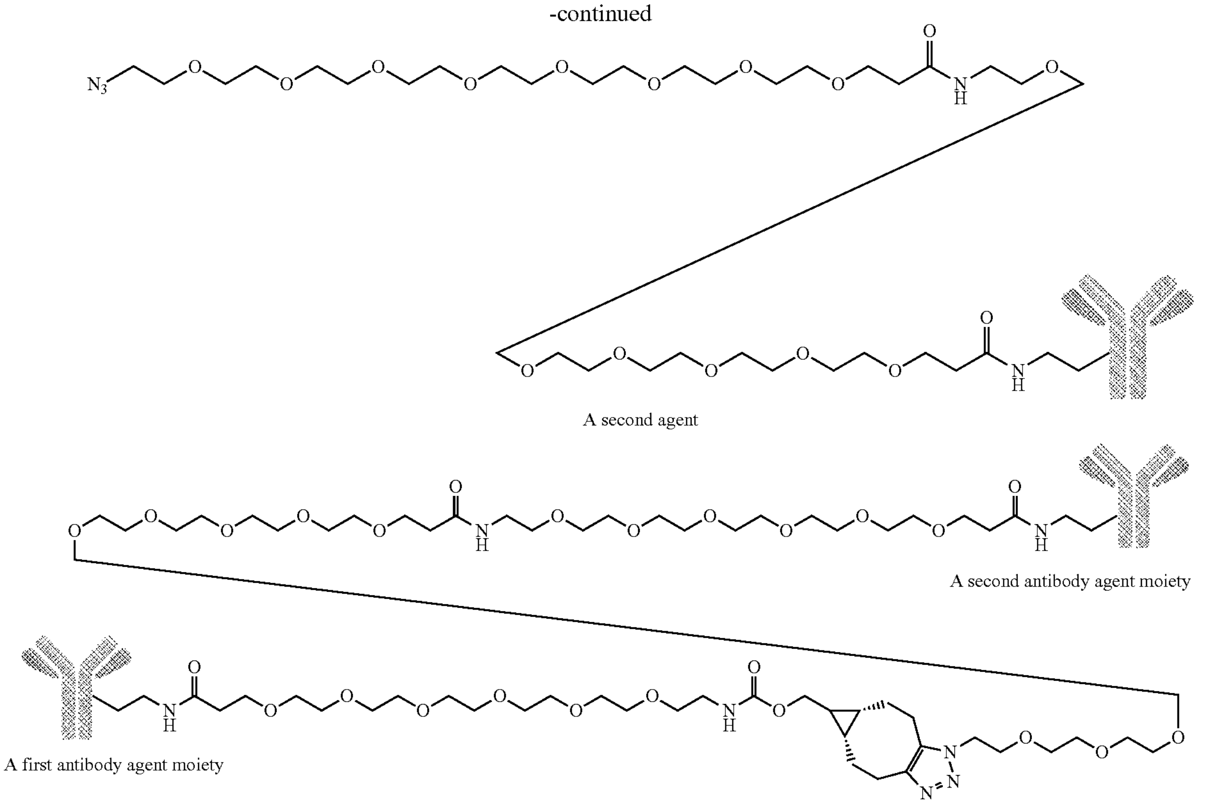

A second agent

A second antibody agent moiety

A first antibody agent moiety

Example of site-specific chemical conjugation of two antibodies (e.g. Trastuzumab-Cetuximab for dual EGFR-HER2 targetting)

In some embodiments, a first agent comprises a reactive moiety which is or comprises (G)n, wherein n is 1-10. In some embodiments, n is 3, 4, or 5. In some embodiments, a (G)n moiety comprises a free N-terminus amino group. A procedure for reparation of pentaglycine-tagged rituximab is described herein as an example. Rituximab (clinical grade) was diluted to 1 mg/mL in 50 mM borate buffer pH 8.2. 2.5 molar equivalents of I-53 was added and mixed thoroughly. The reaction was allowed to proceed for 20 h at 25 C with 800 RPM. The reaction was added to a 15-mL 10,000 MWCO Amicon spin column, and sterile phosphate buffer saline pH 7.4 was added to the top. The spin column was centrifuged for 30 minutes at 2800×g in a swinging bucket rotor. The spin column was then filled with sterile 100 mM Glycine buffer pH 2.7 and spun as above. Glycine buffer wash of pentaglycine-tag conjugated rituximab was repeated, and then solution was brought back to pH 7.4 with buffer exchange to PBS. In some embodiments, a reactive moiety, e.g., which is or comprises (G)n, may be incorporated when expressing an antibody agent.

In some embodiments, a second agent comprises a reactive moiety which is or comprises LPXTG, wherein X is an amino acid residue. In some embodiments, a second agent comprises a reactive moiety which is or comprises LPETG. In some embodiments, a second agent comprises a reactive moiety which is or comprises LPXTG-(X)n, wherein each X is independently an amino acid residue. In some embodiments, a second agent comprises a reactive moiety which is or comprises LPETG-(X)n, wherein each X is independently an amino acid residue. In some embodiments, n is 1-10. In some embodiments, n is 2-10. In some embodiments, n is 3-10. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, a reactive moiety which is or comprises LPXTG may be incorporated as a moiety of interest using a reaction as described herein (e.g., through reacting with suitable compound having the structure of R-I or a salt thereof). In some embodiments, a reactive moiety may be incorporated when expressing an antibody agent. In some embodiments, a second agent was expressed from cells. In some embodiments, a second agent is or comprises METDTLLLWVLLLWVPGSTGEVQLVESGGGLVQPGGSLKLSCAASGFTFNTYAMNWVRQAPG KGLEWVGRIRSKYNNYATYYADSVKGRFTISRDDSKNTLYLQMNSLRAEDTAVYYCVRHGNFG NSYVSWFAYWGQGTLVTVSSGGGGSGGGGSGGGGSQAVVTQEPSLTVSPGGTVTLTCGSSTGA VTTSNYANWVQQKPGQAPRGLIGGTNKRAPGVPARFSGSLLGGKAALTLSGAQPEDEAEYYCA LWYSNLWVFGGGTKLTVLGSEQKLISEEDLGSGGGGSLPETGGSHHHHHH (SEQ ID NO: 1) or a salt thereof. In some embodiments, a second agent is II-I, wherein II-I is a peptide whose sequence is SEQ ID NO: 1, or a salt thereof. In some embodiments, an agent, e.g., II-1, was expressed from expression vectors in HEK293 that was codon optimized under low endotoxin conditions. In some embodiments, affinity purification and size exclusion chromatography was utilized to obtain monomeric scFv for, e.g., MATE. Binding analysis was done using the Octet Data Analysis HT software. Processed data was globally fit to a 1:1 binding model for determination of the equilibrium dissociation constant ($K_d$).

Various technologies can conjugate a first and a second agents, e.g., through contacting a first and a second reactive moiety. In some embodiments, a reaction is an enzymatic reaction. In some embodiments, a reaction is promoted by a sortase. In some embodiments, a method comprises contacting I-53 or a salt thereof with II-I or a salt thereof in the presence of a sortase. In some embodiments, a product agent is a CD20×CD3 agent. In some embodiments, a product comprises a product linker moiety which is or comprises LPXTG. In some embodiments, a product comprises a product linker moiety which is or comprises LPXT(G)n, wherein n is as described herein. In some embodiments, a product comprises a product linker moiety which is or comprises LPETG. In some embodiments, a product comprises a product linker moiety which is or comprises LPET (G)n, wherein n is as described herein. In some embodiments, a produce agent, comprised to similar agent prepared otherwise, provides a number of benefits such as maintenance of properties/activities of antibody agent moieties, low levels of damages to antibody agent moieties (e.g., in some embodiments due to fewer steps and/or milder reaction conditions), homogeneity, site-specificity, linkers of various properties/activities (e.g., those that cannot by provided by natural amino acid peptide linkers), etc. In some embodiments, antibody agent moieties maintain various functions, e.g., binding to targets, biding to FcRs (e.g., via Fc domain), etc. In some embodiments, antibody agent moieties maintain activities, e.g., Fc effector mechanisms like ADCC, ACDP, etc. In some embodiments, incorporation of a second type of antibody agent moieties introduce additional properties and/or activities, e.g., T cell-mediated immune activities (e.g., T cell-mediated cytotoxicity, target-dependent T cell activation and recruitment, etc). In some embodiments, agents comprising multiple types of antibody agent moieties provide increased activities relative to one or more or all individual type of antibody agent moieties, e.g., in some embodiments, increased killing of target cells such as cancer cells. A procedure for conjugation is described below as an example.

Figure 17:
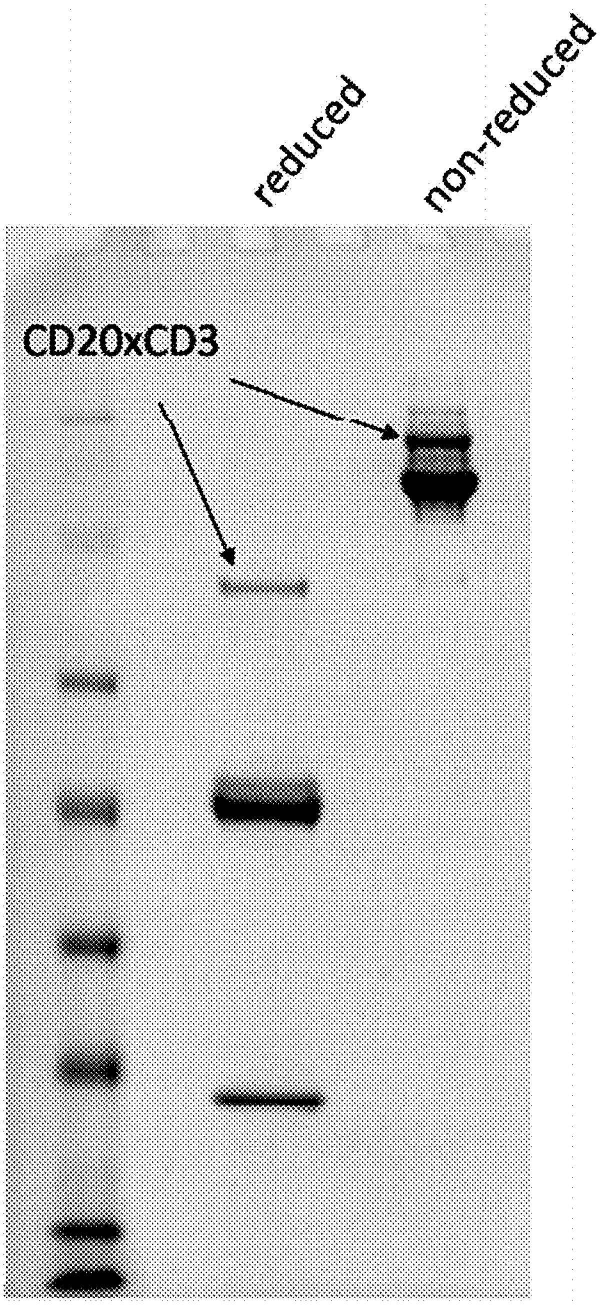
FIG. 17. SDS-PAGE of chemically conjugated product III-1 (CD20×CD3) reduced and non-reduced.
Figure 18:
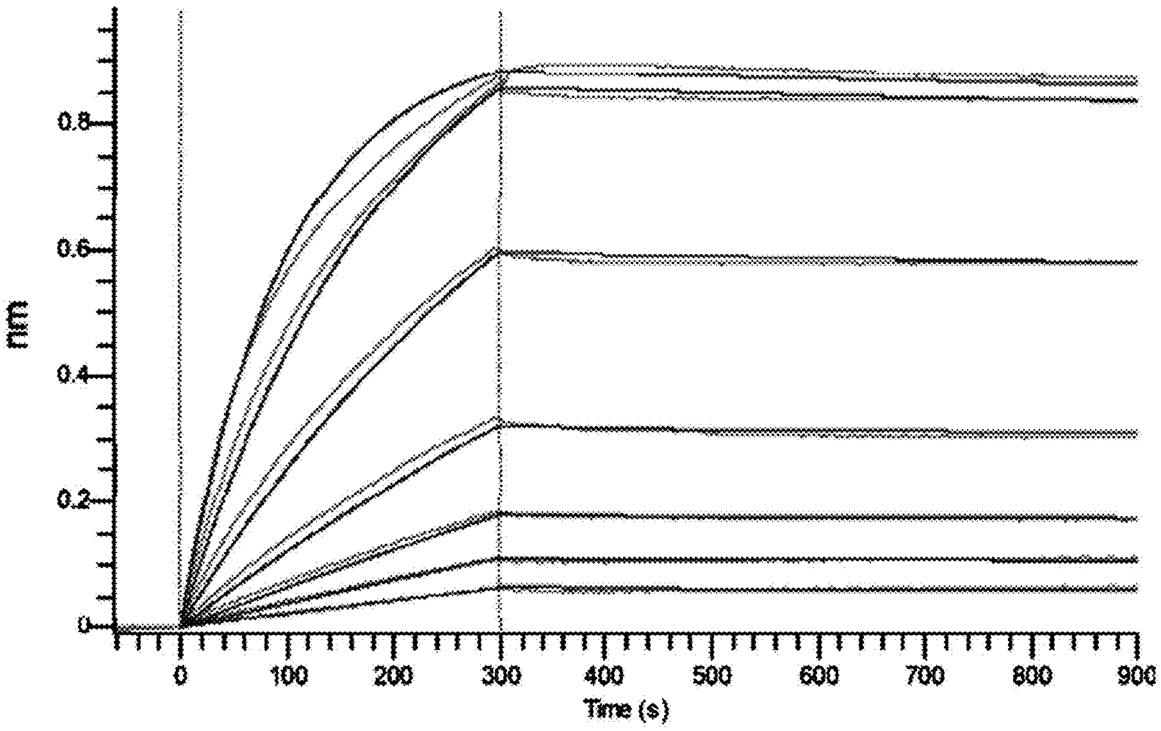
FIG. 18. Provided agents comprising multiple antibody agent moieties maintain properties and/or activities of individual antibody agent moieties. For example, III-1 (CD20×CD3) can bind to CD20 with high affinity. Shown are Octet assay data as examples. $K_d$=1.06 nM. $R^2$=0.9983.
Figure 19:
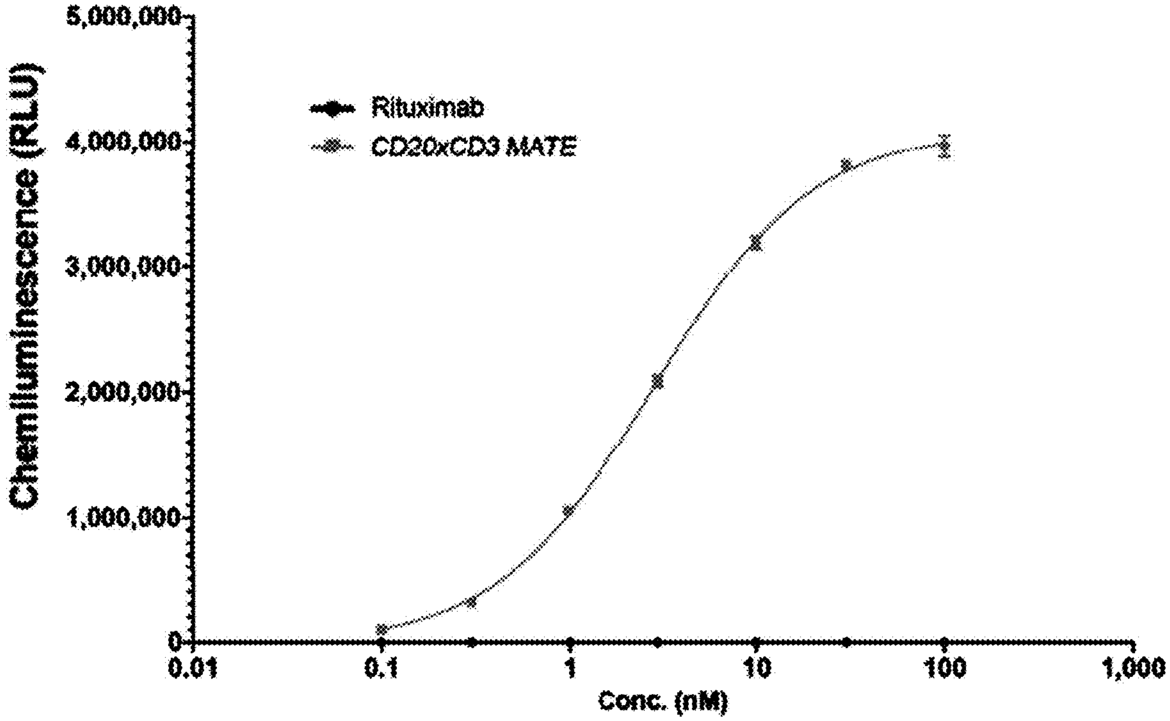
FIG. 19. Provided agents comprising multiple antibody agent moieties can provide additional properties and/or activities compared to individual antibody agent moieties. For example, III-1 (CD20×CD3) can gain binding to CD3, which can be a component of T-cell receptor complex. Among other things, incorporation of CD3 can provide antibody function responsible for T-cell recruitment and activities. Shown are certain data from ELISA assay.
Figure 20:
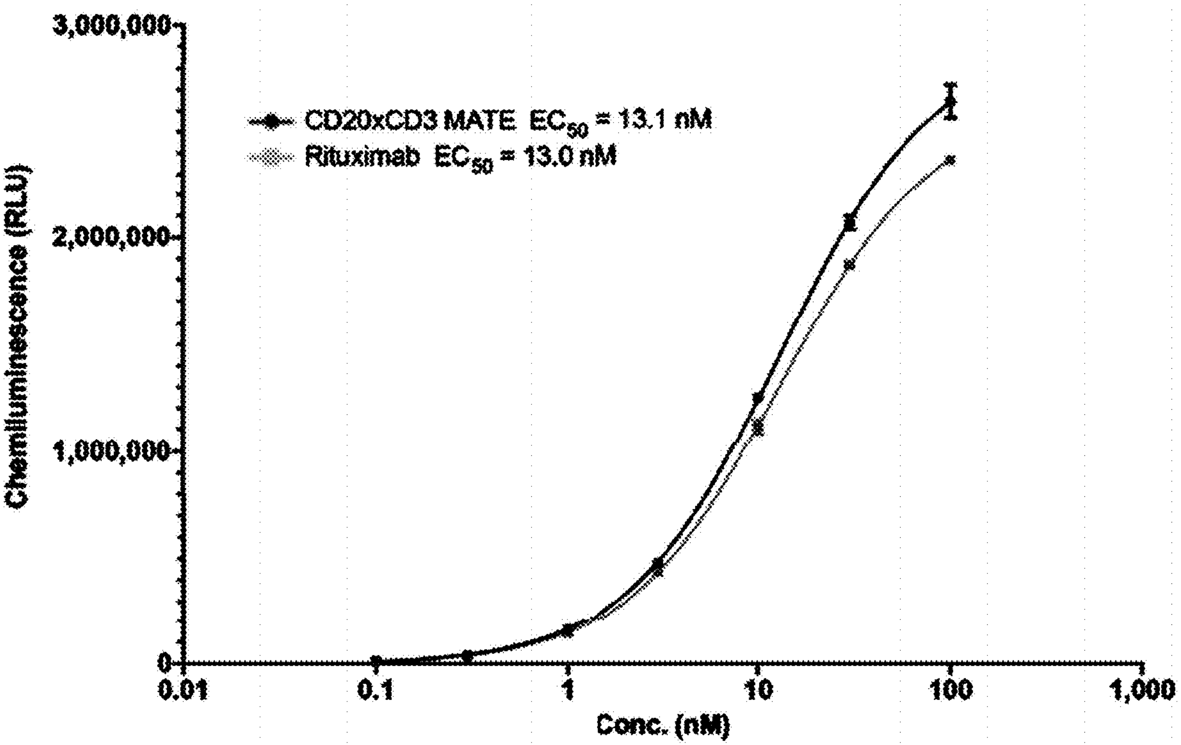
FIG. 20. Provided agents comprising multiple antibody agent moieties maintain properties and/or activities of individual antibody agent moieties. For example, III-1 (CD20×CD3) maintains its binding to CD16 Fc receptor (CD16a-V158), and its function responsible for NK cell recruitment. Shown are ELISA data.
Figure 21:
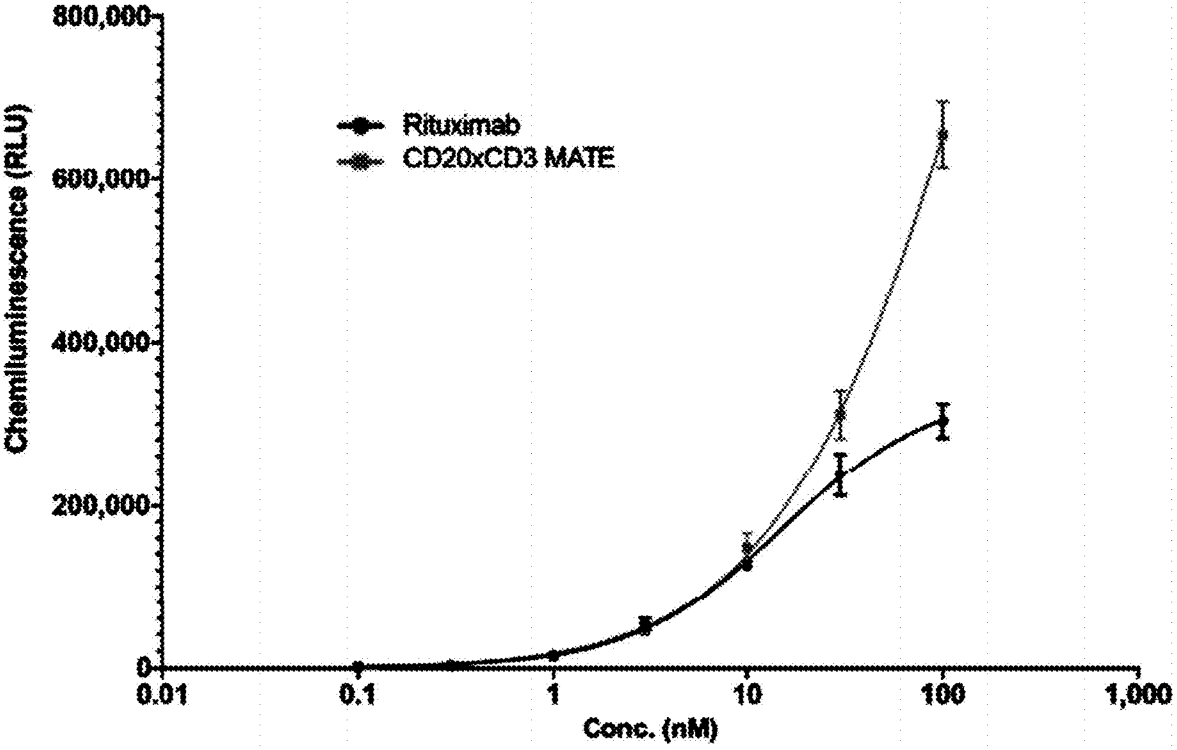
FIG. 21. Provided agents comprising multiple antibody agent moieties maintain or improve properties and/or activities of individual antibody agent moieties. For example, III-1 (CD20×CD3) maintains or even improved its binding to FcRn Fc receptor, indicating that antibody recycling mechanism is maintained.

Conjugation of anti-CD3 scFv to rituximab. Sortase reaction used Active Motif Recombinant Sortase A5 pentamutant enzyme to add SP34 ScFv. 2.5 molar equivalents of scFv was added to conjugated rituximab with I-53 (see above). 5 molar equivalents of $NiCl_2$ was added to the mixture to yield 2:1 $Ni^{2+}$ to scFv. $CaCl_2$ was added to 1 mM. 250 ug of Sortase A5 was added per 6 mg labeled rituximab (3 mg scFv). Reaction ran for 1 h at 30° C. with 800 RPM. Reaction was stopped with 50 mM EDTA. Sample was purified by size-exclusion chromatography to provide compositions of rituximab×SP34 scFv (III-1). In some embodiments, a product agent composition may comprises certain levels of unreacted first and/or second agents. For example, in some embodiments, a product agent composition comprises rituximab in addition to rituximab conjugated with SP34 ScFv. Certain results were illustrated in FIG. 17. Sample were run on a 4-12% NuPAGE gel at 150 V for 1.5 hours in MOPS running buffer, then stained with Coomassie Blue. The reduced lane shows unconjugated light chain (~30 kDa) and heavy chain (~50 kDa), and CD20×CD3 (rituximab×SP34 scFv, III-1) at ~80 kDa. The non-reduced lane shows unconjugated rituximab (lower band) and CD20×CD3 (upper band). In some embodiments, product agents were utilized without removal of rituximab that is not conjugated to SP34 ScFv (e.g., in various assay results described below).

Provided agents comprising more than one antibody agent moieties, e.g., CD20×CD3 agents (e.g., rituximab×SP34 scFv described above), may be assessed utilizing various suitable technologies in accordance with the present disclosure, both in vivo and in intro. Certain assays are described below.

In some embodiments, binding of CD20 to rituximab×SP34 scFv (III-1) was assessed and confirmed by Bio-Layer Interferometry using Octet (Fortebio). Binding assays were performed using Protein A biosensors. The binding of CD3εδ, CD16a, and FcRn were determined by ELISA using neutravidin-coated plates. Biotinylated Human CD3ε & CD3δ heterodimer protein (Avi tag), CD16a (Avi Tag) and human CD16a were used. Readout was determined with anti-human F(ab) HRP.

In some embodiments, an assay is in vitro T cell-mediated cytotoxicity assay. In some embodiments, unfractionated and NK-cell depleted PBMCs were prepared from freshly-thawed and PHA+IL-2 prestimulated PBMCs. Daudi ($CD38^+$) B lymphoblast cells were engineered to stably express a beta-gal reporter fragment using KILR retroparticles (Eurofins). Target cells were treated with III-1, rituximab, and controls. PBMCs were introduced at an effector: target ratio of 15:1 and incubated for 18 h. Luminescence signal was obtained with luminometer to reflect target cell death.

In some embodiments, provided technologies were assessed in animal models. In some embodiments, Cynomolgus monkeys were intravenously injected with rituximab or III-1 (30 ug/kg). Endpoints included clinical observations, cytokine profile and flow cytometric immunophenotyping of T cells, monocytes, granulocytes, NK cells, and B cells (CD45, CD3, CD16, CD14, NKG2A, HLA DR) and cellular activation (CD44 and CD69).

In some embodiments, the present disclosure provides data confirming various properties and/or activities of agents comprising multiple antibody agent moieties, e.g., bispecific agents. For example, in some embodiments, the present disclosure provide data confirming that after conjugation antibody agent moieties can still effectively bind their targets. In some embodiments, it was observed that binding affinity of CD20 to III-1 was 0.75 nM. CD20 binding to rituximab and III-1 was similar, thus conjugation of the CD3-binding ScFv did not negatively affect affinity to CD20. ELISA results showed III-1 binds to CD3εδ, FcRn, and CD16a, indicating that the conjugation does not interfere with binding to their various moieties.

In some embodiments, the present disclosure provides data, e.g., in vitro T cell-mediated cytotoxicity results, which showed activity of Fc/FcR and CD20 binding by the rituximab moiety versus CD3 binding to effector T cells. In some embodiments, T cell enrichment by functionally prestimulating PBMCs increased killing of target cells by 2-fold. In some embodiments, mechanically depleting NK cells indicated that target cell death was induced by T cells, and may not or to a relatively lesser extent by NK cells via ADCC. In some embodiments, it was observed that III-1 elicited target cell killing with an $EC_{50}$ of 0.03-0.07 nM or 0.09-021 nM for prestimulated or freshly thawed PBMCs, respectively.

Various properties and/or activities of provided agents were also confirmed in animal models. In some embodiments, studies in Cynomolgus monkeys showed that III-1 can activate immune cells, e.g., T cells in vivo as shown by, e.g., increased CD69 and CD44 expression (in some embodiments, 3- and 2-fold observed, respectively) with a peak at, in some cases, 4 h post-dose compared to equivalent dose rituximab. In some embodiments, a pronounced depletion of B cells was observed in III-1 treated animals as early as half an hour post-dose, with a partial recovery by days 7-14, while an equivalent dose of rituximab induced a transient B-cell depletion followed by a quicker return to baseline levels.

Among other things, the Example confirms that present disclosure can provide agents comprising multiple types of antibody agent moieties, e.g., bispecifics such as III-1, by, for example, chemical conjugation of CD3-specific ScFv to "off-the-shelf" rituximab using provided technologies, e.g., MATE™ technology. As confirmed herein, provided technologies can maintain and/or improve properties and/or activities (e.g., target binding, immune activities, etc.) of individual antibody agent moieties. For example, III-1 can maintain binding of rituximab to FcRs via its Fc domain and its binding to CD20 on target cells, and can retain rituximab native ability to target B lymphoid malignancies via Fc effector mechanisms like ADCC and ADCP. Provided technologies, by conjugation of more than one types of antibody agent moieties, can provide additional properties and/or activities, e.g., additional immune activities such as T-cell mediated cytotoxicity. For example, III-1 can provide T cell-mediated cytotoxicity. Among other things, certain in vitro data shows increased target cell killing by III-1 compared to rituximab, and in vivo study confirms that III-1 can induce target dependent T cell activation and recruitment, making it superior to unconjugated rituximab. CD3 conjugates generated with other antibody agents show similar increased T cell-mediated cytotoxicity, confirming that provided technologies can be applied to generate improved agents, including from "off-the-shelf" antibodies.

As those skilled in the art appreciate, various technologies are available for assessing provided compositions and methods. Certain data from such technologies are provided in FIG. 18, FIG. 19, FIG. 20 and FIG. 21 as examples. In some embodiments, provided technologies are assessed in animals. Certain examples were described below.

In some embodiments, animals are naive purpose bred female cynomolgus monkeys ((*Macaca fascicularis*) 2-3 years old at dosing. In some embodiments, two animals per group received an intravenous (slow bolus) injection of either rituximab 30 ug/kg or III-1 (30 ug/kg). In some embodiments, blood was collected at intervals as indicated below.

Immunophenotyping Sample Collection

| Sample Collection Time Points | | |
|---|---|---|
| Group Nos. | Study Day/Week | Time Points (Relative to Dosing) |
| 1 and 2 | Day 1 | Pre; 0.5 hr, 2 hr, 4 hr, and 8 hr post |
| | Day 2 | Day 1, 24 hr post |
| | Day 7 | — |
| | Day 15 | Pre; 0.5 hr, 2 hr, 4 hr, and 8 hr post |

Immuno-phenotyping was performed by staining with fluorescently labeled antibodies, including:

| Marker | Color | clone |
|---|---|---|
| CD45 | APC-R700 | D058-1283 |
| CD14 | BV605 | M5E2 |
| CD3 | PeCy7 | SP-34-2 |
| CD16 | BV421 | 3G8 |
| NKG2A | APC | REA110 |
| CD44 | FITC | IM7 |
| CD69 | PE | FN50 |
| HLA DR | BV786 | G46-6 |

-continued

In some embodiments, T cells and B cells were identified according to the gating strategy outlined below. In some embodiments, T cells were identified as CD45+CD3+. In some embodiments, T cell activation was marked by CD69 and CD44. In some embodiments, B cells were identified as CD45+CD3−CD14−NKG2A−HLADR+. In some embodiments, absolute numbers and frequency of immune cell subsets was monitored. In some embodiments, as comparison, human PBMCs were treated in vitro for 18 hrs and identified as $CD19^+$, and percent of PBMCs was calculated. In some embodiments, blood was collected and plasma was obtained for cytokine analyses at intervals according to the below:

Cytokine Sample Collection

| Sample Collection Time Points | | |
|---|---|---|
| Group Nos. | Study Day/Week | Time Points (Relative to Dosing) |
| 1 and 2 | Day 1 | Pre; 0.5 hr, 2 hr, 4 hr, and 8 hr post |
| | Day 2 | Day 1, 24 hr post |
| | Day 7 | — |
| | Day 15 | Pre; 0.5 hr, 2 hr, 4 hr, and 8 hr post |

Figure 29A:
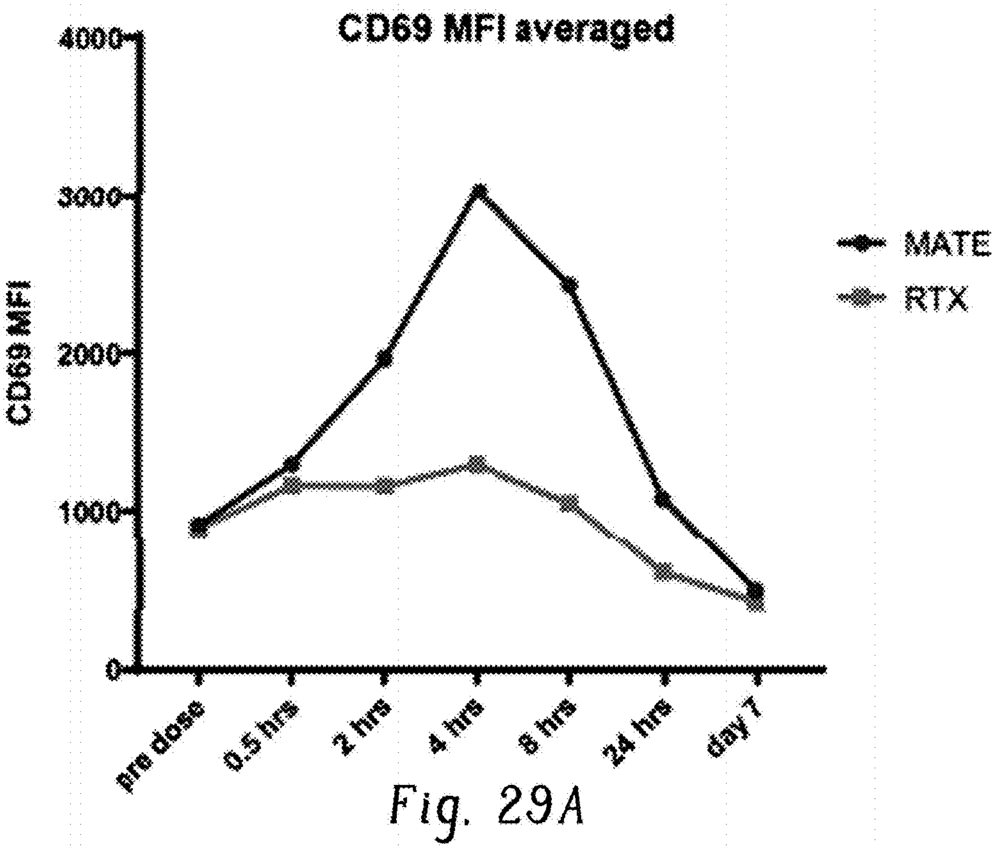
FIG. 29. Provided technologies can provide scFv-antibody conjugates with high activities. For example, a CD3 (scFv)-rituximab conjugate can activate T-cells (A) with minimal IL6 (B) increase, and can be up to 10× more potent in B-cell depletion (C).
Figure 29B:
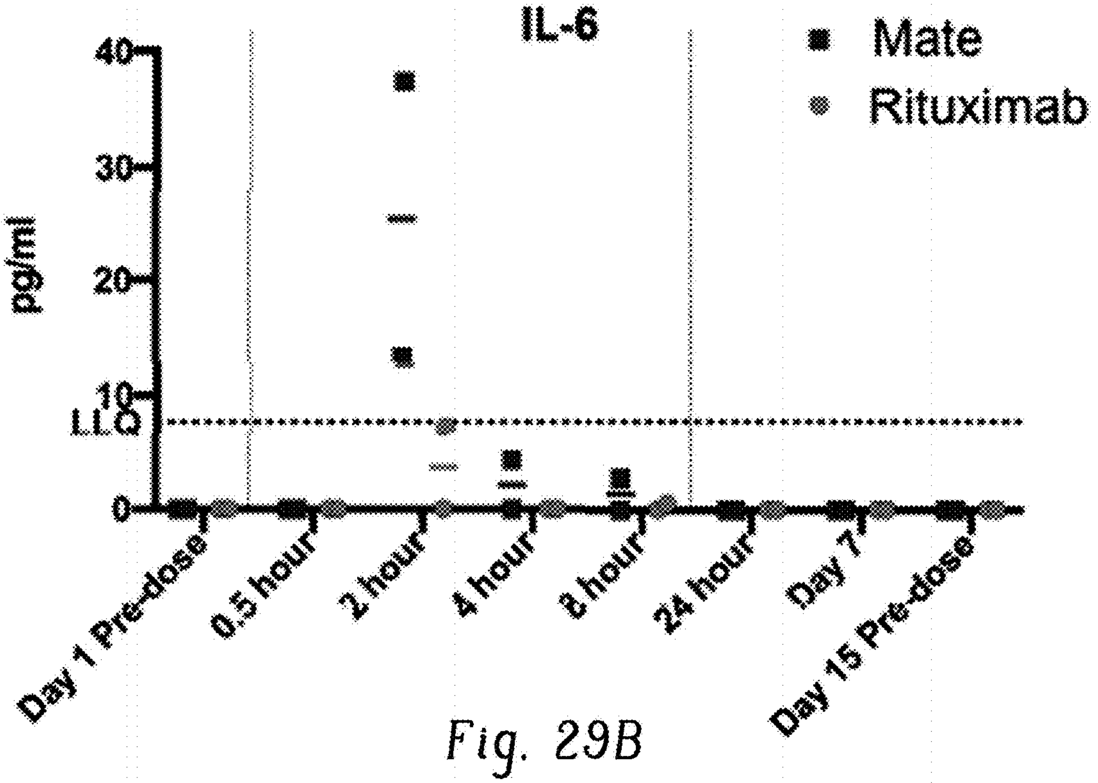
Figure 29C:
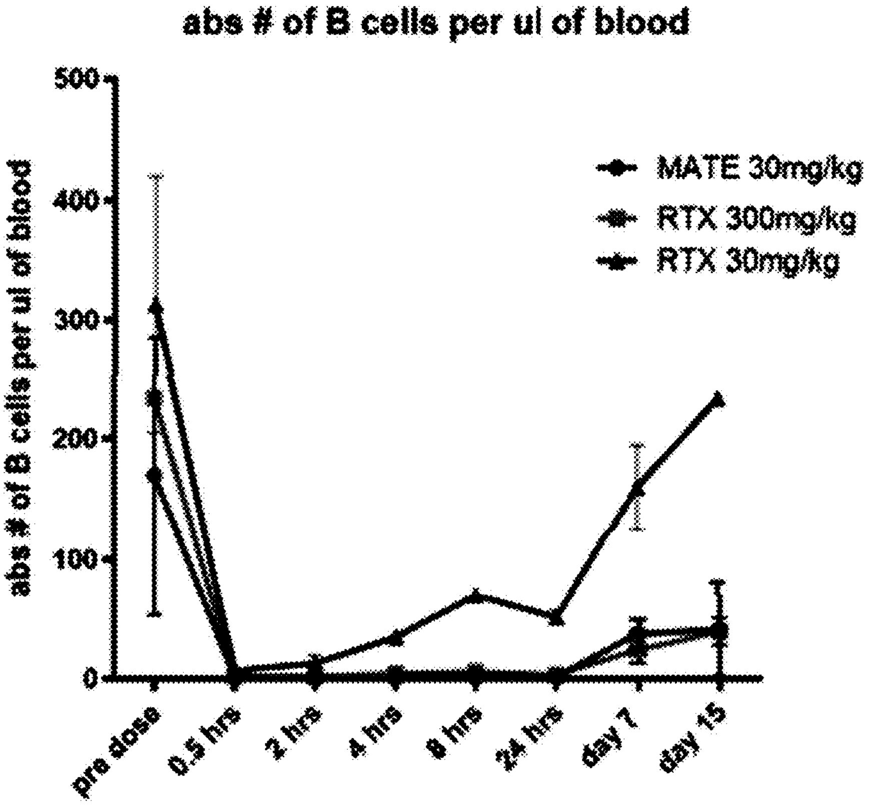
Figure 33A:
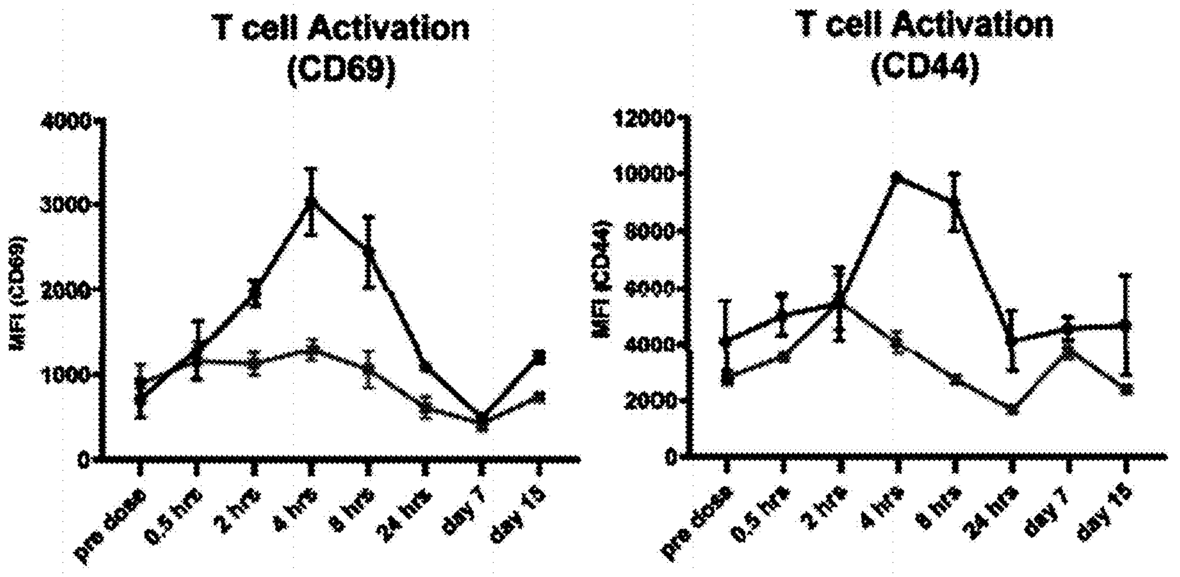
FIG. 33. Provided technologies can provide activities with minimal increase of pro-inflamatory cytokines/chemokines levels in vivo. (A): T cells were identified as $CD45^+CD3^+$, and activation was marked by CD69 and CD44. (B): B cells were identified as $CD45^+CD3^-CD14^-NKG2A^-HLADR^+$. Absolute numbers and frequency of immune cell subsets were monitored. As comparison, human PBMCs were treated in vitro for 18 hrs and identified as $CD19^+$, and percent of PBMCs was calculated. (C): Select levels of cytokines/chemokines.
Figure 33B:
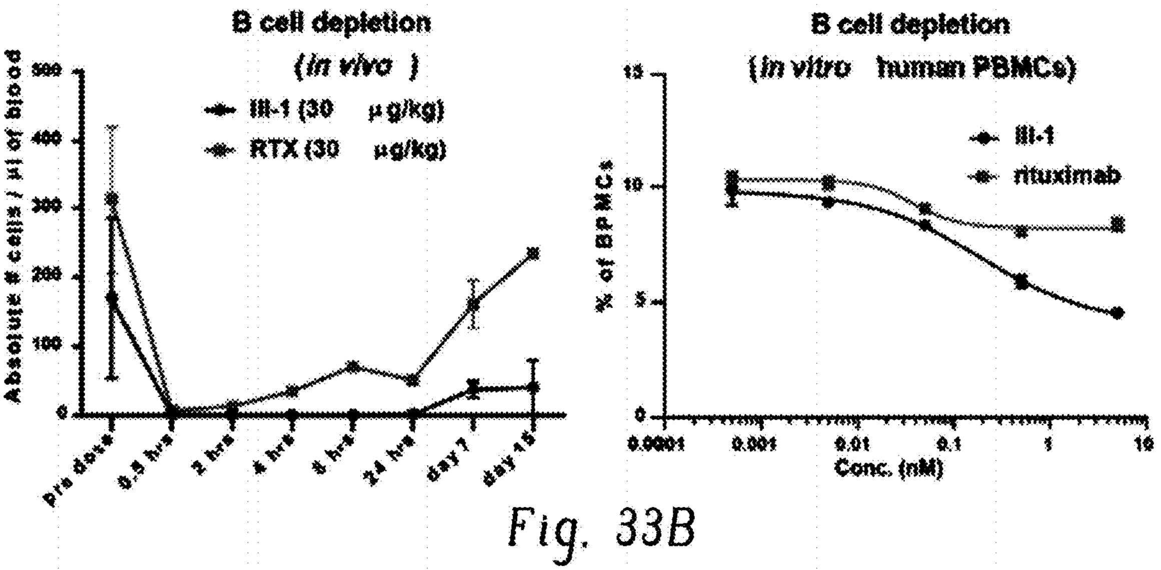
Figure 33C:
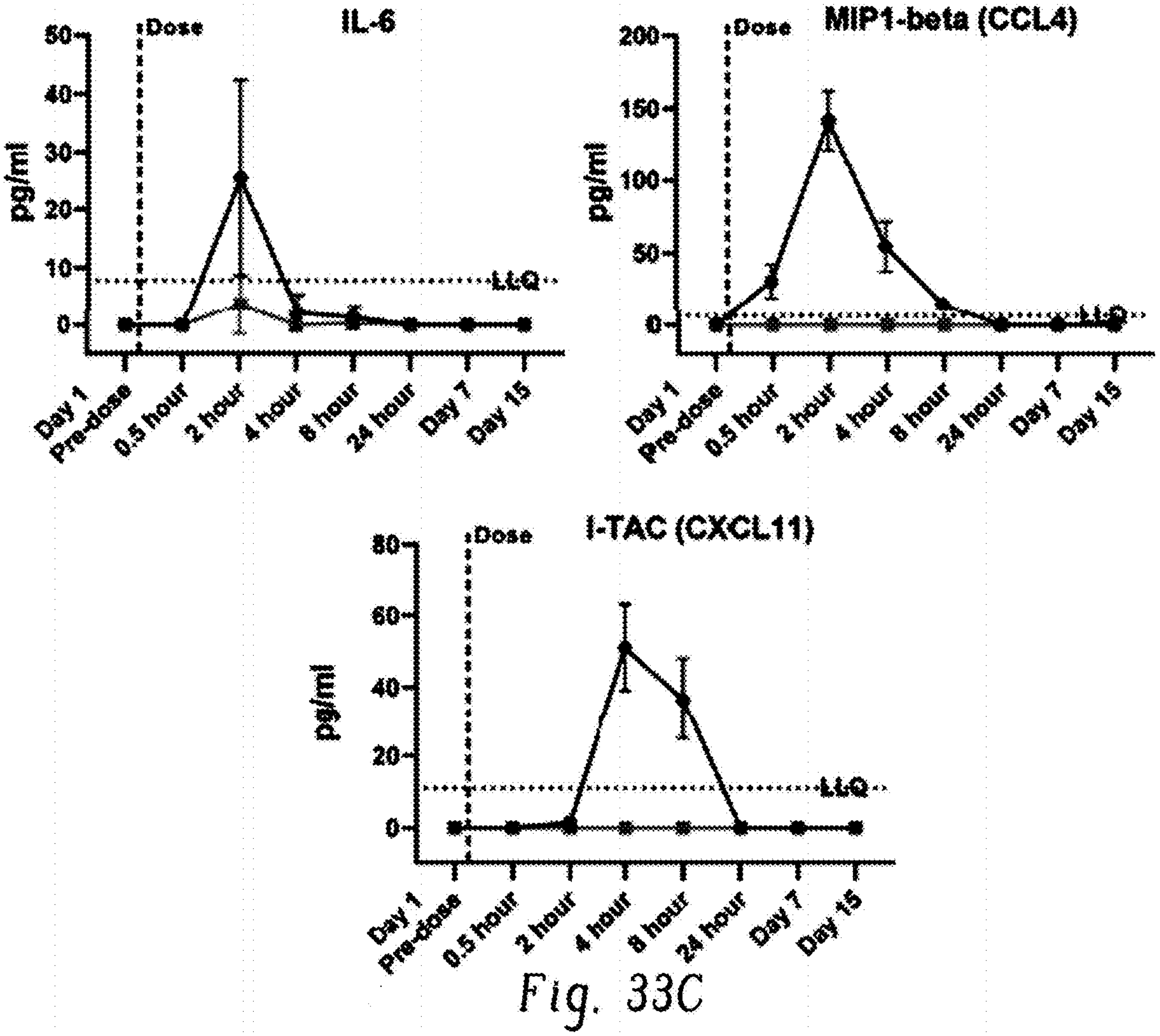

In some embodiments, cytokine multiplex panel for non-human primates (ThermoFisher) was used to determine the levels of inflammatory cytokines and chemokines. As confirmed in FIG. 29 and FIG. 33, provided technologies can activate immune activities (e.g., T-cells) with minimal increase of levels of cytokines/chemokines (e.g., IL6) and can provide improved potency (e.g., 10 fold or more) in target (e.g., B-cell) depletion (e.g., Mate (III-1) compared to rituximab (RTX)). In some embodiments, it was observed that III-1 increased CD69 and CD44 expression (3- and 2-fold, respectively) with a peak at 4 h post-dose compared to equivalent dose RTX. In some embodiments, it was observed that a pronounced depletion of B cells was observed in III-1-treated animals as early as 0.5 hour post-dose, in some embodiments, with a partial recovery by days 7-14. In some embodiments, for human PBMCs, III-1 also induced B cell depletion in vitro. In some embodiments, an equivalent dose of RTX induced a transient B-cell depletion followed by a quicker return to baseline levels. In some embodiments, III-1 induced a minimal increase in IL-6. In some embodiments, III-1 may provide T cell activation and augmented depletion of B cells without inflammatory toxicity to animals. In some embodiments, III-1 induced CCL4 and CXCL11. In some embodiments, III-1 may activate T cells promoting chemotactic activity of effector cells (i.e. monocytes, NK cells).

Figure 30A:
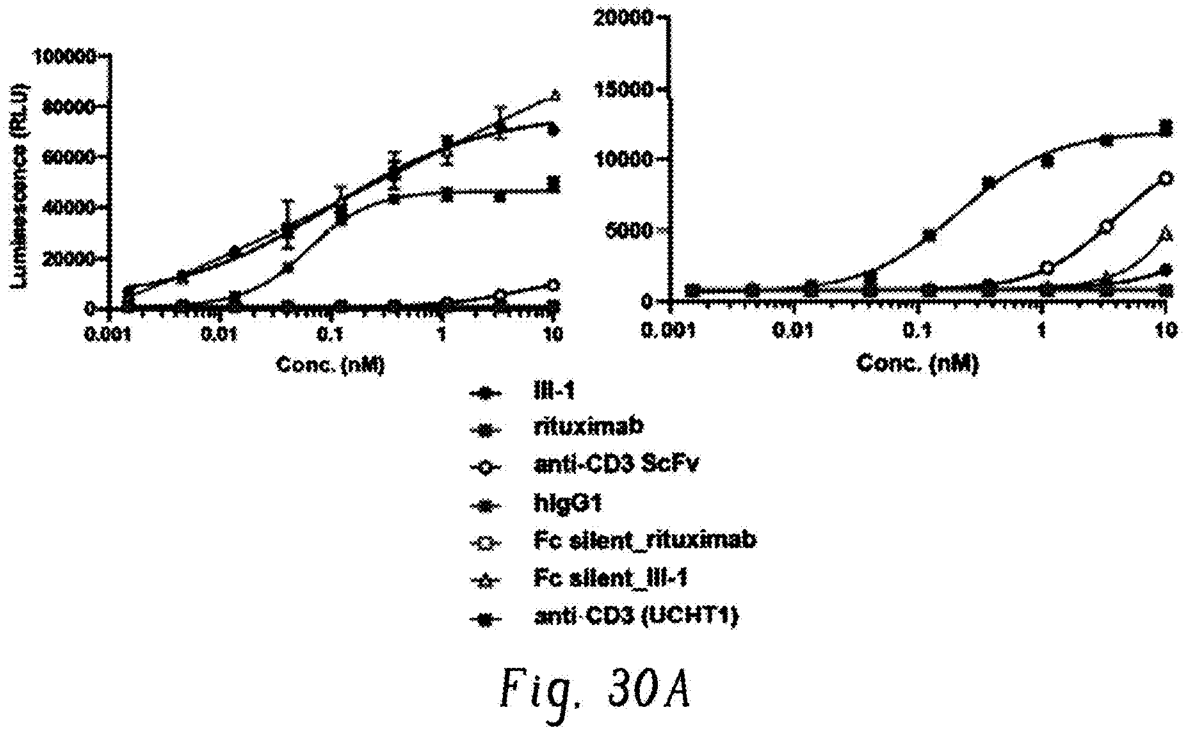
FIG. 30. Provided technologies can activates various effector cells. In some embodiments, as shown in FIG. 30 III-1 can activate PBMC effector cells. (A): In some embodiments, to measure T cell receptor (TCR)/CD3 engagement and T cell activation, effector Jurkat cells stably expressing NFAT-RE upstream of luciferase were used. Activation was measured by luminescence. For effector+target, EC50 is 0.10 nM for III-1, and 0.56 nM for Fc silent III-1. For effector only, EC 50 is >10 nM for both III-1 and Fc silent III-1. (B): In some embodiments, PBMCs were stained with fluorescently-labeled anti-human antibodies specific for CD2, CD56, CD14, and CD19, and PBMC subpopulations were analyzed for CD69 activation marker by flow cytometry.

In some embodiments, III-1 induces functional activation of effector cells. In some embodiments, T cells or PBMCs were treated with varying concentrations of III-1, mAbs, scFv, or control MATE. Effector cells were cultured with or without $CD20^+$ Daudi target cells. In some embodiments, to measure T cell receptor (TCR)/CD3 engagement and T cell activation, effector Jurkat cells stably expressing NFAT-RE upstream of luciferase were used. Activation was measured by luminescence. In some embodiments, PBMCs were stained with fluorescently-labeled anti-human antibodies specific for CD2, CD56, CD14, and CD19, and PBMC subpopulations were analyzed for CD69 activation marker by flow cytometry. In some embodiments, III-1 induced target cell dependent (100-fold higher) activation of T cells. In some embodiments, III-1 functions as a bispecific molecule that recruits and activates effector T cells to kill CD20+ tumor cells. In some embodiments, III-1 induced target cell-dependent activation of T cells, in some embodiments, with co-stimulation by accessory immune cells in a dose-dependent manner. In some embodiments, RTX alone did not induce any activation of PBMC effector cells in vitro. Certain data were provided in FIG. 30. In some embodiments, useful protocols for assessing provided technologies are described below.

Daudi B lymphoblast cells were plated at $1.0\times10^4$ cells/well of a 96-well round-bottom white-walled plate and treated with varying concentrations of III-1, control MATE (anti-CD3 scFv conjugated to Fc silent rituximab (e.g., Ab00126-10.3 Anti-CD20 [10F381 (rituximab)] from Absolute Antibody), "Fc silent III-1"), anti-CD3 single-chain variable fragment (scFv), or control monoclonal antibodies diluted in assay media (RPMI, 10% fetal bovine serum, 100 U/mL Penicillin-Streptomycin). Alternatively, test agents were added to assay media containing no Daudi cells ("Effector only" condition). Both conditions were incubated for 30 min. at 37° C. A genetically engineered Jurkat T cell line (Promega #J1621) expressing a luciferase reporter driven by an NFAT-response element (NFAT-RE) was introduced at an effector:target ratio of 8:1 (or equivalent number of T cells for no Daudi condition) and incubated for 18 hrs. Bio-Glo reagent was added to each well per manufacturer's recommendations (Promega). Luminescence signal was obtained with luminometer to reflect the induction of NFAT, and T cell activation was calculated utilizing GraphPad Prism software.

Daudi cells were plated at $1.0\times10^4$ cells/well of a 96-well round-bottom plate and treated with varying concentrations of III-1 or rituximab diluted in assay media (RPMI, 5% Low IgG bovine serum, 100 U/mL Penicillin-Streptomycin). Alternatively, test agents were added to assay media containing no Daudi cells. Both conditions were incubated for 30 min. at 37° C. Freshly thawed PBMC effector cells were introduced at an effector:target ratio of 20:1 (or equivalent number of PBMCs for no Daudi condition) and incubated for 18 hr. Cells were harvested and stained with fluorescently-labeled anti-human antibodies specific for CD2, CD56, CD14, and CD19, and PBMC subpopulations were analyzed for CD69 activation marker by flow cytometry.

Figure 31B:
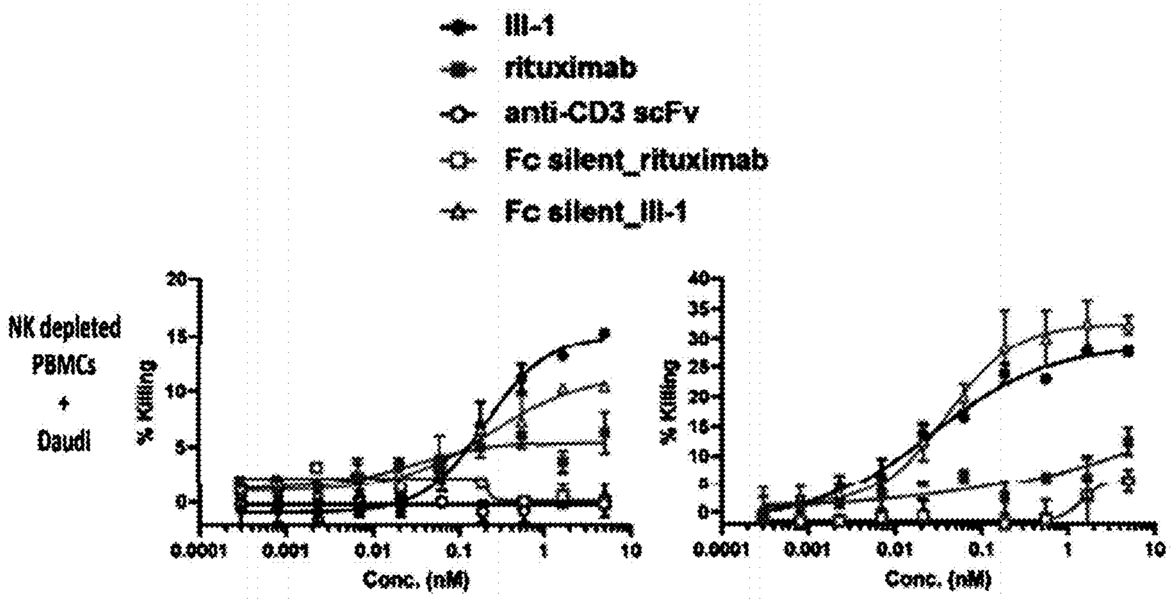
FIG. 31. Provided technologies can effectively kill target cells such as cancer cells. (A): Daudi ($CD20^+$) B lymphoblast cells were engineered to stably express a beta-gal reporter fragment using KILR retroparticles (Eurofins DiscoverX). Target cells were treated with III-1, rituximab, and relevant controls at varying concentrations. Effector cells from unfractionated and NK cell-depleted PBMCs were prepared from freshly-thawed or PHA+IL-2 prestimulated (5 days) PBMCs. Cells were cultured at an effector:target ratio of 15:1 and incubated for 18 hrs. Luminescence signal was obtained with luminometer to reflect target cell death. (B): A-431 ($EGFR^+$) epidermoid carcinoma cells were treated with varying concentrations of cetuximab (CTX)-CD3 MATE, control mAbs, or scFv. Target cell death was measured using CytoTox-Glo reagent (Promega).
Figure 31B:
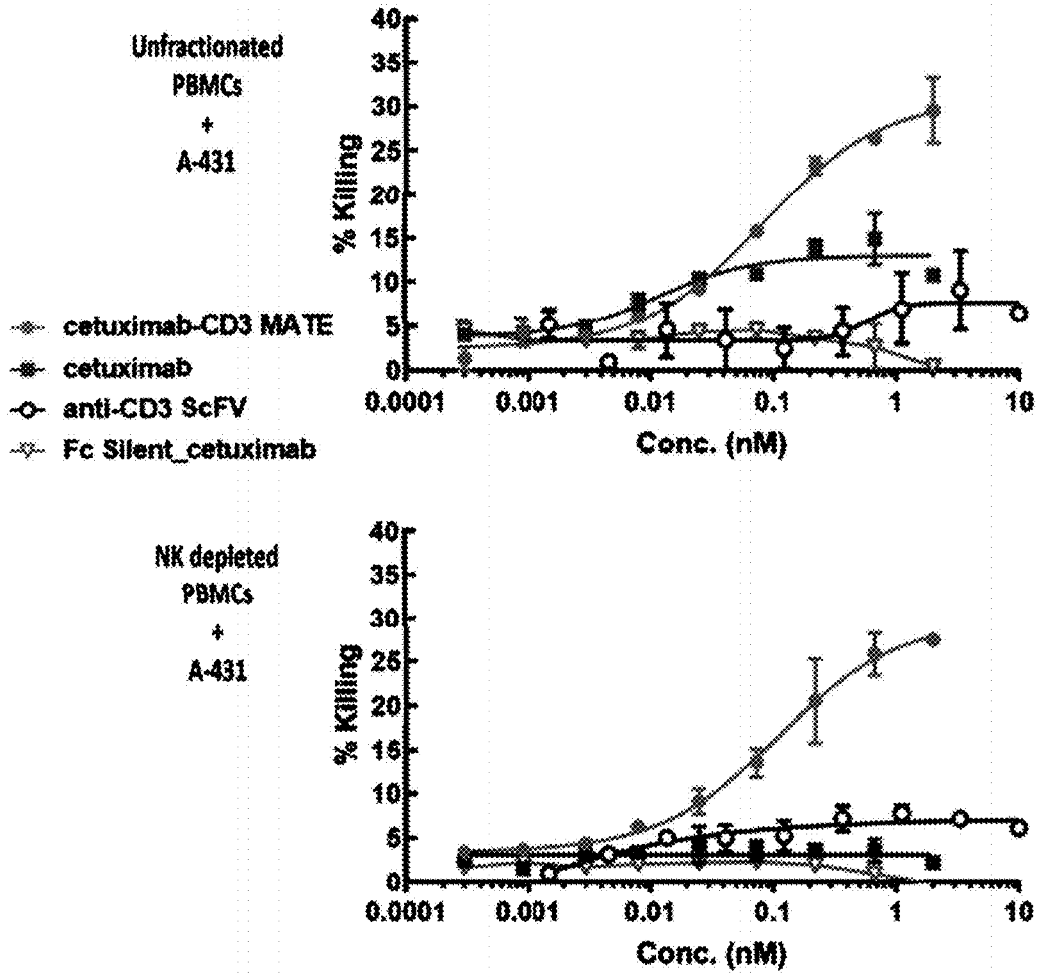

In some embodiments, T cell enrichment by functional prestimulation of PBMCs or by NK cell depletion increases T cell-mediated killing of tumor cells. In some embodiments, Daudi ($CD20^+$) B lymphoblast cells were engineered to stably express a beta-gal reporter fragment using KILR retroparticles (Eurofins DiscoverX). Target cells were treated with III-1, rituximab, and relevant controls at varying concentrations. Effector cells from unfractionated and NK cell-depleted PBMCs were prepared from freshly-thawed or PHA+IL-2 prestimulated (5 days) PBMCs. Cells were cultured at an effector:target ratio of 15:1 and incubated for 18 hrs. Luminescence signal was obtained with luminometer to reflect target cell death. In some embodiments, A-431 ($EGFR^+$) epidermoid carcinoma cells were treated with varying concentrations of cetuximab (CTX)-CD3 MATE (CTX-CD3 conjugate), control mAbs, or scFv. Target cell death was measured using CytoTox-Glo reagent (Promega). In some embodiments, III-1 induced tumor cell killing of Daudi cells (in some embodiments, may be through T Cell-mediated cytotoxicity over ADCC or ADCP). In some embodiments, provided technologies provide 2-3 fold higher max killing of tumor cells compared to native antibody agents, e.g., RTX. In some embodiments, similar site-directed chemistry to conjugate anti-CD3 scFv to RTX was applied to cetuximab, which provides cetuximab-CD3 conjugates that can elicit superior killing compared to native Ab. Certain data were provided in FIG. 31. In some embodiments, useful protocols for assessing provided technologies are described below.

PBMCs were prepared by various methods to serve as effector cells. In some embodiments, PBMCs were thawed and treated for 3 days with phytohemagglutinin (PHA) (Sigma #L8754) at final concentration 4 ug/mL and interleukin 2 (IL-2) (R&D System #202-IL) at a final concentration 5 ng/mL. On day 3, IL-2 was replenished with an additional 5 ug/mL, and PBMCs were incubated for an additional 2 days. These "prestimulated" T cell-enriched PBMCs were harvested and used as effector cells on day 5. In a second method, PBMCs were simply thawed on the day of experimental setup. In both methods, PBMCs were utilized as is and termed "unfractionated," or depleted for NK cells using an immunomagnetic positive selection cell isolation kit for CD56-positive cells (StemCell Technologies #17855). Daudi B lymphoblast cells were engineered to stably express a beta-gal reporter fragment using KILR retroparticles (DiscoverX #97-0002). Daudi cells were plated at $1.0\times10^4$ cells/well of a 96-well round-bottom white-walled plate and treated with varying concentrations of MATEs, control MATEs, anti-CD3 single-chain variable fragment (scFv), or control monoclonal antibodies (mAbs) diluted in assay media (RPMI, 5% Low IgG bovine serum, 100 U/mL Penicillin-Streptomycin). Target Daudi cells were incubated for 30 min. at 37° C. PBMC effector cells, prepared as described above, were introduced at an effector:target ratio of 15:1 and incubated for 18 hr. KILR detection reagent (DiscoverX #97-0001L) was added to each well per manufacturer's recommendations. Luminescence signal was obtained with luminometer to reflect Daudi cell death, and percent killing was calculated utilizing GraphPad Prism software.

A-431 cells were plated at $1.0\times10^4$ cells/well of a 96-well flat-bottom white-walled plate and treated with varying concentrations of MATE, anti-CD3 scFv, or control mAbs diluted in assay media (RPMI, 10% bovine serum, 100 U/mL Penicillin-Streptomycin). Target A-431 cells were incubated for 30 min. at 37° C. PBMCs were thawed on the day of experimental setup and utilized as is ("unfractionated") or depleted for NK cells using an immunomagnetic positive selection cell isolation kit for CD56-positive cells (StemCell Technologies #17855). PBMC effector cells were introduced at an effector:target ratio of 10:1 and incubated for 18 hr. CytoTox-Glo reagent (Promega #G9292) was added to each well per manufacturer's recommendations. Luminescence signal was obtained with luminometer to reflect A-431 cell death, and percent killing was calculated utilizing GraphPad Prism software.

Figure 32:
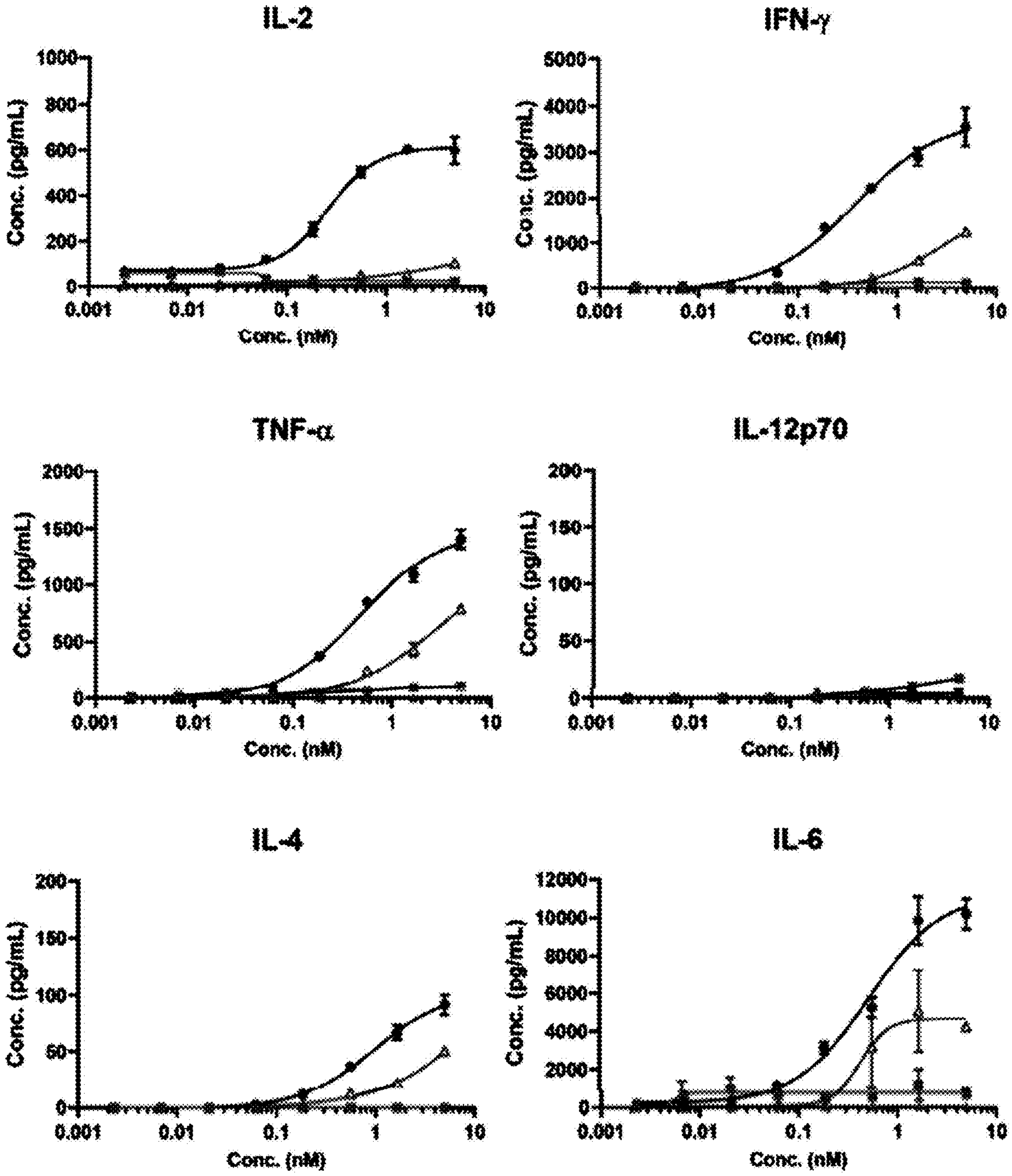
FIG. 32. Certain compositions may induce activating and inflammatory cytokines in a target cell-dependent manner in vitro. Freshly-thawed unfractionated PBMCs were cultured with (20:1 effector-to-target ratio) or without Daudi target cells, and treated with varying concentrations of III-1, rituximab, or control scFv (not shown) for 18 hrs. Supernatants were collected and evaluated with a multiplex immunoassay human cytokine panel (Invitrogen, ProcartaPlex).
Figure 32:
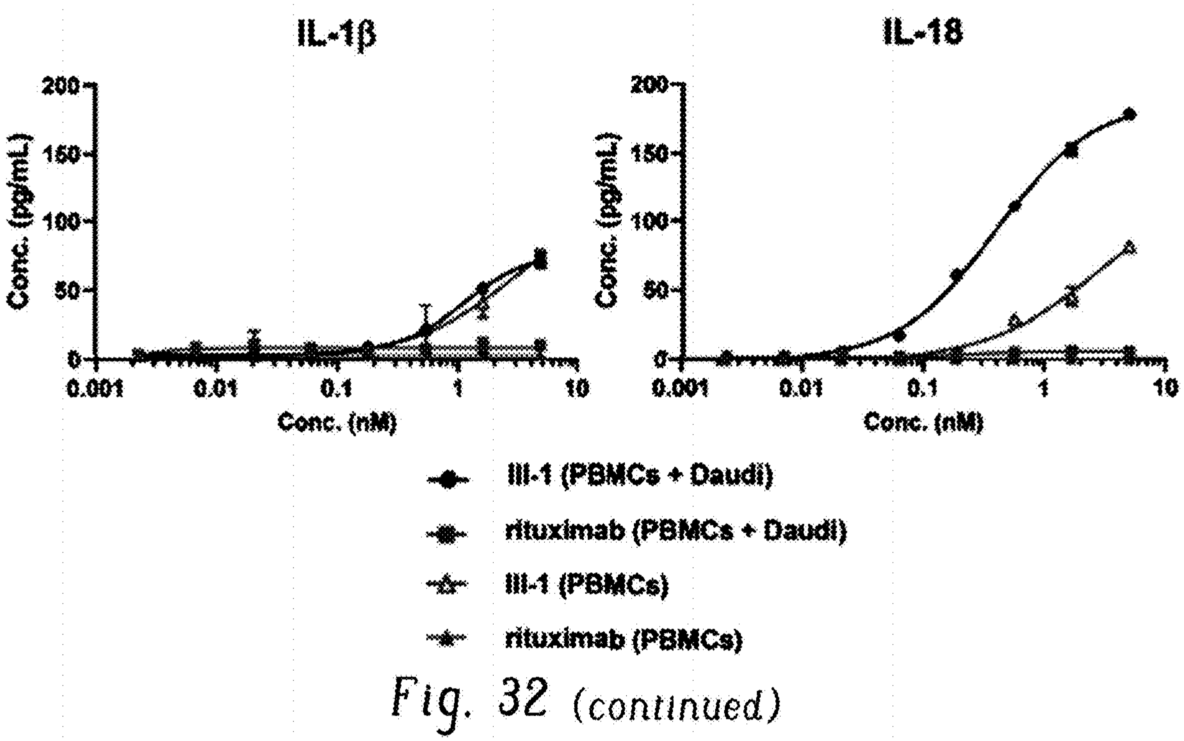

In some embodiments, III-1 induces production of cytokines consistent with effector cell activation in vitro. In some embodiments, freshly-thawed unfractionated PBMCs were cultured with (20:1 effector-to-target ratio) or without Daudi target cells, and treated with varying concentrations of III-1, rituximab, or control scFv (not shown) for 18 hrs. Supernatants were collected and evaluated with a multiplex immunoassay human cytokine panel (Invitrogen, ProcartaPlex). In some embodiments, III-1 preferentially induces an increase in inflammatory and activating cytokines in the presence of Daudi target cells. In some embodiments, no cytokine induction is evident with RTX alone or scFv alone. In some embodiments, T cells, NK cells, and/or macrophages are activated. In some embodiments, III-1 may induce activating and inflammatory cytokines in a target cell-dependent manner. It is noted that other conjugates, e.g., anti-CD3×anti-CD20 trifunctional bispecific mAb "Lymphonum" (TRION Pharma, a.k.a. Bi20, FBTA05) also report higher or similar IL-6 levels, e.g., when exposing PBMCS+B lymphoid cell lines in vitro. It is further noted that these in vitro data may not reflect in vivo results—as shown in aminal data (e.g., see FIG. 33), IL-6 increases were minimal, and it was reported that IL-6 levels in animals can corroborate with human data (e.g., Winkler, et. al. Blood, Vol 94, No 7 (October 1), 1999: pp 2217-2224). In various embodiments, data confirmed that provided antibody-antibody conjugate agents showed comparable or lower levels of undesirable cytokines/chemokines (e.g., IL-6) compared to other reported similar conjugate agents (e.g., Lymphonum). Certain data were provided in FIG. 32. In some embodiments, useful protocols for assessing provided technologies are described below.

Freshly-thawed unfractionated PBMCs were cultured with (20:1 effector-to-target ratio) or without Daudi target cells, and treated with varying concentrations of III-1, rituximab, or control scFv (not shown) for 18 hrs. Supernatants were collected and evaluated with a multiplex immunoassay human cytokine panel (Invitrogen, ProcartaPlex).

Daudi cells were plated at $1.0\times10^4$ cells/well of a 96-well round-bottom plate and treated with varying concentrations of antibody-antibody conjugates (III-1) or rituximab diluted in assay media (RPMI, 5% Low IgG bovine serum, 100 U/mL Penicillin-Streptomycin). Alternatively, test agents were added to assay media containing no Daudi cells. Both conditions were incubated for 30 min. at 37° C. Freshly thawed PBMC effector cells were introduced at an effector: target ratio of 20:1 (or equivalent number of PBMCs for no Daudi condition) and incubated for 18 hrs. Supernatants were harvested and stored at −80° C. until further analysis, and evaluated with a multiplex immunoassay human cytokine panel (Invitrogen, #EPX110-10810-901). Cytokine data was analyzed with Affymetrix ProcartaPlex Analyst 1.0 software.

Using III-1 and other conjugates as examples, it is confirmed that provided technologies can provide various benefits and advantages.

Figure 24:
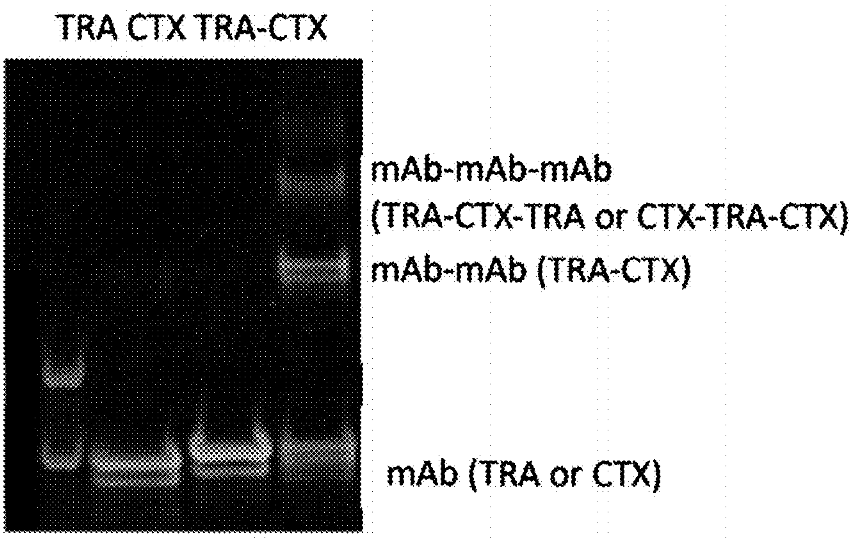
FIG. 24. Provided technologies can provide antibody-antibody conjugates. Illustrated are certain data for trastuzumab (TRA)-cetuximab (CTX) bispecific antibodies.
Figure 25:
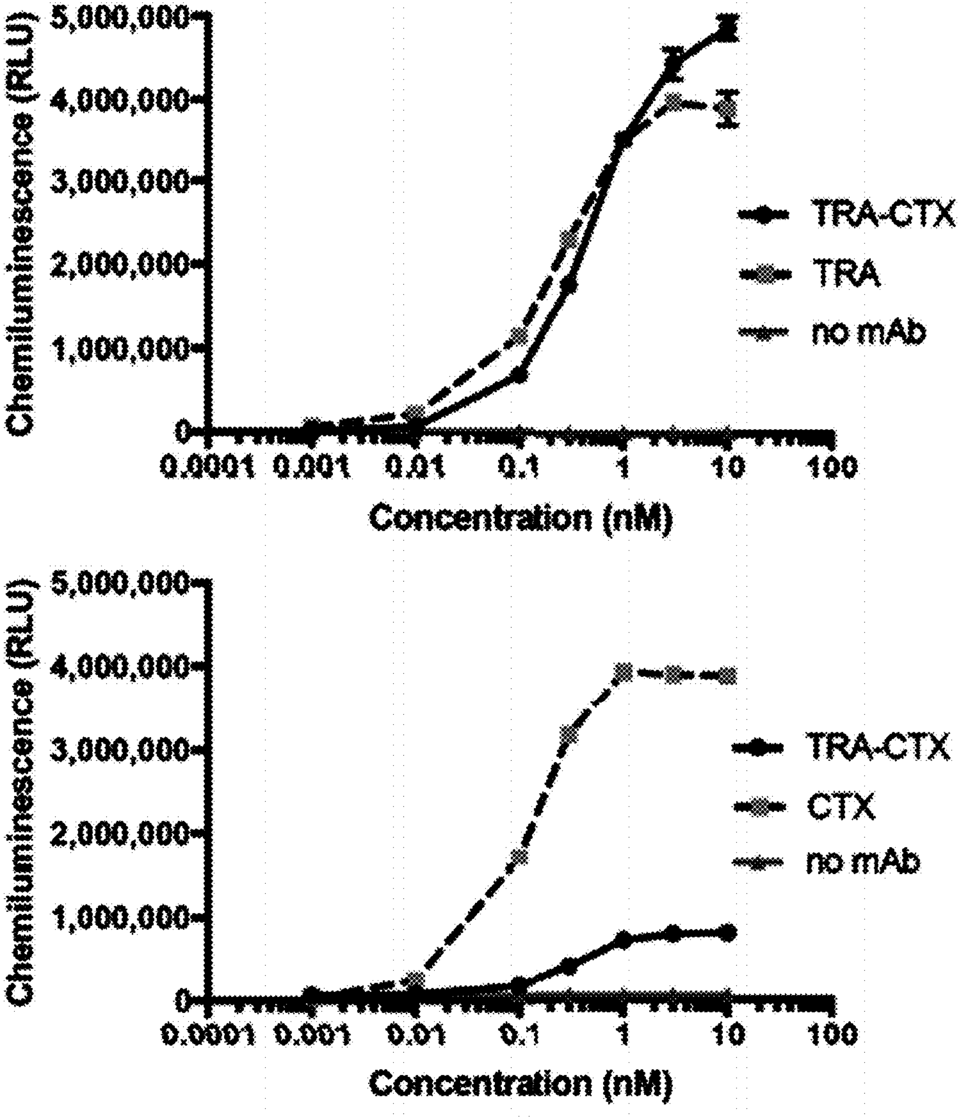
FIG. 25. Provided antibody-antibody conjugates bind to targets of each antibody. For example, certain data from ELISA binding assays confirm that a trastuzumab (TRA)-cetuximab (CTX) conjugate binds to both HER2 and EGFR.
Figure 26:
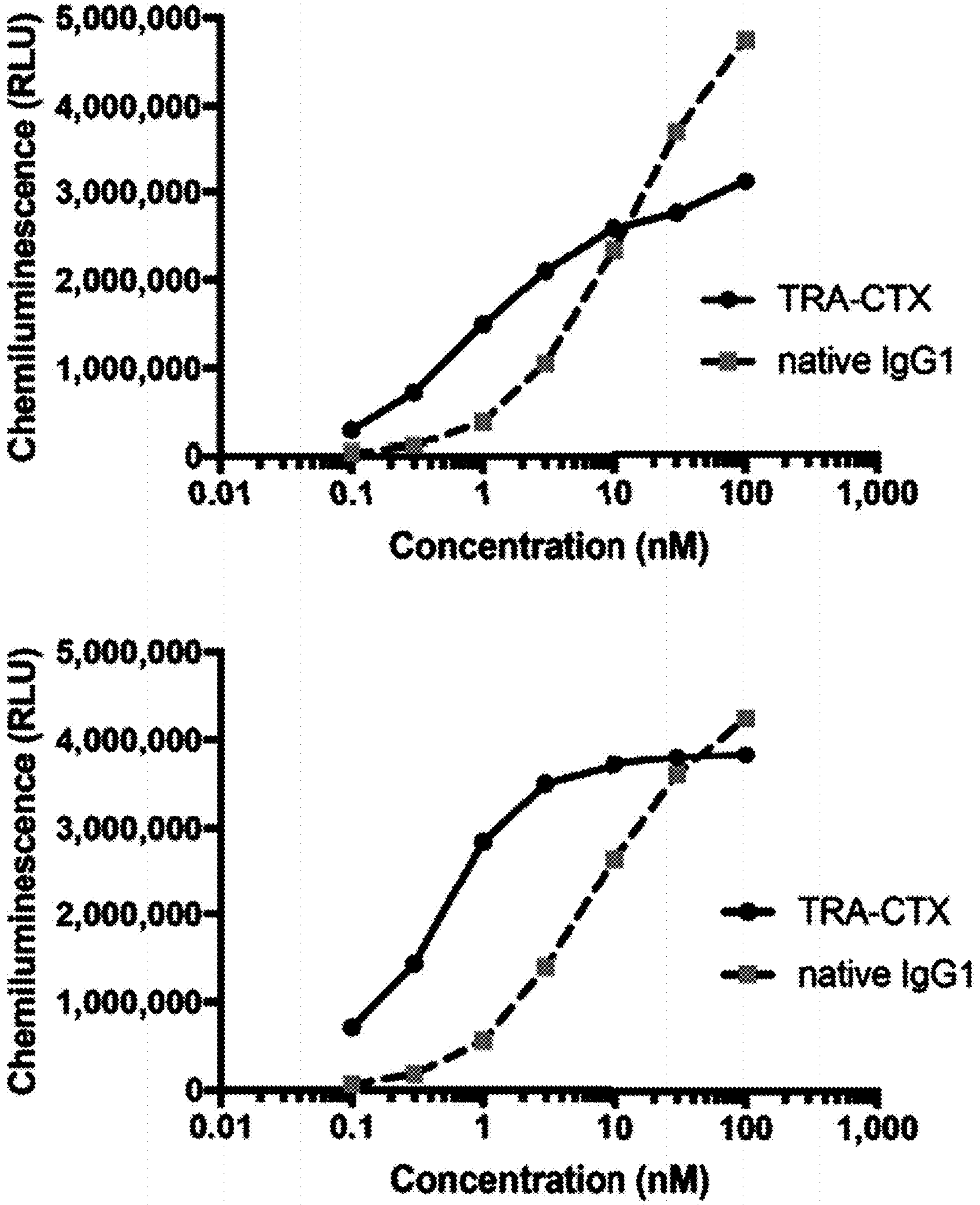
FIG. 26. Provided antibody-antibody conjugates bind to Fc receptors. For example, certain data from ELISA binding assays confirm that a trastuzumab (TRA)-cetuximab (CTX) conjugate maintains binding to Fc receptors FcRn and FcRIII with similar levels to IgG1 control.

In some embodiments, a Trastuzumab-Cetuximab conjugate was provided. In some embodiments, Trastuzumab was conjugated with I-56, and Cetuximab was conjugated with I-65 which was prepared using similar chemistries as described in the Examples. The conjugation products were cleaned up and incubated for 72 h for click reaction to provide Trastuzumab (TRA)-Cetuximab (CTX) conjugate. Certain results were illustrated in FIG. 24, confirming formation of antibody conjugates. Among other things, provided antibody-antibody conjugates maintain binding to targets of each antibody (e.g., see FIG. 25), and bind to Fc receptors (e.g., see FIG. 26).

Example 35. Exemplary Synthesis of Compound I-59

General Procedure for Preparation of Compound 2:

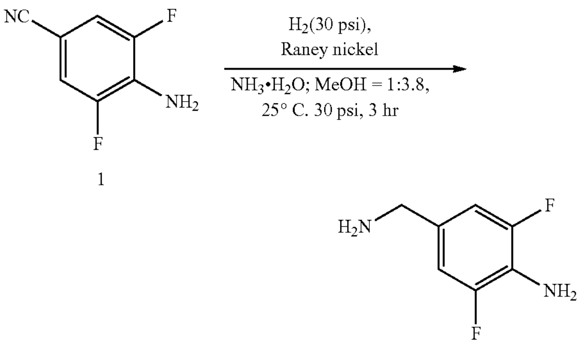

1

2

To a solution of compound 1 (5 g, 32.4 mmol, 1 eq) in MeOH (50 mL) $NH_3.H_2O$ (13 mL) was added nickel (5 g) under $N_2$. The suspension was degassed under vacuum and purged with $H_2$ several times. The mixture was stirred under $H_2$ (30 psi) at 25° C. for 3 hours. TLC (Petroleum ether: Ethyl acetate=1:1 $R_f$=0.01) indicated compound 1 was consumed completely. The reaction mixture was filtered and the filter was concentrated. Compound 2 (10 g, 63.23 mmol, yield: 97.45%) was obtained as a brown solid.

General Procedure for Preparation of Compound 3:

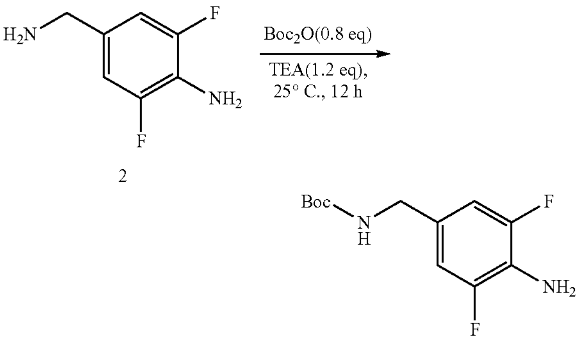

2

3

A mixture of compound 2 (5 g, 31.62 mmol, 1 eq), $Boc_2O$ (5.52 g, 25.2 mmol, 5.81 mL, 0.8 eq) in THF (50 mL) was degassed and purged with $N_2$ for 3 times, and then the mixture was stirred at 25° C. for 12 hr under $N_2$ atmosphere. TLC (Petroleum ether:Ethyl acetate=1:1 $R_f$=0.69) indicated compound 2 was consumed completely. The residue was diluted with $H_2O$ (20 mL) and extracted with ethyl acetate (50 ml*2). The reaction mixture was poured into separatory funnel and separated. The combined organic layers were washed with brine (50 mL), dried over $Na_2SO_4$, filtered and concentrated under reduced pressure to give a residue. The residue was purified by column chromatography ($SiO_2$, Petroleum ether:Ethyl acetate=100:1 to 0:1). Compound 3 (5 g, 19.36 mmol, yield: 61.24%) was obtained as a white solid. $^1$H NMR (400 MHz, DMSO-d6): δ ppm 7.31 (br t, J=5.96 Hz, 1H) 6.76 (br d, J=7.87 Hz, 2H) 5.05 (s, 2H) 3.97 (br d, J=5.01 Hz, 2H) 1.38 (s, 9H).

General Procedure for Preparation of Compound 6:

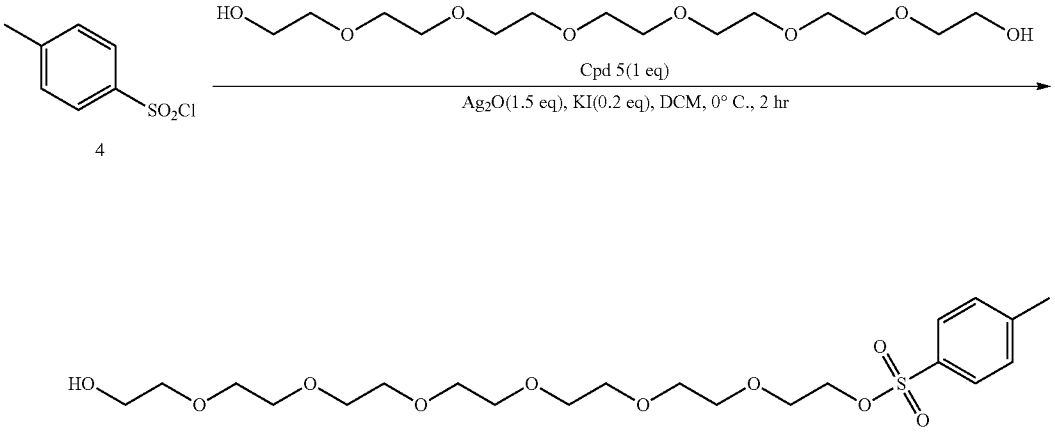

4

6

To a solution of compound 4 (5 g, 15.32 mmol, 1 eq) in DCM (80 mL) was added $Ag_2O$ (5.33 g, 22.98 mmol, 1.5 eq) and KI (508.61 mg, 3.06 mmol, 0.2 eq). The mixture was added with compound 5 (2.92 g, 15.32 mmol, 1 eq) in DCM (20 mL) at 0° C. The mixture was stirred at 0° C. for 2 hr. TLC (Dichloromethane:Methanol=10:1, $R_f$=0.65) indicated compound 4 was consumed completely and one new spot formed. The reaction was clean according to TLC. The suspension was filtered and the filter cake was washed with EtOAc (30 mL×3). The combined filtrates were concentrated to dryness to give product. The residue was purified by column chromatography ($SiO_2$, Dichloromethane:Methanol=100:1 to 2:1). Compound 6 (4.45 g, 9.26 mmol, yield: 60.45%) was obtained as a colorless oil.

General Procedure for Preparation of Compound 9:

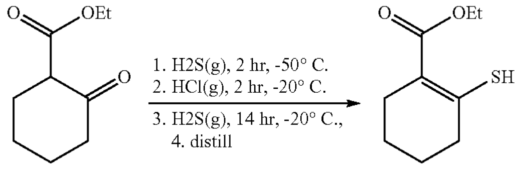

8

9

$H_2S$ gas was bubbled through a solution of compound 8 (40 g, 235 mmol, 37.7 mL, 1 eq) in ethanol (400 mL) at −50° C. for 2 h. HCl gas was then bubbled into the reaction mixture at −20° C. for 2 h, followed by the bubbling of $H_2S$ gas at −20° C. for 2 h. The mixture was then allowed to stand at 25° C. for 14 hr. TLC (Petroleum ether:Ethyl acetate=10:1 $R_f$=0.52) indicated compound 8 was consumed completely. The reaction mixture was poured into an ice-water bath (300 mL) and worked up with petroleum ether (500 ml) and water (500 mL*2). The reaction mixture was poured into separatory funnel and separated. The combined organic layers were washed with brine (500 mL), dried over $Na_2SO_4$, filtered and concentrated under reduced pressure to give a residue. Compound 9 (43 g, 230 mmol, yield 98.23%) was obtained as a red oil. $^1H$ NMR (400 MHz, CHLOROFORM-d): δ ppm 4.21 (q, J=7.06 Hz, 2H) 3.97 (s, 1H) 2.43-2.53 (m, 2H) 2.29-2.38 (m, 2H) 1.59-1.71 (m, 4H) 1.30 (t, J=7.17 Hz, 3H).

General Procedure for Preparation of Compound 7:

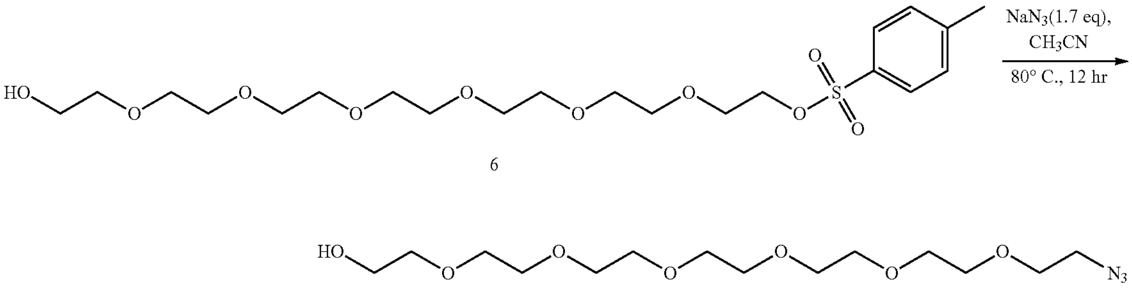

6

7

To a solution of compound 6 (4.3 g, 8.95 mmol, 1 eq) in $CH_3CN$ (50 mL) was added with $NaN_3$ (988.88 mg, 15.21 mmol, 1.7 eq). The mixture was stirred at 80° C. for 12 hr. TLC (Dichloromethane:Methanol=10:1, $R_f$=0.40) indicated compound 6 was consumed completely and one new spot formed. The reaction mixture was diluted with $H_2O$ 100 mL and extracted with EtOAc (50 mL*3). The combined organic layers were washed with brine 50 mL, dried over $Na_2SO_4$, filtered and concentrated under reduced pressure to give a residue. Compound 7 (3 g, 8.54 mmol, yield 95.41%) was obtained as yellow oil.

General Procedure for Preparation of Compound 10:

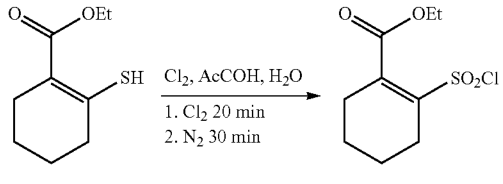

9 10

Chlorine (10 g) was bubbled into a solution of compound 9 (25 g, 134.2 mmol, 1 eq) in AcOH (360 mL) $H_2O$ (40 mL) at 15° C. for 20 min. The reaction mixture was then stirred for 30 min. After excess $Cl_2$ was purged by $N_2$, TLC (Petroleum ether:Ethyl acetate=10:1 $R_f$=0.4) indicated compound 9 was consumed completely. The residue was diluted with $NH_4Cl$ (500 mL*5) and extracted with ethyl acetate (500 ml). The reaction mixture was poured into separatory funnel and separated. The combined organic layers were washed with brine (500 mL), dried over $Na_2SO_4$, filtered and concentrated under reduced pressure to give a residue. Compound 10 (28 g, 110 mmol, yield: 82.5%) was obtained as a yellow oil. $^1H$ NMR (400 MHz, CHLOROFORM-d): δ ppm 4.19-4.31 (m, 2H) 2.52-2.61 (m, 2H) 2.44-2.52 (m, 2H) 1.72-1.82 (m, 2H) 1.62-1.72 (m, 2H) 1.21-1.33 (m, 3H).

General Procedure for Preparation of Compound 11:

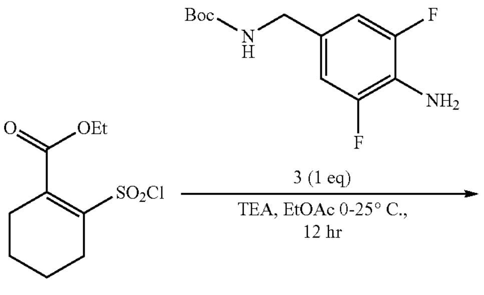

10

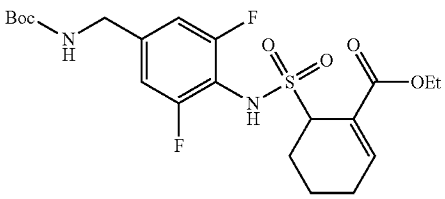

11

To a solution of compound 10 (7.83 g, 30.98 mmol, 2 eq) in EtOAc (20 mL) was added dropwise compound 3 (4 g, 15.49 mmol, 42.63 uL, 1 eq) and TEA (3.13 g, 30.98 mmol, 4.31 mL, 2 eq) in EtOAc (20 mL) at 0° C. After addition, the mixture was stirred at 25° C. for 12 hr. TLC (Petroleum ether:Ethyl acetate=3:1 $R_f$=0.32) indicated compound 3 was consumed completely. The residue was diluted with $H_2O$ 100 mL and extracted with ethyl acetate (200 ml*2). The reaction mixture was poured into separatory funnel and separated. The combined organic layers were washed with brine (100 mL), dried over $Na_2SO_4$, filtered and concentrated under reduced pressure to give a residue. The residue was purified by column chromatography ($SiO_2$, Petroleum ether:Ethyl acetate=10:1 to 0:1). Compound 11 (5.5 g, 11.5 mmol, yield: 74.84%) was obtained as a white solid.

General Procedure for Preparation of Compound 12:

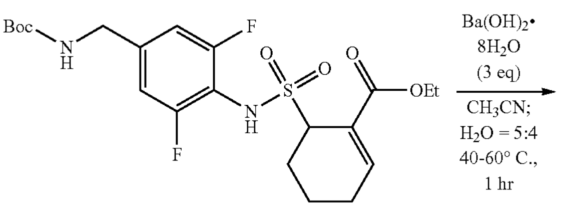

11

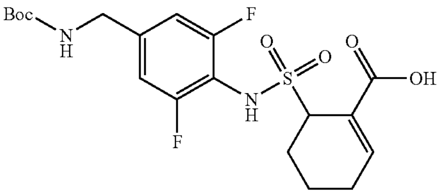

12

To a solution of compound 11 (3.5 g, 7.38 mmol, 1 eq) in $CH_3CN$ (30 mL) $H_2O$ (20 mL) was added barium hydroxide octahydrate (6.98 g, 22.13 mmol, 3 eq). The mixture was stirred at 40-60° C. for 1 hr. LCMS showed the starting material was consumed completely. The reaction mixture was partitioned between ethyl acetate (200 mL). The organic phase was separated. The water phase was diluted with $H_2O$ (100 mL), and 0.5 M HCl was added to adjust pH=3-4. The organic phase of the mixture was separated, and the aqueous phase was extracted with ethyl acetate twice, each time 100 mL. All organic phases were combined, washed once with 50 mL saturated salt water, dried over anhydrous sodium sulfate, filtered, and spun dry. The crude product was purified by reversed-phase HPLC (column: Phenomenex luna c18 250 mm*100 mm*10 um; mobile phase: [water (0.05% HCl)-ACN]; B %: 15%-60%, 20 min). Compound 12 (1.7 g, 3.81 mmol, yield: 51.62%) was obtained as a white solid. LCMS: Rt=1.997 min, MS (ESI): m/z [M+H$^+$] calcd for $C_{19}H_{24}F_2N_2O_6S$, 447.1; found 464.2.

General Procedure for Preparation of Compound 13:

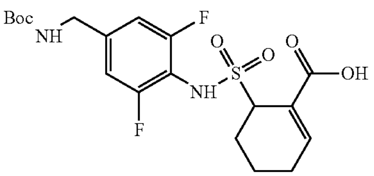

12

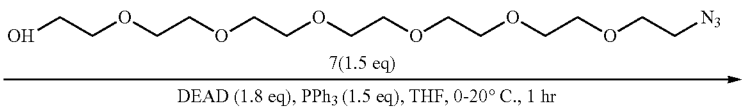

-continued

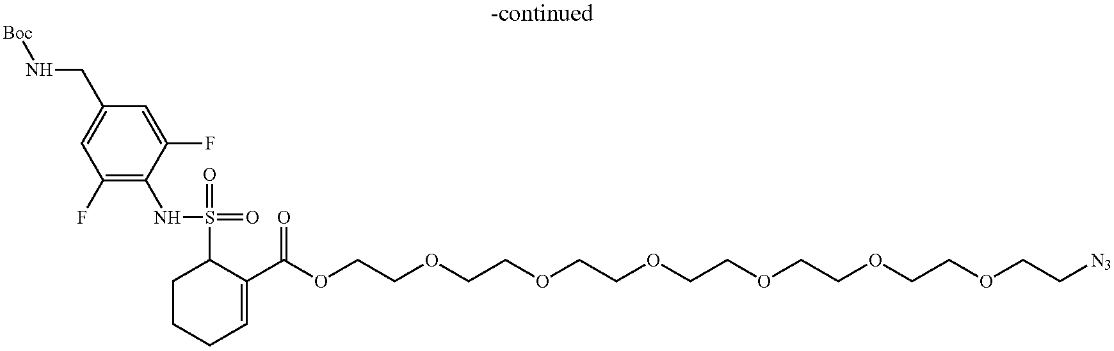

13

To a solution of compound 12 (200 mg, 447.96 umol, 1 eq) in THF (2 mL) was added compound 7 (236 mg, 671.9 umol, 1.5 eq), $PPh_3$ (176.24 mg, 671.95 umol, 1.5 eq) and DEAD (140 mg, 806 umol, 146 uL, 1.8 eq) at 0° C. The mixture was stirred at 20° C. for 12 hr. LCMS showed the starting material was consumed completely. HPLC showed the starting material was consumed completely. The reaction mixture was filtered and the filter was concentrated. The crude product was purified by reversed-phase HPLC (column: Phenomenex luna C18 250*50 mm*10 um; mobile phase: [water (0.1% TFA)-ACN]; B %: 50%-80%, 10 min). Compound 13 (200 mg, 256.46 umol, yield: 57.25%) was obtained as a white solid. $^1H$ NMR (400 MHz, DMSO-d6) δ ppm 9.62 (s, 1H) 7.51 (br t, J=6.32 Hz, 1H) 7.10 (br s, 1H) 7.03 (br d, J=8.58 Hz, 2H) 4.37 (br d, J=4.65 Hz, 1H) 4.14 (br d, J=5.72 Hz, 2H) 4.01-4.11 (m, 2H) 3.57-3.62 (m, 4H) 3.43-3.57 (m, 26H) 2.14-2.28 (m, 1H) 2.10 (br s, 1H) 1.80 (br d, J=13.35 Hz, 1H) 1.64 (br s, 2H) 1.34-1.48 (m, 9H) 1.31 (br s, 1H). LCMS: Rt=1.452 min, MS (ESI): m/z [M+H$^+$] calcd for $C_{33}H_{51}F_2N_5O_{12}S$, 780.3; found 797.3. HPLC: RT=3.718 min.

General Procedure for Preparation of Compound 14:

A mixture of compound 13 (200 mg, 256.46 umol, 1 eq) Zn (167.70 mg, 2.56 mmol, 10 eq) and ammonia; formic acid (161.71 mg, 2.56 mmol, 10 eq) in MeOH (3 mL) was degassed and purged with $N_2$ for 3 times, and then the mixture was stirred at 20° C. for 15 min under $N_2$ atmosphere. LCMS showed the starting material was consumed completely. The reaction mixture was concentrated. The crude product was dissolved in THF (20 ml) and added DCM (20 ml), the mixture was precipitated by solids. The mixture was filtered and the filter cake was washed with DCM (20 mL×2). The combined filtrates were concentrated to dryness to give crude product. Compound 14 (195 mg, crude) was obtained as a white solid. LCMS: Rt=0.678 min, MS (ESI): m/z [M+H$^+$] calcd for $C_{33}H_{53}F_2N_3O_{12}S$, 754.3; found 754.3.

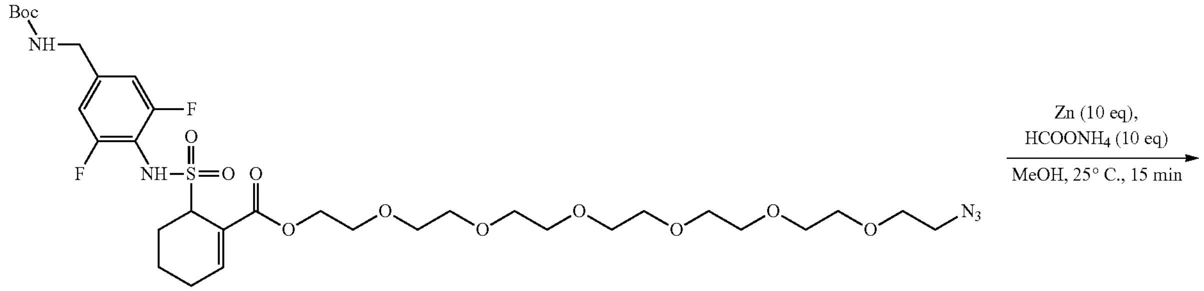

13

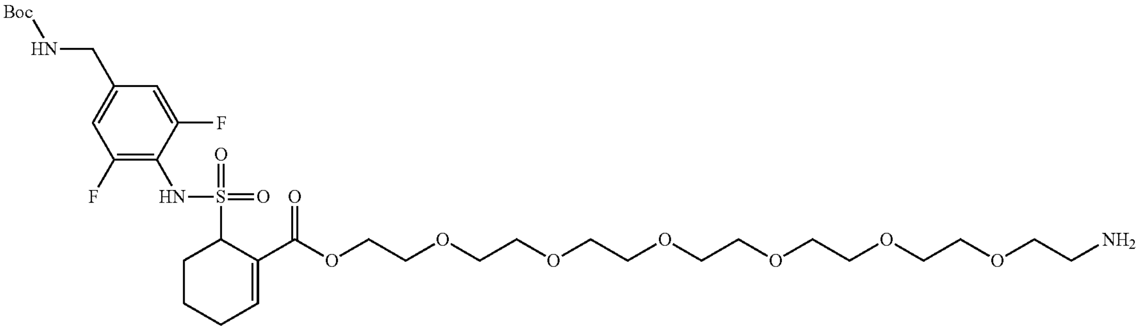

14

General Procedure for Preparation of Compound 16:

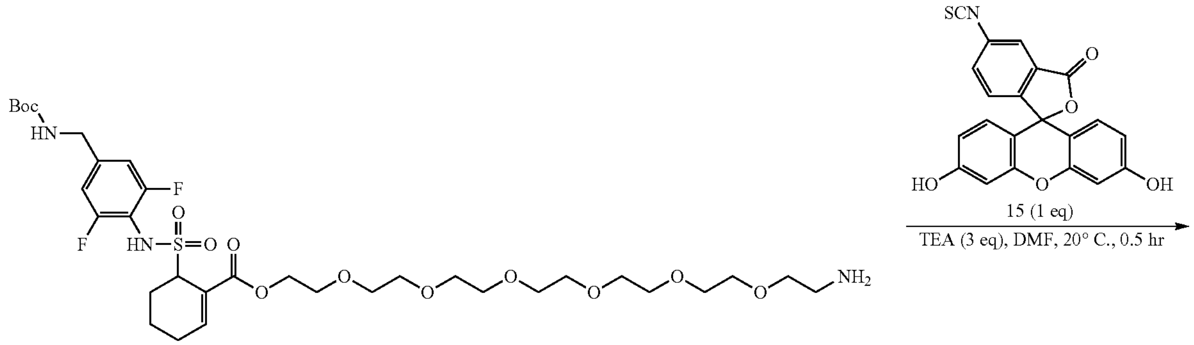

14

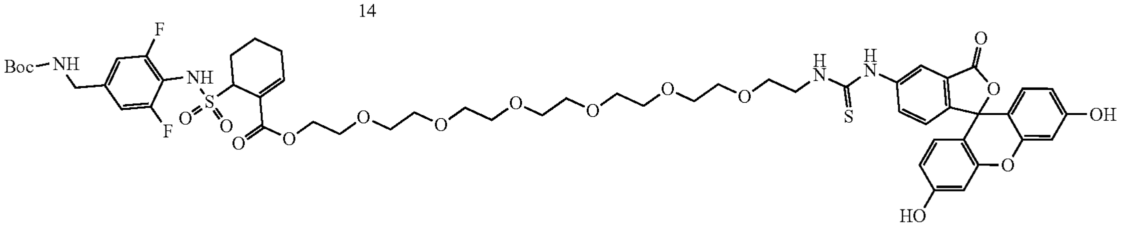

16

A mixture of compound 14 (193 mg, 256 umol, 1 eq), compound 15 (99.6 mg, 256 umol, 1 eq), and TEA (77.7 mg, 768 umol, 106 uL, 3 eq) in DMF (1 mL) was degassed and purged with $N_2$ for 3 times, and then the mixture was stirred at 20° C. for 0.5 hr under $N_2$ atmosphere. LCMS showed the starting material was consumed completely. The reaction mixture was filtered and the filter was concentrated. The crude product was purified by reversed-phase HPLC (column: Nano-micro Kromasil C18 100*40 mm 10 um; mobile phase: [water (0.1% TFA)-ACN]; B %: 35%-65%, 8 min). Compound 16 (170 mg, 148.70 umol, yield: 58.08%) was obtained as a yellow solid. LCMS: Rt=0.788 min, MS (ESI): m/z [M/2+H$^+$] calcd for $C_{54}H_{64}F_2N_4O_{17}S_2$, 1142.3; found 572.8.

General Procedure for Preparation of Compound 17:

A mixture of compound 16 (100 mg, 87.4 umol, 1 eq), TFA (539 mg, 4.73 mmol, 350 uL, 54.0 eq) in DCM (2 mL) was degassed and purged with $N_2$ for 3 times, and then the mixture was stirred at 25° C. for 0.5 hr under $N_2$ atmosphere. LCMS showed the starting material was consumed completely. HPLC showed the starting material was consumed completely. The reaction mixture was filtered and the filter was concentrated. The crude product was purified by reversed-phase HPLC (column: Nano-micro Kromasil C18 100*40 mm 10 um; mobile phase: [water (0.1% TFA)-ACN]; B %: 23%-58%, 8 min). Compound 17 (54.78 mg, 51.87 umol, yield: 59.30%, 98.77% purity) was obtained as a yellow solid. $^1$H NMR (400 MHz, DMSO-d6) δ ppm 10.04 (br s, 3H) 9.73 (br s, 1H) 8.15-8.36 (m, 4H) 8.10 (br s, 1H) 7.75 (br s, 1H) 7.33 (br d, J=8.07 Hz, 2H) 7.18 (br d, J=8.44

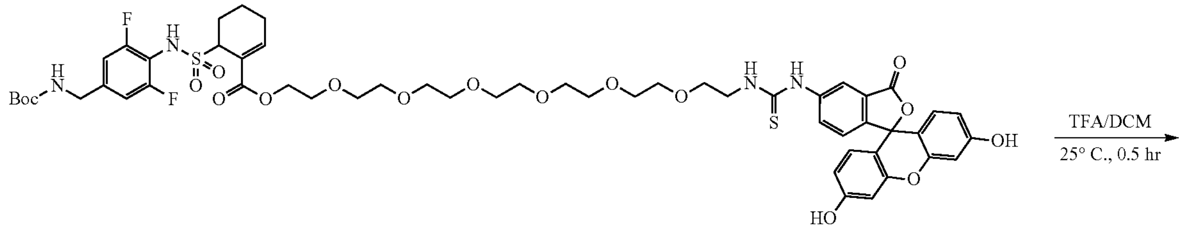

16

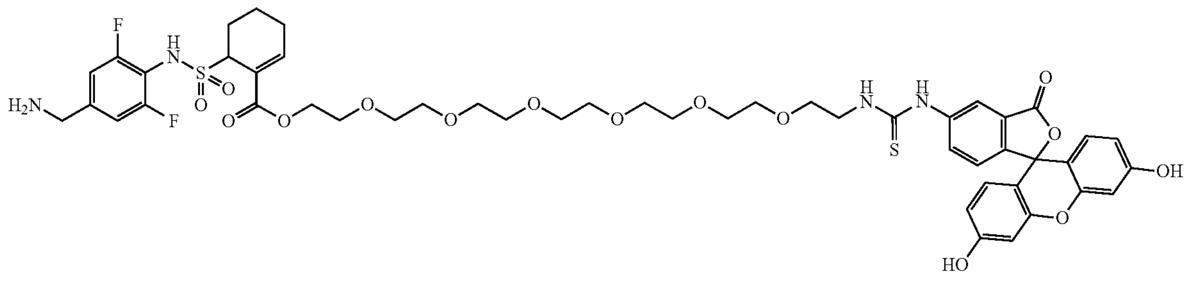

17

Hz, 1H) 7.12 (br s, 1H) 6.67 (br s, 2H) 6.49-6.64 (m, 4H) 4.41 (br s, 1H) 4.09 (br d, J=4.16 Hz, 4H) 3.35-3.64 (m, 31H) 2.24 (br s, 2H) 2.08 (br s, 1H) 1.79 (br s, 1H) 1.62 (br s, 1H). LCMS: Rt=0.655 min, MS (ESI): m/z [M+H$^+$] calcd for $C_{49}H_{56}F_2N_4O_{15}S_2$, 1042.3; found 522.6. HPLC:
RT=3.146 min. QC data for compound 17: HPLC: Rt=1.574 min, purity: 98.83%. QC LCMS: MS (ESI): m/z [M+H$^+$] calcd for $C_{49}H_{56}F_2N_4O_{15}S_2$, 1042.3; found 522.3.
General Procedure for Preparation of Compound 4a:
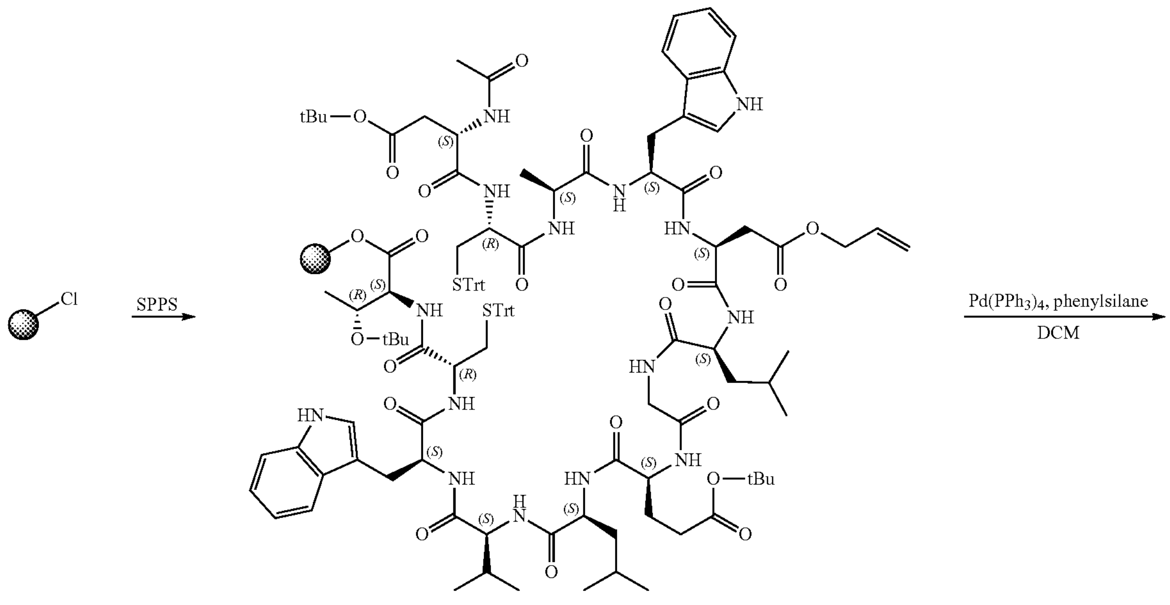
1a
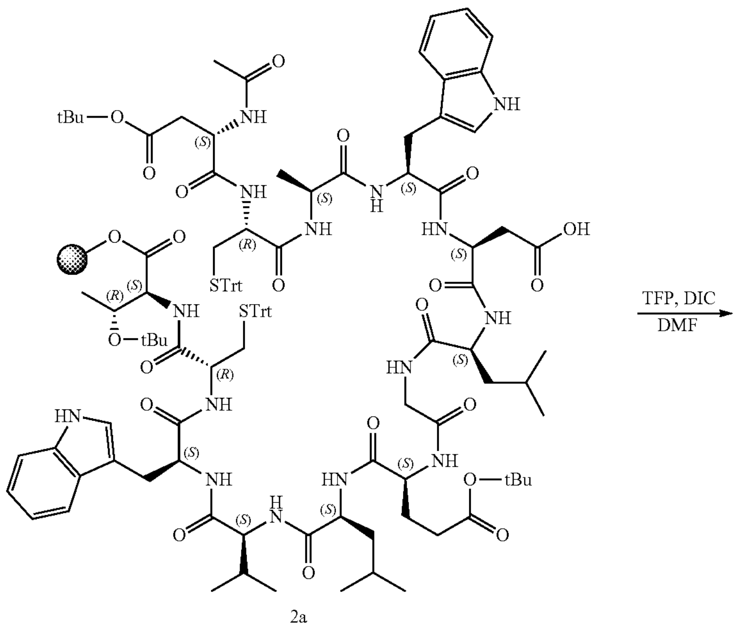
2a -continued

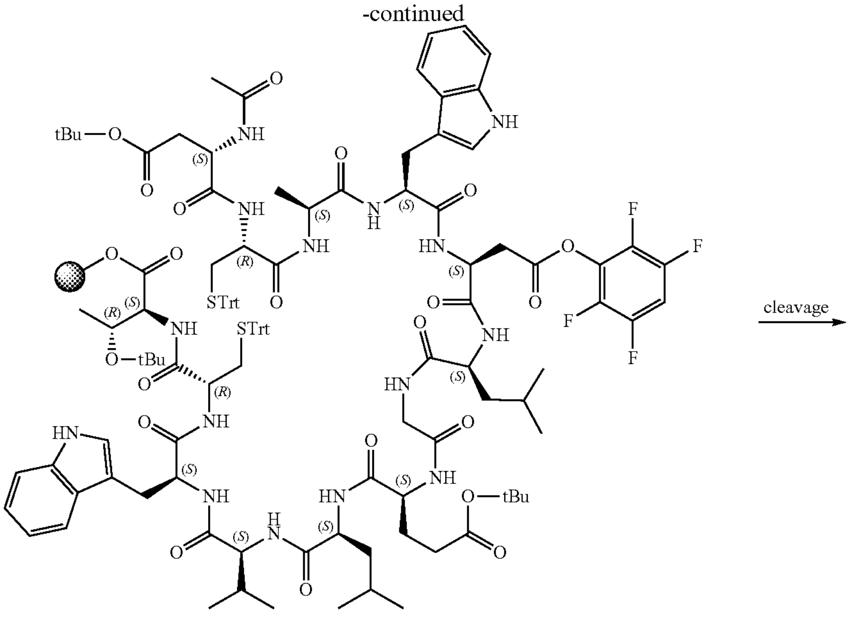

3a

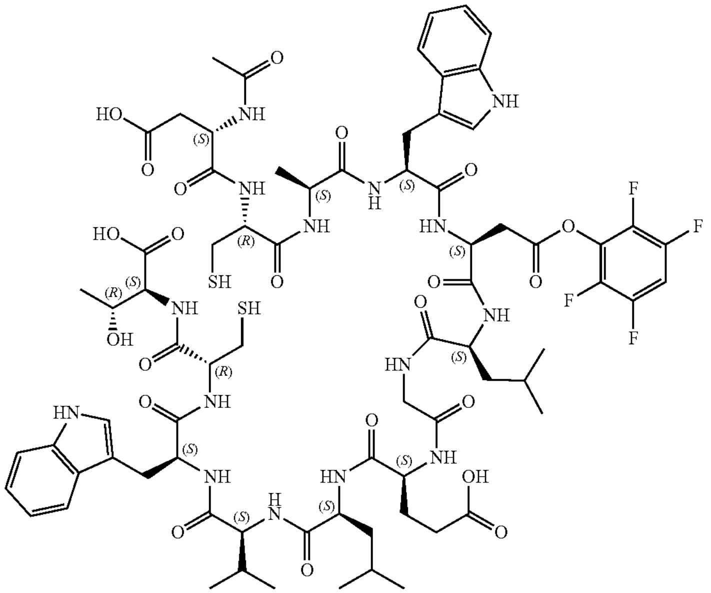

4a

The peptide was synthesized using standard Fmoc chemistry:

1) Resin preparation: To the vessel containing CTC Resin (1.00 mmol, 0.97 g, 1.05 mmol/g, 1.00 eq) and Fmoc-Thr(tBu)-OH (0.40 g, 1.00 mmol, 1.00 eq) in DCM (20.0 mL) was added DIEA (4.00 eq) dropwise and mixed for 2 hrs with $N_2$ bubbling at 15° C. Then MeOH (1.0 mL) was added and bubbled with $N_2$ for another 30 min. The resin was washed with DMF (20.0 mL)*5. Then 20% piperidine in DMF (20.0 mL) was added and the mixture was bubbled with $N_2$ for 30 min at 15° C. The mixture was filtered to obtain the resin, which was washed with DMF (20.0 mL)*5 before proceeding to next step.
2) Coupling: A solution of Fmoc-Cys(Trt)-OH (1.19 g, 3.00 mmol, 3.00 eq), HBTU (1.08 g, 2.85 mmol, 2.85 eq) in DMF (10.0 mL) was added to the resin with $N_2$ bubbling. Then DIEA (6.00 eq) was added to the mixture dropwise and bubbled with $N_2$ for 30 min at 15° C. The coupling reaction was monitored by ninhydrin test, if it showed colorless, the coupling was complete. The resin was then washed with DMF (20.0 mL)*5.
3) De-protection: 20% piperidine in DMF (20.0 mL) was added to the resin and the mixture was bubbled with $N_2$ for 30 mins at 15° C. The resin was then washed with DMF (20.0 mL)*5. The de-protection reaction was monitored by ninhydrin test, if it showed blue or other brownish red, the reaction was completed.
4) Repeat Step 2 and 3 for all other amino acids: (2-13 in the table below).
5) Acetylation (compound 1a): A solution of 10% $AC_2O$/5% NMM/85% DMF (20.0 mL) was added to resin and the mixture was bubbled with $N_2$ for 20 mins. The coupling reaction was monitored by ninhydrin test, if it showed colorless, the coupling was completed. The resin was then washed with DMF (20.0 mL)*5 DCM (10.0 mL)*5.

6) De-OAll (compound 2a): A mixture of phenylsilane (10.0 eq), $Pd(PPh_3)_4$ (0.10 eq) in DCM (10.0 mL) was added to resin with $N_2$ bubbling for 15 m. The resin was then washed with DCM (20.0 mL)*3 Repeat this procedure twice and the de-protection reaction was monitored by LCMS of a cleavage test.

7) TFP coupling (compound 3a): A mixture of TFP (20.00 eq), DMAP (1.00 eq) in DMF (15.0 mL) was added to resin with $N_2$ bubbling. Then DIC (10.00 eq) was added dropwise to resin and the mixture was bubbled with $N_2$ for 3 hrs. The reaction was monitored by LCMS of a cleavage test. After the last position completed, the resin was washed with DMF (20.0 mL)*5, isopropyl ether (20.0 mL)*5 and dried under vacuum.

| # | Materials | Coupling reagents |
|---|---|---|
| 1 | Fmoc-Thr(tBu)-OH (1.00 eq) | DIEA (4.00 eq) |
| 2 | Fmoc-Cys(Trt)-OH (3.00 eq) | HATU(2.85 eq) and DIEA (6.00 eq) |
| 3 | Fmoc-Trp-OH (3.00 eq) | HBTU(2.85 eq) and DIEA (6.00 eq) |
| 4 | Fmoc-Val-OH (3.00 eq) | HBTU(2.85 eq) and DIEA (6.00 eq) |
| 5 | Fmoc-Leu-OH (3.00 eq) | HBTU(2.85 eq) and DIEA (6.00 eq) |
| 6 | Fmoc-Glu(OtBu)-OH (3.00 eq) | HBTU(2.85 eq) and DIEA (6.00 eq) |

-continued

| # | Materials | Coupling reagents |
|---|---|---|
| 7 | Fmoc-Gly-OH (3.00 eq) | HBTU(2.85 eq) and DIEA (6.00 eq) |
| 8 | Fmoc-Leu-OH (3.00 eq) | HBTU(2.85 eq) and DIEA (6.00 eq) |
| 9 | Fmoc-Asp(OAll)-OH (3.00 eq) | HBTU(2.85 eq) and DIEA (6.00 eq) |
| 10 | Fmoc-Trp-OH (3.00 eq) | HBTU(2.85 eq) and DIEA (6.00 eq) |
| 11 | Fmoc-Ala-OH (3.00 eq) | HBTU(2.85 eq) and DIEA (6.00 eq) |
| 12 | Fmoc-Cys(Trt)-OH (3.00 eq) | HBTU(2.85 eq) and DIEA (6.00 eq) |
| 13 | Fmoc-Asp(OtBu)-OH (3.00 eq) | HATU(2.85 eq) and DIEA (6.00 eq) |
| 14 | Acetylation | 10% $Ac_2O$/5% NMM/85% DMF (20 mL) |
| 15 | De-OAll | phenylsilane (10.00 eq), $Pd(PPh_3)_4$ (0.10 eq) |
| 16 | TFP (20.00 eq) | DIC (10.00 eq), DMAP (1.00 eq) |

Peptide Cleavage and Purification:

16) Cleavage buffer (95% TFA/2.5% Tis/2.5% $H_2O$) was added to the flask containing the side chain protected peptide at room temperature and stirred for 1 hr.

17) The solution was combined after filtration.

18) The peptide was precipitated with cold isopropyl ether (100 mL) and centrifuged (3 mins at 3000 rpm).

19) The solid was washed twice with isopropyl ether, and dried under vacuum for 2 hrs.

20) Compound 4a (1.50 g, crude) was obtained as a white solid.

General Procedure for Preparation of Compound 5a:

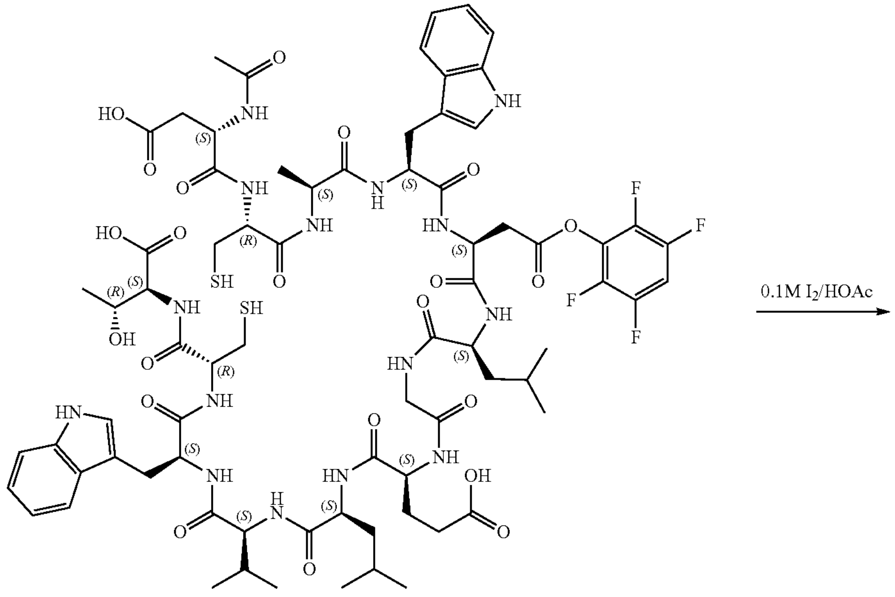

4a

-continued

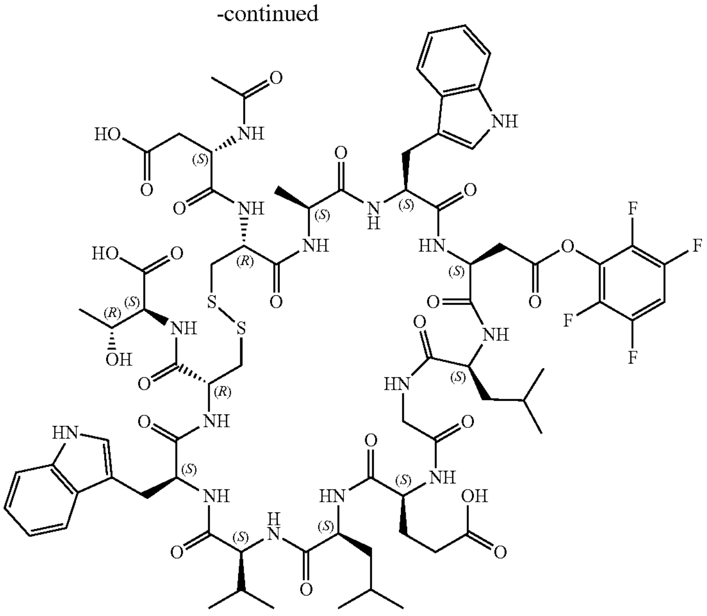

5a

To a mixture of compound 4a (1.51 g, crude) in MeCN/$H_2O$ (1/1, 1 L) was added 0.1 M $I_2$/HOAc dropwise until the color of mixture turned to light yellow. The mixture was stirred at 15° C. for 5 min and the reaction was quenched with 0.1 M $Na_2S_2O_3$ dropwise until the color of mixture turned to colorless. The mixture was dried under lyophilization. The residue was purified by prep-HPLC (acid condition, TFA) directly to get compound 5a (22.01 mg, 90.0% purity, 1.30% yield) as a white solid.

General Procedure for Preparation of Compound I-59:

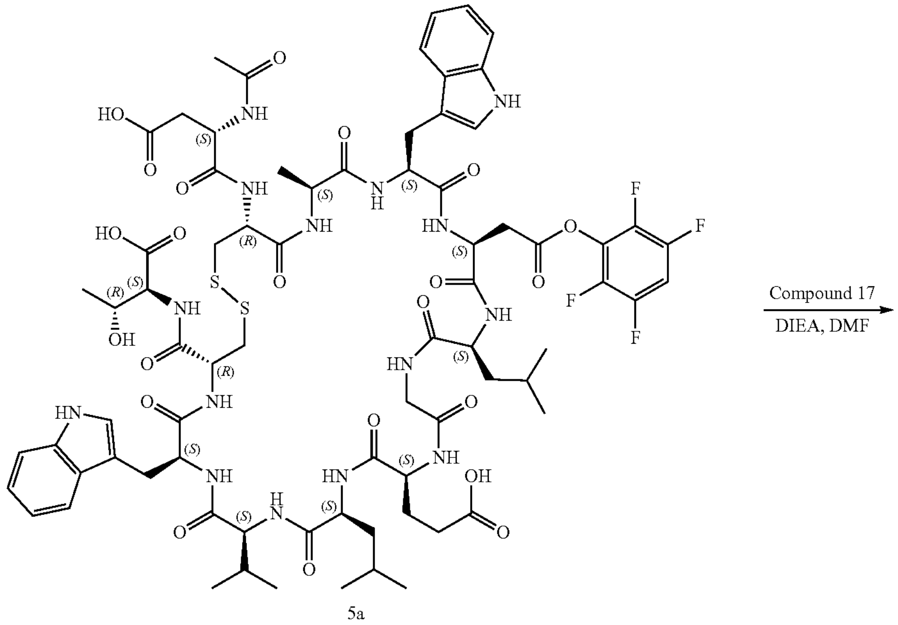

5a

-continued

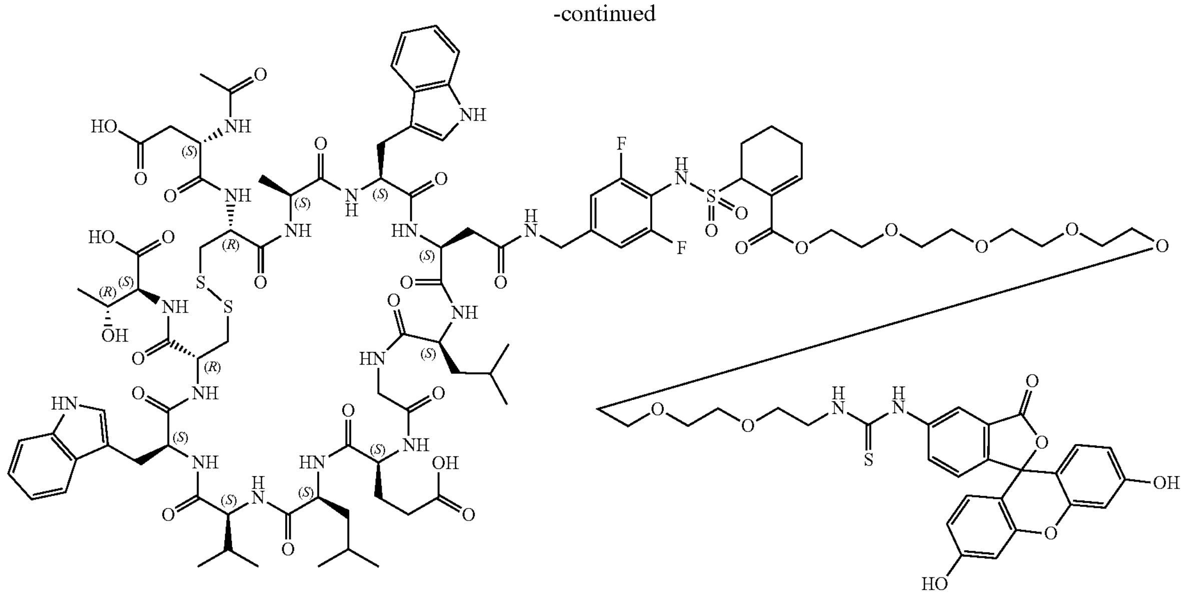

Compound I-59

A mixture of compound 5a (22.01 mg, 12.90 umol, 1.00 eq), and compound 17 (13.50 mg, 12.90 umol, 1.00 eq), DIEA (5.01 mg, 38.90 umol, 6.7 uL, 3.00 eq) in DMF (0.1 mL) was stirred at 15° C. for 1 hr. The mixture was quenched with 1 M HCl to pH=3. The mixture was purified by prep-HPLC (acid condition, TFA) directly to get compound I-59 (0.90 mg, 0.32 umol, 92.4% purity, 2.45% yield) as a white solid, and compound I-59 (1.4 mg, 0.50 umol, 91.2% purity, 3.82% yield) as a yellow solid.

Purification Conditions:

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$) |
| | B: MeCN |
| Gradient | 25-55%-60 min. Retention time: 45 min |
| Column | Luna 25 * 200 mm, C 18 10 um, 110 A + Gemin150 * 30 mm, C 18 5 um, 110 Å |
| Flow Rate | 20 mL/min |
| Wavelength | 220/254 nm |
| Oven Tem. | Room temperature |

Example 36. Exemplary Synthesis of Compound I-60

General Procedure for Preparation of Compound 2:

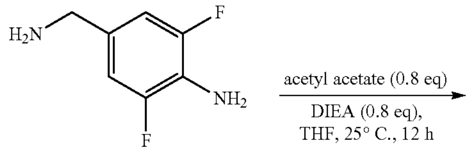

1

-continued

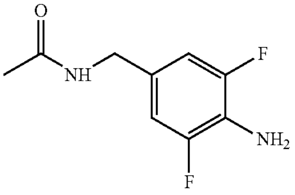

2

A mixture of compound 1 (3 g, 18.9 mmol, 1 eq), acetyl acetate (1.55 g, 15.1 mmol, 1.42 mL, 0.8 eq), DIEA (1.96 g, 15.1 mmol, 2.64 mL, 0.8 eq) in THF (30 mL) was degassed and purged with $N_2$ for 3 times, and then the mixture was stirred at 25° C. for 12 hr under $N_2$ atmosphere. TLC (Petroleum ether:Ethyl acetate=1:1 $R_f$=0.24) indicated compound 1 was consumed completely. The residue was diluted with $H_2O$ (20 mL) and extracted with ethyl acetate (50 ml*2). The reaction mixture was poured into separatory funnel and separated. The combined organic layers were washed with brine (50 mL), dried over $Na_2SO_4$, filtered and concentrated under reduced pressure to give a residue. The residue was purified by column chromatography ($SiO_2$, Petroleum ether:Ethyl acetate=100:1 to 0:1). Compound 2 (3 g, 14.99 mmol, yield: 79.00%) was obtained as a white solid. $^1H$ NMR (400 MHz, DMSO-d6): δ ppm 8.25 (br s, 1H) 6.71-6.85 (m, 2H) 5.07 (s, 2H) 4.09 (d, J=5.96 Hz, 2H) 1.84 (s, 3H).

General Procedure for Preparation of Compound 4:

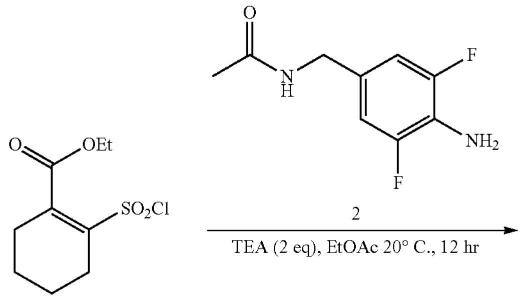

2

3

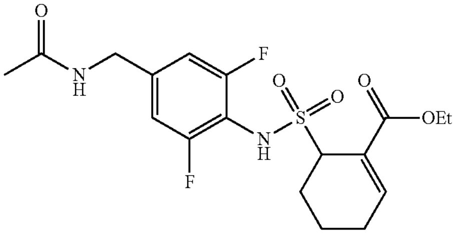

4

To a solution of compound 3 (4.29 g, 16.98 mmol, 2 eq) in EtOAc (20 mL) was added compound 2 (1.7 g, 8.49 mmol, 42.63 uL, 1 eq) TEA (1.72 g, 16.98 mmol, 2.36 mL, 2 eq) in EtOAc (20 mL) at 0° C. over 2 min. After addition, the mixture was stirred at 20° C. for 12 hr. TLC indicated compound 2 was consumed completely. LCMS showed the starting material was consumed completely. The residue was diluted with $H_2O$ (100 mL) and extracted with ethyl acetate (200 ml*2). The reaction mixture was poured into separatory funnel and separated. The combined organic layers were washed with brine (100 mL), dried over $Na_2SO_4$, filtered and concentrated under reduced pressure to give a residue. The residue was purified by column chromatography ($SiO_2$, Petroleum ether:Ethyl acetate=5:1 to 0:1). Compound 4 (4 g, crude) was obtained as a white solid. $^1H$ NMR (400 MHz, DMSO-d6) δ ppm 9.64 (s, 1H) 8.41-8.55 (m, 1H) 7.18-7.31 (m, 1H) 7.07 (br d, J=8.46 Hz, 1H) 4.31-4.40 (m, 1H) 4.26 (d, J=6.08 Hz, 1H) 3.92-4.06 (m, 2H) 2.30-2.44 (m, 2H) 2.04-2.18 (m, 2H) 2.00 (s, 1H) 1.77-1.96 (m, 4H) 1.64 (br s, 1H) 1.15-1.21 (m, 1H) 1.08 (t, J=7.09 Hz, 1H) 1.02 (td, J=7.12, 1.85 Hz, 2H).

General Procedure for Preparation of Compound 5:

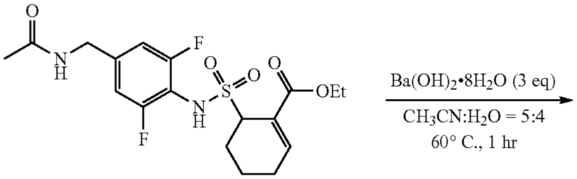

4

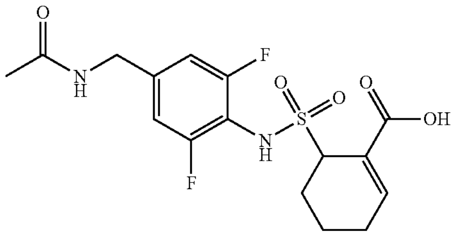

5

To a solution of compound 4 (1.5 g, 3.60 mmol, 1 eq) in $CH_3CN$ (20 mL) H2O (15 mL) was added dihydroxybarium octahydrate (3.41 g, 10.81 mmol, 3 eq). The mixture was stirred at 60° C. for 1 hr. LCMS showed the starting material was consumed completely. The reaction mixture was partitioned between EtOAc (100 mL). The organic phase was separated. The water phase was diluted with $H_2O$ (100 mL), and it was then added with 0.5 M HCl to adjust pH=3-4. The organic phase of the mixture was separated, and the aqueous phase was extracted with ethyl acetate twice, each time 200 mL. Combine all organic phases, wash once with 50 mL saturated salt water, dry anhydrous sodium sulfate, filter and spin dry. The crude product was purified by reversed-phase HPLC (column: Phenomenex luna C18 80*40 mm*3 um; mobile phase: [water (0.04% HCl)-ACN]; B %: 17%-35%, 7 min). Compound 5 (600 mg, 1.54 mmol, yield: 42.89%) was obtained as a white solid. $^1H$ NMR (400 MHz, DMSO-d6) δ ppm 12.28 (br s, 1H) 9.52 (s, 1H) 8.42 (br t, J=5.81 Hz, 1H) 7.05 (br d, J=8.68 Hz, 3H) 4.37 (br d, J=5.38 Hz, 1H) 4.25 (d, J=5.99 Hz, 2H) 2.33 (br d, J=3.67 Hz, 1H) 2.29 (br t, J=4.58 Hz, 1H) 2.17-2.25 (m, 1H) 2.03-2.17 (m, 1H) 1.90 (s, 3H) 1.67-1.81 (m, 1H) 1.54-1.67 (m, 1H). LCMS: Rt=1.232 min, MS (ESI): m/z [M*2+H$^+$] calcd for $C_{16}H_{18}F_2N_2O_5S$, 388.0; found 777.2.

General Procedure for Preparation of Compound 6:

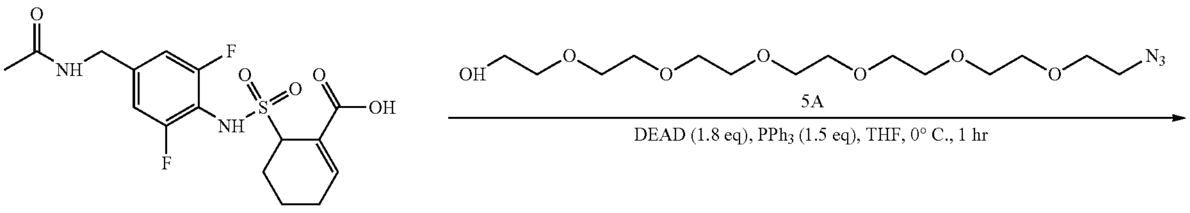

5

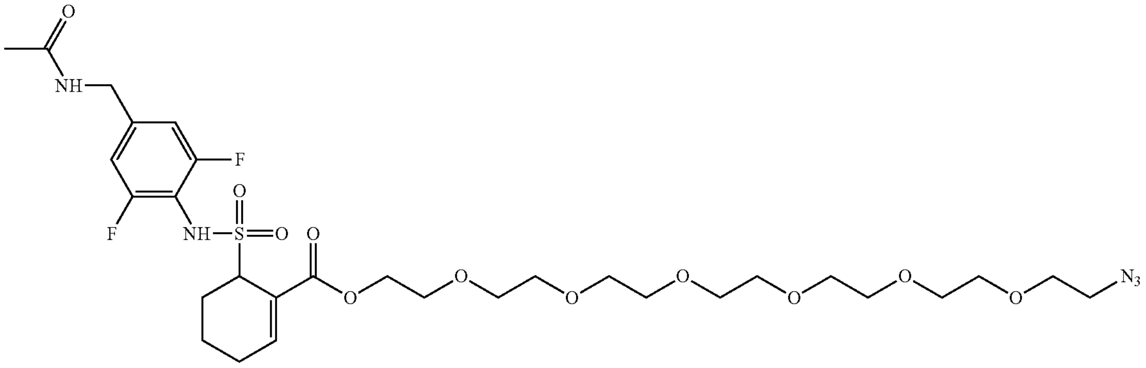

6

To a solution of compound 5 (200 mg, 514 umol, 1 eq) in THF (2 mL) was added $PPh_3$ (202 mg, 772 umol, 1.5 eq) and DEAD (161 mg, 926 umol, 168 uL, 1.8 eq) and compound 5A (361 mg, 1.03 mmol, 2 eq). The mixture was stirred at 15° C. for 1 hr. LCMS showed the starting material was consumed completely. HPLC showed the starting material was consumed completely. The reaction mixture was filtered and the filter was concentrated. The crude product was purified by reversed-phase HPLC (column: Kromasil C18 (250*50 mm*10 um); mobile phase: [water (10 mM $NH_4HCO_3$)-ACN]; B %: 20%-45%, 10 min). Compound 6 (170 mg, 235 umol, yield: 45.74%) was obtained as a white solid. $^1H$ NMR (400 MHz, DMSO-d6): δ ppm 8.42 (br s, 1H) 7.07 (br s, 2H) 4.36 (br s, 1H) 4.25 (br s, 2H) 4.07 (br s, 2H) 3.50 (br s, 16H) 2.10 (br s, 5H) 1.89 (br s, 3H) 1.61 (br s, 3H). LCMS: Rt=1.239 min, MS (ESI): m/z [M+$H_2O^+$] calcd for $C_{30}H_{45}F_2N_5O_{11}S$, 721.2; found 739.3. HPLC: Rt=1.983 min.

General Procedure for Preparation of Compound 7:

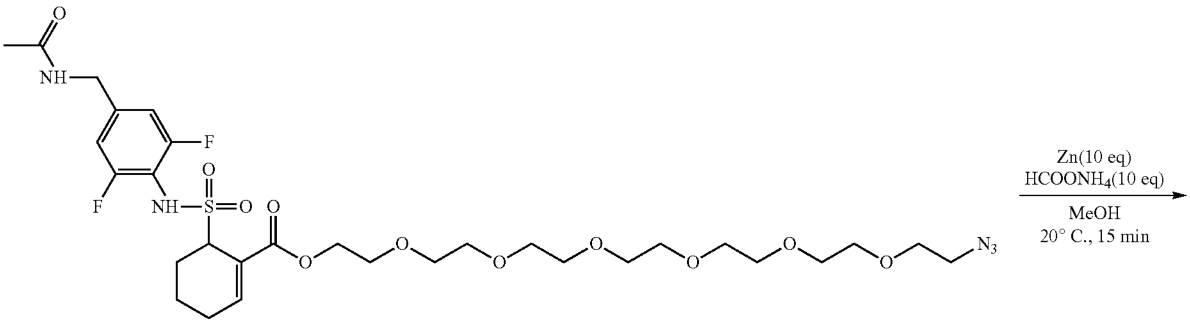

6

-continued

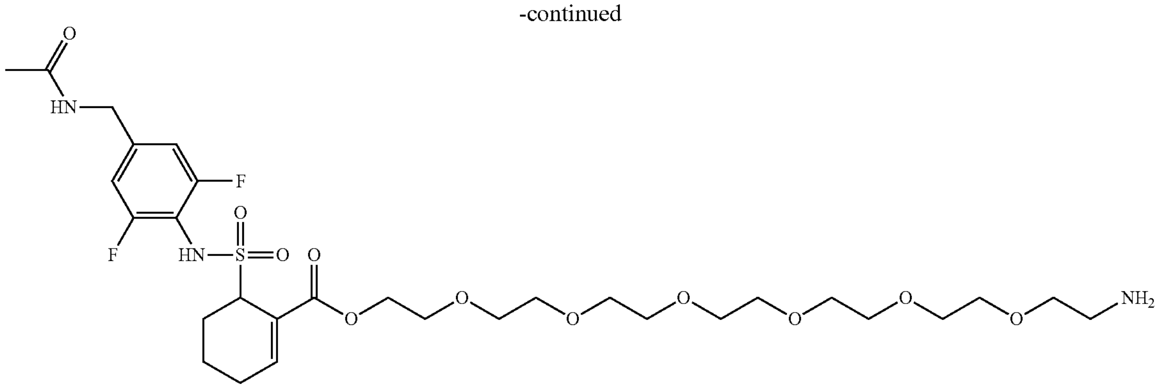

7

A mixture of compound 6 (50 mg, 69.2 umol, 1 eq), Zn (45.30 mg, 692.75 umol, 10 eq), ammonia; formic acid (43.68 mg, 692.75 umol, 10 eq) in MeOH (0.5 mL) was degassed and purged with $N_2$ for 3 times, and then the mixture was stirred at 20° C. for 15 min under $N_2$ atmosphere. LCMS showed the starting material was consumed completely. The reaction mixture was concentrated. The crude product was dissolved in THF (2 ml) and added DCM (2 ml), the mixture was precipitated by solids. The mixture was filtered and the filter cake was washed with DCM (3 mL×2). The combined filtrates were concentrated to dryness to give crude product. Compound 7 (30 mg, 43.12 umol, yield: 62.24%) was obtained as a white oil. LCMS: Rt=0.580 min, MS (ESI): m/z [M+H+] calcd for $C_{30}H_{47}F_2N_3O_{11}S$, 695.5; found 696.2.

General Procedure for Preparation of Compound I-60:

A mixture of compound 7 (30 mg, 43.1 umol, 1 eq), compound 7A (20.15 mg, 51.74 umol, 1.2 eq), and TEA (13.0 mg, 129 umol, 18.0 uL, 3 eq) in DMF (1 mL) was degassed and purged with $N_2$ for 3 times, and then the mixture was stirred at 20° C. for 0.5 hr under $N_2$ atmosphere. LCMS showed the starting material was consumed completely. HPLC showed the starting material was consumed completely. The reaction mixture was filtered and the filtrate was concentrated. The crude product was purified by reversed-phase HPLC (column: Nano-micro Kromasil C18 100*40 mm 10 um; mobile phase: [water (0.1% TFA)-ACN]; B %: 30%-58%, 8 min). The crude product was purified by reversed-phase HPLC (column: Waters Xbridge BEH C18 100*30 mm*10 um; mobile phase: [water (10 mM $NH_4HCO_3$)-ACN]; B %: 5%-40%, 8 min). Compound I-60 (5.27 mg, 5.01 umol, yield: 11.61%, purity 96.00%) was

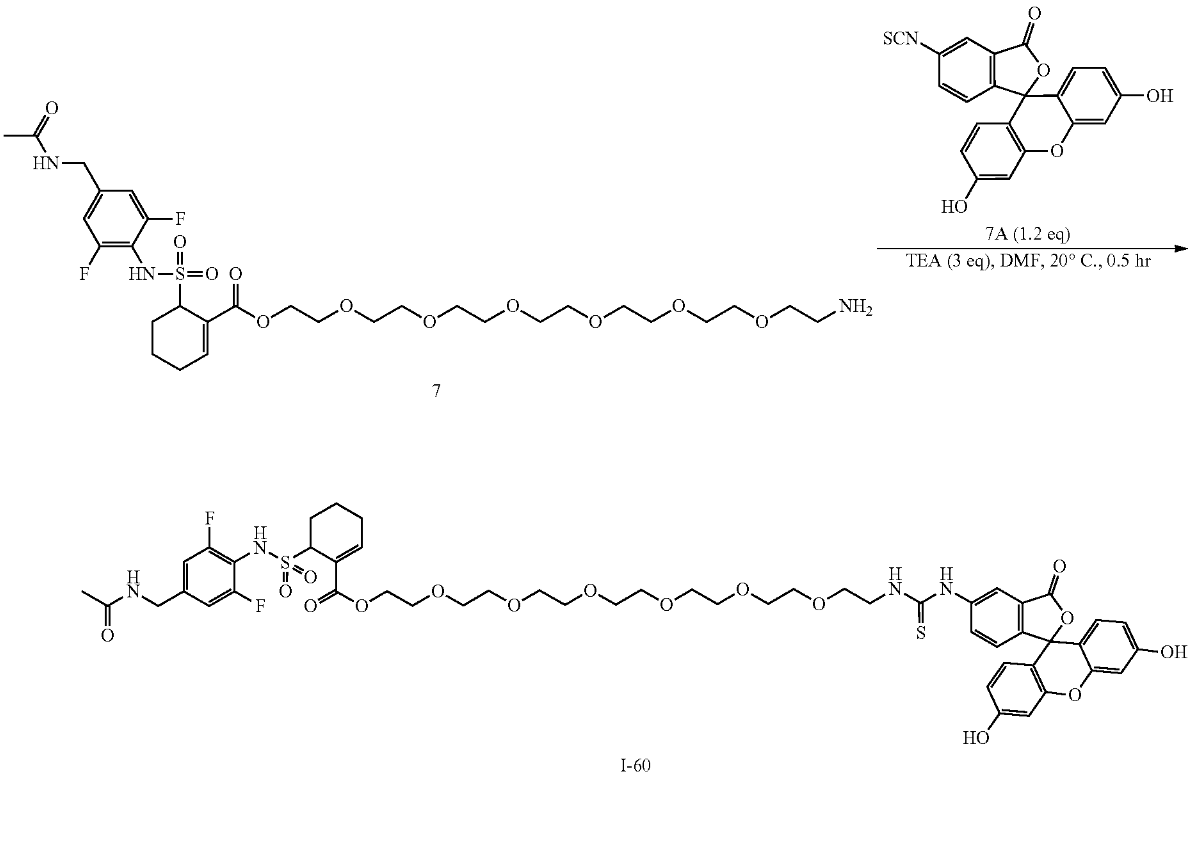

7

I-60 obtained as a yellow solid. $^1H$ NMR (400 MHz, DMSO-d6): δ ppm 10.05 (s, 1H) 8.40 (br s, 1H) 8.27 (s, 1H) 8.14 (br s, 1H) 7.73 (s, 1H) 7.17 (d, J=8.16 Hz, 1H) 6.96-7.07 (m, 3H) 6.67 (s, 2H) 6.52-6.62 (m, 4H) 4.31 (br s, 1H) 4.23 (br d, J=5.95 Hz, 2H) 4.05 (br d, J=4.41 Hz, 2H) 3.68 (br s, 2H) 3.60 (br s, 2H) 3.56 (s, 4H) 3.41-3.54 (m, 20H) 2.25-2.31 (m, 1H) 2.20 (s, 1H) 2.15 (br s, 2H) 1.89 (s, 3H) 1.74 (s, 1H) 1.59 (s, 1H). LCMS: Rt=0.716 min, MS (ESI): m/z [M/2+$H^+$] calcd for $C_{51}H_{58}F_2N_4O_{16}S_2$, 1084.3; found 543.9. HPLC: Rt=1.481 min. QC data for compound I-60: HPLC: Rt=3.047 min, purity: 96.00%. MS: MS (ESI): m/z [M+$H^+$] calcd for $C_{51}H_{58}F_2N_4O_{16}S_2$, 1084.3; [M+$H^+$]=1085.1; [M/2+$H^+$]=543.1; found 1085.1.

Example 37. Exemplary Synthesis of Compound I-61

General Procedure for Preparation of Compound 2

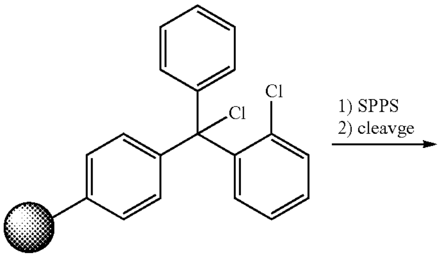

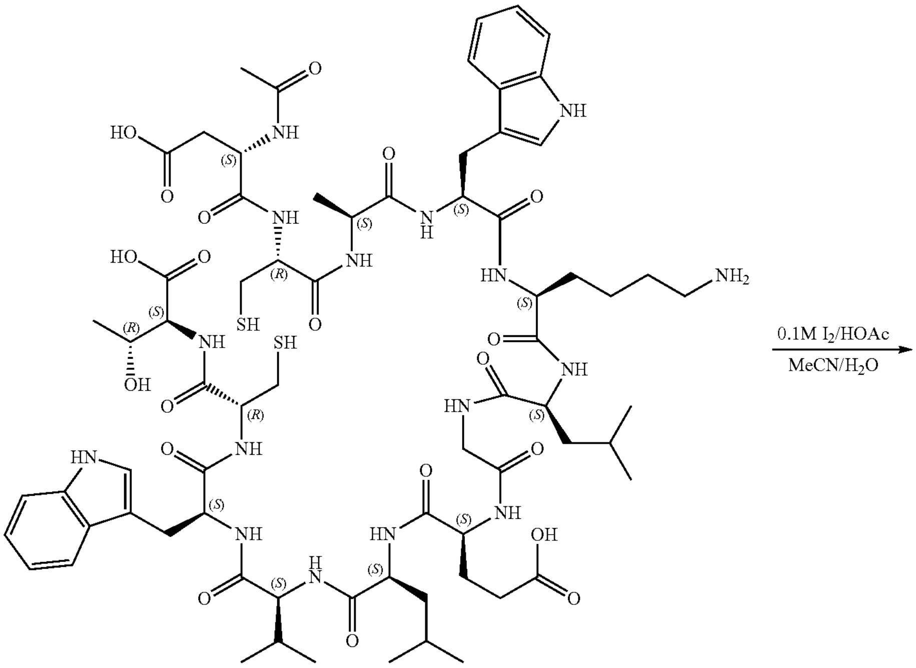

1

-continued

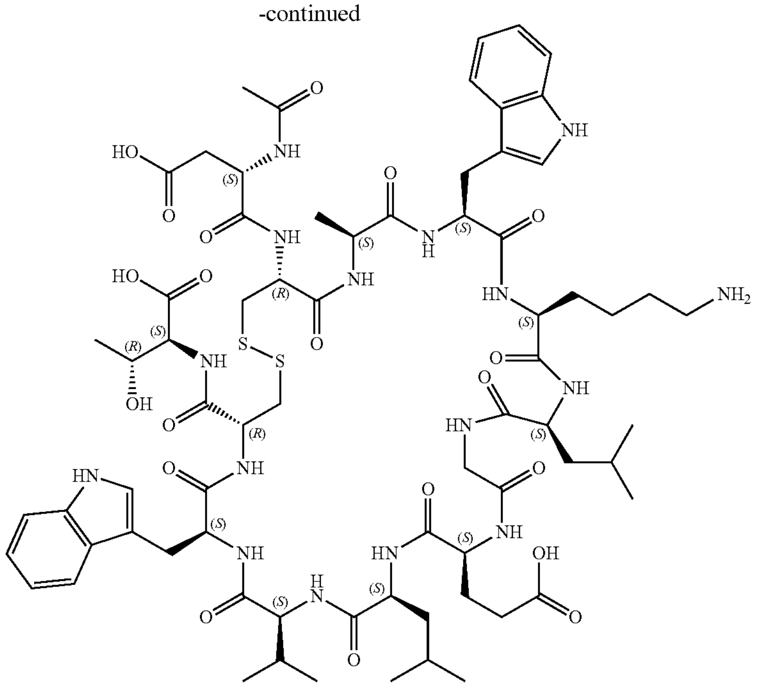

2

The peptide was synthesized using standard Fmoc chemistry:

8) Resin preparation: To the vessel containing CTC Resin (0.50 mmol, 0.50 g, 1.00 mmol/g) and Fmoc-Thr(tBu)-OH (0.20 g, 0.50 mmol, 1.00 eq) in DCM (5.0 mL) was added DIEA (4.00 eq) dropwise and mixed for 2 hrs with $N_2$ bubbling at 15° C. Then added MeOH (0.5 mL) and bubbled with $N_2$ for another 30 mins. The resin was washed with DMF (10.0 mL)*5, followed by adding 20% piperidine in DMF (10.0 mL) to the vessel and the mixture was bubbled with $N_2$ for 30 mins at 15° C. After filtration the resin was washed with DMF (10.0 mL)*5 before proceeding to next step.

9) Coupling: A solution of Fmoc-Cys(Trt)-OH (3.00 eq), HBTU (2.85 eq) in DMF (5.0 mL) was added to the resin with $N_2$ bubbling. Then DIEA (6.00 eq) was added to the mixture dropwise and bubbled with $N_2$ for 30 mins at 15° C. The coupling reaction was monitored by ninhydrin test, if it showed colorless, the coupling was completed. The resin was then washed with DMF (10.0 mL)*5.

10) De-protection: 20% piperidine in DMF (10.0 mL) was added to the resin and the mixture was bubbled with $N_2$ for 30 mins at 15° C. The resin was then washed with DMF (10.0 mL)*5. The de-protection reaction was monitored by ninhydrin test, if it showed blue or other brownish red, the reaction was completed.

11) Repeat Step 2 and 3 for all other amino acids: (2-13 in the table below).

12) Acetylation: A solution of 10% $Ac_2O$/5% NMM/85% DMF (10.0 mL) was added to resin and the mixture was bubbled with $N_2$ for 20 mins. The coupling reaction was monitored by ninhydrin test, if it showed colorless, the coupling was completed. The resin was then washed with DMF (10.0 mL)*5, MeOH (10.0 mL)*5 and dried under vacuum.

| # | Materials | Coupling reagents |
|---|---|---|
| 1 | Fmoc-Thr(tBu)-OH (1.00 eq) | DIEA (4.00 eq) |
| 2 | Fmoc-Cys(Trt)-OH (3.00 eq) | HBTU (2.85 eq) and DIEA (6.00 eq) |
| 3 | Fmoc-Trp-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OtBu)-OH (3.00 eq) | HBTU (2.85 eq) and DIEA (6.00 eq) |
| 7 | Fmoc-Gly-OH (3.00 eq) | HBTU (2.85 eq) and DIEA (6.00 eq) |
| 8 | Fmoc-Leu-OH (3.00 eq) | HBTU (2.85 eq) and DIEA (6.00 eq) |
| 9 | Fmoc-Lys(Boc)-OH (3.00 eq) | HBTU (2.85 eq) and DIEA (6.00 eq) |
| 10 | Fmoc-Trp-OH (3.00 eq) | HBTU (2.85 eq) and DIEA (6.00 eq) |
| 11 | Fmoc-Ala-OH (3.00 eq) | HBTU (2.85 eq) and DIEA (6.00 eq) |
| 12 | Fmoc-Cys(Trt)-OH (3.00 eq) | HBTU (2.85 eq) and DIEA (6.00 eq) |
| 13 | Fmoc-Asp(OtBu)-OH (3.00 eq) | HBTU (2.85 eq) and DIEA (6.00 eq) |
| 14 | Acetylation | 10% $Ac_2O$/5% NMM/85% DMF (20 mL) |

Peptide Cleavage and Purification:

21) Cleavage buffer (95% TFA/2.5% Tis/2.5% $H_2O$) was added to the flask containing the side chain protected peptide at room temperature and stirred for 1 hr.

22) The solution was combined after filtration.

23) The peptide was precipitated with cold isopropyl ether (100 mL) and centrifuged (3 mins at 3000 rpm).

24) The solid was washed twice with isopropyl ether, and dried under vacuum for 2 hrs to get compound 1 (600.0 mg, crude) as a white solid.

To a mixture of compound 1 (600.0 mg, crude) in MeCN/$H_2O$ (1/1, 500.0 mL) was added 0.1 M $I_2$/HOAc dropwise until the light yellow persisted, then the mixture was quenched with 0.1 M $Na_2S_2O_3$ dropwise until the light yellow disappeared. The mixture was lyophilized, followed by prep-HPLC (acid condition, TFA) purification to get compound 2 (245.0 mg) as a white solid.

General Procedure for Preparation of Compound 4:

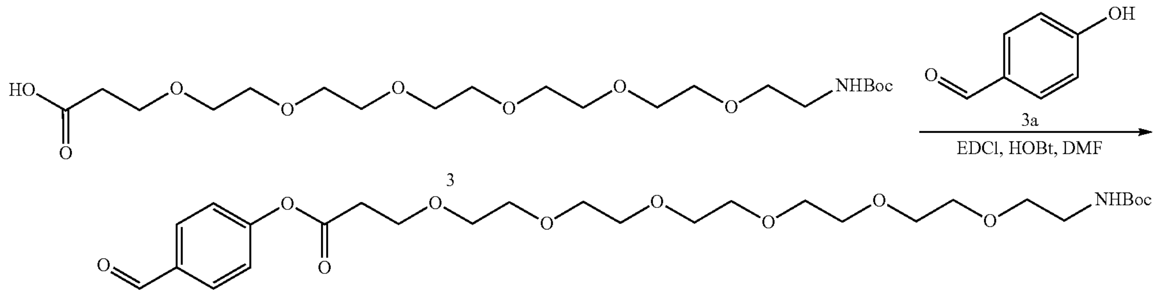

3

4

A mixture of compound 3a (323.1 mg, 2.65 mmol, 3.00 eq), compound 3 (400.0 mg, 881.98 umol, 1.00 eq), DIC (333.9 mg, 2.65 mmol, 409.71 uL, 3.00 eq), HOBt (357.5 mg, 2.65 mmol, 3.00 eq), and DMAP (215.5 mg, 1.76 mmol, 2.00 eq) in DMF (4 mL) was stirred at 15° C. for 16 hrs. The residue was purified by flash C18 (ISCO®; 120 g Sepa-Flash® C18 Flash Column, Eluent of 0~90% MeCN/$H_2O$ ether gradient @ 75 mL/min) directly to get compound 4 (400.0 mg, 717.3 umol, 81.3% yield) as a colorless oil. $^1$HNMR (400 MHz $CD_3Cl$): δ ppm 9.99-10.04 (m, 1H) 7.88-7.97 (m, 2H) 7.29-7.34 (m, 2H) 5.12 (s, 1H) 3.90 (t, J=6.27 Hz, 2H) 3.68-3.71 (m, 4H) 3.66-3.68 (m, 12H) 3.61-3.65 (m, 4H) 3.52-3.58 (m, 2H) 3.33 (d, J=4.77 Hz, 2H) 2.89 (t, J=6.27 Hz, 2H) 1.46 (s, 9H).

General Procedure for Preparation of Compound 5:

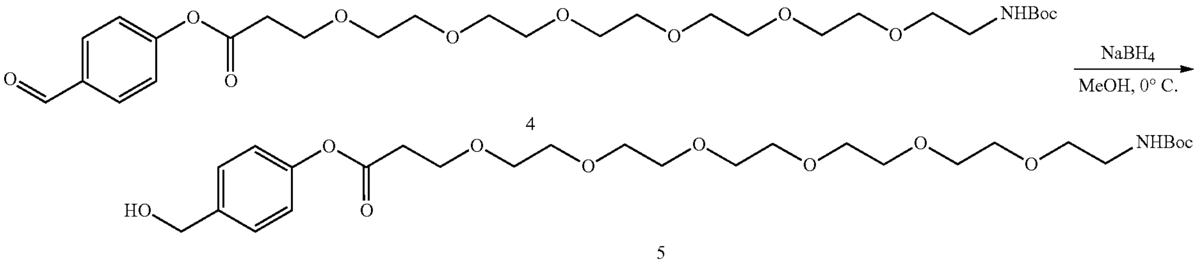

4

5

To a mixture of compound 4 (360.0 mg, 645.5 umol, 1.00 eq) in MeOH (5 mL) was added a solution of $NaBH_4$ (24.4 mg, 645.50 umol, 1.00 eq) in MeOH (0.2 mL) at 0° C., then the mixture was stirred at 0° C. for 0.5 hr. The residue was purified by flash C18 (ISCO®; 120 g SepaFlash® C18 Flash Column, Eluent of 0~90% MeCN/H2O ether gradient @ 75 mL/min) directly to get compound 5 (330.0 mg, 589.61 umol, 91.34% yield) as a colorless oil.

General Procedure for Preparation of Compound 6:

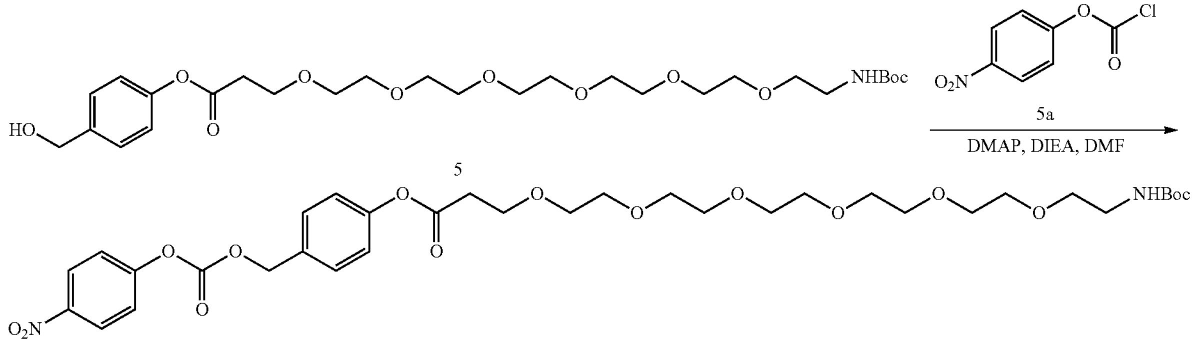

5

6

A mixture of compound 5a (237.7 mg, 1.18 mmol, 2.00 eq), compound 5 (330.0 mg, 589.61 umol, 1.00 eq), and DIEA (304.8 mg, 2.36 mmol, 410.8 uL, 4.00 eq) in THF (5 mL) was stirred at 15° C. for 2 hrs. The residue was purified by flash C18 (ISCO®; 120 g SepaFlash® C18 Flash Column, Eluent of 0~90% MeCN/$H_2O$ ether gradient @ 75 mL/min) directly to get compound 6 (200.0 mg, 275.91 umol, 46.8% yield) as a light yellow oil.

General Procedure for Preparation of Compound 7:

A mixture of compound 2 (92.6 mg, 55.19 umol, 1.00 eq, TFA), compound 6 (40.0 mg, 55.19 umol, 1.00 eq), and DIEA (35.6 mg, 275.91 umol, 48.0 uL, 5.00 eq) in DMF (2 mL) was stirred at 15° C. for 1 hr. The residue was purified by flash C18 (ISCO®; 120 g SepaFlash® C18 Flash Column, Eluent of 0~90% MeCN/$H_2O$ ether gradient @ 75 mL/min) directly to get compound 7 (40.0 mg, 18.6 umol, 33.7% yield) as a white solid.

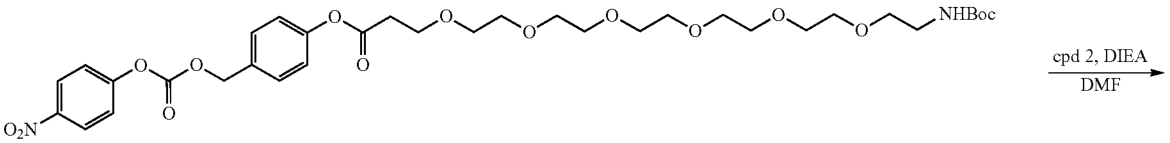

6

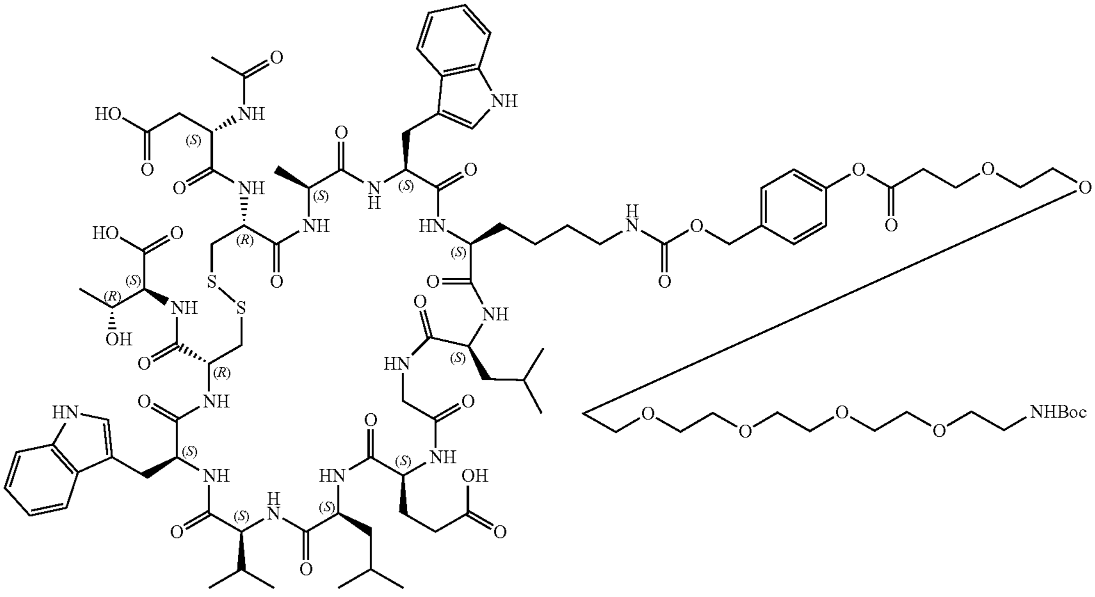

7

General Procedure for Preparation of Compound 8:

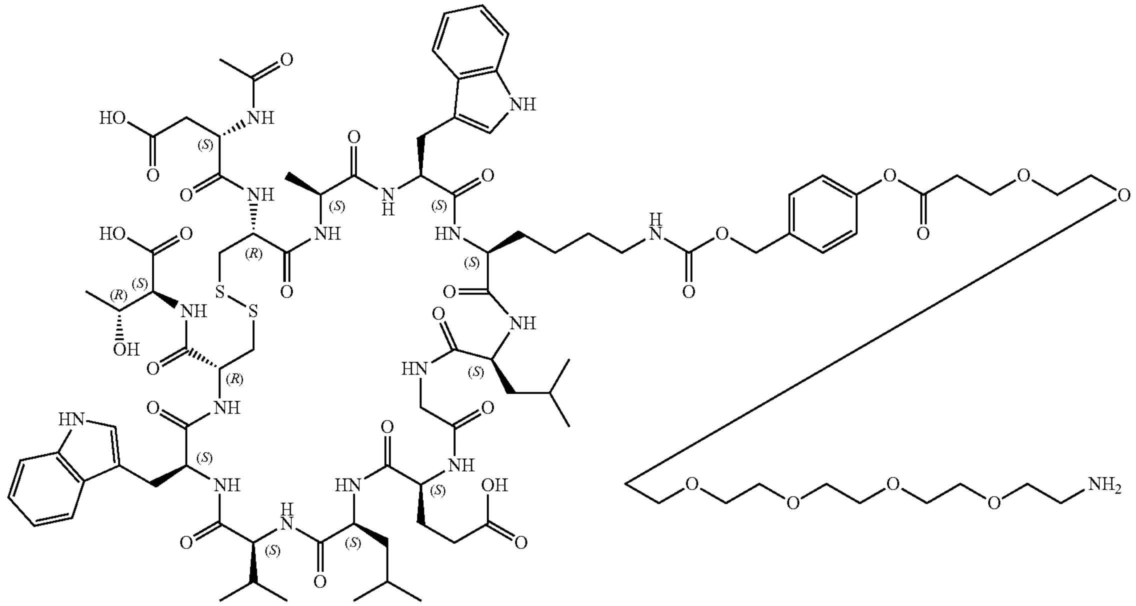

8

A mixture of compound 7 (40.0 mg, 18.61 umol, 1.00 eq) in 25% TFA/DCM (1:4, 5.0 mL) was stirred at 0° C. for 2 hr. The solvent was removed under reduced pressure at 0° C. The residue was purified by flash C18 (ISCO®; 120 g SepaFlash® C18 Flash Column, Eluent of 0~90% MeCN/$H_2O$ ether gradient @ 75 mL/min) directly to get compound 8 (30.0 mg, 13.80 umol, 74.5% yield, TFA) as a white solid.

General Procedure for Preparation of Compound I-61:

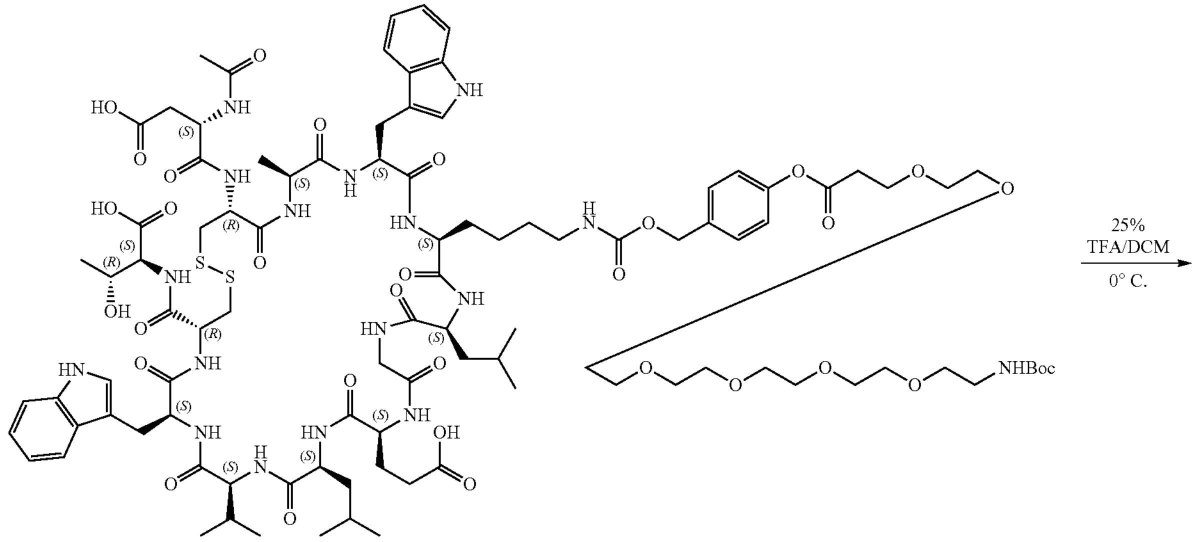

7

-continued

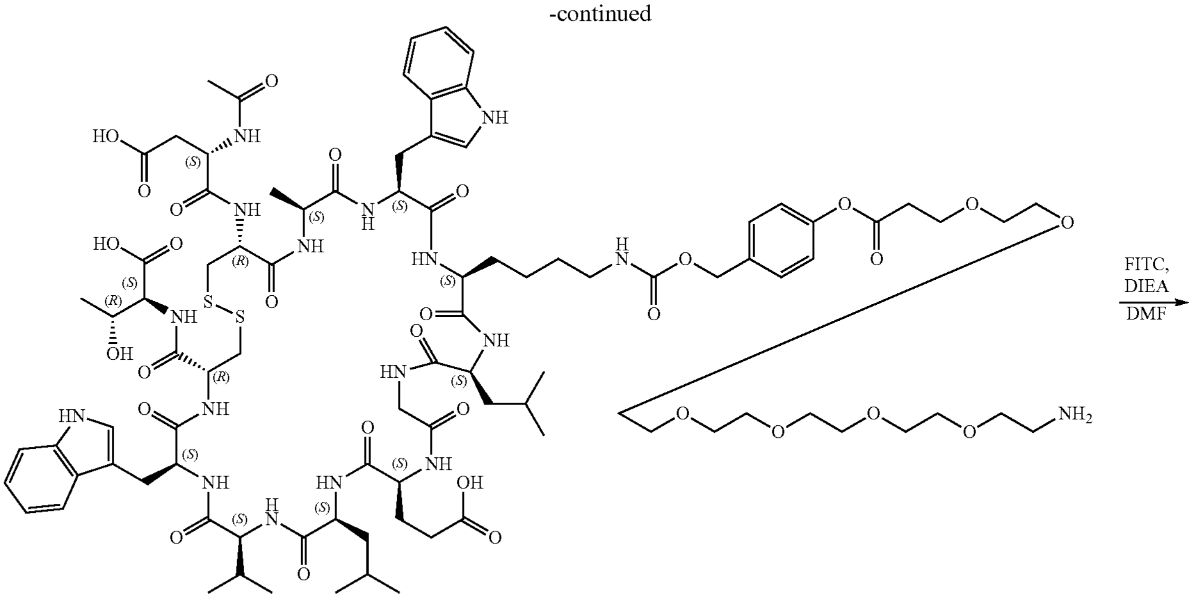

8

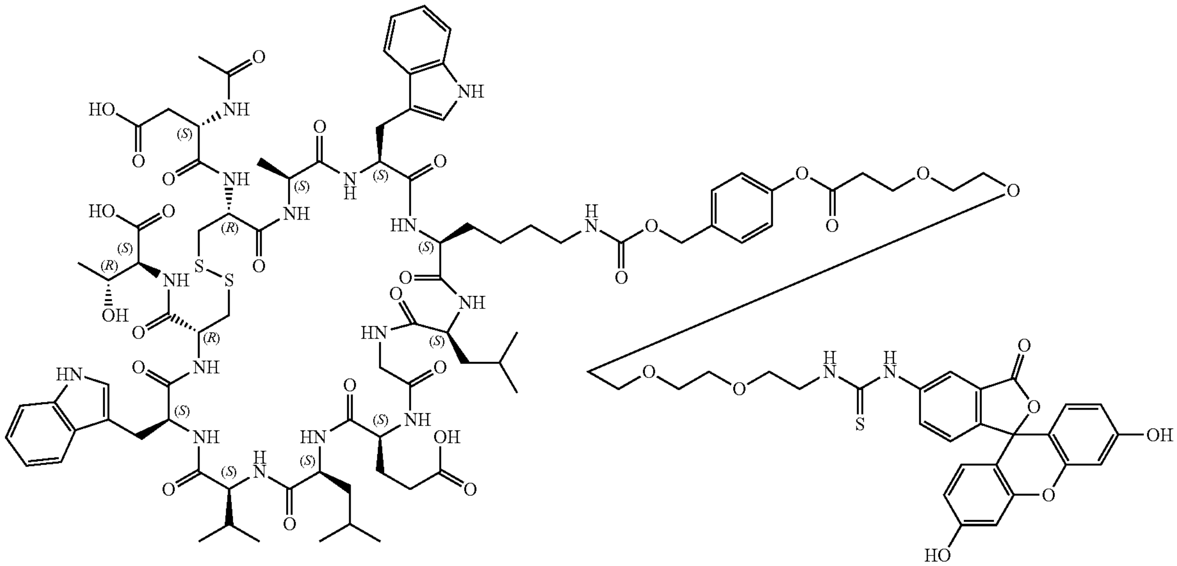

I-61

A mixture of compound 8 (30.0 mg, 13.80 umol, 1.00 eq, TFA), FITC (8.1 mg, 20.80 umol, 1.50 eq), DIEA (7.12 mg, 55.40 umol, 9.6 uL, 4.00 eq) in DMF (0.5 mL) was stirred at 15° C. for 1 hr. The solution was purified by prep-HPLC (acid condition, TFA) directly to get compound I-61 (14.3 mg, 5.05 umol, 36.4% yield, 86.2% purity) as a yellow solid.

Purification Conditions:

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$)<br>B: MeCN |
| Gradient | 20-50%-60 min. Retention time: 45 min |
| Column | Luna 75*200 mm, C18 10 um, 110 Å +<br>Gemin 150*30 mm, C18 5 um, 110 Å |
| Flow Rate | 20 mL/min |
| Wavelength | 220/254 nm |
| Oven Tem. | Room temperature |

Example 38. Exemplary Synthesis of Compound I-62

General Procedure for Preparation of Compound 2:

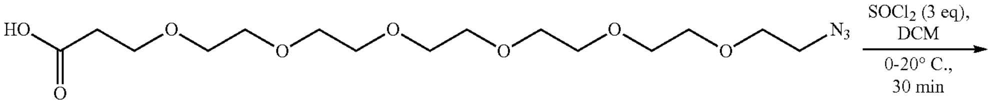

1

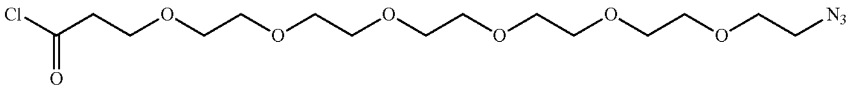

2

To a solution of compound 1 (500 mg, 1.32 mmol, 1 eq) in DCM (3 mL) was added $SOCl_2$ (470.36 mg, 3.95 mmol, 286.80 uL, 3 eq) at 0° C. The mixture was stirred at 20° C. for 30 min. TLC indicated compound 1 was consumed completely and one new spot formed. The reaction mixture was concentrated to dryness. The crude product compound 2 (524 mg, crude) was used into the next step without further purification.

General procedure for preparation of compound 4:

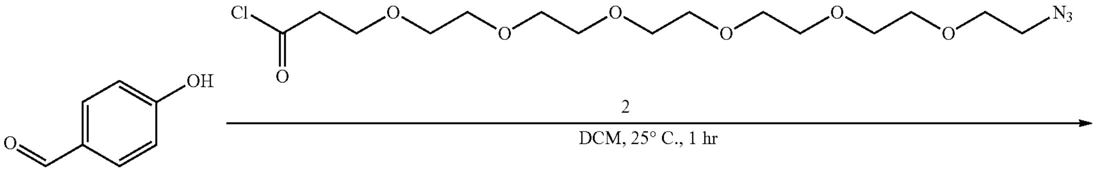

2

3

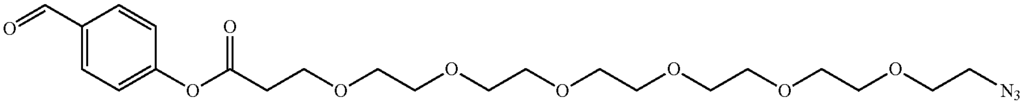

4

To a solution of compound 3 (160 mg, 1.31 mmol, 1 eq) in DCM (3 mL) was added TEA (397.73 mg, 3.93 mmol, 547.08 uL, 3 eq) at 0° C. The mixture was added with compound 2 (521.25 mg, 1.31 mmol, 1 eq) in DCM (1 mL) at 0° C. The mixture was stirred at 25° C. for 1 hr. TLC indicated compound 3 was consumed completely and one new spot formed. The reaction was clean according to TLC. The mixture was diluted with $H_2O$ (10 mL), extracted with DCM (20 mL*3). The combined organic layer was washed with 5 mL $H_2O$, 5 mL brine, dried over $Na_2SO_4$, filtered and the filtrate was concentrated to give a crude product. Compound 4 (550 mg, 1.14 mmol, yield: 86.82%) was obtained as yellow oil. $^1H$ NMR (CHLOROFORM-d, 400 MHz): δ 10.00 (s, 1H), 7.93 (d, 2H, J=8.7 Hz), 7.2-7.3 (m, 3H), 3.89 (t, 2H, J=6.2 Hz), 3.6-3.7 (m, 24H), 3.39 (t, 2H, J=5.1 Hz), 2.88 (t, 2H, J=6.2 Hz).

General Procedure for Preparation of Compound 5:

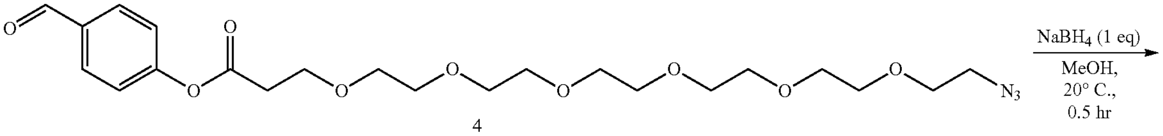

4

-continued

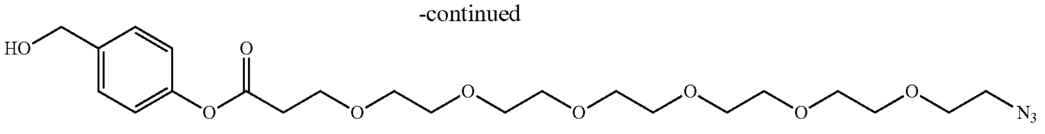

5

To a solution of compound 4 (250 mg, 517.05 umol, 1 eq) in THF (1 mL) was added $NaBH_4$ (19.56 mg, 517.05 umol, 1 eq) at 0° C. The mixture was stirred at 20° C. for 30 min. LC-MS showed compound 4 was consumed completely. The reaction was quenched by addition of 1 mL of HCl (0.5M) to PH=4-5 at 0° C. The mixture was purified directly. The residue was purified by prep-HPLC (TFA condition; column: Phenomenex Synergi C18 150*25*10 um; mobile phase: [water (0.1% TFA)-ACN]; B %: 15%-55%, 10 min). Compound 5 (340 mg, 700.27 umol, yield: 67.72%) was obtained as colourless oil. LCMS: RT=1.748 min, MS (ESI): m/z [M+H$^+$] calcd for $C_{22}H_{35}N_3O_9$, 485.24; found 440.3. $^1$H NMR (CHLOROFORM-d, 400 MHz): δ 7.38 (br s, 2H), 7.2-7.3 (m, 1H), 7.09 (br d, 2H, J=4.6 Hz), 4.70 (br s, 2H), 3.8-3.9 (m, 2H), 3.6-3.8 (m, 23H), 3.39 (br s, 2H), 2.8-2.9 (m, 2H), 1.8-2.2 (m, 3H).

General Procedure for Preparation of Compound 6:

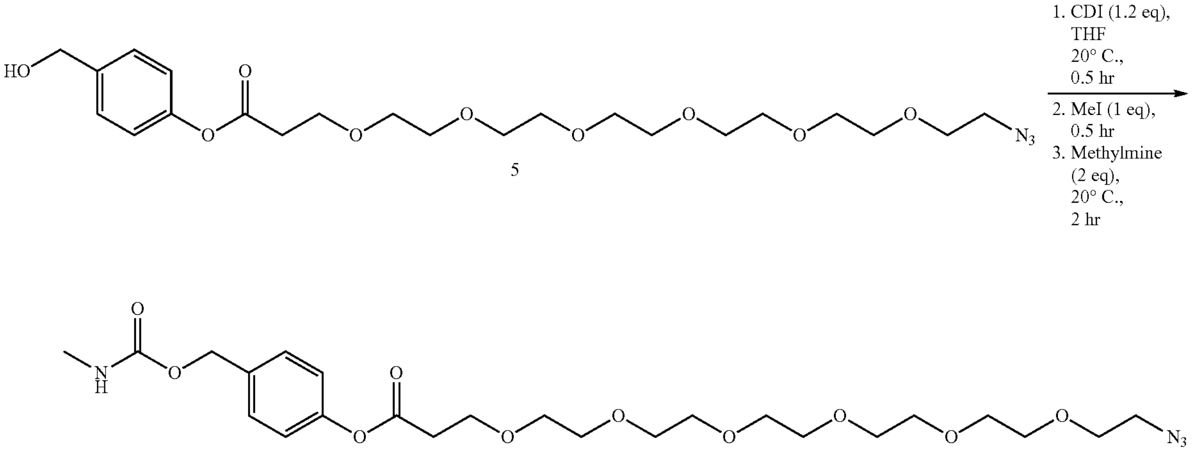

5

6

To a solution of compound 5 (100 mg, 205.96 umol, 1 eq) in THF (1 mL) was added CDI (40.08 mg, 247.15 umol, 1.2 eq) for 0.5 hr. The mixture was added with MeI (29.23 mg, 205.96 umol, 12.82 uL, 1 eq) for 0.5 hr. The mixture was added with methanamine (0.5 M, 823.85 uL, 2 eq). The mixture was stirred at 20° C. for 2 hr. LC-MS showed desired mass was detected. The reaction mixture was dried under nitrogen gas. The mixture was purified directly. The residue was purified by prep-HPLC (TFA condition; column: Phenomenex luna C18 100*40 mm*3 um; mobile phase: [water (0.1% TFA)-ACN]; B %: 35%-65%, 10 min). Compound 6 (50 mg, 92.15 umol, yield: 44.74%) was obtained as yellow oil. LCMS: Rt=1.277 min, MS (ESI): m/z [M+H$^+$] calcd for $C_{24}H_{38}N_4O_{10}$, 543.26; found 543.3. $^1$H NMR (CHLOROFORM-d, 400 MHz): δ 7.38 (br d, 2H, J=8.2 Hz), 7.09 (d, 2H, J=8.4 Hz), 5.09 (s, 2H), 3.87 (t, 2H, J=6.4 Hz), 3.6-3.7 (m, 23H), 3.39 (t, 2H, J=5.1 Hz), 2.8-2.9 (m, 5H).

General Procedure for Preparation of Compound 7:

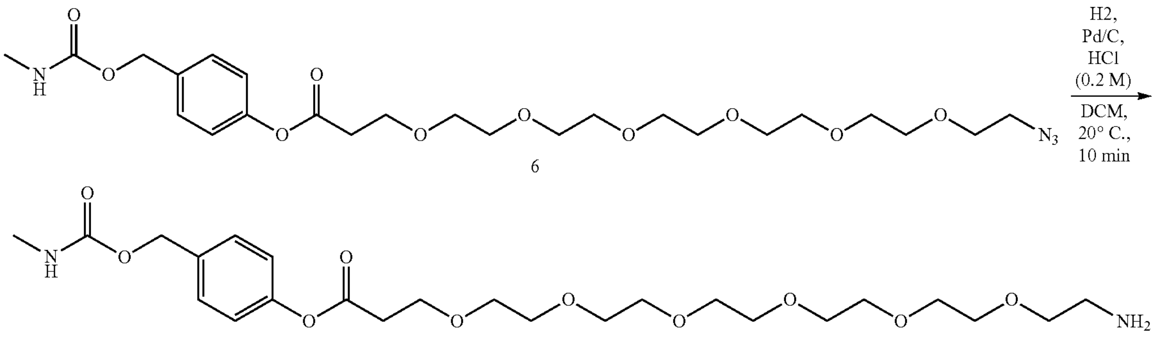

6

7

To a solution of compound 6 (30 mg, 55.29 umol, 1 eq) in THF (0.5 mL) was added Pd/C (15 mg, 10% purity) and HCl (0.2 M, 276.46 uL, 1 eq) under $N_2$ atmosphere. The suspension was degassed and purged with $H_2$ for 3 times. The mixture was stirred under $H_2$ (15 Psi) at 20° C. for 5 min. LC-MS showed compound 6 was consumed completely and desired mass was detected. The suspension was filtered and the filter cake was washed with THF (2 mL×2). The combined filtrates were dried under nitrogen gas. The residue was purified by prep-HPLC (TFA condition; column: Nano-micro Kromasil C18 100*40 mm 10 um; mobile phase: [water (0.1% TFA)-ACN]; B %: 1%-34%, 8 min). Compound 7 (10 mg, 18.00 umol, 32.56% yield, 93% purity) was obtained as colorless oil. LCMS: Rt=1.465 min, MS (ESI): m/z [M+H$^+$] calcd for $C_{24}H_{40}N_2O_{10}$, 517.27; found 517.3.

General Procedure for Preparation of Compound I-62:

To a solution of compound 7 (5 mg, 7.93 umol, 1 eq, TFA) and compound 8 (2.78 mg, 7.14 umol, 0.9 eq) in DMF (0.5 mL) was added TEA (1.60 mg, 15.86 umol, 2.21 uL, 2 eq). The mixture was stirred at 20° C. for 30 min. LC-MS showed compound 7 was consumed completely and desired mass was detected. The mixture was purified directly. The residue was purified by prep-HPLC (TFA condition; column: Phenomenex Synergi C18 150*25*10 um; mobile phase: [water (0.1% TFA)-ACN]; B %: 25%-50%, 10 min). Compound I-62 (5.34 mg, 5.77 umol, yield: 36.39%, 97.91% purity) was obtained as a yellow solid. $^1$H NMR (DMSO-d6, 400 MHz): δ 8.27 (s, 1H), 7.9-8.2 (m, 1H), 7.74 (br d, 1H, J=7.6 Hz), 7.37 (br d, 2H, J=8.4 Hz), 7.18 (d, 1H, J=8.3 Hz), 7.09 (br d, 3H, J=8.3 Hz), 6.67 (d, 2H, J=2.0 Hz), 6.5-6.6 (m, 4H), 5.00 (s, 2H), 3.73 (br t, 3H, J=6.2 Hz), 3.68 (br s, 2H), 3.6-3.6 (m, 3H), 3.5-3.6 (m, 22H), 2.8-2.8 (m, 2H), 2.57 (br d, 4H, J=4.5 Hz). LCMS: Rt=2.430 min, MS (ESI): m/z [M+H$^+$] calcd for $C_{45}H_{51}N_3O_{15}S$, 906.30; found 906.6. QC data for compound I-62: HPLC: Rt=2.907 min, purity: 97.91%. LCMS: Rt=2.330 min. MS (ESI): m/z [M+H$^+$] calcd for $C_{45}H_{51}N_3O_{15}S$, 906.30; found 906.3.

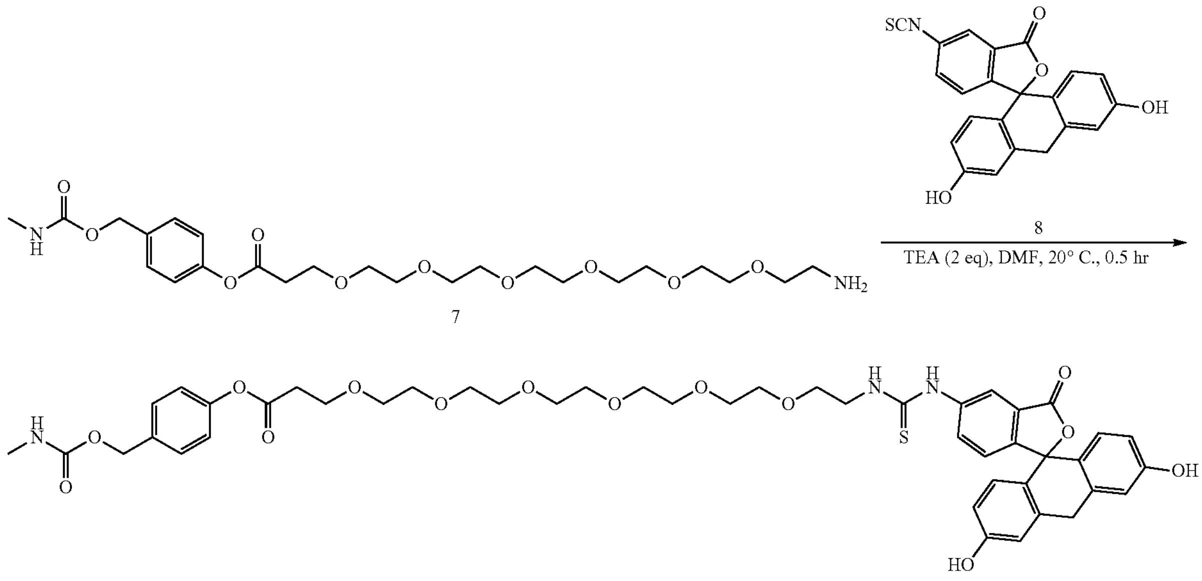

8

7

I-62

Example 39. Exemplary Synthesis of Compound I-63
General Procedure for Preparation of Compound 2:
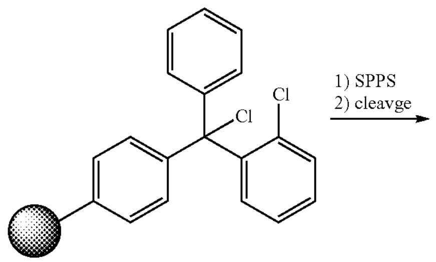
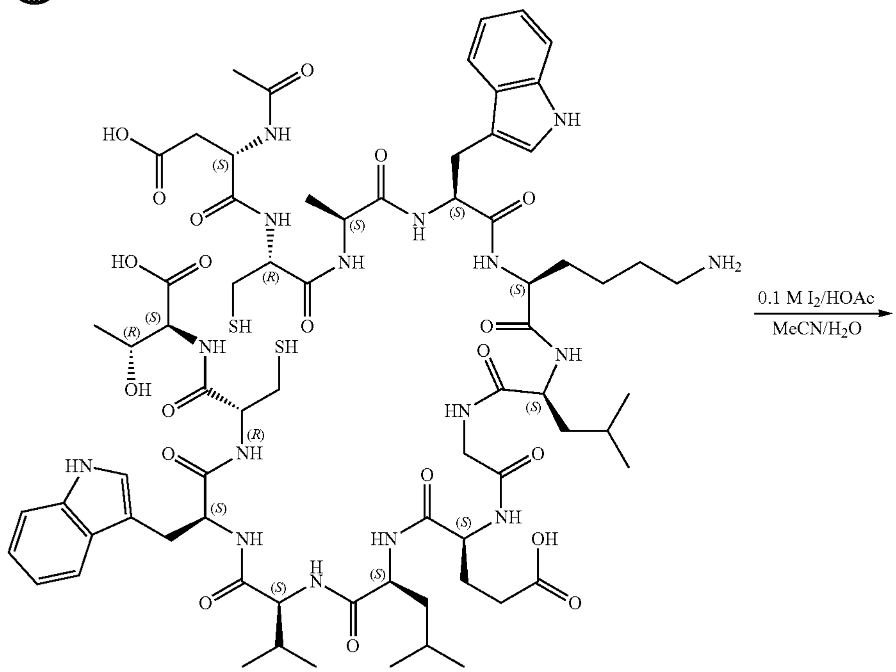
1
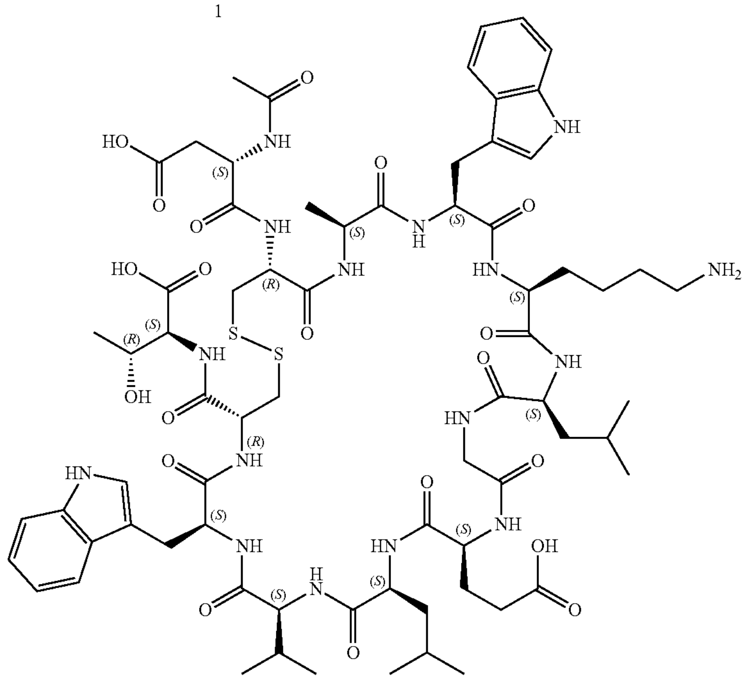
2

The peptide was synthesized using standard Fmoc chemistry.

1) Resin preparation: To the vessel containing CTC Resin (0.50 mmol, 0.50 g, 1.0 mmol/g) and Fmoc-Thr(tBu)-OH (0.20 g, 0.50 mmol, 1.00 eq) in DCM (5.0 mL) was added DIEA (4.00 eq) dropwise and mixed for 2 hrs with $N_2$ bubbling at 15° C. Then added MeOH (0.5 mL) and bubbled with $N_2$ for another 30 mins. The resin was washed with DMF (10.0 mL)*5, followed by adding 20% piperidine in DMF (10.0 mL) to the vessel and the mixture was bubbled with $N_2$ for 30 mins at 15° C. After filtration the resin was washed with DMF (10.0 mL)*5 before proceeding to next step.
2) Coupling: A solution of Fmoc-Cys(Trt)-OH (3.00 eq), HBTU (2.85 eq) in DMF (5.0 mL) was added to the resin with $N_2$ bubbling. Then DIEA (6.00 eq) was added to the mixture dropwise and bubbled with $N_2$ for 30 mins at 15 T. The coupling reaction was monitored by ninhydrin test, if it showed colorless, the coupling was completed. The resin was then washed with DMF (10.0 mL)*5.
3) De-protection: 20% piperidine in DMF (10.0 mL) was added to the resin and the mixture was bubbled with $N_2$ for 30 mins at 15° C. The resin was then washed with DMF (10.0 mL)*5 The de-protection reaction was monitored by ninhydrin test, if it showed blue or other brownish red, the reaction was completed.
4) Repeat Step 2 and 3 for all other amino acids: (2-13 in the table below).
5) Acetylation: A solution of 10% $Ac_2O$/5% NMM/85% DMF (10.0 mL) was added to resin and the mixture was bubbled with $N_2$ for 20 mins. The coupling reaction was monitored by ninhydrin test, if it showed colorless, the coupling was completed. The resin was then washed with DMF (10.0 mL)*5 MeOH (10.0 mL)*5 and dried under vacuum.

| # | Materials | Coupling reagents |
|---|---|---|
| 1 | Fmoc-Thr(tBu)-OH (1.00 eq) | DIEA (4.00 eq) |
| 2 | Fmoc-Cys(Trt)-OH (3.00 eq) | HBTU (2.85 eq) and DIEA (6.00 eq) |
| 3 | Fmoc-Trp-OH (3.00 eq) | HBTU (2.85 eq) and DIEA (6.00 eq) |
| 4 | Fmoc-Val-OH (3.00 eq) | HBTU (2.85 eq) and DIEA (6.00 eq) |
| 5 | Fmoc-Leu-OH (3.00 eq) | HBTU (2.85 eq) and DIEA (6.00 eq) |
| 6 | Fmoc-Glu(OtBu)-OH (3.00 eq) | HBTU (2.85 eq) and DIEA (6.00 eq) |
| 7 | Fmoc-Gly-OH (3.00 eq) | HBTU (2.85 eq) and DIEA (6.00 eq) |
| 8 | Fmoc-Leu-OH (3.00 eq) | HBTU (2.85 eq) and DIEA (6.00 eq) |
| 9 | Fmoc-Lys(Boc)-OH (3.00 eq) | HBTU (2.85 eq) and DIEA (6.00 eq) |
| 10 | Fmoc-Trp-OH (3.00 eq) | HBTU (2.85 eq) and DIEA (6.00 eq) |
| 11 | Fmoc-Ala-OH (3.00 eq) | HBTU (2.85 eq) and DIEA (6.00 eq) |
| 12 | Fmoc-Cys(Trt)-OH (3.00 eq) | HBTU (2.85 eq) and DIEA (6.00 eq) |
| 13 | Fmoc-Asp(OtBu)-OH (3.00 eq) | HBTU (2.85 eq) and DIEA (6.00 eq) |
| 14 | Acetylation | 10% $Ac_2O$/5% NMM/85% DMF (20 mL) |

Peptide Cleavage and Purification:

1) Cleavage buffer (95% TFA/2.5% Tis/2.5% $H_2O$) was added to the flask containing the side chain protected peptide at room temperature and stirred for 1 hr.
2) The solution was combined after filtration.
3) The peptide was precipitated with cold isopropyl ether (100 mL) and centrifuged (3 mins at 3000 rpm).
4) The solid was washed twice with isopropyl ether, and dried under vacuum for 2 hrs to get compound 1 (600.0 mg, crude) as a white solid.
5) To a mixture of compound 1 (600.0 mg, crude) in $MeCN/H_2O$ (1/1, 500.0 mL) was added 0.1 M $I_2$/HOAc dropwise until the light yellow persisted, then the mixture was quenched with 0.1 M $Na_2S_2O_3$ dropwise until the light yellow disappeared. The mixture was lyophilized, followed by prep-HPLC (acid condition, TFA) purification to get compound 2 (245.0 mg) as a white solid.

General Procedure for Preparation of Compound 4

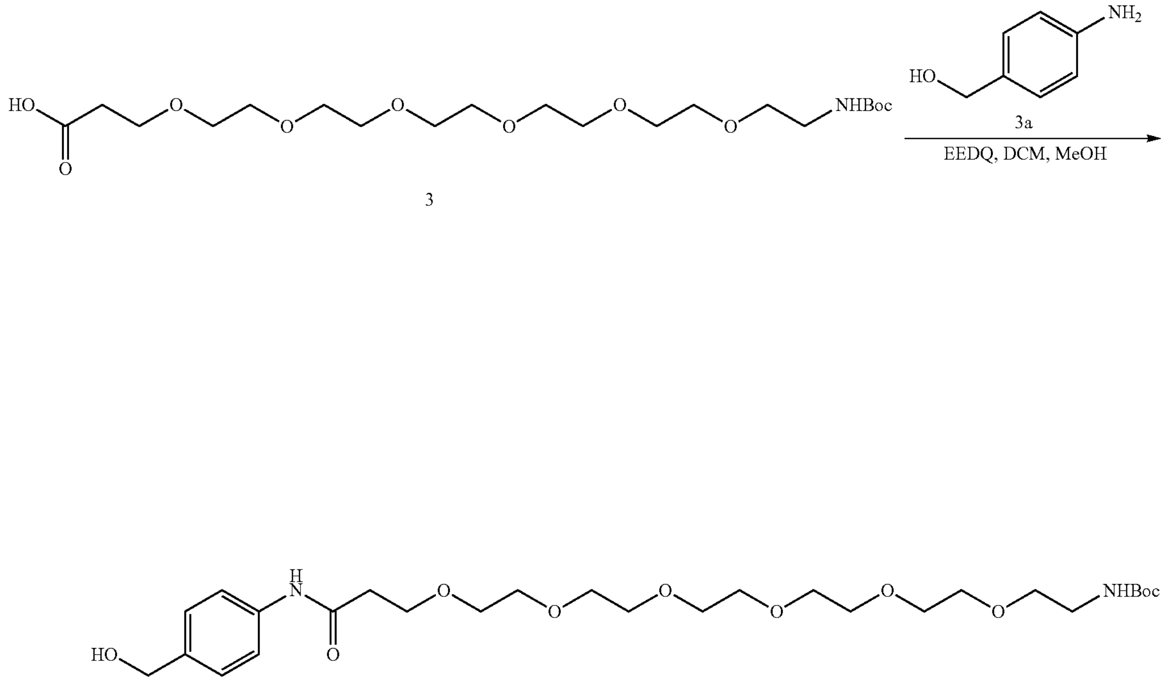

3

4

To a mixture of compound 3a (217.21 mg, 1.76 mmol, 2.00 eq) and compound 3 (400.01 mg, 881.90 umol, 1.00 eq) in DCM (1.0 mL), was added a solution of MeOH (1.0 mL) containing EEDQ (436.20 mg, 1.76 mmol, 2.00 eq) at 15° C. The mixture was stirred at 15° C. for 16 hrs. The solvent was removed under reduced pressure. The residue was purified by flash C18 (ISCO®; 120 g SepaFlash® C18 Flash Column, Eluent of 0~90% MeCN/H2O ether gradient @ 75 mL/min) directly to get compound 4 (270.01 mg, 483.30 umol, 54.8% yield) as a brown oil.

General Procedure for Preparation of Compound 5:

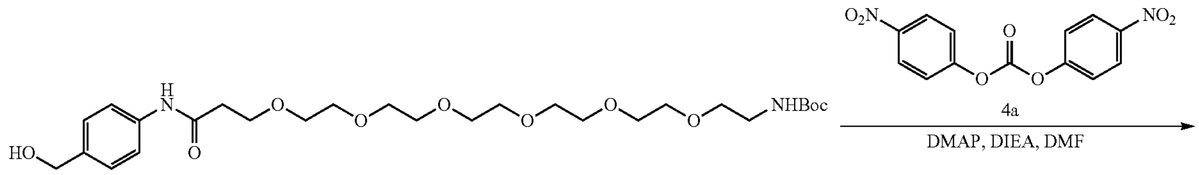

4

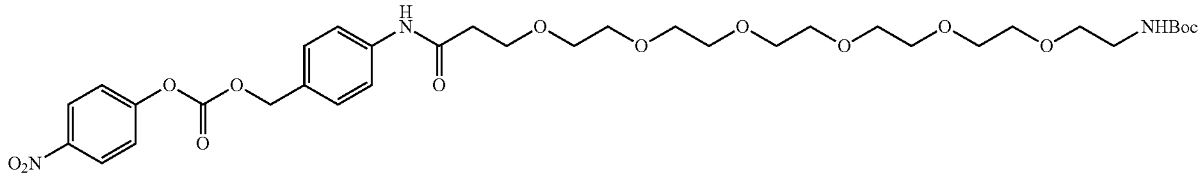

5

A mixture of compound 4a (294.0 mg, 966.60 umol, 2.00 eq), compound 4 (270.0 mg, 483.30 umol, 1.00 eq), and DIEA (249.8 mg, 1.93 mmol, 336.7 uL, 4.00 eq) in DMF (2 mL) was stirred at 15° C. for 3 hrs. The residue was purified by flash C18 (ISCO®; 120 g SepaFlash® C18 Flash Column, Eluent of 0~90% MeCN/$H_2O$ ether gradient @ 75 mL/min) directly to get compound 5 (172.0 mg, 237.6 umol, 49.1% yield) as a yellow oil.

General Procedure for Preparation of Compound 6:

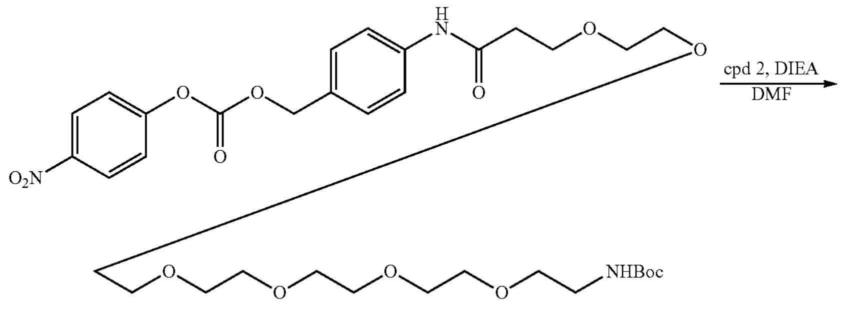

5

-continued
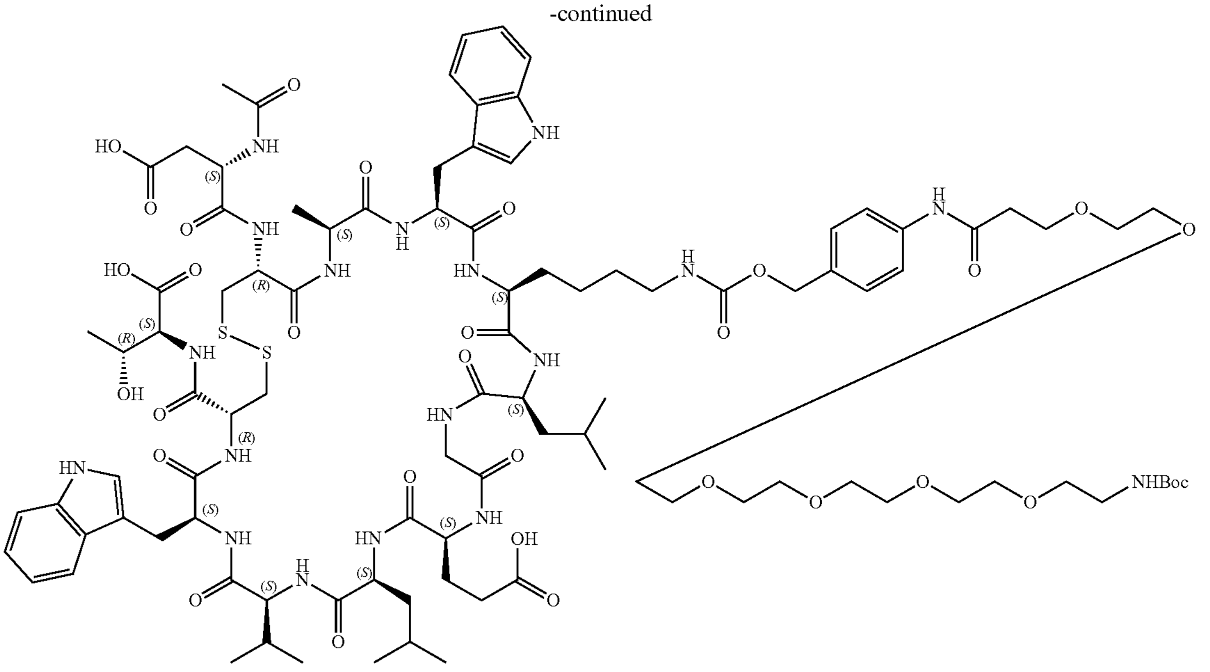
6
A mixture of compound 2 (40.0 mg, 25.58 umol, 1.00 eq), compound 5 (18.5 mg, 25.58 umol, 1.00 eq), and DIEA (16.5 mg, 127.80 umol, 22.28 uL, 5.00 eq) in DMF (0.5 mL) was stirred at 15° C. for 1 hr. The mixture was purified by flash C18 (ISCO®; 120 g SepaFlash® C18 Flash Column, Eluent of 0~90% $MeCN/H_2O$ ether gradient @ 75 mL/min) directly to get compound 6 (28.0 mg, 12.38 umol, 48.3% yield, TFA salt) as a white solid.
General Procedure for Preparation of Compound 7:
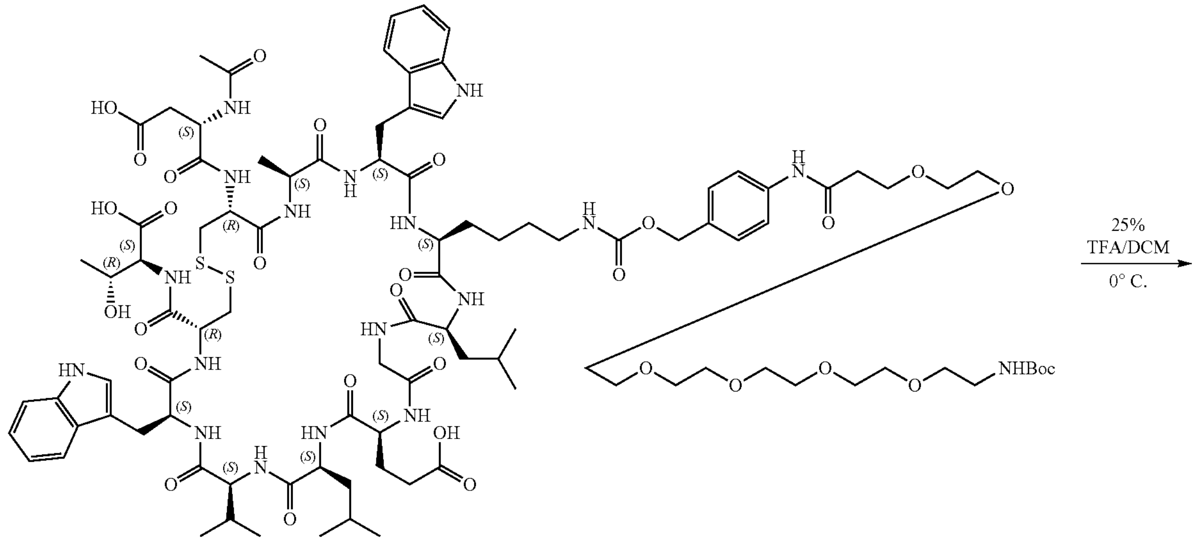
6

-continued

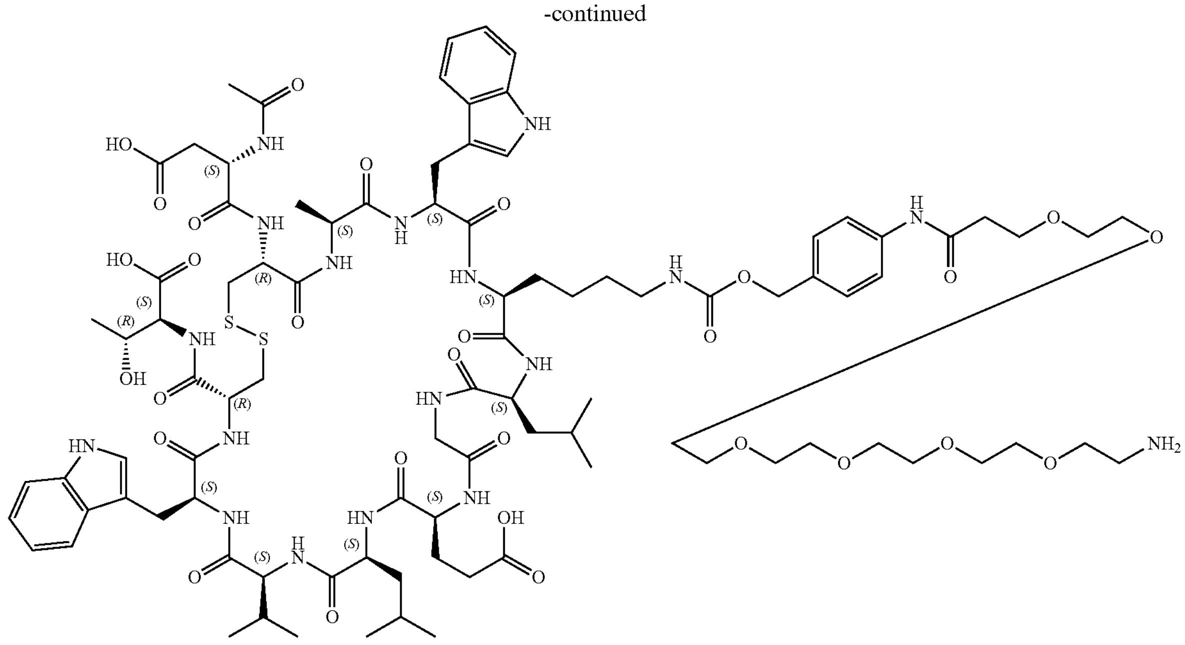

7

A mixture of compound 6 (28.0 mg, 13.00 umol, 1.00 eq) in 25% TFA/DCM (2 mL) was stirred at 0° C. for 2 hr. The solvent was removed under reduced pressure at 0° C. The residue was purified by flash C18 (ISCO®; 120 g Sepa-Flash® C18 Flash Column, Eluent of 0~90% MeCN/$H_2O$ ether gradient @ 75 mL/min) directly to get compound 7 (25.0 mg, 11.50 umol, 88.7% yield, TFA salt) as a white solid.

General Procedure for Preparation of Compound I-63:

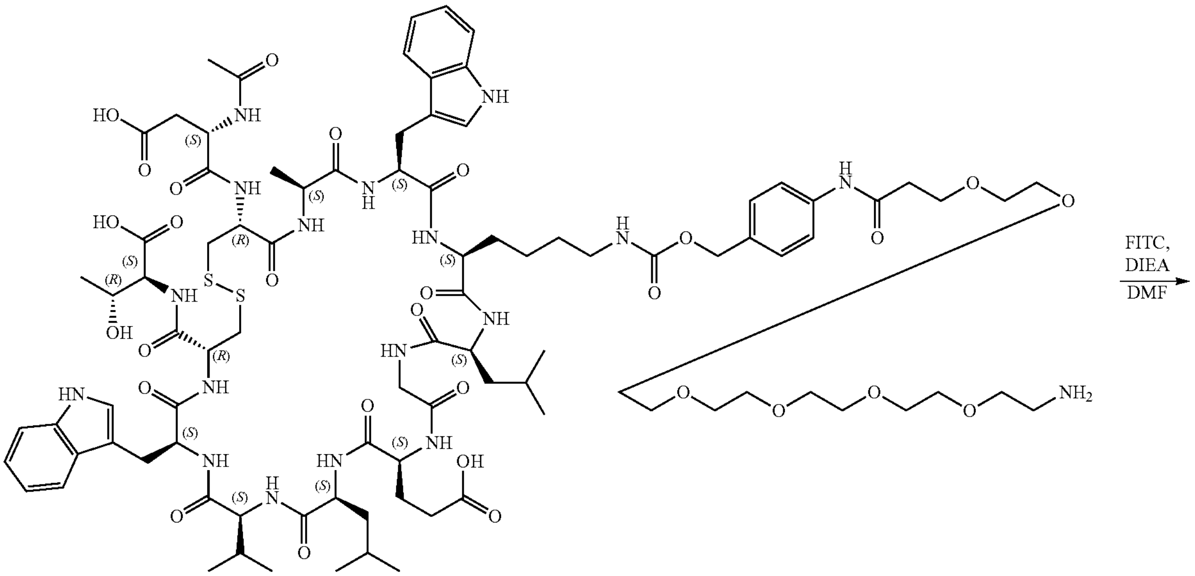

7

-continued

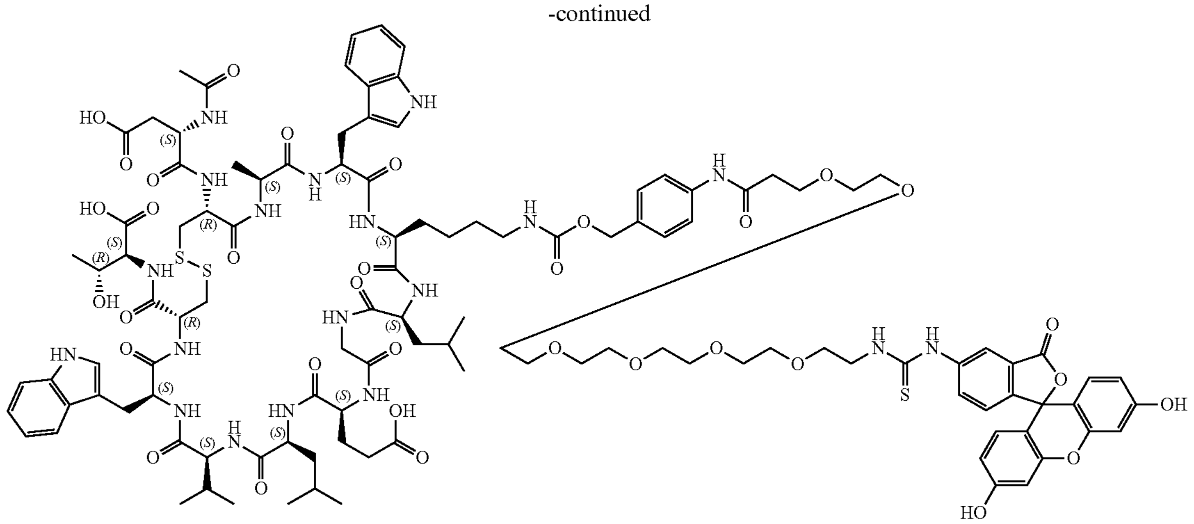

I-63

A mixture of compound 7 (25.0 mg, 12.20 umol, 1.00 eq), FITC (7.1 mg, 18.30 umol, 1.50 eq), and DIEA (7.8 mg, 61.0 umol, 10.6 uL, 5.00 eq) in DMF (0.20 mL) was stirred at 15° C. for 1 hr. The mixture was purified by prep-HPLC (acid condition, TFA) directly to get compound I-63 (6.5 mg, 2.59 umol, 97.0% purity, 21.1% yield) as a yellow solid.
Purification Conditions:

| Purification condition | |
|---|---|
| Sample Preparation | Dissolve in MeCN/$H_2O$ |
| Instrument | Gilson GX-215 |
| Mobile Phase | A: $H_2O$ (0.075% TFA in $H_2O$)<br>B: MeCN |
| Gradient | 20-50%-60 min. Retention time: 48 min |
| Column | Luna 25*200 mm, C 18 10 um, 110 Å + Gemin 150*30 mm, C18 5 um, 110 Å |
| Flow Rate | 20 mL/min |
| Wavelength | 220/254 nm |
| Oven Tem. | Room temperature |

Example 40. Exemplary Synthesis of Compound I-64

General Procedure for Preparation of Compound 2:

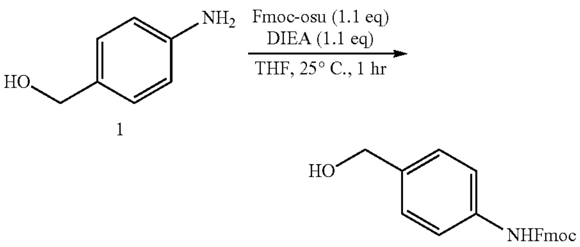

1

2

A mixture of compound (2 g, 16.24 mmol, 1 eq), FMOC-OSU (6.03 g, 17.86 mmol, 1.1 eq), and DIEA (2.31 g, 17.86 mmol, 3.11 mL, 1.1 eq) in THF (30 mL) was degassed and purged with $N_2$ for 3 times, and then the mixture was stirred at 25° C. for 1 hr under $N_2$ atmosphere. TLC (Petroleum ether:Ethyl acetate=1:1 $R_f$=0.6) indicated compound 1 was consumed completely. The reaction mixture was filtered and the filter cake was washed with 20 mL of DCM, dried in vacuum to give or afford product. Compound 2 (2.3 g, 6.66 mmol, yield: 41.00%) was obtained as a white solid.

General Procedure for Preparation of Compound 3:

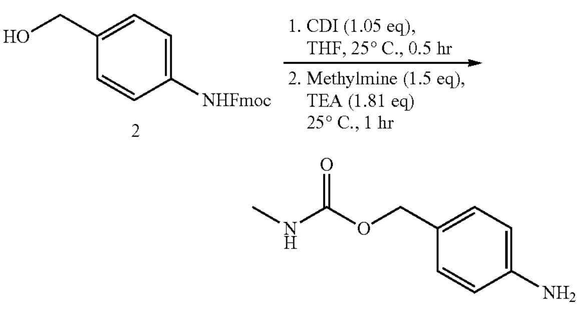

2

3

To a solution of compound 2 (200 mg, 579.05 umol, 1 eq) in THF (2 mL) was added CDI (98.59 mg, 608.01 umol, 1.05 eq) at 25° C. After addition, the mixture was stirred at this temperature for 0.5 hr, and then methanamine (2 M, 1.16 mL, 4 eq) was added at 25° C. The resulting mixture was stirred at 25° C. for 1 hr. TLC (Petroleum ether:Ethyl acetate=1:1 $R_f$=0.4) showed the starting material was consumed completely. The residue was diluted with $H_2O$ (2 mL) and extracted with ethyl acetate (5 ml*2). The reaction mixture was poured into separatory funnel and separated. The combined organic layers were washed with brine (5 mL), dried over $Na_2SO_4$, filtered and concentrated under reduced pressure to give a residue. The residue was purified by column chromatography ($SiO_2$, Petroleum ether:Ethyl acetate=100:1 to 0:1). Compound 3 (20 mg, 110.99 umol, yield: 19.17%) was obtained as a white solid.

General Procedure for Preparation of Compound 4:

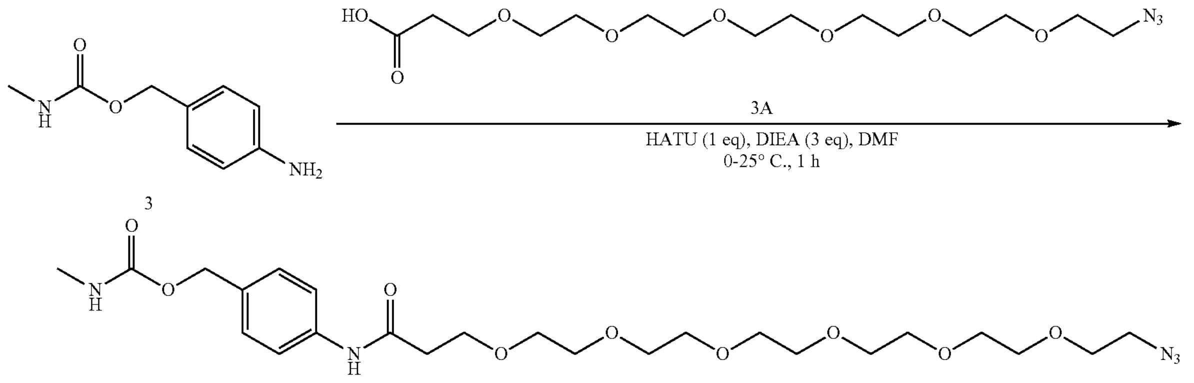

3

4

To a solution of compound 3 (42.11 mg, 110.99 umol, 1 eq) in DMF (0.5 mL) was added HATU (42.20 mg, 110.99 umol, 1 eq) and DIEA (43.03 mg, 332.96 umol, 58.00 uL, 3 eq) at 0° C. After addition, the mixture was stirred at this temperature for 0.5 hr, and compound 3A (20 mg, 110.99 umol, 1 eq) was added at 0° C. The resulting mixture was stirred at 25° C. for 1 hr. LCMS showed the starting material was consumed completely. The reaction mixture was filtered and the filter was concentrated. The residue was purified by prep-HPLC (column: Waters Xbridge BEH C18 100*30 mm*10 um; mobile phase: [water (10 mM $NH_4HCO_3$)-ACN]; B %: 20%-50%, 8 min). Compound 4 (12 mg, 22.16 umol, yield: 19.96%) was obtained as a white solid. LCMS: Rt=1.854 min, MS (ESI): m/z [M+H$^+$] calcd for $C_{24}H_{39}N_5O_9$, 542.2; found 542.2.

General Procedure for Preparation of Compound 5:

A mixture of compound 4 (5 mg, 9.23 umol, 1 eq), Zn (6.04 mg, 92.32 umol, 10 eq), ammonia; formic acid (5.82 mg, 92.32 umol, 10 eq) and in MeOH (0.5 mL) was degassed and purged with $N_2$ for 3 times, and then the mixture was stirred at 25° C. for 5 min under $N_2$ atmosphere. LCMS showed the starting material was consumed completely. The reaction mixture was concentrated. The crude product was dissolved in THF (1 ml) and added DCM (1 ml), the mixture was precipitated by solids. The mixture was filtered and the filter cake was washed with DCM (0.5 mL×2). The combined filtrates were concentrated to dryness to give crude product. The crude product was purified by reversed-phase HPLC (column: Phenomenex Luna C18 150*30 mm*5 um; mobile phase: [water (0.1% TFA)-ACN]; B %: 25%-55%, 10 min). Compound 5 (6 mg, crude) was obtained as a colourless oil. LCMS: Rt=1.233 min, MS (ESI): m/z [M+H$^+$] calcd for $C_{24}H_{41}N_3O_9$, 516.2; found 516.2.

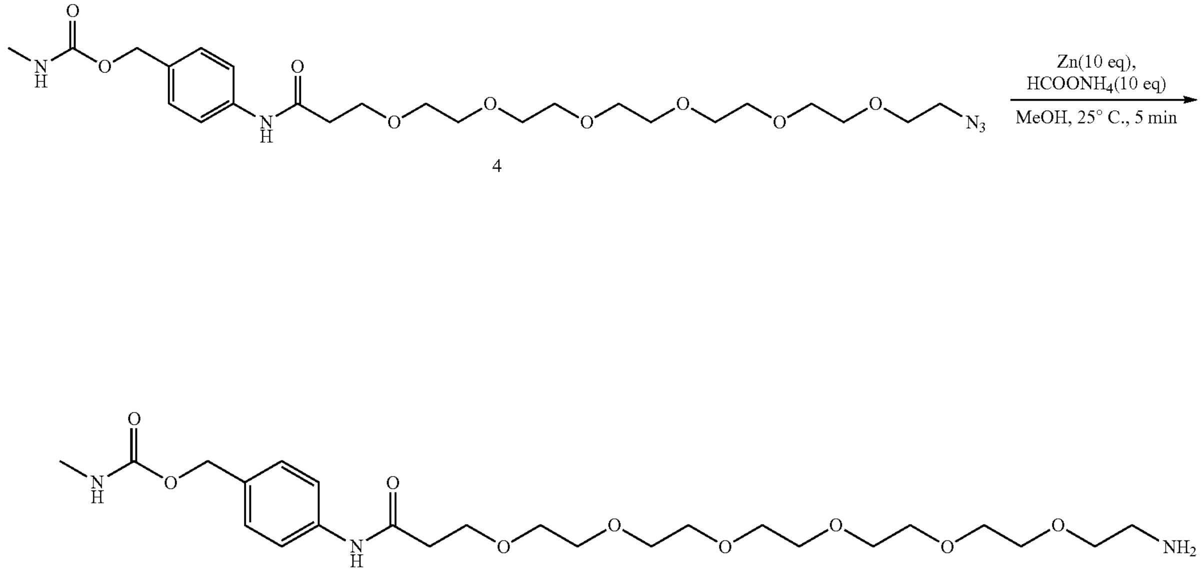

4

5

General Procedure for Preparation of Compound I-64:

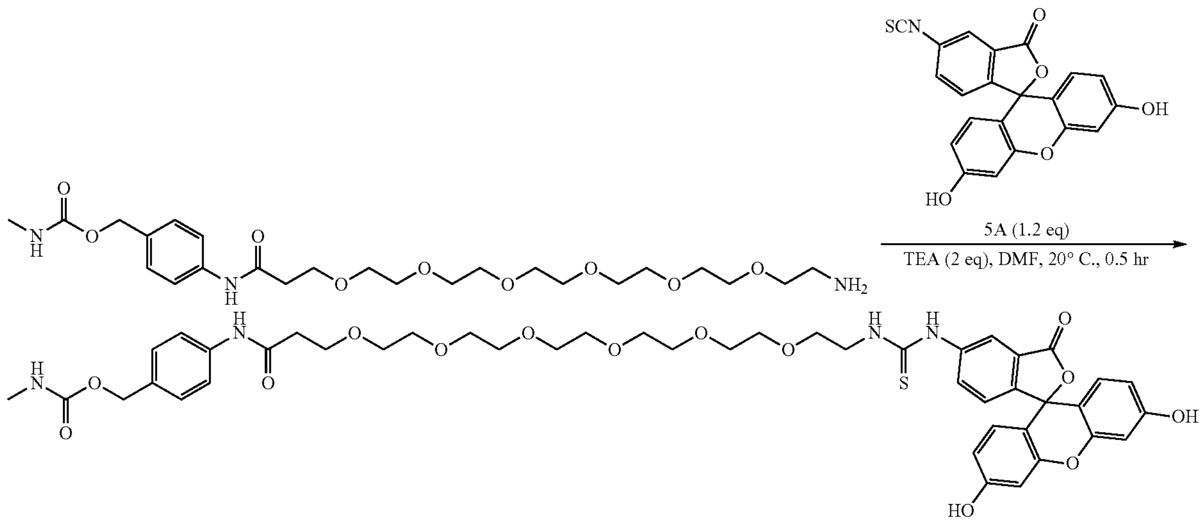

I-64

A mixture of compound 5 (3 mg, 5.82 umol, 1 eq), compound 5A (2.72 mg, 6.98 umol, 1.2 eq), and TEA (1.77 mg, 17.46 umol, 2.43 uL, 3 eq), in DMF (1 mL) was degassed and purged with $N_2$ for 3 times, and then the mixture was stirred at 25° C. for 0.5 hr under $N_2$ atmosphere. LCMS showed the starting material was consumed completely. HPLC showed the starting material was consumed completely. The reaction mixture was filtered and the filtrate was concentrated. The crude product was purified by reversed-phase HPLC (column: Phenomenex Luna C18 150*30 mm*5 um; mobile phase: [water (0.1% TFA)-ACN]; B %: 30%-60%, 10 min). Compound I-64 (3.77 mg, 4.17 umol, yield 71.60%) was obtained as a yellow solid. $^1H$ NMR (400 MHz, DMSO-$d_6$): δ=10.10 (br s, 1H), 10.05-9.97 (m, 1H), 9.94 (s, 1H), 8.26 (s, 1H), 8.07 (br s, 1H), 7.72 (br d, J=8.8 Hz, 1H), 7.56 (d, J=8.4 Hz, 2H), 7.25 (br d, J=8.4 Hz, 2H), 7.17 (d, J=8.4 Hz, 1H), 7.03 (br s, 1H), 6.66 (d, J=2.0 Hz, 2H), 6.62-6.51 (m, 4H), 4.91 (s, 2H), 3.55 (br s, 5H), 3.47 (br d, J=11.5 Hz, 22H), 2.55 (br d, J=4.4 Hz, 5H). LCMS: Rt=1.248 min, MS (ESI): m/z [M+H$^+$] calcd for $C_{45}H_{52}N_4O_{14}S$, 904.3; found 453.3. HPLC: RT=2.746 min. QC data for compound I-64: HPLC: RT=2.763 min purity: 95.42%. MS: MS (ESI): m/z [M+H$^+$] calcd for $C_{45}H_{52}N_4O_{14}S$ 904.3 [M+H$^+$]=905.5 found 905.5.

Example 41. Provided Technologies Provide Efficient Reactions and Removal of Target Binding Moieties Data using various compounds further confirm that provided technologies can provide efficient conjugation:

| Compound | DAR |
|---|---|
| I-10 | 0.07 |
| I-44 | 0.96 |
| I-64 | 0.13 |
| I-63 | 0.81 |
| I-62 | 0.05 |
| I-61 | 0.88 |

-continued

| Compound | DAR |
|---|---|
| I-60 | 0.23 |
| I-59 | 0.71 |

Reactions were set up with daratumumab using 2.5 M eq of indicated reagent in phosphate buffer saline pH 7.4 for 4 h at 25° C. DAR is Drug to antibody ratio, in this case "Drug" is FITC and DAR is measured using FITC absorbance.

Figure 23:
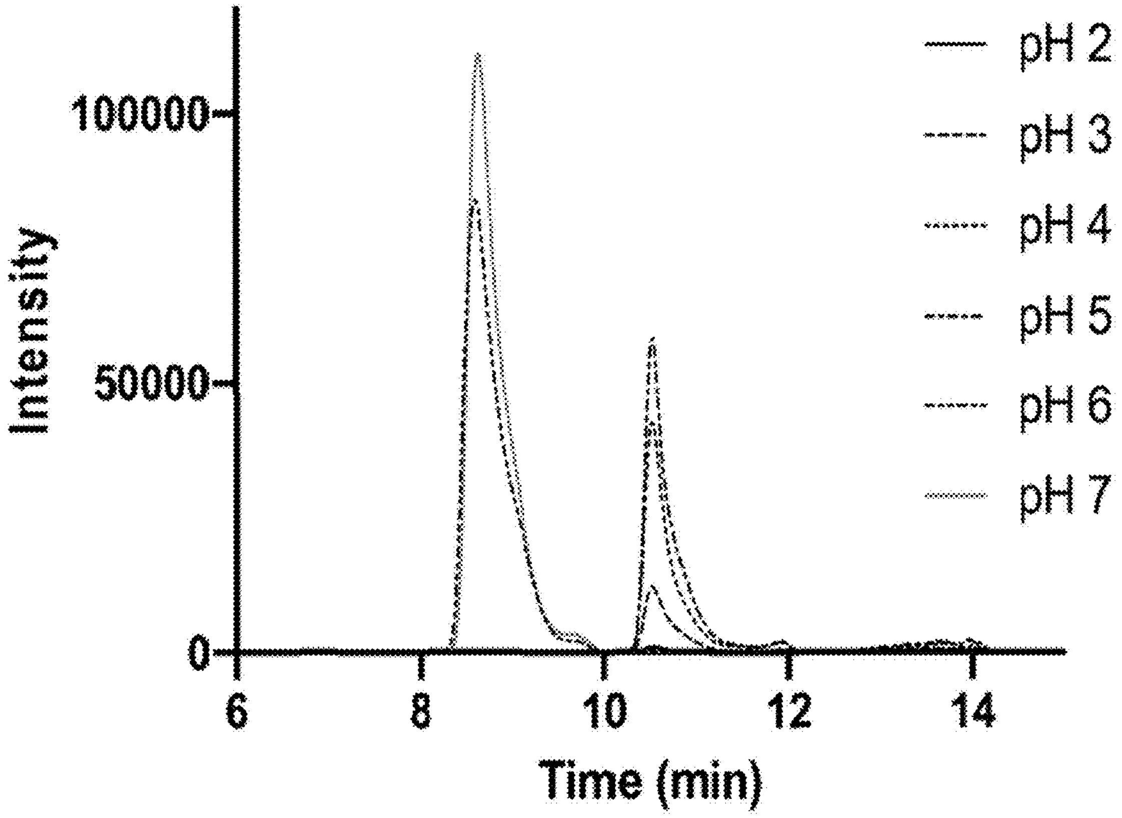
FIG. 23. Provided technologies can effectively remove agents comprising released target binding moieties from reactions. Demonstrated herein is removal of certain target binding moiety by treatment with acidic solutions.

Among other things, the present disclosure provides technologies for removing an agent comprising a target binding moiety (e.g., a reaction product comprising a target binding moiety released after a reaction) from a reaction product (e.g., a product comprising an antibody moiety or a fragment thereof). In some embodiments, a method comprises contacting a composition comprising an agent comprising a target binding moiety and a reaction product wherein the target binding moiety interacts with the reaction product, with an acidic solution. In some embodiments, after contact with an acidic solution, an agent comprising a target binding moiety is separated from a reaction product. In some embodiments, pH of a solution is about 1, 2, 3, or 4. In some embodiments, pH is 1. In some embodiments, pH is 2. In some embodiments, pH is 3. In some embodiments, pH is 4. As confirmed in FIG. 23, agents comprising released target binding moiety from a reaction between I-44 and daratumumab can be effectively removed, e.g., at pH 2. A protocol is described below as an example.

In some embodiments, mass spectrometry analysis of methanol-precipitated antibody conjugates was utilized for assessment of antibody conjugates from provided technologies. In some embodiments, buffers of different pH were utilized to remove bound leaving group from antibody (e.g., antibody conjugate products) after conjugation. In some embodiments, methanol precipitation was performed as below:

1. Combine one volume of purified antibody conjugate and 3 volumes of methanol.
2. Incubate sample at 4° C. for 1 hour.
3. Centrifuge at 15,500×g for 10 min at 4° C.

4. Recover supernatant and dry in speed vac.
5. Re-suspend in 0.10% aqueous formic acid to 30 uL.

In some embodiments, instrument conditions for analysis was:

LC: ExionLC

Mobile phases:

A: 0.10% aqueous formic acid

B: 0.1% formic acid in 95% acetonitrile

Column:

Phenomenex Luna C18(2) column (100×2, 3 um, 100 Å)

Gradient:

Hold 5% B for the $1^{st}$ minute 5-50% B over 1-7 minutes

MS:

Sciex X500B QTOF system

Calibration done with positive calibrant using CDS system. ESI voltage of 5.5 kV, ion source gas 1 and 2 at 40 psi, curtain gas 30 (arbitrary unit), CAD gas 7 (arbitrary unit). Source temperature 350° C., DP 100V, accumulation time 0.25 see, CE 0V. TOF-MS full scan from m/z 300 to m/z 5000 in profile mode. Sciex OS 1.4 used for acquisition.

While a number of embodiments have been described, it is apparent that our basic examples may be altered to provide other embodiments that utilize technologies (e.g., compounds, agents, compositions, methods, etc.) of the present disclosure.

The invention claimed is:
1. A compound having the structure of formula R-I:
$$LG—RG—L^{RM}—MOI, \quad (R\text{-}I)$$
or a salt thereof, wherein:
LG is $R^{LG}$-$L^{LG}$;
$R^{LG}$ is an antibody binding moiety;
$L^{LG}$ is -$L^{LG1}$-, or -$L^{LG1}$-$L^{LG2}$-;
RG comprises one or more groups selected from:
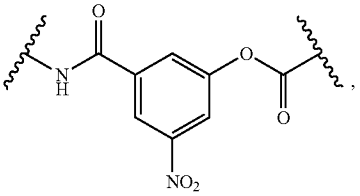
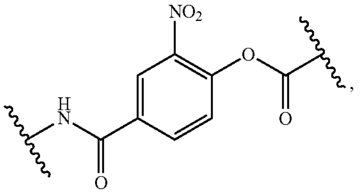
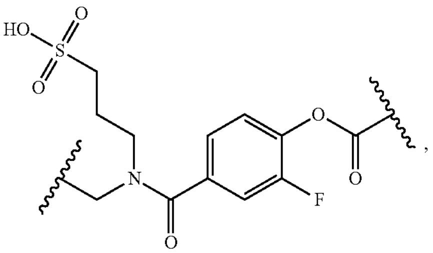
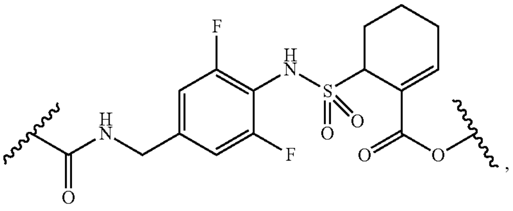
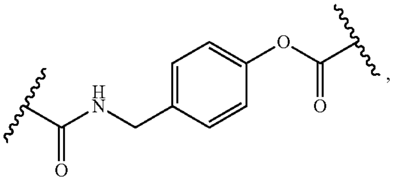
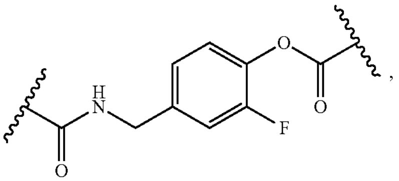
-continued
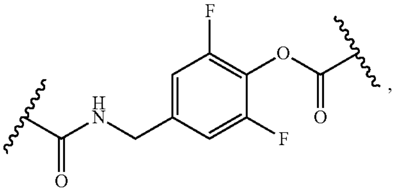
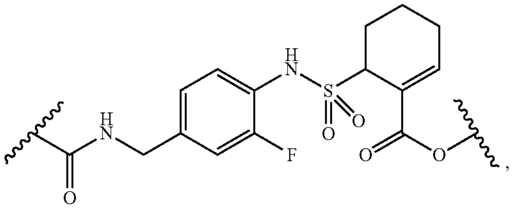
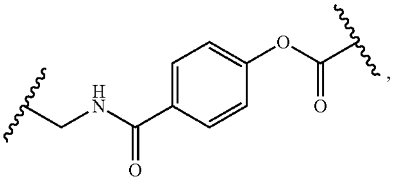
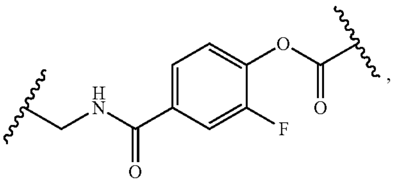
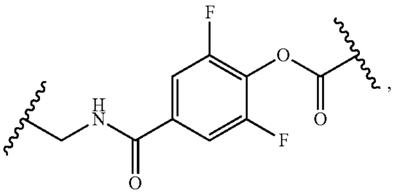
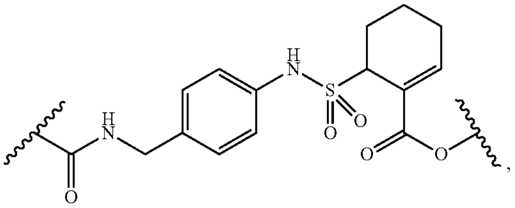
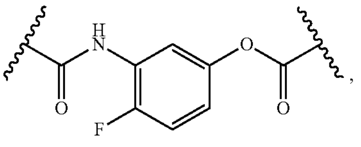
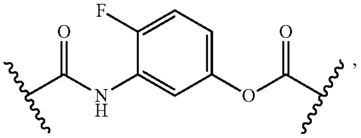
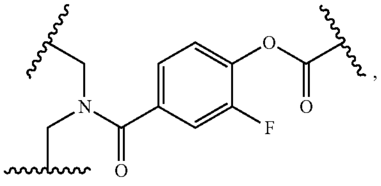

-continued

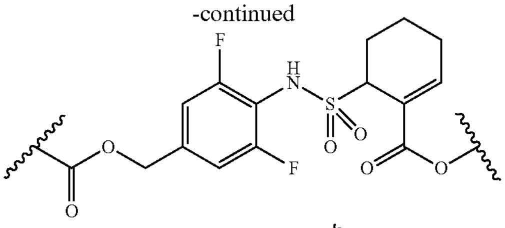,

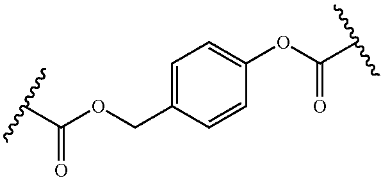,

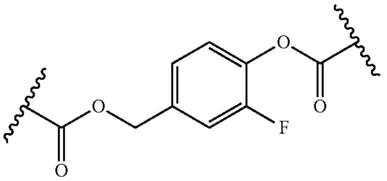,

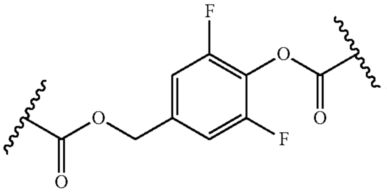,

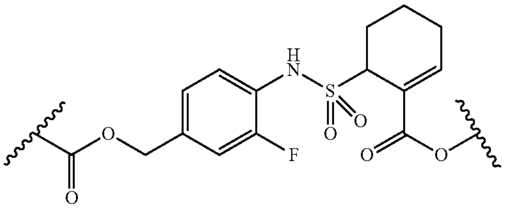,

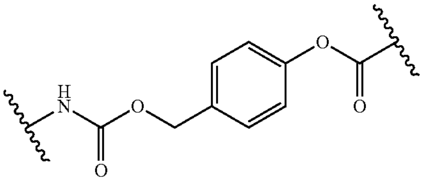,

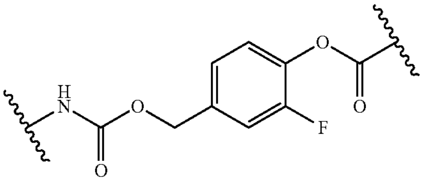,

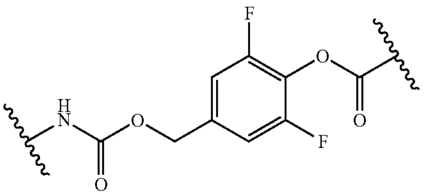,

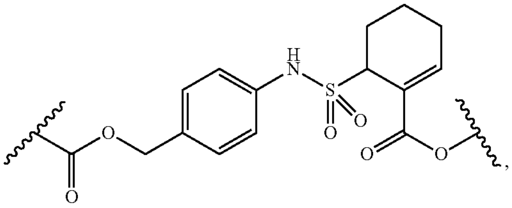,

-continued

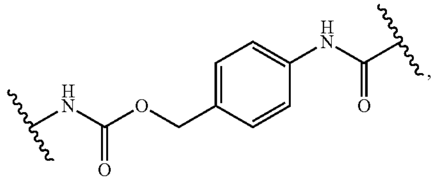,

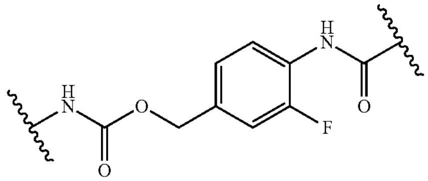, and

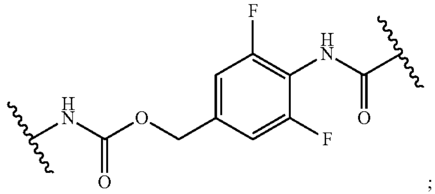;

each of $L^{LG1}$, $L^{LG2}$, and $L^{RM}$ is independently L;

each L is independently a covalent bond, or a bivalent, linear or branched $C_{1-30}$ aliphatic group or heteroaliphatic group having 1-10 heteroatoms, wherein one or more methylene units of the group are optionally and independently replaced with $C_{1-6}$ alkylene, $C_{2-6}$ alkenylene, —C≡C—, -Cy-, —C(R')$_2$—, —O—, —S—, —S—S—, —N(R')—, —C(O)—, —C(S)—, —C(NR')—, —S(O)—, or —S(O)$_2$—;

each -Cy- is independently an optionally substituted bivalent monocyclic, bicyclic or polycyclic group, wherein each monocyclic ring is independently selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —CO$_2$R, or —SO$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups independently taken together to form a covalent bond, or:

two or more R groups on the same atom are independently taken together with the atom to form an optionally substituted, 3-30 membered, monocyclic, bicyclic or polycyclic ring having, in addition to the atom, 0-10 heteroatoms; or two or more R groups on two or more atoms are independently taken together with their intervening atoms to form an optionally substituted, 3-30 membered, monocyclic, bicyclic or polycyclic ring having, in addition to the intervening atoms, 0-10 heteroatoms; and MOI is a moiety of interest, wherein:

the moiety of interest is or comprises GGGGG, LPETG,

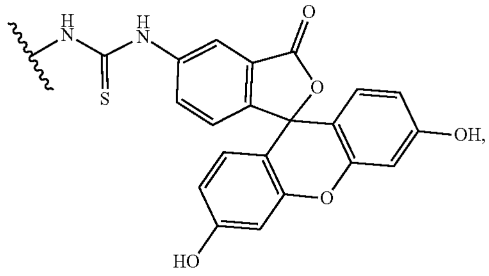
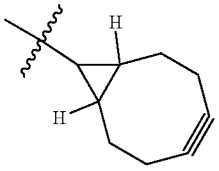
,
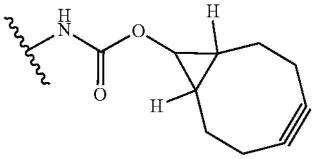
,
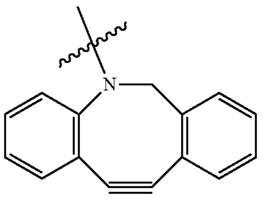
, or
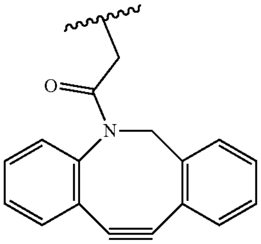
;
the moiety of interest is or comprises a therapeutic agent;
the moiety of interest is an anti-cancer agent,
wherein:
(a) the antibody binding moiety is
(A-1)
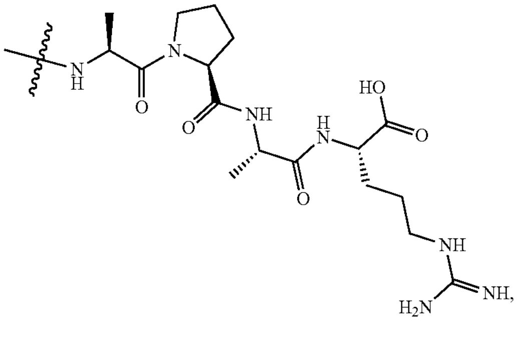
-continued
(A-2)
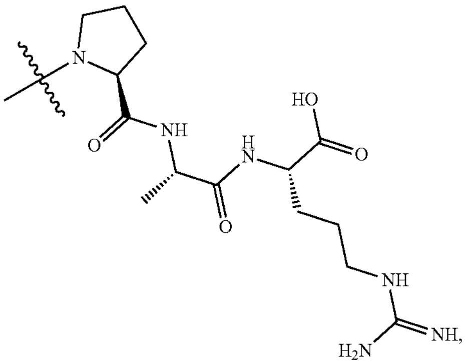
(A-3)
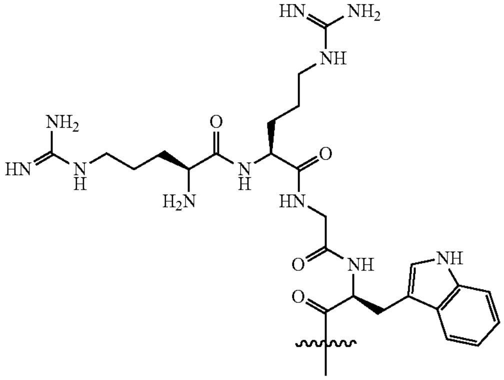
,
(A-4)
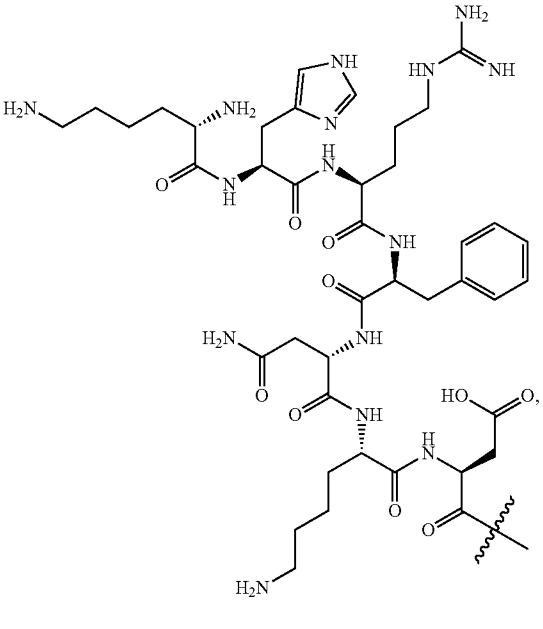

-continued
(A-5)
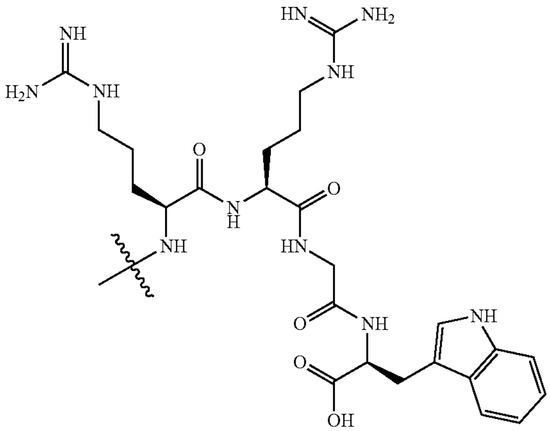
,
(A-6)
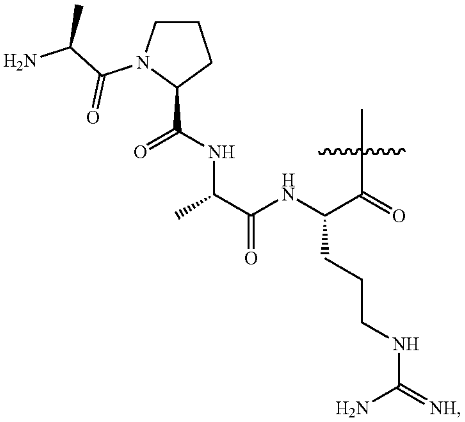
(A-7)
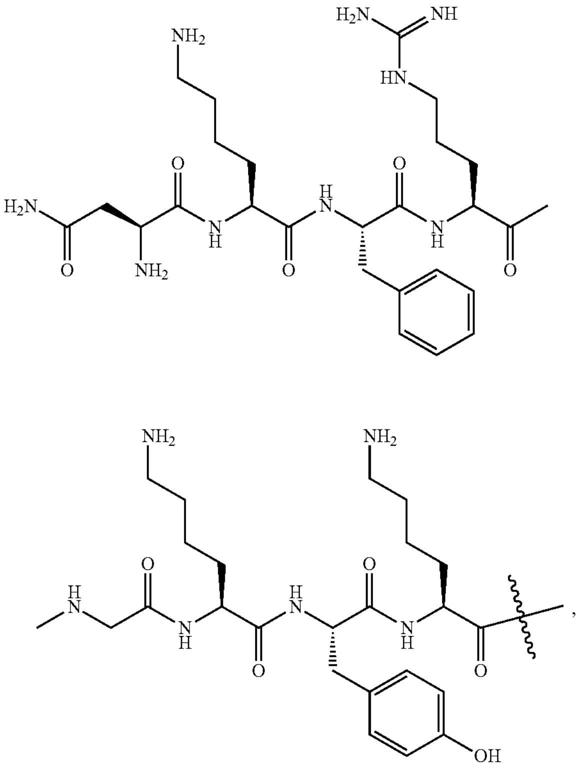
,
-continued
(A-8)
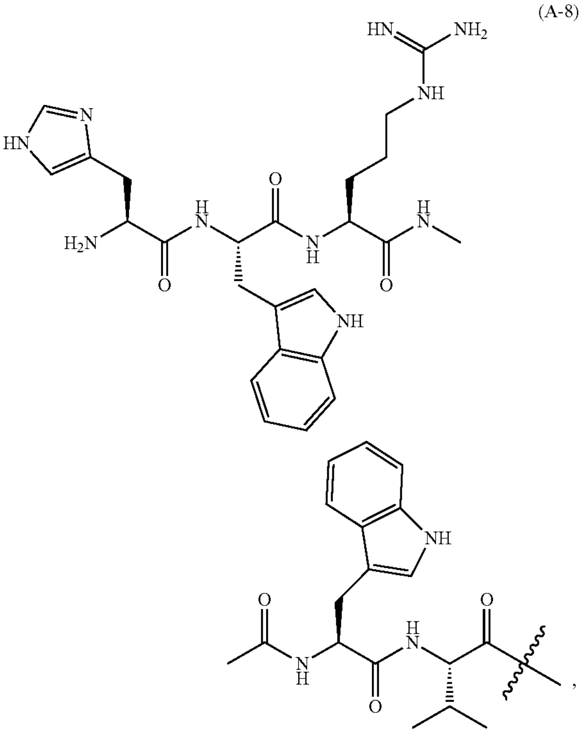
,
(A-9)
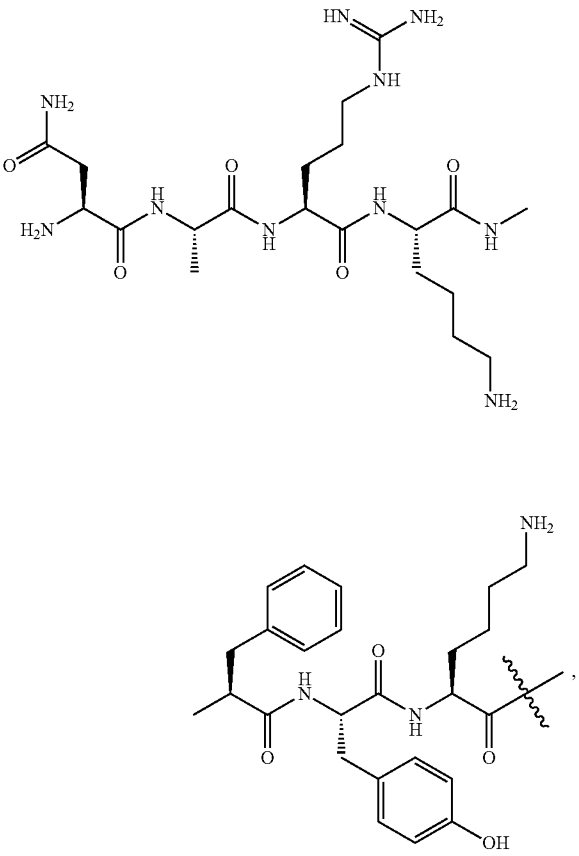
, -continued
(A-10)
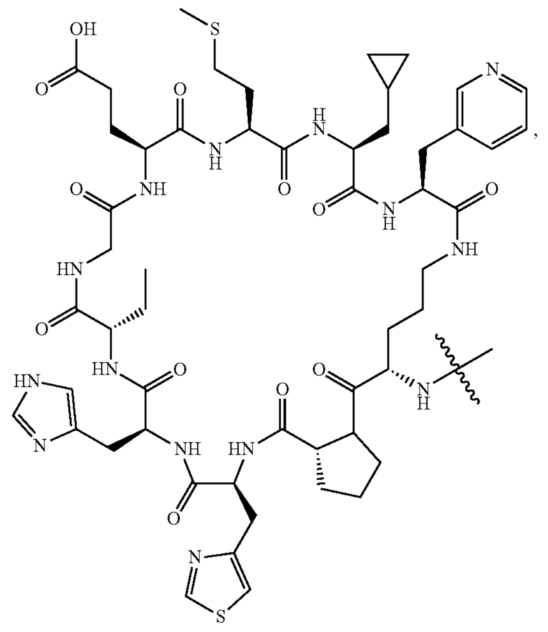
(A-11)
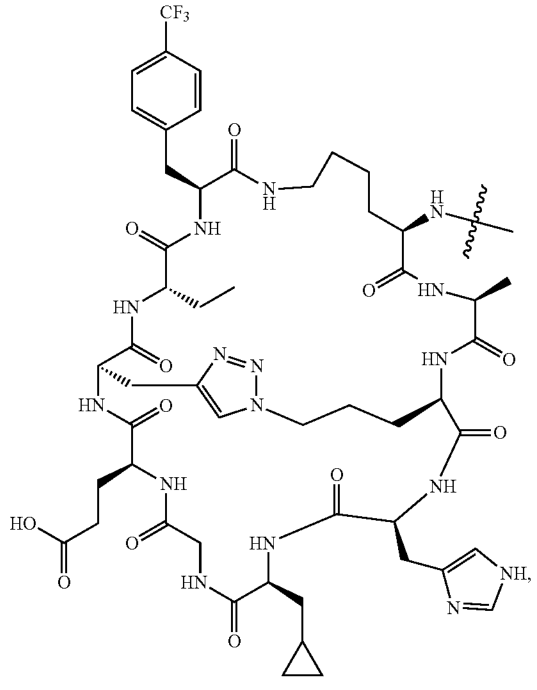
-continued
(A-12)
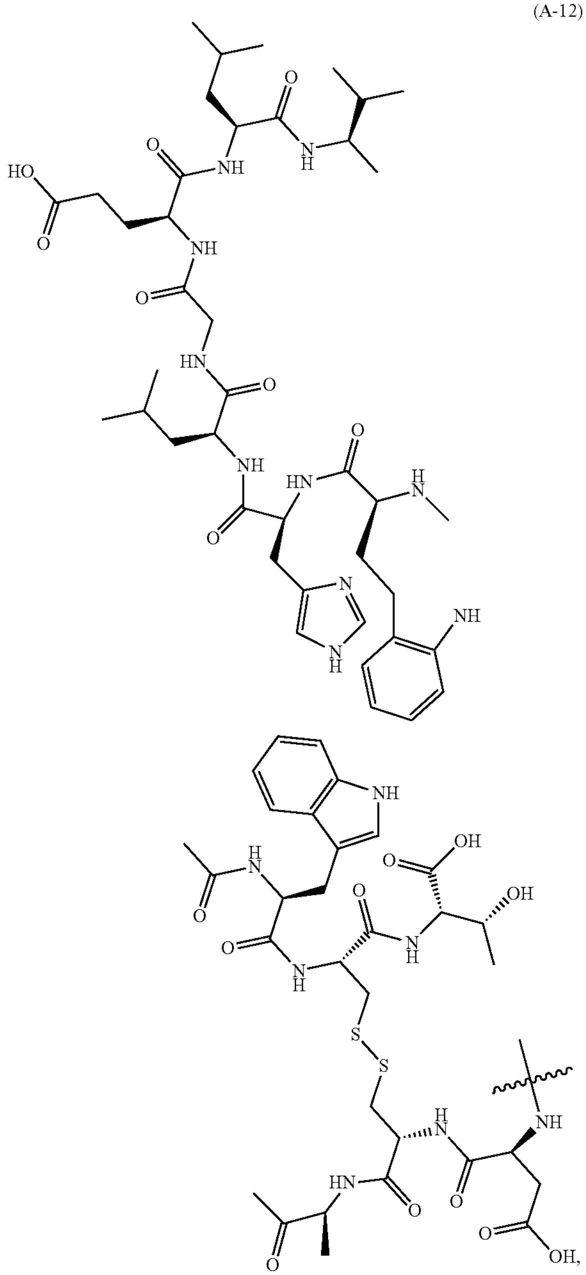
(A-13)
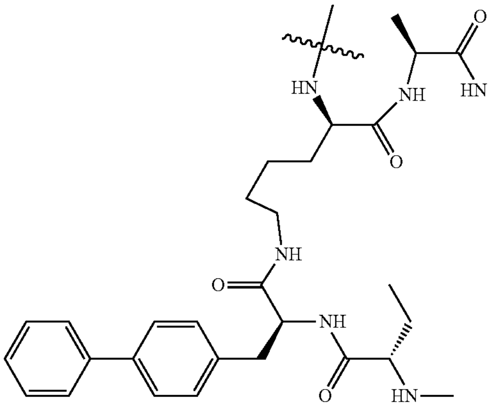

-continued
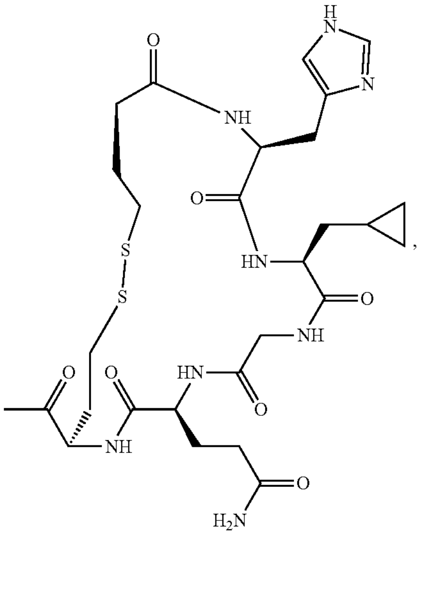
(A-14)
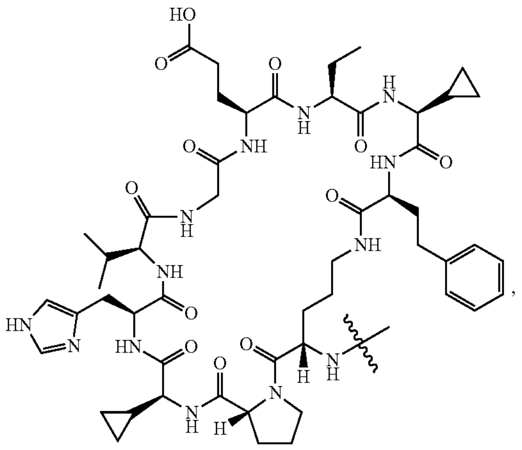
(A-15)
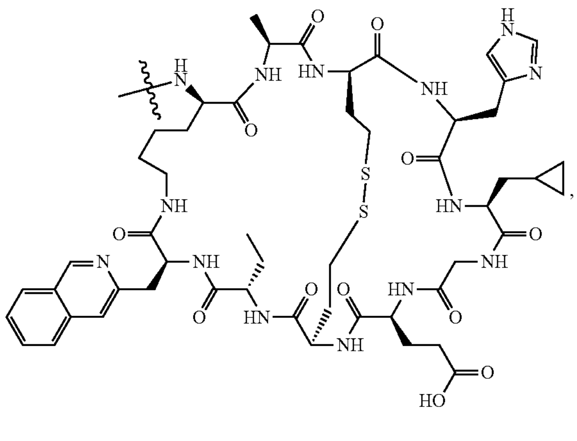
-continued
(A-16)
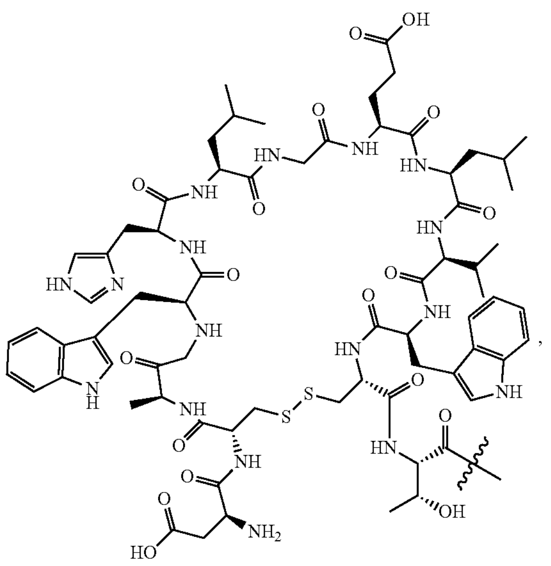
(A-17)
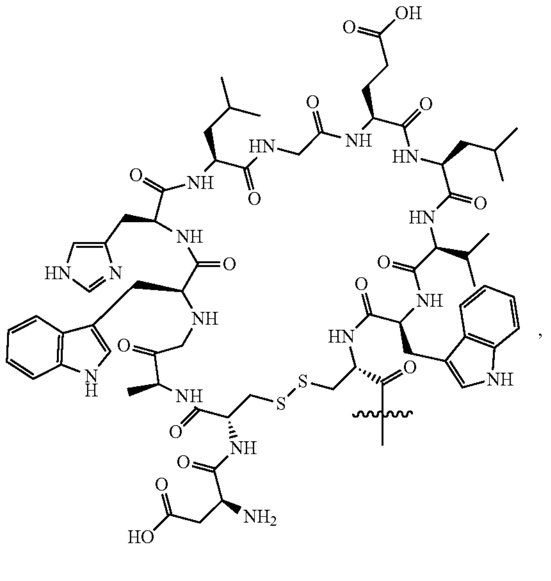

-continued
(A-18)
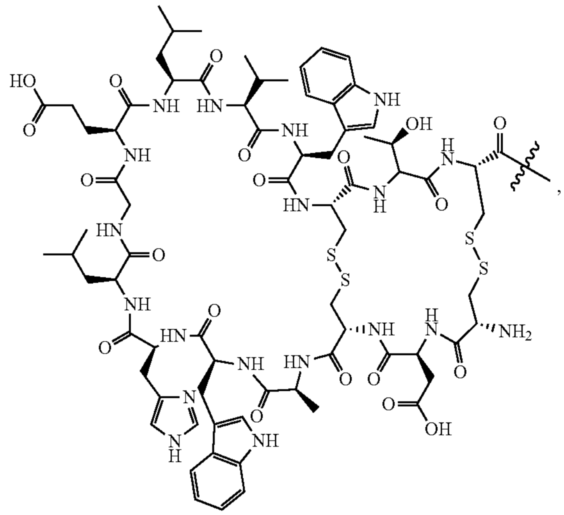
,
(A-19)
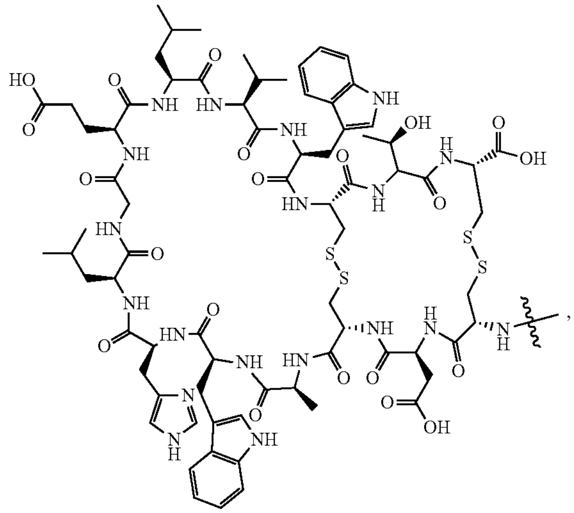
,
(A-20)
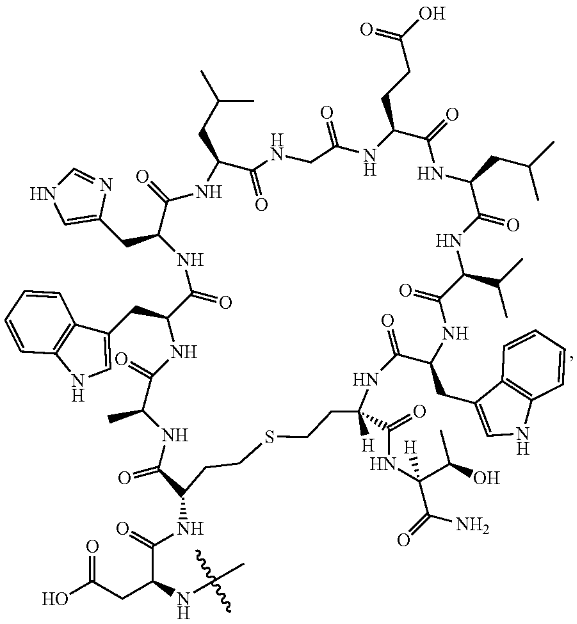
,
(A-21)
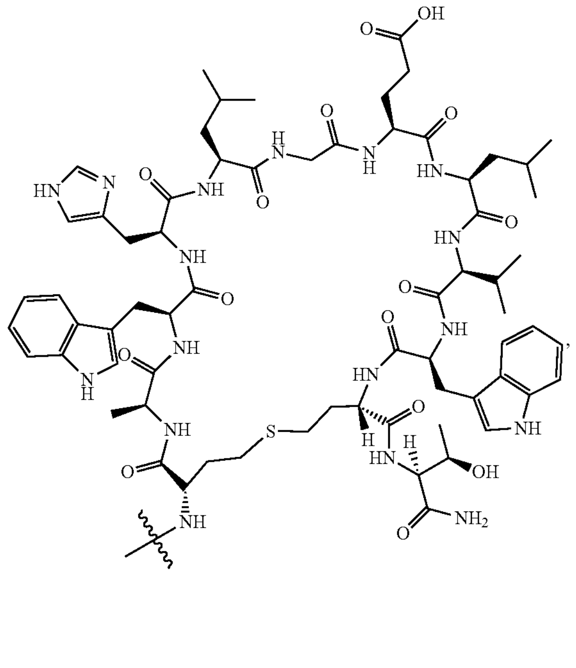
, -continued
(A-22)
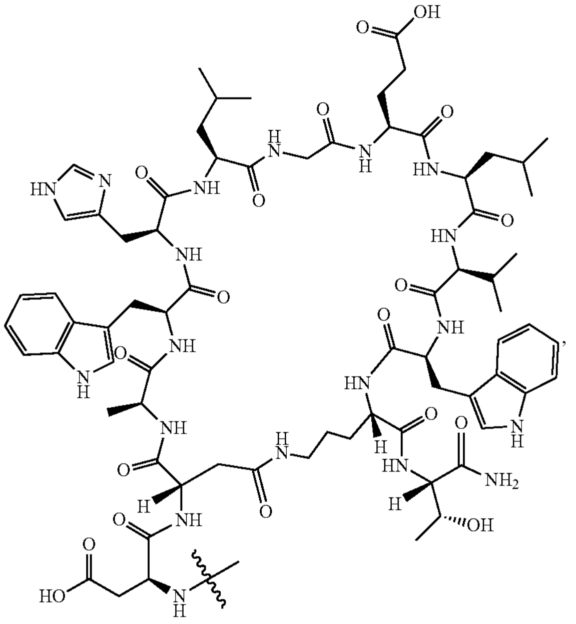
(A-23)
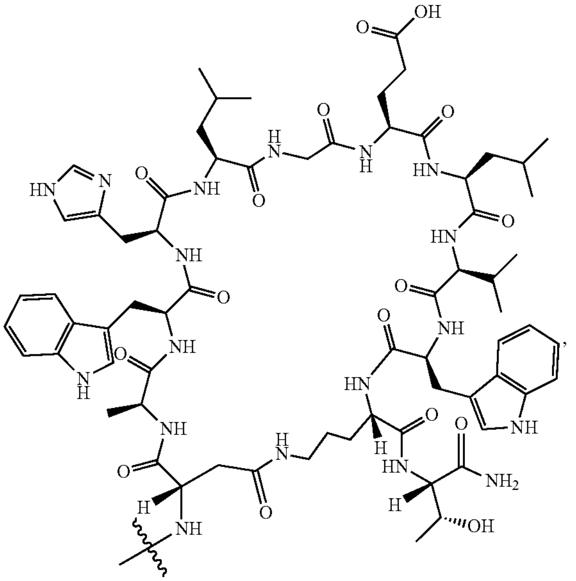
-continued
(A-24)
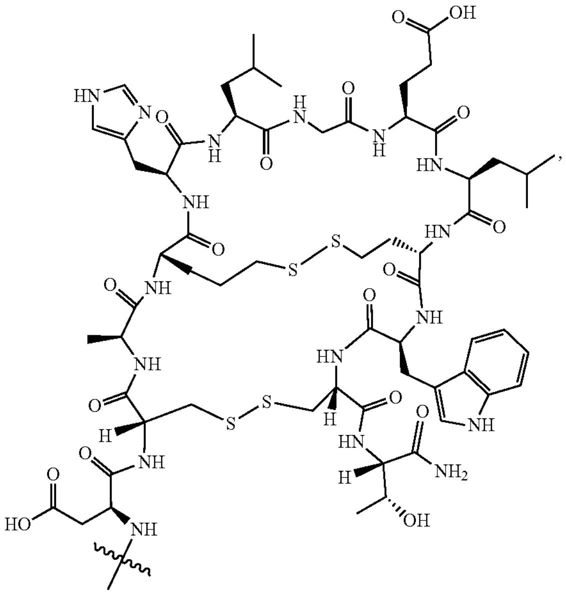
(A-25)
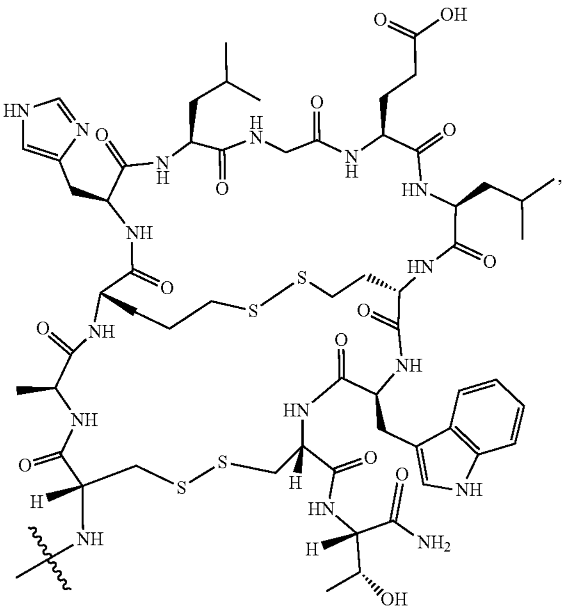

-continued
(A-26)
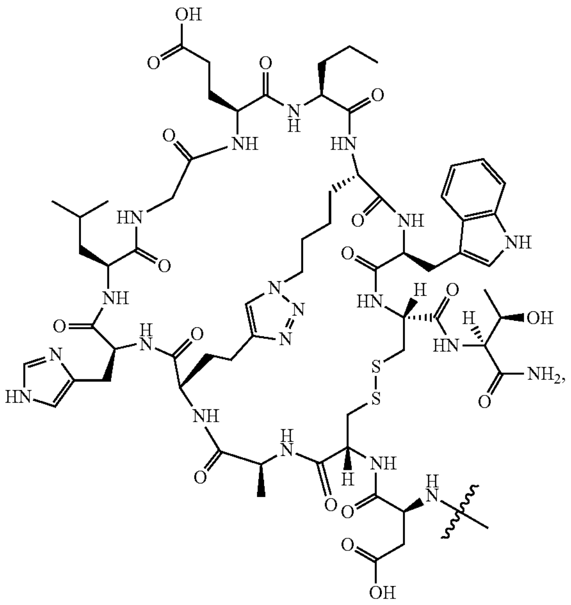
(A-27)
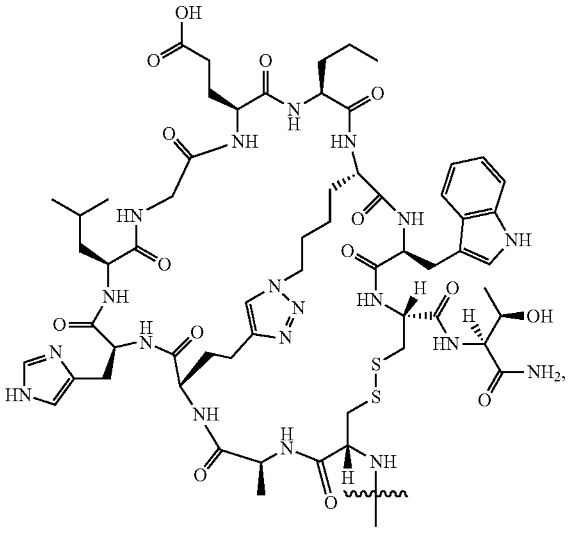
-continued
(A-28)
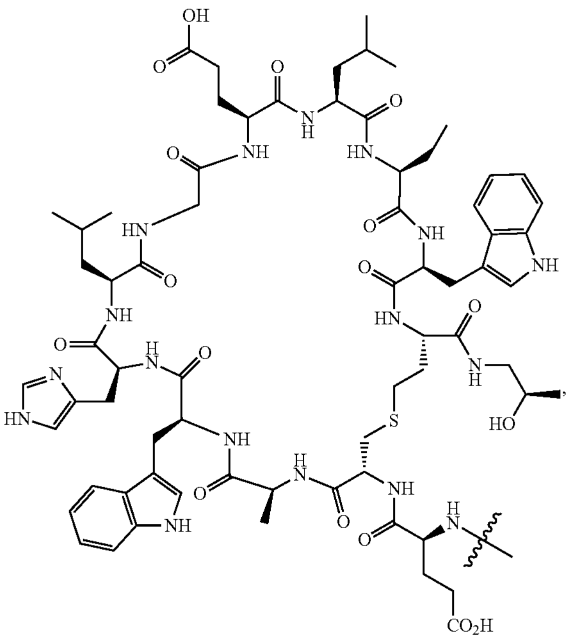
(A-29)
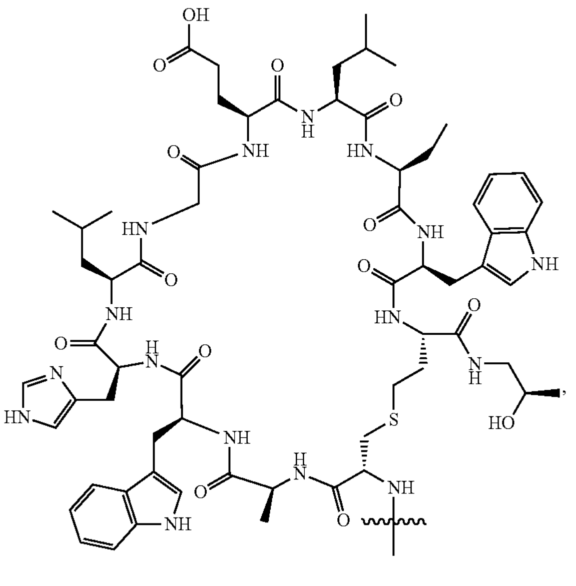

-continued
(A-30)
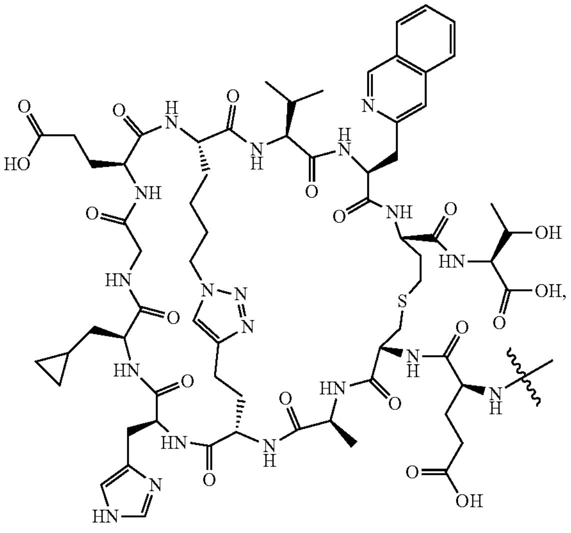
(A-32)
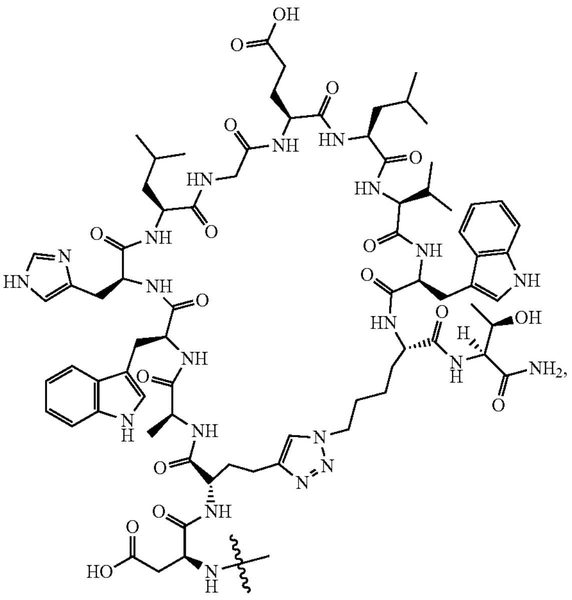
(A-31)
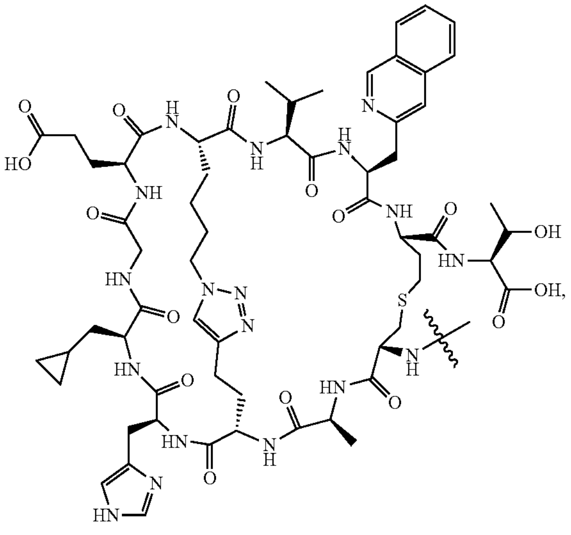
(A-33)
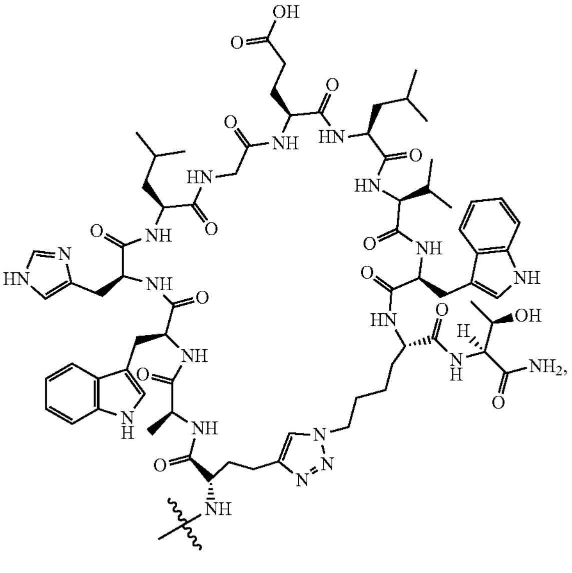

-continued
(A-34)
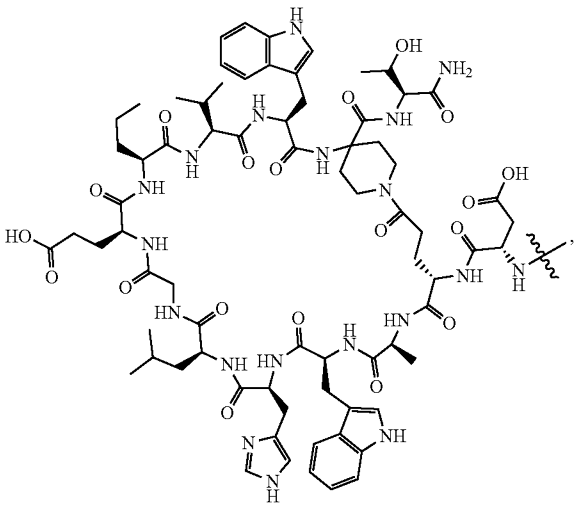
(A-35)
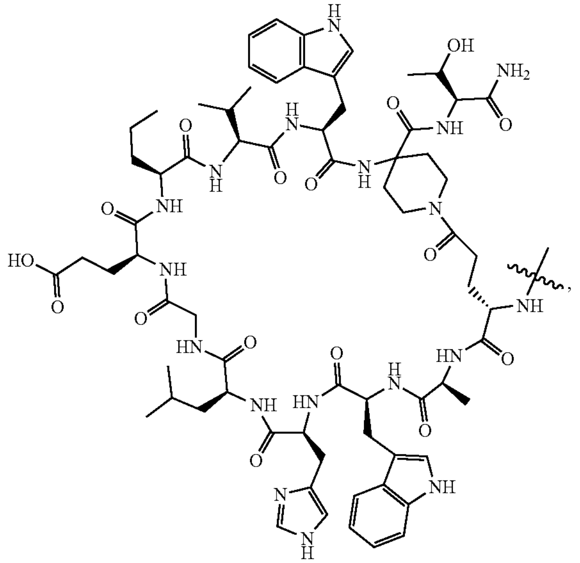
-continued
(A-36)
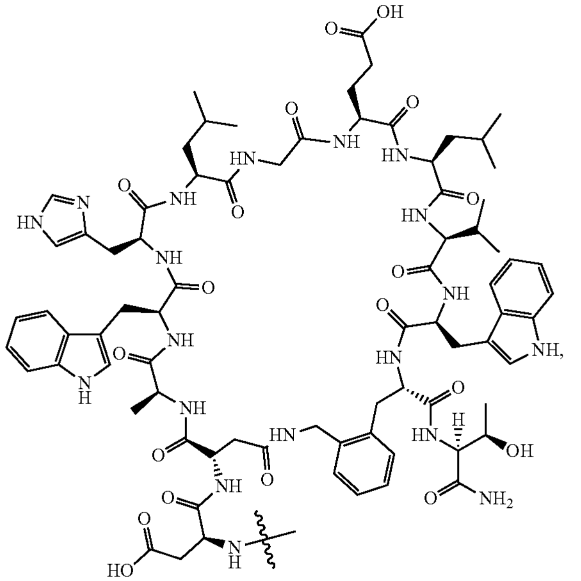
(A-37)
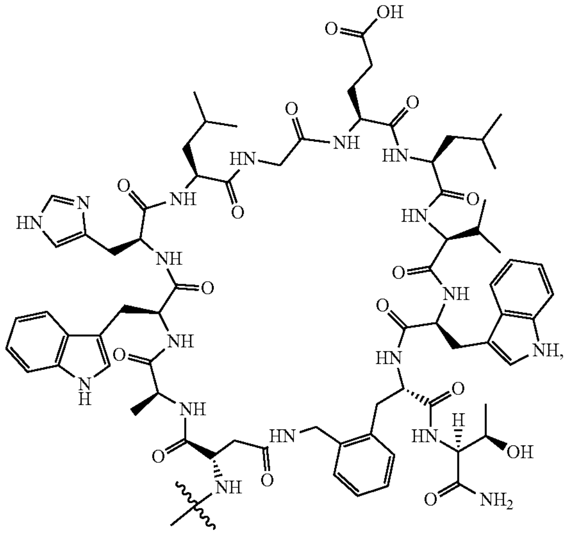

(A-38)
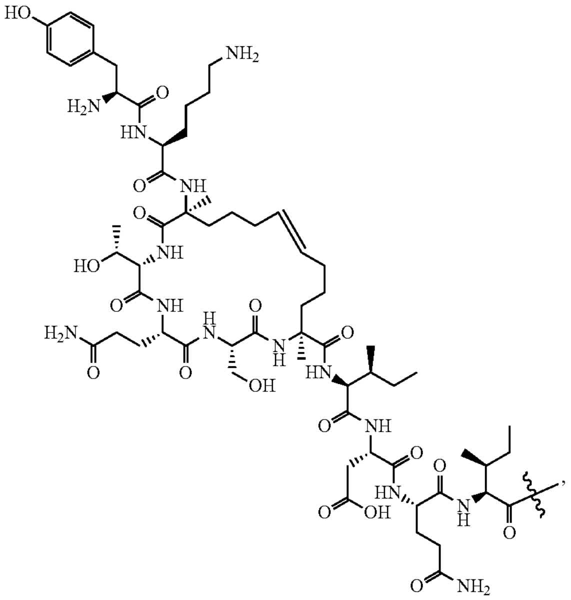
(A-39)
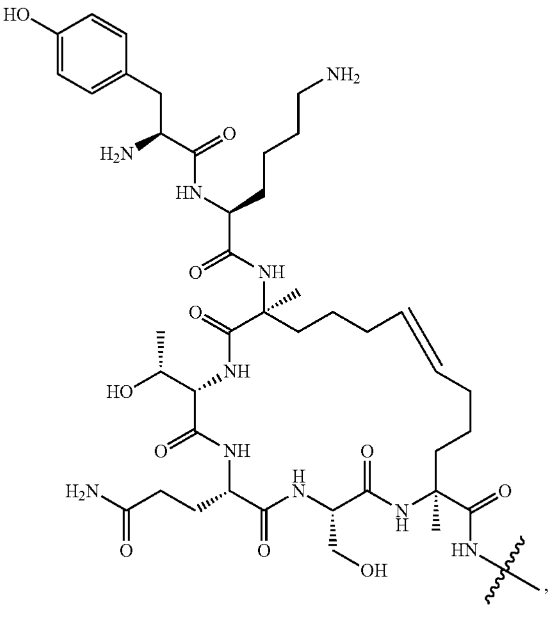
(A-40)
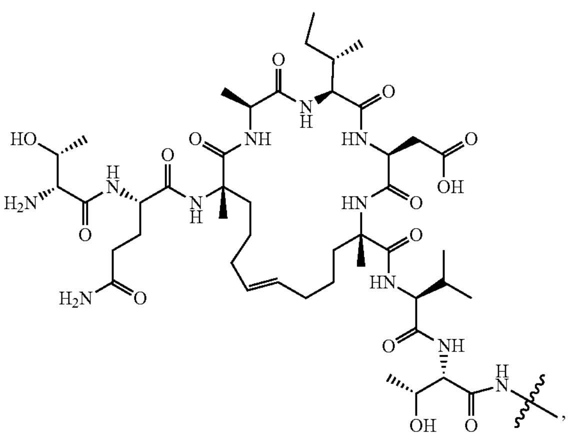
(A-41)
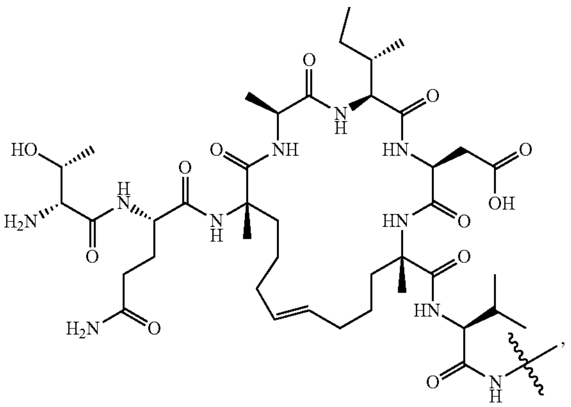
(A-42)
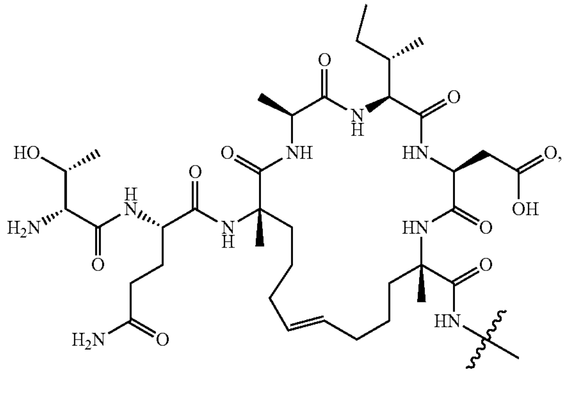

-continued
(A-43)
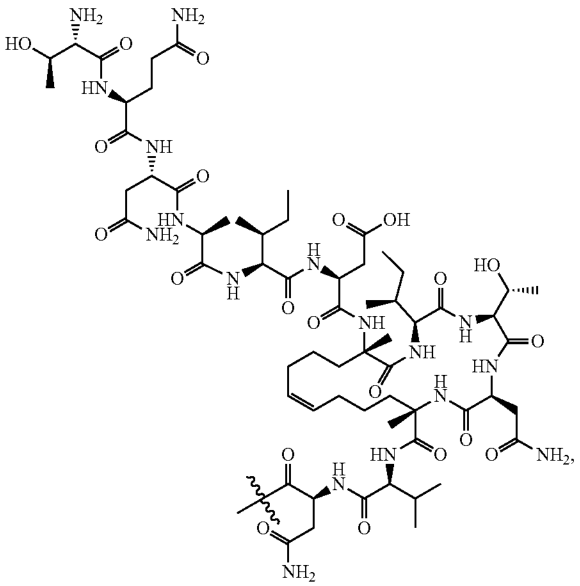
(A-45)
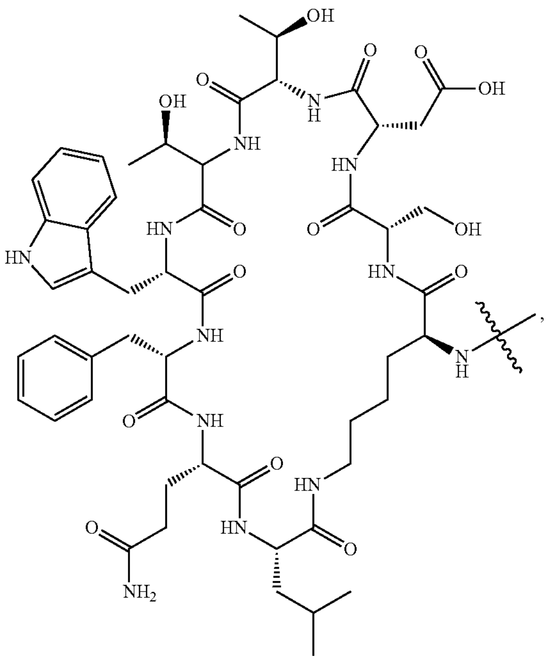
(A-44)
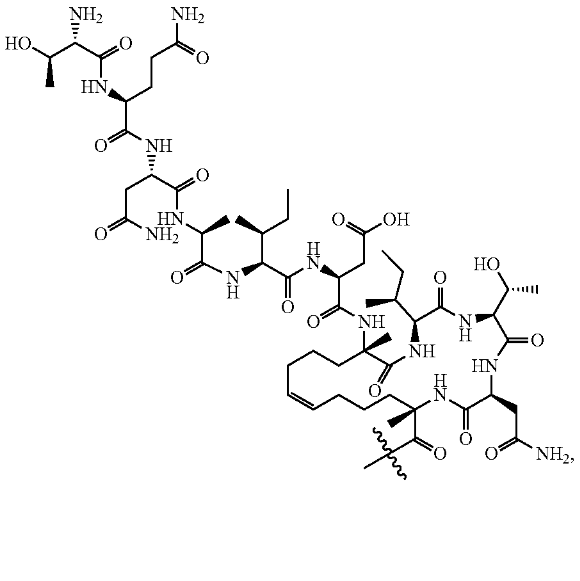
(A-46)
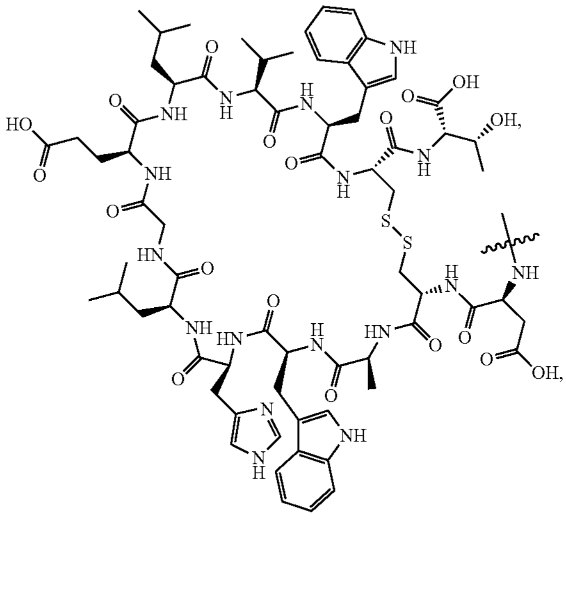

-continued
(A-47)
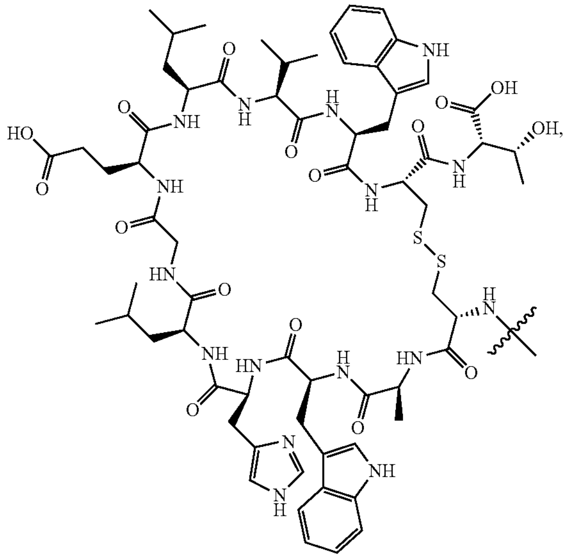
(A-48)
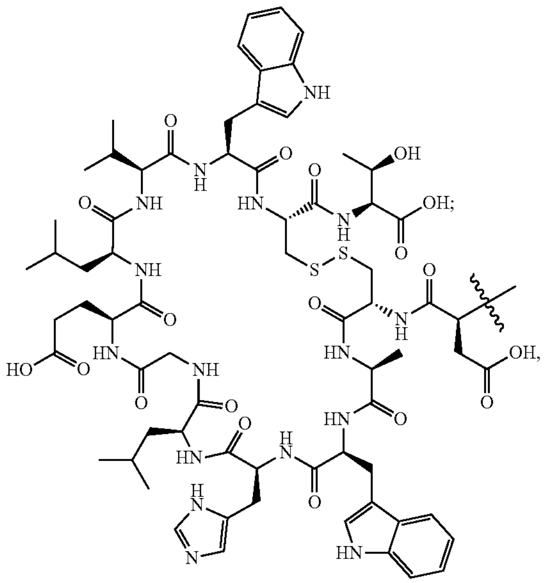
or
-continued
(A-49)
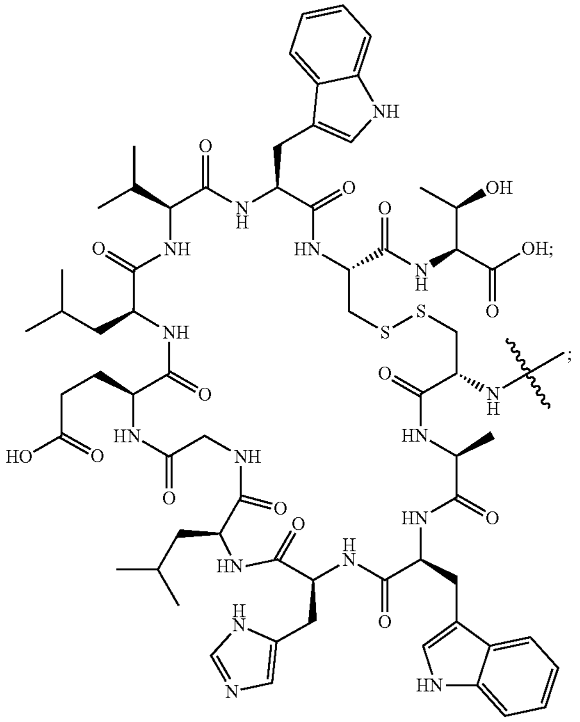
(b) the antibody binding moiety is
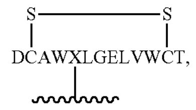
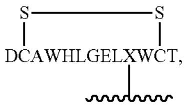
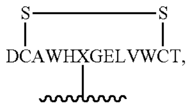
or
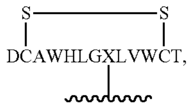
wherein X is an amino acid residue selected from
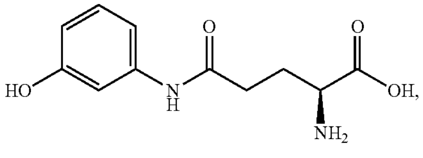
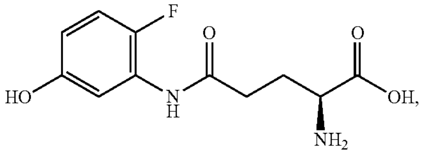
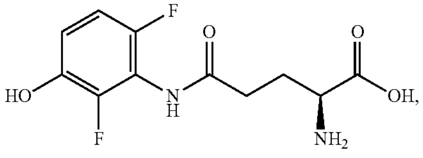

-continued

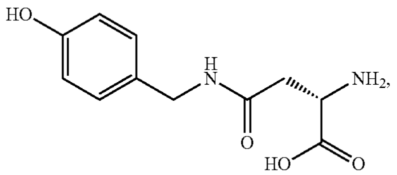

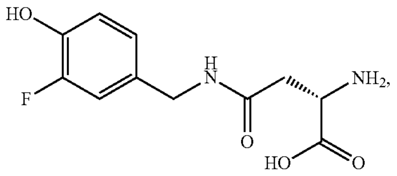

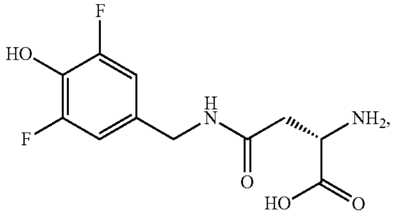

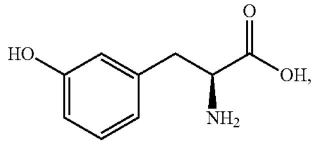

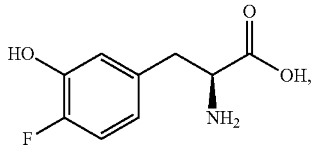

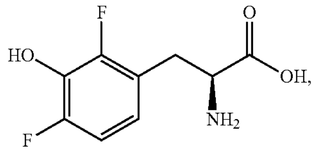

lysine, aspartic acid, glutamic acid, and 2,4-diaminobutyric acid;

(c) the antibody binding moiety is Fc-III, FcBP-2, Fc-III-4C, or

Ac—GPDCAYHXGELVWCTFH—$NH_2$, wherein X is lysine or arginine;

(d) the antibody binding moiety is an antibody binding peptide that comprises DCAWXLGELVWCT, wherein X is an amino acid residue selected from

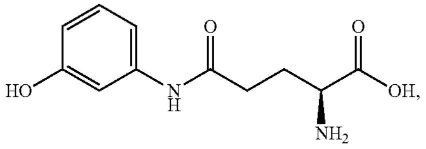

-continued

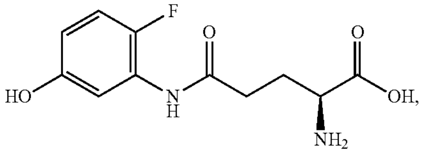

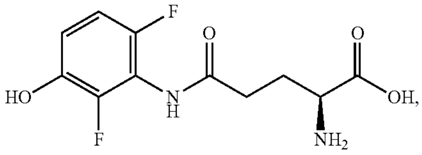

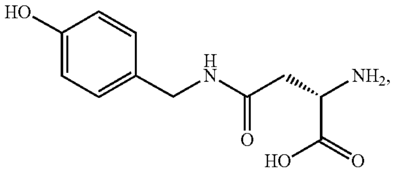

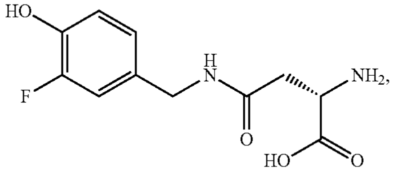

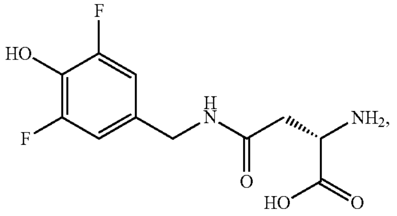

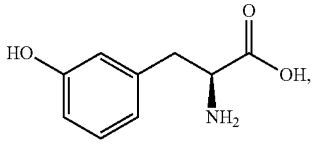

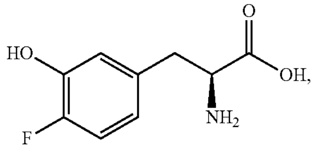

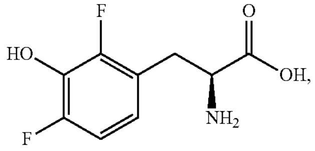

lysine, aspartic acid, glutamic acid, and 2,4-diaminobutyric acid;

(e) the antibody binding moiety comprises DCAWXLGELVWCT, wherein the two cysteine residues optionally form a disulfide bond, and X is an amino acid residue; or (f) the antibody binding moiety is
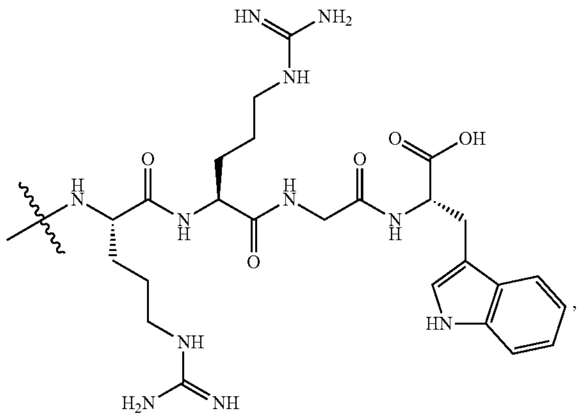
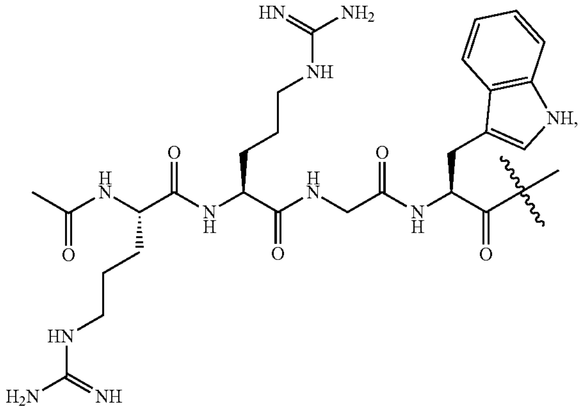
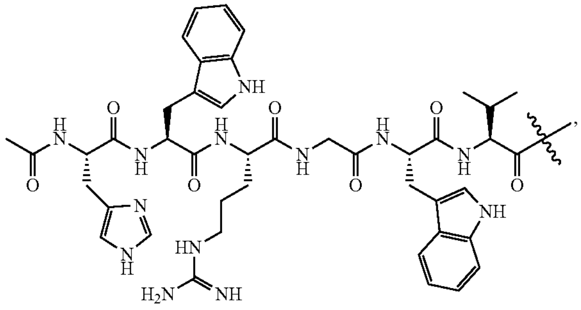
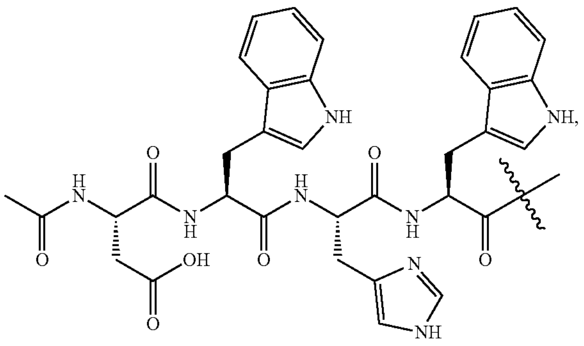
-continued
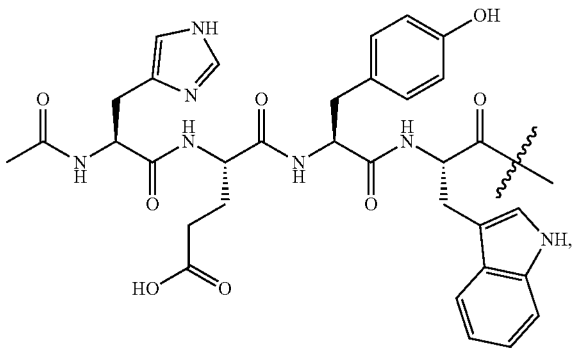
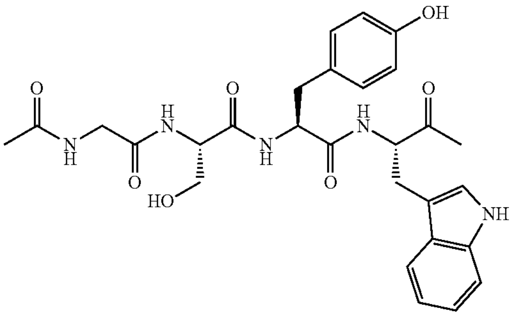
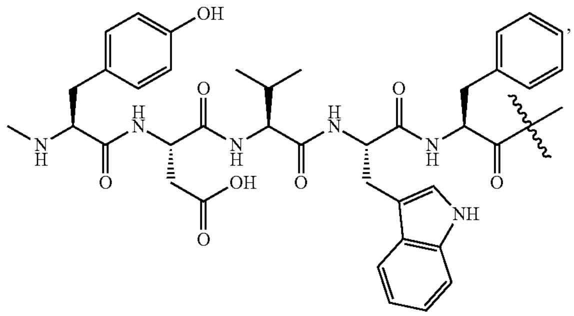
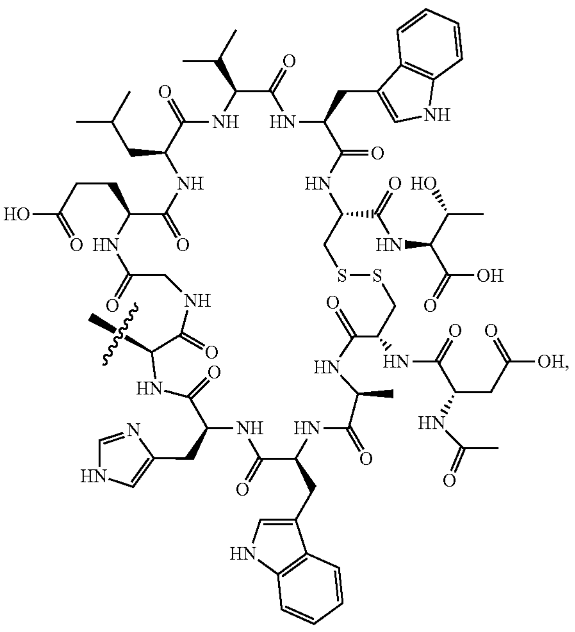

-continued
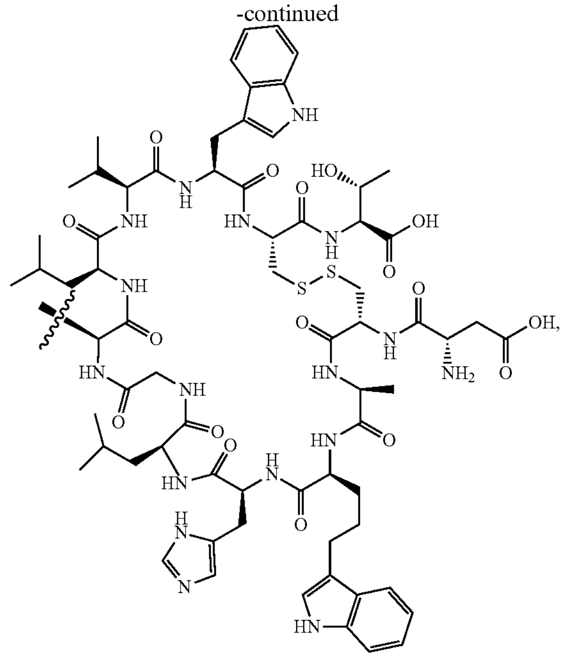
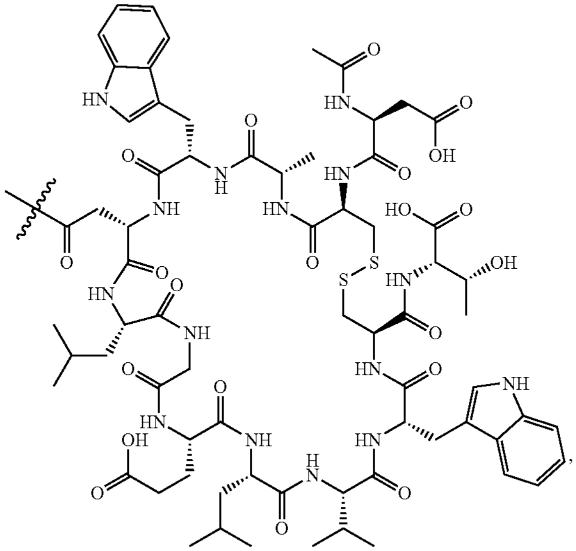
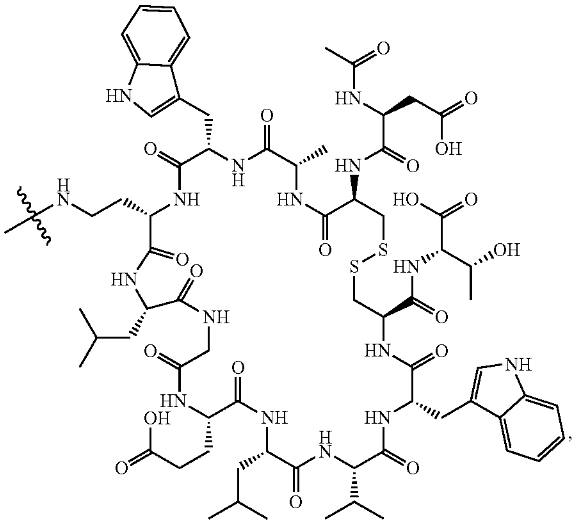
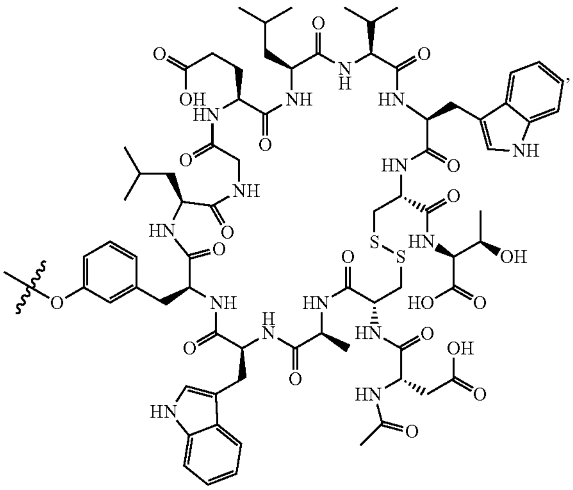
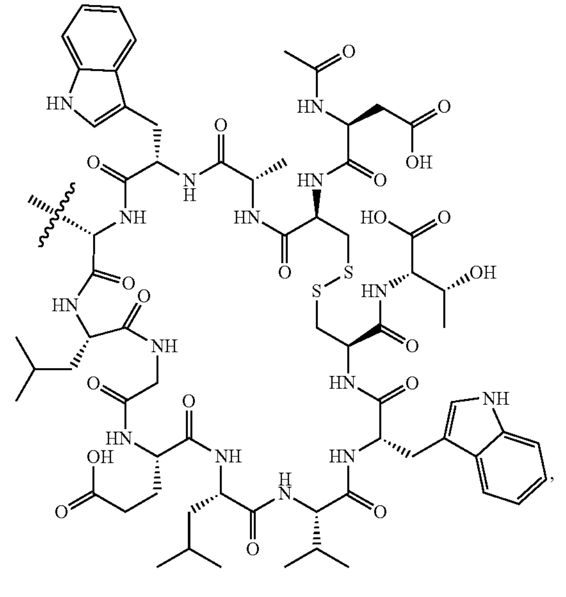
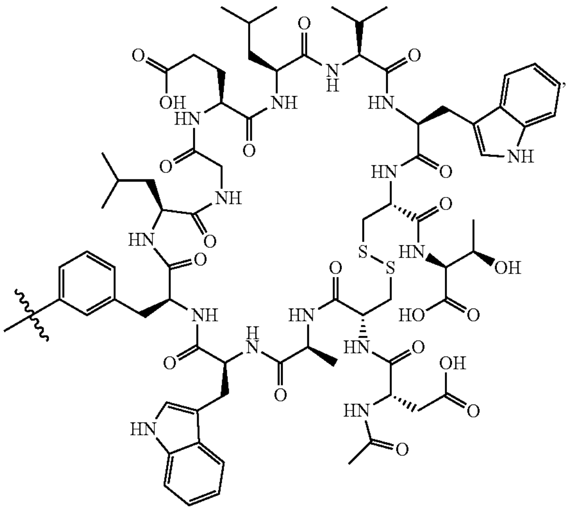

-continued
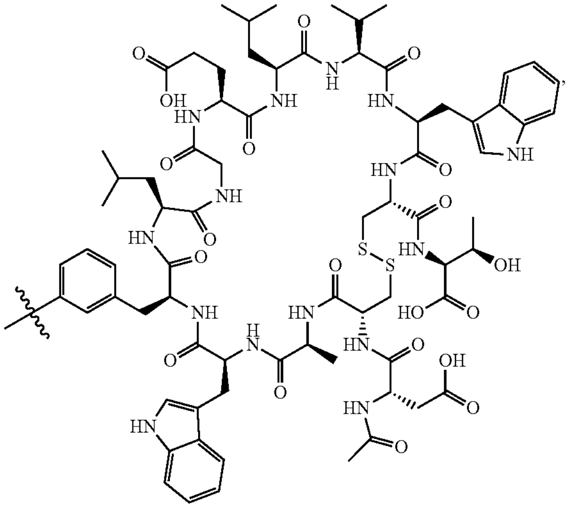
or
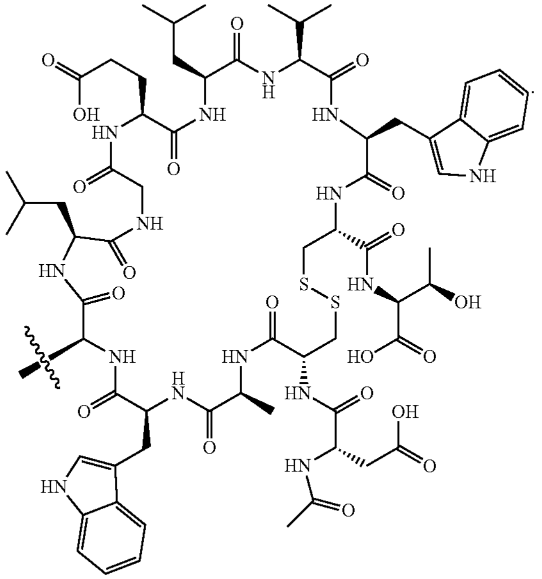
2. The compound of claim 1, wherein RG comprises one or more groups selected from:
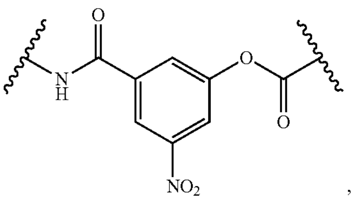
,
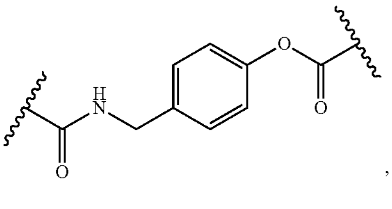
,
-continued
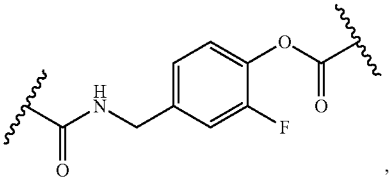
,
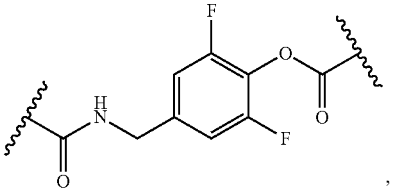
,
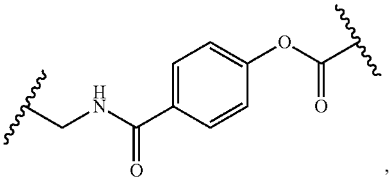
,
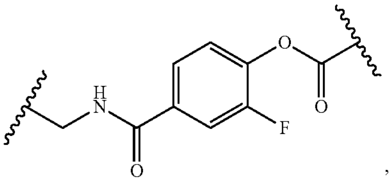
,
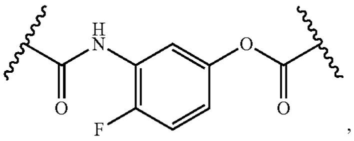
,
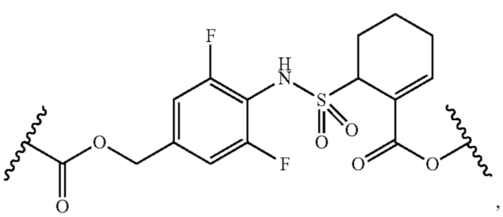
,
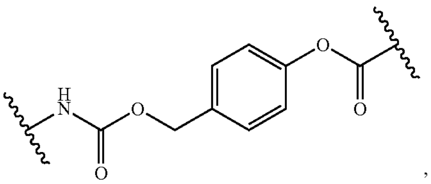
, and
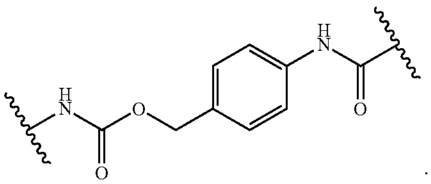
.
3. The compound of claim 1, wherein the antibody binding moiety comprises DCAWXLGELVWCT, wherein the two cysteine residues optionally form a disulfide bond, and X is an amino acid residue.
4. The compound of claim 1, wherein the moiety of interest comprises

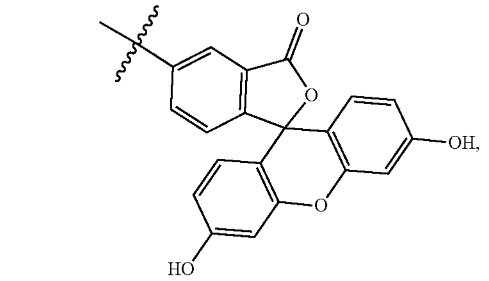

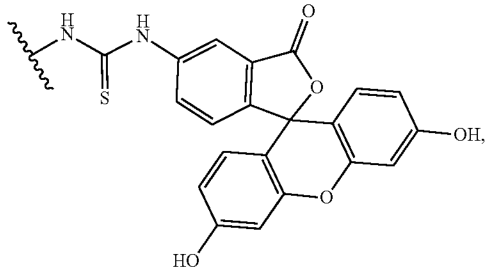

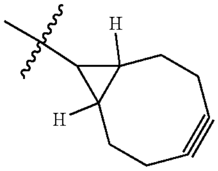

,

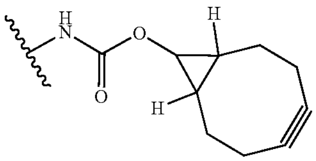

,

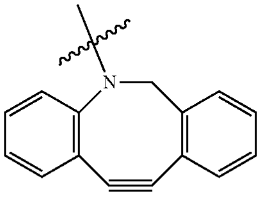

, or

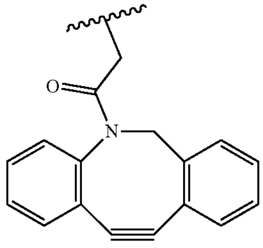

.

5. The compound of claim 1, wherein RG comprises one or more groups selected from:

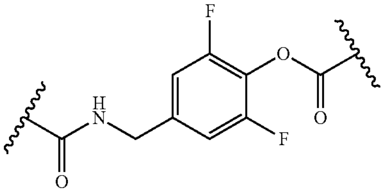

,

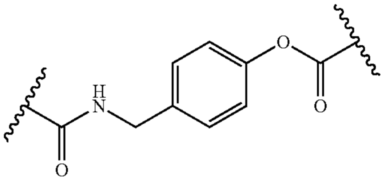

,

-continued

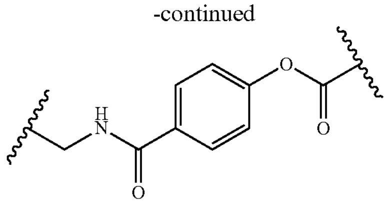

,

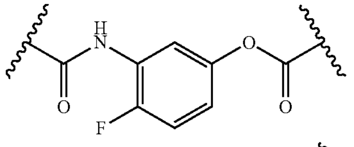

,

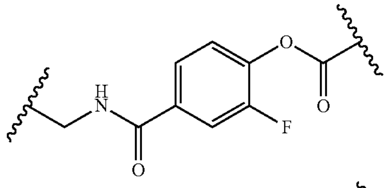

,

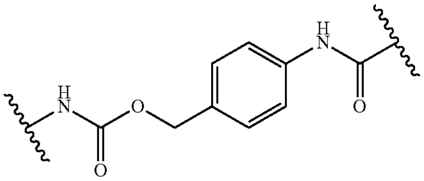

,

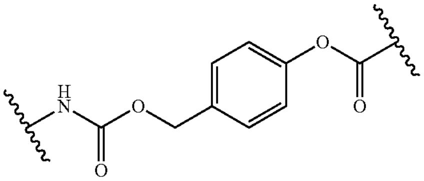

, and

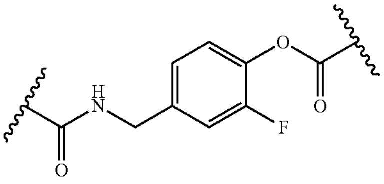

,

6. A method of preparing an agent having the structure of P-I:

$$P—L^{PM}—MOI, \quad (P\text{-}I)$$

or a salt thereof, wherein:

P is a target agent moiety, which is an antibody agent selected from IVIG, IgG1, IgG2, IgG3, IgG4, a monoclonal antibody agent, a polyclonal antibody agent, and an antibody fragment, wherein a conjugation location on the antibody agent is K246 or K248 of the heavy chain of the antibody agent;

$L^{PM}$ is a linker; and

MOI is a moiety of interest, the method comprising:

1) contacting the antibody agent with a reaction partner having the chemical structure of the compound of claim 1 or a salt thereof; and:

2) Forming an agent having the structure of formula P-I.

7. The method of claim 6, wherein RG comprising one or more groups selected from

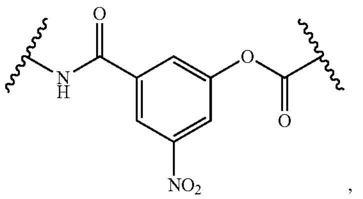

,

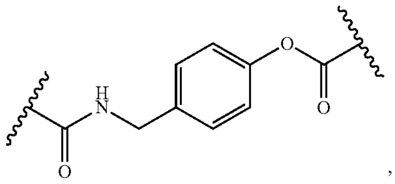

,

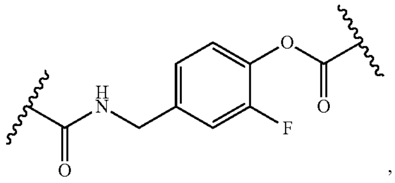

,

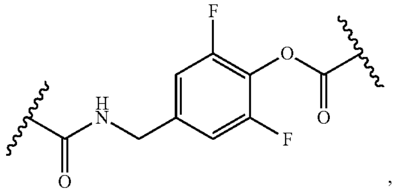

,

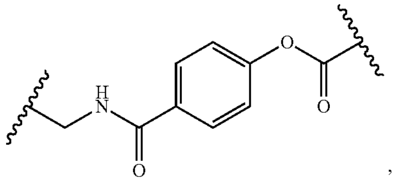

,

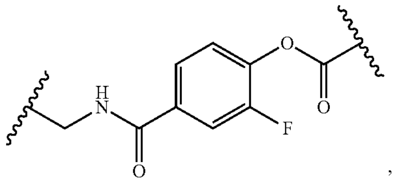

,

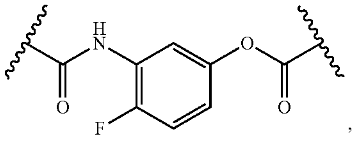

,

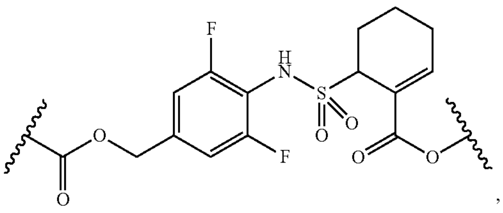

,

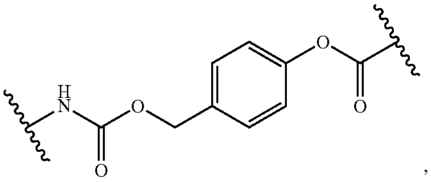

, and

-continued

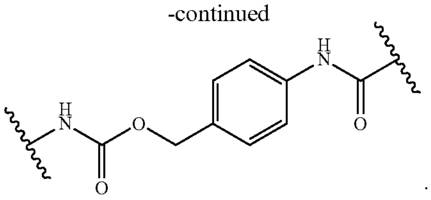

.

8. The method of claim 6, wherein at least one of:

(i) the moiety of interest is selectively attached to the antibody agent at K246 or K248 of an IgG1 heavy chain or a corresponding location;

(ii) the moiety of interest is selectively attached to the antibody agent at K251 or K253 of an IgG2 heavy chain or a corresponding location; or (iii) the moiety of interest is selectively attached to the antibody agent at K239 or K241 of an IgG4 heavy chain or a corresponding location.

9. The method of claim 6, wherein the contacting and forming steps are performed in one chemical reaction.

10. The method of claim 6, wherein RG comprising one or more groups selected from

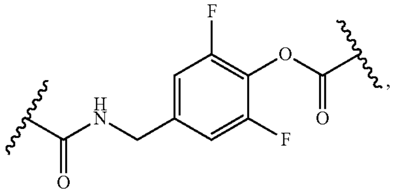

,

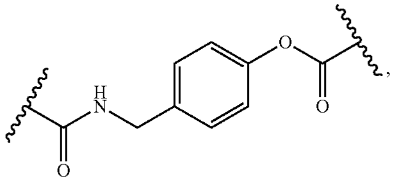

,

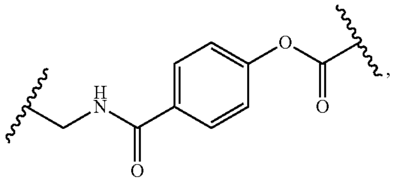

,

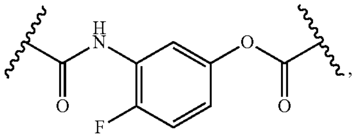

,

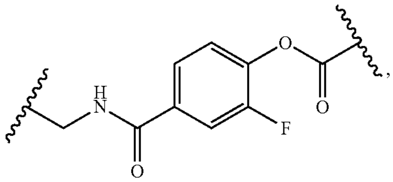

,

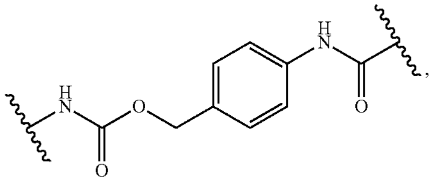

,

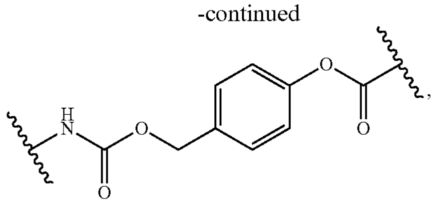, and
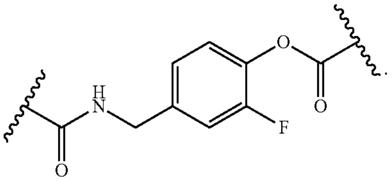.
11. The method of claim 6, wherein the antibody binding moiety comprises DCAWXLGELVWCT, wherein the two cysteine residues optionally form a disulfide bond, and X is an amino acid residue.
12. The method of claim 6, wherein the moiety of interest comprises
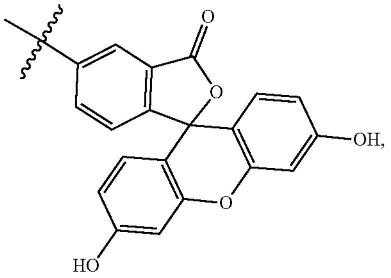
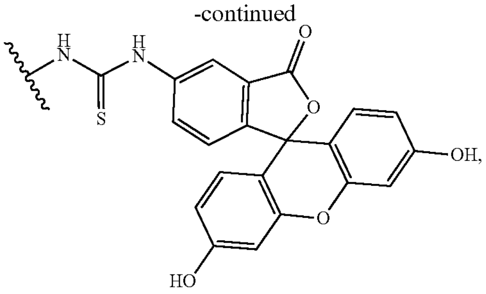
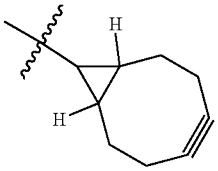,
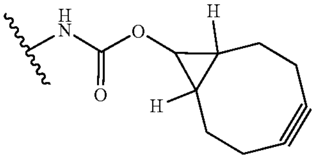,
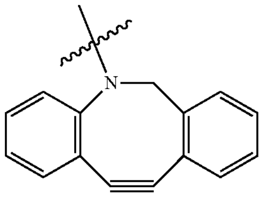, or
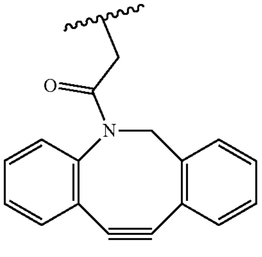.
13. The method of claim 6, wherein the antibody binding moiety is selected from A-1 to A-49
(A-1)
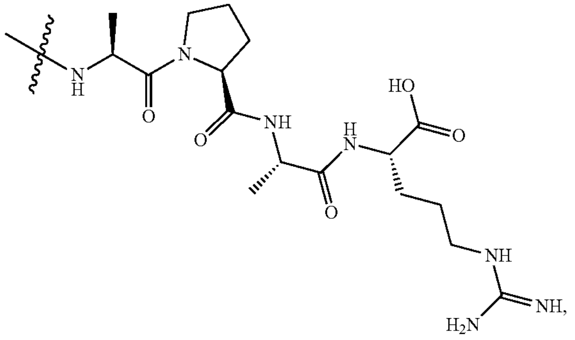
(A-2)
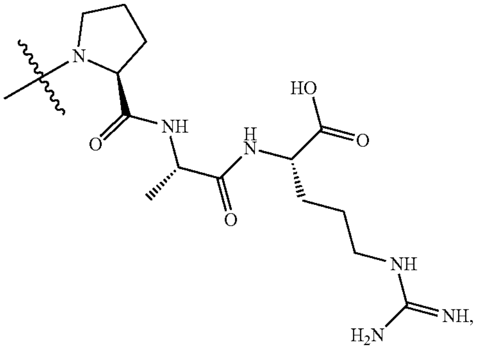

-continued
(A-3)
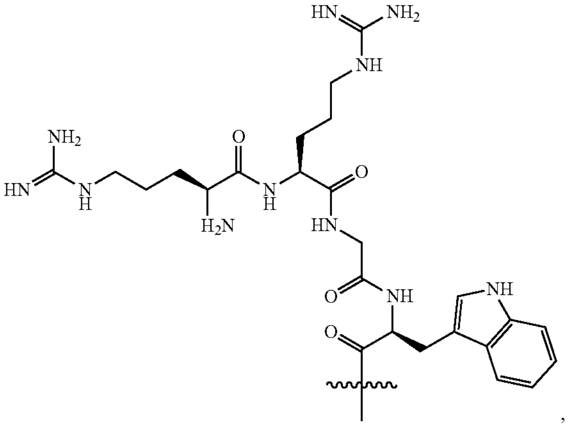
,
(A-4)
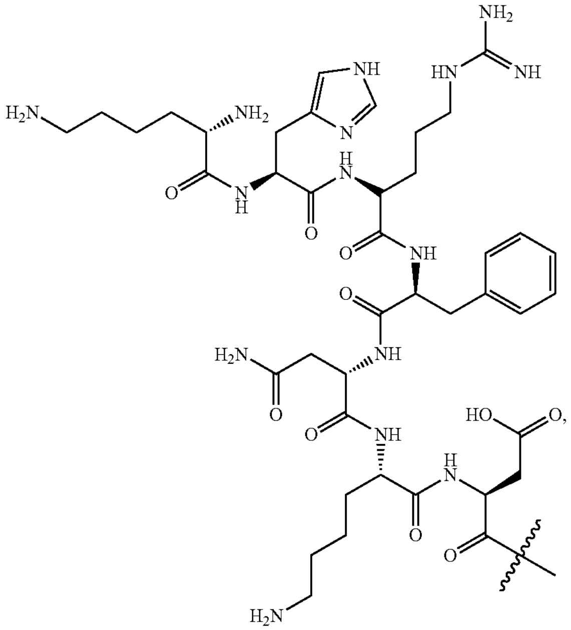
(A-5)
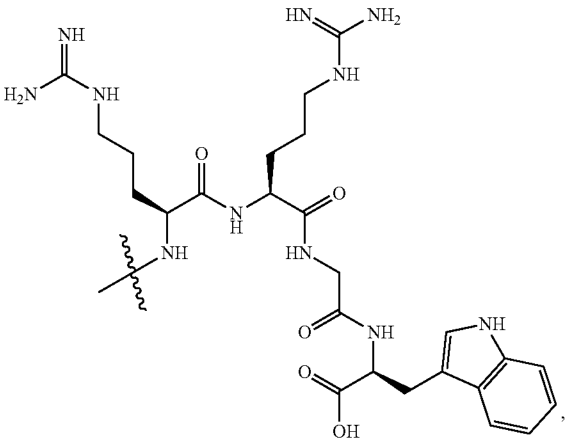
,
(A-6)
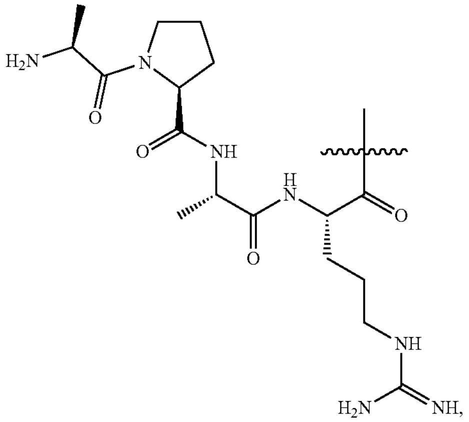
(A-7)
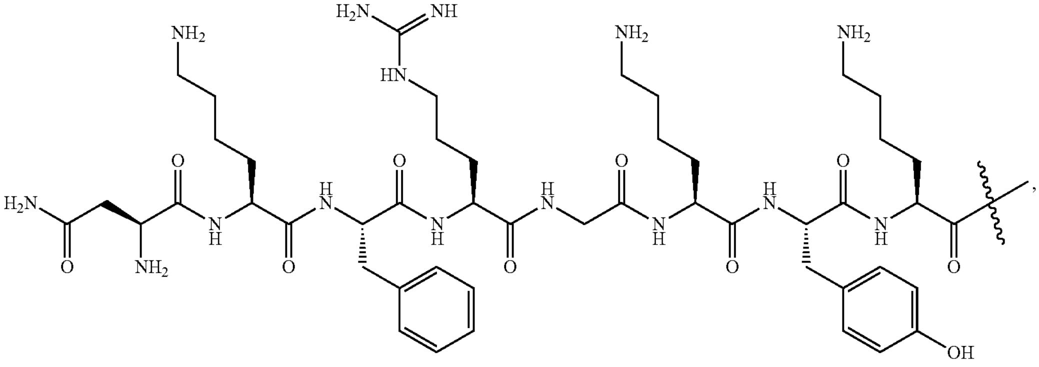
, -continued
(A-8)
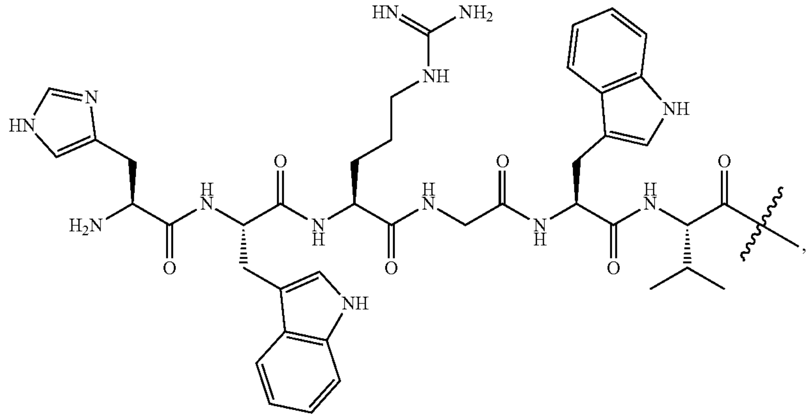
,
(A-9)
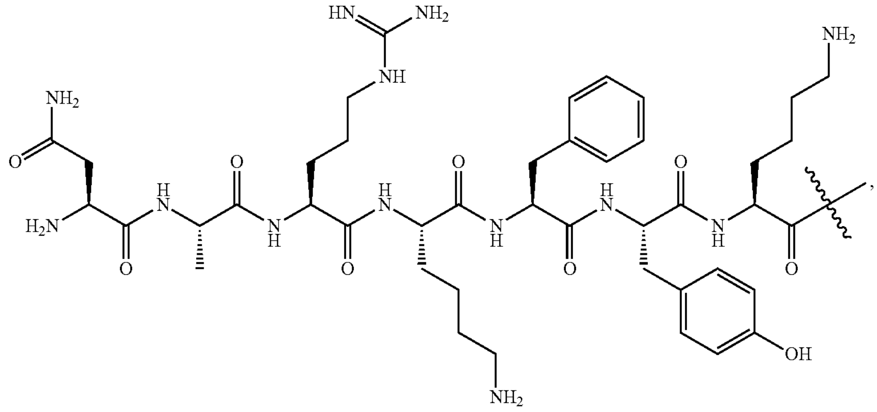
,
(A-10)
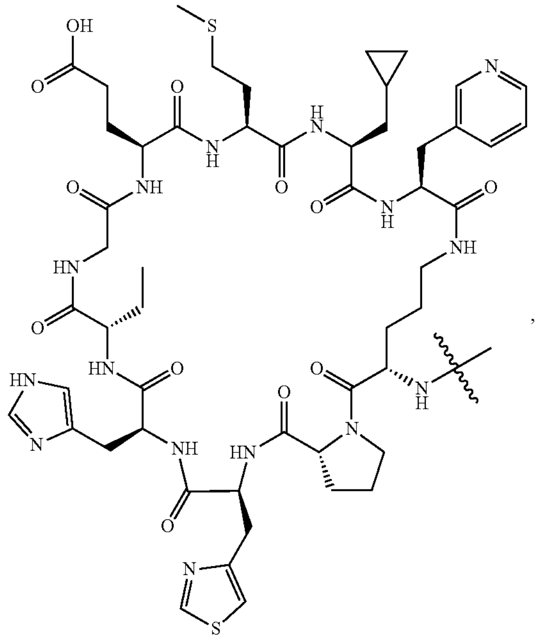
,
(A-11)
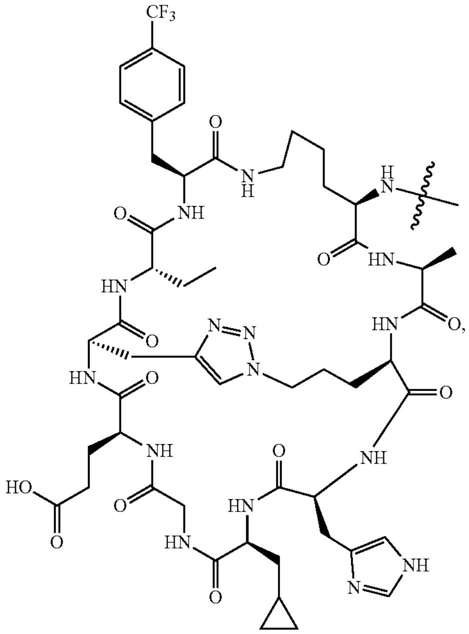
, -continued
(A-12)
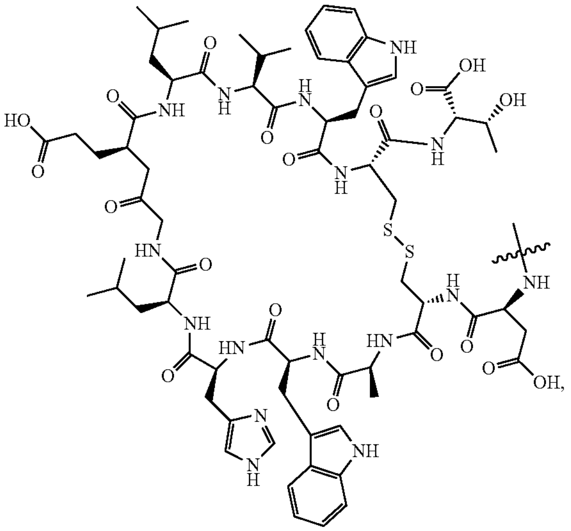
(A-13)
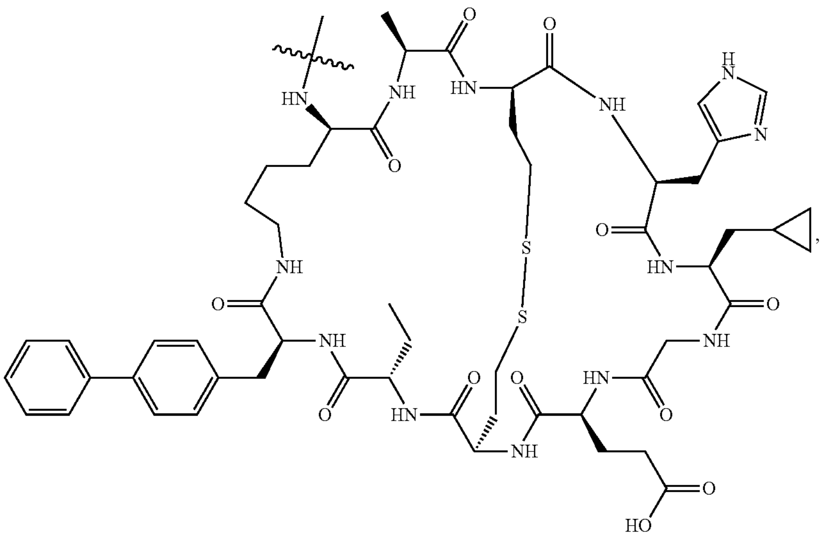
(A-14)
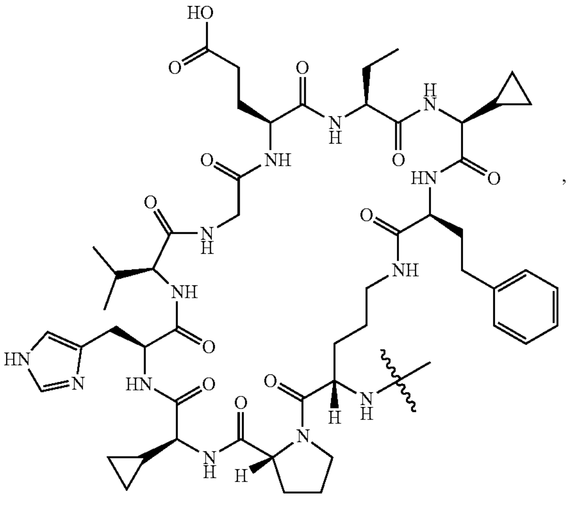
,
(A-15)
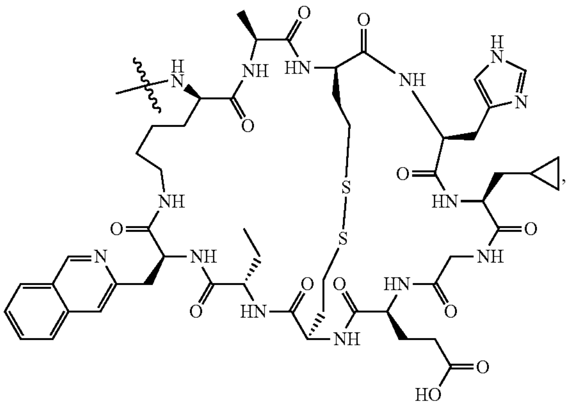

-continued
(A-16)
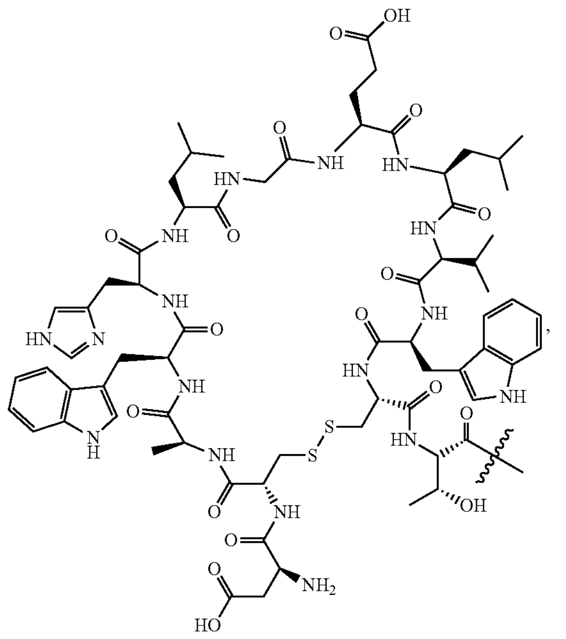
(A-17)
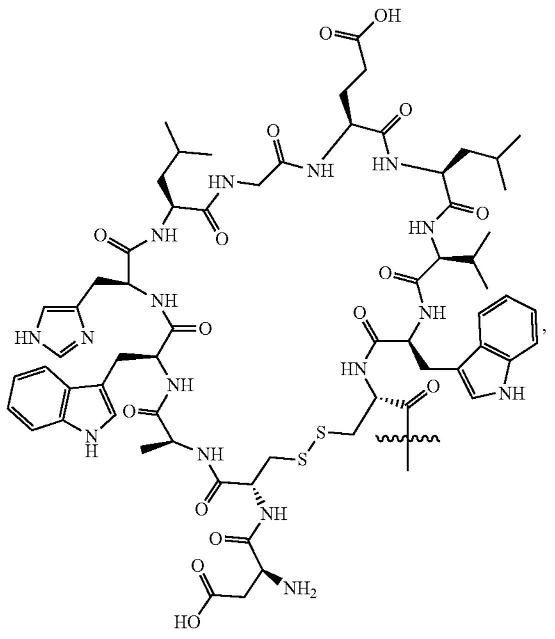
(A-18)
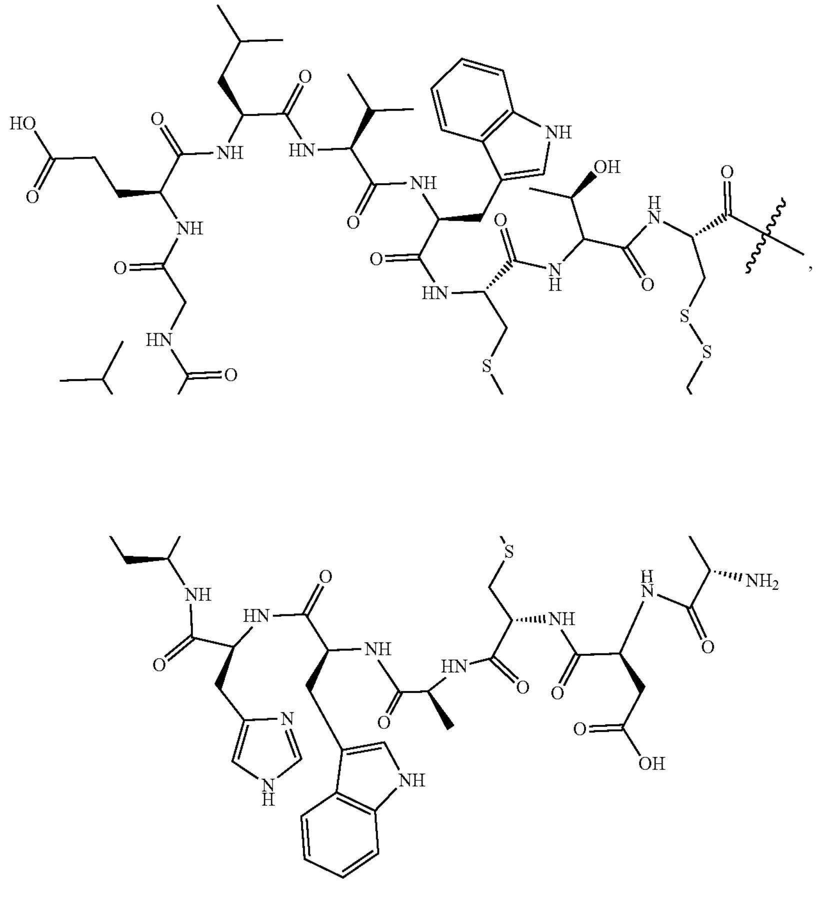

-continued
(A-19)
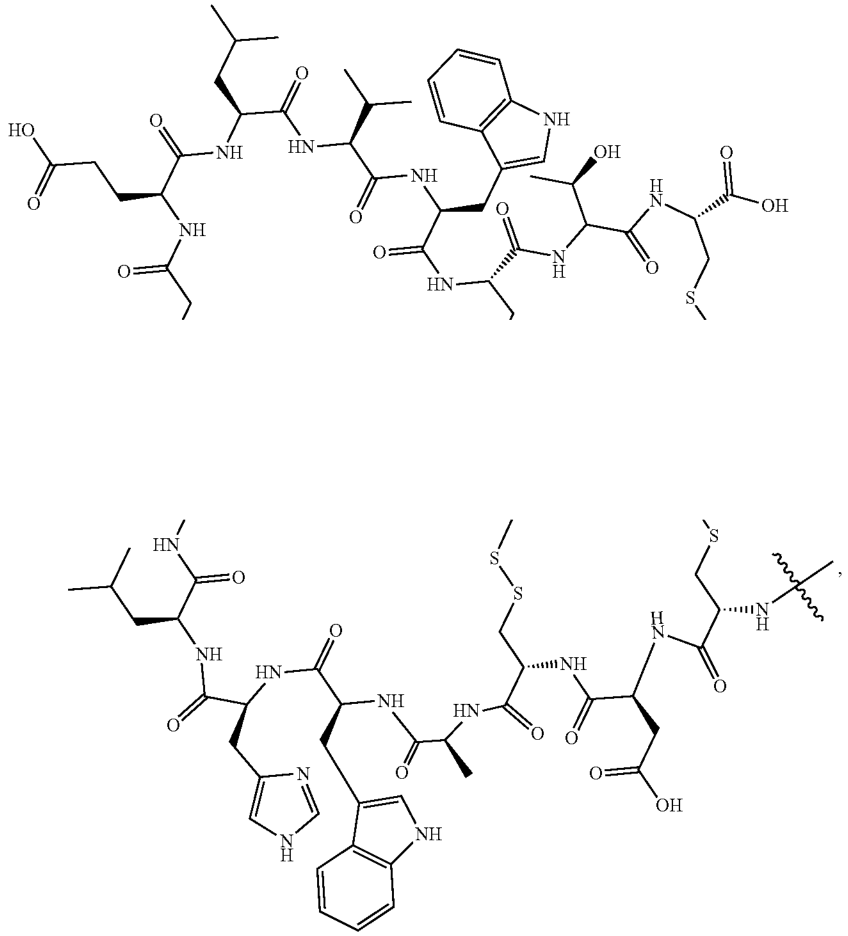
(A-20)
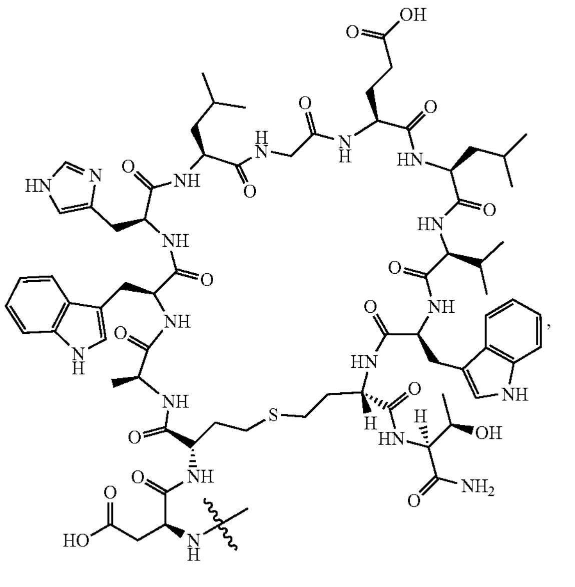
(A-21)
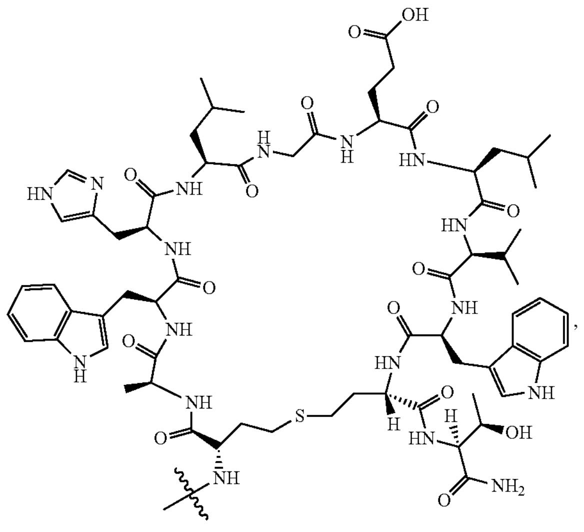

-continued
(A-22)
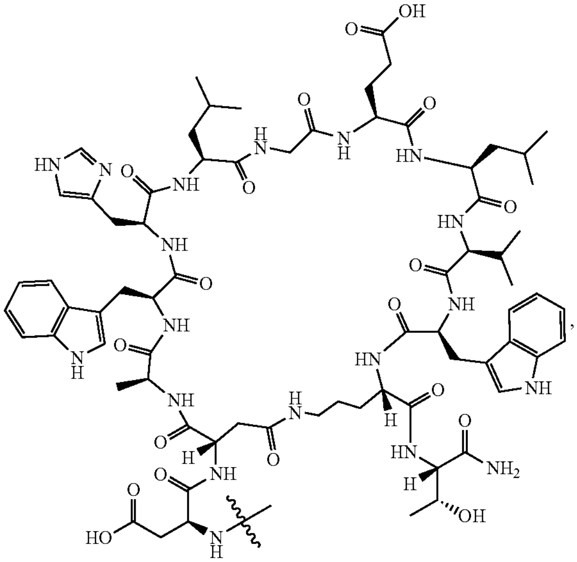
,
(A-23)
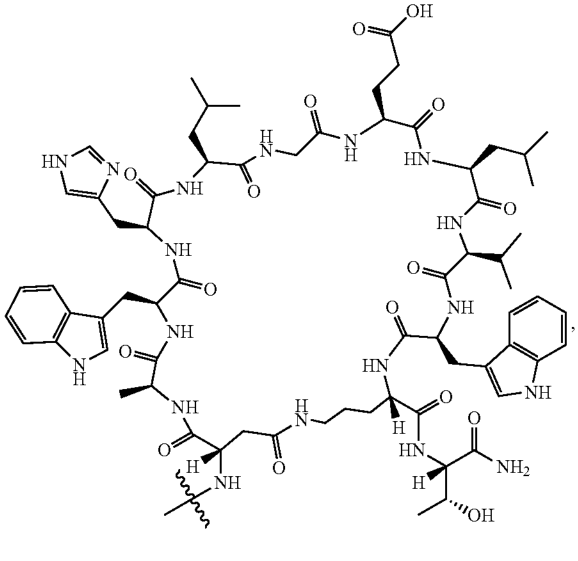
,
(A-24)
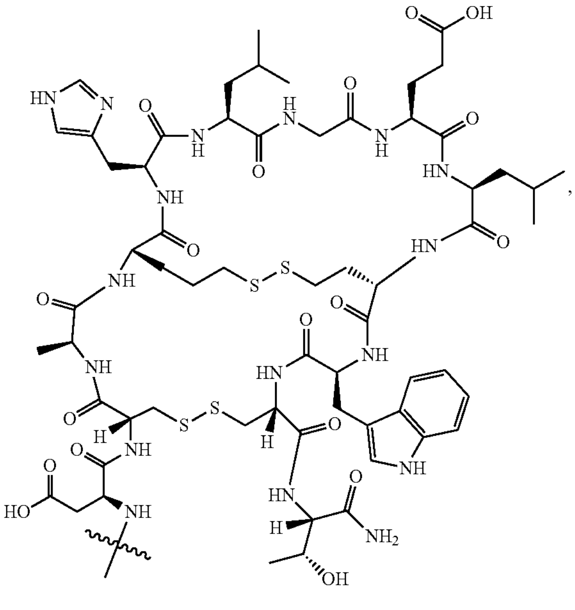
,
(A-25)
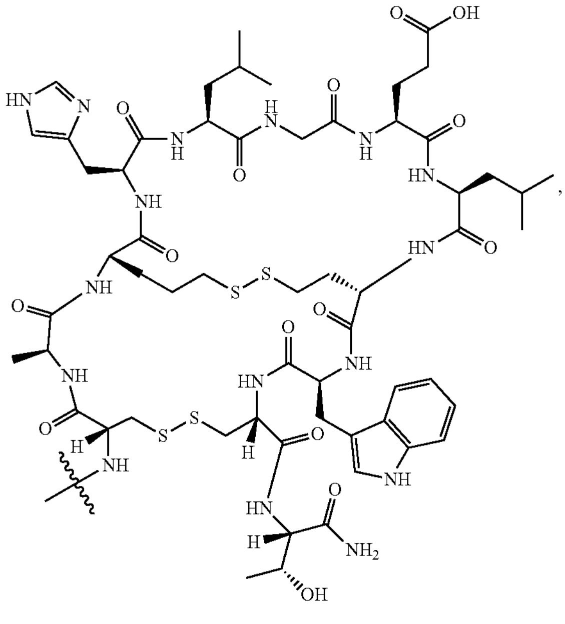
, -continued
(A-26)
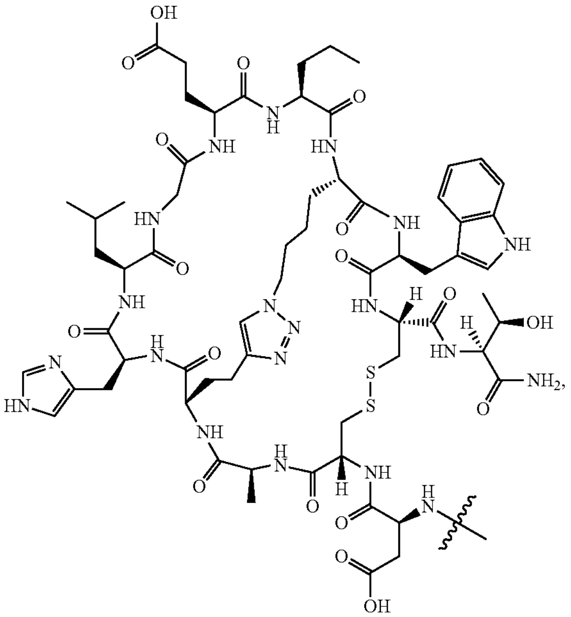
(A-27)
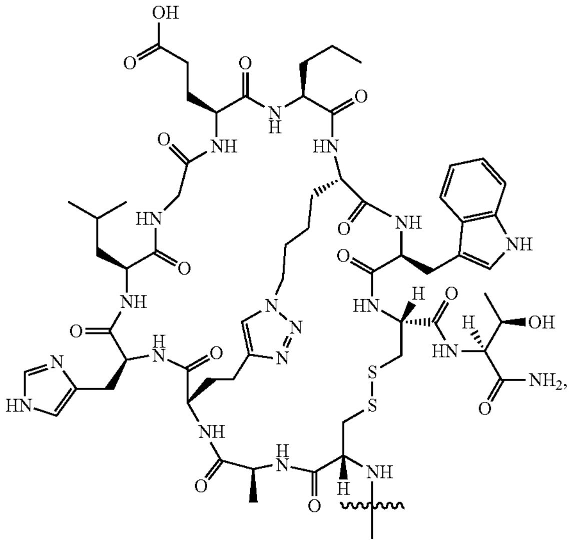
(A-28)
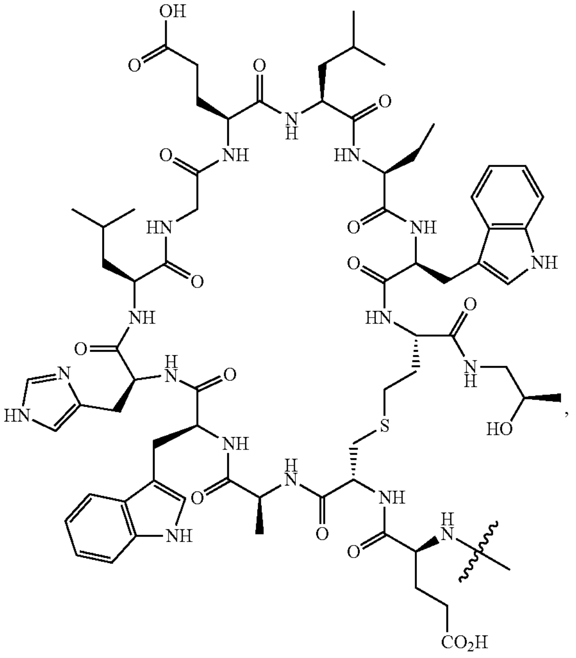

(A-29)
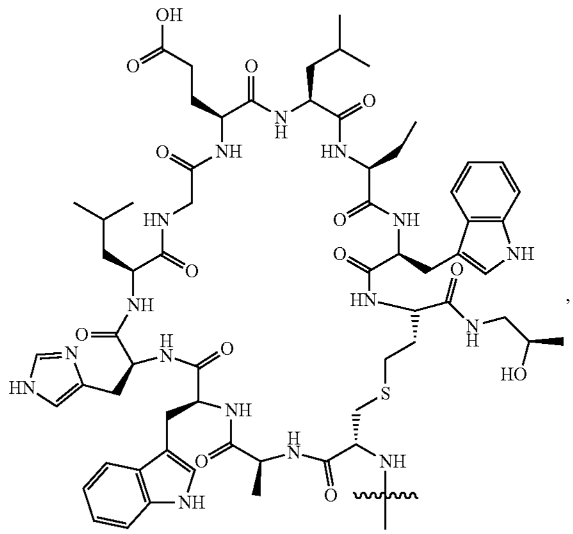
,
(A-30)
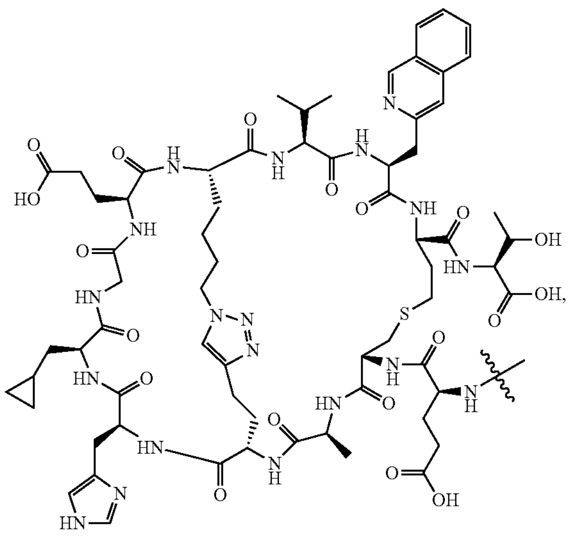
(A-31)
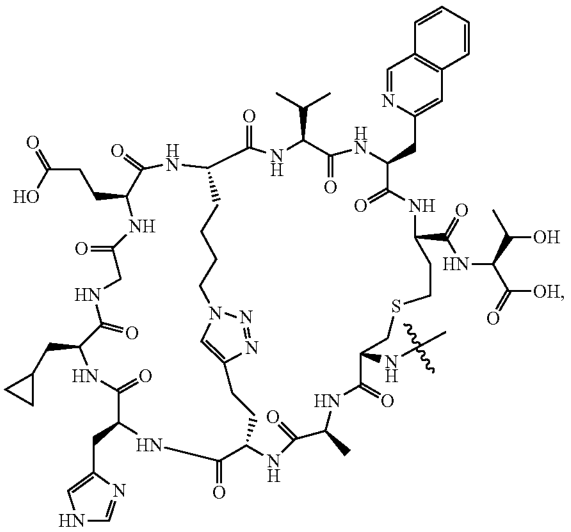
(A-32)
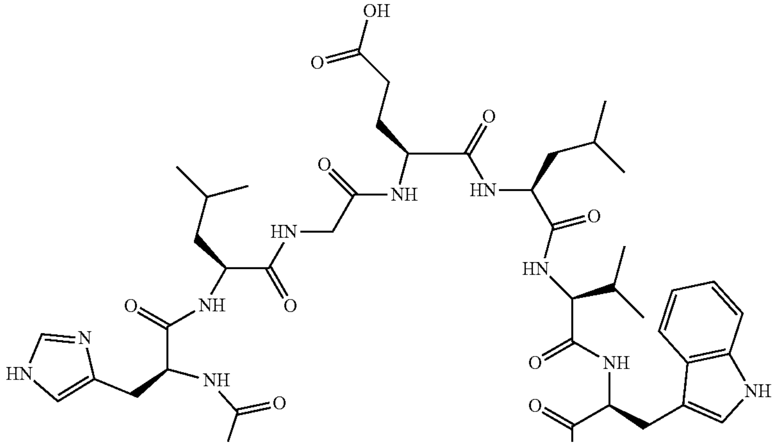

-continued
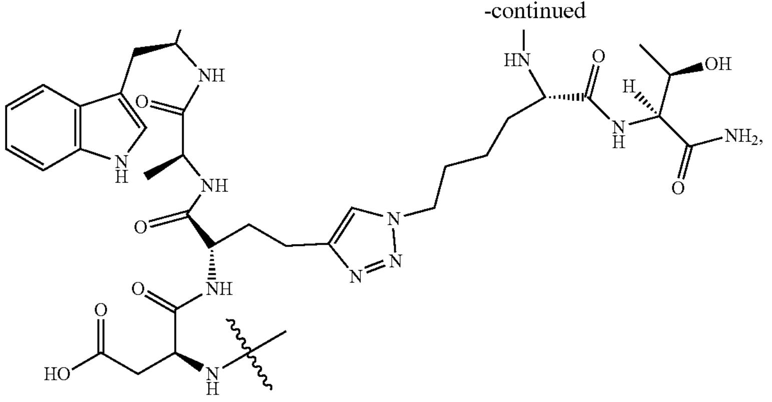
(A-33)
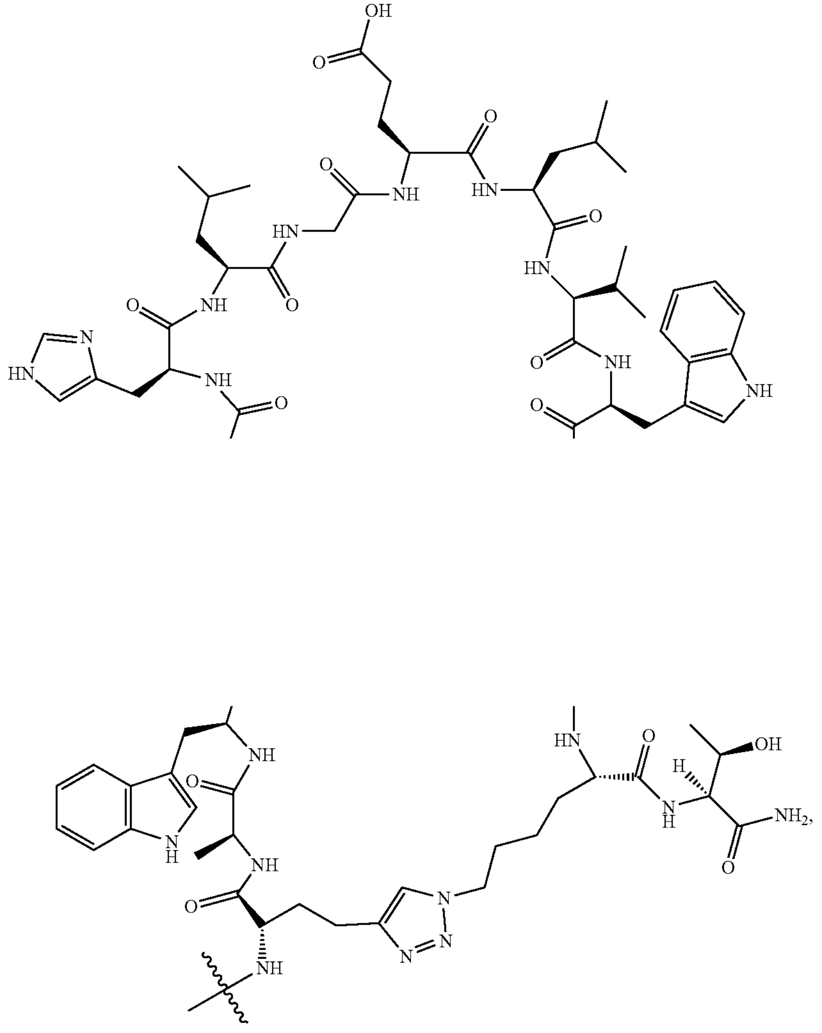

-continued
(A-34)
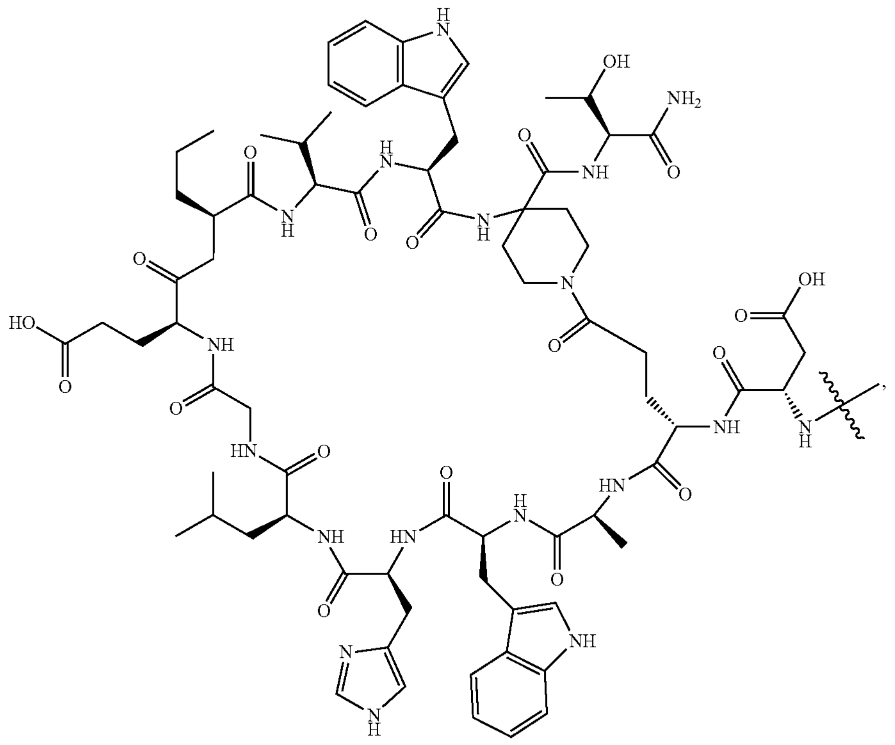
(A-35)
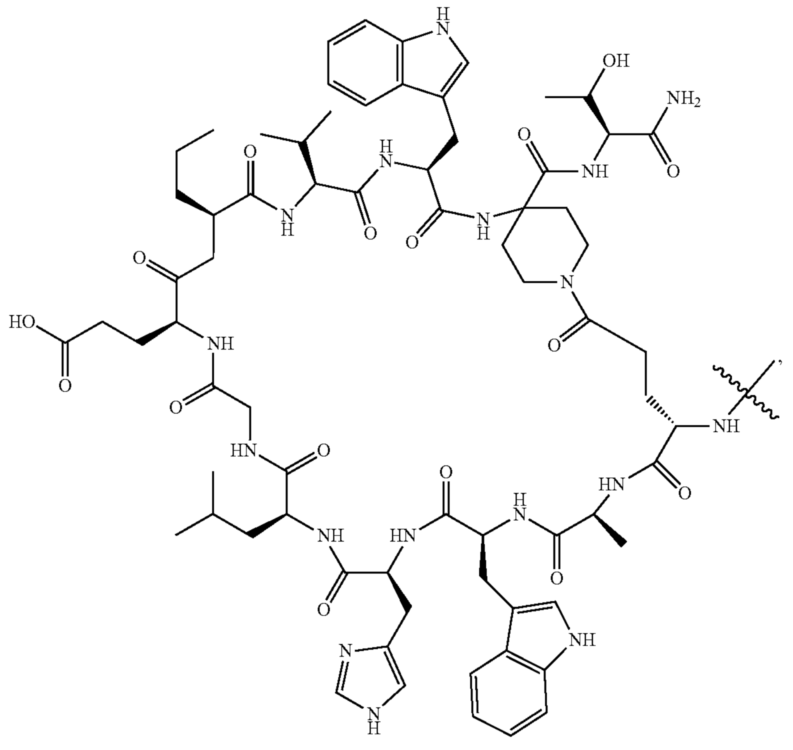

-continued
(A-36)
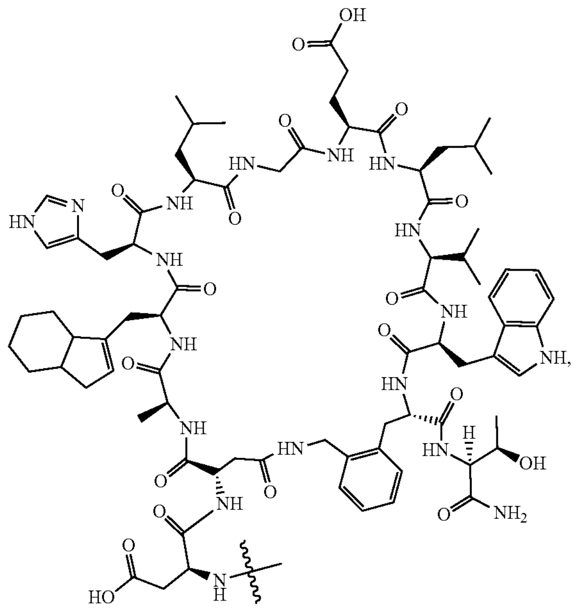
(A-37)
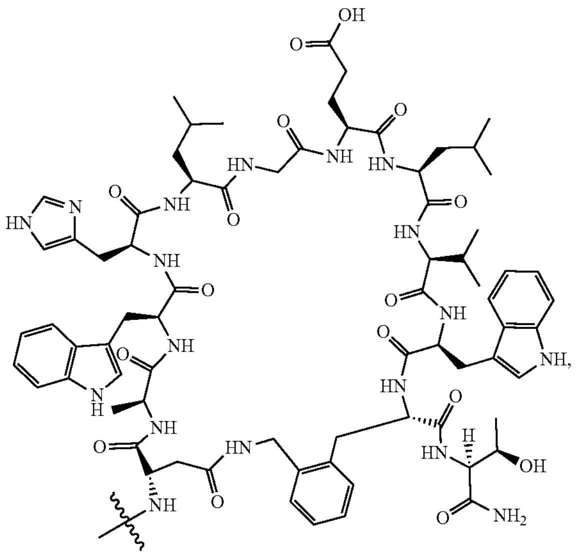
(A-38)
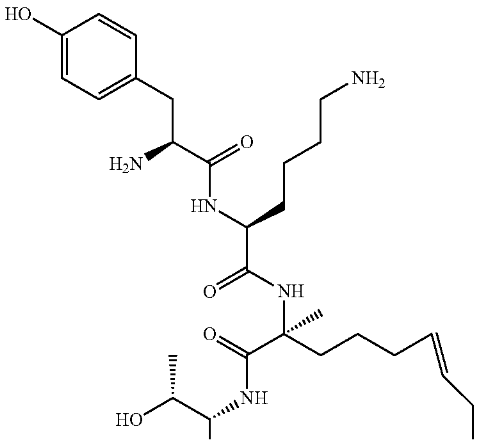
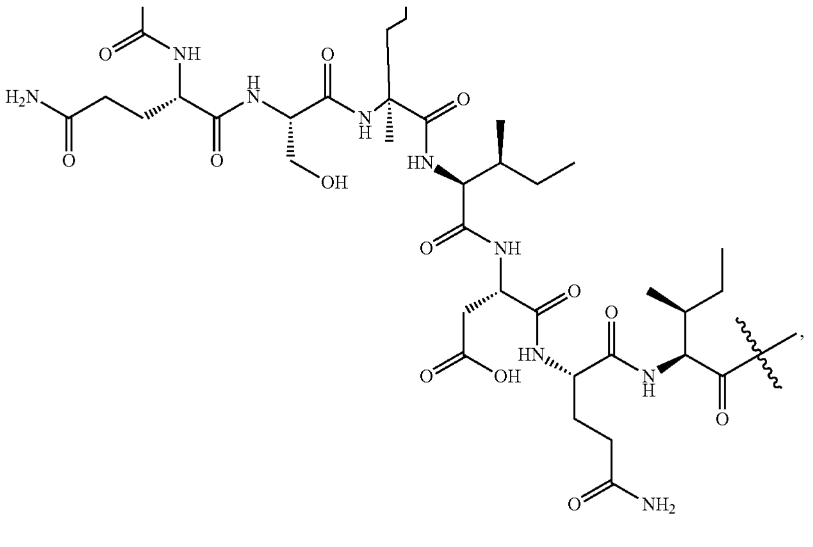

-continued
(A-39)
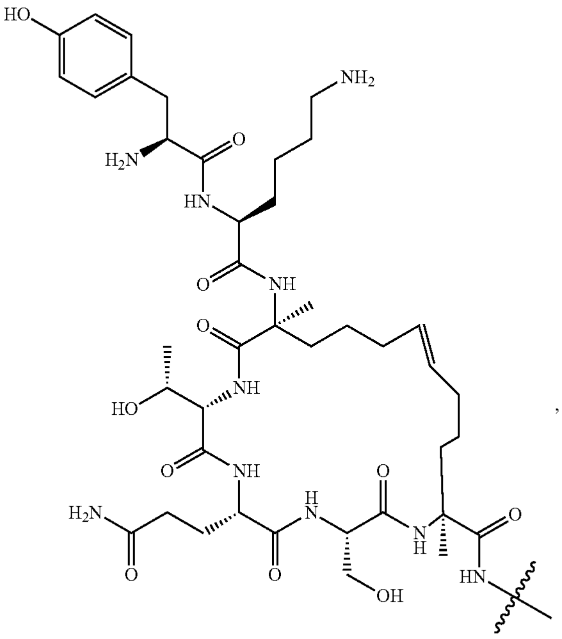
,
(A-40)
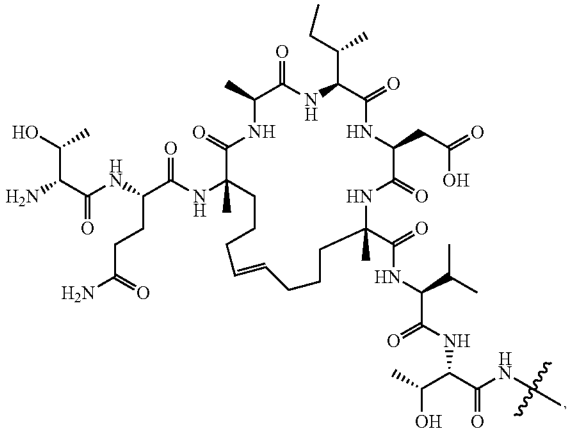
,
(A-41)
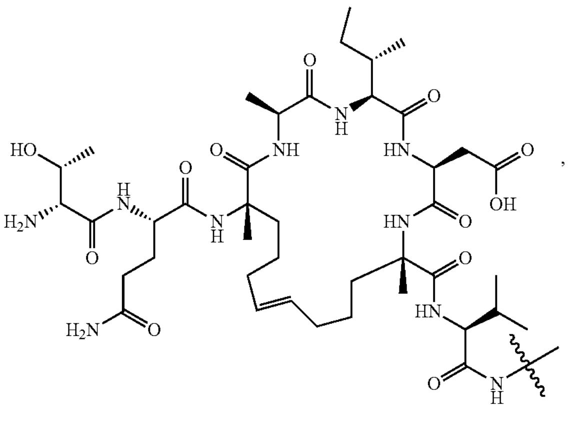
,
(A-42)
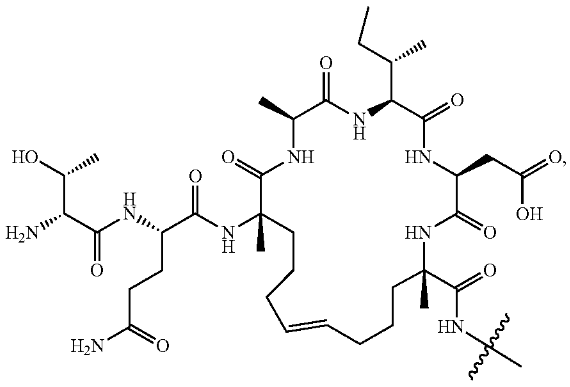
, -continued
(A-43)
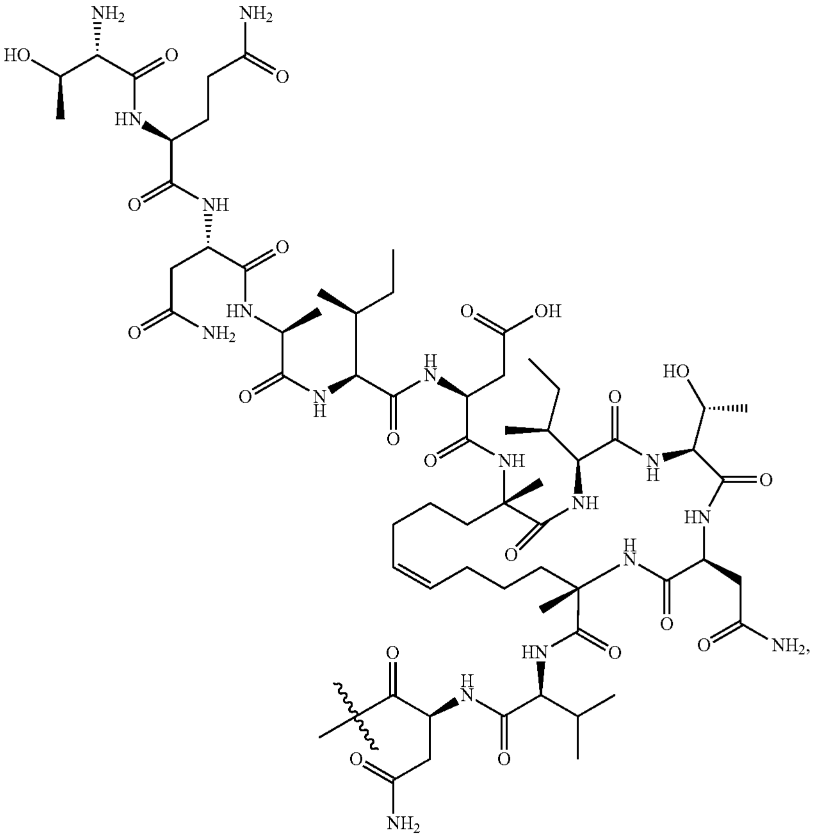
(A-44)
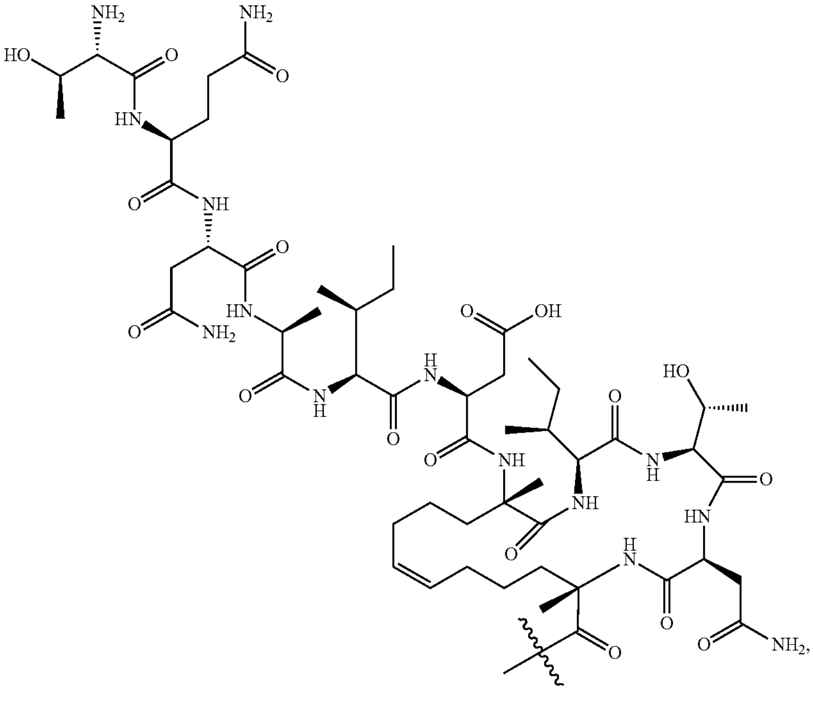

-continued
(A-45)
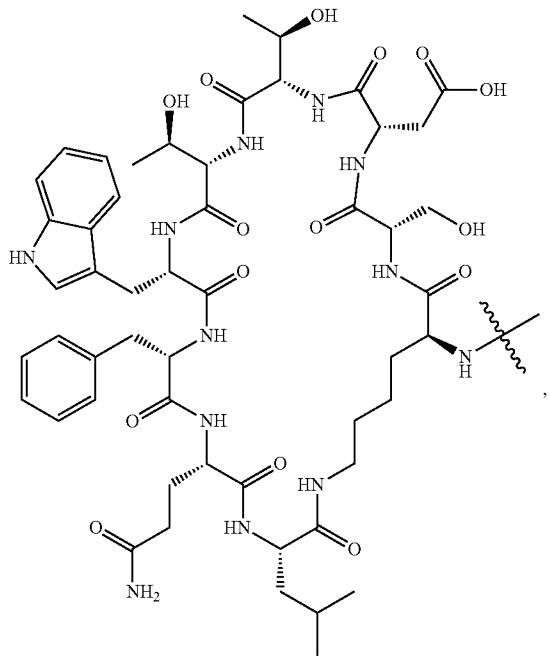
,
(A-46)
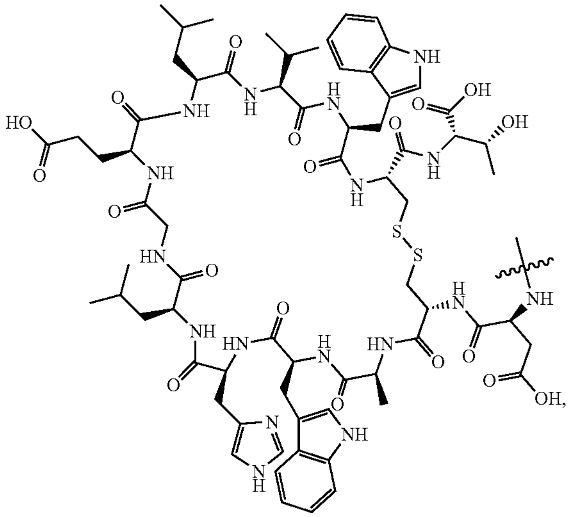
(A-47)
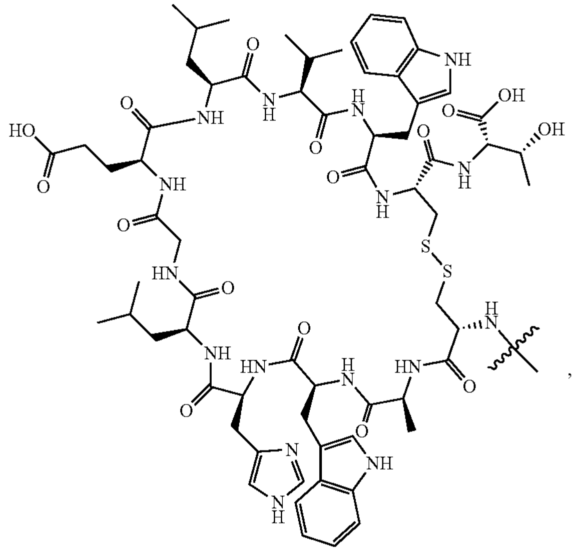
,
(A-48)
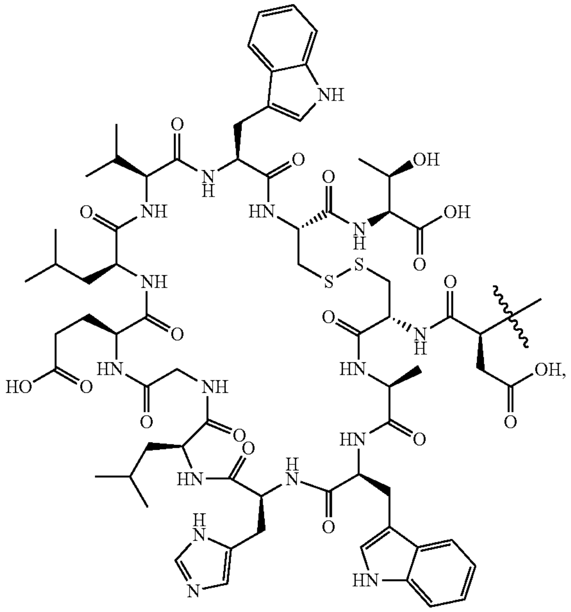

-continued
(A-49)
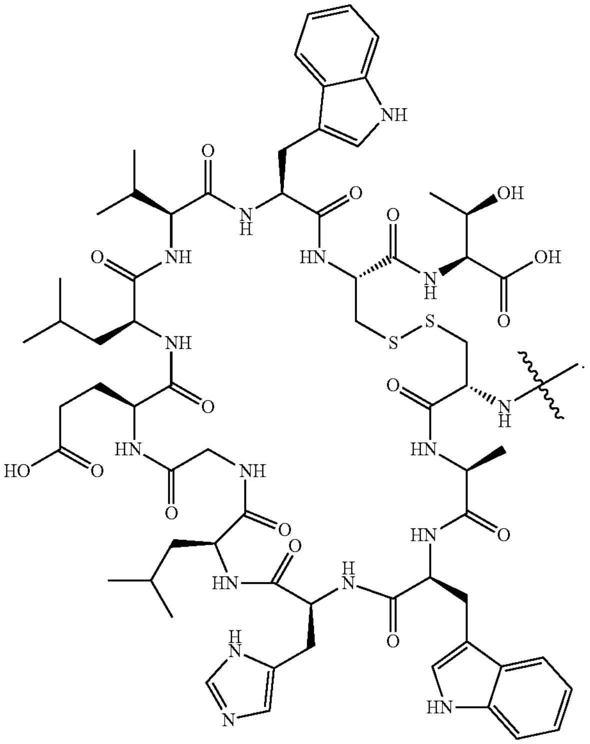
14. The compound of claim 1, wherein the antibody binding moiety is selected from A-1 to A-49:
(A-1)
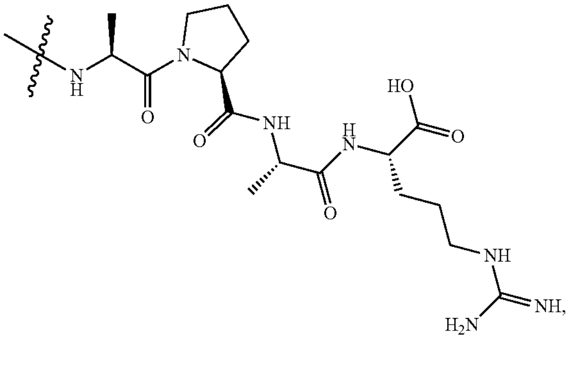
(A-2)
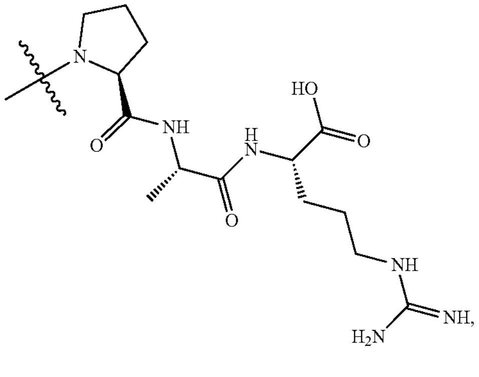

-continued
(A-3)
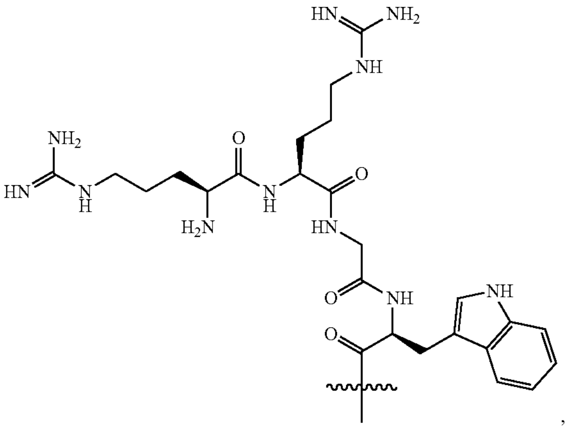
,
(A-4)
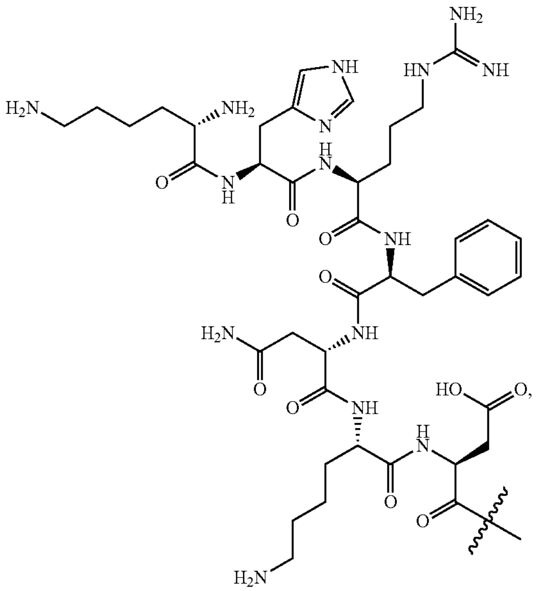
(A-5)
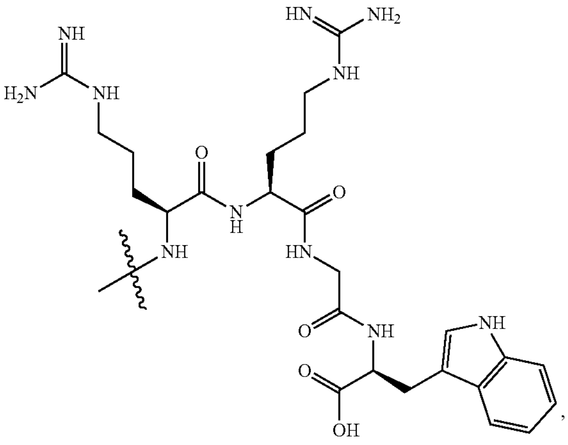
,
(A-6)
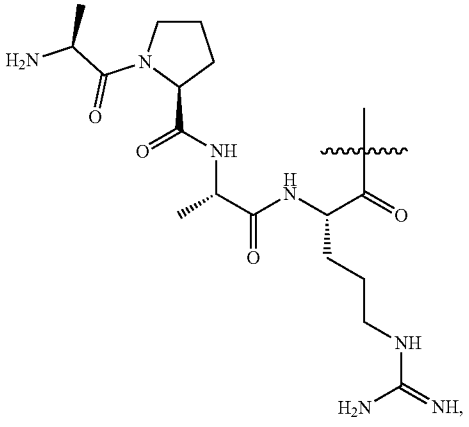
(A-7)
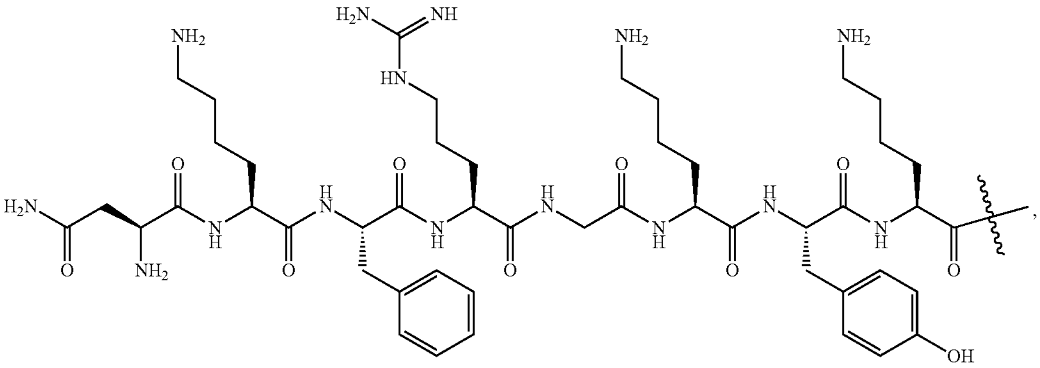
, -continued
(A-8)
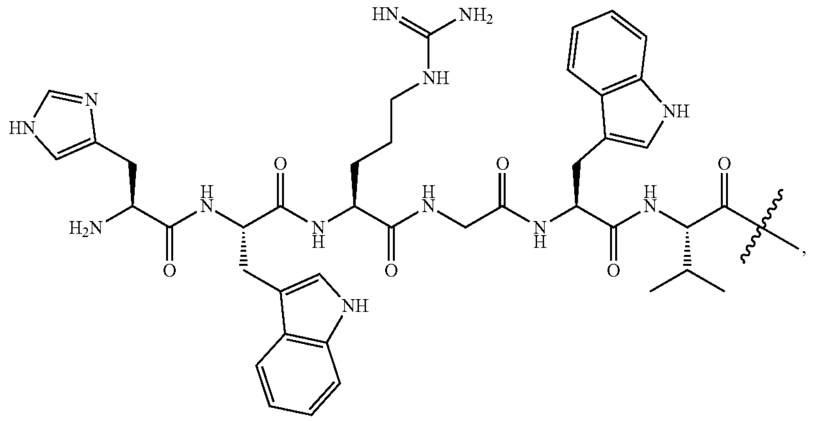
(A-9)
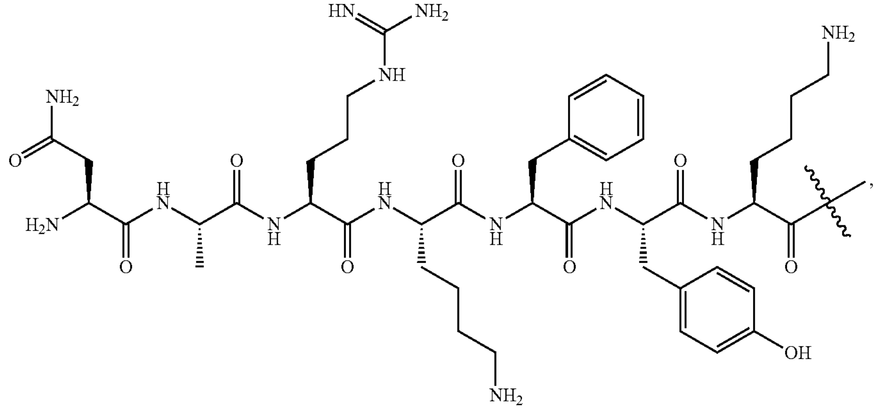
(A-10)
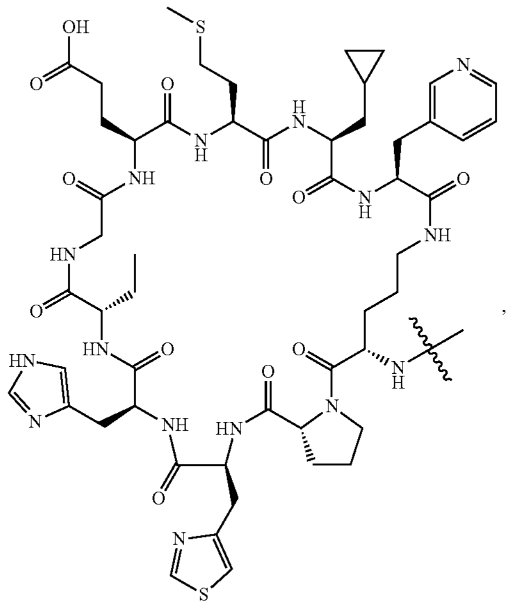
,
(A-11)
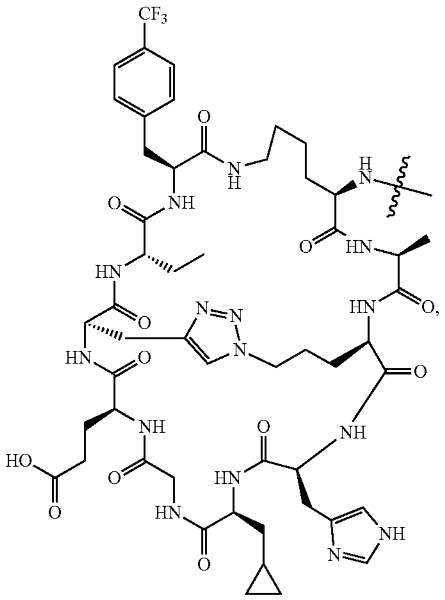

-continued
(A-12)
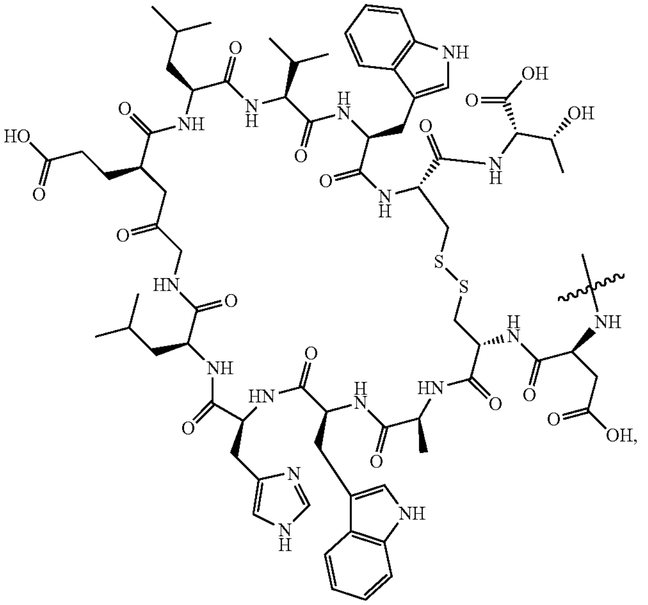
(A-13)
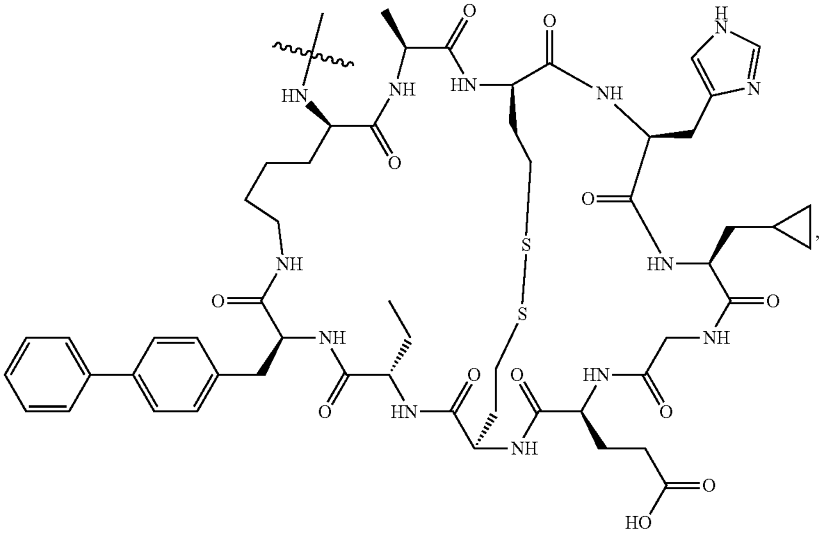
(A-14)
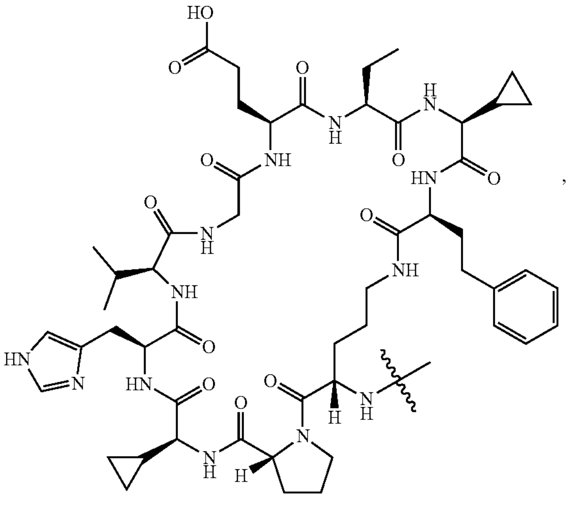
,
(A-15)
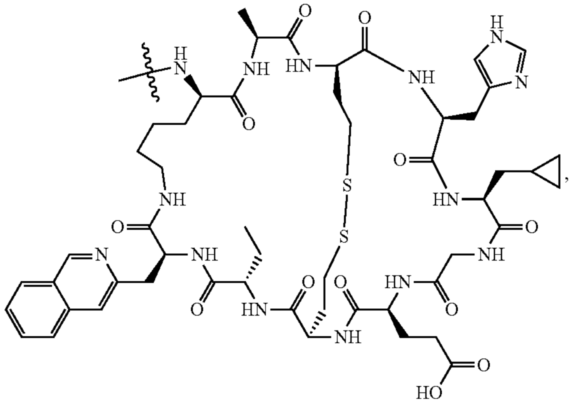

-continued
(A-16)
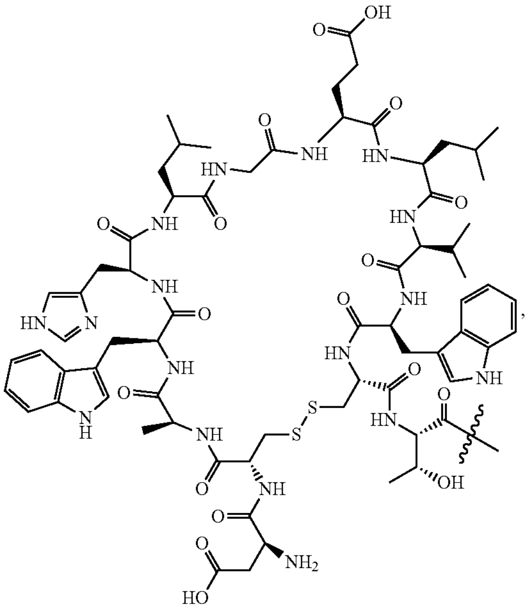
,
(A-17)
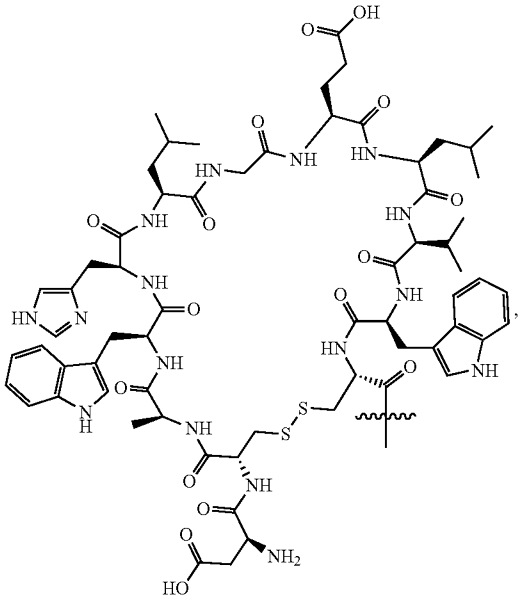
,
(A-18)
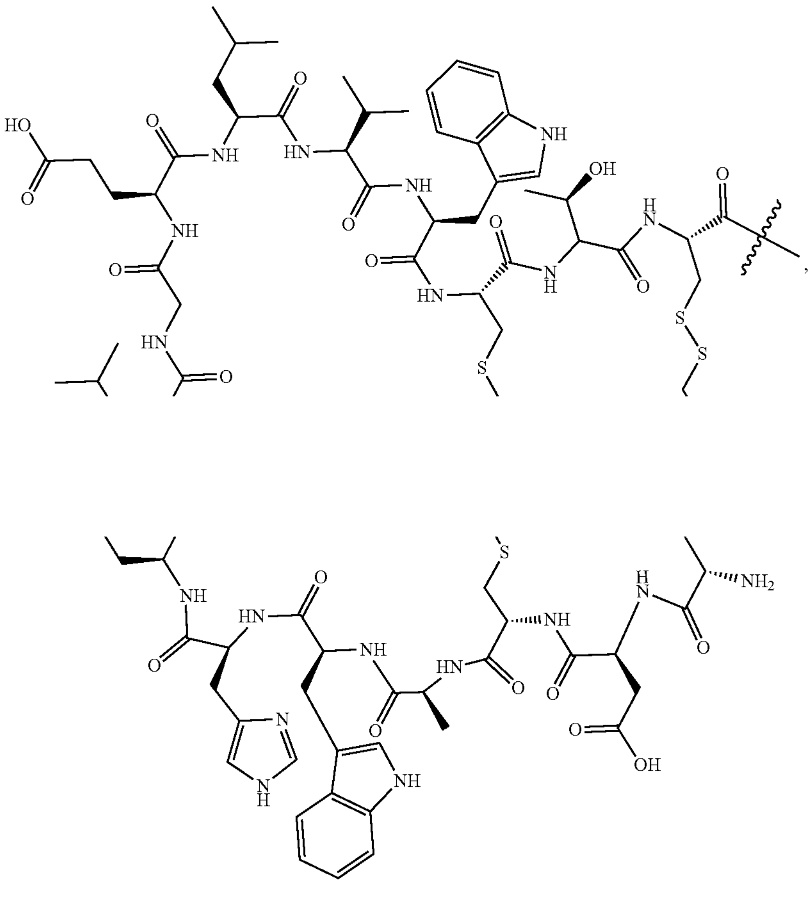
,

-continued
(A-19)
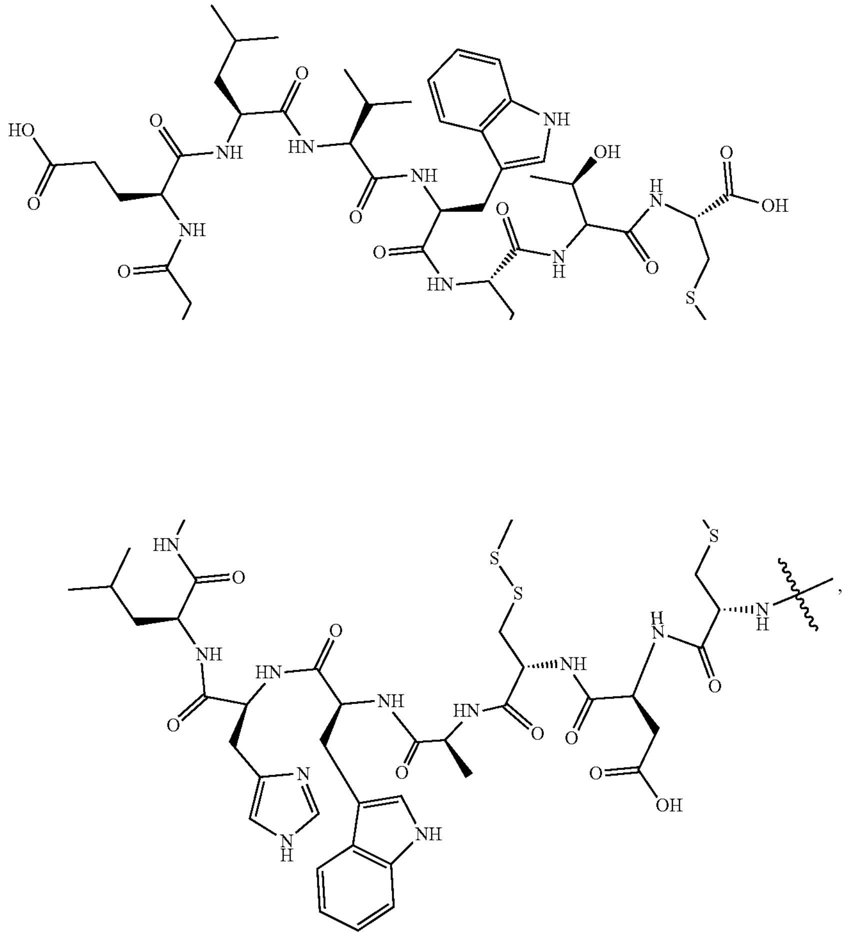
(A-20)
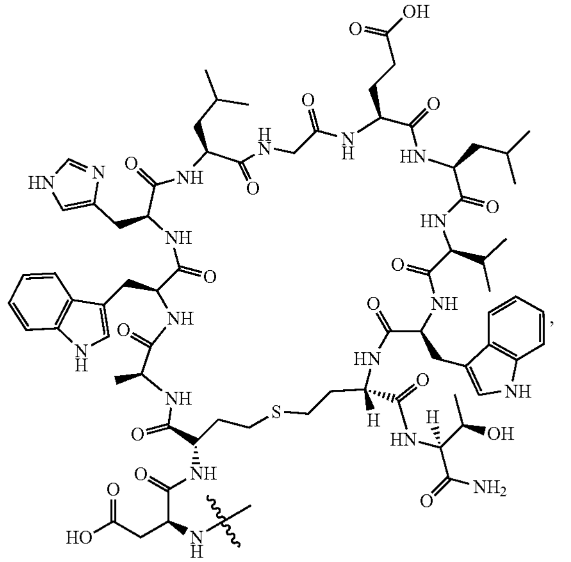
(A-21)
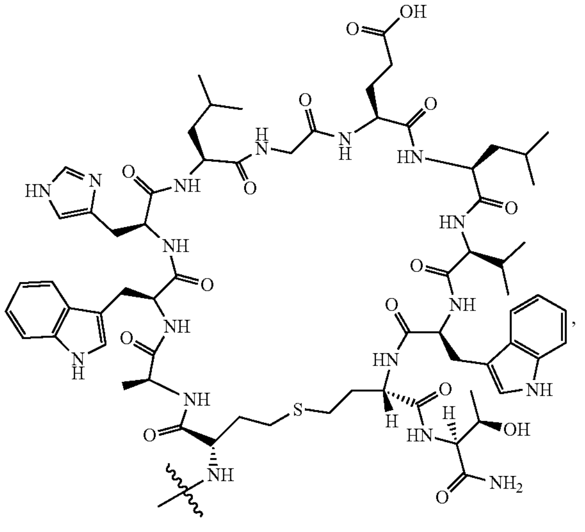

-continued
(A-22)
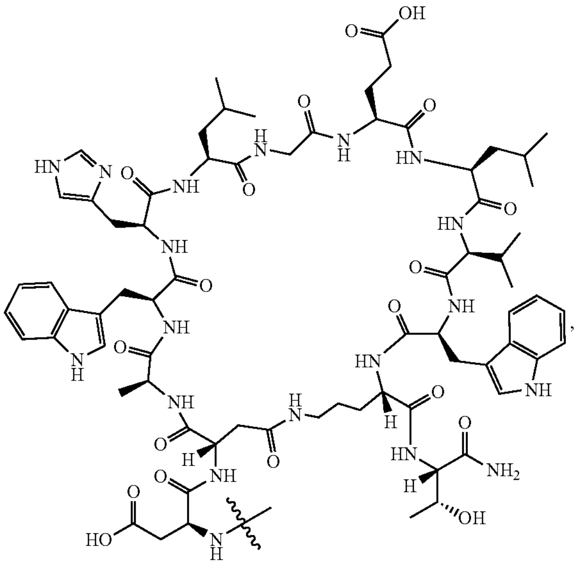
(A-23)
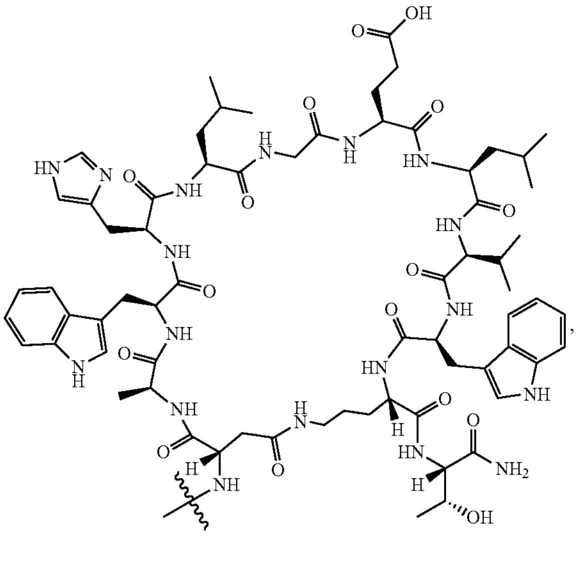
(A-24)
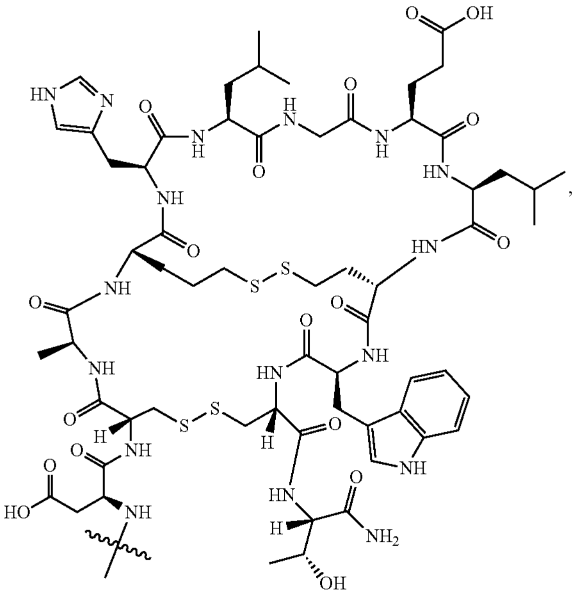

-continued
(A-26)
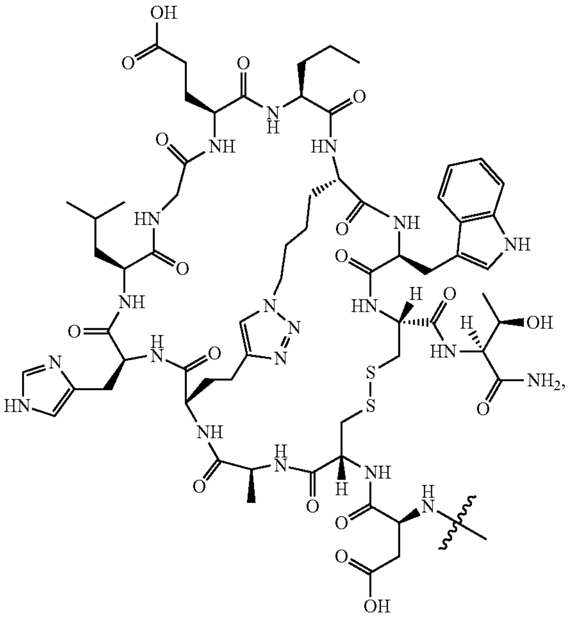
(A-27)
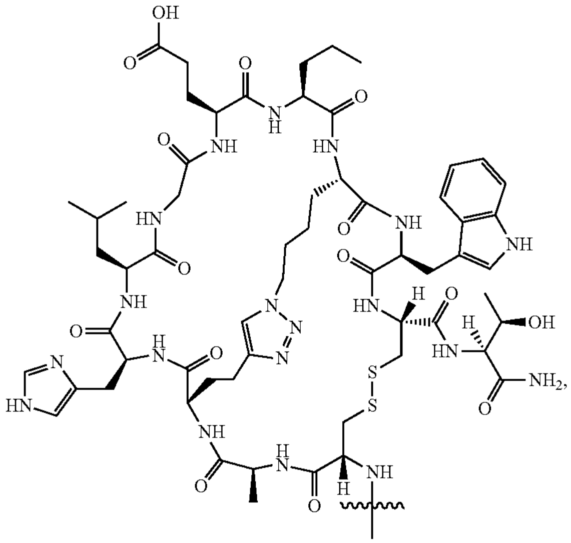
(A-28)
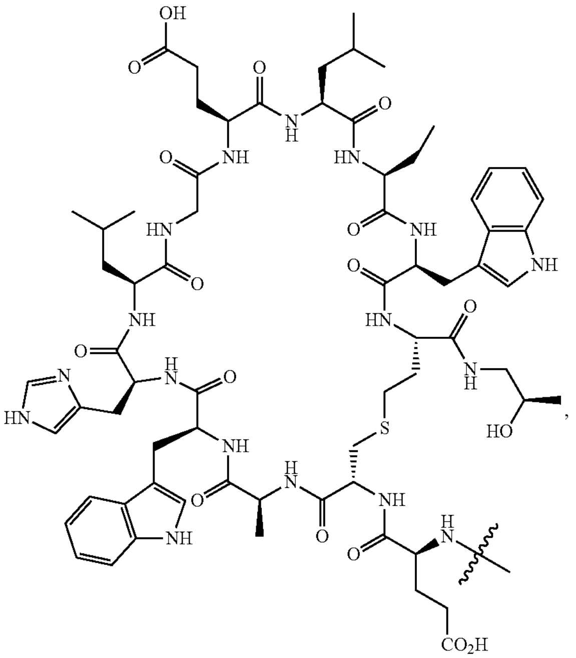

(A-25)
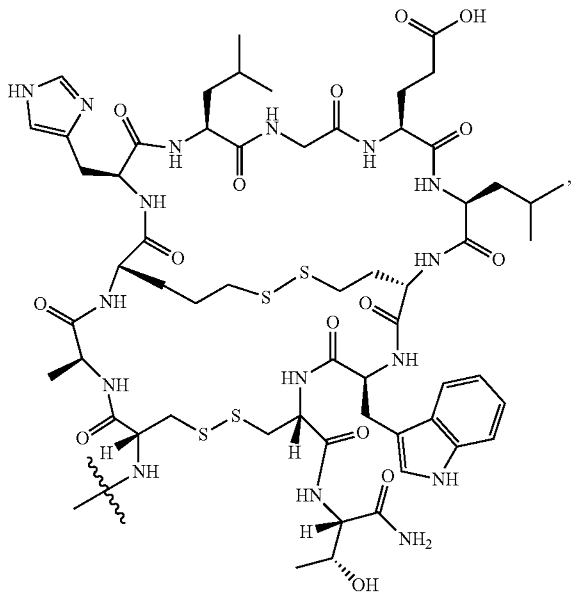
-continued
(A-27)
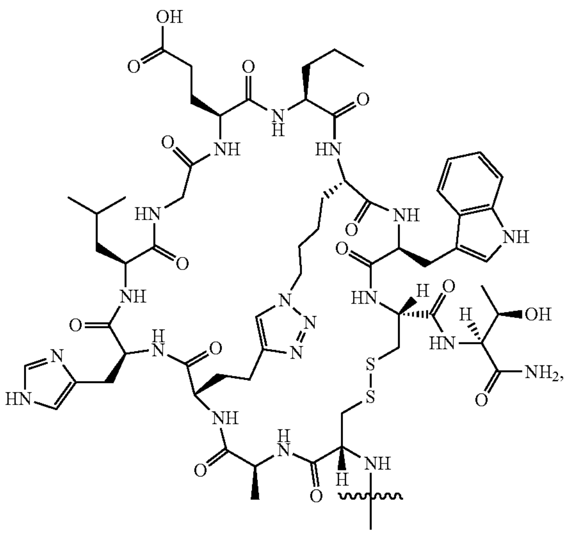
(A-26)
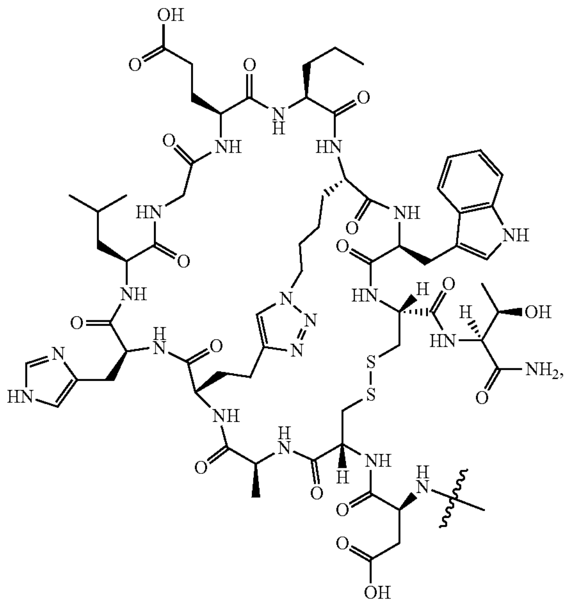
(A-28)
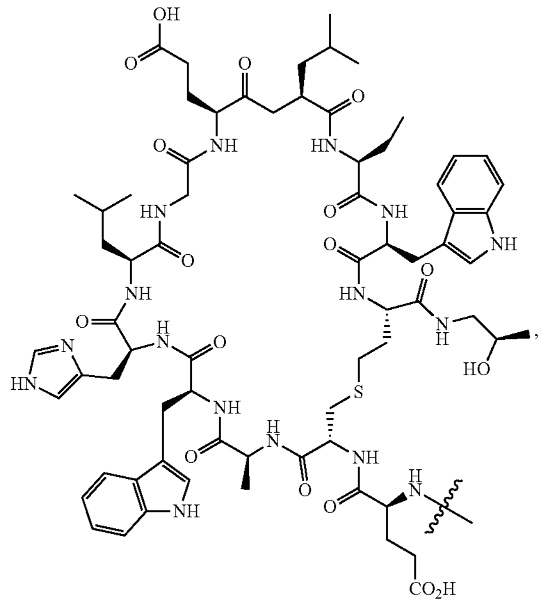

(A-29)
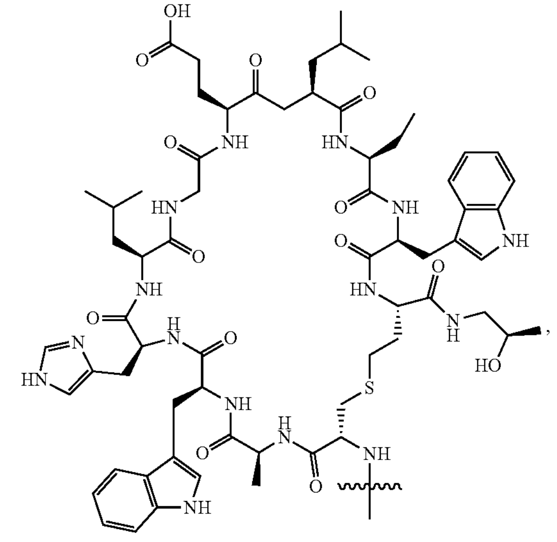
(A-30)
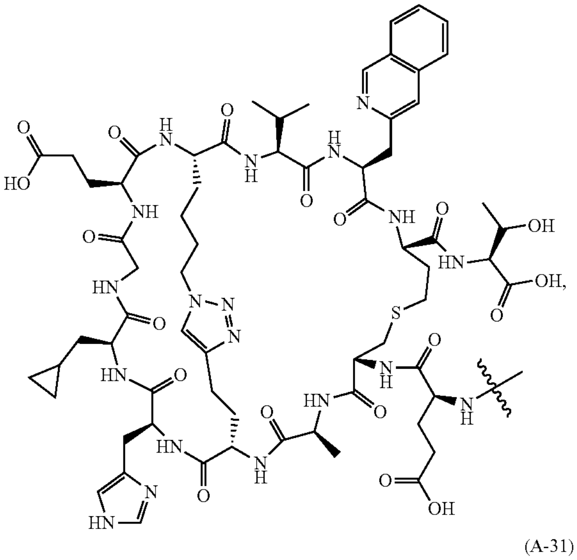
(A-31)
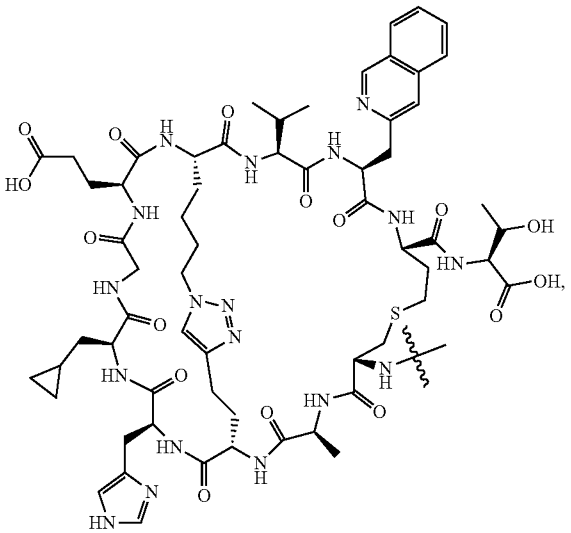
(A-32)
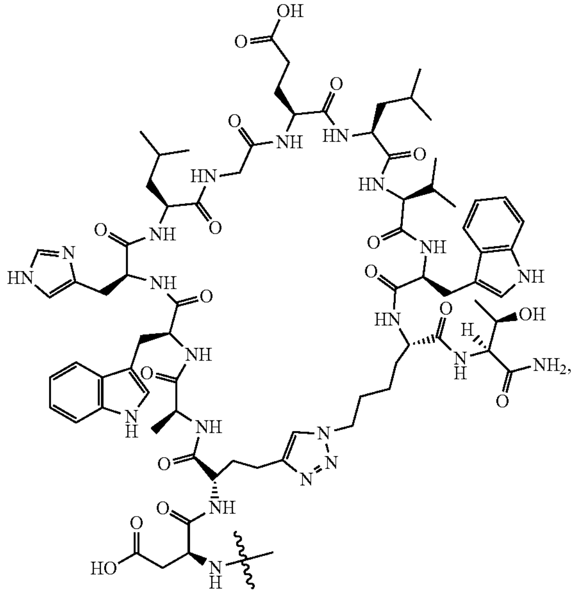
(A-33)
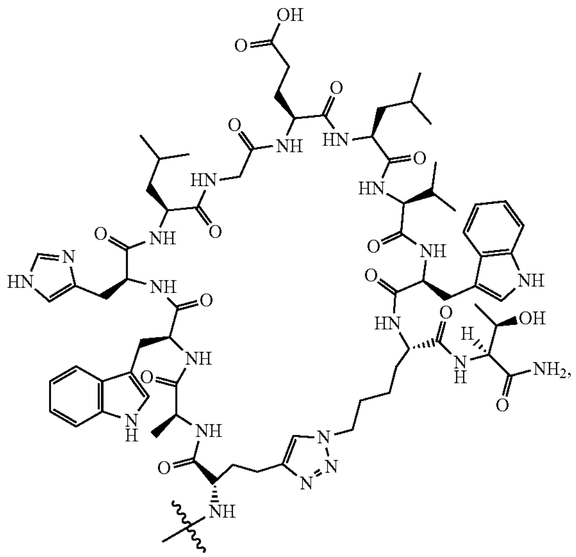

-continued
(A-34)
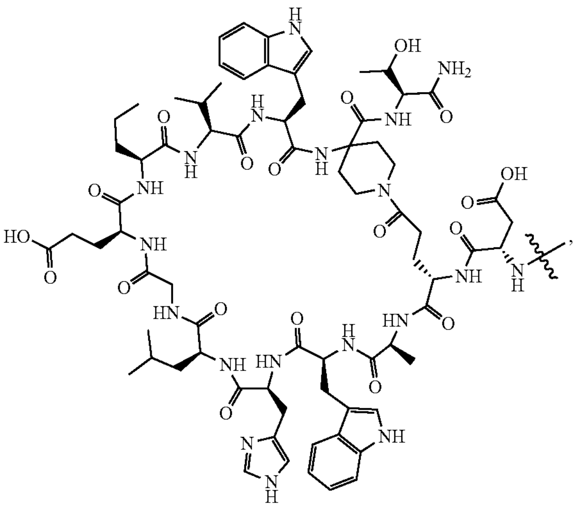
(A-35)
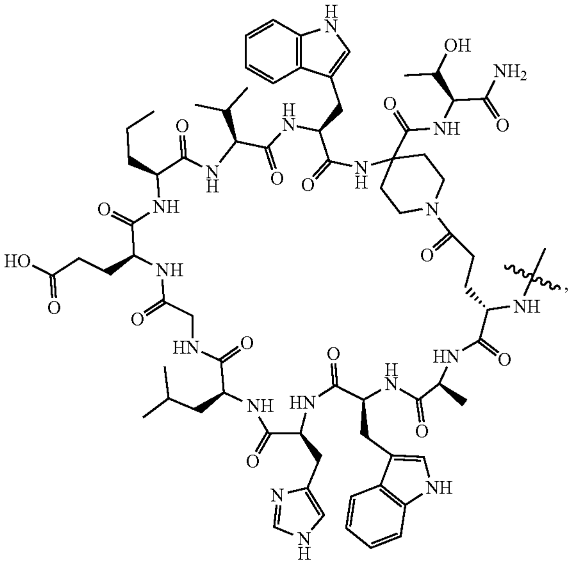
-continued
(A-36)
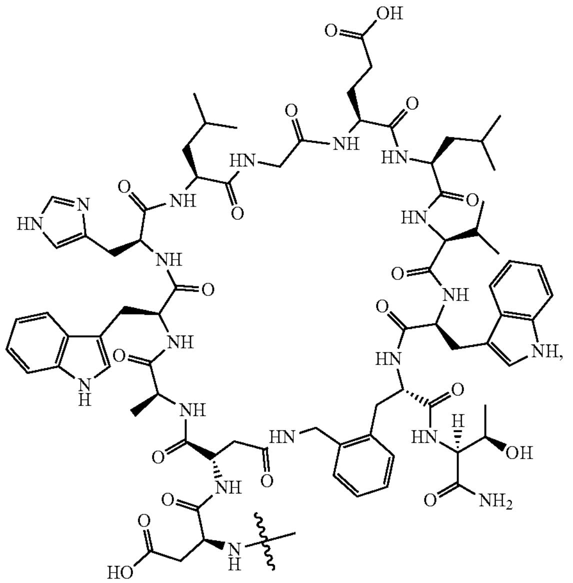
(A-37)
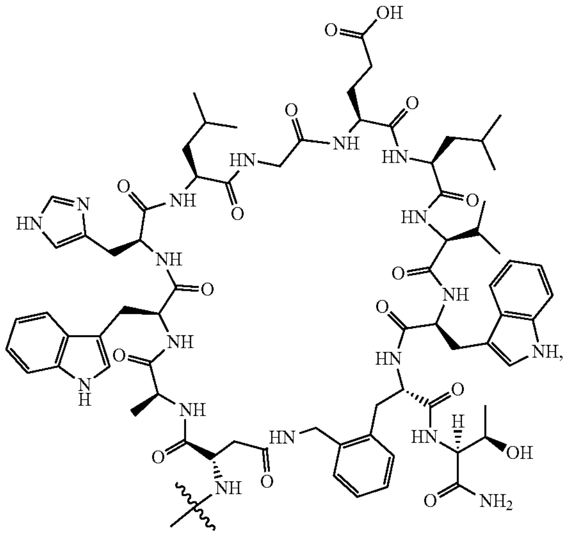

-continued
(A-38)
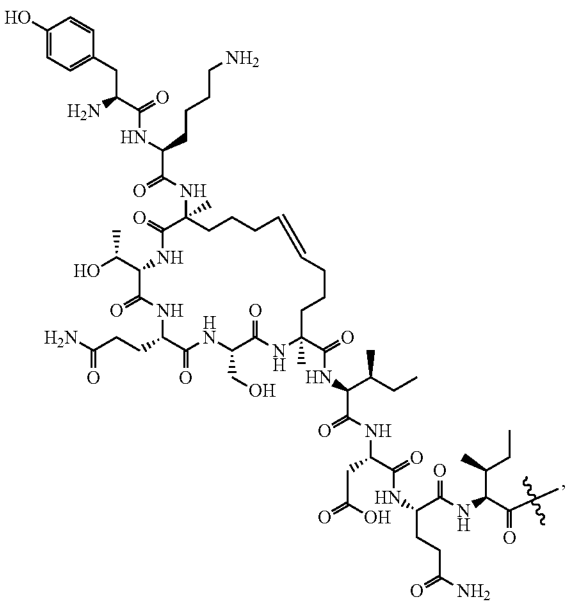
(A-39)
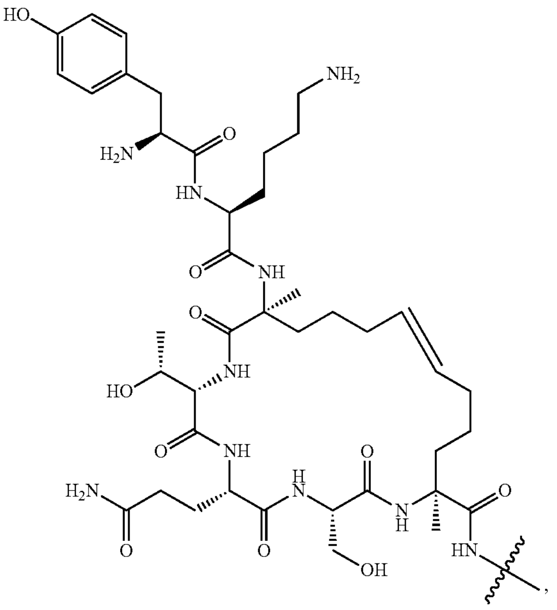
-continued
(A-40)
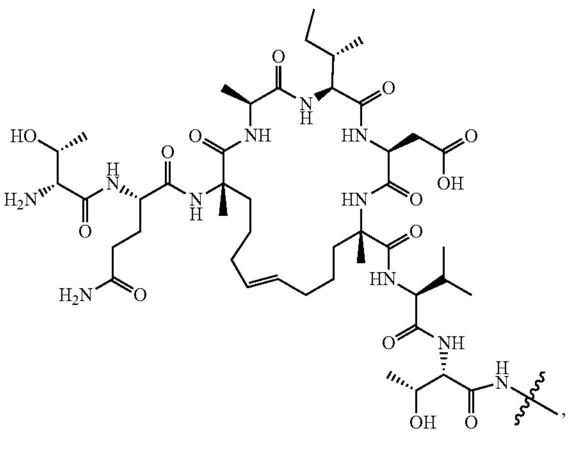
(A-41)
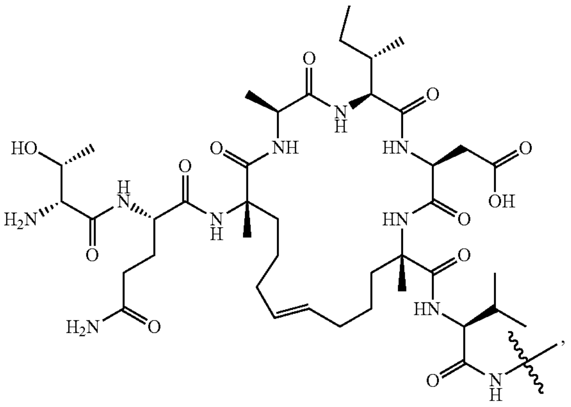
(A-42)
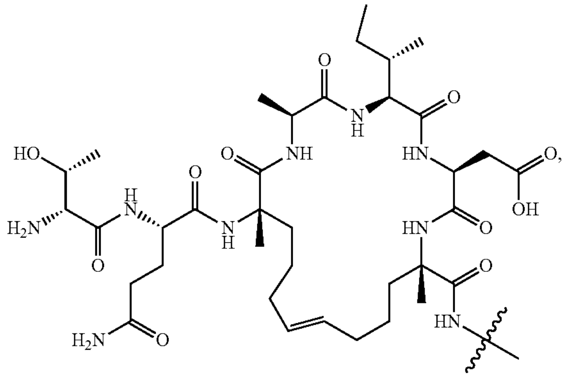

-continued
(A-43)
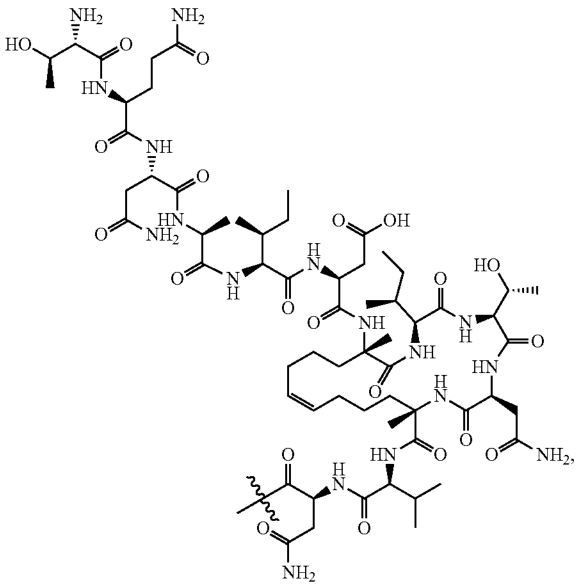
(A-44)
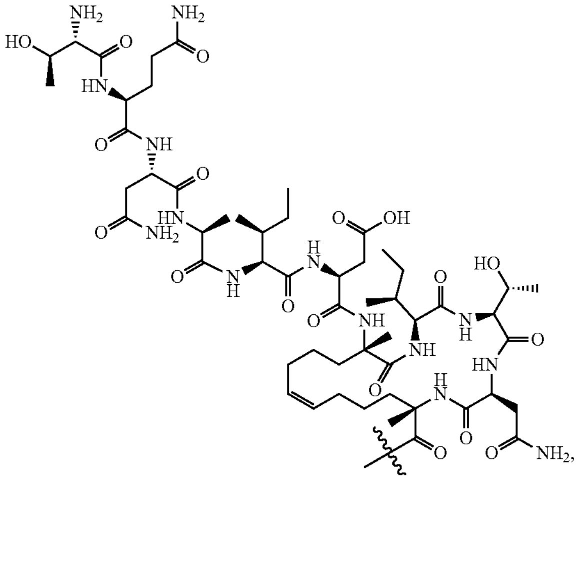
-continued
(A-45)
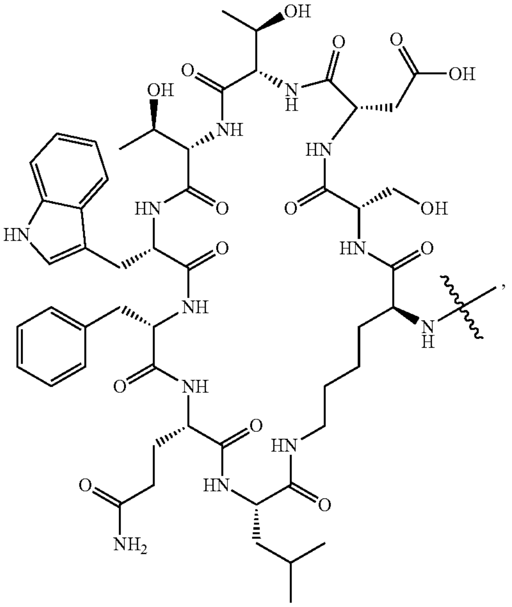
(A-46)
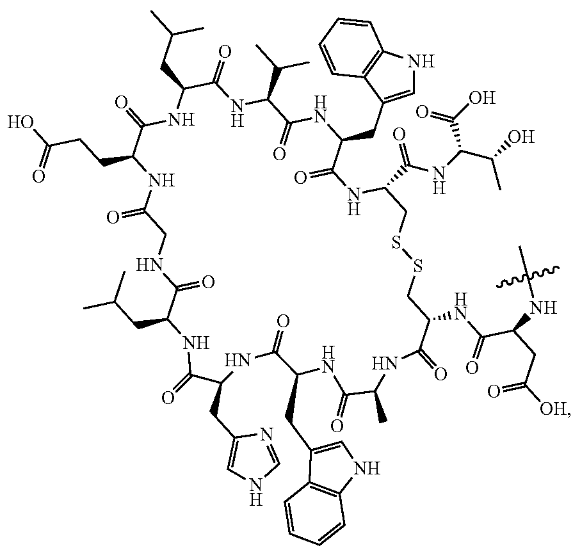

-continued (A-47)

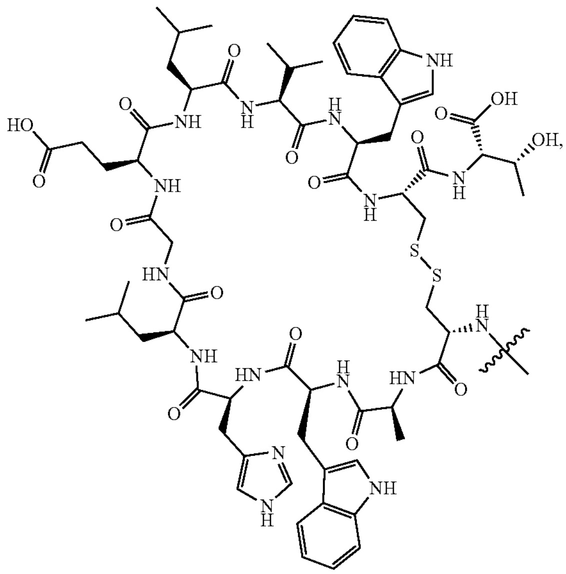

(A-48)

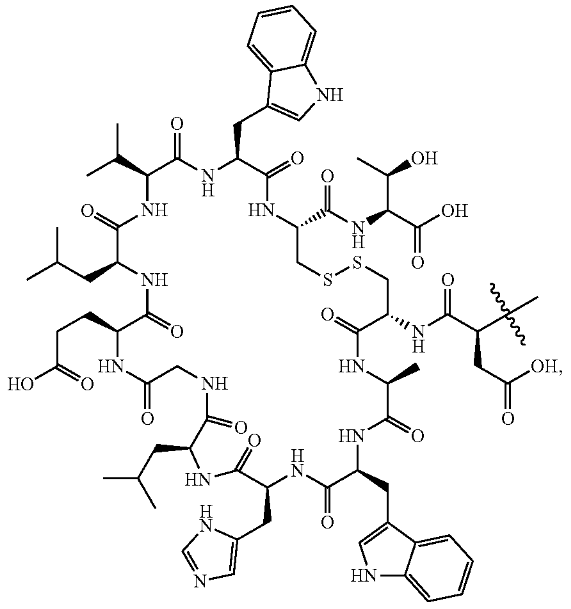

(A-49)

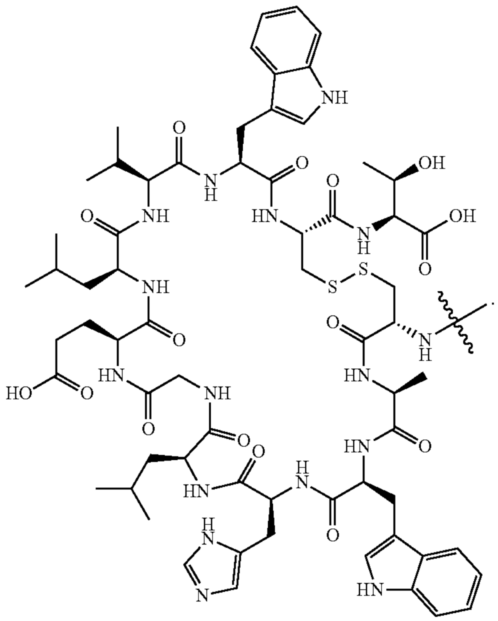

15. The compound of claim 1, wherein the therapeutic agent is a maytansinoid agent, an auristatin agent, or a transcription inhibitor agent.

16. The compound of claim 1, wherein the anti-cancer agent is selected from deoxyribonucleic acid (DNA) injuring agents, antimetabolites, enzyme inhibitors, DNA intercalating agents, DNA cleaving agents, topoisomerase inhibitors, DNA binding inhibitors, tubulin binding inhibitors, cytotoxic nucleosides, platinum compounds, bacteriotoxins, and phytotoxins.

17. The compound of claim 1, wherein the moiety of interest is exatecan or a derivative thereof, a calicheamicin agent, a duocarmycin agent, an amatoxin agent, monomethyl auristatin-E, or monomethyl auristatin-F.

18. The compound of claim 1, wherein the compound has the chemical structure:

(I-21)
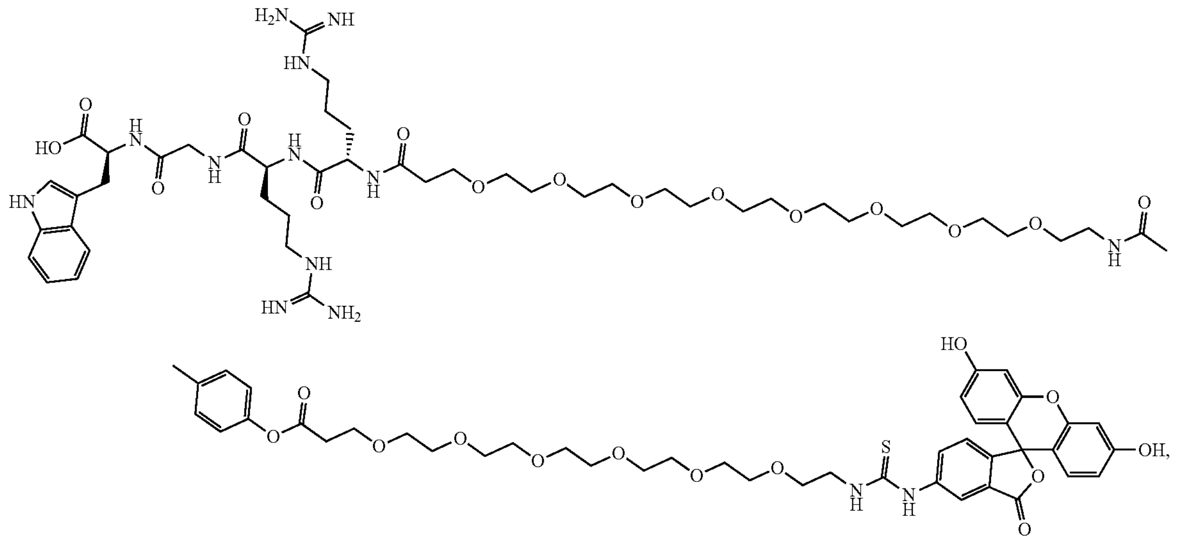
(I-22)
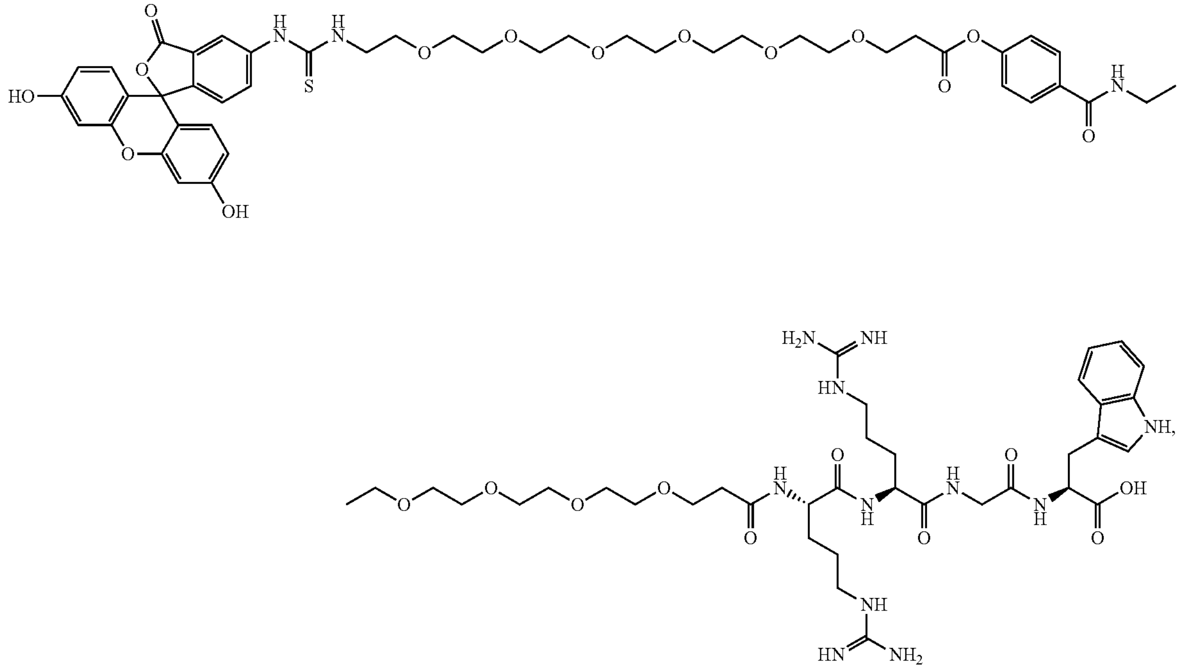
(I-23)
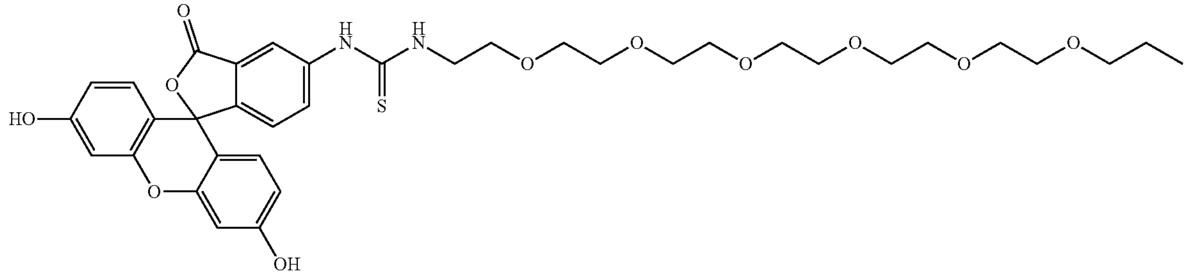

-continued
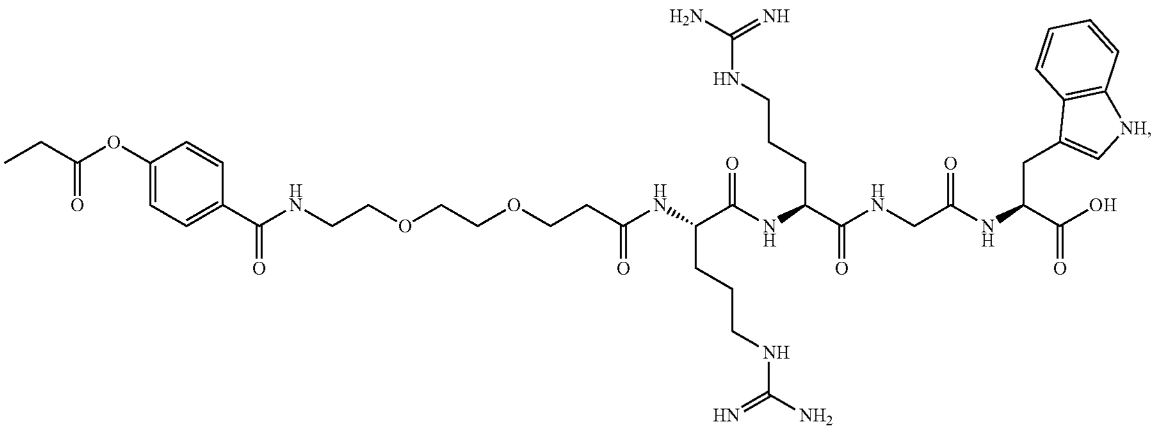
(I-24)
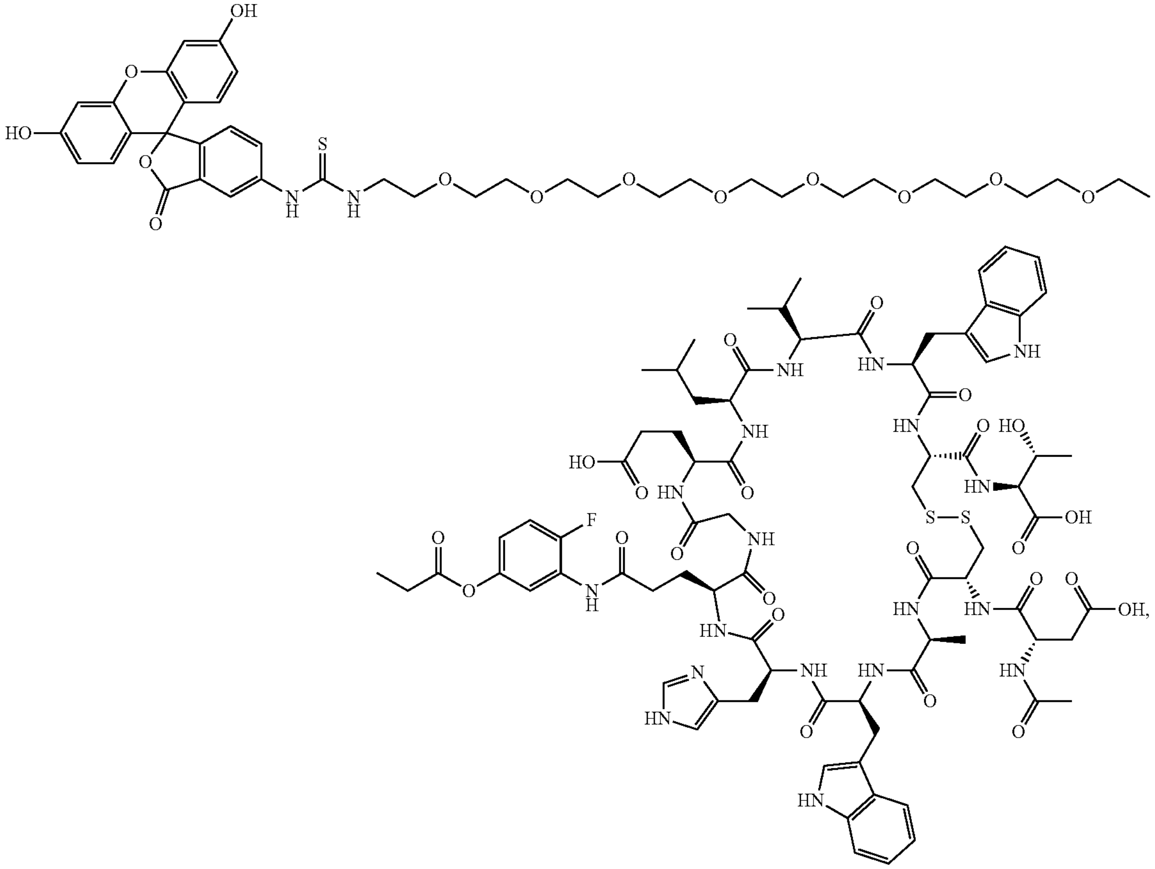
(I-25)
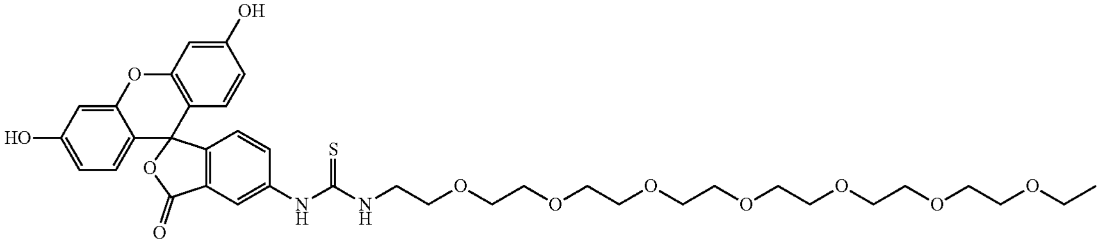

-continued
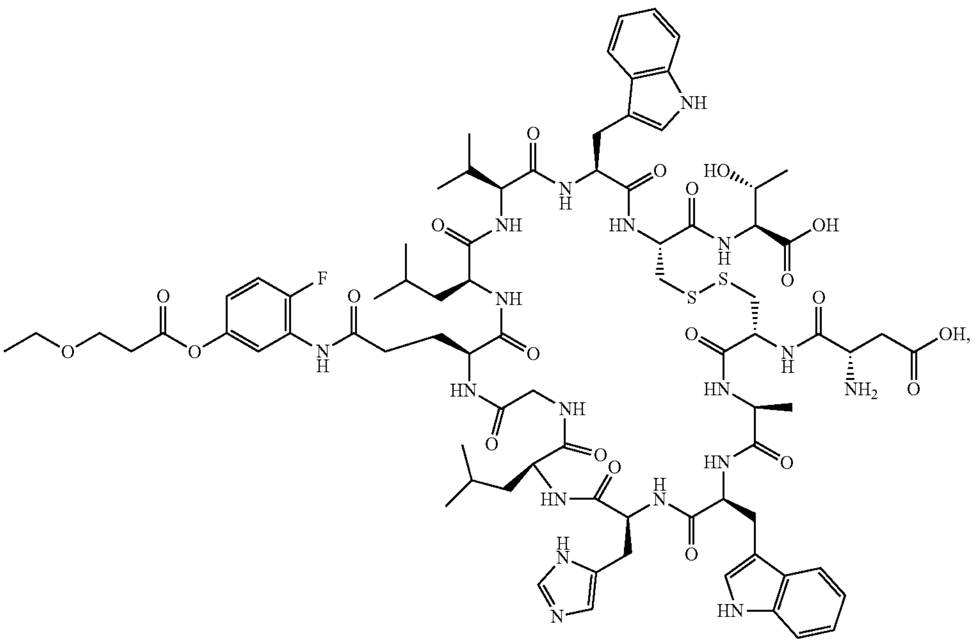
(I-28)
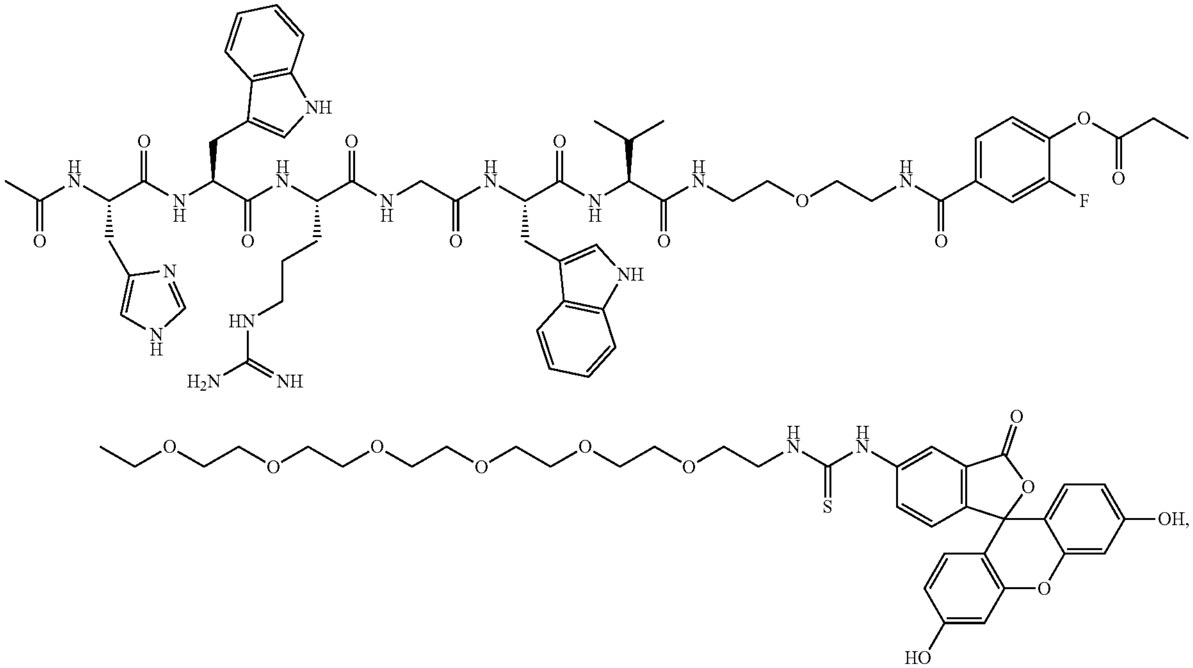
(I-29)
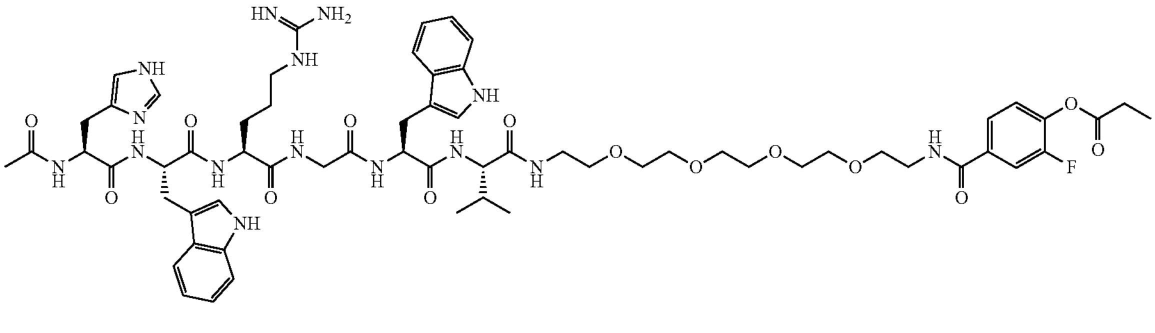

-continued
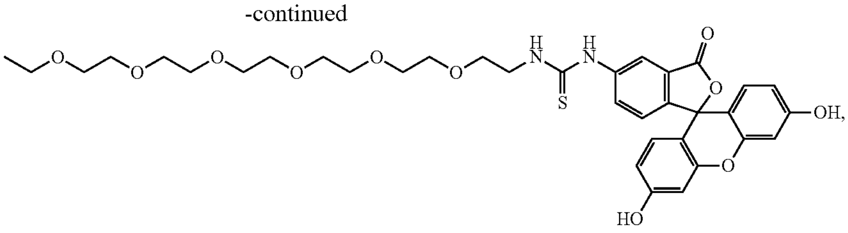
(I-30)
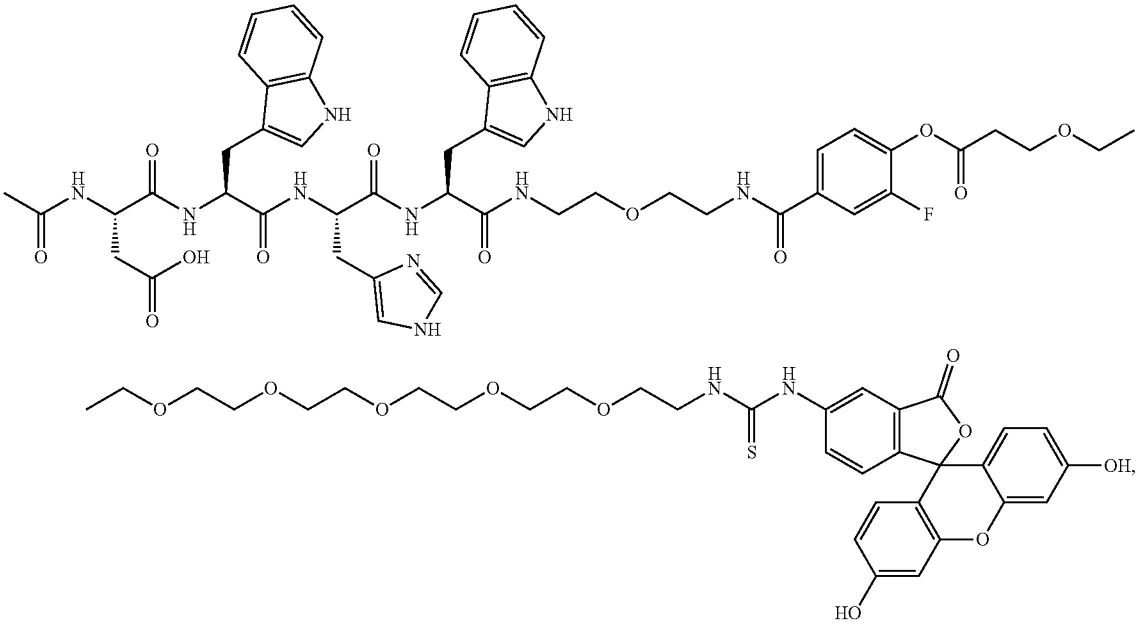
(I-31)
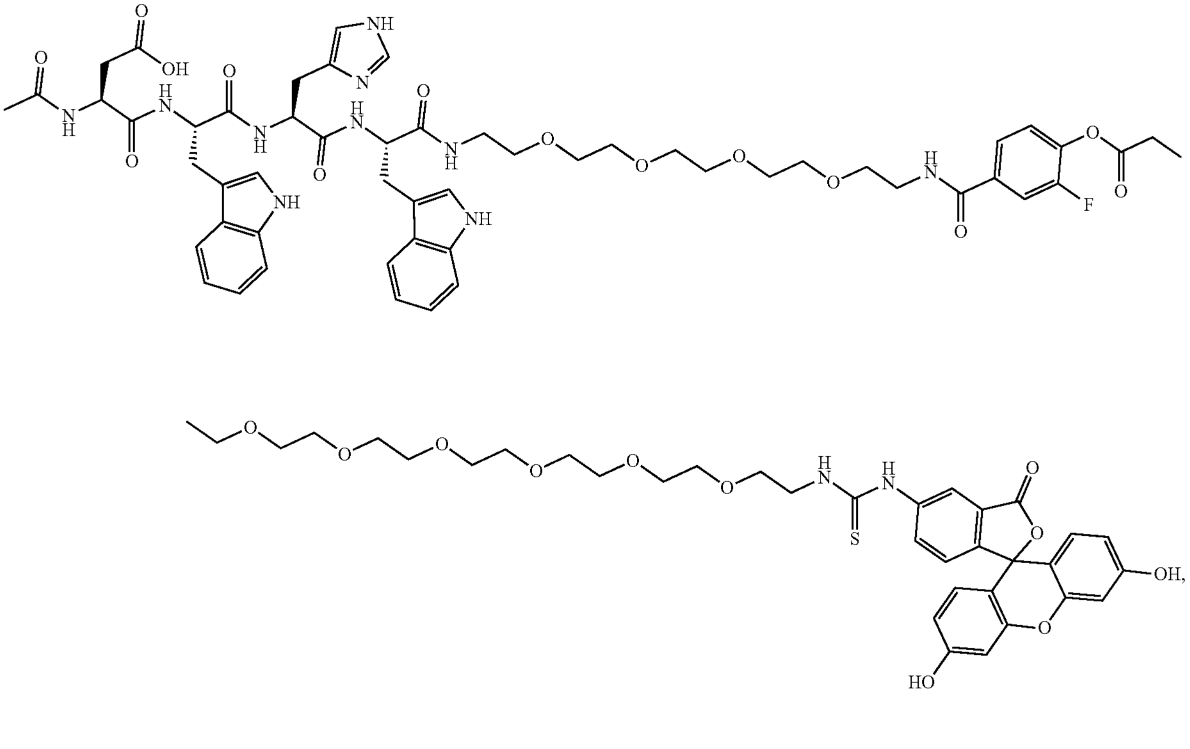

-continued
(I-32)
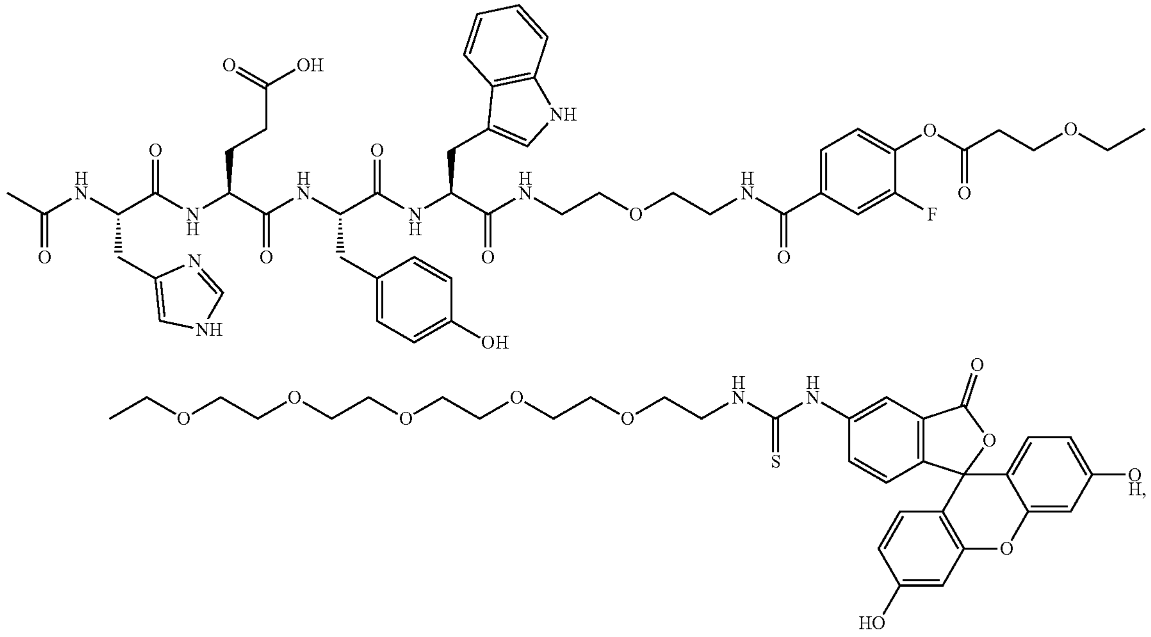
(I-33)
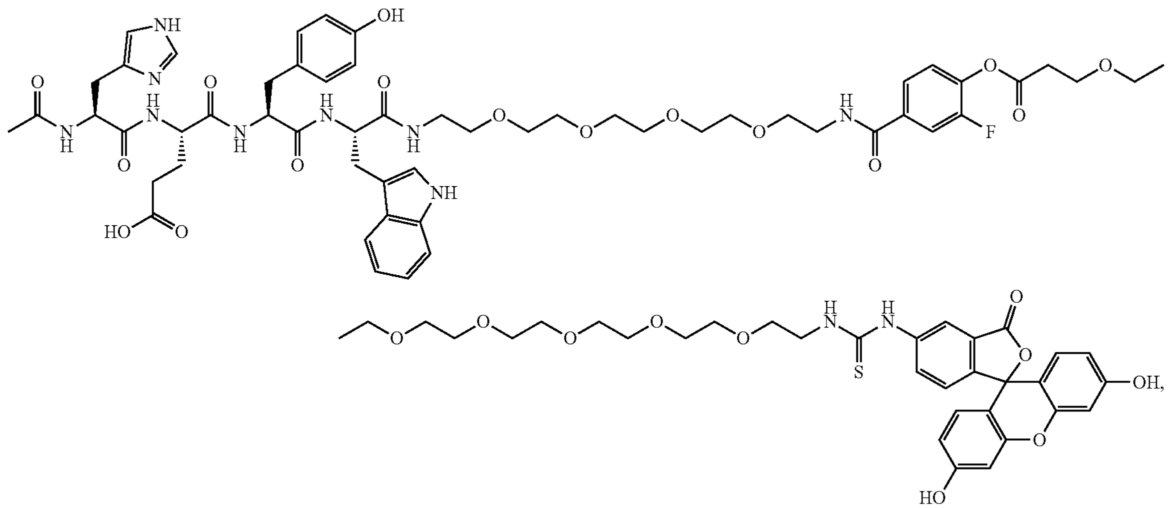
(I-34)
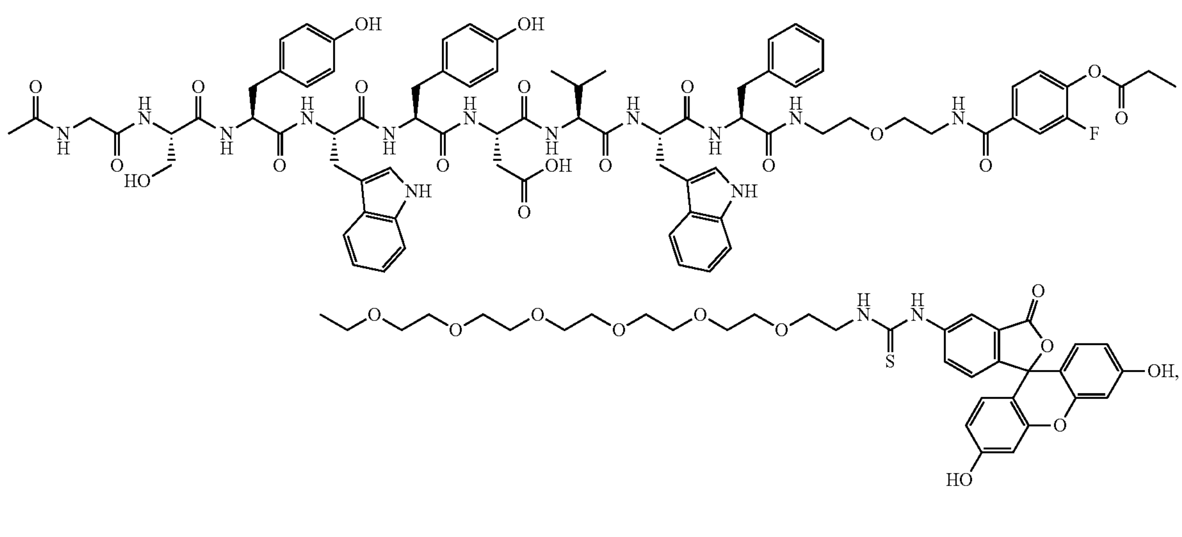

-continued
(I-35)
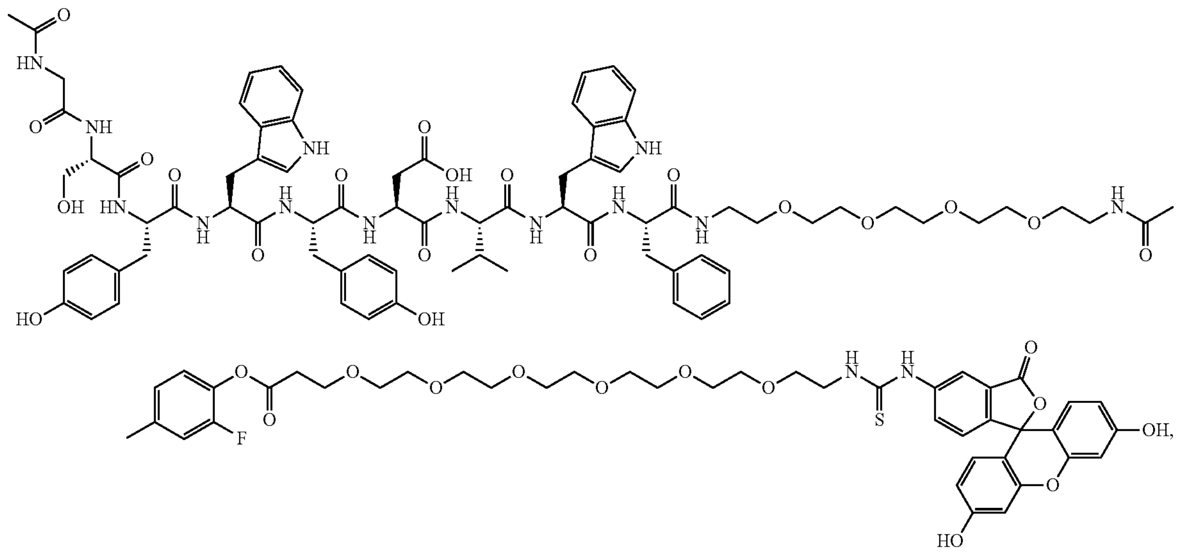
(I-36)
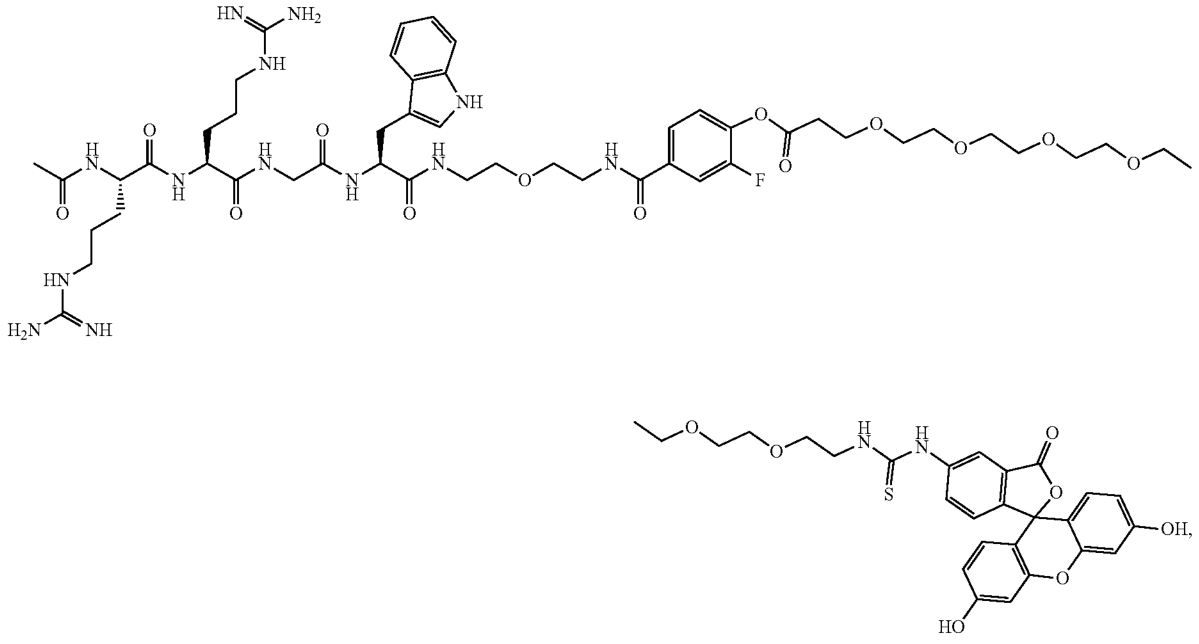
(I-37)
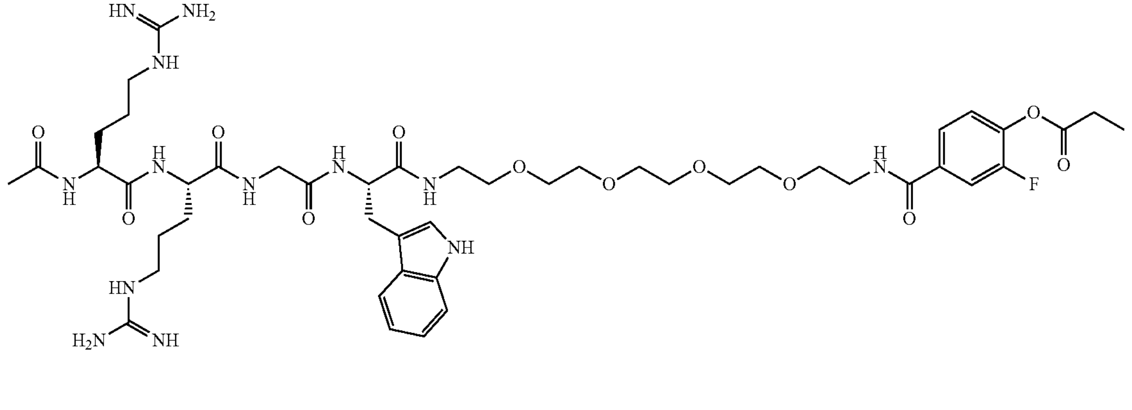

-continued
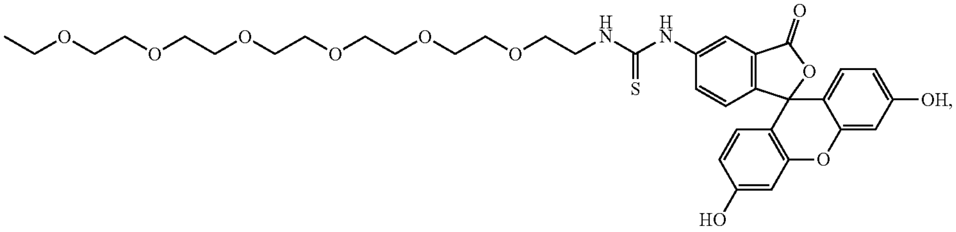
(I-38)
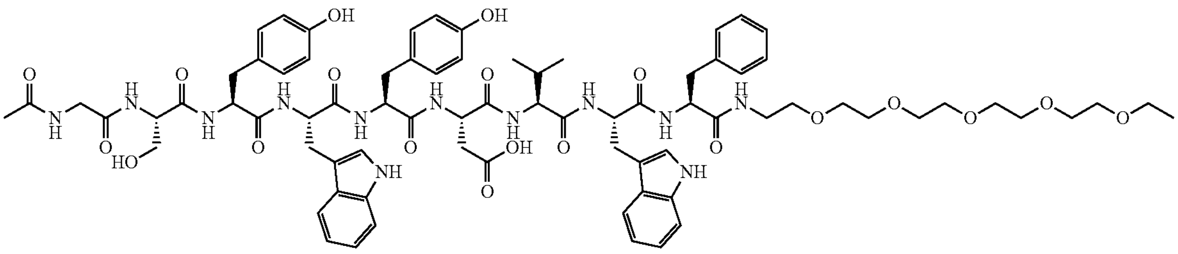
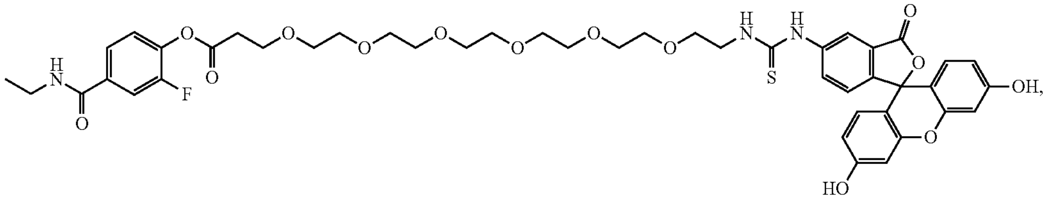
(I-39)
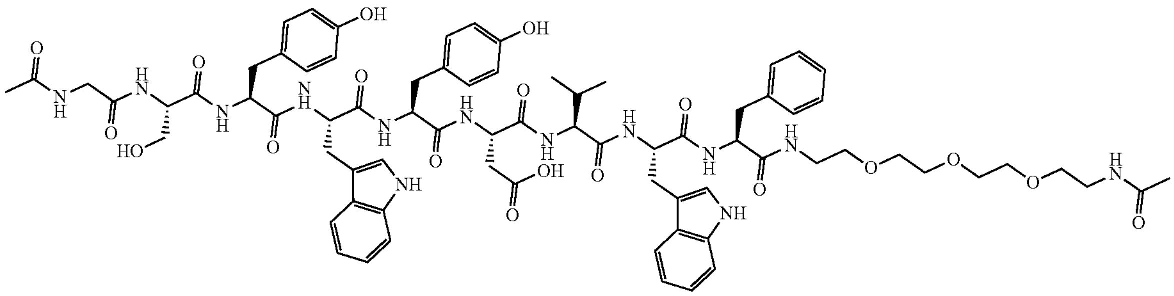
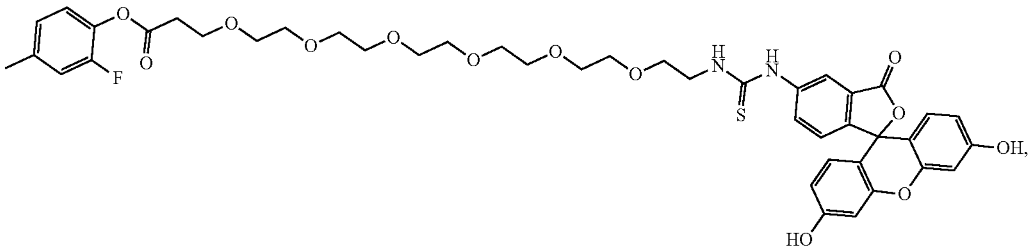
(I-40)
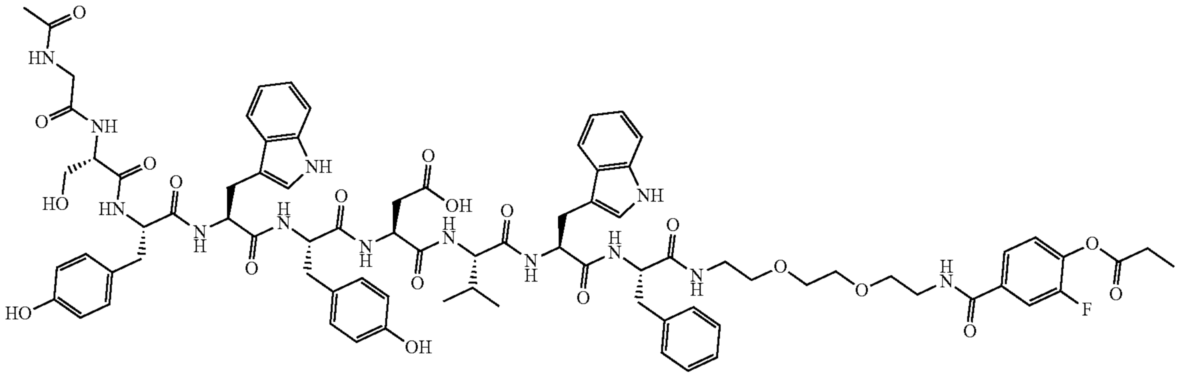

-continued
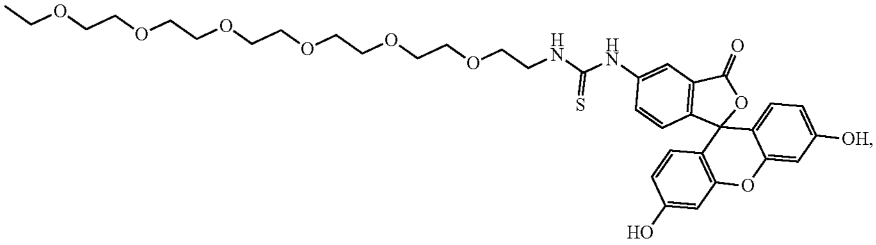
,
(I-41)
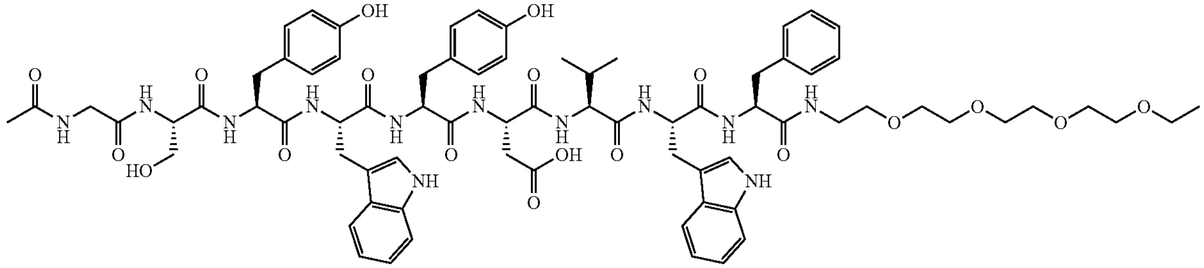
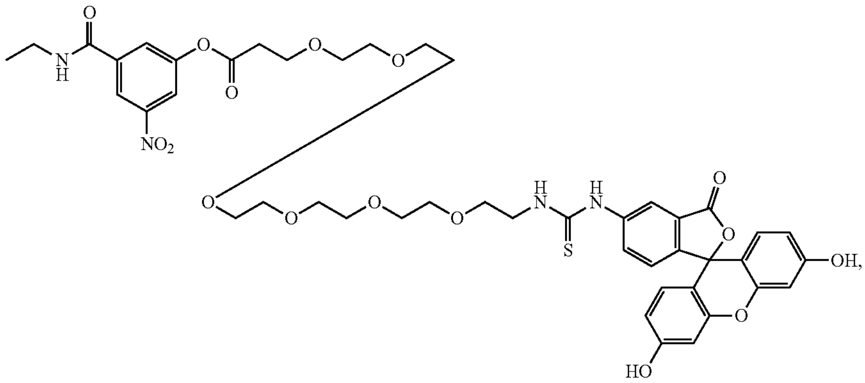
,
(I-42)
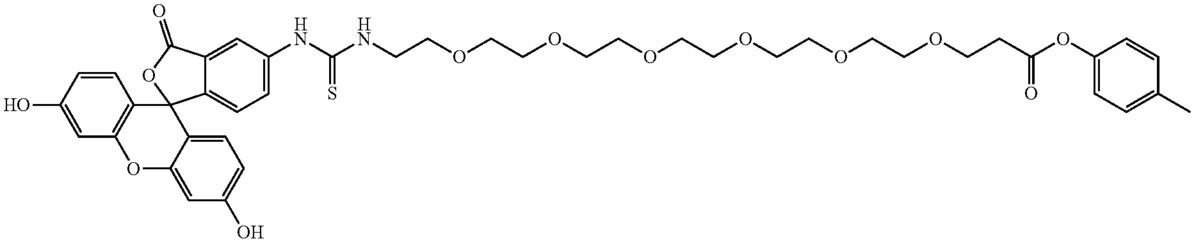

-continued
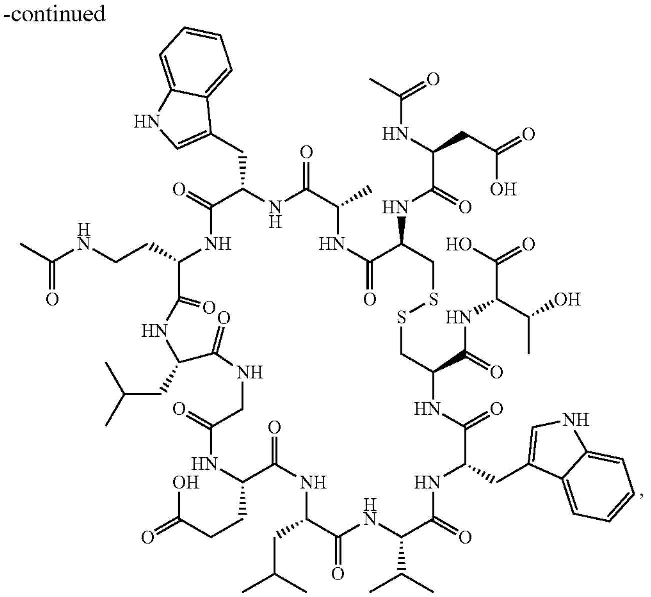
(I-43)
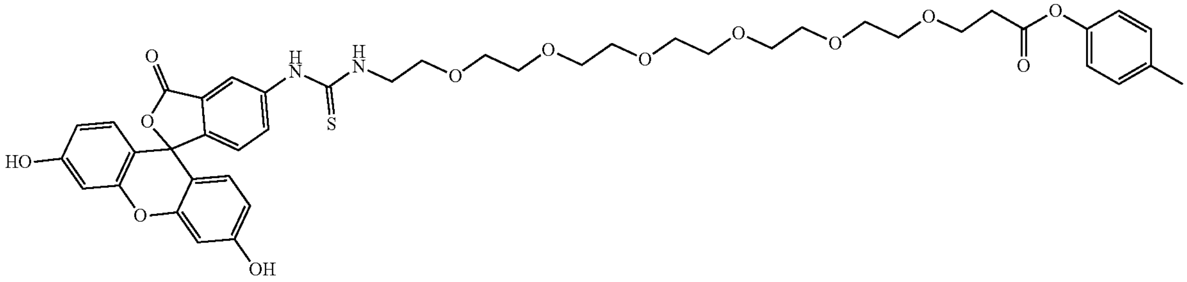
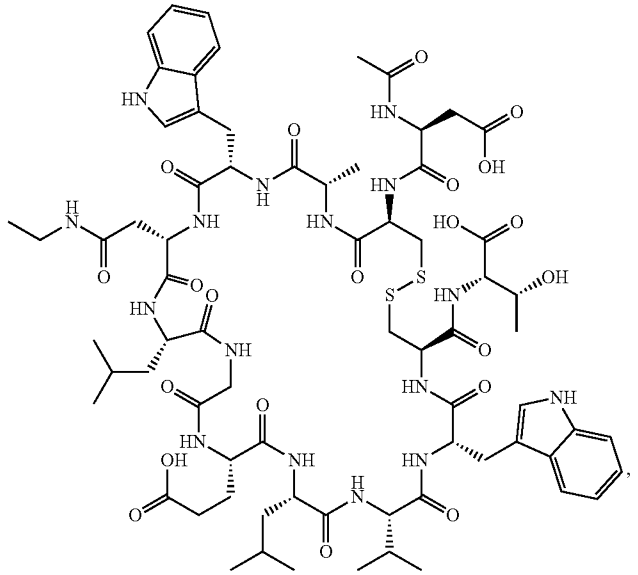
(I-44)
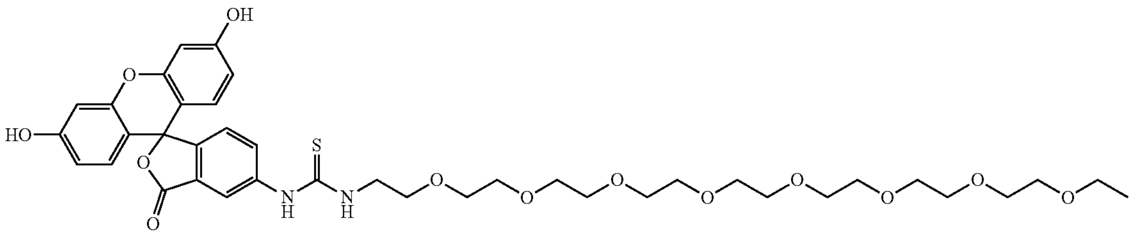

-continued
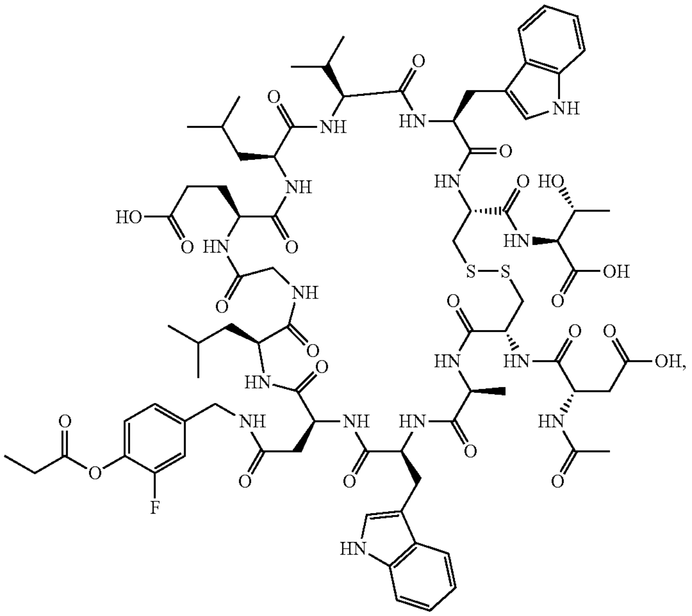
(I-45)
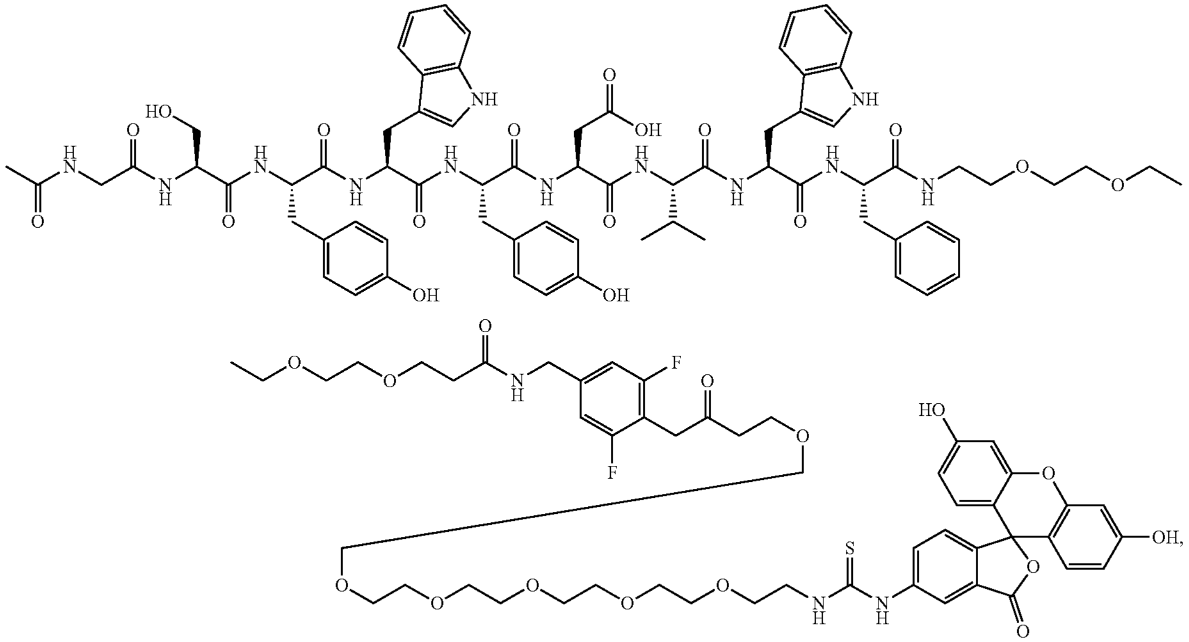
(I-46)
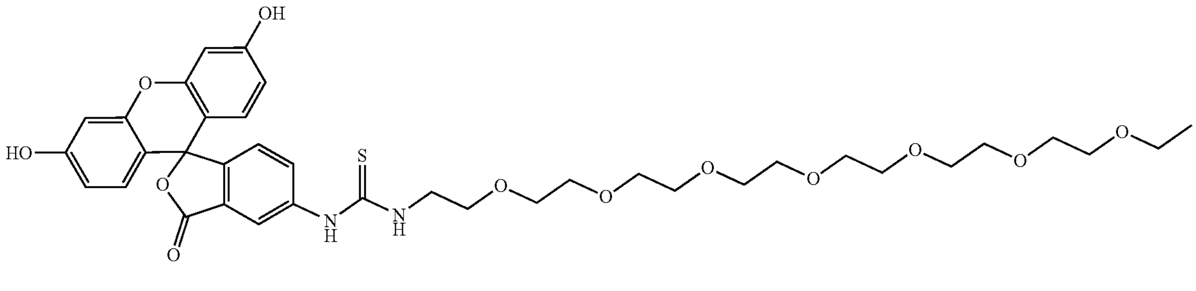

-continued
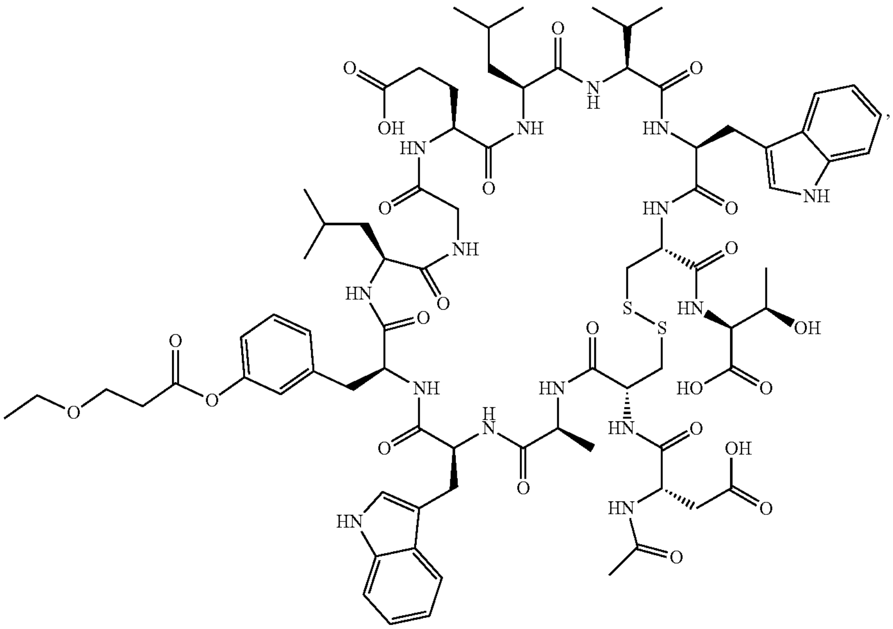
,
(I-47)
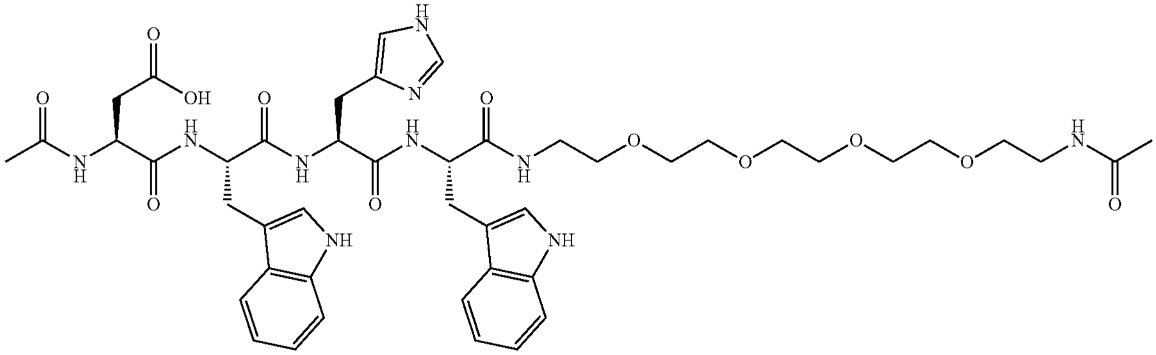
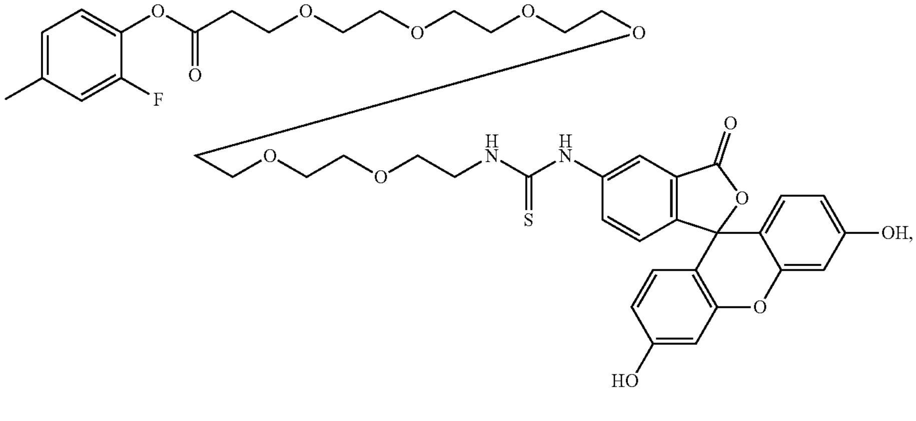
OH,

-continued
(I-49)
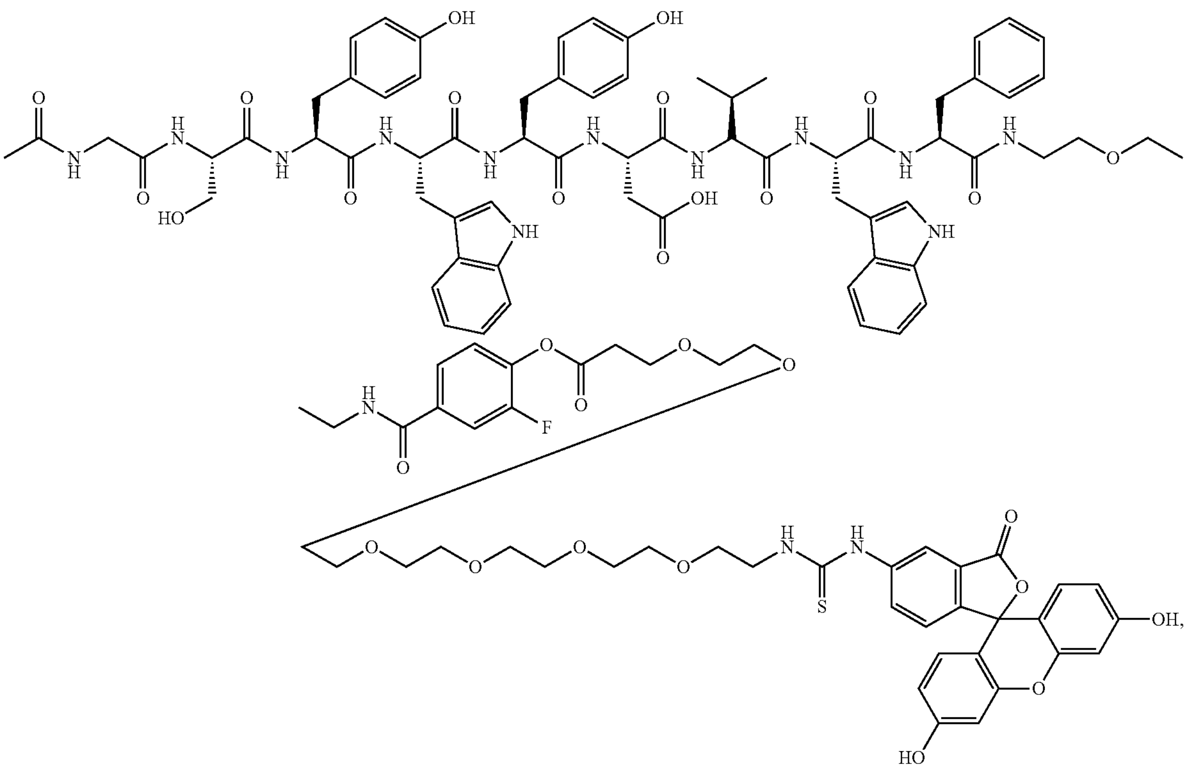
(I-50)
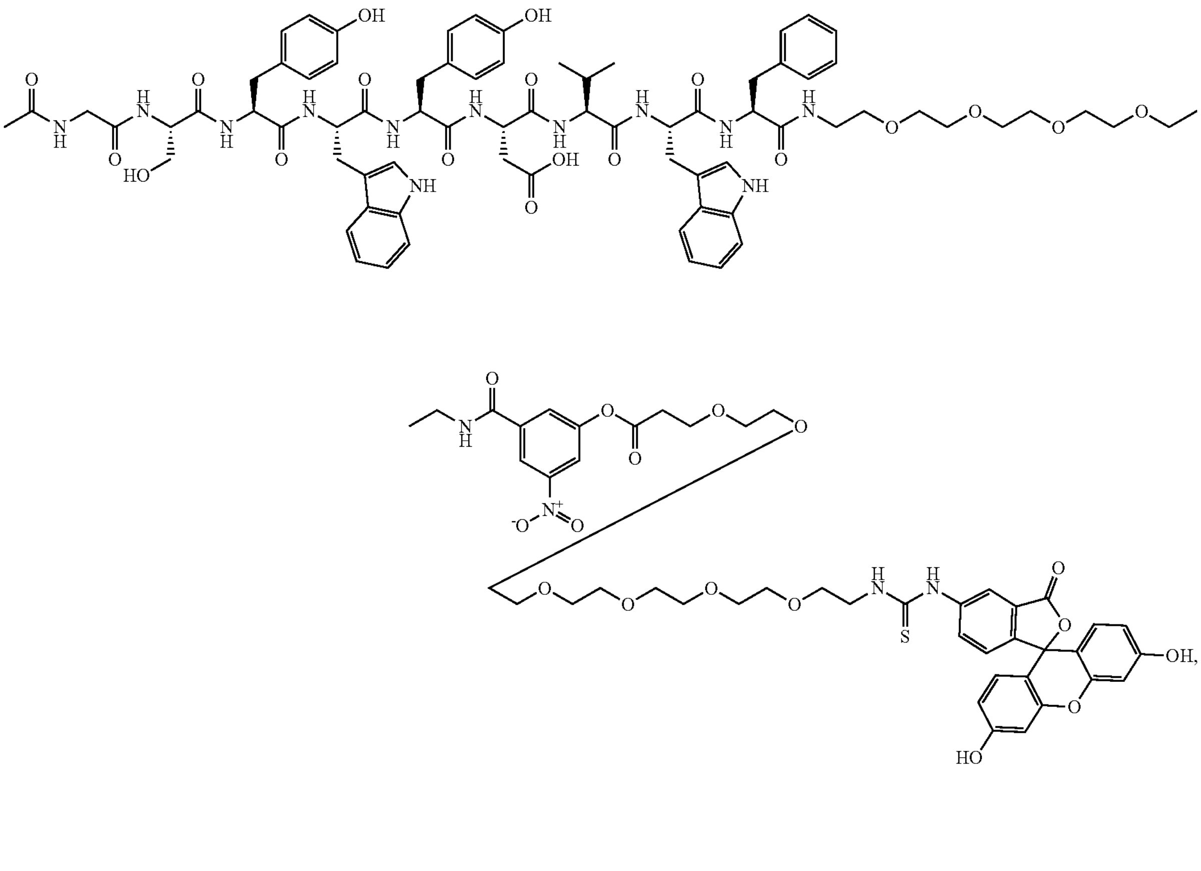

-continued
(I-54)
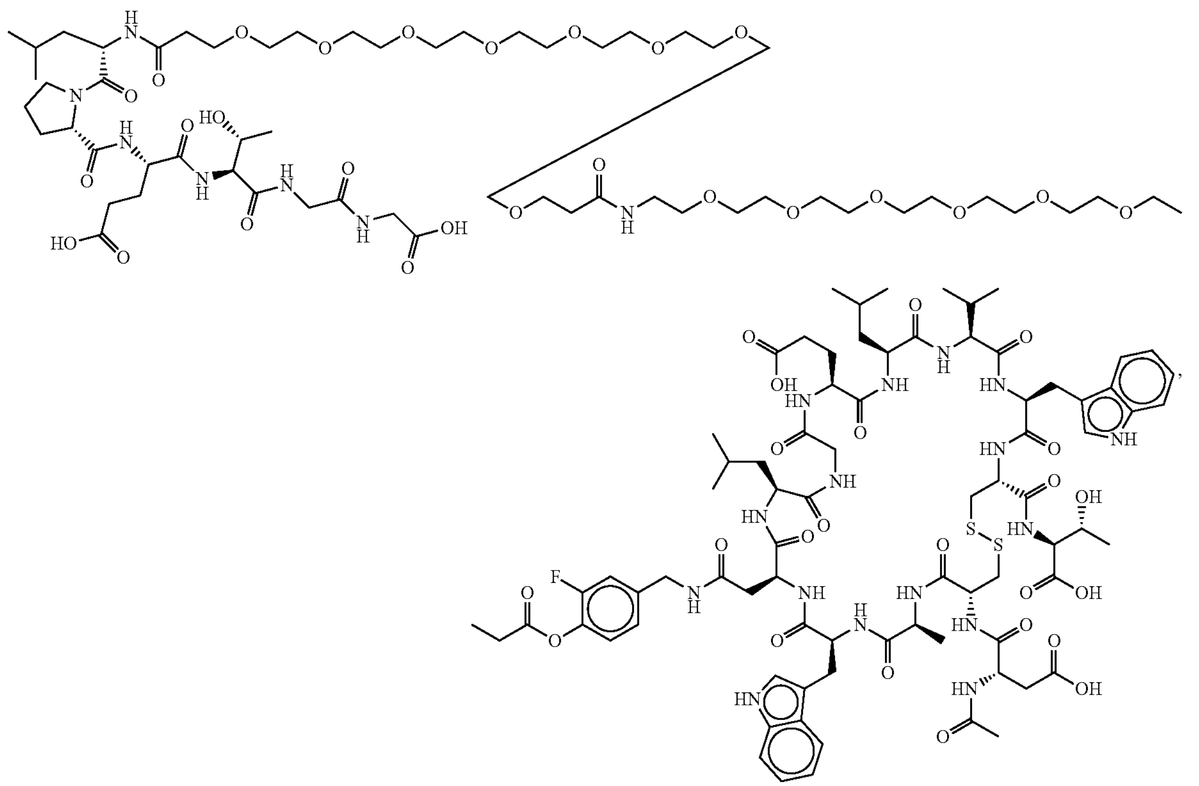
(I-56)
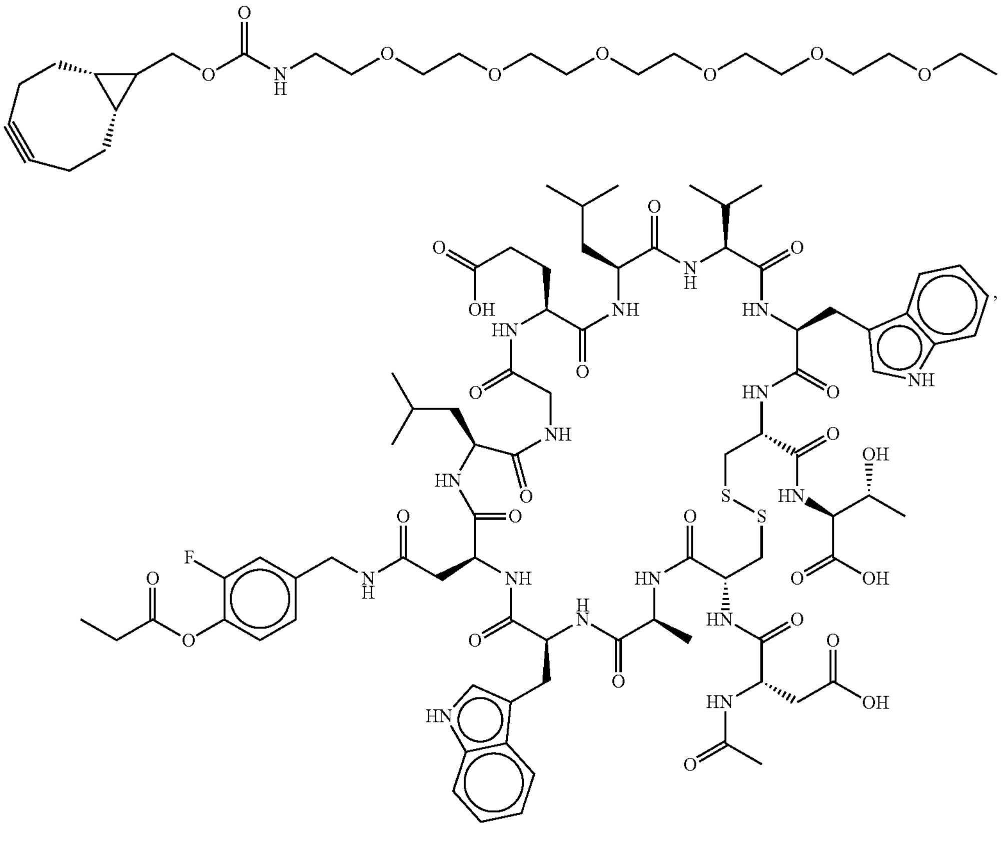

-continued
(I-59)
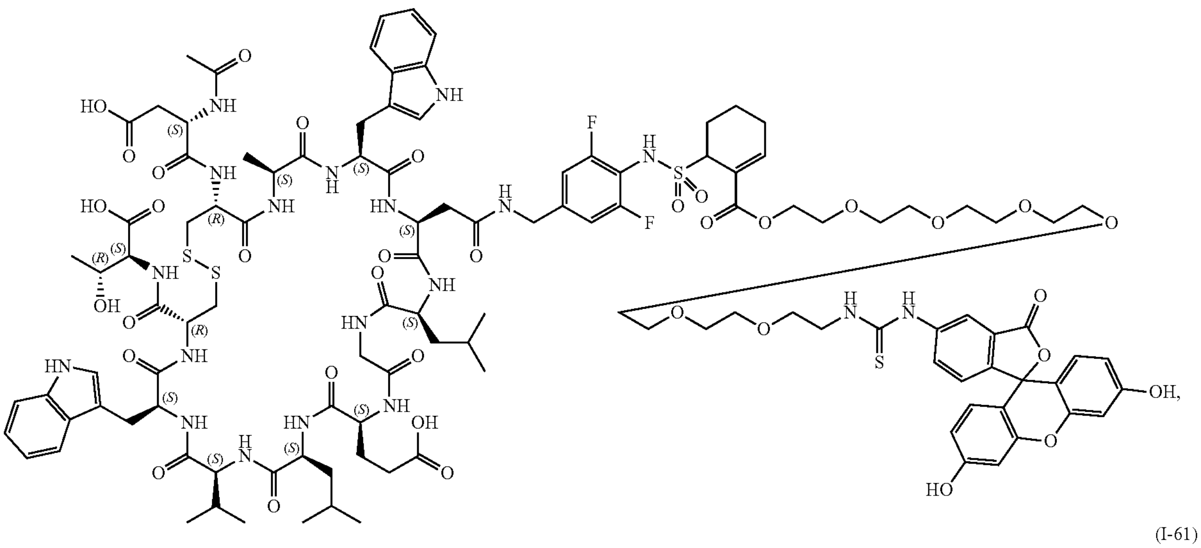
(I-61)
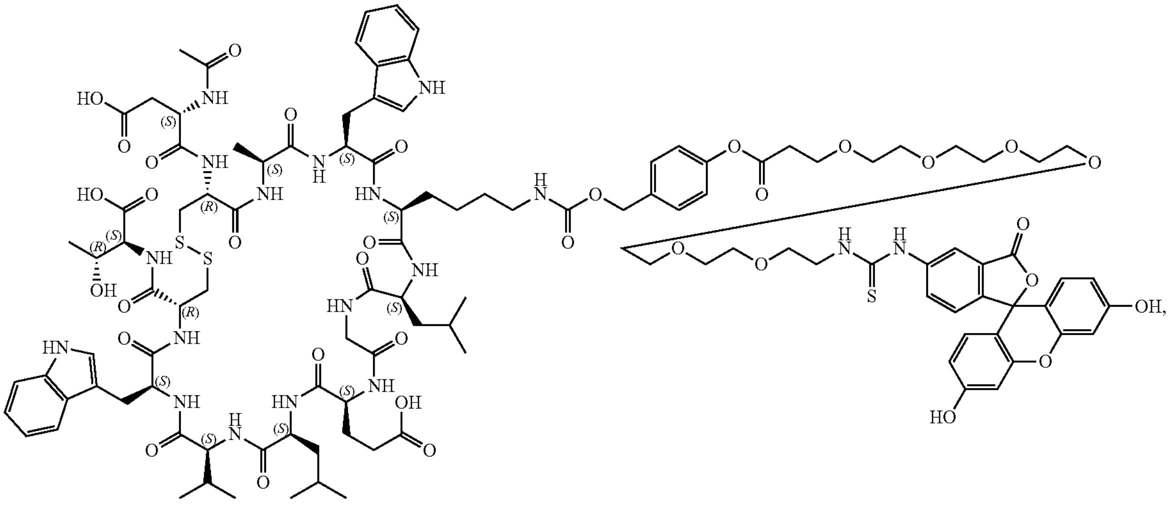
or
(I-63)
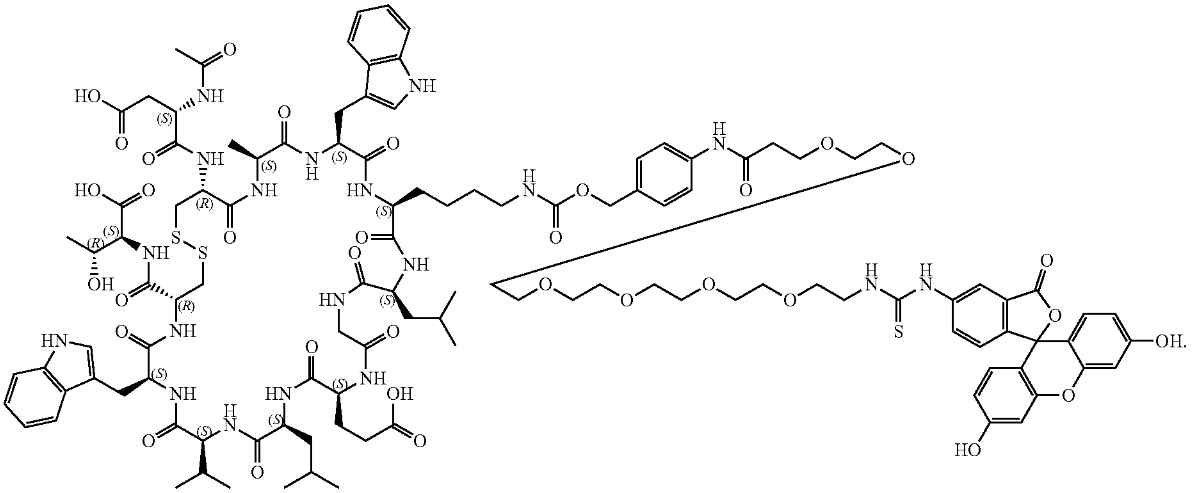
19. The compound of claim 1, wherein the compound has the chemical structure:

(I-45)
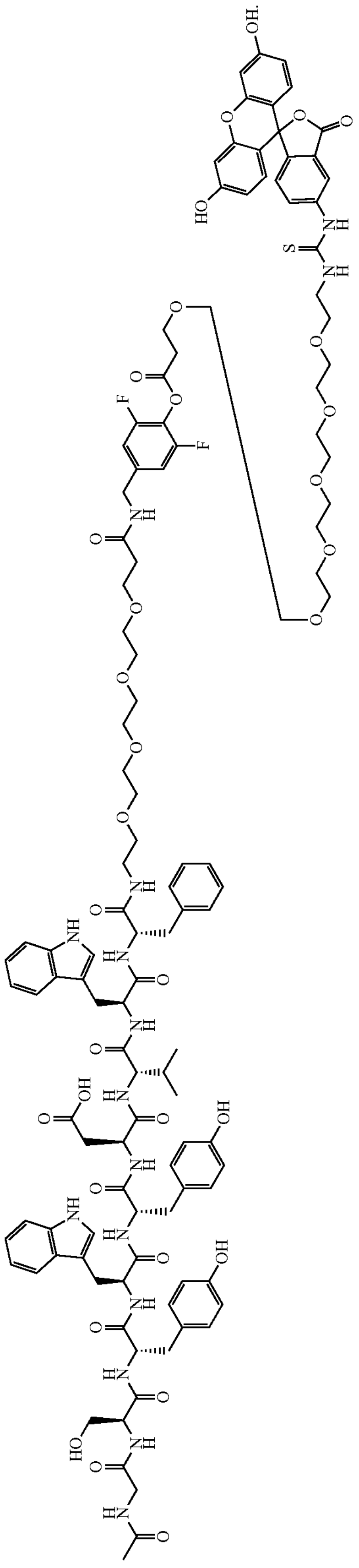

20. A method of preparing an agent having the structure of P-II:

$$P—N—L^{PM}—MOI, \quad (P\text{-}II)$$

wherein:

P—N is a protein agent comprising a lysine residue, wherein the protein agent is an antibody agent selected from IVIG, IgG1, IgG2, IgG3, IgG4, a monoclonal antibody agent, a polyclonal antibody agent, and an antibody fragment, wherein a conjugation location on the antibody agent is K246 or K248 of the heavy chain of the antibody agent;

$L^{PM}$ is a linker; and

MOI is a moiety of interest, the method comprising:

contacting the protein agent with a reaction partner having the chemical structure of the compound of claim 1 or a salt thereof; and forming an agent having the structure of formula (P-II).

* * * * *

SEQUENCE LISTING

```
<160> NUMBER OF SEQ ID NOS: 85

<210> SEQ ID NO 1
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Lys Leu Ser Cys Ala Ala Ser Gly Phe Thr
        35                  40                  45

Phe Asn Thr Tyr Ala Met Asn Trp Val Arg Gln Ala Pro Gly Lys Gly
    50                  55                  60

Leu Glu Trp Val Gly Arg Ile Arg Ser Lys Tyr Asn Asn Tyr Ala Thr
65                  70                  75                  80

Tyr Tyr Ala Asp Ser Val Lys Gly Arg Phe Thr Ile Ser Arg Asp Asp
                85                  90                  95

Ser Lys Asn Thr Leu Tyr Leu Gln Met Asn Ser Leu Arg Ala Glu Asp
            100                 105                 110

Thr Ala Val Tyr Tyr Cys Val Arg His Gly Asn Phe Gly Asn Ser Tyr
        115                 120                 125

Val Ser Trp Phe Ala Tyr Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Gln Ala Val Val Thr Gln Glu Pro Ser Leu Thr Val Ser Pro Gly Gly
                165                 170                 175

Thr Val Thr Leu Thr Cys Gly Ser Ser Thr Gly Ala Val Thr Thr Ser
            180                 185                 190

Asn Tyr Ala Asn Trp Val Gln Gln Lys Pro Gly Gln Ala Pro Arg Gly
        195                 200                 205

Leu Ile Gly Gly Thr Asn Lys Arg Ala Pro Gly Val Pro Ala Arg Phe
    210                 215                 220

Ser Gly Ser Leu Leu Gly Gly Lys Ala Ala Leu Thr Leu Ser Gly Ala
225                 230                 235                 240

Gln Pro Glu Asp Glu Ala Glu Tyr Tyr Cys Ala Leu Trp Tyr Ser Asn
                245                 250                 255

Leu Trp Val Phe Gly Gly Gly Thr Lys Leu Thr Val Leu Gly Ser Glu
```

-continued

```
            260                 265                 270

Gln Lys Leu Ile Ser Glu Glu Asp Leu Gly Ser Gly Gly Gly Gly Ser
        275                 280                 285

Leu Pro Glu Thr Gly Gly Ser His His His His His His
    290                 295                 300


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Pro Ala Arg
1


<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ala Pro Ala
1


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Trp Arg Gly Trp Ala
1               5


<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Gly Arg Arg
1


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Gly Trp
1
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Asn Lys Phe Arg Gly Lys Tyr Lys
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Asn Arg Phe Arg Gly Lys Tyr Lys
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Asn Ala Arg Lys Phe Tyr Lys
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Asn Ala Arg Lys Phe Tyr Lys Gly
1 5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

His Trp Arg Gly Trp Val
1 5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Lys His Phe Arg Asn Lys Asp
1 5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Arg His Arg Phe Asn Lys Asp
1 5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Arg Thr Tyr Lys
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Glu Leu Val Trp
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Gly Glu Leu Val Trp
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Ala Trp His Leu Gly Glu Leu Val Trp
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Trp Asp Leu Gly Glu Leu Val Trp
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 19

Ala Trp Xaa Leu Gly Glu Leu Val Trp
1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(12)
<223> OTHER INFORMATION: May or may not form a disulfide bond
<220> FEATURE:
<223> OTHER INFORMATION: See specification as filed for detailed
      description of substitutions and preferred embodiments

<400> SEQUENCE: 20

Asp Cys Ala Trp His Leu Gly Glu Leu Val Trp Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(12)
<223> OTHER INFORMATION: May or may not form a disulfide bond
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 21

Asp Cys Ala Trp Xaa Leu Gly Glu Leu Val Trp Cys Thr
1               5                   10

<210> SEQ ID NO 22
<211> LENGTH: 13

-continued

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 22

Asp Cys Ala Trp Asp Leu Gly Glu Leu Val Trp Cys Thr
1 5 10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(15)
<223> OTHER INFORMATION: May or may not form a disulfide bond
<220> FEATURE:
<221> NAME/KEY: MISC_FEATURE
<222> LOCATION: (3)..(13)
<223> OTHER INFORMATION: May or may not form a disulfide bond
<220> FEATURE:
<221> NAME/KEY: MOD_RES
<222> LOCATION: (6)..(6)
<223> OTHER INFORMATION: Any amino acid
<220> FEATURE:
<223> OTHER INFORMATION: See specification as filed for detailed
description of substitutions and preferred embodiments

<400> SEQUENCE: 23

Cys Asp Cys Ala Trp Xaa Leu Gly Glu Leu Val Trp Cys Thr Cys
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(15)
<223> OTHER INFORMATION: May or may not form a disulfide bond
<220> FEATURE:
<221> NAME/KEY: MISC_FEATURE
<222> LOCATION: (3)..(13)
<223> OTHER INFORMATION: May or may not form a disulfide bond

<400> SEQUENCE: 24

Cys Asp Cys Ala Trp His Leu Gly Glu Leu Val Trp Cys Thr Cys
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(15)
<223> OTHER INFORMATION: May or may not form a disulfide bond
<220> FEATURE:

<221> NAME/KEY: MISC_FEATURE
<222> LOCATION: (3)..(13)
<223> OTHER INFORMATION: May or may not form a disulfide bond

<400> SEQUENCE: 25

Cys Asp Cys Ala Trp Asp Leu Gly Glu Leu Val Trp Cys Thr Cys
1 5 10 15

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Phe Asn Met Gln Gln Gln Arg Arg Phe Tyr Glu Ala Leu His Asp Pro
1 5 10 15

Asn Leu Asn Glu Glu Gln Arg Asn Ala Lys Ile Lys Ser Ile Arg Asp
20 25 30

Asp

<210> SEQ ID NO 27
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 27

Phe Asn Met Gln Cys Gln Arg Arg Phe Tyr Glu Ala Leu His Asp Pro
1 5 10 15

Asn Leu Asn Glu Glu Gln Arg Asn Ala Lys Ile Lys Ser Ile Arg Asp
20 25 30

Asp Cys

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 28

Arg Gly Asn Cys Ala Tyr His Arg Gly Gln Leu Val Trp Cys Thr Tyr
1 5 10 15

His

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 29

Arg Gly Asn Cys Ala Tyr His Lys Gly Gln Leu Val Trp Cys Thr Tyr
1 5 10 15

His

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 30

Arg Gly Asn Cys Lys Tyr His Arg Gly Gln Leu Val Trp Cys Thr Tyr
1 5 10 15

His

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 31

Arg Gly Asn Cys Ala Trp His Arg Gly Lys Leu Val Trp Cys Thr Tyr
1 5 10 15

His

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 32

Arg Gly Asn Cys Lys Trp His Arg Gly Glu Leu Val Trp Cys Thr Tyr
1 5 10 15

His

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 33

Arg Gly Asn Cys Lys Trp His Arg Gly Gln Leu Val Trp Cys Thr Tyr
1               5                   10                  15

His

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 34

Arg Gly Asn Cys Lys Tyr His Leu Gly Glu Leu Val Trp Cys Thr Tyr
1               5                   10                  15

His

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 35

Arg Gly Asn Cys Lys Tyr His Leu Gly Gln Leu Val Trp Cys Thr Tyr
1               5                   10                  15

His

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 36

Asp Cys Lys Trp His Leu Gly Glu Leu Val Trp Cys Thr
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide <220> FEATURE:
<221> NAME/KEY: MISC_FEATURE
<222> LOCATION: (2)..(12)
<223> OTHER INFORMATION: May or may not form a disulfide bond

<400> SEQUENCE: 37

Asp Cys Lys Tyr His Leu Gly Glu Leu Val Trp Cys Thr
1 5 10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 38

Asp Cys Lys Trp His Arg Gly Glu Leu Val Trp Cys Thr
1 5 10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 39

Asp Cys Lys Trp His Leu Gly Gln Leu Val Trp Cys Thr
1 5 10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 40

Asp Cys Lys Tyr His Arg Gly Glu Leu Val Trp Cys Thr
1 5 10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 41

-continued

Asp Cys Lys Tyr His Leu Gly Gln Leu Val Trp Cys Thr
1 5 10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 42

Asp Cys Lys Trp His Arg Gly Gln Leu Val Trp Cys Thr
1 5 10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond

<400> SEQUENCE: 43

Asp Cys Lys Tyr His Arg Gly Gln Leu Val Trp Cys Thr
1 5 10

<210> SEQ ID NO 44
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 44

Phe Asn Lys Gln Cys Gln Arg Arg Phe Tyr Glu Ala Leu His Asp Pro
1 5 10 15

Asn Leu Asn Glu Glu Gln Arg Asn Ala Arg Ile Arg Ser Ile Arg Asp
20 25 30

Asp Cys

<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 45

Phe Asn Met Gln Cys Gln Arg Arg Phe Tyr Glu Ala Leu His Asp Pro
1 5 10 15

Asn Leu Asn Glu Glu Gln Arg Asn Ala Arg Ile Arg Ser Ile Lys Asp
20 25 30

Asp Cys

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 46

Phe Asn Met Gln Cys Gln Arg Arg Phe Tyr Glu Ala Leu His Asp Pro
1 5 10 15

Asn Leu Asn Lys Glu Gln Arg Asn Ala Arg Ile Arg Ser Ile Arg Asp
20 25 30

Asp Cys

<210> SEQ ID NO 47
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 47

Phe Asn Met Gln Cys Gln Arg Arg Phe Tyr Glu Ala Leu His Asp Pro
1 5 10 15

Asn Leu Asn Glu Glu Gln Arg Asn Ala Arg Ile Arg Ser Ile Arg Asp
20 25 30

Asp Cys

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 48

Arg Gly Asn Cys Ala Trp His Leu Gly Gln Leu Val Trp Cys Lys Tyr
1 5 10 15

His

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 49

Arg Gly Asn Cys Ala Trp His Leu Gly Glu Leu Val Trp Cys Lys Tyr
1               5                   10                  15

His

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 50

Arg Gly Asn Cys Ala Tyr His Leu Gly Gln Leu Val Trp Cys Thr Lys
1               5                   10                  15

His

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 51

Arg Gly Asn Cys Ala Tyr His Leu Gly Gln Leu Val Trp Cys Thr Tyr
1               5                   10                  15

Lys

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(14)
<223> OTHER INFORMATION: May or may not form a disulfide bond

<400> SEQUENCE: 52

Arg Gly Asn Cys Ala Tyr His Arg Gly Gln Leu Val Trp Cys Thr Lys
1               5                   10                  15

His

<210> SEQ ID NO 53
<211> LENGTH: 34
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 53

Lys Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 54
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 54

Phe Asn Met Gln Cys Gln Lys Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 55

Phe Asn Met Gln Cys Gln Arg Arg Phe Tyr Glu Ala Lys His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 56

Phe Asn Met Gln Cys Gln Arg Arg Phe Tyr Glu Ala Leu His Asp Pro

```
1               5                   10                  15

Asn Leu Asn Glu Glu Gln Arg Lys Ala Arg Ile Arg Ser Ile Arg Asp
            20                  25                  30

Asp Cys


<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 57

Phe Asn Met Gln Cys Lys Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys


<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(34)
<223> OTHER INFORMATION: May or may not form a disulfide bond

<400> SEQUENCE: 58

Phe Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Lys
            20                  25                  30

Asp Cys


<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: May or may not form a disulfide bond
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<223> OTHER INFORMATION: See specification as filed for detailed
      description of substitutions and preferred embodiments

<400> SEQUENCE: 59
```

```
Cys Xaa Tyr His Xaa Xaa Xaa Leu Val Trp Cys
1               5                   10


<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MISC_FEATURE
<222> LOCATION: (2)..(12)
<223> OTHER INFORMATION: May or may not form a disulfide bond
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(8)
<223> OTHER INFORMATION: Any amino acid
<220> FEATURE:
<223> OTHER INFORMATION: See specification as filed for detailed
      description of substitutions and preferred embodiments

<400> SEQUENCE: 60

Xaa Cys Xaa Tyr His Xaa Xaa Xaa Leu Val Trp Cys
1               5                   10


<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: May or may not form a disulfide bond
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<223> OTHER INFORMATION: See specification as filed for detailed
      description of substitutions and preferred embodiments

<400> SEQUENCE: 61

Cys Xaa Tyr His Xaa Xaa Xaa Leu Val Trp Cys Xaa
1               5                   10


<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(3)
<223> OTHER INFORMATION: Any amino acid
<220> FEATURE:
<221> NAME/KEY: MISC_FEATURE
<222> LOCATION: (4)..(14)
<223> OTHER INFORMATION: May or may not form a disulfide bond
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<223> OTHER INFORMATION: See specification as filed for detailed
      description of substitutions and preferred embodiments

<400> SEQUENCE: 62

Xaa Xaa Xaa Cys Xaa Tyr His Xaa Xaa Xaa Leu Val Trp Cys Xaa Xaa
1               5                   10                  15

Xaa


<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MISC_FEATURE
<222> LOCATION: (2)..(12)
<223> OTHER INFORMATION: May or may not form a disulfide bond
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 63

Xaa Cys Xaa Tyr His Xaa Xaa Xaa Leu Val Trp Cys Xaa Xaa Xaa
1               5                   10                  15


<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid
<220> FEATURE:
```

<221> NAME/KEY: MISC_FEATURE
<222> LOCATION: (4)..(14)
<223> OTHER INFORMATION: May or may not form a disulfide bond
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<223> OTHER INFORMATION: See specification as filed for detailed
      description of substitutions and preferred embodiments

<400> SEQUENCE: 64

```
Xaa Xaa Xaa Cys Xaa Tyr His Xaa Xaa Xaa Leu Val Trp Cys Xaa Xaa
1               5                   10                  15

Xaa
```

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MISC_FEATURE
<222> LOCATION: (15)..(17)
<223> OTHER INFORMATION: This region may encompass 1-3 residues
<220> FEATURE:
<223> OTHER INFORMATION: See specification as filed for detailed
      description of substitutions and preferred embodiments

<400> SEQUENCE: 65

```
Xaa Xaa Xaa Cys Xaa Xaa His Xaa Gly Xaa Leu Val Trp Cys Xaa Xaa
1               5                   10                  15

Xaa
```

<210> SEQ ID NO 66
<211> LENGTH: 17
<212> TYPE: PRT
<213> ORGANISM: Artificial Sequence
<220> FEATURE:

<223> OTHER INFORMATION: Description of Artificial Sequence: Synthetic
peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<223> OTHER INFORMATION: See specification as filed for detailed
description of substitutions and preferred embodiments

<400> SEQUENCE: 66

Xaa Xaa Xaa Cys Xaa Xaa His Xaa Gly Xaa Leu Val Trp Cys Xaa Xaa
1 5 10 15

Xaa

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<223> OTHER INFORMATION: See specification as filed for detailed
description of substitutions and preferred embodiments

<400> SEQUENCE: 67

Asp Cys Xaa Xaa His Xaa Gly Xaa Leu Val Trp Cys Xaa Xaa Xaa
1 5 10 15

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:

<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<223> OTHER INFORMATION: See specification as filed for detailed description of substitutions and preferred embodiments

<400> SEQUENCE: 68

Asp Cys Xaa Xaa His Xaa Gly Xaa Leu Val Trp Cys Thr
1 5 10

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<223> OTHER INFORMATION: See specification as filed for detailed description of substitutions and preferred embodiments

<400> SEQUENCE: 69

Arg Gly Asn Cys Xaa Xaa His Xaa Gly Xaa Leu Val Trp Cys Xaa Xaa
1 5 10 15

Xaa

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any amino acid

<400> SEQUENCE: 70

Leu Pro Xaa Thr Gly
1 5

<210> SEQ ID NO 71
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MISC_FEATURE
<222> LOCATION: (5)..(14)
<223> OTHER INFORMATION: This region may encompass 1-10 residues

<400> SEQUENCE: 71

Leu Pro Xaa Thr Gly Gly Gly Gly Gly Gly Gly Gly Gly Gly
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(14)
<223> OTHER INFORMATION: This region may encompass 1-10 residues

<400> SEQUENCE: 72

Leu Pro Glu Thr Gly Gly Gly Gly Gly Gly Gly Gly Gly Gly
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Gly Gly Gly
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Pro Glu Thr Gly
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 1-10 residues

<400> SEQUENCE: 75

Gly Gly Gly Gly Gly Gly Gly Gly Gly Gly
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(15)
<223> OTHER INFORMATION: Any amino acid
<220> FEATURE:
<221> NAME/KEY: MISC_FEATURE
<222> LOCATION: (6)..(15)
<223> OTHER INFORMATION: This region may encompass 1-10 residues

<400> SEQUENCE: 76

Leu Pro Xaa Thr Gly Xaa Xaa Xaa Xaa Xaa Xaa Xaa Xaa Xaa Xaa
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(15)
<223> OTHER INFORMATION: Any amino acid
<220> FEATURE:
<221> NAME/KEY: MISC_FEATURE
<222> LOCATION: (6)..(15)
<223> OTHER INFORMATION: This region may encompass 1-10 residues

<400> SEQUENCE: 77

Leu Pro Glu Thr Gly Xaa Xaa Xaa Xaa Xaa Xaa Xaa Xaa Xaa Xaa
1               5                   10                  15

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass 3-5 residues
<220> FEATURE:
<223> OTHER INFORMATION: See specification as filed for detailed
      description of substitutions and preferred embodiments

<400> SEQUENCE: 78

Gly Gly Gly Gly Gly
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<221> NAME/KEY: MOD_RES
<222> LOCATION: (6)..(7)
<223> OTHER INFORMATION: Any amino acid

<400> SEQUENCE: 79

Leu Pro Glu Thr Gly Xaa Xaa
1 5

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond
<220> FEATURE:
<221> NAME/KEY: MOD_RES
<222> LOCATION: (10)..(10)
<223> OTHER INFORMATION: Any amino acid
<220> FEATURE:
<223> OTHER INFORMATION: See specification as filed for detailed description of substitutions and preferred embodiments

<400> SEQUENCE: 80

Asp Cys Ala Trp His Leu Gly Glu Leu Xaa Trp Cys Thr
1 5 10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond
<220> FEATURE:
<221> NAME/KEY: MOD_RES
<222> LOCATION: (6)..(6)
<223> OTHER INFORMATION: Any amino acid
<220> FEATURE:
<223> OTHER INFORMATION: See specification as filed for detailed description of substitutions and preferred embodiments

<400> SEQUENCE: 81

Asp Cys Ala Trp His Xaa Gly Glu Leu Val Trp Cys Thr
1 5 10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(12)
<223> OTHER INFORMATION: May or may not form a disulfide bond
<220> FEATURE:
<221> NAME/KEY: MOD_RES
<222> LOCATION: (8)..(8)
<223> OTHER INFORMATION: Any amino acid
<220> FEATURE:
<223> OTHER INFORMATION: See specification as filed for detailed description of substitutions and preferred embodiments

<400> SEQUENCE: 82

Asp Cys Ala Trp His Leu Gly Xaa Leu Val Trp Cys Thr
1 5 10

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (4)..(14)
<223> OTHER INFORMATION: May or may not form a disulfide bond
<220> FEATURE:
<221> NAME/KEY: MOD_RES
<222> LOCATION: (8)..(8)
<223> OTHER INFORMATION: Lys or Arg

<400> SEQUENCE: 83

Gly Pro Asp Cys Ala Tyr His Xaa Gly Glu Leu Val Trp Cys Thr Phe
1 5 10 15

His

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Leu Pro Glu Thr Gly Gly
1 5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Leu Pro Glu Thr
1